US012780839B2

(12) United States Patent
Li et al.

(10) Patent No.: US 12,780,839 B2
(45) Date of Patent: Nov. 3, 2026

(54) TRICYCLIC DERIVATIVES USEFUL AS PARP7 INHIBITORS

(71) Applicant: Jacobio Pharmaceuticals Co., Ltd., Beijing (CN)

(72) Inventors: Haijun Li, Beijing (CN); Mingming Chen, Beijing (CN); Di Kang, Beijing (CN); Qinglong Li, Beijing (CN); Lei Zhang, Beijing (CN); Man Yan, Beijing (CN); Wei Long, Beijing (CN); Yanping Wang, Beijing (CN); Hao Zhang, Beijing (CN); Cunbo Ma, Beijing (CN); Amin Li, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 450 days.

(21) Appl. No.: 18/276,269

(22) PCT Filed: Jan. 26, 2022

(86) PCT No.: PCT/CN2022/073906

§ 371 (c)(1),
(2) Date: Aug. 8, 2023

(87) PCT Pub. No.: WO2022/170974

PCT Pub. Date: Aug. 18, 2022

(65) Prior Publication Data

US 2024/0336629 A1 Oct. 10, 2024

(30) Foreign Application Priority Data

Feb. 9, 2021 (WO) ................ PCT/CN2021/076144
Apr. 29, 2021 (WO) ................ PCT/CN2021/091050
Sep. 8, 2021 (WO) ................ PCT/CN2021/117189
Sep. 18, 2021 (WO) ................ PCT/CN2021/119368
Oct. 19, 2021 (WO) ................ PCT/CN2021/124714
Nov. 4, 2021 (WO) ................ PCT/CN2021/128807
Nov. 5, 2021 (WO) ................ PCT/CN2021/129056

(51) Int. Cl.
*C07D 513/14* (2006.01)
*C07D 471/14* (2006.01)
*C07D 498/14* (2006.01)
*C12N 9/99* (2006.01)

(52) U.S. Cl.
CPC ......... *C07D 513/14* (2013.01); *C07D 471/14* (2013.01); *C07D 498/14* (2013.01); *C12N 9/99* (2013.01)

(58) Field of Classification Search
CPC .................................................... C07D 513/14
See application file for complete search history.

(56) References Cited

U.S. PATENT DOCUMENTS

2024/0166664 A1* 5/2024 Gu .......................... A61P 35/00

FOREIGN PATENT DOCUMENTS

| | | | |
|---|---|---|---|
| CN | 103570725 | 2/2014 | |
| CN | 103833756 | 6/2014 | |
| EP | 4 289 845 A1 | 12/2023 | |
| WO | 2019055966 | 3/2019 | |
| WO | 2019212937 | 11/2019 | |
| WO | 2020094084 A1 | 5/2020 | |
| WO | 2021047406 A1 | 3/2021 | |
| WO | 2021087018 | 5/2021 | |
| WO | 2021087025 | 5/2021 | |
| WO | WO-2022166749 A1 * | 8/2022 | ............ C07F 9/6561 |
| WO | 2022247839 A1 | 12/2022 | |

OTHER PUBLICATIONS

Pozharskii et al. Heterocycles in Life and Society Wiley, 1997, pp. 1-6.*
Qiu "PARP7: an Emerging Therapeutic Target-Insights into Biological Functions and Advances in Small-Molecule Inhibitor Development" J. Med. Chem. 2025, 68, 19846-19870.*
Zhang "Exploring the structural-activity relationship of hexahydropyrazino[1,2-d]pyrido[3,2-b][1,4]oxazine derivatives as potent and orally-bioavailable PARP7 inhibitors." European Journal of Medicinal Chemistry, 2023, 261, 115836.*
Nov. 22, 2024, Extended European Search Report for European Patent Application No. EP 22 75 2135.
"STN Registry", CAS RN 2417420-76-7 et al.,May 27, 2020 (May 27, 2020).

* cited by examiner

*Primary Examiner* — David K O'Dell
(74) *Attorney, Agent, or Firm* — Baratta Law PLLC; Lawrence A. Baratta, Jr.

(57) ABSTRACT

Provided are a compound of formula (I) that inhibit the activity of PARP7, a stereoisomer thereof, a deuterated derivative thereof, or a pharmaceutically acceptable salt thereof, an intermediate to prepare the compound, a process to prepare the compound, a composition comprising the same, and the methods of using the same.

(I)

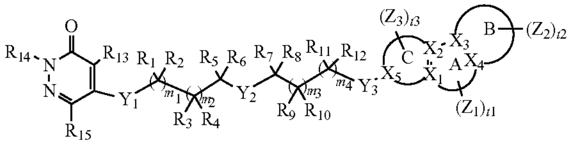

11 Claims, No Drawings

TRICYCLIC DERIVATIVES USEFUL AS PARP7 INHIBITORS

CROSS-REFERENCES TO RELATED APPLICATIONS

This application is a U.S. Nat'l Phase of Int'l Appl. No. PCT/CN2022/073906, filed Jan. 26, 2022, which claims priority to PCT/CN2021/129056, filed Nov. 5, 2021; PCT/CN2021/128807, filed Nov. 4, 2021; PCT/CN2021/124714, filed Oct. 19, 2021; PCT/CN2021/119368, filed Sep. 18, 2021; PCT/CN2021/117189, filed Sep. 8, 2021; PCT/CN2021/091050, filed Apr. 29, 2021; PCT/CN2021/076144, filed Feb. 9, 2021; each of which is incorporated herein in its entirety and for all purposes.

TECHNICAL FIELD

The invention relates to a compound that inhibit the activity of PARP7, a stereoisomer thereof, a deuterated derivative thereof, or a pharmaceutically acceptable salt thereof, an intermediate to prepare the compound, a process to prepare the compound, a composition comprising the same, and the methods of using the same.

BACKGROUND ART

Members of the poly (ADP-ribose) polymerase (PARP) family of enzymes catalyze the post-translational modification of proteins using β-$NAD^+$ as a substrate to successively add ADP-ribose moieties onto target proteins: a process termed PARsylation. In the 1960s, this posttranslational modification was first characterized with the identification of PARP1 and its role in DNA repair. Subsequently, additional 16 members of the PARP family were identified, each of which possesses a structurally similar PARP catalytic domain. Furthermore, in addition to its well-studied role in DNA repair, PARsylation has now been shown to modulate processes as diverse as cellular proliferation, apoptosis, DNA methylation, transcriptional regulation and WNT signaling. According to different catalytic activity, PARP family can be divided into three categories: monoPARPS (catalyze the transfer of mono-ADP-ribose units onto their substrates) including the majority of PARP family members; polyPARPS (catalyze the transfer of poly-ADP-ribose units onto their substrates) including PARP1, PARP2, PARP5A, PARP5b; and PARP13 which is the only PARP family member whose catalytic activity could not be demonstrated either in vitro or in vivo.

The monoPARP protein family plays important roles in multiple stress responses associated with the development of cancer, inflammatory diseases, and neurodegenerative diseases. PARP7 as a monoPARP family member has been demonstrated to be overactive in tumors and to play a key role in cancer cell survival. The study found that many cancer cells rely on PARP7 for internal cellular survival, and that PARP7 allows cancer cells to "hide" from the immune system. Inhibition of PARP7 can effectively inhibit the growth of cancer cells and restore interferon signaling, effectively prevent cancer cells from evading the immune system, and inhibiting the "brake" of innate and adaptive immune mechanisms. In several cancer models, PARP7 inhibitors exhibit persistent tumor growth inhibition, potent anti-proliferative activity, and interferon signaling restoration. At present, few studies have been reported on PARP7 inhibitors. Therefore, there remains a need for therapeutic compounds and methods for treating cancers related to PARP7.

SUMMARY OF THE INVENTION

The present invention provides a compound of formula (I):

(I)

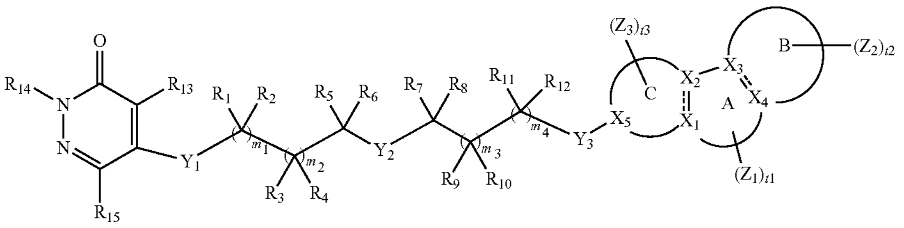

a stereoisomer thereof, a deuterated derivative thereof, or a pharmaceutically acceptable salt thereof, wherein the definition of each of variables is defined as below.

Also provided herein is an intermediate to prepare the compound of the present invention.

Also provided herein is a process to prepare the compound of the present invention.

Also provided herein is a use of the compound of the present invention s a targeting PARP7 protein ligand in a PROTAC compound acting as a degradation modulator of PARP7 protein.

Also provided herein is a pharmaceutical composition comprising an effectively therapeutic amount of the compound of the present invention, a stereoisomer thereof, a deuterated derivatives thereof, or a pharmaceutically acceptable salt thereof, and at least one pharmaceutically acceptably excipient.

Also provided herein is a method of inhibiting the activity of PARP7, comprising contacting an effective amount of the compound of the present invention, a stereoisomer thereof, a deuterated derivative thereof, a pharmaceutically acceptable salt thereof or the pharmaceutical composition of the present invention with PARP7 or a cell in which inhibition of PARP7 is desired.

Also provided herein is a use of the compound of the present invention, a stereoisomer thereof, a deuterated derivative thereof, a pharmaceutically acceptable salt thereof or the pharmaceutical composition of the present invention for the manufacture of a medicament for the treatment of cancer.

Also provided herein is a method of treating a subject having cancer, said method comprising administering to the subject a therapeutically effective amount of the compound of the present invention, a stereoisomer thereof, a deuterated derivative thereof, a pharmaceutically acceptable salt thereof, or the pharmaceutical composition of the present invention.

Also provided herein is a compound of the present invention, a stereoisomer thereof, a deuterated derivative thereof, a pharmaceutically acceptable salt thereof, or the pharmaceutical composition of the present invention for use in the treatment of cancer.

DETAILED DESCRIPTION

Provided herein are the following aspects:

[1]. A compound of formula (I), a stereoisomer thereof, a deuterated derivative thereof, or a pharmaceutically acceptable salt thereof:

(I)

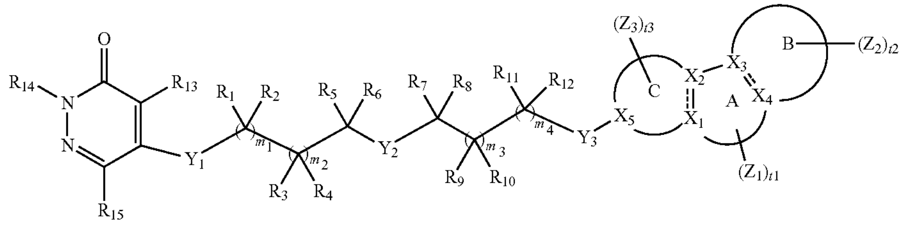

Wherein,

Ring A is selected from a 4-20 membered carbocyclic ring, 4-20 membered heterocyclic ring, 6-12 membered aryl ring or 5-20 membered heteroaryl ring; said ring A is optionally substituted with $t_1$ $Z_1$;

$Z_1$ at each occurrence is independently selected from halogen, —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, —CN, —NO$_2$, —N$_3$, oxo, —OR$_{a1}$, —SR$_{a1}$, —NR$_{c1}$R$_{d1}$, —C(=O)R$_{b1}$, —C(=O)OR$_{a1}$, —OC(=O)R$_{b1}$, —OC(=O)OR$_{a1}$, —C(=O)NR$_{c1}$R$_{d1}$, —OC(=O)NR$_{c1}$R$_{d1}$, —C(=NR$_{e1}$)R$_{b1}$, —C(=NR$_{e1}$)NR$_{c1}$R$_{d1}$, —NR$_{c1}$C(=NR$_{e1}$)NR$_{c1}$R$_{d1}$, —NR$_{c1}$C(=O)R$_{b1}$, —NR$_{c1}$C(=O)OR$_{a1}$, —NR$_{c1}$C(=O)NR$_{c1}$R$_{d1}$, —S(=O)R$_{b1}$, —S(=O)OR$_{a1}$, —OS(=O)R$_{b1}$, —OS(=O)OR$_{a1}$, —S(=O)NR$_{c1}$R$_{d1}$, —NR$_{c1}$S(=O)R$_{b1}$, —NR$_{c1}$S(=O)OR$_{a1}$, —OS(=O)NR$_{c1}$R$_{d1}$, —NR$_{c1}$S(=O)NR$_{c1}$R$_{d1}$, —S(=O)$_2$R$_{b1}$, —S(=O)$_2$OR$_{a1}$, —OS(=O)$_2$R$_{b1}$, —OS(=O)$_2$OR$_{a1}$, —S(=O)$_2$NR$_{c1}$R$_{d1}$, —NR$_{c1}$S(=O)$_2$R$_{b1}$, —NR$_{c1}$S(=O)$_2$OR$_{a1}$, —OS(=O)$_2$NR$_{c1}$R$_{d1}$, —NR$_{c1}$S(=O)$_2$NR$_{c1}$R$_{d1}$, —P(R$_{a1}$)$_2$, —P(=O)(R$_{b1}$)$_2$, —P(=O)$_2$, 3-20 membered carbocyclyl, 3-20 membered heterocyclyl, 6-12 membered aryl or 5-20 membered heteroaryl, wherein, the —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, 3-20 membered carbocyclyl, 3-20 membered heterocyclyl, 6-12 membered aryl or 5-20 membered heteroaryl is independently optionally substituted with one or more substituents selected from halogen, —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, —CN, —NO$_2$, —N$_3$, oxo, —OR$_{a1}$, —SR$_{a1}$, —NR$_{c1}$R$_{d1}$, —C(=O)R$_{b1}$, —C(=O)OR$_{a1}$, —OC(=O)R$_{b1}$, —OC(=O)OR$_{a1}$, —C(=O)NR$_{c1}$R$_{d1}$, —OC(=O)NR$_{c1}$R$_{d1}$, —C(=NR$_{e1}$)R$_{b1}$, —C(=NR$_{e1}$)NR$_{c1}$R$_{d1}$, —NR$_{c1}$C(=NR$_{e1}$)NR$_{c1}$R$_{d1}$, —NR$_{c1}$C(=O)R$_{b1}$, —NR$_{c1}$C(=O)OR$_{a1}$, —NR$_{c1}$C(=O)NR$_{c1}$R$_{d1}$, —S(=O)R$_{b1}$, —S(=O)OR$_{a1}$, —OS(=O)R$_{b1}$, —OS(=O)OR$_{a1}$, —S(=O)NR$_{c1}$R$_{d1}$, —NR$_{c1}$S(=O)R$_{b1}$, —NR$_{c1}$S(=O)OR$_{a1}$, —OS(=O)NR$_{c1}$R$_{d1}$, —NR$_{c1}$S(=O)NR$_{c1}$R$_{d1}$, —S(=O)$_2$R$_{b1}$, —S(=O)$_2$OR$_{a1}$, —OS(=O)$_2$R$_{b1}$, —OS(=O)$_2$OR$_{a1}$, —S(=O)$_2$NR$_{c1}$R$_{d1}$, —NR$_{c1}$S(=O)$_2$R$_{b1}$, —NR$_{c1}$S(=O)$_2$OR$_{a1}$, —OS(=O)$_2$NR$_{c1}$R$_{d1}$, —NR$_{c1}$S(=O)$_2$NR$_{c1}$R$_{d1}$, —P(R$_{a1}$)$_2$, —P(=O)(R$_{b1}$)$_2$, —P(=O)$_2$, 3-20 membered carbocyclyl, 3-20 membered heterocyclyl, 6-12 membered aryl or 5-20 membered heteroaryl;

Optionally, two $Z_1$ together with the atom to which they are both attached form a 3-20 membered carbocyclic ring, or a 3-20 heterocyclic ring, wherein, said 3-20 membered carbocylic ring or 3-20 heterocyclic ring is optionally substituted with one or more R$_{X1}$;

Optionally, two adjacent $Z_1$ together with the atoms to which they are respectively attached form a 3-20 membered carbocyclic ring, a 3-20 membered heterocyclic ring, a 6-12 membered aryl ring or a 5-20 membered heteroaryl ring, wherein, each of rings is independently optionally substituted with one or more R$_{X2}$;

Optionally, two nonadjacent $Z_1$ are connected together to form a C$_{0-6}$alkylene bridge, wherein, each of carbon atoms in the bridge is optionally replaced by 1 or 2 members selected from —CH(R$_{X3}$)—, —C(R$_{X3}$)$_2$—, —HC=CH—, —R$_{X3}$C=CH—, —HC=CR$_{X3}$—, —R$_{X3}$C=CR$_{X3}$—, —C≡C—, —C(=O)—, —O—, —NH—, —NR$_{X3}$—, —S—, —S(=O)—, —S(=O)$_2$—, —PH—, —PR$_{X3}$—, —P(=O)H—, —P(=O)R$_{X3}$—, —C(=O)O—, —OC(=O)—, —C(=O)NH—, —C(=O)NR$_{X3}$—, —NR$_{X3}$C(=O)—, —NHC(=O)—, —S(=O)O—, —OS(=O)—, —S(=O)$_2$O—, —OS(=O)$_2$—, —S(=O)NH—, —S(=O)NR$_{X3}$—, —NHS(=O)—, —NR$_{X3}$S(=O)—, —S(=O)$_2$NH—, —S(=O)$_2$NR$_{X3}$—, —NHS(=O)$_2$—, —NR$_{X3}$S(=O)$_2$—, —OC(=O)O—, —NHC(=O)O—, —NR$_{X3}$C(=O)O—, —OC(=O)NH—, —OC(=O)NR$_{X3}$—, —NHC(=O)NH—, —NHC(=O)NR$_{X3}$—, —NR$_{X3}$C(=O)NH— or —NR$_{X3}$C(=O)NR$_{X3}$—;

R$_{X1}$, R$_{X2}$ or R$_{X3}$ at each occurrence is independently selected from halogen, —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, —CN, —NO$_2$, —N$_3$, oxo, —OR$_{a1}$, —SR$_{a1}$, —NR$_{c1}$R$_{d1}$, —C(=O)R$_{b1}$, —C(=O)OR$_{a1}$, —OC(=O)R$_{b1}$, —OC(=O)OR$_{a1}$, —C(=O)NR$_{c1}$R$_{d1}$, —OC(=O)NR$_{c1}$R$_{d1}$, —C(=NR$_{e1}$)R$_{b1}$, —C(=NR$_{e1}$)NR$_{c1}$R$_{d1}$, —NR$_{c1}$C(=NR$_{e1}$)NR$_{c1}$R$_{d1}$, —NR$_{c1}$C(=O)R$_{b1}$, —NR$_{c1}$C(=O)OR$_{a1}$, —NR$_{c1}$C(=O)NR$_{c1}$R$_{d1}$, —S(=O)$R_{b1}$, —S(=O)O$R_{a1}$, —OS(=O)$R_{b1}$, —OS(=O)O$R_{a1}$, —S(=O)N$R_{c1}R_{d1}$, —N$R_{c1}$S(=O)$R_{b1}$, —N$R_{c1}$S(=O)O$R_{a1}$, —OS(=O)N$R_{c1}R_{d1}$, —N$R_{c1}$S(=O)N$R_{c1}R_{d1}$, —S(=O)$_2R_{b1}$, —S(=O)$_2$O$R_{a1}$, —OS(=O)$_2R_{b1}$, —OS(=O)$_2$O$R_{a1}$, —S(=O)$_2$N$R_{c1}R_{d1}$, —N$R_{c1}$S(=O)$_2R_{b1}$, —N$R_{c1}$S(=O)$_2$O$R_{a1}$, —OS(=O)$_2$N$R_{c1}R_{d1}$, —N$R_{c1}$S(=O)$_2$N$R_{c1}R_{d1}$, —P($R_{a1}$)$_2$, —P(=O)($R_{b1}$)$_2$, —P(=O)$_2$, 3-20 membered carbocyclyl, 3-20 membered heterocyclyl, 6-12 membered aryl or 5-20 membered heteroaryl, wherein, said —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, 3-20 membered carbocyclyl, 3-20 membered heterocyclyl, 6-12 membered aryl or 5-20 membered heteroaryl is optionally independently substituted with one or more substituents selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —O$R_{a1}$, —S$R_{a1}$, —N$R_{c1}R_{d1}$, —C(=O)$R_{b1}$, —C(=O)O$R_{a1}$, —OC(=O)$R_{b1}$, —OC(=O)O$R_{a1}$, —C(=O)N$R_{c1}R_{d1}$, —OC(=O)N$R_{c1}R_{d1}$, —C(=N$R_{e1}$)$R_{b1}$, —C(=N$R_{e1}$)N$R_{c1}R_{d1}$, —N$R_{c1}$C(=N$R_{e1}$)N$R_{c1}R_{d1}$, —N$R_{c1}$C(=O)$R_{b1}$, —N$R_{c1}$C(=O)O$R_{a1}$, —N$R_{c1}$C(=O)N$R_{c1}R_{d1}$, —S(=O)$R_{b1}$, —S(=O)O$R_{a1}$, —OS(=O)$R_{b1}$, —OS(=O)O$R_{a1}$, —S(=O)N$R_{c1}R_{d1}$, —N$R_{c1}$S(=O)$R_{b1}$, —N$R_{c1}$S(=O)O$R_{a1}$, —OS(=O)N$R_{c1}R_{d1}$, —N$R_{c1}$S(=O)N$R_{c1}R_{d1}$, —S(=O)$_2R_{b1}$, —S(=O)$_2$O$R_{a1}$, —OS(=O)$_2R_{b1}$, —OS(=O)$_2$O$R_{a1}$, —S(=O)$_2$N$R_{c1}R_{d1}$, —N$R_{c1}$S(=O)$_2R_{b1}$, —N$R_{c1}$S(=O)$_2$O$R_{a1}$, —OS(=O)$_2$N$R_{c1}R_{d1}$, —N$R_{c1}$S(=O)$_2$N$R_{c1}R_{d1}$, —P($R_{a1}$)$_2$, —P(=O)($R_{b1}$)$_2$, —P(=O)$_2$, 3-20 membered carbocyclyl, 3-20 membered heterocyclyl, 6-12 membered aryl or 5-20 membered heteroaryl;

$t_1$ is selected from 0, 1, 2, 3, 4, 5, 6, 7, 8, 9 or 10;

Ring B is selected from a 3-20 membered carbocyclic ring, 3-20 membered heterocyclic ring, 6-12 membered aryl ring or 5-20 membered heteroaryl ring; said ring B is optionally substituted with $t_2$ $Z_2$;

$Z_2$ at each occurrence is independently selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —O$R_{a2}$, —S$R_{a2}$, —N$R_{c2}R_{d2}$, —C(=O)$R_{b2}$, —C(=O)O$R_{a2}$, —OC(=O)$R_{b2}$, —OC(=O)O$R_{a2}$, —C(=O)N$R_{c2}R_{d2}$, —OC(=O)N$R_{c2}R_{d2}$, —C(=N$R_{e2}$)$R_{b2}$, —C(=N$R_{e2}$)N$R_{c2}R_{d2}$, —N$R_{c2}$C(=N$R_{e2}$)N$R_{c2}R_{d2}$, —N$R_{c2}$C(=O)$R_{b2}$, —N$R_{c2}$C(=O)O$R_{a2}$, —N$R_{c2}$C(=O)N$R_{c2}R_{d2}$, —S(=O)$R_{b2}$, —S(=O)O$R_{a2}$, —OS(=O)$R_{b2}$, —OS(=O)O$R_{a2}$, —S(=O)N$R_{c2}R_{d2}$, —N$R_{c2}$S(=O)$R_{b2}$, —N$R_{c2}$S(=O)O$R_{a2}$, —OS(=O)N$R_{c2}R_{d2}$, —N$R_{c2}$S(=O)N$R_{c2}R_{d2}$, —S(=O)$_2R_{b2}$, —S(=O)$_2$O$R_{a2}$, —OS(=O)$_2R_{b2}$, —OS(=O)$_2$O$R_{a2}$, —S(=O)$_2$N$R_{c2}R_{d2}$, —N$R_{c2}$S(=O)$_2R_{b2}$, —N$R_{c2}$S(=O)$_2$O$R_{a2}$, —OS(=O)$_2$N$R_{c2}R_{d2}$, —N$R_{c2}$S(=O)$_2$N$R_{c2}R_{d2}$, —P($R_{a2}$)$_2$, —P(=O)($R_{b2}$)$_2$, —P(=O)$_2$, 3-20 membered carbocyclyl, 3-20 membered heterocyclyl, 6-12 membered aryl or 5-20 membered heteroaryl ring, wherein, the —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, 3-20 membered carbocyclyl, 3-20 membered heterocyclyl, 6-12 membered aryl or 5-20 membered heteroaryl is independently optionally substituted with one or more substituents selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —O$R_{a2}$, —S$R_{a2}$, —N$R_{c2}R_{d2}$, —C(=O)$R_{b2}$, —C(=O)O$R_{a2}$, —OC(=O)$R_{b2}$, —OC(=O)O$R_{a2}$, —C(=O)N$R_{c2}R_{d2}$, —OC(=O)N$R_{c2}R_{d2}$, —C(=N$R_{e2}$)$R_{b2}$, —C(=N$R_{e2}$)N$R_{c2}R_{d2}$, —N$R_{c2}$C(=N$R_{e2}$)N$R_{c2}R_{d2}$, —N$R_{c2}$C(=O)$R_{b2}$, —N$R_{c2}$C(=O)O$R_{a2}$, —N$R_{c2}$C(=O)N$R_{c2}R_{d2}$, —S(=O)$R_{b2}$, —S(=O)O$R_{a2}$, —OS(=O)$R_{b2}$, —OS(=O)O$R_{a2}$, —S(=O)N$R_{c2}R_{d2}$, —N$R_{c2}$S(=O)$R_{b2}$, —N$R_{c2}$S(=O)O$R_{a2}$, —OS(=O)N$R_{c2}R_{d2}$, —N$R_{c2}$S(=O)N$R_{c2}R_{d2}$, —S(=O)$_2R_{b2}$, —S(=O)$_2$O$R_{a2}$, —OS(=O)$_2R_{b2}$, —OS(=O)$_2$O$R_{a2}$, —S(=O)$_2$N$R_{c2}R_{d2}$, —N$R_{c2}$S(=O)$_2R_{b2}$, —N$R_{c2}$S(=O)$_2$O$R_{a2}$, —OS(=O)$_2$N$R_{c2}R_{d2}$, —N$R_{c2}$S(=O)$_2$N$R_{c2}R_{d2}$, —P($R_{a2}$)$_2$, —P(=O)($R_{b2}$)$_2$, —P(=O)$_2$, 3-20 membered carbocyclyl, 3-20 membered heterocyclyl, 6-12 membered aryl or 5-20 membered heteroaryl;

Optionally, two $Z_2$ together with the atom to which they are both attached form a 3-20 membered carbocyclic ring, or a 3-20 heterocyclic ring, wherein, said 3-20 membered carbocylic ring or 3-20 heterocyclic ring is optionally substituted with one or more $R_{X4}$;

Optionally, two adjacent $Z_2$ together with the atoms to which they are respectively attached form a 3-20 membered carbocyclic ring, a 3-20 membered heterocyclic ring, a 6-12 membered aryl ring or a 5-20 membered heteroaryl ring, wherein, each of rings is independently optionally substituted with one or more $R_{X5}$;

Optionally, two nonadjacent $Z_2$ are connected together to form a $C_{0-6}$ alkylene bridge, wherein, each of the carbon atoms in the bridge is optionally replaced by 1 or 2 members selected from —CH($R_{X6}$)—, —C($R_{X6}$)$_2$—, —HC=CH—, —$R_{X6}$C=CH—, —HC=C$R_{X6}$—, —$R_{X6}$C=C$R_{X6}$—, —C≡C—, —C(=O)—, —O—, —NH—, —N$R_{X6}$—, —S—, —S(=O)—, —S(=O)$_2$—, —PH—, —P$R_{X6}$—, —P(=O)H—, —P(=O)$R_{X6}$—, —C(=O)O—, —OC(=O)—, —C(=O)NH—, —C(=O)N$R_{X6}$—, —N$R_{X6}$C(=O)—, —NHC(=O)—, —S(=O)O—, —OS(=O)—, —S(=O)$_2$O—, —OS(=O)$_2$—, —S(=O)NH—, —S(=O)N$R_{X6}$—, —NHS(=O)—, —N$R_{X6}$S(=O)—, —S(=O)$_2$NH—, —S(=O)$_2$N$R_{X6}$—, —NHS(=O)$_2$—, —N$R_{X6}$S(=O)$_2$—, —OC(=O)O—, —NHC(=O)O—, —N$R_{X6}$C(=O)O—, —OC(=O)NH—, —OC(=O)N$R_{X6}$—, —NHC(=O)NH—, —NHC(=O)N$R_{X6}$—, —N$R_{X6}$C(=O)NH— or —N$R_{X6}$C(=O)N$R_{X6}$—;

$R_{X4}$, $R_{X5}$ or $R_{X6}$ at each occurrence is independently selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —O$R_{a2}$, —S$R_{a2}$, —N$R_{c2}R_{d2}$, —C(=O)$R_{b2}$, —C(=O)O$R_{a2}$, —OC(=O)$R_{b2}$, —OC(=O)O$R_{a2}$, —C(=O)N$R_{c2}R_{d2}$, —OC(=O)N$R_{c2}R_{d2}$, —C(=N$R_{e2}$)$R_{b2}$, —C(=N$R_{e2}$)N$R_{c2}R_{d2}$, —N$R_{c2}$C(=N$R_{e2}$)N$R_{c2}R_{d2}$, —N$R_{c2}$C(=O)$R_{b2}$, —N$R_{c2}$C(=O)O$R_{a2}$, —N$R_{c2}$C(=O)N$R_{c2}R_{d2}$, —S(=O)$R_{b2}$, —S(=O)O$R_{a2}$, —OS(=O)$R_{b2}$, —OS(=O)O$R_{a2}$, —S(=O)N$R_{c2}R_{d2}$, —N$R_{c2}$S(=O)$R_{b2}$, —N$R_{c2}$S(=O)O$R_{a2}$, —OS(=O)N$R_{c2}R_{d2}$, —N$R_{c2}$S(=O)N$R_{c2}R_{d2}$, —S(=O)$_2R_{b2}$, —S(=O)$_2$O$R_{a2}$, —OS(=O)$_2R_{b2}$, —OS(=O)$_2$O$R_{a2}$, —S(=O)$_2$N$R_{c2}R_{d2}$, —N$R_{c2}$S(=O)$_2R_{b2}$, —N$R_{c2}$S(=O)$_2$O$R_{a2}$, —OS(=O)$_2$N$R_{c2}R_{d2}$, —N$R_{c2}$S(=O)$_2$N$R_{c2}R_{d2}$, —P($R_{a2}$)$_2$, —P(=O)($R_{b2}$)$_2$, —P(=O)$_2$, 3-20 membered carbocyclyl, 3-20 membered heterocyclyl, 6-12 membered aryl or 5-20 membered heteroaryl, wherein, the —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, 3-20 membered carbocyclyl, 3-20 membered heterocyclyl, 6-12 membered aryl or 5-20 membered heteroaryl is independently optionally substituted with one or more substituents selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —$OR_{a2}$, —$SR_{a2}$, —$NR_{c2}R_{d2}$, —C(═O)$R_{b2}$, —C(═O)$OR_{a2}$, —OC(═O)$R_{b2}$, —OC(═O)$OR_{a2}$, —C(═O)$NR_{c2}R_{d2}$, —OC(═O)$NR_{c2}R_{d2}$, —C(═$NR_{e2}$)$R_{b2}$, —C(═$NR_{e2}$)$NR_{c2}R_{d2}$, —$NR_{c2}$C(═$NR_{e2}$)$NR_{c2}R_{d2}$, —$NR_{c2}$C(═O)$R_{b2}$, —$NR_{c2}$C(═O)$OR_{a2}$, —$NR_{c2}$C(═O)$NR_{c2}R_{d2}$, —S(═O)$R_{b2}$, —S(═O)$OR_{a2}$, —OS(═O)$R_{b2}$, —OS(═O)$OR_{a2}$, —S(═O)$NR_{c2}R_{d2}$, —$NR_{c2}$S(═O)$R_{b2}$, —$NR_{c2}$S(═O)$OR_{a2}$, —OS(═O)$NR_{c2}R_{d2}$, —$NR_{c2}$S(═O)$NR_{c2}R_{d2}$, —S(═O)$_2R_{b2}$, —S(═O)$_2OR_{a2}$, —OS(═O)$_2R_{b2}$, —OS(═O)$_2OR_{a2}$, —S(═O)$_2NR_{c2}R_{d2}$, —$NR_{c2}$S(═O)$_2R_{b2}$, —$NR_{c2}$S(═O)$_2OR_{a2}$, —OS(═O)$_2NR_{c2}R_{d2}$, —$NR_{c2}$S(═O)$_2NR_{c2}R_{d2}$, —P($R_{a2}$)$_2$, —P(═O)($R_{b2}$)$_2$, —P(═O)$_2$, 3-20 membered carbocyclyl, 3-20 membered heterocyclyl, 6-12 membered aryl or 5-20 membered heteroaryl;

$t_2$ is selected from 0, 1, 2, 3, 4, 5, 6, 7, 8, 9 or 10;

Ring C is selected from a 3-20 membered carbocyclic ring, 3-20 membered heterocyclic ring, 6-12 membered aryl ring or 5-20 membered heteroaryl ring; said ring C is optionally substituted with $t_3$ $Z_3$;

$Z_3$ at each occurrence is independently selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —$OR_{a3}$, —$SR_{a3}$, —$NR_{c3}R_{d3}$, —C(═O)$R_{b3}$, —C(═O)$R_{a3}$, —OC(═O)$R_{b3}$, —OC(═O)$OR_{a3}$, —C(═O)$NR_{c3}R_{d3}$, —OC(═O)$NR_{c3}R_{d3}$, —C(═$NR_{e3}$)$R_{b3}$, —C(═$NR_{e3}$)$NR_{c3}R_{d3}$, —$NR_{c3}$C(═$NR_{e3}$)$NR_{c3}R_{d3}$, —$NR_{c3}$C(═O)$R_{b3}$, —$NR_{c3}$C(═O)$OR_{a3}$, —$NR_{c3}$C(═O)$NR_{c3}R_{d3}$, —S(═O)$R_{b3}$, —S(═O)$OR_{a3}$, —OS(═O)$R_{b3}$, —OS(═O)$OR_{a3}$, —S(═O)$NR_{c3}R_{d3}$, —$NR_{c3}$S(═O)$R_{b3}$, —$NR_{c3}$S(═O)$OR_{a3}$, —OS(═O)$NR_{c3}R_{d3}$, —$NR_{c3}$S(═O)$NR_{c3}R_{d3}$, —S(═O)$_2R_{b3}$, —S(═O)$_2OR_{a3}$, —OS(═O)$_2R_{b3}$, —OS(═O)$_2OR_{a3}$, —S(═O)$_2NR_{c3}R_{d3}$, —$NR_{c3}$S(═O)$_2R_{b3}$, —$NR_{c3}$S(═O)$_2OR_{a3}$, —OS(═O)$_2NR_{c3}R_{d3}$, —$NR_{c3}$S(═O)$_2NR_{c3}R_{d3}$, —P($R_{a3}$)$_2$, —P(═O)($R_{b3}$)$_2$, —P(═O)$_2$, 3-20 membered carbocyclyl, 3-20 membered heterocyclyl, 6-12 membered aryl or 5-20 membered heteroaryl, wherein, the —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, 3-20 membered carbocyclyl, 3-20 membered heterocyclyl, 6-12 membered aryl or 5-20 membered heteroaryl is independently optionally substituted with one or more substituents selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —$OR_{a3}$, —$SR_{a3}$, —$NR_{c3}R_{d3}$, —C(═O)$R_{b3}$, —C(═O)$R_{a3}$, —OC(═O)$R_{b3}$, —OC(═O)$OR_{a3}$, —C(═O)$NR_{c3}R_{d3}$, —OC(═O)$NR_{c3}R_{d3}$, —C(═$NR_{e3}$)$R_{b3}$, —C(═$NR_{e3}$)$NR_{c3}R_{d3}$, —$NR_{c3}$C(═$NR_{e3}$)$NR_{c3}R_{d3}$, —$NR_{c3}$C(═O)$R_{b3}$, —$NR_{c3}$C(═O)$OR_{a3}$, —$NR_{c3}$C(═O)$NR_{c3}R_{d3}$, —S(═O)$R_{b3}$, —S(═O)$OR_{a3}$, —OS(═O)$R_{b3}$, —OS(═O)$OR_{a3}$, —S(═O)$NR_{c3}R_{d3}$, —$NR_{c3}$S(═O)$R_{b3}$, —$NR_{c3}$S(═O)$OR_{a3}$, —OS(O)$NR_{c3}R_{d3}$, —$NR_{c3}$S(═O)$NR_{c3}R_{d3}$, —S(═O)$_2R_{b3}$, —S(═O)$_2OR_{a3}$, —OS(═O)$_2R_{b3}$, —OS(═O)$_2OR_{a3}$, —S(═O)$_2NR_{c3}R_{d3}$, —$NR_{c3}$S(═O)$_2R_{b3}$, —$NR_{c3}$S(═O)$_2OR_{a3}$, —OS(═O)$_2NR_{c3}R_{d3}$, —$NR_{c3}$S(═O)$_2NR_{c3}R_{d3}$, —P($R_{a3}$)$_2$, —P(═O)($R_{b3}$)$_2$, —P(═O)$_2$, 3-20 membered carbocyclyl, 3-20 membered heterocyclyl, 6-12 membered aryl or 5-20 membered heteroaryl;

Optionally, two $Z_3$ together with the atom to which they are both attached form a 3-20 membered carbocyclic ring, or a 3-20 heterocyclic ring, wherein, said 3-20 membered carbocylic ring or 3-20 heterocyclic ring is optionally substituted with one or more $R_{X7}$;

Optionally, two adjacent $Z_3$ together with the atoms to which they are respectively attached form a 3-20 membered carbocyclic ring, a 3-20 membered heterocyclic ring, a 6-12 membered aryl ring or a 5-20 membered heteroaryl ring, wherein, each of rings is independently optionally substituted with one or more $R_{X5}$;

Optionally, two nonadjacent $Z_3$ are connected together to form a $C_{0-6}$ alkylene bridge, wherein, each of the carbon atoms in the bridge is optionally replaced by 1 or 2 members selected from —CH($R_{X9}$)—, —C($R_{X9}$)$_2$—, —HC═CH—, —$R_{X9}$C═CH—, —HC═C$R_{X9}$—, —$R_{X9}$C═C$R_{X9}$—, —C≡C—, —C(═O)—, —O—, —NH—, —$NR_{X9}$—, —S—, —S(═O)—, —S(═O)$_2$—, —PH—, —$PR_{X9}$—, —P(═O)H—, —P(═O)$R_{X9}$—, —C(═O)O—, —OC(═O)—, —C(═O)NH—, —C(═O)$NR_{X9}$—, —$NR_{X9}$C(═O)—, —NHC(═O)—, —S(═O)O—, —OS(═O)—, —S(═O)$_2$O—, —OS(═O)$_2$—, —S(═O)NH—, —S(═O)$NR_{X9}$—, —NHS(═O)—, —$NR_{X9}$S(═O)—, —S(═O)$_2$NH—, —S(═O)$_2NR_{X9}$—, —NHS(═O)$_2$—, —$NR_{X9}$S(═O)$_2$—, —OC(═O)O—, —NHC(═O)O—, —$NR_{X9}$C(═O)O—, —OC(═O)NH—, —OC(═O)$NR_{X9}$—, —NHC(═O)NH—, —NHC(═O)$NR_{X9}$—, —$NR_{X9}$C(═O)NH— or —$NR_{X9}$C(═O)$NR_{X9}$—;

$R_{X7}$, $R_{X5}$ or $R_{X9}$ at each occurrence is independently selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, OXO, —$OR_{a3}$, —$SR_{a3}$, —$NR_{c3}R_{d3}$, —C(═O)$R_{b3}$, —C(═O)$OR_{a3}$, —OC(═O)$R_{b3}$, —OC(═O)$OR_{a3}$, —C(═O)$NR_{c3}R_{d3}$, —OC(═O)$NR_{c3}R_{d3}$, —C(═$NR_{e3}$)$R_{b3}$, —C(═$NR_{e3}$)$NR_{c3}R_{d3}$, —$NR_{c3}$C(═$NR_{e3}$)$NR_{c3}R_{d3}$, —$NR_{c3}$C(═O)$R_{b3}$, —$NR_{c3}$C(═O)$OR_{a3}$, —$NR_{c3}$C(═O)$NR_{c3}R_{d3}$, —S(═O)$R_{b3}$, —S(═O)$OR_{a3}$, —OS(═O)$R_{b3}$, —OS(═O)$OR_{a3}$, —S(═O)$NR_{c3}R_{d3}$, —$NR_{c3}$S(═O)$R_{b3}$, —$NR_{c3}$S(═O)$OR_{a3}$, —OS(═O)$NR_{c3}R_{d3}$, —$NR_{c3}$S(═O)$NR_{c3}R_{d3}$, —S(═O)$_2R_{b3}$, —S(═O)$_2OR_{a3}$, —OS(═O)$_2R_{b3}$, —OS(═O)$_2OR_{a3}$, —S(═O)$_2NR_{c3}R_{d3}$, —$NR_{c3}$S(═O)$_2R_{b3}$, —$NR_{c3}$S(═O)$_2OR_{a3}$, —OS(═O)$_2NR_{c3}R_{d3}$, —$NR_{c3}$S(═O)$_2NR_{c3}R_{d3}$, —P($R_{a3}$)$_2$, —P(═O)($R_{b3}$)$_2$, —P(═O)$_2$, 3-20 membered carbocyclyl, 3-20 membered heterocyclyl, 6-12 membered aryl or 5-20 membered heteroaryl, wherein, the —$C_{1-10}$alkyl, —$C_{2-6}$alkenyl, —$C_{2-6}$alkynyl, —$C_{1-10}$alkoxy, halo$C_{1-10}$alkyl, halo$C_{2-10}$alkenyl, halo$C_{2-10}$alkynyl, halo$C_{1-10}$alkoxy, 3-20 membered carbocyclyl, 3-20 membered heterocyclyl, 6-12 membered aryl or 5-20 membered heteroaryl ring is independently optionally substituted with one or more substituents selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, haloC$_{2-6}$alkynyl, haloC$_{1-10}$alkoxy, —CN, —NO$_2$, —N$_3$, OXO, —OR$_{a3}$, —SR$_{a3}$, —NR$_{c3}$R$_{d3}$, —C(═O)R$_{b3}$, —C(═O)OR$_{a3}$, —OC(═O)R$_{b3}$, —OC(═O)OR$_{a3}$, —C(═O)NR$_{c3}$R$_{d3}$, —OC(═O)NR$_{c3}$R$_{d3}$, —C(═NR$_{e3}$)R$_{b3}$, —C(═NR$_{e3}$)NR$_{c3}$R$_{d3}$, —NR$_{c3}$C(═NR$_{e3}$)NR$_{c3}$R$_{d3}$, —NR$_{c3}$C(═O)R$_{b3}$, —NR$_{c3}$C(═O)OR$_{a3}$, —NR$_{c3}$C(═O)NR$_{c3}$R$_{d3}$, —S(═O)R$_{b3}$, —S(═O)OR$_{a3}$, —OS(═O)R$_{b3}$, —OS(═O)OR$_{a3}$, —S(═O)NR$_{c3}$R$_{d3}$, —NR$_{c3}$S(O)R$_{b3}$, —NR$_{c3}$S(═O)OR$_{a3}$, —OS(═O)NR$_{c3}$R$_{d3}$, —NR$_{c3}$S(═O)NR$_{c3}$R$_{d3}$, —S(═O)$_2$R$_{b3}$, —S(═O)$_2$OR$_{a3}$, —OS(═O)$_2$R$_{b3}$, —OS(═O)$_2$OR$_{a3}$, —S(═O)$_2$NR$_{c3}$R$_{d3}$, —NR$_{c3}$S(═O)$_2$R$_{b3}$, —NR$_{c3}$S(═O)$_2$OR$_{a3}$, —OS(═O)$_2$NR$_{c3}$R$_{d3}$, —NR$_{c3}$S(═O)$_2$NR$_{c3}$R$_{d3}$, —P(R$_{a3}$)$_2$, —P(═O)(R$_{b3}$)$_2$, —P(═O)$_2$, 3-20 membered carbocyclyl, 3-20 membered heterocyclyl, 6-12 membered aryl or 5-20 membered heteroaryl;

t$_3$ is selected from 0, 1, 2, 3, 4, 5, 6, 7, 8, 9 or 10;

When X$_1$ --- X$_2$ is X$_1$—X$_2$, X$_1$ and X$_2$ are independently selected from C, N or CH;

When X$_1$ --- X$_2$ is X$_1$═X$_2$, X$_1$ is C, and X$_2$ is C;

When X$_3$ --- X$_4$ is X$_3$—X$_4$, X$_3$ and X$_4$ are independently selected from C, N or CH;

When X$_3$ --- X$_4$ is X$_3$═X$_4$, X$_3$ is C, and X$_4$ is C;

X$_5$ is selected from C, N or CH;

Y$_1$ is selected from —C(R$_{Y1}$)$_2$—, —R$_{Y1}$C═CR$_{Y1}$—, —C≡C—, —C(═O)—, —O—, —NR$_{Y1}$—, —S—, —S(═O)—, —S(═O)$_2$—, —PR$_{Y1}$—, —P(═O)R$_{Y1}$—, —C(═O)O—, —OC(═O)—, —C(═O)NR$_{Y1}$—, —NR$_{Y1}$C(═O)—, —S(═O)O—, —OS(═O)—, —S(═O)$_2$O—, —OS(═O)$_2$—, —S(═O)NR$_{Y1}$—, —NR$_{Y1}$S(═O)—, —S(═O)$_2$NR$_{Y1}$—, —NR$_{Y1}$S(═O)$_2$—, —OC(═O)O—, —NR$_{Y1}$C(═O)O—, —OC(═O)NR$_{Y1}$— or —NR$_{Y1}$C(═O)NR$_{Y1}$—;

Y$_2$ is selected from —C(R$_{Y2}$)$_2$—, —R$_{Y2}$C═CR$_{Y2}$—, —C≡C—, —C(═O)—, —O—, —NR$_{Y2}$—, —S—, —S(═O)—, —S(═O)$_2$—, —PR$_{Y2}$—, —P(═O)R$_{Y2}$—, —C(═O)O—, —OC(═O)—, —C(═O)NR$_{Y2}$—, —NR$_{Y2}$C(═O)—, —S(═O)O—, —OS(═O)—, —S(═O)$_2$O—, —OS(═O)$_2$—, —S(═O)NR$_{Y2}$—, —NR$_{Y2}$S(═O)—, —S(═O)$_2$NR$_{Y2}$—, —NR$_{Y2}$S(═O)$_2$—, —OC(═O)O—, —NR$_{Y2}$C(═O)O—, —OC(═O)NR$_{Y2}$— or —NR$_{Y2}$C(═O)NR$_{Y2}$—;

Y$_3$ is selected from —C(R$_{Y3}$)$_2$—, —R$_{Y3}$C═CR$_{Y3}$—, —C≡C—, —C(═O)—, —O—, —NR$_{Y3}$—, —S—, —S(═O)—, —S(═O)$_2$—, —PR$_{Y3}$—, —P(═O)R$_{Y3}$—, —C(═O)O—, —OC(═O)—, —C(═O)NR$_{Y3}$—, —NR$_{Y3}$C(═O)—, —S(═O)O—, —OS(═O)—, —S(═O)$_2$O—, —OS(═O)$_2$—, —S(═O)NR$_{Y3}$—, —NR$_{Y3}$S(═O)—, —S(═O)$_2$NR$_{Y3}$—, —NR$_{Y3}$S(═O)$_2$—, —OC(═O)O—, —NR$_{Y3}$C(═O)O—, —OC(═O)NR$_{Y3}$— or —NR$_{Y3}$C(═O)NR$_{Y3}$—;

R$_{Y1}$, R$_{Y2}$ or R$_{Y3}$ at each occurrence is independently selected from hydrogen, halogen, —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, —CN, —NO$_2$, —N$_3$, OXO, —OR$_{a4}$, —SR$_{a4}$, —NR$_{c4}$R$_{d4}$, —C(═O)R$_{b4}$, —C(═O)OR$_{a4}$, —OC(═O)R$_{b4}$, —OC(═O)OR$_{a4}$, —C(═O)NR$_{c4}$R$_{d4}$, —OC(═O)NR$_{c4}$R$_{d4}$, —C(═NR$_{c4}$)R$_{b4}$, —C(═NR$_{e4}$)NR$_{c4}$R$_{d4}$, —NR$_{c4}$C(═NR$_{e4}$)NR$_{c4}$R$_{d4}$, —NR$_{c4}$C(═O)R$_{b4}$, —NR$_{c4}$C(═O)OR$_{a4}$, —NR$_{c4}$C(═O)NR$_{c4}$R$_{d4}$, —S(═O)R$_{b4}$, —S(═O)OR$_{a4}$, —OS(═O)R$_{b4}$, —OS(═O)OR$_{a4}$, —S(═O)NR$_{c4}$R$_{d4}$, —NR$_{c4}$S(═O)R$_{b4}$, —NR$_{c4}$S(═O)OR$_{a4}$, —OS(═O)NR$_{c4}$R$_{d4}$, —NR$_{c4}$S(═O)NR$_{c4}$R$_{d4}$, —S(═O)$_2$R$_{b4}$, —S(═O)$_2$OR$_{a4}$, —OS(═O)$_2$R$_{b4}$, —OS(═O)$_2$OR$_{a4}$, —S(═O)$_2$NR$_{c4}$R$_{d4}$, —NR$_{c4}$S(═O)$_2$R$_{b4}$, —NR$_{c4}$S(═O)$_2$OR$_{a4}$, —OS(═O)$_2$NR$_{c4}$R$_{d4}$, —NR$_{c4}$S(═O)$_2$NR$_{c4}$R$_{d4}$, —P(R$_{a4}$)$_2$, —P(═O)(R$_{b4}$)$_2$, —P(═O)$_2$, 3-20 membered carbocyclyl, 3-20 membered heterocyclyl, 6-12 membered aryl or 5-20 membered heteroaryl, wherein, the —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, 3-20 membered carbocyclyl, 3-20 membered heterocyclyl, 6-12 membered aryl or 5-20 membered heteroaryl is independently optionally substituted with one or more substituents selected from halogen, —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, —CN, —NO$_2$, —N$_3$, oxo, —OR$_{a4}$, —SR$_{a4}$, —NR$_{c4}$R$_{d4}$, —C(═O)R$_{b4}$, —C(═O)OR$_{a4}$, —OC(═O)R$_{b4}$, —OC(═O)OR$_{a4}$, —C(═O)NR$_{c4}$R$_{d4}$, —OC(═O)NR$_{c4}$R$_{d4}$, —C(═NR$_{e4}$)R$_{b4}$, —C(═NR$_{e4}$)NR$_{c4}$R$_{d4}$, —NR$_{c4}$C(═NR$_{e4}$)NR$_{c4}$R$_{d4}$, —NR$_{c4}$C(═O)R$_{b4}$, —NR$_{c4}$C(═O)OR$_{a4}$, —NR$_{c4}$C(═O)NR$_{c4}$R$_{d4}$, —S(═O)R$_{b4}$, —S(═O)OR$_{a4}$, —OS(═O)R$_{b4}$, —OS(═O)OR$_{a4}$, —S(═O)NR$_{c4}$R$_{d4}$, —NR$_{c4}$S(═O)R$_{b4}$, —NR$_{c4}$S(═O)OR$_{a4}$, —OS(═O)NR$_{c4}$R$_{d4}$, —NR$_{c4}$S(═O)NR$_{c4}$R$_{d4}$, —S(═O)$_2$R$_{b4}$, —S(═O)$_2$OR$_{a4}$, —OS(═O)$_2$R$_{b4}$, —OS(═O)$_2$OR$_{a4}$, —S(═O)$_2$NR$_{c4}$R$_{d4}$, —NR$_{c4}$S(═O)$_2$R$_{b4}$, —NR$_{c4}$S(═O)$_2$OR$_{a4}$, —OS(═O)$_2$NR$_{c4}$R$_{d4}$, —NR$_{c4}$S(═O)$_2$NR$_{c4}$R$_{d4}$, —P(R$_{a4}$)$_2$, —P(═O)(R$_{b4}$)$_2$, —P(═O)$_2$, 3-20 membered carbocyclyl, 3-20 membered heterocyclyl, 6-12 membered aryl or 5-20 membered heteroaryl;

m$_1$ is selected from 0, 1, 2, 3, 4, 5 or 6;

m$_2$ is selected from 0, 1, 2, 3, 4, 5 or 6;

m$_3$ is selected from 0, 1, 2, 3, 4, 5 or 6;

m$_4$ is selected from 0, 1, 2, 3, 4, 5 or 6;

R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$ or R$_{15}$ is independently selected from hydrogen, halogen, —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, —CN, —NO$_2$, —N$_3$, oxo, —OR$_{a5}$, —SR$_{a5}$, —NR$_{c5}$R$_{d5}$, —C(═O)R$_{b5}$, —C(═O)OR$_{a5}$, —OC(═O)R$_{b5}$, —OC(═O)OR$_{a5}$, —C(═O)NR$_{c5}$R$_{d5}$, —OC(═O)NR$_{c5}$R$_{d5}$, —C(═NR$_{e5}$)R$_{b5}$, —C(═NR$_{e5}$)NR$_{c5}$R$_{d5}$, —NR$_{c5}$C(═NR$_{e5}$)NR$_{c5}$R$_{d5}$, —NR$_{c5}$C(═O)R$_{b5}$, —NR$_{c5}$C(═O)OR$_{a5}$, —NR$_{c5}$C(═O)NR$_{c5}$R$_{d5}$, —S(═O)R$_{b5}$, —S(═O)OR$_{a5}$, —OS(═O)R$_{b5}$, —OS(═O)OR$_{a5}$, —S(═O)NR$_{c5}$R$_{d5}$, —NR$_{c5}$S(═O)R$_{b5}$, —NR$_{c5}$S(═O)OR$_{a5}$, —OS(═O)NR$_{c5}$R$_{d5}$, —NR$_{c5}$S(═O)NR$_{c5}$R$_{d5}$, —S(═O)$_2$R$_{b5}$, —S(═O)$_2$OR$_{a5}$, —OS(═O)$_2$R$_{b5}$, —OS(═O)$_2$OR$_{a5}$, —S(═O)$_2$NR$_{c5}$R$_{d5}$, —NR$_{c5}$S(═O)$_2$R$_{b5}$, —NR$_{c5}$S(═O)$_2$OR$_{a5}$, —OS(═O)$_2$NR$_{c5}$R$_{d5}$, —NR$_{c5}$S(═O)$_2$NR$_{c5}$R$_{d5}$, —P(R$_{a5}$)$_2$, —P(═O)(R$_{b5}$)$_2$, —P(═O)$_2$, 3-20 membered carbocyclyl, 3-20 membered heterocyclyl, 6-12 membered aryl or 5-20 membered heteroaryl, wherein, the —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, 3-20 membered carbocyclyl, 3-20 membered heterocyclyl, 6-12 membered aryl or 5-20 membered heteroaryl ring is independently optionally substituted with one or more substituents selected from halogen, —C$_{1-10}$alkyl, —C$_{2-6}$alkenyl, —C$_{2-6}$alkynyl, —C$_{1-10}$alkoxy, haloC$_{1-10}$alkyl, haloC$_{2-6}$alkenyl, haloC$_{2-6}$alkynyl, haloC$_{1-10}$alkoxy, —CN, —NO$_2$, —N$_3$, oxo, —OR$_{a5}$, —SR$_{a5}$, —NR$_{c5}$R$_{d5}$, —C(═O)R$_{b5}$, —C(═O)OR$_{a5}$, —OC(═O)R$_{b5}$, —OC(═O)OR$_{a5}$, —C(═O)NR$_{c5}$R$_{d5}$, —OC(═O)NR$_{c5}$R$_{d5}$, $-C(=NR_{e5})R_{b5}$, $-C(=NR_{e5})NR_{c5}R_{d5}$, $-NR_{c5}C(=NR_{e5})NR_{c5}R_{d5}$, $-NR_{c5}C(=O)R_{b5}$, $-NR_{c5}C(=O)OR_{a5}$, $-NR_{c5}C(=O)NR_{c5}R_{d5}$, $-S(=O)R_{b5}$, $-S(=O)OR_{a5}$, $-OS(=O)R_{b5}$, $-OS(=O)OR_{a5}$, $-S(=O)NR_{c5}R_{d5}$, $-NR_{c5}S(=O)R_{b5}$, $-NR_{c5}S(=O)OR_{a5}$, $-OS(=O)NR_{c5}R_{d5}$, $-NR_{c5}S(=O)NR_{c5}R_{d5}$, $-S(=O)_2R_{b5}$, $-S(=O)_2OR_{a5}$, $-OS(=O)_2R_{b5}$, $-OS(=O)_2OR_{a5}$, $-S(=O)_2NR_{c5}R_{d5}$, $-NR_{c5}S(=O)_2R_{b5}$, $-NR_{c5}S(=O)_2OR_{a5}$, $-OS(=O)_2NR_{c5}R_{d5}$, $-NR_{c5}S(=O)_2NR_{c5}R_{d5}$, $-P(R_{a5})_2$, $-P(=O)(R_{b5})_2$, $-P(=O)_2$, 3-20 membered carbocyclyl, 3-20 membered heterocyclyl, 6-12 membered aryl or 5-20 membered heteroaryl;

Optionally, ($R_{Y1}$ in $Y_1$) and $R_{13}$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_4$ $Z_4$;

Optionally, ($R_{Y1}$ in $Y_1$) and $R_{15}$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_5$ $Z_5$;

Optionally, ($R_{Y1}$ in $Y_1$) and $R_1$ together with the atoms to which they are respectively attached form ring D, ring D is selected from a 3-20 membered carbocyclic ring, a 3-20 membered heterocyclic ring, a 6-12 membered aryl ring or a 5-20 membered heteroaryl ring; said ring D is optionally substituted with $t_6$ $Z_6$;

Optionally, ($R_{Y1}$ in $Y_1$) and $R_3$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_7$ $Z_7$;

Optionally, ($R_{Y1}$ in $Y_1$) and $R_5$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_8$ $Z_8$;

Optionally, $R_1$ and $R_3$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_9$ $Z_9$;

Optionally, $R_1$ and $R_5$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{10}$ $Z_{10}$;

Optionally, $R_1$ and ($R_{Y2}$ in $Y_2$) together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{11}$ $Z_{11}$;

Optionally, $R_3$ and $R_5$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{12}$ $Z_{12}$;

Optionally, $R_3$ and ($R_{Y2}$ in $Y_2$) together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{13}$ $Z_{13}$;

Optionally, $R_3$ and $R_7$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{14}$ $Z_{14}$;

Optionally, $R_5$ and ($R_{Y2}$ in $Y_2$) together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{15}$ $Z_5$;

Optionally, $R_5$ and $R_7$ together with the atoms to which they are respectively attached form ring G, said ring G is selected from a 3-20 membered carbocyclic ring, a 3-20 membered heterocyclic ring, a 6-12 membered aryl ring or a 5-20 membered heteroaryl ring; said ring G is optionally substituted with $t_{16}$ $Z_{16}$;

Optionally, $R_5$ and $R_9$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{17}$ $Z_{17}$;

Optionally, ($R_{Y2}$ in $Y_2$) and $R_7$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{18}$ $Z_{18}$;

Optionally, ($R_{Y2}$ in $Y_2$) and $R_9$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{19}$ $Z_{19}$;

Optionally, ($R_{Y2}$ in $Y_2$) and $R_{11}$ together with the atoms to which they are respectively attached form ring F, said ring F is selected from a 3-20 membered carbocyclic ring, a 3-20 membered heterocyclic ring, a 6-12 membered aryl ring or a 5-20 membered heteroaryl ring; said ring F is optionally substituted with $t_{20}$ $Z_{20}$;

Optionally, $R_7$ and $R_9$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{21}$ $Z_{21}$;

Optionally, $R_7$ and $R_{11}$ together with the atoms to which they are respectively attached form ring H, said ring H is selected from a 3-20 membered carbocyclic ring, a 3-20 membered heterocyclic ring, a 6-12 membered aryl ring or a 5-20 membered heteroaryl ring; said ring H is optionally substituted with $t_{22}$ $Z_{22}$;

Optionally, $R_7$ and ($R_{Y3}$ in $Y_3$) together with the atoms to which they are respectively attached form ring E, said ring E is selected from a 3-20 membered carbocyclic ring, a 3-20 membered heterocyclic ring, a 6-12 membered aryl ring or a 5-20 membered heteroaryl ring; each said ring is independently optionally substituted with $t_{23}$ $Z_{23}$;

Optionally, $R_9$ and $R_{11}$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{24}$ $Z_{24}$;

Optionally, $R_9$ and ($R_{Y3}$ in $Y_3$) together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{25}$ $Z_{25}$;

Optionally, $R_9$ and $Z_3$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{26}$ $Z_{26}$;

Optionally, $R_{10}$ and ($R_{Y3}$ in $Y_3$) together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{27}$ $Z_{27}$;

Optionally, $R_{11}$ and $Z_3$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{28}$ $Z_{28}$;

Optionally, ($R_{Y3}$ in $Y_3$) and $Z_3$ together with the atoms to which they are respectively attached form a 3-20 membered carbocyclic ring, a 3-20 membered heterocyclic ring, a 6-12 membered aryl ring or a 5-20 membered heteroaryl ring; each said ring is independently optionally substituted with $t_{29}$ $Z_{29}$;

Optionally, $R_1$ and $R_2$ together with the atom to which they are both attached form a 3-20 membered carbocyclic ring, a 3-20 membered heterocyclic ring, a 6-12 membered aryl ring or a 5-20 membered heteroaryl ring; each said ring is independently optionally substituted with $t_{30}$ $Z_{30}$;

Optionally, $R_3$ and $R_4$ together with the atom to which they are both attached form a 3-20 membered carbocyclic ring, a 3-20 membered heterocyclic ring, a 6-12 membered aryl ring or a 5-20 membered heteroaryl ring; each said ring is independently optionally substituted with $t_{31}$ $Z_{31}$;

Optionally, $R_5$ and $R_6$ together with the atom to which they are both attached form a 3-20 membered carbocyclic ring, a 3-20 membered heterocyclic ring, a 6-12 membered aryl ring or a 5-20 membered heteroaryl ring; each said ring is independently optionally substituted with $t_{32}$ $Z_{32}$;

Optionally, $R_7$ and $R_8$ together with the atom to which they are both attached form a 3-20 membered carbocyclic ring, a 3-20 membered heterocyclic ring, a 6-12 membered aryl ring or a 5-20 membered heteroaryl ring; each said ring is independently optionally substituted with $t_{33}$ $Z_{33}$;

Optionally, $R_9$ and $R_{10}$ together with the atom to which they are both attached form a 3-20 membered carbocyclic ring, a 3-20 membered heterocyclic ring, a 6-12 membered aryl ring or a 5-20 membered heteroaryl ring; each said ring is independently optionally substituted with $t_{34}$ $Z_{34}$;

Optionally, $R_{11}$ and $R_{12}$ together with the atom to which they are both attached form a 3-20 membered carbocyclic ring, a 3-20 membered heterocyclic ring, a 6-12 membered aryl ring or a 5-20 membered heteroaryl ring; each said ring is independently optionally substituted with $t_{35}$ $Z_{35}$;

$t_4$, $t_5$, $t_6$, $t_7$, $t_8$, $t_9$, $t_{10}$, $t_{11}$, $t_{12}$, $t_{13}$, $t_{14}$, $t_{15}$, $t_{16}$, $t_{17}$, $t_{18}$, $t_{19}$, $t_{20}$, $t_{21}$, $t_{22}$, $t_{23}$, $t_{24}$, $t_{25}$, $t_{26}$, $t_{27}$, $t_{28}$, $t_{29}$, $t_{30}$, $t_{31}$, $t_{32}$, $t_{33}$, $t_{34}$, or $t_{35}$ is independently selected from 0, 1, 2, 3, 4, 5, 6, 7, 8, 9 or 10;

$Z_4$, $Z_5$, $Z_6$, $Z_7$, $Z_8$, $Z_9$, $Z_{10}$, $Z_{11}$, $Z_{12}$, $Z_{13}$, $Z_{14}$, $Z_{15}$, $Z_{16}$, $Z_{17}$, $Z_{18}$, $Z_{19}$, $Z_{20}$, $Z_{21}$, $Z_{22}$, $Z_{23}$, $Z_{24}$, $Z_{25}$, $Z_{26}$, $Z_{27}$, $Z_{28}$, $Z_{29}$, $Z_{30}$, $Z_{31}$, $Z_{32}$, $Z_{33}$, $Z_{34}$, or $Z_{35}$ is independently selected from halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —$OR_{a6}$, —$SR_{a6}$, —$NR_{c6}R_{d6}$, —C(═O)$R_{b6}$, —C(═O)$OR_{a6}$, —OC(═O)$R_{b6}$, —OC(═O)$OR_{a6}$, —C(═O)$NR_{c6}R_{d6}$, —OC(═O)$NR_{c6}R_{d6}$, —C(═$NR_{e6}$)$R_{b6}$, —C(═$NR_{e6}$)$NR_{c6}R_{d6}$, —$NR_{c6}$C(═$NR_{e6}$)$NR_{c6}R_{d6}$, —$NR_{c6}$C(═O)$R_{b6}$, —$NR_{c6}$C(═O)$OR_{a6}$, —$NR_{c6}$C(═O)$NR_{c6}R_{d6}$, —S(═O)$R_{b6}$, —S(═O)$OR_{a6}$, —OS(═O)$R_{b6}$, —OS(═O)$OR_{a6}$, —S(═O)$NR_{c6}R_{d6}$, —$NR_{c6}$S(═O)$R_{b6}$, —$NR_{c6}$S(═O)$OR_{a6}$, —OS(═O)$NR_{c6}R_{d6}$, —$NR_{c6}$S(═O)$NR_{c6}R_{d6}$, —$S(═O)_2R_{b6}$, —$S(═O)_2OR_{a6}$, —$OS(═O)_2R_{b6}$, —$OS(═O)_2OR_{a6}$, —$S(═O)_2NR_{c6}R_{d6}$, —$NR_{c6}S(═O)_2R_{b6}$, —$NR_{c6}S(═O)_2OR_{a6}$, —$OS(═O)_2NR_{c6}R_{d6}$, —$NR_{c6}S(═O)_2NR_{c6}R_{d6}$, —$P(R_{a6})_2$, —$P(═O)(R_{b6})_2$, —$P(═O)_2$, 3-20 membered carbocyclyl, 3-20 membered heterocyclyl, 6-12 membered aryl or 5-20 membered heteroaryl, wherein, the —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, 3-20 membered carbocyclyl, 3-20 membered heterocyclyl, 6-12 membered aryl or 5-20 membered heteroaryl is independently optionally substituted with one or more substituents halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —$OR_{a6}$, —$SR_{a6}$, —$NR_{c6}R_{d6}$, —C(═O)$R_{b6}$, —C(═O)$OR_{a6}$, —OC(═O)$R_{b6}$, —OC(═O)$OR_{a6}$, —C(═O)$NR_{c6}R_{d6}$, —OC(═O)$NR_{c6}R_{d6}$, —C(═$NR_{e6}$)$R_{b6}$, —C(═$NR_{e6}$)$NR_{c6}R_{d6}$, —$NR_{c6}$C(═$NR_{e6}$)$NR_{c6}R_{d6}$, —$NR_{c6}$C(═O)$R_{b6}$, —$NR_{c6}$C(═O)$OR_{a6}$, —$NR_{c6}$C(═O)$NR_{c6}R_{d6}$, —S(═O)$R_{b6}$, —S(═O)$OR_{a6}$, —OS(═O)$R_{b6}$, —OS(═O)$OR_{a6}$, —S(═O)$NR_{c6}R_{d6}$, —$NR_{c6}$S(═O)$R_{b6}$, —$NR_{c6}$S(═O)$OR_{a6}$, —OS(═O)$NR_{c6}R_{d6}$, —$NR_{c6}$S(═O)$NR_{c6}R_{d6}$, —$S(═O)_2R_{b6}$, —$S(═O)_2OR_{a6}$, —$OS(═O)_2R_{b6}$, —$OS(═O)_2OR_{a6}$, —$S(═O)_2NR_{c6}R_{d6}$, —$NR_{c6}S(═O)_2R_{b6}$, —$NR_{c6}S(═O)_2OR_{a6}$, —$OS(═O)_2NR_{c6}R_{d6}$, —$NR_{c6}S(═O)_2NR_{c6}R_{d6}$, —$P(R_{a6})_2$, —$P(═O)(R_{b6})_2$, —$P(═O)_2$, 3-20 membered carbocyclyl, 3-20 membered heterocyclyl, 6-12 membered aryl or 5-20 membered heteroaryl;

$R_{a1}$, $R_{b1}$, $R_{c1}$, $R_{d1}$, $R_{e1}$, $R_{a2}$, $R_{b2}$, $R_{c2}$, $R_{d2}$, $R_{e2}$, $R_{a3}$, $R_{b3}$, $R_{c3}$, $R_{d3}$, $R_{e3}$, $R_{a4}$, $R_{b4}$, $R_{c4}$, $R_{d4}$, $R_{e4}$, $R_{a5}$, $R_{b5}$, $R_{c5}$, $R_{d5}$, $R_{e5}$, $R_{a6}$, $R_{b6}$, $R_{c6}$, $R_{d6}$ or $R_{e6}$ at each occurrence is independently selected from hydrogen, halogen, —$C_{1-10}$alkyl, —$C_{2-6}$alkenyl, —$C_{2-6}$alkynyl, —$C_{1-10}$alkoxy, halo$C_{1-10}$alkyl, halo$C_{2-6}$alkenyl, halo$C_{2-6}$alkynyl, halo$C_{1-10}$alkoxy, —CN, —$NO_2$, —$N_3$, oxo, —$N(R_{16})_2$, —$OR_{16}$, —$SR_{16}$, —S(═O)$R_{17}$, —$S(═O)_2R_{17}$, —C(═O)$R_{17}$, —C(═O)$OR_{16}$, —OC(═O)$R_{17}$, —C(═O)$N(R_{16})_2$, —$NR_{16}$C(═O)$R_{17}$, —OC(═O)$OR_{16}$, —$NR_{16}$C(═O)$OR_{16}$, —OC(═O)$N(R_{16})_2$, $—NR_{16}C(=O)N(R_{16})_2$, $—S(=O)OR_{16}$, $—OS(=O)R_{17}$, $—S(=O)N(R_{16})_2$, $—NR_{16}S(=O)R_{17}$, $—S(=O)_2OR_{16}$, $—OS(=O)_2R_{17}$, $—S(=O)_2R_{17}$, $—NR_{16}S(=O)_2R_{17}$, $—OS(=O)_2OR_{16}$, $—NR_{16}S(=O)_2OR_{16}$, $—OS(=O)_2N(R_{16})_2$, $—NR_{16}S(=O)_2N(R_{16})_2$, $—P(R_{16})_2$, $—P(=O)(R_{17})_2$, 3-20 membered carbocyclyl, 3-20 membered heterocyclyl, 6-12 membered aryl or 5-20 membered heteroaryl, wherein, the $—C_{1-10}$alkyl, $—C_{2-6}$alkenyl, $—C_{2-6}$alkynyl, $—C_{1-10}$alkoxy, halo$C_{1-10}$alkyl, halo$C_{2-6}$alkenyl, halo$C_{2-6}$alkynyl, halo$C_{1-10}$alkoxy, 3-20 membered carbocyclyl, 3-20 membered heterocyclyl, 6-12 membered aryl or 5-20 membered heteroaryl ring is optionally independently substituted with one or more substituents selected from halogen, $—C_{1-10}$alkyl, $—C_{2-6}$alkenyl, $—C_{2-6}$alkynyl, $—C_{1-10}$alkoxy, halo$C_{1-10}$alkyl, halo$C_{2-6}$alkenyl, halo$C_{2-6}$alkynyl, halo$C_{1-10}$alkoxy, —CN, $—NO_2$, $—N_3$, oxo, $—N(R_{16})_2$, $—OR_{16}$, $—SR_{16}$, $—S(=O)R_{17}$, $—S(=O)_2R_{17}$, $—C(=O)R_{17}$, $—C(=O)OR_{16}$, $—OC(=O)R_{17}$, $—C(=O)N(R_{16})_2$, $—NR_{16}C(=O)R_{17}$, $—OC(=O)OR_{16}$, $—NR_{16}C(=O)OR_{16}$, $—OC(=O)N(R_{16})_2$, $—NR_{16}C(=O)N(R_{16})_2$, $—S(=O)OR_{16}$, $—OS(=O)R_{17}$, $—S(=O)N(R_{16})_2$, $—NR_{16}S(=O)R_{17}$, $—S(=O)_2OR_{16}$, $—OS(=O)_2R_{17}$, $—S(=O)_2R_{17}$, $—NR_{16}S(=O)_2R_{17}$, $—OS(=O)_2OR_{16}$, $—NR_{16}S(=O)_2OR_{16}$, $—OS(=O)_2N(R_{16})_2$, $—NR_{16}S(=O)_2N(R_{16})_2$, $—P(R_{16})_2$, $—P(=O)(R_{17})_2$, 3-20 membered carbocyclyl, 3-20 membered heterocyclyl, 6-12 membered aryl or 5-20 membered heteroaryl;

Heterocyclyl or heterocyclic at each occurrence independently contains one or more ring members selected from —C(=O)—, —O—, —C(=O)O—, —OC(=O)—, $—NR_{16}—$, $—C(=O)NR_{16}—$, $—NR_{16}C(=O)—$, —S—, —S(=O)—, —S(=O)O—, —OS(=O)—, $—S(=O)NR_{16}—$, $—NR_{16}S(=O)—$, $—S(=O)_2—$, $—S(=O)_2O—$, $—OS(=O)_2—$, $—S(=O)_2NR_{16}—$, $—NR_{16}S(=O)_2—$, $—PR_{16}—$, $—P(=O)R_{17}—$, $—P(=O)R_{17}—NR_{16}—$, $—NR_{16}—P(=O)R_{17}—$, $—P(=O)_2—$, $—NR_{16}—P(=O)_2—$ or $—P(=O)_2—NR_{16}—$;

Heteroaryl at each occurrence independently contains one or more heteroatoms selected from N, O or S;

Each $R_{16}$ or $R_{17}$ is independently selected from hydrogen, halogen, $—C_{1-6}$alkyl, $—C_{2-6}$alkenyl, $—C_{2-6}$alkynyl, $—C_{1-6}$alkoxy, $—C_{1-6}$haloalkyl, halo$C_{2-6}$alkenyl, halo$C_{2-6}$alkynyl, halo$C_{1-6}$alkoxy, —CN, $—NO_2$, $—N_3$, oxo, $—NH_2$, $—NH(C_{1-6}alkyl)$, $—N(C_{1-6}alkyl)_2$, —OH, $—O(C_{1-6}alkyl)$, —SH, $—S(C_{1-6}alkyl)$, $—S(=O)(C_{1-6}alkyl)$, $—S(=O)_2(C_{1-6}alkyl)$, $—C(=O)(C_{1-6}alkyl)$, —C(=O)OH, $—C(=O)(OC_{1-6}alkyl)$, $—OC(=O)(C_{1-6}alkyl)$, $—C(=O)NH_2$, $—C(=O)NH(C_{1-6}alkyl)$, $—C(=O)N(C_{1-6}alkyl)_2$, $—NHC(=O)(C_{1-6}alkyl)$, $—N(C_{1-6}alkyl)C(=O)(C_{1-6}alkyl)$, $—OC(=O)O(C_{1-6}alkyl)$, $—NHC(=O)(OC_{1-6}alkyl)$, $—N(C_{1-6}alkyl)C(=O)(OC_{1-6}alkyl)$, $—OC(=O)NH(C_{1-6}alkyl)$, $—OC(=O)N(C_{1-6}alkyl)_2$, $—NHC(=O)NH_2$, $—NHC(=O)NH(C_{1-6}alkyl)$, $—NHC(=O)N(C_{1-6}alkyl)_2$, $—N(C_{1-6}alkyl)C(=O)NH_2$, $—N(C_{1-6}alkyl)C(=O)NH(C_{1-6}alkyl)$, $—N(C_{1-6}alkyl)C(=O)N(C_{1-6}alkyl)_2$, $—S(=O)(OC_{1-6}alkyl)$, $—OS(=O)(C_{1-6}alkyl)$, $—S(=O)NH_2$, $—S(=O)NH(C_{1-6}alkyl)$, $—S(=O)N(C_{1-6}alkyl)_2$, $—NHS(=O)(C_{1-6}alkyl)$, $—N(C_{1-6}alkyl)S(=O)(C_{1-6}alkyl)$, $—S(=O)_2(OC_{1-6}alkyl)$, $—OS(=O)_2(C_{1-6}alkyl)$, $—S(=O)_2NH_2$, $—S(=O)_2NH(C_{1-6}alkyl)$, $—S(=O)_2N(C_{1-6}alkyl)_2$, $—NHS(=O)_2(C_{1-6}alkyl)$, $—N(C_{1-6}alkyl)S(=O)_2(C_{1-6}alkyl)$, $—OS(=O)_2O(C_{1-6}alkyl)$, $—NHS(=O)_2O(C_{1-6}alkyl)$, $—N(C_{1-6}alkyl)S(=O)_2O(C_{1-6}alkyl)$, $—OS(=O)_2NH_2$, $—OS(=O)_2NH(C_{1-6}alkyl)$, $—OS(=O)_2N(C_{1-6}alkyl)_2$, $—NHS(=O)_2NH_2$, $—NHS(=O)_2NH(C_{1-6}alkyl)$, $—NHS(=O)_2N(C_{1-6}alkyl)_2$, $—N(C_{1-6}alkyl)S(=O)_2NH_2$, $—N(C_{1-6}alkyl)S(=O)_2NH(C_{1-6}alkyl)$, $—N(C_{1-6}alkyl)S(=O)_2N(C_{1-6}alkyl)_2$, $—PH(C_{1-6}alkyl)$, $—P(C_{1-6}alkyl)_2$, $—P(=O)H(C_{1-6}alkyl)$, $—P(=O)(C_{1-6}alkyl)_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl, wherein, said $—C_{1-6}$alkyl, halo$C_{1-6}$alkyl, halo$C_{1-6}$alkoxy, $—C_{2-6}$alkenyl, $—C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl is optionally substituted with one or more substituents selected from halogen, $—C_{1-3}$alkyl, halo$C_{1-3}$alkyl, halo$C_{1-3}$alkoxy, $—C_{2-3}$alkenyl, $—C_{2-3}$alkynyl, —CN, $—NO_2$, $—N_3$, oxo, $—NH_2$, $—NH(C_{1-3}alkyl)$, $—N(C_{1-3}alkyl)_2$, —OH, $—O(C_{1-3}alkyl)$, —SH, $—S(C_{1-3}alkyl)$, $—S(=O)(C_{1-3}alkyl)$, $—S(=O)_2(C_{1-3}alkyl)$, $—C(=O)(C_{1-3}alkyl)$, —C(=O)OH, $—C(=O)(OC_{1-3}alkyl)$, $—OC(=O)(C_{1-3}alkyl)$, $—C(=O)NH_2$, $—C(=O)NH(C_{1-3}alkyl)$, $—C(=O)N(C_{1-3}alkyl)_2$, $—NHC(=O)(C_{1-3}alkyl)$, $—N(C_{1-3}alkyl)C(=O)(C_{1-3}alkyl)$, $—OC(=O)O(C_{1-3}alkyl)$, $—NHC(=O)(OC_{1-3}alkyl)$, $—N(C_{1-3}alkyl)C(=O)(OC_{1-3}alkyl)$, $—OC(=O)NH(C_{1-3}alkyl)$, $—OC(=O)N(C_{1-3}alkyl)_2$, $—NHC(=O)NH_2$, $—NHC(=O)NH(C_{1-3}alkyl)$, $—NHC(=O)N(C_{1-3}alkyl)_2$, $—N(C_{1-3}alkyl)C(=O)NH_2$, $—N(C_{1-3}alkyl)C(=O)NH(C_{1-3}alkyl)$, $—N(C_{1-3}alkyl)C(=O)N(C_{1-3}alkyl)_2$, $—S(=O)(OC_{1-3}alkyl)$, $—OS(=O)(C_{1-3}alkyl)$, $—S(=O)NH_2$, $—S(=O)NH(C_{1-3}alkyl)$, $—S(=O)N(C_{1-3}alkyl)_2$, $—NHS(=O)(C_{1-3}alkyl)$, $—N(C_{1-3}alkyl)S(=O)(C_{1-3}alkyl)$, $—S(=O)_2(OC_{1-3}alkyl)$, $—OS(=O)_2(C_{1-3}alkyl)$, $—S(=O)_2NH_2$, $—S(=O)_2NH(C_{1-3}alkyl)$, $—S(=O)_2N(C_{1-3}alkyl)_2$, $—NHS(=O)_2(C_{1-3}alkyl)$, $—N(C_{1-3}alkyl)S(=O)_2(C_{1-3}alkyl)$, $—OS(=O)_2O(C_{1-3}alkyl)$, $—NHS(=O)_2O(C_{1-3}alkyl)$, $—N(C_{1-3}alkyl)S(=O)_2O(C_{1-3}alkyl)$, $—OS(=O)_2NH_2$, $—OS(=O)_2NH(C_{1-3}alkyl)$, $—OS(=O)_2N(C_{1-3}alkyl)_2$, $—NHS(=O)_2NH_2$, $—NHS(=O)_2NH(C_{1-3}alkyl)$, $—NHS(=O)_2N(C_{1-3}alkyl)_2$, $—N(C_{1-3}alkyl)S(=O)_2NH_2$, $—N(C_{1-3}alkyl)S(=O)_2NH(C_{1-3}alkyl)$, $—N(C_{1-3}alkyl)S(=O)_2N(C_{1-3}alkyl)_2$, $—PH(C_{1-3}alkyl)$, $—P(C_{1-3}alkyl)_2$, $—P(=O)H(C_{1-3}alkyl)$, $—P(=O)(C_{1-3}alkyl)_2$, 3-6 membered cycloalkyl, 3-6 membered cycloalkenyl, 3-6 membered cycloalkynyl, 3-6 membered heterocyclyl, 6 membered aryl or 5-6 membered heteroaryl.

[2]. The compound according to [1], wherein, the moiety of

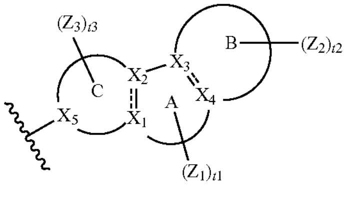

is selected from
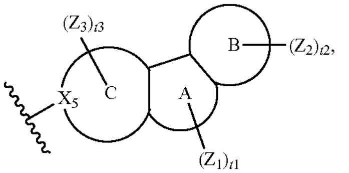
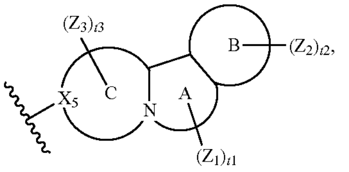
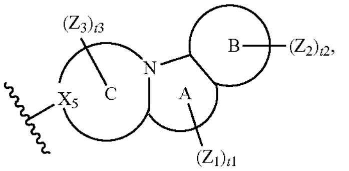
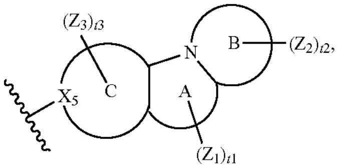
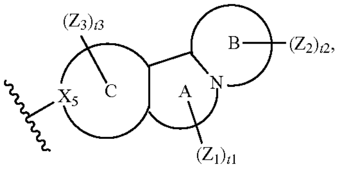
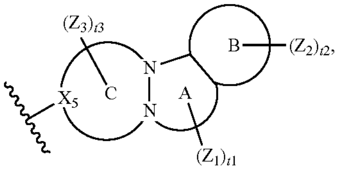
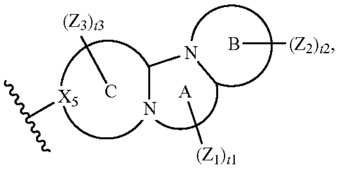
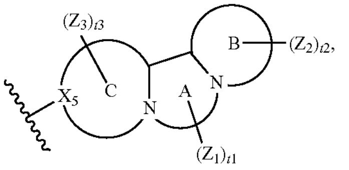
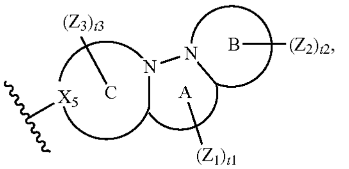
-continued
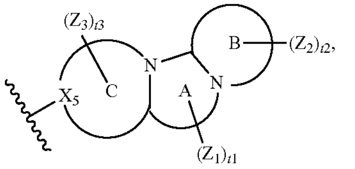
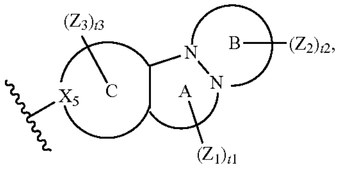
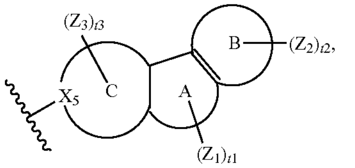
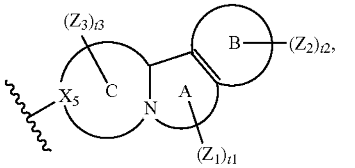
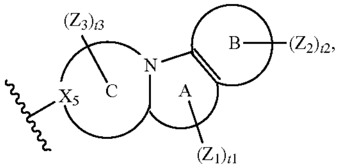
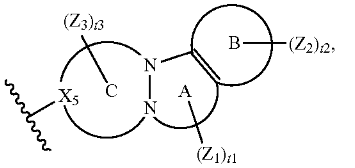
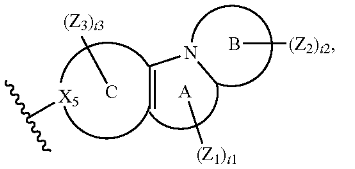
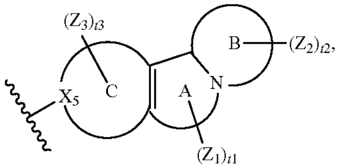
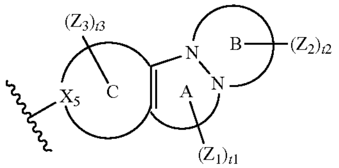
or
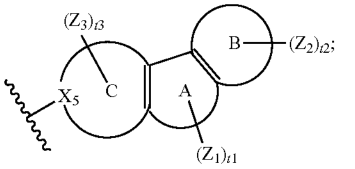

$X_5$ at each occurrence is independently selected from C, N, or CH.

[3]. The compound according to [1] or [2], wherein, the moiety of

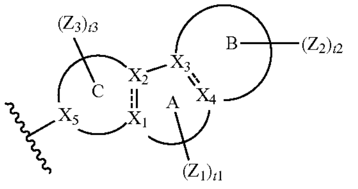

is selected from

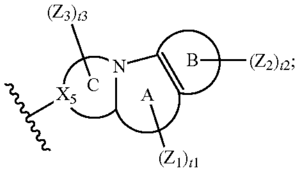

$X_5$ at each occurrence is independently selected from N.

[4]. The compound according to any one of [1] to [3], wherein, ring A is selected from a 4-10 membered cycloalkyl ring, a 4-10 membered cycloalkenyl ring, a 4-10 membered heterocycloalkyl ring, a 4-10 membered heterocycloalkenyl ring, a 6-10 membered aryl ring or a 5-12 member heteroaryl ring.

[5]. The compound according to any one of [1] to [4], wherein, ring A is selected from a 4 membered monocyclic cycloalkyl ring, a 4 membered monocyclic cycloalkenyl ring, a 4 membered monocyclic heterocycloalkyl ring, a 4 membered monocyclic heterocycloalkenyl ring, a 5 membered monocyclic cycloalkyl ring, a 5 membered monocyclic cycloalkenyl ring, a 5 membered bridged cycloalkyl ring, a 5 membered bridged cycloalkenyl ring, a 5 membered fused cycloalkyl ring, a 5 membered fused cycloalkenyl ring, a 5 membered monocyclic heterocycloalkyl ring, a 5 membered monocyclic heterocycloalkenyl ring, a 5 membered bridged heterocycloalkyl ring, a 5 membered bridged heterocycloalkenyl ring, a 5 membered fused heterocycloalkyl ring, a 5 membered fused heterocycloalkenyl ring, a 6 membered monocyclic cycloalkyl ring, a 6 membered monocyclic cycloalkenyl ring, a 6 membered bridged cycloalkyl ring, a 6 membered bridged cycloalkenyl ring, a 6 membered fused cycloalkyl ring, a 6 membered fused cycloalkenyl ring, a 6 membered monocyclic heterocycloalkyl ring, a 6 membered monocyclic heterocycloalkenyl ring, a 6 membered bridged heterocycloalkyl ring, a 6 membered bridged heterocycloalkenyl ring, a 6 membered fused heterocycloalkyl ring, a 6 membered fused heterocycloalkenyl ring, a 7 membered monocyclic cycloalkyl ring, a 7 membered monocyclic cycloalkenyl ring, a 7 membered spirocyclic cycloalkyl ring, a 7 membered spirocyclic cycloalkenyl ring, a 7 membered fused cycloalkyl ring, a 7 membered fused cycloalkenyl ring, a 7 membered bridged cycloalkyl ring, a 7 membered bridged cycloalkenyl ring, a 7 membered monocyclic heterocycloalkyl ring, a 7 membered monocyclic heterocycloalkenyl ring, a 7 membered spirocyclic heterocycloalkyl ring, a 7 membered spirocyclic heterocycloalkenyl ring, a 7 membered fused heterocycloalkyl ring, a 7 membered fused heterocycloalkenyl ring, a 7 membered bridged heterocycloalkyl ring, a 7 membered bridged heterocycloalkenyl ring, a 8 membered monocyclic cycloalkyl ring, a 8 membered monocyclic cycloalkenyl ring, a 8 membered spirocyclic cycloalkyl ring, a 8 membered spirocyclic cycloalkenyl ring, a 8 membered fused cycloalkyl ring, a 8 membered fused cycloalkenyl ring, a 8 membered bridged cycloalkyl ring, a 8 membered bridged cycloalkenyl ring, a 8 membered monocyclic heterocycloalkyl ring, a 8 membered monocyclic heterocycloalkenyl ring, a 8 membered spirocyclic heterocycloalkyl ring, a 8 membered spirocyclic heterocycloalkenyl ring, a 8 membered fused heterocycloalkyl ring, a 8 membered fused heterocycloalkenyl ring, a 8 membered bridged heterocycloalkyl ring, a 8 membered bridged heterocycloalkenyl ring, a 9 membered monocyclic cycloalkyl ring, a 9 membered monocyclic cycloalkenyl ring, a 9 membered spirocyclic cycloalkyl ring, a 9 membered spirocyclic cycloalkenyl ring, a 9 membered fused cycloalkyl ring, a 9 membered fused cycloalkenyl ring, a 9 membered bridged cycloalkyl ring, a 9 membered bridged cycloalkenyl ring, a 9 membered monocyclic heterocycloalkyl ring, a 9 membered monocyclic heterocycloalkenyl ring, a 9 membered spirocyclic heterocycloalkyl ring, a 9 membered spirocyclic heterocycloalkenyl ring, a 9 membered fused heterocycloalkyl ring, a 9 membered fused heterocycloalkenyl ring, a 9 membered bridged heterocycloalkyl ring, a 9 membered bridged heterocycloalkenyl ring, a 10 membered monocyclic cycloalkyl ring, a 10 membered monocyclic cycloalkenyl ring, a 10 membered spirocyclic cycloalkyl ring, a 10 membered spirocyclic cycloalkenyl ring, a 10 membered fused cycloalkyl ring, a 10 membered fused cycloalkenyl ring, a 10 membered bridged cycloalkyl ring, a 10 membered bridged cycloalkenyl ring, a 10 membered monocyclic heterocycloalkyl ring, a 10 membered monocyclic heterocycloalkenyl ring, a 10 membered spirocyclic heterocycloalkyl ring, a 10 membered spirocyclic heterocycloalkenyl ring, a 10 membered fused heterocycloalkyl ring, a 10 membered fused heterocycloalkenyl ring, a 10 membered bridged heterocycloalkyl ring, a 10 membered bridged heterocycloalkenyl ring, a phenyl ring, a naphthalene ring, a 5 membered heteroaryl ring, a 6 membered heteroaryl ring, a 7 membered heteroaryl ring, a 8 membered heteroaryl ring, a 9 membered heteroaryl ring or a 10 membered heteroaryl ring; said heterocycloalkyl or heterocycloalkenyl at each occurrence independently contains one or more ring members selected from N, O, S, —C(═O)—, —C(═O)O—, —OC(═O)—, —C(═O)NH—, —NHC(═O)—, —S(═O)—, —S(═O)O—, —OS(═O)—, —S(═O)NH—, —NHS(═O)—, $—S(═O)_2—$, $—S(═O)_2O—$, $—OS(═O)_2—$, $—S(═O)_2NH—$, or $—NHS(═O)_2—$; said heteroaryl at each occurrence independently contains one or more heteroatoms selected from N, O or S.

[6]. The compound according to any one of [1] to [5], wherein, ring A is selected from a 5 membered monocyclic heterocycloalkyl ring, a 6 membered monocyclic heterocycloalkyl ring, a 7 membered monocyclic heterocycloalkyl ring, a 8 membered monocyclic heterocycloalkyl ring, a 5 membered monocyclic heterocycloalkenyl ring, a 6 membered monocyclic heterocycloalkenyl ring, a 7 membered monocyclic heterocycloalkenyl ring, a 8 membered monocyclic heterocycloalkenyl ring, a 5 membered heteroaryl ring or a 6 membered heteroaryl ring, said heterocycloalkyl or heterocycloalkenyl at each occurrence independently contains 1, 2, or 3 ring members selected from N, O, S, —C(═O)—, —C(═O)NH—, —NHC(═O)—, —S(═O)—, —S(═O)NH—, —NHS(═O)—, $—S(═O)_2—$, $—S(═O)_2NH—$, or $—NHS(═O)_2—$; said heteroaryl at each occurrence independently contains 1, 2, 3 or 4 heteroatoms selected from N, O or S.

[7]. The compound according to any one of [1] to [6], wherein, ring A is selected from a 5 membered monocyclic heterocycloalkyl ring containing 1 N, a 6 membered monocyclic heterocycloalkyl ring containing 1 N, a 7 membered monocyclic heterocycloalkyl ring containing 1 N, a 8 membered monocyclic heterocycloalkyl ring containing 1 N, a 5 membered monocyclic heterocycloalkenyl ring containing 1 N, a 6 membered monocyclic heterocycloalkenyl ring containing 1 N, a 7 membered monocyclic heterocycloalkenyl ring containing 1 N, a 8 membered monocyclic heterocycloalkenyl ring containing 1 N, a 5 membered heteroaryl ring containing 1 N or a 6 membered heteroaryl ring containing 1 N, said heterocycloalkyl or heterocycloalkenyl at each occurrence optionally independently further contains 1 or 2 ring members selected from N, O, S, —C(═O)—, —C(═O)NH—, —NHC(═O)—, —S(═O)—, —S(═O)NH—, —NHS(═O)—, $—S(═O)_2—$, $—S(═O)_2NH—$ or $—NHS(═O)_2—$; said heteroaryl at each occurrence optionally independently further contains 1, 2 or 3 heteroatoms selected from N, O or S.

[8]. The compound according to any one of [1] to [7], wherein, ring A is selected from a 5 membered monocyclic heterocycloalkyl ring containing 1 N at position $X_2$, a 6 membered monocyclic heterocycloalkyl ring containing 1 N at position $X_2$, a 7 membered monocyclic heterocycloalkyl ring containing 1 N at position $X_2$, a 8 membered monocyclic heterocycloalkyl ring containing 1 N at position $X_2$, a 5 membered monocyclic heterocycloalkenyl ring containing 1 N at position $X_2$, a 6 membered monocyclic heterocycloalkenyl ring containing 1 N at position $X_2$, a 7 membered monocyclic heterocycloalkenyl ring containing 1 N at position $X_2$, a 8 membered monocyclic heterocycloalkenyl ring containing 1 N at position $X_2$, a 5 membered heteroaryl ring containing 1 N at position $X_2$ or a 6 membered heteroaryl ring containing 1 N, said heterocycloalkyl or heterocycloalkenyl at each occurrence optionally independently further contains 1 or 2 ring members selected from N, O, S, —C(═O)—, —C(═O)NH—, —NHC(═O)—, —S(═O)—, —S(═O)NH—, —NHS(═O)—, $—S(═O)_2—$, $—S(═O)_2NH—$ or $—NHS(═O)_2—$; said heteroaryl at each occurrence optionally independently further contains 1, 2 or 3 heteroatoms selected from N, O or S.

[9]. The compound according to any one of [1] to [8], wherein, ring B is selected from a 6-10 membered aryl ring or a 5-10 membered heteroaryl ring.

[10]. The compound according to any one of [1] to [9], wherein, ring B is selected from a phenyl ring, a naphthalene ring, a 5 membered heteroaryl ring, a 6 membered heteroaryl ring, or a 10 membered heteroaryl ring, said heteroaryl ring contains 1, 2, 3, 4, 5 or 6 heteroatoms selected from N, O or S.

[11]. The compound according to any one of [1] to [10], wherein, ring B is selected from a phenyl ring, a naphthalene ring, a 5 membered heteroaryl ring or a 6 membered heteroaryl ring, said heteroaryl ring independently contains 1, 2, 3 or 4 heteroatoms selected from N, O or S.

[12]. The compound according to any one of [1] to [11], wherein, ring B is selected from a 5 membered heteroaryl ring containing 1 N or a 6 membered heteroaryl ring containing 1 N, said heteroaryl ring optionally further contains 1, 2 or 3 heteroatoms selected from N, O or S.

[13]. The compound according to any one of [1] to [12], wherein, ring B is selected from a 5 membered heteroaryl ring containing 1 N adjacent to $X_3$ or a 6 membered heteroaryl ring containing 1 N adjacent to $X_3$, said heteroaryl ring optionally further contains 1, 2 or 3 heteroatoms selected from N, O or S.

[14]. The compound according to any one of [1] to [13], wherein, ring C is selected from a 3-10 membered carbocyclic ring, a 3-10 membered heterocyclic ring.

[15]. The compound according to any one of [1] to [14], wherein, ring C is selected from a 3 membered carbocyclic ring, a 4 membered carbocyclic ring, a 5 membered carbocyclic ring, a 6 membered carbocyclic ring, a 7 membered carbocyclic ring, a 8 membered carbocyclic ring, a 9 membered carbocyclic ring, a 10 membered carbocyclic ring, a 3 membered heterocyclic ring, a 4 membered heterocyclic ring, a 5 membered heterocyclic ring, a 6 membered heterocyclic ring, a 7 membered heterocyclic ring, a 8 membered heterocyclic ring, a 9 membered heterocyclic ring or a 10 membered heterocyclic ring, said heterocyclic at each occurrence independently contains one or more ring members selected from N, O, S, —C(═O)—, —C(═O)O—, —OC(═O)—, —C(═O)NH—, —NHC(═O)—, —S(═O)—, —S(═O)O—, —OS(═O)—, —S(═O)NH—, —NHS(═O)—, $—S(═O)_2—$, $—S(═O)_2O—$, $—OS(═O)_2—$, $—S(═O)_2NH—$, or $—NHS(═O)_2—$.

[16]. The compound according to any one of [1] to [15], wherein, ring C is selected from a 5 membered heterocyclic ring, a 6 membered heterocyclic ring or a 7 membered heterocyclic ring, said heterocyclic at each occurrence independently contains one ring member selected from N and further optionally contains 1, 2 or 3 ring members selected from N, O or S.

[17]. The compound according to any one of [1] to [16], wherein, ring C is selected from a 5 membered heterocyclic ring containing 1 N and further containing 1 or 2 ring members selected from N, O or S; a 6 membered heterocyclic ring containing 1 N and further containing 1 or 2 ring members selected from N, O or S; or a 7 membered heterocyclic ring containing 1 N and further containing 1 or 2 ring members selected from N, O or S.

[18]. The compound according to any one of [1] to [16], wherein, ring C is selected from a 5 membered heterocyclic ring containing 1 N at position $X_2$ and further containing 1 or 2 ring members selected from N, O or S; a 6 membered heterocyclic ring containing 1 N at position $X_2$ and further containing 1 or 2 ring members selected from N, O or S; or a 7 membered heterocyclic ring containing 1 N at position $X_2$ and further containing 1 or 2 ring members selected from N, O or S.

[19]. The compound according to any one of [1] to [18], wherein,

Ring A is selected from a 5 membered monocyclic heterocycloalkyl ring containing 1 N, a 6 membered monocyclic heterocycloalkyl ring containing 1 N, a 7 membered monocyclic heterocycloalkyl ring containing 1 N, a 8 membered monocyclic heterocycloalkyl ring containing 1 N, a 5 membered monocyclic heterocycloalkenyl ring containing 1 N, a 6 membered monocyclic heterocycloalkenyl ring containing 1 N, a 7 membered monocyclic heterocycloalkenyl ring containing 1 N, a 8 membered monocyclic heterocycloalkenyl ring containing 1 N, a 5 membered heteroaryl ring containing 1 N or a 6 membered heteroaryl ring containing 1 N, said heterocycloalkyl or heterocycloalkenyl at each occurrence optionally independently further contains 1 or 2 ring members selected from N, O, S, —C(═O)—, —C(═O)NH—, —NHC(═O)—, —S(═O)—, —S(═O)NH—, —NHS(═O)—, $—S(═O)_2—$, $—S(═O)_2NH—$, $—NHS(═O)_2—$; said heteroaryl at each occurrence optionally independently contains 1, 2 or 3 heteroatoms selected from N, O or S;

Ring B is selected from a 5 membered heteroaryl ring containing 1 N or a 6 membered heteroaryl ring containing 1 N, said heteroaryl ring optionally further contains 1 or 2 heteroatoms selected from N, O or S;

Ring C is selected from a 5 membered heterocyclic ring containing 1 N and further containing 1 or 2 ring members selected from N, O or S; a 6 membered heterocyclic ring containing 1 N and further containing 1 or 2 ring members selected from N, O or S; or a 7 membered heterocyclic ring containing 1 N and further containing 1 or 2 ring members selected from N, O or S.

[20]. The compound according to any one of [1] to [19], wherein,

Ring A is selected from a 5 membered monocyclic heterocycloalkenyl ring containing 1 N at position $X_2$, a 6 membered monocyclic heterocycloalkenyl ring containing 1 N at position $X_2$ or a 7 membered monocyclic heterocycloalkenyl ring containing 1 N at position $X_2$, a 8 membered monocyclic heterocycloalkenyl ring containing 1 N at position $X_2$, a 5 membered heteroaryl ring containing 1 N at position $X_2$ or a 6 membered heteroaryl ring containing 1 N, said heterocycloalkenyl at each occurrence optionally independently further contains 1 or 2 ring members selected from N, O, S, —C(═O)—, —C(═O)NH—, —NHC(═O)—, —S(═O)—, —S(═O)NH—, —NHS(═O)—, —$S(═O)_2$—, —$S(═O)_2NH$—, —$NHS(═O)_2$—; said heteroaryl at each occurrence optionally independently further contains 1, 2 or 3 heteroatoms selected from N, O or S;

Ring B is selected from a 5 membered heteroaryl ring containing 1 N adjacent to $X_3$ or a 6 membered heteroaryl ring containing 1 N adjacent to $X_3$, said heteroaryl ring optionally further contains 1 or 2 heteroatoms selected from N, O or S;

Ring C is selected from a 5 membered heterocyclic ring containing 1 N at position $X_2$ and further containing 1 or 2 ring members selected from N, O or S; a 6 membered heterocyclic ring containing 1 N adjacent to $X_3$ and further containing 1 or 2 ring members selected from N, O or S; or a 7 membered heterocyclic ring containing 1 N adjacent to $X_3$ and further containing 1 or 2 ring members selected from N, O or S.

[21]. The compound according to any one of [1] to [20], wherein, the moiety of

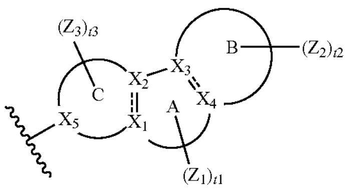

is selected from

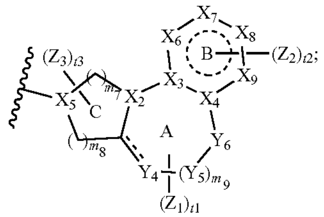

Wherein:

--- indicates a — or ═;

 indicates that ring B is a 5-6 membered aromatic ring;

$X_5$ is selected from N or CH; in some embodiments, $X_5$ is selected from N;

$X_2$ is selected from N or CH; in some embodiments, $X_2$ is selected from N;

$m_7$ is selected from 0, 1, 2, 3, 4, 5, or 6; in some embodiments, $m_7$ is selected from 1, 2 or 3; in some embodiments, $m_7$ is selected from 1 or 2; in some embodiments, $m_7$ is selected from 2;

$m_8$ is selected from 0, 1, 2, 3, 4, 5, or 6; in some embodiments, $m_8$ is selected from 1, 2 or 3; in some embodiments, $m_8$ is selected from 1 or 2; in some embodiments, $m_8$ is selected from 1;

$X_3$ is selected from N or C, $X_4$ is selected from N or C, and provided that $X_3$ and $X_4$ are not N at the same time;

$X_7$ is selected from a bond, N or CH;

$X_6$, $X_8$ and $X_9$ are each independently selected from N, CH, NH, O or S;

When $X_7$ is selected from a bond, $X_6$, $X_8$ and $X_9$ are independently selected from N, CH, NH, O or S to form a 5 membered aromatic heteroaryl ring B;

When $X_7$ is selected from N or CH, $X_6$, $X_8$ and $X_9$ are independently selected from N, CH to form a 6 membered aromatic ring B;

$Y_4$ is selected from absent, CH, $CH_2$, HC═CH, C≡C, C(═O), N, NH, O, S, S(═O), $S(═O)_2$, PH, P(═O)H, C(═O)O, OC(═O), C(═O)NH, NHC(═O), S(═O)O, OS(═O), $S(═O)_2O$, $OS(═O)_2$, S(═O)NH, NHS(═O), $S(═O)_2NH$, $NHS(═O)_2$, OC(═O)O, NH—C(═O)O, OC(═O)NH, or NH—C(═O)—NH; in some embodiments, $Y_4$ is selected from absent, CH, $CH_2$, O, N, NH, S, C(═O), S(═O), $S(═O)_2$, C(═O)NH, NHC(═O), S(═O)NH, NHS(═O), $S(═O)_2NH$, or $NHS(═O)_2$; in some embodiments, $Y_4$ is selected from absent or $CH_2$;

$Y_5$ at each occurrence is independently selected from absent, CH, $CH_2$, HC═CH, C≡C, C(═O), N, NH, O, S, S(═O), $S(═O)_2$, PH, P(═O)H, C(═O)O, OC(═O), C(═O)NH, NHC(═O), S(═O)O, OS(═O), $S(═O)_2O$, $OS(═O)_2$, S(═O)NH, NHS(═O), $S(═O)_2NH$, $NHS(═O)_2$, OC(═O)O, NH—C(═O)O, OC(═O)NH, or NH—C(═O)—NH; in some embodiments, $Y_5$ at each occurrence is independently selected from absent, CH, $CH_2$, O, N, NH, S, C(═O), S(═O), $S(═O)_2$, C(═O)NH, NHC(═O), S(═O)NH, NHS(═O), $S(═O)_2NH$, or $NHS(═O)_2$; in some embodiments, $Y_5$ at each occurrence is independently selected from absent or $CH_2$;

$m_9$ is selected from 0, 1, 2, 3, 4, 5, or 6; in some embodiments, $m_9$ is selected from 0, 1, 2 or 3; in some embodiments, $m_9$ is selected from 0, 1 or 2;

$Y_6$ is selected from CH, $CH_2$, $CF_2$, CH(OH), HC═CH, C≡C, C(═O), N, NH, O, S, S(═O), $S(═O)_2$, PH, P(═O)H, C(═O)O, OC(═O), C(═O)NH, NHC(═O), S(═O)O, OS(═O), $S(═O)_2O$, $OS(═O)_2$, S(═O)NH, NHS(═O), $S(═O)_2NH$, $NHS(═O)_2$, OC(═O)O, NH—C(═O)O, OC(═O)NH, or NH—C(═O)—NH; in some embodiments, $Y_6$ is selected from CH, $CH_2$, $CF_2$, CH(OH), C(═O), O, N, NH, S, S(═O), $S(═O)_2$, C(═O)NH, NHC(═O), S(═O)NH, NHS(═O), $S(═O)_2NH$, or $NHS(═O)_2$; in some embodiments, $Y_6$ is selected from CH, $CH_2$, $CF_2$, CH(OH), C(═O), O, N, NH, S, S(═O), $S(═O)_2$, C(═O)NH or NHC(═O).

[22]. The compound according to any one of [1] to [21], wherein, the moiety of

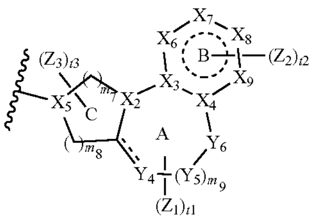

is selected from

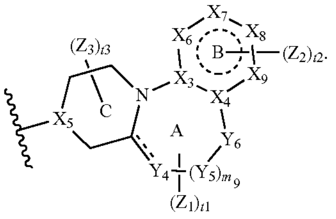

[23]. The compound according to any one of [1] to [22], wherein, the moiety of

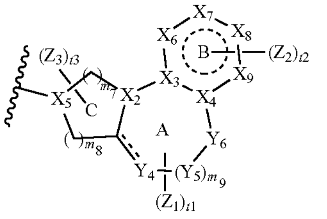

is selected from

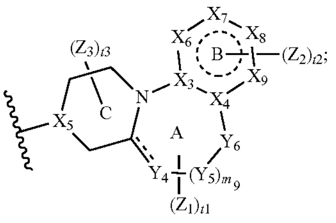

Wherein:

$X_3$ is selected from C;

$X_4$ is selected from C;

$X_5$ is CH or N; in some embodiments, $X_5$ is N;

$X_6$ is selected from N, CH, NH, O or S; in some embodiments, $X_6$ is selected from N;

$X_7$ is selected from a bond, N or CH;

$X_8$ is selected from N, CH, NH, O or S;

$X_9$ is selected from N, CH, NH, O or S;

When $X_7$ is selected from a bond, $X_6$, $X_8$ and $X_9$ are each independently selected from N, CH, NH, O or S to form a 5 membered aromatic heteroaryl ring B;

When $X_7$ is selected from N or CH, $X_6$, $X_8$ and $X_9$ are each independently selected from N, CH to form a phenyl ring or a 6 membered aromatic heteroaryl ring B;

$Y_4$ is selected from absent or $CH_2$;

Each $Y_5$ is independently selected from $CH_2$;

$m_9$ is selected from 0, 1, 2, 3 or 4;

$Y_6$ is selected from CH, $CH_2$, $CF_2$, CH(OH), C(═O), O, N, NH, S, S(═O), $S(═O)_2$, *NHC(═O) or NHC(═O)*;

* indicates the attached point to the aromatic ring B, and ** indicates the attached point to the $Y_5$;

With proviso that:

When ⋯ indicates ═, $Y_4$ is absent, $m_9$ is 0, $Y_6$ is selected from CH, N (in other words, when ⋯ indicates ═, this ⋯ joined with $Y_6$ directly to form ═$Y_6$);

When ⋯ indicates —, $Y_4$ is absent or $CH_2$, $m_9$ is 0, 1, 2, 3 or 4, $Y_6$ is selected from $CH_2$, $CF_2$, CH(OH), C(═O), O, NH, S, S(═O), $S(═O)_2$, *NHC(═O) or NHC(═O)*.

[24]. The compound according to [22] or [23], wherein, the moiety of

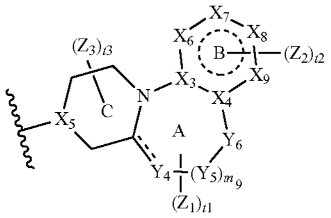

is selected from

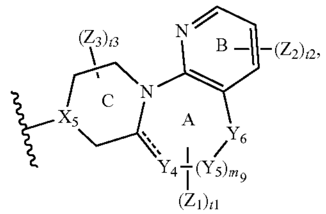

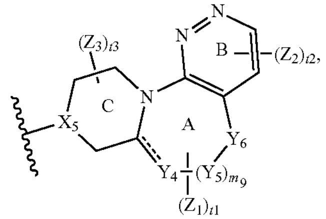

-continued

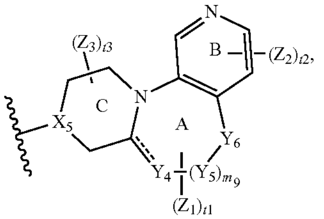

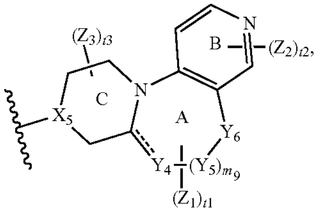

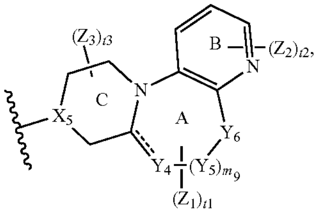

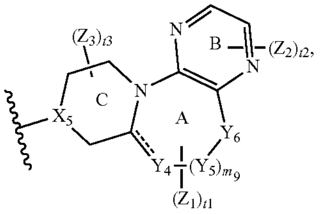

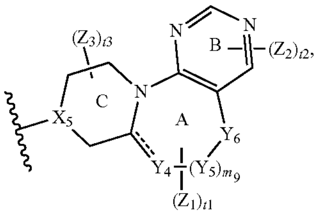

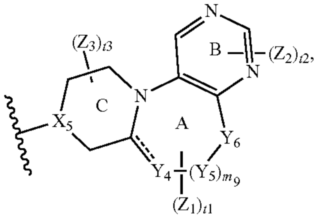

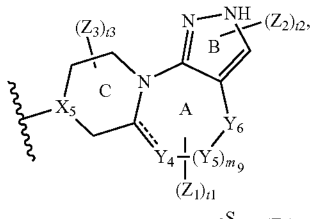

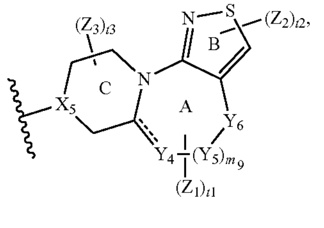

-continued

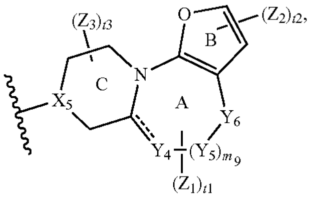

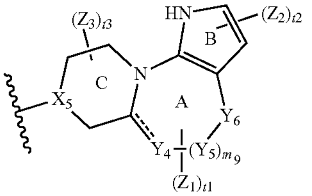

or

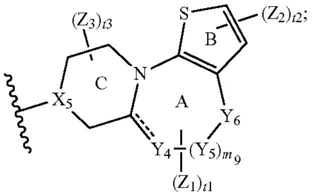

Preferably:

$X_5$ at each occurrence is independently selected from CH or N; in some embodiments, $X_5$ at each occurrence is independently N;

$Y_4$ at each occurrence is independently selected from absent or $CH_2$;

$Y_5$ at each occurrence is independently selected from $CH_2$;

$m_9$ is selected from 0, 1, 2, 3 or 4;

$Y_6$ at each occurrence is independently selected from CH, $CH_2$, $CF_2$, CH(OH), C(=O), O, N, NH, S, S(=O), $S(=O)_2$, *NHC(=O) or NHC(=O)*;

* indicates the attached point to the aromatic ring B, and ** indicates the attached point to the $Y_5$;

With proviso that:

When --- indicates =, $Y_4$ is absent, $m_9$ is 0, $Y_6$ is selected from CH, N (in other words, when --- indicates =, this = joined with $Y_6$ directly to form =$Y_6$);

When --- indicates —, $Y_4$ is absent or $CH_2$, $m_9$ is 0, 1, 2, 3 or 4, $Y_6$ is selected from $CH_2$, $CF_2$, CH(OH), C(=O), O, NH, S, S(=O), $S(=O)_2$, *NHC(=O) or NHC(=O)*.

[25]. The compound according to any one of [22] to [24], wherein, the moiety of

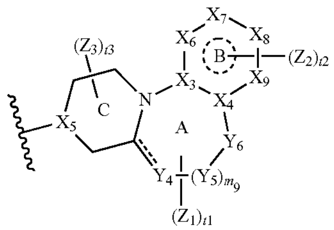

is selected from

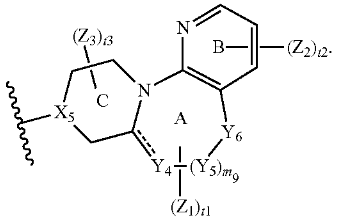

[26]. The compound according to any one of [24] to [25], wherein, the moiety of

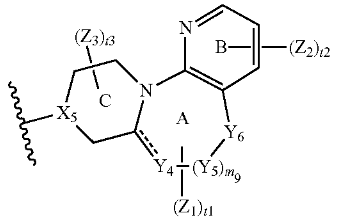

is selected from

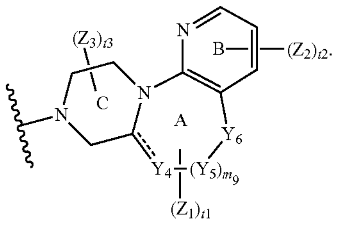

[27]. The compound according to any one of [24] to [26], wherein, the moiety of

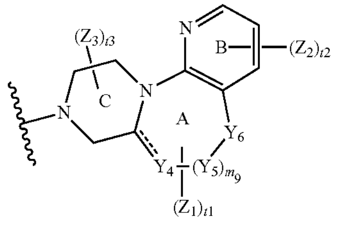

is selected from

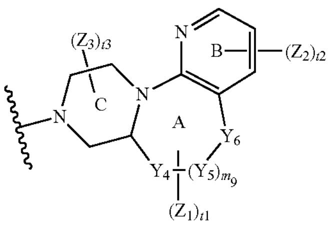

or

-continued

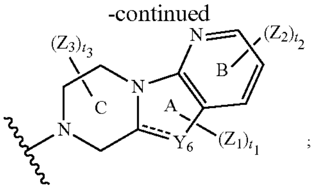

;

Wherein:

$Y_4$ is selected from absent or $CH_2$, $Y_5$ is selected from $CH_2$, $m_9$ is selected from 0, 1 or 2;

$Y_6$ in

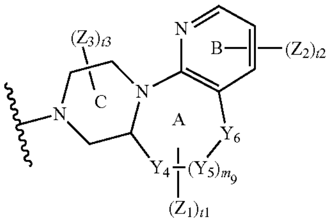

is selected from $CH_2$, $CF_2$, CH(OH), C(=O), O, NH, S, S(=O), $S(=O)_2$, *NHC(=O) or NHC(=O)*; * indicates the attached point to the aromatic ring B, and ** indicates the attached point to the $Y_5$;

$Y_6$ in

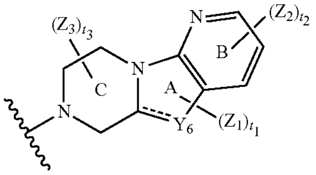

is selected from $CH_2$, CH, N or NH.

[28]. The compound according to any one of [26] or [27], wherein, the moiety of

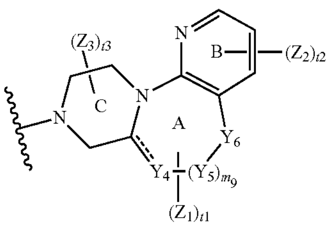

is selected from

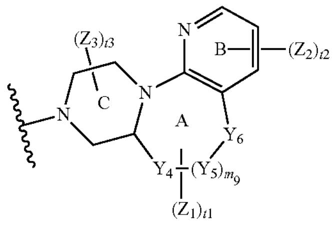

;

$Y_4$ is selected from absent or $CH_2$;

$Y_5$ at each occurrence is independently selected from $CH_2$;

$m_9$ is selected from 0, 1 or 2;

$Y_6$ is selected from $CH_2$, $CF_2$, CHF, CH(OH), C(=O), O, NH, S, S(=O), S(=O)$_2$, *NHC(=O) or NHC(=O)*; * indicates the attached point to the aromatic ring B, and ** indicates the attached point to the $Y_5$.

[29]. The compound according to [28], wherein, the moiety of

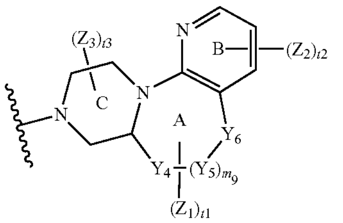

is selected from

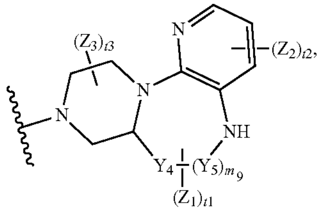

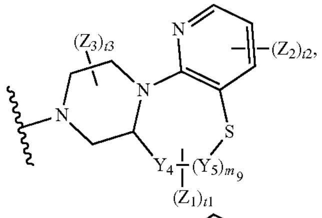

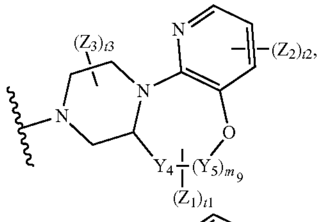

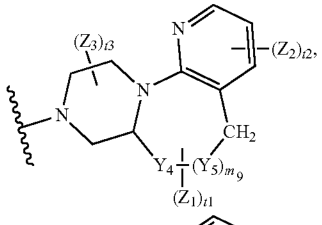

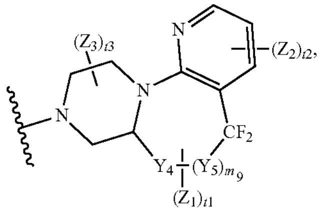

-continued

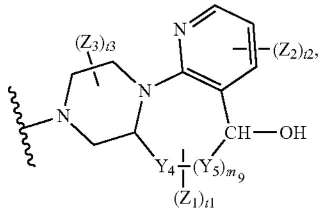

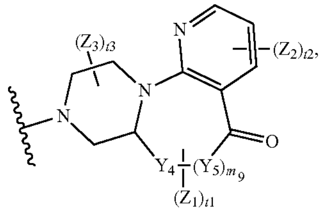

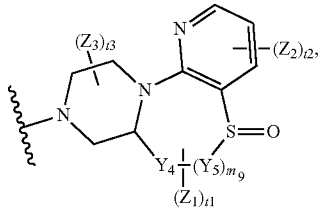

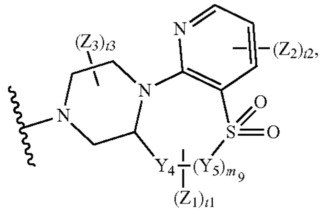

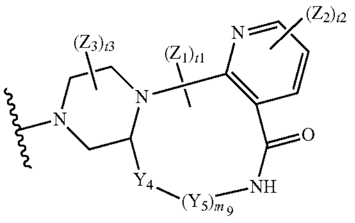

or

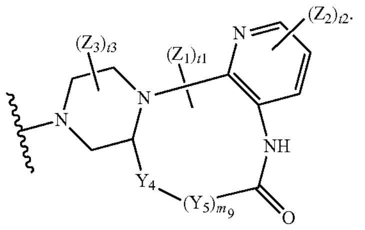

[30]. The compound according to any one of [27] to [29], wherein, the moiety of

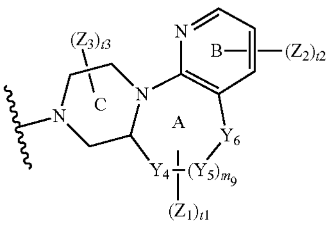

is selected from
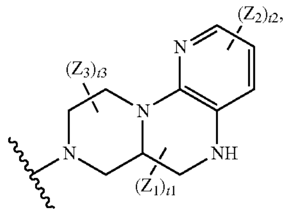
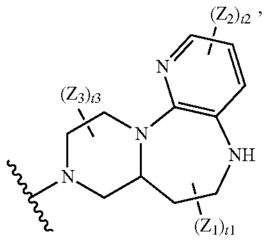
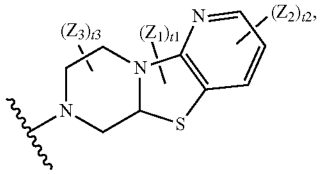
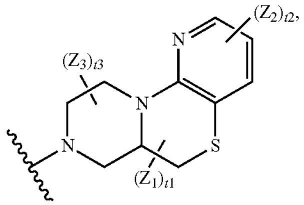
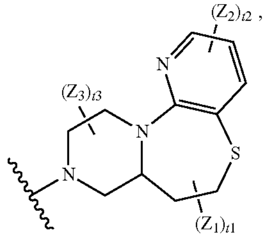
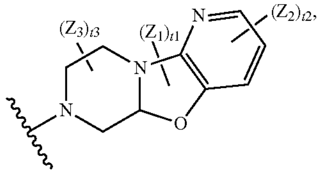
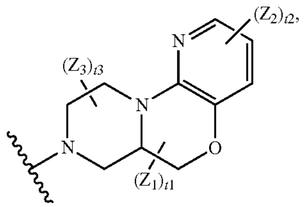
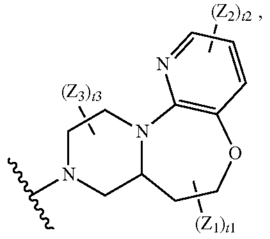
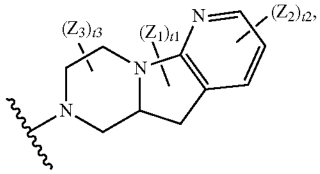
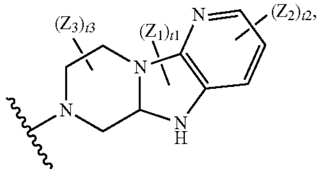
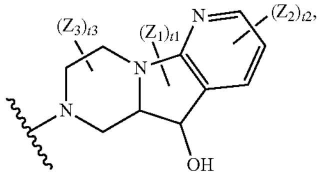
-continued
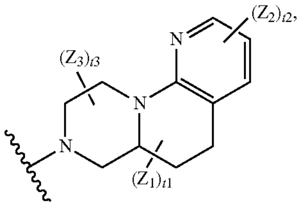
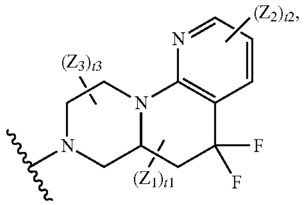
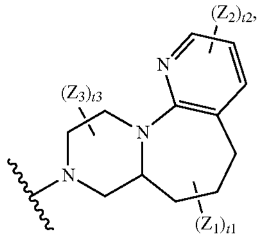
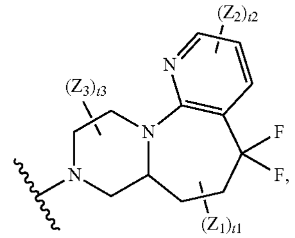
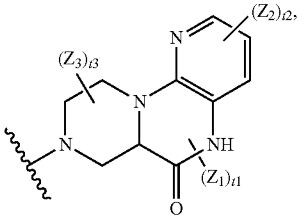
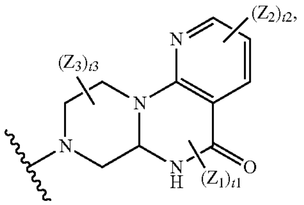
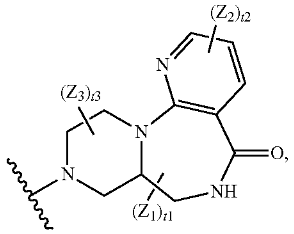
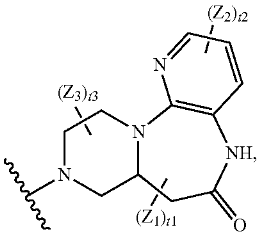
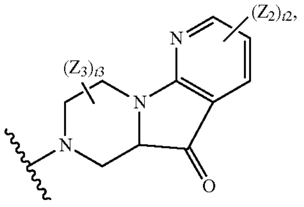

-continued
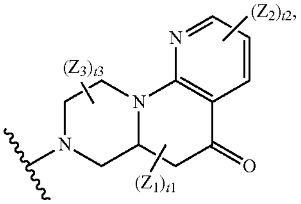
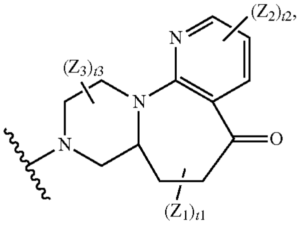
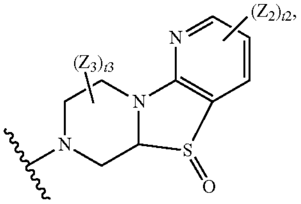
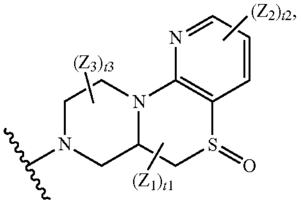
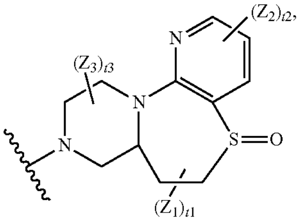
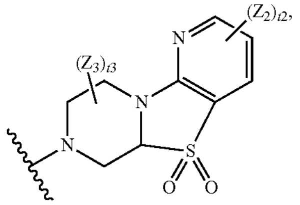
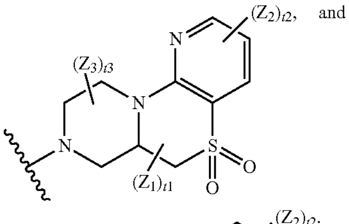
and
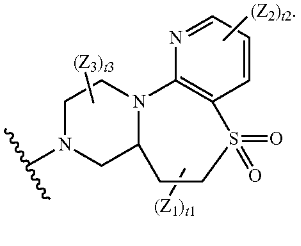
[31]. The compound according to any one of [27] to [30], wherein, the moiety of
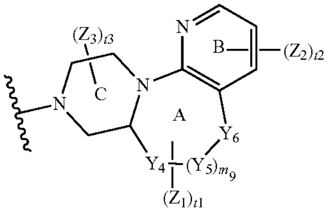
is selected from
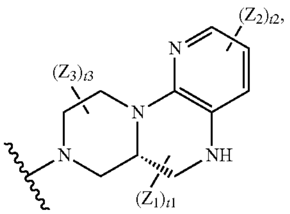
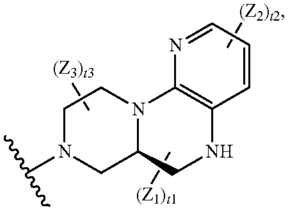
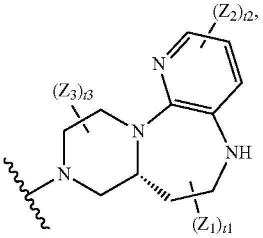
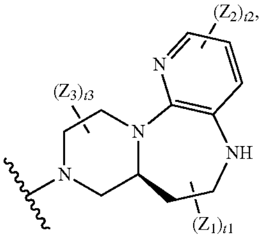
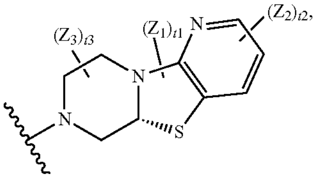
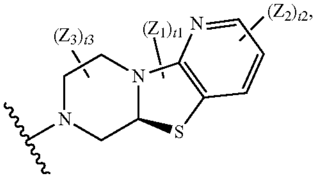
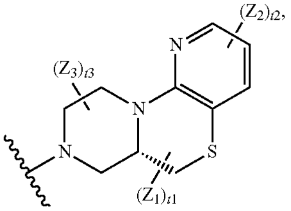

-continued
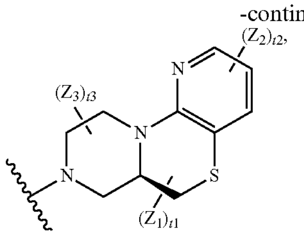
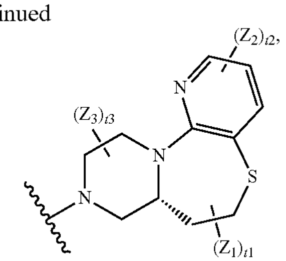
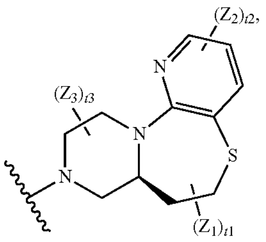
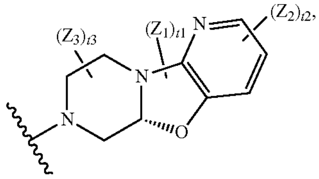
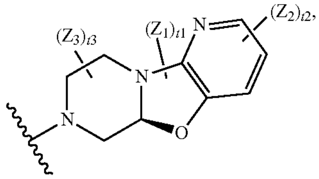
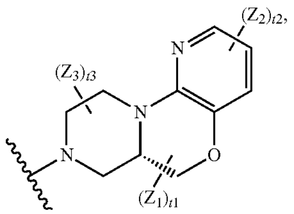
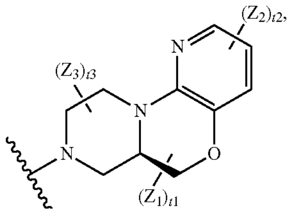
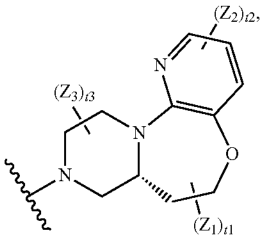
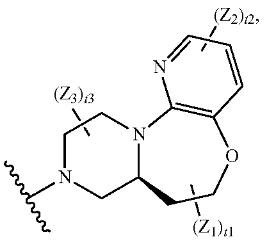
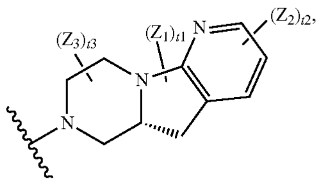
-continued
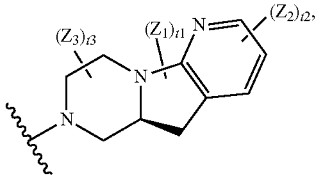
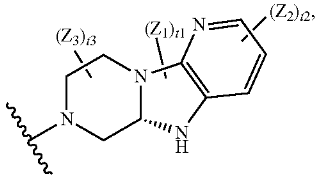
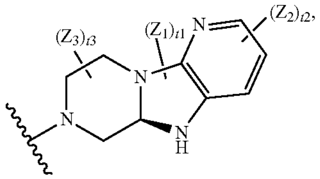
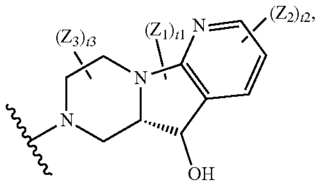
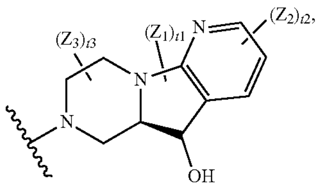
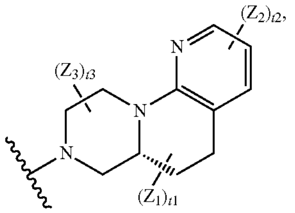
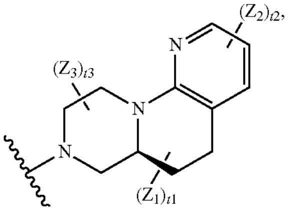
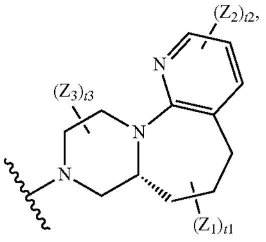
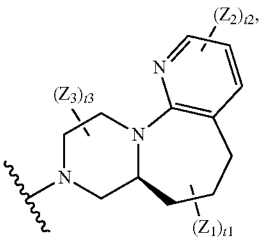

-continued
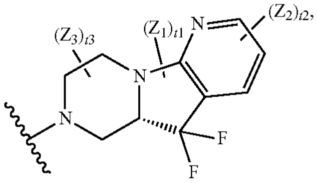
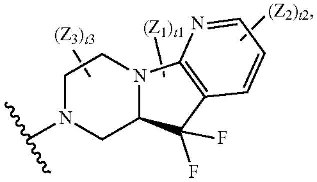
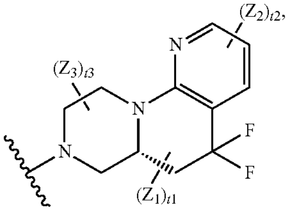
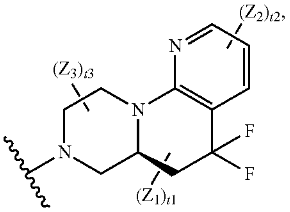
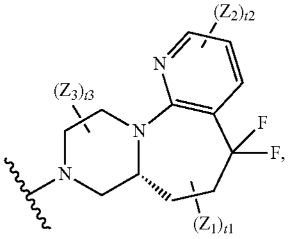
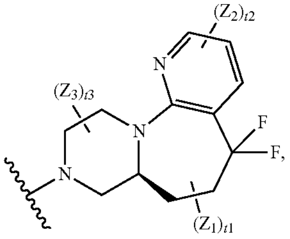
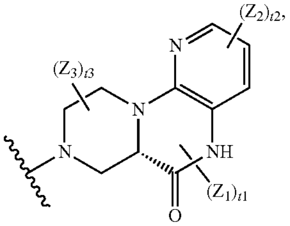
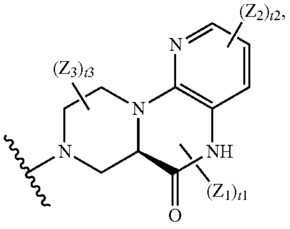
-continued
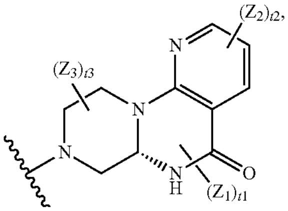
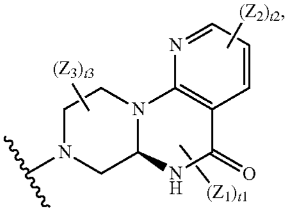
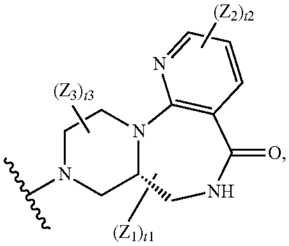
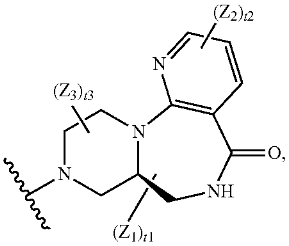
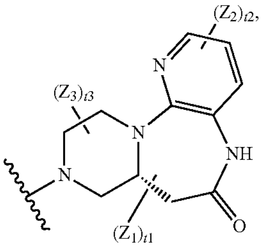
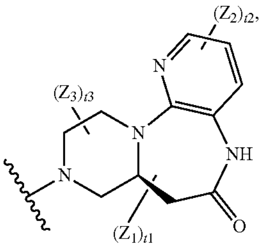
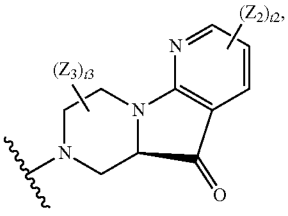

-continued
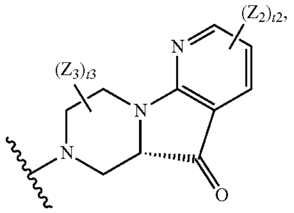
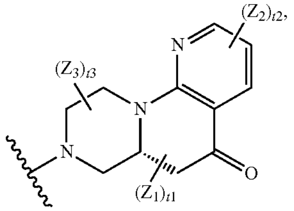
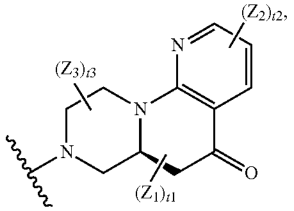
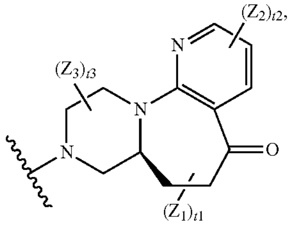
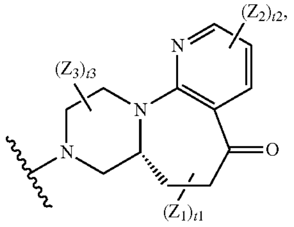
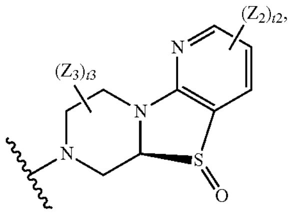
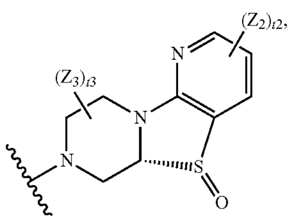
-continued
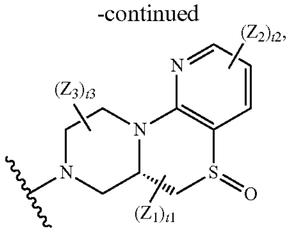
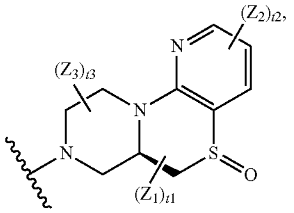
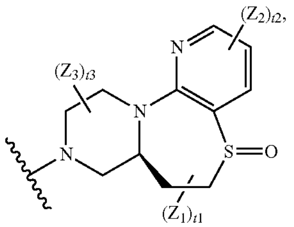
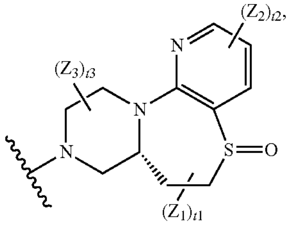
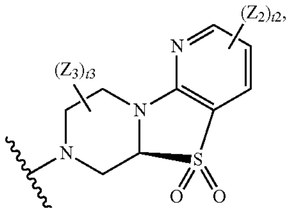
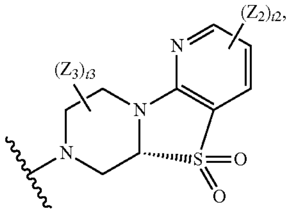
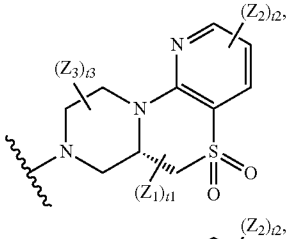
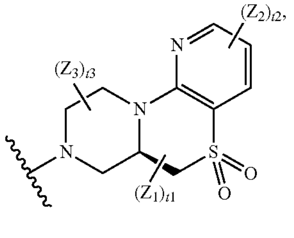

-continued
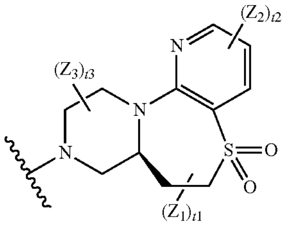
or
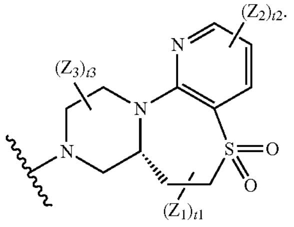
[32]. The compound according to [27], wherein, the moiety of
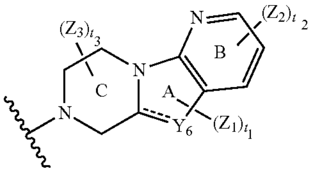
is selected from
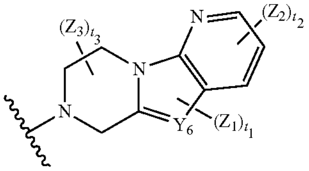
or
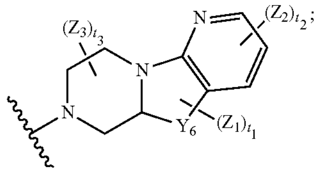
Wherein,
The moiety of
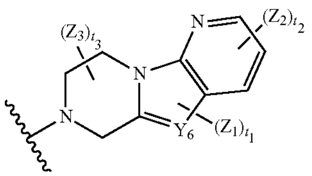
is selected from
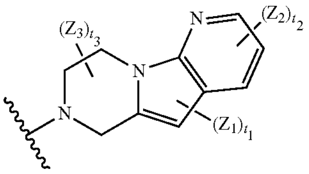
or
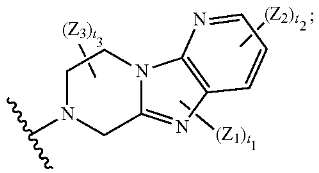
The moiety of
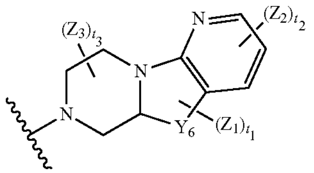
is selected from
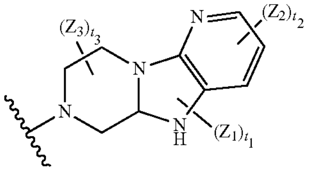
or
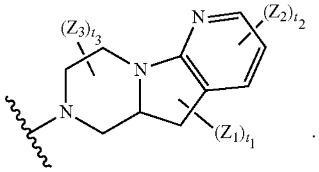
.
[33]. The compound according to [32], wherein, The moiety of
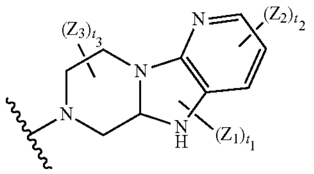
is selected from
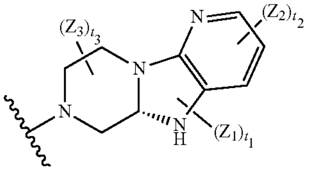
or -continued
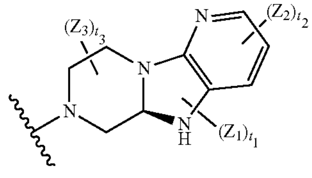
;
The moiety of
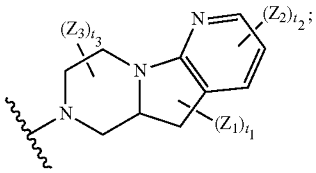
is selected from
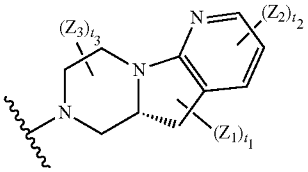
or
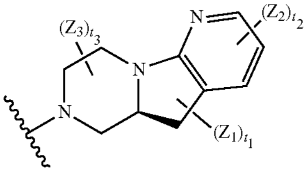
.
[34]. The compound according to any one of [1] to [33], wherein, the moiety of
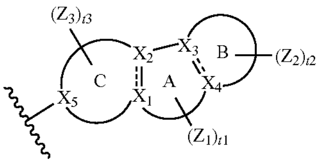
is selected from
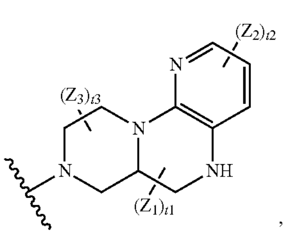
,
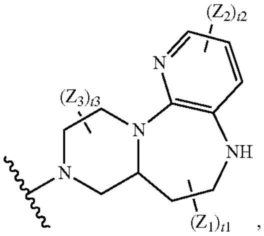
,
-continued
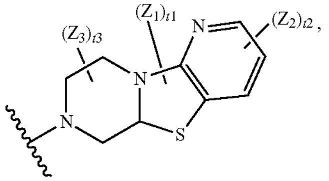
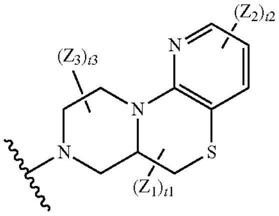
,
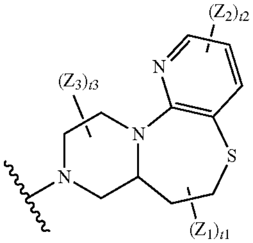
,
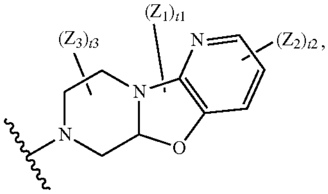
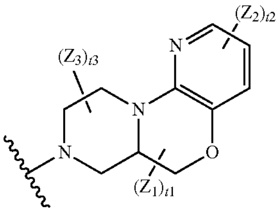
,
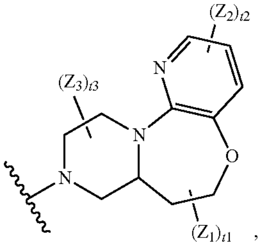
,
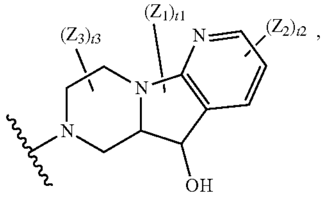
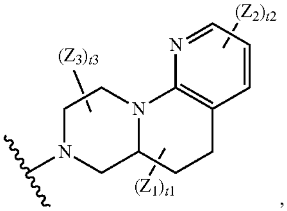
,
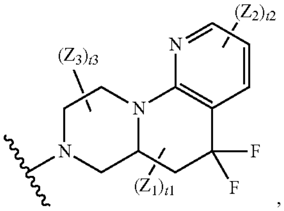
,
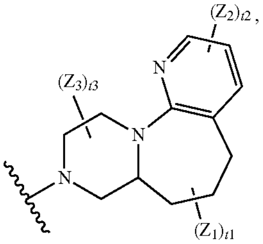

-continued
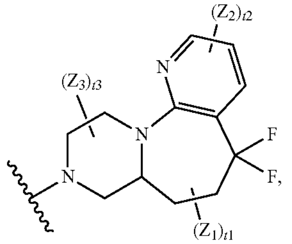
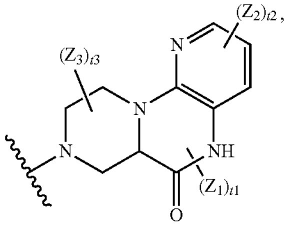
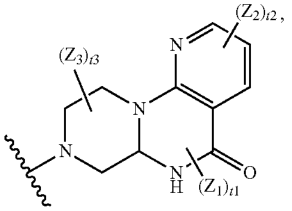
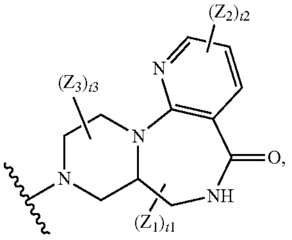
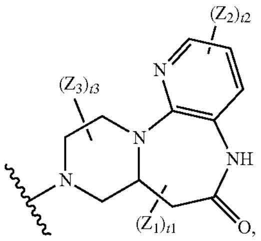
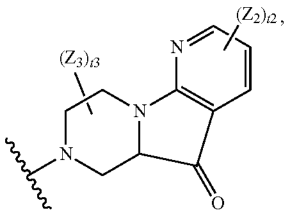
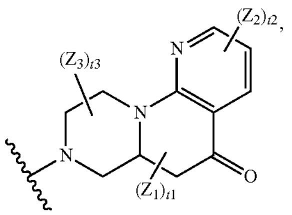
-continued
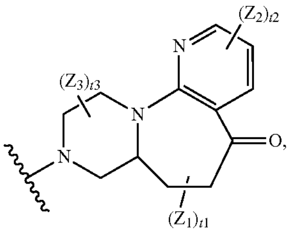
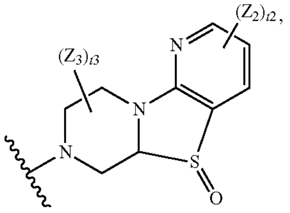
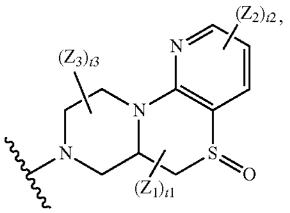
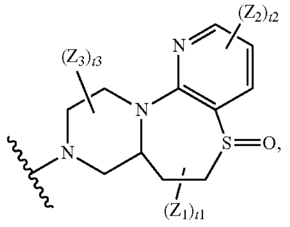
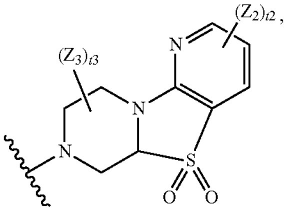
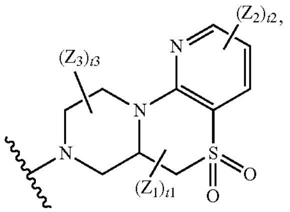
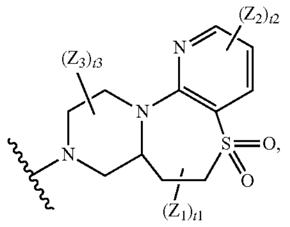

-continued
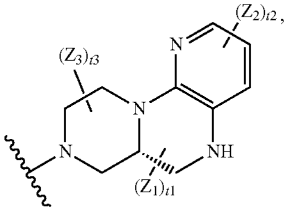
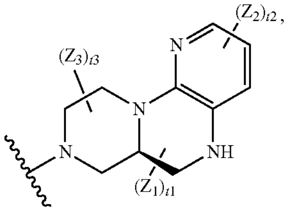
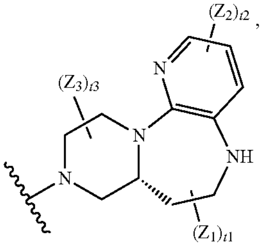
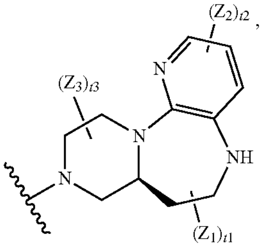
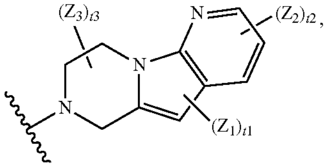
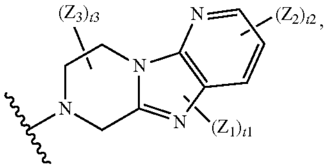
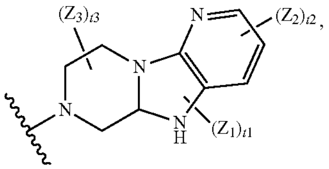
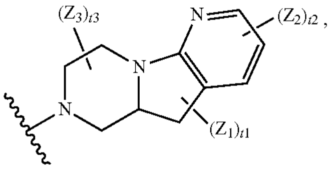
-continued
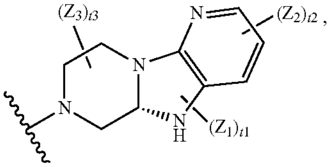
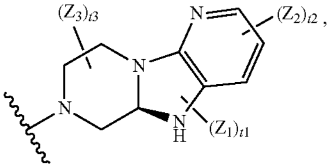
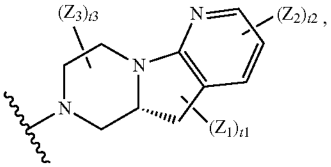
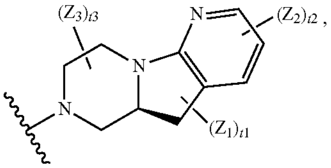
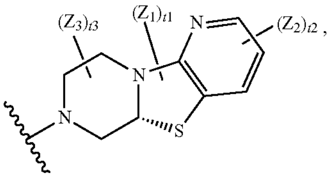
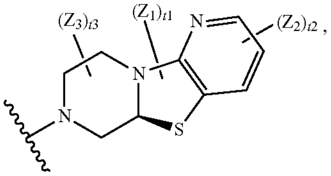
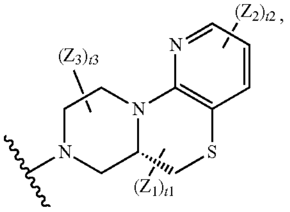
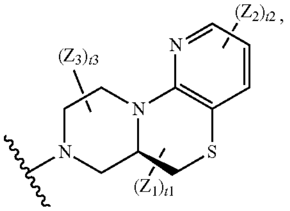
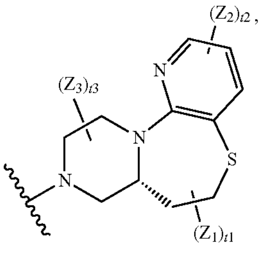

-continued
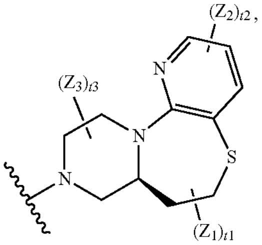
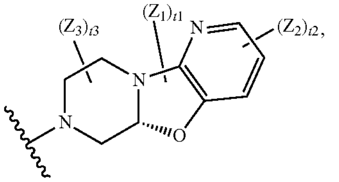
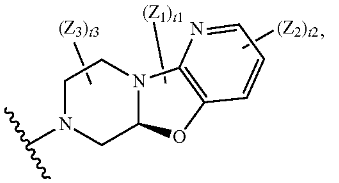
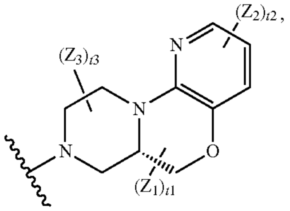
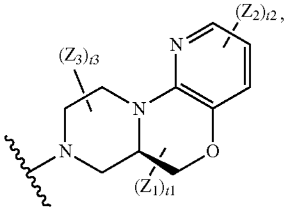
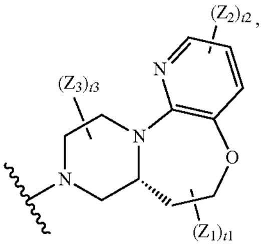
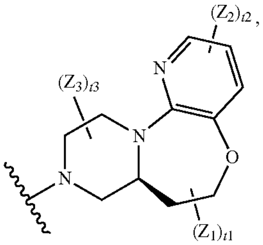
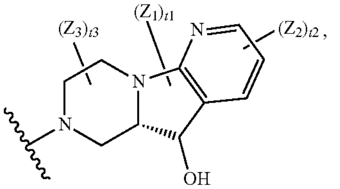
-continued
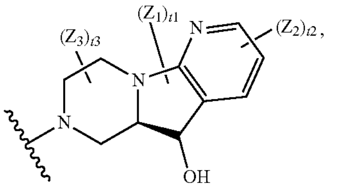
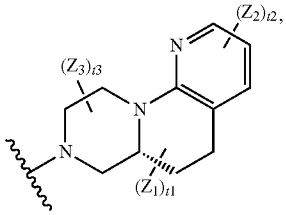
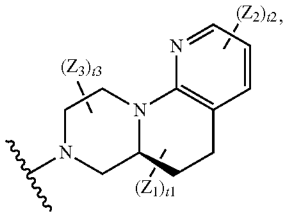
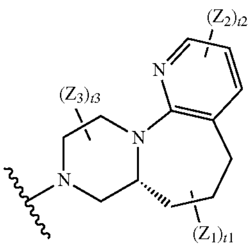
,
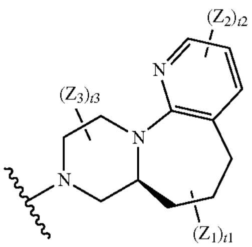
,
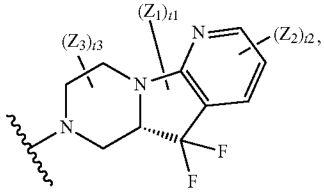
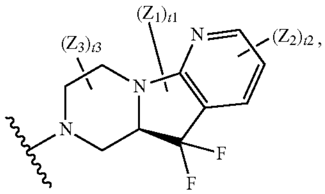
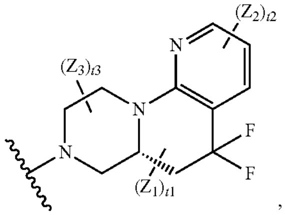
,
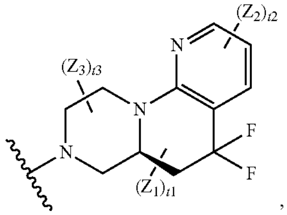
,
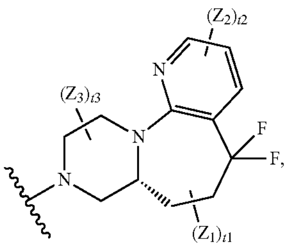

-continued
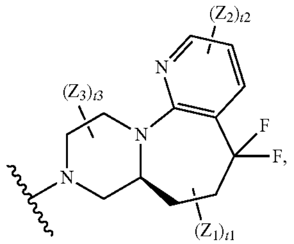
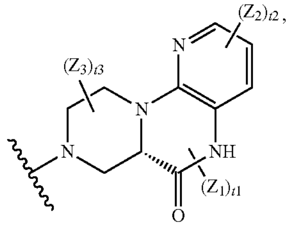
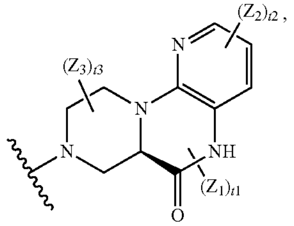
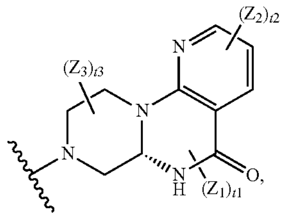
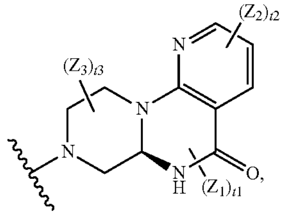
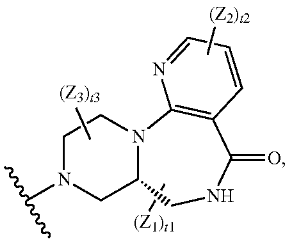
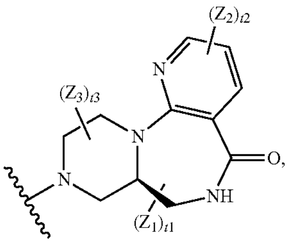
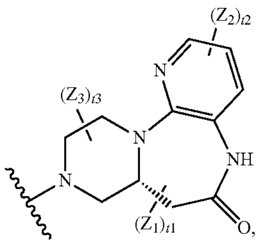
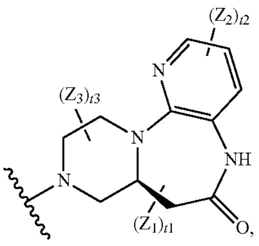
-continued
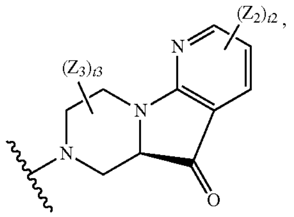
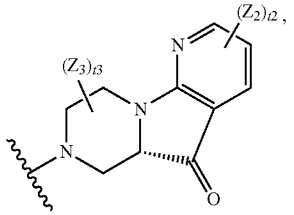
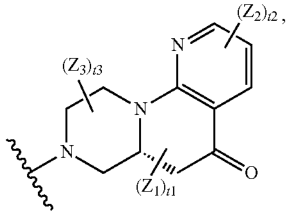
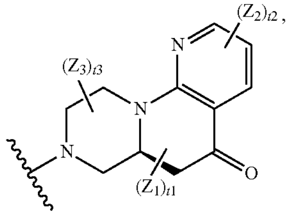
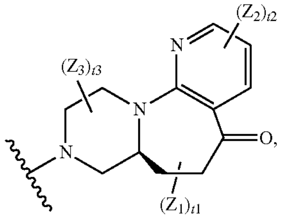
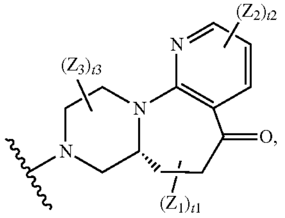
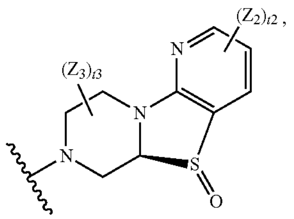
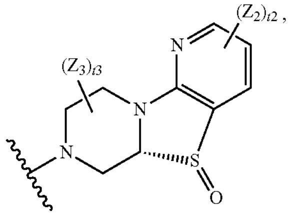

-continued
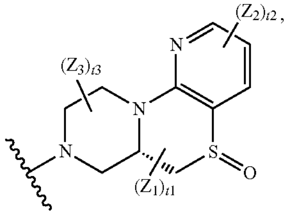
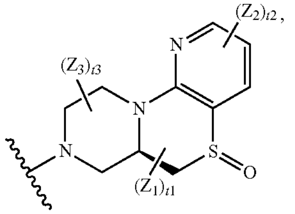
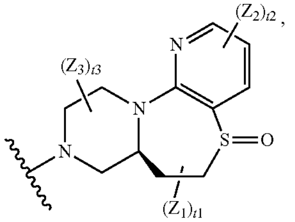
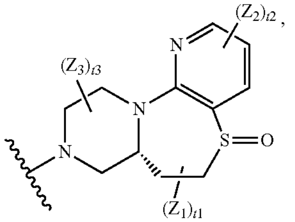
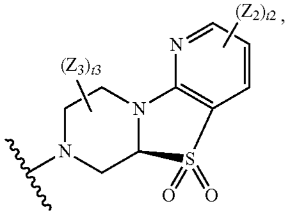
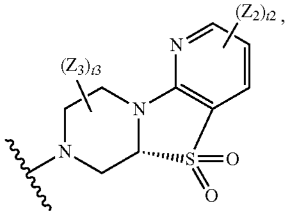
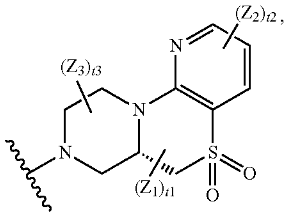
-continued
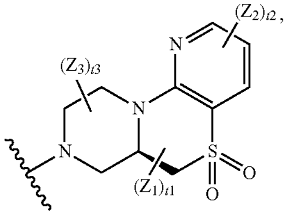
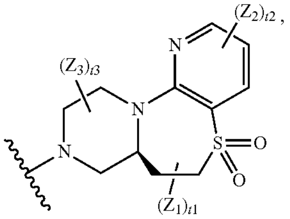
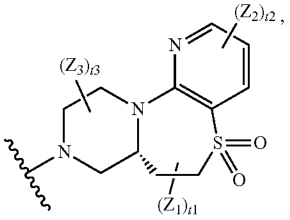
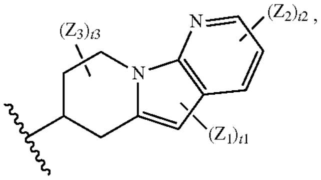
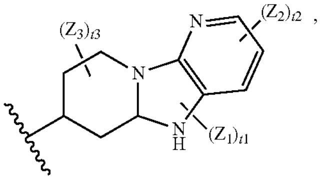
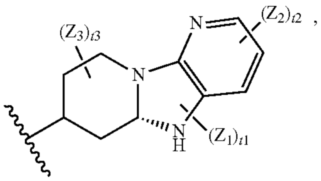
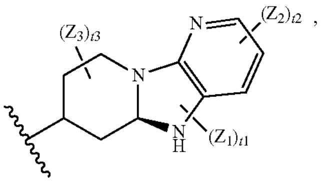
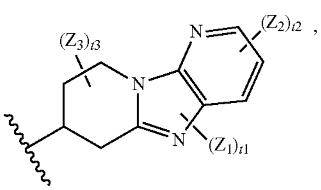

-continued
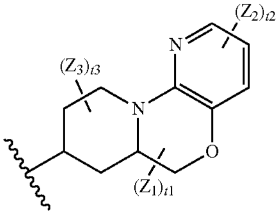,
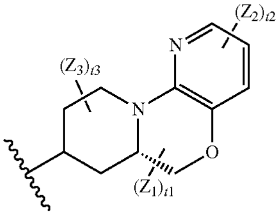,
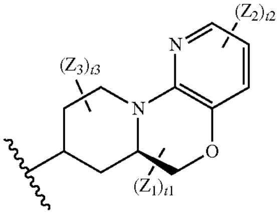,
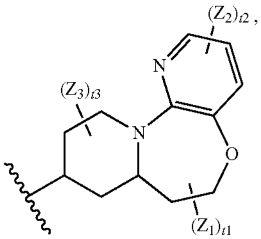,
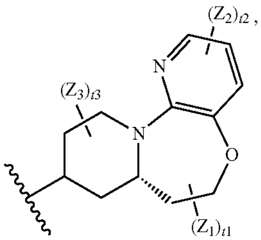,
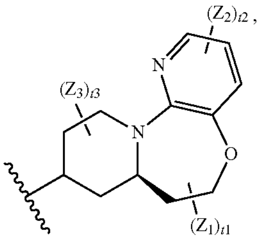,
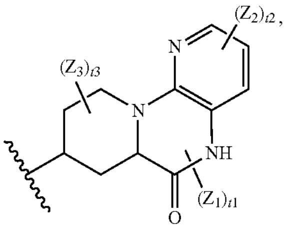,
-continued
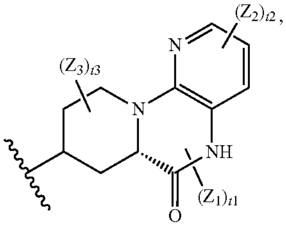,
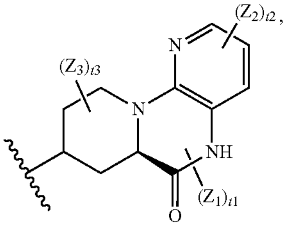,
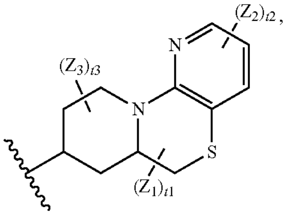,
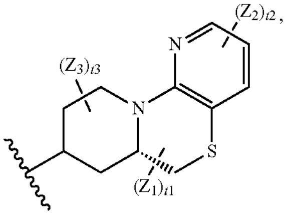,
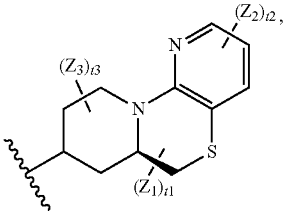,
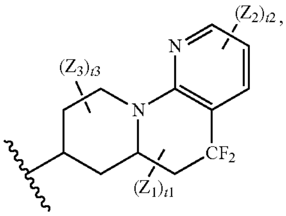,
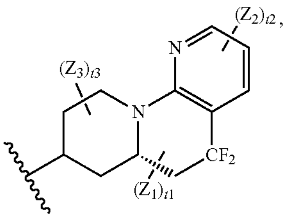, -continued
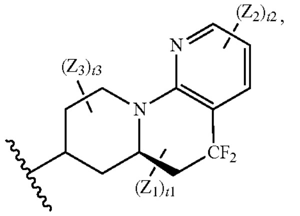
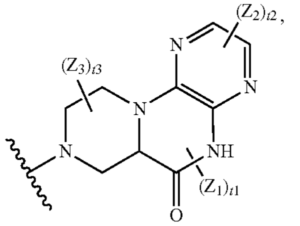
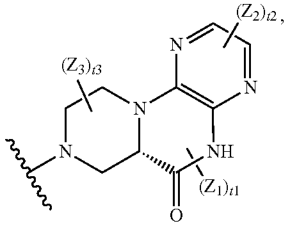
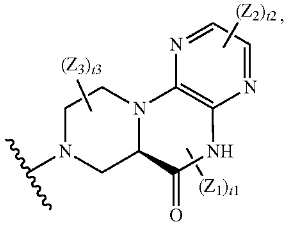
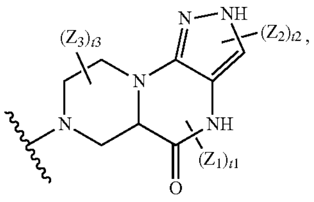
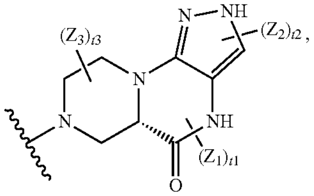
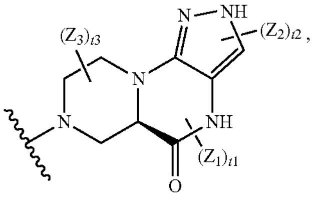
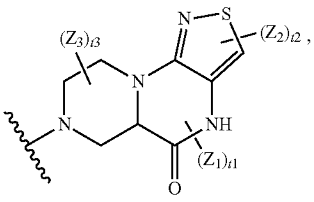
-continued
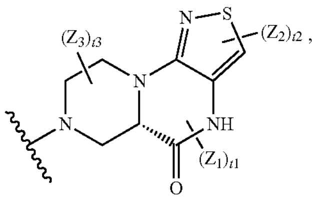
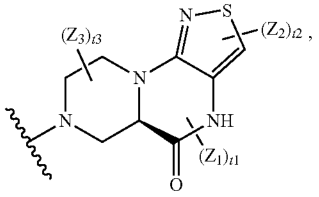
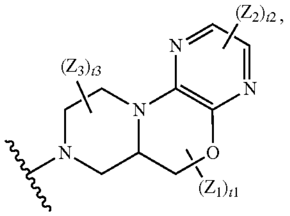
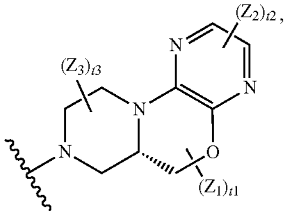
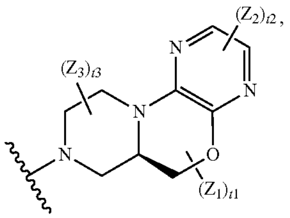
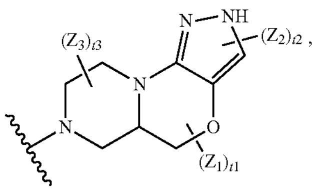
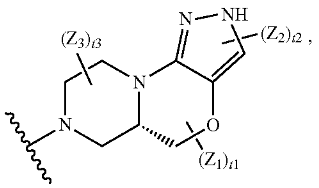
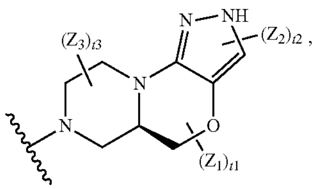

-continued
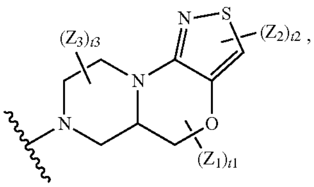
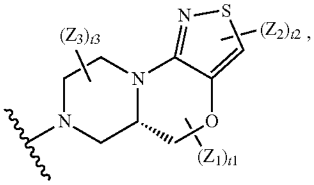
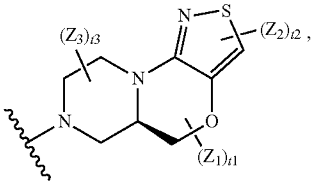
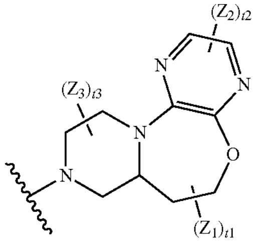
,
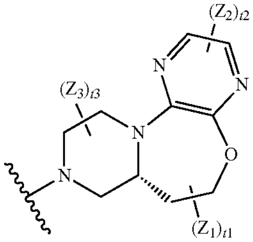
,
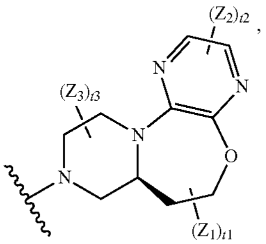
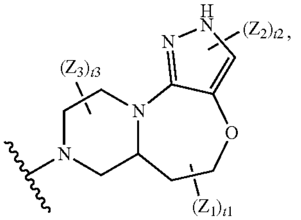
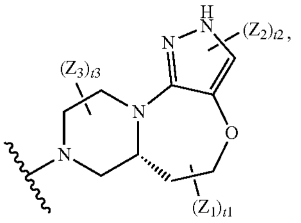
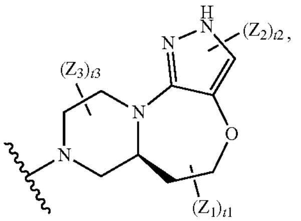
-continued
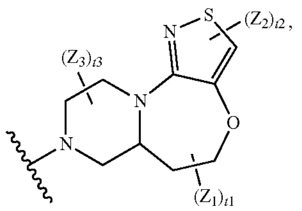
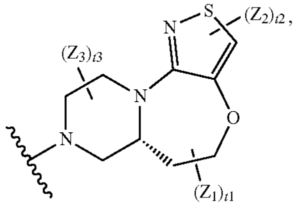
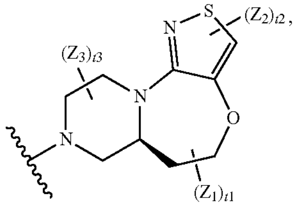
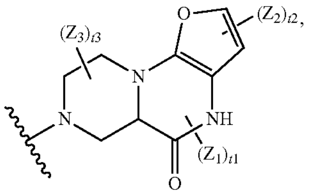
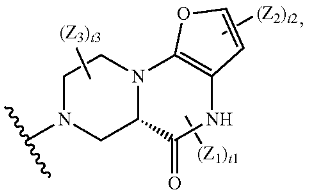
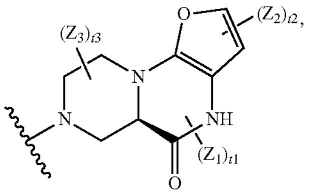
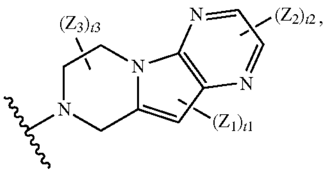
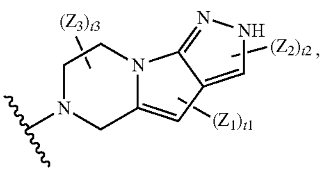
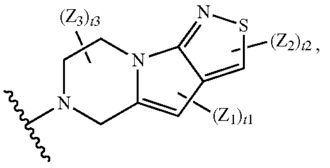

-continued
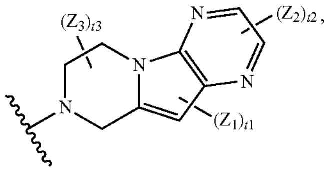,
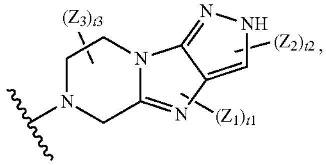,
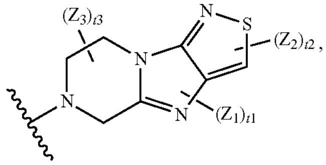,
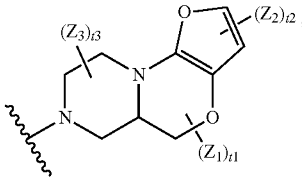,
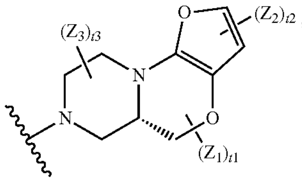,
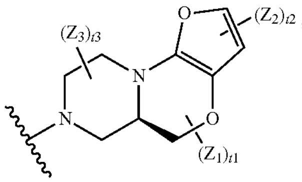,
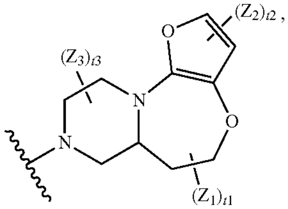,
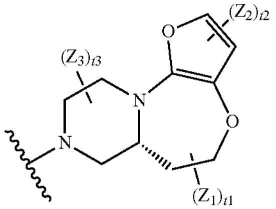,
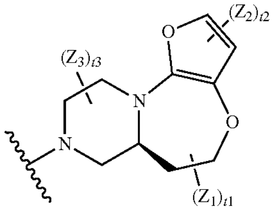,
-continued
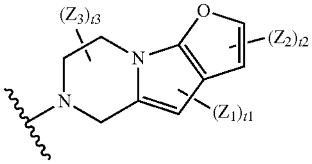,
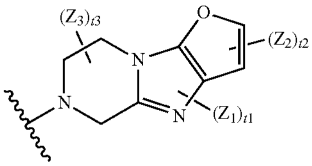,
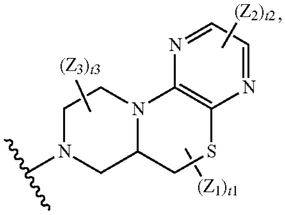,
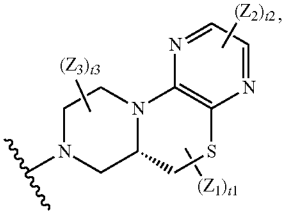,
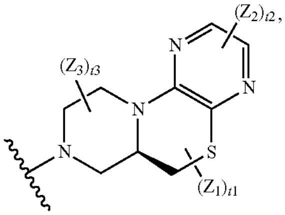,
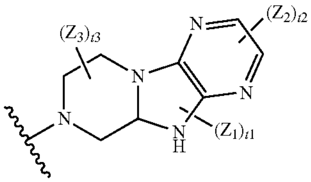,
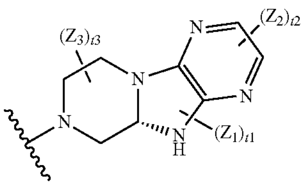,
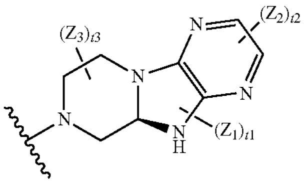,
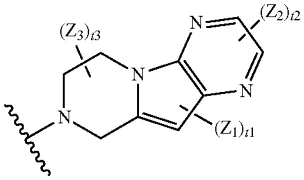, -continued

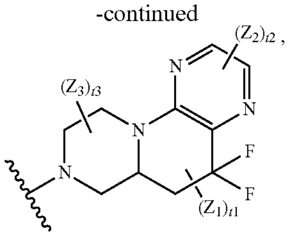

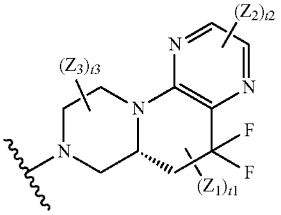

or

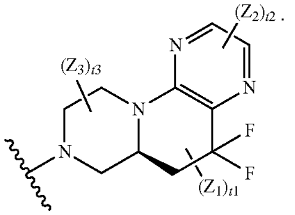

[35]. The compound according to any one of [1] to [34], wherein, $Z_1$, $Z_2$ or $Z_3$ at each occurrence is independently selected from halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, —$NH_2$, —NH($C_{1-6}$alkyl), —N($C_{1-6}$alkyl)$_2$, —NH(3-10 membered cycloalkyl), —N($C_{1-6}$alkyl)(3-10 membered cycloalkyl), —OH, —O($C_{1-6}$alkyl), —O-(3-10 membered cycloalkyl), —SH, —S($C_{1-6}$alkyl), —S(3-10 membered cycloalkyl), —S(═O)($C_{1-6}$alkyl), —S(═O)(3-10 membered cycloalkyl), —S(═O)$_2$($C_{1-6}$alkyl), —S(═O)$_2$(3-10 membered cycloalkyl), —C(═O)($C_{1-6}$alkyl), —C(═O)-(3-10 membered cycloalkyl), —C(═O)OH, —C(═O)(O$C_{1-6}$alkyl), —OC(═O)($C_{1-6}$alkyl), —C(═O)$NH_2$, —C(═O)NH($C_{1-6}$alkyl), —C(═O)N($C_{1-6}$alkyl)$_2$, —NHC(═O)($C_{1-6}$alkyl), —N($C_{1-6}$alkyl)C(═O)($C_{1-6}$alkyl), —OC(═O)O($C_{1-6}$alkyl), —NHC(═O)(O$C_{1-6}$alkyl), —N($C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)$NH_2$, —NHC(═O)NH($C_{1-6}$alkyl), —NHC(═O)N($C_{1-6}$alkyl)$_2$, —N($C_{1-6}$alkyl)C(═O)$NH_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)$NH_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —OS(═O)O($C_{1-6}$alkyl), —NHS(═O)O($C_{1-6}$alkyl), —N($C_{1-6}$alkyl)S(═O)O($C_{1-6}$alkyl), —OS(═O)$NH_2$, —OS(═O)NH($C_{1-6}$alkyl), —OS(═O)N($C_{1-6}$alkyl)$_2$, —NHS(═O)$NH_2$, —NHS(═O)NH($C_{1-6}$alkyl), —NHS(═O)N($C_{1-6}$alkyl)$_2$, —N($C_{1-6}$alkyl)S(═O)$NH_2$, —N($C_{1-6}$alkyl)S(═O)NH($C_{1-6}$alkyl), —N($C_{1-6}$alkyl)S(═O)N($C_{1-6}$alkyl)$_2$, —S(═O)$_2$(O$C_{1-6}$alkyl), —OS(═O)$_2$($C_{1-6}$alkyl), —S(═O)$_2NH_2$, —S(═O)$_2$NH($C_{1-6}$alkyl), —S(═O)$_2$N($C_{1-6}$alkyl)$_2$, —NHS(═O)$_2$($C_{1-6}$alkyl), —N($C_{1-6}$alkyl)S(═O)$_2$($C_{1-6}$alkyl), —OS(═O)$_2$O($C_{1-6}$alkyl), —NHS(═O)$_2$O($C_{1-6}$alkyl), —N($C_{1-6}$alkyl)S(═O)$_2$O($C_{1-6}$alkyl), —OS(═O)$_2NH_2$, —OS(═O)$_2$NH($C_{1-6}$alkyl), —OS(═O)$_2$N($C_{1-6}$alkyl)$_2$, —NHS(═O)$_2NH_2$, —NHS(═O)$_2$NH($C_{1-6}$alkyl), —NHS(═O)$_2$N($C_{1-6}$alkyl)$_2$, —N($C_{1-6}$alkyl)S(═O)$_2NH_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-10 membered cycloalkyl, 3-10 membered heterocyclyl, 6-10 membered aryl or 5-10 membered heteroaryl, wherein said —$C_{1-6}$alkyl, —$C_{1-6}$haloalkyl, —$C_{1-6}$haloalkoxy, —$C_{2-6}$alkenyl, —$C_{2-6}$alkynyl, 3-10 membered cycloalkyl, 3-6 membered heterocyclyl, 6-10 membered aryl or 5-10 membered heteroaryl is independently optionally substituted with 1, 2, 3, 4, 5 or 6 substituents selected from halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —$NH_2$, —NH($C_{1-6}$alkyl), —N($C_{1-6}$alkyl)$_2$, —NH(3-10 membered cycloalkyl), —N($C_{1-6}$alkyl)(3-10 membered cycloalkyl), —OH, —O($C_{1-6}$alkyl), —O(3-10 membered cycloalkyl), —SH, —S($C_{1-6}$alkyl), —S(3-10 membered cycloalkyl), —S(═O)($C_{1-6}$alkyl), —S(═O)(3-10 membered cycloalkyl), —S(═O)$_2$($C_{1-6}$alkyl), —S(═O)$_2$(3-10 membered cycloalkyl), —C(═O)($C_{1-6}$alkyl), —C(═O)-(3-10 membered cycloalkyl), —C(═O)OH, —C(═O)(O$C_{1-6}$alkyl), —OC(═O)($C_{1-6}$alkyl), —C(═O)$NH_2$, —C(═O)NH($C_{1-6}$alkyl), —C(═O)N($C_{1-6}$alkyl)$_2$, —NHC(═O)($C_{1-6}$alkyl), —N($C_{1-6}$alkyl)C(═O)($C_{1-6}$alkyl), —OC(═O)O($C_{1-6}$alkyl), —NHC(═O)(O$C_{1-6}$alkyl), —N($C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)$NH_2$, —NHC(═O)NH($C_{1-6}$alkyl), —NHC(═O)N($C_{1-6}$alkyl)$_2$, —N($C_{1-6}$alkyl)C(═O)$NH_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)$NH_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —OS(═O)O($C_{1-6}$alkyl), —NHS(═O)O($C_{1-6}$alkyl), —N($C_{1-6}$alkyl)S(═O)O($C_{1-6}$alkyl), —OS(═O)$NH_2$, —OS(═O)NH($C_{1-6}$alkyl), —OS(═O)N($C_{1-6}$alkyl)$_2$, —NHS(═O)$NH_2$, —NHS(═O)NH($C_{1-6}$alkyl), —NHS(═O)N($C_{1-6}$alkyl)$_2$, —N($C_{1-6}$alkyl)S(═O)$NH_2$, —N($C_{1-6}$alkyl)S(═O)NH($C_{1-6}$alkyl), —N($C_{1-6}$alkyl)S(═O)N($C_{1-6}$alkyl)$_2$, —S(═O)$_2$(O$C_{1-6}$alkyl), —OS(═O)$_2$($C_{1-6}$alkyl), —S(═O)$_2NH_2$, —S(═O)$_2$NH($C_{1-6}$alkyl), —S(═O)$_2$N($C_{1-6}$alkyl)$_2$, —NHS(═O)$_2$($C_{1-6}$alkyl), —N($C_{1-6}$alkyl)S(═O)$_2$($C_{1-6}$alkyl), —OS(═O)$_2$O($C_{1-6}$alkyl), —NHS(═O)$_2$O($C_{1-6}$alkyl), —N($C_{1-6}$alkyl)S(═O)$_2$O($C_{1-6}$alkyl), —OS(═O)$_2NH_2$, —OS(═O)$_2$NH($C_{1-6}$alkyl), —OS(═O)$_2$N($C_{1-6}$alkyl)$_2$, —NHS(═O)$_2NH_2$, —NHS(═O)$_2$NH($C_{1-6}$alkyl), —NHS(═O)$_2$N($C_{1-6}$alkyl)$_2$, —N($C_{1-6}$alkyl)S(═O)$_2NH_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-10 membered cycloalkyl, 3-6 membered heterocyclyl, 6-10 membered aryl or 5-10 membered heteroaryl;

$t_1$, $t_2$ or $t_3$ at each occurrence is independently selected from 0, 1, 2, 3, 4, 5, or 6.

[36]. The compound according to any one of [1] to [35], wherein, $Z_1$, $Z_2$ or $Z_3$ at each occurrence is independently selected from —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, —$NH_2$, —NH($C_{1-3}$alkyl), —N($C_{1-3}$alkyl)$_2$, —NH(3-6 membered cycloalkyl), —N($C_{1-3}$alkyl)(3-6 membered cycloalkyl), —OH, —O($C_{1-3}$alkyl), —O-(3-6 membered cycloalkyl), —SH, —S($C_{1-3}$alkyl), —S-(3-6 membered cycloalkyl), —S(═O)($C_{1-3}$alkyl), —S(═O)(3-6 membered cycloalkyl), —S(═O)$_2$($C_{1-3}$alkyl), —S(═O)$_2$-(3-6 membered cycloalkyl), —C(═O)($C_{1-3}$alkyl), —C(═O)-(3-6 membered cycloalkyl), —C(═O)OH, —C(═O)(O$C_{1-3}$alkyl), —OC(═O)($C_{1-3}$alkyl), —C(═O)$NH_2$, —C(═O)NH($C_{1-3}$alkyl), —C(═O)N($C_{1-3}$alkyl)$_2$, —NHC(═O)($C_{1-3}$alkyl), —N($C_{1-3}$alkyl)C(═O)($C_{1-3}$alkyl), —S(═O)(O$C_{1-3}$alkyl), —OS(═O)($C_{1-3}$alkyl), —S(═O)$NH_2$, —S(═O)NH ($C_{1-3}$alkyl), —S(=O)N($C_{1-3}$alkyl)$_2$, —NHS(=O)($C_{1-3}$alkyl), —N($C_{1-3}$alkyl)S(=O)($C_{1-3}$alkyl), —S(=O)$_2$(O$C_{1-3}$alkyl), —OS(=O)$_2$($C_{1-3}$alkyl), —S(=O)$_2$NH$_2$, —S(=O)$_2$NH($C_{1-3}$alkyl), —S(=O)$_2$N($C_{1-3}$alkyl)$_2$, —NHS(=O)$_2$($C_{1-3}$alkyl), —N($C_{1-3}$alkyl)S(=O)$_2$($C_{1-3}$alkyl), —P(=O)H($C_{1-3}$alkyl), —P(=O)($C_{1-3}$alkyl)$_2$, 3-6 membered cycloalkyl, 3-6 membered heterocyclyl, 6-10 membered aryl or 5-10 membered heteroaryl, wherein said —$C_{1-3}$alkyl, —$C_{1-3}$haloalkyl, —$C_{1-3}$haloalkoxy, —$C_{2-6}$alkenyl, —$C_{2-6}$alkynyl, 3-6 membered cycloalkyl, 3-6 membered heterocyclyl, 6-10 membered aryl or 5-10 membered heteroaryl is independently optionally substituted with 1, 2, 3, 4, 5 or 6 substituents selected from —F, —Cl, —Br, —$C_{1-3}$alkyl, —$C_{1-3}$haloalkyl, —CN, —NH$_2$, —NH($C_{1-3}$alkyl), —N($C_{1-3}$alkyl)$_2$, —OH, —O($C_{1-3}$alkyl), —SH, —S($C_{1-3}$alkyl), —S(=O)($C_{1-3}$alkyl), —S(=O)$_2$($C_{1-3}$alkyl), —C(=O)($C_{1-3}$alkyl), —C(=O)OH, —C(=O)(O$C_{1-3}$alkyl), —OC(=O)($C_{1-3}$alkyl), —C(=O)NH$_2$, —C(=O)NH($C_{1-3}$alkyl), —C(=O)N($C_{1-3}$alkyl)$_2$, —NHC(=O)($C_{1-3}$alkyl), —N($C_{1-3}$alkyl)C(=O)($C_{1-3}$alkyl), —S(=O)(O$C_{1-3}$alkyl), —OS(=O)($C_{1-3}$alkyl), —S(=O)NH$_2$, —S(=O)NH($C_{1-3}$alkyl), —S(=O)N($C_{1-3}$alkyl)$_2$, —NHS(=O)($C_{1-3}$alkyl), —N($C_{1-3}$alkyl)S(=O)($C_{1-3}$alkyl), —S(=O)$_2$(O$C_{1-3}$alkyl), —OS(=O)$_2$($C_{1-3}$alkyl), —S(=O)$_2$NH$_2$, —S(=O)$_2$NH($C_{1-3}$alkyl), —S(=O)$_2$N($C_{1-3}$alkyl)$_2$, —NHS(=O)$_2$($C_{1-3}$alkyl), —N($C_{1-3}$alkyl)S(=O)$_2$($C_{1-3}$alkyl), —P(=O)H($C_{1-3}$alkyl), —P(=O)($C_{1-3}$alkyl)$_2$ or 3-6 membered cycloalkyl;

$t_1$, $t_2$ or $t_3$ at each occurrence is independently selected from 0, 1, 2, or 3.

[37]. The compound according to any one of [1] to [36], wherein, $Z_1$, $Z_2$ or $Z_3$ at each occurrence is independently selected from —Cl, —F, —Br, —CH$_3$, —CD$_3$, —CH$_2$CH$_3$, —CH$_2$CH$_2$CH$_3$, —CH(CH$_3$)$_2$, —C(CH$_3$)$_3$,

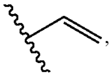, 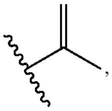, 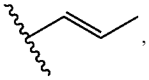, 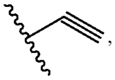,

—CH$_2$F, —CHF$_2$, —CF$_3$, —CH$_2$CH$_2$F, —CH$_2$CHF$_2$, —CH$_2$CF$_3$, —CHFCH$_3$, —CF$_2$CH$_3$, —CN, —NH$_2$, —NH(CH$_3$), —N(CH$_3$)$_2$, —NH(CH$_2$CH$_3$), —OH, —O—CH$_3$, —O—CH$_2$CH$_3$, —O—CH$_2$CH$_2$CH$_3$, —O—CH(CH$_3$)$_2$, —O—CF$_3$, —SH, —S—CH$_3$, —S—CH$_2$CH$_3$, —S—CH$_2$CH$_2$CH$_3$, —S—CH(CH$_3$)$_2$, —S—CF$_3$, —S(=O)CH$_3$, —S(=O)(CH$_2$CH$_3$), —S(=O)(CH$_2$CH$_2$CH$_3$), —S(=O)(CH(CH$_3$)$_2$), —S(=O)$_2$CH$_3$, —S(=O)$_2$(CH$_2$CH$_3$), —S(=O)$_2$(CH$_2$CH$_2$CH$_3$), —S(=O)$_2$(CH(CH$_3$)$_2$), —COOH, —C(=O)(CH$_3$), —C(=O)(CH$_2$CH$_3$), —C(=O)(CH(CH$_3$)$_2$), —C(=O)(CF$_3$), —C(=O)(OCH$_3$), —C(=O)(OCH$_2$CH$_3$), —C(=O)(OCH$_2$CH$_2$CH$_3$), —C(=O)(OCH(CH$_3$)$_2$), —OC(=O)(CH$_3$), —OC(=O)(CH$_2$CH$_3$), —OC(=O)(CH$_2$CH$_2$CH$_3$), —OC(=O)(CH(CH$_3$)$_2$), —C(=O)NH$_2$, —C(=O)NH(CH$_3$), —C(=O)NH(CH$_2$CH$_3$), —C(=O)NH(CH$_2$CH$_2$CH$_3$), —C(=O)NH(CH(CH$_3$)$_2$), —C(=O)N(CH$_3$)$_2$, —C(=O)N(CH$_2$CH$_3$)$_2$, —NHC(=O)(CH$_3$), —NHC(=O)(CH$_2$CH$_3$), —NHC(=O)(CH$_2$CH$_2$CH$_3$), —NHC(=O)(CH(CH$_3$)$_2$), —N(CH$_3$)C(=O)(CH$_3$), —S(=O)(OCH$_3$), —S(=O)(OCH$_2$CH$_3$), —S(=O)(OCH$_2$CH$_2$CH$_3$), —S(=O)(OCH(CH$_3$)$_2$), —OS(=O)(CH$_3$), —OS(=O)(CH$_2$CH$_3$), —OS(=O)(CH$_2$CH$_2$CH$_3$), —OS(=O)(CH(CH$_3$)$_2$), —S(=O)NH$_2$, —S(=O)NH(CH$_3$), —S(=O)NH(CH$_2$CH$_3$), —S(=O)NH(CH$_2$CH$_2$CH$_3$), —S(=O)NH(CH(CH$_3$)$_2$), —S(=O)N(CH$_3$)$_2$, —S(=O)N(CH$_3$)(CH$_2$CH$_3$), —NHS(=O)(CH$_3$), —NHS(=O)(CH$_2$CH$_3$), —NHS(=O)(CH$_2$CH$_2$CH$_3$), —NHS(=O)(CH(CH$_3$)$_2$), —N(CH$_3$)S(=O)(CH$_3$), —S(=O)$_2$(OCH$_3$), —S(=O)$_2$(OCH$_2$CH$_3$), —S(=O)$_2$(OCH$_2$CH$_2$CH$_3$), —S(=O)$_2$(OCH(CH$_3$)$_2$), —OS(=O)$_2$(CH$_3$), —OS(=O)$_2$(CH$_2$CH$_3$), —OS(=O)$_2$(CH$_2$CH$_2$CH$_3$), —OS(=O)$_2$(CH(CH$_3$)$_2$), —S(=O)$_2$NH$_2$, —S(=O)$_2$NH(CH$_3$), —S(=O)$_2$NH(CH$_2$CH$_3$), —S(=O)$_2$NH(CH$_2$CH$_2$CH$_3$), —S(=O)$_2$NH(CH(CH$_3$)$_2$), —S(=O)$_2$N(CH$_3$)$_2$, —S(=O)$_2$N(CH$_3$)(CH$_2$CH$_3$), —NHS(=O)$_2$(CH$_3$), —NHS(=O)$_2$(CH$_2$CH$_3$), —NHS(=O)$_2$(CH$_2$CH$_2$CH$_3$), —NHS(=O)$_2$(CH(CH$_3$)$_2$), —N(CH$_3$)S(=O)$_2$(CH$_3$), —P(=O)H(CH$_3$), —P(=O)H(CH$_2$CH$_3$), —P(=O)H(CH$_2$CH$_2$CH$_3$), —P(=O)H(CH(CH$_3$)$_2$), —P(=O)(CH$_3$)$_2$, —P(=O)(CH$_3$)(CH$_2$CH$_3$), —CH$_2$—OH, —CH$_2$CH$_2$—OH, —CH(CH$_3$)—OH, —CH$_2$—SH, —CH$_2$CH$_2$—SH, —CH(CH$_3$)—SH, —CH$_2$—NH$_2$, —CH$_2$CH$_2$—NH$_2$, —CH(CH$_3$)—NH$_2$, —CH$_2$—CN, —CH$_2$CH$_2$—CN, —CH(CH$_3$)—CN, —O—CH$_3$—O—CH$_3$, —O—CH$_2$CH$_3$—O—CH$_3$, —O—CH(CH$_3$)—O—CH$_3$, —O—CH$_2$CH$_2$CH$_3$—O—CH$_3$, —O—CH$_2$CH(CH$_3$)—O—CH$_3$, —O—CH(CH$_3$)CH$_2$—O—CH$_3$, —NH—O—CH$_3$, —N(CH$_3$)—O—CH$_3$, —N(CH$_2$CH$_3$)—O—CH$_3$,

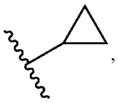, 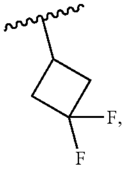, 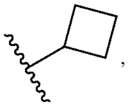, 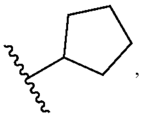,

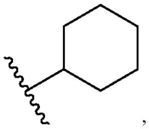, 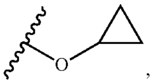, 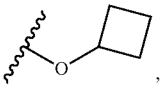,

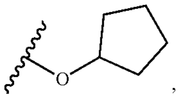, 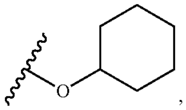, 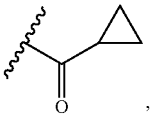,

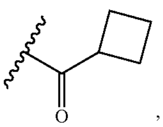, 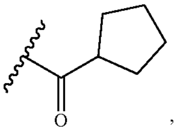, 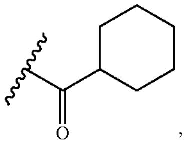,

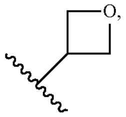, 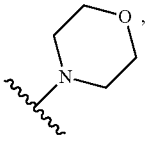, 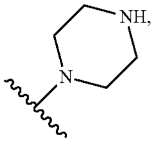

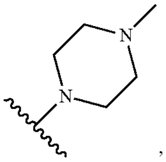, 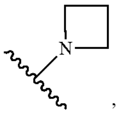, 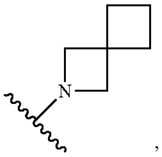,

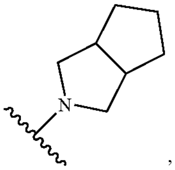, 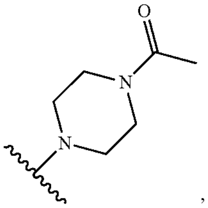, 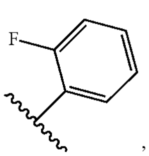,

-continued

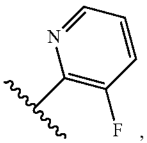
,
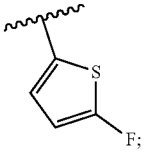

$t_1$, $t_2$ or $t_3$ at each occurrence is independently selected from 0, 1 or 2.

[38]. The compound according to any one of [1] to [37], wherein, $Z_1$ at each occurrence is independently selected from $—CH_3$, —F, —CN, $—CD_3$, $—CH_2CH_3$, —Cl, $—CH(CH_3)_2$,

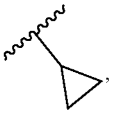 [SMILES: *C1CC1]

$—CHF_2$, $—CH_2CF_3$,

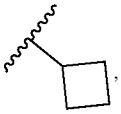
,
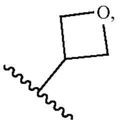
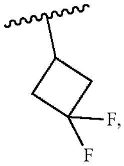

$—CO—CH_3$ or

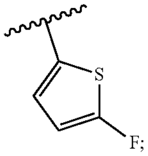 [SMILES: *c1ccc(F)s1]

$t_1$ at each occurrence is independently selected from 0 or 1.

[39]. The compound according to any one of [1] to [38], wherein, $Z_2$ at each occurrence is independently selected from $—CF_3$, —F, —Cl, —Br, $—CH_3$, $—OCH_3$, —CN, $—NH_2$,

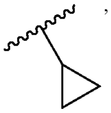
,
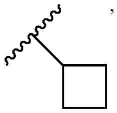
,
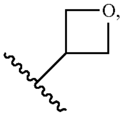
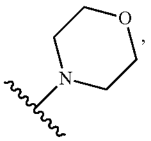
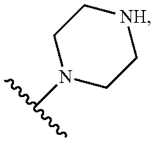
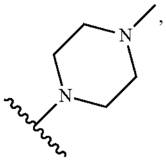
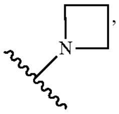

-continued

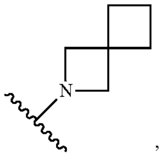
,
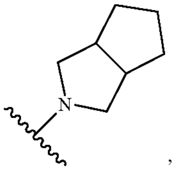
,
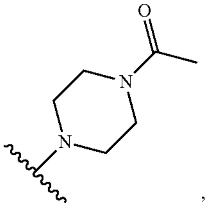
,
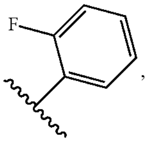
,
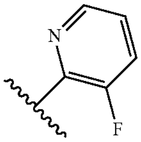

or $—CO—CH_3$;

$t_2$ at each occurrence is independently selected from 0, 1, 2, or 3.

[40]. The compound according to any one of [1] to [39], wherein, $Z_3$ at each occurrence is independently selected from —F, —OH, —CN;

$t_3$ at each occurrence is independently selected from 0, 1 or 2.

[41]. The compound according to any one of [1] to [40], wherein, the moiety of

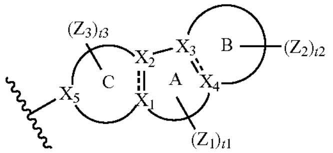

is selected from

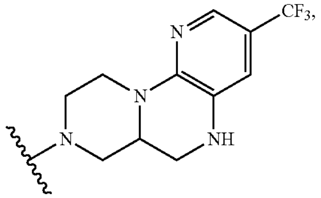

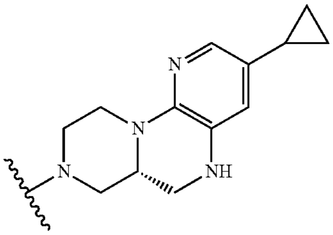
,
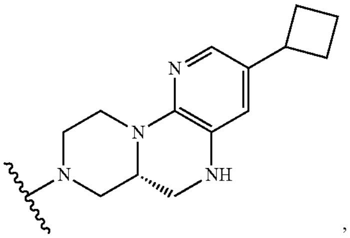
,

-continued
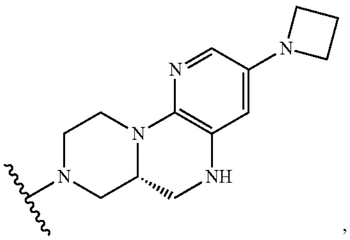
,
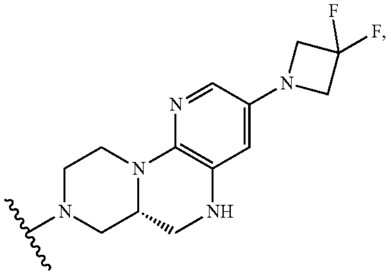
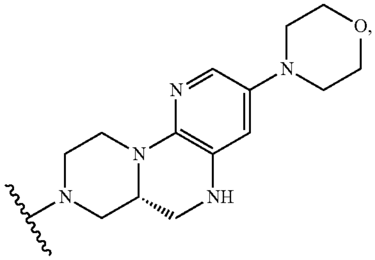
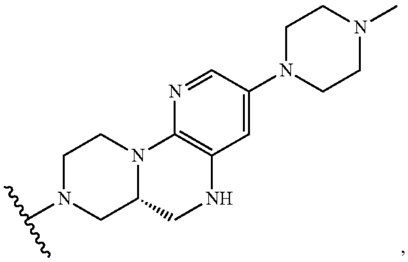
,
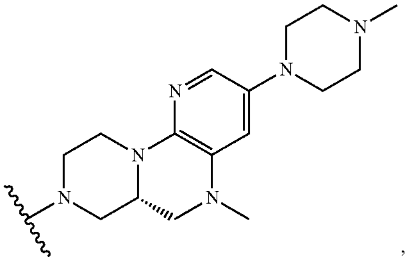
,
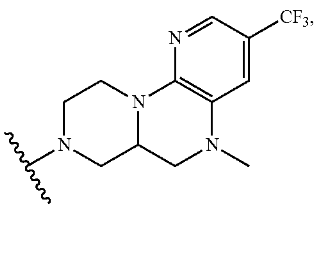
-continued
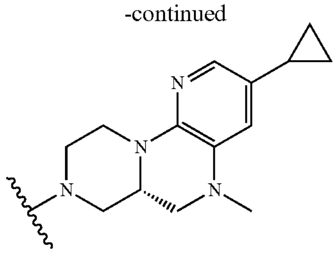
,
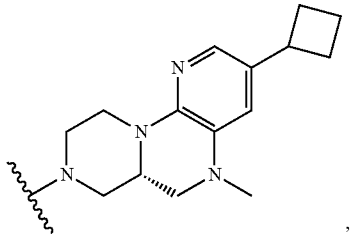
,
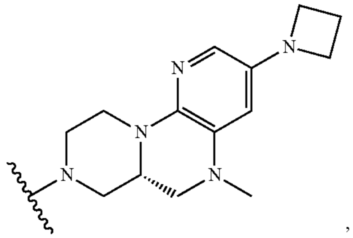
,
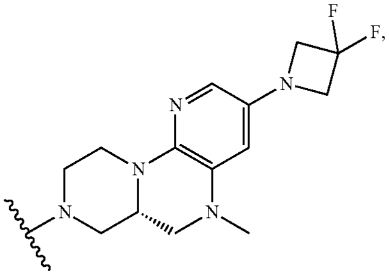
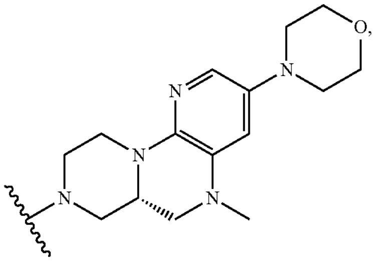
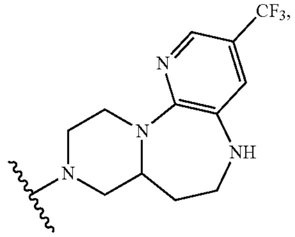
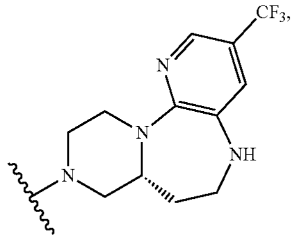

-continued
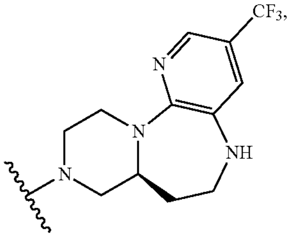
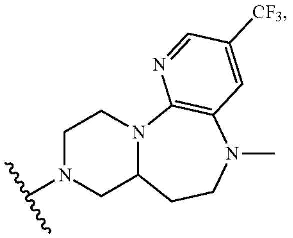
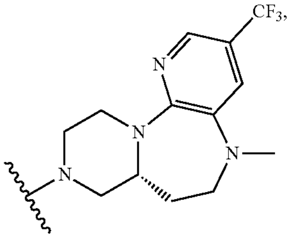
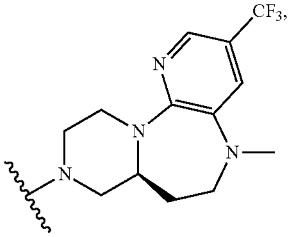
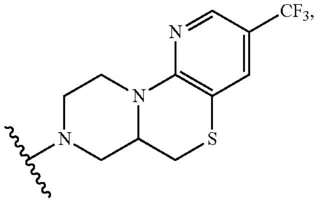
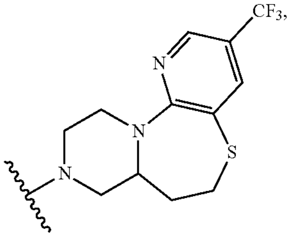
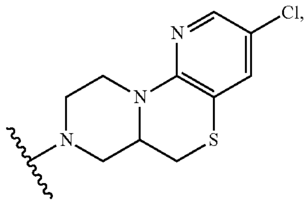
-continued
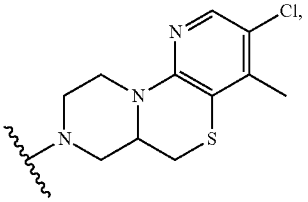
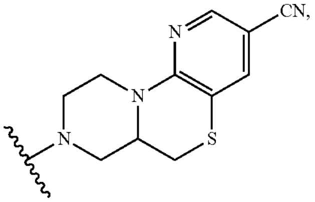
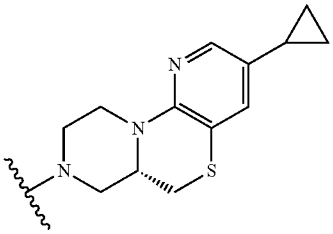
,
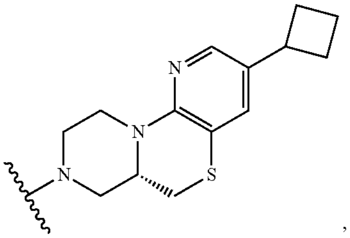
,
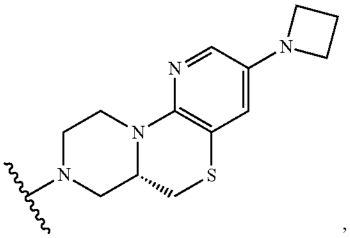
,
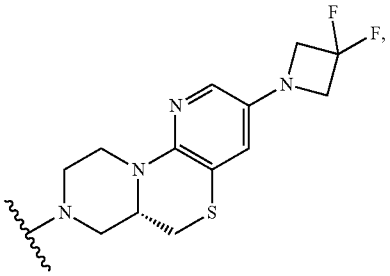
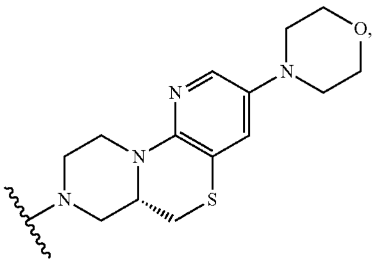

-continued
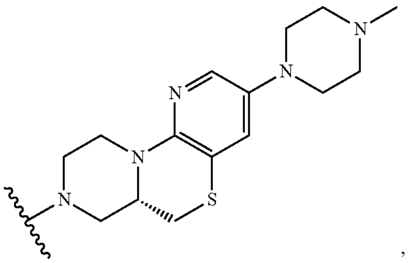
,
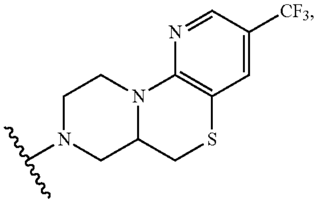
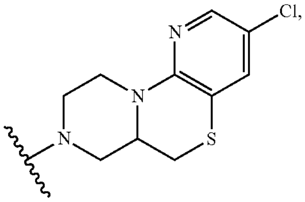
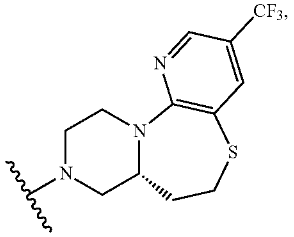
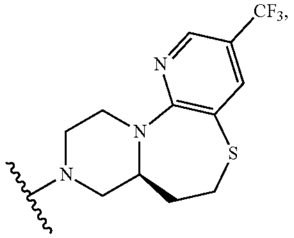
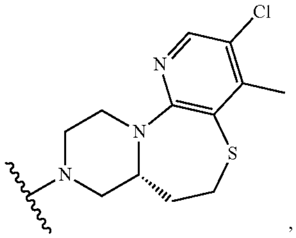
,
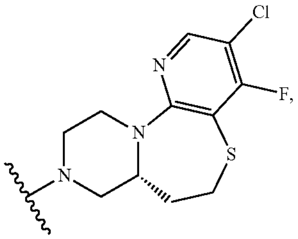
-continued
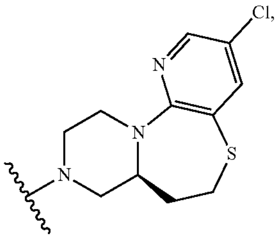
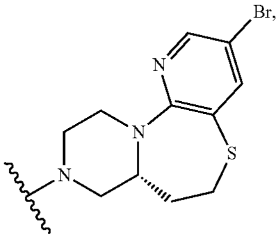
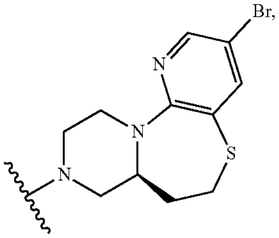
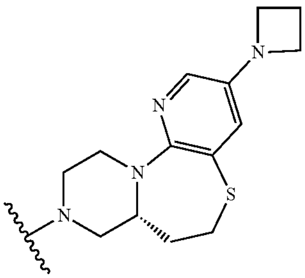
,
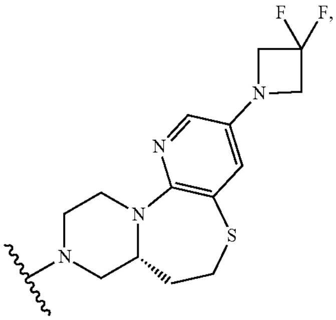
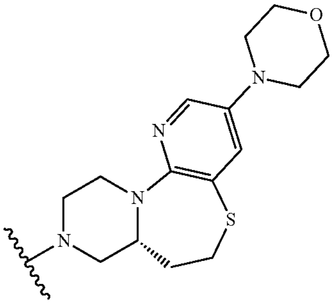
,
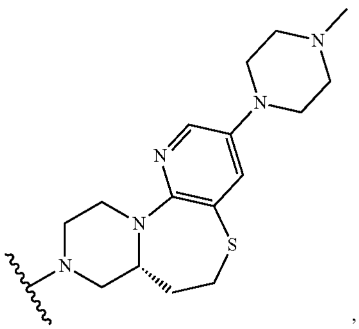
, -continued
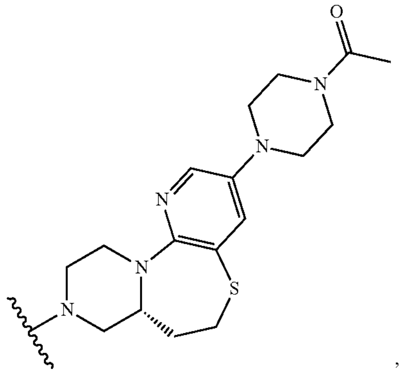
,
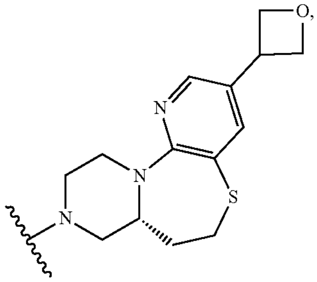
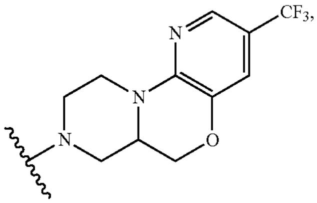
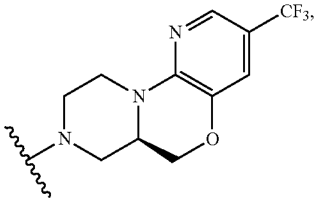
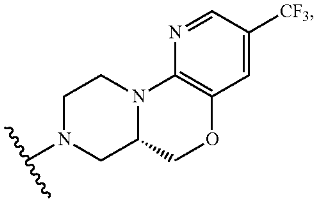
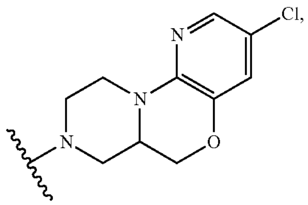
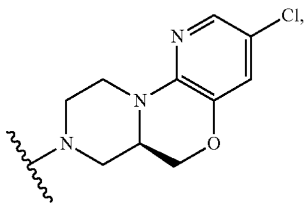
-continued
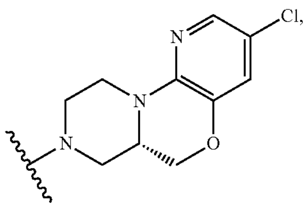
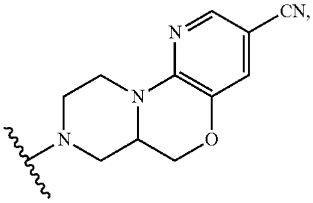
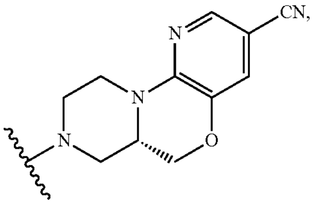
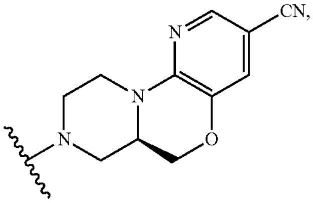
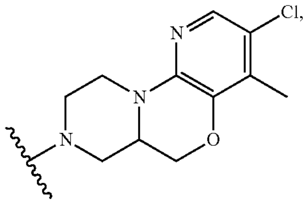
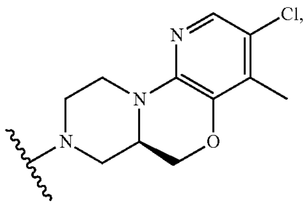
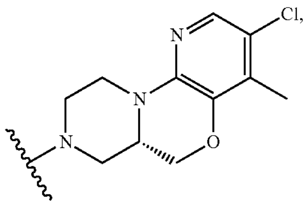
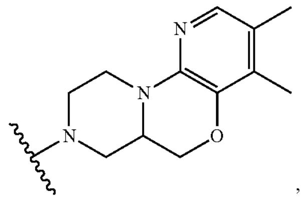
, -continued
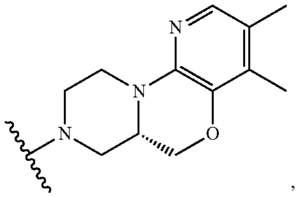
,
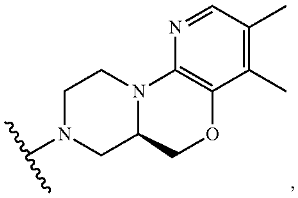
,
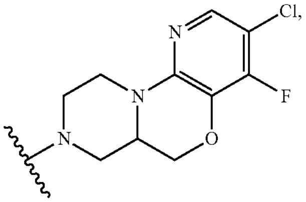
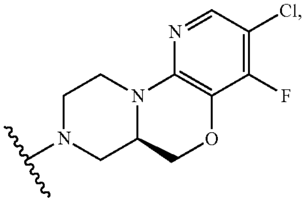
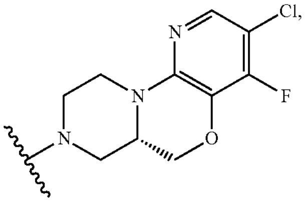
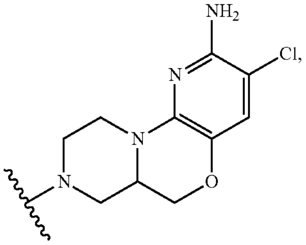
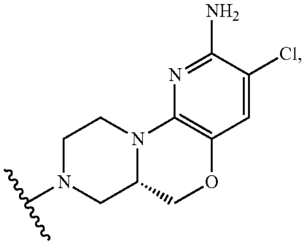
-continued
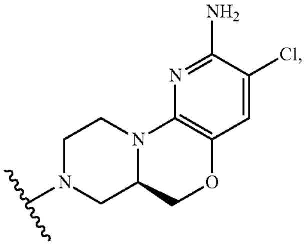
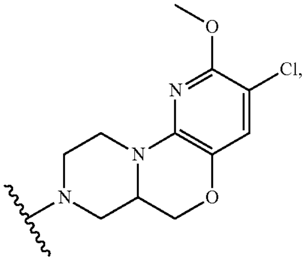
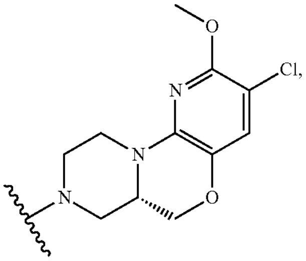
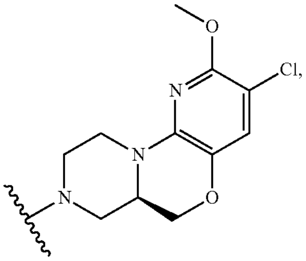
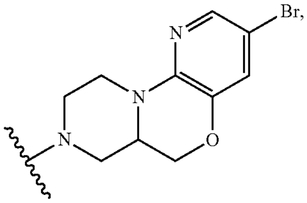
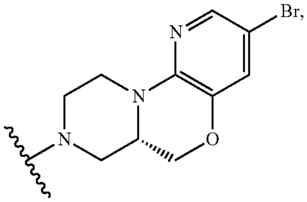
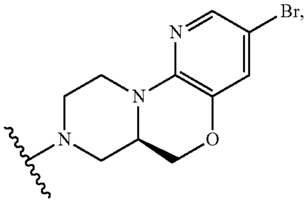

-continued
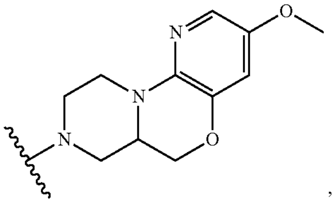
,
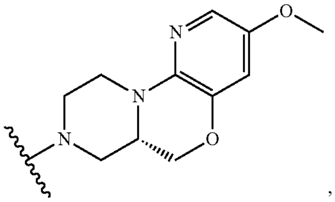
,
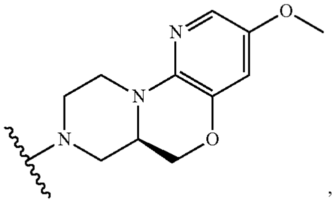
,
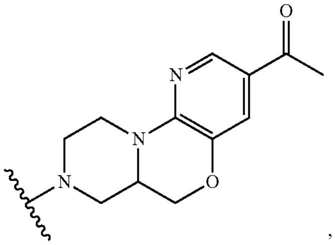
,
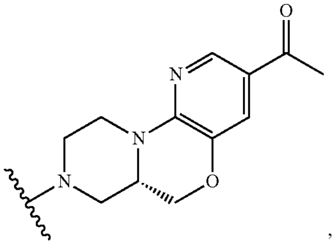
,
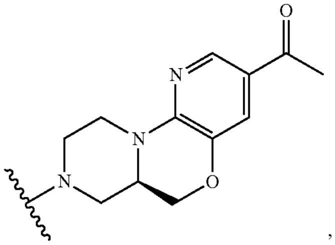
,
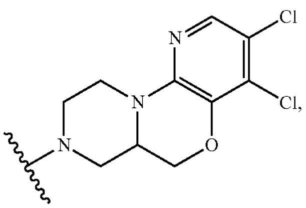
-continued
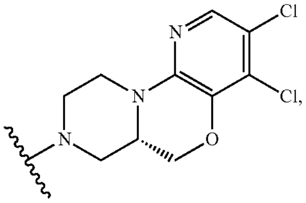
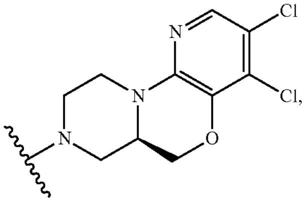
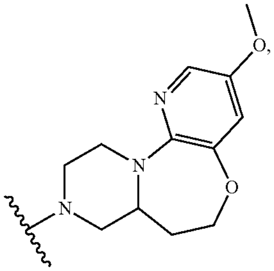
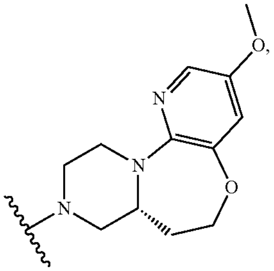
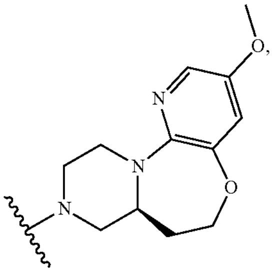
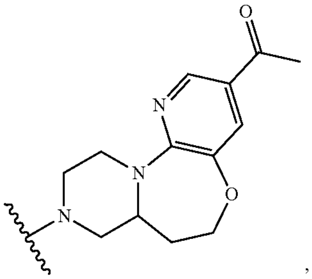
,
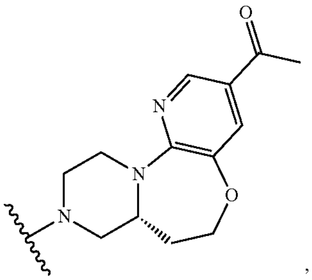
, -continued
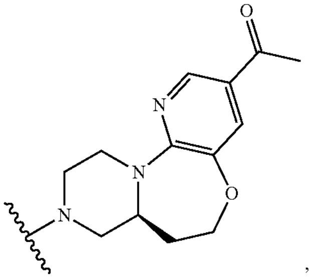
,
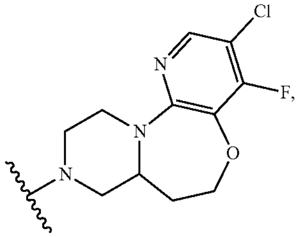
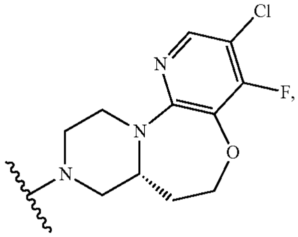
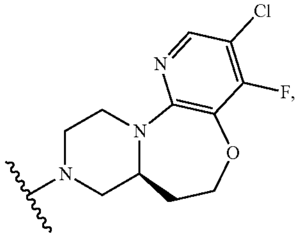
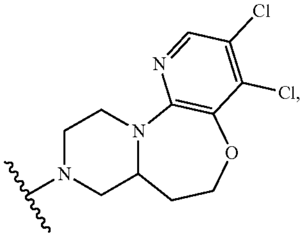
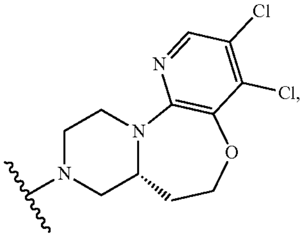
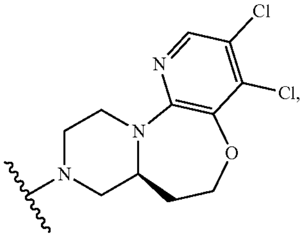
-continued
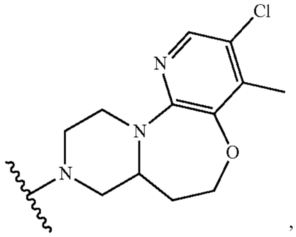
,
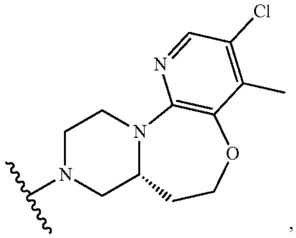
,
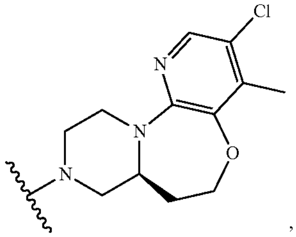
,
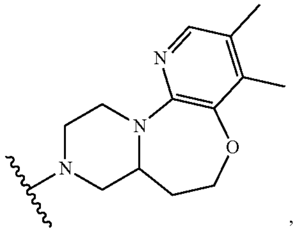
,
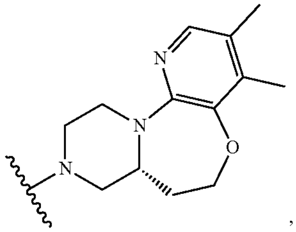
,
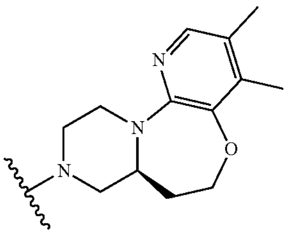
,
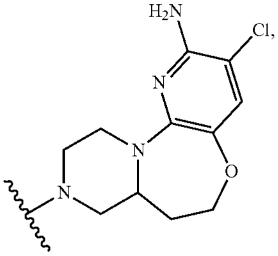
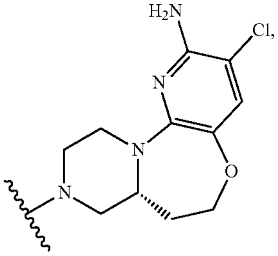
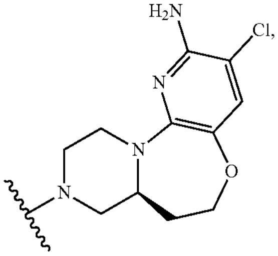

-continued
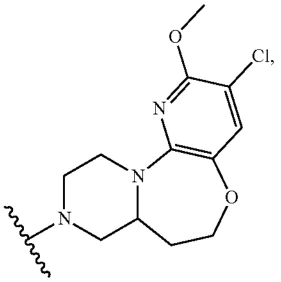
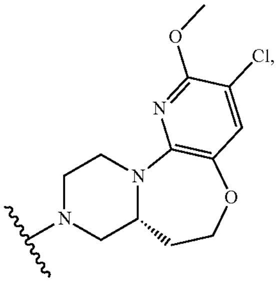
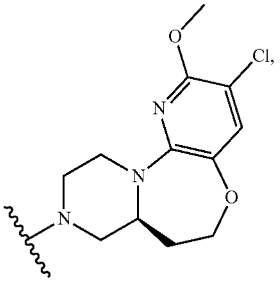
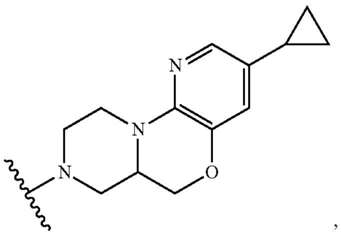
,
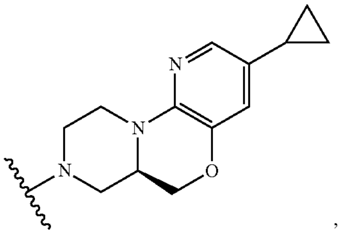
,
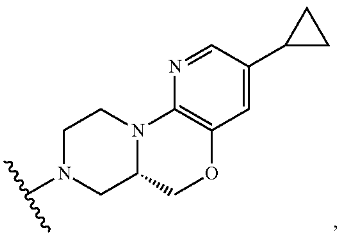
,
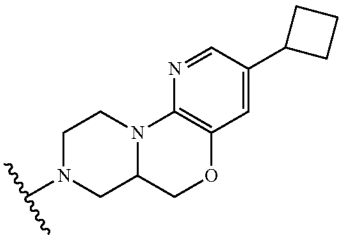
,
-continued
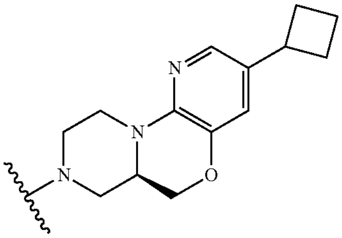
,
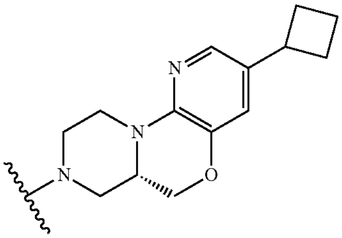
,
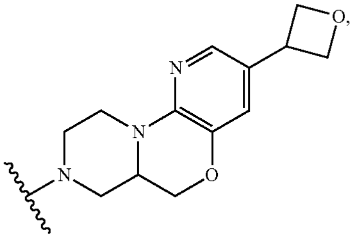
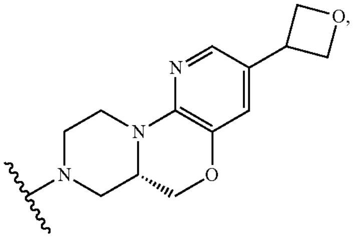
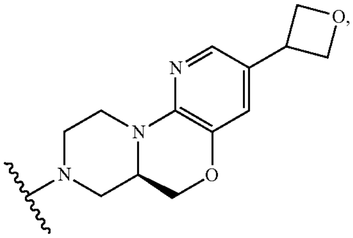
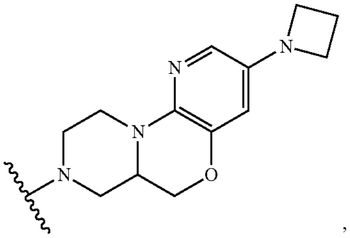
,
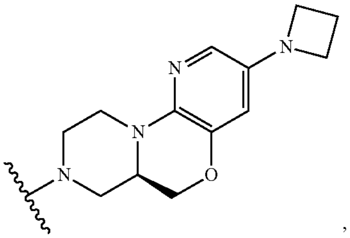
, -continued
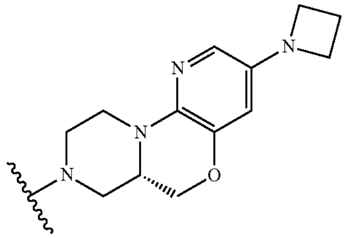
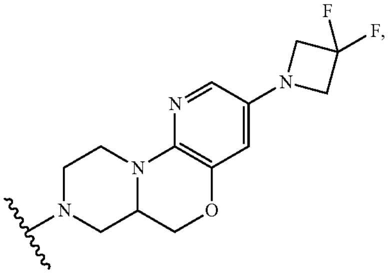
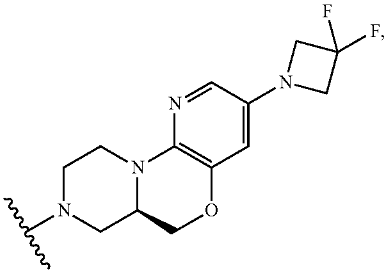
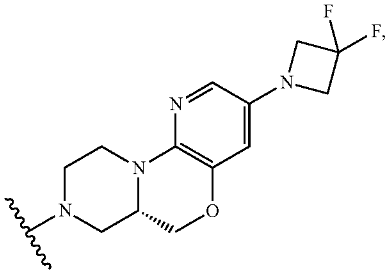
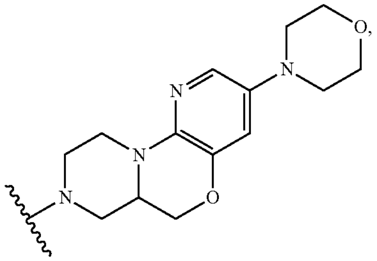
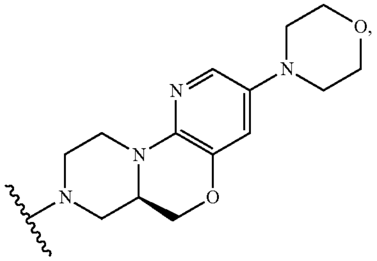
-continued
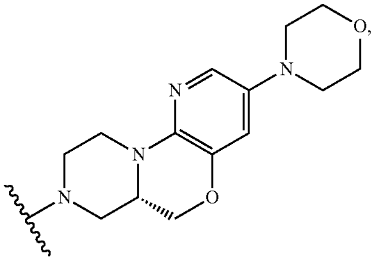
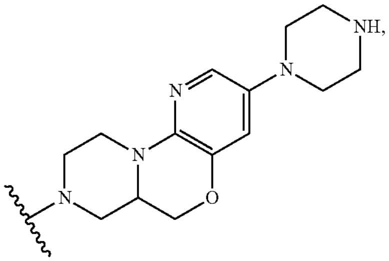
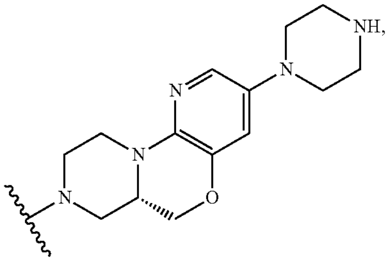
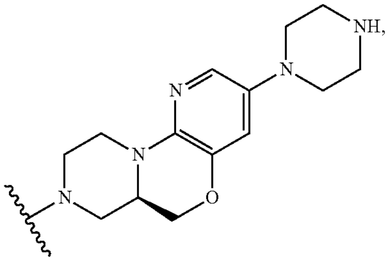
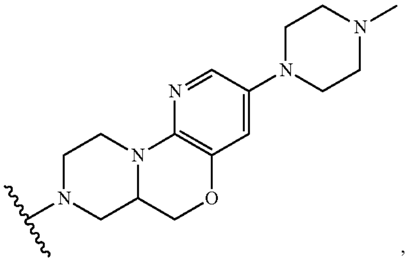
,
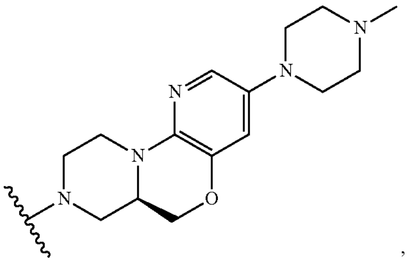
, -continued
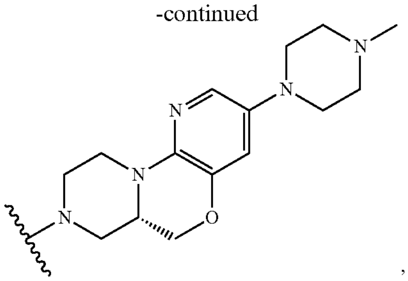
,
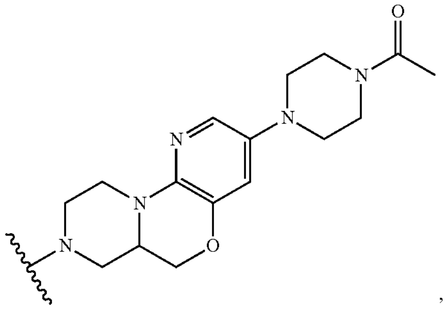
,
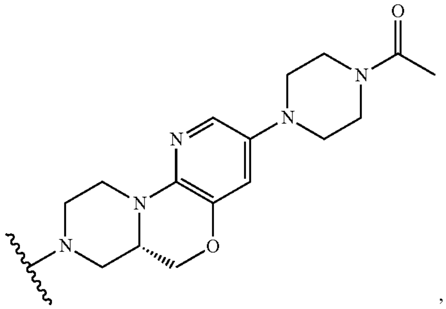
,
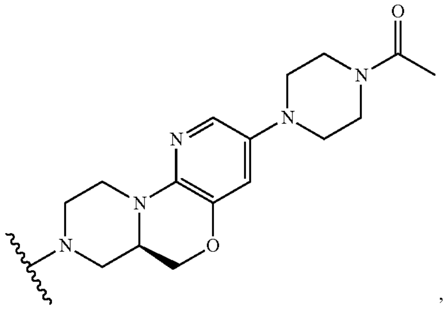
,
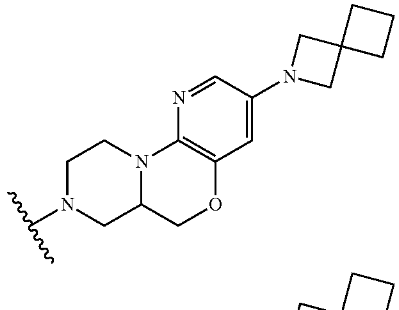
,
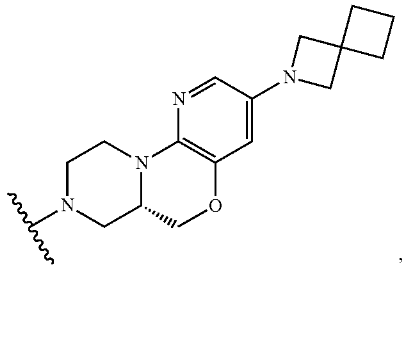
,
-continued
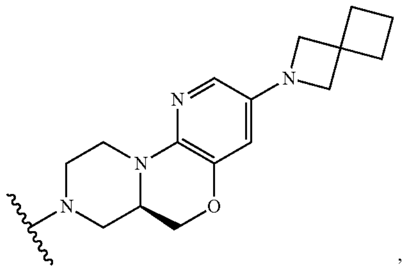
,
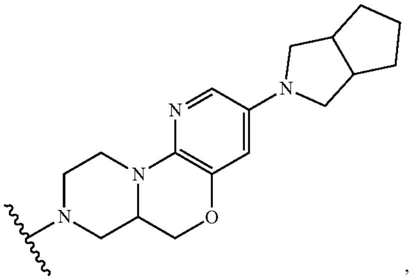
,
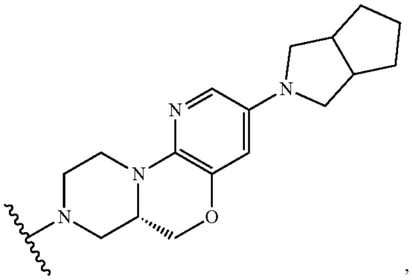
,
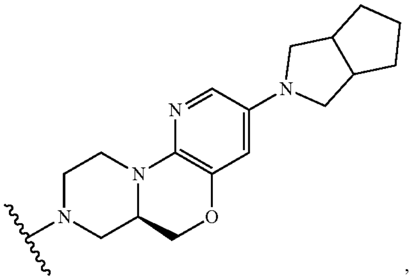
,
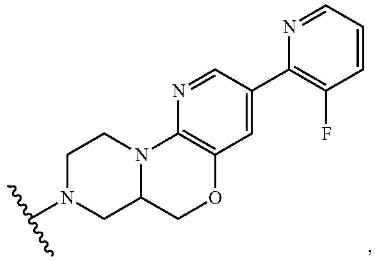
,
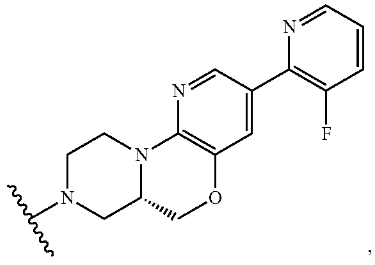
, -continued
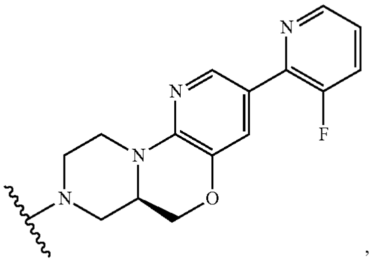
,
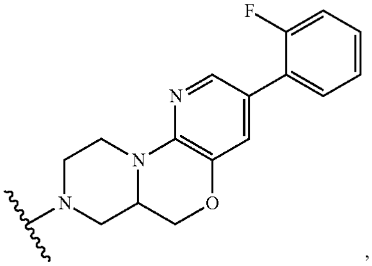
,
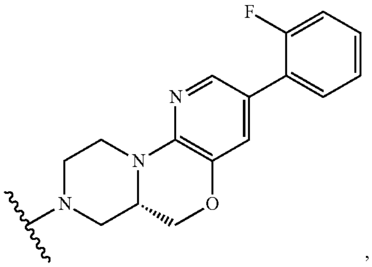
,
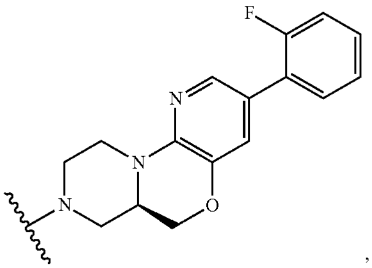
,
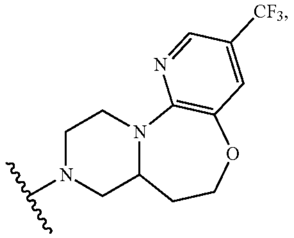
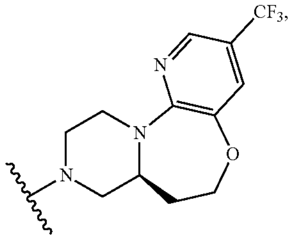
-continued
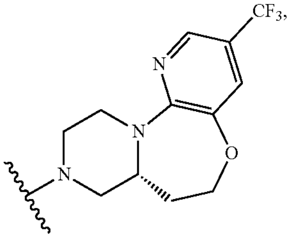
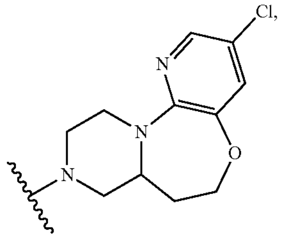
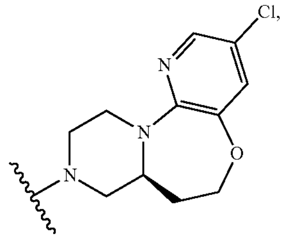
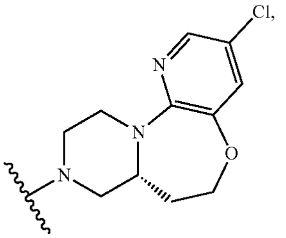
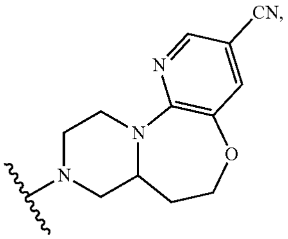
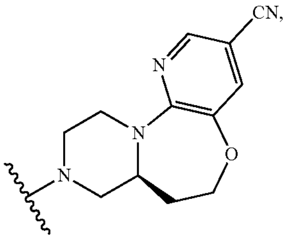
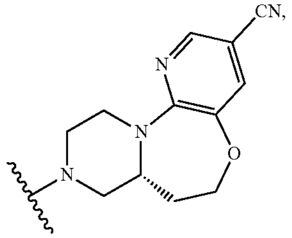
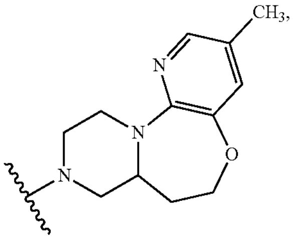
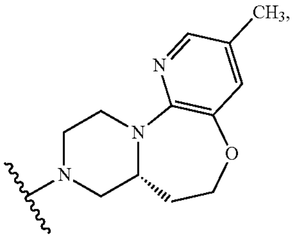
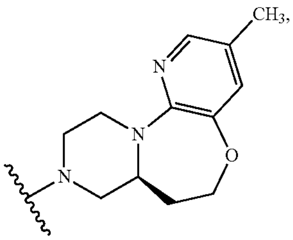

-continued
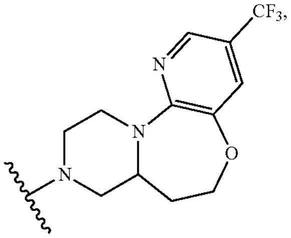
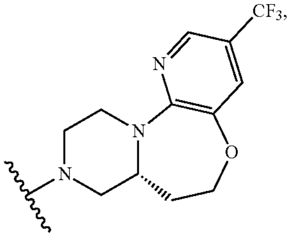
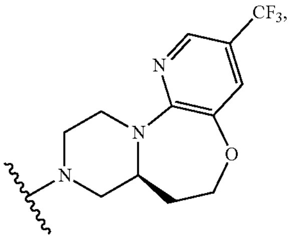
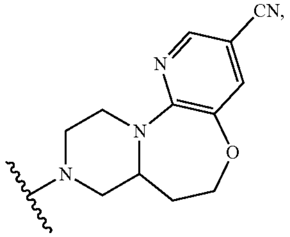
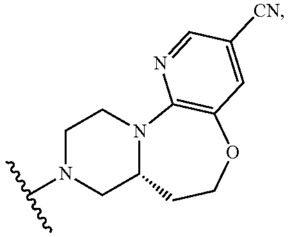
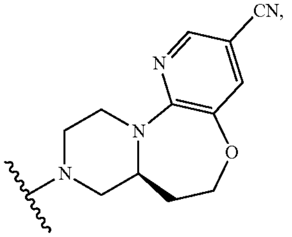
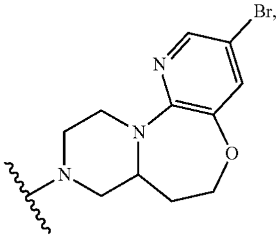
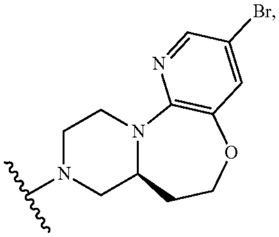
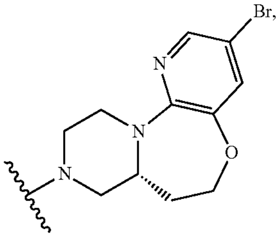
-continued
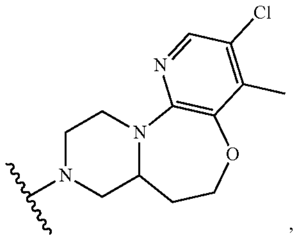
,
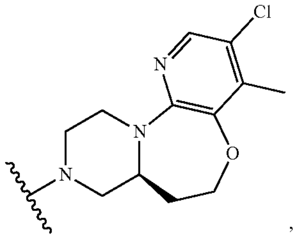
,
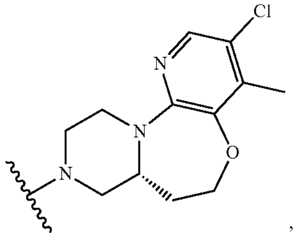
,
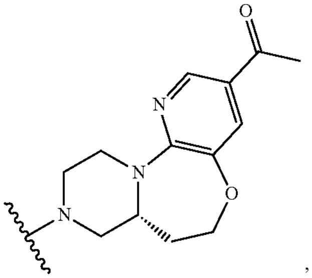
,
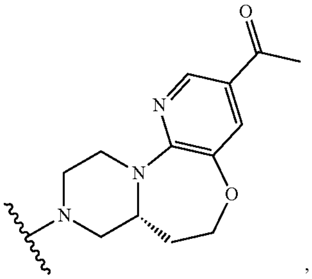
,
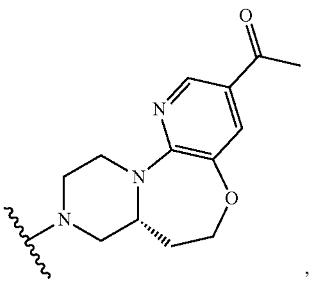
, -continued
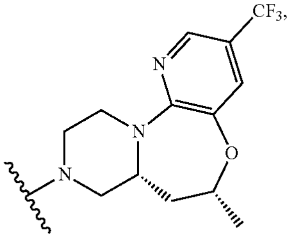
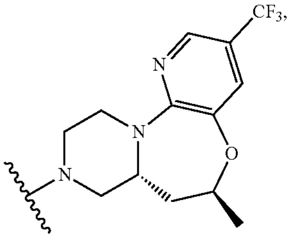
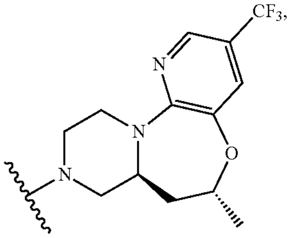
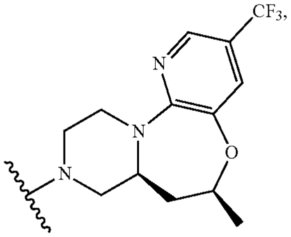
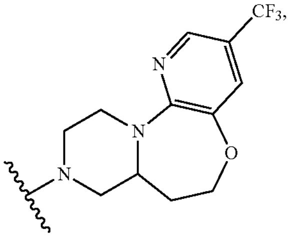
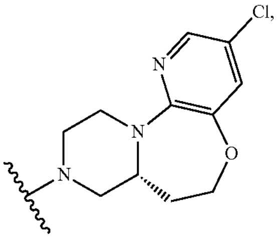
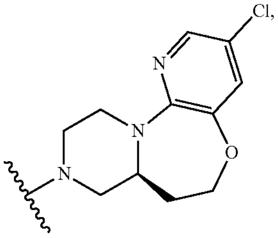
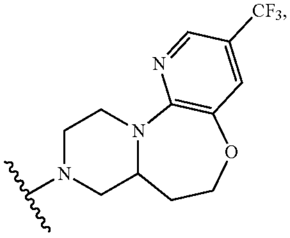
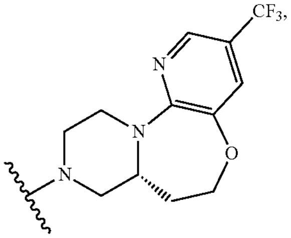
-continued
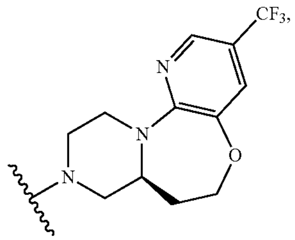
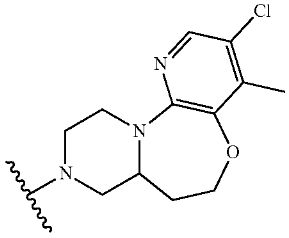
,
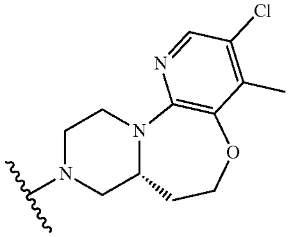
,
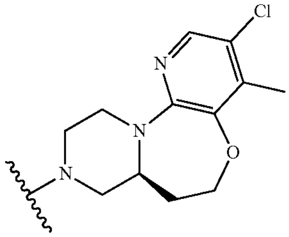
,
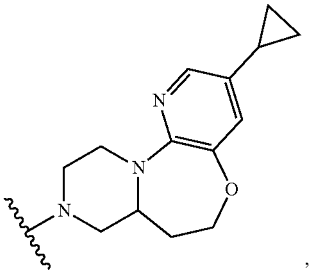
,
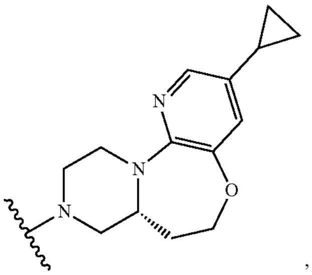
, -continued
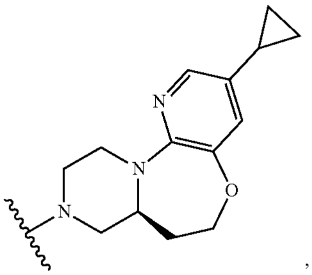
,
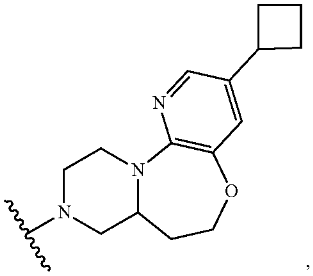
,
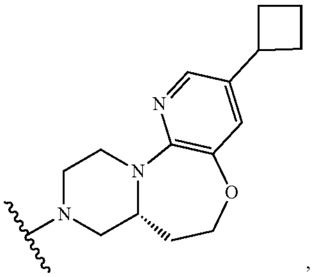
,
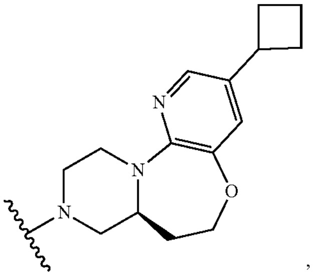
,
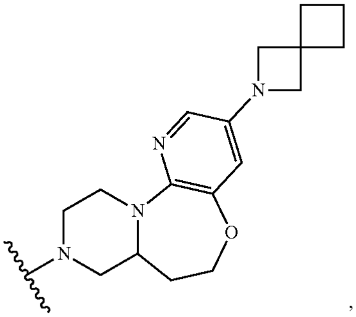
,
-continued
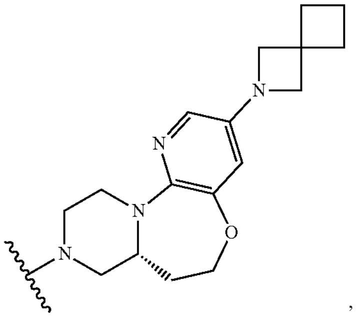
,
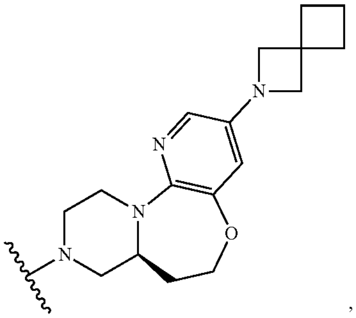
,
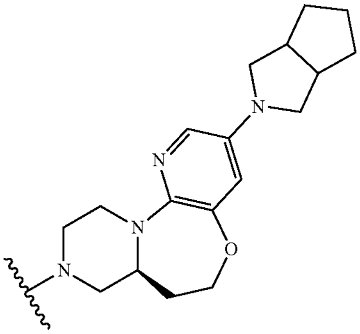
,
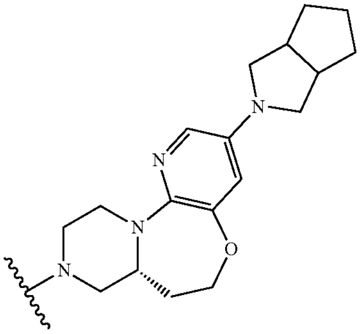
,
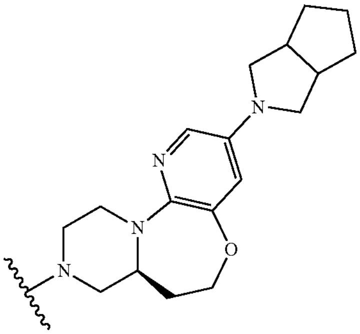
, -continued
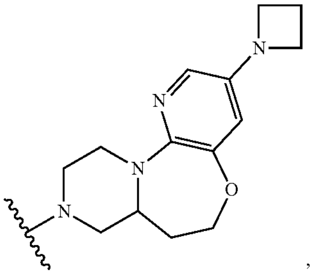
,
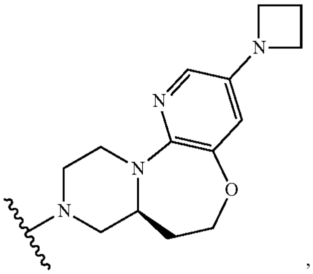
,
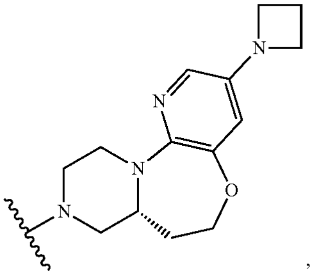
,
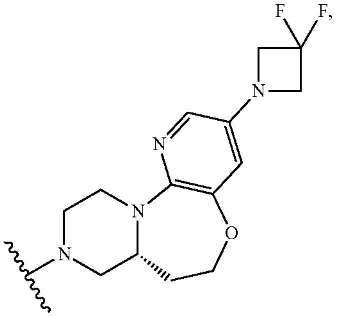
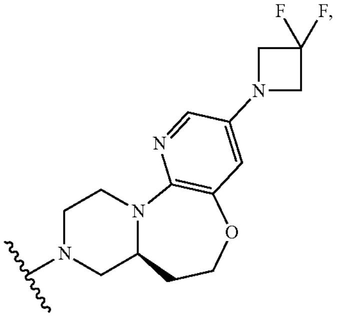
-continued
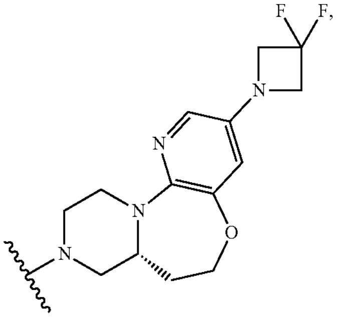
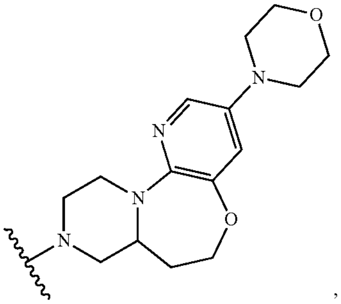
,
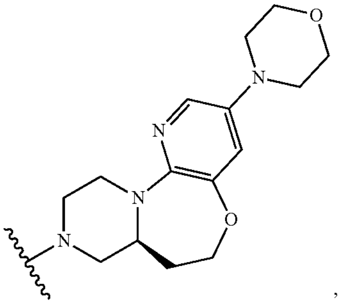
,
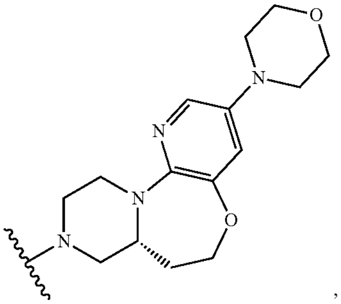
,
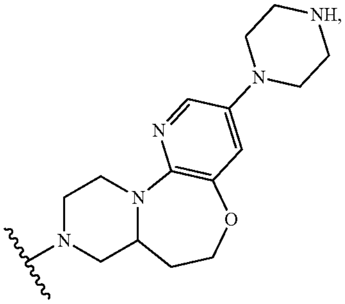

-continued
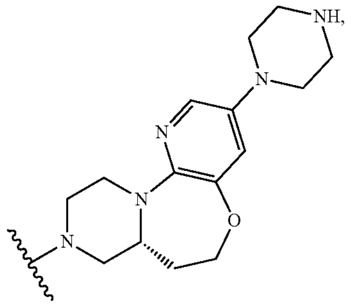
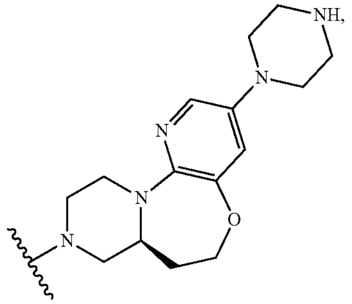
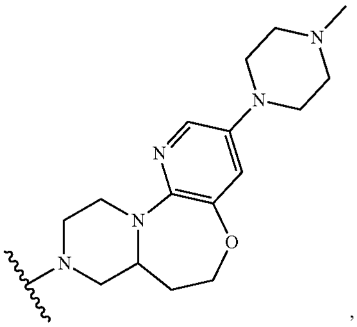
,
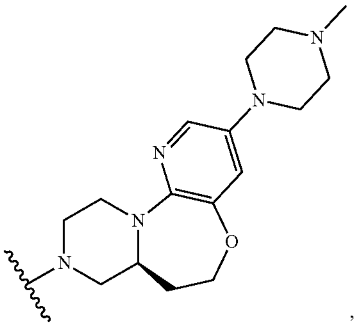
,
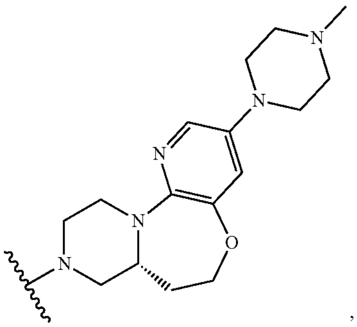
,
-continued
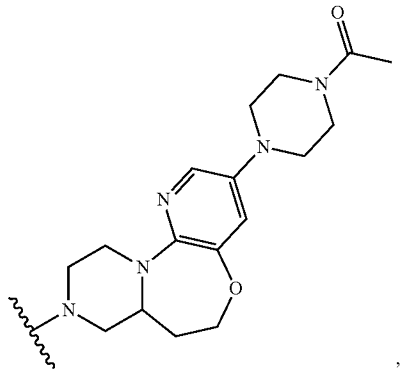
,
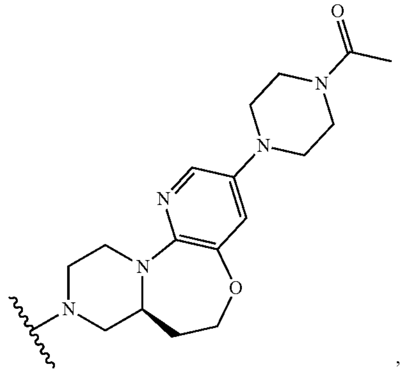
,
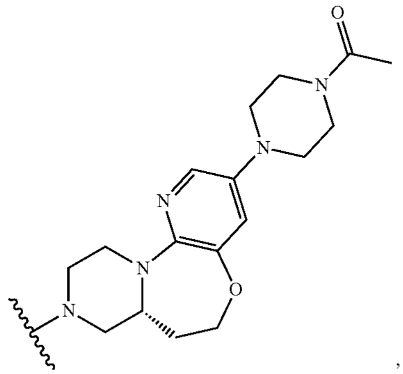
,
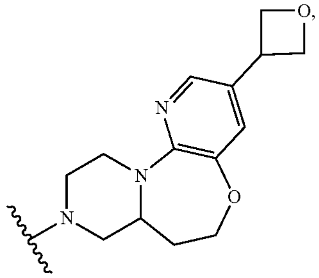
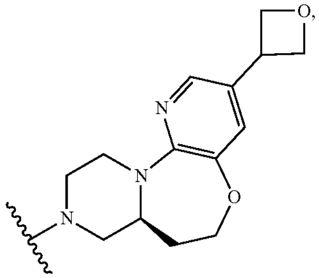

-continued
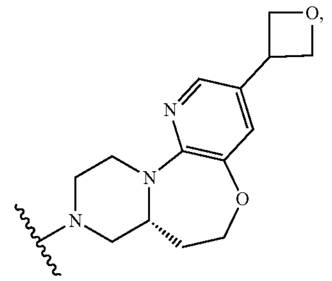
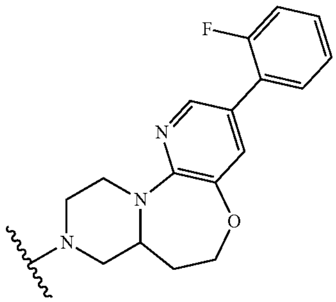
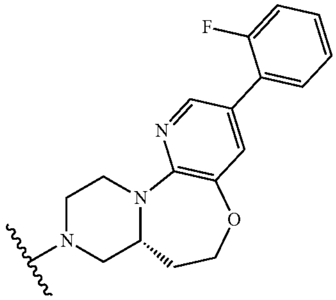
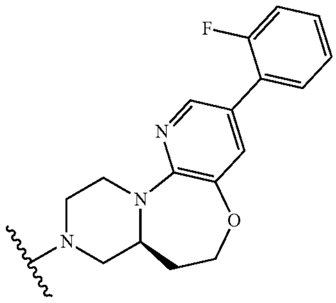
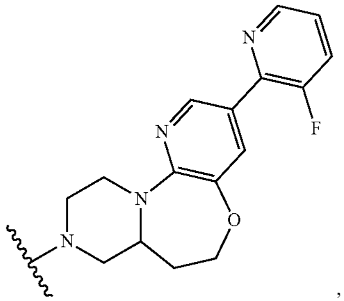
,
-continued
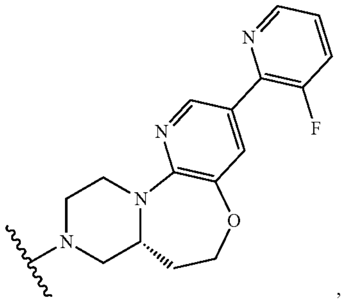
,
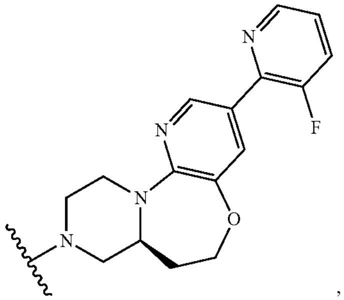
,
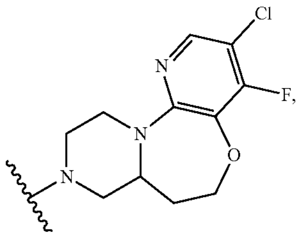
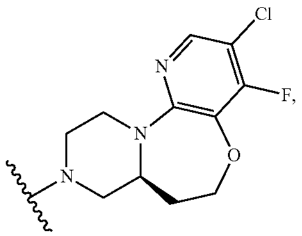
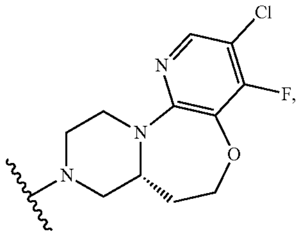
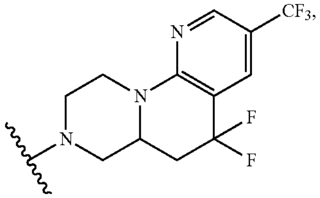
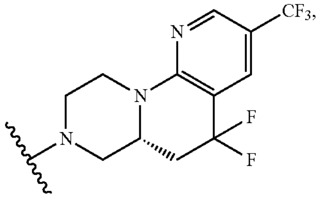

-continued
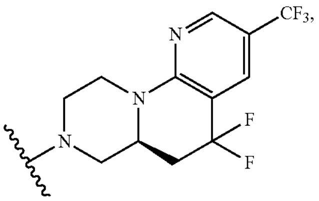
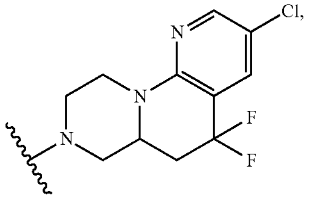
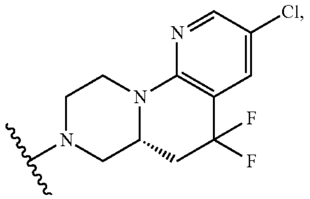
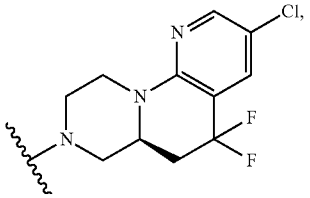
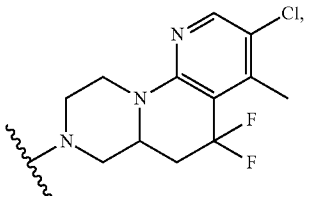
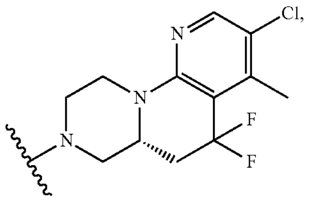
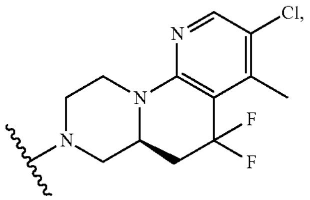
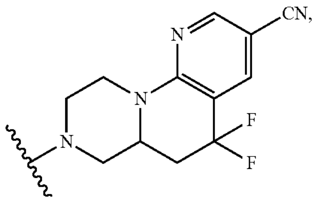
-continued
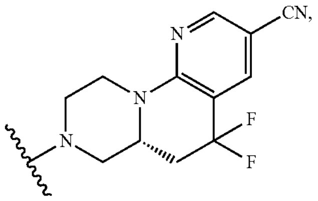
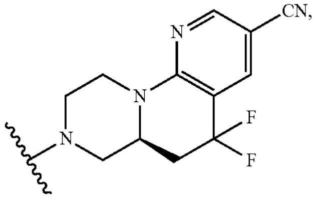
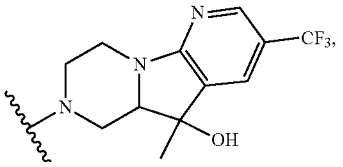
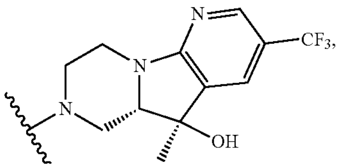
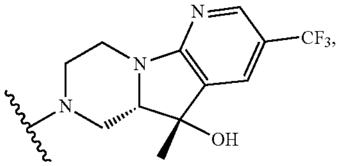
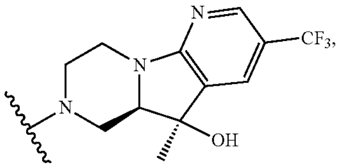
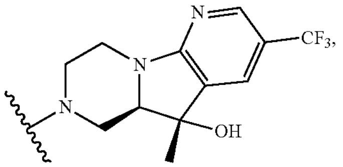
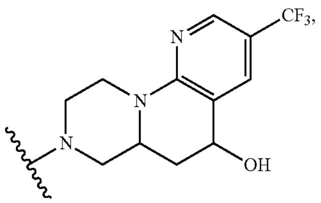
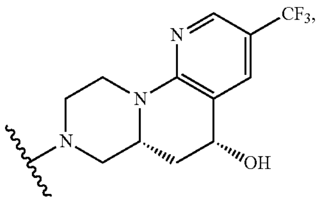

-continued
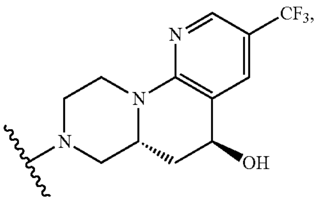
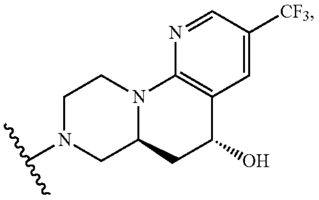
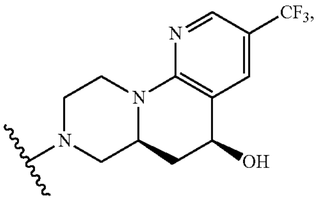
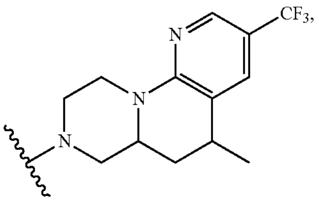
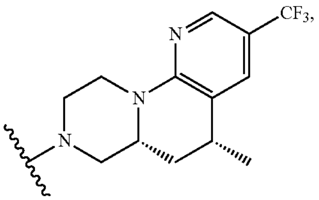
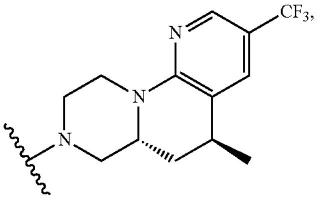
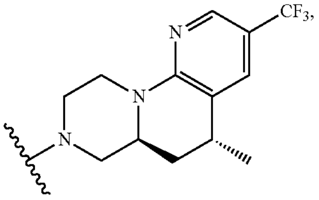
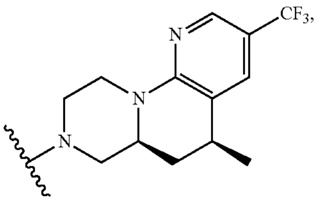
-continued
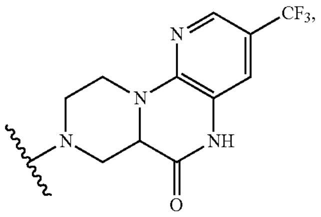
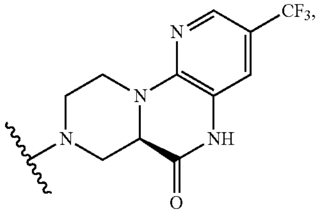
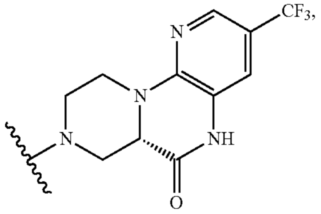
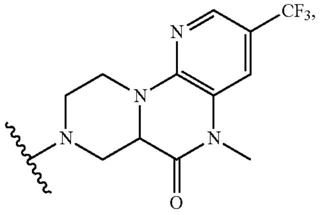
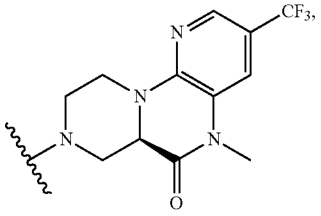
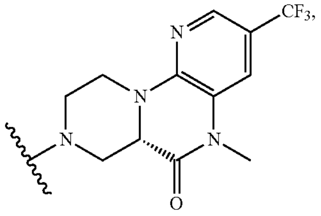
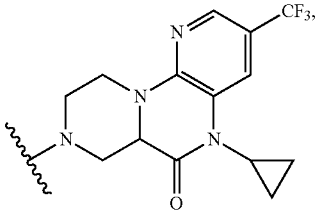
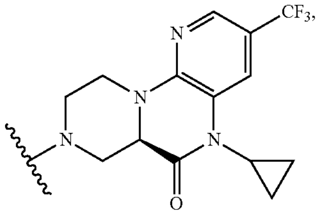

-continued
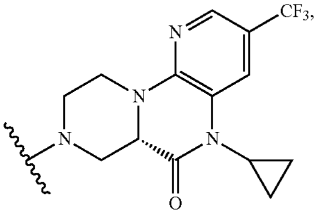
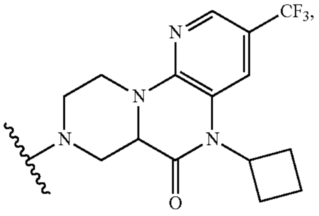
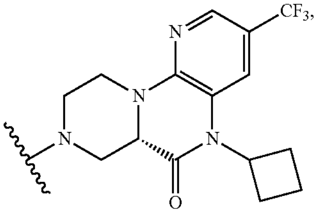
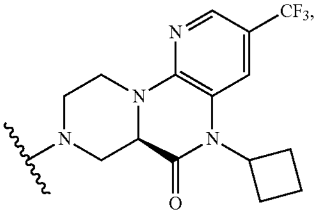
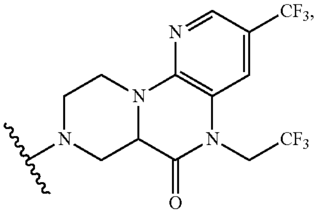
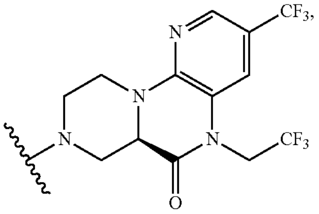
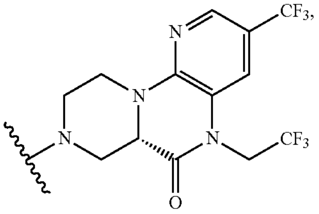
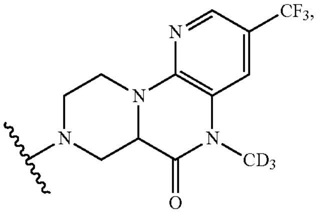
-continued
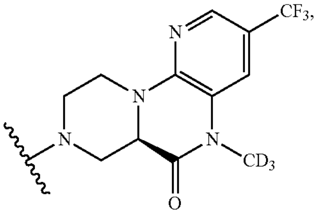
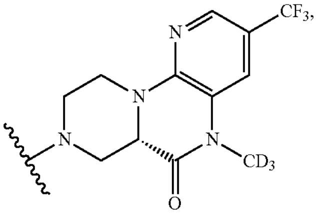
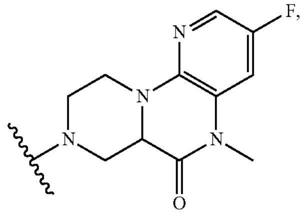
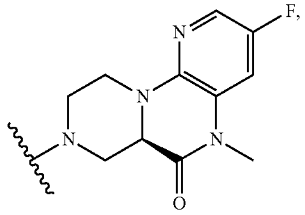
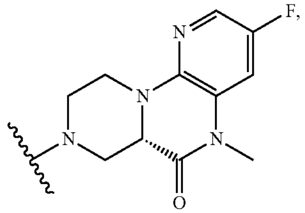
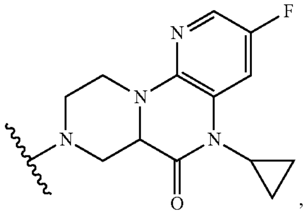
,
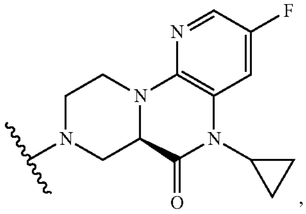
,
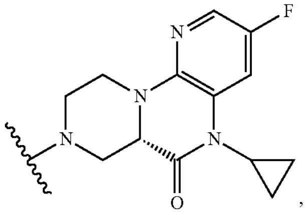
, -continued
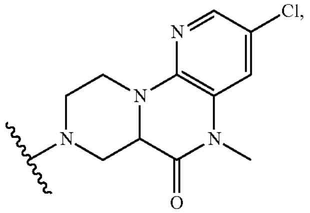
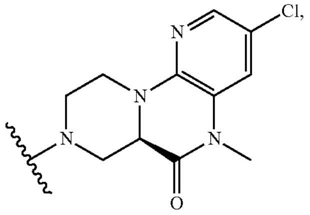
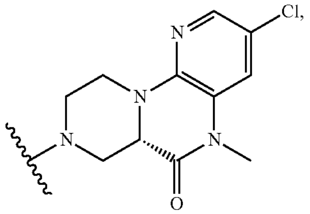
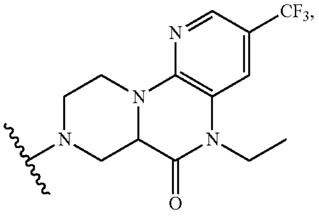
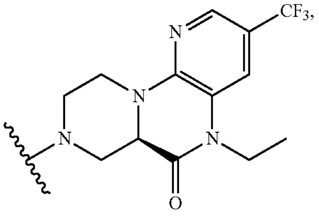
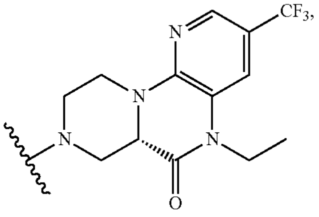
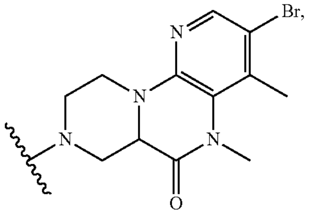
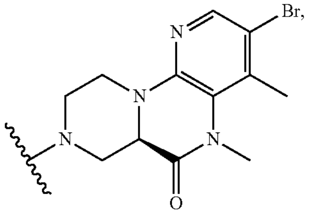
-continued
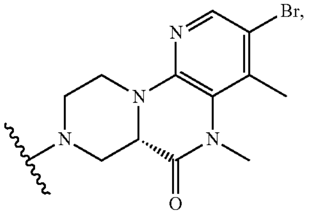
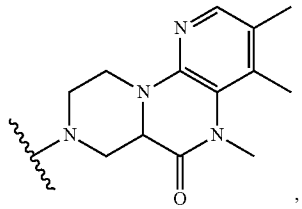
,
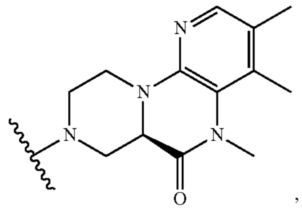
,
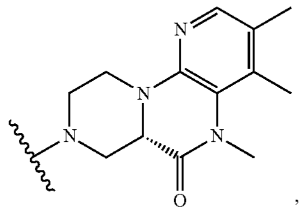
,
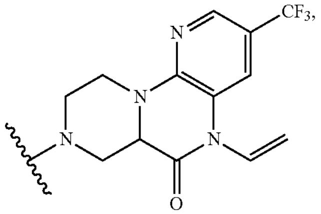
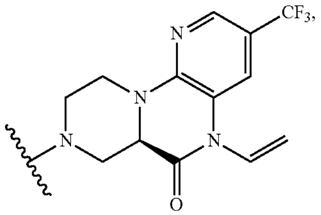
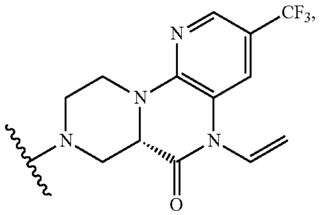
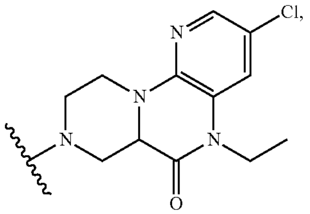

-continued
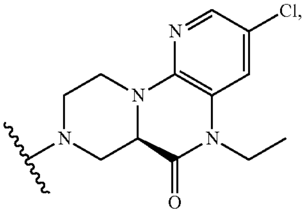
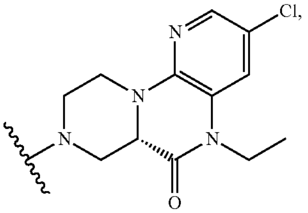
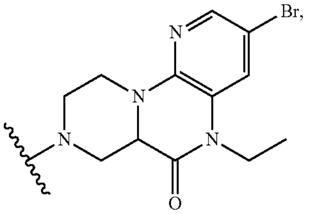
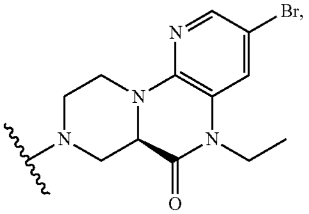
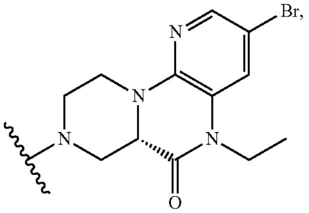
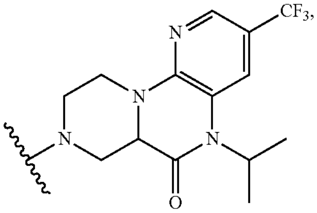
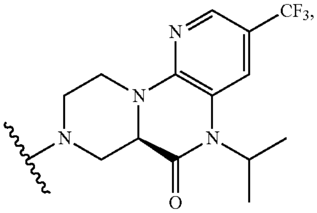
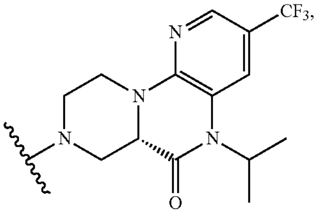
-continued
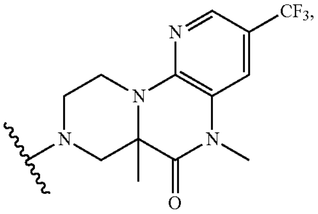
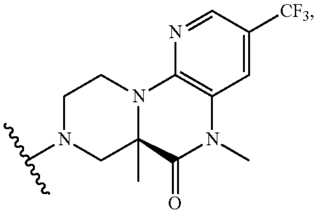
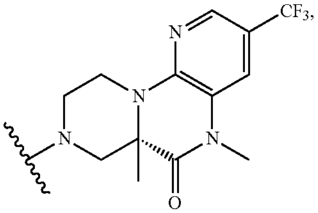
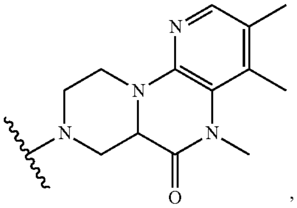
,
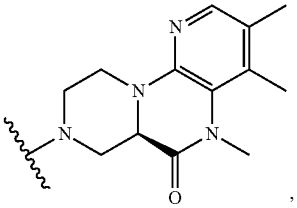
,
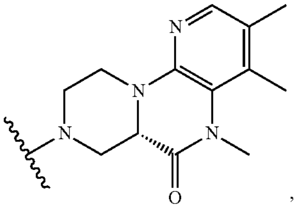
,
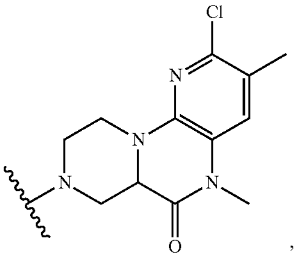
, -continued
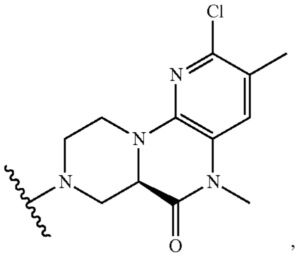
,
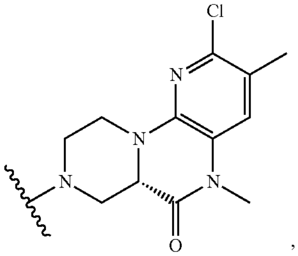
,
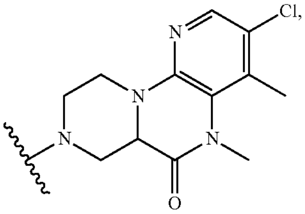
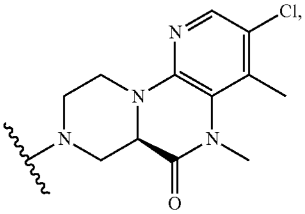
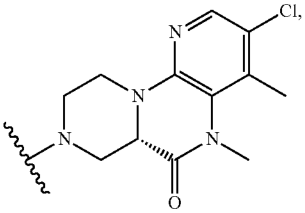
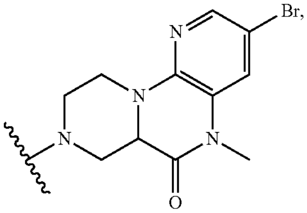
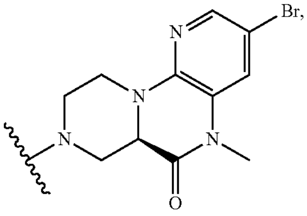
-continued
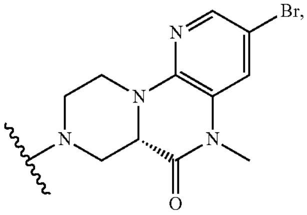
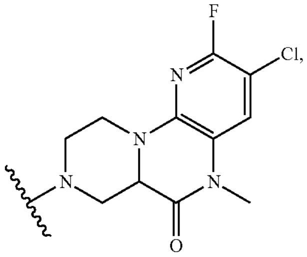
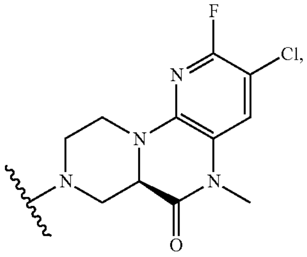
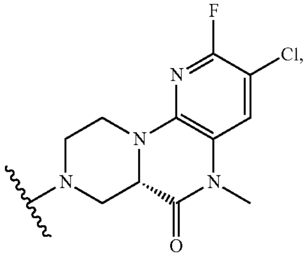
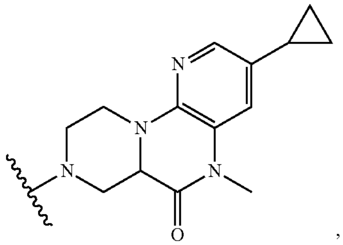
,
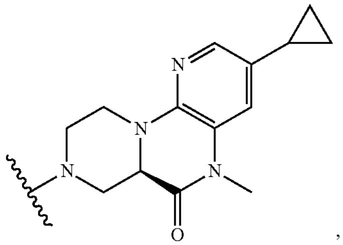
,
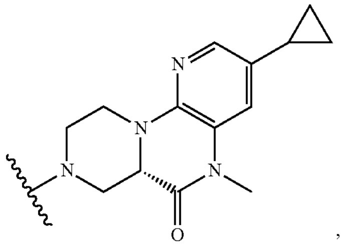
, -continued
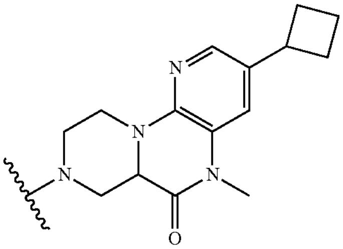
,
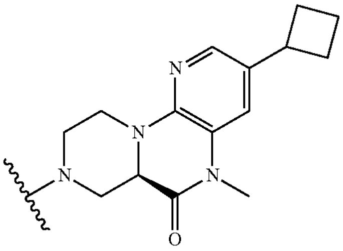
,
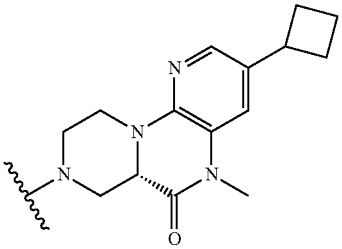
,
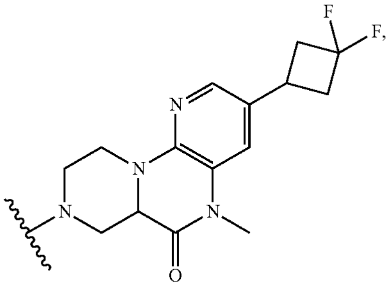
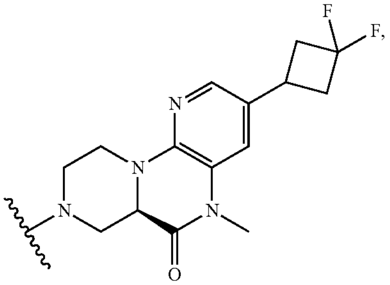
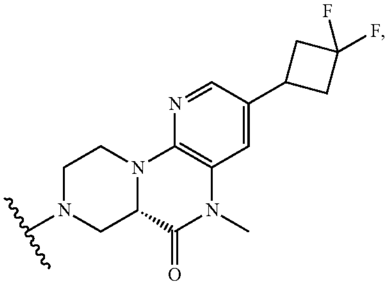
-continued
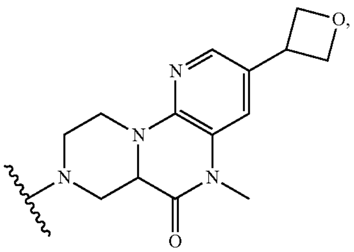
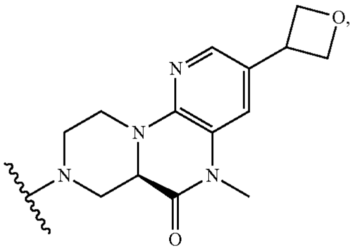
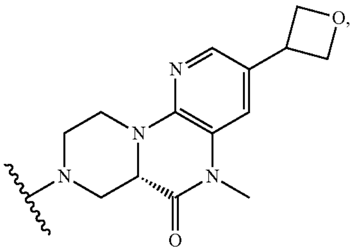
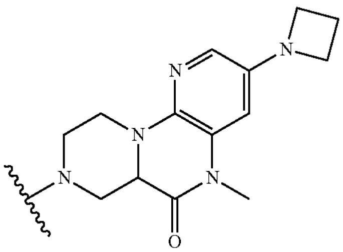
,
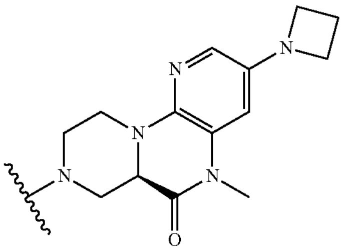
,
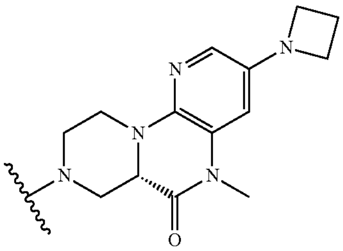
, -continued
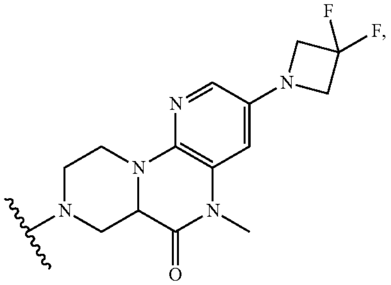
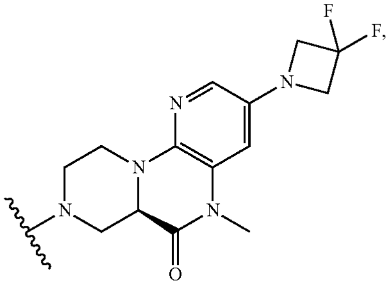
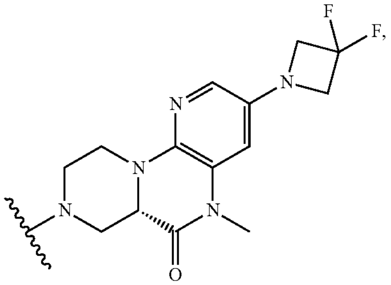
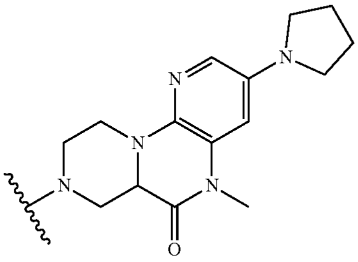
,
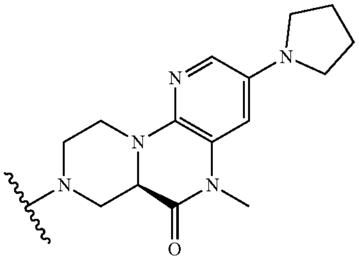
,
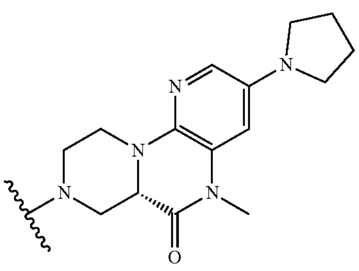
,
-continued
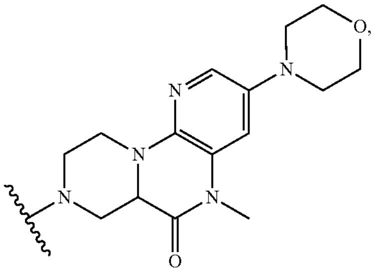
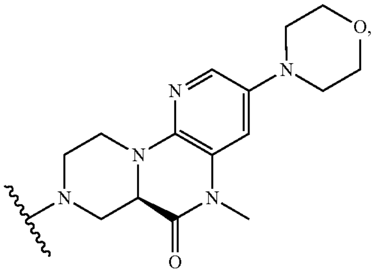
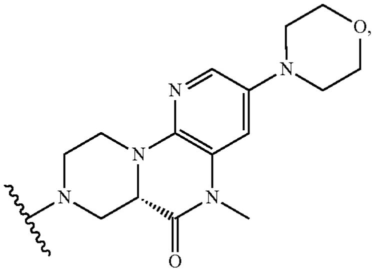
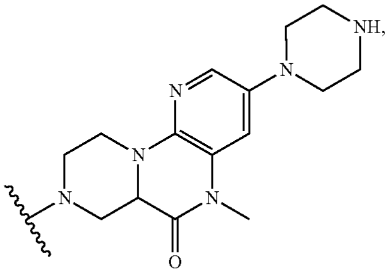
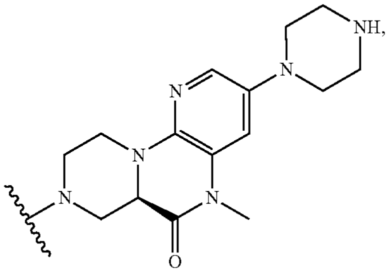
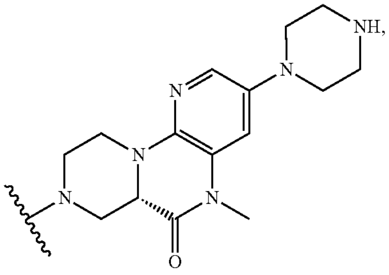

-continued
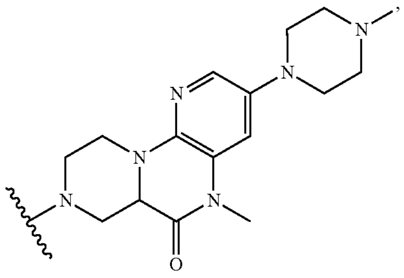
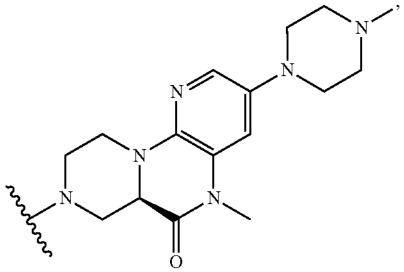
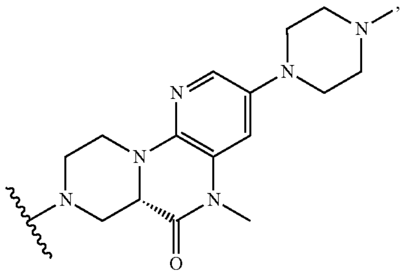
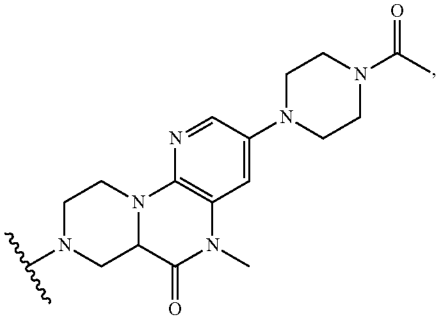
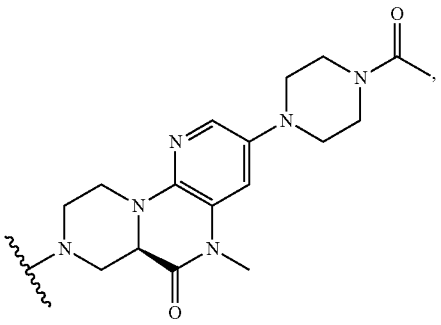
-continued
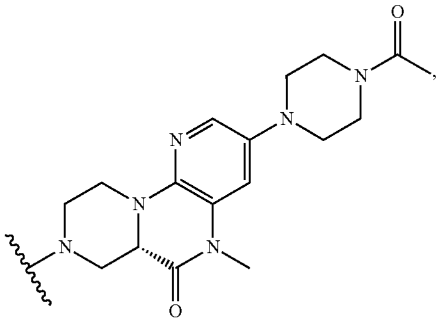
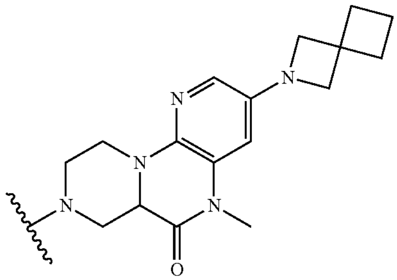
,
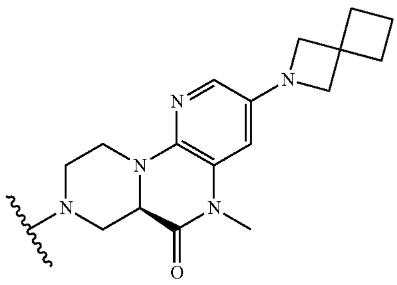
,
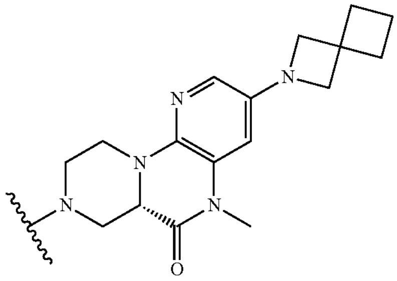
,
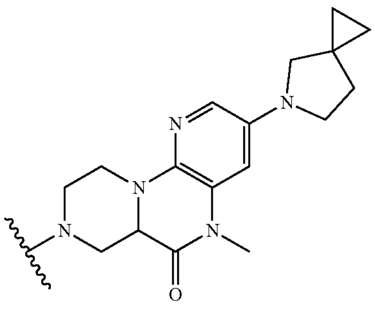
, -continued
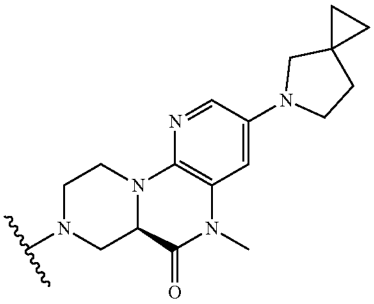
,
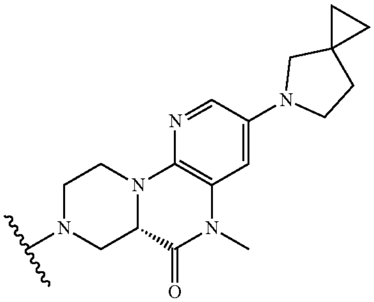
,
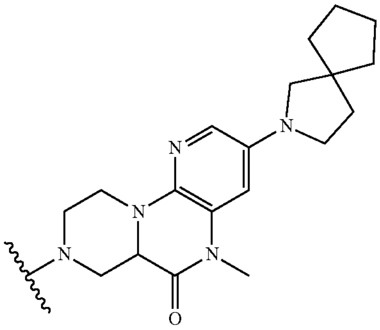
,
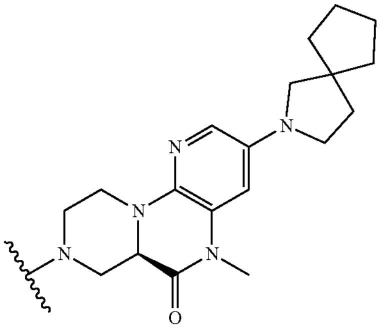
,
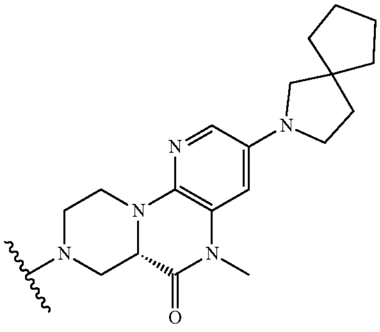
,
-continued
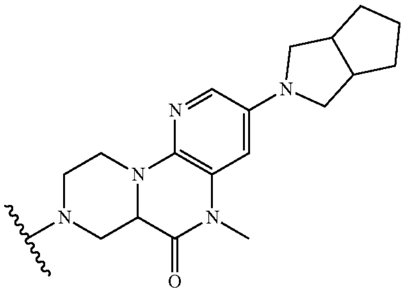
,
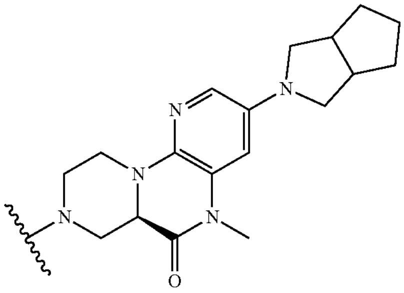
,
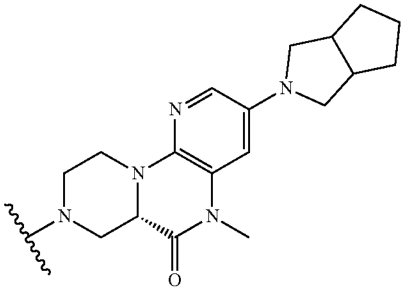
,
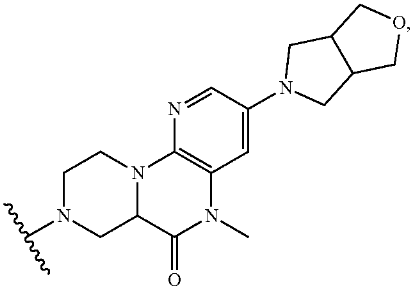
,
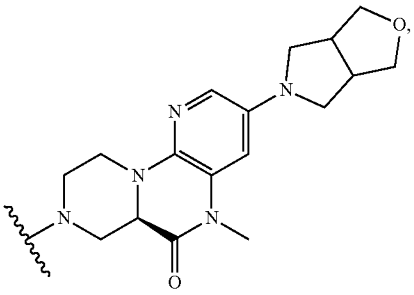

-continued
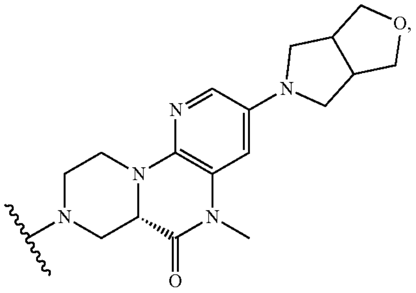
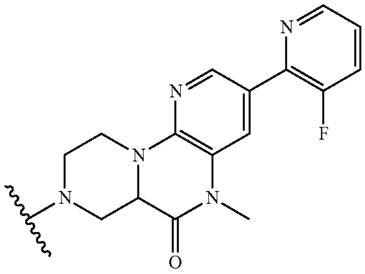
,
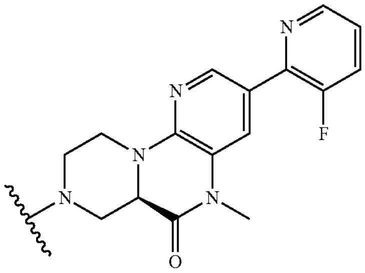
,
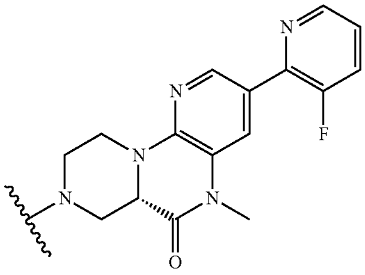
,
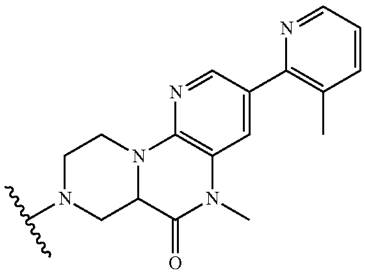
,
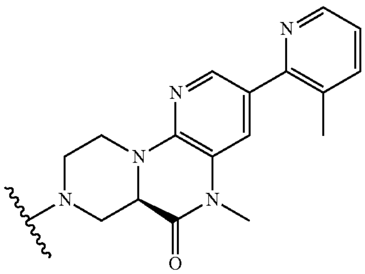
,
-continued
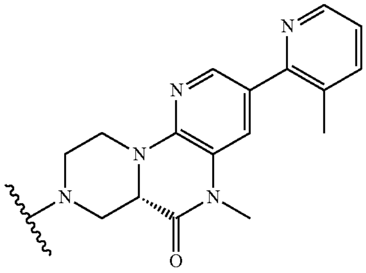
,
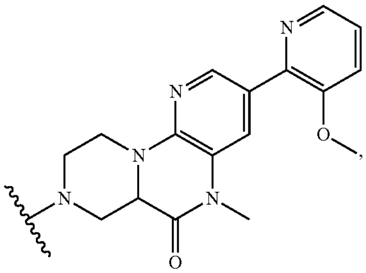
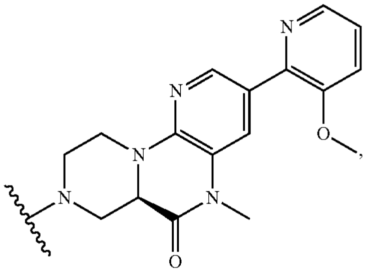
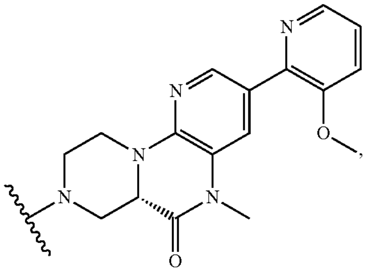
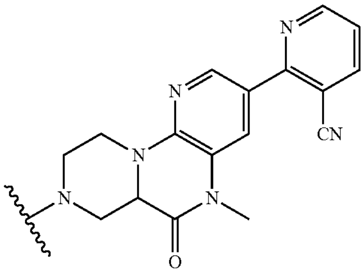
,
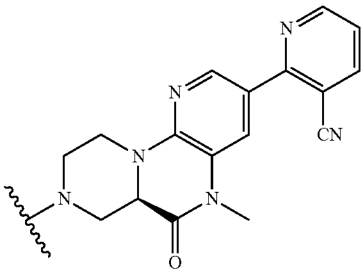
, -continued
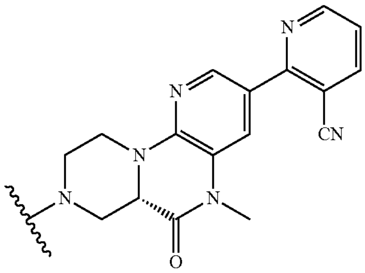
,
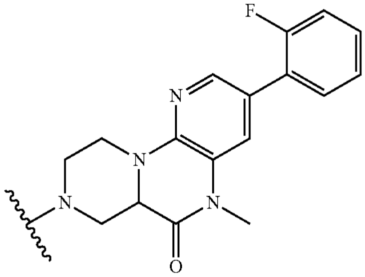
,
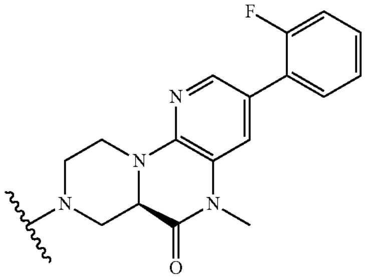
,
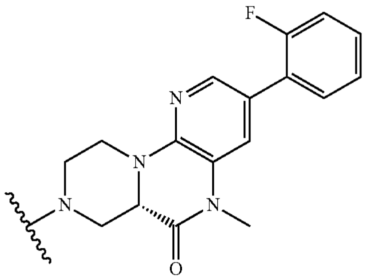
,
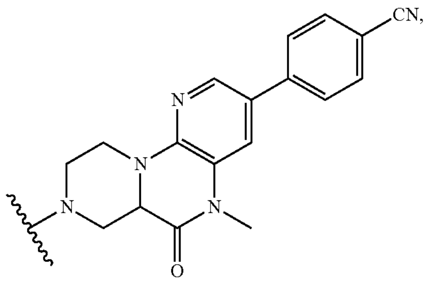
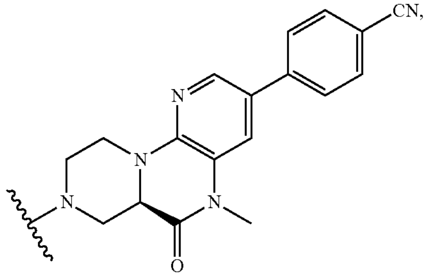
-continued
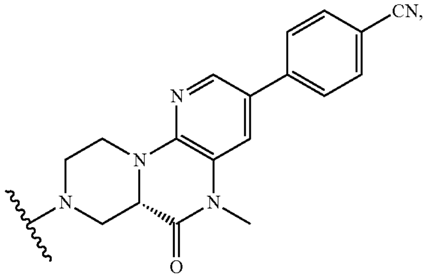
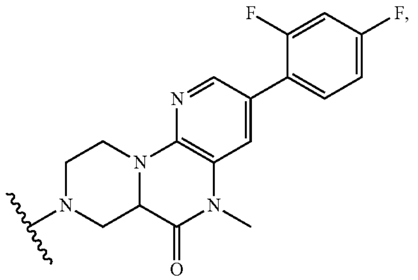
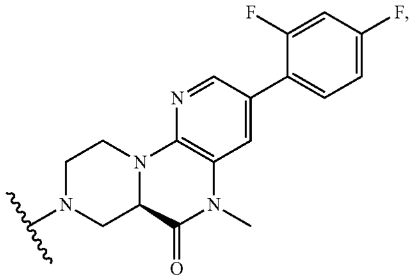
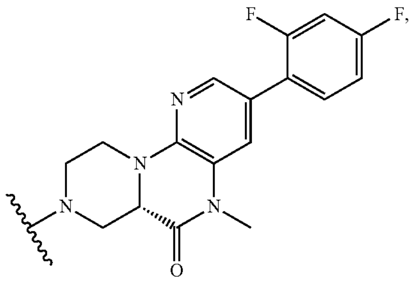
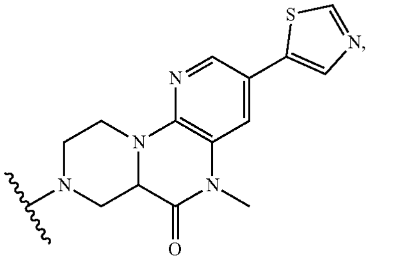
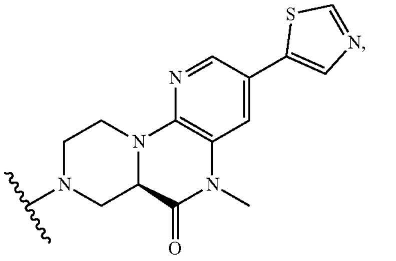

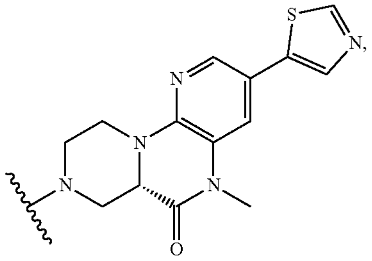
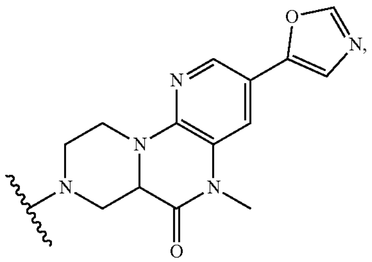
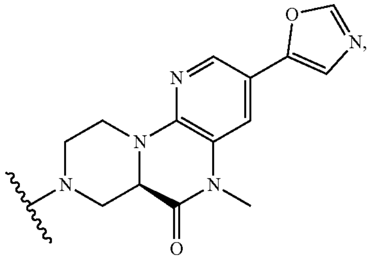
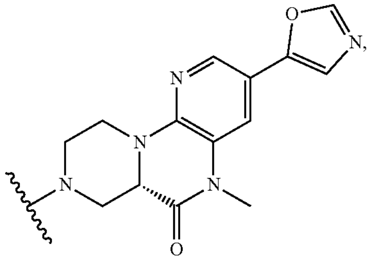
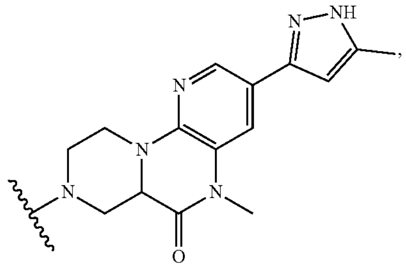
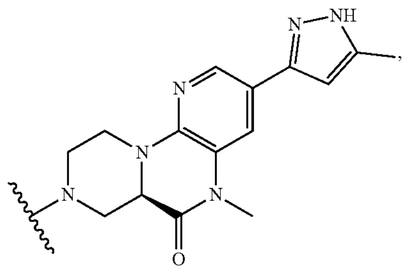
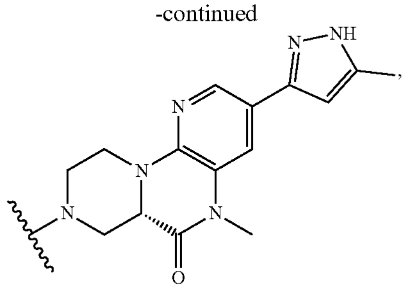
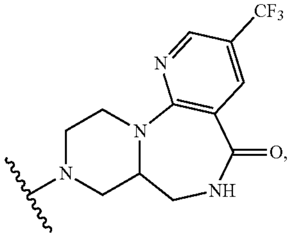
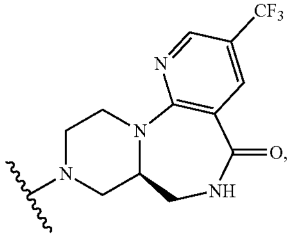
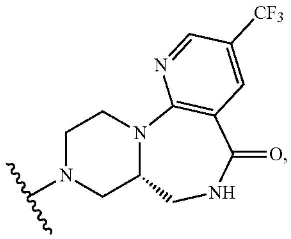
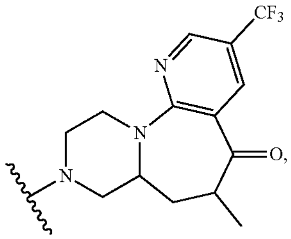
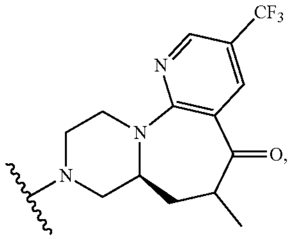
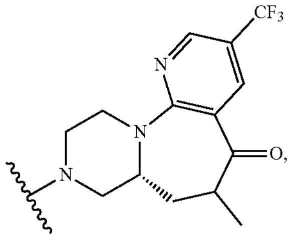

-continued
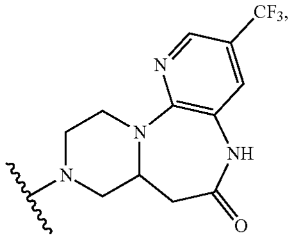
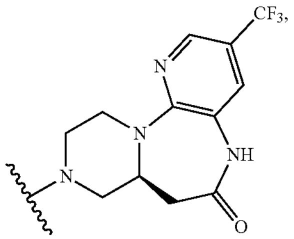
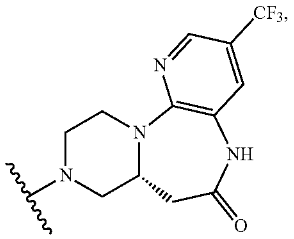
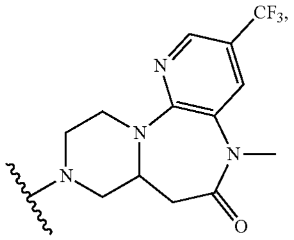
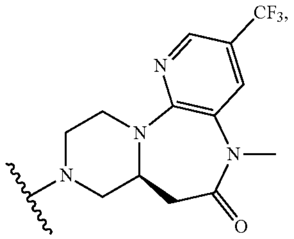
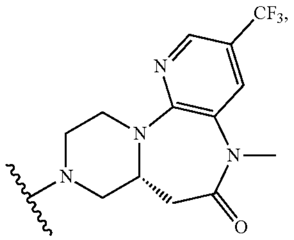
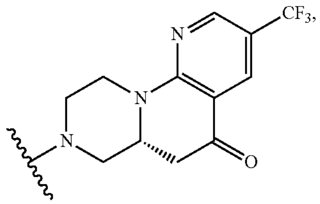
-continued
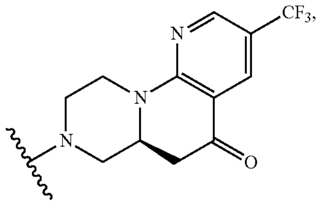
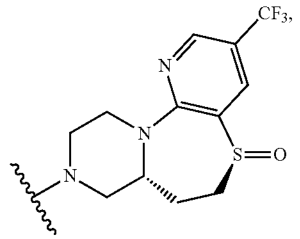
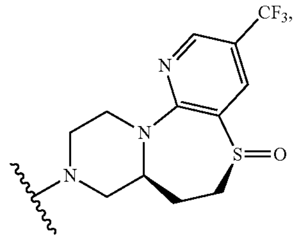
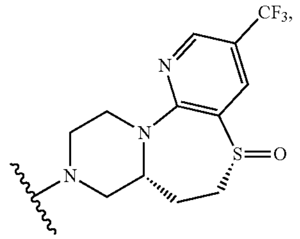
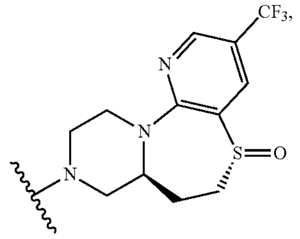
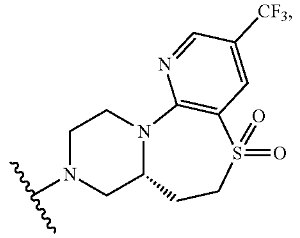
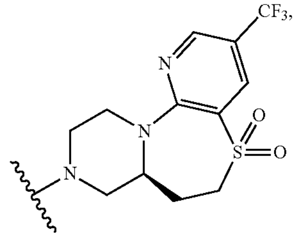

-continued
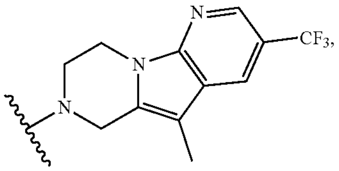
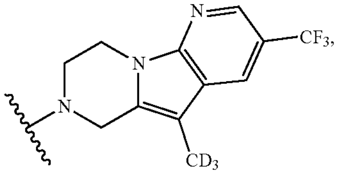
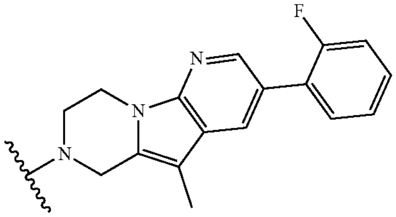
,
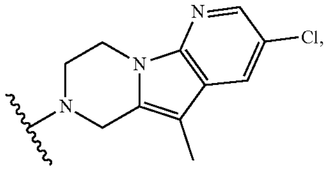
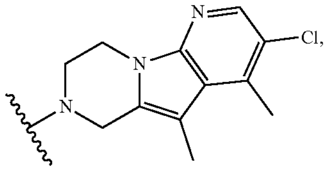
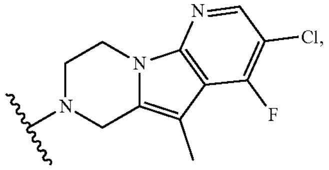
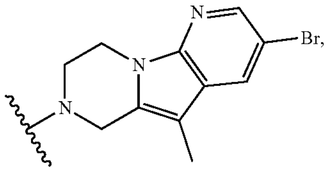
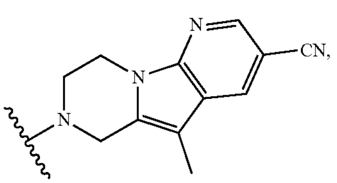
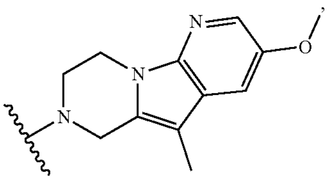
-continued
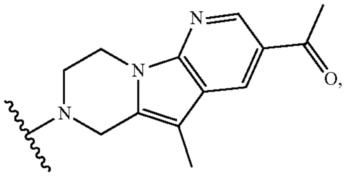
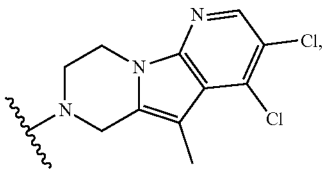
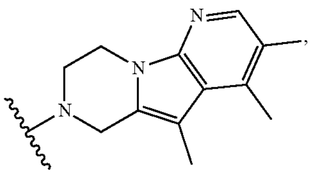
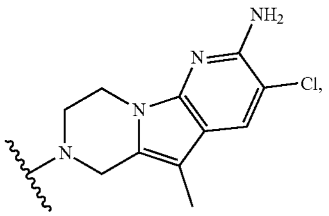
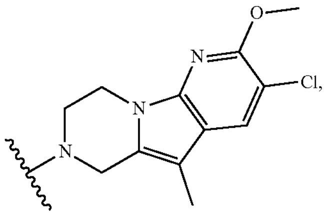
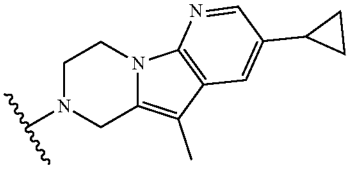
,
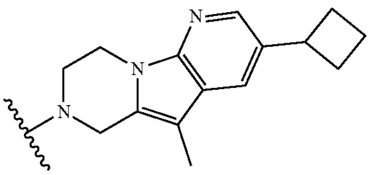
,
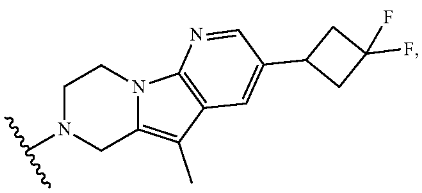
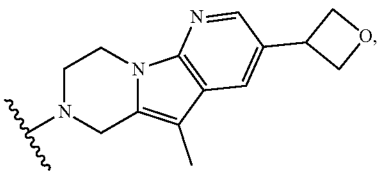

-continued
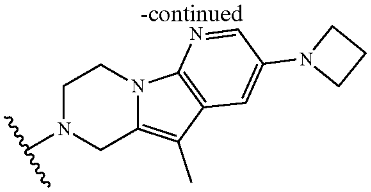
,
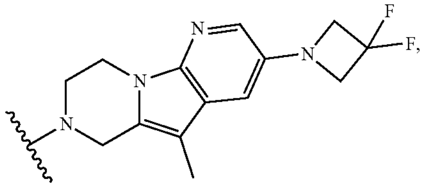
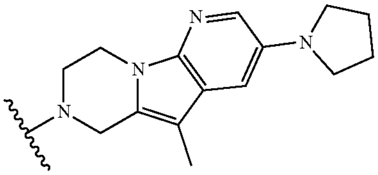
,
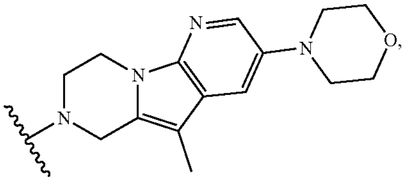
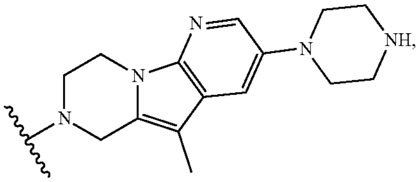
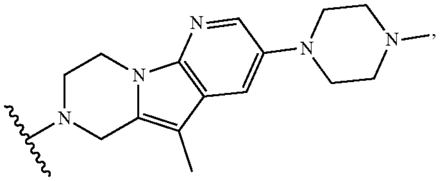
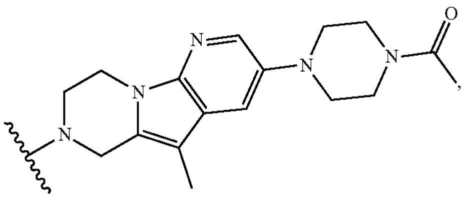
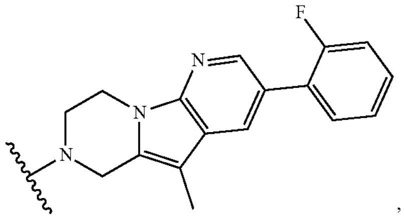
,
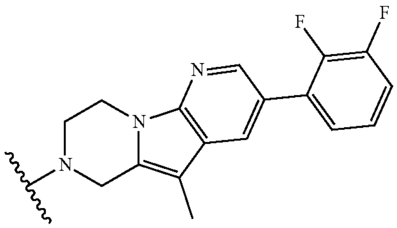
,
-continued
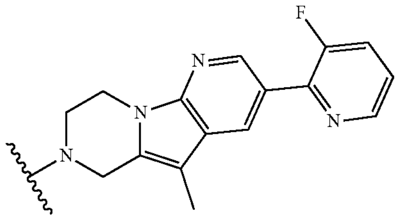
,
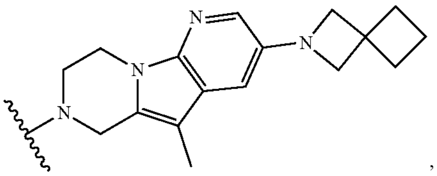
,
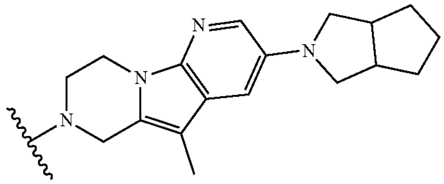
,
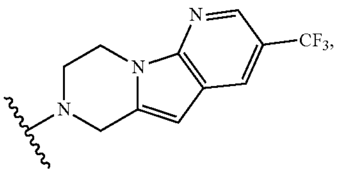
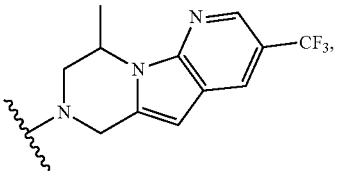
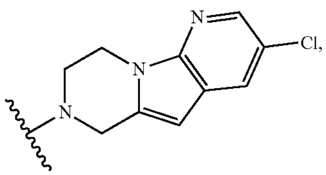
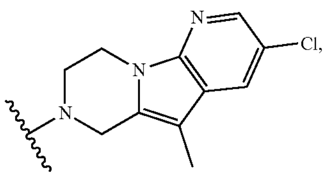
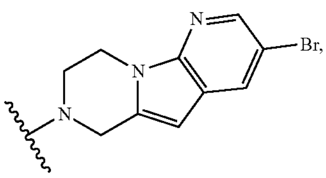
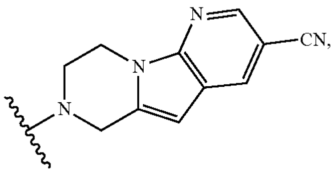

-continued
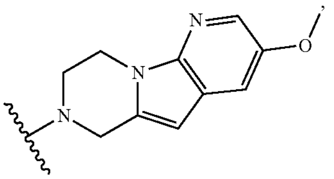
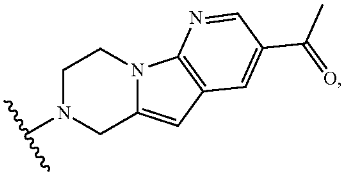
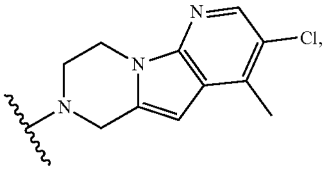
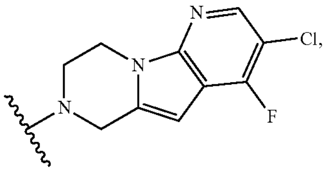
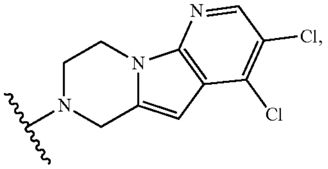
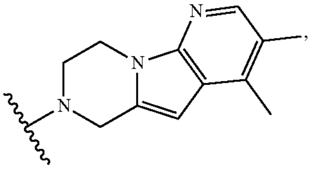
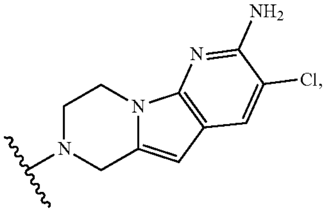
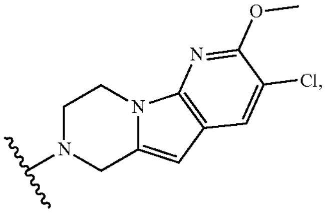
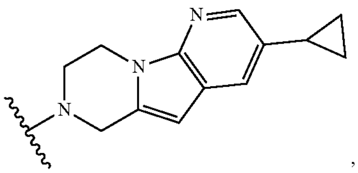
,
-continued
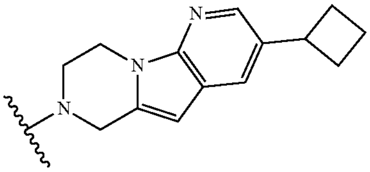
,
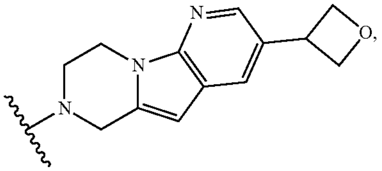
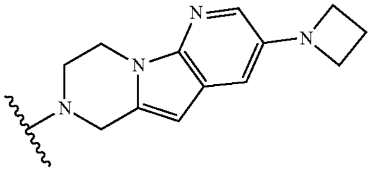
,
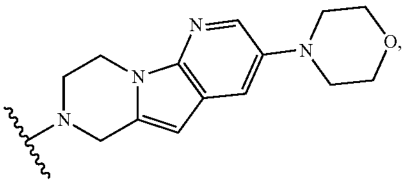
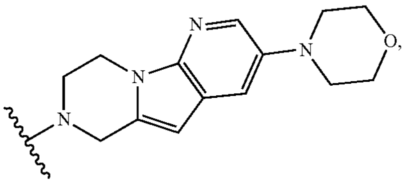
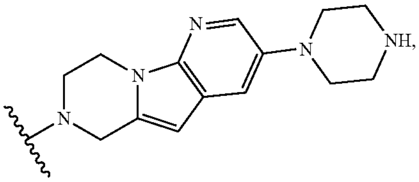
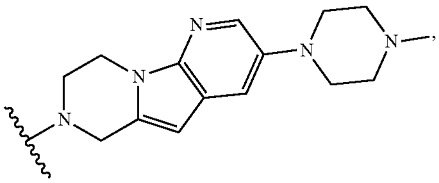
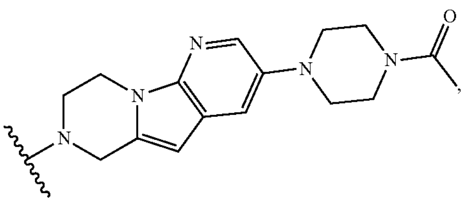
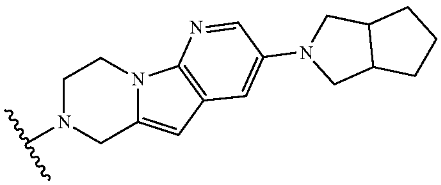
, -continued
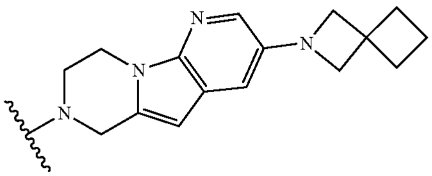
,
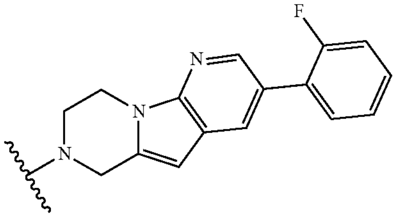
,
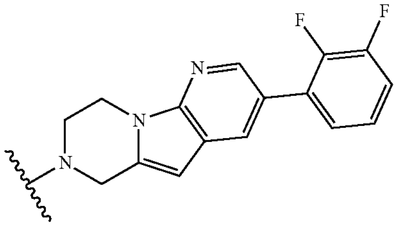
,
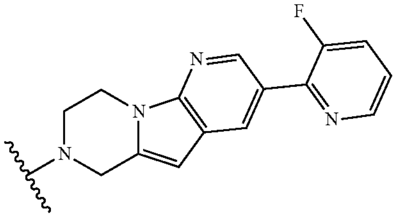
,
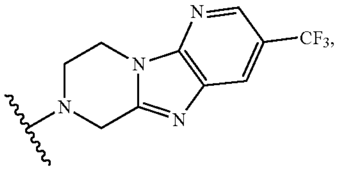
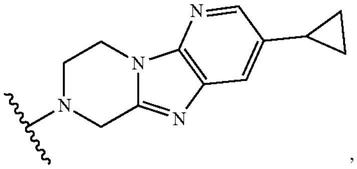
,
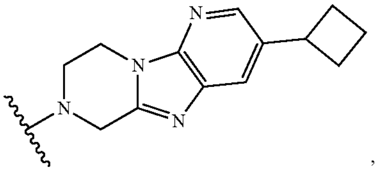
,
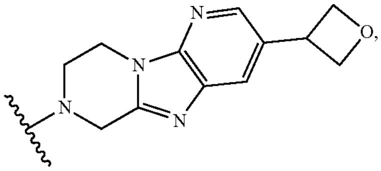
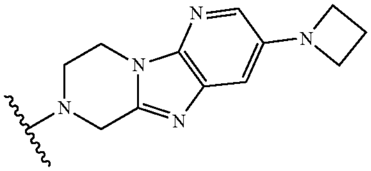
,
-continued
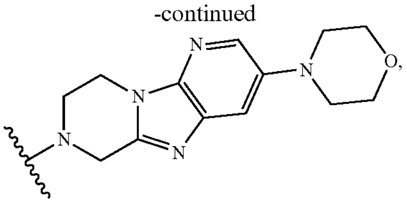
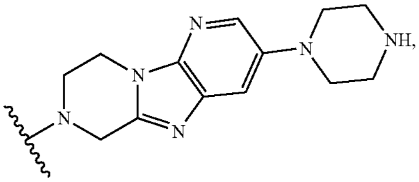
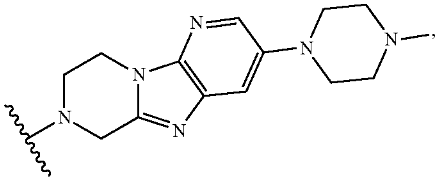
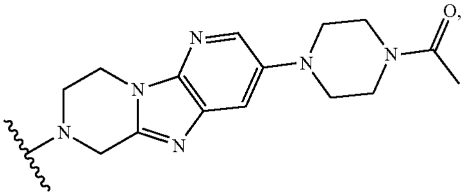
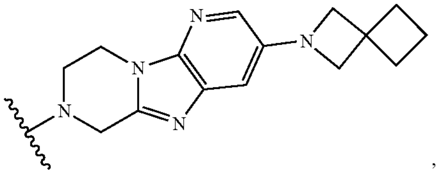
,
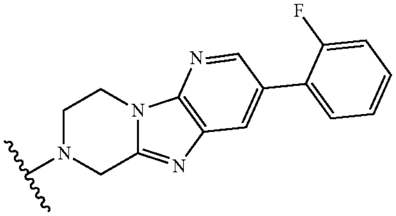
,
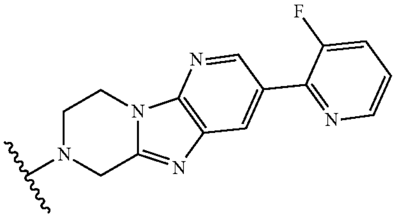
,
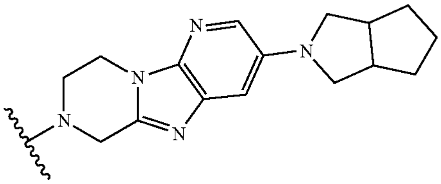
,
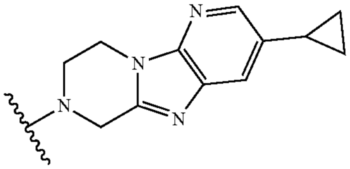
, -continued
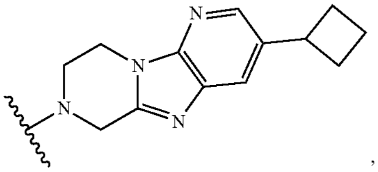
,
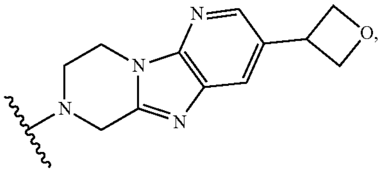
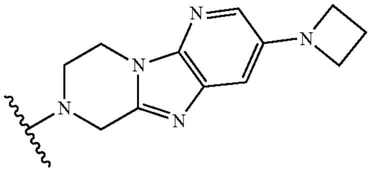
,
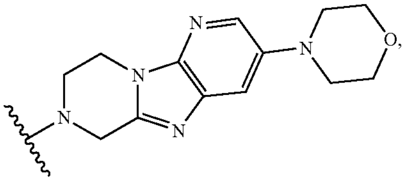
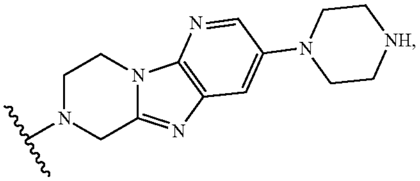
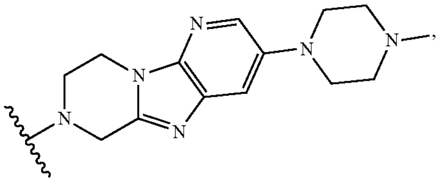
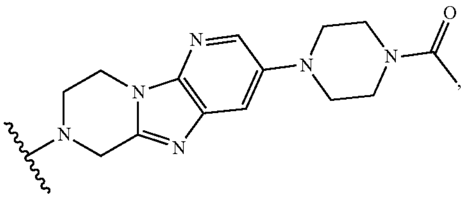
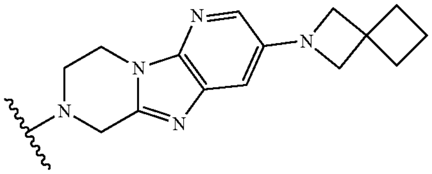
,
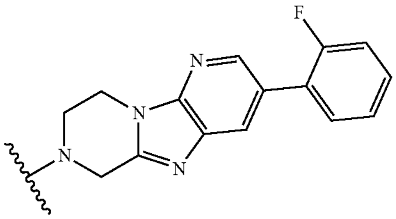
,
-continued
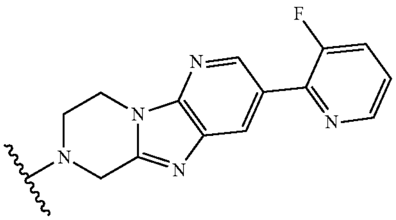
,
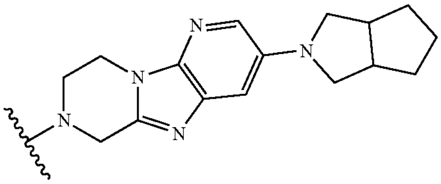
,
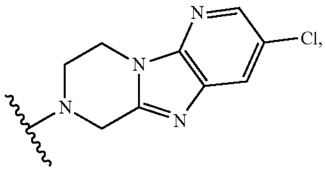
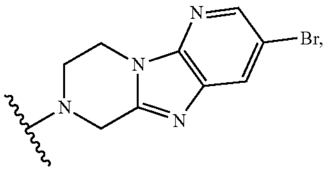
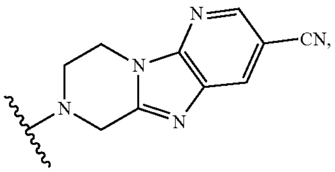
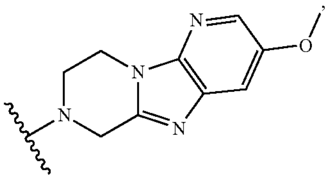
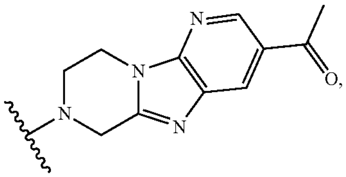
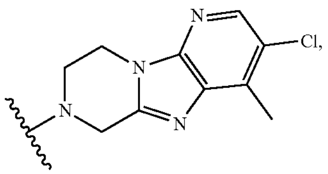
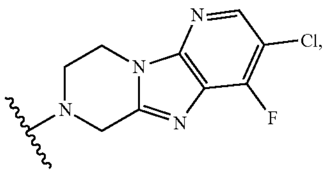

-continued
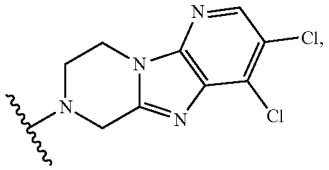
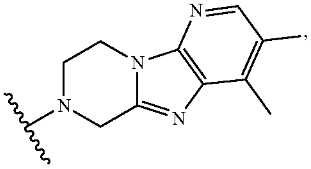
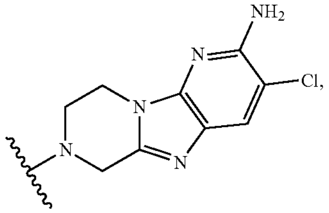
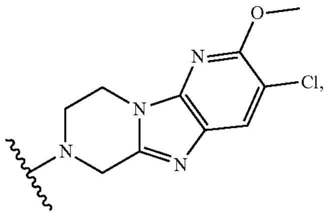
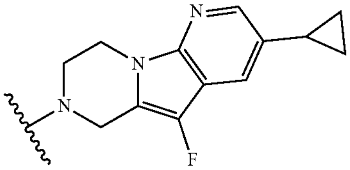
,
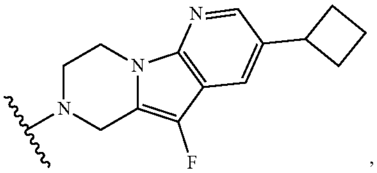
,
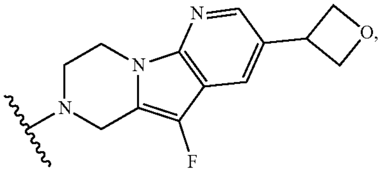
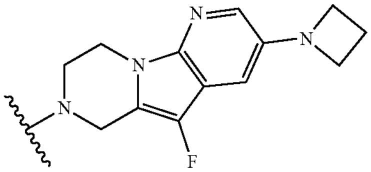
,
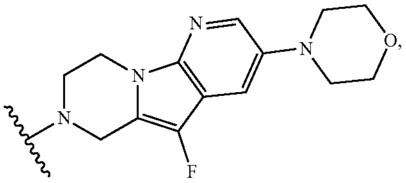
-continued
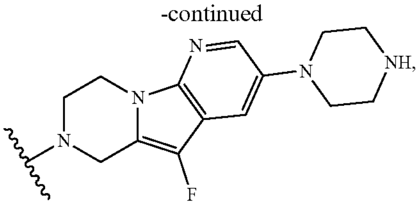
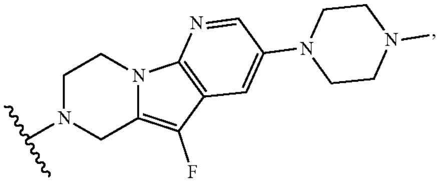
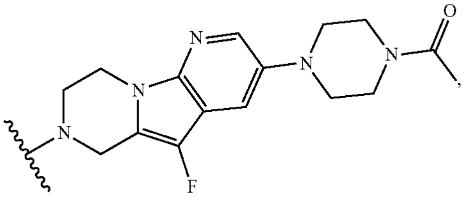
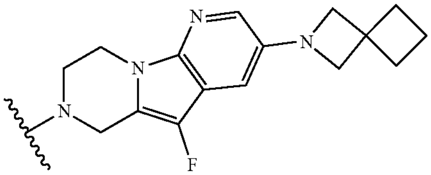
,
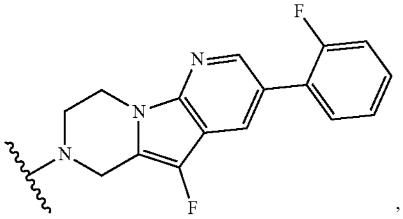
,
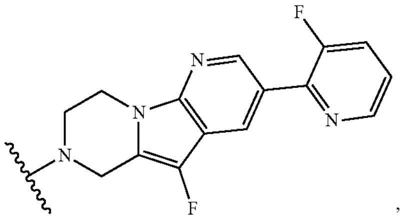
,
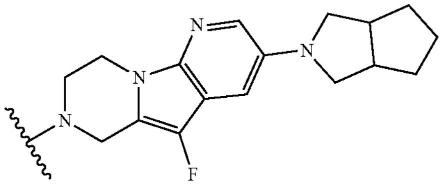
,
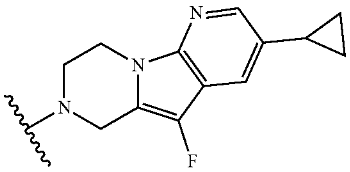
,
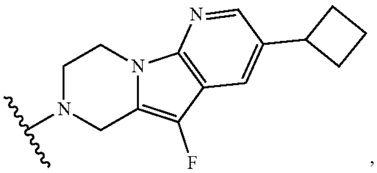
, -continued
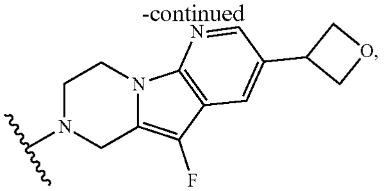
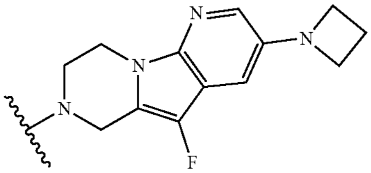
,
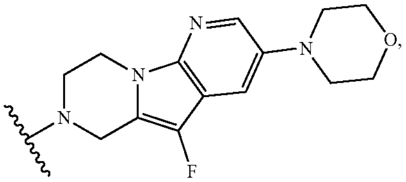
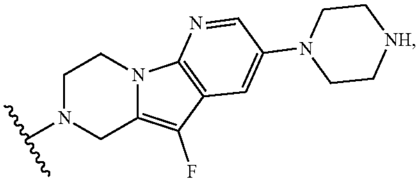
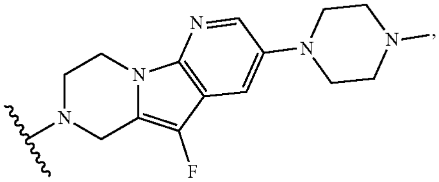
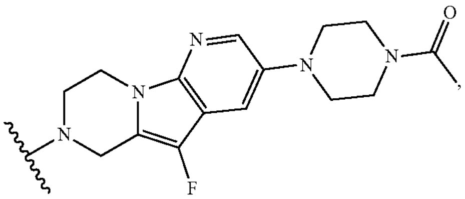
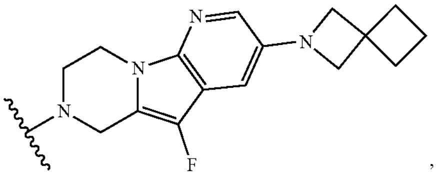
,
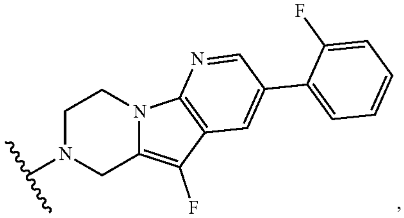
,
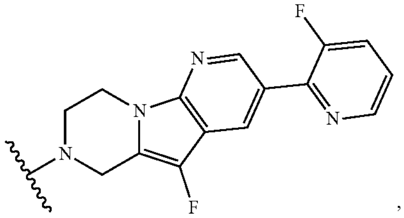
,
-continued
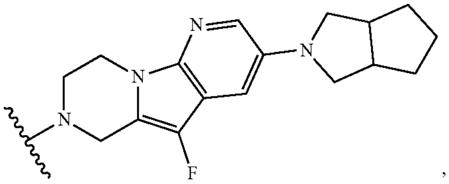
,
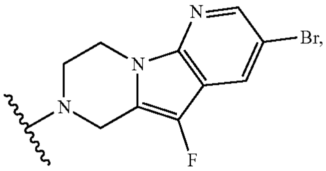
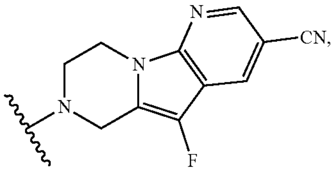
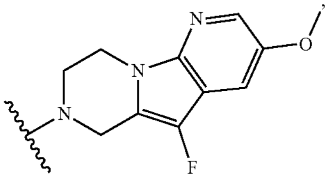
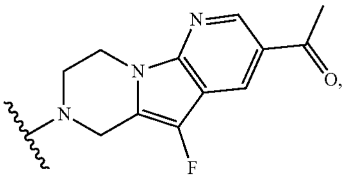
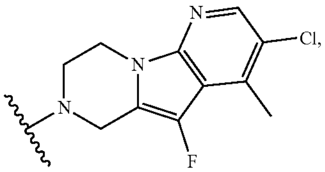
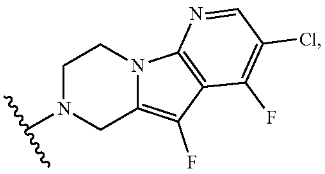
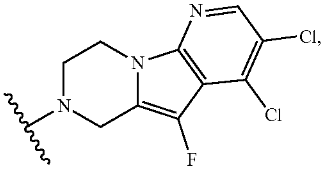
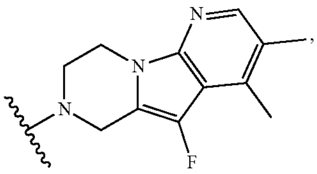

-continued
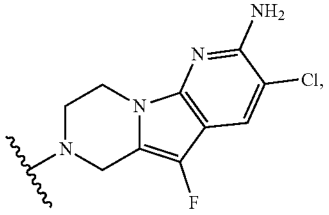
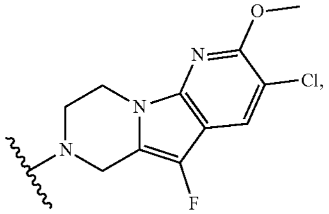
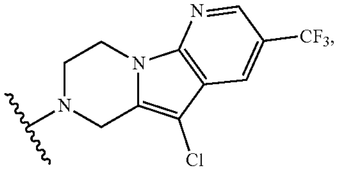
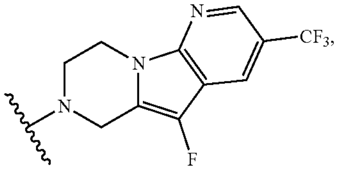
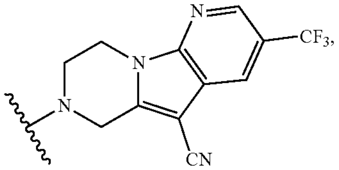
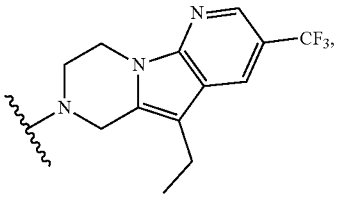
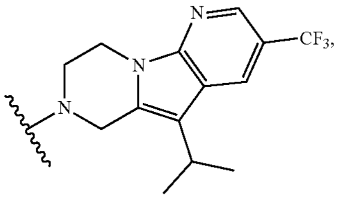
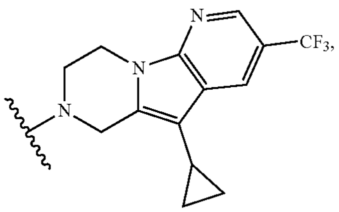
-continued
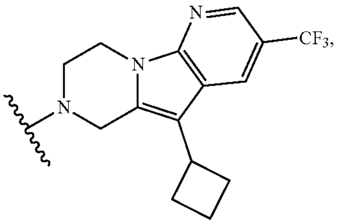
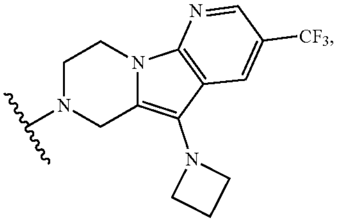
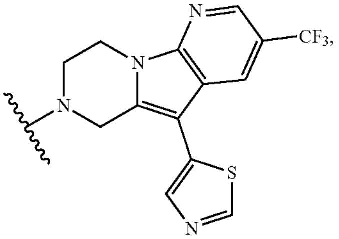
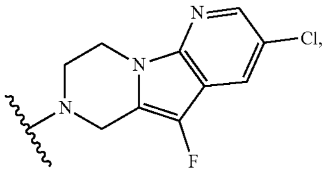
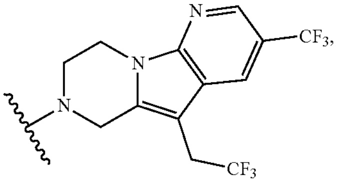
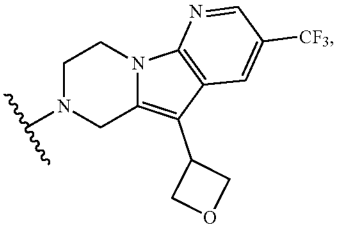
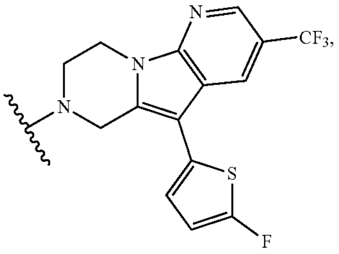
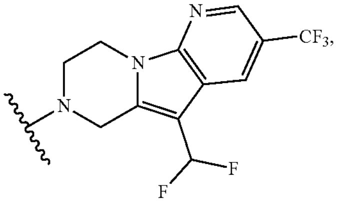

-continued
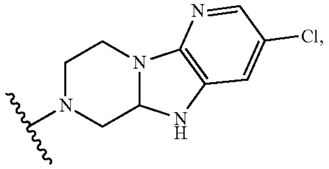
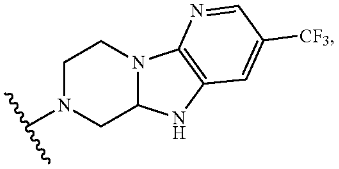
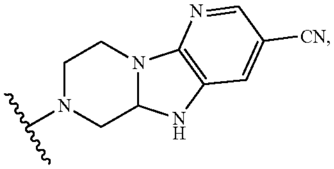
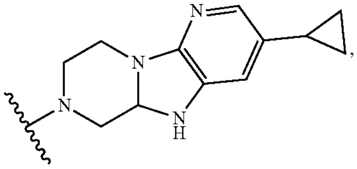
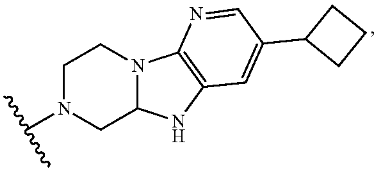
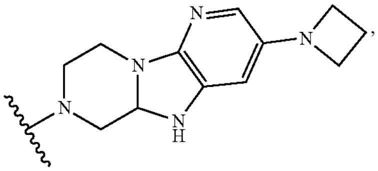
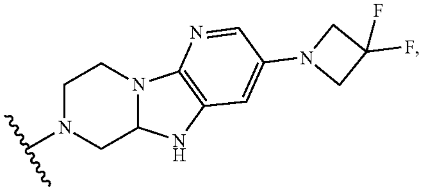
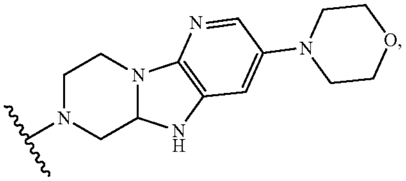
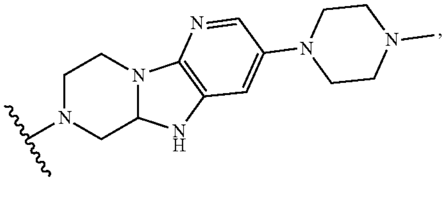
-continued
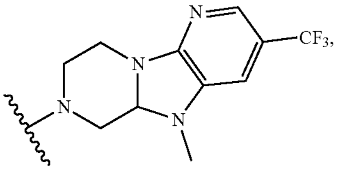
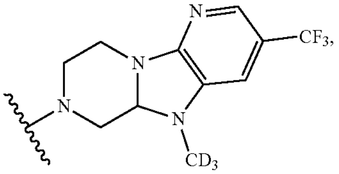
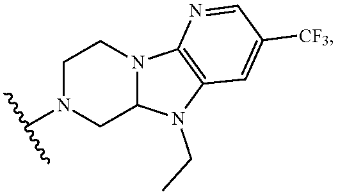
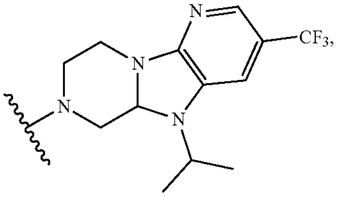
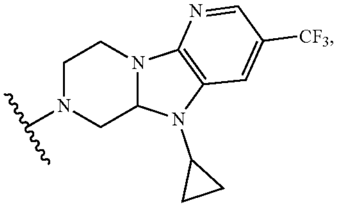
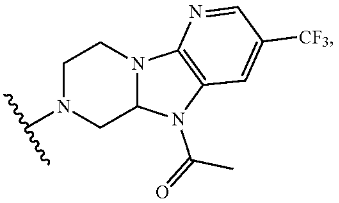
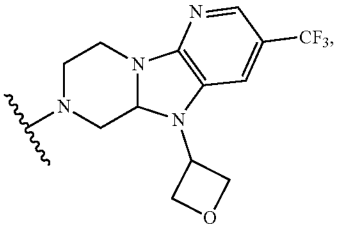
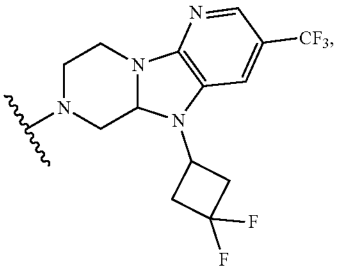

-continued
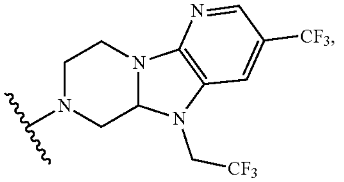
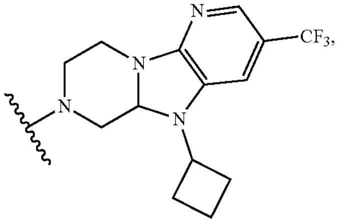
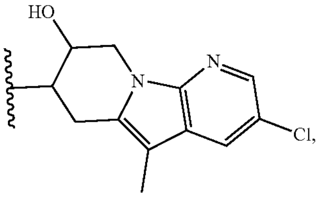
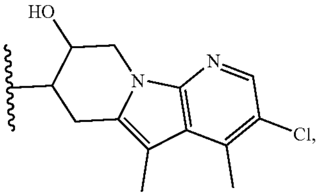
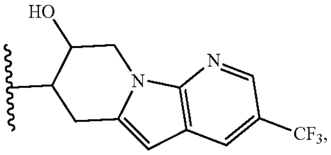
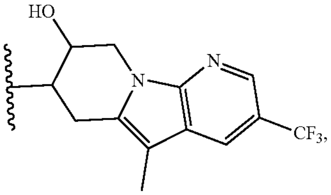
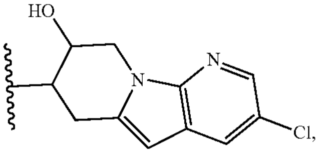
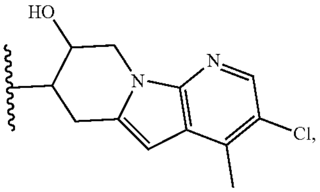
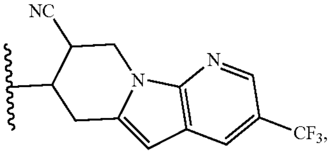
-continued
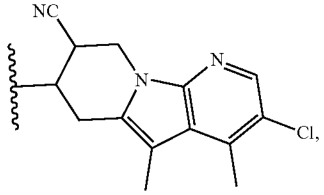
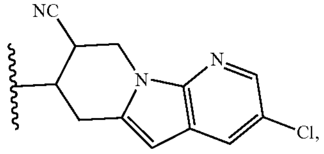
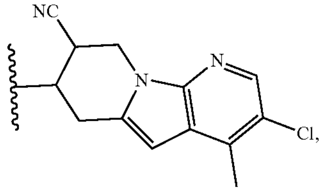
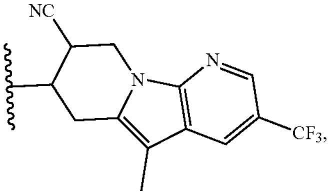
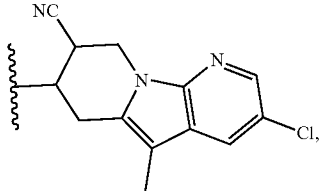
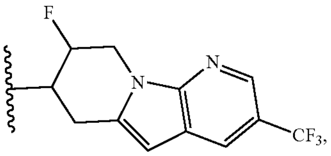
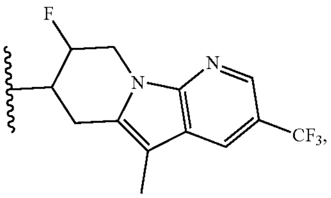
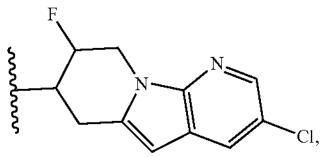
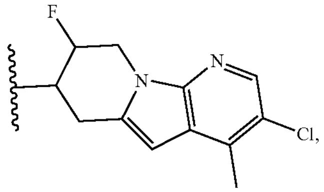

-continued
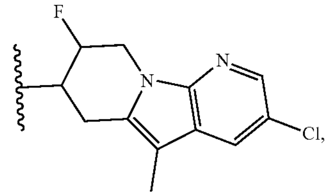,
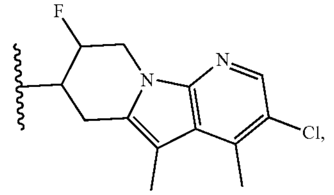,
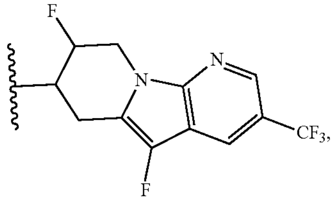,
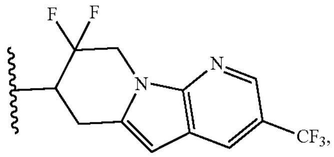,
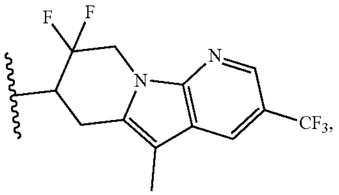,
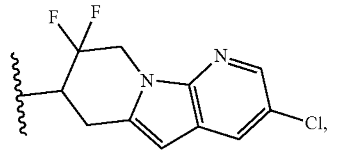,
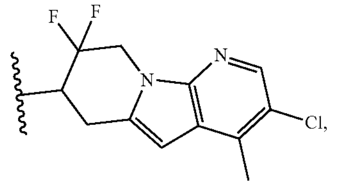,
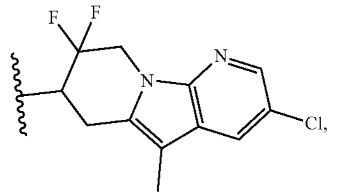,
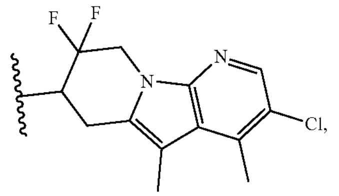,
-continued
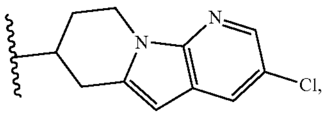,
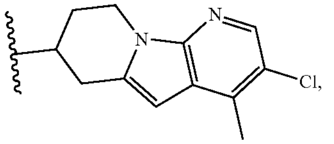,
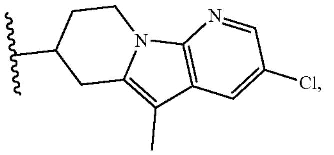,
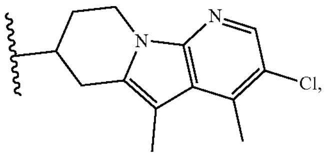,
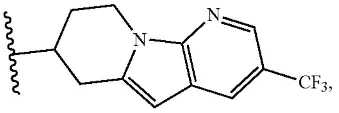,
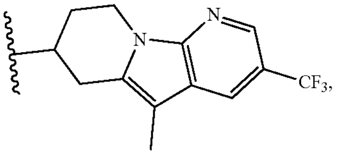,
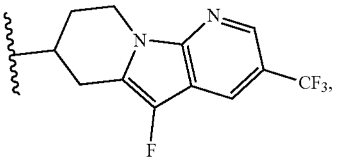,
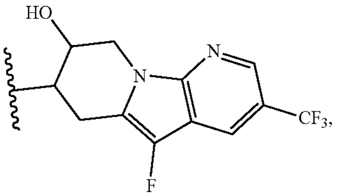,
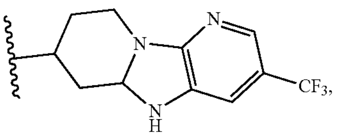,
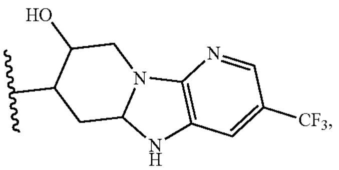,
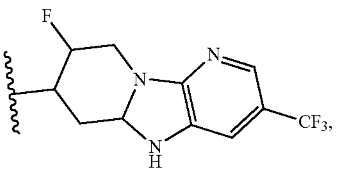, -continued
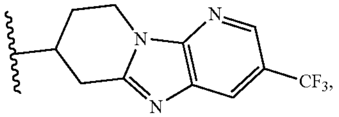
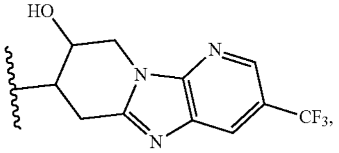
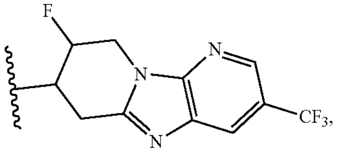
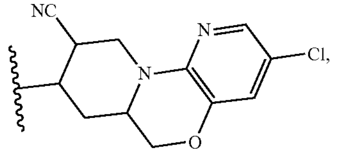
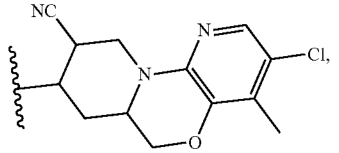
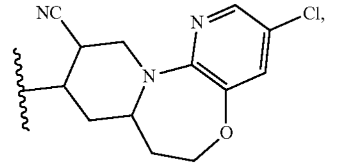
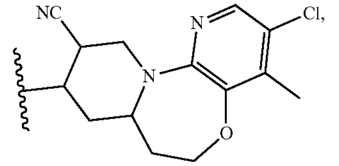
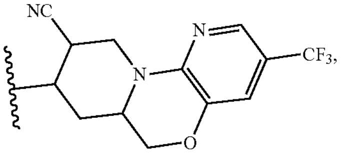
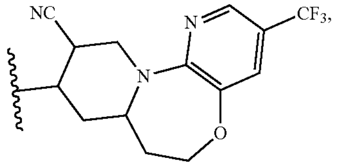
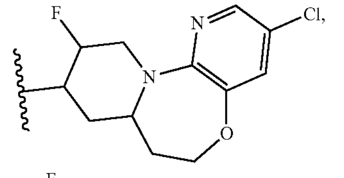
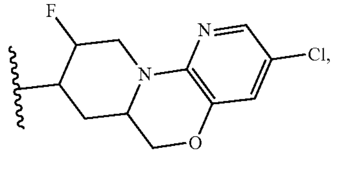
-continued
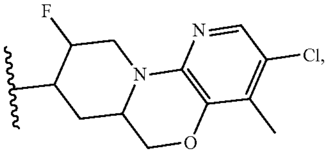
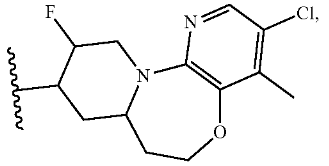
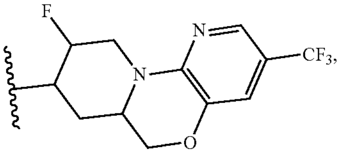
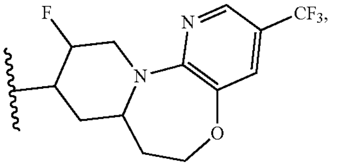
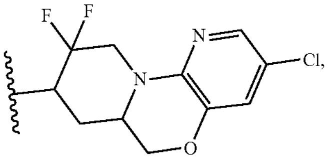
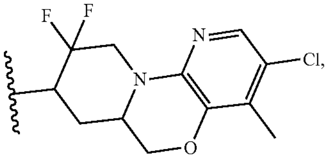
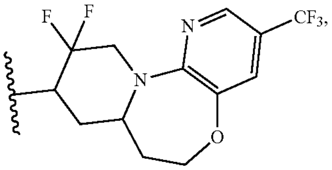
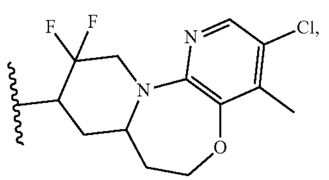
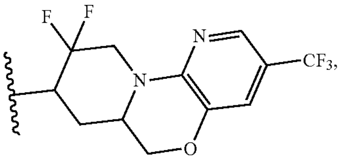
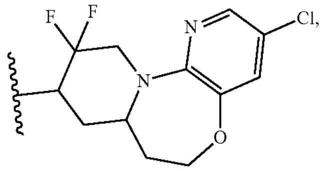

-continued
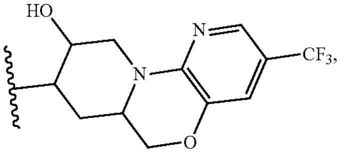
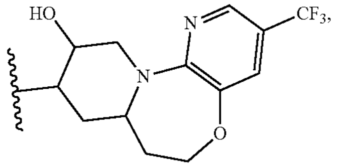
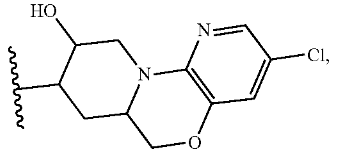
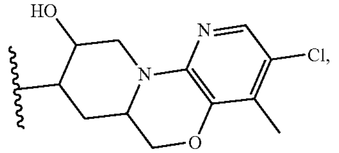
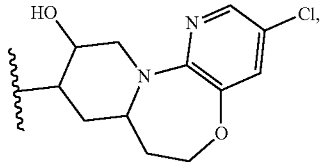
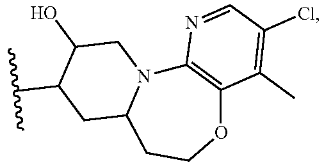
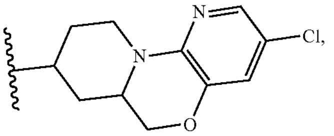
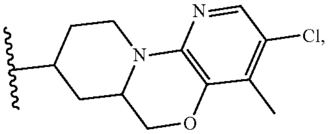
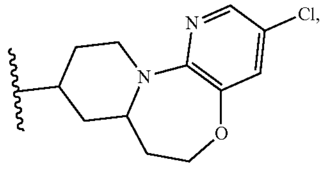
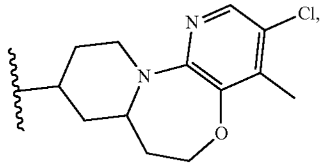
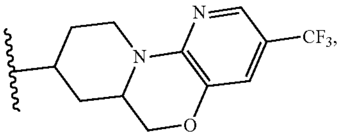
-continued
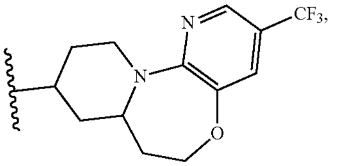
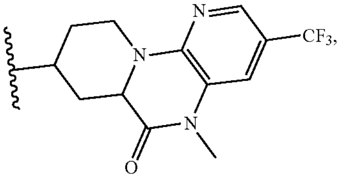
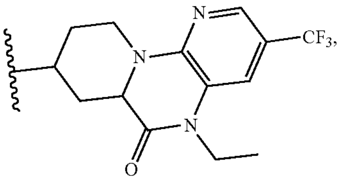
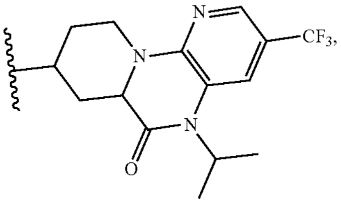
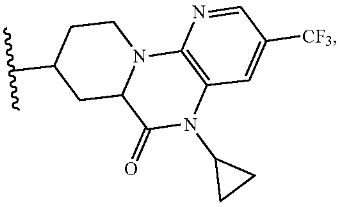
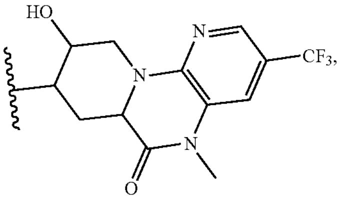
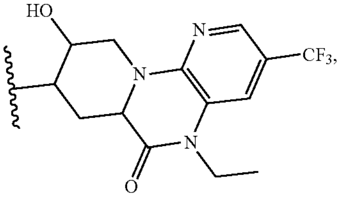
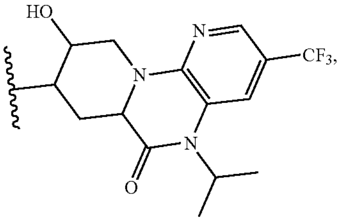

-continued
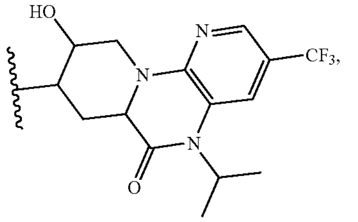
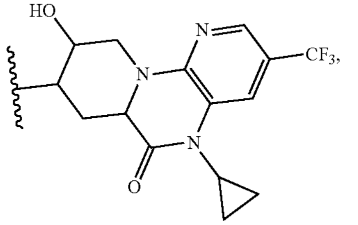
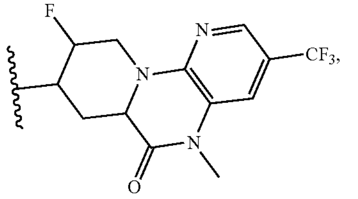
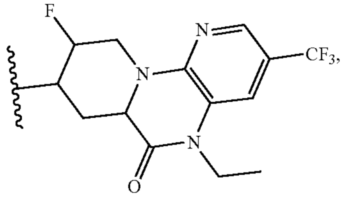
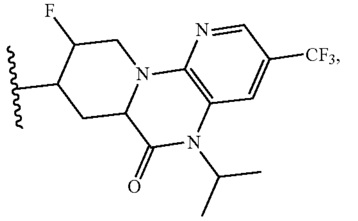
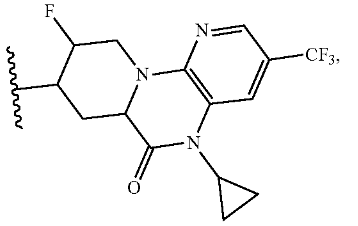
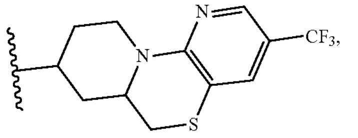
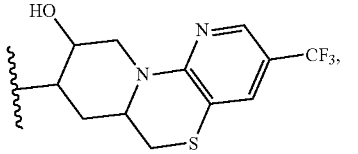
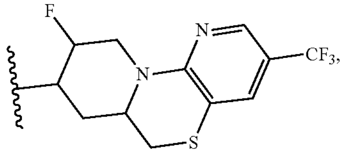
-continued
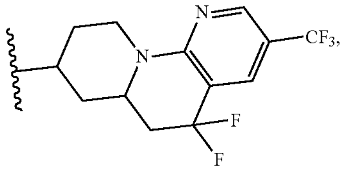
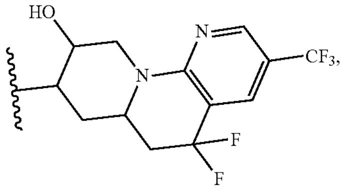
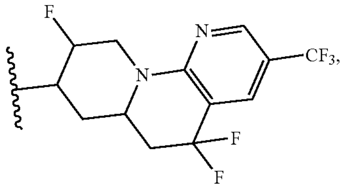
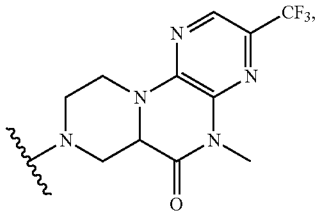
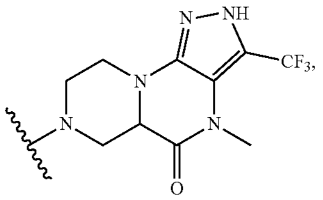
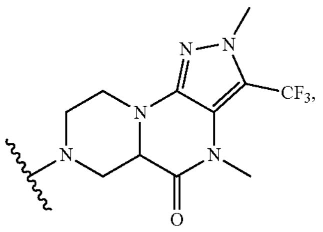
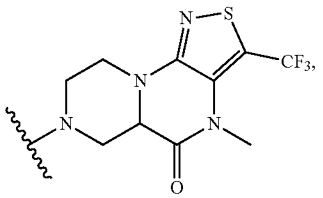
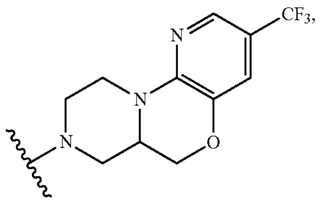

-continued
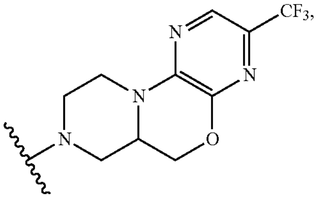
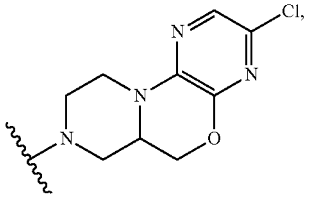
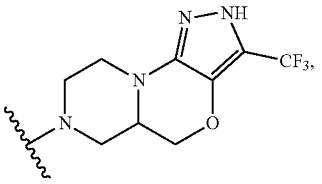
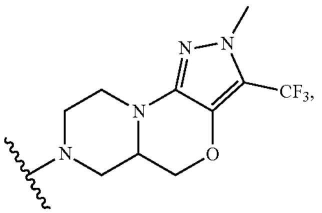
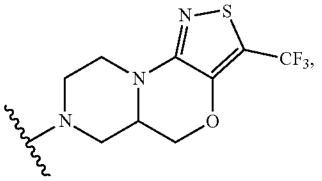
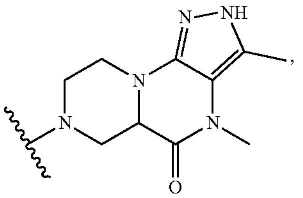
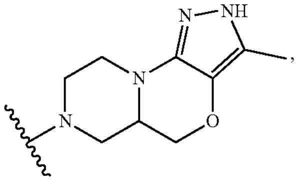
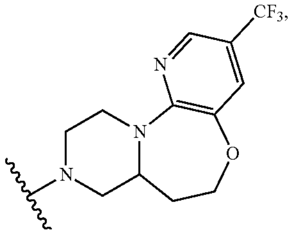
-continued
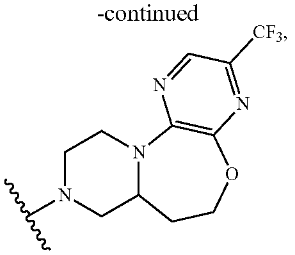
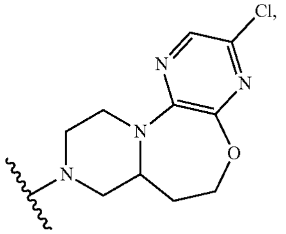
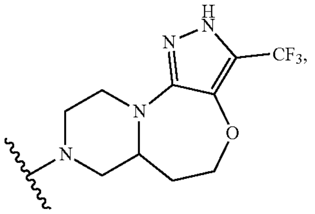
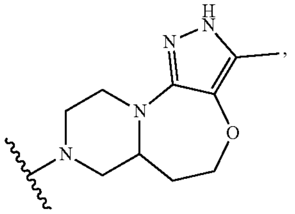
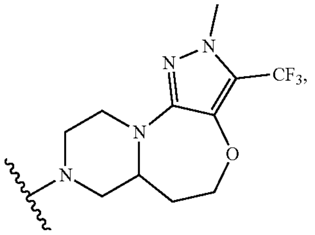
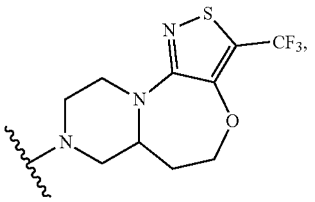
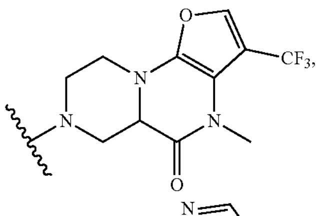
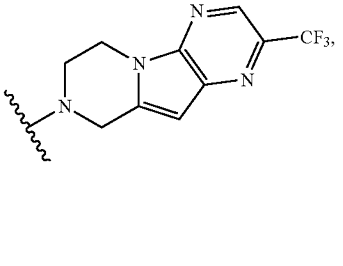

-continued
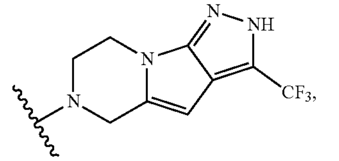
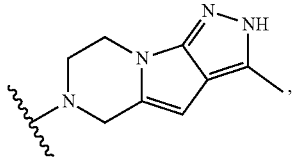
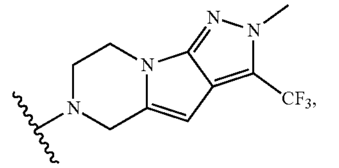
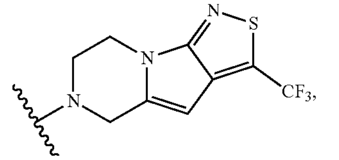
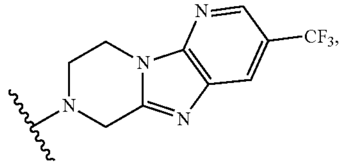
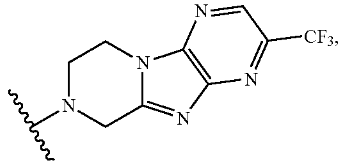
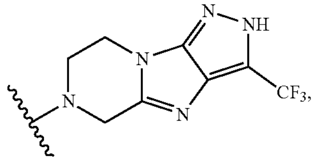
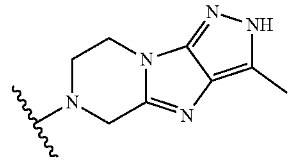
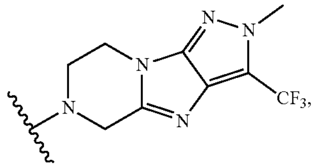
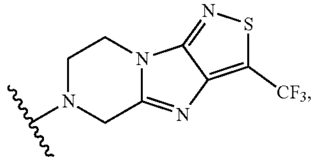
-continued
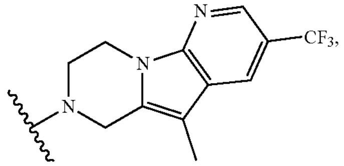
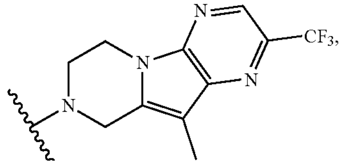
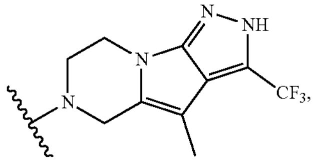
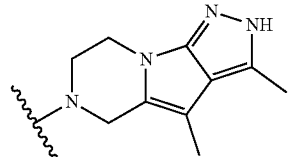
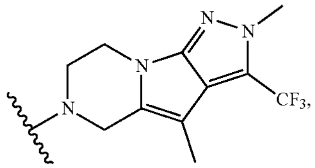
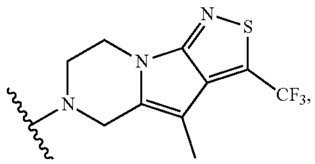
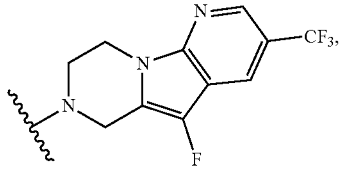
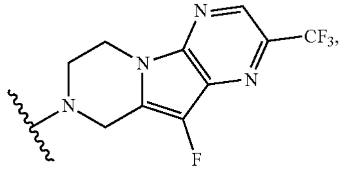
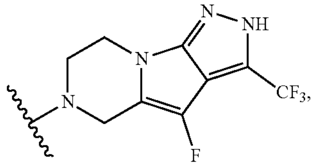
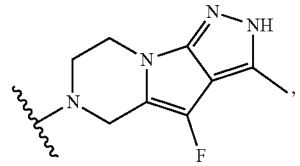

-continued
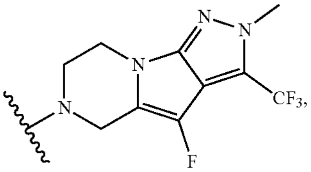
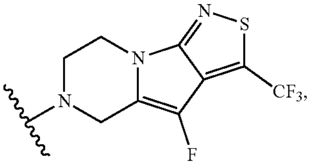
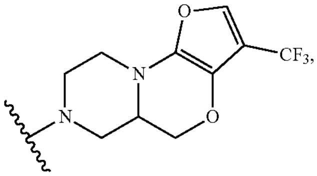
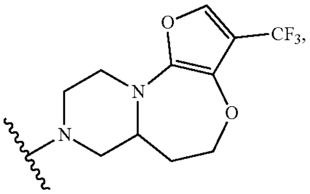
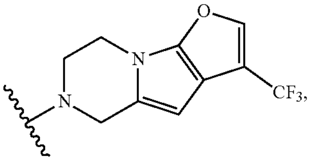
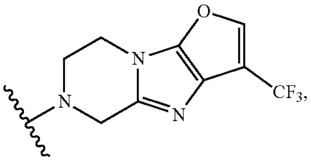
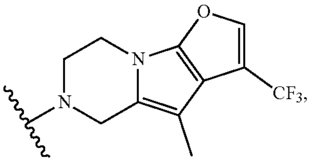
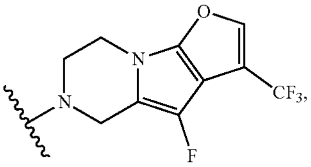
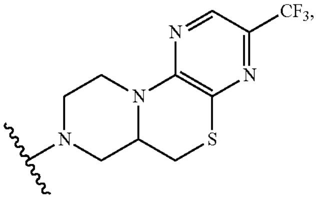
-continued
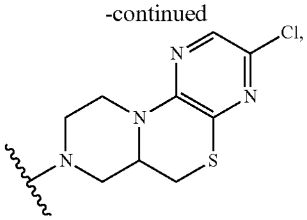
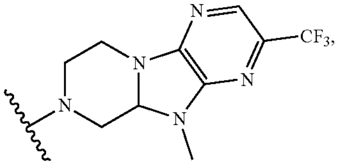
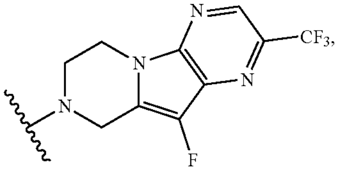
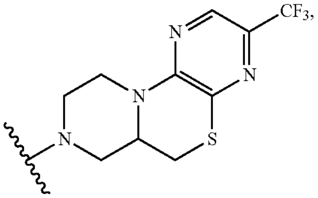
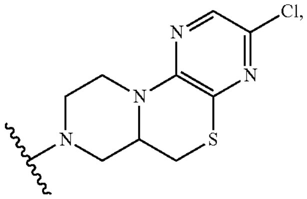
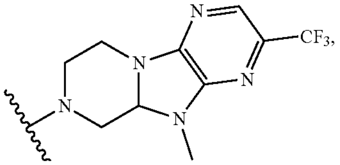
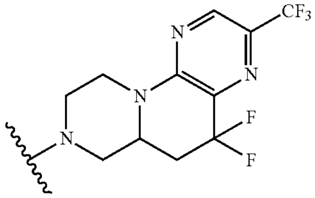
or
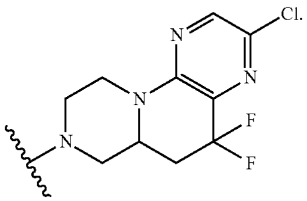 [SMILES: *N1CCN2c3ncc(Cl)nc3C(F)(F)CC2C1]
[42]. The compound according to any one of [1] to [41], wherein,
($R_{Y1}$ in $Y_1$), ($R_{Y2}$ in $Y_2$) or ($R_{Y3}$ in $Y_3$) at each occurrence is independently selected from hydrogen, halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, —$NH_2$, —NH($C_{1-6}$alkyl), —N($C_{1-6}$alkyl)$_2$, —NH(3-10 membered cycloalkyl), —N($C_{1-6}$alkyl)(3-10 membered cycloalkyl), —OH, —O($C_{1-6}$alkyl), —O-(3-10 membered cycloalkyl), —SH, —S($C_{1-6}$alkyl), —S(3-10 membered cycloalkyl), —S(=O)($C_{1-6}$alkyl), —S(=O)(3-10 membered cycloalkyl), —S(=O)$_2$($C_{1-6}$alkyl), —S(=O)$_2$(3-10 membered cycloalkyl), —C(=O)($C_{1-6}$alkyl), —C(=O)-(3-10 membered cycloalkyl), —C(=O)OH, —C(=O)(O$C_{1-6}$alkyl), —OC(=O)($C_{1-6}$alkyl), —C(=O)NH$_2$, —C(=O)NH($C_{1-6}$alkyl), —C(=O)N($C_{1-6}$alkyl)$_2$, —NHC(=O)($C_{1-6}$alkyl), —N($C_{1-6}$alkyl)C(=O)($C_{1-6}$alkyl), —OC(=O)O($C_{1-6}$alkyl), —NHC(=O)(O$C_{1-6}$alkyl), —N($C_{1-6}$alkyl)C(=O)(O$C_{1-6}$alkyl), —OC(=O)NH($C_{1-6}$alkyl), —OC(=O)N($C_{1-6}$alkyl)$_2$, —NHC(=O)NH$_2$, —NHC(=O)NH($C_{1-6}$alkyl), —NHC(=O)N($C_{1-6}$alkyl)$_2$, —N($C_{1-6}$alkyl)C(=O)NH$_2$, —N($C_{1-6}$alkyl)C(=O)NH($C_{1-6}$alkyl), —N($C_{1-6}$alkyl)C(=O)N($C_{1-6}$alkyl)$_2$, —S(=O)(O$C_{1-6}$alkyl), —OS(=O)($C_{1-6}$alkyl), —S(=O)NH$_2$, —S(=O)NH($C_{1-6}$alkyl), —S(=O)N($C_{1-6}$alkyl)$_2$, —NHS(=O)($C_{1-6}$alkyl), —N($C_{1-6}$alkyl)S(=O)($C_{1-6}$alkyl), —OS(=O)O($C_{1-6}$alkyl), —NHS(=O)O($C_{1-6}$alkyl), —N($C_{1-6}$alkyl)S(=O)O($C_{1-6}$alkyl), —OS(=O)NH$_2$, —OS(=O)NH($C_{1-6}$alkyl), —OS(=O)N($C_{1-6}$alkyl)$_2$, —NHS(=O)NH$_2$, —NHS(=O)NH($C_{1-6}$alkyl), —NHS(=O)N($C_{1-6}$alkyl)$_2$, —N($C_{1-6}$alkyl)S(=O)NH$_2$, —N($C_{1-6}$alkyl)S(=O)NH($C_{1-6}$alkyl), —N($C_{1-6}$alkyl)S(=O)N($C_{1-6}$alkyl)$_2$, —S(=O)$_2$(O$C_{1-6}$alkyl), —OS(=O)$_2$($C_{1-6}$alkyl), —S(=O)$_2$NH$_2$, —S(=O)$_2$NH($C_{1-6}$alkyl), —S(=O)$_2$N($C_{1-6}$alkyl)$_2$, —NHS(=O)$_2$($C_{1-6}$alkyl), —N($C_{1-6}$alkyl)S(=O)$_2$($C_{1-6}$alkyl), —OS(=O)$_2$O($C_{1-6}$alkyl), —NHS(=O)$_2$O($C_{1-6}$alkyl), —N($C_{1-6}$alkyl)S(=O)$_2$O($C_{1-6}$alkyl), —OS(=O)$_2$NH$_2$, —OS(=O)$_2$NH($C_{1-6}$alkyl), —OS(=O)$_2$N($C_{1-6}$alkyl)$_2$, —NHS(=O)$_2$NH$_2$, —NHS(=O)$_2$NH($C_{1-6}$alkyl), —NHS(=O)$_2$N($C_{1-6}$alkyl)$_2$, —N($C_{1-6}$alkyl)S(=O)$_2$NH$_2$, —N($C_{1-6}$alkyl)S(=O)$_2$NH($C_{1-6}$alkyl), —N($C_{1-6}$alkyl)S(=O)$_2$N($C_{1-6}$alkyl)$_2$, —PH($C_{1-6}$alkyl), —P($C_{1-6}$alkyl)$_2$, —P(=O)H($C_{1-6}$alkyl), —P(=O)($C_{1-6}$alkyl)$_2$, 3-10 membered cycloalkyl, 3-10 membered heterocyclyl, 6-10 membered aryl or 5-10 membered heteroaryl, wherein said —$C_{1-6}$alkyl, —$C_{1-6}$haloalkyl, —$C_{1-6}$haloalkoxy, —$C_{2-6}$alkenyl, —$C_{2-6}$alkynyl, 3-10 membered cycloalkyl, 3-6 membered heterocyclyl, 6-10 membered aryl or 5-10 membered heteroaryl is independently optionally substituted with 1, 2, 3, 4, 5 or 6 substituents selected from halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —NH$_2$, —NH($C_{1-6}$alkyl), —N($C_{1-6}$alkyl)$_2$, —NH(3-10 membered cycloalkyl), —N($C_{1-6}$alkyl)(3-10 membered cycloalkyl), —OH, —O($C_{1-6}$alkyl), —O(3-10 membered cycloalkyl), —SH, —S($C_{1-6}$alkyl), —S(3-10 membered cycloalkyl), —S(=O)($C_{1-6}$alkyl), —S(=O)(3-10 membered cycloalkyl), —S(=O)$_2$($C_{1-6}$alkyl), —S(=O)$_2$(3-10 membered cycloalkyl), —C(=O)($C_{1-6}$alkyl), —C(=O)-(3-10 membered cycloalkyl), —C(=O)OH, —C(=O)(O$C_{1-6}$alkyl), —OC(=O)($C_{1-6}$alkyl), —C(=O)NH$_2$, —C(=O)NH($C_{1-6}$alkyl), —C(=O)N($C_{1-6}$alkyl)$_2$, —NHC(=O)($C_{1-6}$alkyl), —N($C_{1-6}$alkyl)C(=O)($C_{1-6}$alkyl), —OC(=O)O($C_{1-6}$alkyl), —NHC(=O)(O$C_{1-6}$alkyl), —N($C_{1-6}$alkyl)C(=O)(O$C_{1-6}$alkyl), —OC(=O)NH($C_{1-6}$alkyl), —OC(=O)N($C_{1-6}$alkyl)$_2$, —NHC(=O)NH$_2$, —NHC(=O)NH($C_{1-6}$alkyl), —NHC(=O)N($C_{1-6}$alkyl)$_2$, —N($C_{1-6}$alkyl)C(=O)NH$_2$, —N($C_{1-6}$alkyl)C(=O)NH($C_{1-6}$alkyl), —N($C_{1-6}$alkyl)C(=O)N($C_{1-6}$alkyl)$_2$, —S(=O)(O$C_{1-6}$alkyl), —OS(=O)($C_{1-6}$alkyl), —S(=O)NH$_2$, —S(=O)NH($C_{1-6}$alkyl), —S(=O)N($C_{1-6}$alkyl)$_2$, —NHS(=O)($C_{1-6}$alkyl), —N($C_{1-6}$alkyl)S(=O)($C_{1-6}$alkyl), —OS(=O)O($C_{1-6}$alkyl), —NHS(=O)O($C_{1-6}$alkyl), —N($C_{1-6}$alkyl)S(=O)O($C_{1-6}$alkyl), —OS(=O)NH$_2$, —OS(=O)NH($C_{1-6}$alkyl), —OS(=O)N($C_{1-6}$alkyl)$_2$, —NHS(=O)NH$_2$, —NHS(=O)NH($C_{1-6}$alkyl), —NHS(=O)N($C_{1-6}$alkyl)$_2$, —N($C_{1-6}$alkyl)S(=O)NH$_2$, —N($C_{1-6}$alkyl)S(=O)NH($C_{1-6}$alkyl), —N($C_{1-6}$alkyl)S(=O)N($C_{1-6}$alkyl)$_2$, —S(=O)$_2$(O$C_{1-6}$alkyl), —OS(=O)$_2$($C_{1-6}$alkyl), —S(=O)$_2$NH$_2$, —S(=O)$_2$NH($C_{1-6}$alkyl), —S(=O)$_2$N($C_{1-6}$alkyl)$_2$, —NHS(=O)$_2$($C_{1-6}$alkyl), —N($C_{1-6}$alkyl)S(=O)$_2$($C_{1-6}$alkyl), —OS(=O)$_2$O($C_{1-6}$alkyl), —NHS(=O)$_2$O($C_{1-6}$alkyl), —N($C_{1-6}$alkyl)S(=O)$_2$O($C_{1-6}$alkyl), —OS(=O)$_2$NH$_2$, —OS(=O)$_2$NH($C_{1-6}$alkyl), —OS(=O)$_2$N($C_{1-6}$alkyl)$_2$, —NHS(=O)$_2$NH$_2$, —NHS(=O)$_2$NH($C_{1-6}$alkyl), —NHS(=O)$_2$N($C_{1-6}$alkyl)$_2$, —N($C_{1-6}$alkyl)S(=O)$_2$NH$_2$, —N($C_{1-6}$alkyl)S(=O)$_2$NH($C_{1-6}$alkyl), —N($C_{1-6}$alkyl)S(=O)$_2$N($C_{1-6}$alkyl)$_2$, —PH($C_{1-6}$alkyl), —P($C_{1-6}$alkyl)$_2$, —P(=O)H($C_{1-6}$alkyl), —P(=O)($C_{1-6}$alkyl)$_2$, 3-10 membered cycloalkyl, 3-6 membered heterocyclyl, 6-10 membered aryl or 5-10 membered heteroaryl.

[43]. The compound according to any one of [1] to [42], wherein, ($R_{Y1}$ in $Y_1$), ($R_{Y2}$ in $Y_2$) or ($R_{Y3}$ in $Y_3$) at each occurrence is independently selected from —H, -D, —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, —NH$_2$, —NH($C_{1-3}$alkyl), —N($C_{1-3}$alkyl)$_2$, —NH(3-6 membered cycloalkyl), —N($C_{1-3}$alkyl)(3-6 membered cycloalkyl), —OH, —O($C_{1-3}$alkyl), —O-(3-6 membered cycloalkyl), —SH, —S($C_{1-3}$alkyl), —S-(3-6 membered cycloalkyl), —S(=O)($C_{1-3}$alkyl), —S(=O)(3-6 membered cycloalkyl), —S(=O)$_2$($C_{1-3}$alkyl), —S(=O)$_2$-(3-6 membered cycloalkyl), —C(=O)($C_{1-3}$alkyl), —C(=O)-(3-6 membered cycloalkyl), —C(=O)OH, —C(=O)(O$C_{1-3}$alkyl), —OC(=O)($C_{1-3}$alkyl), —C(=O)NH$_2$, —C(=O)NH($C_{1-3}$alkyl), —C(=O)N($C_{1-3}$alkyl)$_2$, —NHC(=O)($C_{1-3}$alkyl), —N($C_{1-3}$alkyl)C(=O)($C_{1-3}$alkyl), —S(=O)(O$C_{1-3}$alkyl), —OS(=O)($C_{1-3}$alkyl), —S(=O)NH$_2$, —S(=O)NH($C_{1-3}$alkyl), —S(=O)N($C_{1-3}$alkyl)$_2$, —NHS(=O)($C_{1-3}$alkyl), —N($C_{1-3}$alkyl)S(=O)($C_{1-3}$alkyl), —S(=O)$_2$(O$C_{1-3}$alkyl), —OS(=O)$_2$($C_{1-3}$alkyl), —S(=O)$_2$NH$_2$, —S(=O)$_2$NH($C_{1-3}$alkyl), —S(=O)$_2$N($C_{1-3}$alkyl)$_2$, —NHS(=O)$_2$($C_{1-3}$alkyl), —N($C_{1-3}$alkyl)S(=O)$_2$($C_{1-3}$alkyl), —P(=O)H($C_{1-3}$alkyl), —P(=O)($C_{1-3}$alkyl)$_2$, 3-6 membered cycloalkyl, 3-6 membered heterocyclyl, 6-10 membered aryl or 5-10 membered heteroaryl, wherein said —$C_{1-3}$alkyl, —$C_{1-3}$haloalkyl, —$C_{1-3}$haloalkoxy, —$C_{2-6}$alkenyl, —$C_{2-6}$alkynyl, 3-6 membered cycloalkyl, 3-6 membered heterocyclyl, 6-10 membered aryl or 5-10 membered heteroaryl is independently optionally substituted with 1, 2, 3, 4, 5 or 6 substituents selected from —F, —Cl, —Br, —$C_{1-3}$alkyl, —$C_{1-3}$haloalkyl, —CN, —NH$_2$, —NH($C_{1-3}$alkyl), —N($C_{1-3}$alkyl)$_2$, —OH, —O($C_{1-3}$alkyl), —SH, —S($C_{1-3}$alkyl), —S(=O)($C_{1-3}$alkyl), —S(=O)$_2$($C_{1-3}$alkyl), —C(=O)($C_{1-3}$alkyl), —C(=O)OH, —C(=O)(O$C_{1-3}$alkyl), —OC(=O)($C_{1-3}$alkyl), —C(=O)NH$_2$, —C(=O)NH($C_{1-3}$alkyl), —C(=O)N($C_{1-3}$alkyl)$_2$, —NHC(=O)($C_{1-3}$alkyl), —N($C_{1-3}$alkyl)C(=O)($C_{1-3}$alkyl), —S(=O)(OC$_{1-3}$alkyl), —OS(=O)(C$_{1-3}$alkyl), —S(=O)NH$_2$, —S(=O)NH(C$_{1-3}$alkyl), —S(=O)N(C$_{1-3}$alkyl)$_2$, —NHS(=O)(C$_{1-3}$alkyl), —N(C$_{1-3}$alkyl)S(=O)(C$_{1-3}$alkyl), —S(=O)$_2$(OC$_{1-3}$alkyl), —OS(=O)$_2$(C$_{1-3}$alkyl), —S(=O)$_2$NH$_2$, —S(=O)$_2$NH(C$_{1-3}$alkyl), —S(=O)$_2$N(C$_{1-3}$alkyl)$_2$, —NHS(=O)$_2$(C$_{1-3}$alkyl), —N(C$_{1-3}$alkyl)S(=O)$_2$(C$_{1-3}$alkyl), —P(=O)H(C$_{1-3}$alkyl), —P(=O)(C$_{1-3}$alkyl)$_2$ or 3-6 membered cycloalkyl.

[44]. The compound according to any one of [1] to [43], wherein, (R$_{Y1}$ in Y$_1$), (R$_{Y2}$ in Y$_2$) or (R$_{Y3}$ in Y$_3$) at each occurrence is independently selected from —H, -D, —Cl, —F, —Br, —CH$_3$, —CD$_3$, —CH$_2$CH$_3$, —CH$_2$CH$_2$CH$_3$, —CH(CH$_3$)$_2$, —C(CH$_3$)$_3$,

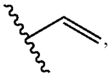, 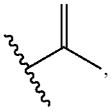, 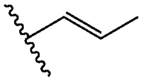, 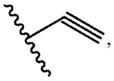,

—CH$_2$F, —CHF$_2$, —CF$_3$, —CH$_2$CH$_2$F, —CH$_2$CHF$_2$, —CH$_2$CF$_3$, —CHFCH$_3$, —CF$_2$CH$_3$, —CN, —NH$_2$, —NH(CH$_3$), —N(CH$_3$)$_2$, —NH(CH$_2$CH$_3$), —OH, —O—CH$_3$, —O—CH$_2$CH$_3$, —O—CH$_2$CH$_2$CH$_3$, —O—CH(CH$_3$)$_2$, —O—CF$_3$, —SH, —S—CH$_3$, —S—CH$_2$CH$_3$, —S—CH$_2$CH$_2$CH$_3$, —S—CH(CH$_3$)$_2$, —S—CF$_3$, —S(=O)CH$_3$, —S(=O)(CH$_2$CH$_3$), —S(=O)(CH$_2$CH$_2$CH$_3$), —S(=O)(CH(CH$_3$)$_2$), —S(=O)$_2$CH$_3$, —S(=O)$_2$(CH$_2$CH$_3$), —S(=O)$_2$(CH$_2$CH$_2$CH$_3$), —S(=O)$_2$(CH(CH$_3$)$_2$), —COOH, —C(=O)(CH$_3$), —C(=O)(CH$_2$CH$_3$), —C(=O)(CH(CH$_3$)$_2$), —C(=O)(CF$_3$), —C(=O)(OCH$_3$), —C(=O)(OCH$_2$CH$_3$), —C(=O)(OCH$_2$CH$_2$CH$_3$), —C(=O)(OCH(CH$_3$)$_2$), —OC(=O)(CH$_3$), —OC(=O)(CH$_2$CH$_3$), —OC(=O)(CH$_2$CH$_2$CH$_3$), —OC(=O)(CH(CH$_3$)$_2$), —C(=O)NH$_2$, —C(=O)NH(CH$_3$), —C(=O)NH(CH$_2$CH$_3$), —C(=O)NH(CH$_2$CH$_2$CH$_3$), —C(=O)NH(CH(CH$_3$)$_2$), —C(=O)N(CH$_3$)$_2$, —C(=O)N(CH$_2$CH$_3$)$_2$, —NHC(=O)(CH$_3$), —NHC(=O)(CH$_2$CH$_3$), —NHC(=O)(CH$_2$CH$_2$CH$_3$), —NHC(=O)(CH(CH$_3$)$_2$), —N(CH$_3$)C(=O)(CH$_3$), —S(=O)(OCH$_3$), —S(=O)(OCH$_2$CH$_3$), —S(=O)(OCH$_2$CH$_2$CH$_3$), —S(=O)(OCH(CH$_3$)$_2$), —OS(=O)(CH$_3$), —OS(=O)(CH$_2$CH$_3$), —OS(=O)(CH$_2$CH$_2$CH$_3$), —OS(=O)(CH(CH$_3$)$_2$), —S(=O)NH$_2$, —S(=O)NH(CH$_3$), —S(=O)NH(CH$_2$CH$_3$), —S(=O)NH(CH$_2$CH$_2$CH$_3$), —S(=O)NH(CH(CH$_3$)$_2$), —S(=O)N(CH$_3$)$_2$, —S(=O)N(CH$_3$)(CH$_2$CH$_3$), —NHS(=O)(CH$_3$), —NHS(=O)(CH$_2$CH$_3$), —NHS(=O)(CH$_2$CH$_2$CH$_3$), —NHS(=O)(CH(CH$_3$)$_2$), —N(CH$_3$)S(=O)(CH$_3$), —S(=O)$_2$(OCH$_3$), —S(=O)$_2$(OCH$_2$CH$_3$), —S(=O)$_2$(OCH$_2$CH$_2$CH$_3$), —S(=O)$_2$(OCH(CH$_3$)$_2$), —OS(=O)$_2$(CH$_3$), —OS(=O)$_2$(CH$_2$CH$_3$), —OS(=O)$_2$(CH$_2$CH$_2$CH$_3$), —OS(=O)$_2$(CH(CH$_3$)$_2$), —S(=O)$_2$NH$_2$, —S(=O)$_2$NH(CH$_3$), —S(=O)$_2$NH(CH$_2$CH$_3$), —S(=O)$_2$NH(CH$_2$CH$_2$CH$_3$), —S(=O)$_2$NH(CH(CH$_3$)$_2$), —S(=O)$_2$N(CH$_3$)$_2$, —S(=O)$_2$N(CH$_3$)(CH$_2$CH$_3$), —NHS(=O)$_2$(CH$_3$), —NHS(=O)$_2$(CH$_2$CH$_3$), —NHS(=O)$_2$(CH$_2$CH$_2$CH$_3$), —NHS(=O)$_2$(CH(CH$_3$)$_2$), —N(CH$_3$)S(=O)$_2$(CH$_3$), —P(=O)H(CH$_3$), —P(=O)H(CH$_2$CH$_3$), —P(=O)H(CH$_2$CH$_2$CH$_3$), —P(=O)H(CH(CH$_3$)$_2$), —P(=O)(CH$_3$)$_2$, —P(=O)(CH$_3$)(CH$_2$CH$_3$), —CH$_2$—OH, —CH$_2$CH$_2$—OH, —CH(CH$_3$)—OH, —CH$_2$—SH, —CH$_2$CH$_2$—SH, —CH(CH$_3$)—SH, —CH$_2$—NH$_2$, —CH$_2$CH$_2$—NH$_2$, —CH(CH$_3$)—NH$_2$, —CH$_2$—CN, —CH$_2$CH$_2$—CN, —CH(CH$_3$)—CN, —O—CH$_3$—O—CH$_3$, —O—CH$_2$CH$_3$—O—CH$_3$, —O—CH(CH$_3$)—O—CH$_3$, —O—CH$_2$CH$_2$CH$_3$—O—CH$_3$, —O—CH$_2$CH(CH$_3$)—O—CH$_3$, —O—CH(CH$_3$)CH$_2$—O—CH$_3$, —NH—O—CH$_3$, —N(CH$_3$)—O—CH$_3$, —N(CH$_2$CH$_3$)—O—CH$_3$,

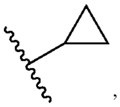, 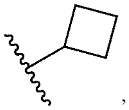, 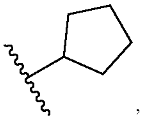, 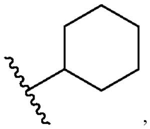, 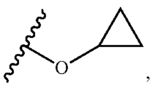, 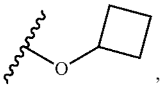, 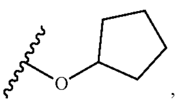, 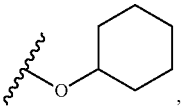, 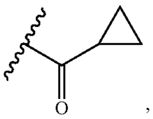, 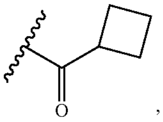, 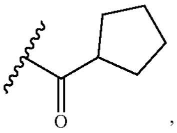, 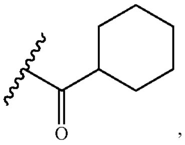, 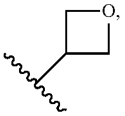 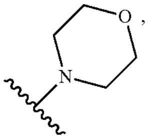 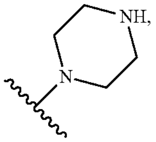 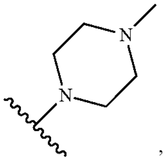, 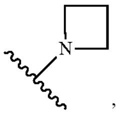, 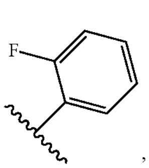, 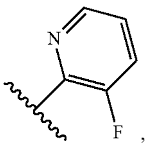, 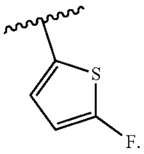.

[45]. The compound according to any one of [1] to [44], wherein, (R$_{Y1}$ in Y$_1$), (R$_{Y2}$ in Y$_2$) or (R$_{Y3}$ in Y$_3$) at each occurrence is independently selected from —H, -D, —Cl, —F, —Br, —CH$_3$, —CD$_3$, —CH$_2$CH$_3$, —CH(CH$_3$)$_2$, —C(CH$_3$)$_3$, —CH$_2$F, —CHF$_2$, —CF$_3$, —CH$_2$CH$_2$F, —CH$_2$CHF$_2$, —CH$_2$CF$_3$, —CHFCH$_3$, —CF$_2$CH$_3$, —CN, —NH$_2$, —NH(CH$_3$), —N(CH$_3$)$_2$, —OH, —O—CH$_3$, —O—CH(CH$_3$)$_2$, —O—CF$_3$, —SH, —S—CH$_3$, —S—CH(CH$_3$)$_2$, —S—CF$_3$, —S(=O)CH$_3$, —S(=O)$_2$CH$_3$, —C(=O)(CH$_3$), —C(=O)(CH$_2$CH$_3$), —C(=O)(CH(CH$_3$)$_2$), —C(=O)(CF$_3$), —C(=O)NH$_2$, —C(=O)NH(CH$_3$), —NHC(=O)(CH$_3$), —S(=O)NH$_2$, —S(=O)NH(CH$_3$), —NHS(=O)(CH$_3$), —S(=O)$_2$NH$_2$, —S(=O)$_2$NH(CH$_3$), —NHS(=O)$_2$(CH$_3$), —CH$_2$—OH, —CH$_2$CH$_2$—OH, —CH(CH$_3$)—OH, —CH$_2$—NH$_2$, —CH$_2$CH$_2$—NH$_2$, —CH(CH$_3$)—NH$_2$, —CH$_2$—CN, —CH$_2$CH$_2$—CN, —CH(CH$_3$)—CN,

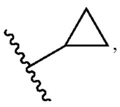, 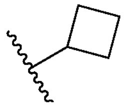, 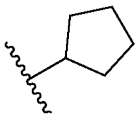 or

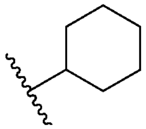.

[46]. The compound according to any one of [1] to [45], wherein, ($R_{Y1}$ in $Y_1$), ($R_{Y2}$ in $Y_2$) or ($R_{Y3}$ in $Y_3$) at each occurrence is independently selected from —H, -D, —$CH_3$, or —$CD_3$.

[47]. The compound according to any one of [1] to [46], wherein, $Y_1$ at each occurrence is independently selected from —$C(R_{Y1})_2$—, —C(═O)—, —O—, —$NR_{Y1}$—, —S—, —S(═O)—, —$S(═O)_2$—, —$PR_{Y1}$—, —P(═O)$R_{Y1}$—, —C(═O)$NR_{Y1}$—, —$NR_{Y1}$C(═O)—, —S(═O)$NR_{Y1}$—, —$NR_{Y1}$S(═O)—, —$S(═O)_2NR_{Y1}$—, or —$NR_{Y1}S(═O)_2$—; in some embodiments, $Y_1$ at each occurrence is independently selected from —$C(R_{Y1})_2$—, —C(═O)—, —O—, —$NR_{Y1}$—, —S—, —S(═O)—, —$S(═O)_2$—, —C(═O)$NR_{Y1}$—, —$NR_{Y1}$C(═O)—, —S(═O)$NR_{Y1}$—, —$NR_{Y1}$S(═O)—, —$S(═O)_2NR_{Y1}$—, or —$NR_{Y1}S(═O)_2$—; in some embodiments, $Y_1$ at each occurrence is independently selected from —$CH_2$—, —$CH(CH_3)$—, —$CH(CH_2CH_3)$—, —$C(CH_3)_2$—, —O—, —NH—, —$N(CH_3)$—, —$N(CH_2CH_3)$—, —$N(CH(CH_3)_2)$—, —C(═O)—, —C(═O)NH—, —C(═O)$N(CH_3)$—, —NH—C(═O)—, —$N(CH_3)$—C(═O)—, —S—, —S(═O)—, —NH—S(═O)—, —$N(CH_3)$—S(═O)—, —$S(═O)_2$—, —NH—$S(═O)_2$— or —$N(CH_3)$—$S(═O)_2$—; in some embodiments, $Y_1$ is selected from —O— or —NH—;

Optionally, ($R_{Y1}$ in $Y_1$) and $R_1$ on the adjacent carbon atom together with the atoms to which they are respectively attached form ring D, ring D is selected from a 3-10 membered cycloalkyl ring, a 3-10 membered cycloalkenyl ring, a 3-10 membered heterocycloalkyl ring, a 3-10 membered heterocycloalkenyl ring, a 6-10 membered aryl ring or a 5-12 member heteroaryl ring; in some embodiments, ring D is selected from a 3 membered monocyclic cycloalkyl ring, a 3 membered monocyclic cycloalkenyl ring, a 3 membered monocyclic heterocycloalkyl ring, a 3 membered monocyclic heterocycloalkenyl ring, 4 membered monocyclic cycloalkyl ring, a 4 membered monocyclic cycloalkenyl ring, a 4 membered monocyclic heterocycloalkyl ring, a 4 membered monocyclic heterocycloalkenyl ring, 4 membered fused cycloalkyl ring, a 4 membered fused cycloalkenyl ring, a 4 membered fused heterocycloalkyl ring, a 4 membered fused heterocycloalkenyl ring, a 5 membered monocyclic cycloalkyl ring, a 5 membered monocyclic cycloalkenyl ring, a 5 membered bridged cycloalkyl ring, a 5 membered bridged cycloalkenyl ring, a 5 membered fused cycloalkyl ring, a 5 membered fused cycloalkenyl ring, a 5 membered spirocyclic cycloalkyl ring, a 5 membered spirocyclic cycloalkenyl ring, a 5 membered monocyclic heterocycloalkyl ring, a 5 membered monocyclic heterocycloalkenyl ring, a 5 membered bridged heterocycloalkyl ring, a 5 membered bridged heterocycloalkenyl ring, a 5 membered fused heterocycloalkyl ring, a 5 membered fused heterocycloalkenyl ring, a 5 membered spirocyclic heterocycloalkyl ring, a 5 membered spirocyclic heterocycloalkenyl ring, a 6 membered monocyclic cycloalkyl ring, a 6 membered monocyclic cycloalkenyl ring, a 6 membered bridged cycloalkyl ring, a 6 membered bridged cycloalkenyl ring, a 6 membered fused cycloalkyl ring, a 6 membered fused cycloalkenyl ring, a 6 membered spirocyclic cycloalkyl ring, a 6 membered spirocyclic cycloalkenyl ring, a 6 membered monocyclic heterocycloalkyl ring, a 6 membered monocyclic heterocycloalkenyl ring, a 6 membered bridged heterocycloalkyl ring, a 6 membered bridged heterocycloalkenyl ring, a 6 membered fused heterocycloalkyl ring, a 6 membered fused heterocycloalkenyl ring, a 6 membered spirocyclic heterocycloalkyl ring, a 6 membered spirocyclic heterocycloalkenyl ring, a 7 membered monocyclic cycloalkyl ring, a 7 membered monocyclic cycloalkenyl ring, a 7 membered spirocyclic cycloalkyl ring, a 7 membered spirocyclic cycloalkenyl ring, a 7 membered fused cycloalkyl ring, a 7 membered fused cycloalkenyl ring, a 7 membered bridged cycloalkyl ring, a 7 membered bridged cycloalkenyl ring, a 7 membered monocyclic heterocycloalkyl ring, a 7 membered monocyclic heterocycloalkenyl ring, a 7 membered spirocyclic heterocycloalkyl ring, a 7 membered spirocyclic heterocycloalkenyl ring, a 7 membered fused heterocycloalkyl ring, a 7 membered fused heterocycloalkenyl ring, a 7 membered bridged heterocycloalkyl ring, a 7 membered bridged heterocycloalkenyl ring, a 8 membered monocyclic cycloalkyl ring, a 8 membered monocyclic cycloalkenyl ring, a 8 membered spirocyclic cycloalkyl ring, a 8 membered spirocyclic cycloalkenyl ring, a 8 membered fused cycloalkyl ring, a 8 membered fused cycloalkenyl ring, a 8 membered bridged cycloalkyl ring, a 8 membered bridged cycloalkenyl ring, a 8 membered monocyclic heterocycloalkyl ring, a 8 membered monocyclic heterocycloalkenyl ring, a 8 membered spirocyclic heterocycloalkyl ring, a 8 membered spirocyclic heterocycloalkenyl ring, a 8 membered fused heterocycloalkyl ring, a 8 membered fused heterocycloalkenyl ring, a 8 membered bridged heterocycloalkyl ring, a 8 membered bridged heterocycloalkenyl ring, a 9 membered monocyclic cycloalkyl ring, a 9 membered monocyclic cycloalkenyl ring, a 9 membered spirocyclic cycloalkyl ring, a 9 membered spirocyclic cycloalkenyl ring, a 9 membered fused cycloalkyl ring, a 9 membered fused cycloalkenyl ring, a 9 membered bridged cycloalkyl ring, a 9 membered bridged cycloalkenyl ring, a 9 membered monocyclic heterocycloalkyl ring, a 9 membered monocyclic heterocycloalkenyl ring, a 9 membered spirocyclic heterocycloalkyl ring, a 9 membered spirocyclic heterocycloalkenyl ring, a 9 membered fused heterocycloalkyl ring, a 9 membered fused heterocycloalkenyl ring, a 9 membered bridged heterocycloalkyl ring, a 9 membered bridged heterocycloalkenyl ring, a 10 membered monocyclic cycloalkyl ring, a 10 membered monocyclic cycloalkenyl ring, a 10 membered spirocyclic cycloalkyl ring, a 10 membered spirocyclic cycloalkenyl ring, a 10 membered fused cycloalkyl ring, a 10 membered fused cycloalkenyl ring, a 10 membered bridged cycloalkyl ring, a 10 membered bridged cycloalkenyl ring, a 10 membered monocyclic heterocycloalkyl ring, a 10 membered monocyclic heterocycloalkenyl ring, a 10 membered spirocyclic heterocycloalkyl ring, a 10 membered spirocyclic heterocycloalkenyl ring, a 10 membered fused heterocycloalkyl ring, a 10 membered fused heterocycloalkenyl ring, a 10 membered bridged heterocycloalkyl ring, a 10 membered bridged heterocycloalkenyl ring, a phenyl ring, a naphthalene ring, a 5 membered heteroaryl ring, a 6 membered heteroaryl ring, a 7 membered heteroaryl ring, a 8 membered heteroaryl ring, a 9 membered heteroaryl ring or a 10 membered heteroaryl ring; said heterocycloalkyl or heterocycloalkenyl at each occurrence contains one or more ring members selected from N, O, S, —C(=O)—, —C(=O)O—, —OC(=O)—, —C(=O)NH—, —NHC(=O)—, —S(=O)—, —S(=O)O—, —OS(=O)—, —S(=O)NH—, —NHS(=O)—, $—S(=O)_2—$, $—S(=O)_2O—$, $—OS(=O)_2—$, $—S(=O)_2NH—$, or $—NHS(=O)_2—$; said heteroaryl at each occurrence independently contains one or more heteroatoms selected from N, O or S; in some embodiments, ring D is selected from a 4 membered monocyclic heterocycloalkyl ring, 5 membered monocyclic heterocycloalkyl ring, a 6 membered monocyclic heterocycloalkyl ring, a 7 membered monocyclic heterocycloalkyl ring, a 9 membered spirocyclic heterocycloalkyl ring, a 9 membered fused heterocycloalkyl ring, a 9 membered bridged heterocycloalkyl ring, said heterocycloalkyl at each occurrence optionally further contains one or more ring members selected from N, O, S; in some embodiments, ring D is selected from a 4 membered monocyclic heterocycloalkyl ring containing 1 N, a 5 membered monocyclic heterocycloalkyl ring containing 1 N, a 6 membered monocyclic heterocycloalkyl ring containing 1 N and optionally further containing 1 O, a 9 membered fused heterocycloalkyl ring containing 1 N.

[48]. The compound according to any one of [1] to [47], wherein, $Y_1$ is selected from $—C(R_{Y1})_2—$, —O—, $—NR_{Y1}—$, —S—, —S(=O)—, $—S(=O)_2—$;

Wherein:

$R_{Y1}$ is selected from hydrogen or $—C_{1-3}alkyl$; or $R_{Y1}$ and $R_1$ on the adjacent carbon atom together with the atoms to which they are respectively attached form

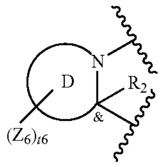

when $Y_1$ is selected from $—NR_{Y1}—$;

& indicates that the carbon atom in ring D is R configuration or S configuration when the carbon atom is a chiral carbon atom; in some embodiments, & indicates that the carbon atom in ring D is R configuration when the carbon atom is a chiral carbon atom; in some embodiments, & indicates that the carbon atom in ring D is S configuration when the carbon atom is a chiral carbon atom.

[49]. The compound according to any one of [1] to [48], wherein, $Y_1$ is selected from —O— or $—NR_{Y1}—$;

Wherein:

$R_{Y1}$ is selected from hydrogen or $—C_{1-3}alkyl$; or $R_{Y1}$ and $R_1$ on the adjacent carbon atom together with the atoms to which they are respectively attached form

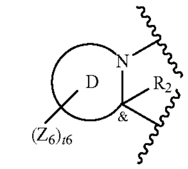

;

& indicates that the carbon atom in ring D is R configuration or S configuration when the carbon atom is a chiral carbon atom; in some embodiments, & indicates that the carbon atom in ring D is R configuration when the carbon atom is a chiral carbon atom; in some embodiments, & indicates that the carbon atom in ring D is S configuration when the carbon atom is a chiral carbon atom;

In some embodiments, the moiety of

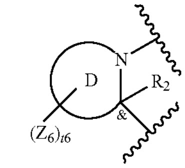

is selected from

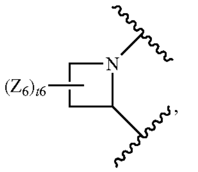

,

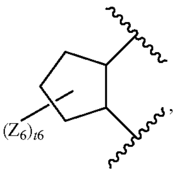

,

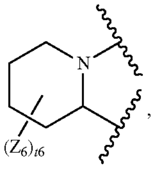

,

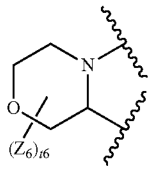

or

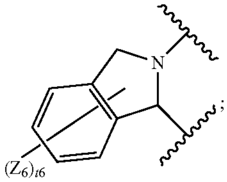

;

in some embodiments, the moiety of

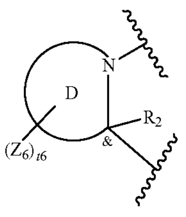

is selected from

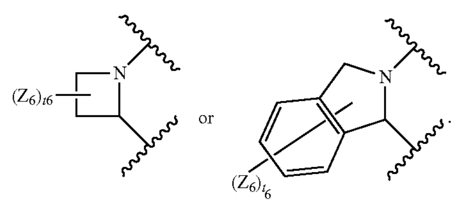

[50]. The compound according to any one of [1] to [49], wherein, the compound is selected from the following formula (II), formula (III) or formula (IV):

Wherein,

& in any one of formulas indicates that the carbon atom is R configuration or S configuration when the carbon atom is a chiral carbon atom; in some embodiments, & in any one of formulas indicates that the carbon atom is R configuration when the carbon atom is a chiral carbon atom; in some embodiments, & in any one of formulas indicates that the carbon atom is S configuration when the carbon atom is a chiral carbon atom;

$m_5$ is selected from 0, 1, 2, 3, 4, 5 or 6; in some embodiments, $m_5$ is selected from 0, 1, or 2, in some embodiments, $m_5$ is selected from 0; in some embodiments, $m_5$ is selected from 1; in some embodiments, $m_5$ is selected from 2.

[51]. The compound according to [50], wherein, the compound is selected from the following formula (V), formula (VI) or formula (VII):

(II)

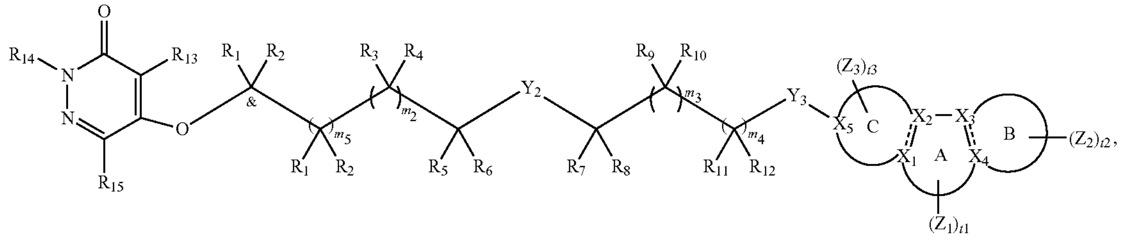

(III)

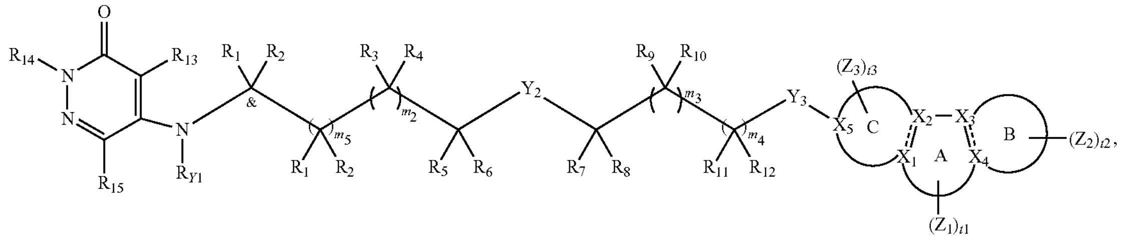

or (IV)

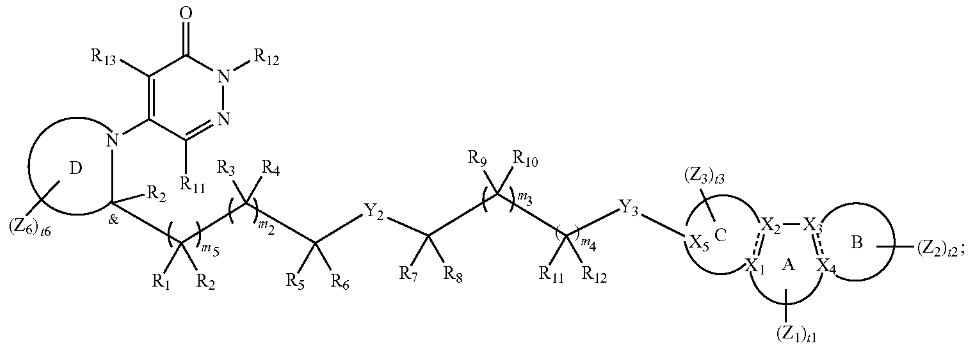

;

(V)

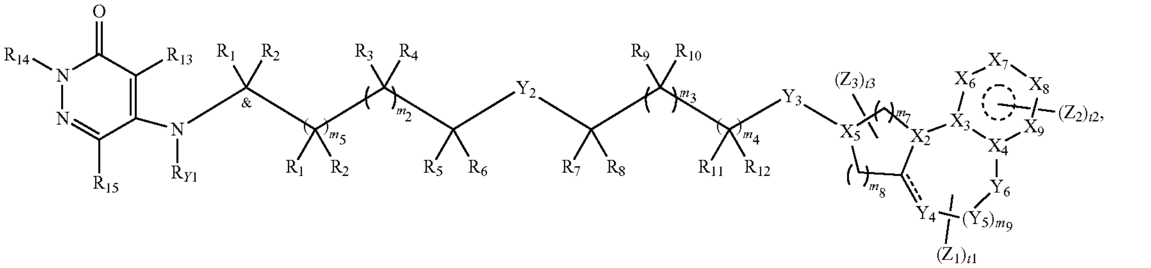

(VI)

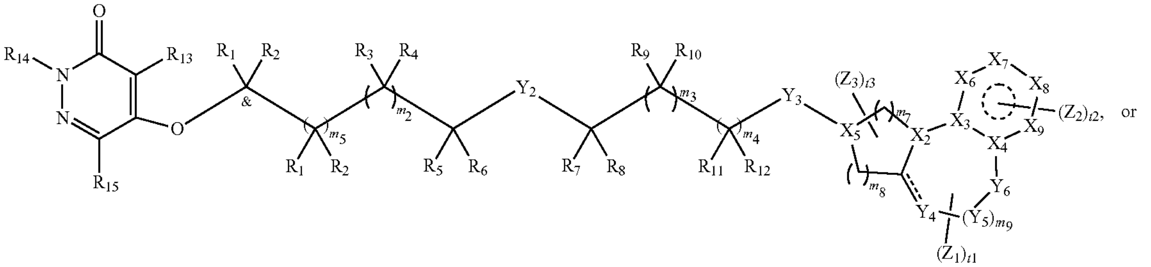

or (VII)

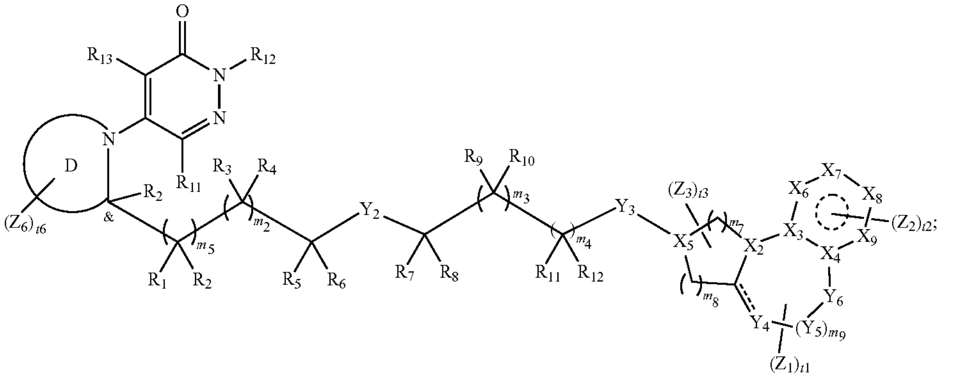

& in any one of formulas indicates that the carbon atom is R configuration or S configuration when the carbon atom is a chiral carbon atom; in some embodiments, & in any one of formulas indicates that the carbon atom is R configuration when the carbon atom is a chiral carbon atom; in some embodiments, & in any one of formulas indicates that the carbon atom is S configuration when the carbon atom is a chiral carbon atom.

[52]. The compound according to [50] or [51], wherein, the compound is selected from any one of the following formulas:

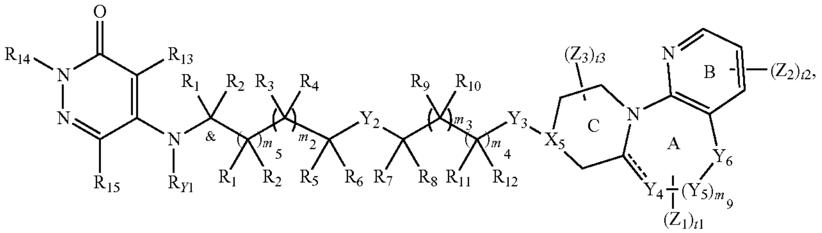

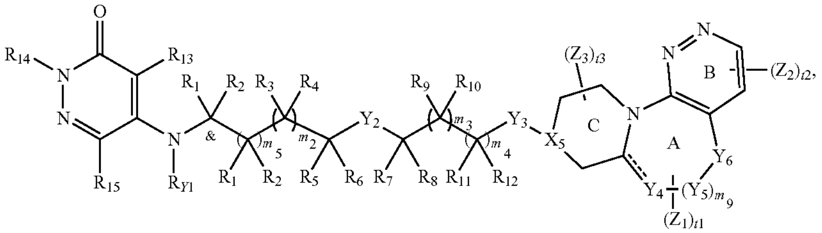

-continued
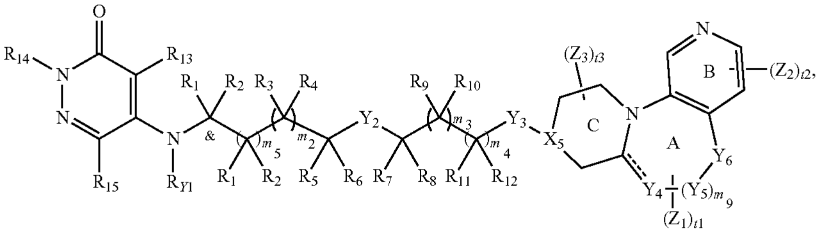
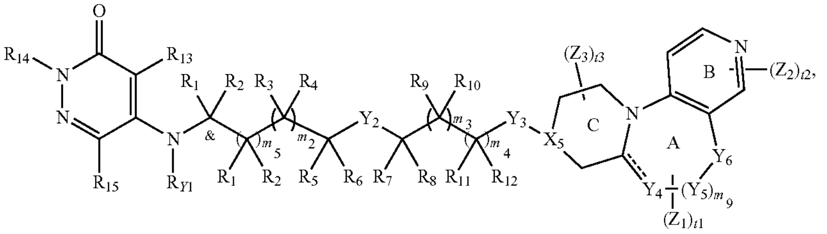
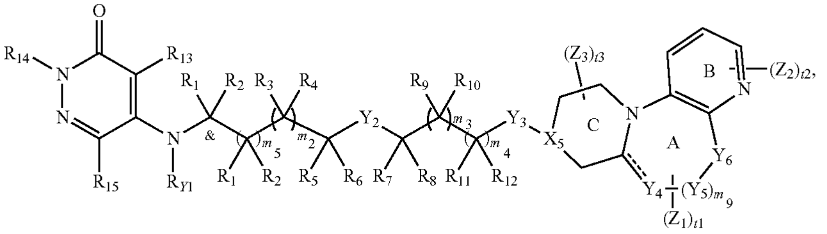
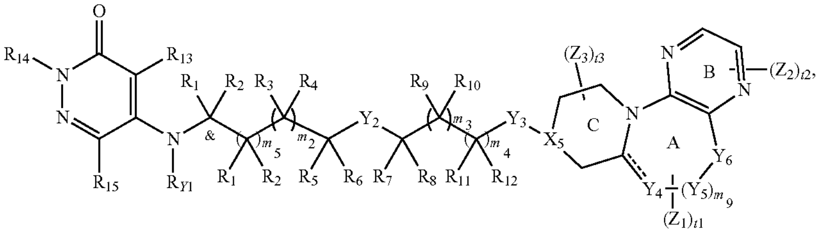
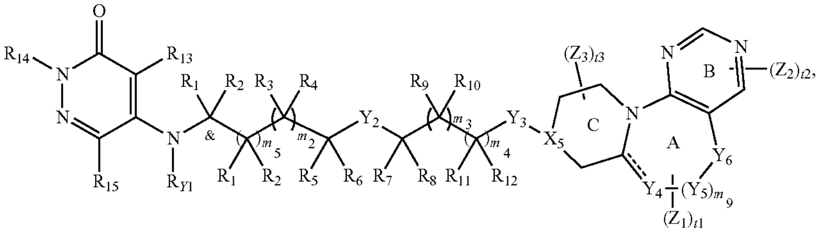
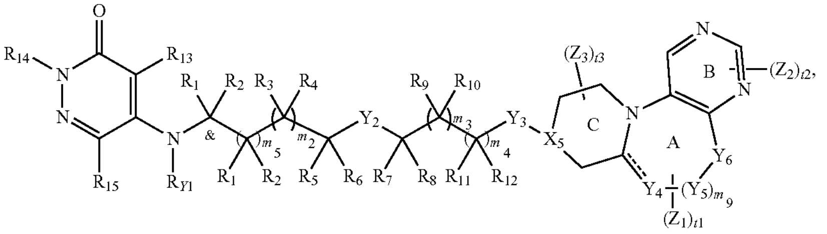
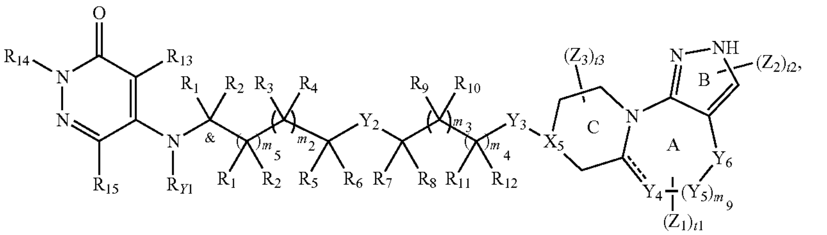

-continued
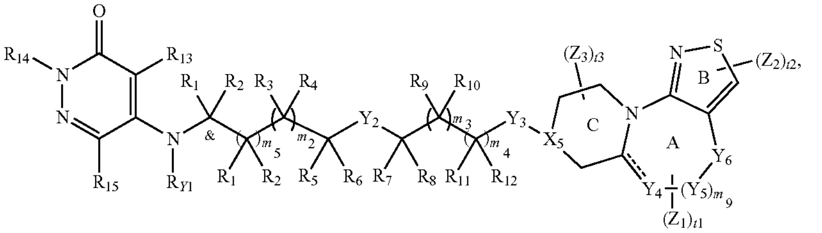
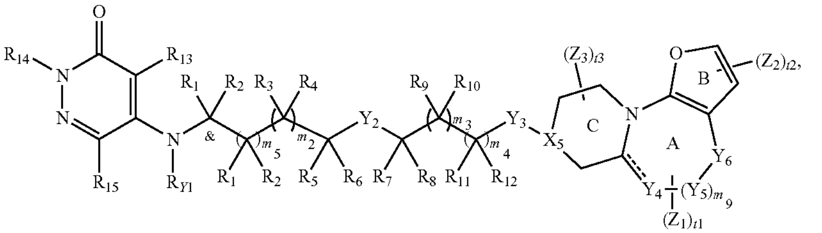
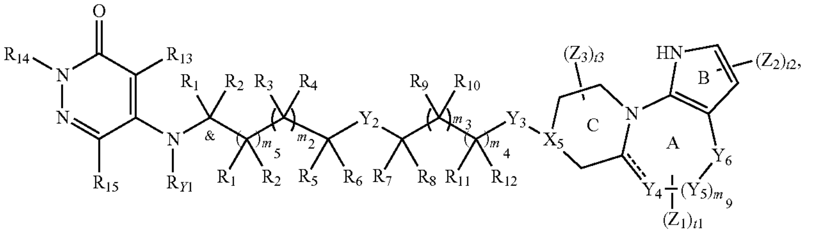
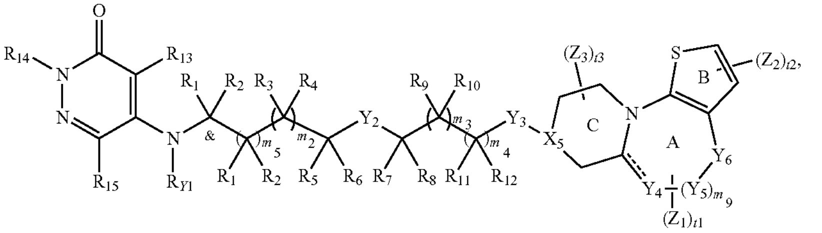
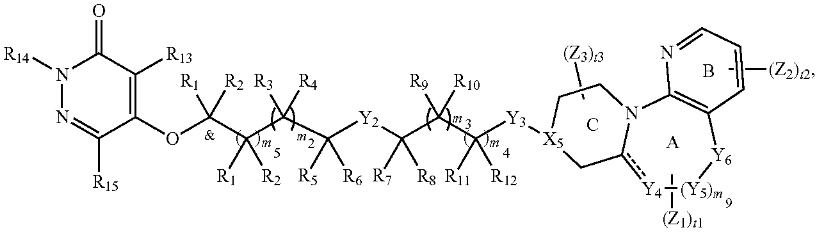
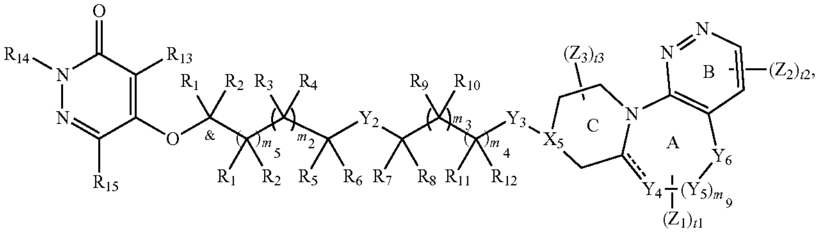
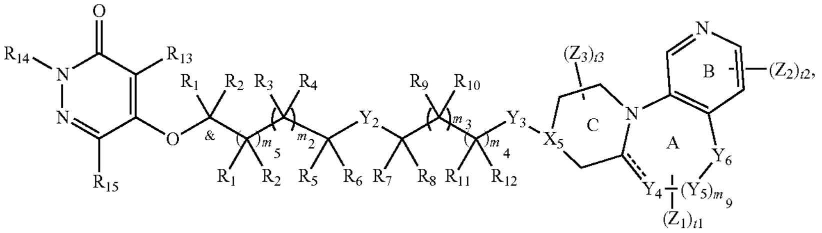

-continued
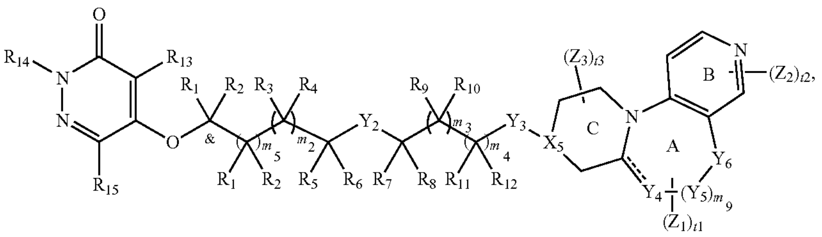
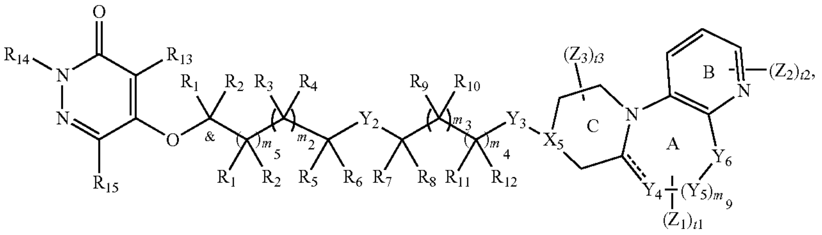
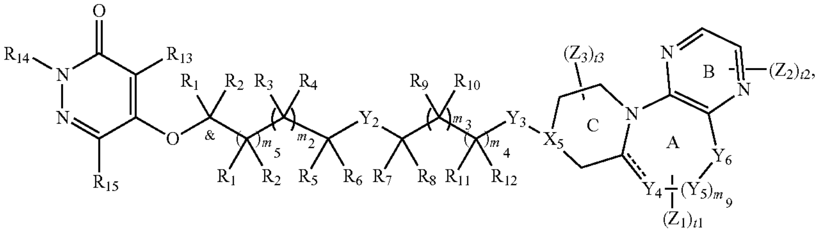
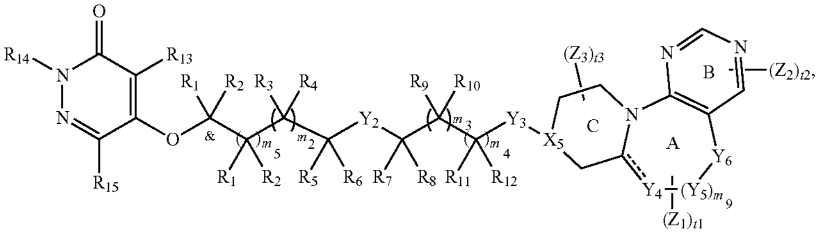
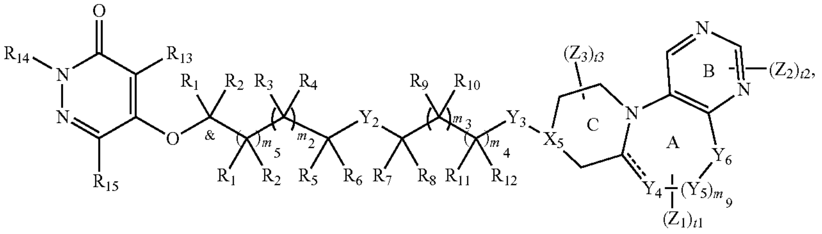
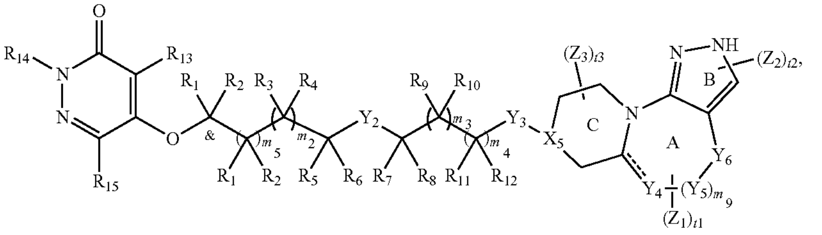
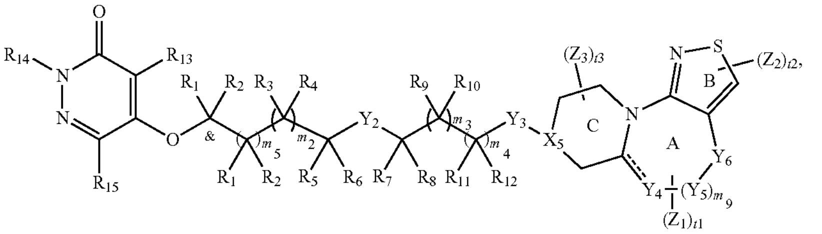

-continued
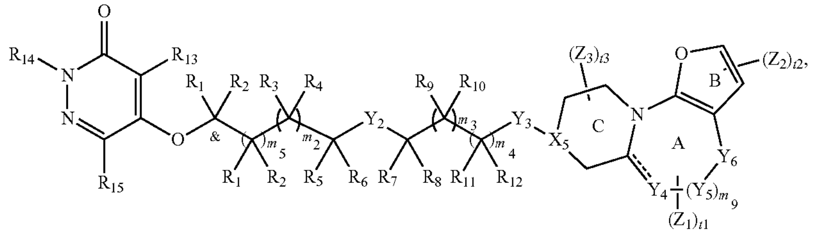
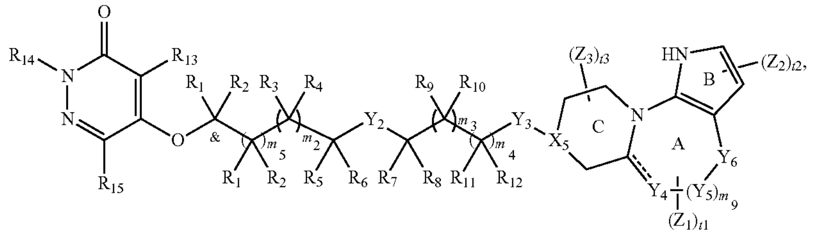
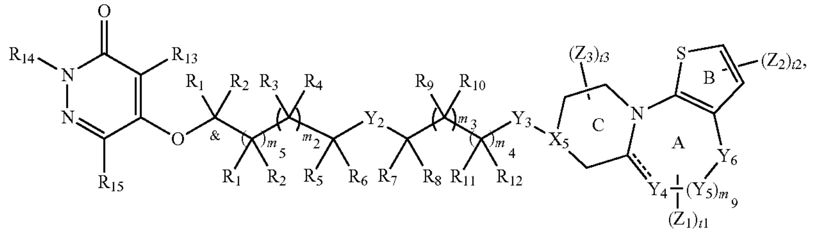
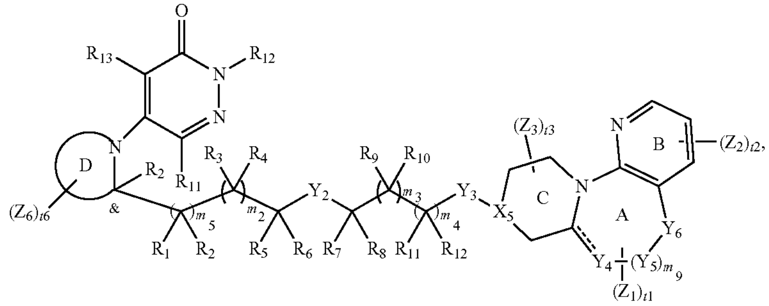
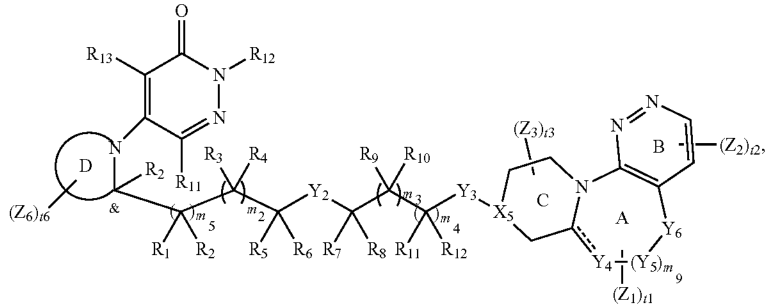
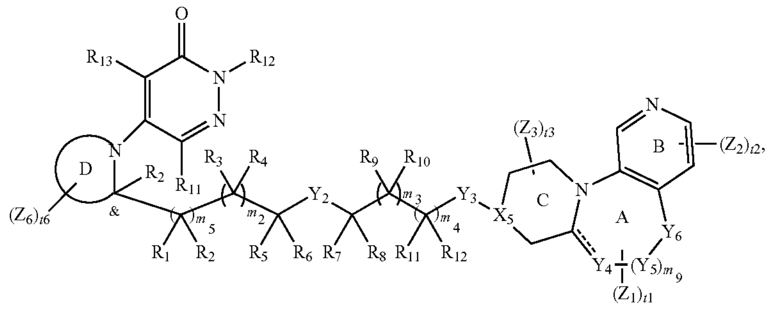

-continued
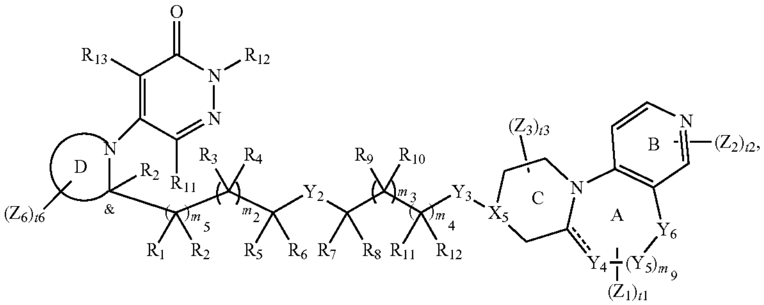
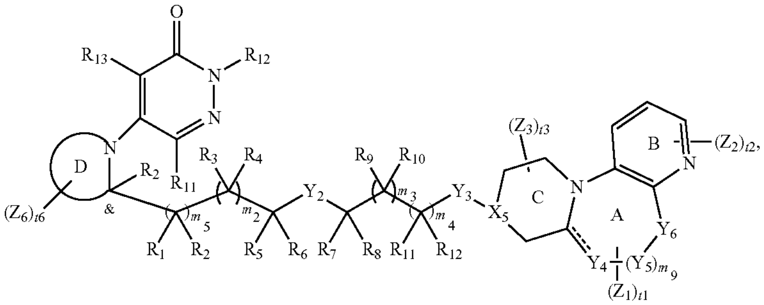
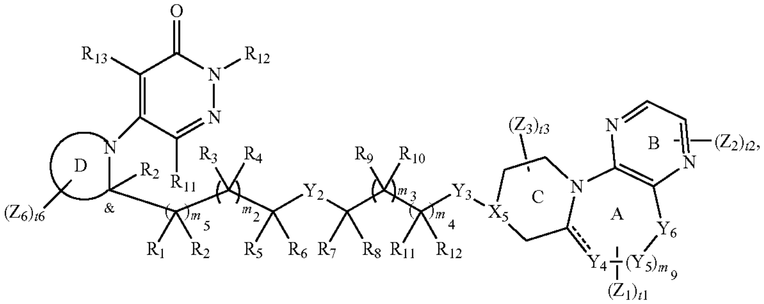
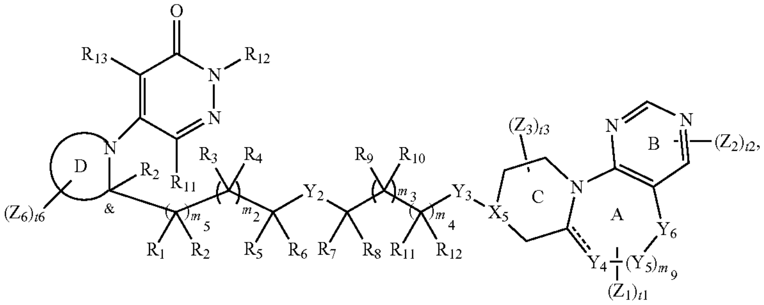
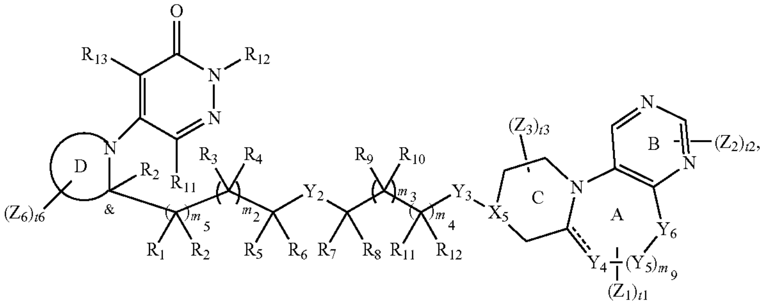

-continued
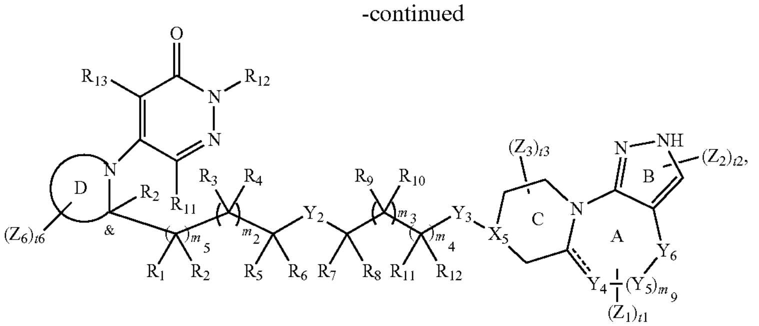
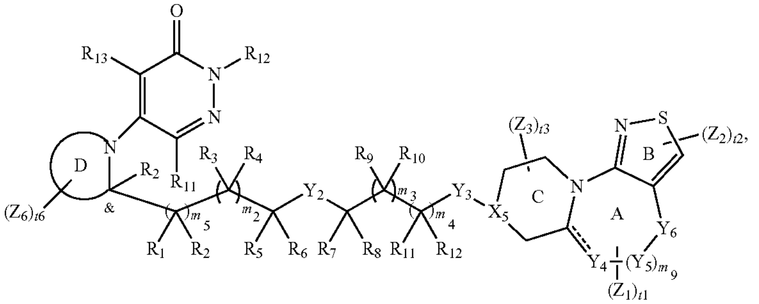
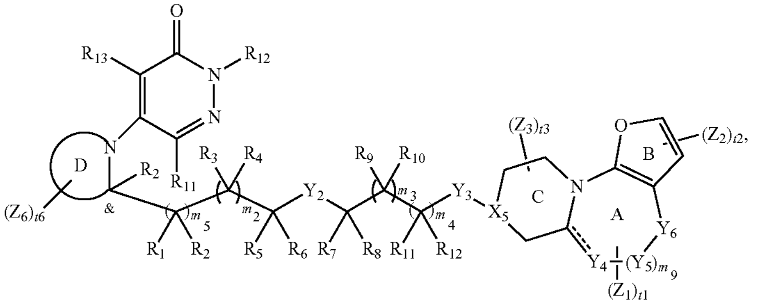
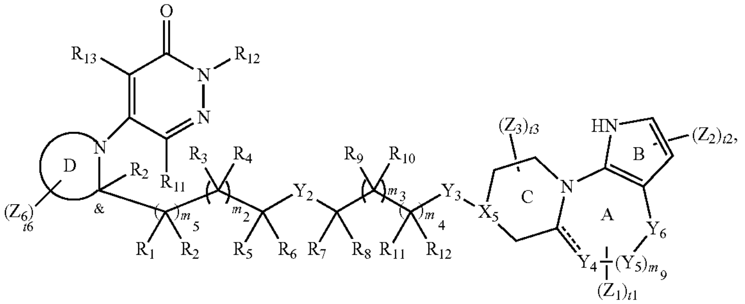
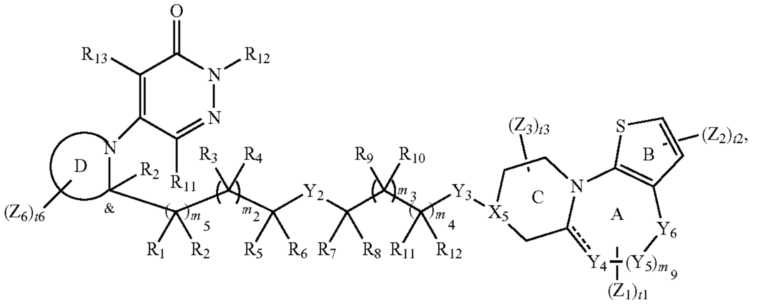
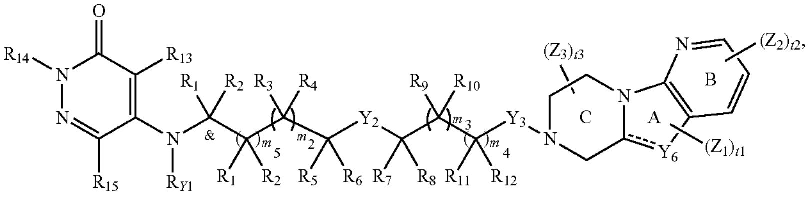

-continued
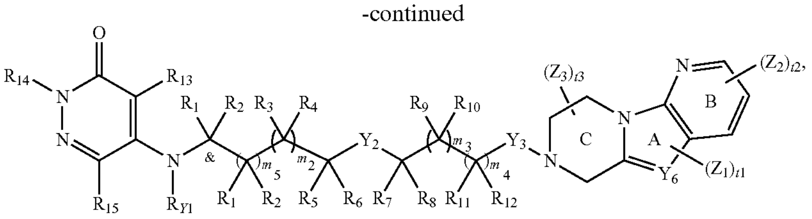
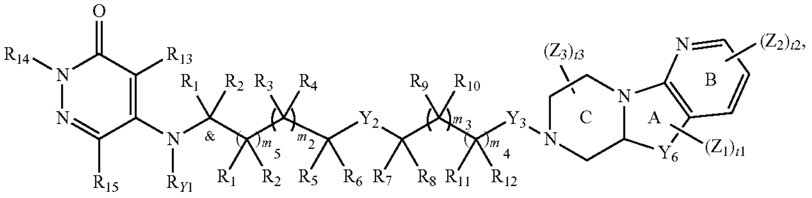
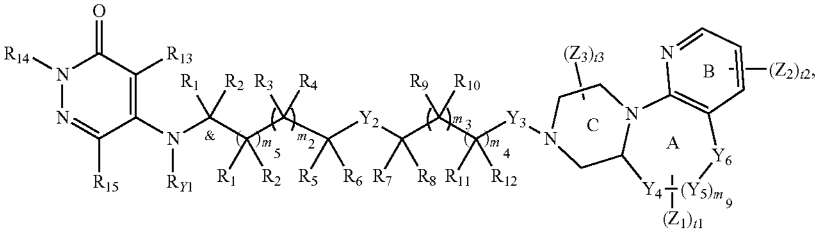
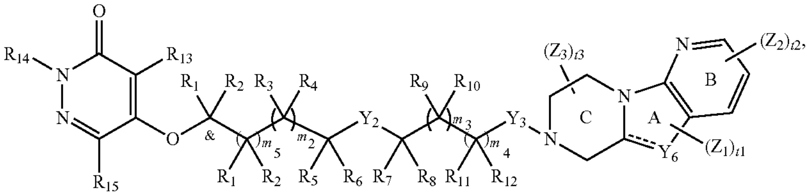
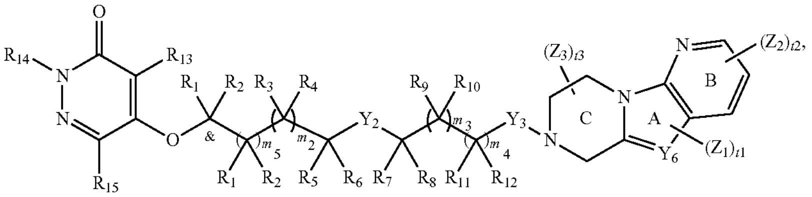
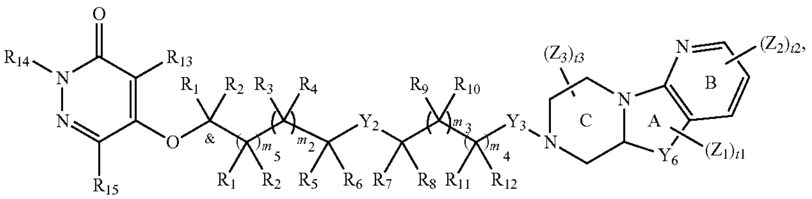
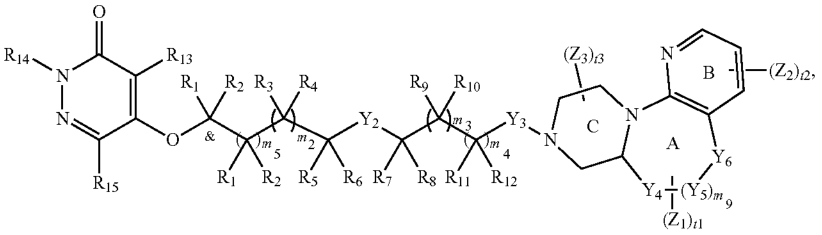
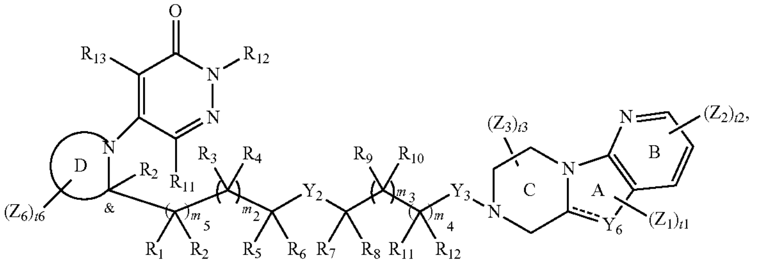

-continued

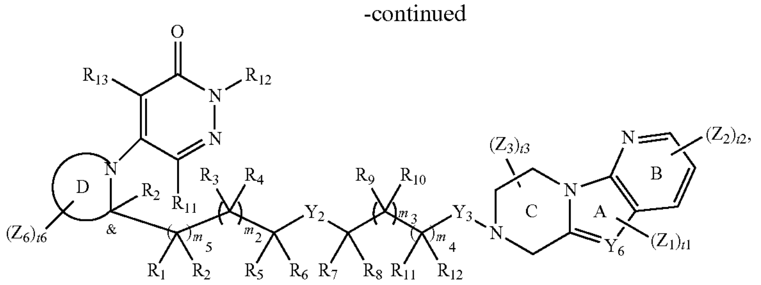

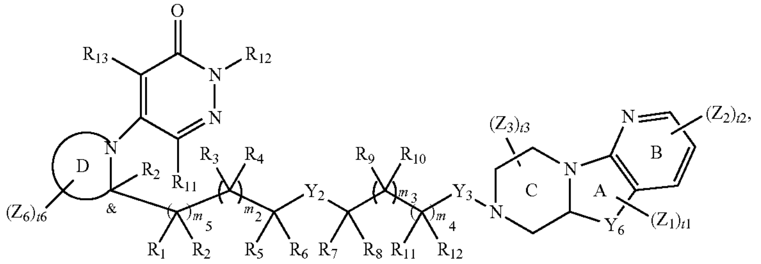

or

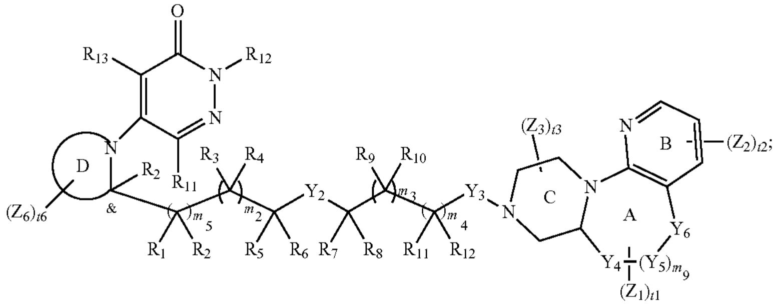

& in any one of formulas indicates that the carbon atom is R configuration or S configuration when the carbon atom is a chiral carbon atom; in some embodiments, & in any one of formulas indicates that the carbon atom is R configuration when the carbon atom is a chiral carbon atom; in some embodiments, & in any one of formulas indicates that the carbon atom is S configuration when the carbon atom is a chiral carbon atom.

[53]. The compound according to any one of [50] to [52], wherein, the compound is selected from any one of the following formulas:

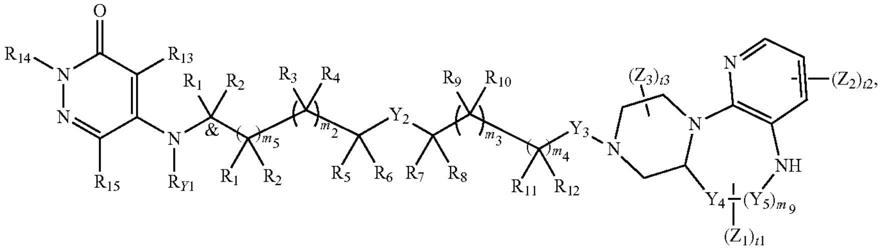

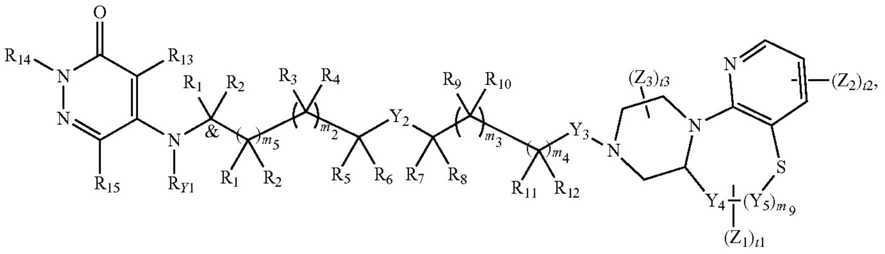

-continued
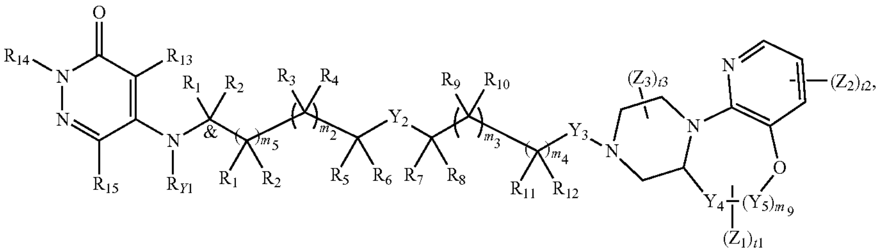
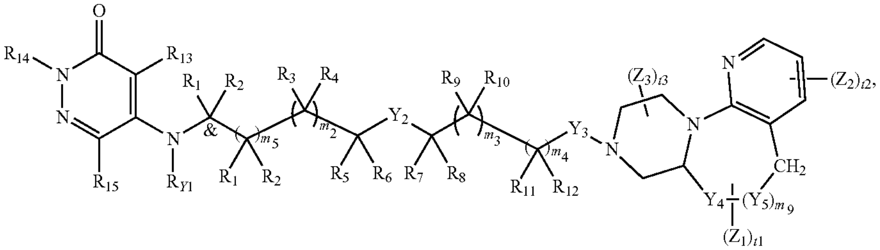
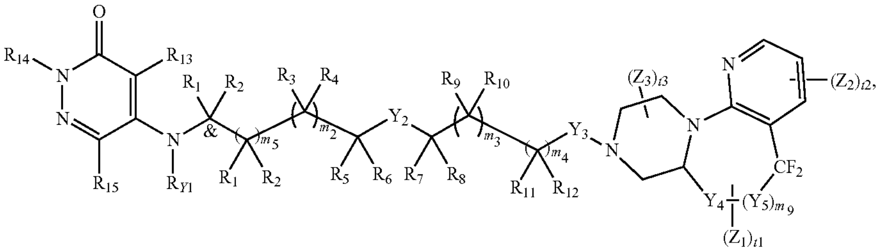
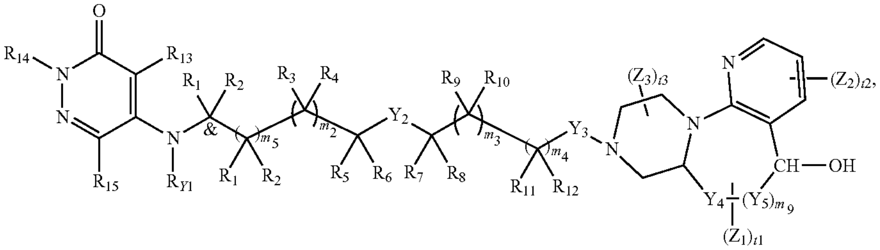
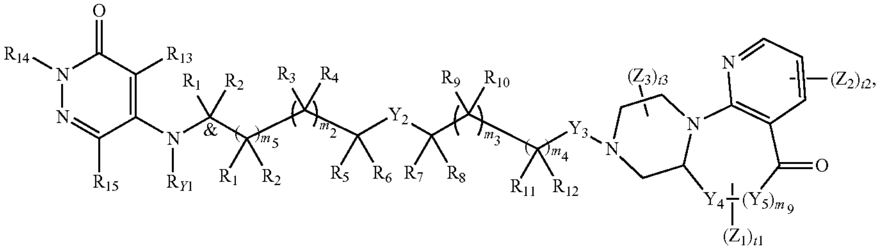
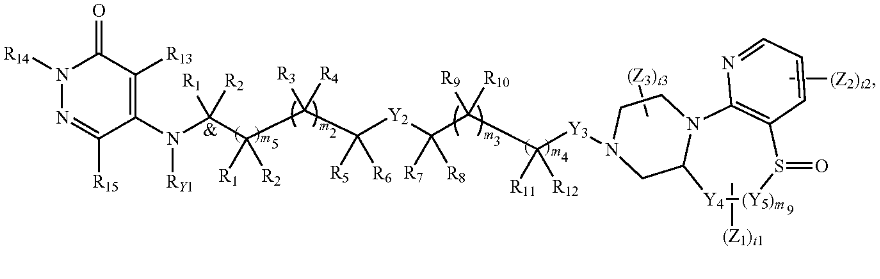

-continued
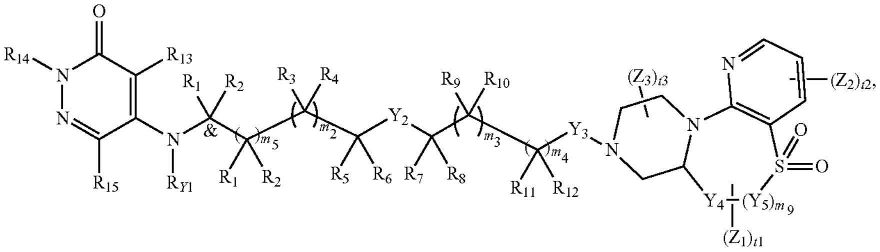
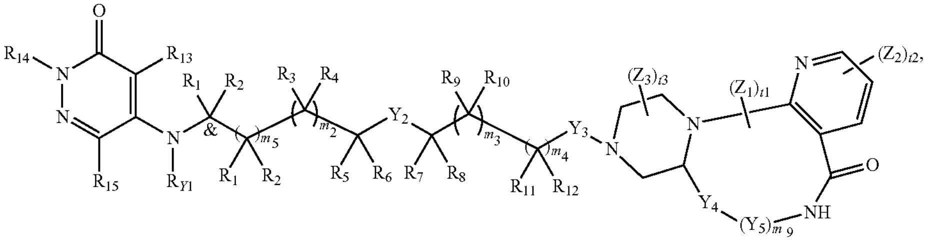
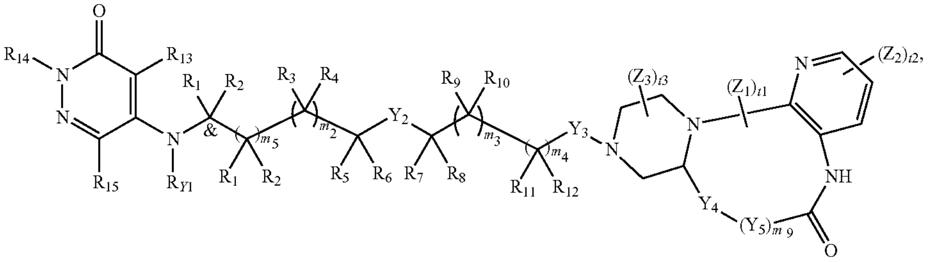
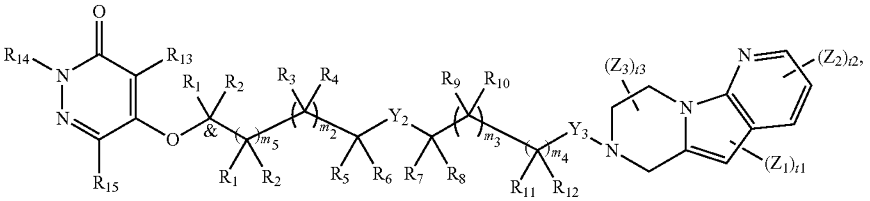
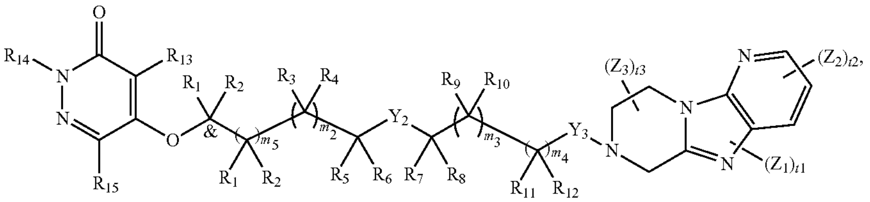
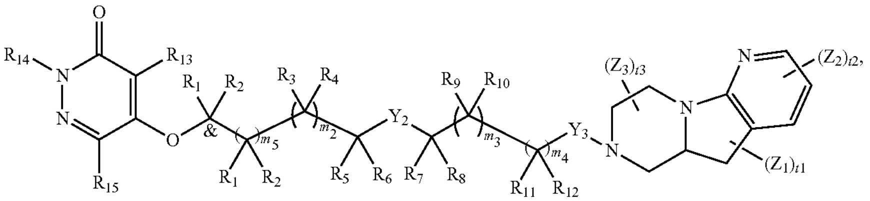
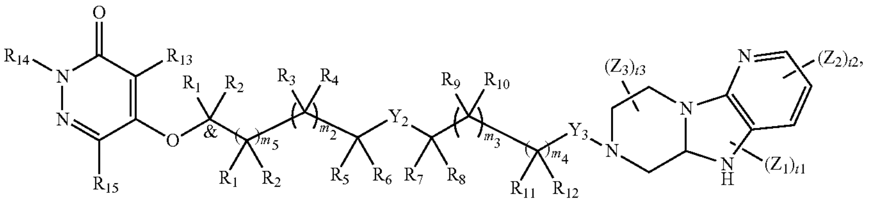

-continued
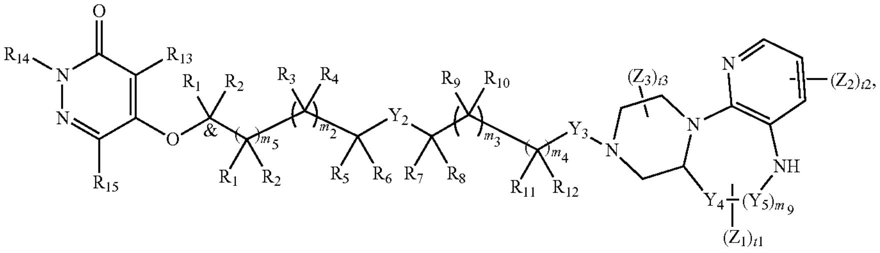
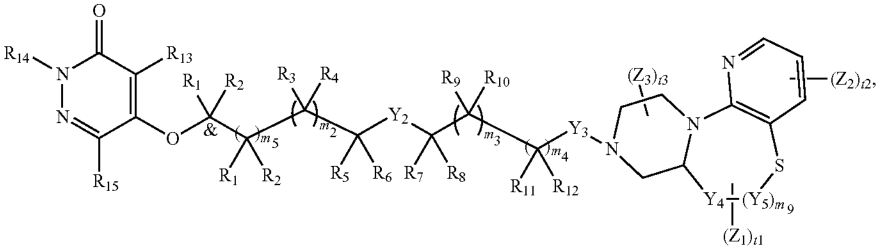
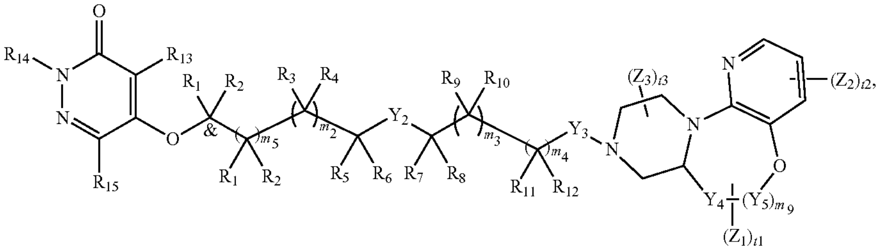
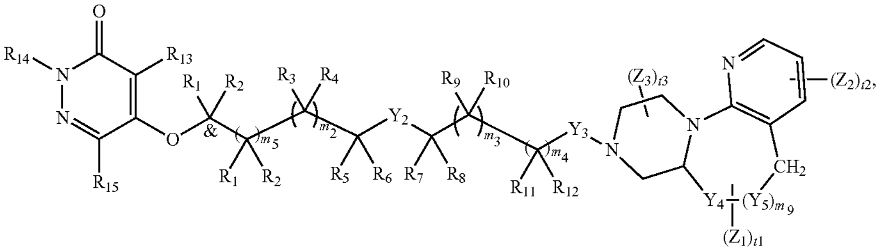
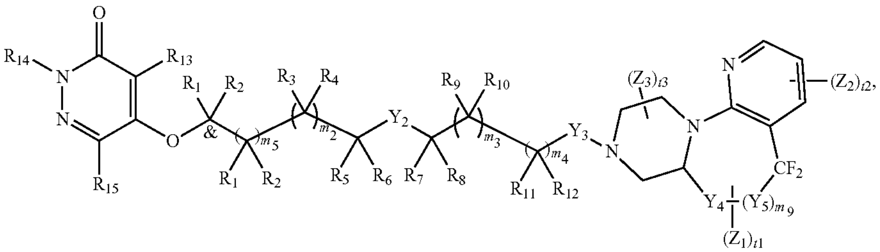
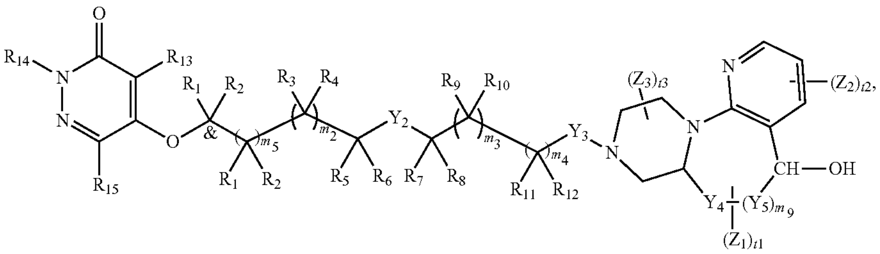

-continued
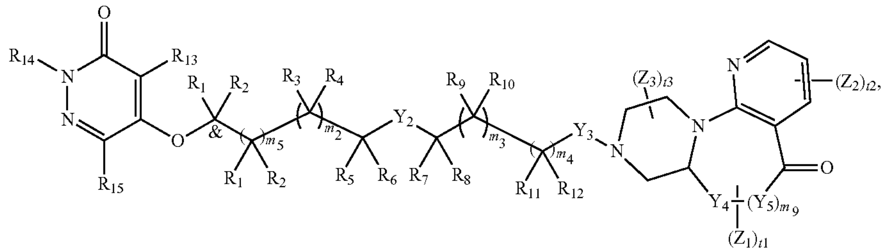
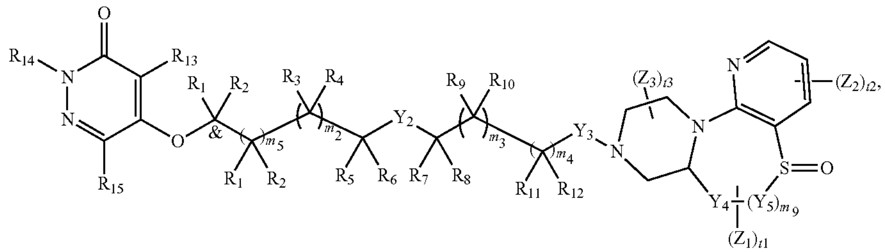
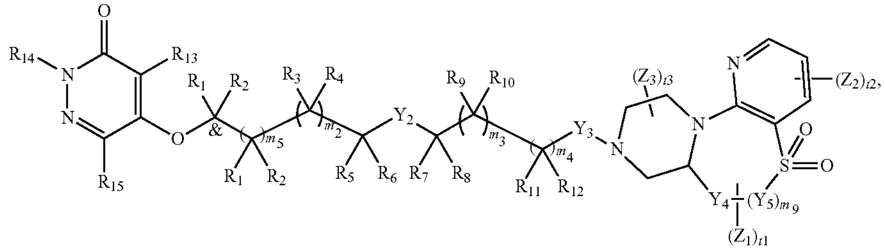
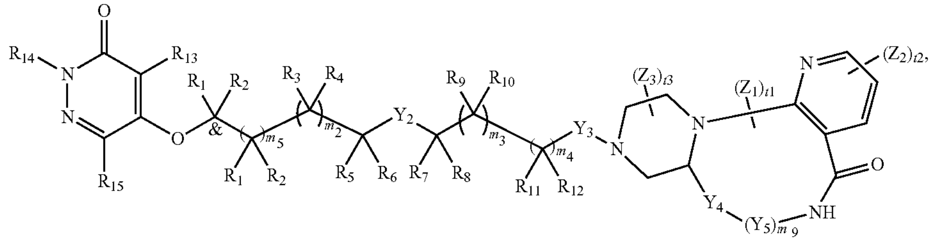
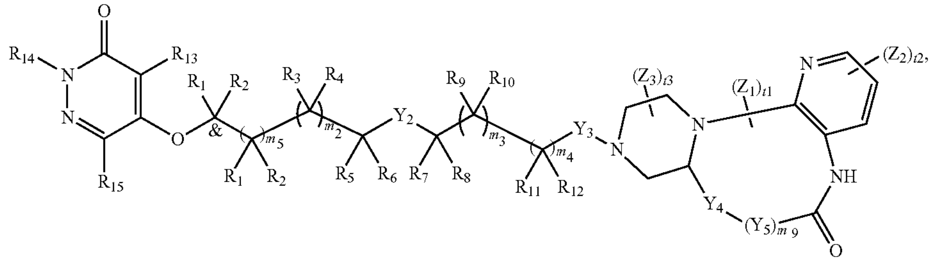
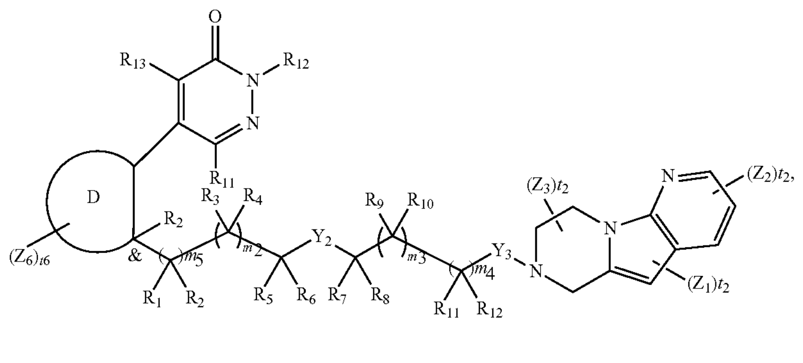

-continued
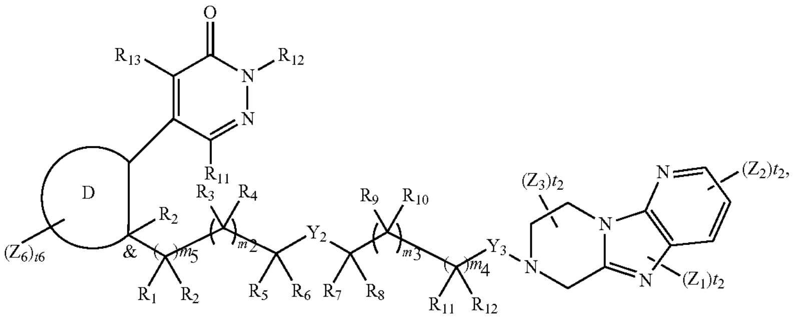
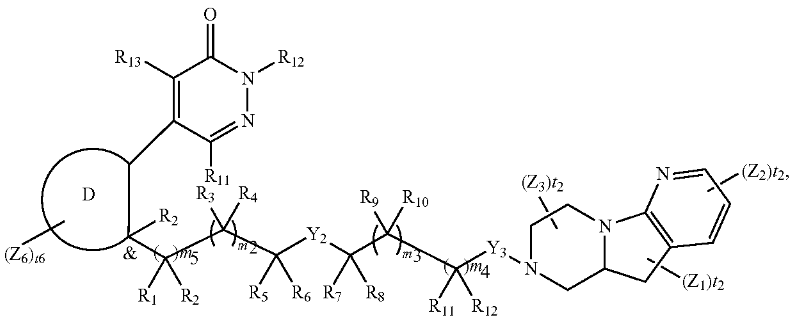
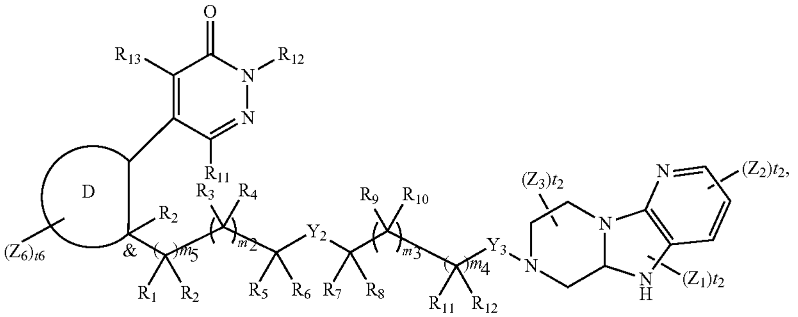
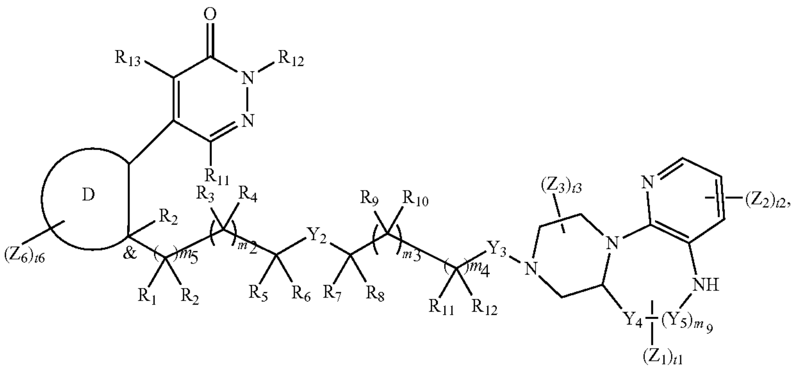
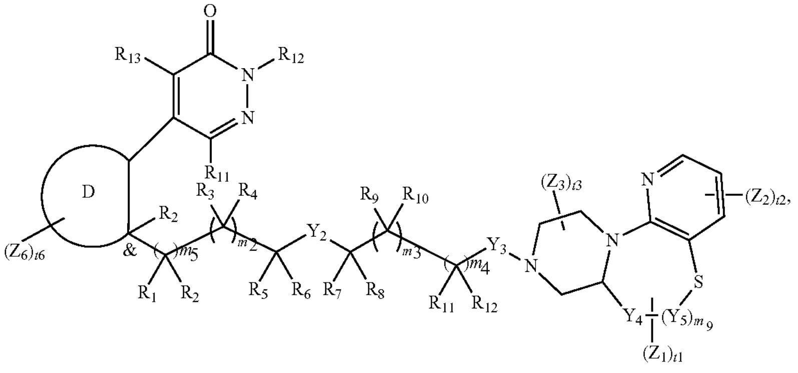

-continued
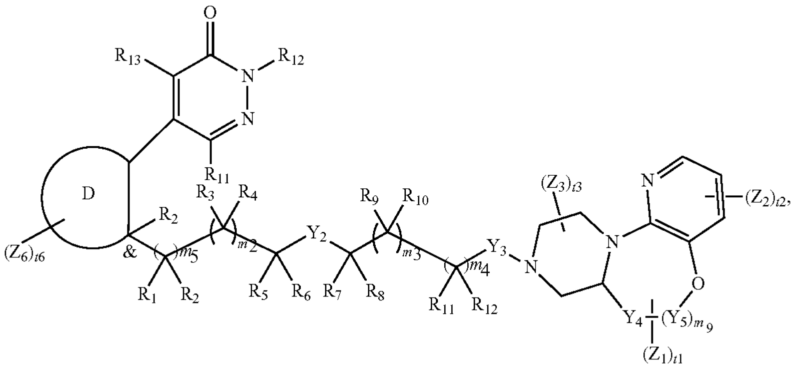
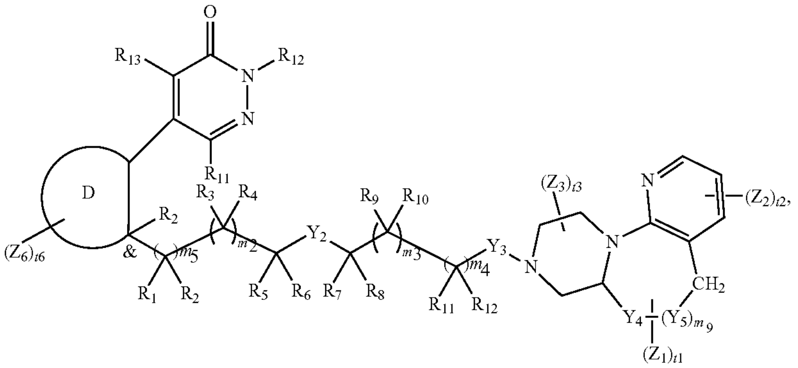
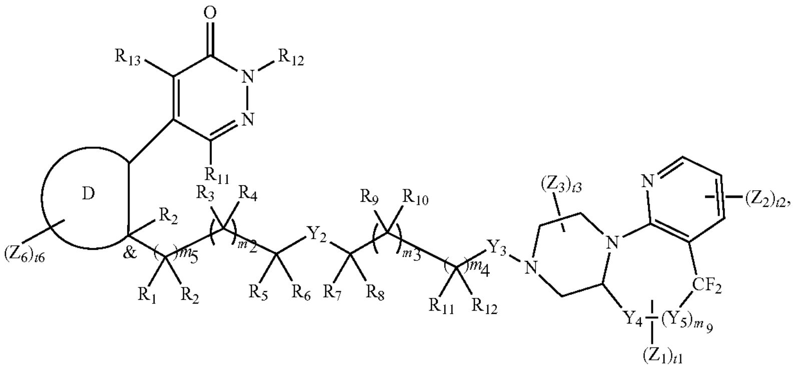
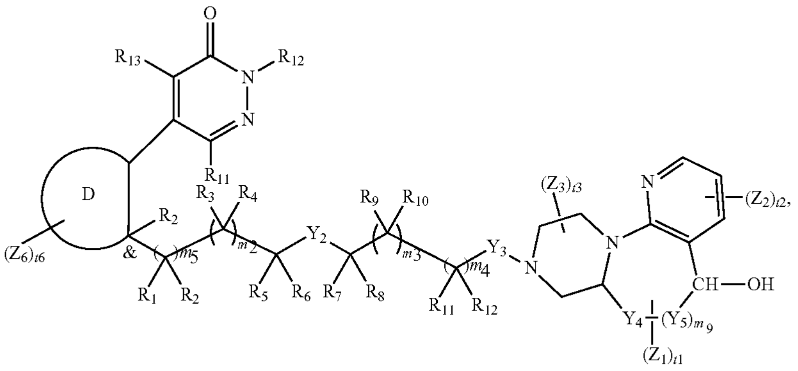

-continued
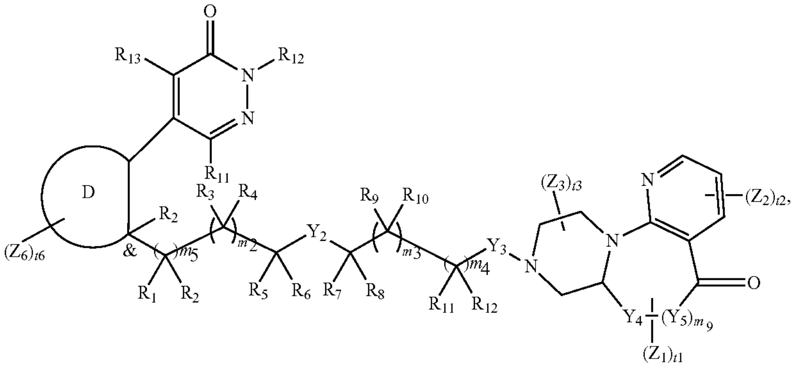
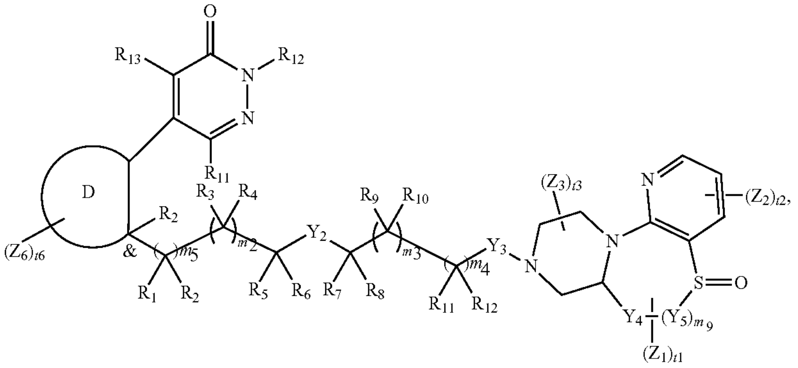
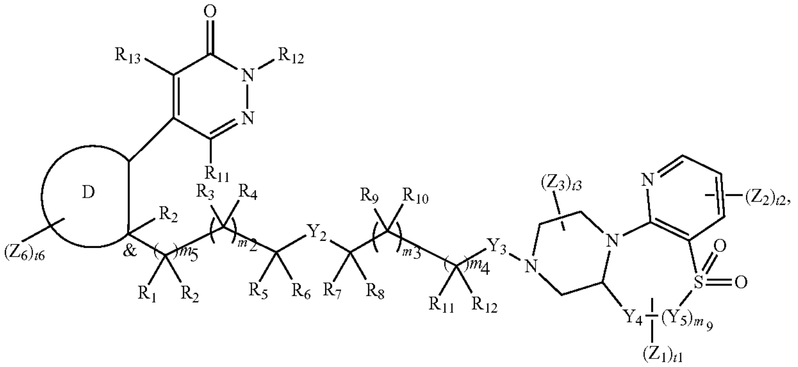
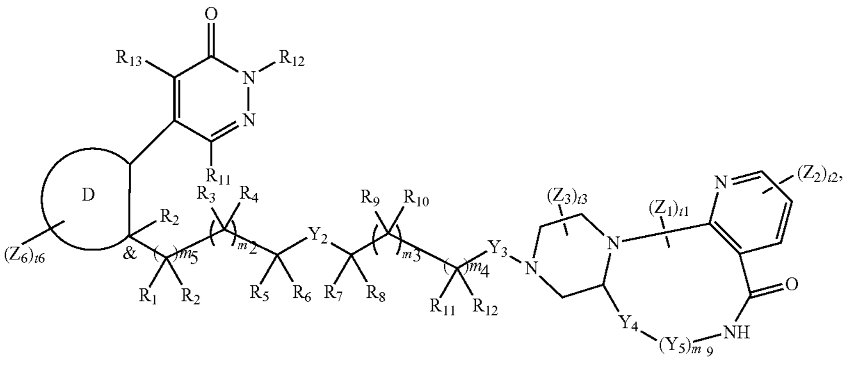

-continued
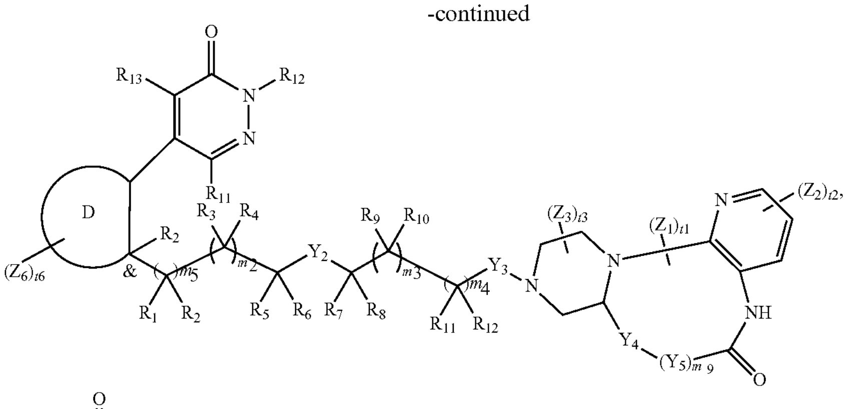
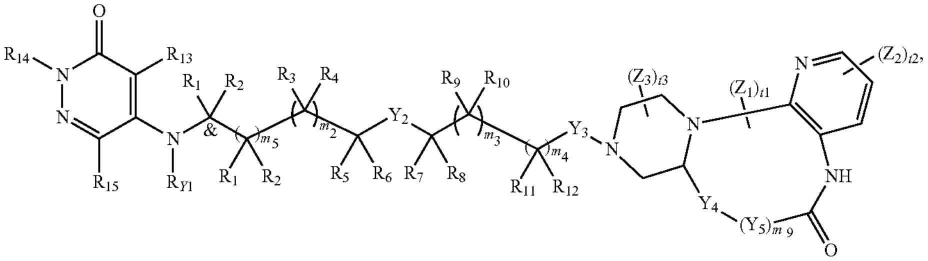
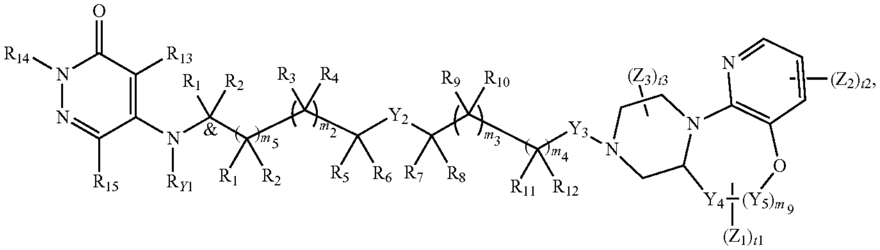
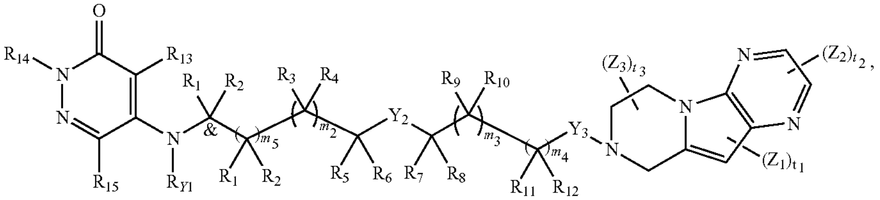
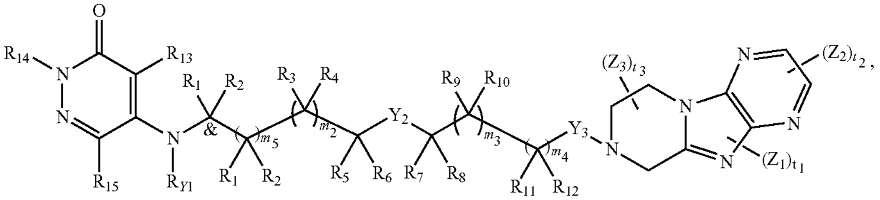
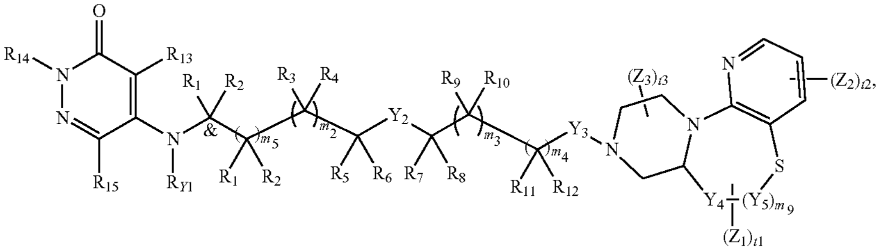
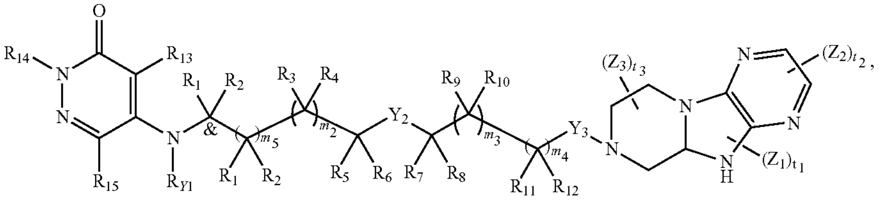

-continued
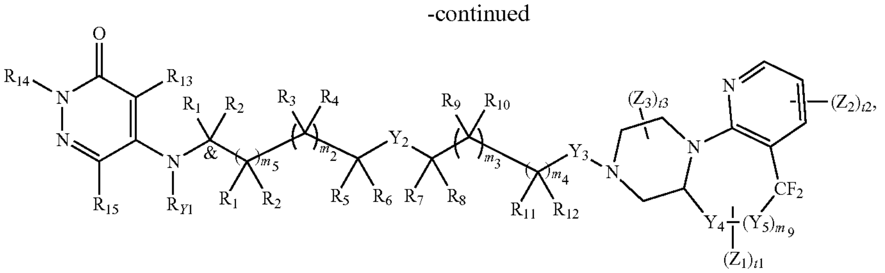
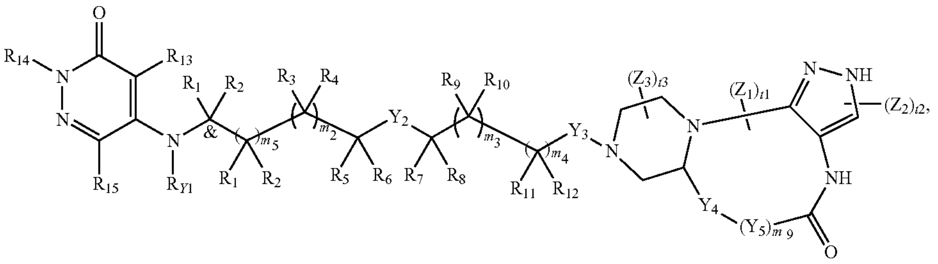
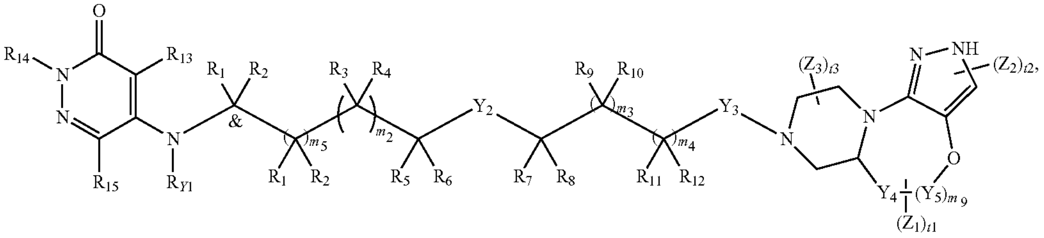
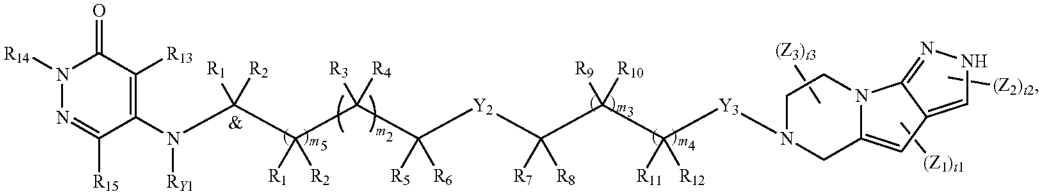
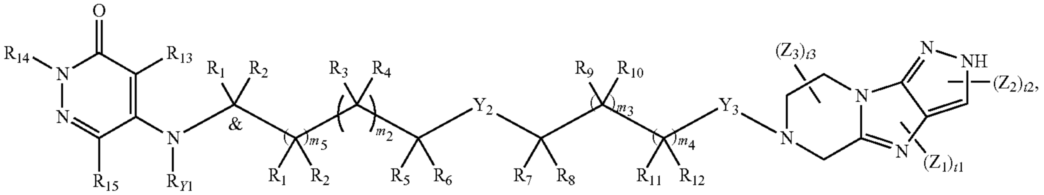
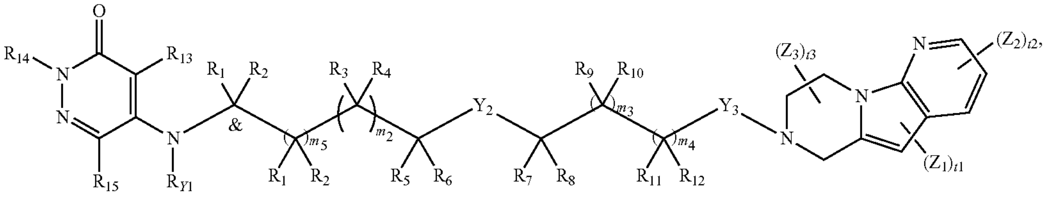
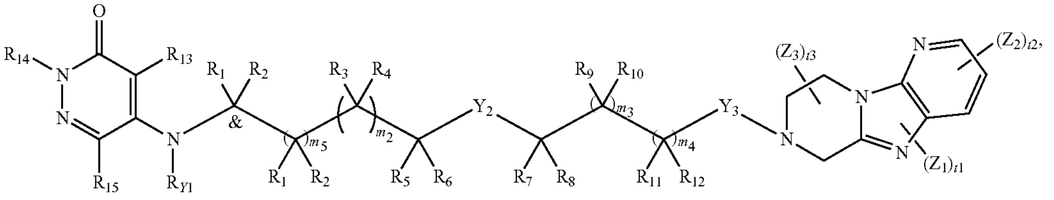

-continued
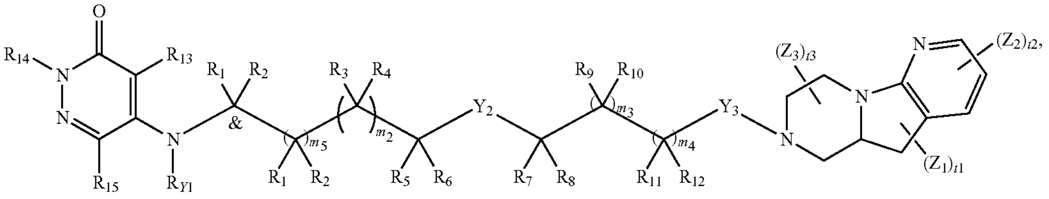
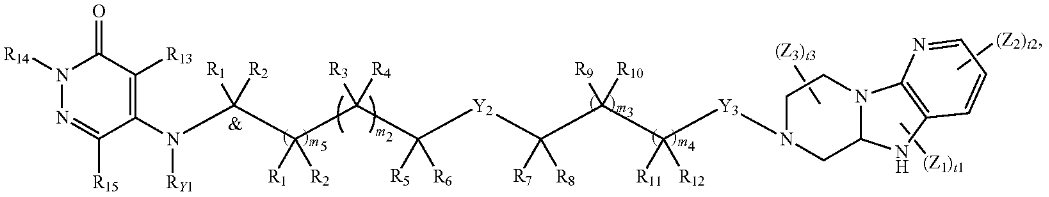
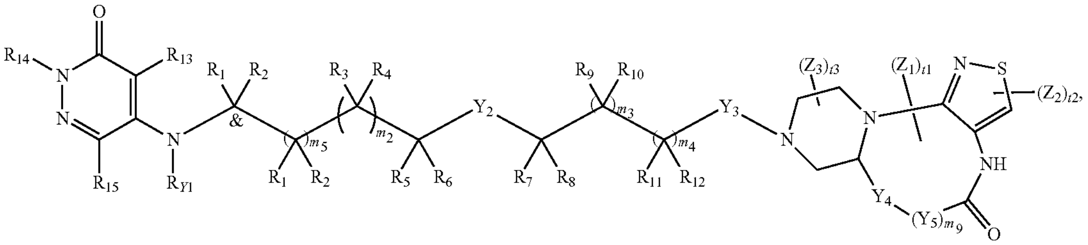
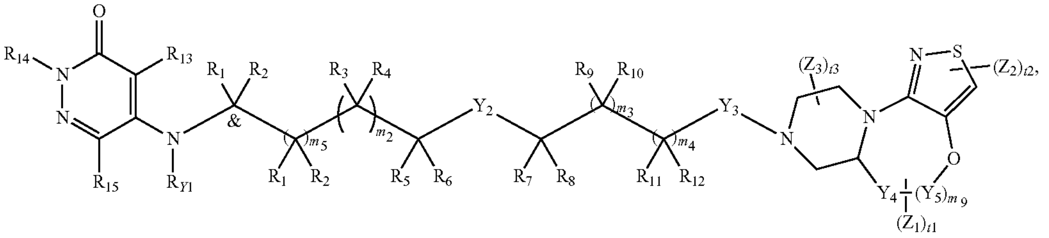
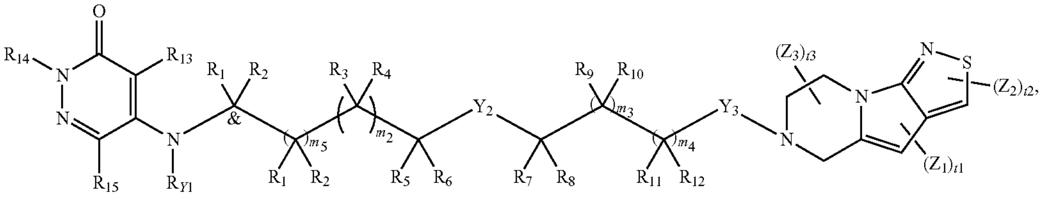
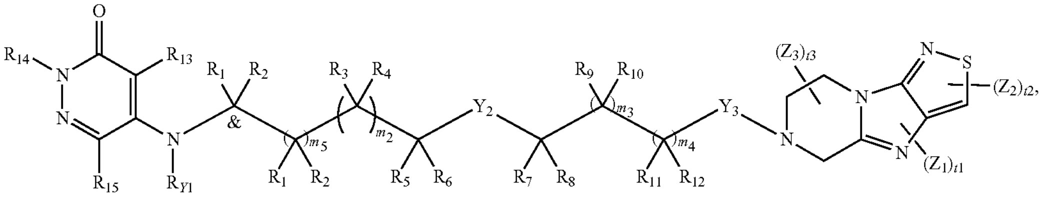
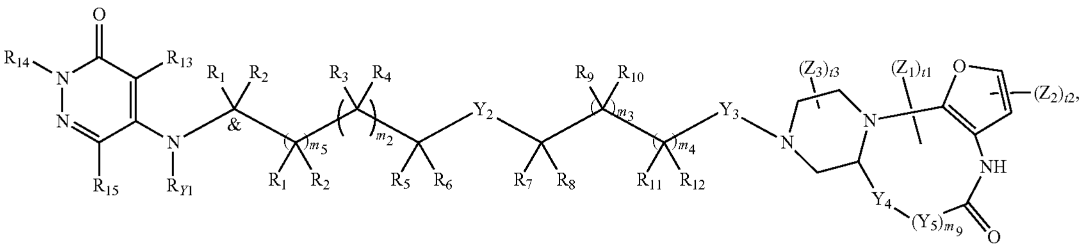

-continued
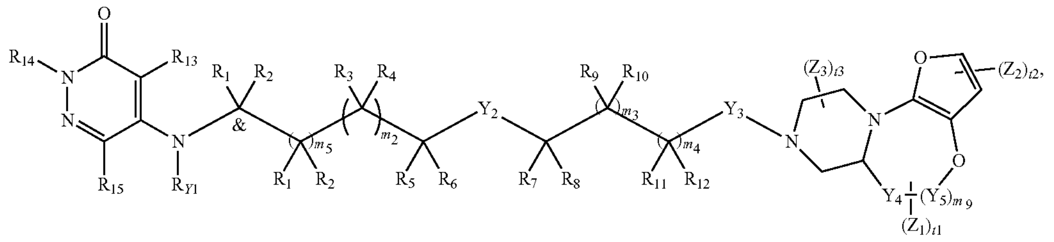
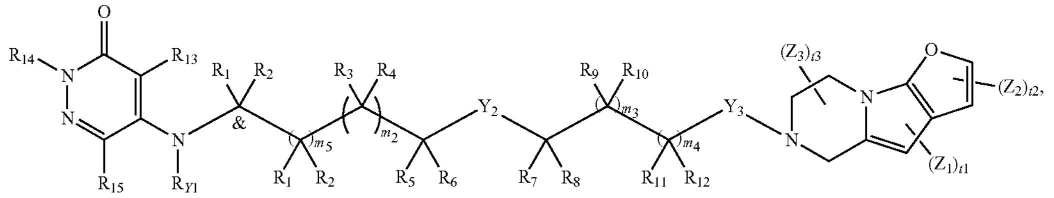
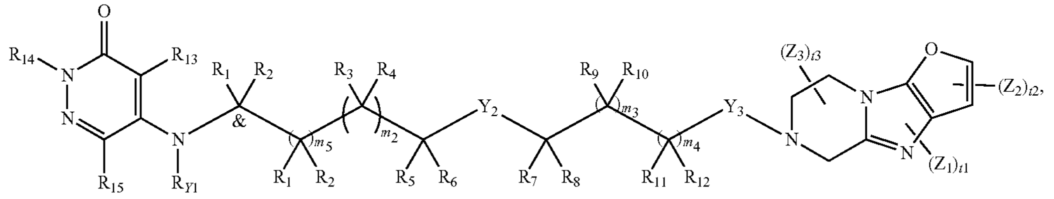
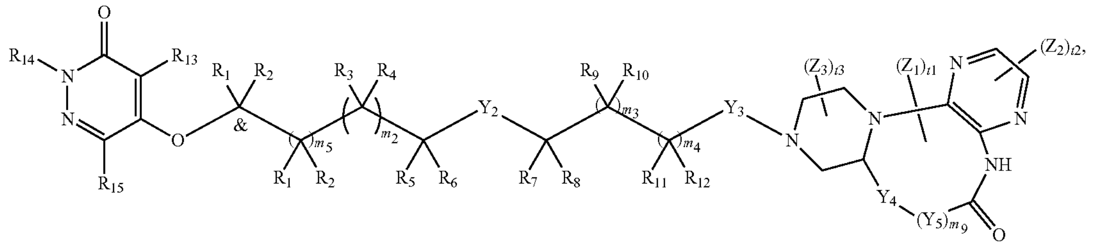
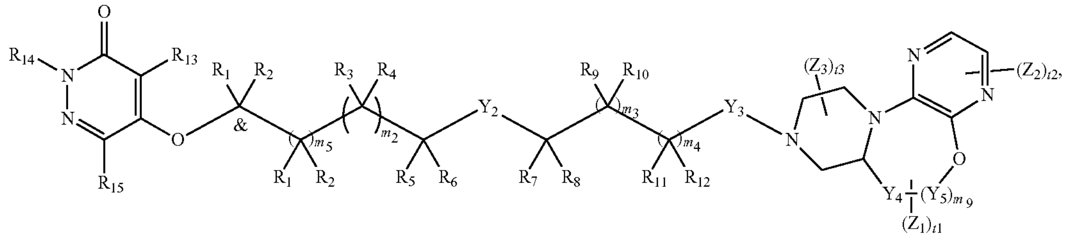
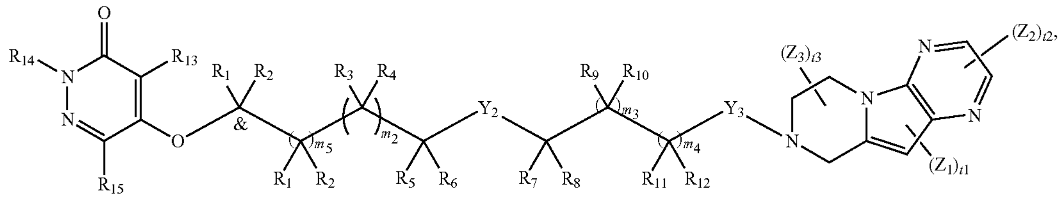
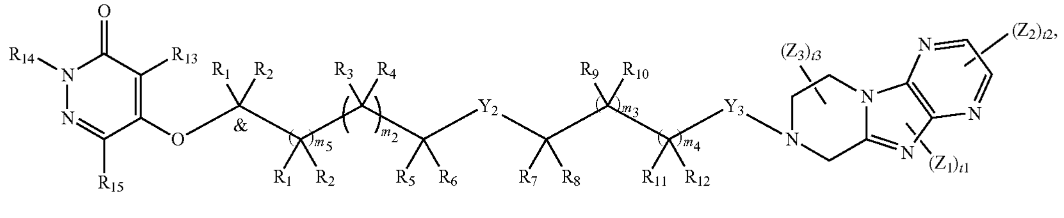

-continued
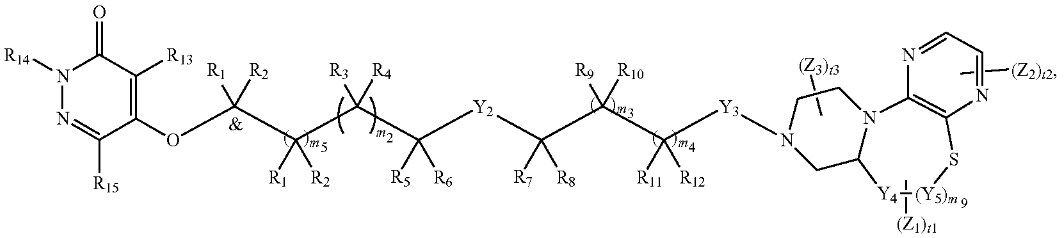
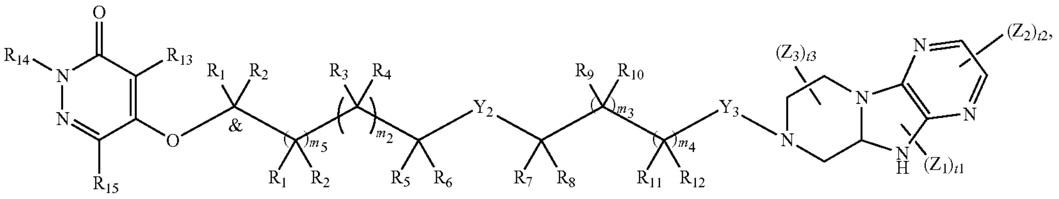
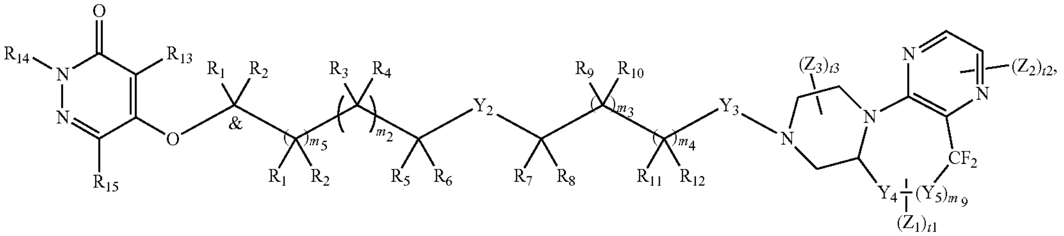
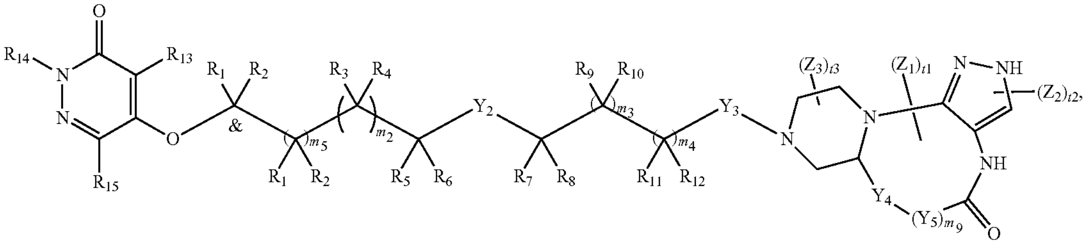
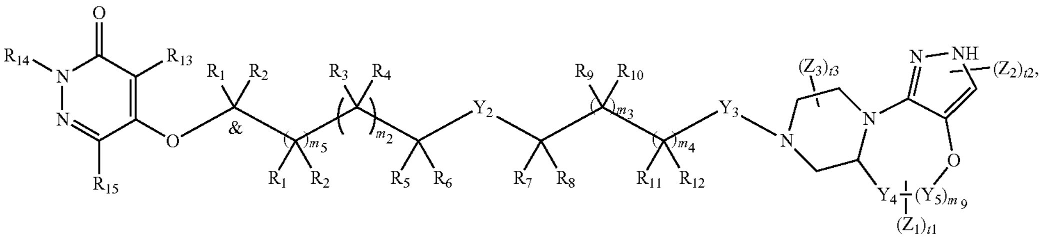
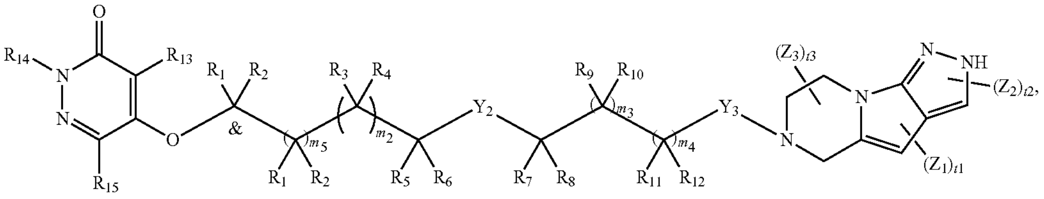
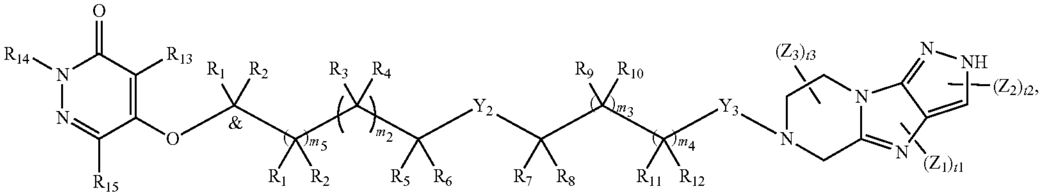

-continued
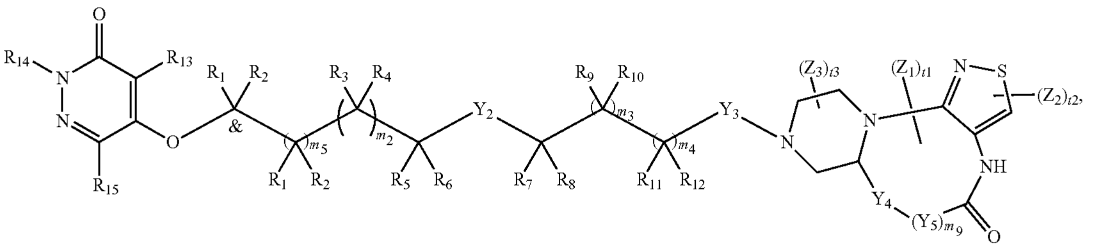
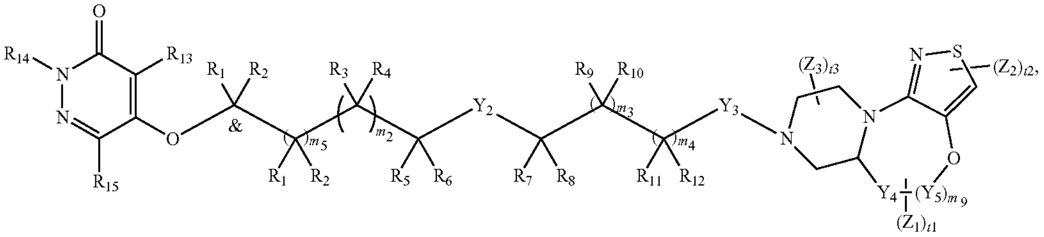
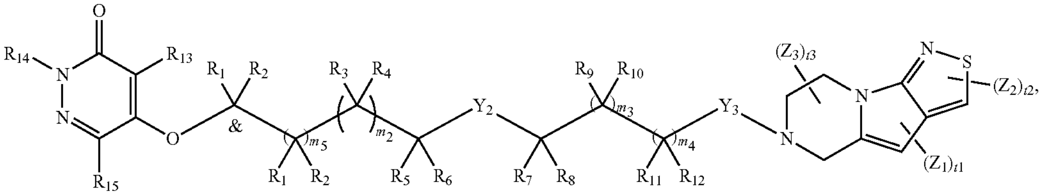
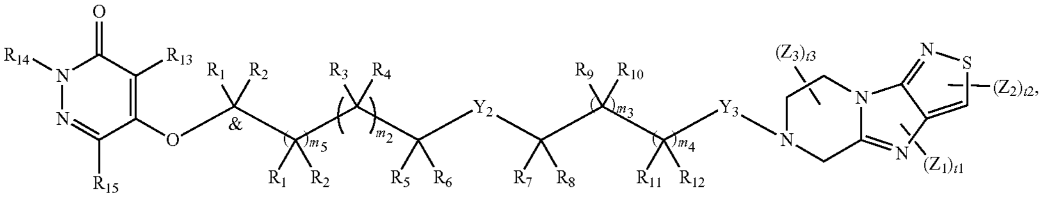
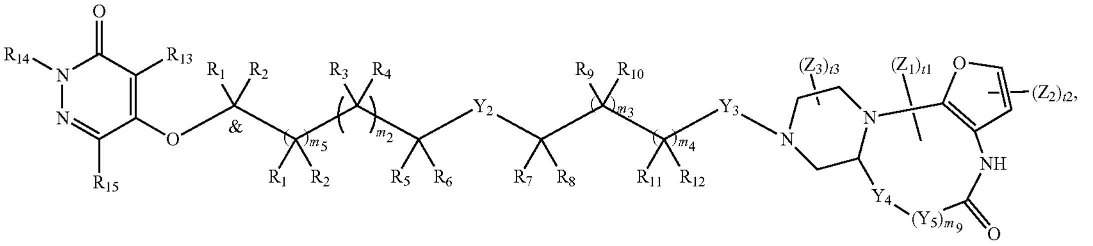
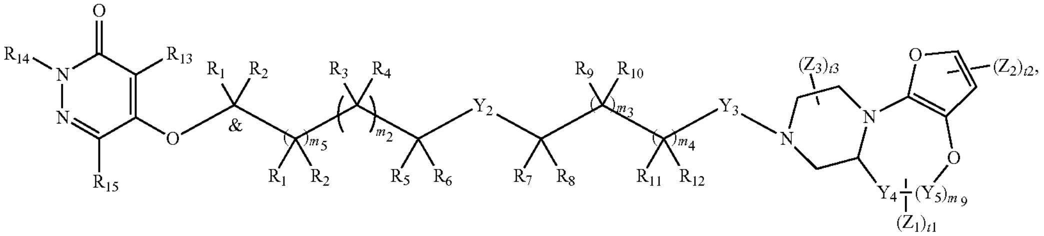
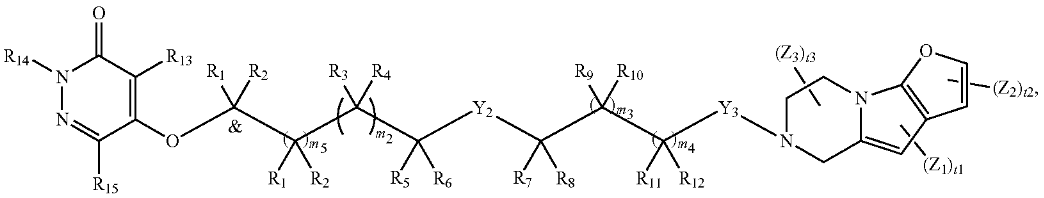

-continued
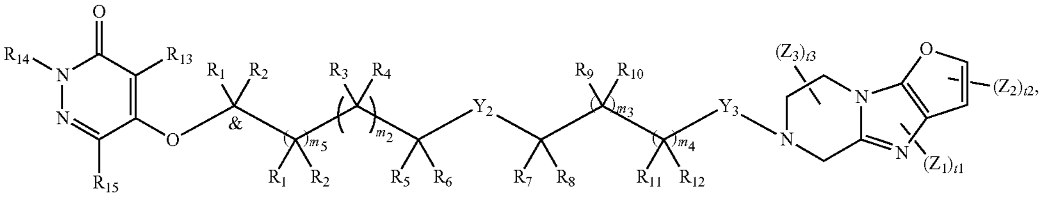
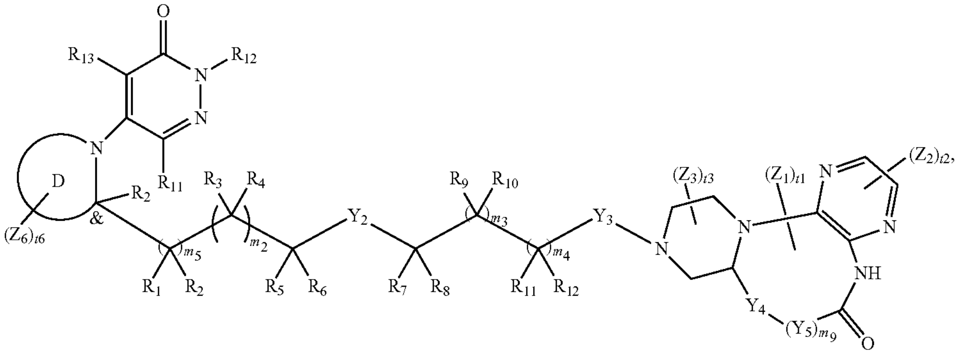
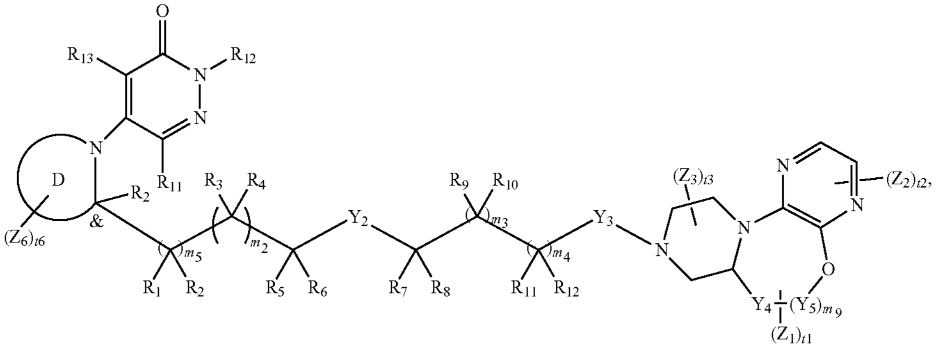
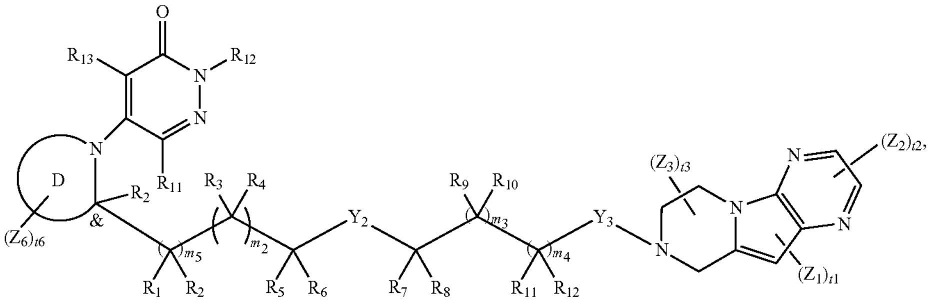
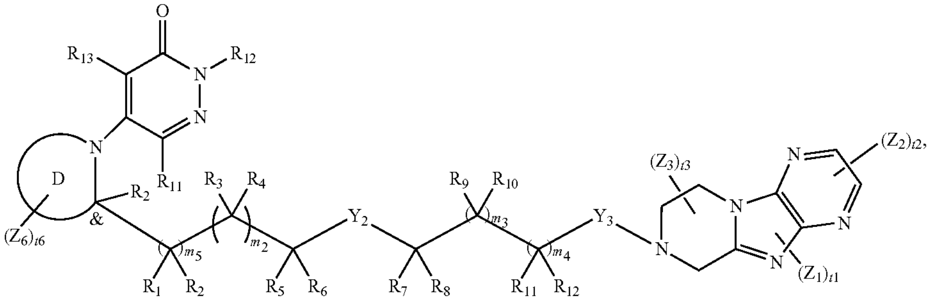

-continued
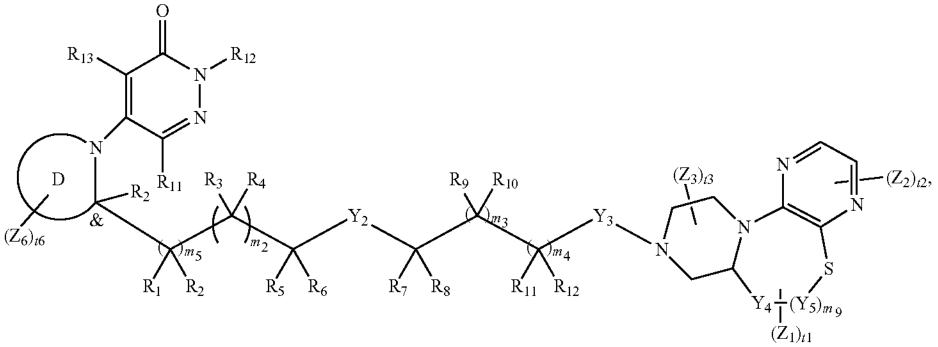
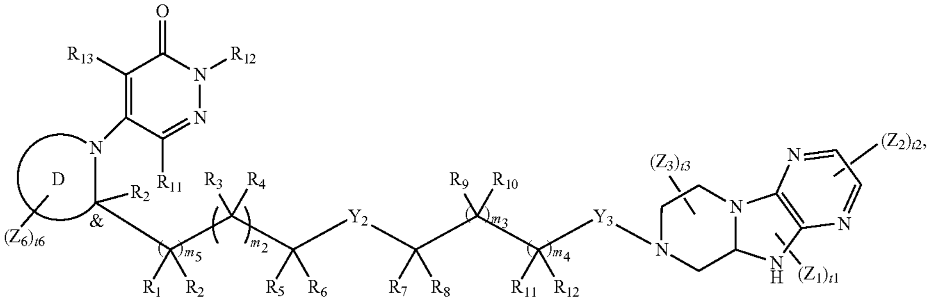
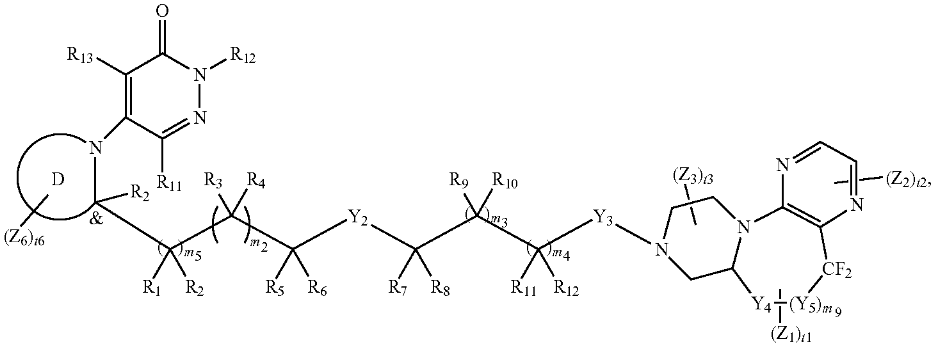
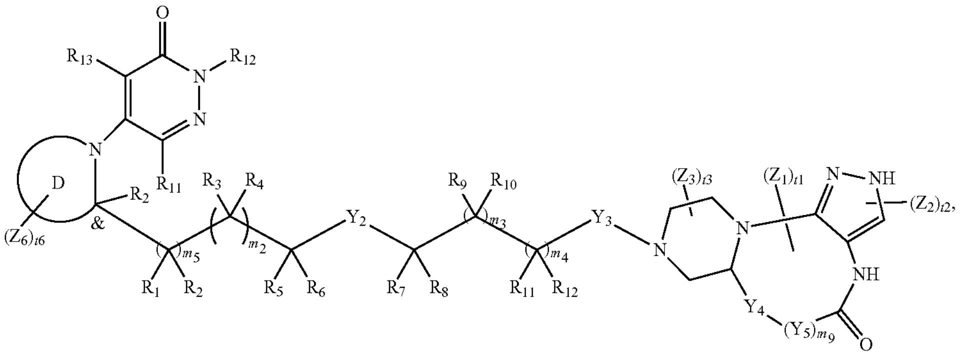
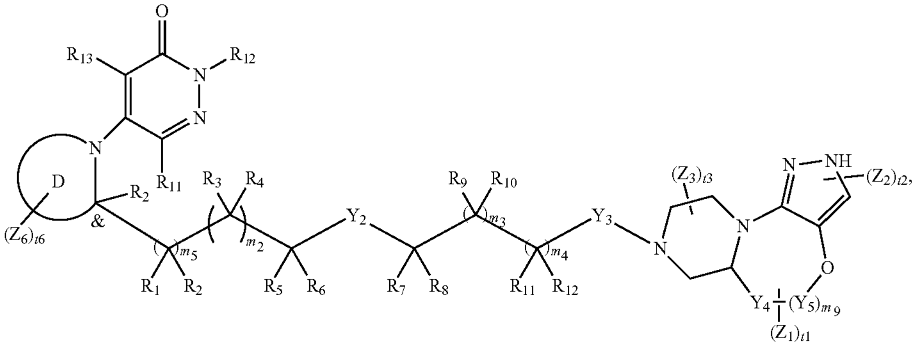

-continued
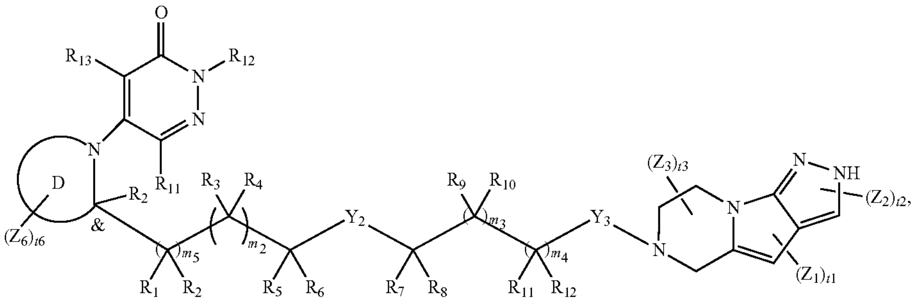
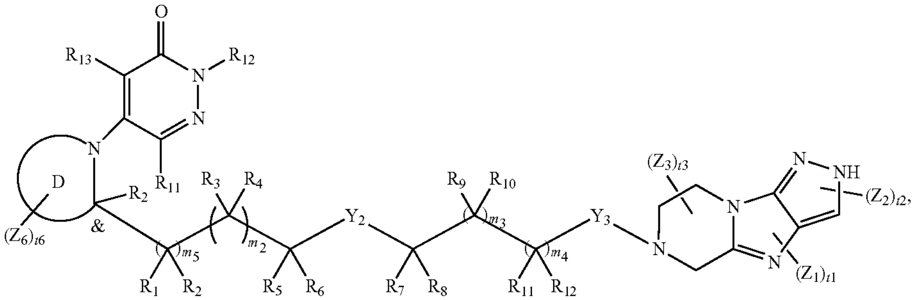
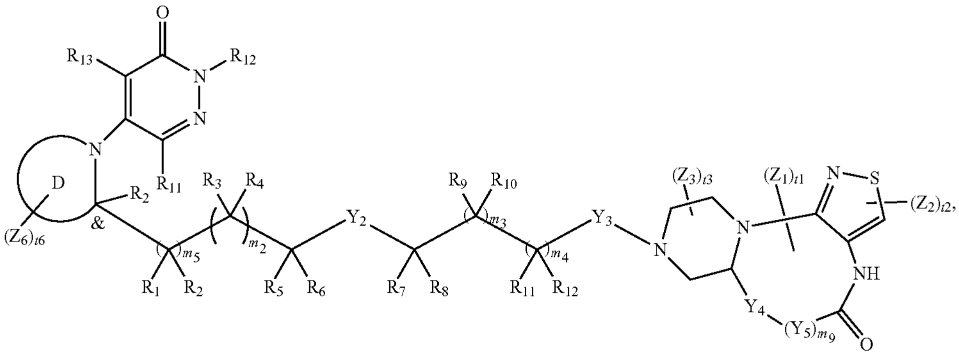
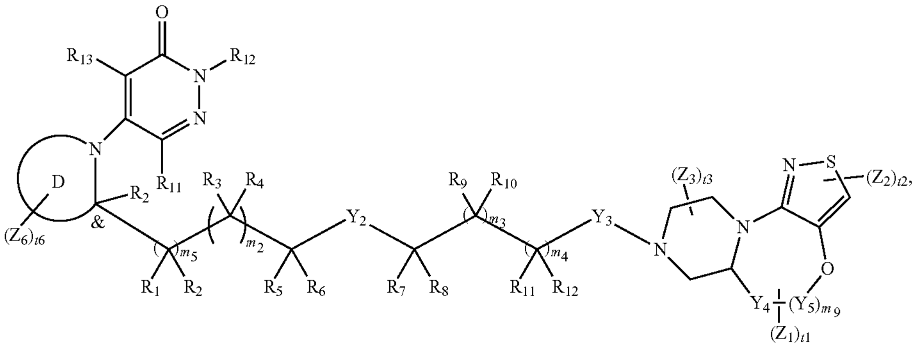
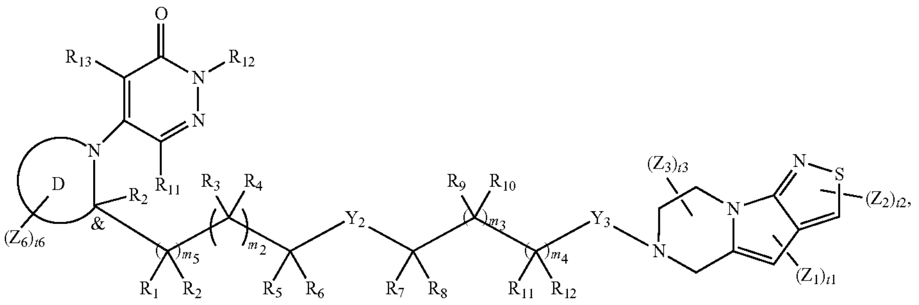

-continued
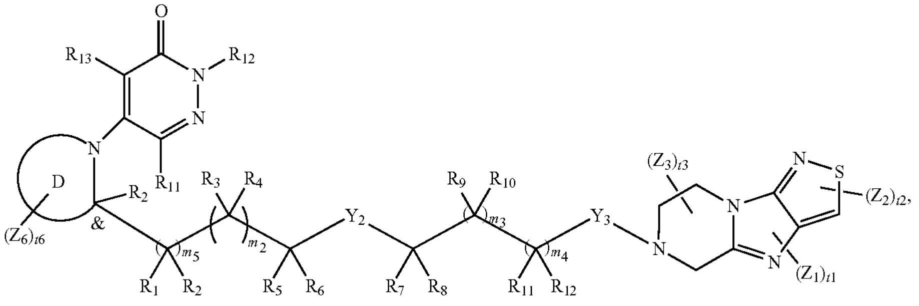
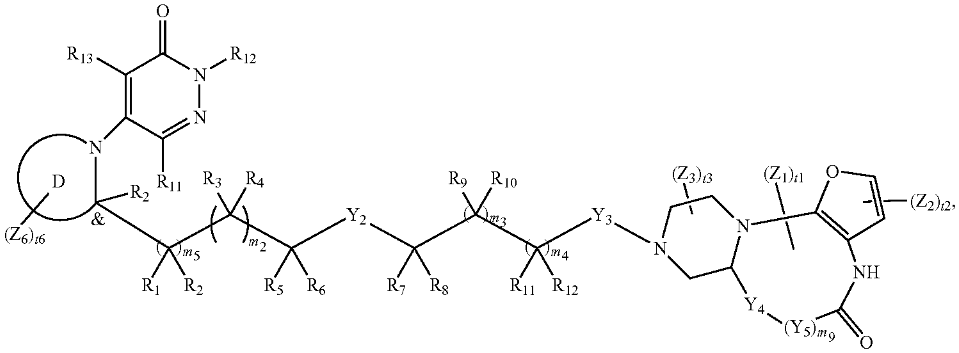
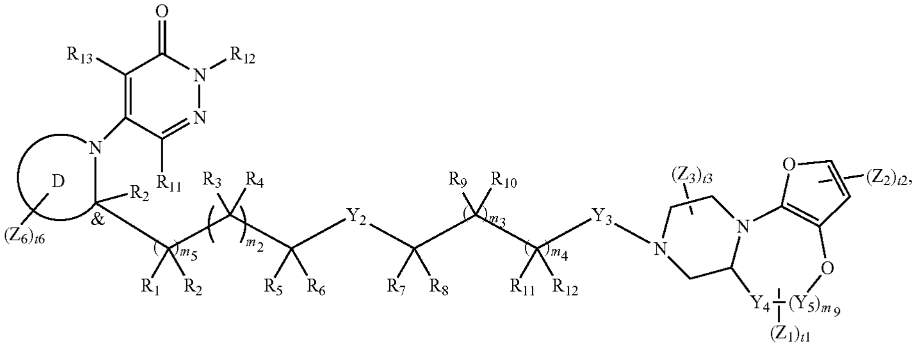
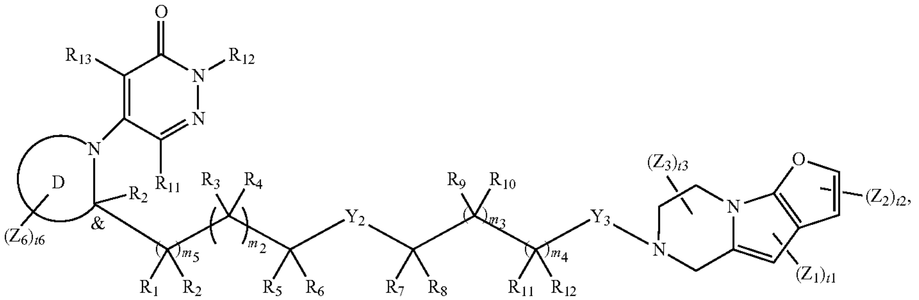
or
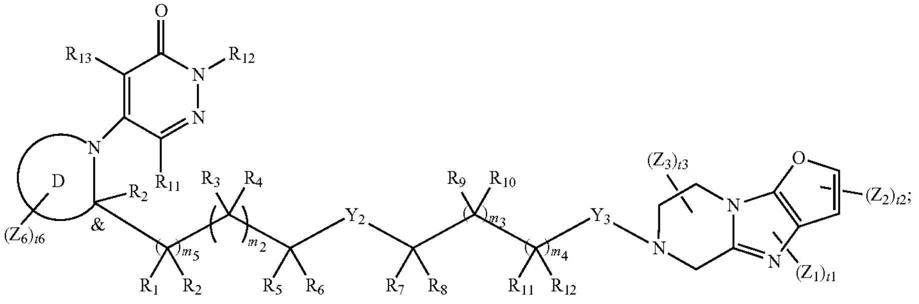
;

& in any one of formulas indicates that the carbon atom is R configuration or S configuration when the carbon atom is a chiral carbon atom; in some embodiments, & in any one of formulas indicates that the carbon atom is R configuration when the carbon atom is a chiral carbon atom; in some embodiments, & in any one of formulas indicates that the carbon atom is S configuration when the carbon atom is a chiral carbon atom.

[54]. The compound according to any one of [50] to [53], wherein, the compound is selected from any one of the following formulas:

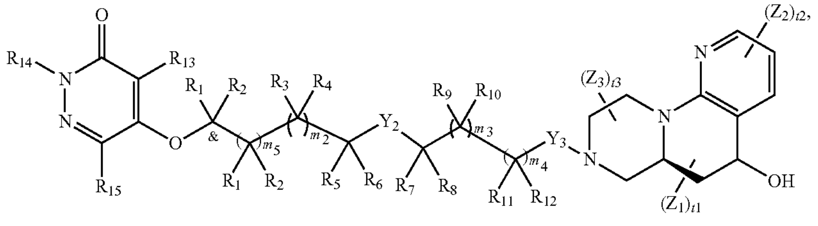

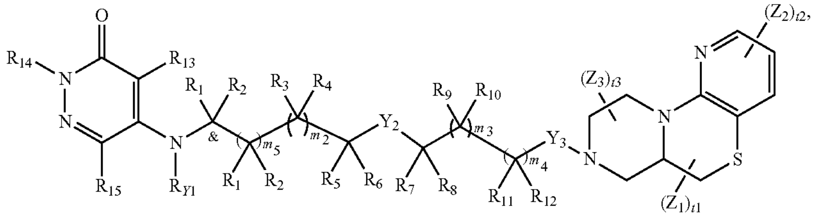

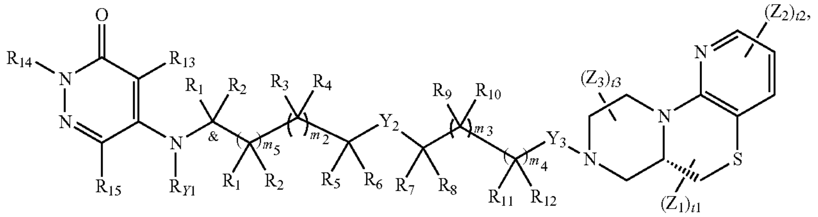

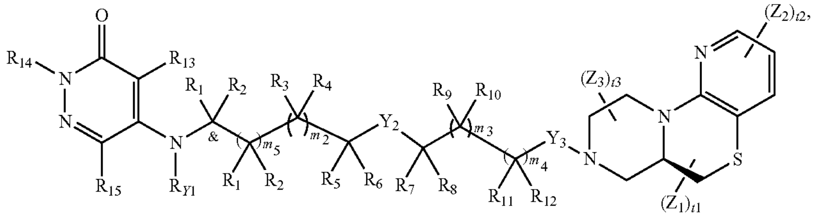

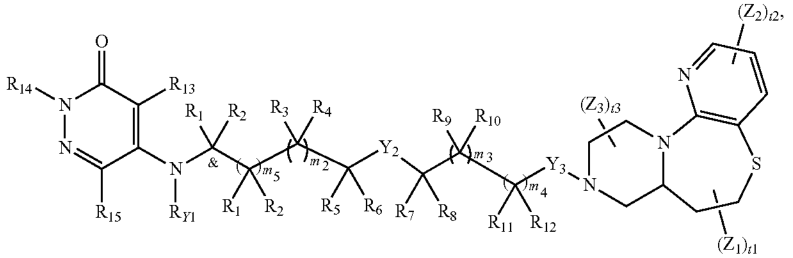

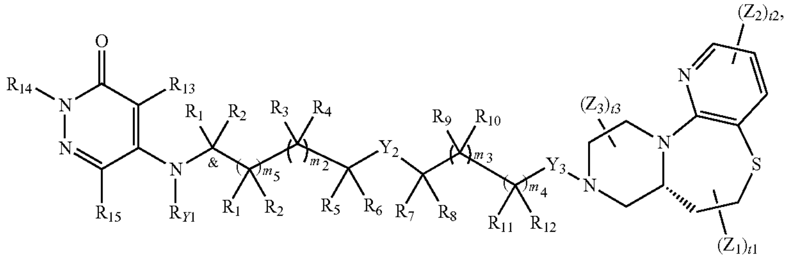

-continued
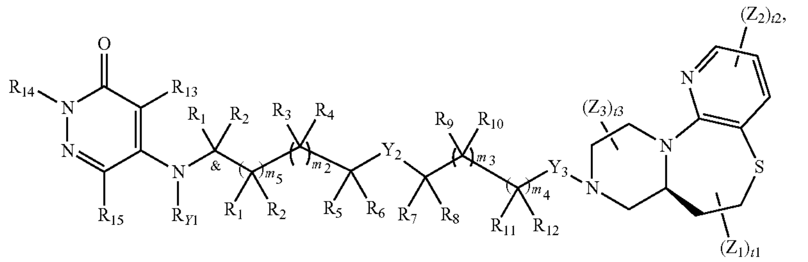
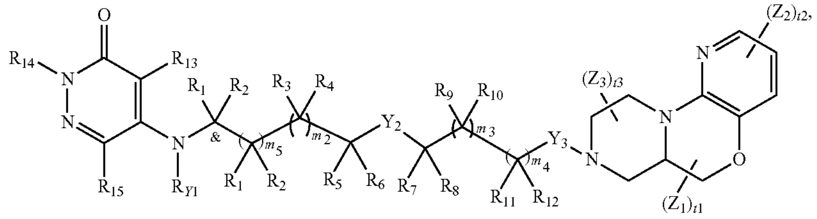
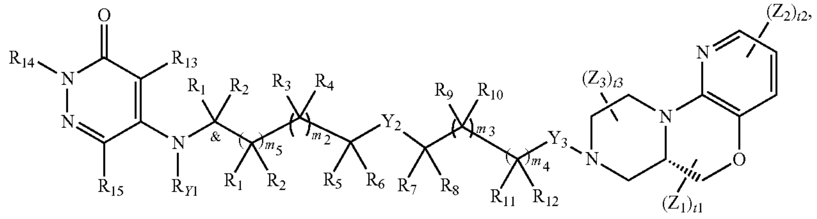
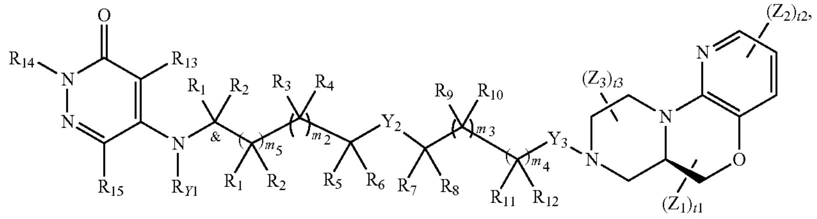
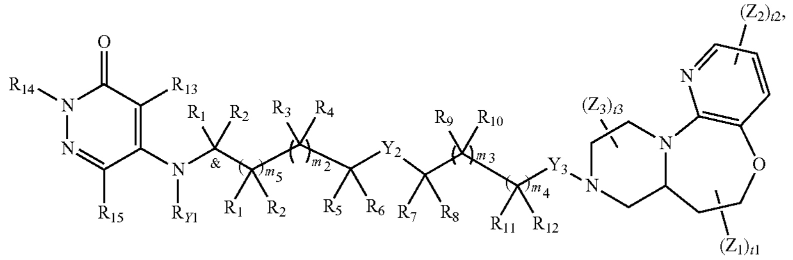
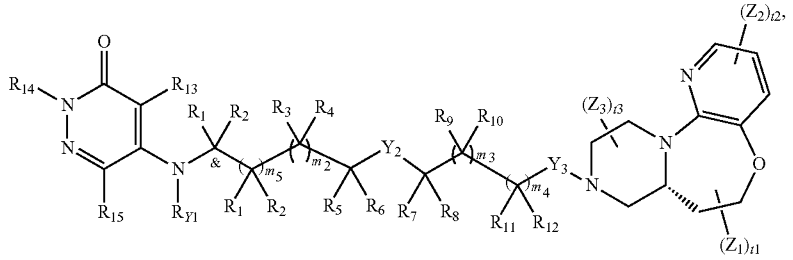
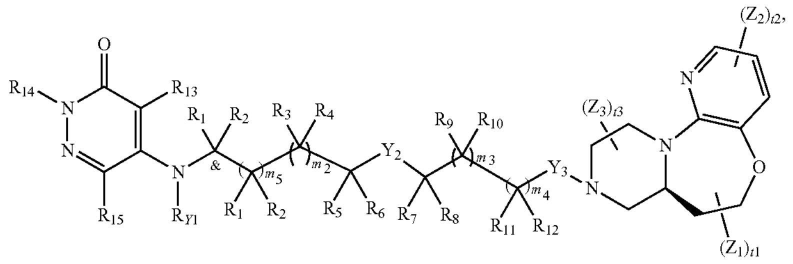

-continued
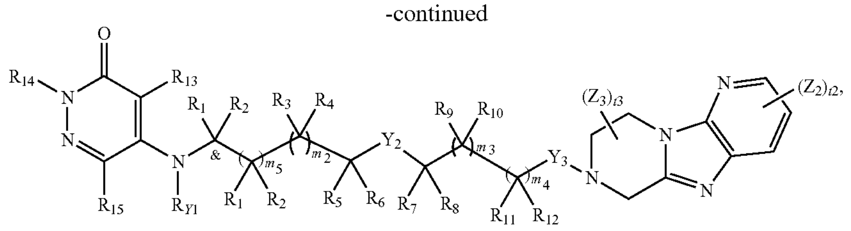
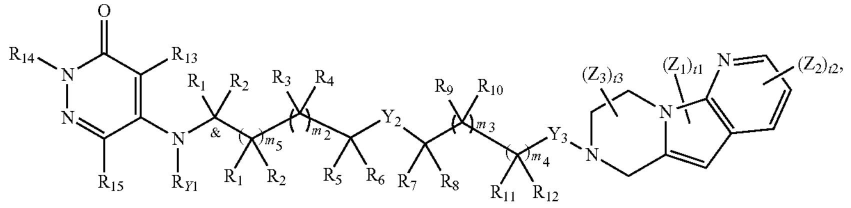
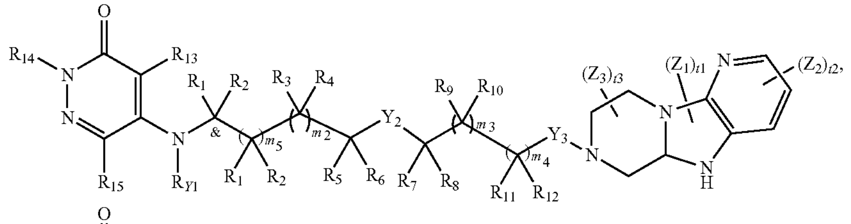
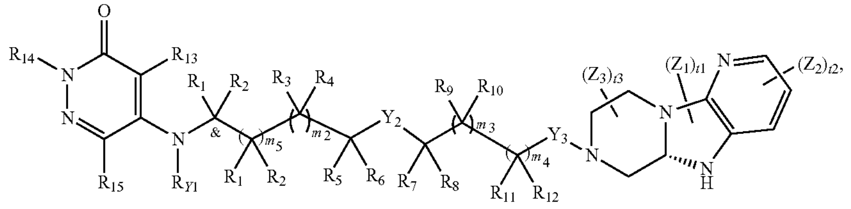
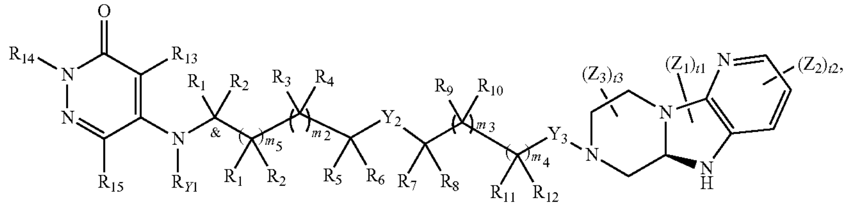
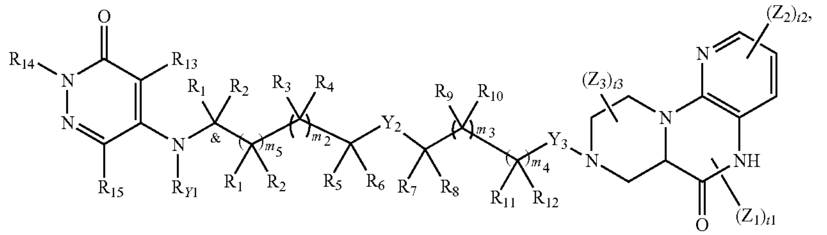
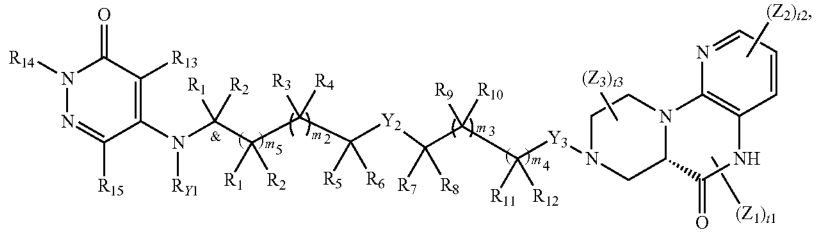
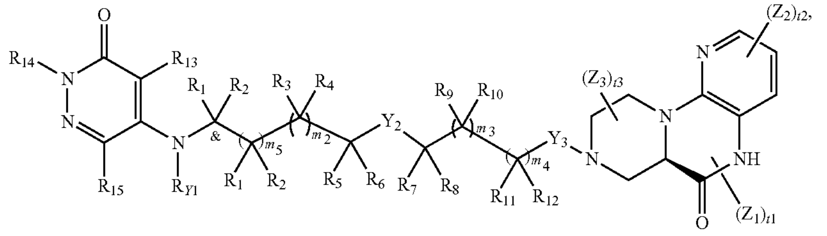

-continued
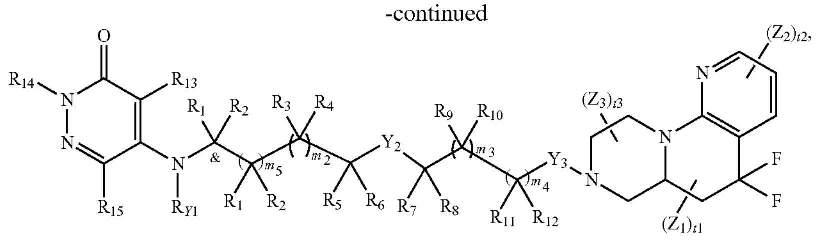
,
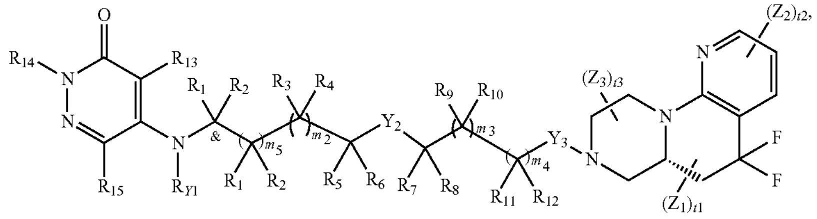
,
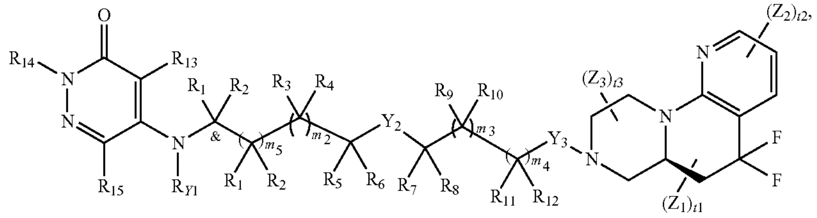
,
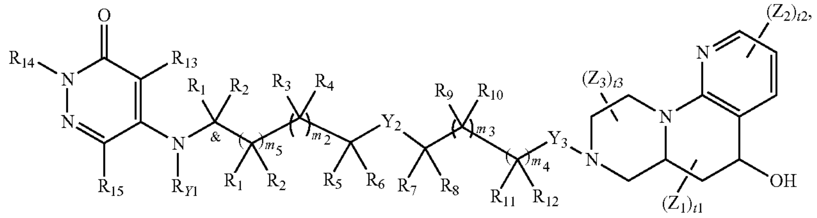
,
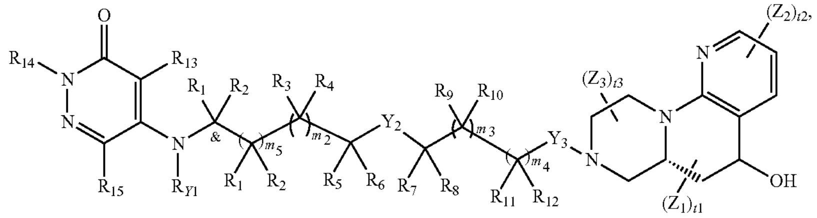
,
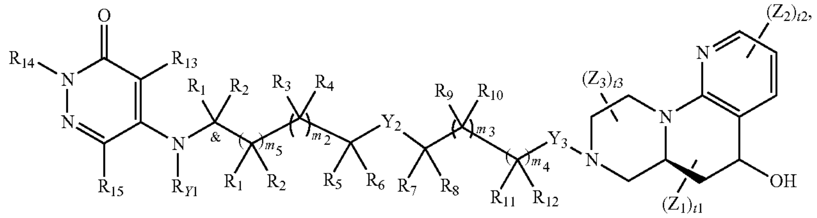
,
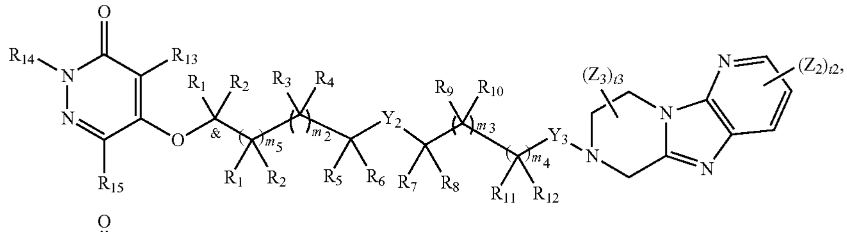
,
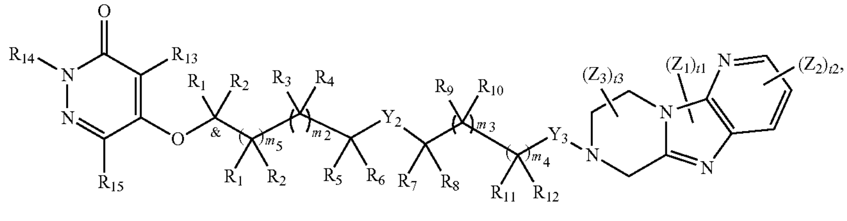
, -continued
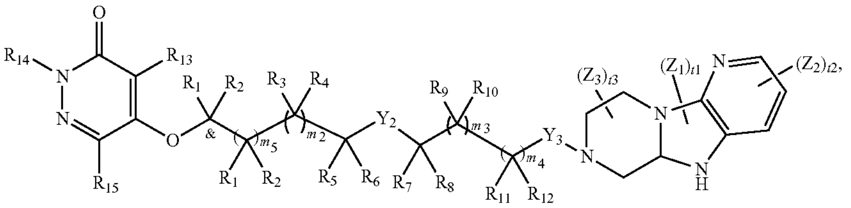
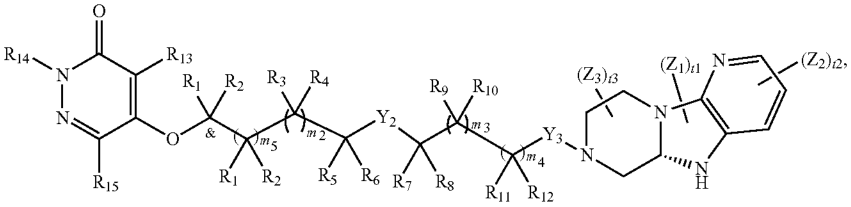
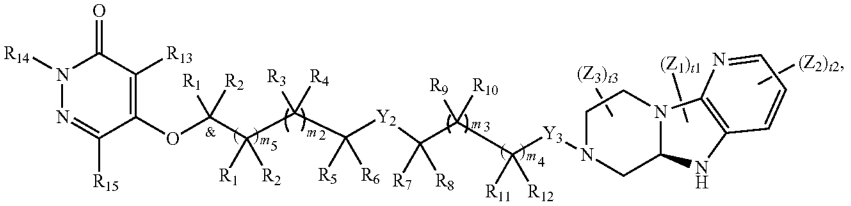
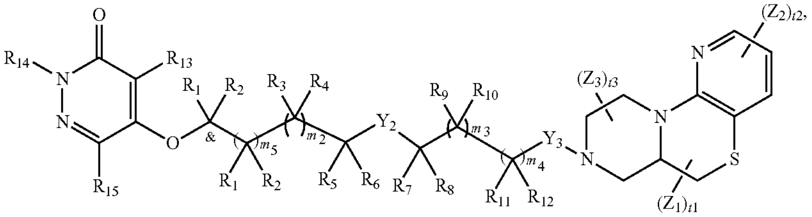
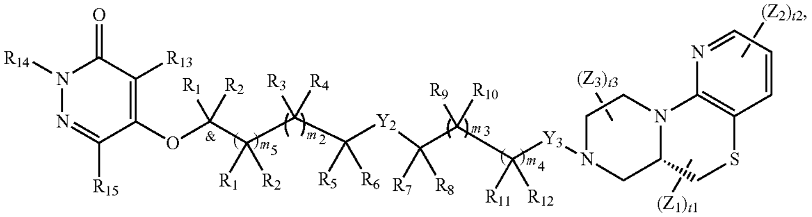
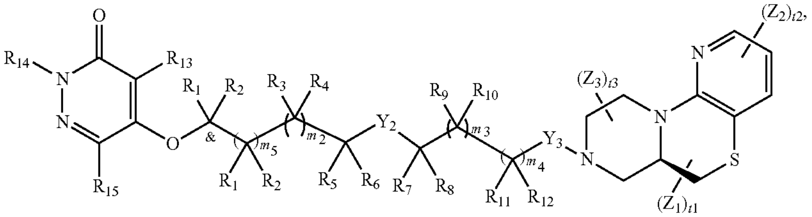
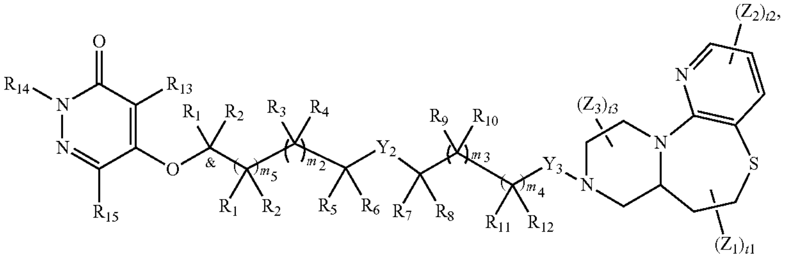

-continued
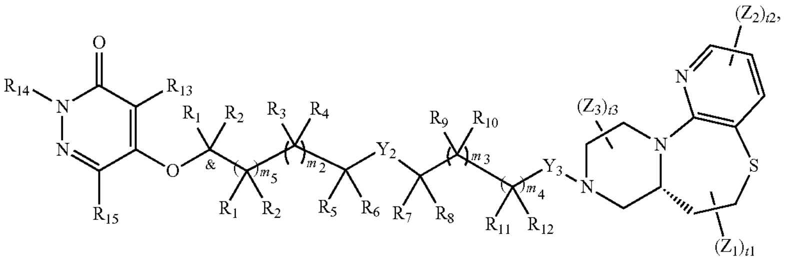
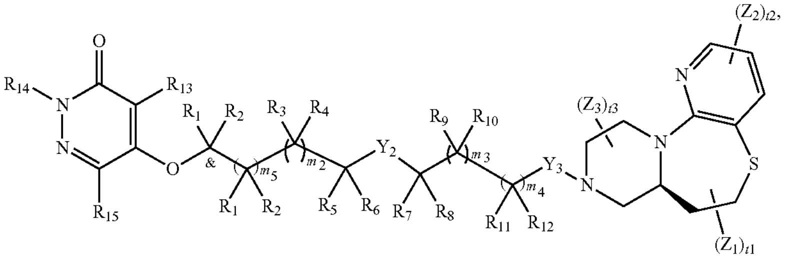
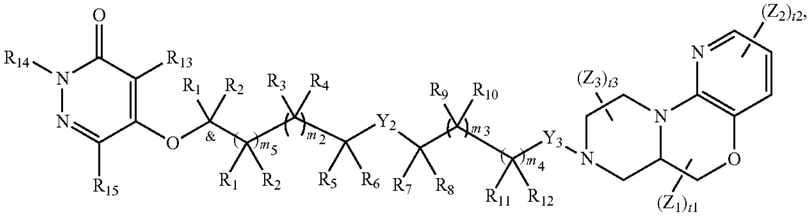
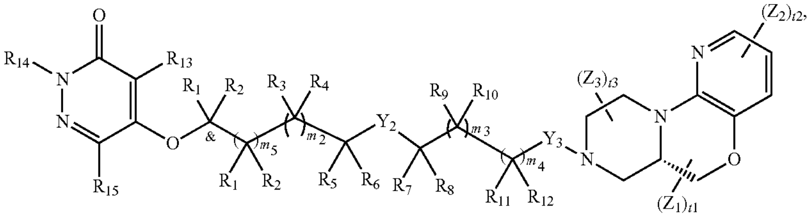
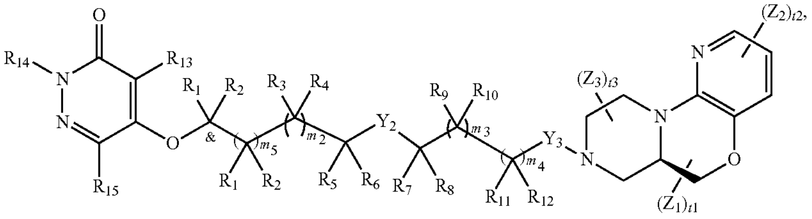
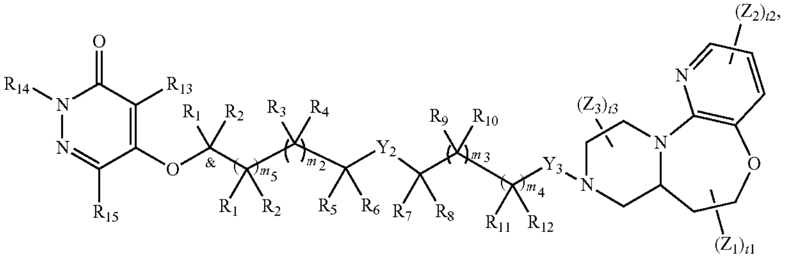
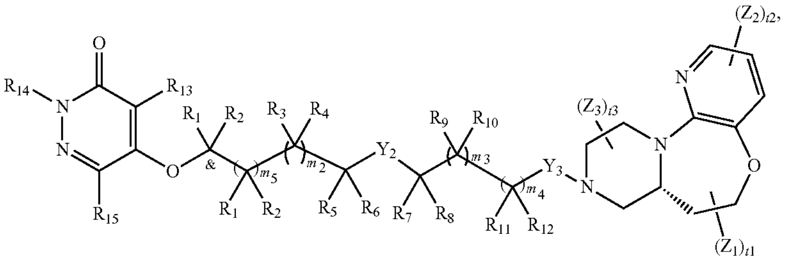

-continued
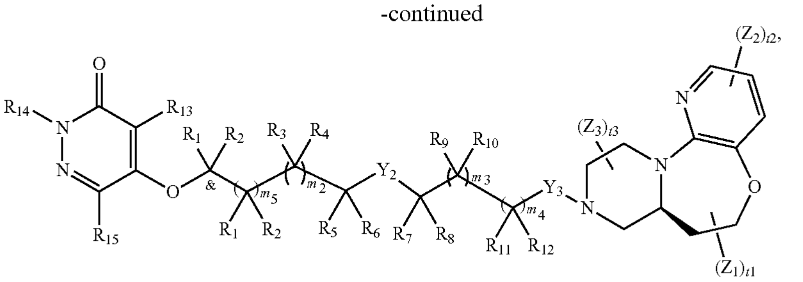
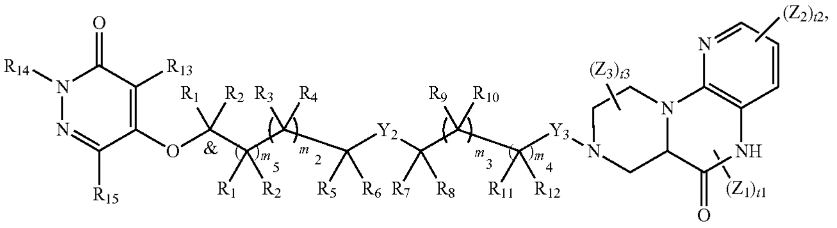
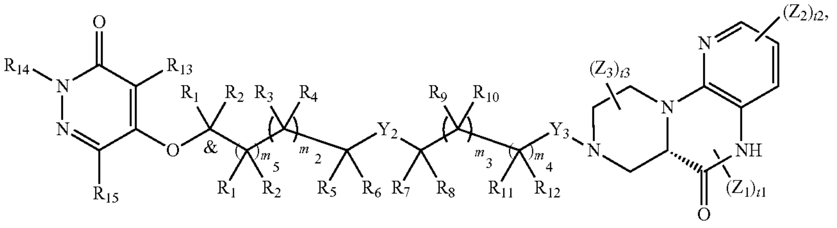
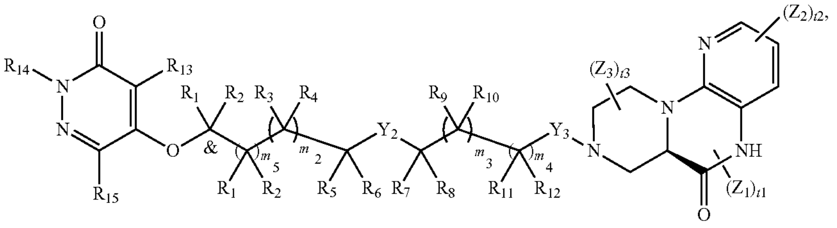
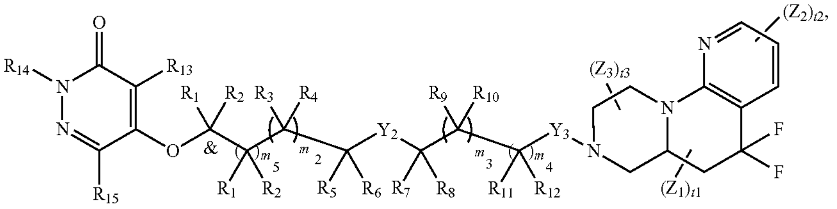
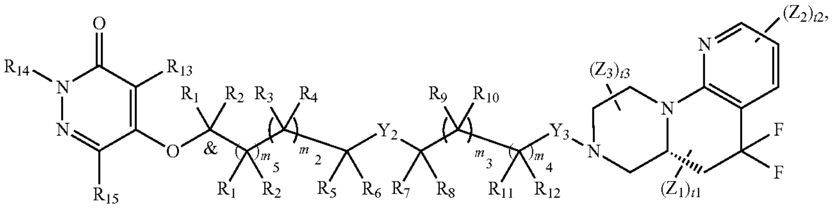
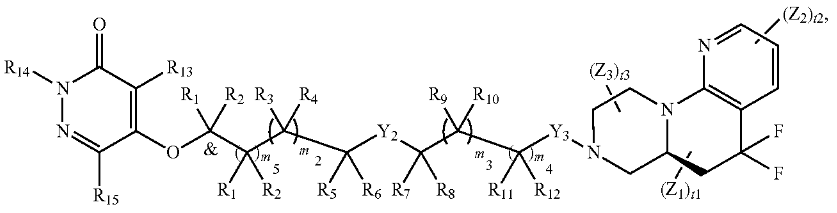

-continued
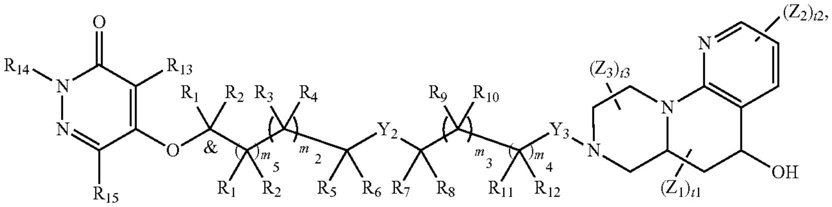
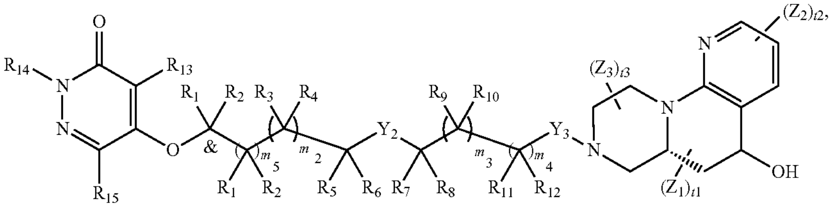
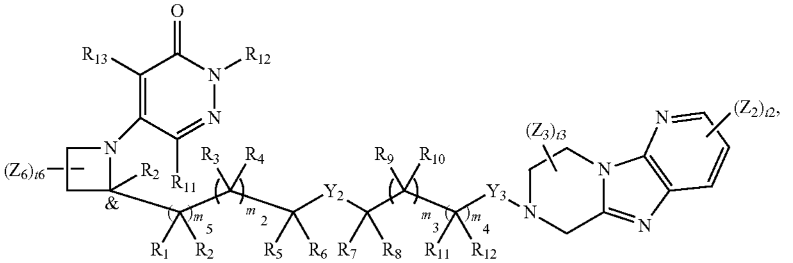
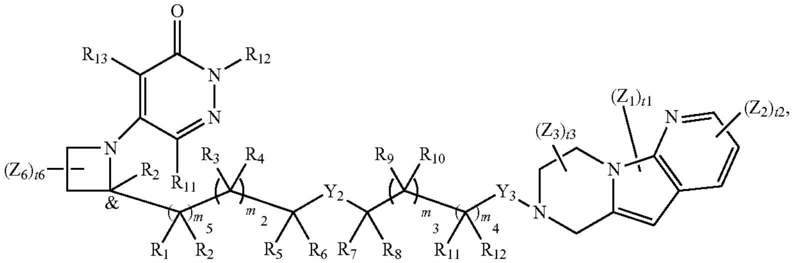
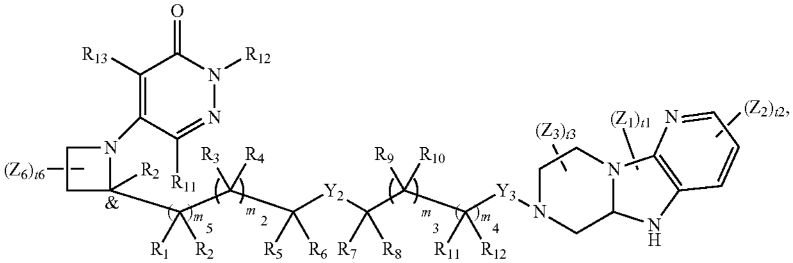
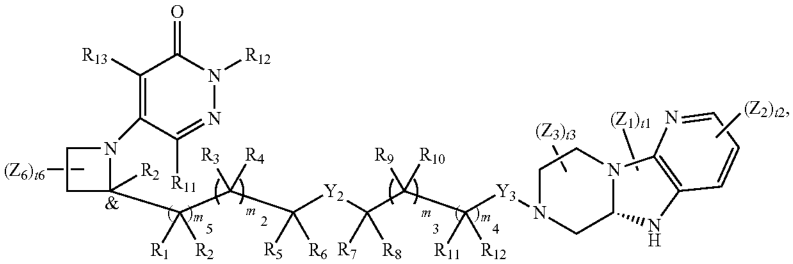

-continued
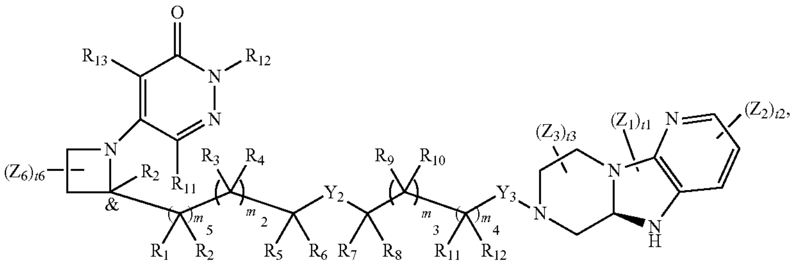
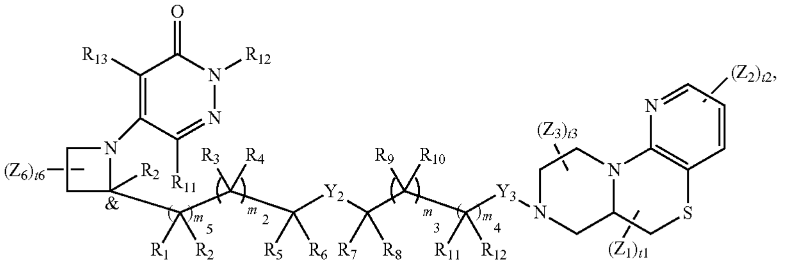
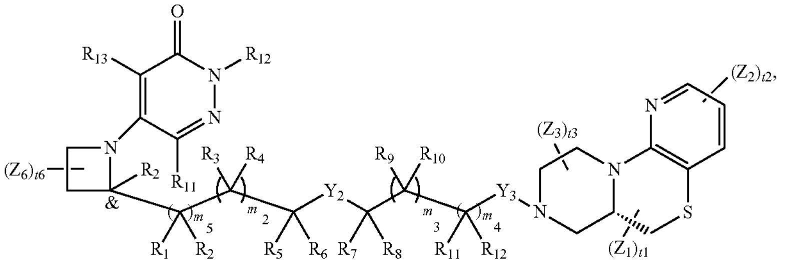
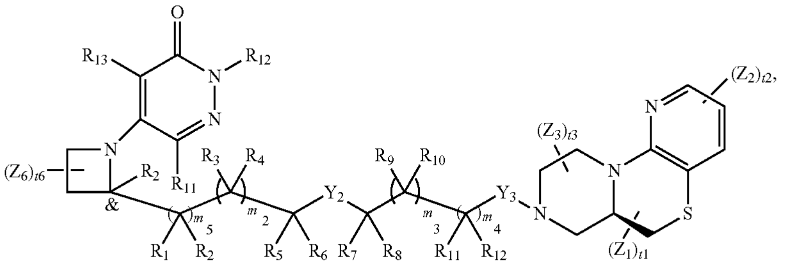
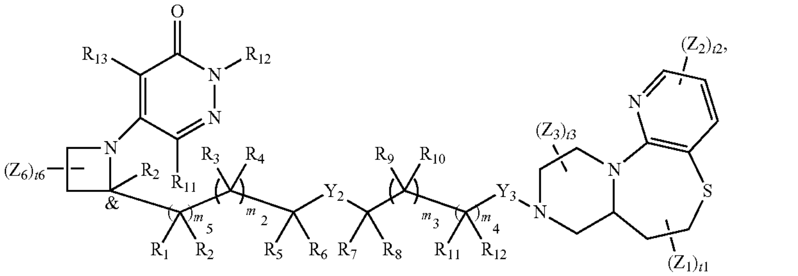
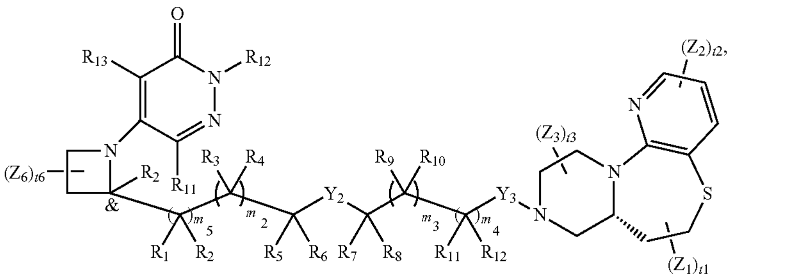

-continued
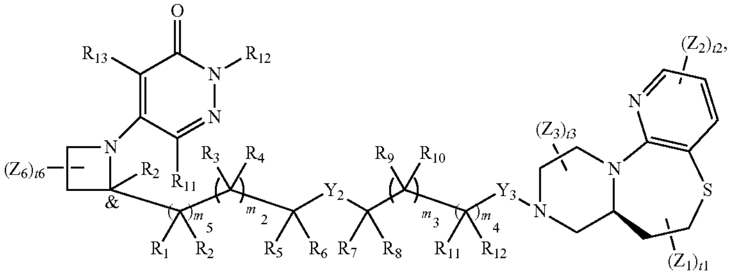
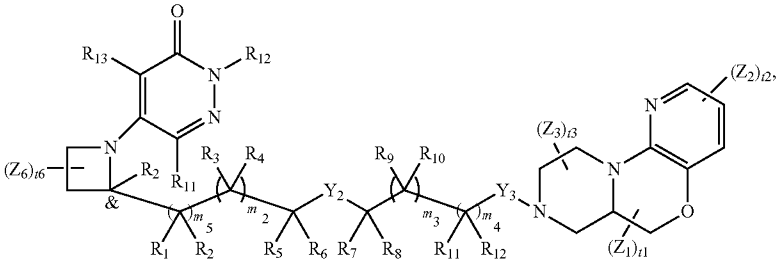
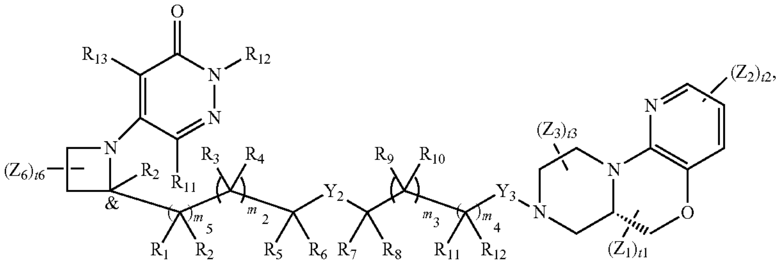
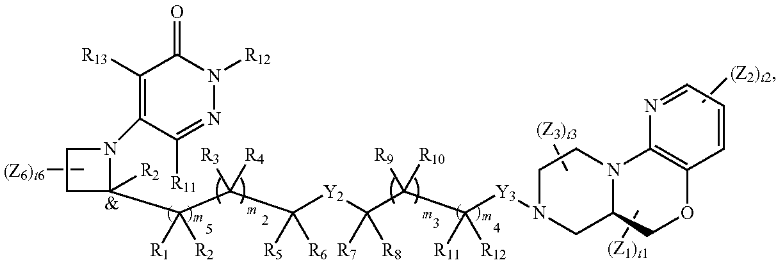
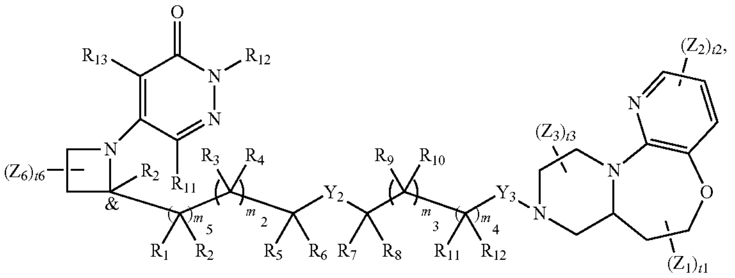
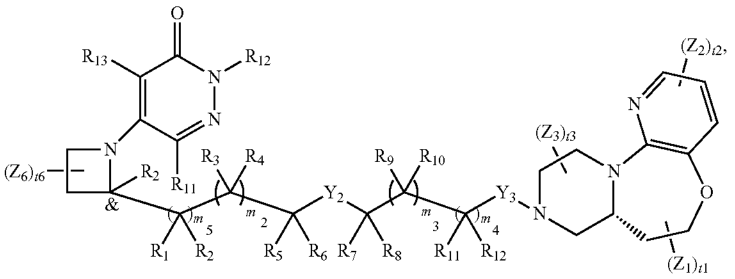

-continued
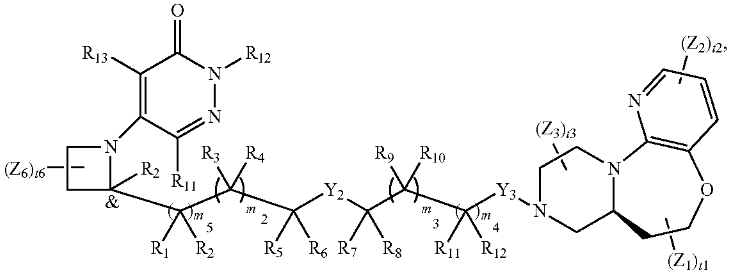
,
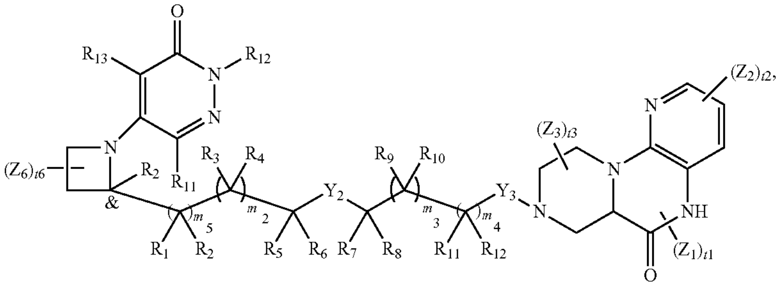
,
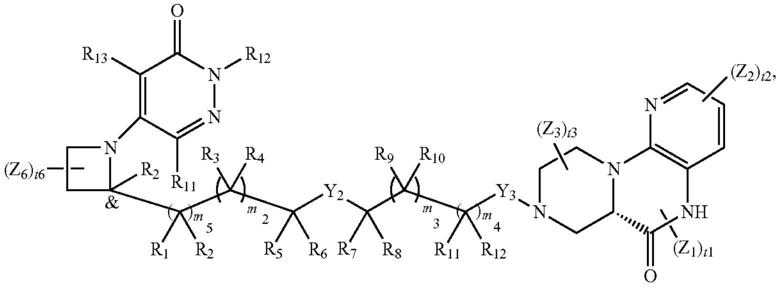
,
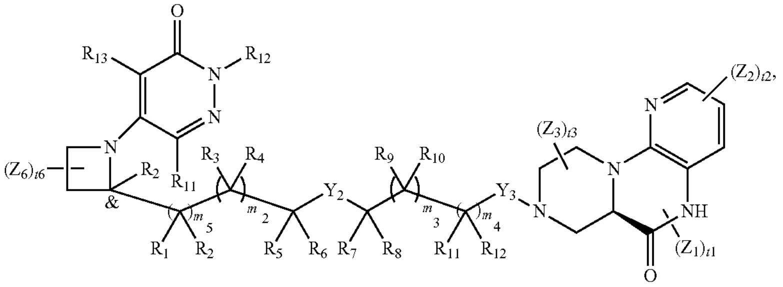
,
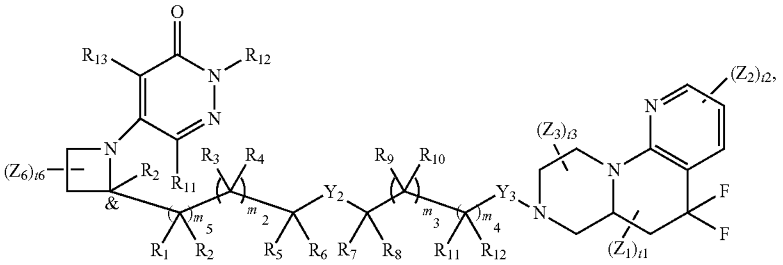
,
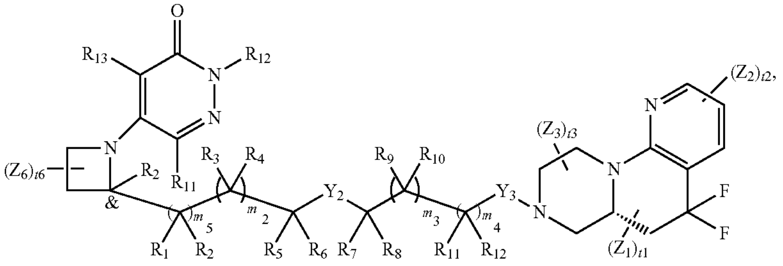
, -continued

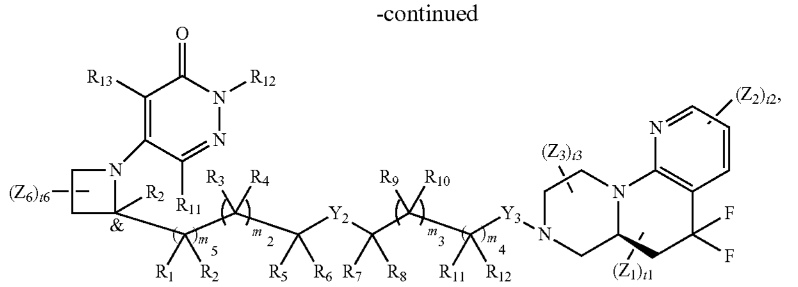

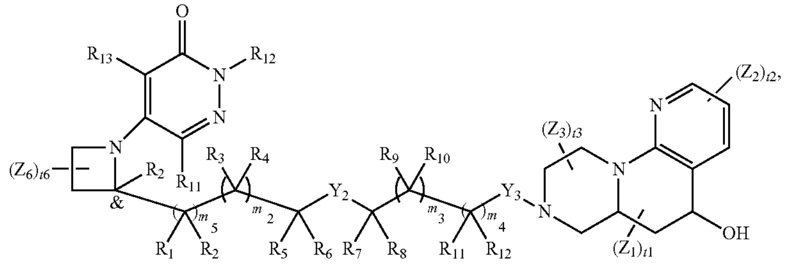

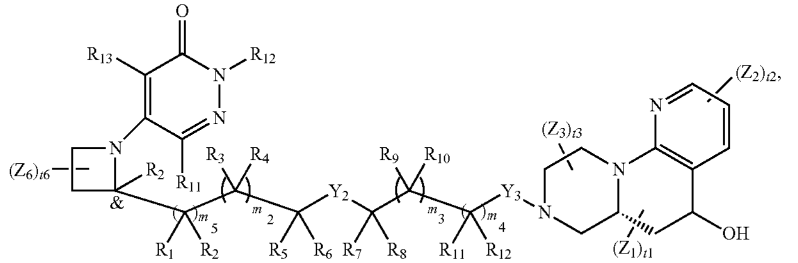

or

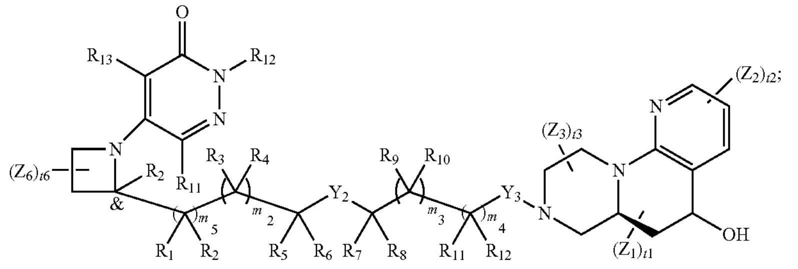

& in any one of formulas indicates that the carbon atom is R configuration or S configuration when the carbon atom is a chiral carbon atom; in some embodiments, & in any one of formulas indicates that the carbon atom is R configuration when the carbon atom is a chiral carbon atom; in some embodiments, & in any one of formulas indicates that the carbon atom is S configuration when the carbon atom is a chiral carbon atom.

[55]. The compound according to any one of [1] to [50], wherein, the compound is selected from the following formula (VIII):

Wherein, the definition of $R_1$, $R_2$, $R_3$, $R_4$, $R_5$, $R_6$, $R_8$, $R_9$, $R_{10}$, $R_{11}$, $R_{12}$, $R_{13}$, $R_{14}$, $R_{15}$, $Y_1$, $Y_2$, $X_1$, $X_2$, $X_3$, $X_4$, $Z_1$, $Z_2$, $Z_3$, $Z_{23}$, ring A, ring B, ring C, $m_1$, $m_2$, $m_3$, $m_4$, $t_1$, $t_2$, $t_3$ or $t_{23}$ is same as any one of [1] to [50];

Ring E is selected from a 3-15 membered carbocyclic ring, 3-15 membered heterocyclic ring, —$C_{6-10}$ aryl ring or 5-15 membered heteroaryl ring; in some embodiments, ring E is selected from a 4-10 membered cycloalkyl ring, 4-10 membered cycloalkenyl ring, 4-10 membered cycloalkynyl ring, 4-10 membered heterocycloalkyl ring, 4-10 membered heterocycloalk- (VIII)

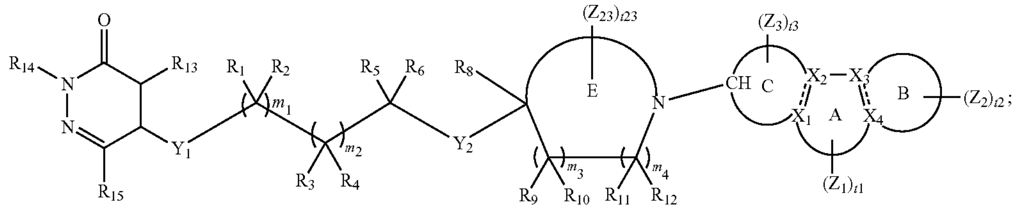

enyl ring, —$C_{6-10}$ aryl ring or 5-10 membered heteroaryl ring; said heterocycloalkyl ring or heterocycloalkenyl ring at each occurrence is independently contain 1, 2, 3 or 4 ring members selected from N, O, S, C(=O), C(=O)NH, NHC(=O), S(=O), S(=O)NH, NH—S(=O), $S(=O)_2$, $S(=O)_2NH$, $NHS(=O)_2$; said heteroaryl ring contain 1, 2, 3 or 4 ring members selected from N, O, S;

In some embodiments, ring E is selected from 4 membered cycloalkyl ring; 5 membered cycloalkyl ring; 6 membered cycloalkyl ring; 7 membered cycloalkyl ring; 4 membered cycloalkenyl ring; 5 membered cycloalkenyl ring; 6 membered cycloalkenyl ring; 7 membered cycloalkenyl ring; 4 membered cycloalkynyl ring; 5 membered cycloalkynyl ring; 6 membered cycloalkynyl ring; 7 membered cycloalkynyl ring; 4 membered heterocycloalkyl ring; 5 membered heterocycloalkyl ring; 6 membered heterocycloalkyl ring; 7 membered heterocycloalkyl ring; 4 membered heterocycloalkenyl ring; 5 membered heterocycloalkenyl ring; 6 membered heterocycloalkenyl ring; 7 membered heterocycloalkenyl ring; benzene ring; naphthalene ring; 5 membered heteroaryl ring; 6 membered heteroaryl ring; 7 membered heteroaryl ring; 8 membered heteroaryl ring; 9 membered heteroaryl ring; 10 membered heteroaryl ring; said heterocycloalkyl ring or heterocycloalkenyl ring at each occurrence independently contains 1 N and further contains 1, 2, 3, or 4 ring members selected from N, O, S, C(=O), S(=O), $S(=O)_2$; said heteroaryl ring contain 1, 2, 3 or 4 ring members selected from N, O, S;

In some embodiments, ring E is selected from 5 membered heterocycloalkyl ring containing 1 N and further containing 1, 2, or 3 ring members selected from C(=O), S(=O) or $S(=O)_2$; or 6 membered heterocycloalkyl ring containing 1 N and further containing 1, 2, or 3 ring members selected from C(=O), S(=O), $S(=O)_2$.

[56]. The compound according to [55], wherein, the compound is selected from any one of the following formula:

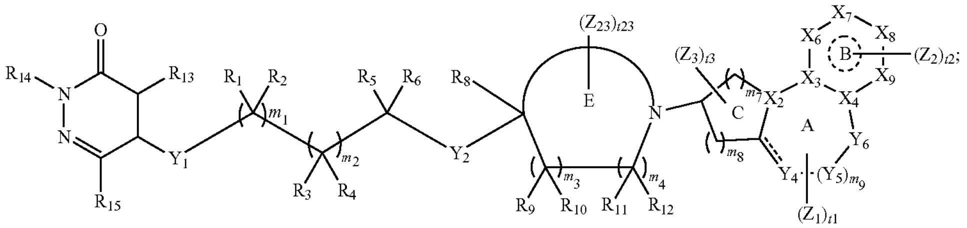

In some embodiments, the compound is selected from any one of the following formulas:

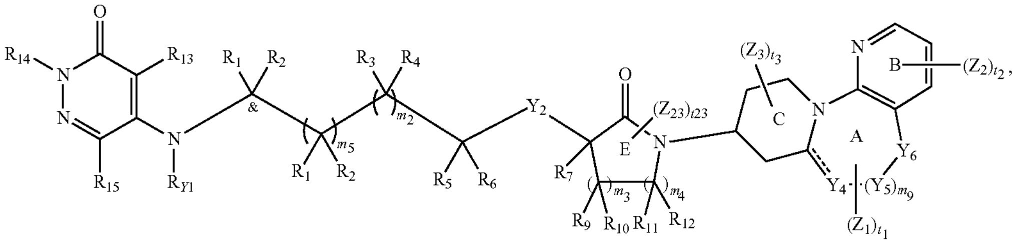

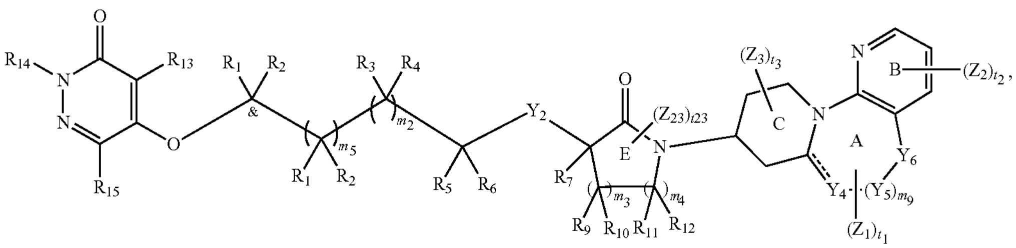
or

-continued
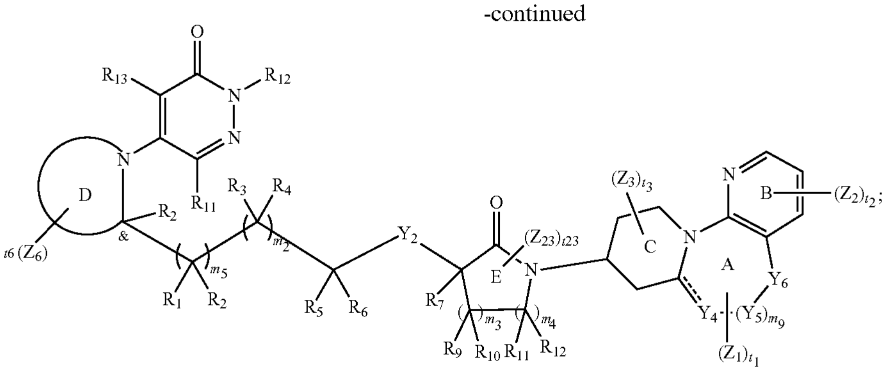
In some embodiments, the compound is selected from the following formulas:
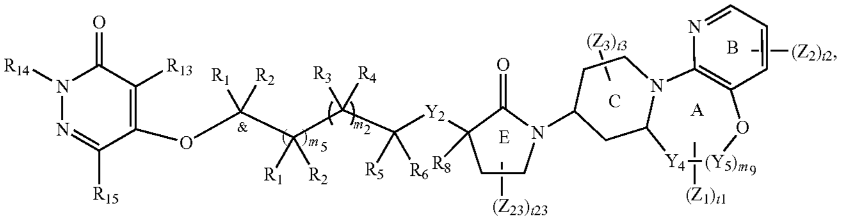
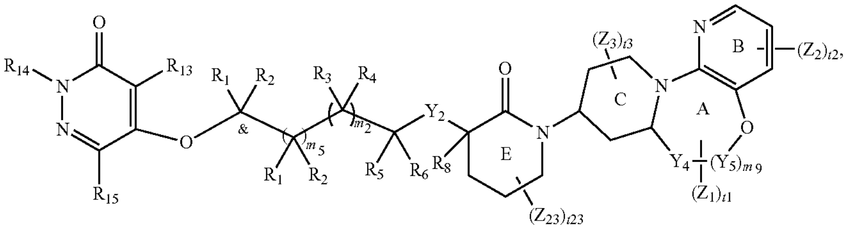
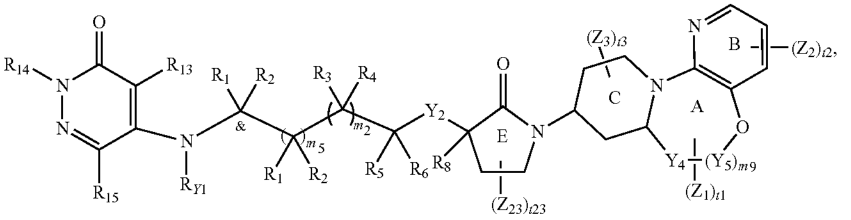
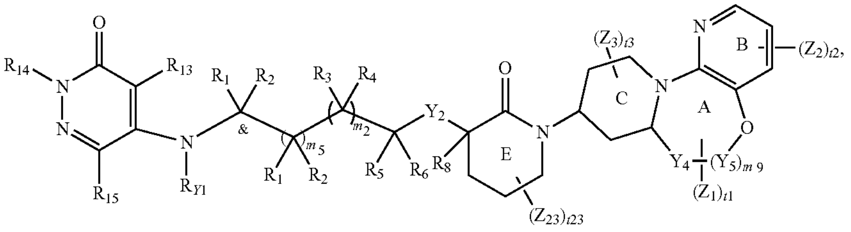
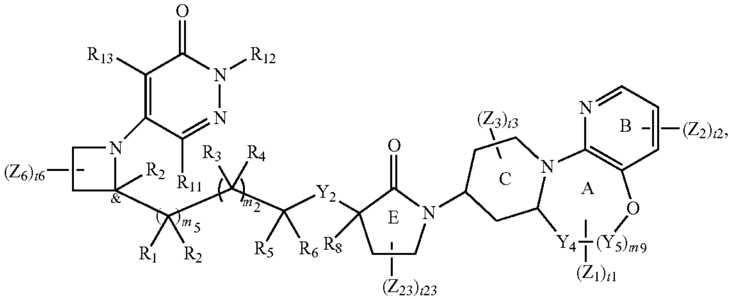
or -continued

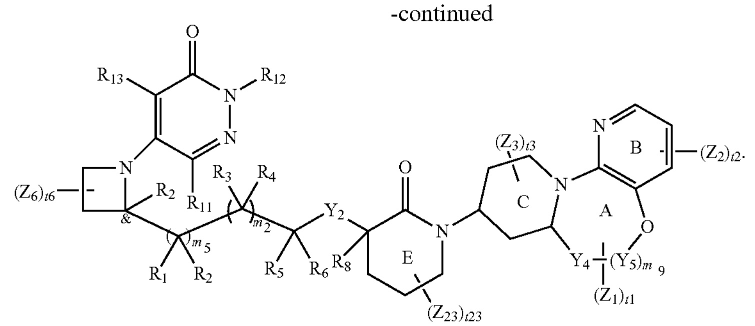

[57]. The compound according to any one of [1] to [50], wherein, the compound is selected from the following formula (IX):

(IX)

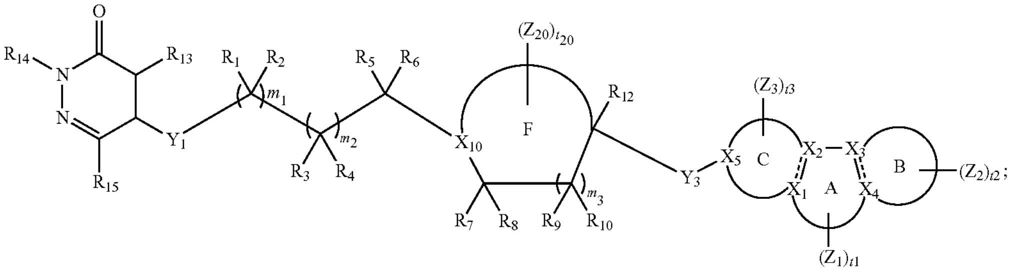

Wherein, the definition of $R_1$, $R_2$, $R_3$, $R_4$, $R_5$, $R_6$, $R_7$, $R_8$, $R_9$, $R_{10}$, $R_{12}$, $R_{13}$, $R_{14}$, $R_{15}$, $Y_1$, $Y_3$, $X_1$, $X_2$, $X_3$, $X_4$, $X_5$, $Z_1$, $Z_2$, $Z_3$, $Z_{20}$, ring A, ring B, ring C, $m_1$, $m_2$, $m_3$, $t_1$, $t_2$, $t_3$ or $t_2$ is same as any one of[1] to [50];

$X_{10}$ is selected from C, N or CH;

Ring F is selected from a 3-20 membered carbocyclic ring, 3-20 membered heterocyclic ring, —$C_{6-10}$ aryl ring or 5-20 membered heteroaryl ring;

In some embodiments, ring F is selected from a 3-10 membered cycloalkyl ring, 3-10 membered cycloalkenyl ring, 3-10 membered heterocycloalkyl ring, 3-10 membered heterocycloalkenyl ring, —$C_{6-10}$ aryl ring or 5-10 membered heteroaryl ring;

In some embodiments, ring F is selected from a 3-10 membered heterocycloalkyl ring, 3-10 membered heterocycloalkenyl ring or 5-10 membered heteroaryl ring; said heterocycloalkyl ring or heterocycloalkenyl ring at each occurrence contains 1 N and optionally further contains 1, 2, 3 or 4 ring members selected from N, O, S, C(═O), S(═O) or $S(═O)_2$; said heteroaryl ring contain 1, 2, 3 or 4 ring members selected from N, O, S;

In some embodiments, ring F is selected from 3 membered heterocycloalkyl ring; 4 membered heterocycloalkyl ring; 5 membered heterocycloalkyl ring; 6 membered heterocycloalkyl ring; 7 membered heterocycloalkyl ring; 3 membered heterocycloalkenyl ring; 4 membered heterocycloalkenyl ring; 5 membered heterocycloalkenyl ring; 6 membered heterocycloalkenyl ring; 7 membered heterocycloalkenyl ring; 5 membered heteroaryl ring; 6 membered heteroaryl ring; 7 membered heteroaryl ring; 8 membered heteroaryl ring; 9 membered heteroaryl ring; 10 membered heteroaryl ring; said heterocycloalkyl ring or heterocycloalkenyl ring at each occurrence independently contains 1 N and optionally further contains 1, 2, 3, or 4 ring members selected from N, O, S, C(═O), S(═O), $S(═O)_2$; said heteroaryl ring contain 1, 2, 3 or 4 ring members selected from N, O or S;

In some embodiments, ring F is selected from 5 membered heterocycloalkyl ring containing 1 N.

[58]. The compound according to [57], wherein, the compound is selected from the following formula:

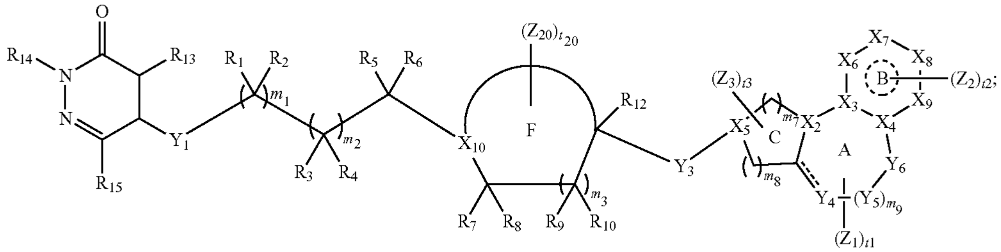

In some embodiments, the compound is selected from any one of the following formulas:
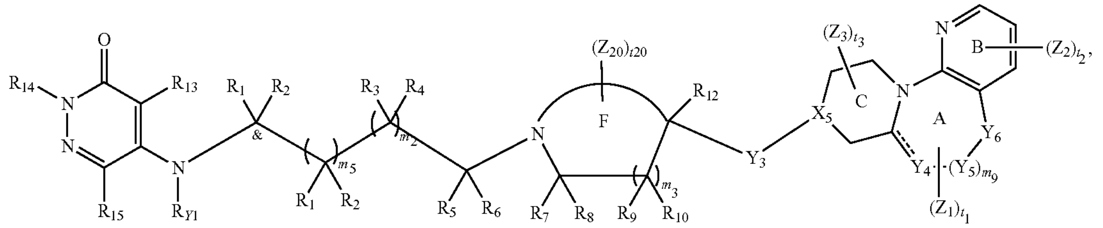
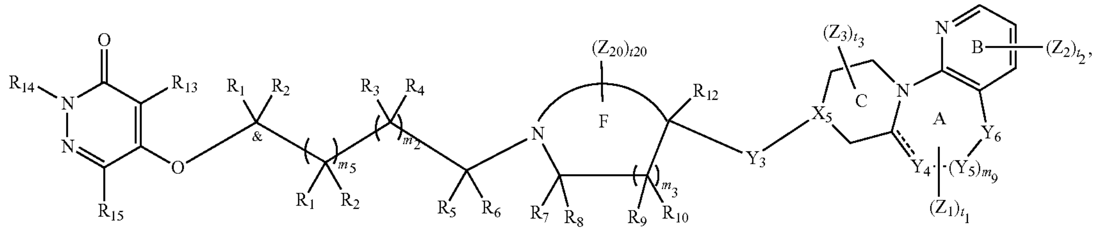
or
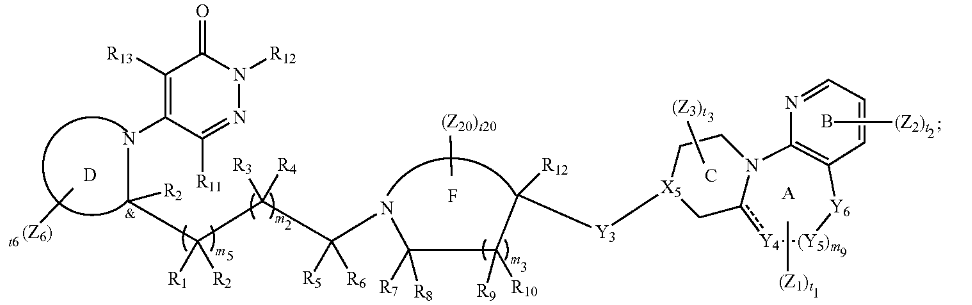
In some embodiments, the compound is selected from any one of the following formulas:
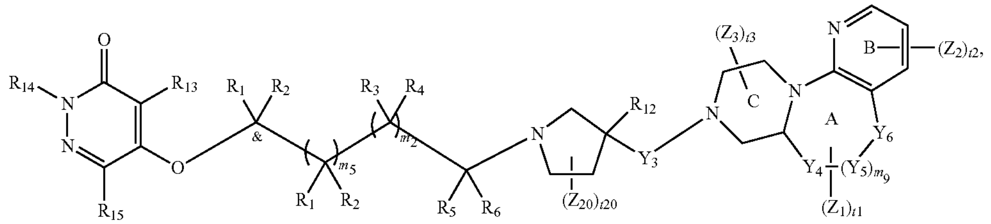
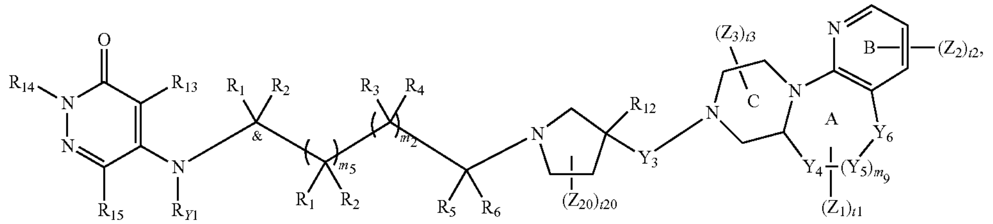
or -continued
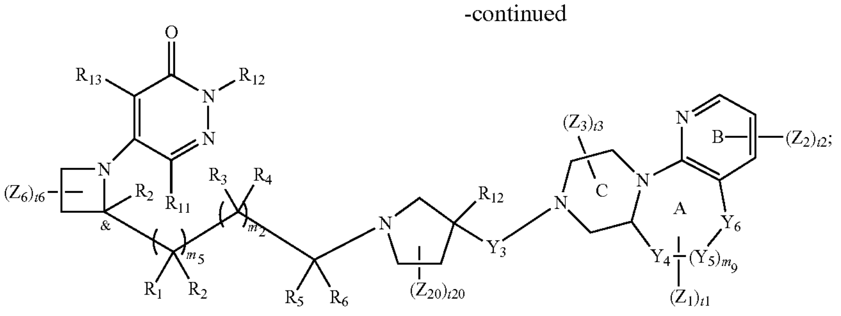
In some embodiments, the compound is selected from any one of the following formulas:
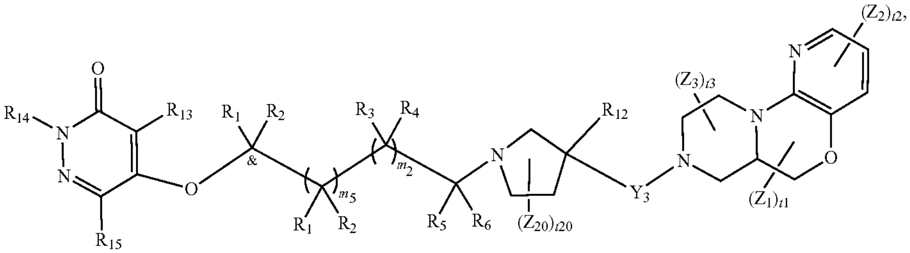
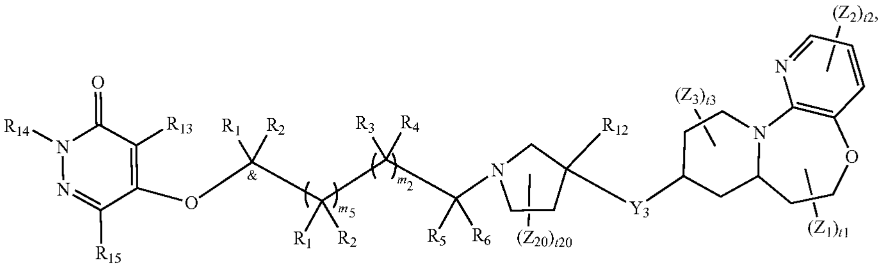
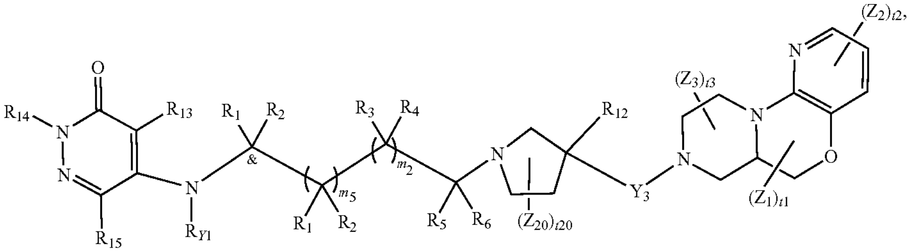
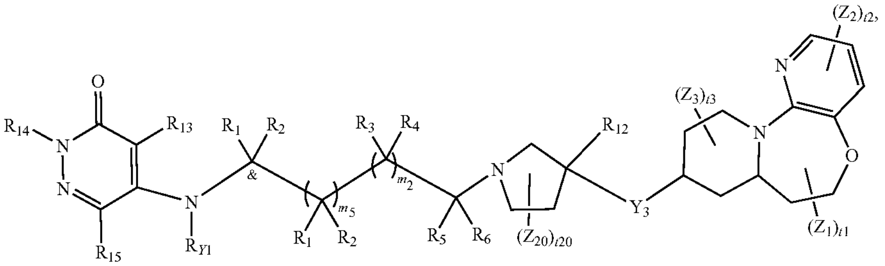

-continued

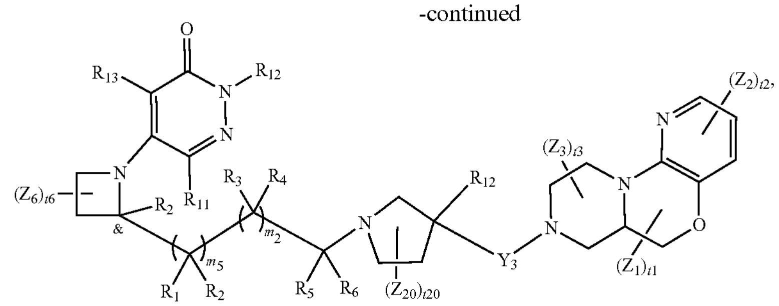

or

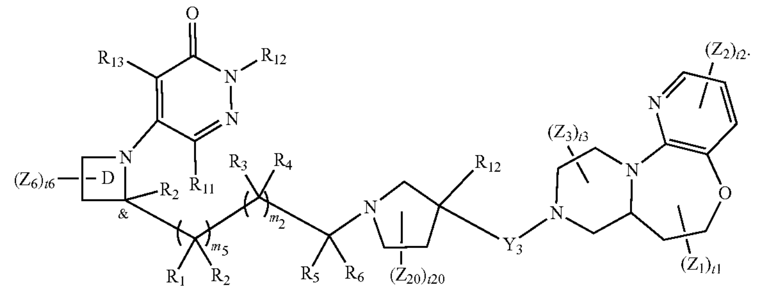

[59]. The compound according to any one of [1] to [50], wherein, the compound is selected from the following formula (X):

(X)

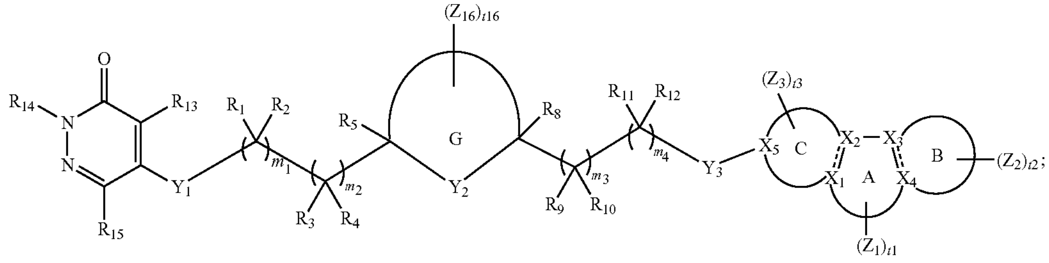

Wherein, the definition of $R_1$, $R_2$, $R_3$, $R_4$, $R_6$, $R_8$, $R_9$, $R_{10}$, $R_{11}$, $R_{12}$, $R_{13}$, $R_{14}$, $R_{15}$, $Y_1$, $Y_2$, $Y_3$, $X_1$, $X_2$, $X_3$, $X_4$, $X_5$, $Z_1$, $Z_2$, $Z_3$, $Z_{16}$, ring A, ring B, ring C, $m_1$, $m_2$, $m_3$, $m_4$, $t_1$, $t_2$, $t_3$ or $t_{16}$ is same as any one of [1] to [50];

Ring G is selected from a 3-20 membered carbocyclic ring, 3-20 membered heterocyclic ring, —$C_{6-10}$ aryl ring or 5-20 membered heteroaryl ring;

In some embodiments, ring G is selected from a 3-10 membered cycloalkyl ring, 3-10 membered cycloalkenyl ring, 3-10 membered heterocycloalkyl ring, 3-10 membered heterocycloalkenyl ring, —$C_{6-10}$ aryl ring or 5-10 membered heteroaryl ring;

In some embodiments, ring G is selected from a 3-10 membered heterocycloalkyl ring, 3-10 membered heterocycloalkenyl ring or 5-10 membered heteroaryl ring; said heterocycloalkyl ring or heterocycloalkenyl ring at each occurrence contains 1 O and optionally further contains 1, 2, 3 or 4 ring members selected from N, O, S, C(═O), S(═O) or S(═O)$_2$; said heteroaryl ring contain 1, 2, 3 or 4 ring members selected from N, O, S;

In some embodiments, ring G is selected from 3 membered heterocycloalkyl ring; 4 membered heterocycloalkyl ring; 5 membered heterocycloalkyl ring; 6 membered heterocycloalkyl ring; 7 membered heterocycloalkyl ring; 3 membered heterocycloalkenyl ring; 4 membered heterocycloalkenyl ring; 5 membered heterocycloalkenyl ring; 6 membered heterocycloalkenyl ring; 7 membered heterocycloalkenyl ring; 5 membered heteroaryl ring; 6 membered heteroaryl ring; 7 membered heteroaryl ring; 8 membered heteroaryl ring; 9 membered heteroaryl ring; 10 membered heteroaryl ring; said heterocycloalkyl ring or heterocycloalkenyl ring at each occurrence independently contains 1 O and optionally further contains 1, 2, 3, or 4 ring members selected from N, O, S, C(═O), S(═O), S(═O)$_2$; said heteroaryl ring contain 1, 2, 3 or 4 ring members selected from N, O or S;

In some embodiments, ring G is selected from 5 membered heterocycloalkyl ring containing 1 O.

[60]. The compound according to [59], wherein, the compound is selected from the following formula:

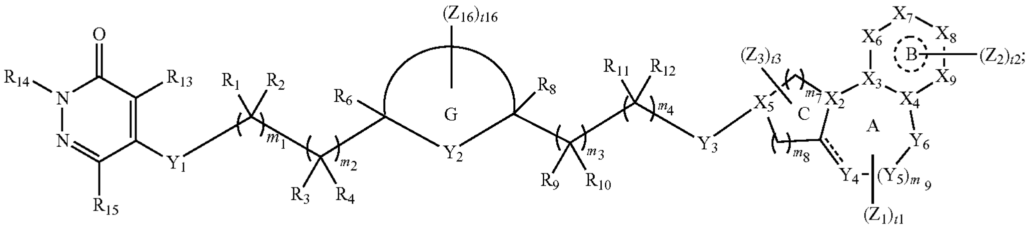
In some embodiments, the compound is selected from any one of the following formulas:
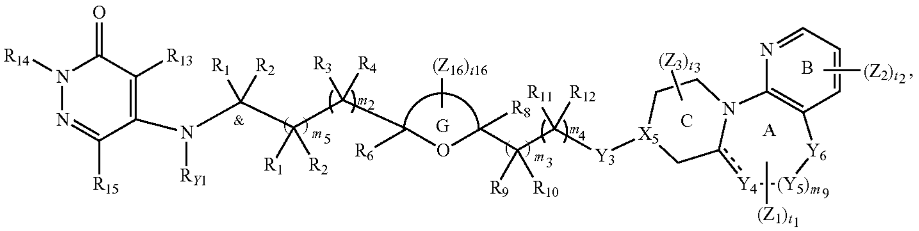
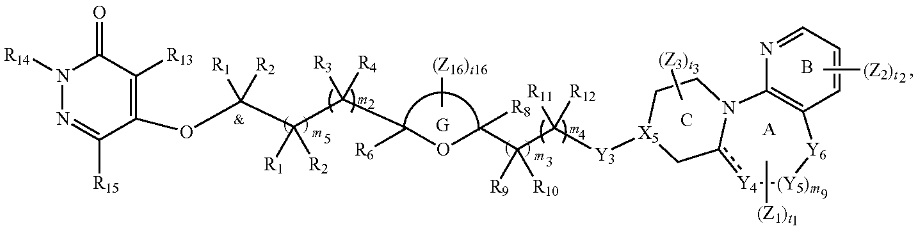
or
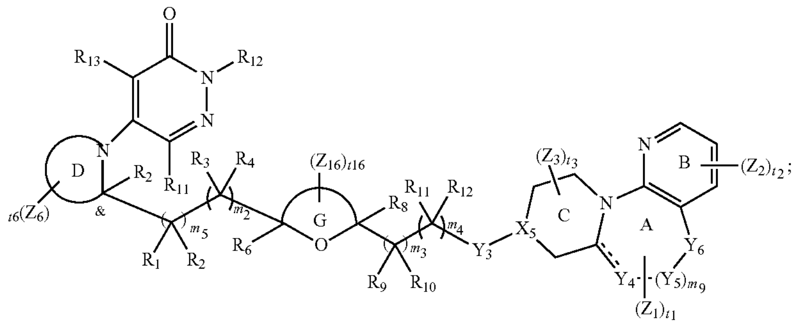
In some embodiments, the compound is selected from any one of the following formulas:
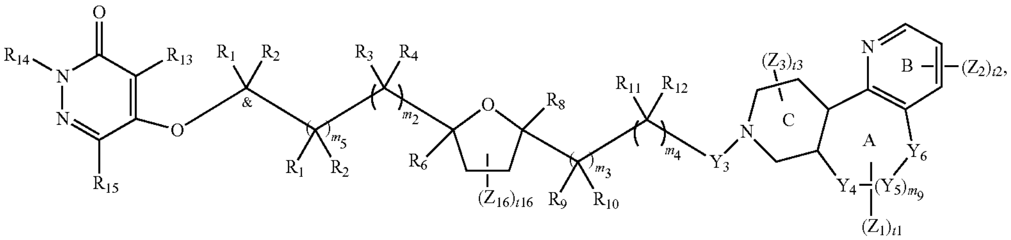

-continued
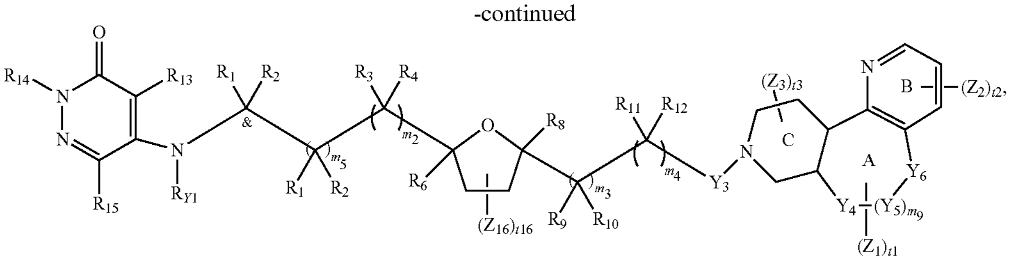
or
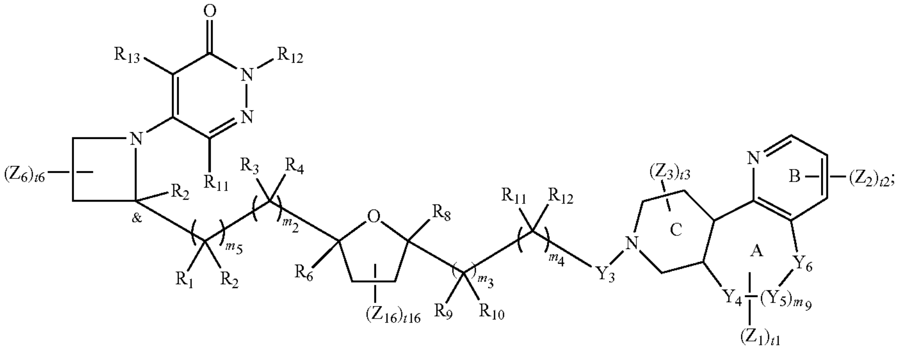
;
In some embodiments, the compound is selected from any one of the following formulas:
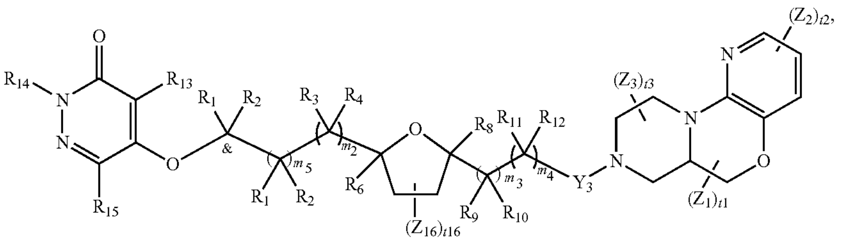
,
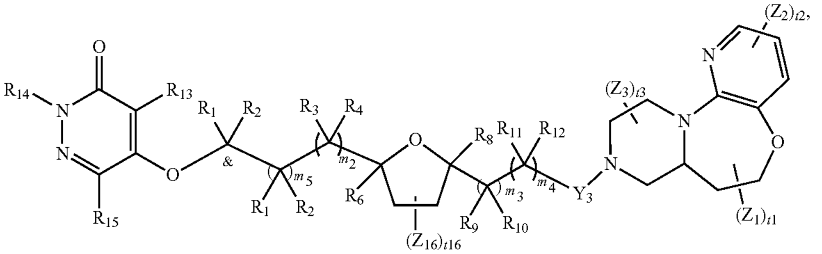
,
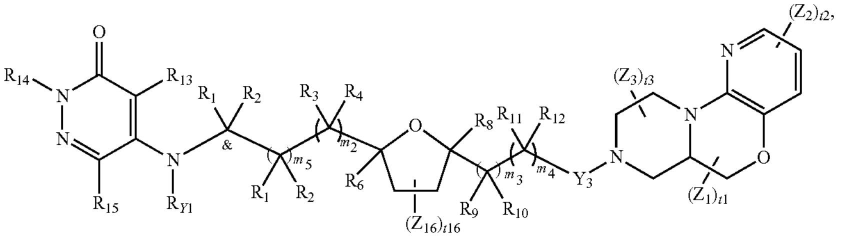
, -continued

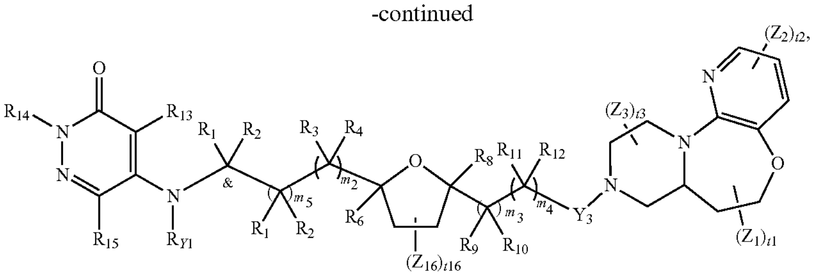

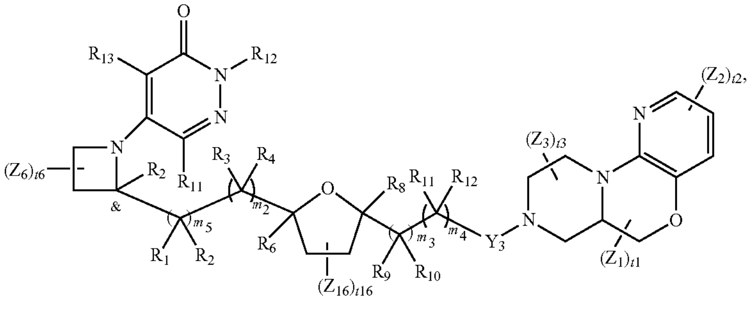

or

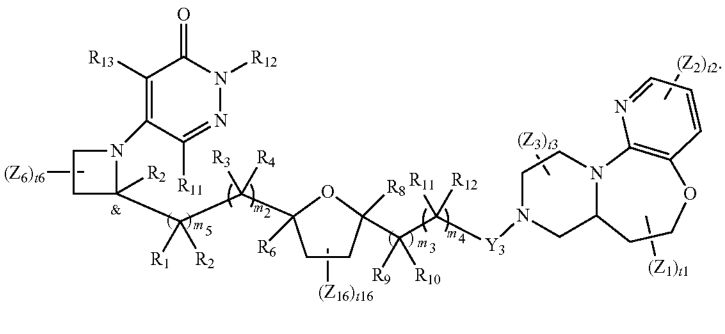

[61]. The compound according to any one of [1] to [50], wherein, the compound is selected from the following formula (XI):

(XI)

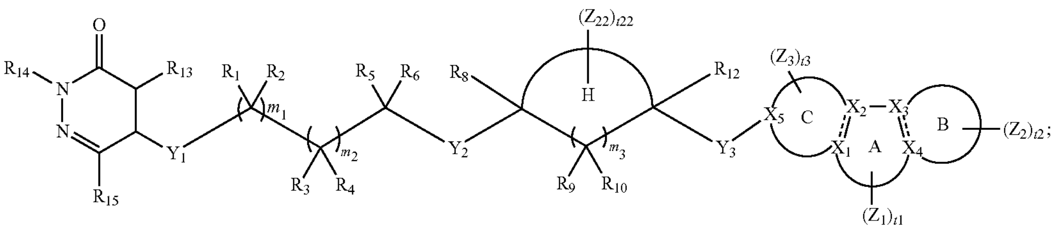

Wherein, the definition of $R_1$, $R_2$, $R_3$, $R_4$, $R_5$, $R_6$, $R_8$, $R_9$, $R_{10}$, $R_{12}$, $R_{13}$, $R_{14}$, $R_{15}$, $Y_1$, $Y_2$, $Y_3$, $X_1$, $X_2$, $X_3$, $X_4$, $X_5$, $Z_1$, $Z_2$, $Z_3$, $Z_{22}$, ring A, ring B, ring C, $m_1$, $m_2$, $m_3$, $t_1$, $t_2$, $t_3$ or $t_{22}$ is same as any one of [1] to [50];

Ring H is selected from a 3-20 membered carbocyclic ring, 3-20 membered heterocyclic ring, —$C_{6-10}$ aryl ring or 5-20 membered heteroaryl ring;

In some embodiments, ring H is selected from a 3-10 membered cycloalkyl ring, 3-10 membered cycloalkenyl ring, 3-10 membered heterocycloalkyl ring, 3-10 membered heterocycloalkenyl ring, —$C_{6-10}$ aryl ring or 5-10 membered heteroaryl ring;

In some embodiments, ring H is selected from a —$C_{6-10}$ aryl ring or 5-10 membered heteroaryl ring; said heteroaryl ring contain 1, 2, 3 or 4 ring members selected from N, O, S;

In some embodiments, ring H is selected from benzene ring; naphthalene ring; 5 membered heteroaryl ring; 6 membered heteroaryl ring; 7 membered heteroaryl ring; 8 membered heteroaryl ring; 9 membered heteroaryl ring; 10 membered heteroaryl ring; said heteroaryl ring contain 1, 2, 3 or 4 ring members selected from N, O, S;

In some embodiments, ring H is selected from a benzene ring.

[62]. The compound according to [61], wherein, the compound is selected from the following formula:

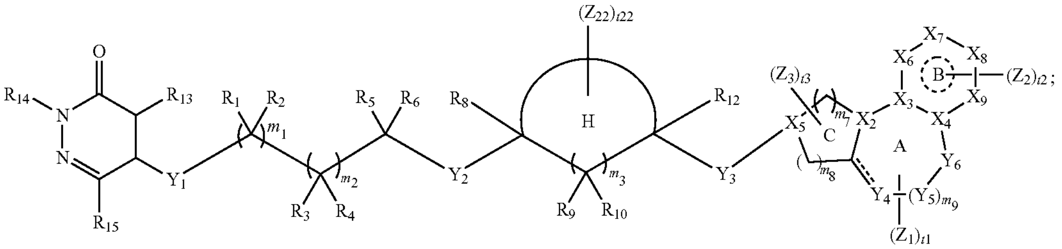
In some embodiments, the compound is selected from any one of the following formulas:
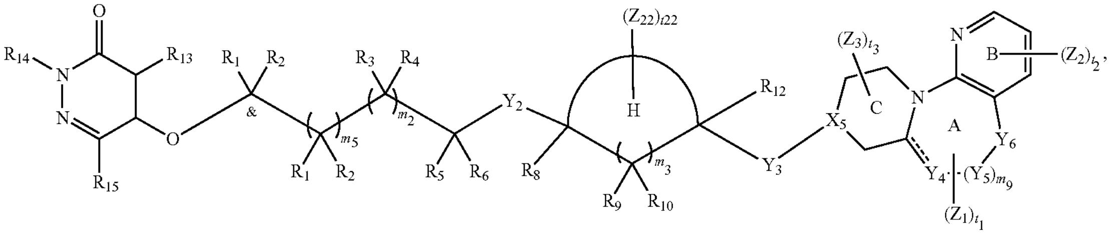
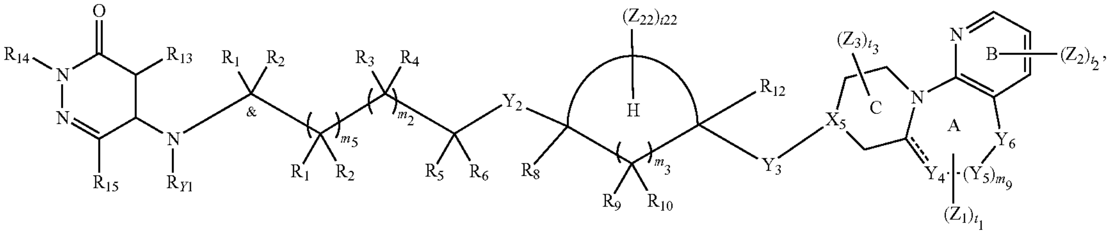
or
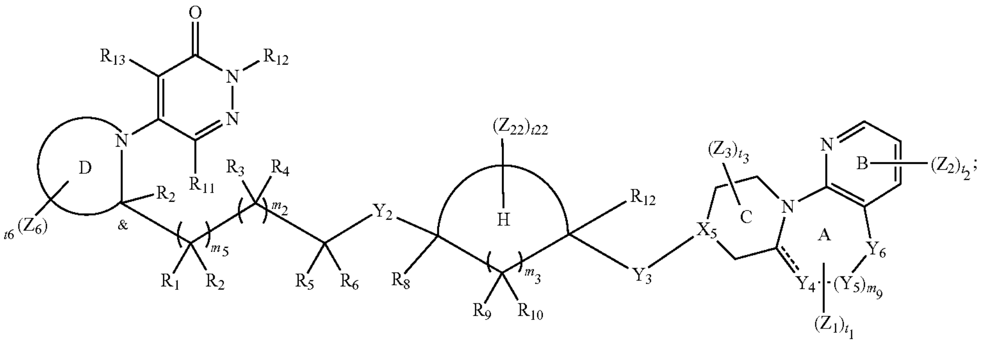
In some embodiments, the compound of is selected from any one of the following formulas:
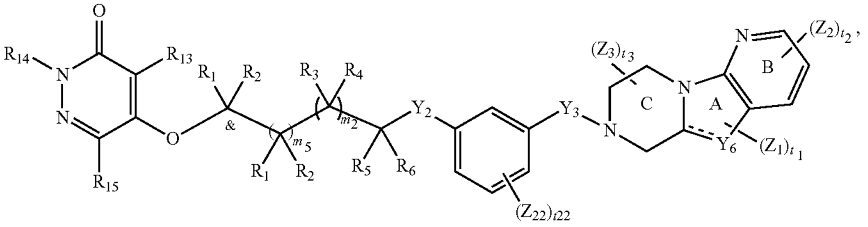

-continued
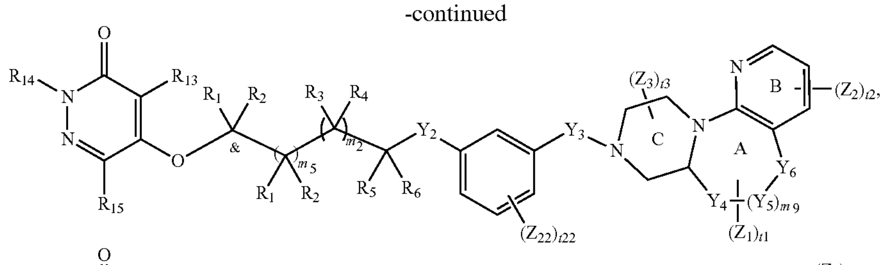
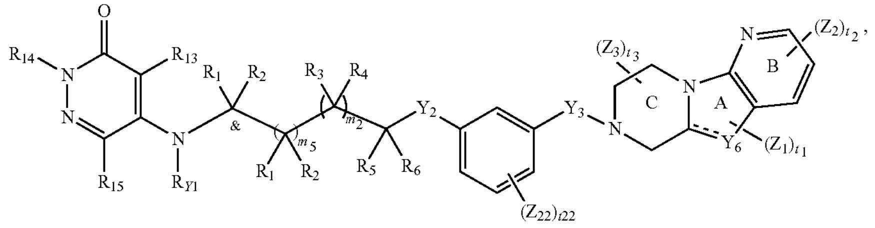
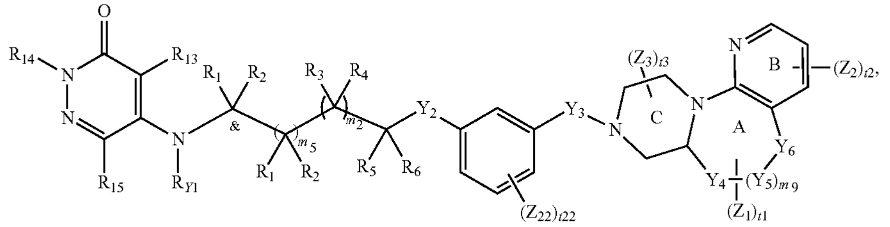
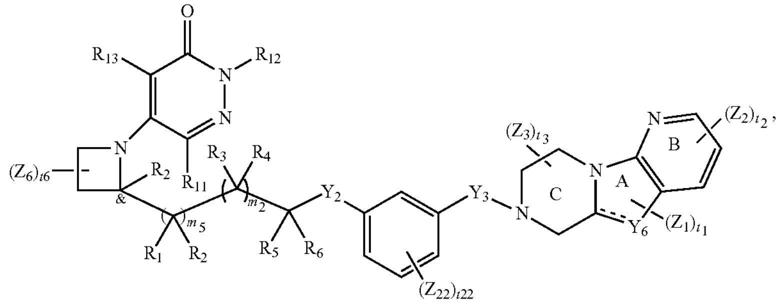
or
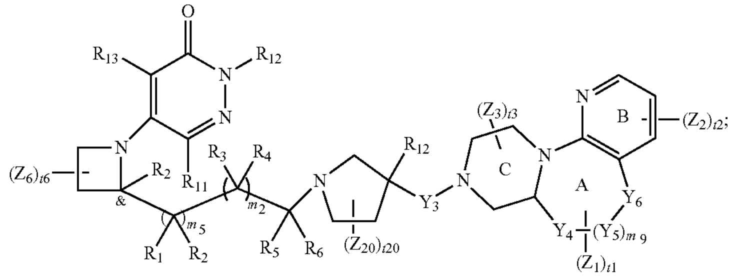
In some embodiments, the compound is selected from any one of the following formulas:
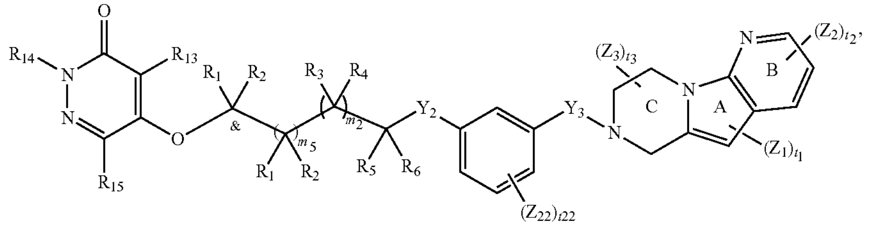

-continued
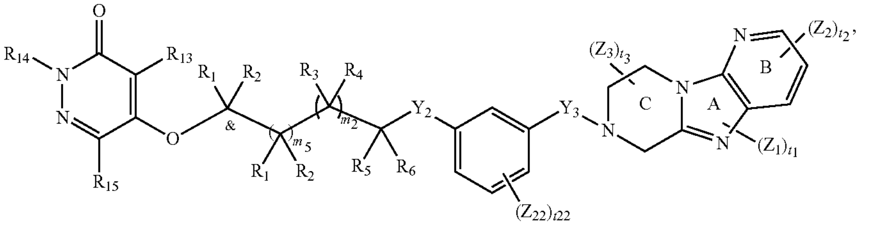,
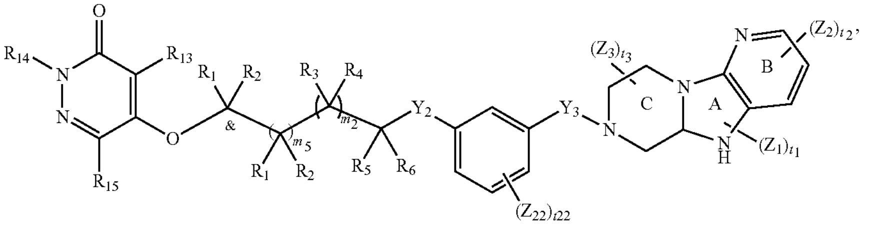,
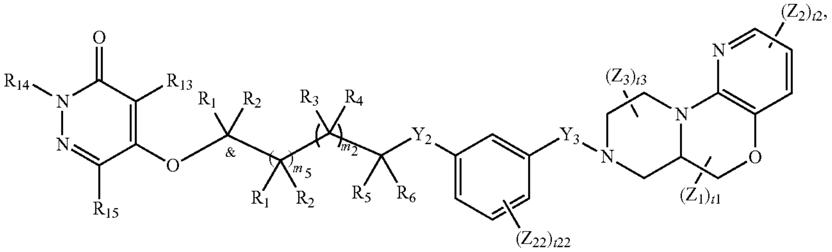,
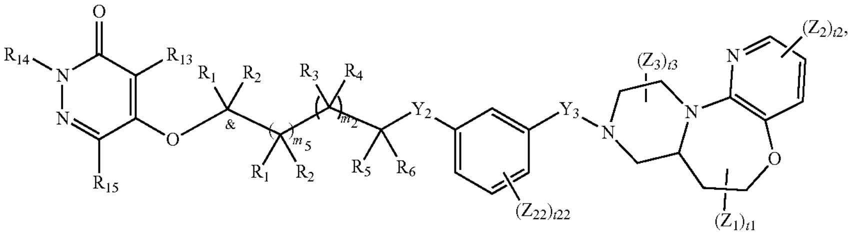,
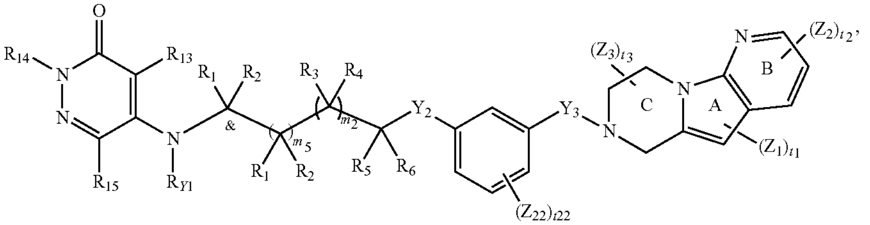,
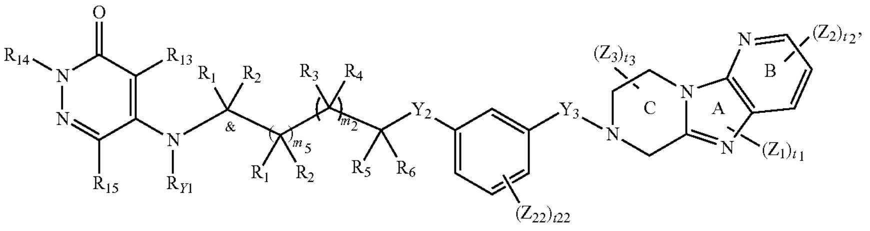,
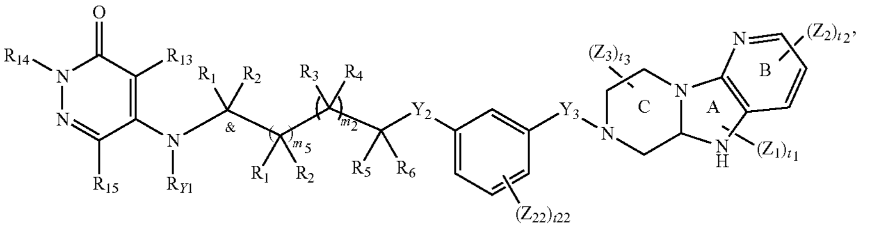, -continued
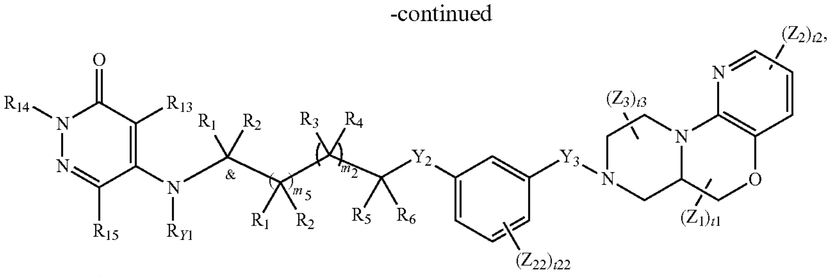
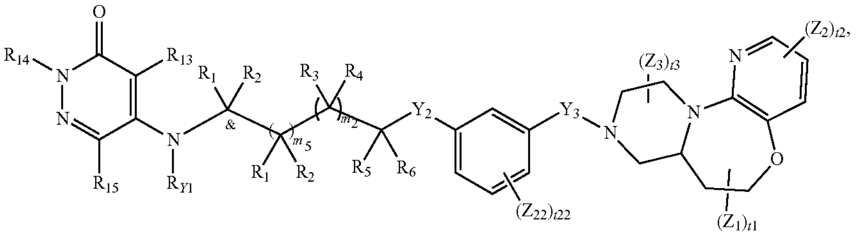
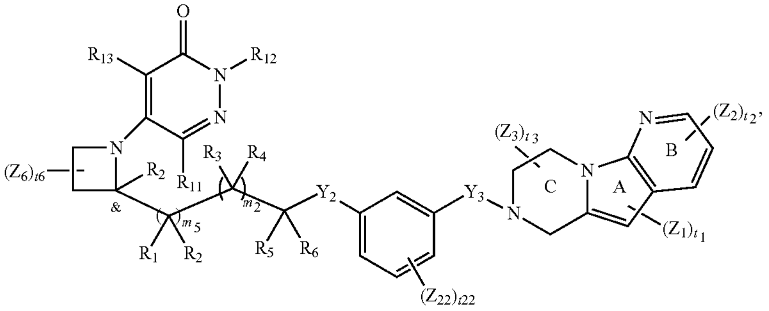
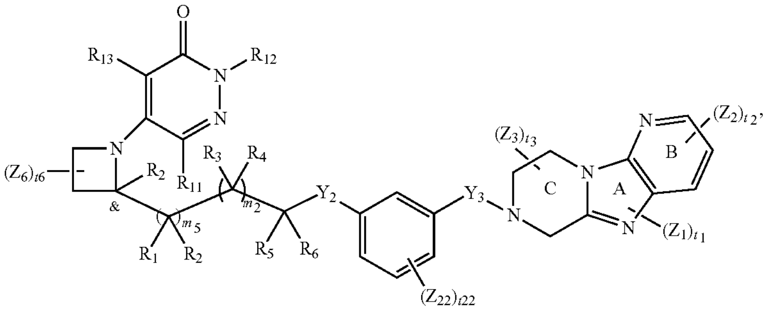
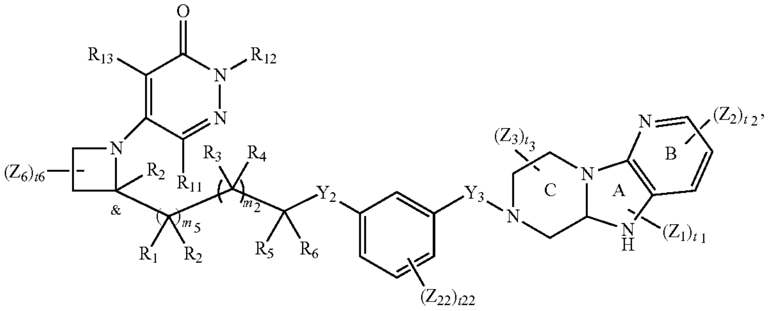
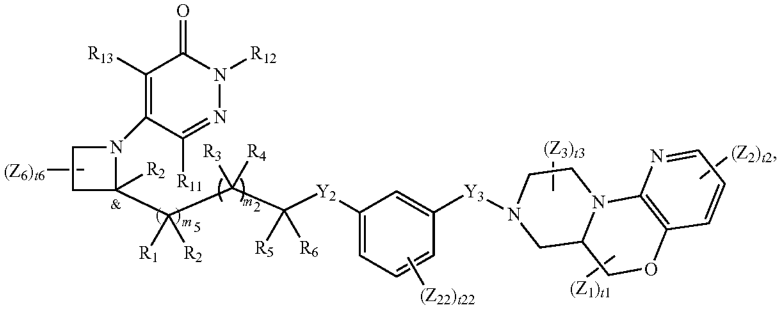
or -continued

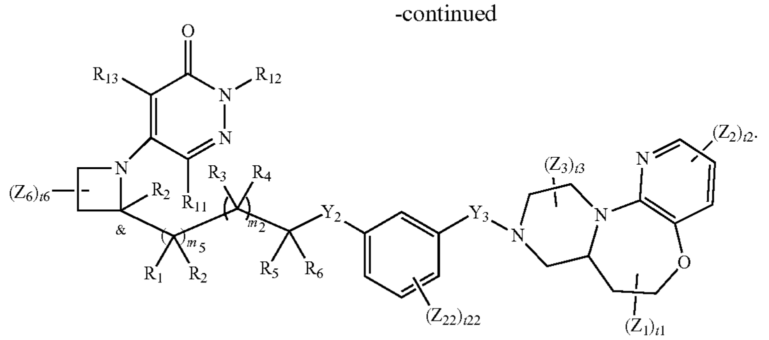

[63]. The compound according to any one of [1] to [50], wherein, the compound is selected from the following formula (XII):

(XII)

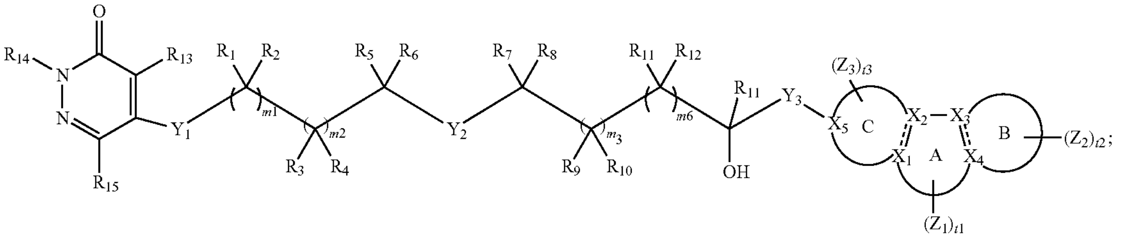

Wherein, the definition of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $Y_1$, $Y_2$, $Y_3$, $X_1$, $X_2$, $X_3$, $X_4$, $X_5$, $Z_1$, $Z_2$, $Z_3$, ring A, ring B, ring C, $m_1$, $m_2$, $m_3$, $t_1$, $t_2$, or $t_3$ is same as any one of [1] to [50];

$m_6$ is selected from 0, 1, 2, 3, 4, 5 or 6.

[64]. The compound according to [63], wherein, the compound is selected from any one of the following formulas:

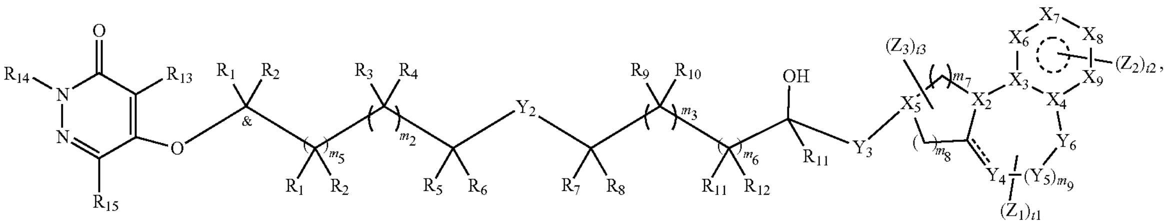

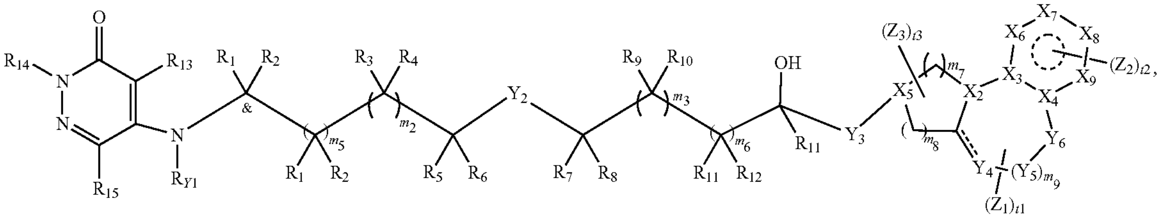

or

-continued
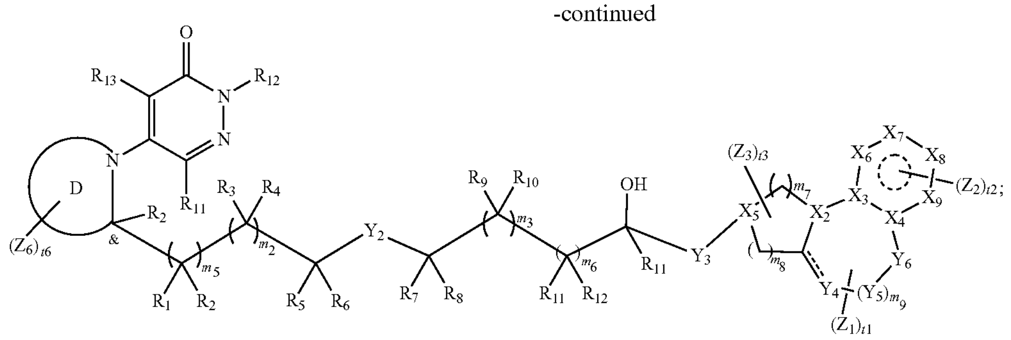
In some embodiments, the compound is selected from any one of the following formulas:
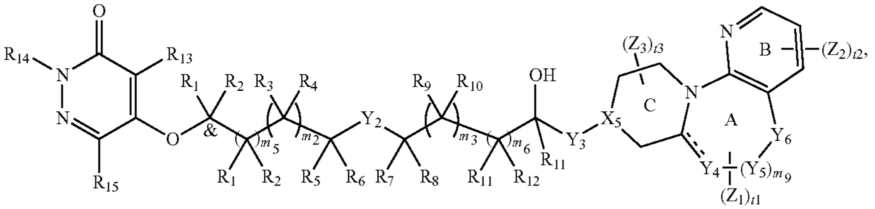
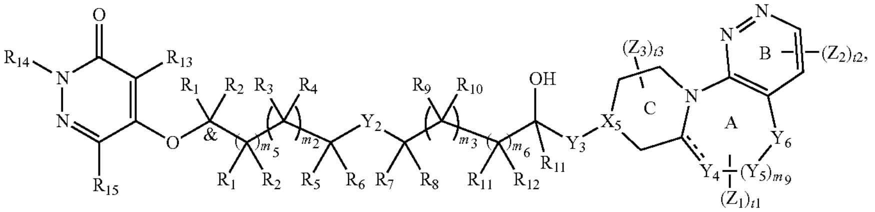
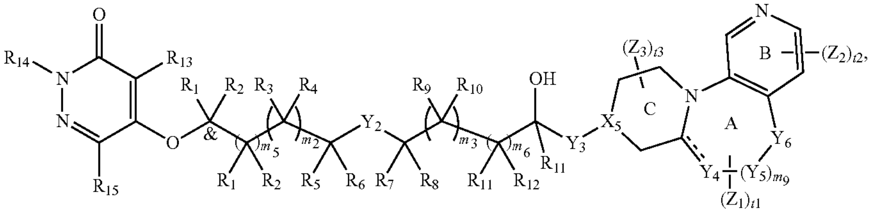
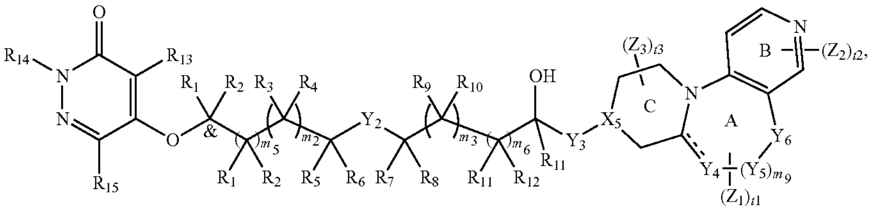
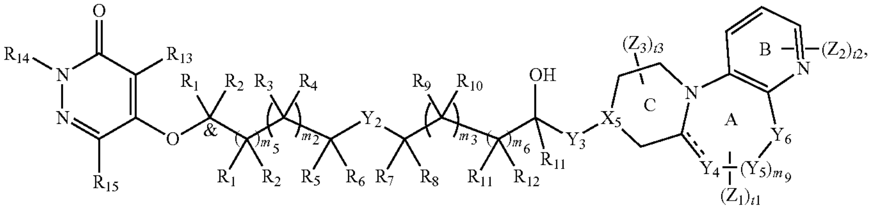

-continued
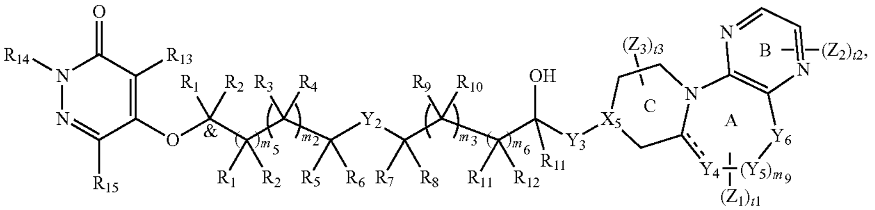
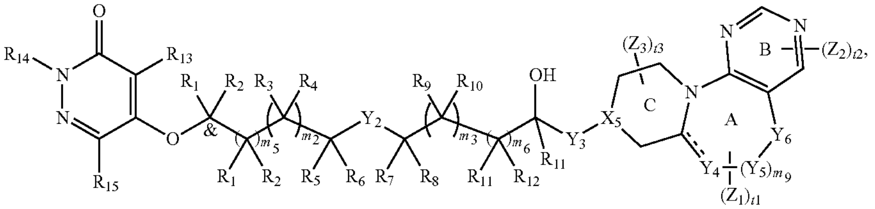
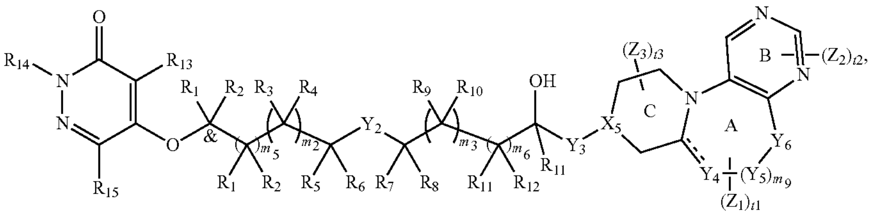
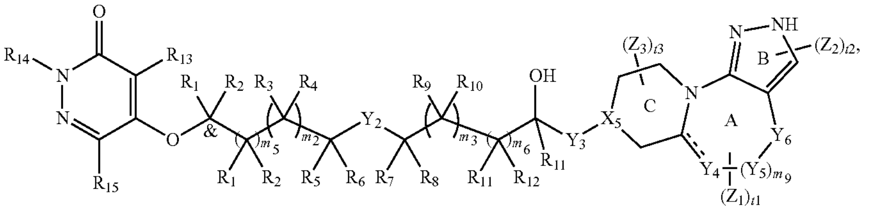
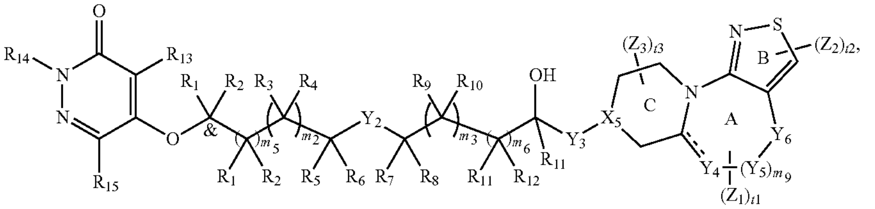
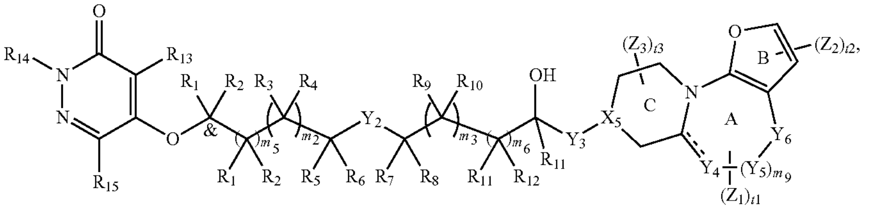
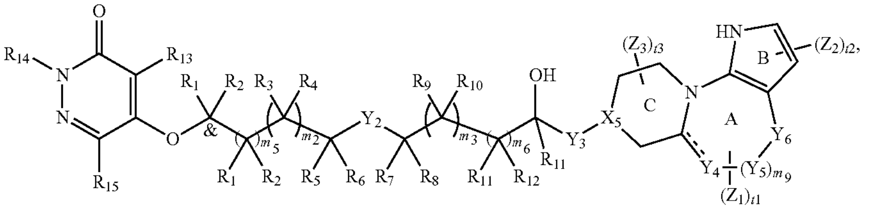
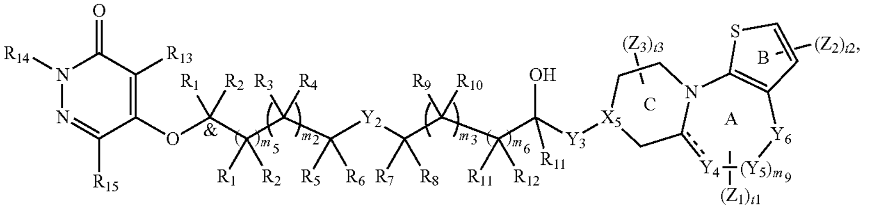

-continued
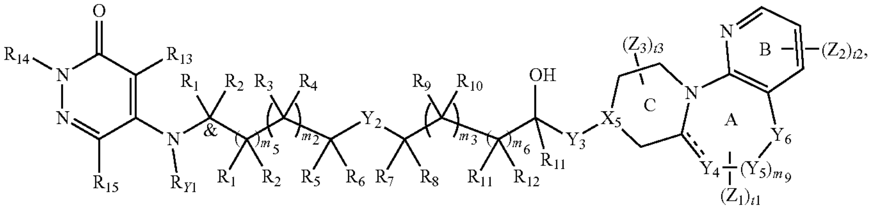
,
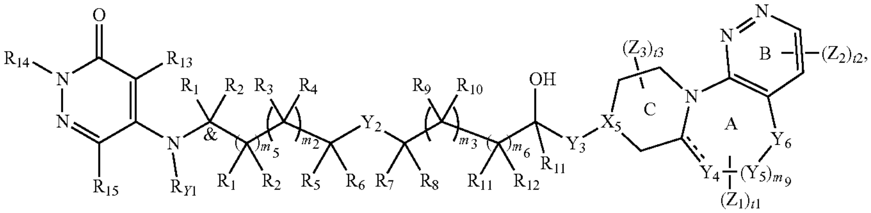
,
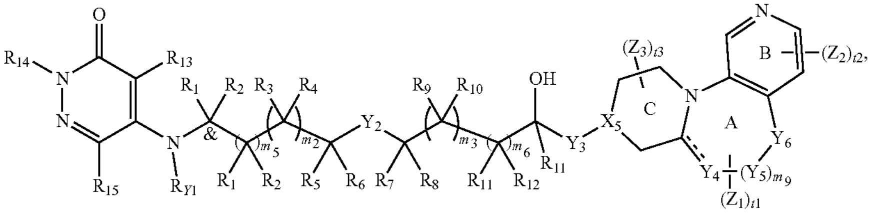
,
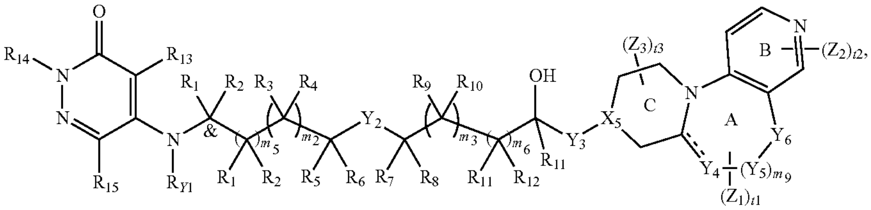
,
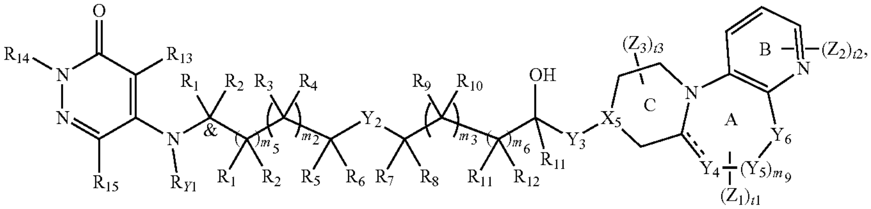
,
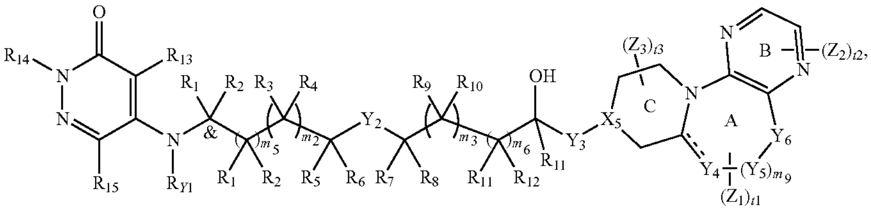
,
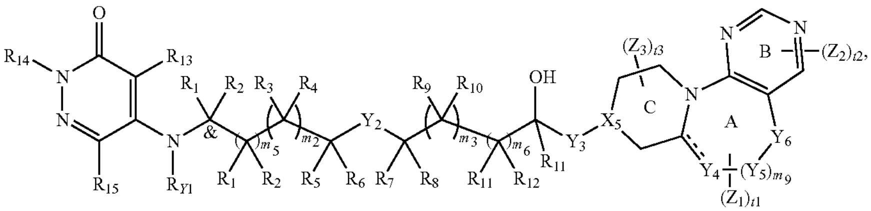
,
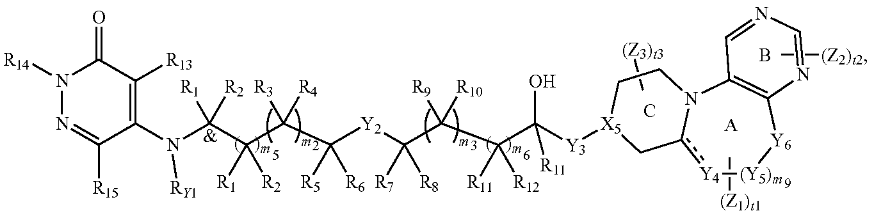
, -continued
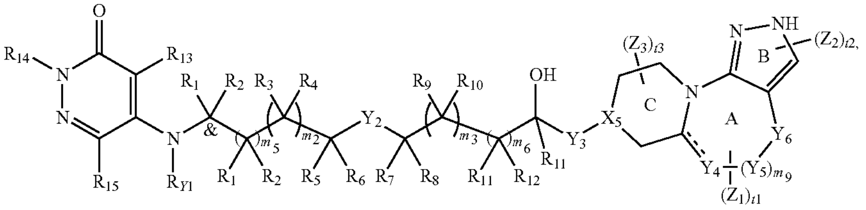
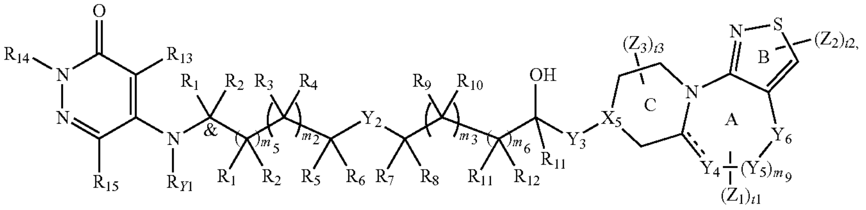
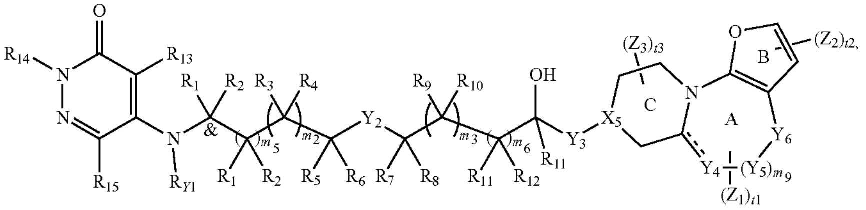
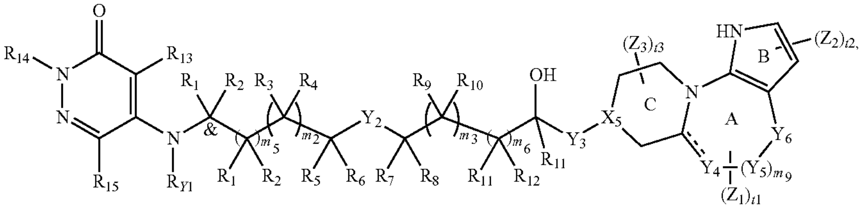
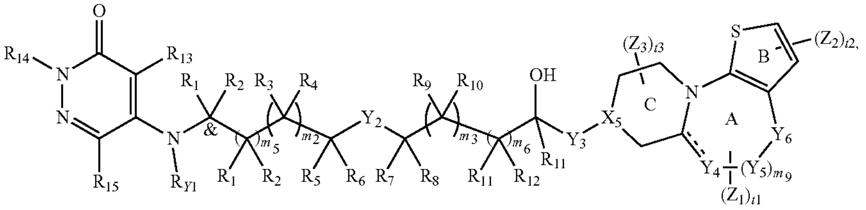
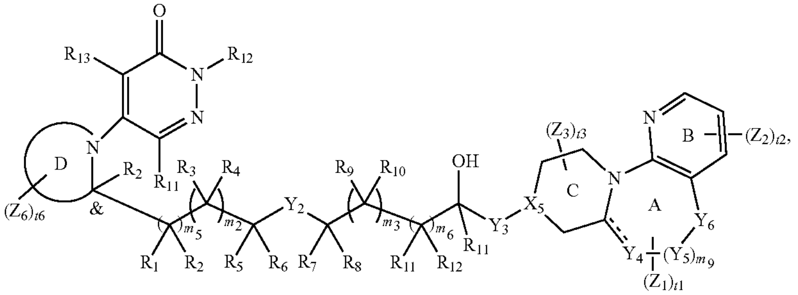
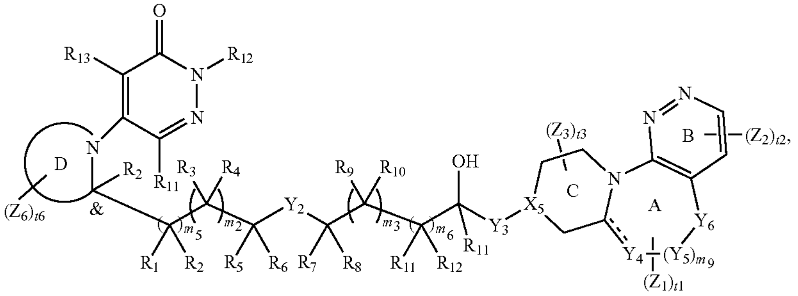

-continued
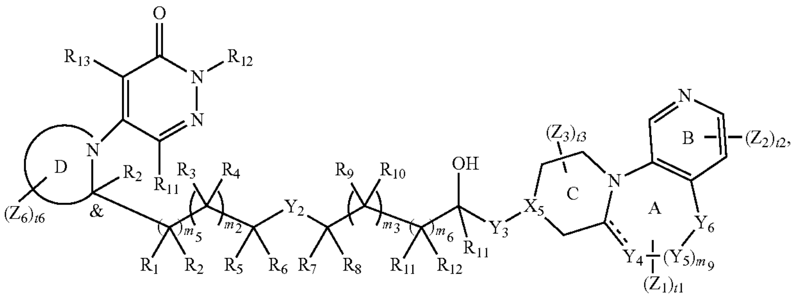
,
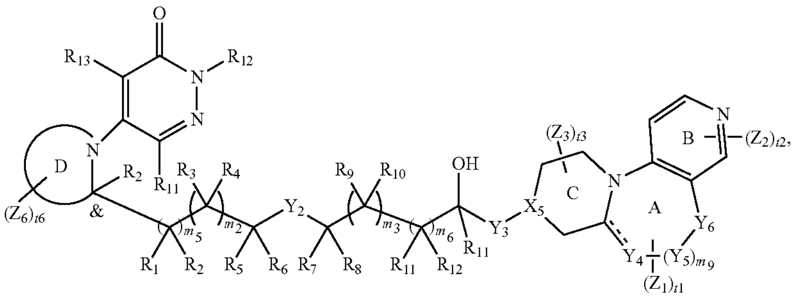
,
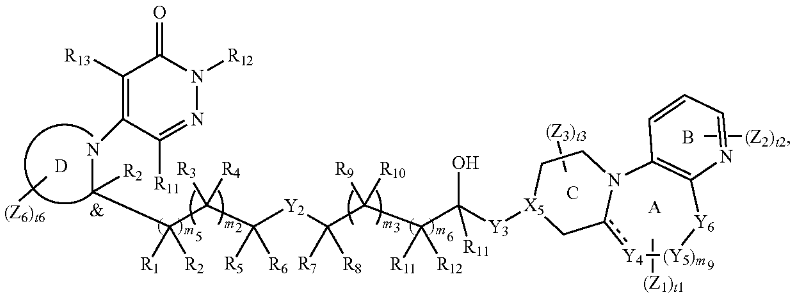
,
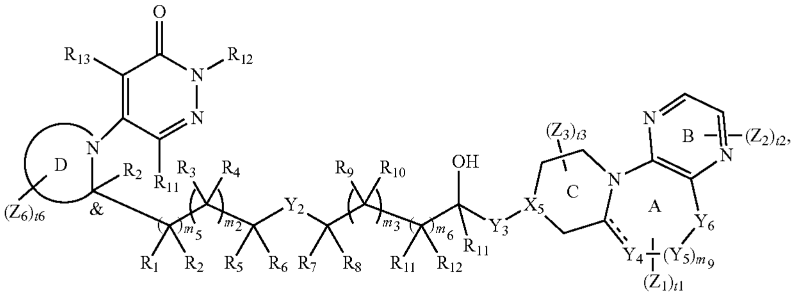
,
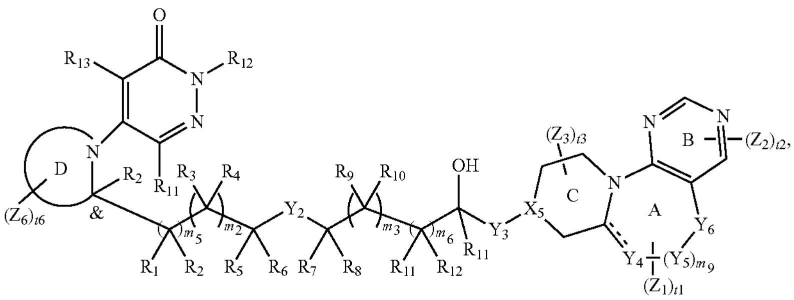
, -continued
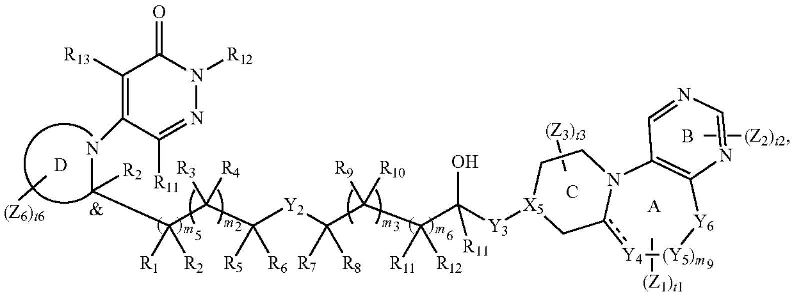
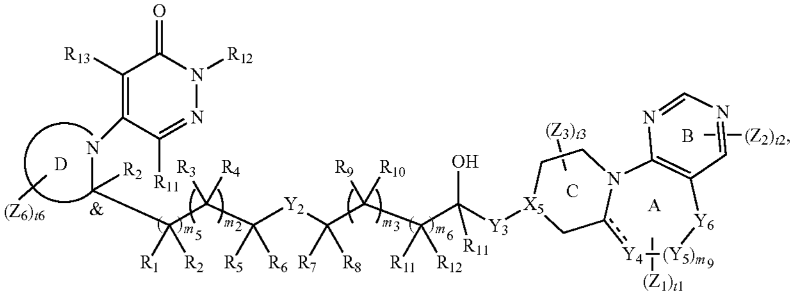
or
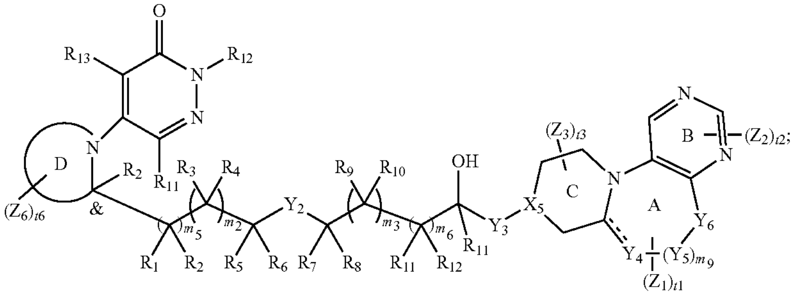
In some embodiments, the compound is selected from any one of the following formulas:
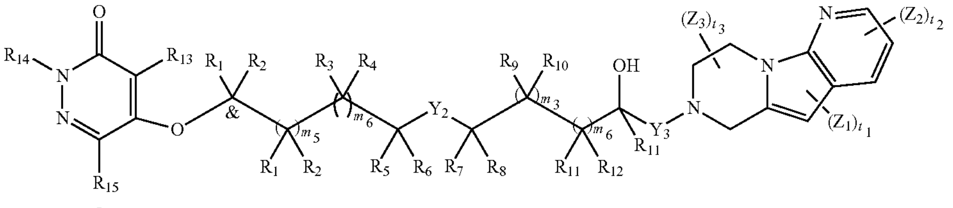
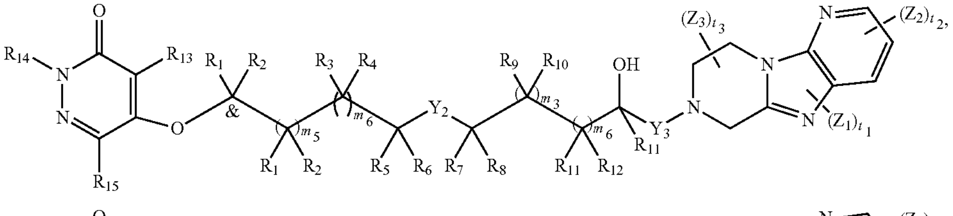
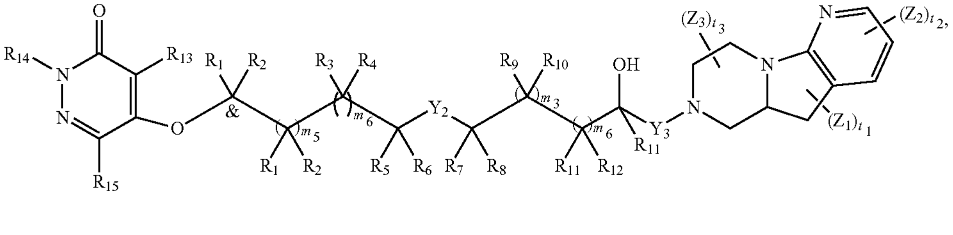

-continued
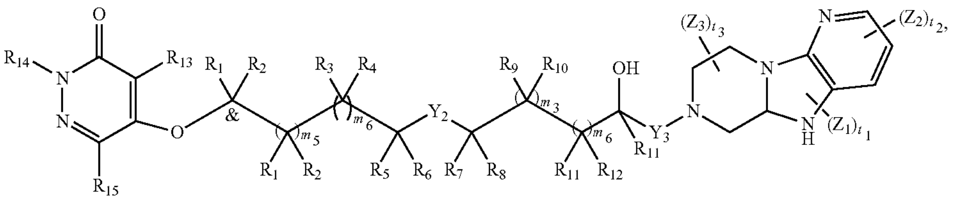
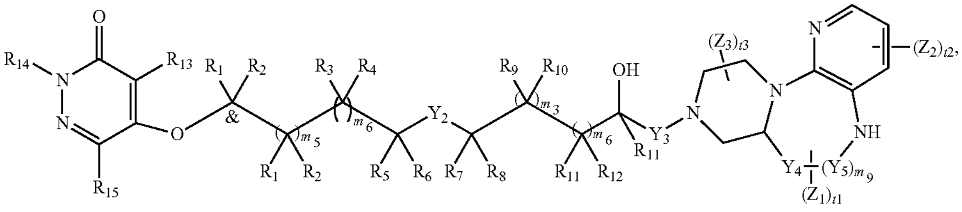
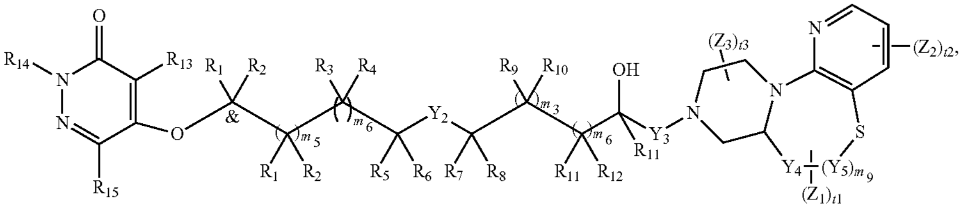
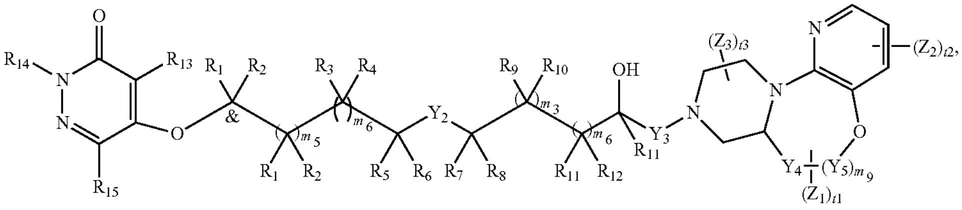
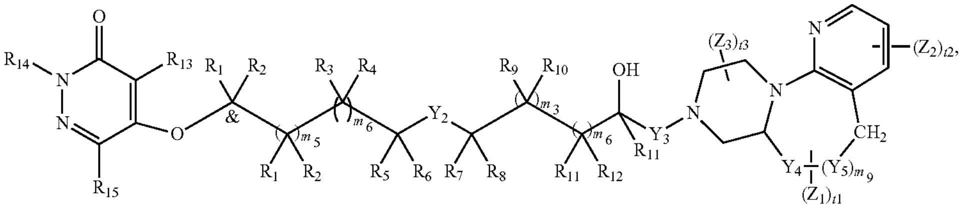
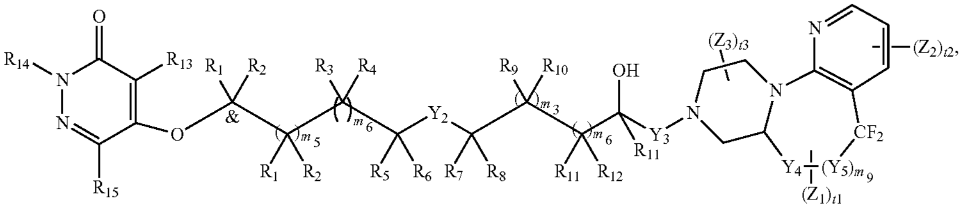
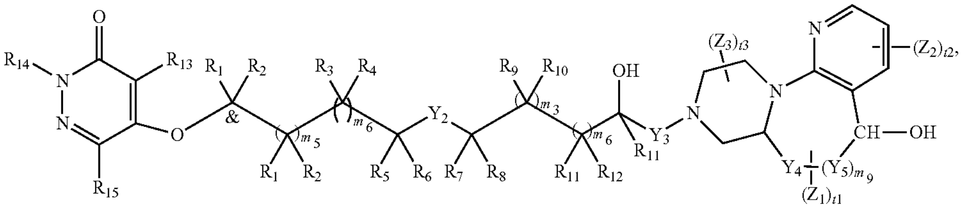
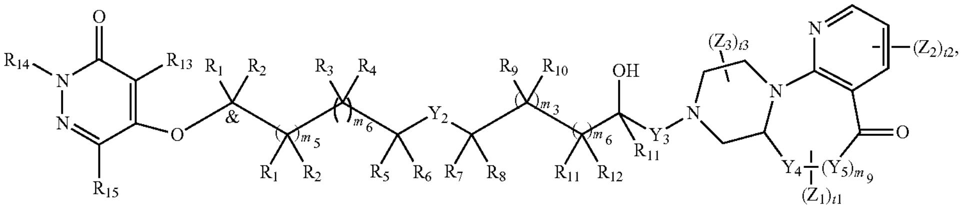

-continued
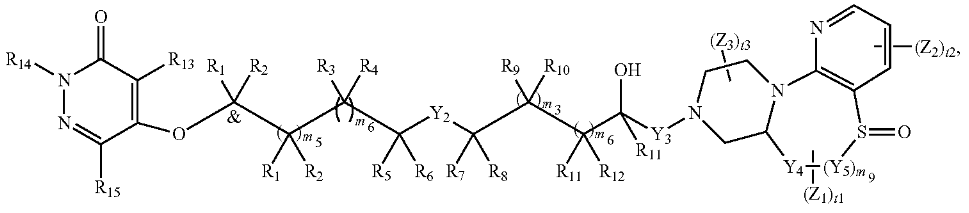
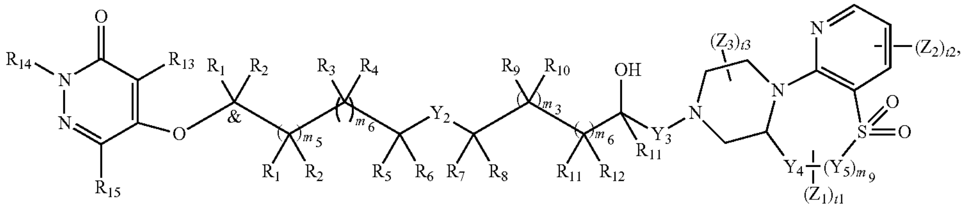
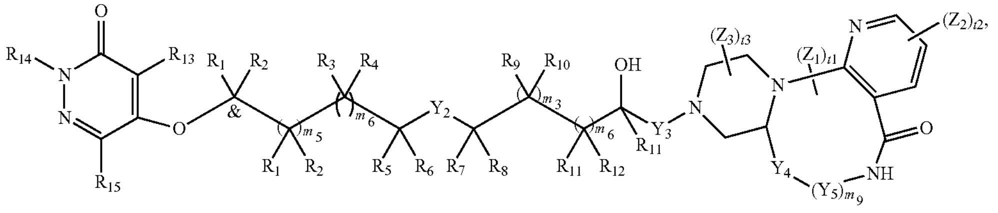
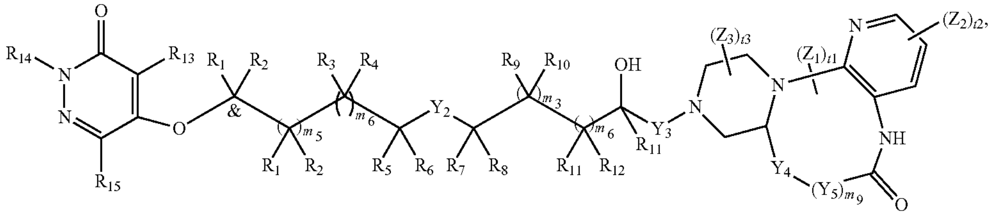
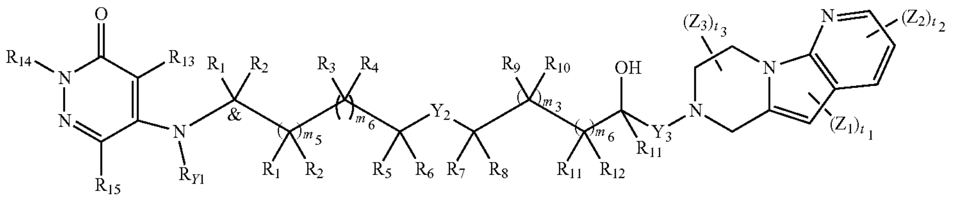
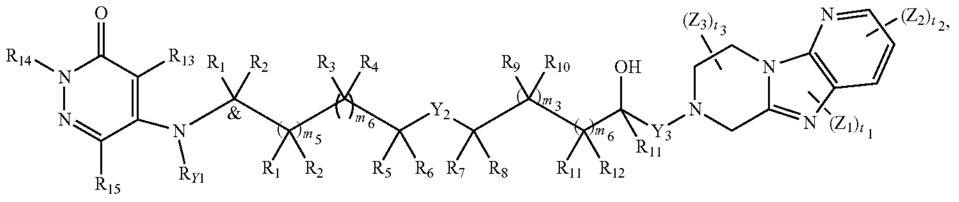
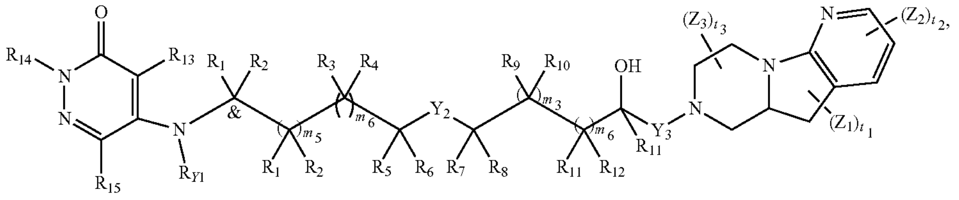
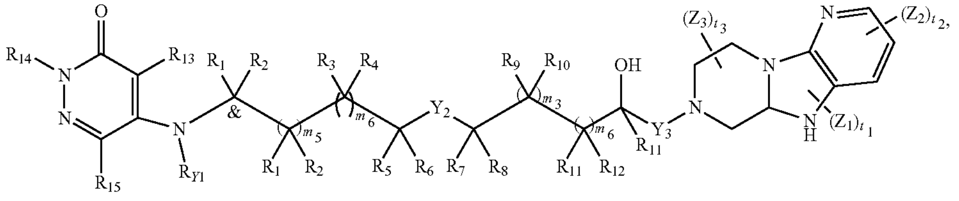

-continued
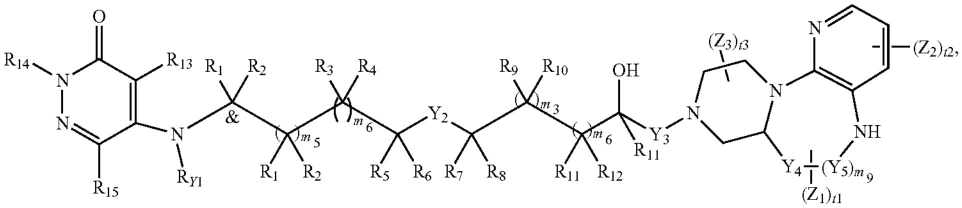
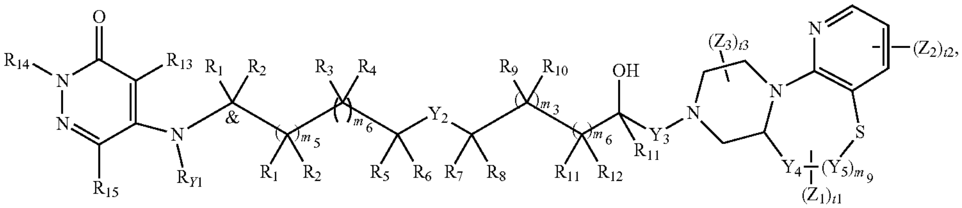
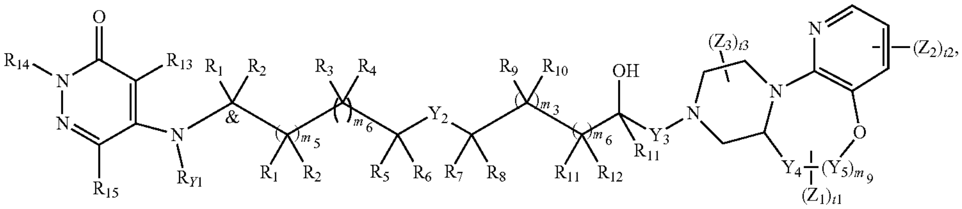
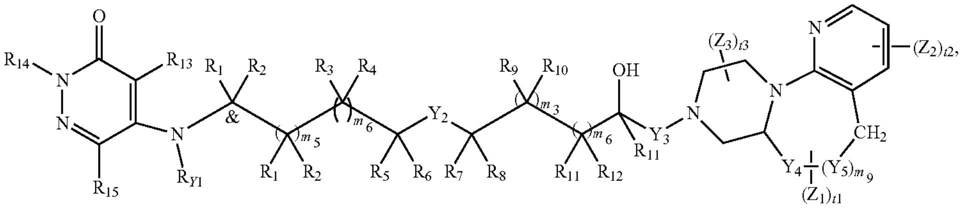
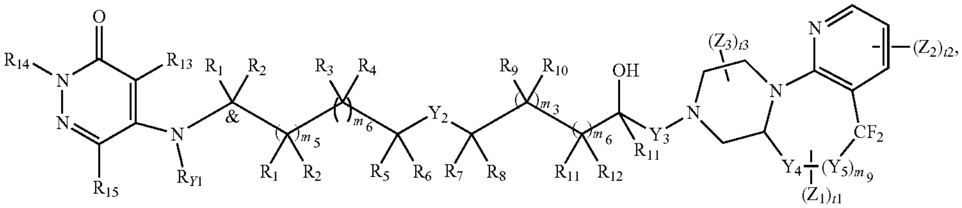
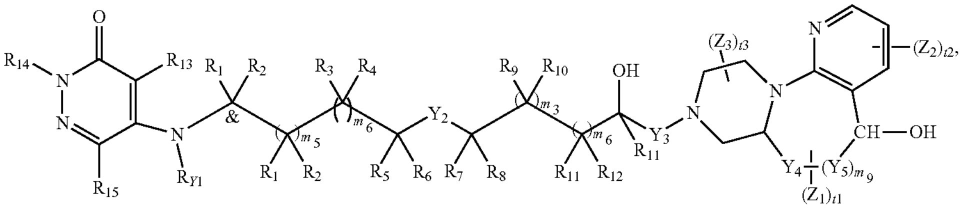
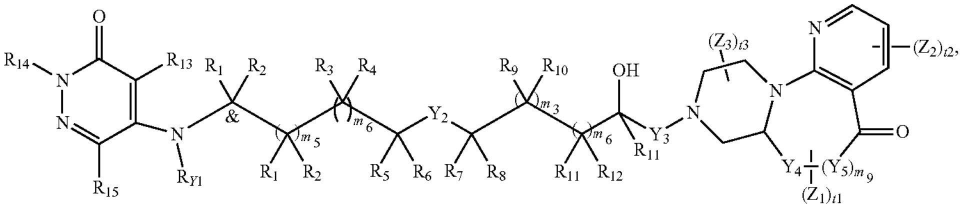
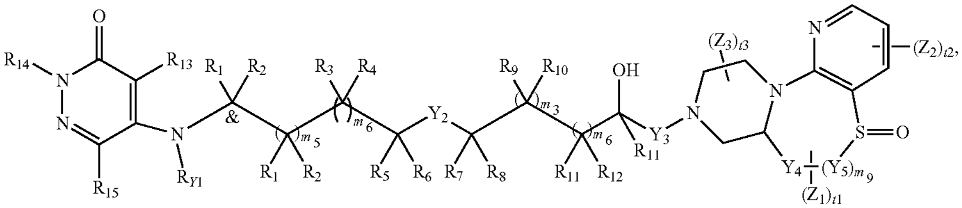

-continued
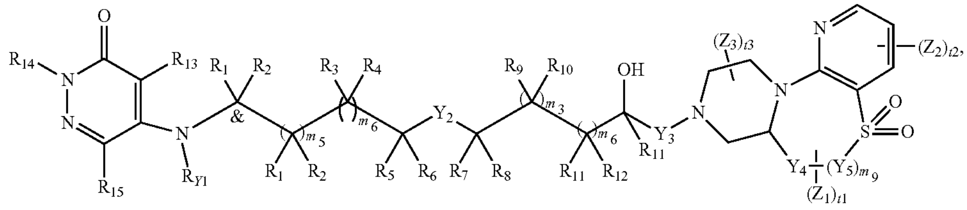
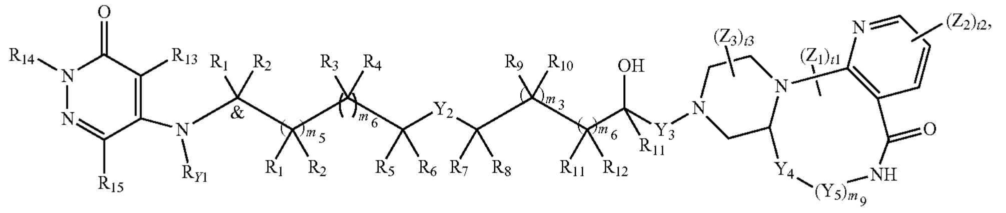
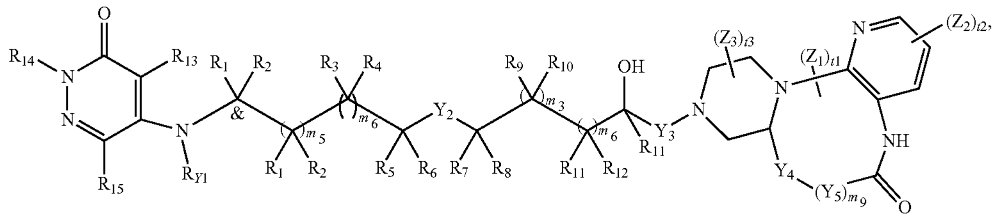
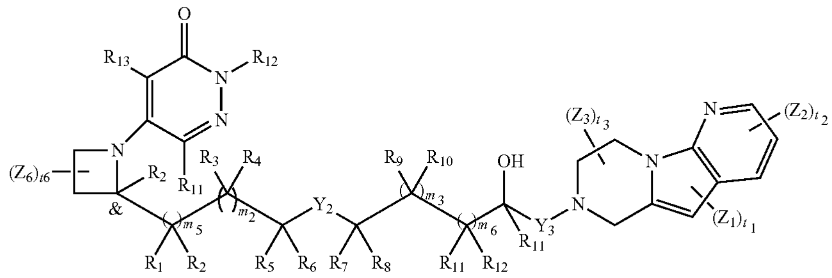
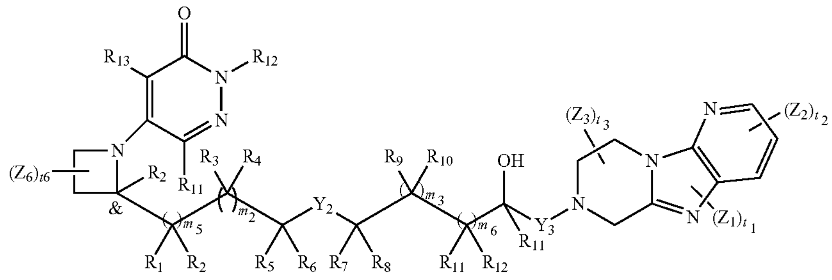
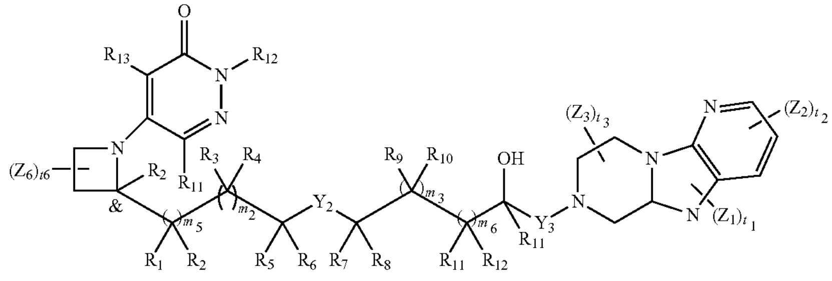

-continued
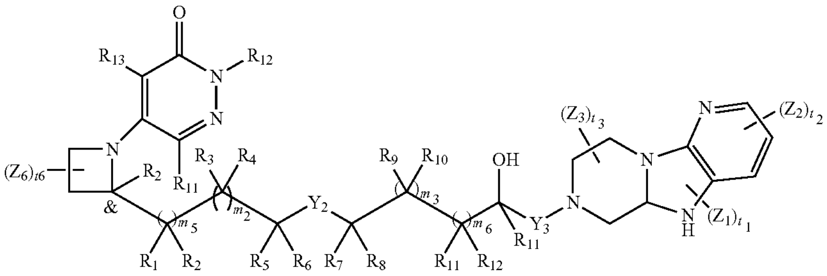
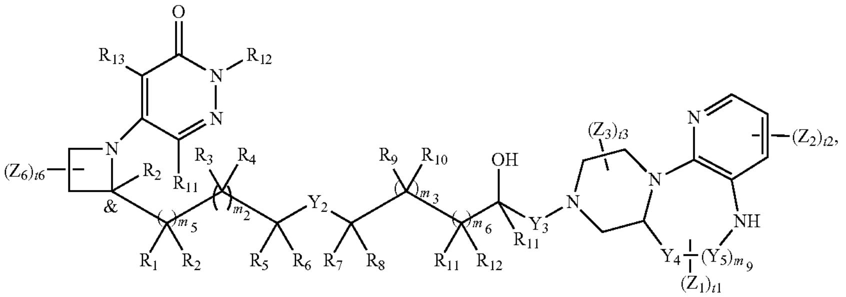
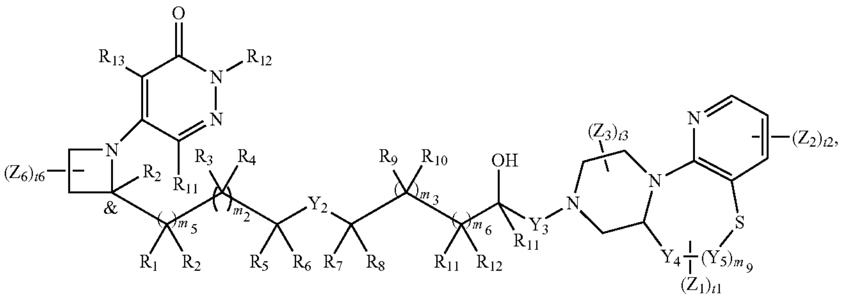
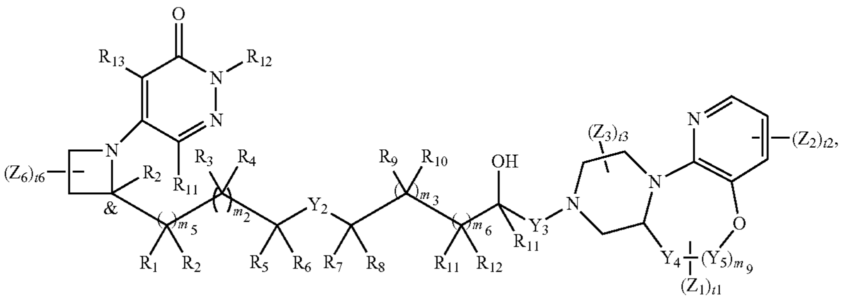
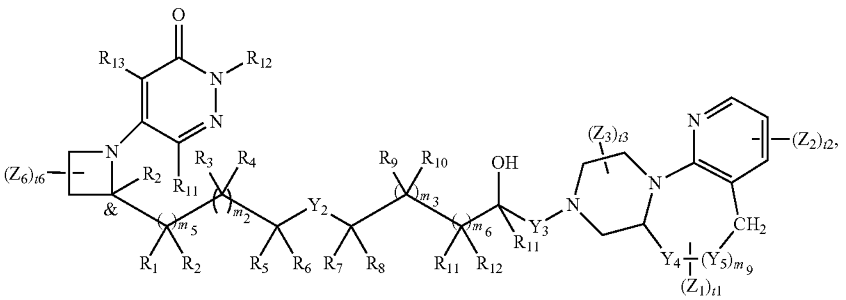

-continued
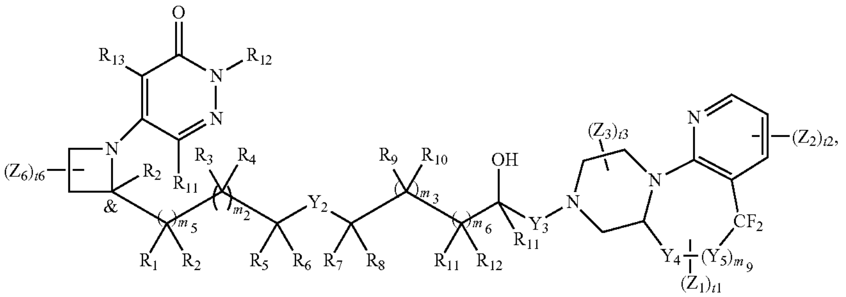
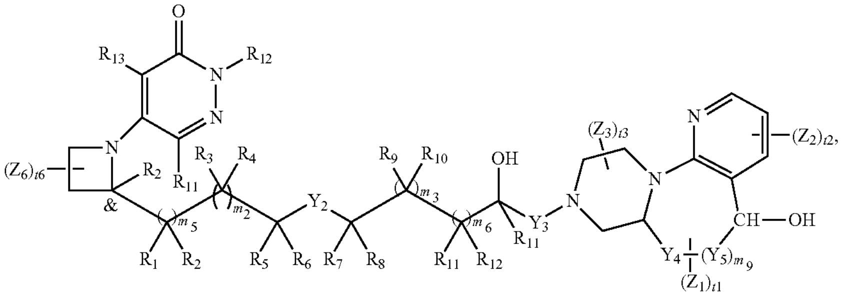
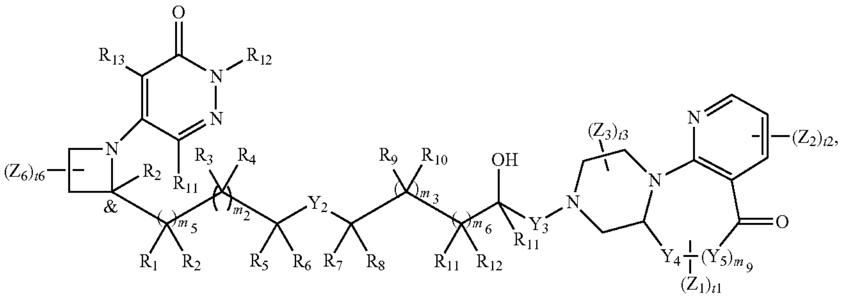
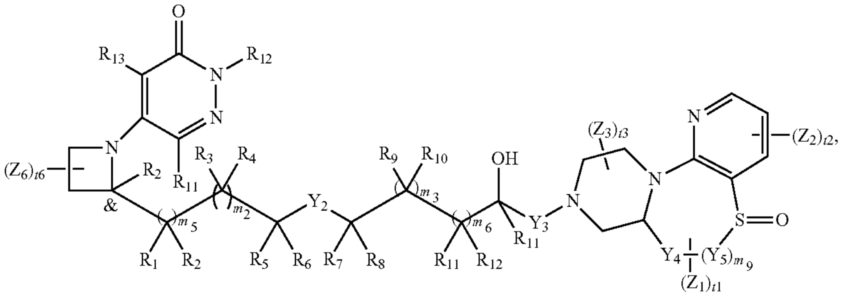
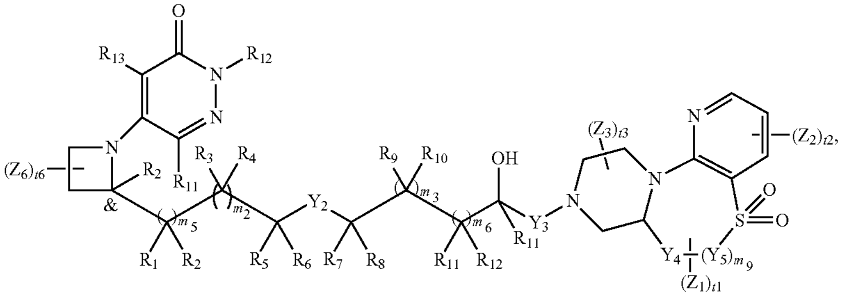

-continued
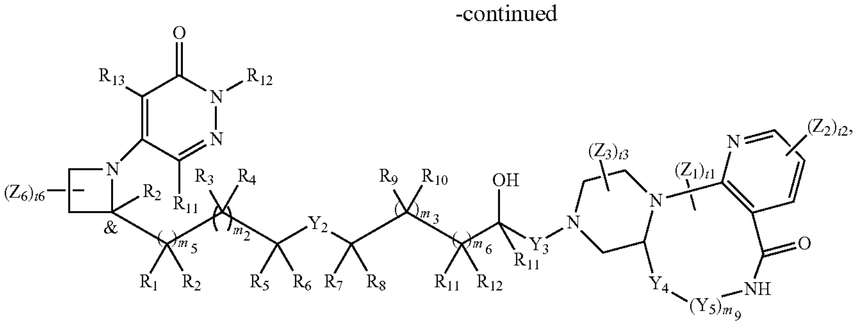
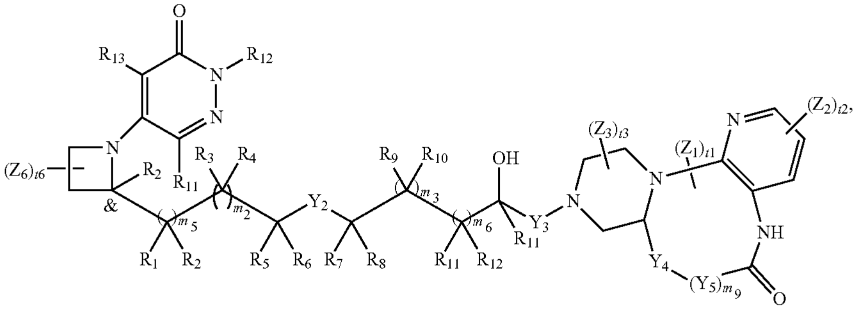
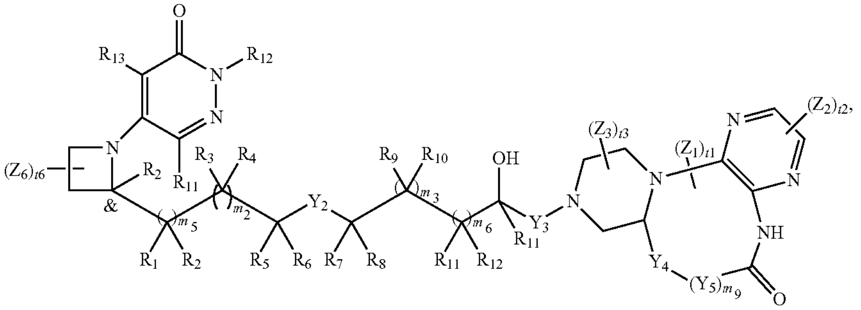
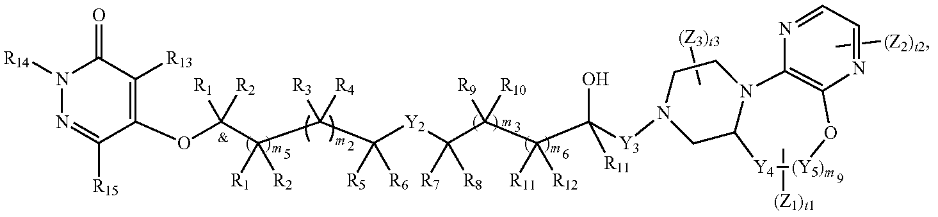
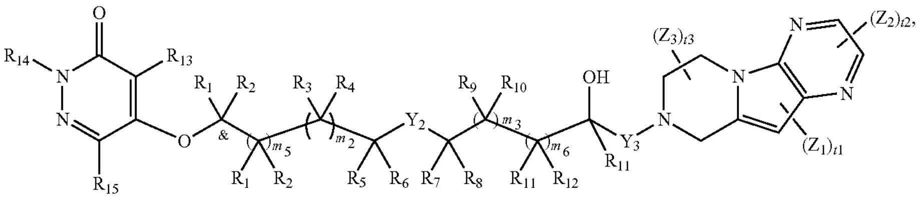
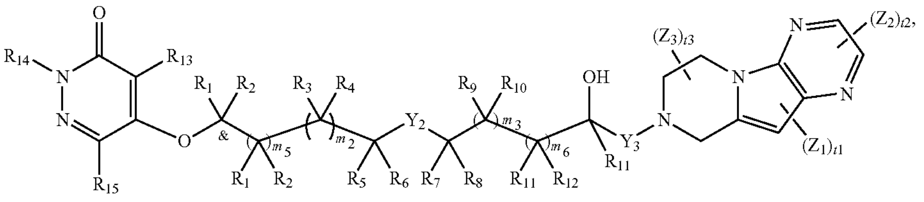

-continued
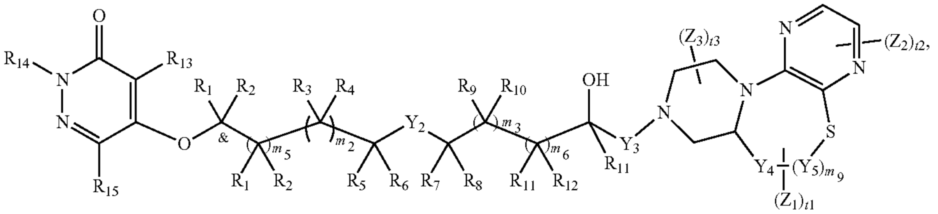
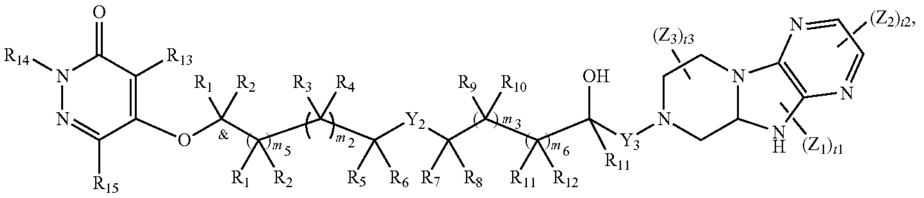
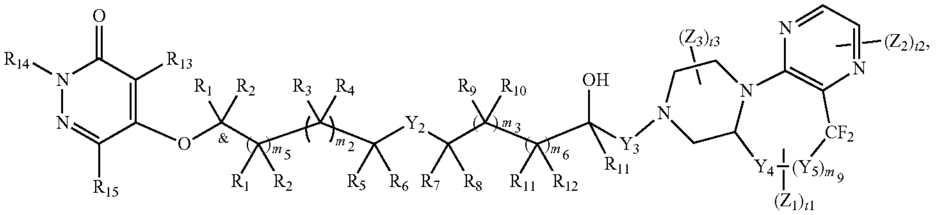
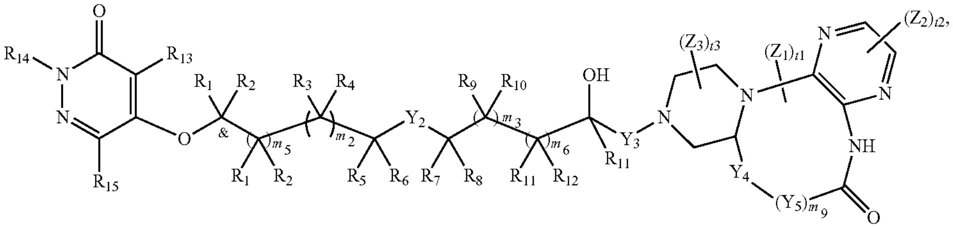
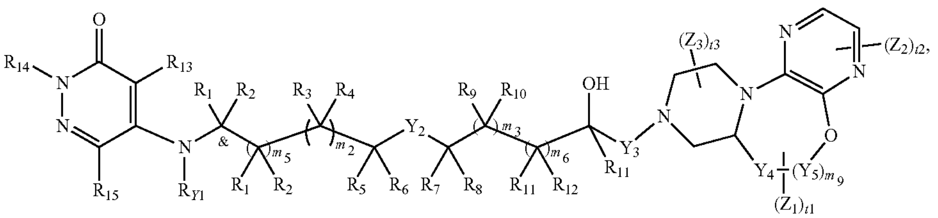
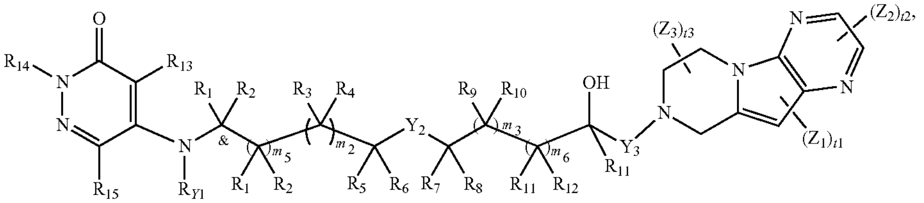
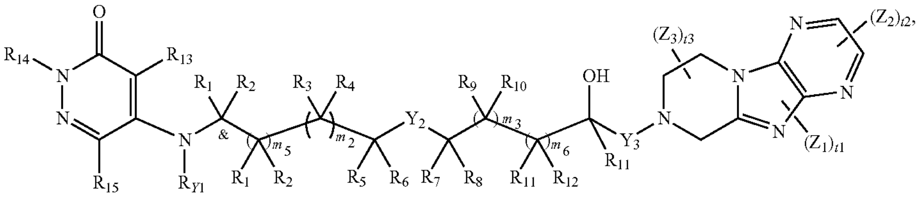
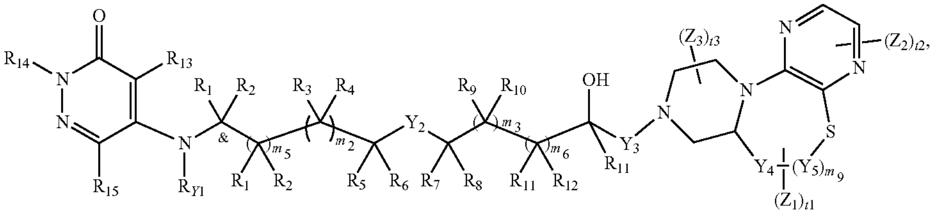

-continued
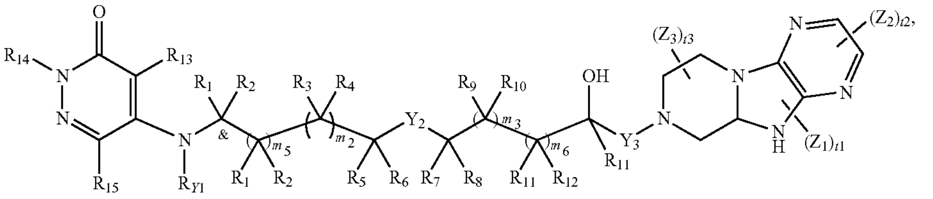
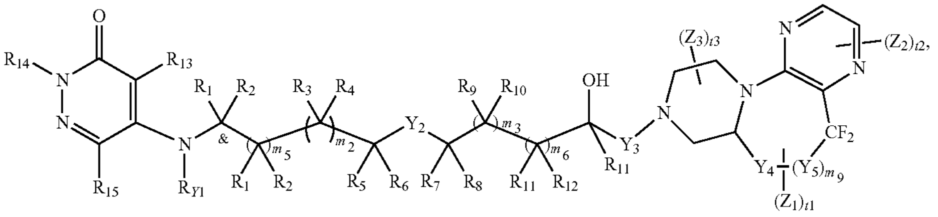
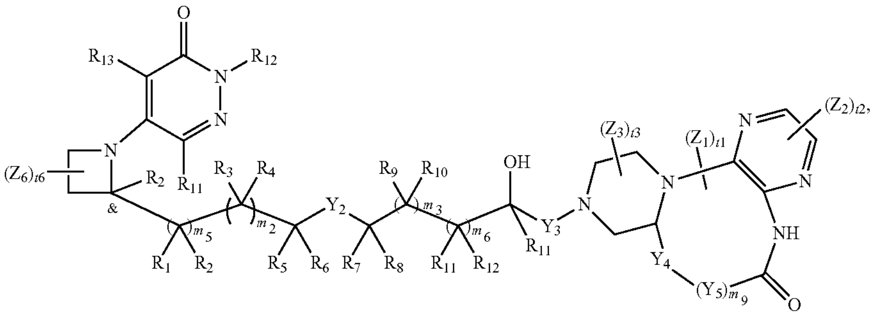
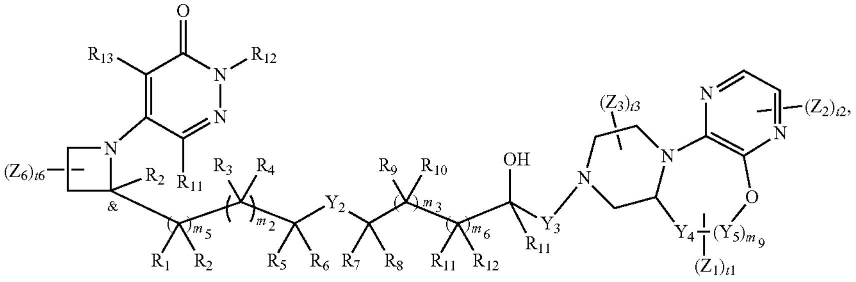
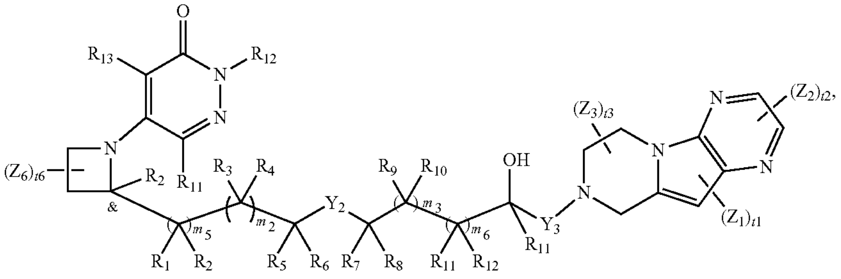
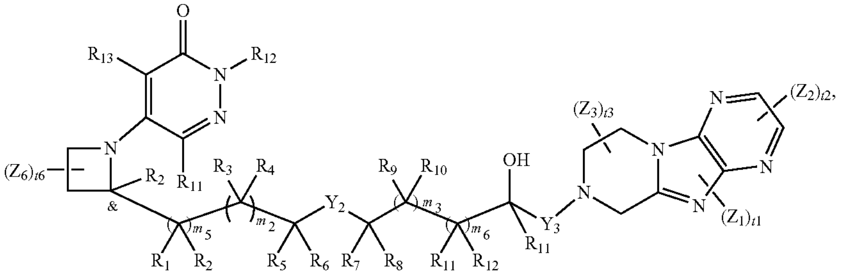

-continued
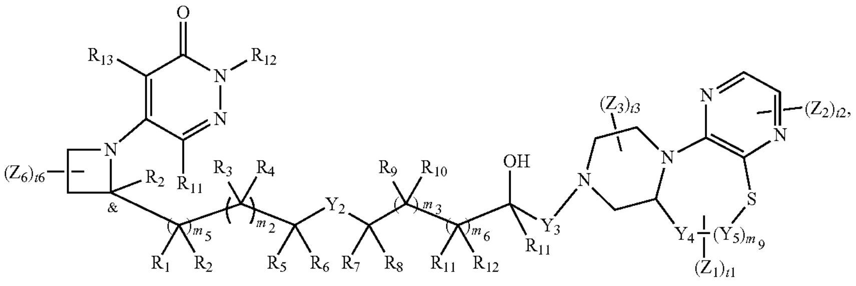
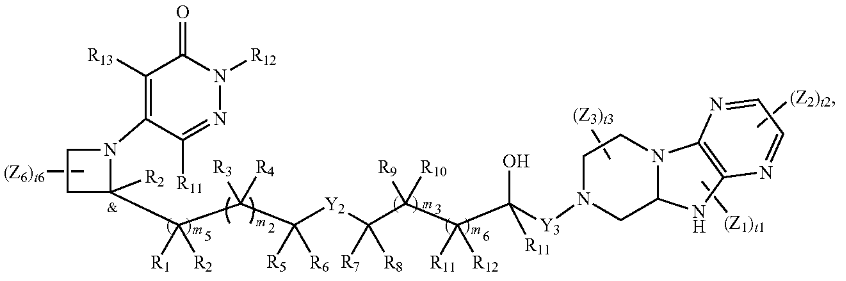
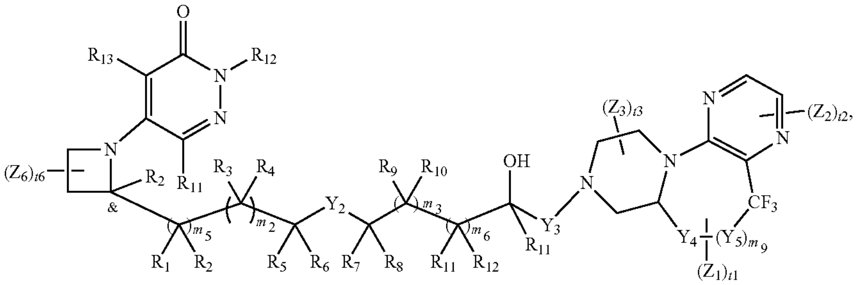
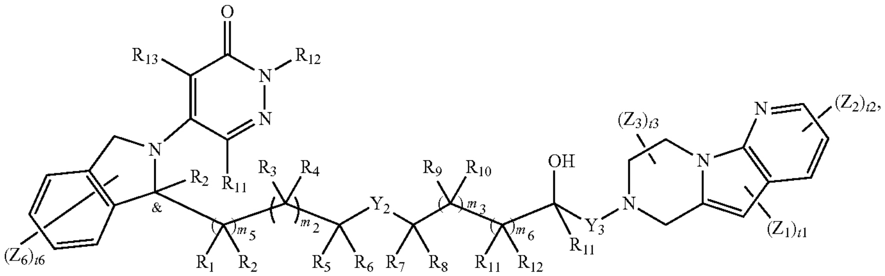
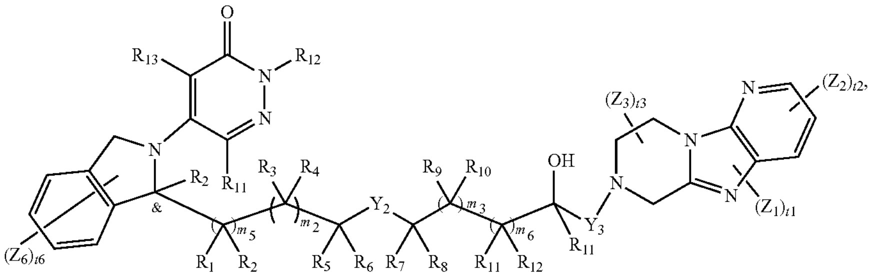
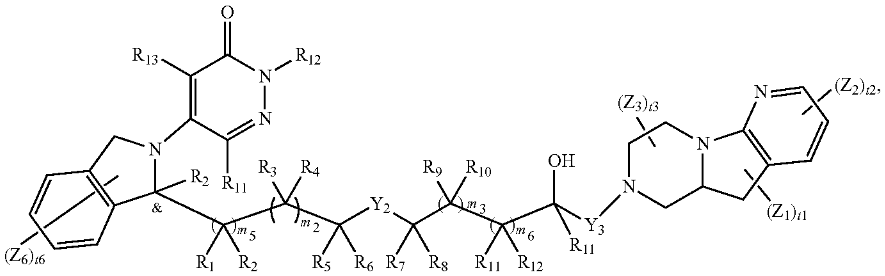

-continued
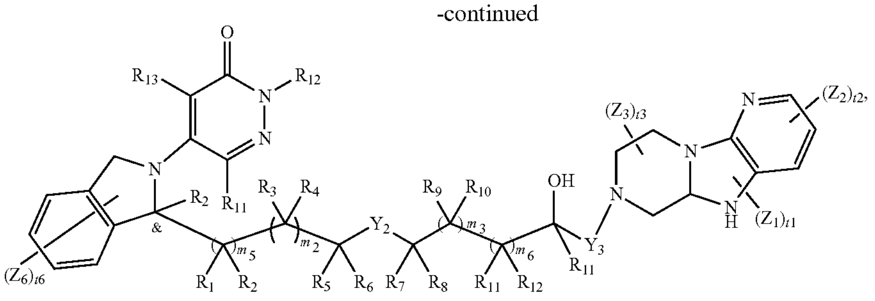
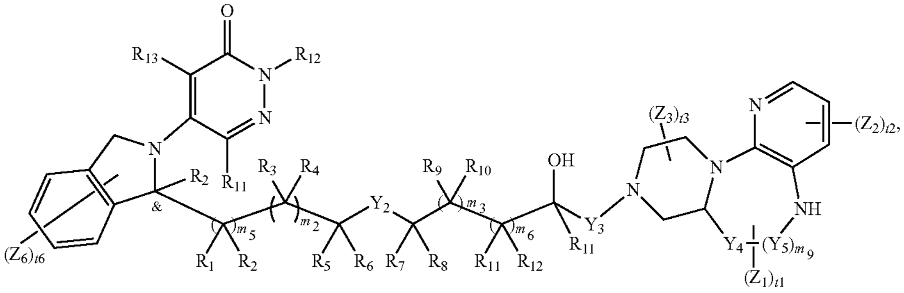
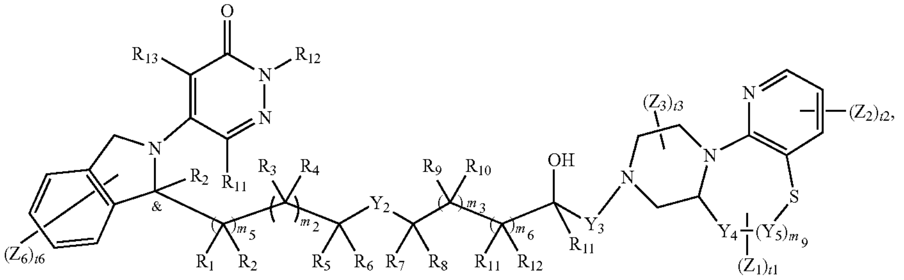
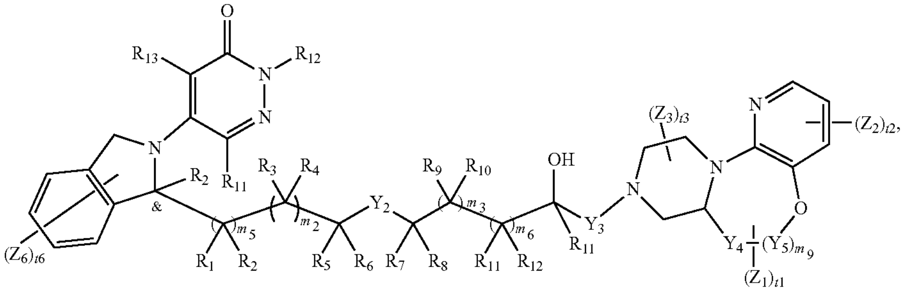
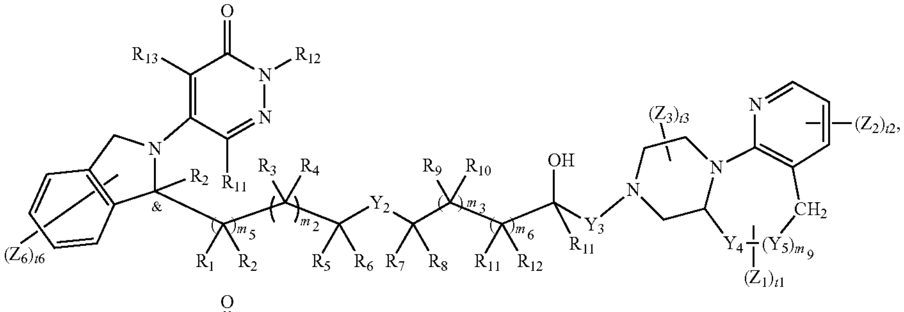
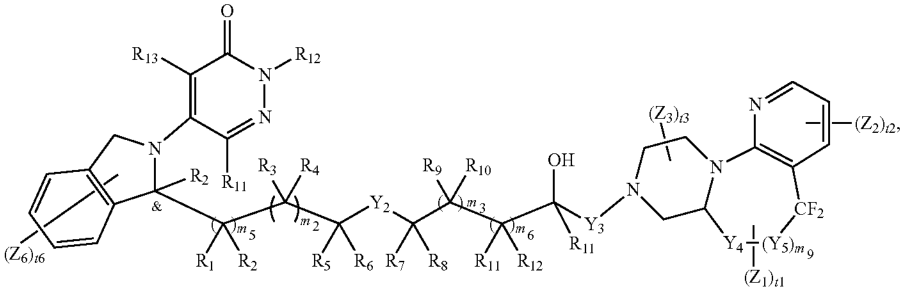

-continued
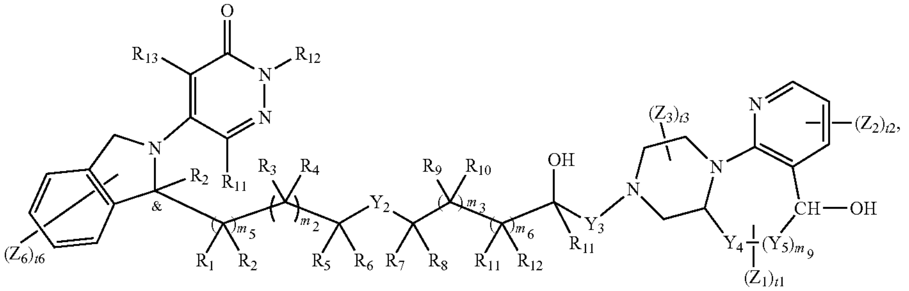
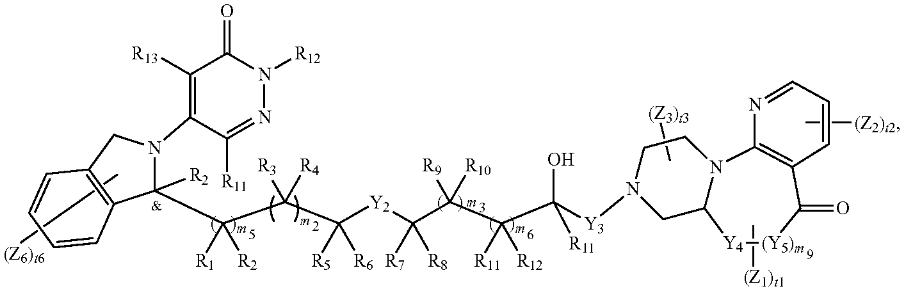
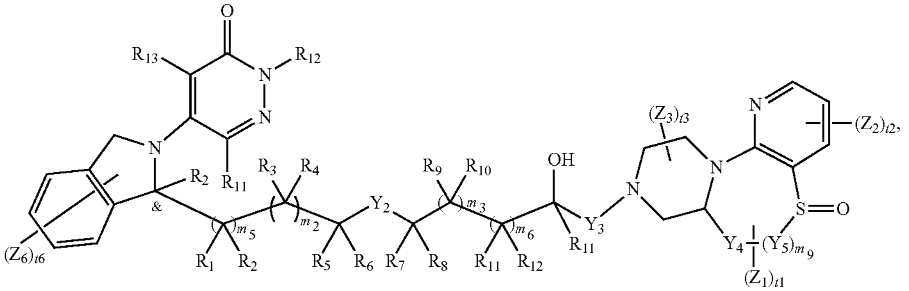
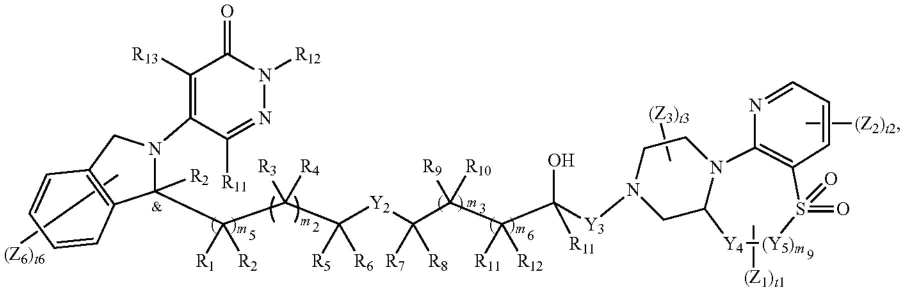
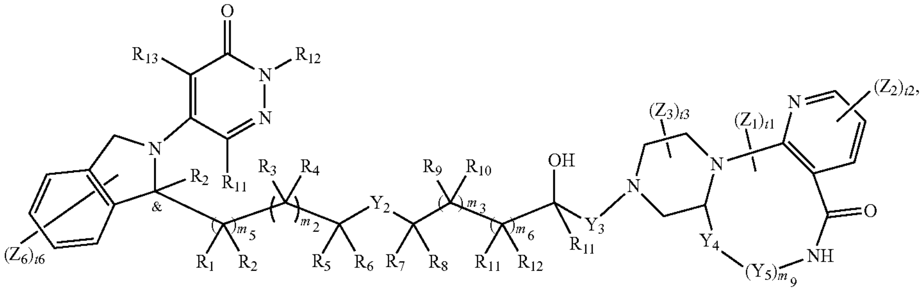

-continued
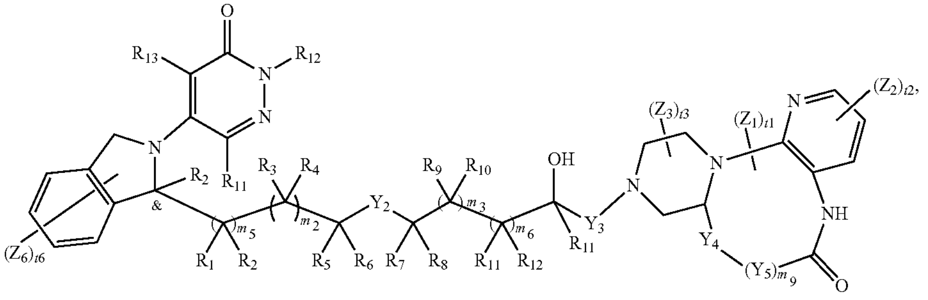
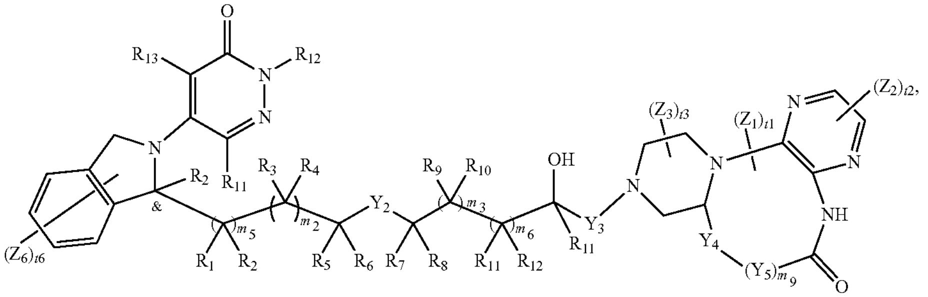
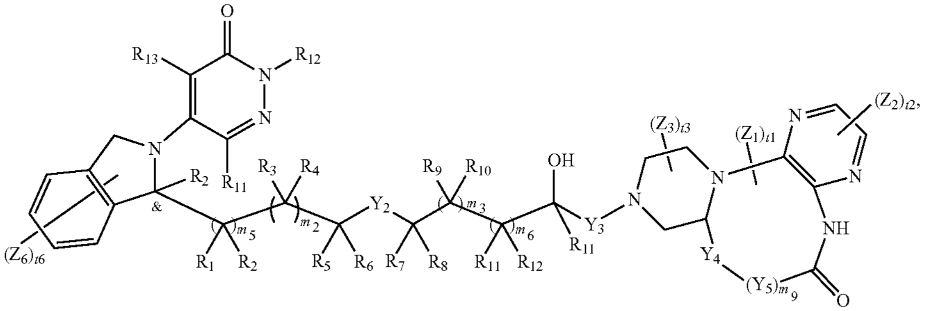
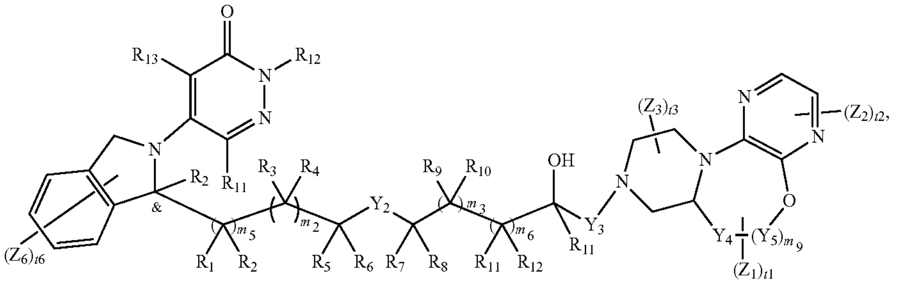
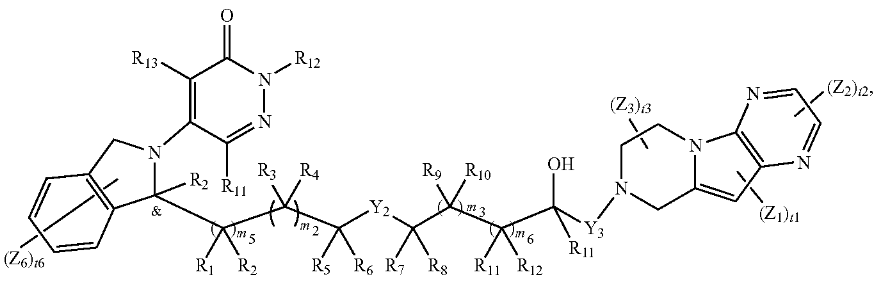

-continued

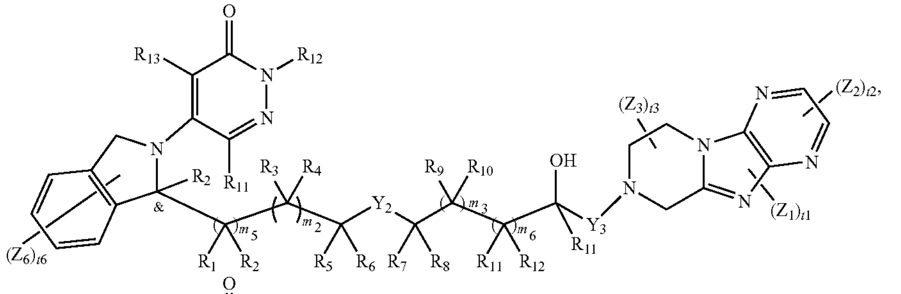

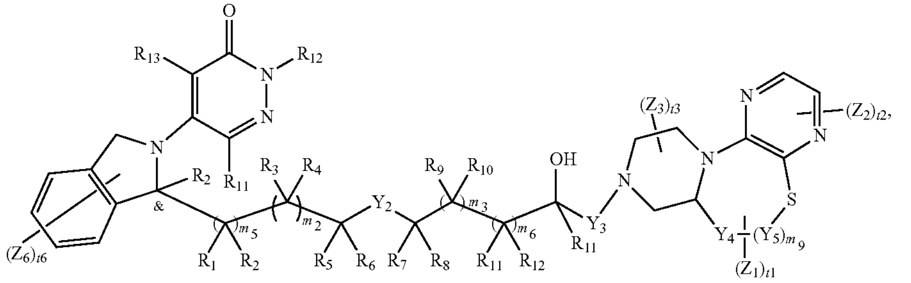

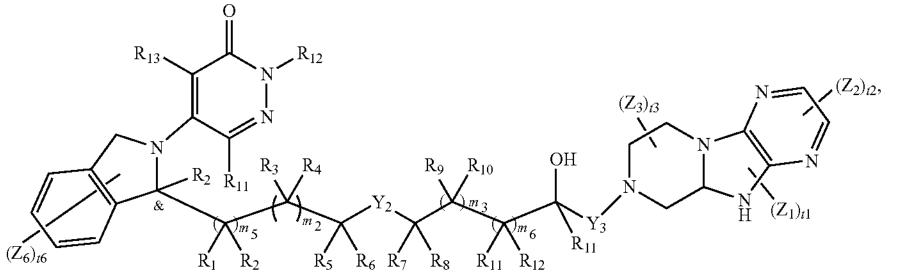

or

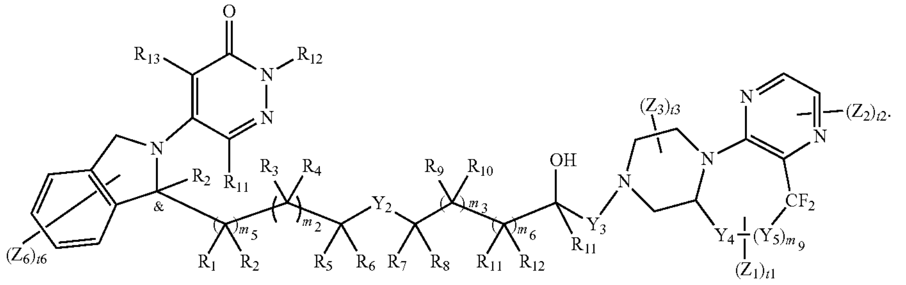

[65]. The compound according to any one of [1] to [64], wherein, $Y_2$ at each occurrence is independently selected from —$C(R_{Y2})_2$—, —C(═O)—, —O—, —$NR_{Y2}$—, —S—, —S(═O)—, —$S(═O)_2$—, —$PR_{Y2}$—, —P(═O)$R_{Y2}$—, —C(═O)$NR_{Y2}$—, —$NR_{Y2}$C(═O)—, —S(═O)$NR_{Y2}$—, —$NR_{Y2}$S(═O)—, —$S(═O)_2NR_{Y2}$—, or —$NR_{Y2}$ $S(═O)_2$—.

[66]. The compound according to any one of [1] to [65], wherein, $Y_2$ at each occurrence is independently selected from —$C(R_{Y2})_2$—, —C(═O)—, —O—, —$NR_{Y2}$—, —S—, —S(═O)—, —$S(═O)_2$—, —C(═O)$NR_{Y2}$—, —$NR_{Y2}$C (═O)—, —S(═O)$NR_{Y2}$—, —$NR_{Y2}$S(═O)—, —$S(═O)_2NR_{Y2}$—, or —$NR_{Y2}S(═O)_2$—.

[67]. The compound according to any one of [1] to [66], wherein, $Y_2$ at each occurrence is independently selected from —$CH_2$—, —$CH(CH_3)$—, —$CH(CH_2CH_3)$—, —$C(CH_3)_2$—, —O—, —NH—, —$N(CH_3)$—, —$N(CH_2CH_3)$—, —$N(CH(CH_3)_2)$—, —C(═O)—, —C(═O)NH—, —C(═O)$N(CH_3)$—, —NH—C(═O)—, —$N(CH_3)$—C(═O)—, —S—, —S(═O)—, —NH—S (═O)—, —$N(CH_3)$—S(═O)—, —$S(═O)_2$—, —NH—S $(═O)_2$— or —$N(CH_3)$—$S(═O)_2$—.

[68]. The compound according to any one of [1] to [67], wherein, $Y_2$ at each occurrence is independently selected from —O—, —CO—NH—, or —NH—CO—.

[69]. The compound according to any one of [1] to [68], wherein, $Y_2$ at each occurrence is independently selected from —O—.

[70]. The compound according to any one of [1] to [69], wherein, $Y_3$ at each occurrence is independently selected from —$C(R_{Y3})_2$—, —C(═O)—, —O—, —$NR_{Y3}$—, —S—, —S(═O)—, —$S(═O)_2$—, —$PR_{Y3}$—, —P(═O)$R_{Y3}$—, —C(═O)$NR_{Y3}$—, —$NR_{Y3}$C(═O)—, —S(═O)$NR_{Y3}$—, —$NR_{Y3}$S(═O)—, —$S(═O)_2NR_{Y3}$—, or —$NR_{Y3}S(═O)_2$—.

[71]. The compound according to any one of [1] to [70], wherein, $Y_3$ at each occurrence is independently selected from —$C(R_{Y3})_2$—, —C(═O)—, —O—, —$NR_{Y3}$—, —S—, —S(═O)—, —$S(═O)_2$—, —C(═O)$NR_{Y3}$—, —$NR_{Y3}$C (═O)—, —S(═O)$NR_{Y3}$—, —$NR_{Y3}$S(═O)—, —$S(═O)_2NR_{Y3}$—, or —$NR_{Y3}S(═O)_2$—.

[72]. The compound according to any one of [1] to [71], wherein, $Y_3$ at each occurrence is independently selected from —$CH_2$—, —$CH(CH_3)$—, —$CH(CH_2CH_3)$—, —$C(CH_3)_2$—, —O—, —NH—, —$N(CH_3)$—, —$N(CH_2CH_3)$—, —$N(CH(CH_3)_2)$—, —C(═O)—, —C(═O)NH—, —C(═O)$N(CH_3)$—, —NH—C(═O)—, —$N(CH_3)$—C(═O)—, —S—, —S(═O)—, —NH—S(═O)—, —$N(CH_3)$—S(═O)—, —$S(═O)_2$—, —NH—$S(═O)_2$— or —$N(CH_3)$—$S(═O)_2$—.

[73]. The compound according to any one of [1] to [72], wherein, $Y_3$ at each occurrence is independently selected from —C(═O)—, —$S(═O)_2$—, —C(═O)—NH—, —NH—C(═O)—, —C(═O)—$N(CH_3)$— or —$N(CH_3)$—C(═O)—.

[74]. The compound according to any one of [1] to [73], wherein, $Y_3$ at each occurrence is independently selected from —C(═O)—.

[75]. The compound according to any one of [1] to [54], and [61] to [74], wherein, $Y_2$ at each occurrence is independently selected from —O—, and $Y_3$ at each occurrence is independently selected from —C(═O)—.

[76]. The compound according to any one of [1] to [75], wherein, $R_1$, $R_2$, $R_3$, $R_4$, $R_5$, $R_6$, $R_7$, $R_8$, $R_9$, $R_{10}$, $R_{11}$, or $R_{12}$ at each occurrence is independently selected from hydrogen, halogen, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —$NH_2$, —NH($C_{1-6}$alkyl), —N($C_{1-6}$alkyl)$_2$, —OH, —O($C_{1-6}$alkyl), —SH, —S($C_{1-6}$alkyl), —S(halo$C_{1-6}$alkyl), —S(═O)($C_{1-6}$alkyl), —$S(═O)_2$($C_{1-6}$alkyl), —C(═O)($C_{1-6}$alkyl), —C(═O)OH, —C(═O)(O$C_{1-6}$alkyl), —OC(═O)($C_{1-6}$alkyl), —C(═O)$NH_2$, —C(═O)NH($C_{1-6}$alkyl), —C(═O)N($C_{1-6}$alkyl)$_2$, —NHC(═O)($C_{1-6}$alkyl), —N($C_{1-6}$alkyl)C(═O)($C_{1-6}$alkyl), —OC(═O)O($C_{1-6}$alkyl), —NHC(═O)(O$C_{1-6}$alkyl), —N($C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)$NH_2$, —NHC(═O)NH($C_{1-6}$alkyl), —NHC(═O)N($C_{1-6}$alkyl)$_2$, —N($C_{1-6}$alkyl)C(═O)$NH_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)$NH_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —$S(═O)_2$(O$C_{1-6}$alkyl), —$OS(═O)_2$($C_{1-6}$alkyl), —$S(═O)_2NH_2$, —$S(═O)_2$NH($C_{1-6}$alkyl), —$S(═O)_2$N($C_{1-6}$alkyl)$_2$, —$NHS(═O)_2$($C_{1-6}$alkyl), —N($C_{1-6}$alkyl)$S(═O)_2$($C_{1-6}$alkyl), —$OS(═O)_2$O($C_{1-6}$alkyl), —$NHS(═O)_2$O($C_{1-6}$alkyl), —N($C_{1-6}$alkyl)$S(═O)_2$O($C_{1-6}$alkyl), —$OS(═O)_2NH_2$, —$OS(═O)_2$NH($C_{1-6}$alkyl), —$OS(═O)_2$N($C_{1-6}$alkyl)$_2$, —$NHS(═O)_2NH_2$, —$NHS(═O)_2$NH($C_{1-6}$alkyl), —$NHS(═O)_2$N($C_{1-6}$alkyl)$_2$, —N($C_{1-6}$alkyl)$S(═O)_2NH_2$, —N($C_{1-6}$alkyl)$S(═O)_2$NH($C_{1-6}$alkyl), —N($C_{1-6}$alkyl)$S(═O)_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-6 membered cycloalkyl, 3-6 membered heterocyclyl, 6-10 membered aryl or 5-10 membered heteroaryl, wherein said —$C_{1-6}$alkyl, —$C_{1-6}$haloalkyl, —$C_{1-6}$haloalkoxy, —$C_{2-6}$alkenyl, —$C_{2-6}$alkynyl, 3-6 membered cycloalkyl, 3-6 membered heterocyclyl, 6-10 membered aryl or 5-10 membered heteroaryl is independently optionally substituted with 1, 2, 3, 4, 5 or 6 substituents selected from —F, —Cl, —Br, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —$NH_2$, —NH($C_{1-6}$alkyl), —N($C_{1-6}$alkyl)$_2$, —OH, —O($C_{1-6}$alkyl), —SH, —S($C_{1-6}$alkyl), —S(halo$C_{1-6}$alkyl), —S(═O)($C_{1-6}$alkyl), —$S(═O)_2$($C_{1-6}$alkyl), —C(═O)($C_{1-6}$alkyl), —C(═O)OH, —C(═O)(O$C_{1-6}$alkyl), —OC(═O)($C_{1-6}$alkyl), —C(═O)$NH_2$, —C(═O)NH($C_{1-6}$alkyl), —C(═O)N($C_{1-6}$alkyl)$_2$, —NHC(═O)($C_{1-6}$alkyl), —N($C_{1-6}$alkyl)C(═O)($C_{1-6}$alkyl), —OC(═O)O($C_{1-6}$alkyl), —NHC(═O)(O$C_{1-6}$alkyl), —N($C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)$NH_2$, —NHC(═O)NH($C_{1-6}$alkyl), —NHC(═O)N($C_{1-6}$alkyl)$_2$, —N($C_{1-6}$alkyl)C(═O)$NH_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)$NH_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —$S(═O)_2$(O$C_{1-6}$alkyl), —$OS(═O)_2$($C_{1-6}$alkyl), —$S(═O)_2NH_2$, —$S(═O)_2$NH($C_{1-6}$alkyl), —$S(═O)_2$N($C_{1-6}$alkyl)$_2$, —$NHS(═O)_2$($C_{1-6}$alkyl), —N($C_{1-6}$alkyl)$S(═O)_2$($C_{1-6}$alkyl), —$OS(═O)_2$O($C_{1-6}$alkyl), —$NHS(═O)_2$O($C_{1-6}$alkyl), —N($C_{1-6}$alkyl)$S(═O)_2$O($C_{1-6}$alkyl), —$OS(═O)_2NH_2$, —$OS(═O)_2$NH($C_{1-6}$alkyl), —$OS(═O)_2$N($C_{1-6}$alkyl)$_2$, —$NHS(═O)_2NH_2$, —$NHS(═O)_2$NH($C_{1-6}$alkyl), —$NHS(═O)_2$N($C_{1-6}$alkyl)$_2$, —N($C_{1-6}$alkyl)$S(═O)_2NH_2$, —N($C_{1-6}$alkyl)$S(═O)_2$NH($C_{1-6}$alkyl), —N($C_{1-6}$alkyl)$S(═O)_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-6 membered cycloalkyl, 3-6 membered heterocyclyl, 6-10 membered aryl or 5-10 membered heteroaryl;

$m_1$ is 0, 1, 2, 3, 4, 5, or 6;

$m_2$ is 0, 1, 2, 3, 4, 5, or 6;

$m_3$ is 0, 1, 2, 3, 4, 5, or 6;

$m_4$ is 0, 1, 2, 3, 4, 5, or 6.

[77]. The compound according to any one of [1] to [76], wherein, $R_1$, $R_2$, $R_3$, $R_4$, $R_5$, $R_6$, $R_7$, $R_8$, $R_9$, $R_{10}$, $R_{11}$, or $R_{12}$ at each occurrence is independently selected from —H, -D, —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, oxo, —$NH_2$, —NH($C_{1-3}$alkyl), —N($C_{1-3}$alkyl)$_2$, —OH, —O($C_{1-3}$alkyl), —SH, —S($C_{1-3}$alkyl), —S(═O)($C_{1-3}$alkyl), —$S(═O)_2$($C_{1-3}$alkyl), —C(═O)($C_{1-3}$alkyl), —C(═O)OH, —C(═O)(O$C_{1-3}$alkyl), —OC(═O)($C_{1-3}$alkyl), —C(═O)$NH_2$, —C(═O)NH($C_{1-3}$alkyl), —C(═O)N($C_{1-3}$alkyl)$_2$, —NHC(═O)($C_{1-3}$alkyl), —N($C_{1-3}$alkyl)C(═O)($C_{1-3}$alkyl), —S(═O)(O$C_{1-3}$alkyl), —OS(═O)($C_{1-3}$alkyl), —S(═O)$NH_2$, —S(═O)NH($C_{1-3}$alkyl), —S(═O)N($C_{1-3}$alkyl)$_2$, —NHS(═O)($C_{1-3}$alkyl), —N($C_{1-3}$alkyl)S(═O)($C_{1-3}$alkyl), —$S(═O)_2$(O$C_{1-3}$alkyl), —$OS(═O)_2$($C_{1-3}$alkyl), —$S(═O)_2NH_2$, —$S(═O)_2$NH($C_{1-3}$alkyl), —$S(═O)_2$N($C_{1-3}$alkyl)$_2$, —$NHS(═O)_2$($C_{1-3}$alkyl), —N($C_{1-3}$alkyl)$S(═O)_2$($C_{1-3}$alkyl), —P(═O)H($C_{1-3}$alkyl), —P(═O)($C_{1-3}$alkyl)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl, wherein said —$C_{1-3}$alkyl, —$C_{1-3}$haloalkyl, —$C_{1-3}$haloalkoxy, —$C_{2-6}$alkenyl, —$C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl is independently optionally substituted with 1, 2, 3, 4, 5 or 6 substituents selected from hydrogen, —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, oxo, —$NH_2$, —NH($C_{1-3}$alkyl), —N($C_{1-3}$alkyl)$_2$, —OH, —O($C_{1-3}$alkyl), —SH, —S($C_{1-3}$alkyl), —S(═O)($C_{1-3}$alkyl), —S(═O)$_2$($C_{1-3}$alkyl), —C(═O)($C_{1-3}$alkyl), —C(═O)OH, —C(═O)(O$C_{1-3}$alkyl), —OC(═O)($C_{1-3}$alkyl), —C(═O)$NH_2$, —C(═O)NH($C_{1-3}$alkyl), —C(═O)N($C_{1-3}$alkyl)$_2$, —NHC(═O)($C_{1-3}$alkyl), —N($C_{1-3}$alkyl)C(═O)($C_{1-3}$alkyl), —S(═O)(O$C_{1-3}$alkyl), —OS(═O)($C_{1-3}$alkyl), —S(═O)$NH_2$, —S(═O)NH($C_{1-3}$alkyl), —S(═O)N($C_{1-3}$alkyl)$_2$, —NHS(═O)($C_{1-3}$alkyl), —N($C_{1-3}$alkyl)S(═O)($C_{1-3}$alkyl), —S(═O)$_2$(O$C_{1-3}$alkyl), —OS(═O)$_2$($C_{1-3}$alkyl), —S(═O)$_2NH_2$, —S(═O)$_2$NH($C_{1-3}$alkyl), —S(═O)$_2$N($C_{1-3}$alkyl)$_2$, —NHS(═O)$_2$($C_{1-3}$alkyl), —N($C_{1-3}$alkyl)S(═O)$_2$($C_{1-3}$alkyl), —P(═O)H($C_{1-3}$alkyl), —P(═O)($C_{1-3}$alkyl)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl;

$m_1$ is 0, 1, 2, or 3;

$m_2$ is 0, 1, 2, or 3;

$m_3$ is 0, 1, 2, or 3;

$m_4$ is 0, 1, 2, or 3.

[78]. The compound according to any one of [1] to [77], wherein, $R_1$, $R_2$, $R_3$, $R_4$, $R_5$, $R_6$, $R_7$, $R_8$, $R_9$, $R_{10}$, $R_{11}$, or $R_{12}$ at each occurrence is independently selected from —H, -D, —Cl, —F, —Br, —$CH_3$, —$CD_3$, —$CH_2CH_3$, —$CH_2CH_2CH_3$, —CH($CH_3$)$_2$, —O—$CH_2F$, —O—$CHF_2$, —O—$CF_3$, —S—$CH_2F$, —S—$CHF_2$, —S—$CF_3$,

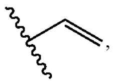, 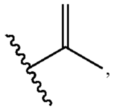, 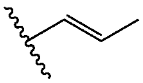,

—$CH_2F$, —$CHF_2$, —$CF_3$, —$CH_2CH_2F$, —$CH_2CHF_2$, —$CH_2CF_3$, —$CHFCH_3$, —$CF_2CH_3$, —CN, oxo, —$NH_2$, —NH($CH_3$), —N($CH_3$)$_2$, —NH($CH_2CH_3$), —OH, —O—$CH_3$, —O—$CH_2CH_3$, —O—$CH_2CH_2CH_3$, —O—CH($CH_3$)$_2$, —SH, —S—$CH_3$, —S—$CH_2CH_3$, —S—$CH_2CH_2CH_3$, —S—CH($CH_3$)$_2$, —S(═O)$CH_3$, —S(═O)($CH_2CH_3$), —S(═O)($CH_2CH_2CH_3$), —S(═O)(CH($CH_3$)$_2$), —S(═O)$_2CH_3$, —S(═O)$_2$($CH_2CH_3$), —S(═O)$_2$($CH_2CH_2CH_3$), —S(═O)$_2$(CH($CH_3$)$_2$), —COOH, —C(═O)($CH_3$), —C(═O)($CH_2CH_3$), —C(═O)(CH($CH_3$)$_2$), —C(═O)($CF_3$), —C(═O)($OCH_3$), —C(═O)($OCH_2CH_3$), —C(═O)($OCH_2CH_2CH_3$), —C(═O)(OCH($CH_3$)$_2$), —OC(═O)($CH_3$), —OC(═O)($CH_2CH_3$), —OC(═O)($CH_2CH_2CH_3$), —OC(═O)(CH($CH_3$)$_2$), —C(═O)$NH_2$, —C(═O)NH($CH_3$), —C(═O)NH($CH_2CH_3$), —C(═O)NH($CH_2CH_2CH_3$), —C(═O)NH(CH($CH_3$)$_2$), —C(═O)N($CH_3$)$_2$, —C(═O)N($CH_2CH_3$)$_2$, —NHC(═O)($CH_3$), —NHC(═O)($CH_2CH_3$), —NHC(═O)($CH_2CH_2CH_3$), —NHC(═O)(CH($CH_3$)$_2$), —N($CH_3$)C(═O)($CH_3$), —S(═O)($OCH_3$), —S(═O)($OCH_2CH_3$), —S(═O)($OCH_2CH_2CH_3$), —S(═O)(OCH($CH_3$)$_2$), —OS(═O)($CH_3$), —OS(═O)($CH_2CH_3$), —OS(═O)($CH_2CH_2CH_3$), —OS(═O)(CH($CH_3$)$_2$), —S(═O)$NH_2$, —S(═O)NH($CH_3$), —S(═O)NH($CH_2CH_3$), —S(═O)NH($CH_2CH_2CH_3$), —S(═O)NH(CH($CH_3$)$_2$), —S(═O)N($CH_3$)$_2$, —S(═O)N($CH_3$)($CH_2CH_3$), —NHS(═O)($CH_3$), —NHS(═O)($CH_2CH_3$), —NHS(═O)($CH_2CH_2CH_3$), —NHS(═O)(CH($CH_3$)$_2$), —N($CH_3$)S(═O)($CH_3$), —S(═O)$_2$($OCH_3$), —S(═O)$_2$($OCH_2CH_3$), —S(═O)$_2$($OCH_2CH_2CH_3$), —S(═O)$_2$(OCH($CH_3$)$_2$), —OS(═O)$_2$($CH_3$), —OS(═O)$_2$($CH_2CH_3$), —OS(═O)$_2$($CH_2CH_2CH_3$), —OS(═O)$_2$(CH($CH_3$)$_2$), —S(═O)$_2NH_2$, —S(═O)$_2$NH($CH_3$), —S(═O)$_2$NH($CH_2CH_3$), —S(═O)$_2$NH($CH_2CH_2CH_3$), —S(═O)$_2$NH(CH($CH_3$)$_2$), —S(═O)$_2$N($CH_3$)$_2$, —S(═O)$_2$N($CH_3$)($CH_2CH_3$), —NHS(═O)$_2$($CH_3$), —NHS(═O)$_2$($CH_2CH_3$), —NHS(═O)$_2$($CH_2CH_2CH_3$), —NHS(═O)$_2$(CH($CH_3$)$_2$), —N($CH_3$)S(═O)$_2$($CH_3$), —P(═O)H($CH_3$), —P(═O)H($CH_2CH_3$), —P(═O)H($CH_2CH_2CH_3$), —P(═O)H(CH($CH_3$)$_2$), —P(═O)($CH_3$)$_2$, —P(═O)($CH_3$)($CH_2CH_3$), —$CH_2$—OH, —$CH_2CH_2$—OH, —CH($CH_3$)—OH, —$CH_2$—$OCH_3$, —$CH_2$—$OCH_2CH_3$, —$CH_2$—OCH($CH_3$)$_2$, —$CH_2$—$NH_2$, —$CH_2CH_2$—$NH_2$, —CH($CH_3$)—$NH_2$, —$CH_2$—NH—C(═O)($CH_3$), —$CH_2$—NH—C(═O)($CH_2CH_3$), —$CH_2$—NH—C(═O)(CH($CH_3$)$_2$), —$CH_2$—N($CH_3$)—C(═O)($CH_2CH_3$), —$CH_2$—CN, —$CH_2CH_2$—CN, —CH($CH_3$)—CN,

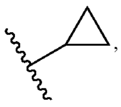 [SMILES: *C1CC1], 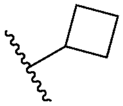, 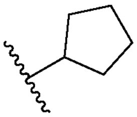, or

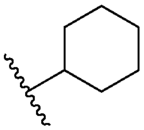.

[79]. The compound according to any one of [1] to [78], wherein, $R_1$, $R_2$, $R_3$, $R_4$, $R_5$, $R_6$, $R_7$, $R_8$, $R_9$, $R_{10}$, $R_{11}$, or $R_{12}$ at each occurrence is independently selected from —H, -D, —Cl, —F, —Br, —$CH_3$, —$CD_3$, —$CH_2CH_3$, —$CH_2CH_2CH_3$, —CH($CH_3$)$_2$, —$CF_3$, —O—$CF_3$, —S—$CF_3$, —$CF_3$, —CN, oxo, —$NH_2$, —NH($CH_3$), —N($CH_3$)$_2$, —OH, —O—$CH_3$, —O—$CH_2CH_3$, —O—$CH_2CH_2CH_3$, —O—CH($CH_3$)$_2$, —SH, —S—$CH_3$, —S—CH($CH_3$)$_2$, —S(═O)$CH_3$, —S(═O)$_2CH_3$, —COOH, —C(═O)($CH_3$), —C(═O)($CH_2CH_3$), —C(═O)($CF_3$), —C(═O)$NH_2$, —C(═O)NH($CH_3$), —NHC(═O)($CH_3$), —S(═O)$NH_2$, —S(═O)NH($CH_3$), —NHS(═O)($CH_3$), —S(═O)$_2NH_2$, —S(═O)$_2$NH($CH_3$), —NHS(═O)$_2$($CH_3$), —$CH_2$—OH, —$CH_2CH_2$—OH, —CH(OH)($CH_3$), —$CH_2$—$OCH_3$, —$CH_2$—$OCH_2CH_3$, —$CH_2$—$NH_2$, —$CH_2CH_2$—$NH_2$, —CH($CH_3$)—$NH_2$, —$CH_2$—NH—C(═O)($CH_3$), —$CH_2$—CN, —$CH_2CH_2$—CN, —CH($CH_3$)—CN, or

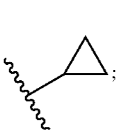;

$m_1$ is 0, or 1;

$m_2$ is 0, or 1;

$m_3$ is 0, or 1;

$m_4$ is 0, or 1.

[80]. The compound according to any one of [1] to [79], wherein, $R_1$ or $R_2$ at each occurrence is independently selected from —H, -D, —$CH_3$, —$CD_3$, —$CH_2CH_3$, —$CH_2CH_2CH_3$, —CH($CH_3$)$_2$, —$CF_3$, —$CH_2$—

$OCH_3$, $—CH_2—OCH_2CH_3$, $—CH_2—OH$, $—CH_2CH_2—OH$, $—CH(OH)(CH_3)$ or $—CH_2—NH—C(=O)(CH_3)$;
$m_1$ is 1;
$R_3$, $R_4$, $R_5$, $R_6$, $R_7$, $R_8$, $R_9$, $R_{10}$, $R_{11}$, or $R_{12}$ at each occurrence is independently selected from —H, -D, —OH, $—CH_3$, $—CD_3$, $—CH_2CH_3$, $—CH_2CH_2CH_3$ or $—CH(CH_3)_2$;
$m_2$ is 0
$m_3$ is 1; and
$m_4$ is 0.
[81]. The compound according to any one of [1] to [80], wherein, the moiety of
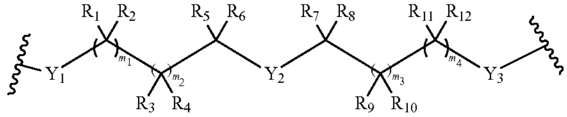
is selected from:
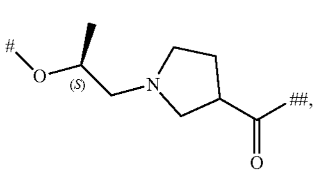
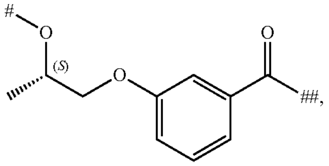
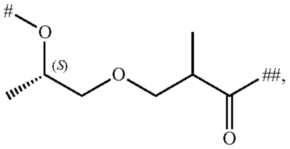
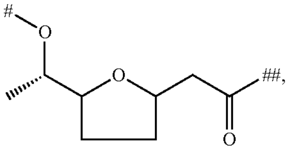
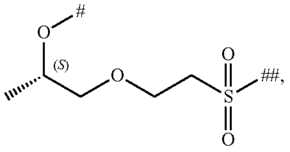
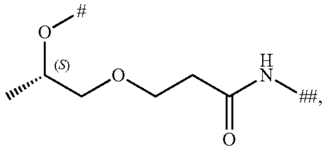
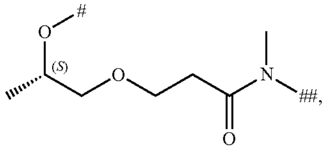
-continued
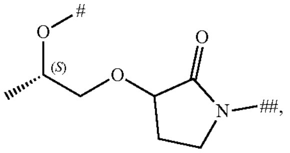
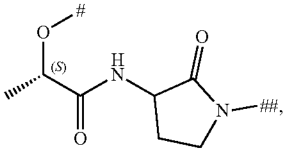
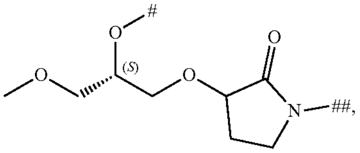
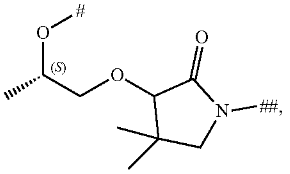
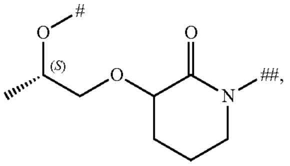
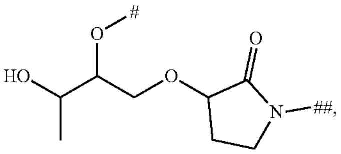
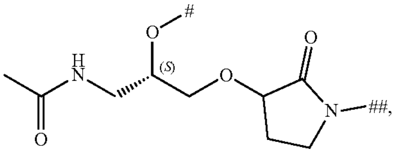
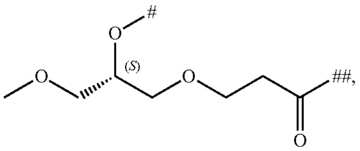
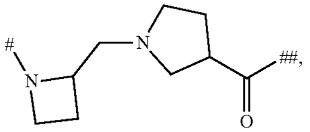
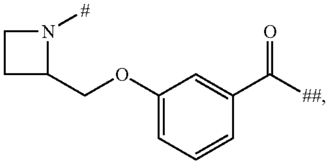
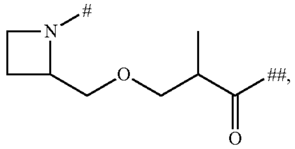

-continued

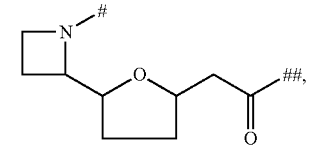

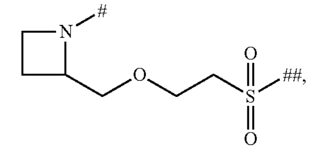

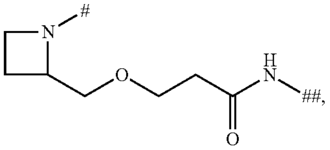

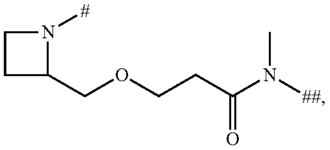

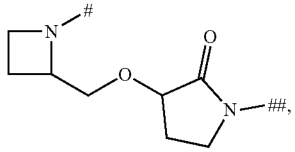

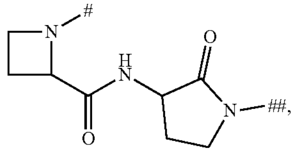

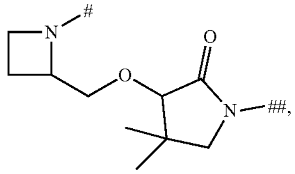

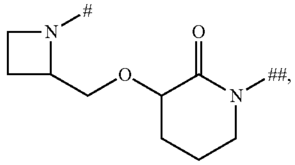

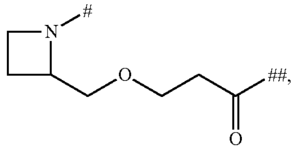

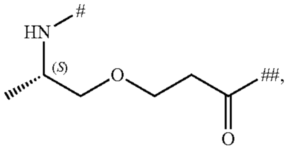

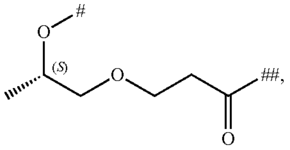

-continued

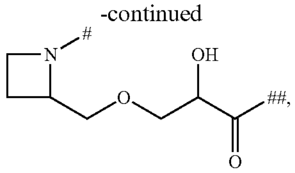

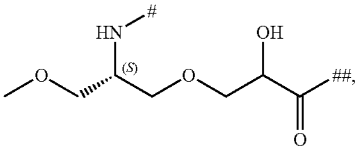

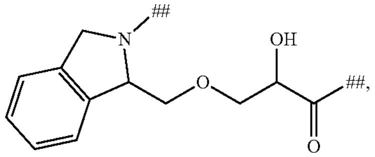

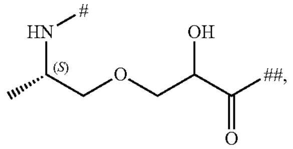

or

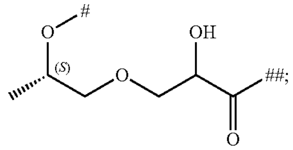

Wherein, # indicates the attached point to the moiety of

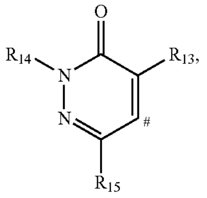

the ## indicates the attached point to the moiety of

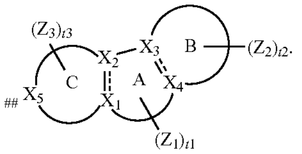

[82]. The compound according to any one of [1] to [81], wherein, $R_{13}$, $R_{14}$ or $R_{15}$ at each occurrence is independently selected from hydrogen, halogen, $-C_{1-6}$alkyl, $-C_{1-6}$haloalkyl, $-C_{1-6}$haloalkoxy, $-C_{2-6}$alkenyl, $-C_{2-6}$alkynyl, —CN, oxo, $-NH_2$, $-NH(C_{1-6}$alkyl), $-N(C_{1-6}$alkyl$)_2$, —OH, $-O(C_{1-6}$alkyl), —SH, $-S(C_{1-6}$alkyl), $-S($halo$C_{1-6}$alkyl), $-S(=O)(C_{1-6}$alkyl), $-S(=O)_2(C_{1-6}$alkyl), $-C(=O)(C_{1-6}$alkyl), $-C(=O)OH$, $-C(=O)(OC_{1-6}$alkyl), $-OC(=O)(C_{1-6}$alkyl), $-C(=O)NH_2$, $-C(=O)NH(C_{1-6}$alkyl), $-C(=O)N(C_{1-6}$alkyl$)_2$, $-NHC(=O)(C_{1-6}$alkyl), $-N(C_{1-6}$alkyl)$C(=O)(C_{1-6}$alkyl), $-OC(=O)O(C_{1-6}$alkyl), $-NHC(=O)(OC_{1-6}$alkyl), $-N(C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)NH$_2$, —NHC(═O)NH($C_{1-6}$alkyl), —NHC(═O)N($C_{1-6}$alkyl)$_2$, —N($C_{1-6}$alkyl)C(═O)NH$_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)NH$_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —S(═O)$_2$(O$C_{1-6}$alkyl), —OS(═O)$_2$($C_{1-6}$alkyl), —S(═O)$_2$NH$_2$, —S(═O)$_2$NH($C_{1-6}$alkyl), —S(═O)$_2$N($C_{1-6}$alkyl)$_2$, —NHS(═O)$_2$($C_{1-6}$alkyl), —N($C_{1-6}$alkyl)S(═O)$_2$($C_{1-6}$alkyl), —OS(═O)$_2$O($C_{1-6}$alkyl), —NHS(═O)$_2$O($C_{1-6}$alkyl), —N($C_{1-6}$alkyl)S(═O)$_2$O($C_{1-6}$alkyl), —OS(═O)$_2$NH$_2$, —OS(═O)$_2$NH($C_{1-6}$alkyl), —OS(═O)$_2$N($C_{1-6}$alkyl)$_2$, —NHS(═O)$_2$NH$_2$, —NHS(═O)$_2$NH($C_{1-6}$alkyl), —NHS(═O)$_2$N($C_{1-6}$alkyl)$_2$, —N($C_{1-6}$alkyl)S(═O)$_2$NH$_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-6 membered cycloalkyl, 3-6 membered heterocyclyl, 6-10 membered aryl or 5-10 membered heteroaryl, wherein said —$C_{1-6}$alkyl, —$C_{1-6}$haloalkyl, —$C_{1-6}$haloalkoxy, —$C_{2-6}$alkenyl, —$C_{2-6}$alkynyl, 3-6 membered cycloalkyl, 3-6 membered heterocyclyl, 6-10 membered aryl or 5-10 membered heteroaryl is independently optionally substituted with 1, 2, 3, 4, 5 or 6 substituents selected from —F, —Cl, —Br, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —NH$_2$, —NH($C_{1-6}$alkyl), —N($C_{1-6}$alkyl)$_2$, —OH, —O($C_{1-6}$alkyl), —SH, —S($C_{1-6}$alkyl), —S(halo$C_{1-6}$alkyl), —S(═O)($C_{1-6}$alkyl), —S(═O)$_2$($C_{1-6}$alkyl), —C(═O)($C_{1-6}$alkyl), —C(═O)OH, —C(═O)(O$C_{1-6}$alkyl), —OC(═O)($C_{1-6}$alkyl), —C(═O)NH$_2$, —C(═O)NH($C_{1-6}$alkyl), —C(═O)N($C_{1-6}$alkyl)$_2$, —NHC(═O)($C_{1-6}$alkyl), —N($C_{1-6}$alkyl)C(═O)($C_{1-6}$alkyl), —OC(═O)O($C_{1-6}$alkyl), —NHC(═O)(O$C_{1-6}$alkyl), —N($C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)NH$_2$, —NHC(═O)NH($C_{1-6}$alkyl), —NHC(═O)N($C_{1-6}$alkyl)$_2$, —N($C_{1-6}$alkyl)C(═O)NH$_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)NH$_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —S(═O)$_2$(O$C_{1-6}$alkyl), —OS(═O)$_2$($C_{1-6}$alkyl), —S(═O)$_2$NH$_2$, —S(═O)$_2$NH($C_{1-6}$alkyl), —S(═O)$_2$N($C_{1-6}$alkyl)$_2$, —NHS(═O)$_2$($C_{1-6}$alkyl), —N($C_{1-6}$alkyl)S(═O)$_2$($C_{1-6}$alkyl), —OS(═O)$_2$O($C_{1-6}$alkyl), —NHS(═O)$_2$O($C_{1-6}$alkyl), —N($C_{1-6}$alkyl)S(═O)$_2$O($C_{1-6}$alkyl), —OS(═O)$_2$NH$_2$, —OS(═O)$_2$NH($C_{1-6}$alkyl), —OS(═O)$_2$N($C_{1-6}$alkyl)$_2$, —NHS(═O)$_2$NH$_2$, —NHS(═O)$_2$NH($C_{1-6}$alkyl), —NHS(═O)$_2$N($C_{1-6}$alkyl)$_2$, —N($C_{1-6}$alkyl)S(═O)$_2$NH$_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-6 membered cycloalkyl, 3-6 membered heterocyclyl, 6-10 membered aryl or 5-10 membered heteroaryl.

[83]. The compound according to any one of [1] to [82], wherein, $R_{13}$, $R_{14}$ or $R_{15}$ at each occurrence is independently selected from —H, -D, —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, oxo, —NH$_2$, —NH($C_{1-3}$alkyl), —N($C_{1-3}$alkyl)$_2$, —OH, —O($C_{1-3}$alkyl), —SH, —S($C_{1-3}$alkyl), —S(═O)($C_{1-3}$alkyl), —S(═O)$_2$($C_{1-3}$alkyl), —C(═O)($C_{1-3}$alkyl), —C(═O)OH, —C(═O)(O$C_{1-3}$alkyl), —OC(═O)($C_{1-3}$alkyl), —C(═O)NH$_2$, —C(═O)NH($C_{1-3}$alkyl), —C(═O)N($C_{1-3}$alkyl)$_2$, —NHC(═O)($C_{1-3}$alkyl), —N($C_{1-3}$alkyl)C(═O)($C_{1-3}$alkyl), —S(═O)(O$C_{1-3}$alkyl), —OS(═O)($C_{1-3}$alkyl), —S(═O)NH$_2$, —S(═O)NH($C_{1-3}$alkyl), —S(═O)N($C_{1-3}$alkyl)$_2$, —NHS(═O)($C_{1-3}$alkyl), —N($C_{1-3}$alkyl)S(═O)($C_{1-3}$alkyl), —S(═O)$_2$(O$C_{1-3}$alkyl), —OS(═O)$_2$($C_{1-3}$alkyl), —S(═O)$_2$NH$_2$, —S(═O)$_2$NH($C_{1-3}$alkyl), —S(═O)$_2$N($C_{1-3}$alkyl)$_2$, —NHS(═O)$_2$($C_{1-3}$alkyl), —N($C_{1-3}$alkyl)S(═O)$_2$($C_{1-3}$alkyl), —P(═O)H($C_{1-3}$alkyl), —P(═O)($C_{1-3}$alkyl)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl, wherein said —$C_{1-3}$alkyl, —$C_{1-3}$haloalkyl, —$C_{1-3}$haloalkoxy, —$C_{2-6}$alkenyl, —$C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl is independently optionally substituted with 1, 2, 3, 4, 5 or 6 substituents selected from hydrogen, —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, oxo, —NH$_2$, —NH($C_{1-3}$alkyl), —N($C_{1-3}$alkyl)$_2$, —OH, —O($C_{1-3}$alkyl), —SH, —S($C_{1-3}$alkyl), —S(═O)($C_{1-3}$alkyl), —S(═O)$_2$($C_{1-3}$alkyl), —C(═O)($C_{1-3}$alkyl), —C(═O)OH, —C(═O)(O$C_{1-3}$alkyl), —OC(═O)($C_{1-3}$alkyl), —C(═O)NH$_2$, —C(═O)NH($C_{1-3}$alkyl), —C(═O)N($C_{1-3}$alkyl)$_2$, —NHC(═O)($C_{1-3}$alkyl), —N($C_{1-3}$alkyl)C(═O)($C_{1-3}$alkyl), —S(═O)(O$C_{1-3}$alkyl), —OS(═O)($C_{1-3}$alkyl), —S(═O)NH$_2$, —S(═O)NH($C_{1-3}$alkyl), —S(═O)N($C_{1-3}$alkyl)$_2$, —NHS(═O)($C_{1-3}$alkyl), —N($C_{1-3}$alkyl)S(═O)($C_{1-3}$alkyl), —S(═O)$_2$(O$C_{1-3}$alkyl), —OS(═O)$_2$($C_{1-3}$alkyl), —S(═O)$_2$NH$_2$, —S(═O)$_2$NH($C_{1-3}$alkyl), —S(═O)$_2$N($C_{1-3}$alkyl)$_2$, —NHS(═O)$_2$($C_{1-3}$alkyl), —N($C_{1-3}$alkyl)S(═O)$_2$($C_{1-3}$alkyl), —P(═O)H($C_{1-3}$alkyl), —P(═O)($C_{1-3}$alkyl)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl;

[84]. The compound according to any one of [1] to [83], wherein, $R_{13}$, $R_{14}$ or $R_{15}$ at each occurrence is independently selected from —H, -D, —Cl, —F, —Br, —$CH_3$, —$CD_3$, —$CH_2CH_3$, —$CH_2CH_2CH_3$, —$CH(CH_3)_2$, —O—$CH_2F$, —O—$CHF_2$, —O—$CF_3$, —S—$CH_2F$, —S—$CHF_2$, —S—$CF_3$,

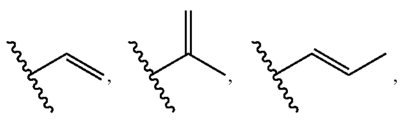

—$CH_2F$, —$CHF_2$, —$CF_3$, —$CH_2CH_2F$, —$CH_2CHF_2$, —$CH_2CF_3$, —$CHFCH_3$, —$CF_2CH_3$, —CN, oxo, —NH$_2$, —NH($CH_3$), —N($CH_3$)$_2$, —NH($CH_2CH_3$), —OH, —O—$CH_3$, —O—$CH_2CH_3$, —O—$CH_2CH_2CH_3$, —O—$CH(CH_3)_2$, —SH, —S—$CH_3$, —S—$CH_2CH_3$, —S—$CH_2CH_2CH_3$, —S—$CH(CH_3)_2$, —S(═O)$CH_3$, —S(═O)($CH_2CH_3$), —S(═O)($CH_2CH_2CH_3$), —S(═O)($CH(CH_3)_2$), —S(═O)$_2$$CH_3$, —S(═O)$_2$($CH_2CH_3$), —S(═O)$_2$($CH_2CH_2CH_3$), —S(═O)$_2$($CH(CH_3)_2$), $—COOH$, $—C(=O)(CH_3)$, $—C(=O)(CH_2CH_3)$, $—C(=O)(CH(CH_3)_2)$, $—C(=O)(CF_3)$, $—C(=O)(OCH_3)$, $—C(=O)(OCH_2CH_3)$, $—C(=O)(OCH_2CH_2CH_3)$, $—C(=O)(OCH(CH_3)_2)$, $—OC(=O)(CH_3)$, $—OC(=O)(CH_2CH_3)$, $—OC(=O)(CH_2CH_2CH_3)$, $—OC(=O)(CH(CH_3)_2)$, $—C(=O)NH_2$, $—C(=O)NH(CH_3)$, $—C(=O)NH(CH_2CH_3)$, $—C(=O)NH(CH_2CH_2CH_3)$, $—C(=O)NH(CH(CH_3)_2)$, $—C(=O)N(CH_3)_2$, $—C(=O)N(CH_2CH_3)_2$, $—NHC(=O)(CH_3)$, $—NHC(=O)(CH_2CH_3)$, $—NHC(=O)(CH_2CH_2CH_3)$, $—NHC(=O)(CH(CH_3)_2)$, $—N(CH_3)C(=O)(CH_3)$, $—S(=O)(OCH_3)$, $—S(=O)(OCH_2CH_3)$, $—S(=O)(OCH_2CH_2CH_3)$, $—S(=O)(OCH(CH_3)_2)$, $—OS(=O)(CH_3)$, $—OS(=O)(CH_2CH_3)$, $—OS(=O)(CH_2CH_2CH_3)$, $—OS(=O)(CH(CH_3)_2)$, $—S(=O)NH_2$, $—S(=O)NH(CH_3)$, $—S(=O)NH(CH_2CH_3)$, $—S(=O)NH(CH_2CH_2CH_3)$, $—S(=O)NH(CH(CH_3)_2)$, $—S(=O)N(CH_3)_2$, $—S(=O)N(CH_3)(CH_2CH_3)$, $—NHS(=O)(CH_3)$, $—NHS(=O)(CH_2CH_3)$, $—NHS(=O)(CH_2CH_2CH_3)$, $—NHS(=O)(CH(CH_3)_2)$, $—N(CH_3)S(=O)(CH_3)$, $—S(=O)_2(OCH_3)$, $—S(=O)_2(OCH_2CH_3)$, $—S(=O)_2(OCH_2CH_2CH_3)$, $—S(=O)_2(OCH(CH_3)_2)$, $—OS(=O)_2(CH_3)$, $—OS(=O)_2(CH_2CH_3)$, $—OS(=O)_2(CH_2CH_2CH_3)$, $—OS(=O)_2(CH(CH_3)_2)$, $—S(=O)_2NH_2$, $—S(=O)_2NH(CH_3)$, $—S(=O)_2NH(CH_2CH_3)$, $—S(=O)_2NH(CH_2CH_2CH_3)$, $—S(=O)_2NH(CH(CH_3)_2)$, $—S(=O)_2N(CH_3)_2$, $—S(=O)_2N(CH_3)(CH_2CH_3)$, $—NHS(=O)_2(CH_3)$, $—NHS(=O)_2(CH_2CH_3)$, $—NHS(=O)_2(CH_2CH_2CH_3)$, $—NHS(=O)_2(CH(CH_3)_2)$, $—N(CH_3)S(=O)_2(CH_3)$, $—P(=O)H(CH_3)$, $—P(=O)H(CH_2CH_3)$, $—P(=O)H(CH_2CH_2CH_3)$, $—P(=O)H(CH(CH_3)_2)$, $—P(=O)(CH_3)_2$, $—P(=O)(CH_3)(CH_2CH_3)$, $—CH_2—OH$, $—CH_2CH_2—OH$, $—CH(CH_3)—OH$, $—CH_2—OCH_3$, $—CH_2—OCH_2CH_3$, $—CH_2—OCH(CH_3)_2$, $—CH_2—NH_2$, $—CH_2CH_2—NH_2$, $—CH(CH_3)—NH_2$, $—CH_2—NH—C(=O)(CH_3)$, $—CH_2—NH—C(=O)(CH_2CH_3)$, $—CH_2—NH—C(=O)(CH(CH_3)_2)$, $—CH_2—N(CH_3)—C(=O)(CH_2CH_3)$, $—CH_2—CN$, $—CH_2CH_2—CN$, $—CH(CH_3)—CN$

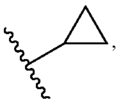, 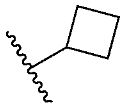, 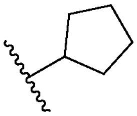, or

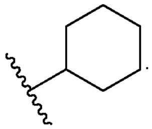.

[85]. The compound according to any one of [1] to [84], wherein, $R_{13}$, $R_{14}$ or $R_{15}$ at each occurrence is independently selected from —H, -D, —Cl, —F, —Br, $—CH_3$, $—CD_3$, $—CH_2CH_3$, $—CH_2CH_2CH_3$, $—CH(CH_3)_2$, $—CF_3$, $—O—CF_3$, $—S—CF_3$, $—CF_3$, —CN, oxo, $—NH_2$, $—NH(CH_3)$, $—N(CH_3)_2$, —OH, $—O—CH_3$, $—O—CH_2CH_3$, $—O—CH_2CH_2CH_3$, $—O—CH(CH_3)_2$, —SH, $—S—CH_3$, $—S—CH(CH_3)_2$, $—S(=O)CH_3$, $—S(=O)_2CH_3$, —COOH, $—C(=O)(CH_3)$, $—C(=O)(CH_2CH_3)$, $—C(=O)(CF_3)$, $—C(=O)NH_2$, $—C(=O)NH(CH_3)$, $—NHC(=O)(CH_3)$, $—S(=O)NH_2$, $—S(=O)NH(CH_3)$, $—NHS(=O)(CH_3)$, $—S(=O)_2NH_2$, $—S(=O)_2NH(CH_3)$, $—NHS(=O)_2(CH_3)$, $—CH_2—OH$, $—CH_2CH_2—OH$, $—CH(OH)(CH_3)$, $—CH_2—OCH_3$, $—CH_2—OCH_2CH_3$, $—CH_2—NH_2$, $—CH_2CH_2—NH_2$, $—CH(CH_3)—NH_2$, $—CH_2—NH—C(=O)(CH_3)$, $—CH_2—CN$, $—CH_2CH_2—CN$, $—CH(CH_3)—CN$, or

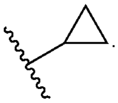.

[86]. The compound according to any one of [1] to [85], wherein, $R_{13}$ is selected from —F, —Cl, —Br, $—CH_3$, $—CD_3$, $—CH_2CH_3$, $—CH(CH_3)_2$, $—CF_3$, $—C(=O)—CH_3$, $—CO—CF_3$, $—OCH_3$,

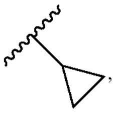, $—S—CH_3$, $—S—CH_2CH_3$ or $—S—CH(CH_3)_2$; in some embodiments, $R_{13}$ is selected from $—CF_3$; and $R_{14}$ or $R_{15}$ at each occurrence is independently selected from —H, -D, —OH, $—CH_3$, $—CD_3$, $—CH_2$ $CH_3$, $—CH_2CH_2CH_3$ or $—CH(CH_3)_2$;

In some embodiments, $R_{13}$ is selected from $—CF_3$ and $R_{14}$ or $R_{15}$ at each occurrence is independently selected from —H.

[87]. The compound according to any one of [1] to [86], wherein, $Y_2$ at each occurrence is independently selected from —O—, —CO—NH—, or —NH—CO—; in some embodiments, $Y_2$ at each occurrence is independently selected from —O—;

$Y_3$ at each occurrence is independently selected from —C(=O)—, $—S(=O)_2—$, —C(=O)—NH—, —NH—C(=O)—, $—C(=O)—N(CH_3)—$, or $—N(CH_3)—C(=O)—$; in some embodiments, $Y_3$ at each occurrence is independently selected from —C(=O)—;

$R_{13}$ is selected from —F, —Cl, —Br, $—CH_3$, $—CD_3$, $—CH_2CH_3$, $—CH(CH_3)_2$, $—CF_3$, $—C(=O)—CH_3$, $—C(=O)—CF_3$, $—OCH_3$,

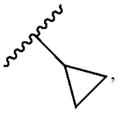 [SMILES: *C1CC1], $—S—CH_3$, $—S—CH_2CH_3$ or $—S—CH(CH_3)_2$; in some embodiments, $R_{13}$ is selected from $—CF_3$;

$R_1$ or $R_2$ at each occurrence is independently selected from —H, -D, $—CH_3$, $—CD_3$, $—CH_2CH_3$, $—CH_2CH_2CH_3$, $—CH(CH_3)_2$, $—CF_3$, $—CH_2—OCH_3$, $—CH_2—OCH_2CH_3$, $—CH_2—OH$, $—CH_2CH_2—OH$, $—CH(OH)(CH_3)$ or $—CH_2—NH—C(=O)(CH_3)$; in some embodiments, $R_1$ at each occurrence is independently selected from $—CH_3$, $—CD_3$, $—CH_2—O—CH_3$, $—CH(OH)(CH_3)$ or $—CH_2—NH—C(=O)(CH_3)$; and $R_2$ at each occurrence is independently selected from —H, -D, $—CH_3$, $—CD_3$, $—CH_2CH_3$, $—CH_2CH_2CH_3$;

$R_3$, $R_4$, $R_5$, $R_6$, $R_7$, $R_8$, $R_9$, $R_{10}$, $R_{11}$, $R_{12}$, $R_{14}$ or $R_{15}$ at each occurrence is independently selected from —H, -D, —OH, —$CH_3$, —$CD_3$, —$CH_2CH_3$, —$CH_2CH_2CH_3$ or —$CH(CH_3)_2$; in some embodiments, $R_3$, $R_4$, $R_5$, $R_6$, $R_7$, $R_8$, $R_9$, $R_{10}$, $R_{11}$, $R_{12}$, $R_{14}$ or $R_{15}$ at each occurrence is independently selected from —H, -D, —OH, —$CH_3$ or —$CD_3$;

$m_1$ is selected from 1 or 2;

$m_2$ is 0 or 1;

$m_3$ is 1 or 2;

$m_4$ is 0 or 1.

[88]. The compound according to any one of [1] to [87], wherein, $Y_2$ at each occurrence is independently selected from —O—;

$Y_3$ at each occurrence is independently selected from —C(═O)—;

$R_{13}$ is selected from —$CF_3$;

$R_1$ at each occurrence is independently selected from —$CH_3$ and $R_2$ at each occurrence is independently selected from —H;

$R_3$, $R_4$, $R_5$, $R_6$, $R_7$, $R_8$, $R_9$, $R_{10}$, $R_{11}$, $R_{12}$, $R_{14}$ or $R_{15}$ at each occurrence is independently selected from —H;

$m_1$ is 1;

$m_2$ is 0;

$m_3$ is 1;

$m_4$ is 0.

[89]. The compound according to any one of [1] to [88], wherein, $R_{16}$ or $R_{17}$ at each occurrence is independently selected from hydrogen, halogen —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —$NH_2$, —NH($C_{1-6}$alkyl), —N($C_{1-6}$alkyl)$_2$, —OH, —O($C_{1-6}$alkyl), —SH, —S($C_{1-6}$alkyl), —S(halo$C_{1-6}$alkyl), —S(═O)($C_{1-6}$alkyl), —S(═O)$_2$($C_{1-6}$alkyl), —C(═O)($C_{1-6}$alkyl), —C(═O)OH, —C(═O)(O$C_{1-6}$alkyl), —OC(═O)($C_{1-6}$alkyl), —C(═O)$NH_2$, —C(═O)NH($C_{1-6}$alkyl), —C(═O)N($C_{1-6}$alkyl)$_2$, —NHC(═O)($C_{1-6}$alkyl), —N($C_{1-6}$alkyl)C(═O)($C_{1-6}$alkyl), —OC(═O)O($C_{1-6}$alkyl), —NHC(═O)(O$C_{1-6}$alkyl), —N($C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)$NH_2$, —NHC(═O)NH($C_{1-6}$alkyl), —NHC(═O)N($C_{1-6}$alkyl)$_2$, —N($C_{1-6}$alkyl)C(═O)$NH_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)$NH_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —S(═O)$_2$(O$C_{1-6}$alkyl), —OS(═O)$_2$($C_{1-6}$alkyl), —S(═O)$_2NH_2$, —S(═O)$_2$NH($C_{1-6}$alkyl), —S(═O)$_2$N($C_{1-6}$alkyl)$_2$, —NHS(═O)$_2$($C_{1-6}$alkyl), —N($C_{1-6}$alkyl)S(═O)$_2$($C_{1-6}$alkyl), —OS(═O)$_2$O($C_{1-6}$alkyl), —NHS(═O)$_2$O($C_{1-6}$alkyl), —N($C_{1-6}$alkyl)S(═O)$_2$O($C_{1-6}$alkyl), —OS(═O)$_2NH_2$, —OS(═O)$_2$NH($C_{1-6}$alkyl), —OS(═O)$_2$N($C_{1-6}$alkyl)$_2$, —NHS(═O)$_2NH_2$, —NHS(═O)$_2$NH($C_{1-6}$alkyl), —NHS(═O)$_2$N($C_{1-6}$alkyl)$_2$, —N($C_{1-6}$alkyl)S(═O)$_2NH_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-6 membered cycloalkyl, 3-6 membered heterocyclyl, 6-10 membered aryl or 5-10 membered heteroaryl, wherein said —$C_{1-6}$alkyl, —$C_{1-6}$haloalkyl, —$C_{1-6}$haloalkoxy, —$C_{2-6}$alkenyl, —$C_{2-6}$alkynyl, 3-6 membered cycloalkyl, 3-6 membered heterocyclyl, 6-10 membered aryl or 5-10 membered heteroaryl is independently optionally substituted with 1, 2, 3, 4, 5 or 6 substituents selected from —F, —Cl, —Br, —$C_{1-6}$alkyl, —$C_{1-6}$haloalkyl, —$C_{1-6}$haloalkoxy, —$C_{2-6}$alkenyl, —$C_{2-6}$alkynyl, —CN, oxo, —$NH_2$, —NH($C_{1-6}$alkyl), —N($C_{1-6}$alkyl)$_2$, —OH, —O($C_{1-6}$alkyl), —SH, —S($C_{1-6}$alkyl), —S(halo$C_{1-6}$alkyl), —S(═O)($C_{1-6}$alkyl), —S(═O)$_2$($C_{1-6}$alkyl), —C(═O)($C_{1-6}$alkyl), —C(═O)OH, —C(═O)(O$C_{1-6}$alkyl), —OC(═O)($C_{1-6}$alkyl), —C(═O)$NH_2$, —C(═O)NH($C_{1-6}$alkyl), —C(═O)N($C_{1-6}$alkyl)$_2$, —NHC(═O)($C_{1-6}$alkyl), —N($C_{1-6}$alkyl)C(═O)($C_{1-6}$alkyl), —OC(═O)O($C_{1-6}$alkyl), —NHC(═O)(O$C_{1-6}$alkyl), —N($C_{1-6}$alkyl)C(═O)(O$C_{1-6}$alkyl), —OC(═O)NH($C_{1-6}$alkyl), —OC(═O)N($C_{1-6}$alkyl)$_2$, —NHC(═O)$NH_2$, —NHC(═O)NH($C_{1-6}$alkyl), —NHC(═O)N($C_{1-6}$alkyl)$_2$, —N($C_{1-6}$alkyl)C(═O)$NH_2$, —N($C_{1-6}$alkyl)C(═O)NH($C_{1-6}$alkyl), —N($C_{1-6}$alkyl)C(═O)N($C_{1-6}$alkyl)$_2$, —S(═O)(O$C_{1-6}$alkyl), —OS(═O)($C_{1-6}$alkyl), —S(═O)$NH_2$, —S(═O)NH($C_{1-6}$alkyl), —S(═O)N($C_{1-6}$alkyl)$_2$, —NHS(═O)($C_{1-6}$alkyl), —N($C_{1-6}$alkyl)S(═O)($C_{1-6}$alkyl), —S(═O)$_2$(O$C_{1-6}$alkyl), —OS(═O)$_2$($C_{1-6}$alkyl), —S(═O)$_2NH_2$, —S(═O)$_2$NH($C_{1-6}$alkyl), —S(═O)$_2$N($C_{1-6}$alkyl)$_2$, —NHS(═O)$_2$($C_{1-6}$alkyl), —N($C_{1-6}$alkyl)S(═O)$_2$($C_{1-6}$alkyl), —OS(═O)$_2$O($C_{1-6}$alkyl), —NHS(═O)$_2$O($C_{1-6}$alkyl), —N($C_{1-6}$alkyl)S(═O)$_2$O($C_{1-6}$alkyl), —OS(═O)$_2NH_2$, —OS(═O)$_2$NH($C_{1-6}$alkyl), —OS(═O)$_2$N($C_{1-6}$alkyl)$_2$, —NHS(═O)$_2NH_2$, —NHS(═O)$_2$NH($C_{1-6}$alkyl), —NHS(═O)$_2$N($C_{1-6}$alkyl)$_2$, —N($C_{1-6}$alkyl)S(═O)$_2NH_2$, —N($C_{1-6}$alkyl)S(═O)$_2$NH($C_{1-6}$alkyl), —N($C_{1-6}$alkyl)S(═O)$_2$N($C_{1-6}$alkyl)$_2$, —PH($C_{1-6}$alkyl), —P($C_{1-6}$alkyl)$_2$, —P(═O)H($C_{1-6}$alkyl), —P(═O)($C_{1-6}$alkyl)$_2$, 3-6 membered cycloalkyl, 3-6 membered heterocyclyl, 6-10 membered aryl or 5-10 membered heteroaryl.

[90]. The compound according to any one of [1] to [89], wherein, $R_{16}$ or $R_{17}$ at each occurrence is independently selected from —H, -D, —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, oxo, —$NH_2$, —NH($C_{1-3}$alkyl), —N($C_{1-3}$alkyl)$_2$, —OH, —O($C_{1-3}$alkyl), —SH, —S($C_{1-3}$alkyl), —S(═O)($C_{1-3}$alkyl), —S(═O)$_2$($C_{1-3}$alkyl), —C(═O)($C_{1-3}$alkyl), —C(═O)OH, —C(═O)(O$C_{1-3}$alkyl), —OC(═O)($C_{1-3}$alkyl), —C(═O)$NH_2$, —C(═O)NH($C_{1-3}$alkyl), —C(═O)N($C_{1-3}$alkyl)$_2$, —NHC(═O)($C_{1-3}$alkyl), —N($C_{1-3}$alkyl)C(═O)($C_{1-3}$alkyl), —S(═O)(O$C_{1-3}$alkyl), —OS(═O)($C_{1-3}$alkyl), —S(═O)$NH_2$, —S(═O)NH($C_{1-3}$alkyl), —S(═O)N($C_{1-3}$alkyl)$_2$, —NHS(═O)($C_{1-3}$alkyl), —N($C_{1-3}$alkyl)S(═O)($C_{1-3}$alkyl), —S(═O)$_2$(O$C_{1-3}$alkyl), —OS(═O)$_2$($C_{1-3}$alkyl), —S(═O)$_2NH_2$, —S(═O)$_2$NH($C_{1-3}$alkyl), —S(═O)$_2$N($C_{1-3}$alkyl)$_2$, —NHS(═O)$_2$($C_{1-3}$alkyl), —N($C_{1-3}$alkyl)S(═O)$_2$($C_{1-3}$alkyl), —P(═O)H($C_{1-3}$alkyl), —P(═O)($C_{1-3}$alkyl)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl, wherein said —$C_{1-3}$alkyl, —$C_{1-3}$haloalkyl, —$C_{1-3}$haloalkoxy, —$C_{2-6}$alkenyl, —$C_{2-6}$alkynyl, 3-6 membered cycloalkyl, 3-6 membered cycloalkenyl, 3-6 membered cycloalkynyl, 3-6 membered heterocyclyl, 6-10 membered aryl or 5-10 membered heteroaryl is independently optionally substituted with 1, 2, 3, 4, 5 or 6 substituents selected from hydrogen, —F, —Cl, —Br, —$C_{1-3}$alkyl, —$C_{1-3}$haloalkyl, —$C_{1-3}$haloalkoxy, —$C_{2-3}$alkenyl, —$C_{2-3}$alkynyl, —CN, oxo, —$NH_2$, —NH (C$_{1-3}$alkyl), —N(C$_{1-3}$alkyl)$_2$, —OH, —O(C$_{1-3}$alkyl), —SH, —S(C$_{1-3}$alkyl), —S(═O)(C$_{1-3}$alkyl), —S(═O)$_2$(C$_{1-3}$alkyl), —C(═O)(C$_{1-3}$alkyl), —C(═O)OH, —C(═O)(OC$_{1-3}$alkyl), —OC(═O)(C$_{1-3}$alkyl), —C(═O)NH$_2$, —C(═O)NH(C$_{1-3}$alkyl), —C(═O)N(C$_{1-3}$alkyl)$_2$, —NHC(═O)(C$_{1-3}$alkyl), —N(C$_{1-3}$alkyl)C(═O)(C$_{1-3}$alkyl), —S(═O)(OC$_{1-3}$alkyl), —OS(═O)(C$_{1-3}$alkyl), —S(═O)NH$_2$, —S(═O)NH(C$_{1-3}$alkyl), —S(═O)N(C$_{1-3}$alkyl)$_2$, —NHS(═O)(C$_{1-3}$alkyl), —N(C$_{1-3}$alkyl)S(═O)(C$_{1-3}$alkyl), —S(═O)$_2$(OC$_{1-3}$alkyl), —OS(═O)$_2$(C$_{1-3}$alkyl), —S(═O)$_2$NH$_2$, —S(═O)$_2$NH(C$_{1-3}$alkyl), —S(═O)$_2$N(C$_{1-3}$alkyl)$_2$, —NHS(═O)$_2$(C$_{1-3}$alkyl), —N(C$_{1-3}$alkyl)S(═O)$_2$(C$_{1-3}$alkyl), —P(═O)H(C$_{1-3}$alkyl), —P(═O)(C$_{1-3}$alkyl)$_2$, 3-6 membered cycloalkyl, 3-6 membered cycloalkenyl, 3-6 membered cycloalkynyl, 3-6 membered heterocyclyl, 6-10 membered aryl or 5-10 membered heteroaryl.

[91]. The compound according to any one of [1] to [90], wherein,

R$_{16}$ or R$_{17}$ at each occurrence is independently selected from —H, -D, —Cl, —F, —Br, —CH$_3$, —CD$_3$, —CH$_2$CH$_3$, —CH$_2$CH$_2$CH$_3$, —CH(CH$_3$)$_2$, —C(CH$_3$)$_3$, —O—CH$_2$F, —O—CHF$_2$, —O—CF$_3$, —S—CH$_2$F, —S—CHF$_2$, —S—CF$_3$,

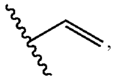, 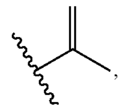, 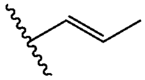,

—CH$_2$F, —CHF$_2$, —CF$_3$, —CH$_2$CH$_2$F, —CH$_2$CHF$_2$, —CH$_2$CF$_3$, —CHFCH$_3$, —CF$_2$CH$_3$, —CN, oxo, —NH$_2$, —NH(CH$_3$), —N(CH$_3$)$_2$, —NH(CH$_2$CH$_3$), —OH, —O—CH$_3$, —O—CH$_2$CH$_3$, —O—CH$_2$CH$_2$CH$_3$, —O—CH(CH$_3$)$_2$, —SH, —S—CH$_3$, —S—CH$_2$CH$_3$, —S—CH$_2$CH$_2$CH$_3$, —S—CH(CH$_3$)$_2$, —S(═O)CH$_3$, —S(═O)(CH$_2$CH$_3$), —S(═O)(CH$_2$CH$_2$CH$_3$), —S(═O)(CH(CH$_3$)$_2$), —S(═O)$_2$CH$_3$, —S(═O)$_2$(CH$_2$CH$_3$), —S(═O)$_2$(CH$_2$CH$_2$CH$_3$), —S(═O)$_2$(CH(CH$_3$)$_2$), —COOH, —C(═O)(CH$_3$), —C(═O)(CH$_2$CH$_3$), —C(═O)(CH(CH$_3$)$_2$), —C(═O)(CF$_3$), —C(═O)(OCH$_3$), —C(═O)(OCH$_2$CH$_3$), —C(═O)(OCH$_2$CH$_2$CH$_3$), —C(═O)(OCH(CH$_3$)$_2$), —OC(═O)(CH$_3$), —OC(═O)(CH$_2$CH$_3$), —OC(═O)(CH$_2$CH$_2$CH$_3$), —OC(═O)(CH(CH$_3$)$_2$), —C(═O)NH$_2$, —C(═O)NH(CH$_3$), —C(═O)NH(CH$_2$CH$_3$), —C(═O)NH(CH$_2$CH$_2$CH$_3$), —C(═O)NH(CH(CH$_3$)$_2$), —C(═O)N(CH$_3$)$_2$, —C(═O)N(CH$_2$CH$_3$)$_2$, —NHC(═O)(CH$_3$), —NHC(═O)(CH$_2$CH$_3$), —NHC(═O)(CH$_2$CH$_2$CH$_3$), —NHC(═O)(CH(CH$_3$)$_2$), —N(CH$_3$)C(═O)(CH$_3$), —S(═O)(OCH$_3$), —S(═O)(OCH$_2$CH$_3$), —S(═O)(OCH$_2$CH$_2$CH$_3$), —S(═O)(OCH(CH$_3$)$_2$), —OS(═O)(CH$_3$), —OS(═O)(CH$_2$CH$_3$), —OS(═O)(CH$_2$CH$_2$CH$_3$), —OS(═O)(CH(CH$_3$)$_2$), —S(═O)NH$_2$, —S(═O)NH(CH$_3$), —S(═O)NH(CH$_2$CH$_3$), —S(═O)NH(CH$_2$CH$_2$CH$_3$), —S(═O)NH(CH(CH$_3$)$_2$), —S(═O)N(CH$_3$)$_2$, —S(═O)N(CH$_3$)(CH$_2$CH$_3$), —NHS(═O)(CH$_3$), —NHS(═O)(CH$_2$CH$_3$), —NHS(═O)(CH$_2$CH$_2$CH$_3$), —NHS(═O)(CH(CH$_3$)$_2$), —N(CH$_3$)S(═O)(CH$_3$), —S(═O)$_2$(OCH$_3$), —S(═O)$_2$(OCH$_2$CH$_3$), —S(═O)$_2$(OCH$_2$CH$_2$CH$_3$), —S(═O)$_2$(OCH(CH$_3$)$_2$), —OS(═O)$_2$(CH$_3$), —OS(═O)$_2$(CH$_2$CH$_3$), —OS(═O)$_2$(CH$_2$CH$_2$CH$_3$), —OS(═O)$_2$(CH(CH$_3$)$_2$), —S(═O)$_2$NH$_2$, —S(═O)$_2$NH(CH$_3$), —S(═O)$_2$NH(CH$_2$CH$_3$), —S(═O)$_2$NH(CH$_2$CH$_2$CH$_3$), —S(═O)$_2$NH(CH(CH$_3$)$_2$), —S(═O)$_2$N(CH$_3$)$_2$, —S(═O)$_2$N(CH$_3$)(CH$_2$CH$_3$), —NHS(═O)$_2$(CH$_3$), —NHS(═O)$_2$(CH$_2$CH$_3$), —NHS(═O)$_2$(CH$_2$CH$_2$CH$_3$), —NHS(═O)$_2$(CH(CH$_3$)$_2$), —N(CH$_3$)S(═O)$_2$(CH$_3$), —P(═O)H(CH$_3$), —P(═O)H(CH$_2$CH$_3$), —P(═O)H(CH$_2$CH$_2$CH$_3$), —P(═O)H(CH(CH$_3$)$_2$), —P(═O)(CH$_3$)$_2$, —P(═O)(CH$_3$)(CH$_2$CH$_3$), —CH$_2$—OH, —CH$_2$CH$_2$—OH, —CH(CH$_3$)—OH, —CH$_2$—NH$_2$, —CH$_2$CH$_2$—NH$_2$, —CH(CH$_3$)—NH$_2$, —CH$_2$—CN, —CH$_2$CH$_2$—CN, —CH(CH$_3$)—CN,

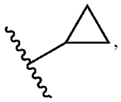, 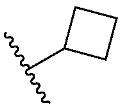, 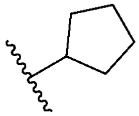, or

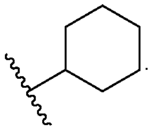.

[92]. The compound according to any one of [1] to [91], wherein,

R$_{16}$ or R$_{17}$ at each occurrence is independently selected from —H, -D, —Cl, —F, —Br, —CH$_3$, —CD$_3$, —CH$_2$CH$_3$, —CH(CH$_3$)$_2$, —C(CH$_3$)$_3$, —O—CF$_3$, —S—CF$_3$, —CF$_3$, —CN, oxo, —NH$_2$, —NH(CH$_3$), —N(CH$_3$)$_2$, —OH, —O—CH$_3$, —O—CH(CH$_3$)$_2$, —SH, —S—CH$_3$, —S—CH(CH$_3$)$_2$, —S(═O)CH$_3$, —S(═O)$_2$CH$_3$, —COOH, —C(═O)(CH$_3$), —C(═O)(CH$_2$CH$_3$), —C(═O)(CF$_3$), —C(═O)NH$_2$, —C(═O)NH(CH$_3$), —NHC(═O)(CH$_3$), —S(═O)NH$_2$, —S(═O)NH(CH$_3$), —NHS(═O)(CH$_3$), —S(═O)$_2$NH$_2$, —S(═O)$_2$NH(CH$_3$), —NHS(═O)$_2$(CH$_3$), —P(═O)H(CH$_3$), —P(═O)(CH$_3$)$_2$, —CH$_2$—OH, —CH$_2$CH$_2$—OH, —CH(CH$_3$)—OH, —CH$_2$—NH$_2$, —CH$_2$CH$_2$—NH$_2$, —CH(CH$_3$)—NH$_2$, —CH$_2$—CN, —CH$_2$CH$_2$—CN, —CH(CH$_3$)—CN, or

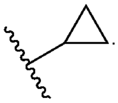 [SMILES: *C1CC1].

[93]. The compound according to any one of [1] to [92], wherein, the compound is selected from any one of the following compounds:

5-(((2S)-1-((1-(3-chloro-8-hydroxy-5-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;

5-(((2S)-1-((1-(3-chloro-8-hydroxy-4,5-dimethyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;

3-chloro-8-(2-oxo-3-((S)-2-((6-oxo-5-(trifluoromethyl)-1,6-dihydropyridazin-4-yl)oxy)propoxy)pyrrolidin-1-yl)-6,6a,7,8,9,10-hexahydrodipyrido[3,2-b:1',2'-d][1,4]oxazine-9-carbonitrile;

3-chloro-4-methyl-8-(2-oxo-3-((S)-2-((6-oxo-5-(trifluoromethyl)-1,6-dihydropyridazin-4-yl)oxy)propoxy)pyrrolidin-1-yl)-6,6a,7,8,9,10-hexahydrodipyrido[3,2-b:1',2'-d][1,4]oxazine-9-carbonitrile;

-continued 3-chloro-9-(2-oxo-3-((S)-2-((6-oxo-5-(trifluoromethyl)-1,6-dihydropyridazin-4-yl)oxy)propoxy)pyrrolidin-1-yl)-7,7a,8,9,10,11-hexahydro-6H-dipyrido[3,2-b:1',2'-d][1,4]oxazepine-10-carbonitrile;
3-chloro-4-methyl-9-(2-oxo-3-((S)-2-((6-oxo-5-(trifluoromethyl)-1,6-dihydropyridazin-4-yl)oxy)propoxy)pyrrolidin-1-yl)-7,7a,8,9,10,11-hexahydro-6H-dipyrido[3,2-b:1',2'-d][1,4]oxazepine-10-carbonitrile;
3-chloro-7-(2-oxo-3-((S)-2-((6-oxo-5-(trifluoromethyl)-1,6-dihydropyridazin-4-yl)oxy)propoxy)pyrrolidin-1-yl)-6,7,8,9-tetrahydropyrido[3,2-b]indolizine-8-carbonitrile;
3-chloro-4-methyl-7-(2-oxo-3-((S)-2-((6-oxo-5-(trifluoromethyl)-1,6-dihydropyridazin-4-yl)oxy)propoxy)pyrrolidin-1-yl)-6,7,8,9-tetrahydropyrido[3,2-b]indolizine-8-carbonitrile;
5-methyl-7-(2-oxo-3-((S)-2-((6-oxo-5-(trifluoromethyl)-1,6-dihydropyridazin-4-yl)oxy)propoxy)pyrrolidin-1-yl)-3-(trifluoromethyl)-6,7,8,9-tetrahydropyrido[3,2-b]indolizine-8-carbonitrile;
3-chloro-5-methyl-7-(2-oxo-3-((S)-2-((6-oxo-5-(trifluoromethyl)-1,6-dihydropyridazin-4-yl)oxy)propoxy)pyrrolidin-1-yl)-6,7,8,9-tetrahydropyrido[3,2-b]indolizine-8-carbonitrile;
(2S)-N-(1-(3-chloro-6,6a,7,8,9,10-hexahydrodipyrido[3,2-b:1',2'-d][1,4]oxazin-8-yl)-2-oxopyrrolidin-3-yl)-2-((6-oxo-5-(trifluoromethyl)-1,6-dihydropyridazin-4-yl)oxy)propanamide;
(2S)-N-(1-(3-chloro-4-methyl-6,6a,7,8,9,10-hexahydrodipyrido[3,2-b:1',2'-d][1,4]oxazin-8-yl)-2-oxopyrrolidin-3-yl)-2-((6-oxo-5-(trifluoromethyl)-1,6-dihydropyridazin-4-yl)oxy)propanamide;
(2S)-N-(1-(3-chloro-7,7a,8,9,10,11-hexahydro-6H-dipyrido[3,2-b:1',2'-d][1,4]oxazepin-9-yl)-2-oxopyrrolidin-3-yl)-2-((6-oxo-5-(trifluoromethyl)-1,6-dihydropyridazin-4-yl)oxy)propanamide;
(2S)-N-(1-(3-chloro-4-methyl-7,7a,8,9,10,11-hexahydro-6H-dipyrido[3,2-b:1',2'-d][1,4]oxazepin-9-yl)-2-oxopyrrolidin-3-yl)-2-((6-oxo-5-(trifluoromethyl)-1,6-dihydropyridazin-4-yl)oxy)propanamide;
(2S)-N-(1-(3-chloro-6,7,8,9-tetrahydropyrido[3,2-b]indolizin-7-yl)-2-oxopyrrolidin-3-yl)-2-((6-oxo-5-(trifluoromethyl)-1,6-dihydropyridazin-4-yl)oxy)propanamide;
(2S)-N-(1-(3-chloro-4-methyl-6,7,8,9-tetrahydropyrido[3,2-b]indolizin-7-yl)-2-oxopyrrolidin-3-yl)-2-((6-oxo-5-(trifluoromethyl)-1,6-dihydropyridazin-4-yl)oxy)propanamide;
(2S)-N-(1-(3-chloro-5-methyl-6,7,8,9-tetrahydropyrido[3,2-b]indolizin-7-yl)-2-oxopyrrolidin-3-yl)-2-((6-oxo-5-(trifluoromethyl)-1,6-dihydropyridazin-4-yl)oxy)propanamide;
(2S)-N-(1-(3-chloro-4,5-dimethyl-6,7,8,9-tetrahydropyrido[3,2-b]indolizin-7-yl)-2-oxopyrrolidin-3-yl)-2-((6-oxo-5-(trifluoromethyl)-1,6-dihydropyridazin-4-yl)oxy)propanamide;
5-(((2S)-1-((1-(3-chloro-6,6a,7,8,9,10-hexahydrodipyrido[3,2-b:1',2'-d][1,4]oxazin-8-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-4-methyl-6,6a,7,8,9,10-hexahydrodipyrido[3,2-b:1',2'-d][1,4]oxazin-8-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-7,7a,8,9,10,11-hexahydro-6H-dipyrido[3,2-b:1',2'-d][1,4]oxazepin-9-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-4-methyl-7,7a,8,9,10,11-hexahydro-6H-dipyrido[3,2-b:1',2'-d][1,4]oxazepin-9-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-6,7,8,9-tetrahydropyrido[3,2-b]indolizin-7-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-4-methyl-6,7,8,9-tetrahydropyrido[3,2-b]indolizin-7-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-5-methyl-6,7,8,9-tetrahydropyrido[3,2-b]indolizin-7-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-4,5-dimethyl-6,7,8,9-tetrahydropyrido[3,2-b]indolizin-7-yl)-2-oxopyrrolidin-3-yl)oxy)-3-methoxypropan-2-yl)oxy)-4-(trifluoromethyl)pyridazin-3(2H)-one;
5-(((2S)-1-((1-(3-chloro-4-methyl-7,7a,8,9,10,11-hexahydro-6H-dipyrido[3,2-b:1',2'-d][1,4]oxazepin-9-yl)-4,4-dimethyl-2-oxopyrrolidin-3-yl)oxy)propan-2-yl)oxy)-4-(trifluoromethyl)pyridazin-3(2H)-one;
5-(((2S)-1-((1-(3-chloro-6,6a,7,8,9,10-hexahydrodipyrido[3,2-b:1',2'-d][1,4]oxazin-8-yl)-4,4-dimethyl-2-oxopyrrolidin-3-yl)oxy)propan-2-yl)oxy)-4-(trifluoromethyl)pyridazin-3(2H)-one;
5-(((2S)-1-((1-(3-chloro-4-methyl-6,6a,7,8,9,10-hexahydrodipyrido[3,2-b:1',2'-d][1,4]oxazin-8-yl)-4,4-dimethyl-2-oxopyrrolidin-3-yl)oxy)propan-2-yl)oxy)-4-(trifluoromethyl)pyridazin-3(2H)-one;
5-(((2S)-1-((1-(3-chloro-6,7,8,9-tetrahydropyrido[3,2-b]indolizin-7-yl)-4,4-dimethyl-2-oxopyrrolidin-3-yl)oxy)propan-2-yl)oxy)-4-(trifluoromethyl)pyridazin-3(2H)-one;
5-(((2S)-1-((1-(3-chloro-4-methyl-6,7,8,9-tetrahydropyrido[3,2-b]indolizin-7-yl)-4,4-dimethyl-2-oxopyrrolidin-3-yl)oxy)propan-2-yl)oxy)-4-(trifluoromethyl)pyridazin-3(2H)-one;
5-(((2S)-1-((1-(3-chloro-5-methyl-6,7,8,9-tetrahydropyrido[3,2-b]indolizin-7-yl)-4,4-dimethyl-2-oxopyrrolidin-3-yl)oxy)propan-2-yl)oxy)-4-(trifluoromethyl)pyridazin-3(2H)-one;
5-(((2S)-1-((4,4-dimethyl-2-oxo-1-(3-(trifluoromethyl)-6,6a,7,8,9,10-hexahydrodipyrido[3,2-b:1',2'-d][1,4]oxazin-8-yl)pyrrolidin-3-yl)oxy)propan-2-yl)oxy)-4-(trifluoromethyl)pyridazin-3(2H)-one;
5-(((2S)-1-((4,4-dimethyl-2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)oxy)propan-2-yl)oxy)-4-(trifluoromethyl)pyridazin-3(2H)-one;
5-(((2S)-1-((1-(3-chloro-7,7a,8,9,10,11-hexahydro-6H-dipyrido[3,2-b:1',2'-d][1,4]oxazepin-9-yl)-4,4-dimethyl-2-oxopyrrolidin-3-yl)oxy)propan-2-yl)oxy)-4-(trifluoromethyl)pyridazin-3(2H)-one;
5-(((2S)-1-((4,4-dimethyl-2-oxo-1-(3-(trifluoromethyl)-6,7,8,9-tetrahydropyrido[3,2-b]indolizin-7-yl)pyrrolidin-3-yl)oxy)propan-2-yl)oxy)-4-(trifluoromethyl)pyridazin-3(2H)-one;
5-(((2S)-1-((4,4-dimethyl-1-(5-methyl-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-4,5-dimethyl-6,7,8,9-tetrahydropyrido[3,2-b]indolizin-7-yl)-4,4-dimethyl-2-oxopyrrolidin-3-yl)oxy)propan-2-yl)oxy)-4-(trifluoromethyl)pyridazin-3(2H)-one;
5-(((2S)-1-((1-(3-chloro-6,6a,7,8,9,10-hexahydrodipyrido[3,2-b:1',2'-d][1,4]oxazin-8-yl)-2-oxopiperidin-3-yl)oxy)propan-2-yl)oxy)-4-(trifluoromethyl)pyridazin-3(2H)-one;
5-(((2S)-1-((1-(3-chloro-4-methyl-6,6a,7,8,9,10-hexahydrodipyrido[3,2-b:1',2'-d][1,4]oxazin-8-yl)-2-oxopiperidin-3-yl)oxy)propan-2-yl)oxy)-4-(trifluoromethyl)pyridazin-3(2H)-one;
5-(((2S)-1-((1-(3-chloro-7,7a,8,9,10,11-hexahydro-6H-dipyrido[3,2-b:1',2'-d][1,4]oxazepin-9-yl)-2-oxopiperidin-3-yl)oxy)propan-2-yl)oxy)-4-(trifluoromethyl)pyridazin-3(2H)-one;
5-(((2S)-1-((1-(3-chloro-4-methyl-7,7a,8,9,10,11-hexahydro-6H-dipyrido[3,2-b:1',2'-d][1,4]oxazepin-9-yl)-2-oxopiperidin-3-yl)oxy)propan-2-yl)oxy)-4-(trifluoromethyl)pyridazin-3(2H)-one;
5-(((2S)-1-((1-(3-chloro-6,7,8,9-tetrahydropyrido[3,2-b]indolizin-7-yl)-2-oxopiperidin-3-yl)oxy)propan-2-yl)oxy)-4-(trifluoromethyl)pyridazin-3(2H)-one;

-continued 5-(((2S)-1-((1-(3-chloro-4-methyl-6,7,8,9-tetrahydropyrido[3,2-b]indolizin-7-yl)-2-oxopiperidin-3-yl)oxy) propan-2-yl)oxy)-4-(trifluoromethyl)pyridazin-3(2H)-one;
5-(((2S)-1-((1-(3-chloro-5-methyl-6,7,8,9-tetrahydropyrido[3,2-b]indolizin-7-yl)-2-oxopiperidin-3-yl)oxy) propan-2-yl)oxy)-4-(trifluoromethyl)pyridazin-3(2H)-one;
5-(((2S)-1-((1-(3-chloro-4,5-dimethyl-6,7,8,9-tetrahydropyrido[3,2-b]indolizin-7-yl)-2-oxopiperidin-3-yl) oxy)propan-2-yl)oxy)-4-(trifluoromethyl)pyridazin-3(2H)-one;
5-((1-((1-(3-chloro-6,6a,7,8,9,10-hexahydrodipyrido[3,2-b:1',2'-d][1,4]oxazin-8-yl)-2-oxopyrrolidin-3-yl) oxy)-3-hydroxybutan-2-yl)oxy)-4-(trifluoromethyl)pyridazin-3(2H)-one;
5-((1-((1-(3-chloro-4-methyl-6,6a,7,8,9,10-hexahydrodipyrido[3,2-b:1',2'-d][1,4]oxazin-8-yl)-2-oxopyrrolidin-3-yl)oxy)-3-hydroxybutan-2-yl)oxy)-4-(trifluoromethyl)pyridazin-3(2H)-one;
5-((1-((1-(3-chloro-7,7a,8,9,10,11-hexahydro-6H-dipyrido[3,2-b:1',2'-d][1,4]oxazepin-9-yl)-2-oxopyrrolidin-3-yl)oxy)-3-hydroxybutan-2-yl)oxy)-4-(trifluoromethyl)pyridazin-3(2H)-one;
5-((1-((1-(3-chloro-4-methyl-7,7a,8,9,10,11-hexahydro-6H-dipyrido[3,2-b:1',2'-d][1,4]oxazepin-9-yl)-2-oxopyrrolidin-3-yl)oxy)-3-hydroxybutan-2-yl)oxy)-4-(trifluoromethyl)pyridazin-3(2H)-one;
5-((1-((1-(3-chloro-6,7,8,9-tetrahydropyrido[3,2-b]indolizin-7-yl)-2-oxopyrrolidin-3-yl)oxy)-3-hydroxybutan-2-yl)oxy)-4-(trifluoromethyl)pyridazin-3(2H)-one;
5-((1-((1-(3-chloro-4-methyl-6,7,8,9-tetrahydropyrido[3,2-b]indolizin-7-yl)-2-oxopyrrolidin-3-yl)oxy)-3-hydroxybutan-2-yl)oxy)-4-(trifluoromethyl)pyridazin-3(2H)-one;
5-((1-((1-(3-chloro-5-methyl-6,7,8,9-tetrahydropyrido[3,2-b]indolizin-7-yl)-2-oxopyrrolidin-3-yl)oxy)-3-hydroxybutan-2-yl)oxy)-4-(trifluoromethyl)pyridazin-3(2H)-one;
5-((1-((1-(3-chloro-4,5-dimethyl-6,7,8,9-tetrahydropyrido[3,2-b]indolizin-7-yl)-2-oxopyrrolidin-3-yl)oxy)-3-hydroxybutan-2-yl)oxy)-4-(trifluoromethyl)pyridazin-3(2H)-one;
N-((2S)-3-((2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-6,6a,7,8,9,10-hexahydrodipyrido[3,2-b:l',2'-d][1,4]oxazin-8-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-4-methyl-6,6a,7,8,9,10-hexahydrodipyrido[3,2-b:1',2'-d][1,4]oxazin-8-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-7,7a,8,9,10,11-hexahydro-6H-dipyrido[3,2-b:1',2'-d][1,4]oxazepin-9-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-4-methyl-7,7a,8,9,10,11-hexahydro-6H-dipyrido[3,2-b:1',2'-d][1,4]oxazepin-9-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((2-oxo-1-(3-(trifluoromethyl)-6,7,8,9-tetrahydropyrido[3,2-b]indolizin-7-yl)pyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-6,7,8,9-tetrahydropyrido[3,2-b]indolizin-7-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-4-methyl-6,7,8,9-tetrahydropyrido[3,2-b]indolizin-7-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((1-(5-methyl-3-(trifluoromethyl)-6,7,8,9-tetrahydropyrido[3,2-b]indolizin-7-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-5-methyl-6,7,8,9-tetrahydropyrido[3,2-b]indolizin-7-yl)-2-oxopyrrolidin-3-yl)oxy)-2-((6-oxo-5-(trifluoromethyl)-1,6-dihydropyridazin-4-yl)oxy)propyl)acetamide;
N-((2S)-3-((1-(3-chloro-4,5-dimethyl-6,7,8,9-tetrahydropyrido[3,2-b]indolizin-7-yl)-2-oxopyrrolidin-3-yl) oxy)-2-((6-oxo-5-(trifluoromethyl)-1,6-dihydropyridazin-4-yl)oxy)propyl)acetamide;
4-(trifluoromethyl)-5-(((2S)-1-(3-(3-(trifluoromethyl)-6,7,8,9-tetrahydropyrido[3',2':4,5]pyrrolo[1,2-a]pyrazine-7-carbonyl)pyrrolidin-1-yl)propan-2-yl)oxy)pyridazin-3(2H)-one;
4-(trifluoromethyl)-5-(((2S)-1-(3-(3-(trifluoromethyl)-6,6a,7,8,9,10-hexahydropyrazino[1,2-d]pyrido[3,2-b][1,4]oxazine-8-carbonyl)phenoxy)propan-2-yl)oxy)pyridazin-3(2H)-one;
(S)-4-(trifluoromethyl)-5-((1-(3-(3-(trifluoromethyl)-6,7,8,9-tetrahydropyrido[3',2':4,5]pyrrolo[1,2-a]pyrazine-7-carbonyl)phenoxy)propan-2-yl)oxy)pyridazin-3(2H)-one;
(S)-5-((1-(3-(5-methyl-3-(trifluoromethyl)-6,7,8,9-tetrahydropyrido[3',2':4,5]pyrrolo[1,2-a]pyrazine-7-carbonyl)phenoxy)propan-2-yl)oxy)-4-(trifluoromethyl)pyridazin-3(2H)-one;
(S)-5-((1-(3-(3-chloro-4,5-dimethyl-6,7,8,9-tetrahydropyrido[3',2':4,5]pyrrolo[1,2-a]pyrazine-7-carbonyl) phenoxy)propan-2-yl)oxy)-4-(trifluoromethyl)pyridazin-3(2H)-one;
5-(((2S)-1-(3-(3-chloro-4,5-dimethyl-8,9-dihydropyrido[3',2':4,5]pyrrolo[1,2-a]pyrazin-7(6H)-yl)-2-methyl-3-oxopropoxy)propan-2-yl)oxy)-4-(trifluoromethyl)pyridazin-3(2H)-one;
5-(((2S)-1-(2-methyl-3-oxo-3-(3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
5-((1S)-1-(5-(2-(3-chloro-4,5-dimethyl-8,9-dihydropyrido[3',2':4,5]pyrrolo[1,2-a]pyrazin-7(6H)-yl)-2-oxoethyl)tetrahydrofuran-2-yl)ethoxy)-4-(trifluoromethyl)pyridazin-3(2H)-one;
5-((1S)-1-(5-(2-oxo-2-(3-(trifluoromethyl)-8,9-dihydropyrido[3',2':4,5]pyrrolo[1,2-a]pyrazin-7(6H)-yl)ethyl)tetrahydrofuran-2-yl)ethoxy)-4-(trifluoromethyl)pyridazin-3(2H)-one;
5-((1S)-1-(5-(2-oxo-2-(3-(trifluoromethyl)-6a,7,9,10-tetrahydropyrazino[1,2-d]pyrido[3,2-b][1,4]oxazin-8 (6H)-yl)ethyl)tetrahydrofuran-2-yl)ethoxy)-4-(trifluoromethyl)pyridazin-3(2H)-one;
5-((1S)-1-(5-(2-oxo-2-(3-(trifluoromethyl)-6,7,7a,8,10,11-hexahydro-9H-pyrazino[1,2-d]pyrido[3,2-b][1,4]oxazepin-9-yl)ethyl)tetrahydrofuran-2-yl)ethoxy)-4-(trifluoromethyl)pyridazin-3(2H)-one;
5-((1S)-1-(5-(2-(3-chloro-6,7,7a,8,10,11-hexahydro-9H-pyrazino[1,2-d]pyrido[3,2-b][1,4]oxazepin-9-yl)-2-oxoethyl)tetrahydrofuran-2-yl)ethoxy)-4-(trifluoromethyl)pyridazin-3(2H)-one;
(S)-5-((1-(2-((5-methyl-3-(trifluoromethyl)-8,9-dihydropyrido[3',2':4,5]pyrrolo[1,2-a]pyrazin-7(6H)-yl)sulfonyl)ethoxy)propan-2-yl)oxy)-4-(trifluoromethyl)pyridazin-3(2H)-one;
(S)-4-(trifluoromethyl)-5-((1-(2-((3-(trifluoromethyl)-8,9-dihydropyrido[3',2':4,5]pyrrolo[1,2-a]pyrazin-7(6H)-yl)sulfonyl)ethoxy)propan-2-yl)oxy)pyridazin-3(2H)-one;
4-(trifluoromethyl)-5-(((2S)-1-(2-((3-(trifluoromethyl)-6a,7,9,10-tetrahydropyrazino[1,2-d]pyrido[3,2-b][1,4]oxazin-8(6H)-yl)sulfonyl)ethoxy)propan-2-yl)oxy)pyridazin-3(2H)-one;
4-(trifluoromethyl)-5-(((2S)-1-(2-((3-(trifluoromethyl)-6,7,7a,8,10,11-hexahydro-9H-pyrazino[1,2-d]pyrido[3,2-b][1,4]oxazepin-9-yl)sulfonyl)ethoxy)propan-2-yl)oxy)pyridazin-3(2H)-one;
5-(((2S)-1-(2-((3-chloro-6,7,7a,8,10,11-hexahydro-9H-pyrazino[1,2-d]pyrido[3,2-b][1,4]oxazepin-9-yl)sulfonyl)ethoxy)propan-2-yl)oxy)-4-(trifluoromethyl)pyridazin-3(2H)-one;

-continued

N-(3-chloro-4,5-dimethyl-6,7,8,9-tetrahydropyrido[3,2-b]indolizin-7-yl)-3-((S)-2-((6-oxo-5-(trifluoromethyl)-1,6-dihydropyridazin-4-yl)oxy)propoxy)propanamide;
3-((S)-2-((6-oxo-5-(trifluoromethyl)-1,6-dihydropyridazin-4-yl)oxy)propoxy)-N-(3-(trifluoromethyl)-6,6a,7,8,9,10-hexahydrodipyrido[3,2-b:1',2'-d][1,4]oxazin-8-yl)propanamide;
3-((S)-2-((6-oxo-5-(trifluoromethyl)-1,6-dihydropyridazin-4-yl)oxy)propoxy)-N-(3-(trifluoromethyl)-6,7,8,9-tetrahydropyrido[3,2-b]indolizin-7-yl)propanamide;
3-((S)-2-((6-oxo-5-(trifluoromethyl)-1,6-dihydropyridazin-4-yl)oxy)propoxy)-N-(3-(trifluoromethyl)-7,7a,8,9,10,11-hexahydro-6H-dipyrido[3,2-b:1',2'-d][1,4]oxazepin-9-yl)propanamide;
N-(3-chloro-7,7a,8,9,10,11-hexahydro-6H-dipyrido[3,2-b:1',2'-d][1,4]oxazepin-9-yl)-3-((S)-2-((6-oxo-5-(trifluoromethyl)-1,6-dihydropyridazin-4-yl)oxy)propoxy)propanamide;
5-(((2S)-1-((2-oxo-1-(3-(trifluoromethyl)-6,6a,7,8,9,10-hexahydrodipyrido[3,2-b:1',2'-d][1,4]oxazin-8-yl)pyrrolidin-3-yl)oxy)propan-2-yl)oxy)-4-(trifluoromethyl)pyridazin-3(2H)-one;
5-(((2S)-1-((2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)oxy)propan-2-yl)oxy)-4-(trifluoromethyl)pyridazin-3(2H)-one;
5-(((2S)-1-((1-(3-chloro-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((2-oxo-1-(3-(trifluoromethyl)-6,7,8,9-tetrahydropyrido[3,2-b]indolizin-7-yl)pyrrolidin-3-yl)oxy)propan-2-yl)oxy)-4-(trifluoromethyl)pyridazin-3(2H)-one;
5-(((2S)-1-((1-(5-methyl-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-4,5-dimethyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(9-fluoro-3-(trifluoromethyl)-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(10-fluoro-3-(trifluoromethyl)-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(3-chloro-10-fluoro-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(8-fluoro-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(8-fluoro-5-methyl-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(9,9-difluoro-3-(trifluoromethyl)-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(3-chloro-10,10-difluoro-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(8,8-difluoro-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(8,8-difluoro-5-methyl-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(9-hydroxy-3-(trifluoromethyl)-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(10-hydroxy-3-(trifluoromethyl)-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(8-hydroxy-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(8-hydroxy-5-methyl-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
8-(2-oxo-3-((S)-2-((6-oxo-5-(trifluoromethyl)-1,6-dihydropyridazin-4-yl)oxy)propoxy)pyrrolidin-1-yl)-3-(trifluoromethyl)-6,6a,7,8,9,10-hexahydrodipyrido[3,2-b:1',2'-d][1,4]oxazine-9-carbonitrile;
9-(2-oxo-3-((S)-2-((6-oxo-5-(trifluoromethyl)-1,6-dihydropyridazin-4-yl)oxy)propoxy)pyrrolidin-1-yl)-3-(trifluoromethyl)-7,7a,8,9,10,11-hexahydro-6H-dipyrido[3,2-b:1',2'-d][1,4]oxazepine-10-carbonitrile;
7-(2-oxo-3-((S)-2-((6-oxo-5-(trifluoromethyl)-1,6-dihydropyridazin-4-yl)oxy)propoxy)pyrrolidin-1-yl)-3-(trifluoromethyl)-6,7,8,9-tetrahydropyrido[3,2-b]indolizine-8-carbonitrile;
3-chloro-4,5-dimethyl-7-(2-oxo-3-((S)-2-((6-oxo-5-(trifluoromethyl)-1,6-dihydropyridazin-4-yl)oxy)propoxy)pyrrolidin-1-yl)-6,7,8,9-tetrahydropyrido[3,2-b]indolizine-8-carbonitrile;
(2S)-N-(2-oxo-1-(3-(trifluoromethyl)-6,6a,7,8,9,10-hexahydrodipyrido[3,2-b:1',2'-d][1,4]oxazin-8-yl)pyrrolidin-3-yl)-2-((6-oxo-5-(trifluoromethyl)-1,6-dihydropyridazin-4-yl)oxy)propanamide;
(2S)-N-(2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)-2-((6-oxo-5-(trifluoromethyl)-1,6-dihydropyridazin-4-yl)oxy)propanamide;
(2S)-N-(2-oxo-1-(3-(trifluoromethyl)-6,7,8,9-tetrahydropyrido[3,2-b]indolizin-7-yl)pyrrolidin-3-yl)-2-((6-oxo-5-(trifluoromethyl)-1,6-dihydropyridazin-4-yl)oxy)propanamide;
(2S)-N-(1-(5-methyl-3-(trifluoromethyl)-6,7,8,9-tetrahydropyrido[3,2-b]indolizin-7-yl)-2-oxopyrrolidin-3-yl)-2-((6-oxo-5-(trifluoromethyl)-1,6-dihydropyridazin-4-yl)oxy)propanamide;
5-(((2S)-1-methoxy-3-((2-oxo-1-(3-(trifluoromethyl)-6,6a,7,8,9,10-hexahydrodipyrido[3,2-b:1',2'-d][1,4]oxazin-8-yl)pyrrolidin-3-yl)oxy)propan-2-yl)oxy)-4-(trifluoromethyl)pyridazin-3(2H)-one;
5-(((2S)-1-methoxy-3-((2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)oxy)propan-2-yl)oxy)-4-(trifluoromethyl)pyridazin-3(2H)-one;
5-(((2S)-1-methoxy-3-((2-oxo-1-(3-(trifluoromethyl)-6,7,8,9-tetrahydropyrido[3,2-b]indolizin-7-yl)pyrrolidin-3-yl)oxy)propan-2-yl)oxy)-4-(trifluoromethyl)pyridazin-3(2H)-one;
5-(((2S)-1-methoxy-3-((1-(5-methyl-3-(trifluoromethyl)-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
4-(trifluoromethyl)-5-(((2S)-1-(3-(3-(trifluoromethyl)-7,7a,8,9,10,11-hexahydro-6H-pyrazino[1,2-d]pyrido[3,2-b][1,4]oxazepine-9-carbonyl)pyrrolidin-1-yl)propan-2-yl)oxy)pyridazin-3(2H)-one;
5-(((2S)-1-((2-oxo-1-(3-(trifluoromethyl)-6,6a,7,8,9,10-hexahydrodipyrido[3,2-b:1',2'-d][1,4]oxazin-8-yl)piperidin-3-yl)oxy)propan-2-yl)oxy)-4-(trifluoromethyl)pyridazin-3(2H)-one;
5-(((2S)-1-((2-oxo-1-(3-(trifluoromethyl)-7,7a,8,9,10,11-hexahydro-6H-dipyrido[3,2-b:1',2'-d][1,4]oxazepin-9-yl)piperidin-3-yl)oxy)propan-2-yl)oxy)-4-(trifluoromethyl)pyridazin-3(2H)-one;

-continued 5-(((2S)-1-((2-oxo-1-(3-(trifluoromethyl)-6,7,8,9-tetrahydropyrido[3,2-b]indolizin-7-yl)piperidin-3-yl)oxy)propan-2-yl)oxy)-4-(trifluoromethyl)pyridazin-3(2H)-one;
5-(((2S)-1-((1-(5-methyl-3-(trifluoromethyl)-6,7,8,9-tetrahydropyrido[3,2-b]indolizin-7-yl)-2-oxopiperidin-3-yl)oxy)propan-2-yl)oxy)-4-(trifluoromethyl)pyridazin-3(2H)-one;
5-((3-hydroxy-1-((2-oxo-1-(3-(trifluoromethyl)-6,6a,7,8,9,10-hexahydrodipyrido[3,2-b:1',2'-d][1,4]oxazin-8-yl)pyrrolidin-3-yl)oxy)butan-2-yl)oxy)-4-(trifluoromethyl)pyridazin-3(2H)-one;
5-((3-hydroxy-1-((2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)oxy)butan-2-yl)oxy)-4-(trifluoromethyl)pyridazin-3(2H)-one;
5-((3-hydroxy-1-((2-oxo-1-(3-(trifluoromethyl)-6,7,8,9-tetrahydropyrido[3,2-b]indolizin-7-yl)pyrrolidin-3-yl)oxy)butan-2-yl)oxy)-4-(trifluoromethyl)pyridazin-3(2H)-one;
5-((3-hydroxy-1-((1-(5-methyl-3-(trifluoromethyl)-6,7,8,9-tetrahydropyrido[3,2-b]indolizin-7-yl)-2-oxopyrrolidin-3-yl)oxy)butan-2-yl)oxy)-4-(trifluoromethyl)pyridazin-3(2H)-one;
4-(trifluoromethyl)-5-(((2S)-1-(3-(3-(trifluoromethyl)-7,7a,8,9,10,11-hexahydro-6H-pyrazino[1,2-d]pyrido[3,2-b][1,4]oxazepine-9-carbonyl)phenoxy)propan-2-yl)oxy)pyridazin-3(2H)-one;
5-(((2S)-1-(3-(3-chloro-7,7a,8,9,10,11-hexahydro-6H-pyrazino[1,2-d]pyrido[3,2-b][1,4]oxazepine-9-carbonyl)phenoxy)propan-2-yl)oxy)-4-(trifluoromethyl)pyridazin-3(2H)-one;
5-(((2S)-1-(3-(3-chloro-4-methyl-7,7a,8,9,10,11-hexahydro-6H-pyrazino[1,2-d]pyrido[3,2-b][1,4]oxazepine-9-carbonyl)phenoxy)propan-2-yl)oxy)-4-(trifluoromethyl)pyridazin-3(2H)-one;
(S)-5-((1-(3-(3-chloro-4-methyl-6,7,8,9-tetrahydropyrido[3',2':4,5]pyrrolo[1,2-a]pyrazine-7-carbonyl)phenoxy)propan-2-yl)oxy)-4-(trifluoromethyl)pyridazin-3(2H)-one;
(S)-5-((1-(3-(3-chloro-5-methyl-6,7,8,9-tetrahydropyrido[3',2':4,5]pyrrolo[1,2-a]pyrazine-7-carbonyl)phenoxy)propan-2-yl)oxy)-4-(trifluoromethyl)pyridazin-3(2H)-one;
N-((2S)-3-((2-oxo-1-(3-(trifluoromethyl)-6,6a,7,8,9,10-hexahydrodipyrido[3,2-b:1',2'-d][1,4]oxazin-8-yl)pyrrolidin-3-yl)oxy)-2-((6-oxo-5-(trifluoromethyl)-1,6-dihydropyridazin-4-yl)oxy)propyl)acetamide;
5-(((2S)-1-(2-methyl-3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((2S)-1-(2-methyl-3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)-4-(trifluoromethyl)pyridazin-3(2H)-one;
4-(trifluoromethyl)-5-(((2S)-1-(3-(3-(trifluoromethyl)-6,6a,7,8,9,10-hexahydropyrazino[1,2-d]pyrido[3,2-b][1,4]oxazine-8-carbonyl)pyrrolidin-1-yl)propan-2-yl)oxy)pyridazin-3(2H)-one;
5-(((2S)-1-(3-(3-chloro-5-methyl-6,7,8,9-tetrahydropyrido[3',2':4,5]pyrrolo[1,2-a]pyrazine-7-carbonyl)pyrrolidin-1-yl)propan-2-yl)oxy)-4-(trifluoromethyl)pyridazin-3(2H)-one;
5-(((2S)-1-(3-(3-chloro-4-methyl-6,7,8,9-tetrahydropyrido[3',2':4,5]pyrrolo[1,2-a]pyrazine-7-carbonyl)pyrrolidin-1-yl)propan-2-yl)oxy)-4-(trifluoromethyl)pyridazin-3(2H)-one;
5-(((2S)-1-(3-(3-chloro-4,5-dimethyl-6,7,8,9-tetrahydropyrido[3',2':4,5]pyrrolo[1,2-a]pyrazine-7-carbonyl)pyrrolidin-1-yl)propan-2-yl)oxy)-4-(trifluoromethyl)pyridazin-3(2H)-one;
5-(((2S)-1-(3-(3-chloro-6,6a,7,8,9,10-hexahydropyrazino[1,2-d]pyrido[3,2-b][1,4]oxazine-8-carbonyl)pyrrolidin-1-yl)propan-2-yl)oxy)-4-(trifluoromethyl)pyridazin-3(2H)-one;
5-(((2S)-1-(3-(3-chloro-7,7a,8,9,10,11-hexahydro-6H-pyrazino[1,2-d]pyrido[3,2-b][1,4]oxazepine-9-carbonyl)pyrrolidin-1-yl)propan-2-yl)oxy)-4-(trifluoromethyl)pyridazin-3(2H)-one;
5-(((2S)-1-(3-(3-chloro-6,7,8,9-tetrahydropyrido[3',2':4,5]pyrrolo[1,2-a]pyrazine-7-carbonyl)pyrrolidin-1-yl)propan-2-yl)oxy)-4-(trifluoromethyl)pyridazin-3(2H)-one;
5-(((2S)-1-(3-(3-chloro-4-methyl-6,6a,7,8,9,10-hexahydropyrazino[1,2-d]pyrido[3,2-b][1,4]oxazine-8-carbonyl)pyrrolidin-1-yl)propan-2-yl)oxy)-4-(trifluoromethyl)pyridazin-3(2H)-one;
5-(((2S)-1-(3-(3-chloro-4-methyl-7,7a,8,9,10,11-hexahydro-6H-pyrazino[1,2-d]pyrido[3,2-b][1,4]oxazepine-9-carbonyl)pyrrolidin-1-yl)propan-2-yl)oxy)-4-(trifluoromethyl)pyridazin-3(2H)-one;
5-(((2S)-1-(3-(5-methyl-3-(trifluoromethyl)-6,7,8,9-tetrahydropyrido[3',2':4,5]pyrrolo[1,2-a]pyrazine-7-carbonyl)pyrrolidin-1-yl)propan-2-yl)oxy)-4-(trifluoromethyl)pyridazin-3(2H)-one;
5-(((2S)-1-(3-(3-chloro-6,6a,7,8,9,10-hexahydropyrazino[1,2-d]pyrido[3,2-b][1,4]oxazine-8-carbonyl)phenoxy)propan-2-yl)oxy)-4-(trifluoromethyl)pyridazin-3(2H)-one;
5-(((2S)-1-(3-(3-chloro-4-methyl-6,6a,7,8,9,10-hexahydropyrazino[1,2-d]pyrido[3,2-b][1,4]oxazine-8-carbonyl)phenoxy)propan-2-yl)oxy)-4-(trifluoromethyl)pyridazin-3(2H)-one;
(S)-5-((1-methoxy-3-(3-oxo-3-(3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)-3-methoxypropan-2-yl)oxy)-4-(trifluoromethyl)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)-3-methoxypropan-2-yl)oxy)-4-(trifluoromethyl)pyridazin-3(2H)-one;
(S)-5-((1-methoxy-3-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-methoxy-3-(3-(5-(methyl-d3)-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-ethyl-3-(trifluoromethyl)-8,9-dihydropyrido[3',2':4,5]pyrrolo[1,2-a]pyrazin-7(6H)-yl)-3-oxopropoxy)-3-methoxypropan-2-yl)oxy)-4-(trifluoromethyl)pyridazin-3(2H)-one;
(S)-7-(3-(3-methoxy-2-((6-oxo-5-(trifluoromethyl)-1,6-dihydropyridazin-4-yl)oxy)propoxy)propanoyl)-3-(trifluoromethyl)-6,7,8,9-tetrahydropyrido[3',2':4,5]pyrrolo[1,2-a]pyrazine-5-carbonitrile;
(S)-5-((1-methoxy-3-(3-oxo-3-(3-(trifluoromethyl)-8,9-dihydropyrido[3',2':4,5]imidazo[1,2-a]pyrazin-7(6H)-yl)propoxy)propan-2-yl)oxy)-4-(trifluoromethyl)pyridazin-3(2H)-one;
5-(((2S)-1-methoxy-3-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-(((2S)-1-methoxy-3-(3-(5-methyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-methoxy-3-(3-(5-(methyl-d3)-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-ethyl-3-(trifluoromethyl)-5a,6,8,9-tetrahydropyrido[3',2':4,5]imidazo[1,2-a]pyrazin-7(5H)-yl)-3-oxopropoxy)-3-methoxypropan-2-yl)oxy)-4-(trifluoromethyl)pyridazin-3(2H)-one;
5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)-4-(trifluoromethyl)pyridazin-3(2H)-one;

-continued 5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-(methyl-d3)-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-ethyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
7-(3-((1-(6-oxo-5-(trifluoromethyl)-1,6-dihydropyridazin-4-yl)azetidin-2-yl)methoxy)propanoyl)-3-(trifluoromethyl)-6,7,8,9-tetrahydropyrido[3',2':4,5]pyrrolo[1,2-a]pyrazine-5-carbonitrile;
5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)-4-(trifluoromethyl)pyridazin-3(2H)-one;
5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)-4-(trifluoromethyl)pyridazin-3(2H)-one;
5-(2-((3-(5-methyl-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(5-(methyl-d3)-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(5-ethyl-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(3-chloro-6,7,8,9-tetrahydropyrido[3',2':4,5]pyrrolo[1,2-a]pyrazine-7-carbonyl)phenoxy)methyl)azetidin-1-yl)-4-(trifluoromethyl)pyridazin-3(2H)-one;
5-(3-(2-methyl-3-(5-methyl-3-(trifluoromethyl)-8,9-dihydropyrido[3',2':4,5]pyrrolo[1,2-a]pyrazin-7(6H)-yl)-3-oxopropoxy)propyl)-4-(trifluoromethyl)pyridazin-3(2H)-one;
5-(2-((3-(3-chloro-6a,7,9,10-tetrahydropyrazino[1,2-d]pyrido[3,2-b][1,4]oxazin-8(6H)-yl)-2-methyl-3-oxopropoxy)methyl)azetidin-1-yl)-4-(trifluoromethyl)pyridazin-3(2H)-one;
5-(2-((3-(3-chloro-4-methyl-6a,7,9,10-tetrahydropyrazino[1,2-d]pyrido[3,2-b][1,4]oxazin-8(6H)-yl)-2-methyl-3-oxopropoxy)methyl)azetidin-1-yl)-4-(trifluoromethyl)pyridazin-3(2H)-one;
5-(2-((3-(3-chloro-6,7,7a,8,10,11-hexahydro-9H-pyrazino[1,2-d]pyrido[3,2-b][1,4]oxazepin-9-yl)-2-methyl-3-oxopropoxy)methyl)azetidin-1-yl)-4-(trifluoromethyl)pyridazin-3(2H)-one;
5-(2-((3-(3-chloro-4-methyl-6,7,7a,8,10,11-hexahydro-9H-pyrazino[1,2-d]pyrido[3,2-b][1,4]oxazepin-9-yl)-2-methyl-3-oxopropoxy)methyl)azetidin-1-yl)-4-(trifluoromethyl)pyridazin-3(2H)-one;
5-(3-(3-(3-chloro-8,9-dihydropyrido[3',2':4,5]pyrrolo[1,2-a]pyrazin-7(6H)-yl)-2-methyl-3-oxopropoxy)propyl)-4-(trifluoromethyl)pyridazin-3(2H)-one;
5-(3-(3-(3-chloro-4-methyl-8,9-dihydropyrido[3',2':4,5]pyrrolo[1,2-a]pyrazin-7(6H)-yl)-2-methyl-3-oxopropoxy)propyl)-4-(trifluoromethyl)pyridazin-3(2H)-one;
5-(3-(3-(3-chloro-5-methyl-8,9-dihydropyrido[3',2':4,5]pyrrolo[1,2-a]pyrazin-7(6H)-yl)-2-methyl-3-oxopropoxy)propyl)-4-(trifluoromethyl)pyridazin-3(2H)-one;
5-(2-(5-(2-(5-methyl-3-(trifluoromethyl)-8,9-dihydropyrido[3',2':4,5]pyrrolo[1,2-a]pyrazin-7(6H)-yl)-2-oxoethyl)tetrahydrofuran-2-yl)azetidin-1-yl)-4-(trifluoromethyl)pyridazin-3(2H)-one;
5-(2-(5-(2-(3-chloro-5-methyl-8,9-dihydropyrido[3',2':4,5]pyrrolo[1,2-a]pyrazin-7(6H)-yl)-2-oxoethyl)tetrahydrofuran-2-yl)azetidin-1-yl)-4-(trifluoromethyl)pyridazin-3(2H)-one;
5-(2-(5-(2-(3-chloro-4-methyl-6,7,7a,8,10,11-hexahydro-9H-pyrazino[1,2-d]pyrido[3,2-b][1,4]oxazepin-9-yl)-2-oxoethyl)tetrahydrofuran-2-yl)azetidin-1-yl)-4-(trifluoromethyl)pyridazin-3(2H)-one;
5-(2-(5-(2-(3-chloro-6a,7,9,10-tetrahydropyrazino[1,2-d]pyrido[3,2-b][1,4]oxazin-8(6H)-yl)-2-oxoethyl)tetrahydrofuran-2-yl)azetidin-1-yl)-4-(trifluoromethyl)pyridazin-3(2H)-one;
5-(2-(5-(2-(3-chloro-4-methyl-6a,7,9,10-tetrahydropyrazino[1,2-d]pyrido[3,2-b][1,4]oxazin-8(6H)-yl)-2-oxoethyl)tetrahydrofuran-2-yl)azetidin-1-yl)-4-(trifluoromethyl)pyridazin-3(2H)-one;
5-(2-(5-(2-(3-chloro-8,9-dihydropyrido[3',2':4,5]pyrrolo[1,2-a]pyrazin-7(6H)-yl)-2-oxoethyl)tetrahydrofuran-2-yl)azetidin-1-yl)-4-(trifluoromethyl)pyridazin-3(2H)-one;
5-(2-(5-(2-(3-chloro-4-methyl-8,9-dihydropyrido[3',2':4,5]pyrrolo[1,2-a]pyrazin-7(6H)-yl)-2-oxoethyl)tetrahydrofuran-2-yl)azetidin-1-yl)-4-(trifluoromethyl)pyridazin-3(2H)-one;
5-(2-((2-((3-chloro-6a,7,9,10-tetrahydropyrazino[1,2-d]pyrido[3,2-b][1,4]oxazin-8(6H)-yl)sulfonyl)ethoxy)methyl)azetidin-1-yl)-4-(trifluoromethyl)pyridazin-3(2H)-one;
5-(2-((2-((3-chloro-4-methyl-6a,7,9,10-tetrahydropyrazino[1,2-d]pyrido[3,2-b][1,4]oxazin-8(6H)-yl)sulfonyl)ethoxy)methyl)azetidin-1-yl)-4-(trifluoromethyl)pyridazin-3(2H)-one;
5-(2-((2-((3-chloro-8,9-dihydropyrido[3',2':4,5]pyrrolo[1,2-a]pyrazin-7(6H)-yl)sulfonyl)ethoxy)methyl)azetidin-1-yl)-4-(trifluoromethyl)pyridazin-3(2H)-one;
5-(2-((2-((3-chloro-4-methyl-8,9-dihydropyrido[3',2':4,5]pyrrolo[1,2-a]pyrazin-7(6H)-yl)sulfonyl)ethoxy)methyl)azetidin-1-yl)-4-(trifluoromethyl)pyridazin-3(2H)-one;
5-(2-((2-((3-chloro-4-methyl-6,7,7a,8,10,11-hexahydro-9H-pyrazino[1,2-d]pyrido[3,2-b][1,4]oxazepin-9-yl)sulfonyl)ethoxy)methyl)azetidin-1-yl)-4-(trifluoromethyl)pyridazin-3(2H)-one;
5-(2-((2-((3-chloro-5-methyl-8,9-dihydropyrido[3',2':4,5]pyrrolo[1,2-a]pyrazin-7(6H)-yl)sulfonyl)ethoxy)methyl)azetidin-1-yl)-4-(trifluoromethyl)pyridazin-3(2H)-one;
5-(2-((2-((3-chloro-4,5-dimethyl-8,9-dihydropyrido[3',2':4,5]pyrrolo[1,2-a]pyrazin-7(6H)-yl)sulfonyl)ethoxy)methyl)azetidin-1-yl)-4-(trifluoromethyl)pyridazin-3(2H)-one;
N-(5-methyl-3-(trifluoromethyl)-6,7,8,9-tetrahydropyrido[3,2-b]indolizin-7-yl)-3-((1-(6-oxo-5-(trifluoromethyl)-1,6-dihydropyridazin-4-yl)azetidin-2-yl)methoxy)propanamide;
N-(3-chloro-5-methyl-6,7,8,9-tetrahydropyrido[3,2-b]indolizin-7-yl)-3-((1-(6-oxo-5-(trifluoromethyl)-1,6-dihydropyridazin-4-yl)azetidin-2-yl)methoxy)propanamide;
N-(3-chloro-4-methyl-7,7a,8,9,10,11-hexahydro-6H-dipyrido[3,2-b:1',2'-d][1,4]oxazepin-9-yl)-3-((1-(6-oxo-5-(trifluoromethyl)-1,6-dihydropyridazin-4-yl)azetidin-2-yl)methoxy)propanamide;
N-(3-chloro-6,6a,7,8,9,10-hexahydrodipyrido[3,2-b:1',2'-d][1,4]oxazin-8-yl)-3-((1-(6-oxo-5-(trifluoromethyl)-1,6-dihydropyridazin-4-yl)azetidin-2-yl)methoxy)propanamide;
N-(3-chloro-4-methyl-6,6a,7,8,9,10-hexahydrodipyrido[3,2-b:1',2'-d][1,4]oxazin-8-yl)-3-((1-(6-oxo-5-(trifluoromethyl)-1,6-dihydropyridazin-4-yl)azetidin-2-yl)methoxy)propanamide;

-continued

N-(3-chloro-6,7,8,9-tetrahydropyrido[3,2-b]indolizin-7-yl)-3-((1-(6-oxo-5-(trifluoromethyl)-1,6-dihydropyridazin-4-yl)azetidin-2-yl)methoxy)propanamide;
N-(3-chloro-4-methyl-6,7,8,9-tetrahydropyrido[3,2-b]indolizin-7-yl)-3-((1-(6-oxo-5-(trifluoromethyl)-1,6-dihydropyridazin-4-yl)azetidin-2-yl)methoxy)propanamide;
N-methyl-N-(5-methyl-3-(trifluoromethyl)-6,7,8,9-tetrahydropyrido[3,2-b]indolizin-7-yl)-3-((1-(6-oxo-5-(trifluoromethyl)-1,6-dihydropyridazin-4-yl)azetidin-2-yl)methoxy)propanamide;
N-(3-chloro-5-methyl-6,7,8,9-tetrahydropyrido[3,2-b]indolizin-7-yl)-N-methyl-3-((1-(6-oxo-5-(trifluoromethyl)-1,6-dihydropyridazin-4-yl)azetidin-2-yl)methoxy)propanamide;
N-(3-chloro-4-methyl-7,7a,8,9,10,11-hexahydro-6H-dipyrido[3,2-b:1',2'-d][1,4]oxazepin-9-yl)-N-methyl-3-((1-(6-oxo-5-(trifluoromethyl)-1,6-dihydropyridazin-4-yl)azetidin-2-yl)methoxy)propanamide;
N-(3-chloro-6,6a,7,8,9,10-hexahydrodipyrido[3,2-b:1',2'-d][1,4]oxazin-8-yl)-N-methyl-3-((1-(6-oxo-5-(trifluoromethyl)-1,6-dihydropyridazin-4-yl)azetidin-2-yl)methoxy)propanamide;
N-(3-chloro-4-methyl-6,6a,7,8,9,10-hexahydrodipyrido[3,2-b:1',2'-d][1,4]oxazin-8-yl)-N-methyl-3-((1-(6-oxo-5-(trifluoromethyl)-1,6-dihydropyridazin-4-yl)azetidin-2-yl)methoxy)propanamide;
N-(3-chloro-6,7,8,9-tetrahydropyrido[3,2-b]indolizin-7-yl)-N-methyl-3-((1-(6-oxo-5-(trifluoromethyl)-1,6-dihydropyridazin-4-yl)azetidin-2-yl)methoxy)propanamide;
N-(3-chloro-4-methyl-6,7,8,9-tetrahydropyrido[3,2-b]indolizin-7-yl)-N-methyl-3-((1-(6-oxo-5-(trifluoromethyl)-1,6-dihydropyridazin-4-yl)azetidin-2-yl)methoxy)propanamide;
N-(3-chloro-4,5-dimethyl-6,7,8,9-tetrahydropyrido[3,2-b]indolizin-7-yl)-N-methyl-3-((1-(6-oxo-5-(trifluoromethyl)-1,6-dihydropyridazin-4-yl)azetidin-2-yl)methoxy)propanamide;
N-methyl-3-((1-(6-oxo-5-(trifluoromethyl)-1,6-dihydropyridazin-4-yl)azetidin-2-yl)methoxy)-N-(3-(trifluoromethyl)-6,6a,7,8,9,10-hexahydrodipyrido[3,2-b:1',2'-d][1,4]oxazin-8-yl)propanamide;
N-methyl-3-((1-(6-oxo-5-(trifluoromethyl)-1,6-dihydropyridazin-4-yl)azetidin-2-yl)methoxy)-N-(3-(trifluoromethyl)-6,7,8,9-tetrahydropyrido[3,2-b]indolizin-7-yl)propanamide;
N-methyl-3-((1-(6-oxo-5-(trifluoromethyl)-1,6-dihydropyridazin-4-yl)azetidin-2-yl)methoxy)-N-(3-(trifluoromethyl)-7,7a,8,9,10,11-hexahydro-6H-dipyrido[3,2-b:1',2'-d][1,4]oxazepin-9-yl)propanamide;
N-(3-chloro-7,7a,8,9,10,11-hexahydro-6H-dipyrido[3,2-b:1',2'-d][1,4]oxazepin-9-yl)-N-methyl-3-((1-(6-oxo-5-(trifluoromethyl)-1,6-dihydropyridazin-4-yl)azetidin-2-yl)methoxy)propanamide;
5-(2-(((1-(3-chloro-4-methyl-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(3-chloro-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-4-methyl-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-4-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-5-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-9-fluoro-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-9-fluoro-4-methyl-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-10-fluoro-4-methyl-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(3-chloro-8-fluoro-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8-fluoro-4-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8-fluoro-5-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8-fluoro-4,5-dimethyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-9,9-difluoro-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-9,9-difluoro-4-methyl-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(10,10-difluoro-3-(trifluoromethyl)-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(3-chloro-10,10-difluoro-4-methyl-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(3-chloro-8,8-difluoro-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8,8-difluoro-4-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8,8-difluoro-5-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8,8-difluoro-4,5-dimethyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-9-hydroxy-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-9-hydroxy-4-methyl-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-10-hydroxy-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(3-chloro-10-hydroxy-4-methyl-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;

-continued 5-(2-(((1-(3-chloro-8-hydroxy-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8-hydroxy-4-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8-hydroxy-5-methyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-8-hydroxy-4,5-dimethyl-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
3-chloro-8-(2-oxo-3-((1-(6-oxo-5-(trifluoromethyl)-1,6-dihydropyridazin-4-yl)azetidin-2-yl)methoxy)pyrrolidin-1-yl)-6,6a,7,8,9,10-hexahydrodipyrido[3,2-b:1',2'-d][1,4]oxazine-9-carbonitrile;
3-chloro-4-methyl-8-(2-oxo-3-((1-(6-oxo-5-(trifluoromethyl)-1,6-dihydropyridazin-4-yl)azetidin-2-yl)methoxy)pyrrolidin-1-yl)-6,6a,7,8,9,10-hexahydrodipyrido[3,2-b:1',2'-d][1,4]oxazine-9-carbonitrile;
3-chloro-9-(2-oxo-3-((1-(6-oxo-5-(trifluoromethyl)-1,6-dihydropyridazin-4-yl)azetidin-2-yl)methoxy)pyrrolidin-1-yl)-7,7a,8,9,10,11-hexahydro-6H-dipyrido[3,2-b:1',2'-d][1,4]oxazepine-10-carbonitrile;
3-chloro-4-methyl-9-(2-oxo-3-((1-(6-oxo-5-(trifluoromethyl)-1,6-dihydropyridazin-4-yl)azetidin-2-yl)methoxy)pyrrolidin-1-yl)-7,7a,8,9,10,11-hexahydro-6H-dipyrido[3,2-b: 1',2'-d][1,4]oxazepine-10-carbonitrile;
3-chloro-7-(2-oxo-3-((1-(6-oxo-5-(trifluoromethyl)-1,6-dihydropyridazin-4-yl)azetidin-2-yl)methoxy)pyrrolidin-1-yl)-6,7,8,9-tetrahydropyrido[3,2-b]indolizine-8-carbonitrile;
3-chloro-4-methyl-7-(2-oxo-3-((1-(6-oxo-5-(trifluoromethyl)-1,6-dihydropyridazin-4-yl)azetidin-2-yl)methoxy)pyrrolidin-1-yl)-6,7,8,9-tetrahydropyrido[3,2-b]indolizine-8-carbonitrile;
5-methyl-7-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-6,7,8,9-tetrahydropyrido[3,2-b]indolizine-8-carbonitrile;
3-chloro-5-methyl-7-(2-oxo-3-((1-(6-oxo-5-(trifluoromethyl)-1,6-dihydropyridazin-4-yl)azetidin-2-yl)methoxy)pyrrolidin-1-yl)-6,7,8,9-tetrahydropyrido[3,2-b]indolizine-8-carbonitrile;
N-(1-(3-chloro-6,6a,7,8,9,10-hexahydrodipyrido[3,2-b:1',2'-d][1,4]oxazin-8-yl)-2-oxopyrrolidin-3-yl)-1-(6-oxo-5-(trifluoromethyl)-1,6-dihydropyridazin-4-yl)azetidine-2-carboxamide;
N-(1-(3-chloro-4-methyl-6,6a,7,8,9,10-hexahydrodipyrido[3,2-b:1',2'-d][1,4]oxazin-8-yl)-2-oxopyrrolidin-3-yl)-1-(6-oxo-5-(trifluoromethyl)-1,6-dihydropyridazin-4-yl)azetidine-2-carboxamide;
N-(1-(3-chloro-7,7a,8,9,10,11-hexahydro-6H-dipyrido[3,2-b:1',2'-d][1,4]oxazepin-9-yl)-2-oxopyrrolidin-3-yl)-1-(6-oxo-5-(trifluoromethyl)-1,6-dihydropyridazin-4-yl)azetidine-2-carboxamide;
N-(1-(3-chloro-4-methyl-7,7a,8,9,10,11-hexahydro-6H-dipyrido[3,2-b:1',2'-d][1,4]oxazepin-9-yl)-2-oxopyrrolidin-3-yl)-1-(6-oxo-5-(trifluoromethyl)-1,6-dihydropyridazin-4-yl)azetidine-2-carboxamide;
N-(1-(3-chloro-6,7,8,9-tetrahydropyrido[3,2-b]indolizin-7-yl)-2-oxopyrrolidin-3-yl)-1-(6-oxo-5-(trifluoromethyl)-1,6-dihydropyridazin-4-yl)azetidine-2-carboxamide;
N-(1-(3-chloro-4-methyl-6,7,8,9-tetrahydropyrido[3,2-b]indolizin-7-yl)-2-oxopyrrolidin-3-yl)-1-(6-oxo-5-(trifluoromethyl)-1,6-dihydropyridazin-4-yl)azetidine-2-carboxamide;
N-(1-(3-chloro-5-methyl-6,7,8,9-tetrahydropyrido[3,2-b]indolizin-7-yl)-2-oxopyrrolidin-3-yl)-1-(6-oxo-5-(trifluoromethyl)-1,6-dihydropyridazin-4-yl)azetidine-2-carboxamide;
N-(1-(3-chloro-4,5-dimethyl-6,7,8,9-tetrahydropyrido[3,2-b]indolizin-7-yl)-2-oxopyrrolidin-3-yl)-1-(6-oxo-5-(trifluoromethyl)-1,6-dihydropyridazin-4-yl)azetidine-2-carboxamide;
5-(2-(((1-(3-chloro-4-methyl-7,7a,8,9,10,11-hexahydro-6H-dipyrido[3,2-b:1',2'-d][1,4]oxazepin-9-yl)-4,4-dimethyl-2-oxopyrrolidin-3-yl)oxy)methyl)azetidin-1-yl)-4-(trifluoromethyl)pyridazin-3(2H)-one;
5-(2-(((1-(3-chloro-6,6a,7,8,9,10-hexahydrodipyrido[3,2-b:1',2'-d][1,4]oxazin-8-yl)-4,4-dimethyl-2-oxopyrrolidin-3-yl)oxy)methyl)azetidin-1-yl)-4-(trifluoromethyl)pyridazin-3(2H)-one;
5-(2-(((1-(3-chloro-4-methyl-6,6a,7,8,9,10-hexahydrodipyrido[3,2-b:1',2'-d][1,4]oxazin-8-yl)-4,4-dimethyl-2-oxopyrrolidin-3-yl)oxy)methyl)azetidin-1-yl)-4-(trifluoromethyl)pyridazin-3(2H)-one;
5-(2-(((1-(3-chloro-6,7,8,9-tetrahydropyrido[3,2-b]indolizin-7-yl)-4,4-dimethyl-2-oxopyrrolidin-3-yl)oxy)methyl)azetidin-1-yl)-4-(trifluoromethyl)pyridazin-3(2H)-one;
5-(2-(((1-(3-chloro-4-methyl-6,7,8,9-tetrahydropyrido[3,2-b]indolizin-7-yl)-4,4-dimethyl-2-oxopyrrolidin-3-yl)oxy)methyl)azetidin-1-yl)-4-(trifluoromethyl)pyridazin-3(2H)-one;
5-(2-(((1-(3-chloro-5-methyl-6,7,8,9-tetrahydropyrido[3,2-b]indolizin-7-yl)-4,4-dimethyl-2-oxopyrrolidin-3-yl)oxy)methyl)azetidin-1-yl)-4-(trifluoromethyl)pyridazin-3(2H)-one;
5-(2-(((4,4-dimethyl-2-oxo-1-(3-(trifluoromethyl)-6,6a,7,8,9,10-hexahydrodipyrido[3,2-b:1',2'-d][1,4]oxazin-8-yl)pyrrolidin-3-yl)oxy)methyl)azetidin-1-yl)-4-(trifluoromethyl)pyridazin-3(2H)-one;
5-(2-(((4,4-dimethyl-2-oxo-1-(3-(trifluoromethyl)-7,7a,8,9,10,11-hexahydro-6H-dipyrido[3,2-b: 1',2'-d][1,4]oxazepin-9-yl)pyrrolidin-3-yl)oxy)methyl)azetidin-1-yl)-4-(trifluoromethyl)pyridazin-3(2H)-one;
5-(2-(((1-(3-chloro-7,7a,8,9,10,11-hexahydro-6H-dipyrido[3,2-b:1',2'-d][1,4]oxazepin-9-yl)-4,4-dimethyl-2-oxopyrrolidin-3-yl)oxy)methyl)azetidin-1-yl)-4-(trifluoromethyl)pyridazin-3(2H)-one;
5-(2-(((4,4-dimethyl-2-oxo-1-(3-(trifluoromethyl)-6,7,8,9-tetrahydropyrido[3,2-b]indolizin-7-yl)pyrrolidin-3-yl)oxy)methyl)azetidin-1-yl)-4-(trifluoromethyl)pyridazin-3(2H)-one;
5-(2-(((4,4-dimethyl-1-(5-methyl-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-4,5-dimethyl-6,7,8,9-tetrahydropyrido[3,2-b]indolizin-7-yl)-4,4-dimethyl-2-oxopyrrolidin-3-yl)oxy)methyl)azetidin-1-yl)-4-(trifluoromethyl)pyridazin-3(2H)-one;
5-(2-(((1-(3-chloro-6,6a,7,8,9,10-hexahydrodipyrido[3,2-b:1',2'-d][1,4]oxazin-8-yl)-2-oxopiperidin-3-yl)oxy)methyl)azetidin-1-yl)-4-(trifluoromethyl)pyridazin-3(2H)-one;
5-(2-(((1-(3-chloro-4-methyl-6,6a,7,8,9,10-hexahydrodipyrido[3,2-b:1',2'-d][1,4]oxazin-8-yl)-2-oxopiperidin-3-yl)oxy)methyl)azetidin-1-yl)-4-(trifluoromethyl)pyridazin-3(2H)-one;
5-(2-(((1-(3-chloro-7,7a,8,9,10,11-hexahydro-6H-dipyrido[3,2-b:1',2'-d][1,4]oxazepin-9-yl)-2-oxopiperidin-3-yl)oxy)methyl)azetidin-1-yl)-4-(trifluoromethyl)pyridazin-3(2H)-one;
5-(2-(((1-(3-chloro-4-methyl-7,7a,8,9,10,11-hexahydro-6H-dipyrido[3,2-b:1',2'-d][1,4]oxazepin-9-yl)-2-oxopiperidin-3-yl)oxy)methyl)azetidin-1-yl)-4-(trifluoromethyl)pyridazin-3(2H)-one;
5-(2-(((1-(3-chloro-6,7,8,9-tetrahydropyrido[3,2-b]indolizin-7-yl)-2-oxopiperidin-3-yl)oxy)methyl)azetidin-1-yl)-4-(trifluoromethyl)pyridazin-3(2H)-one;
5-(2-(((1-(3-chloro-4-methyl-6,7,8,9-tetrahydropyrido[3,2-b]indolizin-7-yl)-2-oxopiperidin-3-yl)oxy)methyl)azetidin-1-yl)-4-(trifluoromethyl)pyridazin-3(2H)-one;
5-(2-(((1-(3-chloro-5-methyl-6,7,8,9-tetrahydropyrido[3,2-b]indolizin-7-yl)-2-oxopiperidin-3-yl)oxy)methyl)azetidin-1-yl)-4-(trifluoromethyl)pyridazin-3(2H)-one;

-continued 5-(2-(((1-(3-chloro-4,5-dimethyl-6,7,8,9-tetrahydropyrido[3,2-b]indolizin-7-yl)-2-oxopiperidin-3-yl)oxy) methyl)azetidin-1-yl)-4-(trifluoromethyl)pyridazin-3(2H)-one;
4-(trifluoromethyl)-5-(2-((3-(3-(trifluoromethyl)-6,7,8,9-tetrahydropyrido[3',2':4,5]pyrrolo[1,2-a]pyrazine-7-carbonyl)pyrrolidin-1-yl)methyl)azetidin-1-yl)pyridazin-3(2H)-one;
4-(trifluoromethyl)-5-(2-((3-(3-(trifluoromethyl)-6,6a,7,8,9,10-hexahydropyrazino[1,2-d]pyrido[3,2-b][1,4]oxazine-8-carbonyl)phenoxy)methyl)azetidin-1-yl)pyridazin-3(2H)-one;
4-(trifluoromethyl)-5-(2-((3-(3-(trifluoromethyl)-6,7,8,9-tetrahydropyrido[3',2':4,5]pyrrolo[1,2-a]pyrazine-7-carbonyl)phenoxy)methyl)azetidin-1-yl)pyridazin-3(2H)-one;
5-(2-((3-(5-methyl-3-(trifluoromethyl)-6,7,8,9-tetrahydropyrido[3',2':4,5]pyrrolo[1,2-a]pyrazine-7-carbonyl)phenoxy)methyl)azetidin-1-yl)-4-(trifluoromethyl)pyridazin-3(2H)-one;
5-(3-(3-(3-chloro-4,5-dimethyl-8,9-dihydropyrido[3',2':4,5]pyrrolo[1,2-a]pyrazin-7(6H)-yl)-2-methyl-3-oxopropoxy)propyl)-4-(trifluoromethyl)pyridazin-3(2H)-one;
5-(2-((2-methyl-3-oxo-3-(3-(trifluoromethyl)-8,9-dihydropyrido[3',2':4,5]pyrrolo[1,2-a]pyrazin-7(6H)-yl) propoxy)methyl)azetidin-1-yl)-4-(trifluoromethyl)pyridazin-3(2H)-one;
5-(2-(5-(2-(3-chloro-4,5-dimethyl-8,9-dihydropyrido[3',2':4,5]pyrrolo[1,2-a]pyrazin-7(6H)-yl)-2-oxoethyl) tetrahydrofuran-2-yl)azetidin-1-yl)-4-(trifluoromethyl)pyridazin-3(2H)-one;
5-(2-(5-(2-oxo-2-(3-(trifluoromethyl)-8,9-dihydropyrido[3',2':4,5]pyrrolo[1,2-a]pyrazin-7(6H)-yl)ethyl)tetrahydrofuran-2-yl)azetidin-1-yl)-4-(trifluoromethyl)pyridazin-3(2H)-one;
5-(2-(5-(2-oxo-2-(3-(trifluoromethyl)-6a,7,9,10-tetrahydropyrazino[1,2-d]pyrido[3,2-b][1,4]oxazin-8(6H)-yl)ethyl)tetrahydrofuran-2-yl)azetidin-1-yl)-4-(trifluoromethyl)pyridazin-3(2H)-one;
5-(2-(5-(2-oxo-2-(3-(trifluoromethyl)-6,7,7a,8,10,11-hexahydro-9H-pyrazino[1,2-d]pyrido[3,2-b][1,4]oxazepin-9-yl)ethyl)tetrahydrofuran-2-yl)azetidin-1-yl)-4-(trifluoromethyl)pyridazin-3(2H)-one;
5-(2-(5-(2-(3-chloro-6,7,7a,8,10,11-hexahydro-9H-pyrazino[1,2-d]pyrido[3,2-b][1,4]oxazepin-9-yl)-2-oxoethyl)tetrahydrofuran-2-yl)azetidin-1-yl)-4-(trifluoromethyl)pyridazin-3(2H)-one;
5-(2-((2-((5-methyl-3-(trifluoromethyl)-8,9-dihydropyrido[3',2':4,5]pyrrolo[1,2-a]pyrazin-7(6H)-yl)sulfonyl)ethoxy)methyl)azetidin-1-yl)-4-(trifluoromethyl)pyridazin-3(2H)-one;
4-(trifluoromethyl)-5-(2-((2-((3-(trifluoromethyl)-8,9-dihydropyrido[3',2':4,5]pyrrolo[1,2-a]pyrazin-7(6H)-yl)sulfonyl)ethoxy)methyl)azetidin-1-yl)pyridazin-3(2H)-one;
4-(trifluoromethyl)-5-(2-((2-((3-(trifluoromethyl)-6a,7,9,10-tetrahydropyrazino[1,2-d]pyrido[3,2-b][1,4]oxazin-8(6H)-yl)sulfonyl)ethoxy)methyl)azetidin-1-yl)pyridazin-3(2H)-one;
4-(trifluoromethyl)-5-(2-((2-((3-(trifluoromethyl)-6,7,7a,8,10,11-hexahydro-9H-pyrazino[1,2-d]pyrido[3,2-b][1,4]oxazepin-9-yl)sulfonyl)ethoxy)methyl)azetidin-1-yl)pyridazin-3(2H)-one;
5-(2-((2-((3-chloro-6,7,7a,8,10,11-hexahydro-9H-pyrazino[1,2-d]pyrido[3,2-b][1,4]oxazepin-9-yl)sulfonyl)ethoxy)methyl)azetidin-1-yl)-4-(trifluoromethyl)pyridazin-3(2H)-one;
N-(3-chloro-4,5-dimethyl-6,7,8,9-tetrahydropyrido[3,2-b]indolizin-7-yl)-3-((1-(6-oxo-5-(trifluoromethyl)-1,6-dihydropyridazin-4-yl)azetidin-2-yl)methoxy)propanamide;
3-((1-(6-oxo-5-(trifluoromethyl)-1,6-dihydropyridazin-4-yl)azetidin-2-yl)methoxy)-N-(3-(trifluoromethyl)-6,6a,7,8,9,10-hexahydrodipyrido[3,2-b:1',2'-d][1,4]oxazin-8-yl)propanamide;
3-((1-(6-oxo-5-(trifluoromethyl)-1,6-dihydropyridazin-4-yl)azetidin-2-yl)methoxy)-N-(3-(trifluoromethyl)-6,7,8,9-tetrahydropyrido[3,2-b]indolizin-7-yl)propanamide;
3-((1-(6-oxo-5-(trifluoromethyl)-1,6-dihydropyridazin-4-yl)azetidin-2-yl)methoxy)-N-(3-(trifluoromethyl)-7,7a,8,9,10,11-hexahydro-6H-dipyrido[3,2-b:1',2'-d][1,4]oxazepin-9-yl)propanamide;
N-(3-chloro-7,7a,8,9,10,11-hexahydro-6H-dipyrido[3,2-b:1',2'-d][1,4]oxazepin-9-yl)-3-((1-(6-oxo-5-(trifluoromethyl)-1,6-dihydropyridazin-4-yl)azetidin-2-yl)methoxy)propanamide;
5-(2-(((2-oxo-1-(3-(trifluoromethyl)-6,6a,7,8,9,10-hexahydrodipyrido[3,2-b:1',2'-d][1,4]oxazin-8-yl)pyrrolidin-3-yl)oxy)methyl)azetidin-1-yl)-4-(trifluoromethyl)pyridazin-3(2H)-one;
5-(2-(((2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)oxy)methyl)azetidin-1-yl)-4-(trifluoromethyl)pyridazin-3(2H)-one;
5-(2-(((1-(3-chloro-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((2-oxo-1-(3-(trifluoromethyl)-6,7,8,9-tetrahydropyrido[3,2-b]indolizin-7-yl)pyrrolidin-3-yl)oxy)methyl)azetidin-1-yl)-4-(trifluoromethyl)pyridazin-3(2H)-one;
5-(2-(((1-(5-methyl-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(3-chloro-4,5-dimethyl-6,7,8,9-tetrahydropyrido[3,2-b]indolizin-7-yl)-2-oxopyrrolidin-3-yl)oxy) methyl)azetidin-1-yl)-4-(trifluoromethyl)pyridazin-3(2H)-one;
5-(2-(((1-(9-fluoro-3-(trifluoromethyl)-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(10-fluoro-3-(trifluoromethyl)-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(3-chloro-10-fluoro-7,7a,8,9,10,11-hexahydro-6H-dipyrido[3,2-b: 1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(8-fluoro-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(8-fluoro-5-methyl-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(9,9-difluoro-3-(trifluoromethyl)-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(3-chloro-10,10-difluoro-7,7a,8,9,10,11-hexahydro-6H-dipyrido[3,2-b: 1',2'-d][1,4]oxazepin-9-yl)-2-oxopyrrolidin-3-yl)oxy)methyl)azetidin-1-yl)-4-(trifluoromethyl)pyridazin-3(2H)-one;
5-(2-(((1-(8,8-difluoro-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(8,8-difluoro-5-methyl-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(9-hydroxy-3-(trifluoromethyl)-6,6a,7,8,9,10-hexahydrodipyrido[3,2-b:1',2'-d][1,4]oxazin-8-yl)-2-oxopyrrolidin-3-yl)oxy)methyl)azetidin-1-yl)-4-(trifluoromethyl)pyridazin-3(2H)-one;
5-(2-(((1-(10-hydroxy-3-(trifluoromethyl)-7,7a,8,9,10,11-hexahydro-6H-dipyrido[3,2-b:1',2'-d][1,4]oxazepin-9-yl)-2-oxopyrrolidin-3-yl)oxy)methyl)azetidin-1-yl)-4-(trifluoromethyl)pyridazin-3(2H)-one;

-continued 5-(2-(((1-(8-hydroxy-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-(((1-(8-hydroxy-5-methyl-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-6,6a,7,8,9,10-hexahydrodipyrido[3,2-b:1',2'-d][1,4]oxazine-9-carbonitrile;
9-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,7a,8,9,10,11-hexahydro-6H-dipyrido[3,2-b:1',2'-d][1,4]oxazepine-10-carbonitrile;
7-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-6,7,8,9-tetrahydropyrido[3,2-b]indolizine-8-carbonitrile;
3-chloro-4,5-dimethyl-7-(2-oxo-3-((1-(6-oxo-5-(trifluoromethyl)-1,6-dihydropyridazin-4-yl)azetidin-2-yl)methoxy)pyrrolidin-1-yl)-6,7,8,9-tetrahydropyrido[3,2-b]indolizine-8-carbonitrile;
N-(2-oxo-1-(3-(trifluoromethyl)-6,6a,7,8,9,10-hexahydrodipyrido[3,2-b:1',2'-d][1,4]oxazin-8-yl)pyrrolidin-3-yl)-1-(6-oxo-5-(trifluoromethyl)-1,6-dihydropyridazin-4-yl)azetidine-2-carboxamide;
N-(2-oxo-1-(3-(trifluoromethyl)-7,7a,8,9,10,11-hexahydro-6H-dipyrido[3,2-b:1',2'-d][1,4]oxazepin-9-yl)pyrrolidin-3-yl)-1-(6-oxo-5-(trifluoromethyl)-1,6-dihydropyridazin-4-yl)azetidine-2-carboxamide;
N-(2-oxo-1-(3-(trifluoromethyl)-6,7,8,9-tetrahydropyrido[3,2-b]indolizin-7-yl)pyrrolidin-3-yl)-1-(6-oxo-5-(trifluoromethyl)-1,6-dihydropyridazin-4-yl)azetidine-2-carboxamide;
N-(1-(5-methyl-3-(trifluoromethyl)-6,7,8,9-tetrahydropyrido[3,2-b]indolizin-7-yl)-2-oxopyrrolidin-3-yl)-1-(6-oxo-5-(trifluoromethyl)-1,6-dihydropyridazin-4-yl)azetidine-2-carboxamide;
4-(trifluoromethyl)-5-(2-((3-(3-(trifluoromethyl)-7,7a,8,9,10,11-hexahydro-6H-pyrazino[1,2-d]pyrido[3,2-b][1,4]oxazepine-9-carbonyl)pyrrolidin-1-yl)methyl)azetidin-1-yl)pyridazin-3(2H)-one;
5-(2-(((2-oxo-1-(3-(trifluoromethyl)-6,6a,7,8,9,10-hexahydrodipyrido[3,2-b:1',2'-d][1,4]oxazin-8-yl)piperidin-3-yl)oxy)methyl)azetidin-1-yl)-4-(trifluoromethyl)pyridazin-3(2H)-one;
5-(2-(((2-oxo-1-(3-(trifluoromethyl)-7,7a,8,9,10,11-hexahydro-6H-dipyrido[3,2-b:1',2'-d][1,4]oxazepin-9-yl)piperidin-3-yl)oxy)methyl)azetidin-1-yl)-4-(trifluoromethyl)pyridazin-3(2H)-one;
5-(2-(((2-oxo-1-(3-(trifluoromethyl)-6,7,8,9-tetrahydropyrido[3,2-b]indolizin-7-yl)piperidin-3-yl)oxy)methyl)azetidin-1-yl)-4-(trifluoromethyl)pyridazin-3(2H)-one;
5-(2-(((1-(5-methyl-3-(trifluoromethyl)-6,7,8,9-tetrahydropyrido[3,2-b]indolizin-7-yl)-2-oxopiperidin-3-yl)oxy)methyl)azetidin-1-yl)-4-(trifluoromethyl)pyridazin-3(2H)-one;
4-(trifluoromethyl)-5-(2-((3-(3-(trifluoromethyl)-7,7a,8,9,10,11-hexahydro-6H-pyrazino[1,2-d]pyrido[3,2-b][1,4]oxazepine-9-carbonyl)phenoxy)methyl)azetidin-1-yl)pyridazin-3(2H)-one;
5-(2-((3-(3-chloro-7,7a,8,9,10,11-hexahydro-6H-pyrazino[1,2-d]pyrido[3,2-b][1,4]oxazepine-9-carbonyl)phenoxy)methyl)azetidin-1-yl)-4-(trifluoromethyl)pyridazin-3(2H)-one;
5-(2-((3-(3-chloro-4-methyl-7,7a,8,9,10,11-hexahydro-6H-pyrazino[1,2-d]pyrido[3,2-b][1,4]oxazepine-9-carbonyl)phenoxy)methyl)azetidin-1-yl)-4-(trifluoromethyl)pyridazin-3(2H)-one;
5-(2-((3-(3-chloro-4-methyl-6,7,8,9-tetrahydropyrido[3',2':4,5]pyrrolo[1,2-a]pyrazine-7-carbonyl)phenoxy)methyl)azetidin-1-yl)-4-(trifluoromethyl)pyridazin-3(2H)-one;
5-(2-((3-(3-chloro-5-methyl-6,7,8,9-tetrahydropyrido[3',2':4,5]pyrrolo[1,2-a]pyrazine-7-carbonyl)phenoxy)methyl)azetidin-1-yl)-4-(trifluoromethyl)pyridazin-3(2H)-one;
5-(2-((2-methyl-3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-(2-((2-methyl-3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)-4-(trifluoromethyl)pyridazin-3(2H)-one;
4-(trifluoromethyl)-5-(2-((3-(3-(trifluoromethyl)-6,6a,7,8,9,10-hexahydropyrazino[1,2-d]pyrido[3,2-b][1,4]oxazine-8-carbonyl)pyrrolidin-1-yl)methyl)azetidin-1-yl)pyridazin-3(2H)-one;
5-(2-((3-(3-chloro-5-methyl-6,7,8,9-tetrahydropyrido[3',2':4,5]pyrrolo[1,2-a]pyrazine-7-carbonyl)pyrrolidin-1-yl)methyl)azetidin-1-yl)-4-(trifluoromethyl)pyridazin-3(2H)-one;
5-methyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-ethyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-isopropyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-cyclopropyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-(2-(((2-oxo-1-(3-(trifluoromethyl)-6,6a,7,8,9,10-hexahydrodipyrido[3,2-b:1',2'-d][1,4]thiazin-8-yl)pyrrolidin-3-yl)oxy)methyl)azetidin-1-yl)-4-(trifluoromethyl)pyridazin-3(2H)-one;
5-(2-(((1-(5,5-difluoro-3-(trifluoromethyl)-6,6a,7,8,9,10-hexahydro-5H-pyrido[1,2-a][1,8]naphthyridin-8-yl)-2-oxopyrrolidin-3-yl)oxy)methyl)azetidin-1-yl)-4-(trifluoromethyl)pyridazin-3(2H)-one;
5-(2-(((2-oxo-1-(3-(trifluoromethyl)-5,5a,6,7,8,9-hexahydroimidazo[1,2-a:5,4-b']dipyridin-7-yl)pyrrolidin-3-yl)oxy)methyl)azetidin-1-yl)-4-(trifluoromethyl)pyridazin-3(2H)-one;
5-(2-(((2-oxo-1-(3-(trifluoromethyl)-6,7,8,9-tetrahydroimidazo[1,2-a:5,4-b']dipyridin-7-yl)pyrrolidin-3-yl)oxy)methyl)azetidin-1-yl)-4-(trifluoromethyl)pyridazin-3(2H)-one;
5-(2-(((1-(5-fluoro-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
9-hydroxy-5-methyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-ethyl-9-hydroxy-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
9-hydroxy-5-isopropyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-cyclopropyl-9-hydroxy-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-(2-(((1-(9-hydroxy-3-(trifluoromethyl)-6,6a,7,8,9,10-hexahydrodipyrido[3,2-b:1',2'-d][1,4]thiazin-8-yl)-2-oxopyrrolidin-3-yl)oxy)methyl)azetidin-1-yl)-4-(trifluoromethyl)pyridazin-3(2H)-one;
5-(2-(((1-(5,5-difluoro-9-hydroxy-3-(trifluoromethyl)-6,6a,7,8,9,10-hexahydro-5H-pyrido[1,2-a][1,8]naphthyridin-8-yl)-2-oxopyrrolidin-3-yl)oxy)methyl)azetidin-1-yl)-4-(trifluoromethyl)pyridazin-3(2H)-one;

-continued 5-(2-(((1-(8-hydroxy-3-(trifluoromethyl)-5,5a,6,7,8,9-hexahydroimidazo[1,2-a:5,4-b']dipyridin-7-yl)-2-oxopyrrolidin-3-yl)oxy)methyl)azetidin-1-yl)-4-(trifluoromethyl)pyridazin-3(2H)-one;
5-(2-(((1-(8-hydroxy-3-(trifluoromethyl)-6,7,8,9-tetrahydroimidazo[1,2-a:5,4-b']dipyridin-7-yl)-2-oxopyrrolidin-3-yl)oxy)methyl)azetidin-1-yl)-4-(trifluoromethyl)pyridazin-3(2H)-one;
5-(2-(((1-(5-fluoro-8-hydroxy-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
9-fluoro-5-methyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aHI)-one;
5-ethyl-9-fluoro-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
9-fluoro-5-isopropyl-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-cyclopropyl-9-fluoro-8-(2-oxo-3-((1-(6-oxo-5-(trifluoromethyl)-1,6-dihydropyridazin-4-yl)azetidin-2-yl)methoxy)pyrrolidin-1-yl)-3-(trifluoromethyl)-7,8,9,10-tetrahydro-5H-dipyrido[1,2-a:3',2'-e]pyrazin-6(6aH)-one;
5-(2-(((1-(9-fluoro-3-(trifluoromethyl)-6,6a,7,8,9,10-hexahydrodipyrido[3,2-b:1',2'-d][1,4]thiazin-8-yl)-2-oxopyrrolidin-3-yl)oxy)methyl)azetidin-1-yl)-4-(trifluoromethyl)pyridazin-3(2H)-one;
5-(2-(((2-oxo-1-(5,5,9-trifluoro-3-(trifluoromethyl)-6,6a,7,8,9,10-hexahydro-5H-pyrido[1,2-a][1,8]naphthyridin-8-yl)pyrrolidin-3-yl)oxy)methyl)azetidin-1-yl)-4-(trifluoromethyl)pyridazin-3(2H)-one;
5-(2-(((1-(8-fluoro-3-(trifluoromethyl)-5,5a,6,7,8,9-hexahydroimidazo[1,2-a:5,4-b']dipyridin-7-yl)-2-oxopyrrolidin-3-yl)oxy)methyl)azetidin-1-yl)-4-(trifluoromethyl)pyridazin-3(2H)-one;
5-(2-(((1-(8-fluoro-3-(trifluoromethyl)-6,7,8,9-tetrahydroimidazo[1,2-a:5,4-b']dipyridin-7-yl)-2-oxopyrrolidin-3-yl)oxy)methyl)azetidin-1-yl)-4-(trifluoromethyl)pyridazin-3(2H)-one;
5-(2-(((1-(5,8-difluoro-3-(trifluoromethyl)-6,7,8,9-tetrahydropyrido[3,2-b]indolizin-7-yl)-2-oxopyrrolidin-3-yl)oxy)methyl)azetidin-1-yl)-4-(trifluoromethyl)pyridazin-3(2H)-one;
5-(2-((3-(3-chloro-4-methyl-6,7,8,9-tetrahydropyrido[3',2':4,5]pyrrolo[1,2-a]pyrazine-7-carbonyl)pyrrolidin-1-yl)methyl)azetidin-1-yl)-4-(trifluoromethyl)pyridazin-3(2H)-one;
5-(2-((3-(3-chloro-4,5-dimethyl-6,7,8,9-tetrahydropyrido[3',2':4,5]pyrrolo[1,2-a]pyrazine-7-carbonyl)pyrrolidin-1-yl)methyl)azetidin-1-yl)-4-(trifluoromethyl)pyridazin-3(2H)-one;
5-(2-((3-(3-chloro-6,6a,7,8,9,10-hexahydropyrazino[1,2-d]pyrido[3,2-b][1,4]oxazine-8-carbonyl)pyrrolidin-1-yl)methyl)azetidin-1-yl)-4-(trifluoromethyl)pyridazin-3(2H)-one;
5-(2-((3-(3-chloro-7,7a,8,9,10,11-hexahydro-6H-pyrazino[1,2-d]pyrido[3,2-b][1,4]oxazepine-9-carbonyl)pyrrolidin-1-yl)methyl)azetidin-1-yl)-4-(trifluoromethyl)pyridazin-3(2H)-one;
5-(2-((3-(3-chloro-6,7,8,9-tetrahydropyrido[3',2':4,5]pyrrolo[1,2-a]pyrazine-7-carbonyl)pyrrolidin-1-yl)methyl)azetidin-1-yl)-4-(trifluoromethyl)pyridazin-3(2H)-one;
5-(2-((3-(3-chloro-4-methyl-6,6a,7,8,9,10-hexahydropyrazino[1,2-d]pyrido[3,2-b][1,4]oxazine-8-carbonyl)pyrrolidin-1-yl)methyl)azetidin-1-yl)-4-(trifluoromethyl)pyridazin-3(2H)-one;
5-(2-((3-(3-chloro-4-methyl-7,7a,8,9,10,11-hexahydro-6H-pyrazino[1,2-d]pyrido[3,2-b][1,4]oxazepine-9-carbonyl)pyrrolidin-1-yl)methyl)azetidin-1-yl)-4-(trifluoromethyl)pyridazin-3(2H)-one;
5-(2-((3-(5-methyl-3-(trifluoromethyl)-6,7,8,9-tetrahydropyrido[3',2':4,5]pyrrolo[1,2-a]pyrazine-7-carbonyl)pyrrolidin-1-yl)methyl)azetidin-1-yl)-4-(trifluoromethyl)pyridazin-3(2H)-one;
5-(2-((3-(3-chloro-6,6a,7,8,9,10-hexahydropyrazino[1,2-d]pyrido[3,2-b][1,4]oxazine-8-carbonyl)phenoxy)methyl)azetidin-1-yl)-4-(trifluoromethyl)pyridazin-3(2H)-one;
5-(2-((3-(3-chloro-4-methyl-6,6a,7,8,9,10-hexahydropyrazino[1,2-d]pyrido[3,2-b][1,4]oxazine-8-carbonyl)phenoxy)methyl)azetidin-1-yl)-4-(trifluoromethyl)pyridazin-3(2H)-one;
(S)-5-((1-(3-(3-chloro-6,7,8,9-tetrahydropyrido[3',2':4,5]pyrrolo[1,2-a]pyrazine-7-carbonyl)phenoxy)propan-2-yl)oxy)-4-(trifluoromethyl)pyridazin-3(2H)-one;
5-(((2S)-1-(2-methyl-3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]oxazin-8(6H)-yl)-2-methyl-3-oxopropoxy)propan-2-yl)oxy)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]oxazin-8(6H)-yl)-2-methyl-3-oxopropoxy)propan-2-yl)oxy)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]oxazepin-9-yl)-2-methyl-3-oxopropoxy)propan-2-yl)oxy)-4-(trifluoromethyl)pyridazin-3(2H)-one;
5-(((2S)-1-(3-(3-chloro-4-methyl-6,7,7a,8,10,11-hexahydro-9H-pyrazino[1,2-d]pyrido[3,2-b][1,4]oxazepin-9-yl)-2-methyl-3-oxopropoxy)propan-2-yl)oxy)-4-(trifluoromethyl)pyridazin-3(2H)-one;
5-(((2S)-1-(3-(3-chloro-8,9-dihydropyrido[3',2':4,5]pyrrolo[1,2-a]pyrazin-7(6H)-yl)-2-methyl-3-oxopropoxy)propan-2-yl)oxy)-4-(trifluoromethyl)pyridazin-3(2H)-one;
5-(((2S)-1-(3-(3-chloro-4-methyl-8,9-dihydropyrido[3',2':4,5]pyrrolo[1,2-a]pyrazin-7(6H)-yl)-2-methyl-3-oxopropoxy)propan-2-yl)oxy)-4-(trifluoromethyl)pyridazin-3(2H)-one;
5-(((2S)-1-(3-(3-chloro-5-methyl-8,9-dihydropyrido[3',2':4,5]pyrrolo[1,2-a]pyrazin-7(6H)-yl)-2-methyl-3-oxopropoxy)propan-2-yl)oxy)-4-(trifluoromethyl)pyridazin-3(2H)-one;
5-((1S)-1-(5-(2-(5-methyl-3-(trifluoromethyl)-8,9-dihydropyrido[3',2':4,5]pyrrolo[1,2-a]pyrazin-7(6H)-yl)-2-oxoethyl)tetrahydrofuran-2-yl)ethoxy)-4-(trifluoromethyl)pyridazin-3(2H)-one;
5-((1S)-1-(5-(2-(3-chloro-5-methyl-8,9-dihydropyrido[3',2':4,5]pyrrolo[1,2-a]pyrazin-7(6H)-yl)-2-oxoethyl)tetrahydrofuran-2-yl)ethoxy)-4-(trifluoromethyl)pyridazin-3(2H)-one;
5-((1S)-1-(5-(2-(3-chloro-4-methyl-6,7,7a,8,10,11-hexahydro-9H-pyrazino[1,2-d]pyrido[3,2-b][1,4]oxazepin-9-yl)-2-oxoethyl)tetrahydrofuran-2-yl)ethoxy)-4-(trifluoromethyl)pyridazin-3(2H)-one;
5-((1S)-1-(5-(2-(3-chloro-6a,7,9,10-tetrahydropyrazino[1,2-d]pyrido[3,2-b][1,4]oxazin-8(6H)-yl)-2-oxoethyl)tetrahydrofuran-2-yl)ethoxy)-4-(trifluoromethyl)pyridazin-3(2H)-one;
5-((1S)-1-(5-(2-(3-chloro-4-methyl-6a,7,9,10-tetrahydropyrazino[1,2-d]pyrido[3,2-b][1,4]oxazin-8(6H)-yl)-2-oxoethyl)tetrahydrofuran-2-yl)ethoxy)-4-(trifluoromethyl)pyridazin-3(2H)-one;
5-((1S)-1-(5-(2-(3-chloro-8,9-dihydropyrido[3',2':4,5]pyrrolo[1,2-a]pyrazin-7(6H)-yl)-2-oxoethyl)tetrahydrofuran-2-yl)ethoxy)-4-(trifluoromethyl)pyridazin-3(2H)-one;
5-((1S)-1-(5-(2-(3-chloro-4-methyl-8,9-dihydropyrido[3',2':4,5]pyrrolo[1,2-a]pyrazin-7(6H)-yl)-2-oxoethyl)tetrahydrofuran-2-yl)ethoxy)-4-(trifluoromethyl)pyridazin-3(2H)-one;
5-(((2S)-1-(2-((3-chloro-6a,7,9,10-tetrahydropyrazino[1,2-d]pyrido[3,2-b][1,4]oxazin-8(6H)-yl)sulfonyl)ethoxy)propan-2-yl)oxy)-4-(trifluoromethyl)pyridazin-3(2H)-one;

-continued 5-(((2S)-1-(2-((3-chloro-4-methyl-6a,7,9,10-tetrahydropyrazino[1,2-d]pyrido[3,2-b][1,4]oxazin-8(6H)-yl)sulfonyl)ethoxy)propan-2-yl)oxy)-4-(trifluoromethyl)pyridazin-3(2H)-one;
(S)-5-((1-(2-((3-chloro-8,9-dihydropyrido[3',2':4,5]pyrrolo[1,2-a]pyrazin-7(6H)-yl)sulfonyl)ethoxy)propan-2-yl)oxy)-4-(trifluoromethyl)pyridazin-3(2H)-one;
(S)-5-((1-(2-((3-chloro-4-methyl-8,9-dihydropyrido[3',2':4,5]pyrrolo[1,2-a]pyrazin-7(6H)-yl)sulfonyl)ethoxy)propan-2-yl)oxy)-4-(trifluoromethyl)pyridazin-3(2H)-one;
5-(((2S)-1-(2-((3-chloro-4-methyl-6,7,7a,8,10,11-hexahydro-9H-pyrazino[1,2-d]pyrido[3,2-b][1,4]oxazepin-9-yl)sulfonyl)ethoxy)propan-2-yl)oxy)-4-(trifluoromethyl)pyridazin-3(2H)-one;
(S)-5-((1-(2-((3-chloro-5-methyl-8,9-dihydropyrido[3',2':4,5]pyrrolo[1,2-a]pyrazin-7(6H)-yl)sulfonyl)ethoxy)propan-2-yl)oxy)-4-(trifluoromethyl)pyridazin-3(2H)-one;
(S)-5-((1-(2-((3-chloro-4,5-dimethyl-8,9-dihydropyrido[3',2':4,5]pyrrolo[1,2-a]pyrazin-7(6H)-yl)sulfonyl)ethoxy)propan-2-yl)oxy)-4-(trifluoromethyl)pyridazin-3(2H)-one;
N-(5-methyl-3-(trifluoromethyl)-6,7,8,9-tetrahydropyrido[3,2-b]indolizin-7-yl)-3-((S)-2-((6-oxo-5-(trifluoromethyl)-1,6-dihydropyridazin-4-yl)oxy)propoxy)propanamide;
N-(3-chloro-5-methyl-6,7,8,9-tetrahydropyrido[3,2-b]indolizin-7-yl)-3-((S)-2-((6-oxo-5-(trifluoromethyl)-1,6-dihydropyridazin-4-yl)oxy)propoxy)propanamide;
N-(3-chloro-4-methyl-7,7a,8,9,10,11-hexahydro-6H-dipyrido[3,2-b:1',2'-d][1,4]oxazepin-9-yl)-3-((S)-2-((6-oxo-5-(trifluoromethyl)-1,6-dihydropyridazin-4-yl)oxy)propoxy)propanamide;
N-(3-chloro-6,6a,7,8,9,10-hexahydrodipyrido[3,2-b:1',2'-d][1,4]oxazin-8-yl)-3-((S)-2-((6-oxo-5-(trifluoromethyl)-1,6-dihydropyridazin-4-yl)oxy)propoxy)propanamide;
N-(3-chloro-4-methyl-6,6a,7,8,9,10-hexahydrodipyrido[3,2-b:1',2'-d][1,4]oxazin-8-yl)-3-((S)-2-((6-oxo-5-(trifluoromethyl)-1,6-dihydropyridazin-4-yl)oxy)propoxy)propanamide;
N-(3-chloro-6,7,8,9-tetrahydropyrido[3,2-b]indolizin-7-yl)-3-((S)-2-((6-oxo-5-(trifluoromethyl)-1,6-dihydropyridazin-4-yl)oxy)propoxy)propanamide;
N-(3-chloro-4-methyl-6,7,8,9-tetrahydropyrido[3,2-b]indolizin-7-yl)-3-((S)-2-((6-oxo-5-(trifluoromethyl)-1,6-dihydropyridazin-4-yl)oxy)propoxy)propanamide;
N-methyl-N-(5-methyl-3-(trifluoromethyl)-6,7,8,9-tetrahydropyrido[3,2-b]indolizin-7-yl)-3-((S)-2-((6-oxo-5-(trifluoromethyl)-1,6-dihydropyridazin-4-yl)oxy)propoxy)propanamide;
N-(3-chloro-5-methyl-6,7,8,9-tetrahydropyrido[3,2-b]indolizin-7-yl)-N-methyl-3-((S)-2-((6-oxo-5-(trifluoromethyl)-1,6-dihydropyridazin-4-yl)oxy)propoxy)propanamide;
N-(3-chloro-4-methyl-7,7a,8,9,10,11-hexahydro-6H-dipyrido[3,2-b:1',2'-d][1,4]oxazepin-9-yl)-N-methyl-3-((S)-2-((6-oxo-5-(trifluoromethyl)-1,6-dihydropyridazin-4-yl)oxy)propoxy)propanamide;
N-(3-chloro-6,6a,7,8,9,10-hexahydrodipyrido[3,2-b:1',2'-d][1,4]oxazin-8-yl)-N-methyl-3-((S)-2-((6-oxo-5-(trifluoromethyl)-1,6-dihydropyridazin-4-yl)oxy)propoxy)propanamide;
N-(3-chloro-4-methyl-6,6a,7,8,9,10-hexahydrodipyrido[3,2-b:1',2'-d][1,4]oxazin-8-yl)-N-methyl-3-((S)-2-((6-oxo-5-(trifluoromethyl)-1,6-dihydropyridazin-4-yl)oxy)propoxy)propanamide;
N-(3-chloro-6,7,8,9-tetrahydropyrido[3,2-b]indolizin-7-yl)-N-methyl-3-((S)-2-((6-oxo-5-(trifluoromethyl)-1,6-dihydropyridazin-4-yl)oxy)propoxy)propanamide;
N-(3-chloro-4-methyl-6,7,8,9-tetrahydropyrido[3,2-b]indolizin-7-yl)-N-methyl-3-((S)-2-((6-oxo-5-(trifluoromethyl)-1,6-dihydropyridazin-4-yl)oxy)propoxy)propanamide;
N-(3-chloro-4,5-dimethyl-6,7,8,9-tetrahydropyrido[3,2-b]indolizin-7-yl)-N-methyl-3-((S)-2-((6-oxo-5-(trifluoromethyl)-1,6-dihydropyridazin-4-yl)oxy)propoxy)propanamide;
N-methyl-3-((S)-2-((6-oxo-5-(trifluoromethyl)-1,6-dihydropyridazin-4-yl)oxy)propoxy)-N-(3-(trifluoromethyl)-6,6a,7,8,9,10-hexahydrodipyrido[3,2-b:1',2'-d][1,4]oxazin-8-yl)propanamide;
N-methyl-3-((S)-2-((6-oxo-5-(trifluoromethyl)-1,6-dihydropyridazin-4-yl)oxy)propoxy)-N-(3-(trifluoromethyl)-6,7,8,9-tetrahydropyrido[3,2-b]indolizin-7-yl)propanamide;
N-methyl-3-((S)-2-((6-oxo-5-(trifluoromethyl)-1,6-dihydropyridazin-4-yl)oxy)propoxy)-N-(3-(trifluoromethyl)-7,7a,8,9,10,11-hexahydro-6H-dipyrido[3,2-b:1',2'-d][1,4]oxazepin-9-yl)propanamide;
N-(3-chloro-7,7a,8,9,10,11-hexahydro-6H-dipyrido[3,2-b:1',2'-d][1,4]oxazepin-9-yl)-N-methyl-3-((S)-2-((6-oxo-5-(trifluoromethyl)-1,6-dihydropyridazin-4-yl)oxy)propoxy)propanamide;
5-(((2S)-1-((1-(3-chloro-4-methyl-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(3-chloro-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(3-chloro-4-methyl-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(3-chloro-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-4-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-5-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-9-fluoro-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(3-chloro-9-fluoro-4-methyl-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(3-chloro-10-fluoro-4-methyl-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(3-chloro-8-fluoro-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-8-fluoro-4-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-8-fluoro-5-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-8-fluoro-4,5-dimethyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-9,9-difluoro-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;

-continued 5-(((2S)-1-((1-(3-chloro-9,9-difluoro-4-methyl-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(10,10-difluoro-3-(trifluoromethyl)-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(3-chloro-10,10-difluoro-4-methyl-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(3-chloro-8,8-difluoro-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-8,8-difluoro-4-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-8,8-difluoro-5-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-8,8-difluoro-4,5-dimethyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-9-hydroxy-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(3-chloro-9-hydroxy-4-methyl-6,6a,7,8,9,10-hexahydrodipyrido[3,2-b:1',2'-d][1,4]oxazin-8-yl)-2-oxopyrrolidin-3-yl)oxy)propan-2-yl)oxy)-4-(trifluoromethyl)pyridazin-3(2H)-one;
5-(((2S)-1-((1-(3-chloro-10-hydroxy-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(3-chloro-10-hydroxy-4-methyl-7,7a,8,9,10,11-hexahydro-6H-dipyrido[3,2-b:1',2'-d][1,4]oxazepin-9-yl)-2-oxopyrrolidin-3-yl)oxy)propan-2-yl)oxy)-4-(trifluoromethyl)pyridazin-3(2H)-one;
5-(((2S)-1-((1-(3-chloro-8-hydroxy-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-(((2S)-1-((1-(3-chloro-8-hydroxy-4-methyl-6,7,8,9-tetrahydropyrido[3,2-b]indolizin-7-yl)-2-oxopyrrolidin-3-yl)oxy)propan-2-yl)oxy)-4-(trifluoromethyl)pyridazin-3(2H)-one;
5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)-4-(trifluoromethyl)pyridazin-3(2H)-one;
5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-dipyrazino[1,2-a:2',3'-e]pyrazin-6(6aH)-one;
4-methyl-7-(3-((S)-2-((6-oxo-5-(trifluoromethyl)-1,6-dihydropyridazin-4-yl)amino)propoxy)propanoyl)-3-(trifluoromethyl)-2,4,6,7,8,9-hexahydropyrazino[1,2-a]pyrazolo[4,3-e]pyrazin-5(5aH)-one;
2,4-dimethyl-7-(3-((S)-2-((6-oxo-5-(trifluoromethyl)-1,6-dihydropyridazin-4-yl)amino)propoxy)propanoyl)-3-(trifluoromethyl)-2,4,6,7,8,9-hexahydropyrazino[1,2-a]pyrazolo[4,3-e]pyrazin-5(5aH)-one;
4-methyl-7-(3-((S)-2-((6-oxo-5-(trifluoromethyl)-1,6-dihydropyridazin-4-yl)amino)propoxy)propanoyl)-3-(trifluoromethyl)-6,7,8,9-tetrahydro-4H-isothiazolo[4,3-e]pyrazino[1,2-a]pyrazin-5(5aH)-one;
5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((2S)-1-(3-oxo-3-(3-(trifluoromethyl)-6a,7,9,10-tetrahydrodipyrazino[2,3-b:1',2'-d][1,4]oxazin-8(6H)-yl)propoxy)propan-2-yl)amino)-4-(trifluoromethyl)pyridazin-3(2H)-one;
5-(((2S)-1-(3-oxo-3-(3-(trifluoromethyl)-5a,6,8,9-tetrahydro-2H-pyrazino[1,2-d]pyrazolo[4,3-b][1,4]oxazin-7(5H)-yl)propoxy)propan-2-yl)amino)-4-(trifluoromethyl)pyridazin-3(2H)-one;
5-(((2S)-1-(3-(2-methyl-3-(trifluoromethyl)-5a,6,8,9-tetrahydro-2H-pyrazino[1,2-d]pyrazolo[4,3-b][1,4]oxazin-7(5H)-yl)-3-oxopropoxy)propan-2-yl)amino)-4-(trifluoromethyl)pyridazin-3(2H)-one;
5-(((2S)-1-(3-oxo-3-(3-(trifluoromethyl)-5a,6,8,9-tetrahydroisothiazolo[4,3-b]pyrazino[1,2-d][1,4]oxazin-7(5H)-yl)propoxy)propan-2-yl)amino)-4-(trifluoromethyl)pyridazin-3(2H)-one;
3,4-dimethyl-7-(3-((S)-2-((6-oxo-5-(trifluoromethyl)-1,6-dihydropyridazin-4-yl)amino)propoxy)propanoyl)-2,4,6,7,8,9-hexahydropyrazino[1,2-a]pyrazolo[4,3-e]pyrazin-5(5aH)-one;
5-(((2S)-1-(3-(3-methyl-5a,6,8,9-tetrahydro-2H-pyrazino[1,2-d]pyrazolo[4,3-b][1,4]oxazin-7(5H)-yl)-3-oxopropoxy)propan-2-yl)amino)-4-(trifluoromethyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)-4-(trifluoromethyl)pyridazin-3(2H)-one;
5-(((2S)-1-(3-oxo-3-(3-(trifluoromethyl)-6,7,7a,8,10,11-hexahydro-9H-dipyrazino[2,3-b:1',2'-d][1,4]oxazepin-9-yl)propoxy)propan-2-yl)oxy)-4-(trifluoromethyl)pyridazin-3(2H)-one;
5-(((2S)-1-(3-oxo-3-(3-(trifluoromethyl)-5,6,6a,7,9,10-hexahydro-2H,8H-pyrazino[1,2-d]pyrazolo[4,3-b][1,4]oxazepin-8-yl)propoxy)propan-2-yl)oxy)-4-(trifluoromethyl)pyridazin-3(2H)-one;
5-(((2S)-1-(3-(3-methyl-5,6,6a,7,9,10-hexahydro-2H,8H-pyrazino[1,2-d]pyrazolo[4,3-b][1,4]oxazepin-8-yl)-3-oxopropoxy)propan-2-yl)oxy)-4-(trifluoromethyl)pyridazin-3(2H)-one;
5-(((2S)-1-(3-(2-methyl-3-(trifluoromethyl)-5,6,6a,7,9,10-hexahydro-2H,8H-pyrazino[1,2-d]pyrazolo[4,3-b][1,4]oxazepin-8-yl)-3-oxopropoxy)propan-2-yl)oxy)-4-(trifluoromethyl)pyridazin-3(2H)-one;
5-(((2S)-1-(3-oxo-3-(3-(trifluoromethyl)-5,6,6a,7,9,10-hexahydro-8H-isothiazolo[4,3-b]pyrazino[1,2-d][1,4]oxazepin-8-yl)propoxy)propan-2-yl)oxy)-4-(trifluoromethyl)pyridazin-3(2H)-one;
4-methyl-7-(3-((S)-2-((6-oxo-5-(trifluoromethyl)-1,6-dihydropyridazin-4-yl)amino)propoxy)propanoyl)-3-(trifluoromethyl)-6,7,8,9-tetrahydro-4H-furo[3,2-e]pyrazino[1,2-a]pyrazin-5(5aH)-one;
(S)-5-((1-(3-oxo-3-(2-(trifluoromethyl)-6,7-dihydropyrrolo[1,5-a:2,3-b']dipyrazin-8(9H)-yl)propoxy)propan-2-yl)amino)-4-(trifluoromethyl)pyridazin-3(2H)-one;
(S)-5-((1-(3-oxo-3-(3-(trifluoromethyl)-2,5,7,8-tetrahydro-6H-pyrazolo[4',3':4,5]pyrrolo[1,2-a]pyrazin-6-yl)propoxy)propan-2-yl)amino)-4-(trifluoromethyl)pyridazin-3(2H)-one;
(S)-5-((1-(3-(3-methyl-2,5,7,8-tetrahydro-6H-pyrazolo[4',3':4,5]pyrrolo[1,2-a]pyrazin-6-yl)-3-oxopropoxy)propan-2-yl)amino)-4-(trifluoromethyl)pyridazin-3(2H)-one;
(S)-5-((1-(3-(2-methyl-3-(trifluoromethyl)-2,5,7,8-tetrahydro-6H-pyrazolo[4',3':4,5]pyrrolo[1,2-a]pyrazin-6-yl)-3-oxopropoxy)propan-2-yl)amino)-4-(trifluoromethyl)pyridazin-3(2H)-one;
(S)-5-((1-(3-oxo-3-(3-(trifluoromethyl)-7,8-dihydroisothiazolo[4',3':4,5]pyrrolo[1,2-a]pyrazin-6(5H)-yl)propoxy)propan-2-yl)amino)-4-(trifluoromethyl)pyridazin-3(2H)-one;

-continued (S)-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)-4-(trifluoromethyl)pyridazin-3(2H)-one;
(S)-5-((1-(3-oxo-3-(3-(trifluoromethyl)-8,9-dihydroimidazo[1,2-a:4,5-b']dipyrazin-7(6H)-yl)propoxy)propan-2-yl)amino)-4-(trifluoromethyl)pyridazin-3(2H)-one;
(S)-5-((1-(3-oxo-3-(3-(trifluoromethyl)-2,5,7,8-tetrahydro-6H-pyrazolo[4',3':4,5]imidazo[1,2-a]pyrazin-6-yl)propoxy)propan-2-yl)amino)-4-(trifluoromethyl)pyridazin-3(2H)-one;
(S)-5-((1-(3-(3-methyl-2,5,7,8-tetrahydro-6H-pyrazolo[4',3':4,5]imidazo[1,2-a]pyrazin-6-yl)-3-oxopropoxy)propan-2-yl)amino)-4-(trifluoromethyl)pyridazin-3(2H)-one;
(S)-5-((1-(3-(2-methyl-3-(trifluoromethyl)-2,5,7,8-tetrahydro-6H-pyrazolo[4',3':4,5]imidazo[1,2-a]pyrazin-6-yl)-3-oxopropoxy)propan-2-yl)amino)-4-(trifluoromethyl)pyridazin-3(2H)-one;
(S)-5-((1-(3-oxo-3-(3-(trifluoromethyl)-7,8-dihydroisothiazolo[4',3':4,5]imidazo[1,2-a]pyrazin-6(5H)-yl)propoxy)propan-2-yl)amino)-4-(trifluoromethyl)pyridazin-3(2H)-one;
(S)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(10-methyl-2-(trifluoromethyl)-6,7-dihydropyrrolo[1,5-a:2,3-b']dipyrazin-8(9H)-yl)-3-oxopropoxy)propan-2-yl)amino)-4-(trifluoromethyl)pyridazin-3(2H)-one;
(S)-5-((1-(3-(4-methyl-3-(trifluoromethyl)-2,5,7,8-tetrahydro-6H-pyrazolo[4',3':4,5]pyrrolo[1,2-a]pyrazin-6-yl)-3-oxopropoxy)propan-2-yl)amino)-4-(trifluoromethyl)pyridazin-3(2H)-one;
(S)-5-((1-(3-(3,4-dimethyl-2,5,7,8-tetrahydro-6H-pyrazolo[4',3':4,5]pyrrolo[1,2-a]pyrazin-6-yl)-3-oxopropoxy)propan-2-yl)amino)-4-(trifluoromethyl)pyridazin-3(2H)-one;
(S)-5-((1-(3-(2,4-dimethyl-3-(trifluoromethyl)-2,5,7,8-tetrahydro-6H-pyrazolo[4',3':4,5]pyrrolo[1,2-a]pyrazin-6-yl)-3-oxopropoxy)propan-2-yl)amino)-4-(trifluoromethyl)pyridazin-3(2H)-one;
(S)-5-((1-(3-(4-methyl-3-(trifluoromethyl)-7,8-dihydroisothiazolo[4',3':4,5]pyrrolo[1,2-a]pyrazin-6(5H)-yl)-3-oxopropoxy)propan-2-yl)amino)-4-(trifluoromethyl)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(10-fluoro-2-(trifluoromethyl)-6,7-dihydropyrrolo[1,5-a:2,3-b']dipyrazin-8(9H)-yl)-3-oxopropoxy)propan-2-yl)amino)-4-(trifluoromethyl)pyridazin-3(2H)-one;
(S)-5-((1-(3-(4-fluoro-3-(trifluoromethyl)-2,5,7,8-tetrahydro-6H-pyrazolo[4',3':4,5]pyrrolo[1,2-a]pyrazin-6-yl)-3-oxopropoxy)propan-2-yl)amino)-4-(trifluoromethyl)pyridazin-3(2H)-one;
(S)-5-((1-(3-(4-fluoro-3-methyl-2,5,7,8-tetrahydro-6H-pyrazolo[4',3':4,5]pyrrolo[1,2-a]pyrazin-6-yl)-3-oxopropoxy)propan-2-yl)amino)-4-(trifluoromethyl)pyridazin-3(2H)-one;
(S)-5-((1-(3-(4-fluoro-2-methyl-3-(trifluoromethyl)-2,5,7,8-tetrahydro-6H-pyrazolo[4',3':4,5]pyrrolo[1,2-alpyrazin-6-yl)-3-oxopropoxy)propan-2-yl)amino)-4-(trifluoromethyl)pyridazin-3(2H)-one;
(S)-5-((1-(3-(4-fluoro-3-(trifluoromethyl)-7,8-dihydroisothiazolo[4',3':4,5]pyrrolo[1,2-a]pyrazin-6(5H)-yl)-3-oxopropoxy)propan-2-yl)amino)-4-(trifluoromethyl)pyridazin-3(2H)-one;
5-(((2S)-1-(3-oxo-3-(3-(trifluoromethyl)-5a,6,8,9-tetrahydrofuro[3,2-b]pyrazino[1,2-d][1,4]oxazin-7(5H)-yl)propoxy)propan-2-yl)amino)-4-(trifluoromethyl)pyridazin-3(2H)-one;
5-(((2S)-1-(3-oxo-3-(3-(trifluoromethyl)-5,6,6a,7,9,10-hexahydro-8H-furo[3,2-b]pyrazino[1,2-d][1,4]oxazepin-8-yl)propoxy)propan-2-yl)oxy)-4-(trifluoromethyl)pyridazin-3(2H)-one;
(S)-5-((1-(3-oxo-3-(3-(trifluoromethyl)-7,8-dihydrofuro[3',2':4,5]pyrrolo[1,2-a]pyrazin-6(5H)-yl)propoxy)propan-2-yl)amino)-4-(trifluoromethyl)pyridazin-3(2H)-one;
(S)-5-((1-(3-oxo-3-(3-(trifluoromethyl)-7,8-dihydrofuro[3',2':4,5]imidazo[1,2-a]pyrazin-6(5H)-yl)propoxy)propan-2-yl)amino)-4-(trifluoromethyl)pyridazin-3(2H)-one;
(S)-5-((1-(3-(4-methyl-3-(trifluoromethyl)-7,8-dihydrofuro[3',2':4,5]pyrrolo[1,2-a]pyrazin-6(5H)-yl)-3-oxopropoxy)propan-2-yl)amino)-4-(trifluoromethyl)pyridazin-3(2H)-one;
(S)-5-((1-(3-(4-fluoro-3-(trifluoromethyl)-7,8-dihydrofuro[3',2':4,5]pyrrolo[1,2-a]pyrazin-6(5H)-yl)-3-oxopropoxy)propan-2-yl)amino)-4-(trifluoromethyl)pyridazin-3(2H)-one;
(S)-5-((1-(3-(3-cyclopropyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-cyclobutyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(oxetan-3-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(azetidin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-morpholino-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-oxo-3-(3-(piperazin-1-yl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
(S)-5-((1-(3-(3-(4-methylpiperazin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(4-acetylpiperazin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(2-azaspiro[3,3]heptan-2-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(2-fluorophenyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(3-fluoropyridin-2-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((2S)-1-(3-(3-(hexahydrocyclopenta[c]pyrrol-2(1H)-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-cyclopropyl-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-cyclobutyl-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3-(oxetan-3-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;

-continued (S)-5-((1-(3-(3-(azetidin-1-yl)-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3-morpholino-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3-(piperazin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3-(4-methylpiperazin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(4-acetylpiperazin-1-yl)-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3-(2-azaspiro[3,3]heptan-2-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3-(2-fluorophenyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3-(3-fluoropyridin-2-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((2S)-1-(3-(5-fluoro-3-(hexahydrocyclopenta[c]pyrrol-2(1H)-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-cyclopropyl-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-cyclobutyl-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(oxetan-3-yl)-8,9-dihydropyrido[3',2':4,5]imidazo[1,2-a]pyrazin-7(6H)-yl)-3-oxopropoxy) propan-2-yl)oxy)-4-(trifluoromethyl)pyridazin-3(2H)-one;
(S)-5-((1-(3-(3-(azetidin-1-yl)-8,9-dihydropyrido[3',2':4,5]imidazo[1,2-a]pyrazin-7(6H)-yl)-3-oxopropoxy) propan-2-yl)oxy)-4-(trifluoromethyl)pyridazin-3(2H)-one;
(S)-5-((1-(3-(3-morpholino-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-oxo-3-(3-(piperazin-1-yl)-8,9-dihydropyrido[3',2':4,5]imidazo[1,2-a]pyrazin-7(6H)-yl)propoxy)propan-2-yl)oxy)-4-(trifluoromethyl)pyridazin-3(2H)-one;
(S)-5-((1-(3-(3-(4-methylpiperazin-1-yl)-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(4-acetylpiperazin-1-yl)-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(2-azaspiro[3,3]heptan-2-yl)-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(2-fluorophenyl)-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(3-fluoropyridin-2-yl)-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
5-(((2S)-1-(3-(3-(hexahydrocyclopenta[c]pyrrol-2(1H)-yl)-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
5-(((2S)-1-(3-(3-cyclopropyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-cyclobutyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-(oxetan-3-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-(azetidin-1-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-morpholino-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-oxo-3-(3-(piperazin-1-yl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((2S)-1-(3-(3-(4-methylpiperazin-1-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-(4-acetylpiperazin-1-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-(2-azaspiro[3,3]heptan-2-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-(hexahydrocyclopenta[c]pyrrol-2(1H)-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-(3-fluoropyridin-2-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-(2-fluorophenyl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-cyclopropyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-cyclobutyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-(oxetan-3-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-(azetidin-1-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-(2-azaspiro[3,3]heptan-2-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-(hexahydrocyclopenta[c]pyrrol-2(1H)-yl)-6,7,7a,8,10,11-hexahydro-9H-pyrazino[1,2-d] pyrido[3,2-b][1,4]oxazepin-9-yl)-3-oxopropoxy)propan-2-yl)oxy)-4-(trifluoromethyl)pyridazin-3(2H)-one;

5-(((2S)-1-(3-(3-morpholino-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-oxo-3-(3-(piperazin-1-yl)-6,7,7a,8,10,11-hexahydro-9H-pyrazino[1,2-d]pyrido[3,2-b][1,4]oxazepin-9-yl)propoxy)propan-2-yl)oxy)-4-(trifluoromethyl)pyridazin-3(2H)-one;
5-(((2S)-1-(3-(3-(4-methylpiperazin-1-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-(4-acetylpiperazin-1-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-(2-fluorophenyl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-(3-fluoropyridin-2-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
(S)-5-((1-(3-(3-cyclopropyl-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-cyclobutyl-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-methyl-3-(oxetan-3-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(azetidin-1-yl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-methyl-3-morpholino-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-methyl-3-(piperazin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-methyl-3-(4-methylpiperazin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(4-acetylpiperazin-1-yl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-methyl-3-(2-azaspiro[3,3]heptan-2-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(2-fluorophenyl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(3-fluoropyridin-2-yl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((2S)-1-(3-(3-(hexahydrocyclopenta[c]pyrrol-2(1H)-yl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(2-((3-(3-cyclopropyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-cyclobutyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(oxetan-3-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(azetidin-1-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-morpholino-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-oxo-3-(3-(piperazin-1-yl)-8,9-dihydropyrido[3',2':4,5]pyrrolo[1,2-a]pyrazin-7(6H)-yl)propoxy)methyl)azetidin-1-yl)-4-(trifluoromethyl)pyridazin-3(2H)-one;
5-(2-((3-(3-(4-methylpiperazin-1-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(4-acetylpiperazin-1-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(2-azaspiro[3,3]heptan-2-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(2-fluorophenyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(3-fluoropyridin-2-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(hexahydrocyclopenta[c]pyrrol-2(1H)-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-cyclopropyl-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-cyclobutyl-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3-(oxetan-3-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(azetidin-1-yl)-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3-morpholino-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3-(piperazin-1-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3-(4-methylpiperazin-1-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(4-acetylpiperazin-1-yl)-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3-(2-azaspiro[3,3]heptan-2-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;

-continued 5-(2-((3-(5-fluoro-3-(2-fluorophenyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3-(3-fluoropyridin-2-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3-(hexahydrocyclopenta[c]pyrrol-2(1H)-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-cyclopropyl-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-cyclobutyl-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-(oxetan-3-yl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-(azetidin-1-yl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-morpholino-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-oxo-3-(3-(piperazin-1-yl)-8,9-dihydropyrido[3',2':4,5]imidazo[1,2-a]pyrazin-7(6H)-yl)propoxy)methyl)azetidin-1-yl)-4-(trifluoromethyl)pyridazin-3(2H)-one;
5-(2-((3-(3-(4-methylpiperazin-1-yl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-(4-acetylpiperazin-1-yl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-(2-azaspiro[3,3]heptan-2-yl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-(2-fluorophenyl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-(3-fluoropyridin-2-yl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-(hexahydrocyclopenta[c]pyrrol-2(1H)-yl)-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-cyclopropyl-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-cyclobutyl-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-(oxetan-3-yl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-(azetidin-1-yl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-morpholino-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-oxo-3-(3-(piperazin-1-yl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-(2-((3-(3-(4-methylpiperazin-1-yl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-(4-acetylpiperazin-1-yl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-(2-azaspiro[3,3]heptan-2-yl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-(hexahydrocyclopenta[c]pyrrol-2(1H)-yl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-(3-fluoropyridin-2-yl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-(2-fluorophenyl)-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-cyclopropyl-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-cyclobutyl-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-(oxetan-3-yl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-(azetidin-1-yl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-(2-azaspiro[3,3]heptan-2-yl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-(hexahydrocyclopenta[c]pyrrol-2(1H)-yl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-morpholino-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-oxo-3-(3-(piperazin-1-yl)-6,7,7a,8,10,11-hexahydro-9H-pyrazino[1,2-d]pyrido[3,2-b][1,4]oxazepin-9-yl)propoxy)methyl)azetidin-1-yl)-4-(trifluoromethyl)pyridazin-3(2H)-one;
5-(2-((3-(3-(4-methylpiperazin-1-yl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-(4-acetylpiperazin-1-yl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-(2-fluorophenyl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-(3-fluoropyridin-2-yl)-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;

-continued 5-(2-((3-(3-cyclopropyl-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-cyclobutyl-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-methyl-3-(oxetan-3-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(azetidin-1-yl)-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-methyl-3-morpholino-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-methyl-3-(piperazin-1-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-methyl-3-(4-methylpiperazin-1-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(4-acetylpiperazin-1-yl)-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-methyl-3-(2-azaspiro[3,3]heptan-2-yl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(2-fluorophenyl)-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(3-fluoropyridin-2-yl)-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-(hexahydrocyclopenta[c]pyrrol-2(1H)-yl)-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(3-chloro-4-fluoro-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
9-(3-((S)-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
5-(((2S)-1-(3-(3,4-dimethyl-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(2-amino-3-chloro-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(3-chloro-2-methoxy-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(3-bromo-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
8-(3-((S)-2-((6-oxo-5-(trifluoromethyl)-1,6-dihydropyridazin-4-yl)amino)propoxy)propanoyl)-6,6a,7,8,9,10-hexahydropyrazino[1,2-d]pyrido[3,2-b][1,4]oxazine-3-carbonitrile;
5-(((2S)-1-(3-(3-methoxy-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(3-acetyl-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(3,4-dichloro-6a,7,9,10-tetrahydropyrazino[1,2-d]pyrido[3,2-b][1,4]oxazin-8(6H)-yl)-3-oxopropoxy)propan-2-yl)amino)-4-(trifluoromethyl)pyridazin-3(2H)-one;
5-(((2S)-1-(3-(3-methoxy-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(3-acetyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(3-chloro-4-fluoro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(3,4-dichloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(3,4-dimethyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(2-amino-3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(3-chloro-2-methoxy-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
(S)-5-((1-(3-(3-chloro-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(3-bromo-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-7-(3-(2-((6-oxo-5-(trifluoromethyl)-1,6-dihydropyridazin-4-yl)amino)propoxy)propanoyl)-6,7,8,9-tetrahydropyrido[3',2':4,5]imidazo[1,2-a]pyrazine-3-carbonitrile;
(S)-5-((1-(3-(3-methoxy-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;

-continued (S)-5-((1-(3-(3-acetyl-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-4-methyl-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-4-fluoro-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(3,4-dichloro-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(3,4-dimethyl-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(2-amino-3-chloro-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-2-methoxy-8,9-dihydropyrido[3',2':4,5]imidazo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-bromo-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-7-(3-(2-((6-oxo-5-(trifluoromethyl)-1,6-dihydropyridazin-4-yl)amino)propoxy)propanoyl)-6,7,8,9-tetrahydropyrido[3',2':4,5]pyrrolo[1,2-a]pyrazine-3-carbonitrile;
(S)-5-((1-(3-(3-methoxy-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-acetyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-4-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-4-fluoro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3,4-dichloro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3,4-dimethyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(2-amino-3-chloro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-2-methoxy-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-bromo-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-chloro-4-fluoro-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
9-(3-((S)-2-((6-oxo-5-(trifluoromethyl)-1,6-dihydropyridazin-4-yl)oxy)propoxy)propanoyl)-7,7a,8,9,10,11-hexahydro-6H-pyrazino[1,2-d]pyrido[3,2-b][1,4]oxazepine-3-carbonitrile;
5-(((2S)-1-(3-(3,4-dimethyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(2-amino-3-chloro-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-chloro-2-methoxy-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-bromo-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
8-(3-((S)-2-((6-oxo-5-(trifluoromethyl)-1,6-dihydropyridazin-4-yl)oxy)propoxy)propanoyl)-6,6a,7,8,9,10-hexahydropyrazino[1,2-d]pyrido[3,2-b][1,4]oxazine-3-carbonitrile;
5-(((2S)-1-(3-(3-methoxy-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-acetyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3,4-dichloro-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((2S)-1-(3-(3-methoxy-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-acetyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-chloro-4-fluoro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3,4-dichloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;

-continued 5-(((2S)-1-(3-(3,4-dimethyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(2-amino-3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2S)-1-(3-(3-chloro-2-methoxy-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
(S)-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)-4-(trifluoromethyl)pyridazin-3(2H)-one;
(S)-5-((1-(3-(3-chloro-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-bromo-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-7-(3-(2-((6-oxo-5-(trifluoromethyl)-1,6-dihydropyridazin-4-yl)oxy)propoxy)propanoyl)-6,7,8,9-tetrahydropyrido[3',2':4,5]imidazo[1,2-a]pyrazine-3-carbonitrile;
(S)-5-((1-(3-(3-methoxy-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-acetyl-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-4-methyl-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-4-fluoro-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3,4-dichloro-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3,4-dimethyl-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(2-amino-3-chloro-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-2-methoxy-8,9-dihydropyrido[3',2':4,5]imidazo[1,2-a]pyrazin-7(6H)-yl)-3-oxopropoxy)propan-2-yl)oxy)-4-(trifluoromethyl)pyridazin-3(2H)-one;
(S)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
(S)-5-((1-(3-(3-chloro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-bromo-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-7-(3-(2-((6-oxo-5-(trifluoromethyl)-1,6-dihydropyridazin-4-yl)oxy)propoxy)propanoyl)-6,7,8,9-tetrahydropyrido[3',2':4,5]pyrrolo[1,2-a]pyrazine-3-carbonitrile;
(S)-5-((1-(3-(3-methoxy-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-acetyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-4-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-4-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3,4-dichloro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3,4-dimethyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(2-amino-3-chloro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-2-methoxy-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-bromo-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)-4-(trifluoromethyl)pyridazin-3(2H)-one;
5-(2-((3-(3-chloro-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-chloro-4-methyl-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-chloro-4-fluoro-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
9-(3-((1-(6-oxo-5-(trifluoromethyl)-1,6-dihydropyridazin-4-yl)azetidin-2-yl)methoxy)propanoyl)-7,7a,8,9,10,11-hexahydro-6H-pyrazino[1,2-d]pyrido[3,2-b][1,4]oxazepine-3-carbonitrile;
5-(2-((3-(3,4-dimethyl-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(2-amino-3-chloro-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-chloro-2-methoxy-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-bromo-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;

-continued 8-(3-((1-(6-oxo-5-(trifluoromethyl)-1,6-dihydropyridazin-4-yl)azetidin-2-yl)methoxy)propanoyl)-6,6a,7,8,9,10-hexahydropyrazino[1,2-d]pyrido[3,2-b][1,4]oxazine-3-carbonitrile;
5-(2-((3-(3-methoxy-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-acetyl-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3,4-dichloro-6a,7,9,10-tetrahydropyrazino[1,2-d]pyrido[3,2-b][1,4]oxazin-8(6H)-yl)-3-oxopropoxy)methyl)azetidin-1-yl)-4-(trifluoromethyl)pyridazin-3(2H)-one;
5-(2-((3-(3-methoxy-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-acetyl-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-chloro-4-fluoro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3,4-dichloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-chloro-4-methyl-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3,4-dimethyl-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(2-amino-3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-chloro-2-methoxy-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-(2-((3-(3-chloro-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-bromo-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
7-(3-((1-(6-oxo-5-(trifluoromethyl)-1,6-dihydropyridazin-4-yl)azetidin-2-yl)methoxy)propanoyl)-6,7,8,9-tetrahydropyrido[3',2':4,5]imidazo[1,2-a]pyrazine-3-carbonitrile;
5-(2-((3-(3-methoxy-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-acetyl-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-4-methyl-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-4-fluoro-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3,4-dichloro-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3,4-dimethyl-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(2-amino-3-chloro-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-2-methoxy-8,9-dihydropyrido[3',2':4,5]imidazo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-bromo-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
7-(3-((1-(6-oxo-5-(trifluoromethyl)-1,6-dihydropyridazin-4-yl)azetidin-2-yl)methoxy)propanoyl)-6,7,8,9-tetrahydropyrido[3',2':4,5]pyrrolo[1,2-a]pyrazine-3-carbonitrile;
5-(2-((3-(3-methoxy-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-acetyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-4-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-4-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3,4-dichloro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3,4-dimethyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(2-amino-3-chloro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-2-methoxy-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-bromo-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-fluoro-7-(3-((1-(6-oxo-5-(trifluoromethyl)-1,6-dihydropyridazin-4-yl)azetidin-2-yl)methoxy)propanoyl)-6,7,8,9-tetrahydropyrido[3',2':4,5]pyrrolo[1,2-a]pyrazine-3-carbonitrile;
5-(2-((3-(5-fluoro-3-methoxy-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;

-continued 5-(2-((3-(3-acetyl-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-5-fluoro-4-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-4,5-difluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3,4-dichloro-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-fluoro-3,4-dimethyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(2-amino-3-chloro-5-fluoro-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-5-fluoro-2-methoxy-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-bromo-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-methyl-7-(3-((1-(6-oxo-5-(trifluoromethyl)-1,6-dihydropyridazin-4-yl)azetidin-2-yl)methoxy)propanoyl)-6,7,8,9-tetrahydropyrido[3',2':4,5]pyrrolo[1,2-a]pyrazine-3-carbonitrile;
5-(2-((3-(3-methoxy-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-acetyl-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-4,5-dimethyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-4-fluoro-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3,4-dichloro-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-oxo-3-(3,4,5-trimethyl-8,9-dihydropyrido[3',2':4,5]pyrrolo[1,2-a]pyrazin-7(6H)-yl)propoxy)methyl)azetidin-1-yl)-4-(trifluoromethyl)pyridazin-3(2H)-one;
5-(2-((3-(2-amino-3-chloro-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(3-chloro-2-methoxy-5-methyl-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-bromo-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-fluoro-7-(3-(2-((6-oxo-5-(trifluoromethyl)-1,6-dihydropyridazin-4-yl)oxy)propoxy)propanoyl)-6,7,8,9-tetrahydropyrido[3',2':4,5]pyrrolo[1,2-a]pyrazine-3-carbonitrile;
(S)-5-((1-(3-(5-fluoro-3-methoxy-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-acetyl-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-5-fluoro-4-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-4,5-difluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3,4-dichloro-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-fluoro-3,4-dimethyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(2-amino-3-chloro-5-fluoro-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-5-fluoro-2-methoxy-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-bromo-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-methyl-7-(3-(2-((6-oxo-5-(trifluoromethyl)-1,6-dihydropyridazin-4-yl)oxy)propoxy)propanoyl)-6,7,8,9-tetrahydropyrido[3',2':4,5]pyrrolo[1,2-a]pyrazine-3-carbonitrile;
(S)-5-((1-(3-(3-methoxy-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-acetyl-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-4,5-dimethyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-4-fluoro-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;

-continued (S)-5-((1-(3-(3,4-dichloro-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-oxo-3-(3,4,5-trimethyl-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
(S)-5-((1-(3-(2-amino-3-chloro-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-2-methoxy-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-chloro-5-fluoro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-bromo-5-fluoro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-fluoro-7-(3-(2-((6-oxo-5-(trifluoromethyl)-1,6-dihydropyridazin-4-yl)amino)propoxy)propanoyl)-6,7,8,9-tetrahydropyrido[3',2':4,5]pyrrolo[1,2-a]pyrazine-3-carbonitrile;
(S)-5-((1-(3-(5-fluoro-3-methoxy-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-acetyl-5-fluoro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-5-fluoro-4-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-4,5-difluoro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3,4-dichloro-5-fluoro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(5-fluoro-3,4-dimethyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(2-amino-3-chloro-5-fluoro-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-5-fluoro-2-methoxy-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-bromo-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-methyl-7-(3-(2-((6-oxo-5-(trifluoromethyl)-1,6-dihydropyridazin-4-yl)amino)propoxy)propanoyl)-6,7,8,9-tetrahydropyrido[3',2':4,5]pyrrolo[1,2-a]pyrazine-3-carbonitrile;
(S)-5-((1-(3-(3-methoxy-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-acetyl-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-4,5-dimethyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-4-fluoro-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3,4-dichloro-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-oxo-3-(3,4,5-trimethyl-8,9-dihydropyrido[3',2':4,5]pyrrolo[1,2-a]pyrazin-7(6H)-yl)propoxy)propan-2-yl)amino)-4-(trifluoromethyl)pyridazin-3(2H)-one;
(S)-5-((1-(3-(2-amino-3-chloro-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(3-chloro-2-methoxy-5-methyl-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
8-(3-((S)-2-((5-ethyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-ethyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)pyridazin-3(2H)-one;
(S)-4-ethyl-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-ethylpyridazin-3(2H)-one;
4-ethyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-ethyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-ethyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)pyridazin-3(2H)-one;
5-ethyl-8-(3-((S)-2-((5-ethyl-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-ethyl-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-ethylpyridazin-3(2H)-one;
4-ethyl-5-(((2S)-1-(3-oxo-3-(3-(trifluoromethyl)-5,6,6a,7,9,10-hexahydro-8H-pyrazino[1,2-a]pyrido[3,2-elpyrazin-8-yl)propoxy)propan-2-yl)amino)pyridazin-3(2H)-one;
4-ethyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)pyridazin-3(2H)-one;

-continued 4-ethyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)pyridazin-3(2H)-one;
4-ethyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)pyridazin-3(2H)-one;
(S)-4-ethyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-4-ethyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)pyridazin-3(2H)-one;
8-(3-((S)-2-((5-methoxy-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-methoxy-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)-4-methoxypyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-methoxypyridazin-3(2H)-one;
4-methoxy-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-methoxy-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-methoxy-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)pyridazin-3(2H)-one;
5-ethyl-8-(3-((S)-2-((5-methoxy-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-methoxy-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-methoxypyridazin-3(2H)-one;
4-methoxy-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)pyridazin-3(2H)-one;
4-methoxy-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)pyridazin-3(2H)-one;
4-methoxy-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)pyridazin-3(2H)-one;
(S)-4-methoxy-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-4-methoxy-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)pyridazin-3(2H)-one;
8-(3-((S)-2-((5-acetyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-acetyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)pyridazin-3(2H)-one;
(S)-4-acetyl-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-4-acetyl-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
4-acetyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-acetyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-acetyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)pyridazin-3(2H)-one;
8-(3-((S)-2-((5-acetyl-6-oxo-1,6-dihydropyridazin-4-yl)amino)propoxy)propanoyl)-5-ethyl-3-(trifluoromethyl)-7,8,9,10-tetrahydro-5H-pyrazino[1,2-a]pyrido[3,2-e]pyrazin-6(6aH)-one;
8-(3-((S)-2-((5-acetyl-6-oxo-1,6-dihydropyridazin-4-yl)amino)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
4-acetyl-5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)pyridazin-3(2H)-one;
4-acetyl-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)pyridazin-3(2H)-one;
4-acetyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)pyridazin-3(2H)-one;
4-acetyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)pyridazin-3(2H)-one;
4-acetyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)pyridazin-3(2H)-one;
(S)-4-acetyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-4-acetyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)pyridazin-3(2H)-one;
4-methoxy-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)pyridazin-3(2H)-one;
5-methyl-8-(3-((S)-2-((6-oxo-5-(2,2,2-trifluoroacetyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)-4-(2,2,2-trifluoroacetyl)pyridazin-3(2H)-one;

-continued (S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)-4-(2,2,2-trifluoroacetyl)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-(2,2,2-trifluoroacetyl)pyridazin-3(2H)-one;
5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(2,2,2-trifluoroacetyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(2,2,2-trifluoroacetyl)pyridazin-3(2H)-one;
5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)-4-(2,2,2-trifluoroacetyl)pyridazin-3(2H)-one;
5-ethyl-8-(3-((S)-2-((6-oxo-5-(2,2,2-trifluoroacetyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
8-(3-((S)-2-((5-ethyl-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-ethyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;
(S)-4-ethyl-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)-4-ethylpyridazin-3(2H)-one;
4-ethyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-ethyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-ethyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
5-ethyl-8-(3-((S)-2-((5-ethyl-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-ethyl-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-ethylpyridazin-3(2H)-one;
4-ethyl-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)oxy)pyridazin-3(2H)-one;
4-ethyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)oxy)pyridazin-3(2H)-one;
4-ethyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-ethyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)pyridazin-3(2H)-one;
(S)-4-ethyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-4-ethyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)pyridazin-3(2H)-one;
8-(3-((S)-2-((5-methoxy-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-methoxy-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)-4-methoxypyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)-4-methoxypyridazin-3(2H)-one;
4-methoxy-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-methoxy-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-methoxy-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
5-ethyl-8-(3-((S)-2-((5-methoxy-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-methoxy-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-methoxypyridazin-3(2H)-one;
4-methoxy-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)oxy)pyridazin-3(2H)-one;
4-methoxy-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-methoxy-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)pyridazin-3(2H)-one;
(S)-4-methoxy-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-4-methoxy-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)pyridazin-3(2H)-one;
8-(3-((S)-2-((5-acetyl-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-acetyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;

-continued (S)-4-acetyl-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-4-acetyl-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
4-acetyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-acetyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-acetyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
8-(3-((S)-2-((5-acetyl-6-oxo-1,6-dihydropyridazin-4-yl)oxy)propoxy)propanoyl)-5-ethyl-3-(trifluoromethyl)-7,8,9,10-tetrahydro-5H-pyrazino[1,2-a]pyrido[3,2-e]pyrazin-6(6aH)-one;
8-(3-((S)-2-((5-acetyl-6-oxo-1,6-dihydropyridazin-4-yl)oxy)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
4-acetyl-5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)pyridazin-3(2H)-one;
4-acetyl-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)oxy)pyridazin-3(2H)-one;
4-acetyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)oxy)pyridazin-3(2H)-one;
4-acetyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-acetyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)pyridazin-3(2H)-one;
(S)-4-acetyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-4-acetyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)pyridazin-3(2H)-one;
4-methoxy-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)oxy)pyridazin-3(2H)-one;
5-methyl-8-(3-((S)-2-((6-oxo-5-(2,2,2-trifluoroacetyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)-4-(2,2,2-trifluoroacetyl)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)-4-(2,2,2-trifluoroacetyl)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)-4-(2,2,2-trifluoroacetyl)pyridazin-3(2H)-one;
5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)-4-(2,2,2-trifluoroacetyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)-4-(2,2,2-trifluoroacetyl)pyridazin-3(2H)-one;
5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)-4-(2,2,2-trifluoroacetyl)pyridazin-3(2H)-one;
5-ethyl-8-(3-((S)-2-((6-oxo-5-(2,2,2-trifluoroacetyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((6-oxo-5-(2,2,2-trifluoroacetyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(2,2,2-trifluoroacetyl)pyridazin-3(2H)-one;
5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)oxy)-4-(2,2,2-trifluoroacetyl)pyridazin-3(2H)-one;
5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)oxy)-4-(2,2,2-trifluoroacetyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(2,2,2-trifluoroacetyl)pyridazin-3(2H)-one;
5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)-4-(2,2,2-trifluoroacetyl)pyridazin-3(2H)-one;
(S)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(2,2,2-trifluoroacetyl)pyridazin-3(2H)-one;
(S)-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)-4-(2,2,2-trifluoroacetyl)pyridazin-3(2H)-one;
5-cyclopropyl-8-(3-((S)-2-((6-oxo-5-(2,2,2-trifluoroacetyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(2,2,2-trifluoroacetyl)pyridazin-3(2H)-one;
5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)-4-(2,2,2-trifluoroacetyl)pyridazin-3(2H)-one;
5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(2,2,2-trifluoroacetyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(2,2,2-trifluoroacetyl)pyridazin-3(2H)-one;
5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)-4-(2,2,2-trifluoroacetyl)pyridazin-3(2H)-one;
(S)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(2,2,2-trifluoroacetyl)pyridazin-3(2H)-one;
(S)-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)-4-(2,2,2-trifluoroacetyl)pyridazin-3(2H)-one;

-continued 8-(3-((S)-2-((5-cyclopropyl-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-cyclopropyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;
(S)-4-cyclopropyl-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)-4-cyclopropylpyridazin-3(2H)-one;
4-cyclopropyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-cyclopropyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-cyclopropyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
8-(3-((S)-2-((5-cyclopropyl-6-oxo-1,6-dihydropyridazin-4-yl)oxy)propoxy)propanoyl)-5-ethyl-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-cyclopropyl-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-cyclopropylpyridazin-3(2H)-one;
4-cyclopropyl-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)oxy)pyridazin-3(2H)-one;
4-cyclopropyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)oxy)pyridazin-3(2H)-one;
4-cyclopropyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-cyclopropyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)pyridazin-3(2H)-one;
(S)-4-cyclopropyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-4-cyclopropyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)pyridazin-3(2H)-one;
8-(3-((S)-2-((5-isopropyl-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-isopropyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)-4-isopropylpyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)-4-isopropylpyridazin-3(2H)-one;
4-isopropyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-isopropyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-isopropyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
5-ethyl-8-(3-((S)-2-((5-isopropyl-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-isopropyl-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-isopropylpyridazin-3(2H)-one;
4-isopropyl-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)oxy)pyridazin-3(2H)-one;
4-isopropyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)oxy)pyridazin-3(2H)-one;
4-isopropyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-isopropyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)pyridazin-3(2H)-one;
(S)-4-isopropyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-4-isopropyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)pyridazin-3(2H)-one;
5-methyl-8-(3-((S)-2-((5-(methylthio)-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-4-(methylthio)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)oxy)-4-(methylthio)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)-4-(methylthio)pyridazin-3(2H)-one;
4-(methylthio)-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-(methylthio)-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-(methylthio)-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;

-continued 5-ethyl-8-(3-((S)-2-((5-(methylthio)-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-(methylthio)-6-oxo-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(methylthio)pyridazin-3(2H)-one;
4-(methylthio)-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)oxy)pyridazin-3(2H)-one;
4-(methylthio)-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-(methylthio)-5-(((2S)-1-(3-oxo-3-(3-(trifluoromethyl)-5a,6,8,9-tetrahydropyrido[3',2':4,5]imidazo [1,2-a]pyrazin-7(5H)-yl)propoxy)propan-2-yl)oxy)pyridazin-3(2H)-one;
(S)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(methylthio)pyridazin-3(2H)-one;
(S)-4-(methylthio)-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)pyridazin-3(2H)-one;
4-(methylthio)-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)oxy)pyridazin-3(2H)-one;
8-(3-((1-(5-ethyl-6-oxo-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
4-ethyl-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)pyridazin-3(2H)-one;
4-ethyl-5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-ethylpyridazin-3(2H)-one;
4-ethyl-5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)pyridazin-3(2H)-one;
4-ethyl-5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)pyridazin-3(2H)-one;
4-ethyl-5-(2-((3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)pyridazin-3(2H)-one;
5-ethyl-8-(3-((1-(5-ethyl-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((1-(5-ethyl-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-ethylpyridazin-3(2H)-one;
4-ethyl-5-(2-((3-oxo-3-(3-(trifluoromethyl)-5,6,6a,7,9,10-hexahydro-8H-pyrazino[1,2-a]pyrido[3,2-e]pyrazin-8-yl)propoxy)methyl)azetidin-1-yl)pyridazin-3(2H)-one;
4-ethyl-5-(2-((3-oxo-3-(3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)pyridazin-3(2H)-one;
4-ethyl-5-(2-((3-oxo-3-(3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)pyridazin-3(2H)-one;
4-ethyl-5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)pyridazin-3(2H)-one;
4-ethyl-5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
4-ethyl-5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)pyridazin-3(2H)-one;
8-(3-((1-(5-methoxy-6-oxo-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
4-methoxy-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)pyridazin-3(2H)-one;
5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-methoxypyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-methoxypyridazin-3(2H)-one;
4-methoxy-5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)pyridazin-3(2H)-one;
4-methoxy-5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)pyridazin-3(2H)-one;
4-methoxy-5-(2-((3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)pyridazin-3(2H)-one;
5-ethyl-8-(3-((1-(5-methoxy-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((1-(5-methoxy-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-methoxypyridazin-3(2H)-one;
4-methoxy-5-(2-((3-oxo-3-(3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)pyridazin-3(2H)-one;
4-methoxy-5-(2-((3-oxo-3-(3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)pyridazin-3(2H)-one;
4-methoxy-5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)pyridazin-3(2H)-one;

-continued 4-methoxy-5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
4-methoxy-5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)pyridazin-3(2H)-one;
8-(3-((1-(5-acetyl-6-oxo-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
4-acetyl-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)pyridazin-3(2H)-one;
4-acetyl-5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
4-acetyl-5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
4-acetyl-5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)pyridazin-3(2H)-one;
4-acetyl-5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)pyridazin-3(2H)-one;
4-acetyl-5-(2-((3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)pyridazin-3(2H)-one;
8-(3-((1-(5-acetyl-6-oxo-1,6-dihydropyridazin-4-yl)azetidin-2-yl)methoxy)propanoyl)-5-ethyl-3-(trifluoromethyl)-7,8,9,10-tetrahydro-5H-pyrazino[1,2-a]pyrido[3,2-e]pyrazin-6(6aH)-one;
8-(3-((1-(5-acetyl-6-oxo-1,6-dihydropyridazin-4-yl)azetidin-2-yl)methoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
4-acetyl-5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)pyridazin-3(2H)-one;
4-acetyl-5-(2-((3-oxo-3-(3-(trifluoromethyl)-5,6,6a,7,9,10-hexahydro-8H-pyrazino[1,2-a]pyrido[3,2-e]pyrazin-8-yl)propoxy)methyl)azetidin-1-yl)pyridazin-3(2H)-one;
4-acetyl-5-(2-((3-oxo-3-(3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)pyridazin-3(2H)-one;
4-acetyl-5-(2-((3-oxo-3-(3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)pyridazin-3(2H)-one;
4-acetyl-5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)pyridazin-3(2H)-one;
4-acetyl-5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
4-acetyl-5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)pyridazin-3(2H)-one;
4-methoxy-5-(2-((3-oxo-3-(3-(trifluoromethyl)-5,6,6a,7,9,10-hexahydro-8H-pyrazino[1,2-a]pyrido[3,2-e]pyrazin-8-yl)propoxy)methyl)azetidin-1-yl)pyridazin-3(2H)-one;
5-methyl-8-(3-((1-(6-oxo-5-(2,2,2-trifluoroacetyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)-4-(2,2,2-trifluoroacetyl)pyridazin-3(2H)-one;
5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(2,2,2-trifluoroacetyl)pyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(2,2,2-trifluoroacetyl)pyridazin-3(2H)-one;
5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(2,2,2-trifluoroacetyl)pyridazin-3(2H)-one;
5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)-4-(2,2,2-trifluoroacetyl)pyridazin-3(2H)-one;
5-(2-((3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)-4-(2,2,2-trifluoroacetyl)pyridazin-3(2H)-one;
5-ethyl-8-(3-((1-(6-oxo-5-(2,2,2-trifluoroacetyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((1-(6-oxo-5-(2,2,2-trifluoroacetyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(2,2,2-trifluoroacetyl)pyridazin-3(2H)-one;
5-(2-((3-oxo-3-(3-(trifluoromethyl)-5,6,6a,7,9,10-hexahydro-8H-pyrazino[1,2-a]pyrido[3,2-e]pyrazin-8-yl)propoxy)methyl)azetidin-1-yl)-4-(2,2,2-trifluoroacetyl)pyridazin-3(2H)-one;
5-(2-((3-oxo-3-(3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)-4-(2,2,2-trifluoroacetyl)pyridazin-3(2H)-one;
5-(2-((3-oxo-3-(3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)-4-(2,2,2-trifluoroacetyl)pyridazin-3(2H)-one;
5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)-4-(2,2,2-trifluoroacetyl)pyridazin-3(2H)-one;
5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(2,2,2-trifluoroacetyl)pyridazin-3(2H)-one;
5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)-4-(2,2,2-trifluoroacetyl)pyridazin-3(2H)-one;
8-(3-((1-(5-cyclopropyl-6-oxo-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
4-cyclopropyl-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)pyridazin-3(2H)-one;
4-cyclopropyl-5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-cyclopropylpyridazin-3(2H)-one;

-continued 4-cyclopropyl-5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)pyridazin-3(2H)-one;
4-cyclopropyl-5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)pyridazin-3(2H)-one;
4-cyclopropyl-5-(2-((3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)pyridazin-3(2H)-one;
8-(3-((1-(5-cyclopropyl-6-oxo-1,6-dihydropyridazin-4-yl)azetidin-2-yl)methoxy)propanoyl)-5-ethyl-3-(trifluoromethyl)-7,8,9,10-tetrahydro-5H-pyrazino[1,2-a]pyrido[3,2-e]pyrazin-6(6aH)-one;
5-cyclopropyl-8-(3-((1-(5-cyclopropyl-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-cyclopropylpyridazin-3(2H)-one;
4-cyclopropyl-5-(2-((3-oxo-3-(3-(trifluoromethyl)-5,6,6a,7,9,10-hexahydro-8H-pyrazino[1,2-a]pyrido[3,2-e]pyrazin-8-yl)propoxy)methyl)azetidin-1-yl)pyridazin-3(2H)-one;
4-cyclopropyl-5-(2-((3-oxo-3-(3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)pyridazin-3(2H)-one;
4-cyclopropyl-5-(2-((3-oxo-3-(3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)pyridazin-3(2H)-one;
4-cyclopropyl-5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)pyridazin-3(2H)-one;
4-cyclopropyl-5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
4-cyclopropyl-5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)pyridazin-3(2H)-one;
8-(3-((1-(5-isopropyl-6-oxo-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
4-isopropyl-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)pyridazin-3(2H)-one;
5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-isopropylpyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-isopropylpyridazin-3(2H)-one;
4-isopropyl-5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)pyridazin-3(2H)-one;
4-isopropyl-5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)pyridazin-3(2H)-one;
4-isopropyl-5-(2-((3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)pyridazin-3(2H)-one;
5-ethyl-8-(3-((1-(5-isopropyl-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((1-(5-isopropyl-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-isopropylpyridazin-3(2H)-one;
4-isopropyl-5-(2-((3-oxo-3-(3-(trifluoromethyl)-5,6,6a,7,9,10-hexahydro-8H-pyrazino[1,2-a]pyrido[3,2-e]pyrazin-8-yl)propoxy)methyl)azetidin-1-yl)pyridazin-3(2H)-one;
4-isopropyl-5-(2-((3-oxo-3-(3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)pyridazin-3(2H)-one;
4-isopropyl-5-(2-((3-oxo-3-(3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)pyridazin-3(2H)-one;
4-isopropyl-5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)pyridazin-3(2H)-one;
4-isopropyl-5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
4-isopropyl-5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)pyridazin-3(2H)-one;
5-methyl-8-(3-((1-(5-(methylthio)-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
4-(methylthio)-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)pyridazin-3(2H)-one;
5-(2-((3-(5-fluoro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(methylthio)pyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(methylthio)pyridazin-3(2H)-one;
4-(methylthio)-5-(2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)pyridazin-3(2H)-one;
4-(methylthio)-5-(2-((3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)pyridazin-3(2H)-one;
4-(methylthio)-5-(2-((3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)pyridazin-3(2H)-one;
5-ethyl-8-(3-((1-(5-(methylthio)-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((1-(5-(methylthio)-6-oxo-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(methylthio)pyridazin-3(2H)-one;

-continued 4-(methylthio)-5-(2-((3-oxo-3-(3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)pyridazin-3(2H)-one;
4-(methylthio)-5-(2-((3-oxo-3-(3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)pyridazin-3(2H)-one;
4-(methylthio)-5-(2-((3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)pyridazin-3(2H)-one;
5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(methylthio)pyridazin-3(2H)-one;
4-(methylthio)-5-(2-((3-oxo-3-(3-(trifluoromethyl)-8,9-dihydropyrido[3',2':4,5]imidazo[1,2-a]pyrazin-7(6H)-yl)propoxy)methyl)azetidin-1-yl)pyridazin-3(2H)-one;
4-(methylthio)-5-(2-((3-oxo-3-(3-(trifluoromethyl)-5,6,6a,7,9,10-hexahydro-8H-pyrazino[1,2-a]pyrido[3,2-e]pyrazin-8-yl)propoxy)methyl)azetidin-1-yl)pyridazin-3(2H)-one;
8-(3-((S)-2-((5-cyclopropyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-cyclopropyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)pyridazin-3(2H)-one;
(S)-4-cyclopropyl-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-cyclopropylpyridazin-3(2H)-one;
4-cyclopropyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-cyclopropyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-cyclopropyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)pyridazin-3(2H)-one;
8-(3-((S)-2-((5-cyclopropyl-6-oxo-1,6-dihydropyridazin-4-yl)amino)propoxy)propanoyl)-5-ethyl-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-cyclopropyl-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-cyclopropylpyridazin-3(2H)-one;
4-cyclopropyl-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)pyridazin-3(2H)-one;
4-cyclopropyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)pyridazin-3(2H)-one;
4-cyclopropyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)pyridazin-3(2H)-one;
4-cyclopropyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)pyridazin-3(2H)-one;
(S)-4-cyclopropyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-4-cyclopropyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)pyridazin-3(2H)-one;
8-(3-((S)-2-((5-isopropyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-isopropyl-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)-4-isopropylpyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-isopropylpyridazin-3(2H)-one;
4-isopropyl-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-isopropyl-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-isopropyl-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)pyridazin-3(2H)-one;
5-ethyl-8-(3-((S)-2-((5-isopropyl-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-isopropyl-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-isopropylpyridazin-3(2H)-one;
4-isopropyl-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)pyridazin-3(2H)-one;
4-isopropyl-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)pyridazin-3(2H)-one;
4-isopropyl-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)pyridazin-3(2H)-one;
4-isopropyl-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)pyridazin-3(2H)-one;
(S)-4-isopropyl-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
(S)-4-isopropyl-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)pyridazin-3(2H)-one;

-continued 5-methyl-8-(3-((S)-2-((5-(methylthio)-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-4-(methylthio)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)pyridazin-3(2H)-one;
(S)-5-((1-(3-(5-fluoro-3-(trifluoromethyl)-8,9-dihydropyrido[3',2':4,5]pyrrolo[1,2-a]pyrazin-7(6H)-yl)-3-oxopropoxy)propan-2-yl)amino)-4-(methylthio)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-(methylthio)pyridazin-3(2H)-one;
4-(methylthio)-5-(((2S)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-(methylthio)-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-(methylthio)-5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)pyridazin-3(2H)-one;
5-ethyl-8-(3-((S)-2-((5-(methylthio)-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((5-(methylthio)-6-oxo-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(methylthio)pyridazin-3(2H)-one;
4-(methylthio)-5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)pyridazin-3(2H)-one;
4-(methylthio)-5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)pyridazin-3(2H)-one;
4-(methylthio)-5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)pyridazin-3(2H)-one;
(S)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(methylthio)pyridazin-3(2H)-one;
(S)-4-(methylthio)-5-((1-(3-oxo-3-(3-(trifluoromethyl)-8,9-dihydropyrido[3',2':4,5]imidazo[1,2-a]pyrazin-7(6H)-yl)propoxy)propan-2-yl)amino)pyridazin-3(2H)-one;
4-(methylthio)-5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)pyridazin-3(2H)-one;
8-(2-hydroxy-3-((S)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
5-ethyl-8-(2-hydroxy-3-((S)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-5a,6,8,9-tetrahydropyrido[3',2':4,5]imidazo[1,2-a]pyrazin-7(5H)-yl)propoxy)-3-methoxypropan-2-yl)amino)-4-(trifluoromethyl)pyridazin-3(2H)-one;
5-cyclopropyl-8-(2-hydroxy-3-((S)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-6,7,7a,8,10,11-hexahydro-9H-pyrazino[1,2-d]pyrido[3,2-b][1,4]oxazepin-9-yl)propoxy)-3-methoxypropan-2-yl)amino)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]oxazepin-9-yl)-2-hydroxy-3-oxopropoxy)-3-methoxypropan-2-yl)amino)-4-(trifluoromethyl)pyridazin-3(2H)-one;
5-(((2S)-1-(2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)-3-methoxypropan-2-yl)amino)-4-(trifluoromethyl)pyridazin-3(2H)-one;
8-(2-hydroxy-3-((S)-3-methoxy-2-((6-oxo-5-(trifluoromethyl)-1,6-dihydropyridazin-4-yl)amino)propoxy)propanoyl)-5-isopropyl-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-8,9-dihydropyrido[3',2':4,5]pyrrolo[1,2-a]pyrazin-7(6H)-yl)propoxy)-3-methoxypropan-2-yl)amino)-4-(trifluoromethyl)pyridazin-3(2H)-one;
8-(2-hydroxy-3-((S)-3-methoxy-2-((6-oxo-5-(trifluoromethyl)-1,6-dihydropyridazin-4-yl)amino)propoxy)propanoyl)-5-(methyl-d3)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-4-methyl-6,7,7a,8,10,11-hexahydro-9H-pyrazino[1,2-d]pyrido[3,2-b][1,4]oxazepin-9-yl)-2-hydroxy-3-oxopropoxy)-3-methoxypropan-2-yl)amino)-4-(trifluoromethyl)pyridazin-3(2H)-one;
5-(((2S)-1-(3-(3-chloro-6,7,7a,8,10,11-hexahydro-9H-dipyrazino[2,3-b:1',2'-d][1,4]oxazepin-9-yl)-2-hydroxy-3-oxopropoxy)-3-methoxypropan-2-yl)amino)-4-(trifluoromethyl)pyridazin-3(2H)-one;
5-(((2S)-1-(2-hydroxy-3-oxo-3-(3-(trifluoromethyl)-6,7,7a,8,10,11-hexahydro-9H-dipyrazino[2,3-b:1',2'-d][1,4]oxazepin-9-yl)propoxy)-3-methoxypropan-2-yl)amino)-4-(trifluoromethyl)pyridazin-3(2H)-one;
5-(((2S)-1-(2-hydroxy-3-oxo-3-(3-(trifluoromethyl)-6a,7,9,10-tetrahydrodipyrazino[2,3-b:1',2'-d][1,4]oxazin-8(6H)-yl)propoxy)-3-methoxypropan-2-yl)amino)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]oxazin-8(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]oxazin-8(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-6a,7,9,10-tetrahydrodipyrazino[2,3-b:1',2'-d][1,4]oxazin-8(6H)-yl)-2-hydroxy-3-oxopropoxy)-3-methoxypropan-2-yl)amino)-4-(trifluoromethyl)pyridazin-3(2H)-one;
8-(2-hydroxy-3-((S)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-dipyrazino[1,2-a:2',3'-e]pyrazin-6(6aH)-one;
9-(2-hydroxy-3-((S)-3-methoxy-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
8-(2-hydroxy-3-((S)-3-methoxy-2-((6-oxo-5-(trifluoromethyl)-1,6-dihydropyridazin-4-yl)amino)propoxy)propanoyl)-6,6a,7,8,9,10-hexahydropyrazino[1,2-d]pyrido[3,2-b][1,4]oxazine-3-carbonitrile;
8-(3-((S)-2-((5-chloro-6-oxo-1,6-dihydropyridazin-4-yl)amino)-3-methoxypropoxy)-2-hydroxypropanoyl)-5-methyl-3-(trifluoromethyl)-7,8,9,10-tetrahydro-5H-pyrazino[1,2-a]pyrido[3,2-e]pyrazin-6(6aH)-one;
4-chloro-5-(((2S)-1-(3-(3-chloro-6,7,7a,8,10,11-hexahydro-9H-pyrazino[1,2-d]pyrido[3,2-b][1,4]oxazepin-9-yl)-2-hydroxy-3-oxopropoxy)-3-methoxypropan-2-yl)amino)pyridazin-3(2H)-one;

-continued 4-chloro-5-(((2S)-1-(2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)-3-methoxypropan-2-yl)amino)pyridazin-3(2H)-one;
5-(((2S)-1-(2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)-3-methoxypropan-2-yl)amino)-4-(trifluoromethyl)pyridazin-3(2H)-one;
5-(((2S)-1-(2-hydroxy-3-oxo-3-(3-(trifluoromethyl)-6a,7,9,10-tetrahydrodipyrazino[2,3-b:1',2'-d][1,4]thiazin-8(6H)-yl)propoxy)-3-methoxypropan-2-yl)amino)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]thiazin-8(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]thiazin-8(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-6a,7,9,10-tetrahydrodipyrazino[2,3-b:1',2'-d][1,4]thiazin-8(6H)-yl)-2-hydroxy-3-oxopropoxy)-3-methoxypropan-2-yl)amino)-4-(trifluoromethyl)pyridazin-3(2H)-one;
8-(2-hydroxy-3-((S)-3-methoxy-2-((6-oxo-5-(trifluoromethyl)-1,6-dihydropyridazin-4-yl)amino)propoxy)propanoyl)-6,6a,7,8,9,10-hexahydropyrazino[1,2-d]pyrido[3,2-b][1,4]thiazine-3-carbonitrile;
4-chloro-5-(((2S)-1-(2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)-3-methoxypropan-2-yl)amino)pyridazin-3(2H)-one;
5-(((2S)-1-(3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)-3-methoxypropan-2-yl)amino)-4-(trifluoromethyl)pyridazin-3(2H)-one;
5-(((2S)-1-(3-(5,5-difluoro-3-(trifluoromethyl)-5,6,6a,7,9,10-hexahydro-8H-pyrido[1,6-a:2,3-b']dipyrazin-8-yl)-2-hydroxy-3-oxopropoxy)-3-methoxypropan-2-yl)amino)-4-(trifluoromethyl)pyridazin-3(2H)-one;
5-(((2S)-1-(3-(3-chloro-5,5-difluoro-5,6,6a,7,9,10-hexahydro-8H-pyrazino[1,2-a][1,8]naphthyridin-8-yl)-2-hydroxy-3-oxopropoxy)-3-methoxypropan-2-yl)amino)-4-(trifluoromethyl)pyridazin-3(2H)-one;
5-(((2S)-1-(3-(3-chloro-5,5-difluoro-4-methyl-5,6,6a,7,9,10-hexahydro-8H-pyrazino[1,2-a][1,8]naphthyridin-8-yl)-2-hydroxy-3-oxopropoxy)-3-methoxypropan-2-yl)amino)-4-(trifluoromethyl)pyridazin-3(2H)-one;
5-(((2S)-1-(3-(3-chloro-5,5-difluoro-5,6,6a,7,9,10-hexahydro-8H-pyrido[1,6-a:2,3-b']dipyrazin-8-yl)-2-hydroxy-3-oxopropoxy)-3-methoxypropan-2-yl)amino)-4-(trifluoromethyl)pyridazin-3(2H)-one;
5,5-difluoro-8-(2-hydroxy-3-((S)-3-methoxy-2-((6-oxo-5-(trifluoromethyl)-1,6-dihydropyridazin-4-yl)amino)propoxy)propanoyl)-6,6a,7,8,9,10-hexahydro-5H-pyrazino[1,2-a][1,8]naphthyridine-3-carbonitrile;
4-chloro-5-(((2S)-1-(3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)-3-methoxypropan-2-yl)amino)pyridazin-3(2H)-one;
5-(((2S)-1-(3-(3-chloro-5a,6,8,9-tetrahydropyrido[3',2':4,5]imidazo[1,2-a]pyrazin-7(5H)-yl)-2-hydroxy-3-oxopropoxy)-3-methoxypropan-2-yl)amino)-4-(trifluoromethyl)pyridazin-3(2H)-one;
7-(2-hydroxy-3-((S)-3-methoxy-2-((6-oxo-5-(trifluoromethyl)-1,6-dihydropyridazin-4-yl)amino)propoxy)propanoyl)-5,5a,6,7,8,9-hexahydropyrido[3',2':4,5]imidazo[1,2-a]pyrazine-3-carbonitrile;
4-chloro-5-(((2S)-1-(2-hydroxy-3-oxo-3-(3-(trifluoromethyl)-5a,6,8,9-tetrahydropyrido[3',2':4,5]imidazo[1,2-a]pyrazin-7(5H)-yl)propoxy)-3-methoxypropan-2-yl)amino)pyridazin-3(2H)-one;
5-(((2S)-1-(2-hydroxy-3-(5-methyl-3-(trifluoromethyl)-5a,6,8,9-tetrahydropyrido[3',2':4,5]imidazo[1,2-a]pyrazin-7(5H)-yl)-3-oxopropoxy)-3-methoxypropan-2-yl)amino)-4-(trifluoromethyl)pyridazin-3(2H)-one5-(((2S)-1-(3-(5-cyclopropyl-3-(trifluoromethyl)-5a,6,8,9-tetrahydropyrido[3',2':4,5]imidazo[1,2-a]pyrazin-7(5H)-yl)-2-hydroxy-3-oxopropoxy)-3-methoxypropan-2-yl)amino)-4-(trifluoromethyl)pyridazin-3(2H)-one;
5-(((2S)-1-(2-hydroxy-3-(5-methyl-3-(trifluoromethyl)-5a,6,8,9-tetrahydroimidazo[1,2-a:4,5-b']dipyrazin-7(5H)-yl)-3-oxopropoxy)-3-methoxypropan-2-yl)amino)-4-(trifluoromethyl)pyridazin-3(2H)-one;
5-(((2S)-1-(3-(3-chloro-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
7-(2-hydroxy-3-((S)-3-methoxy-2-((6-oxo-5-(trifluoromethyl)-1,6-dihydropyridazin-4-yl)amino)propoxy)propanoyl)-6,7,8,9-tetrahydropyrido[3',2':4,5]pyrrolo[1,2-a]pyrazine-3-carbonitrile;
5-(((2S)-1-(2-hydroxy-3-oxo-3-(2-(trifluoromethyl)-6,7-dihydropyrrolo[1,5-a:2,3-b']dipyrazin-8(9H)-yl)propoxy)-3-methoxypropan-2-yl)amino)-4-(trifluoromethyl)pyridazin-3(2H)-one;
5-(((2S)-1-(3-(3-chloro-4-methyl-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-4-fluoro-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
4-chloro-5-(((2S)-1-(2-hydroxy-3-oxo-3-(3-(trifluoromethyl)-8,9-dihydropyrido[3',2':4,5]pyrrolo[1,2-a]pyrazin-7(6H)-yl)propoxy)-3-methoxypropan-2-yl)amino)pyridazin-3(2H)-one;
5-(((2S)-1-(2-hydroxy-3-oxo-3-(3-(trifluoromethyl)-8,9-dihydropyrido[3',2':4,5]imidazo[1,2-a]pyrazin-7(6H)-yl)propoxy)-3-methoxypropan-2-yl)amino)-4-(trifluoromethyl)pyridazin-3(2H)-one;
5-(((2S)-1-(3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(3-(5-chloro-3-(trifluoromethyl)-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(2-hydroxy-3-(5-methyl-3-(trifluoromethyl)-8,9-dihydropyrido[3',2':4,5]pyrrolo[1,2-a]pyrazin-7(6H)-yl)-3-oxopropoxy)-3-methoxypropan-2-yl)amino)-4-(trifluoromethyl)pyridazin-3(2H)-one;
5-(((2S)-1-(3-(5-cyclopropyl-3-(trifluoromethyl)-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(3-(5-ethyl-3-(trifluoromethyl)-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
7-(2-hydroxy-3-((S)-3-methoxy-2-((6-oxo-5-(trifluoromethyl)-1,6-dihydropyridazin-4-yl)amino)propoxy)propanoyl)-3-(trifluoromethyl)-6,7,8,9-tetrahydropyrido[3',2':4,5]pyrrolo[1,2-a]pyrazine-5-carbonitrile;
5-(((2S)-1-(3-(3-chloro-5-fluoro-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-4,5-difluoro-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-5-fluoro-4-methyl-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-fluoro-7-(2-hydroxy-3-((S)-3-methoxy-2-((6-oxo-5-(trifluoromethyl)-1,6-dihydropyridazin-4-yl)amino)propoxy)propanoyl)-6,7,8,9-tetrahydropyrido[3',2':4,5]pyrrolo[1,2-a]pyrazine-3-carbonitrile;

5-(((2S)-1-(3-(10-fluoro-2-(trifluoromethyl)-6,7-dihydropyrrolo[1,5-a:2,3-b']dipyrazin-8(9H)-yl)-2-hydroxy-3-oxopropoxy)-3-methoxypropan-2-yl)amino)-4-(trifluoromethyl)pyridazin-3(2H)-one;
4-chloro-5-(((2S)-1-(3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)-3-methoxypropan-2-yl)amino)pyridazin-3(2H)-one;
5-(((2S)-1-(3-(3-chloro-5-methyl-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-4-fluoro-5-methyl-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
5-(((2S)-1-(3-(3-chloro-4,5-dimethyl-8,9-dihydropyrido[3',2':4,5]pyrrolo[1,2-a]pyrazin-7(6H)-yl)-2-hydroxy-3-oxopropoxy)-3-methoxypropan-2-yl)amino)-4-(trifluoromethyl)pyridazin-3(2H)-one;
7-(2-hydroxy-3-((S)-3-methoxy-2-((6-oxo-5-(trifluoromethyl)-1,6-dihydropyridazin-4-yl)amino)propoxy)propanoyl)-5-methyl-6,7,8,9-tetrahydropyrido[3',2':4,5]pyrrolo[1,2-a]pyrazine-3-carbonitrile;
5-(((2S)-1-(2-hydroxy-3-(10-methyl-2-(trifluoromethyl)-6,7-dihydropyrrolo[1,5-a:2,3-b']dipyrazin-8(9H)-yl)-3-oxopropoxy)-3-methoxypropan-2-yl)amino)-4-(trifluoromethyl)pyridazin-3(2H)-one;
4-chloro-5-(((2S)-1-(2-hydroxy-3-(5-methyl-3-(trifluoromethyl)-8,9-dihydropyrido[3',2':4,5]pyrrolo[1,2-a]pyrazin-7(6H)-yl)-3-oxopropoxy)-3-methoxypropan-2-yl)amino)pyridazin-3(2H)-one;
8-(2-hydroxy-3-((2-(6-oxo-5-(trifluoromethyl)-1,6-dihydropyridazin-4-yl)isoindolin-1-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
5-ethyl-8-(2-hydroxy-3-((2-(6-oxo-5-(trifluoromethyl)-1,6-dihydropyridazin-4-yl)isoindolin-1-yl)methoxy)propanoyl)-3-(trifluoromethyl)-7,8,9,10-tetrahydro-5H-pyrazino[1,2-a]pyrido[3,2-e]pyrazin-6(6aH)-one:
5-(1-((2-hydroxy-3-oxo-3-(3-(trifluoromethyl)-5a,6,8,9-tetrahydropyrido[3',2':4,5]imidazo[1,2-a]pyrazin-7(5H)-yl)propoxy)methyl)isoindolin-2-yl)-4-(trifluoromethyl)pyridazin-3(2H)-one;
5-cyclopropyl-8-(2-hydroxy-3-((2-(6-oxo-5-(trifluoromethyl)-1,6-dihydropyridazin-4-yl)isoindolin-1-yl)methoxy)propanoyl)-3-(trifluoromethyl)-7,8,9,10-tetrahydro-5H-pyrazino[1,2-a]pyrido[3,2-e]pyrazin-6(6aH)-one;
5-(1-((2-hydroxy-3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)isoindolin-2-yl)-4-(trifluoromethyl)pyridazin-3(2H)-one;
5-(1-((3-(3-chloro-6,7,7a,8,10,11-hexahydro-9H-pyrazino[1,2-d]pyrido[3,2-b][1,4]oxazepin-9-yl)-2-hydroxy-3-oxopropoxy)methyl)isoindolin-2-yl)-4-(trifluoromethyl)pyridazin-3(2H)-one;
5-(1-((2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)methyl)isoindolin-2-yl)-4-(trifluoromethyl)pyridazin-3(2H)-one;
8-(2-hydroxy-3-((2-(6-oxo-5-(trifluoromethyl)-1,6-dihydropyridazin-4-yl)isoindolin-1-yl)methoxy)propanoyl)-5-isopropyl-3-(trifluoromethyl)-7,8,9,10-tetrahydro-5H-pyrazino[1,2-a]pyrido[3,2-e]pyrazin-6(6aH)-one;
5-(1-((2-hydroxy-3-oxo-3-(3-(trifluoromethyl)-8,9-dihydropyrido[3',2':4,5]pyrrolo[1,2-a]pyrazin-7(6H)-yl)propoxy)methyl)isoindolin-2-yl)-4-(trifluoromethyl)pyridazin-3(2H)-one;
8-(2-hydroxy-3-((2-(6-oxo-5-(trifluoromethyl)-1,6-dihydropyridazin-4-yl)isoindolin-1-yl)methoxy)propanoyl)-5-(methyl-d3)-3-(trifluoromethyl)-7,8,9,10-tetrahydro-5H-pyrazino[1,2-a]pyrido[3,2-e]pyrazin-6(6aH)-one;
5-(1-((3-(3-chloro-4-methyl-6,7,7a,8,10,11-hexahydro-9H-pyrazino[1,2-d]pyrido[3,2-b][1,4]oxazepin-9-yl)-2-hydroxy-3-oxopropoxy)methyl)isoindolin-2-yl)-4-(trifluoromethyl)pyridazin-3(2H)-one;
5-(1-((3-(3-chloro-6,7,7a,8,10,11-hexahydro-9H-dipyrazino[2,3-b:1',2'-d][1,4]oxazepin-9-yl)-2-hydroxy-3-oxopropoxy)methyl)isoindolin-2-yl)-4-(trifluoromethyl)pyridazin-3(2H)-one;
5-(1-((2-hydroxy-3-oxo-3-(3-(trifluoromethyl)-6,7,7a,8,10,11-hexahydro-9H-dipyrazino[2,3-b:1',2'-d][1,4]oxazepin-9-yl)propoxy)methyl)isoindolin-2-yl)-4-(trifluoromethyl)pyridazin-3(2H)-one;
5-(1-((2-hydroxy-3-oxo-3-(3-(trifluoromethyl)-6a,7,9,10-tetrahydrodipyrazino[2,3-b:1',2'-d][1,4]oxazin-8(6H)-yl)propoxy)methyl)isoindolin-2-yl)-4-(trifluoromethyl)pyridazin-3(2H)-one;
5-(1-((3-(3-chloro-6a,7,9,10-tetrahydropyrazino[1,2-d]pyrido[3,2-b][1,4]oxazin-8(6H)-yl)-2-hydroxy-3-oxopropoxy)methyl)isoindolin-2-yl)-4-(trifluoromethyl)pyridazin-3(2H)-one;
5-(1-((3-(3-chloro-4-methyl-6a,7,9,10-tetrahydropyrazino[1,2-d]pyrido[3,2-b][1,4]oxazin-8(6H)-yl)-2-hydroxy-3-oxopropoxy)methyl)isoindolin-2-yl)-4-(trifluoromethyl)pyridazin-3(2H)-one;
5-(1-((3-(3-chloro-6a,7,9,10-tetrahydrodipyrazino[2,3-b:1',2'-d][1,4]oxazin-8(6H)-yl)-2-hydroxy-3-oxopropoxy)methyl)isoindolin-2-yl)-4-(trifluoromethyl)pyridazin-3(2H)-one;
8-(2-hydroxy-3-((2-(6-oxo-5-(trifluoromethyl)-1,6-dihydropyridazin-4-yl)isoindolin-1-yl)methoxy)propanoyl)-5-methyl-3-(trifluoromethyl)-7,8,9,10-tetrahydro-5H-dipyrazino[1,2-a:2',3'-e]pyrazin-6(6aH)-one;
9-(2-hydroxy-3-((2-(6-oxo-5-(trifluoromethyl)-1,6-dihydropyridazin-4-yl)isoindolin-1-yl)methoxy)propanoyl)-7,7a,8,9,10,11-hexahydro-6H-pyrazino[1,2-d]pyrido[3,2-b][1,4]oxazepine-3-carbonitrile;
8-(2-hydroxy-3-((2-(6-oxo-5-(trifluoromethyl)-1,6-dihydropyridazin-4-yl)isoindolin-1-yl)methoxy)propanoyl)-6,6a,7,8,9,10-hexahydropyrazino[1,2-d]pyrido[3,2-b][1,4]oxazine-3-carbonitrile;
8-(3-((2-(5-chloro-6-oxo-1,6-dihydropyridazin-4-yl)isoindolin-1-yl)methoxy)-2-hydroxypropanoyl)-5-methyl-3-(trifluoromethyl)-7,8,9,10-tetrahydro-5H-pyrazino[1,2-a]pyrido[3,2-e]pyrazin-6(6aH)-one;
4-chloro-5-(1-((3-(3-chloro-6,7,7a,8,10,11-hexahydro-9H-pyrazino[1,2-d]pyrido[3,2-b][1,4]oxazepin-9-yl)-2-hydroxy-3-oxopropoxy)methyl)isoindolin-2-yl)pyridazin-3(2H)-one;
4-chloro-5-(1-((2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)methyl)isoindolin-2-yl)pyridazin-3(2H)-one;
5-(1-((2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)methyl)isoindolin-2-yl)-4-(trifluoromethyl)pyridazin-3(2H)-one;
5-(1-((2-hydroxy-3-oxo-3-(3-(trifluoromethyl)-6a,7,9,10-tetrahydrodipyrazino[2,3-b:1',2'-d][1,4]thiazin-8(6H)-yl)propoxy)methyl)isoindolin-2-yl)-4-(trifluoromethyl)pyridazin-3(2H)-one;
5-(1-((3-(3-chloro-6a,7,9,10-tetrahydropyrazino[1,2-d]pyrido[3,2-b][1,4]thiazin-8(6H)-yl)-2-hydroxy-3-oxopropoxy)methyl)isoindolin-2-yl)-4-(trifluoromethyl)pyridazin-3(2H)-one;
5-(1-((3-(3-chloro-4-methyl-6a,7,9,10-tetrahydropyrazino[1,2-d]pyrido[3,2-b][1,4]thiazin-8(6H)-yl)-2-hydroxy-3-oxopropoxy)methyl)isoindolin-2-yl)-4-(trifluoromethyl)pyridazin-3(2H)-one;
5-(1-((3-(3-chloro-6a,7,9,10-tetrahydrodipyrazino[2,3-b:1',2'-d][1,4]thiazin-8(6H)-yl)-2-hydroxy-3-oxopropoxy)methyl)isoindolin-2-yl)-4-(trifluoromethyl)pyridazin-3(2H)-one;
8-(2-hydroxy-3-((2-(6-oxo-5-(trifluoromethyl)-1,6-dihydropyridazin-4-yl)isoindolin-1-yl)methoxy)propanoyl)-6,6a,7,8,9,10-hexahydropyrazino[1,2-d]pyrido[3,2-b][1,4]thiazine-3-carbonitrile;
4-chloro-5-(1-((2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)methyl)isoindolin-2-yl)pyridazin-3(2H)-one;
5-(1-((3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)methyl)isoindolin-2-yl)-4-(trifluoromethyl)pyridazin-3(2H)-one;

-continued 5-(1-((3-(5,5-difluoro-3-(trifluoromethyl)-5,6,6a,7,9,10-hexahydro-8H-pyrido[1,6-a:2,3-b']dipyrazin-8-yl)-2-hydroxy-3-oxopropoxy)methyl)isoindolin-2-yl)-4-(trifluoromethyl)pyridazin-3(2H)-one;
5-(1-((3-(3-chloro-5,5-difluoro-5,6,6a,7,9,10-hexahydro-8H-pyrazino[1,2-a][1,8]naphthyridin-8-yl)-2-hydroxy-3-oxopropoxy)methyl)isoindolin-2-yl)-4-(trifluoromethyl)pyridazin-3(2H)-one;
5-(1-((3-(3-chloro-5,5-difluoro-4-methyl-5,6,6a,7,9,10-hexahydro-8H-pyrazino[1,2-a][1,8]naphthyridin-8-yl)-2-hydroxy-3-oxopropoxy)methyl)isoindolin-2-yl)-4-(trifluoromethyl)pyridazin-3(2H)-one;
5-(1-((3-(3-chloro-5,5-difluoro-5,6,6a,7,9,10-hexahydro-8H-pyrido[1,6-a:2,3-b']dipyrazin-8-yl)-2-hydroxy-3-oxopropoxy)methyl)isoindolin-2-yl)-4-(trifluoromethyl)pyridazin-3(2H)-one;
5,5-difluoro-8-(2-hydroxy-3-((2-(6-oxo-5-(trifluoromethyl)-1,6-dihydropyridazin-4-yl)isoindolin-1-yl)methoxy)propanoyl)-6,6a,7,8,9,10-hexahydro-5H-pyrazino[1,2-a][1,8]naphthyridine-3-carbonitrile;
4-chloro-5-(1-((3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)methyl)isoindolin-2-yl)pyridazin-3(2H)-one;
5-(1-((3-(3-chloro-5a,6,8,9-tetrahydropyrido[3',2':4,5]imidazo[1,2-a]pyrazin-7(5H)-yl)-2-hydroxy-3-oxopropoxy)methyl)isoindolin-2-yl)-4-(trifluoromethyl)pyridazin-3(2H)-one;
7-(2-hydroxy-3-((2-(6-oxo-5-(trifluoromethyl)-1,6-dihydropyridazin-4-yl)isoindolin-1-yl)methoxy)propanoyl)-5,5a,6,7,8,9-hexahydropyrido[3',2':4,5]imidazo[1,2-a]pyrazine-3-carbonitrile;
4-chloro-5-(1-((2-hydroxy-3-oxo-3-(3-(trifluoromethyl)-5a,6,8,9-tetrahydropyrido[3',2':4,5]imidazo[1,2-a]pyrazin-7(5H)-yl)propoxy)methyl)isoindolin-2-yl)pyridazin-3(2H)-one;
5-(1-((2-hydroxy-3-(5-methyl-3-(trifluoromethyl)-5a,6,8,9-tetrahydropyrido[3',2':4,5]imidazo[1,2-a]pyrazin-7(5H)-yl)-3-oxopropoxy)methyl)isoindolin-2-yl)-4-(trifluoromethyl)pyridazin-3(2H)-one;
5-(1-((3-(5-cyclopropyl-3-(trifluoromethyl)-5a,6,8,9-tetrahydropyrido[3',2':4,5]imidazo[1,2-a]pyrazin-7(5H)-yl)-2-hydroxy-3-oxopropoxy)methyl)isoindolin-2-yl)-4-(trifluoromethyl)pyridazin-3(2H)-one;
5-(1-((2-hydroxy-3-(5-methyl-3-(trifluoromethyl)-5a,6,8,9-tetrahydroimidazo[1,2-a:4,5-b']dipyrazin-7(5H)-yl)-3-oxopropoxy)methyl)isoindolin-2-yl)-4-(trifluoromethyl)pyridazin-3(2H)-one;
5-(1-((3-(3-chloro-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
7-(2-hydroxy-3-((2-(6-oxo-5-(trifluoromethyl)-1,6-dihydropyridazin-4-yl)isoindolin-1-yl)methoxy)propanoyl)-6,7,8,9-tetrahydropyrido[3',2':4,5]pyrrolo[1,2-a]pyrazine-3-carbonitrile;
5-(1-((2-hydroxy-3-oxo-3-(2-(trifluoromethyl)-6,7-dihydropyrrolo[1,5-a:2,3-b']dipyrazin-8(9H)-yl)propoxy)methyl)isoindolin-2-yl)-4-(trifluoromethyl)pyridazin-3(2H)-one;
5-(1-((3-(3-chloro-4-methyl-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((3-(3-chloro-4-fluoro-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
4-chloro-5-(1-((2-hydroxy-3-oxo-3-(3-(trifluoromethyl)-8,9-dihydropyrido[3',2':4,5]pyrrolo[1,2-a]pyrazin-7(6H)-yl)propoxy)methyl)isoindolin-2-yl)pyridazin-3(2H)-one;
5-(1-((2-hydroxy-3-oxo-3-(3-(trifluoromethyl)-8,9-dihydropyrido[3',2':4,5]imidazo[1,2-a]pyrazin-7(6H)-yl)propoxy)methyl)isoindolin-2-yl)-4-(trifluoromethyl)pyridazin-3(2H)-one;
5-(1-((3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((3-(5-chloro-3-(trifluoromethyl)-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((2-hydroxy-3-(5-methyl-3-(trifluoromethyl)-8,9-dihydropyrido[3',2':4,5]pyrrolo[1,2-a]pyrazin-7(6H)-yl)-3-oxopropoxy)methyl)isoindolin-2-yl)-4-(trifluoromethyl)pyridazin-3(2H)-one;
5-(1-((3-(5-cyclopropyl-3-(trifluoromethyl)-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((3-(5-ethyl-3-(trifluoromethyl)-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
7-(2-hydroxy-3-((2-(6-oxo-5-(trifluoromethyl)-1,6-dihydropyridazin-4-yl)isoindolin-1-yl)methoxy)propanoyl)-3-(trifluoromethyl)-6,7,8,9-tetrahydropyrido[3',2':4,5]pyrrolo[1,2-a]pyrazine-5-carbonitrile;
5-(1-((3-(3-chloro-5-fluoro-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((3-(3-chloro-4,5-difluoro-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((3-(3-chloro-5-fluoro-4-methyl-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-fluoro-7-(2-hydroxy-3-((2-(6-oxo-5-(trifluoromethyl)-1,6-dihydropyridazin-4-yl)isoindolin-1-yl)methoxy)propanoyl)-6,7,8,9-tetrahydropyrido[3',2':4,5]pyrrolo[1,2-a]pyrazine-3-carbonitrile;
5-(1-((3-(10-fluoro-2-(trifluoromethyl)-6,7-dihydropyrrolo[1,5-a:2,3-b']dipyrazin-8(9H)-yl)-2-hydroxy-3-oxopropoxy)methyl)isoindolin-2-yl)-4-(trifluoromethyl)pyridazin-3(2H)-one;
4-chloro-5-(1-((3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)methyl)isoindolin-2-yl)pyridazin-3(2H)-one;
5-(1-((3-(3-chloro-5-methyl-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((3-(3-chloro-4-fluoro-5-methyl-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
5-(1-((3-(3-chloro-4,5-dimethyl-8,9-dihydropyrido[3',2':4,5]pyrrolo[1,2-a]pyrazin-7(6H)-yl)-2-hydroxy-3-oxopropoxy)methyl)isoindolin-2-yl)-4-(trifluoromethyl)pyridazin-3(2H)-one;
7-(2-hydroxy-3-((2-(6-oxo-5-(trifluoromethyl)-1,6-dihydropyridazin-4-yl)isoindolin-1-yl)methoxy)propanoyl)-5-methyl-6,7,8,9-tetrahydropyrido[3',2':4,5]pyrrolo[1,2-a]pyrazine-3-carbonitrile;
5-(1-((2-hydroxy-3-(10-methyl-2-(trifluoromethyl)-6,7-dihydropyrrolo[1,5-a:2,3-b']dipyrazin-8(9H)-yl)-3-oxopropoxy)methyl)isoindolin-2-yl)-4-(trifluoromethyl)pyridazin-3(2H)-one;
4-chloro-5-(1-((2-hydroxy-3-(5-methyl-3-(trifluoromethyl)-8,9-dihydropyrido[3',2':4,5]pyrrolo[1,2-a]pyrazin-7(6H)-yl)-3-oxopropoxy)methyl)isoindolin-2-yl)pyridazin-3(2H)-one;
8-(2-hydroxy-3-((S)-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
5-ethyl-8-(2-hydroxy-3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;

-continued 5-(((2S)-1-(2-hydroxy-3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)-4-(trifluoromethyl)pyridazin-3(2H)-one;
5-cyclopropyl-8-(2-hydroxy-3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((2S)-1-(2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
8-(2-hydroxy-3-((S)-2-((6-oxo-5-(trifluoromethyl)-1,6-dihydropyridazin-4-yl)amino)propoxy)propanoyl)-5-isopropyl-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-8,9-dihydropyrido[3',2':4,5]pyrrolo[1,2-a]pyrazin-7(6H)-yl)propoxy)propan-2-yl)amino)-4-(trifluoromethyl)pyridazin-3(2H)-one;
8-(2-hydroxy-3-((S)-2-((6-oxo-5-(trifluoromethyl)-1,6-dihydropyridazin-4-yl)amino)propoxy)propanoyl)-5-(methyl-d3)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-4-methyl-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((2S)-1-(3-(3-chloro-6,7,7a,8,10,11-hexahydro-9H-dipyrazino[2,3-b:1',2'-d][1,4]oxazepin-9-yl)-2-hydroxy-3-oxopropoxy)propan-2-yl)amino)-4-(trifluoromethyl)pyridazin-3(2H)-one;
5-(((2S)-1-(2-hydroxy-3-oxo-3-(3-(trifluoromethyl)-6,7,7a,8,10,11-hexahydro-9H-dipyrazino[2,3-b:1',2'-d][1,4]oxazepin-9-yl)propoxy)propan-2-yl)amino)-4-(trifluoromethyl)pyridazin-3(2H)-one;
5-(((2S)-1-(2-hydroxy-3-oxo-3-(3-(trifluoromethyl)-6a,7,9,10-tetrahydrodipyrazino[2,3-b:1',2'-d][1,4]oxazin-8(6H)-yl)propoxy)propan-2-yl)amino)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]oxazin-8(6H)-yl)-2-hydroxy-3-oxopropoxy)propan-2-yl)amino)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]oxazin-8(6H)-yl)-2-hydroxy-3-oxopropoxy)propan-2-yl)amino)-4-(trifluoromethyl)pyridazin-3(2H)-one;
5-(((2S)-1-(3-(3-chloro-6a,7,9,10-tetrahydrodipyrazino[2,3-b:1',2'-d][1,4]oxazin-8(6H)-yl)-2-hydroxy-3-oxopropoxy)propan-2-yl)amino)-4-(trifluoromethyl)pyridazin-3(2H)-one;
8-(2-hydroxy-3-((S)-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-dipyrazino[1,2-a:2',3'-e]pyrazin-6(6aH)-one;
9-(2-hydroxy-3-((S)-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
8-(2-hydroxy-3-((S)-2-((6-oxo-5-(trifluoromethyl)-1,6-dihydropyridazin-4-yl)amino)propoxy)propanoyl)-6,6a,7,8,9,10-hexahydropyrazino[1,2-d]pyrido[3,2-b][1,4]oxazine-3-carbonitrile;
8-(3-((S)-2-((5-chloro-6-oxo-1,6-dihydropyridazin-4-yl)amino)propoxy)-2-hydroxypropanoyl)-5-methyl-3-(trifluoromethyl)-7,8,9,10-tetrahydro-5H-pyrazino[1,2-a]pyrido[3,2-e]pyrazin-6(6aH)-one;
4-chloro-5-(((2S)-1-(3-(3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)pyridazin-3(2H)-one;
4-chloro-5-(((2S)-1-(2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
5-(((2S)-1-(2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)-4-(trifluoromethyl)pyridazin-3(2H)-one;
5-(((2S)-1-(2-hydroxy-3-oxo-3-(3-(trifluoromethyl)-6a,7,9,10-tetrahydrodipyrazino[2,3-b:1',2'-d][1,4]thiazin-8(6H)-yl)propoxy)propan-2-yl)amino)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]thiazin-8(6H)-yl)-2-hydroxy-3-oxopropoxy)propan-2-yl)amino)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]thiazin-8(6H)-yl)-2-hydroxy-3-oxopropoxy)propan-2-yl)amino)-4-(trifluoromethyl)pyridazin-3(2H)-one;
5-(((2S)-1-(3-(3-chloro-6a,7,9,10-tetrahydrodipyrazino[2,3-b:1',2'-d][1,4]thiazin-8(6H)-yl)-2-hydroxy-3-oxopropoxy)propan-2-yl)amino)-4-(trifluoromethyl)pyridazin-3(2H)-one;
8-(2-hydroxy-3-((S)-2-((6-oxo-5-(trifluoromethyl)-1,6-dihydropyridazin-4-yl)amino)propoxy)propanoyl)-6,6a,7,8,9,10-hexahydropyrazino[1,2-d]pyrido[3,2-b][1,4]thiazine-3-carbonitrile;
4-chloro-5-(((2S)-1-(2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)pyridazin-3(2H)-one;
5-(((2S)-1-(3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)propan-2-yl)amino)-4-(trifluoromethyl)pyridazin-3(2H)-one;
5-(((2S)-1-(3-(5,5-difluoro-3-(trifluoromethyl)-5,6,6a,7,9,10-hexahydro-8H-pyrido[1,6-a:2,3-b']dipyrazin-8-yl)-2-hydroxy-3-oxopropoxy)propan-2-yl)amino)-4-(trifluoromethyl)pyridazin-3(2H)-one;
5-(((2S)-1-(3-(3-chloro-5,5-difluoro-5,6,6a,7,9,10-hexahydro-8H-pyrazino[1,2-a][1,8]naphthyridin-8-yl)-2-hydroxy-3-oxopropoxy)propan-2-yl)amino)-4-(trifluoromethyl)pyridazin-3(2H)-one;
5-(((2S)-1-(3-(3-chloro-5,5-difluoro-4-methyl-5,6,6a,7,9,10-hexahydro-8H-pyrazino[1,2-a][1,8]naphthyridin-8-yl)-2-hydroxy-3-oxopropoxy)propan-2-yl)amino)-4-(trifluoromethyl)pyridazin-3(2H)-one;
5-(((2S)-1-(3-(3-chloro-5,5-difluoro-5,6,6a,7,9,10-hexahydro-8H-pyrido[1,6-a:2,3-b']dipyrazin-8-yl)-2-hydroxy-3-oxopropoxy)propan-2-yl)amino)-4-(trifluoromethyl)pyridazin-3(2H)-one;
5,5-difluoro-8-(2-hydroxy-3-((S)-2-((6-oxo-5-(trifluoromethyl)-1,6-dihydropyridazin-4-yl)amino)propoxy)propanoyl)-6,6a,7,8,9,10-hexahydro-5H-pyrazino[1,2-a][1,8]naphthyridine-3-carbonitrile;
4-chloro-5-(((2S)-1-(3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)propan-2-yl)amino)pyridazin-3(2H)-one;
5-(((2S)-1-(3-(3-chloro-5a,6,8,9-tetrahydropyrido[3',2':4,5]imidazo[1,2-a]pyrazin-7(5H)-yl)-2-hydroxy-3-oxopropoxy)propan-2-yl)amino)-4-(trifluoromethyl)pyridazin-3(2H)-one;
7-(2-hydroxy-3-((S)-2-((6-oxo-5-(trifluoromethyl)-1,6-dihydropyridazin-4-yl)amino)propoxy)propanoyl)-5,5a,6,7,8,9-hexahydropyrido[3',2':4,5]imidazo[1,2-a]pyrazine-3-carbonitrile;
4-chloro-5-(((2S)-1-(2-hydroxy-3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)pyridazin-3(2H)-one;
5-(((2S)-1-(2-hydroxy-3-(5-methyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;

-continued 5-(((2S)-1-(3-(5-cyclopropyl-3-(trifluoromethyl)-5a,6,8,9-tetrahydropyrido[3',2':4,5]imidazo[1,2-a]pyrazin-7(5H)-yl)-2-hydroxy-3-oxopropoxy)propan-2-yl)amino)-4-(trifluoromethyl)pyridazin-3(2H)-one;
5-(((2S)-1-(2-hydroxy-3-(5-methyl-3-(trifluoromethyl)-5a,6,8,9-tetrahydroimidazo[1,2-a:4,5-b']dipyrazin-7(5H)-yl)-3-oxopropoxy)propan-2-yl)amino)-4-(trifluoromethyl)pyridazin-3(2H)-one;
5-(((2S)-1-(3-(3-chloro-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
7-(2-hydroxy-3-((S)-2-((6-oxo-5-(trifluoromethyl)-1,6-dihydropyridazin-4-yl)amino)propoxy)propanoyl)-6,7,8,9-tetrahydropyrido[3',2':4,5]pyrrolo[1,2-a]pyrazine-3-carbonitrile;
5-(((2S)-1-(2-hydroxy-3-oxo-3-(2-(trifluoromethyl)-6,7-dihydropyrrolo[1,5-a:2,3-b']dipyrazin-8(9H)-yl)propoxy)propan-2-yl)amino)-4-(trifluoromethyl)pyridazin-3(2H)-one;
5-(((2S)-1-(3-(3-chloro-4-methyl-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(3-(3-chloro-4-fluoro-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
4-chloro-5-(((2S)-1-(2-hydroxy-3-oxo-3-(3-(trifluoromethyl)-8,9-dihydropyrido[3',2':4,5]pyrrolo[1,2-a]pyrazin-7(6H)-yl)propoxy)propan-2-yl)amino)pyridazin-3(2H)-one;
5-(((2S)-1-(2-hydroxy-3-oxo-3-(3-(trifluoromethyl)-8,9-dihydropyrido[3',2':4,5]imidazo[1,2-a]pyrazin-7(6H)-yl)propoxy)propan-2-yl)amino)-4-(trifluoromethyl)pyridazin-3(2H)-one;
5-(((2S)-1-(3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(3-(5-chloro-3-(trifluoromethyl)-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(2-hydroxy-3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
5-(((2S)-1-(3-(5-cyclopropyl-3-(trifluoromethyl)-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(3-(5-ethyl-3-(trifluoromethyl)-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
7-(2-hydroxy-3-((S)-2-((6-oxo-5-(trifluoromethyl)-1,6-dihydropyridazin-4-yl)amino)propoxy)propanoyl)-3-(trifluoromethyl)-6,7,8,9-tetrahydropyrido[3',2':4,5]pyrrolo[1,2-a]pyrazine-5-carbonitrile;
5-(((2S)-1-(3-(3-chloro-5-fluoro-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(3-(3-chloro-4,5-difluoro-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(3-(3-chloro-5-fluoro-4-methyl-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-fluoro-7-(2-hydroxy-3-((S)-2-((6-oxo-5-(trifluoromethyl)-1,6-dihydropyridazin-4-yl)amino)propoxy)propanoyl)-6,7,8,9-tetrahydropyrido[3',2':4,5]pyrrolo[1,2-a]pyrazine-3-carbonitrile;
5-(((2S)-1-(3-(10-fluoro-2-(trifluoromethyl)-6,7-dihydropyrrolo[1,5-a:2,3-b']dipyrazin-8(9H)-yl)-2-hydroxy-3-oxopropoxy)propan-2-yl)amino)-4-(trifluoromethyl)pyridazin-3(2H)-one;
4-chloro-5-(((2S)-1-(3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)propan-2-yl)amino)pyridazin-3(2H)-one;
5-(((2S)-1-(3-(3-chloro-5-methyl-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(3-(3-chloro-4-fluoro-5-methyl-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
5-(((2S)-1-(3-(3-chloro-4,5-dimethyl-8,9-dihydropyrido[3',2':4,5]pyrrolo[1,2-a]pyrazin-7(6H)-yl)-2-hydroxy-3-oxopropoxy)propan-2-yl)amino)-4-(trifluoromethyl)pyridazin-3(2H)-one;
7-(2-hydroxy-3-((S)-2-((6-oxo-5-(trifluoromethyl)-1,6-dihydropyridazin-4-yl)amino)propoxy)propanoyl)-5-methyl-6,7,8,9-tetrahydropyrido[3',2':4,5]pyrrolo[1,2-a]pyrazine-3-carbonitrile;
5-(((2S)-1-(2-hydroxy-3-(10-methyl-2-(trifluoromethyl)-6,7-dihydropyrrolo[1,5-a:2,3-b']dipyrazin-8(9H)-yl)-3-oxopropoxy)propan-2-yl)amino)-4-(trifluoromethyl)pyridazin-3(2H)-one;
4-chloro-5-(((2S)-1-(2-hydroxy-3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)pyridazin-3(2H)-one;
8-(2-hydroxy-3-((S)-2-((6-oxo-5-(trifluoromethyl)-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
5-ethyl-8-(2-hydroxy-3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-cyclopropyl-8-(2-hydroxy-3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)oxy)-4-(trifluoromethyl)pyridazin-3(2H)-one;
5-(((2S)-1-(2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
8-(2-hydroxy-3-((S)-2-((6-oxo-5-(trifluoromethyl)-1,6-dihydropyridazin-4-yl)oxy)propoxy)propanoyl)-5-isopropyl-3-(trifluoromethyl)-7,8,9,10-tetrahydro-5H-pyrazino[1,2-a]pyrido[3,2-e]pyrazin-6(6aH)-one;
5-(((2S)-1-(2-hydroxy-3-oxo-3-(3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
8-(2-hydroxy-3-((S)-2-((6-oxo-5-(trifluoromethyl)-1,6-dihydropyridazin-4-yl)oxy)propoxy)propanoyl)-5-(methyl-d3)-3-(trifluoromethyl)-7,8,9,10-tetrahydro-5H-pyrazino[1,2-a]pyrido[3,2-e]pyrazin-6(6aH)-one;
5-(((2S)-1-(3-(3-chloro-4-methyl-6,7,7a,8,10,11-hexahydro-9H-pyrazino[1,2-d]pyrido[3,2-b][1,4]oxazepin-9-yl)-2-hydroxy-3-oxopropoxy)propan-2-yl)oxy)-4-(trifluoromethyl)pyridazin-3(2H)-one;

-continued 5-(((2S)-1-(3-(3-chloro-6,7,7a,8,10,11-hexahydro-9H-dipyrazino[2,3-b:1',2'-d][1,4]oxazepin-9-yl)-2-hydroxy-3-oxopropoxy)propan-2-yl)oxy)-4-(trifluoromethyl)pyridazin-3(2H)-one;
5-(((2S)-1-(2-hydroxy-3-oxo-3-(3-(trifluoromethyl)-6,7,7a,8,10,11-hexahydro-9H-dipyrazino[2,3-b:1',2'-d][1,4]oxazepin-9-yl)propoxy)propan-2-yl)oxy)-4-(trifluoromethyl)pyridazin-3(2H)-one;
5-(((2S)-1-(2-hydroxy-3-oxo-3-(3-(trifluoromethyl)-6a,7,9,10-tetrahydrodipyrazino[2,3-b:1',2'-d][1,4]oxazin-8(6H)-yl)propoxy)propan-2-yl)oxy)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]oxazin-8(6H)-yl)-2-hydroxy-3-oxopropoxy)propan-2-yl)oxy)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]oxazin-8(6H)-yl)-2-hydroxy-3-oxopropoxy)propan-2-yl)oxy)-4-(trifluoromethyl)pyridazin-3(2H)-one;
5-(((2S)-1-(3-(3-chloro-6a,7,9,10-tetrahydrodipyrazino[2,3-b:1',2'-d][1,4]oxazin-8(6H)-yl)-2-hydroxy-3-oxopropoxy)propan-2-yl)oxy)-4-(trifluoromethyl)pyridazin-3(2H)-one;
8-(2-hydroxy-3-((S)-2-((6-oxo-5-(trifluoromethyl)-1,6-dihydropyridazin-4-yl)oxy)propoxy)propanoyl)-5-methyl-3-(trifluoromethyl)-7,8,9,10-tetrahydro-5H-dipyrazino[1,2-a:2',3'-e]pyrazin-6(6aH)-one;
9-(2-hydroxy-3-((S)-2-((6-oxo-5-(trifluoromethyl)-1,6-dihydropyridazin-4-yl)oxy)propoxy)propanoyl)-7,7a,8,9,10,11-hexahydro-6H-pyrazino[1,2-d]pyrido[3,2-b][1,4]oxazepine-3-carbonitrile;
8-(2-hydroxy-3-((S)-2-((6-oxo-5-(trifluoromethyl)-1,6-dihydropyridazin-4-yl)oxy)propoxy)propanoyl)-6,6a,7,8,9,10-hexahydropyrazino[1,2-d]pyrido[3,2-b][1,4]oxazine-3-carbonitrile;
8-(3-((S)-2-((5-chloro-6-oxo-1,6-dihydropyridazin-4-yl)oxy)propoxy)-2-hydroxypropanoyl)-5-methyl-3-(trifluoromethyl)-7,8,9,10-tetrahydro-5H-pyrazino[1,2-a]pyrido[3,2-e]pyrazin-6(6aH)-one;
4-chloro-5-(((2S)-1-(3-(3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)oxy)pyridazin-3(2H)-one;
4-chloro-5-(((2S)-1-(2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
5-(((2S)-1-(2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)-4-(trifluoromethyl)pyridazin-3(2H)-one;
5-(((2S)-1-(2-hydroxy-3-oxo-3-(3-(trifluoromethyl)-6a,7,9,10-tetrahydrodipyrazino[2,3-b:1',2'-d][1,4]thiazin-8(6H)-yl)propoxy)propan-2-yl)oxy)-4-(trifluoromethyl)pyridazin-3(2H)-one;
5-(((2S)-1-(3-(3-chloro-6a,7,9,10-tetrahydropyrazino[1,2-d]pyrido[3,2-b][1,4]thiazin-8(6H)-yl)-2-hydroxy-3-oxopropoxy)propan-2-yl)oxy)-4-(trifluoromethyl)pyridazin-3(2H)-one;
5-(((2S)-1-(3-(3-chloro-4-methyl-6a,7,9,10-tetrahydropyrazino[1,2-d]pyrido[3,2-b][1,4]thiazin-8(6H)-yl)-2-hydroxy-3-oxopropoxy)propan-2-yl)oxy)-4-(trifluoromethyl)pyridazin-3(2H)-one;
5-(((2S)-1-(3-(3-chloro-6a,7,9,10-tetrahydrodipyrazino[2,3-b:1',2'-d][1,4]thiazin-8(6H)-yl)-2-hydroxy-3-oxopropoxy)propan-2-yl)oxy)-4-(trifluoromethyl)pyridazin-3(2H)-one;
8-(2-hydroxy-3-((S)-2-((6-oxo-5-(trifluoromethyl)-1,6-dihydropyridazin-4-yl)oxy)propoxy)propanoyl)-6,6a,7,8,9,10-hexahydropyrazino[1,2-d]pyrido[3,2-b][1,4]thiazine-3-carbonitrile;
4-chloro-5-(((2S)-1-(2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
5-(((2S)-1-(3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)propan-2-yl)oxy)-4-(trifluoromethyl)pyridazin-3(2H)-one;
5-(((2S)-1-(3-(5,5-difluoro-3-(trifluoromethyl)-5,6,6a,7,9,10-hexahydro-8H-pyrido[1,6-a:2,3-b']dipyrazin-8-yl)-2-hydroxy-3-oxopropoxy)propan-2-yl)oxy)-4-(trifluoromethyl)pyridazin-3(2H)-one;
5-(((2S)-1-(3-(3-chloro-5,5-difluoro-5,6,6a,7,9,10-hexahydro-8H-pyrazino[1,2-a][1,8]naphthyridin-8-yl)-2-hydroxy-3-oxopropoxy)propan-2-yl)oxy)-4-(trifluoromethyl)pyridazin-3(2H)-one;
5-(((2S)-1-(3-(3-chloro-5,5-difluoro-4-methyl-5,6,6a,7,9,10-hexahydro-8H-pyrazino[1,2-a][1,8]naphthyridin-8-yl)-2-hydroxy-3-oxopropoxy)propan-2-yl)oxy)-4-(trifluoromethyl)pyridazin-3(2H)-one;
5-(((2S)-1-(3-(3-chloro-5,5-difluoro-5,6,6a,7,9,10-hexahydro-8H-pyrido[1,6-a:2,3-b']dipyrazin-8-yl)-2-hydroxy-3-oxopropoxy)propan-2-yl)oxy)-4-(trifluoromethyl)pyridazin-3(2H)-one;
5,5-difluoro-8-(2-hydroxy-3-((S)-2-((6-oxo-5-(trifluoromethyl)-1,6-dihydropyridazin-4-yl)oxy)propoxy)propanoyl)-6,6a,7,8,9,10-hexahydro-5H-pyrazino[1,2-a][1,8]naphthyridine-3-carbonitrile;
4-chloro-5-(((2S)-1-(3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)propan-2-yl)oxy)pyridazin-3(2H)-one;
5-(((2S)-1-(3-(3-chloro-5a,6,8,9-tetrahydropyrido[3',2':4,5]imidazo[1,2-a]pyrazin-7(5H)-yl)-2-hydroxy-3-oxopropoxy)propan-2-yl)oxy)-4-(trifluoromethyl)pyridazin-3(2H)-one;
7-(2-hydroxy-3-((S)-2-((6-oxo-5-(trifluoromethyl)-1,6-dihydropyridazin-4-yl)oxy)propoxy)propanoyl)-5,5a,6,7,8,9-hexahydropyrido[3',2':4,5]imidazo[1,2-a]pyrazine-3-carbonitrile;
4-chloro-5-(((2S)-1-(2-hydroxy-3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)pyridazin-3(2H)-one;
5-(((2S)-1-(2-hydroxy-3-(5-methyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-cyclopropyl-3-(trifluoromethyl)-5a,6,8,9-tetrahydropyrido[3',2':4,5]imidazo[1,2-a]pyrazin-7(5H)-yl)-2-hydroxy-3-oxopropoxy)propan-2-yl)oxy)-4-(trifluoromethyl)pyridazin-3(2H)-one;
5-(((2S)-1-(2-hydroxy-3-(5-methyl-3-(trifluoromethyl)-5a,6,8,9-tetrahydroimidazo[1,2-a:4,5-b']dipyrazin-7(5H)-yl)-3-oxopropoxy)propan-2-yl)oxy)-4-(trifluoromethyl)pyridazin-3(2H)-one;
5-(((2S)-1-(3-(3-chloro-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
7-(2-hydroxy-3-((S)-2-((6-oxo-5-(trifluoromethyl)-1,6-dihydropyridazin-4-yl)oxy)propoxy)propanoyl)-6,7,8,9-tetrahydropyrido[3',2':4,5]pyrrolo[1,2-a]pyrazine-3-carbonitrile;
5-(((2S)-1-(2-hydroxy-3-oxo-3-(2-(trifluoromethyl)-6,7-dihydropyrrolo[1,5-a:2,3-b']dipyrazin-8(9H)-yl)propoxy)propan-2-yl)oxy)-4-(trifluoromethyl)pyridazin-3(2H)-one;
5-(((2S)-1-(3-(3-chloro-4-methyl-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(3-(3-chloro-4-fluoro-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
4-chloro-5-(((2S)-1-(2-hydroxy-3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;

-continued 5-(((2S)-1-(2-hydroxy-3-oxo-3-(3-(trifluoromethyl)-8,9-dihydropyrido[3',2':4,5]imidazo[1,2-a]pyrazin-7(6H)-yl)propoxy)propan-2-yl)oxy)-4-(trifluoromethyl)pyridazin-3(2H)-one;
5-(((2S)-1-(3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(3-(5-chloro-3-(trifluoromethyl)-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(2-hydroxy-3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((2S)-1-(3-(5-cyclopropyl-3-(trifluoromethyl)-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(3-(5-ethyl-3-(trifluoromethyl)-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
7-(2-hydroxy-3-((S)-2-((6-oxo-5-(trifluoromethyl)-1,6-dihydropyridazin-4-yl)oxy)propoxy)propanoyl)-3-(trifluoromethyl)-6,7,8,9-tetrahydropyrido[3',2':4,5]pyrrolo[1,2-a]pyrazine-5-carbonitrile;
5-(((2S)-1-(3-(3-chloro-5-fluoro-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(3-(3-chloro-4,5-difluoro-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(3-(3-chloro-5-fluoro-4-methyl-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-fluoro-7-(2-hydroxy-3-((S)-2-((6-oxo-5-(trifluoromethyl)-1,6-dihydropyridazin-4-yl)oxy)propoxy)propanoyl)-6,7,8,9-tetrahydropyrido[3',2':4,5]pyrrolo[1,2-a]pyrazine-3-carbonitrile;
5-(((2S)-1-(3-(10-fluoro-2-(trifluoromethyl)-6,7-dihydropyrrolo[1,5-a:2,3-b']dipyrazin-8(9H)-yl)-2-hydroxy-3-oxopropoxy)propan-2-yl)oxy)-4-(trifluoromethyl)pyridazin-3(2H)-one;
4-chloro-5-(((2S)-1-(3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)propan-2-yl)oxy)pyridazin-3(2H)-one;
5-(((2S)-1-(3-(3-chloro-5-methyl-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(3-(3-chloro-4-fluoro-5-methyl-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
5-(((2S)-1-(3-(3-chloro-4,5-dimethyl-8,9-dihydropyrido[3',2':4,5]pyrrolo[1,2-a]pyrazin-7(6H)-yl)-2-hydroxy-3-oxopropoxy)propan-2-yl)oxy)-4-(trifluoromethyl)pyridazin-3(2H)-one;
7-(2-hydroxy-3-((S)-2-((6-oxo-5-(trifluoromethyl)-1,6-dihydropyridazin-4-yl)oxy)propoxy)propanoyl)-5-methyl-6,7,8,9-tetrahydropyrido[3',2':4,5]pyrrolo[1,2-a]pyrazine-3-carbonitrile;
5-(((2S)-1-(2-hydroxy-3-(10-methyl-2-(trifluoromethyl)-6,7-dihydropyrrolo[1,5-a:2,3-b']dipyrazin-8(9H)-yl)-3-oxopropoxy)propan-2-yl)oxy)-4-(trifluoromethyl)pyridazin-3(2H)-one;
4-chloro-5-(((2S)-1-(2-hydroxy-3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
8-(2-hydroxy-3-((1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one,
5-ethyl-8-(2-hydroxy-3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((2-hydroxy-3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)-4-(trifluoromethyl)pyridazin-3(2H)-one;
5-cyclopropyl-8-(2-hydroxy-3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(2-((2-hydroxy-3-oxo-3-(3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)-4-(trifluoromethyl)pyridazin-3(2H)-one;
5-(2-((3-(3-chloro-6,7,7a,8,10,11-hexahydro-9H-pyrazino[1,2-d]pyrido[3,2-b][1,4]oxazepin-9-yl)-2-hydroxy-3-oxopropoxy)methyl)azetidin-1-yl)-4-(trifluoromethyl)pyridazin-3(2H)-one;
5-(2-((2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
8-(2-hydroxy-3-((1-(6-oxo-5-(trifluoromethyl)-1,6-dihydropyridazin-4-yl)azetidin-2-yl)methoxy)propanoyl)-5-isopropyl-3-(trifluoromethyl)-7,8,9,10-tetrahydro-5H-pyrazino[1,2-a]pyrido[3,2-e]pyrazin-6(6aH)-one;
5-(2-((2-hydroxy-3-oxo-3-(3-(trifluoromethyl)-8,9-dihydropyrido[3',2':4,5]pyrrolo[1,2-a]pyrazin-7(6H)-yl)propoxy)methyl)azetidin-1-yl)-4-(trifluoromethyl)pyridazin-3(2H)-one;
8-(2-hydroxy-3-((1-(6-oxo-5-(trifluoromethyl)-1,6-dihydropyridazin-4-yl)azetidin-2-yl)methoxy)propanoyl)-5-(methyl-d3)-3-(trifluoromethyl)-7,8,9,10-tetrahydro-5H-pyrazino[1,2-a]pyrido[3,2-e]pyrazin-6(6aH)-one;
5-(2-((3-(3-chloro-4-methyl-6,7,7a,8,10,11-hexahydro-9H-pyrazino[1,2-d]pyrido[3,2-b][1,4]oxazepin-9-yl)-2-hydroxy-3-oxopropoxy)methyl)azetidin-1-yl)-4-(trifluoromethyl)pyridazin-3(2H)-one;
5-(2-((3-(3-chloro-6,7,7a,8,10,11-hexahydro-9H-dipyrazino[2,3-b:1',2'-d][1,4]oxazepin-9-yl)-2-hydroxy-3-oxopropoxy)methyl)azetidin-1-yl)-4-(trifluoromethyl)pyridazin-3(2H)-one;
5-(2-((2-hydroxy-3-oxo-3-(3-(trifluoromethyl)-6,7,7a,8,10,11-hexahydro-9H-dipyrazino[2,3-b:1',2'-d][1,4]oxazepin-9-yl)propoxy)methyl)azetidin-1-yl)-4-(trifluoromethyl)pyridazin-3(2H)-one;
5-(2-((2-hydroxy-3-oxo-3-(3-(trifluoromethyl)-6a,7,9,10-tetrahydrodipyrazino[2,3-b:1',2'-d][1,4]oxazin-8(6H)-yl)propoxy)methyl)azetidin-1-yl)-4-(trifluoromethyl)pyridazin-3(2H)-one;
5-(2-((3-(3-chloro-6a,7,9,10-tetrahydropyrazino[1,2-d]pyrido[3,2-b][1,4]oxazin-8(6H)-yl)-2-hydroxy-3-oxopropoxy)methyl)azetidin-1-yl)-4-(trifluoromethyl)pyridazin-3(2H)-one;
5-(2-((3-(3-chloro-4-methyl-6a,7,9,10-tetrahydropyrazino[1,2-d]pyrido[3,2-b][1,4]oxazin-8(6H)-yl)-2-hydroxy-3-oxopropoxy)methyl)azetidin-1-yl)-4-(trifluoromethyl)pyridazin-3(2H)-one;
5-(2-((3-(3-chloro-6a,7,9,10-tetrahydrodipyrazino[2,3-b:1',2'-d][1,4]oxazin-8(6H)-yl)-2-hydroxy-3-oxopropoxy)methyl)azetidin-1-yl)-4-(trifluoromethyl)pyridazin-3(2H)-one;
8-(2-hydroxy-3-((1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-dipyrazino[1,2-a:2',3'-e]pyrazin-6(6aH)-one;
9-(2-hydroxy-3-((1-(6-oxo-5-(trifluoromethyl)-1,6-dihydropyridazin-4-yl)azetidin-2-yl)methoxy)propanoyl)-7,7a,8,9,10,11-hexahydro-6H-pyrazino[1,2-d]pyrido[3,2-b][1,4]oxazepine-3-carbonitrile;
8-(2-hydroxy-3-((1-(6-oxo-5-(trifluoromethyl)-1,6-dihydropyridazin-4-yl)azetidin-2-yl)methoxy)propanoyl)-6,6a,7,8,9,10-hexahydropyrazino[1,2-d]pyrido[3,2-b][1,4]oxazine-3-carbonitrile;

-continued 8-(3-((1-(5-chloro-6-oxo-1,6-dihydropyridazin-4-yl)azetidin-2-yl)methoxy)-2-hydroxypropanoyl)-5-methyl-3-(trifluoromethyl)-7,8,9,10-tetrahydro-5H-pyrazino[1,2-a]pyrido[3,2-e]pyrazin-6(6aH)-one;
4-chloro-5-(2-((3-(3-chloro-6,7,7a,8,10,11-hexahydro-9H-pyrazino[1,2-d]pyrido[3,2-b][1,4]oxazepin-9-yl)-2-hydroxy-3-oxopropoxy)methyl)azetidin-1-yl)pyridazin-3(2H)-one;
4-chloro-5-(2-((2-hydroxy-3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)pyridazin-3(2H)-one;
5-(2-((2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)-4-(trifluoromethyl)pyridazin-3(2H)-one;
5-(2-((2-hydroxy-3-oxo-3-(3-(trifluoromethyl)-6a,7,9,10-tetrahydrodipyrazino[2,3-b:1',2'-d][1,4]thiazin-8(6H)-yl)propoxy)methyl)azetidin-1-yl)-4-(trifluoromethyl)pyridazin-3(2H)-one;
5-(2-((3-(3-chloro-6a,7,9,10-tetrahydropyrazino[1,2-d]pyrido[3,2-b][1,4]thiazin-8(6H)-yl)-2-hydroxy-3-oxopropoxy)methyl)azetidin-1-yl)-4-(trifluoromethyl)pyridazin-3(2H)-one;
5-(2-((3-(3-chloro-4-methyl-6a,7,9,10-tetrahydropyrazino[1,2-d]pyrido[3,2-b][1,4]thiazin-8(6H)-yl)-2-hydroxy-3-oxopropoxy)methyl)azetidin-1-yl)-4-(trifluoromethyl)pyridazin-3(2H)-one;
5-(2-((3-(3-chloro-6a,7,9,10-tetrahydrodipyrazino[2,3-b:1',2'-d][1,4]thiazin-8(6H)-yl)-2-hydroxy-3-oxopropoxy)methyl)azetidin-1-yl)-4-(trifluoromethyl)pyridazin-3(2H)-one;
8-(2-hydroxy-3-((1-(6-oxo-5-(trifluoromethyl)-1,6-dihydropyridazin-4-yl)azetidin-2-yl)methoxy)propanoyl)-6,6a,7,8,9,10-hexahydropyrazino[1,2-d]pyrido[3,2-b][1,4]thiazine-3-carbonitrile;
4-chloro-5-(2-((2-hydroxy-3-oxo-3-(3-(trifluoromethyl)-6a,7,9,10-tetrahydropyrazino[1,2-d]pyrido[3,2-b][1,4]thiazin-8(6H)-yl)propoxy)methyl)azetidin-1-yl)pyridazin-3(2H)-one;
5-(2-((3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)methyl)azetidin-1-yl)-4-(trifluoromethyl)pyridazin-3(2H)-one;
5-(2-((3-(5,5-difluoro-3-(trifluoromethyl)-5,6,6a,7,9,10-hexahydro-8H-pyrido[1,6-a:2,3-b']dipyrazin-8-yl)-2-hydroxy-3-oxopropoxy)methyl)azetidin-1-yl)-4-(trifluoromethyl)pyridazin-3(2H)-one;
5-(2-((3-(3-chloro-5,5-difluoro-5,6,6a,7,9,10-hexahydro-8H-pyrazino[1,2-a][1,8]naphthyridin-8-yl)-2-hydroxy-3-oxopropoxy)methyl)azetidin-1-yl)-4-(trifluoromethyl)pyridazin-3(2H)-one;
5-(2-((3-(3-chloro-5,5-difluoro-4-methyl-5,6,6a,7,9,10-hexahydro-8H-pyrazino[1,2-a][1,8]naphthyridin-8-yl)-2-hydroxy-3-oxopropoxy)methyl)azetidin-1-yl)-4-(trifluoromethyl)pyridazin-3(2H)-one;
5-(2-((3-(3-chloro-5,5-difluoro-5,6,6a,7,9,10-hexahydro-8H-pyrido[1,6-a:2,3-b']dipyrazin-8-yl)-2-hydroxy-3-oxopropoxy)methyl)azetidin-1-yl)-4-(trifluoromethyl)pyridazin-3(2H)-one;
5,5-difluoro-8-(2-hydroxy-3-((1-(6-oxo-5-(trifluoromethyl)-1,6-dihydropyridazin-4-yl)azetidin-2-yl)methoxy)propanoyl)-6,6a,7,8,9,10-hexahydro-5H-pyrazino[1,2-a][1,8]naphthyridine-3-carbonitrile;
4-chloro-5-(2-((3-(5,5-difluoro-3-(trifluoromethyl)-5,6,6a,7,9,10-hexahydro-8H-pyrazino[1,2-a][1,8]naphthyridin-8-yl)-2-hydroxy-3-oxopropoxy)methyl)azetidin-1-yl)pyridazin-3(2H)-one;
5-(2-((3-(3-chloro-5a,6,8,9-tetrahydropyrido[3',2':4,5]imidazo[1,2-a]pyrazin-7(5H)-yl)-2-hydroxy-3-oxopropoxy)methyl)azetidin-1-yl)-4-(trifluoromethyl)pyridazin-3(2H)-one;
7-(2-hydroxy-3-((1-(6-oxo-5-(trifluoromethyl)-1,6-dihydropyridazin-4-yl)azetidin-2-yl)methoxy)propanoyl)-5,5a,6,7,8,9-hexahydropyrido[3',2':4,5]imidazo[1,2-a]pyrazine-3-carbonitrile;
4-chloro-5-(2-((2-hydroxy-3-oxo-3-(3-(trifluoromethyl)-5a,6,8,9-tetrahydropyrido[3',2':4,5]imidazo[1,2-a]pyrazin-7(5H)-yl)propoxy)methyl)azetidin-1-yl)pyridazin-3(2H)-one;
5-(2-((2-hydroxy-3-(5-methyl-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(5-cyclopropyl-3-(trifluoromethyl)-5a,6,8,9-tetrahydropyrido[3',2':4,5]imidazo[1,2-a]pyrazin-7(5H)-yl)-2-hydroxy-3-oxopropoxy)methyl)azetidin-1-yl)-4-(trifluoromethyl)pyridazin-3(2H)-one;
5-(2-((2-hydroxy-3-(5-methyl-3-(trifluoromethyl)-5a,6,8,9-tetrahydroimidazo[1,2-a:4,5-b']dipyrazin-7(5H)-yl)-3-oxopropoxy)methyl)azetidin-1-yl)-4-(trifluoromethyl)pyridazin-3(2H)-one;
5-(2-((3-(3-chloro-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
7-(2-hydroxy-3-((1-(6-oxo-5-(trifluoromethyl)-1,6-dihydropyridazin-4-yl)azetidin-2-yl)methoxy)propanoyl)-6,7,8,9-tetrahydropyrido[3',2':4,5]pyrrolo[1,2-a]pyrazine-3-carbonitrile;
5-(2-((2-hydroxy-3-oxo-3-(2-(trifluoromethyl)-6,7-dihydropyrrolo[1,5-a:2,3-b']dipyrazin-8(9H)-yl)propoxy)methyl)azetidin-1-yl)-4-(trifluoromethyl)pyridazin-3(2H)-one;
5-(2-((3-(3-chloro-4-methyl-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-(2-((3-(3-chloro-4-fluoro-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
4-chloro-5-(2-((2-hydroxy-3-oxo-3-(3-(trifluoromethyl)-8,9-dihydropyrido[3',2':4,5]pyrrolo[1,2-a]pyrazin-7(6H)-yl)propoxy)methyl)azetidin-1-yl)pyridazin-3(2H)-one;
5-(2-((2-hydroxy-3-oxo-3-(3-(trifluoromethyl)-8,9-dihydropyrido[3',2':4,5]imidazo[1,2-a]pyrazin-7(6H)-yl)propoxy)methyl)azetidin-1-yl)-4-(trifluoromethyl)pyridazin-3(2H)-one;
5-(2-((3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-(2-((3-(5-chloro-3-(trifluoromethyl)-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-(2-((2-hydroxy-3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-cyclopropyl-3-(trifluoromethyl)-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-(2-((3-(5-ethyl-3-(trifluoromethyl)-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
7-(2-hydroxy-3-((1-(6-oxo-5-(trifluoromethyl)-1,6-dihydropyridazin-4-yl)azetidin-2-yl)methoxy)propanoyl)-3-(trifluoromethyl)-6,7,8,9-tetrahydropyrido[3',2':4,5]pyrrolo[1,2-a]pyrazine-5-carbonitrile;
5-(2-((3-(3-chloro-5-fluoro-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-(2-((3-(3-chloro-4,5-difluoro-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;

-continued 5-(2-((3-(3-chloro-5-fluoro-4-methyl-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-fluoro-7-(2-hydroxy-3-((1-(6-oxo-5-(trifluoromethyl)-1,6-dihydropyridazin-4-yl)azetidin-2-yl)methoxy)propanoyl)-6,7,8,9-tetrahydropyrido[3',2':4,5]pyrrolo[1,2-a]pyrazine-3-carbonitrile;
5-(2-((3-(10-fluoro-2-(trifluoromethyl)-6,7-dihydropyrrolo[1,5-a:2,3-b']dipyrazin-8(9H)-yl)-2-hydroxy-3-oxopropoxy)methyl)azetidin-1-yl)-4-(trifluoromethyl)pyridazin-3(2H)-one;
4-chloro-5-(2-((3-(5-fluoro-3-(trifluoromethyl)-8,9-dihydropyrido[3',2':4,5]pyrrolo[1,2-a]pyrazin-7(6H)-yl)-2-hydroxy-3-oxopropoxy)methyl)azetidin-1-yl)pyridazin-3(2H)-one;
5-(2-((3-(3-chloro-5-methyl-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-(2-((3-(3-chloro-4-fluoro-5-methyl-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
5-(2-((3-(3-chloro-4,5-dimethyl-8,9-dihydropyrido[3',2':4,5]pyrrolo[1,2-a]pyrazin-7(6H)-yl)-2-hydroxy-3-oxopropoxy)methyl)azetidin-1-yl)-4-(trifluoromethyl)pyridazin-3(2H)-one;
7-(2-hydroxy-3-((1-(6-oxo-5-(trifluoromethyl)-1,6-dihydropyridazin-4-yl)azetidin-2-yl)methoxy)propanoyl)-5-methyl-6,7,8,9-tetrahydropyrido[3',2':4,5]pyrrolo[1,2-a]pyrazine-3-carbonitrile;
5-(2-((2-hydroxy-3-(10-methyl-2-(trifluoromethyl)-6,7-dihydropyrrolo[1,5-a:2,3-b']dipyrazin-8(9H)-yl)-3-oxopropoxy)methyl)azetidin-1-yl)-4-(trifluoromethyl)pyridazin-3(2H)-one;
4-chloro-5-(2-((2-hydroxy-3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)pyridazin-3(2H)-one;
(S)-5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-isopropyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-ethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-cyclopropyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(methyl-d3)-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-((S)-2-((6-oxo-5-(trifluoromethyl)-1,6-dihydropyridazin-4-yl)amino)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
(S)-5-cyclobutyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(6aS)-5-methyl-8-(3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(6aS)-5-isopropyl-8-(3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-ethyl-8-(3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(6aS)-5-cyclopropyl-8-(3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-(methyl-d3)-8-(3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(6aS)-8-(3-((1-(6-oxo-5-(trifluoromethyl)-1,6-dihydropyridazin-4-yl)azetidin-2-yl)methoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
(6aS)-5-cyclobutyl-8-(3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-5-isopropyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-ethyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-5-cyclopropyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(methyl-d3)-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-((S)-2-((6-oxo-5-(trifluoromethyl)-1,6-dihydropyridazin-4-yl)oxy)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
(S)-5-cyclobutyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-5-((1-(3-(5-(methyl-d3)-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(5-ethyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(5-isopropyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-7-(3-(2-((6-oxo-5-(trifluoromethyl)-1,6-dihydropyridazin-4-yl)amino)propoxy)propanoyl)-3-(trifluoromethyl)-6,7,8,9-tetrahydropyrido[3',2':4,5]pyrrolo[1,2-a]pyrazine-5-carbonitrile;
(S)-5-((1-(3-(5-cyclopropyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(5-cyclobutyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;

-continued (S)-5-((1-(3-oxo-3-(5-(2,2,2-trifluoroethyl)-3-(trifluoromethyl)-8,9-dihydropyrido[3',2':4,5]pyrrolo[1,2-a]pyrazin-7(6H)-yl)propoxy)propan-2-yl)amino)-4-(trifluoromethyl)pyridazin-3(2H)-one;
(S)-5-((1-(3-(5-(oxetan-3-yl)-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(5-(5-fluorothiophen-2-yl)-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(5-(difluoromethyl)-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(S)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-(methyl-d3)-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-ethyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-isopropyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-7-(3-(2-((6-oxo-5-(trifluoromethyl)-1,6-dihydropyridazin-4-yl)oxy)propoxy)propanoyl)-3-(trifluoromethyl)-6,7,8,9-tetrahydropyrido[3',2':4,5]pyrrolo[1,2-a]pyrazine-5-carbonitrile;
(S)-5-((1-(3-(5-cyclopropyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-cyclobutyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-oxo-3-(5-(2,2,2-trifluoroethyl)-3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
(S)-5-((1-(3-(5-(oxetan-3-yl)-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-(5-fluorothiophen-2-yl)-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-(difluoromethyl)-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(2-((3-(5-isopropyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-cyclopropyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-cyclobutyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-oxo-3-(5-(2,2,2-trifluoroethyl)-3-(trifluoromethyl)-8,9-dihydropyrido[3',2':4,5]pyrrolo[1,2-a]pyrazin-7(6H)-yl)propoxy)methyl)azetidin-1-yl)-4-(trifluoromethyl)pyridazin-3(2H)-one;
5-(2-((3-(5-(oxetan-3-yl)-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-(5-fluorothiophen-2-yl)-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5-(difluoromethyl)-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(((2S)-1-(3-(5-methyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-ethyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-isopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-cyclopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-cyclobutyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-(oxetan-3-yl)-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-(3,3-difluorocyclobutyl)-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-(methyl-d3)-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-oxo-3-(5-(2,2,2-trifluoroethyl)-3-(trifluoromethyl)-5a,6,8,9-tetrahydropyrido[3',2':4,5]imidazo[1,2-a]pyrazin-7(5H)-yl)propoxy)propan-2-yl)amino)-4-(trifluoromethyl)pyridazin-3(2H)-one;
5-(((2S)-1-(3-(5-acetyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-methyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-ethyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-isopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-cyclopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-cyclobutyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-(oxetan-3-yl)-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(5-(3,3-difluorocyclobutyl)-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;

-continued 5-(((2S)-1-(3-(5-(methyl-d3)-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-oxo-3-(5-(2,2,2-trifluoroethyl)-3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-(((2S)-1-(3-(5-acetyl-3-(trifluoromethyl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(2-((3-(5-isopropyl-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(5-cyclopropyl-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(5-cyclobutyl-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(5-(oxetan-3-yl)-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-(5-(3,3-difluorocyclobutyl)-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(2-((3-oxo-3-(5-(2,2,2-trifluoroethyl)-3-(trifluoromethyl)-5a,6,8,9-tetrahydropyrido[3',2':4,5]imidazo[1,2-a]pyrazin-7(5H)-yl)propoxy)methyl)azetidin-1-yl)-4-(trifluoromethyl)pyridazin-3(2H)-one;
5-(2-((3-(5-acetyl-3-(trifluoromethyl)-5a,6,8,9-tetrahydropyrido[3',2':4,5]imidazo[1,2-a]pyrazin-7(5H)-yl)-3-oxopropoxy)methyl)azetidin-1-yl)-4-(trifluoromethyl)pyridazin-3(2H)-one;
5-(((2S)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(trifluoromethyl)pyridazin-3(2H)-one;
9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
5-(((2S)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)-4-(trifluoromethyl)pyridazin-3(2H)-one;
5-(((S)-1-(3-oxo-3-((S)-3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(trifluoromethyl)pyridazin-3(2H)-one;
5-(((S)-1-(3-oxo-3-((R)-3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(trifluoromethyl)pyridazin-3(2H)-one;
5-(((2S)-1-(3-(5-methyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((2S)-1-(3-(5-methyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-methyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
5-(((S)-1-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((S)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((S)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((S)-1-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
4-acetyl-5-(((S)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-acetyl-5-(((S)-1-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
5-(((S)-1-(3-((R)-3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
(R)-9-(3-((S)-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
(S)-9-(3-((S)-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
3-oxo-5-(((S)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-2,3-dihydropyridazine-4-carbonitrile;
3-oxo-5-(((S)-1-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-2,3-dihydropyridazine-4-carbonitrile;
5-(((S)-1-(3-((R)-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(trifluoromethyl)pyridazin-3(2H)-one;
5-(((S)-1-(3-oxo-3-((S)-3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(trifluoromethyl)pyridazin-3(2H)-one;
5-(((S)-1-(3-((6R,7aR)-6-methyl-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((6S,7aR)-6-methyl-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;

-continued 5-(((S)-1-(3-((S)-3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-((R)-3-((R)-3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((S)-1-((S)-3-((R)-3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((S)-1-(3-((5S,7aR)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((5S,7aS)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((5R,7aR)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((5R,7aS)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2S)-1-(3-((S)-3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((S)-1-(3-((6R,7aS)-6-methyl-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((6S,7aS)-6-methyl-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-acetyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-acetyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-((R)-2-hydroxy-3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((S)-1-((S)-2-hydroxy-3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((S)-1-((R)-2-hydroxy-3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((S)-1-((S)-2-hydroxy-3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((S)-1-(3-((R)-3-chloro-6,7,7a,8,10,11-hexahydro-9H-pyrazino[1,2-d]pyrido[3,2-b][1,4]oxazepin-9-yl)-3-oxopropoxy)-3-methoxypropan-2-yl)amino)-4-(trifluoromethyl)pyridazin-3(2H)-one;
5-(((S)-1-(3-((S)-3-chloro-6,7,7a,8,10,11-hexahydro-9H-pyrazino[1,2-d]pyrido[3,2-b][1,4]oxazepin-9-yl)-3-oxopropoxy)-3-methoxypropan-2-yl)amino)-4-(trifluoromethyl)pyridazin-3(2H)-one;
5-(((S)-1-methoxy-3-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((S)-1-methoxy-3-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((S)-1-methoxy-3-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((S)-1-methoxy-3-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
(R)-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a][1,8]naphthyridin-5-one;
(S)-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a][1,8]naphthyridin-5-one;
5-(((S)-1-(3-((R)-5,5-difluoro-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((S)-1-(3-((S)-5,5-difluoro-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((S)-1-(3-((5S,6aR)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((S)-1-(3-((5R,6aR)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((S)-1-(3-((5R,5aS)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((S)-1-(3-((5S,5aS)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((S)-1-(3-((5R,5aR)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((S)-1-(3-((5S,5aR)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((S)-1-(3-((5R,6aR)-5-hydroxy-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((S)-1-(3-((5S,6aR)-5-hydroxy-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;

-continued 8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-cyclopropyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
8-(3-((S)-2-((6-oxo-5-(trifluoromethyl)-1,6-dihydropyridazin-4-yl)amino)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
(S)-5-(methyl-d3)-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-(methyl-d3)-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-3-fluoro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-fluoro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-5-cyclopropyl-3-fluoro-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-5-cyclopropyl-3-fluoro-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-8-(3-((S)-2-((5-acetyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((S)-2-((5-acetyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5,6a-dimethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5,6a-dimethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-3-chloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-5-ethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-ethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-3-bromo-4,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-4,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3,4,5-trimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3,4,5-trimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-2-chloro-3,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-2-chloro-3,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-4,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-4,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-8-(3-((S)-2-((6-oxo-5-(trifluoromethyl)-1,6-dihydropyridazin-4-yl)amino)propoxy)propanoyl)-3-(trifluoromethyl)-5-vinyl-7,8,9,10-tetrahydro-5H-pyrazino[1,2-a]pyrido[3,2-e]pyrazin-6(6aH)-one;
(R)-8-(3-((S)-2-((6-oxo-5-(trifluoromethyl)-1,6-dihydropyridazin-4-yl)amino)propoxy)propanoyl)-3-(trifluoromethyl)-5-vinyl-7,8,9,10-tetrahydro-5H-pyrazino[1,2-a]pyrido[3,2-e]pyrazin-6(6aH)-one;
(S)-3-chloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-5-isopropyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-((S)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((S)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)amino)butoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-((S)-2-((6-oxo-5-(trifluoromethyl)-1,6-dihydropyridazin-4-yl)amino)butoxy)propanoyl)-3-(trifluoromethyl)-7,8,9,10-tetrahydro-5H-pyrazino[1,2-a]pyrido[3,2-e]pyrazin-6(6aH)-one;

-continued (S)-5-methyl-8-((2-((S)-2-((6-oxo-5-(trifluoromethyl)-1,6-dihydropyridazin-4-yl)amino)propoxy)ethyl)sulfonyl)-3-(trifluoromethyl)-7,8,9,10-tetrahydro-5H-pyrazino[1,2-a]pyrido[3,2-e]pyrazin-6(6aH)-one;
(R)-8-((R)-2-hydroxy-3-((S)-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-((S)-2-hydroxy-3-((S)-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-((R)-2-hydroxy-3-((S)-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-((S)-2-hydroxy-3-((S)-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-isopropyl-8-(3-((S)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-isopropyl-8-(3-((S)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydropyrido[3,4-c][1,5]naphthyridin-6(5H)-one;
(S)-5-methyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydropyrido[3,4-c][1,5]naphthyridin-6(5H)-one;
9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
6-methyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(S)-5-methyl-8-(1-((S)-2-((6-oxo-5-(trifluoromethyl)-1,6-dihydropyridazin-4-yl)amino)propyl)piperidine-4-carbonyl)-3-(trifluoromethyl)-7,8,9,10-tetrahydro-5H-pyrazino[1,2-a]pyrido[3,2-e]pyrazin-6(6aH)-one;
(R)-5-methyl-8-(1-((S)-2-((6-oxo-5-(trifluoromethyl)-1,6-dihydropyridazin-4-yl)amino)propyl)piperidine-4-carbonyl)-3-(trifluoromethyl)-7,8,9,10-tetrahydro-5H-pyrazino[1,2-a]pyrido[3,2-e]pyrazin-6(6aH)-one;
(S)-8-(3-((S)-2-((5-chloro-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((S)-2-((5-chloro-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-((S)-2-((5-bromo-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((S)-2-((5-bromo-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-((R)-1-((R)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(R)-5-methyl-8-((S)-1-((R)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(S)-5-methyl-8-((S)-1-((S)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(R)-5-methyl-8-((R)-1-((S)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(S)-5-methyl-8-((R)-1-((S)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(S)-3-chloro-2-fluoro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-2-fluoro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-5-methyl-8-((S)-1-((S)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(S)-5-methyl-8-((S)-1-((R)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(S)-5-methyl-8-(3-((S)-3,3,3-trifluoro-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-((S)-3,3,3-trifluoro-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-((R)-3,3,3-trifluoro-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-((R)-3,3,3-trifluoro-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-((R)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-((R)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((R)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((R)-1-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((S)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((S)-1-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((S)-1-(3-((R)-3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;

-continued 5-(((S)-1-(3-((S)-3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((R)-1-(3-((R)-3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((R)-1-(3-((S)-3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
(R)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
(S)-3-chloro-5-methyl-8-(3-((R)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(R)-3-chloro-5-methyl-8-(3-((R)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-3-chloro-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(R)-3-chloro-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(R)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((S)-1-(3-((R)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((S)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((R)-1-(3-((R)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((R)-1-(3-((S)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
(R)-5-isopropyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(S)-5-isopropyl-8-(3-((R)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
(R)-5-isopropyl-8-(3-((R)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((S)-1-(3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(trifluoromethyl)pyridazin-3(2H)-one;
5-(((S)-1-(3-oxo-3-((S)-3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(trifluoromethyl)pyridazin-3(2H)-one;
5-(((R)-1-(3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(trifluoromethyl)pyridazin-3(2H)-one;
5-(((R)-1-(3-oxo-3-((S)-3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(trifluoromethyl)pyridazin-3(2H)-one;
5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-(((2R)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
(R)-5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)-4-(trifluoromethyl)pyridazin-3(2H)-one;
(S)-5-ethyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-(((S)-1-(3-oxo-3-((S)-3-(trifluoromethyl)-6a,7,9,10-tetrahydropyrazino[1,2-d]pyrido[3,2-b][1,4]thiazin-8(6H)-yl)propoxy)propan-2-yl)oxy)-4-(trifluoromethyl)pyridazin-3(2H)-one;
5-(((S)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)-4-(trifluoromethyl)pyridazin-3(2H)-one;
5-(((S)-1-(3-((S)-3-chloro-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-chloro-4-methyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-chloro-6a,7,9,10-tetrahydropyrazino[1,2-d]pyrido[3,2-b][1,4]thiazin-8(6H)-yl)-3-oxopropoxy)propan-2-yl)oxy)-4-(trifluoromethyl)pyridazin-3(2H)-one;
5-(((S)-1-(3-((R)-3-chloro-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((2S)-1-(3-(9-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-8-(3-((S)-2-((5-chloro-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-chloro-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)pyridazin-3(2H)-one;
(S)-4-chloro-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)pyridazin-3(2H)-one;
(S)-4-chloro-5-((1-(3-(3-chloro-5-fluoro-8,9-dihydropyrido[3',2':4,5]pyrrolo[1,2-a]pyrazin-7(6H)-yl)-3-oxopropoxy)propan-2-yl)oxy)pyridazin-3(2H)-one;
4-chloro-5-(((S)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-chloro-5-(((S)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-chloro-5-(((S)-1-(3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-chloro-5-(((S)-1-(3-oxo-3-((S)-3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;

-continued (S)-8-(3-((S)-2-((5-acetyl-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-4-acetyl-5-((1-(3-(3-chloro-5-fluoro-8,9-dihydropyrido[3',2':4,5]pyrrolo[1,2-a]pyrazin-7(6H)-yl)-3-oxopropoxy)propan-2-yl)oxy)pyridazin-3(2H)-one;
4-acetyl-5-(((S)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-acetyl-5-(((S)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-acetyl-5-(((S)-1-(3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-acetyl-5-(((S)-1-(3-oxo-3-((S)-3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
(S)-8-(3-((S)-2-((5-ethyl-6-oxo-1,6-dihydropyridazin-4-yl)oxy)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-((1-(3-(3-chloro-5-fluoro-8,9-dihydropyrido[3',2':4,5]pyrrolo[1,2-a]pyrazin-7(6H)-yl)-3-oxopropoxy)propan-2-yl)oxy)-4-ethylpyridazin-3(2H)-one;
4-ethyl-5-(((S)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)oxy)pyridazin-3(2H)-one;
4-ethyl-5-(((S)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)oxy)pyridazin-3(2H)-one;
4-ethyl-5-(((S)-1-(3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)pyridazin-3(2H)-one;
4-ethyl-5-(((S)-1-(3-oxo-3-((S)-3-(trifluoromethyl)-6a,7,9,10-tetrahydropyrazino[1,2-d]pyrido[3,2-b][1,4]thiazin-8(6H)-yl)propoxy)propan-2-yl)oxy)pyridazin-3(2H)-one;
(S)-3-cyclopropyl-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-3-cyclobutyl-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-3-(3,3-difluorocyclobutyl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-methyl-3-(oxetan-3-yl)-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-3-(azetidin-1-yl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-3-(3,3-difluoroazetidin-1-yl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)oxy)propoxy)propanoyl)-3-(pyrrolidin-1-yl)-7,8,9,10-tetrahydro-5H-pyrazino[1,2-a]pyrido[3,2-e]pyrazin-6(6aH)-one;
(S)-5-methyl-3-morpholino-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)oxy)propoxy)propanoyl)-3-(piperazin-1-yl)-7,8,9,10-tetrahydro-5H-pyrazino[1,2-a]pyrido[3,2-e]pyrazin-6(6aH)-one;
(S)-5-methyl-3-(4-methylpiperazin-1-yl)-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-3-(4-acetylpiperazin-1-yl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)oxy)propoxy)propanoyl)-3-(2-azaspiro[3,3]heptan-2-yl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)oxy)propoxy)propanoyl)-3-(5-azaspiro[2.4]heptan-5-yl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)oxy)propoxy)propanoyl)-3-(2-azaspiro[4.4]nonan-2-yl)-7,8,9,10-tetrahydro-5H-pyrazino[1,2-a]pyrido[3,2-e]pyrazin-6(6aH)-one;
(6aS)-3-(hexahydrocyclopenta[c]pyrrol-2(1H)-yl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(6aS)-5-methyl-8-(3-((S)-2-((6-oxo-5-(trifluoromethyl)-1,6-dihydropyridazin-4-yl)oxy)propoxy)propanoyl)-3-(tetrahydro-1H-furo[3,4-c]pyrrol-5(3H)-yl)-7,8,9,10-tetrahydro-5H-pyrazino[1,2-a]pyrido[3,2-e]pyrazin-6(6aH)-one;
(S)-5-((1-(3-(3-(3,3-difluorocyclobutyl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(3-(3,3-difluoroazetidin-1-yl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-(5-methyl-3-(pyrrolidin-1-yl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-3-(3-fluoropyridin-2-yl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-methyl-3-(3-methylpyridin-2-yl)-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-3-(3-methoxypyridin-2-yl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
2-((S)-5-methyl-6-oxo-8-(3-((S)-2-((6-oxo-5-(trifluoromethyl)-1,6-dihydropyridazin-4-yl)oxy)propoxy)propanoyl)-6,6a,7,8,9,10-hexahydro-5H-pyrazino[1,2-a]pyrido[3,2-e]pyrazin-3-yl)nicotinonitrile;
(S)-3-(2-fluorophenyl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
4-((S)-5-methyl-6-oxo-8-(3-((S)-2-((6-oxo-5-(trifluoromethyl)-1,6-dihydropyridazin-4-yl)oxy)propoxy)propanoyl)-6,6a,7,8,9,10-hexahydro-5H-pyrazino[1,2-a]pyrido[3,2-e]pyrazin-3-yl)benzonitrile;
(S)-3-(2,4-difluorophenyl)-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-methyl-8-(3-((S)-2-((6-oxo-5-(trifluoromethyl)-1,6-dihydropyridazin-4-yl)oxy)propoxy)propanoyl)-3-(thiazol-5-yl)-7,8,9,10-tetrahydro-5H-pyrazino[1,2-a]pyrido[3,2-e]pyrazin-6(6aH)-one;

-continued (S)-5-methyl-3-(5-methyl-1H-pyrazol-3-yl)-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-methyl-3-(oxazol-5-yl)-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
(S)-5-((1-(3-(3-(2,3-difluorophenyl)-5-methyl-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((S)-1-(3-((R)-3-(azetidin-1-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((R)-3-(3,3-difluoroazetidin-1-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((R)-3-morpholino-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((R)-3-(4-methylpiperazin-1-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((R)-3-(4-acetylpiperazin-1-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((R)-3-(oxetan-3-yl)-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((R)-3-(azetidin-1-yl)-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((S)-1-(3-((R)-3-(3,3-difluoroazetidin-1-yl)-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((S)-1-(3-((R)-3-morpholino-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((S)-1-(3-((R)-3-(4-methylpiperazin-1-yl)-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((S)-1-(3-((R)-3-(4-acetylpiperazin-1-yl)-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((S)-1-(3-((R)-3-(oxetan-3-yl)-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((S)-1-(3-((S)-3-cyclopropyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-cyclobutyl-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-(azetidin-1-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-(3,3-difluoroazetidin-1-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-morpholino-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-(4-methylpiperazin-1-yl)-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((S)-3-cyclopropyl-6a,7,9,10-tetrahydropyrazino[1,2-d]pyrido[3,2-b][1,4]thiazin-8(6H)-yl)-3-oxopropoxy)propan-2-yl)oxy)-4-(trifluoromethyl)pyridazin-3(2H)-one;
5-(((S)-1-(3-((S)-3-cyclobutyl-6a,7,9,10-tetrahydropyrazino[1,2-d]pyrido[3,2-b][1,4]thiazin-8(6H)-yl)-3-oxopropoxy)propan-2-yl)oxy)-4-(trifluoromethyl)pyridazin-3(2H)-one;
5-(((S)-1-(3-((S)-3-(azetidin-1-yl)-6a,7,9,10-tetrahydropyrazino[1,2-d]pyrido[3,2-b][1,4]thiazin-8(6H)-yl)-3-oxopropoxy)propan-2-yl)oxy)-4-(trifluoromethyl)pyridazin-3(2H)-one;
5-(((S)-1-(3-((S)-3-(3,3-difluoroazetidin-1-yl)-6a,7,9,10-tetrahydropyrazino[1,2-d]pyrido[3,2-b][1,4]thiazin-8(6H)-yl)-3-oxopropoxy)propan-2-yl)oxy)-4-(trifluoromethyl)pyridazin-3(2H)-one;
5-(((S)-1-(3-((S)-3-morpholino-6a,7,9,10-tetrahydropyrazino[1,2-d]pyrido[3,2-b][1,4]thiazin-8(6H)-yl)-3-oxopropoxy)propan-2-yl)oxy)-4-(trifluoromethyl)pyridazin-3(2H)-one;
5-(((S)-1-(3-((S)-3-(4-methylpiperazin-1-yl)-6a,7,9,10-tetrahydropyrazino[1,2-d]pyrido[3,2-b][1,4]thiazin-8(6H)-yl)-3-oxopropoxy)propan-2-yl)oxy)-4-(trifluoromethyl)pyridazin-3(2H)-one;
(S)-5-((1-(3-(3-(2,3-difluorophenyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-(((S)-1-(3-((R)-3-cyclopropyl-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-cyclobutyl-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-(azetidin-1-yl)-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-(3,3-difluoroazetidin-1-yl)-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-morpholino-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-(4-methylpiperazin-1-yl)-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-cyclopropyl-5-methyl-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-cyclobutyl-5-methyl-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-(azetidin-1-yl)-5-methyl-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-3-(3,3-difluoroazetidin-1-yl)-5-methyl-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((S)-1-(3-((R)-5-methyl-3-morpholino-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;

-continued 5-(((S)-1-(3-((R)-5-methyl-3-(4-methylpiperazin-1-yl)-5,6,6a,7,9,10-hexahydro-8H-pyrazino[1,2-a]pyrido[3,2-e]pyrazin-8-yl)-3-oxopropoxy)propan-2-yl)oxy)-4-(trifluoromethyl)pyridazin-3(2H)-one;
5-(((2S)-1-(3-(3-cyclopropyl-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(3-cyclobutyl-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(3-(azetidin-1-yl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(3-(3,3-difluoroazetidin-1-yl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(3-morpholino-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((2S)-1-(3-(3-(4-methylpiperazin-1-yl)-5a,6,8,9-tetrahydropyrido[3',2':4,5]imidazo[1,2-a]pyrazin-7(5H)-yl)-3-oxopropoxy)propan-2-yl)oxy)-4-(trifluoromethyl)pyridazin-3(2H)-one;
5-(((S)-1-(3-((S)-3-chloro-4-fluoro-6a,7,9,10-tetrahydropyrazino[1,2-d]pyrido[3,2-b][1,4]oxazin-8(6H)-yl)-3-oxopropoxy)propan-2-yl)oxy)-4-(trifluoromethyl)pyridazin-3(2H)-one;
5-(((S)-1-(3-((R)-3-chloro-4-fluoro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((S)-1-(3-((R)-3-chloro-4-methyl-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
5-(((S)-1-(3-((R)-3-chloro-4-fluoro-6,7,7a,8,10,11-hexahydro-9H-pyrazino[1,2-d]pyrido[3,2-b][1,4]thiazepin-9-yl)-3-oxopropoxy)propan-2-yl)oxy)-4-(trifluoromethyl)pyridazin-3(2H)-one;
(S)-5-((1-(3-(5-(azetidin-1-yl)-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
(S)-5-((1-(3-oxo-3-(5-(thiazol-5-yl)-3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
(R)-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-5-methyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(R)-5-methyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
5-ethyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-5-ethyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(R)-5-ethyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
5-isopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-5-isopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(R)-5-isopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
5-cyclopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-5-cyclopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(R)-5-cyclopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(R)-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(S)-6-methyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(R)-6-methyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
6-ethyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(R)-6-ethyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(S)-6-ethyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
6-isopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(R)-6-isopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(S)-6-isopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
6-cyclopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(R)-6-cyclopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(S)-6-cyclopropyl-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;

-continued 5-(((2S)-1-(3-oxo-3-(3-(trifluoromethyl)-6,7,7a,8,10,11-hexahydropyrazino[1,2-a]pyrido[3,2-f][1,4]diazepin-9(5H)-yl)propoxy)propan-2-yl)amino)-4-(trifluoromethyl)pyridazin-3(2H)-one;
5-(((S)-1-(3-oxo-3-((S)-3-(trifluoromethyl)-6,7,7a,8,10,11-hexahydropyrazino[1,2-a]pyrido[3,2-f][1,4]diazepin-9(5H)-yl)propoxy)propan-2-yl)amino)-4-(trifluoromethyl)pyridazin-3(2H)-one;
5-(((S)-1-(3-oxo-3-((R)-3-(trifluoromethyl)-6,7,7a,8,10,11-hexahydropyrazino[1,2-a]pyrido[3,2-f][1,4]diazepin-9(5H)-yl)propoxy)propan-2-yl)amino)-4-(trifluoromethyl)pyridazin-3(2H)-one;
5-(((2S)-1-(3-(6-methyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((S)-6-methyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((R)-6-methyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((2S)-1-(3-(6-ethyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((S)-6-ethyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((R)-6-ethyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((2S)-1-(3-(6-isopropyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((S)-6-isopropyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((R)-6-isopropyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((2S)-1-(3-(6-cyclopropyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((S)-6-cyclopropyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((R)-6-cyclopropyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((2S)-1-(3-(6-acetyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((S)-6-acetyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((R)-6-acetyl-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((2S)-1-(3-(6-(methylsulfonyl)-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((R)-6-(methylsulfonyl)-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((S)-6-(methylsulfonyl)-3-(trifluoromethyl)-6,7,7a,8,10,11-hexahydropyrazino[1,2-a]pyrido[3,2-f][1,4]diazepin-9(5H)-yl)-3-oxopropoxy)propan-2-yl)amino)-4-(trifluoromethyl)pyridazin-3(2H)-one;
5-(((S)-1-(3-((S)-5-methyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((R)-5-methyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((2S)-1-(3-(5-ethyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((S)-5-ethyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((R)-5-ethyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((2S)-1-(3-(5-isopropyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((S)-5-isopropyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((R)-5-isopropyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((2S)-1-(3-(5-cyclopropyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((S)-5-cyclopropyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((R)-5-cyclopropyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((2S)-1-(3-(5-acetyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((S)-5-acetyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((R)-5-acetyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((2S)-1-(3-(5-(methylsulfonyl)-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((S)-5-(methylsulfonyl)-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((S)-1-(3-((R)-5-(methylsulfonyl)-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
(R)-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;

-continued (S)-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-isopropyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(R)-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(S)-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
6-methyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(S)-6-methyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(R)-6-methyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
6-ethyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(S)-6-ethyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(R)-6-ethyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
6-isopropyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(S)-6-isopropyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(R)-6-isopropyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
6-cyclopropyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(S)-6-cyclopropyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
(R)-6-cyclopropyl-8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a]pyrido[3,2-e]pyrimidin-5-one;
5-(((2S)-1-(3-oxo-3-(3-(trifluoromethyl)-5,6,6a,7,9,10-hexahydro-8H-pyrazino[1,2-a]pyrido[3,2-e]pyrimidin-8-yl)propoxy)propan-2-yl)amino)-4-(trifluoromethyl)pyridazin-3(2H)-one;
5-(((S)-1-(3-oxo-3-((R)-3-(trifluoromethyl)-5,6,6a,7,9,10-hexahydro-8H-pyrazino[1,2-a]pyrido[3,2-e]pyrimidin-8-yl)propoxy)propan-2-yl)amino)-4-(trifluoromethyl)pyridazin-3(2H)-one;
5-(((S)-1-(3-oxo-3-((S)-3-(trifluoromethyl)-5,6,6a,7,9,10-hexahydro-8H-pyrazino[1,2-a]pyrido[3,2-e]pyrimidin-8-yl)propoxy)propan-2-yl)amino)-4-(trifluoromethyl)pyridazin-3(2H)-one;
5-(((2S)-1-(3-(6-methyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((R)-6-methyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((S)-6-methyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((2S)-1-(3-(6-ethyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((R)-6-ethyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((S)-6-ethyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((2S)-1-(3-(6-isopropyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((R)-6-isopropyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((S)-6-isopropyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((2S)-1-(3-(6-cyclopropyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((R)-6-cyclopropyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((S)-6-cyclopropyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((2S)-1-(3-(6-acetyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((S)-6-acetyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((R)-6-acetyl-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((2S)-1-(3-(6-(methylsulfonyl)-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((S)-6-(methylsulfonyl)-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;
5-(((S)-1-(3-((R)-6-(methylsulfonyl)-3-(trifluoromethyl)-5,6,6a,7,9,10-hexahydro-8H-pyrazino[1,2-a]pyrido[3,2-e]pyrimidin-8-yl)-3-oxopropoxy)propan-2-yl)amino)-4-(trifluoromethyl)pyridazin-3(2H)-one;

-continued 5-(((S)-1-(3-oxo-3-((S)-3-(trifluoromethyl)-5,6,6a,7,9,10-hexahydro-8H-pyrazino[1,2-a]pyrido[3,2-e]pyrazin-8-yl)propoxy)propan-2-yl)amino)-4-(trifluoromethyl)pyridazin-3(2H)-one;
5-(((S)-1-(3-oxo-3-((R)-3-(trifluoromethyl)-5,6,6a,7,9,10-hexahydro-8H-pyrazino[1,2-a]pyrido[3,2-e]pyrazin-8-yl)propoxy)propan-2-yl)amino)-4-(trifluoromethyl)pyridazin-3(2H)-one;
5-(((S)-1-(3-((S)-5-methyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((S)-1-(3-((R)-5-methyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((2S)-1-(3-(5-ethyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((S)-1-(3-((S)-5-ethyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((S)-1-(3-((R)-5-ethyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((2S)-1-(3-(5-isopropyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((S)-1-(3-((S)-5-isopropyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((S)-1-(3-((R)-5-isopropyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((2S)-1-(3-(5-cyclopropyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((S)-1-(3-((S)-5-cyclopropyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((S)-1-(3-((R)-5-cyclopropyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((2S)-1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)amino)-4-(trifluoromethyl)pyridazin-3(2H)-one;
5-(((S)-1-(3-oxo-3-((R)-3-(trifluoromethyl)-5a,6,8,9-tetrahydropyrido[3',2':4,5]imidazo[1,2-a]pyrazin-7(5H)-yl)propoxy)propan-2-yl)amino)-4-(trifluoromethyl)pyridazin-3(2H)-one;
5-(((S)-1-(3-oxo-3-((S)-3-(trifluoromethyl)-5a,6,8,9-tetrahydropyrido[3',2':4,5]imidazo[1,2-a]pyrazin-7(5H)-yl)propoxy)propan-2-yl)amino)-4-(trifluoromethyl)pyridazin-3(2H)-one;
5-(((S)-1-(3-((R)-5-methyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((S)-5-methyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((R)-5-ethyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((S)-5-ethyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((R)-5-isopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((S)-5-isopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((R)-5-cyclopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((S)-5-cyclopropyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((S)-5-acetyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((R)-5-acetyl-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-(5-(methylsulfonyl)-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((S)-5-(methylsulfonyl)-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((S)-1-(3-((R)-5-(methylsulfonyl)-3-(trifluoromethyl)-5a,6,8,9-tetrahydropyrido[3',2':4,5]imidazo[1,2-a]pyrazin-7(5H)-yl)-3-oxopropoxy)propan-2-yl)amino)-4-(trifluoromethyl)pyridazin-3(2H)-one;
5-(((2S)-1-(3-oxo-3-(3-(trifluoromethyl)-6,7,7a,8,10,11-hexahydropyrazino[1,2-a]pyrido[3,2-f]azepin-9(5H)-yl)propoxy)propan-2-yl)amino)-4-(trifluoromethyl)pyridazin-3(2H)-one;
5-(((S)-1-(3-oxo-3-((S)-3-(trifluoromethyl)-6,7,7a,8,10,11-hexahydropyrazino[1,2-a]pyrido[3,2-f]azepin-9(5H)-yl)propoxy)propan-2-yl)amino)-4-(trifluoromethyl)pyridazin-3(2H)-one;
5-(((S)-1-(3-oxo-3-((R)-3-(trifluoromethyl)-6,7,7a,8,10,11-hexahydropyrazino[1,2-a]pyrido[3,2-f]azepin-9(5H)-yl)propoxy)propan-2-yl)amino)-4-(trifluoromethyl)pyridazin-3(2H)-one;
9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f]azepin-5(6H)-one;
(S)-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f]azepin-5(6H)-one;
(R)-9-(3-((S)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f]azepin-5(6H)-one;
5-(((2S)-1-(3-(5,5-difluoro-3-(trifluoromethyl)-6,7,7a,8,10,11-hexahydropyrazino[1,2-a]pyrido[3,2-f]azepin-9(5H)-yl)-3-oxopropoxy)propan-2-yl)amino)-4-(trifluoromethyl)pyridazin-3(2H)-one;
5-(((S)-1-(3-((S)-5,5-difluoro-3-(trifluoromethyl)-6,7,7a,8,10,11-hexahydropyrazino[1,2-a]pyrido[3,2-f]azepin-9(5H)-yl)-3-oxopropoxy)propan-2-yl)amino)-4-(trifluoromethyl)pyridazin-3(2H)-one;
5-(((S)-1-(3-((R)-5,5-difluoro-3-(trifluoromethyl)-6,7,7a,8,10,11-hexahydropyrazino[1,2-a]pyrido[3,2-f]azepin-9(5H)-yl)-3-oxopropoxy)propan-2-yl)amino)-4-(trifluoromethyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(trifluoromethyl)pyridazin-3(2H)-one;

-continued 5-(((2S)-1-(3-(5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2S)-1-(3-((7aS)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2S)-1-(3-((7aR)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2S)-1-(3-(5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2S)-1-(3-oxo-3-(3-(trifluoromethyl)-5,6,6a,7,9,10-hexahydro-8H-pyrazino[1,2-a][1,8]naphthyridin-8-yl)propoxy)propan-2-yl)amino)-4-(trifluoromethyl)pyridazin-3(2H)-one;
5-(((S)-1-(3-oxo-3-((S)-3-(trifluoromethyl)-5,6,6a,7,9,10-hexahydro-8H-pyrazino[1,2-a][1,8]naphthyridin-8-yl)propoxy)propan-2-yl)amino)-4-(trifluoromethyl)pyridazin-3(2H)-one;
5-(((S)-1-(3-oxo-3-((R)-3-(trifluoromethyl)-5,6,6a,7,9,10-hexahydro-8H-pyrazino[1,2-a][1,8]naphthyridin-8-yl)propoxy)propan-2-yl)amino)-4-(trifluoromethyl)pyridazin-3(2H)-one;
8-(3-((S)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a][1,8]naphthyridin-5-one;
5-(((2S)-1-(3-(5,5-difluoro-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2S)-1-(3-oxo-3-(3-(trifluoromethyl)-6a,7,9,10-tetrahydropyrazino[1,2-d]pyrido[3,2-b][1,4]thiazin-8(6H)-yl)propoxy)propan-2-yl)amino)-4-(trifluoromethyl)pyridazin-3(2H)-one;
5-(((S)-1-(3-oxo-3-((R)-3-(trifluoromethyl)-6a,7,9,10-tetrahydropyrazino[1,2-d]pyrido[3,2-b][1,4]thiazin-8(6H)-yl)propoxy)propan-2-yl)amino)-4-(trifluoromethyl)pyridazin-3(2H)-one;
5-(((S)-1-(3-oxo-3-((S)-3-(trifluoromethyl)-6a,7,9,10-tetrahydropyrazino[1,2-d]pyrido[3,2-b][1,4]thiazin-8(6H)-yl)propoxy)propan-2-yl)amino)-4-(trifluoromethyl)pyridazin-3(2H)-one;
5-(((2S)-1-(3-(5-oxido-3-(trifluoromethyl)-6a,7,9,10-tetrahydropyrazino[1,2-d]pyrido[3,2-b][1,4]thiazin-8(6H)-yl)-3-oxopropoxy)propan-2-yl)amino)-4-(trifluoromethyl)pyridazin-3(2H)-one;
5-(((2S)-1-(3-((6aR)-5-oxido-3-(trifluoromethyl)-6a,7,9,10-tetrahydropyrazino[1,2-d]pyrido[3,2-b][1,4]thiazin-8(6H)-yl)-3-oxopropoxy)propan-2-yl)amino)-4-(trifluoromethyl)pyridazin-3(2H)-one;
5-(((2S)-1-(3-((6aS)-5-oxido-3-(trifluoromethyl)-6a,7,9,10-tetrahydropyrazino[1,2-d]pyrido[3,2-b][1,4]thiazin-8(6H)-yl)-3-oxopropoxy)propan-2-yl)amino)-4-(trifluoromethyl)pyridazin-3(2H)-one;
5-(((2S)-1-(3-(5,5-dioxido-3-(trifluoromethyl)-6a,7,9,10-tetrahydropyrazino[1,2-d]pyrido[3,2-b][1,4]thiazin-8(6H)-yl)-3-oxopropoxy)propan-2-yl)amino)-4-(trifluoromethyl)pyridazin-3(2H)-one;
5-(((S)-1-(3-((R)-5,5-dioxido-3-(trifluoromethyl)-6a,7,9,10-tetrahydropyrazino[1,2-d]pyrido[3,2-b][1,4]thiazin-8(6H)-yl)-3-oxopropoxy)propan-2-yl)amino)-4-(trifluoromethyl)pyridazin-3(2H)-one;
5-(((S)-1-(3-((S)-5,5-dioxido-3-(trifluoromethyl)-6a,7,9,10-tetrahydropyrazino[1,2-d]pyrido[3,2-b][1,4]thiazin-8(6H)-yl)-3-oxopropoxy)propan-2-yl)amino)-4-(trifluoromethyl)pyridazin-3(2H)-one;
5-(((2S)-1-(3-oxo-3-(3-(trifluoromethyl)-5a,6,8,9-tetrahydro-7H-pyrido[2',3':4,5]oxazolo[3,2-a]pyrazin-7-yl)propoxy)propan-2-yl)amino)-4-(trifluoromethyl)pyridazin-3(2H)-one;
5-(((S)-1-(3-oxo-3-((S)-3-(trifluoromethyl)-5a,6,8,9-tetrahydro-7H-pyrido[2',3':4,5]oxazolo[3,2-a]pyrazin-7-yl)propoxy)propan-2-yl)amino)-4-(trifluoromethyl)pyridazin-3(2H)-one;
5-(((S)-1-(3-oxo-3-((R)-3-(trifluoromethyl)-5a,6,8,9-tetrahydro-7H-pyrido[2',3':4,5]oxazolo[3,2-a]pyrazin-7-yl)propoxy)propan-2-yl)amino)-4-(trifluoromethyl)pyridazin-3(2H)-one;
5-(((2S)-1-(3-oxo-3-(3-(trifluoromethyl)-5a,6,8,9-tetrahydropyrido[3',2':4,5]pyrrolo[1,2-a]pyrazin-7(5H)-yl)propoxy)propan-2-yl)amino)-4-(trifluoromethyl)pyridazin-3(2H)-one;
5-(((S)-1-(3-oxo-3-((S)-3-(trifluoromethyl)-5a,6,8,9-tetrahydropyrido[3',2':4,5]pyrrolo[1,2-a]pyrazin-7(5H)-yl)propoxy)propan-2-yl)amino)-4-(trifluoromethyl)pyridazin-3(2H)-one;
5-(((S)-1-(3-oxo-3-((R)-3-(trifluoromethyl)-5a,6,8,9-tetrahydropyrido[3',2':4,5]pyrrolo[1,2-a]pyrazin-7(5H)-yl)propoxy)propan-2-yl)amino)-4-(trifluoromethyl)pyridazin-3(2H)-one;
7-(3-((S)-2-((6-oxo-5-(trifluoromethyl)-1,6-dihydropyridazin-4-yl)amino)propoxy)propanoyl)-3-(trifluoromethyl)-6,7,8,9-tetrahydropyrido[3',2':4,5]pyrrolo[1,2-a]pyrazin-5(5aH)-one;
(R)-7-(3-((S)-2-((6-oxo-5-(trifluoromethyl)-1,6-dihydropyridazin-4-yl)amino)propoxy)propanoyl)-3-(trifluoromethyl)-6,7,8,9-tetrahydropyrido[3',2':4,5]pyrrolo[1,2-a]pyrazin-5(5aH)-one;
(S)-7-(3-((S)-2-((6-oxo-5-(trifluoromethyl)-1,6-dihydropyridazin-4-yl)amino)propoxy)propanoyl)-3-(trifluoromethyl)-6,7,8,9-tetrahydropyrido[3',2':4,5]pyrrolo[1,2-a]pyrazin-5(5aH)-one;
5-(((2S)-1-(3-(5,5-difluoro-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((S)-1-(3-((R)-5,5-difluoro-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((S)-1-(3-((S)-5,5-difluoro-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((2S)-1-(3-oxo-3-(3-(trifluoromethyl)-5a,6,8,9-tetrahydro-7H-pyrido[2',3':4,5]thiazolo[3,2-a]pyrazin-7-yl)propoxy)propan-2-yl)amino)-4-(trifluoromethyl)pyridazin-3(2H)-one;
5-(((S)-1-(3-oxo-3-((S)-3-(trifluoromethyl)-5a,6,8,9-tetrahydro-7H-pyrido[2',3':4,5]thiazolo[3,2-a]pyrazin-7-yl)propoxy)propan-2-yl)amino)-4-(trifluoromethyl)pyridazin-3(2H)-one;
5-(((S)-1-(3-oxo-3-((R)-3-(trifluoromethyl)-5a,6,8,9-tetrahydro-7H-pyrido[2',3':4,5]thiazolo[3,2-a]pyrazin-7-yl)propoxy)propan-2-yl)amino)-4-(trifluoromethyl)pyridazin-3(2H)-one;
5-(((2S)-1-(3-(5-oxido-3-(trifluoromethyl)-5a,6,8,9-tetrahydro-7H-pyrido[2',3':4,5]thiazolo[3,2-a]pyrazin-7-yl)-3-oxopropoxy)propan-2-yl)amino)-4-(trifluoromethyl)pyridazin-3(2H)-one;
5-(((S)-1-(3-((5S,5aS)-5-oxido-3-(trifluoromethyl)-5a,6,8,9-tetrahydro-7H-pyrido[2',3':4,5]thiazolo[3,2-a]pyrazin-7-yl)-3-oxopropoxy)propan-2-yl)amino)-4-(trifluoromethyl)pyridazin-3(2H)-one;
5-(((S)-1-(3-((5R,5aR)-5-oxido-3-(trifluoromethyl)-5a,6,8,9-tetrahydro-7H-pyrido[2',3':4,5]thiazolo[3,2-a]pyrazin-7-yl)-3-oxopropoxy)propan-2-yl)amino)-4-(trifluoromethyl)pyridazin-3(2H)-one;
5-(((2S)-1-(3-(5,5-dioxido-3-(trifluoromethyl)-5a,6,8,9-tetrahydro-7H-pyrido[2',3':4,5]thiazolo[3,2-a]pyrazin-7-yl)-3-oxopropoxy)propan-2-yl)amino)-4-(trifluoromethyl)pyridazin-3(2H)-one;
5-(((S)-1-(3-((S)-5,5-dioxido-3-(trifluoromethyl)-5a,6,8,9-tetrahydro-7H-pyrido[2',3':4,5]thiazolo[3,2-a]pyrazin-7-yl)-3-oxopropoxy)propan-2-yl)amino)-4-(trifluoromethyl)pyridazin-3(2H)-one;
5-(((S)-1-(3-((R)-5,5-dioxido-3-(trifluoromethyl)-5a,6,8,9-tetrahydro-7H-pyrido[2',3':4,5]thiazolo[3,2-a]pyrazin-7-yl)-3-oxopropoxy)propan-2-yl)amino)-4-(trifluoromethyl)pyridazin-3(2H)-one;

-continued 8-(3-((S)-2-((6-oxo-5-(trifluoromethyl)-1,6-dihydropyridazin-4-yl)amino)propoxy)propanoyl)-3,5-bis(trifluoromethyl)-7,8,9,10-tetrahydro-5H-pyrazino[1,2-a]pyrido[3,2-e]pyrazin-6(6aH)-one;
(R)-8-(3-((S)-2-((6-oxo-5-(trifluoromethyl)-1,6-dihydropyridazin-4-yl)amino)propoxy)propanoyl)-3,5-bis(trifluoromethyl)-7,8,9,10-tetrahydro-5H-pyrazino[1,2-a]pyrido[3,2-e]pyrazin-6(6aH)-one;
(S)-8-(3-((S)-2-((6-oxo-5-(trifluoromethyl)-1,6-dihydropyridazin-4-yl)amino)propoxy)propanoyl)-3,5-bis(trifluoromethyl)-7,8,9,10-tetrahydro-5H-pyrazino[1,2-a]pyrido[3,2-e]pyrazin-6(6aH)-one;
(R)-8-(3-((S)-2-((6-oxo-5-(trifluoromethyl)-1,6-dihydropyridazin-4-yl)amino)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
(S)-4-chloro-3,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-4-chloro-3,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3,4-dichloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3,4-dichloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-4-chloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-4-chloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-2,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-2,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-2,3-dichloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-2,3-dichloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-2-amino-3-chloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-2-amino-3-chloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-5-ethyl-3,4-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-5-ethyl-3,4-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-4-chloro-5-ethyl-3-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-4-chloro-5-ethyl-3-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-5-ethyl-3-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-5-ethyl-3-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-5-ethyl-4-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-5-ethyl-4-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-5-ethyl-4-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-5-ethyl-4-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3,4-dichloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3,4-dichloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-4-chloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-4-chloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-5-ethyl-2-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-5-ethyl-2-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-2,3-dichloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-2,3-dichloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-2-amino-3-chloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-2-amino-3-chloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-4,5-dimethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;

-continued (R)-4,5-dimethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-4-chloro-5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-4-chloro-5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-2-amino-5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-2-amino-5-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-ethyl-4-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-ethyl-4-methyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-4-chloro-5-ethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-4-chloro-5-ethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-2-amino-5-ethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-2-amino-5-ethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(((S)-1-(3-((R)-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3,4-dimethyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3,4-dimethyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-bromo-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-bromo-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3,4-dimethyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3,4-dimethyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-chloro-4-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-chloro-4-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-bromo-4-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-bromo-4-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-4-chloro-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-4-chloro-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3,4-dichloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3,4-dichloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-bromo-4-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-bromo-4-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-4-chloro-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-4-chloro-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3,4-dichloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3,4-dichloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-bromo-4-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-bromo-4-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2,3-dimethyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-2,3-dimethyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-chloro-2-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;

-continued 5-(((S)-1-(3-((S)-3-chloro-2-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-bromo-2-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-bromo-2-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-2,3-dimethyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2,3-dimethyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-chloro-2-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-chloro-2-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-bromo-2-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-bromo-2-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2-chloro-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-2-chloro-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-2,3-dichloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-2,3-dichloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-3-bromo-2-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-3-bromo-2-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-2-chloro-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2-chloro-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2,3-dichloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2,3-dichloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-3-bromo-2-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-3-bromo-2-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2-amino-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-2-amino-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-2-amino-3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-2-amino-3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-2-amino-3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-2-amino-3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-2-amino-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2-amino-3-methyl-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2-amino-3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2-amino-3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2-amino-3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2-amino-3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2-amino-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((S)-2-amino-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((S)-1-(3-((R)-2-amino-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2-amino-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((R)-2-amino-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((S)-1-(3-((S)-2-amino-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;

-continued (R)-8-(3-(((S)-1-(6-oxo-5-(trifluoromethyl)-1,6-dihydropyridazin-4-yl)azetidin-2-yl)methoxy)propanoyl)-3-(trifluoromethyl)-6,6a,7,8,9,10-hexahydro-5H-pyrazino[1,2-a][1,8]naphthyridin-5-one;
5-((S)-2-((3-((R)-5,5-difluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aR)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
(R)-6-methyl-8-(3-(((S)-1-(6-oxo-5-(trifluoromethyl)-1,6-dihydropyridazin-4-yl)azetidin-2-yl)methoxy)propanoyl)-3-(trifluoromethyl)-6,6a,7,8,9,10-hexahydro-5H-pyrazino[1,2-a]pyrido[3,2-e]pyrimidin-5-one;
(S)-5-methyl-8-(3-(((S)-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-((S)-2-((3-((5R,6aR)-5-fluoro-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-oxo-3-((R)-3-(trifluoromethyl)-5,6,6a,7,9,10-hexahydro-8H-pyrazino[1,2-a][1,8]naphthyridin-8-yl)propoxy)methyl)azetidin-1-yl)-4-(trifluoromethyl)pyridazin-3(2H)-one;
5-((S)-2-((3-((5R,6aR)-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-oxo-3-((S)-3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-((S)-2-((3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)-4-(trifluoromethyl)pyridazin-3(2H)-one;
5-((S)-2-((3-((R)-3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-((S)-2-((3-((R)-3-bromo-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
(R)-9-(3-(((S)-1-(6-oxo-5-(trifluoromethyl)-1,6-dihydropyridazin-4-yl)azetidin-2-yl)methoxy)propanoyl)-7,7a,8,9,10,11-hexahydro-6H-pyrazino[1,2-d]pyrido[3,2-b][1,4]oxazepine-3-carbonitrile;
5-((S)-2-((3-((R)-3-methyl-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-((S)-2-((3-oxo-3-((R)-3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)-4-(trifluoromethyl)pyridazin-3(2H)-one;
5-((S)-2-((3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)-4-(trifluoromethyl)pyridazin-3(2H)-one;
5-((2S)-2-((3-((7aR)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)methyl)azetidin-1-yl)-4-(trifluoromethyl)pyridazin-3(2H)-one;
5-((S)-2-((3-((R)-5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)methyl)azetidin-1-yl)-4-(trifluoromethyl)pyridazin-3(2H)-one;
(R)-5-methyl-8-(3-(((S)-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-3-chloro-5-methyl-8-(3-(((S)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
(S)-3-bromo-5-methyl-8-(3-(((S)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
(S)-5-methyl-6-oxo-8-(3-(((S)-1-(6-oxo-5-(trifluoromethyl)-1,6-dihydropyridazin-4-yl)azetidin-2-yl)methoxy)propanoyl)-6,6a,7,8,9,10-hexahydro-5H-pyrazino[1,2-a]pyrido[3,2-e]pyrazine-3-carbonitrile;
(S)-3-cyclopropyl-5-methyl-8-(3-(((S)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
5-((S)-2-((3-((5R,6aR)-5-hydroxy-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5R,6aR)-5-fluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-oxo-3-((R)-3-(trifluoromethyl)-5,6,6a,7,9,10-hexahydro-8H-pyrazino[1,2-a]pyrido[3,2-e]pyrazin-8-yl)propoxy)methyl)azetidin-1-yl)-4-(trifluoromethyl)pyridazin-3(2H)-one;
5-((S)-2-((3-oxo-3-((S)-3-(trifluoromethyl)-6a,7,9,10-tetrahydropyrazino[1,2-d]pyrido[3,2-b][1,4]thiazin-8(6H)-yl)propoxy)methyl)azetidin-1-yl)-4-(trifluoromethyl)pyridazin-3(2H)-one;
5-((S)-2-((3-((5R,5aS)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
(S)-7-(3-(((S)-1-(6-oxo-5-(trifluoromethyl)-1,6-dihydropyridazin-4-yl)azetidin-2-yl)methoxy)propanoyl)-3-(trifluoromethyl)-6,7,8,9-tetrahydropyrido[3',2':4,5]pyrrolo[1,2-a]pyrazin-5(5aH)-one;
5-((S)-2-((3-((S)-5,5-difluoro-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((R)-5,5-dimethyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-oxo-3-((R)-3-(trifluoromethyl)-5a,6,8,9-tetrahydropyrido[3',2':4,5]pyrrolo[1,2-a]pyrazin-7(5H)-yl)propoxy)methyl)azetidin-1-yl)-4-(trifluoromethyl)pyridazin-3(2H)-one;
5-((S)-2-((3-((5S,5aS)-5-hydroxy-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aS)-5-fluoro-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aR)-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aS)-5-fluoro-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
(S)-5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
(S)-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)-4-(trifluoromethyl)pyridazin-3(2H)-one;

-continued 5-((S)-2-((3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)methyl)azetidin-1-yl)-4-(trifluoromethyl)pyridazin-3(2H)-one;
5-((S)-2-((3-((S)-3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-((S)-2-((3-((S)-3-bromo-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
(S)-9-(3-(((S)-1-(6-oxo-5-(trifluoromethyl)-1,6-dihydropyridazin-4-yl)azetidin-2-yl)methoxy)propanoyl)-7,7a,8,9,10,11-hexahydro-6H-pyrazino[1,2-d]pyrido[3,2-b][1,4]oxazepine-3-carbonitrile;
5-((S)-2-((3-((S)-3-methyl-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-((S)-2-((3-oxo-3-((S)-3-(trifluoromethyl)-6,7,7a,8,10,11-hexahydropyrazino[1,2-d]pyrido[3,2-b][1,4]diazepin-9(5H)-yl)propoxy)methyl)azetidin-1-yl)-4-(trifluoromethyl)pyridazin-3(2H)-one;
5-((S)-2-((3-oxo-3-((S)-3-(trifluoromethyl)-6,7,7a,8,10,11-hexahydro-9H-pyrazino[1,2-d]pyrido[3,2-b][1,4]thiazepin-9-yl)propoxy)methyl)azetidin-1-yl)-4-(trifluoromethyl)pyridazin-3(2H)-one;
5-((2S)-2-((3-((7aS)-5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)methyl)azetidin-1-yl)-4-(trifluoromethyl)pyridazin-3(2H)-one;
5-((S)-2-((3-((S)-5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)methyl)azetidin-1-yl)-4-(trifluoromethyl)pyridazin-3(2H)-one;
(S)-8-(3-(((S)-1-(6-oxo-5-(trifluoromethyl)-1,6-dihydropyridazin-4-yl)azetidin-2-yl)methoxy)propanoyl)-3-(trifluoromethyl)-6,6a,7,8,9,10-hexahydro-5H-pyrazino[1,2-a][1,8]naphthyridin-5-one;
5-((S)-2-((3-((S)-5,5-difluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aS)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
(S)-6-methyl-8-(3-(((S)-1-(6-oxo-5-(trifluoromethyl)-1,6-dihydropyridazin-4-yl)azetidin-2-yl)methoxy)propanoyl)-3-(trifluoromethyl)-6,6a,7,8,9,10-hexahydro-5H-pyrazino[1,2-a]pyrido[3,2-e]pyrimidin-5-one;
5-((S)-2-((3-((5R,6aS)-5-fluoro-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-oxo-3-((S)-3-(trifluoromethyl)-5,6,6a,7,9,10-hexahydro-8H-pyrazino[1,2-a][1,8]naphthyridin-8-yl)propoxy)methyl)azetidin-1-yl)-4-(trifluoromethyl)pyridazin-3(2H)-one;
5-((S)-2-((3-((5R,6aS)-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-oxo-3-((R)-3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
(R)-3-chloro-5-methyl-8-(3-(((S)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
(R)-3-bromo-5-methyl-8-(3-(((S)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
(R)-5-methyl-6-oxo-8-(3-(((S)-1-(6-oxo-5-(trifluoromethyl)-1,6-dihydropyridazin-4-yl)azetidin-2-yl)methoxy)propanoyl)-6,6a,7,8,9,10-hexahydro-5H-pyrazino[1,2-a]pyrido[3,2-e]pyrazine-3-carbonitrile;
(R)-3-cyclopropyl-5-methyl-8-(3-(((S)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
5-((S)-2-((3-((5R,6aS)-5-hydroxy-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5R,6aS)-5-fluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-oxo-3-((S)-3-(trifluoromethyl)-5,6,6a,7,9,10-hexahydro-8H-pyrazino[1,2-a]pyrido[3,2-e]pyrazin-8-yl)propoxy)methyl)azetidin-1-yl)-4-(trifluoromethyl)pyridazin-3(2H)-one;
5-((S)-2-((3-oxo-3-((R)-3-(trifluoromethyl)-6a,7,9,10-tetrahydropyrazino[1,2-d]pyrido[3,2-b][1,4]thiazin-8(6H)-yl)propoxy)methyl)azetidin-1-yl)-4-(trifluoromethyl)pyridazin-3(2H)-one;
5-((S)-2-((3-((5R,6aS)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5R,6aR)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aR)-5-fluoro-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aS)-5-fluoro-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aR)-5-hydroxy-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aS)-5-hydroxy-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aR)-5-fluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aS)-5-fluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aR)-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5S,6aS)-5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((5R,5aR)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
(R)-7-(3-(((S)-1-(6-oxo-5-(trifluoromethyl)-1,6-dihydropyridazin-4-yl)azetidin-2-yl)methoxy)propanoyl)-3-(trifluoromethyl)-6,7,8,9-tetrahydropyrido[3',2':4,5]pyrrolo[1,2-a]pyrazin-5(5aH)-one;
5-((S)-2-((3-((S)-5,5-dimethyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-oxo-3-((S)-3-(trifluoromethyl)-5a,6,8,9-tetrahydropyrido[3',2':4,5]pyrrolo[1,2-a]pyrazin-7(5H)-yl)propoxy)methyl)azetidin-1-yl)-4-(trifluoromethyl)pyridazin-3(2H)-one;

-continued 5-((S)-2-((3-((5S,5aR)-5-hydroxy-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aR)-5-fluoro-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aS)-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aR)-5-fluoro-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aS)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aR)-5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aS)-5-fluoro-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5S,5aR)-5-fluoro-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aS)-5-hydroxy-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aR)-5-hydroxy-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aR)-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aS)-5-methyl-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aS)-5-fluoro-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
5-((S)-2-((3-((5R,5aR)-5-fluoro-3-(trifluoromethyl)-5a,6,8,9-tetrahydropyrido[3',2':4,5]pyrrolo[1,2-a]pyrazin-7(5H)-yl)-3-oxopropoxy)methyl)azetidin-1-yl)-4-(trifluoromethyl)pyridazin-3(2H)-one;
(S)-5-methyl-8-(3-(((S)-4-oxo-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-(((R)-3,3-difluoro-4-oxo-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-(3-(((2S,3S)-3-methyl-4-oxo-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((S)-2-(6-oxo-5-(trifluoromethyl)-1,6-dihydropyridazin-4-yl)-2-azaspiro[3,3]heptan-1-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((1R,4R,5S)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((2S,4S)-4-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-(((S)-4,4-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-(((S)-4,4-difluoro-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-(3-(((S)-2-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((2S,3R)-3-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-(((S)-3,3-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-(((2R,3S)-3-fluoro-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-(((2R,3R)-3-methoxy-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-(3-(((2R,3R)-1-(6-oxo-5-(trifluoromethyl)-1,6-dihydropyridazin-4-yl)-3-(trifluoromethoxy)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-(((S)-3,3-dimethyl-4-oxo-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-(((R)-3,3-difluoro-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-5-methyl-8-(3-(((S)-4-oxo-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-8-(3-(((R)-3,3-difluoro-4-oxo-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;

-continued (R)-5-methyl-8-(3-(((2S,3S)-3-methyl-4-oxo-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((S)-2-(6-oxo-5-(trifluoromethyl)-1,6-dihydropyridazin-4-yl)-2-azaspiro[3,3]heptan-1-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((1R,4R,5S)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((2S,4S)-4-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-8-(3-(((S)-4,4-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-5-methyl-8-(3-(((2S,3R)-3-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-8-(3-(((S)-3,3-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-(((2R,3S)-3-fluoro-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-(((2R,3R)-3-methoxy-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-(((S)-3,3-dimethyl-4-oxo-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-(((R)-3,3-difluoro-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-(3-(((2S,4R)-4-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((2S,4R)-4-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((2S,3S)-3-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((2S,3S)-3-methyl-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one(S)-5-methyl-8-(3-(((2S,3R)-3-methyl-4-oxo-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((2S,3R)-3-methyl-4-oxo-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-(((2R,3S)-3-methoxy-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-(((2R,3S)-3-methoxy-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-(3-(((2R,3S)-1-(6-oxo-5-(trifluoromethyl)-1,6-dihydropyridazin-4-yl)-3-(trifluoromethoxy)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((2R,3S)-1-(6-oxo-5-(trifluoromethyl)-1,6-dihydropyridazin-4-yl)-3-(trifluoromethoxy)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-(((2R,3R)-3-fluoro-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-(((2R,3R)-3-fluoro-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-5-methyl-8-(3-(((1S,4R,5R)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((1R,4R,5R)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-elpyrazin-6(6aH)-one;
(S)-5-methyl-8-(3-(((1S,4R,5S)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-e]pyrazin-6(6aH)-one;

-continued (R)-5-methyl-8-(3-(((1S,4R,5R)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((1S,4R,5S)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-e]pyrazin-6(6aH)-one;
5-((2S)-2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-((2S)-2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
3-chloro-5-methyl-8-(3-(((S)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
5-methyl-8-(3-(((S)-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((1R,4R,5R)-6-(6-oxo-5-(trifluoromethyl)-1,6-dihydropyridazin-4-yl)-6-azabicyclo[3.2.0]heptan-4-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-4-acetyl-5-(2-((3-oxo-3-(4-(5-(trifluoromethyl)pyrimidin-2-yl)piperazin-1-yl)propoxy)methyl)azetidin-1-yl)pyridazin-3(2H)-one;
(S)-5-(2-((3-(4-(5-cyclopropylpyrimidin-2-yl)piperazin-1-yl)-3-oxopropoxy)methyl)azetidin-1-yl)-4-(trifluoromethyl)pyridazin-3(2H)-one;
(S)-5-methyl-8-(3-((R)-1-((S)-1-(6-oxo-5-(trifluoromethyl)-1,6-dihydropyridazin-4-yl)azetidin-2-yl)ethoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((S)-4-(6-oxo-5-(trifluoromethyl)-1,6-dihydropyridazin-4-yl)morpholin-3-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((R)-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((S)-1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((S)-1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
9-(3-(2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(R)-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
8-(3-(2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
3-chloro-4,5-dimethyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-4,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-4,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-4,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-4,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-4,5-dimethyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-4,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-4,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-4,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-4,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3,4,5-trimethyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3,4,5-trimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;

-continued 3,4,5-trimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3,4,5-trimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3,4,5-trimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
2-chloro-3,5-dimethyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
2-chloro-3,5-dimethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
2-chloro-3,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-2-chloro-3,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-2-chloro-3,5-dimethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
8-(3-(2-((6-oxo-5-(trifluoromethyl)-1,6-dihydropyridazin-4-yl)amino)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
8-(3-((R)-2-((6-oxo-5-(trifluoromethyl)-1,6-dihydropyridazin-4-yl)amino)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
(R)-8-(3-((S)-2-((6-oxo-5-(trifluoromethyl)-1,6-dihydropyridazin-4-yl)amino)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
(S)-8-(3-((R)-2-((6-oxo-5-(trifluoromethyl)-1,6-dihydropyridazin-4-yl)amino)propoxy)propanoyl)-5-(2,2,2-trifluoroethyl)-3-(trifluoromethyl)-7,8,9,10-tetrahydro-5H-pyrazino[1,2-a]pyrido[3,2-e]pyrazin-6(6aH)-one;
8-(3-(2-((6-oxo-5-(trifluoromethyl)-1,6-dihydropyridazin-4-yl)amino)propoxy)propanoyl)-3-(trifluoromethyl)-5-vinyl-7,8,9,10-tetrahydro-5H-pyrazino[1,2-a]pyrido[3,2-e]pyrazin-6(6aH)-one;
8-(3-((S)-2-((6-oxo-5-(trifluoromethyl)-1,6-dihydropyridazin-4-yl)amino)propoxy)propanoyl)-3-(trifluoromethyl)-5-vinyl-7,8,9,10-tetrahydro-5H-pyrazino[1,2-a]pyrido[3,2-e]pyrazin-6(6aH)-one;
8-(3-((R)-2-((6-oxo-5-(trifluoromethyl)-1,6-dihydropyridazin-4-yl)amino)propoxy)propanoyl)-3-(trifluoromethyl)-5-vinyl-7,8,9,10-tetrahydro-5H-pyrazino[1,2-a]pyrido[3,2-e]pyrazin-6(6aH)-one;
(S)-8-(3-((R)-2-((6-oxo-5-(trifluoromethyl)-1,6-dihydropyridazin-4-yl)amino)propoxy)propanoyl)-3-(trifluoromethyl)-5-vinyl-7,8,9,10-tetrahydro-5H-pyrazino[1,2-a]pyrido[3,2-e]pyrazin-6(6aH)-one;
(R)-8-(3-((R)-2-((6-oxo-5-(trifluoromethyl)-1,6-dihydropyridazin-4-yl)amino)propoxy)propanoyl)-3-(trifluoromethyl)-5-vinyl-7,8,9,10-tetrahydro-5H-pyrazino[1,2-a]pyrido[3,2-e]pyrazin-6(6aH)-one;
9-(3-(2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(R)-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(S)-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
6-methyl-9-(3-(2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
6-methyl-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(R)-6-methyl-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
(S)-6-methyl-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-a]pyrido[3,2-f][1,4]diazepin-5(6H)-one;
5-methyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydropyrido[3,4-c][1,5]naphthyridin-6(5H)-one;
8-(3-(2-((5-acetyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-((R)-2-((5-acetyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-((R)-2-((5-acetyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((R)-2-((5-acetyl-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
3-chloro-2-fluoro-5-methyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-2-fluoro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-2-fluoro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-2-fluoro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-2-fluoro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
5-methyl-8-(3-(2-((6-oxo-5-(trifluoromethyl)-1,6-dihydropyridazin-4-yl)amino)butoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((S)-2-((6-oxo-5-(trifluoromethyl)-1,6-dihydropyridazin-4-yl)amino)butoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((R)-2-((6-oxo-5-(trifluoromethyl)-1,6-dihydropyridazin-4-yl)amino)butoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-((R)-2-((6-oxo-5-(trifluoromethyl)-1,6-dihydropyridazin-4-yl)amino)butoxy)propanoyl)-3-(trifluoromethyl)-7,8,9,10-tetrahydro-5H-pyrazino[1,2-a]pyrido[3,2-e]pyrazin-6(6aH)-one;

-continued (R)-5-methyl-8-(3-((R)-2-((6-oxo-5-(trifluoromethyl)-1,6-dihydropyridazin-4-yl)amino)butoxy)propanoyl)-3-(trifluoromethyl)-7,8,9,10-tetrahydro-5H-pyrazino[1,2-a]pyrido[3,2-e]pyrazin-6(6aH)-one;
5-methyl-9-(3-(2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
5-methyl-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(R)-5-methyl-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
(S)-5-methyl-9-(3-((R)-2-((6-oxo-5-(trifluoromethyl)-1,6-dihydropyridazin-4-yl)amino)propoxy)propanoyl)-3-(trifluoromethyl)-7,7a,8,9,10,11-hexahydropyrazino[1,2-d]pyrido[3,2-b][1,4]diazepin-6(5H)-one;
5-ethyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-ethyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-ethyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-ethyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(methyl-d3)-8-(3-(2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-(methyl-d3)-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-(methyl-d3)-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-(methyl-d3)-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
3-fluoro-5-methyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-fluoro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-fluoro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-fluoro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-fluoro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-5-methyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-5-methyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-5-methyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-5-methyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-5-ethyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-chloro-5-ethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-chloro-5-ethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-chloro-5-ethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-5-ethyl-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-5-ethyl-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
3-bromo-5-ethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-3-bromo-5-ethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-3-bromo-5-ethyl-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
5-isopropyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;

-continued 5-isopropyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-isopropyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-isopropyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-isopropyl-8-(3-(3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-isopropyl-8-(3-((S)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-isopropyl-8-(3-((R)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one(S)-5-isopropyl-8-(3-((R)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-isopropyl-8-(3-((R)-3-methoxy-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-cyclopropyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5-cyclopropyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5-cyclopropyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
8-(3-(2-((5-acetyl-6-oxo-1,6-dihydropyridazin-4-yl)amino)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
8-(3-((R)-2-((5-acetyl-6-oxo-1,6-dihydropyridazin-4-yl)amino)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
(S)-8-(3-((S)-2-((5-acetyl-6-oxo-1,6-dihydropyridazin-4-yl)amino)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
(R)-8-(3-((S)-2-((5-acetyl-6-oxo-1,6-dihydropyridazin-4-yl)amino)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
(S)-8-(3-((R)-2-((5-acetyl-6-oxo-1,6-dihydropyridazin-4-yl)amino)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
(R)-8-(3-((R)-2-((5-acetyl-6-oxo-1,6-dihydropyridazin-4-yl)amino)propoxy)propanoyl)-5-cyclopropyl-3-(trifluoromethyl)-7,8,9,10-tetrahydro-5H-pyrazino[1,2-a]pyrido[3,2-e]pyrazin-6(6aH)-one;
5-cyclopropyl-3-fluoro-8-(3-(2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
5-cyclopropyl-3-fluoro-8-(3-((S)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
5-cyclopropyl-3-fluoro-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(S)-5-cyclopropyl-3-fluoro-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
(R)-5-cyclopropyl-3-fluoro-8-(3-((R)-2-((6-oxo-5-(trifluoromethyl)-1,6-dihydropyridazin-4-yl)amino)propoxy)propanoyl)-7,8,9,10-tetrahydro-5H-pyrazino[1,2-a]pyrido[3,2-e]pyrazin-6(6aH)-one;
8-(3-(3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-((S)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-((R)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-((R)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((R)-3-methoxy-2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
5-methyl-8-(3-(3,3,3-trifluoro-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((R)-3,3,3-trifluoro-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one5-methyl-8-(3-((S)-3,3,3-trifluoro-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
8-(3-(2-((5-chloro-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-((S)-2-((5-chloro-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-((R)-2-((5-chloro-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-((R)-2-((5-chloro-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((R)-2-((5-chloro-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-(2-((5-bromo-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-((S)-2-((5-bromo-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-((R)-2-((5-bromo-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;

-continued (S)-8-(3-((R)-2-((5-bromo-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-((R)-2-((5-bromo-6-oxo-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
5,6a-dimethyl-8-(3-(2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5,6a-dimethyl-8-(3-((S)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5,6a-dimethyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(S)-5,6a-dimethyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
(R)-5,6a-dimethyl-8-(3-((R)-2-((6-oxo-5-(trifluoromethyl)-1,6-dihydropyridazin-4-yl)amino)propoxy)propanoyl)-3-(trifluoromethyl)-7,8,9,10-tetrahydro-5H-pyrazino[1,2-a]pyrido[3,2-e]pyrazin-6(6aH)-one;
5-methyl-8-((2-(2-((6-oxo-5-(trifluoromethyl)-1,6-dihydropyridazin-4-yl)amino)propoxy)ethyl)sulfonyl)-3-(trifluoromethyl)-7,8,9,10-tetrahydro-5H-pyrazino[1,2-a]pyrido[3,2-e]pyrazin-6(6aH)-one;
5-methyl-8-((2-((S)-2-((6-oxo-5-(trifluoromethyl)-1,6-dihydropyridazin-4-yl)amino)propoxy)ethyl)sulfonyl)-3-(trifluoromethyl)-7,8,9,10-tetrahydro-5H-pyrazino[1,2-a]pyrido[3,2-e]pyrazin-6(6aH)-one;
5-methyl-8-((2-((R)-2-((6-oxo-5-(trifluoromethyl)-1,6-dihydropyridazin-4-yl)amino)propoxy)ethyl)sulfonyl)-3-(trifluoromethyl)-7,8,9,10-tetrahydro-5H-pyrazino[1,2-a]pyrido[3,2-e]pyrazin-6(6aH)-one;
(R)-5-methyl-8-((2-((S)-2-((6-oxo-5-(trifluoromethyl)-1,6-dihydropyridazin-4-yl)amino)propoxy)ethyl)sulfonyl)-3-(trifluoromethyl)-7,8,9,10-tetrahydro-5H-pyrazino[1,2-a]pyrido[3,2-e]pyrazin-6(6aH)-one;
(S)-5-methyl-8-((2-((R)-2-((6-oxo-5-(trifluoromethyl)-1,6-dihydropyridazin-4-yl)amino)propoxy)ethyl)sulfonyl)-3-(trifluoromethyl)-7,8,9,10-tetrahydro-5H-pyrazino[1,2-a]pyrido[3,2-e]pyrazin-6(6aH)-one;
(R)-5-methyl-8-((2-((R)-2-((6-oxo-5-(trifluoromethyl)-1,6-dihydropyridazin-4-yl)amino)propoxy)ethyl)sulfonyl)-3-(trifluoromethyl)-7,8,9,10-tetrahydro-5H-pyrazino[1,2-a]pyrido[3,2-e]pyrazin-6(6aH)-one;
5-methyl-8-(1-(2-((6-oxo-5-(trifluoromethyl)-1,6-dihydropyridazin-4-yl)amino)propyl)piperidine-4-carbonyl)-3-(trifluoromethyl)-7,8,9,10-tetrahydro-5H-pyrazino[1,2-a]pyrido[3,2-e]pyrazin-6(6aH)-one;
5-methyl-8-(1-((S)-2-((6-oxo-5-(trifluoromethyl)-1,6-dihydropyridazin-4-yl)amino)propyl)piperidine-4-carbonyl)-3-(trifluoromethyl)-7,8,9,10-tetrahydro-5H-pyrazino[1,2-a]pyrido[3,2-e]pyrazin-6(6aH)-one;
5-methyl-8-(1-((R)-2-((6-oxo-5-(trifluoromethyl)-1,6-dihydropyridazin-4-yl)amino)propyl)piperidine-4-carbonyl)-3-(trifluoromethyl)-7,8,9,10-tetrahydro-5H-pyrazino[1,2-a]pyrido[3,2-e]pyrazin-6(6aH)-one;
(S)-5-methyl-8-(1-((R)-2-((6-oxo-5-(trifluoromethyl)-1,6-dihydropyridazin-4-yl)amino)propyl)piperidine-4-carbonyl)-3-(trifluoromethyl)-7,8,9,10-tetrahydro-5H-pyrazino[1,2-a]pyrido[3,2-e]pyrazin-6(6aH)-one;
(R)-5-methyl-8-(1-((R)-2-((6-oxo-5-(trifluoromethyl)-1,6-dihydropyridazin-4-yl)amino)propyl)piperidine-4-carbonyl)-3-(trifluoromethyl)-7,8,9,10-tetrahydro-5H-pyrazino[1,2-a]pyrido[3,2-e]pyrazin-6(6aH)-one;
5-methyl-8-(1-(2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
5-methyl-8-(1-((R)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
5-methyl-8-(1-((S)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(6aS)-5-methyl-8-(1-((R)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(6aR)-5-methyl-8-(1-((R)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(6aS)-5-methyl-8-(1-((S)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
(6aR)-5-methyl-8-(1-((S)-2-((6-oxo-5-(trifluoromethyl)-1,6-dihydropyridazin-4-yl)amino)propyl)pyrrolidine-3-carbonyl)-3-(trifluoromethyl)-7,8,9,10-tetrahydro-5H-pyrazino[1,2-a]pyrido[3,2-e]pyrazin-6(6aH)-one;
5-((1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(trifluoromethyl)pyridazin-3(2H)-one;
5-(((2R)-1-(3-oxo-3-(3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(trifluoromethyl)pyridazin-3(2H)-one;
5-(((R)-1-(3-oxo-3-((R)-3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(trifluoromethyl)pyridazin-3(2H)-one;
5-(((R)-1-(3-oxo-3-((S)-3-(trifluoromethyl)-6,7,7a,8,10,11-hexahydropyrazino[1,2-d]pyrido[3,2-b][1,4]diazepin-9(5H)-yl)propoxy)propan-2-yl)amino)-4-(trifluoromethyl)pyridazin-3(2H)-one;
5-((1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)-4-(trifluoromethyl)pyridazin-3(2H)-one;
5-(((2R)-1-(3-oxo-3-(3-(trifluoromethyl)-5,6,6a,7,9,10-hexahydro-8H-pyrazino[1,2-a]pyrido[3,2-e]pyrazin-8-yl)propoxy)propan-2-yl)amino)-4-(trifluoromethyl)pyridazin-3(2H)-one;
5-(((R)-1-(3-oxo-3-((R)-3-(trifluoromethyl)-5,6,6a,7,9,10-hexahydro-8H-pyrazino[1,2-a]pyrido[3,2-e]pyrazin-8-yl)propoxy)propan-2-yl)amino)-4-(trifluoromethyl)pyridazin-3(2H)-one;
5-(((R)-1-(3-oxo-3-((S)-3-(trifluoromethyl)-5,6,6a,7,9,10-hexahydro-8H-pyrazino[1,2-a]pyrido[3,2-e]pyrazin-8-yl)propoxy)propan-2-yl)amino)-4-(trifluoromethyl)pyridazin-3(2H)-one;
5-((1-(3-(5-methyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((2R)-1-(3-(5-methyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((R)-1-(3-((R)-5-methyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-(((R)-1-(3-((S)-5-methyl-3-(trifluoromethyl)-5,6,6a,7,9,10-hexahydro-8H-pyrazino[1,2-a]pyrido[3,2-e]pyrazin-8-yl)-3-oxopropoxy)propan-2-yl)amino)-4-(trifluoromethyl)pyridazin-3(2H)-one;
5-((1-(3-(5-methyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((2R)-1-(3-(5-methyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;

-continued 5-(((R)-1-(3-((R)-5-methyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-(((R)-1-(3-((S)-5-methyl-3-(trifluoromethyl)-6,7,7a,8,10,11-hexahydropyrazino[1,2-d]pyrido[3,2-b][1,4]diazepin-9(5H)-yl)-3-oxopropoxy)propan-2-yl)amino)-4-(trifluoromethyl)pyridazin-3(2H)-one;
5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)-4-(trifluoromethyl)pyridazin-3(2H)-one;
(R)-5-((1-(3-oxo-3-(3-(trifluoromethyl)-8,9-dihydropyrido[3',2':4,5]pyrrolo[1,2-a]pyrazin-7(6H)-yl)propoxy)propan-2-yl)amino)-4-(trifluoromethyl)pyridazin-3(2H)-one;
5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(R)-5-((1-(3-(5-chloro-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
(R)-5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)amino)-4-(trifluoromethyl)pyridazin-3(2H)-one;
5-((1-(3-(5-methyl-3-(trifluoromethyl)-8,9-dihydropyrido[3',2':4,5]pyrrolo[1,2-a]pyrazin-7(6H)-yl)-3-oxopropoxy)propan-2-yl)oxy)-4-(trifluoromethyl)pyridazin-3(2H)-one;
5-((1-(3-oxo-3-(3-(trifluoromethyl)-8,9-dihydropyrido[3',2':4,5]pyrrolo[1,2-a]pyrazin-7(6H)-yl)propoxy)propan-2-yl)oxy)-4-(trifluoromethyl)pyridazin-3(2H)-one;
5-((1-(3-oxo-3-(3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-(((S)-1-(3-oxo-3-((S)-3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-(((S)-1-(3-oxo-3-((R)-3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-(((R)-1-(3-oxo-3-((S)-3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-(((R)-1-(3-oxo-3-((R)-3-(trifluoromethyl)-5a,6,8,9-tetrahydropyrido[3',2':4,5]imidazo[1,2-a]pyrazin-7(5H)-yl)propoxy)propan-2-yl)oxy)-4-(trifluoromethyl)pyridazin-3(2H)-one;
5-((1-(3-oxo-3-(3-(trifluoromethyl)-8,9-dihydropyrido[3',2':4,5]imidazo[1,2-a]pyrazin-7(6H)-yl)propoxy)propan-2-yl)oxy)-4-(trifluoromethyl)pyridazin-3(2H)-one;
5-((1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-(((2R)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)oxy)-4-(trifluoromethyl)pyridazin-3(2H)-one;
5-((1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((2R)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((R)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((R)-1-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-((1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((2R)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((R)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((R)-1-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-((1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2R)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((R)-3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((S)-3-chloro-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
9-(3-(2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
9-(3-((R)-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
(R)-9-(3-((R)-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
(S)-9-(3-((R)-2-((6-oxo-5-(trifluoromethyl)-1,6-dihydropyridazin-4-yl)amino)propoxy)propanoyl)-7,7a,8,9,10,11-hexahydro-6H-pyrazino[1,2-d]pyrido[3,2-b][1,4]oxazepine-3-carbonitrile;
5-((1-(3-(3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2R)-1-(3-(3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((R)-3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((S)-3-bromo-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-((1-(3-(3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;

-continued 5-(((2S)-1-(3-(3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2R)-1-(3-(3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((R)-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((S)-3-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-((1-(3-(3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2R)-1-(3-(3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((R)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((S)-3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
3-oxo-5-((1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-2,3-dihydropyridazine-4-carbonitrile;
3-oxo-5-(((2S)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-2,3-dihydropyridazine-4-carbonitrile;
3-oxo-5-(((2R)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-2,3-dihydropyridazine-4-carbonitrile;
3-oxo-5-(((R)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-2,3-dihydropyridazine-4-carbonitrile;
3-oxo-5-(((R)-1-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-2,3-dihydropyridazine-4-carbonitrile;
5-((1-(3-(3-acetyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2R)-1-(3-(3-acetyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((R)-3-acetyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((R)-1-(3-((S)-3-acetyl-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-((1-(3-(6-methyl-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-(((2S)-1-(3-(6-methyl-3-(trifluoromethyl)-6,7,7a,8,10,11-hexahydro-9H-pyrazino[1,2-d]pyrido[3,2-b][1,4]oxazepin-9-yl)-3-oxopropoxy)propan-2-yl)amino)-4-(trifluoromethyl)pyridazin-3(2H)-one;
5-((1-(2-hydroxy-3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-((1-(3-(3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((2S)-1-((2R)-3-(3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((2S)-1-((2S)-3-(3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((S)-1-((R)-3-((S)-3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
5-(((S)-1-((S)-3-((S)-3-chloro-6,7,7a,8,10,11-hexahydro-9H-pyrazino[1,2-d]pyrido[3,2-b][1,4]oxazepin-9-yl)-2-hydroxy-3-oxopropoxy)propan-2-yl)amino)-4-(trifluoromethyl)pyridazin-3(2H)-one;
8-(2-hydroxy-3-(2-((6-oxo-5-(trifluoromethyl)-1,6-dihydropyridazin-4-yl)amino)propoxy)propanoyl)-5-methyl-3-(trifluoromethyl)-7,8,9,10-tetrahydro-5H-pyrazino[1,2-a]pyrido[3,2-e]pyrazin-6(6aH)-one;
5-((1-methoxy-3-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((2S)-1-methoxy-3-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((2R)-1-methoxy-3-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((R)-1-methoxy-3-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-(((R)-1-methoxy-3-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)amino)-4-(trifluoromethyl)pyridazin-3(2H)-one;
5-((1-(3-(3-chloro-6,7,7a,8,10,11-hexahydro-9H-pyrazino[1,2-d]pyrido[3,2-b][1,4]oxazepin-9-yl)-3-oxopropoxy)-3-methoxypropan-2-yl)amino)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]oxazepin-9-yl)-3-oxopropoxy)-3-methoxypropan-2-yl)amino)-4-(trifluoromethyl)pyridazin-3(2H)-one;
5-(((2R)-1-(3-(3-chloro-6,7,7a,8,10,11-hexahydro-9H-pyrazino[1,2-d]pyrido[3,2-b][1,4]oxazepin-9-yl)-3-oxopropoxy)-3-methoxypropan-2-yl)amino)-4-(trifluoromethyl)pyridazin-3(2H)-one;
5-(((R)-1-(3-((R)-3-chloro-6,7,7a,8,10,11-hexahydro-9H-pyrazino[1,2-d]pyrido[3,2-b][1,4]oxazepin-9-yl)-3-oxopropoxy)-3-methoxypropan-2-yl)amino)-4-(trifluoromethyl)pyridazin-3(2H)-one;
5-(((R)-1-(3-((S)-3-chloro-6,7,7a,8,10,11-hexahydro-9H-pyrazino[1,2-d]pyrido[3,2-b][1,4]oxazepin-9-yl)-3-oxopropoxy)-3-methoxypropan-2-yl)amino)-4-(trifluoromethyl)pyridazin-3(2H)-one;
5-((1-methoxy-3-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((2S)-1-methoxy-3-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((2R)-1-methoxy-3-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;

-continued 5-(((R)-1-methoxy-3-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
5-(((R)-1-methoxy-3-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)-4-(trifluoromethyl)pyridazin-3(2H)-one;
4-acetyl-5-((1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-acetyl-5-(((2R)-1-(3-oxo-3-(3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-acetyl-5-(((S)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-acetyl-5-(((S)-1-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-acetyl-5-(((R)-1-(3-oxo-3-((S)-3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-acetyl-5-(((R)-1-(3-oxo-3-((R)-3-(trifluoromethyl)-6a,7,9,10-tetrahydropyrazino[1,2-d]pyrido[3,2-b][1,4]oxazin-8(6H)-yl)propoxy)propan-2-yl)amino)pyridazin-3(2H)-one;
4-acetyl-5-((1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-acetyl-5-(((2R)-1-(3-oxo-3-(3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-acetyl-5-(((R)-1-(3-oxo-3-((R)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
4-acetyl-5-(((R)-1-(3-oxo-3-((S)-3-(trifluoromethyl)-6,7,7a,8,10,11-hexahydro-9H-pyrazino[1,2-d]pyrido[3,2-b][1,4]oxazepin-9-yl)propoxy)propan-2-yl)amino)pyridazin-3(2H)-one;
5-((1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(trifluoromethyl)pyridazin-3(2H)-one;
5-(((2R)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(trifluoromethyl)pyridazin-3(2H)-one;
5-(((R)-1-(3-oxo-3-((R)-3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(trifluoromethyl)pyridazin-3(2H)-one;
5-(((R)-1-(3-oxo-3-((S)-3-(trifluoromethyl)-6,7,7a,8,10,11-hexahydro-9H-pyrazino[1,2-d]pyrido[3,2-b][1,4]thiazepin-9-yl)propoxy)propan-2-yl)amino)-4-(trifluoromethyl)pyridazin-3(2H)-one;
5-((1-(3-(3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2S)-1-(3-(3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2R)-1-(3-(3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((R)-1-(3-((R)-3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((R)-1-(3-((S)-3-bromo-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-((1-(3-(3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2S)-1-(3-(3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2R)-1-(3-(3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((R)-1-(3-((R)-3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((R)-1-(3-((S)-3-chloro-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-((1-(3-(5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2R)-1-(3-(5-oxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-((1-(3-(5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((2R)-1-(3-(5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((R)-1-(3-((R)-5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
5-(((R)-1-(3-((S)-5,5-dioxido-3-(trifluoromethyl)-6,7,7a,8,10,11-hexahydro-9H-pyrazino[1,2-d]pyrido[3,2-b][1,4]thiazepin-9-yl)-3-oxopropoxy)propan-2-yl)amino)-4-(trifluoromethyl)pyridazin-3(2H)-one;
8-(3-(2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a][1,8]naphthyridin-5-one;
8-(3-((R)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a][1,8]naphthyridin-5-one;
(R)-8-(3-((R)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a][1,8]naphthyridin-5-one;
(S)-8-(3-((R)-2-((6-oxo-5-(trifluoromethyl)-1,6-dihydropyridazin-4-yl)amino)propoxy)propanoyl)-3-(trifluoromethyl)-6,6a,7,8,9,10-hexahydro-5H-pyrazino[1,2-a][1,8]naphthyridin-5-one;
5-((1-(3-(5,5-difluoro-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2R)-1-(3-(5,5-difluoro-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((R)-1-(3-((R)-5,5-difluoro-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;

-continued 5-(((R)-1-(3-((S)-5,5-difluoro-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2S)-1-(3-(5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-((1-(3-(5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2R)-1-(3-(5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2S)-1-(3-((6aR)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2R)-1-(3-((6aR)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2S)-1-(3-((6aS)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2R)-1-(3-((6aS)-5-hydroxy-5-methyl-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-((1-(3-(5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-(((2S)-1-(3-(5-hydroxy-5-methyl-3-(trifluoromethyl)-5a,6,8,9-tetrahydropyrido[3',2':4,5]pyrrolo[1,2-a]pyrazin-7(5H)-yl)-3-oxopropoxy)propan-2-yl)amino)-4-(trifluoromethyl)pyridazin-3(2H)-one;
5-((1-(3-(5-hydroxy-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((2S)-1-(3-(5-hydroxy-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((S)-1-(3-((5R,6aS)-5-hydroxy-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-(((S)-1-(3-((5S,6aS)-5-hydroxy-3-(trifluoromethyl)-5,6,6a,7,9,10-hexahydro-8H-pyrazino[1,2-a][1,8]naphthyridin-8-yl)-3-oxopropoxy)propan-2-yl)amino)-4-(trifluoromethyl)pyridazin-3(2H)-one;
5-methyl-8-(3-(2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((R)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
3-chloro-5-methyl-8-(3-(2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
3-chloro-5-methyl-8-(3-((S)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
3-chloro-5-methyl-8-(3-((R)-2-((6-oxo-5-(trifluoromethyl)-1,6-dihydropyridazin-4-yl)oxy)propoxy)propanoyl)-7,8,9,10-tetrahydro-5H-pyrazino[1,2-a]pyrido[3,2-e]pyrazin-6(6aH)-one;
5-isopropyl-8-(3-(2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-isopropyl-8-(3-((S)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-isopropyl-8-(3-((R)-2-((6-oxo-5-(trifluoromethyl)-1,6-dihydropyridazin-4-yl)oxy)propoxy)propanoyl)-3-(trifluoromethyl)-7,8,9,10-tetrahydro-5H-pyrazino[1,2-a]pyrido[3,2-e]pyrazin-6(6aH)-one;
5-((1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2R)-1-(3-(3-chloro-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-((1-(3-(3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-(((2R)-1-(3-(3-chloro-4-methyl-6,7,7a,8,10,11-hexahydro-9H-pyrazino[1,2-d]pyrido[3,2-b][1,4]oxazepin-9-yl)-3-oxopropoxy)propan-2-yl)oxy)-4-(trifluoromethyl)pyridazin-3(2H)-one;
5-((1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(trifluoromethyl)pyridazin-3(2H)-one;
5-(((2S)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(trifluoromethyl)pyridazin-3(2H)-one;
5-(((2R)-1-(3-oxo-3-(3-(trifluoromethyl)-6,7,7a,8,10,11-hexahydro-9H-pyrazino[1,2-d]pyrido[3,2-b][1,4]thiazepin-9-yl)propoxy)propan-2-yl)oxy)-4-(trifluoromethyl)pyridazin-3(2H)-one;
5-methyl-8-(3-((1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-(((S)-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-(((R)-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((R)-1-(6-oxo-5-(trifluoromethyl)-1,6-dihydropyridazin-4-yl)azetidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
3-chloro-5-methyl-8-(3-((1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
3-chloro-5-methyl-8-(3-(((R)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
(S)-3-chloro-5-methyl-8-(3-(((R)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;
(R)-3-chloro-5-methyl-8-(3-(((R)-1-(6-oxo-5-(trifluoromethyl)-1,6-dihydropyridazin-4-yl)azetidin-2-yl)methoxy)propanoyl)-7,8,9,10-tetrahydro-5H-pyrazino[1,2-a]pyrido[3,2-e]pyrazin-6(6aH)-one;

-continued 5-((2R)-2-((3-oxo-3-(3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-((R)-2-((3-oxo-3-((S)-3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-((R)-2-((3-oxo-3-((R)-3-(trifluoromethyl)-6a,7,9,10-tetrahydropyrazino[1,2-d]pyrido[3,2-b][1,4]oxazin-8(6H)-yl)propoxy)methyl)azetidin-1-yl)-4-(trifluoromethyl)pyridazin-3(2H)-one;
5-((2R)-2-((3-(3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-((R)-2-((3-((R)-3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
5-((R)-2-((3-((S)-3-chloro-6,7,7a,8,10,11-hexahydro-9H-pyrazino[1,2-d]pyrido[3,2-b][1,4]oxazepin-9-yl)-3-oxopropoxy)methyl)azetidin-1-yl)-4-(trifluoromethyl)pyridazin-3(2H)-one;
(R)-5-(2-((3-oxo-3-(3-(trifluoromethyl)-8,9-dihydropyrido[3',2':4,5]pyrrolo[1,2-a]pyrazin-7(6H)-yl)propoxy)methyl)azetidin-1-yl)-4-(trifluoromethyl)pyridazin-3(2H)-one;
(R)-5-(2-((3-(5-methyl-3-(trifluoromethyl)-8,9-dihydropyrido[3',2':4,5]pyrrolo[1,2-a]pyrazin-7(6H)-yl)-3-oxopropoxy)methyl)azetidin-1-yl)-4-(trifluoromethyl)pyridazin-3(2H)-one;
5-(2-((3-(5,5-difluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((2S)-2-((3-(5,5-difluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((2R)-2-((3-(5,5-difluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((R)-2-((3-((R)-5,5-difluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((R)-2-((3-((S)-5,5-difluoro-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-(2-((3-(5-methyl-3-(trifluoromethyl)-6a,7,9,10-tetrahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((2S)-2-((3-(5-methyl-3-(trifluoromethyl)-6a,7,9,10-tetrahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((2R)-2-((3-(5-methyl-3-(trifluoromethyl)-6a,7,9,10-tetrahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((R)-5-methyl-3-(trifluoromethyl)-6a,7,9,10-tetrahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((S)-2-((3-((S)-5-methyl-3-(trifluoromethyl)-6a,7,9,10-tetrahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((R)-2-((3-((R)-5-methyl-3-(trifluoromethyl)-6a,7,9,10-tetrahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((R)-2-((3-((S)-5-methyl-3-(trifluoromethyl)-6a,7,9,10-tetrahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-(2-((3-(5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
5-((2S)-2-((3-(5-methyl-3-(trifluoromethyl)-5,6,6a,7,9,10-hexahydro-8H-pyrazino[1,2-a][1,8]naphthyridin-8-yl)-3-oxopropoxy)methyl)azetidin-1-yl)-4-(trifluoromethyl)pyridazin-3(2H)-one;
8-(3-((3,3-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-(((S)-3,3-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
8-(3-(((R)-3,3-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(S)-8-(3-(((R)-3,3-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
(R)-8-(3-(((R)-3,3-dimethyl-1-(6-oxo-5-(trifluoromethyl)-1,6-dihydropyridazin-4-yl)azetidin-2-yl)methoxy)propanoyl)-5-methyl-3-(trifluoromethyl)-7,8,9,10-tetrahydro-5H-pyrazino[1,2-a]pyrido[3,2-e]pyrazin-6(6aH)-one;
5-methyl-8-(3-(1-(1-(6-oxo-5-(trifluoromethyl)-1,6-dihydropyridazin-4-yl)azetidin-2-yl)ethoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-(1-((S)-1-(6-oxo-5-(trifluoromethyl)-1,6-dihydropyridazin-4-yl)azetidin-2-yl)ethoxy)propanoyl)-3-(trifluoromethyl)-7,8,9,10-tetrahydro-5H-pyrazino[1,2-a]pyrido[3,2-e]pyrazin-6(6aH)-one;
(6aS)-5-methyl-8-(3-(1-((S)-1-(6-oxo-5-(trifluoromethyl)-1,6-dihydropyridazin-4-yl)azetidin-2-yl)ethoxy)propanoyl)-3-(trifluoromethyl)-7,8,9,10-tetrahydro-5H-pyrazino[1,2-a]pyrido[3,2-e]pyrazin-6(6aH)-one;
(6aR)-5-methyl-8-(3-(1-((S)-1-(6-oxo-5-(trifluoromethyl)-1,6-dihydropyridazin-4-yl)azetidin-2-yl)ethoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((4-(6-oxo-5-(trifluoromethyl)-1,6-dihydropyridazin-4-yl)morpholin-3-yl)methoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-(((S)-4-(6-oxo-5-(trifluoromethyl)-1,6-dihydropyridazin-4-yl)morpholin-3-yl)methoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-(((R)-4-(6-oxo-5-(trifluoromethyl)-1,6-dihydropyridazin-4-yl)morpholin-3-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((S)-4-(6-oxo-5-(trifluoromethyl)-1,6-dihydropyridazin-4-yl)morpholin-3-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((R)-4-(6-oxo-5-(trifluoromethyl)-1,6-dihydropyridazin-4-yl)morpholin-3-yl)methoxy)propanoyl)-3-(trifluoromethyl)-7,8,9,10-tetrahydro-5H-pyrazino[1,2-a]pyrido[3,2-e]pyrazin-6(6aH)-one;
(R)-5-methyl-8-(3-(((R)-4-(6-oxo-5-(trifluoromethyl)-1,6-dihydropyridazin-4-yl)morpholin-3-yl)methoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-((1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one;

-continued 5-methyl-8-(3-(((S)-1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
5-methyl-8-(3-(((R)-1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((S)-1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
(S)-5-methyl-8-(3-(((R)-1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one;
or
(R)-5-methyl-8-(3-(((R)-1-(6-oxo-5-(trifluoromethyl)-1,6-dihydropyridazin-4-yl)pyrrolidin-2-yl)methoxy)propanoyl)-3-(trifluoromethyl)-7,8,9,10-tetrahydro-5H-pyrazino[1,2-a]pyrido[3,2-e]pyrazin-6(6aH)-one.

[94]. An intermediate selected from any one of the following formulas:

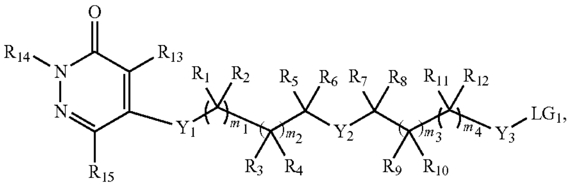

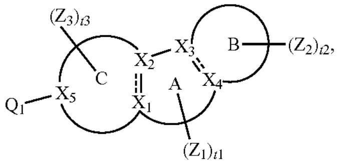

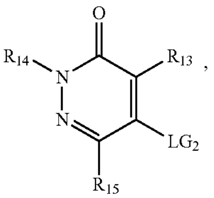

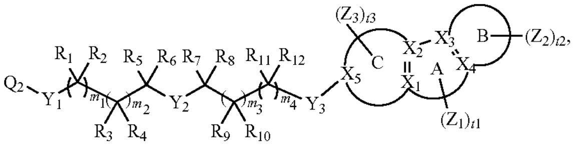

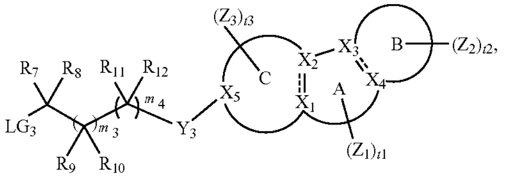

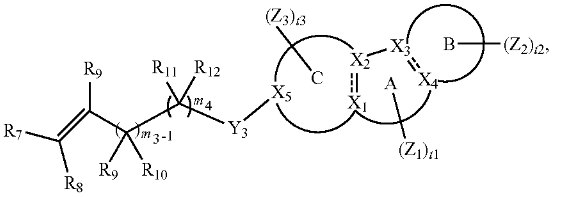

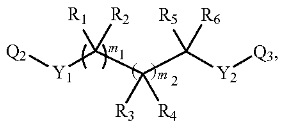

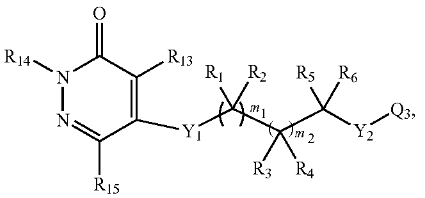

-continued

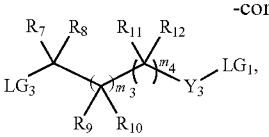

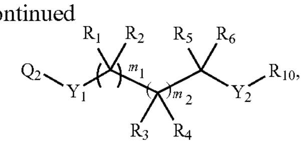

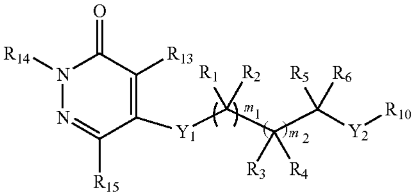

or

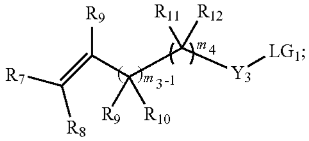

Wherein, $LG_1$ is a leaving group or a group that can be converted to the leaving group; in some embodiments, the leaving group is selected from halogen (such as —Cl, —Br or —I), —OS(═O)$_2$CH$_3$ or

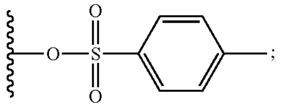 [SMILES: *OS(=O)(=O)c1ccc(C)cc1]

in some embodiments, the group that can be converted to the leaving group is selected from —OH;

When $X_5$ is selected from N, said $Q_1$ is selected from —H or a protecting group of N, in some embodiments, said protecting group of N is selected from -Boc;

$LG_2$ is a leaving group or a group that can be converted to the leaving group; in some embodiments, the leaving group is selected from halogen (such as —Cl, —Br or —I), —OS(═O)$_2$CH$_3$ or

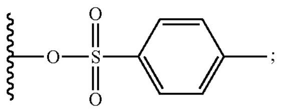 [SMILES: *OS(=O)(=O)c1ccc(C)cc1]

in some embodiments, the group that can be converted to the leaving group is selected from —OH;

$Q_2$ is selected from —H;

$Q_3$ is selected from —H;

$LG_3$ is a leaving group or a group that can be converted to the leaving group; in some embodiments the leaving group is selected from halogen (such as —Cl, —Br or —I), —OS(=O)$_2$CH$_3$ or

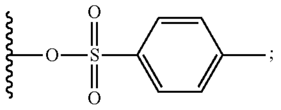

in some embodiments, the group that can be converted to the leaving group is selected from —OH;

The definition of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $Y_1$, $Y_2$, $Y_3$, $X_1$, $X_2$, $X_3$, $X_4$, $X_5$, ring A, ring B, ring C, $Z_1$, $Z_2$, $Z_3$, $m_1$, $m_2$, $m_3$, $m_4$, $t_1$, $t_2$, or $t_3$ at each occurrence is same as any one of [1] to [93].

[95]. The intermediate according to [94], wherein, the intermediate is selected from:

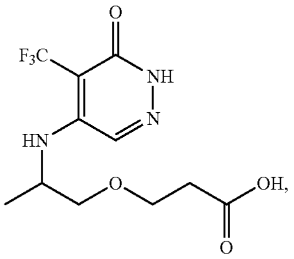

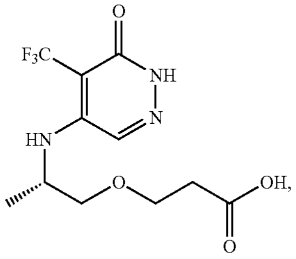

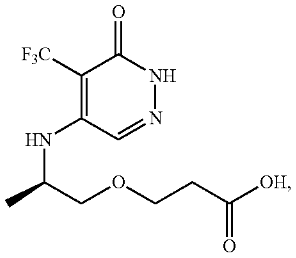

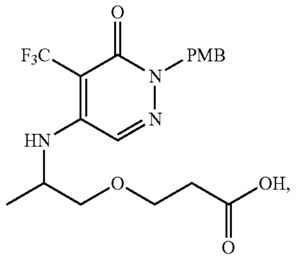

-continued

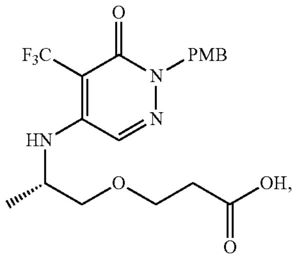

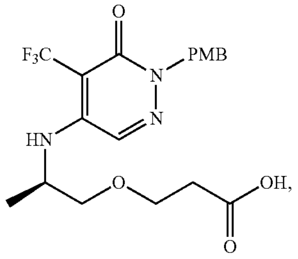

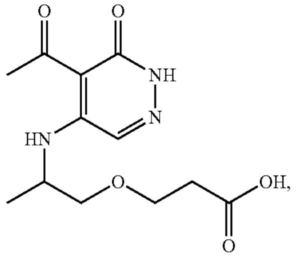

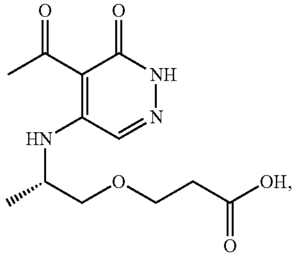

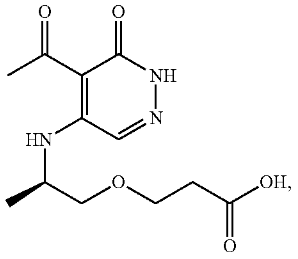

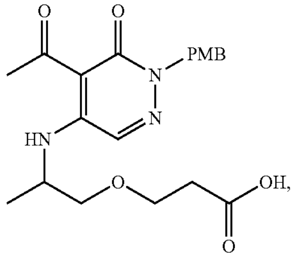

-continued
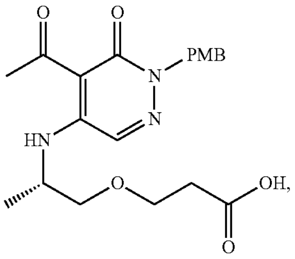
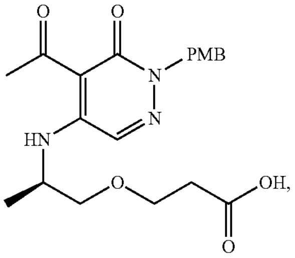
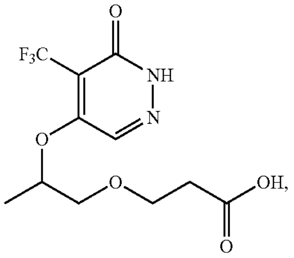
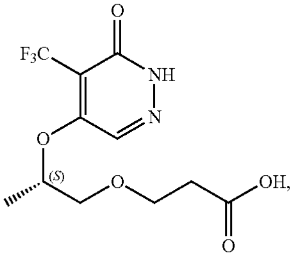
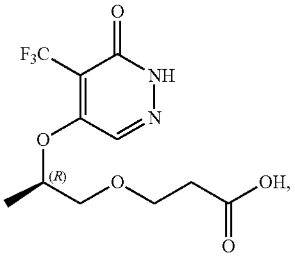
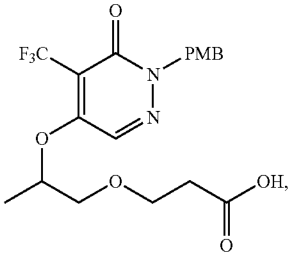
-continued
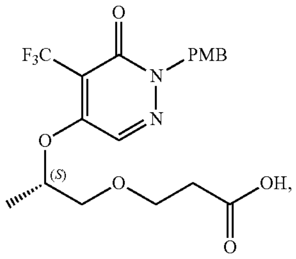
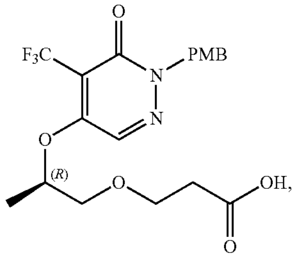
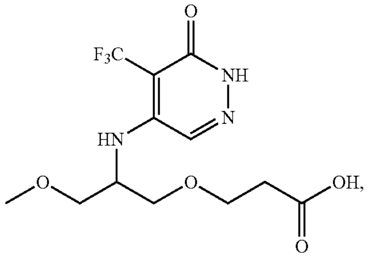
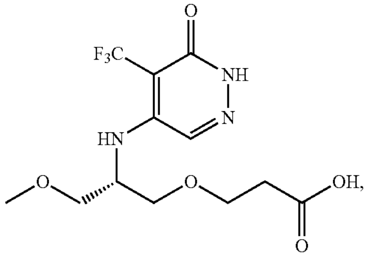
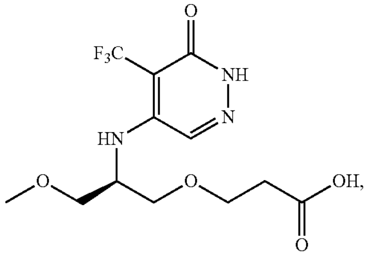
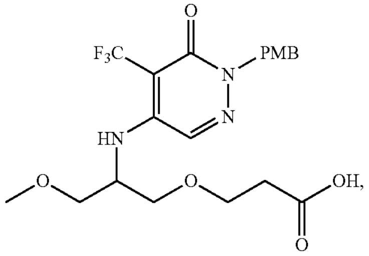

-continued
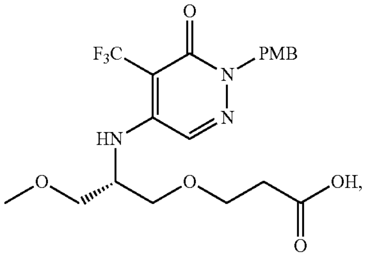
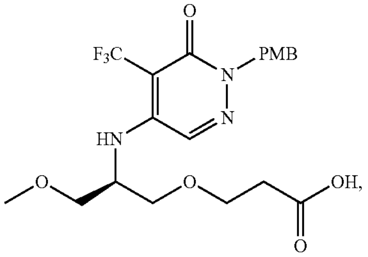
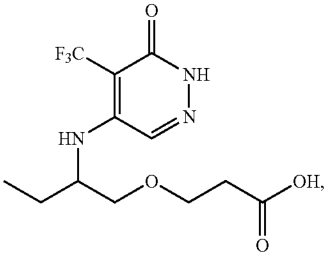
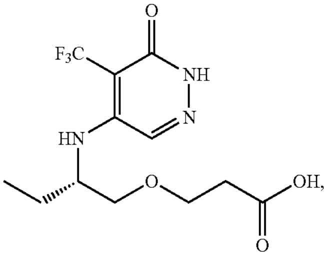
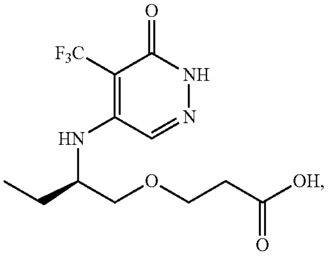
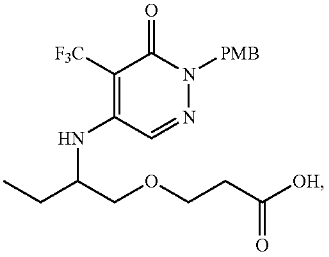
-continued
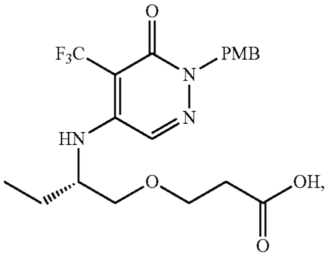
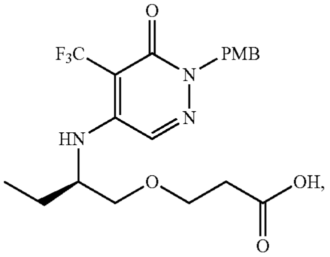
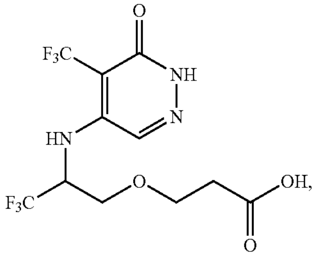
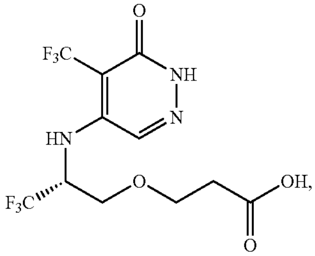
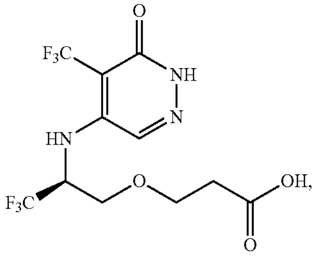
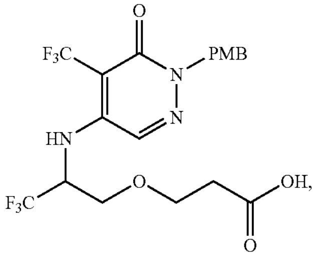

-continued
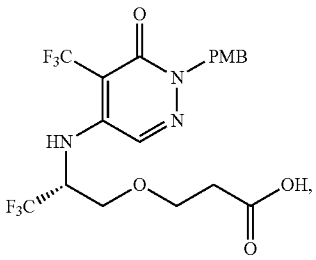
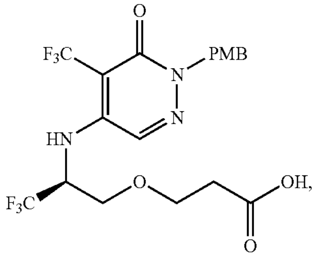
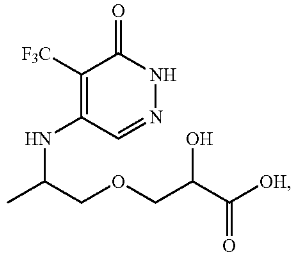
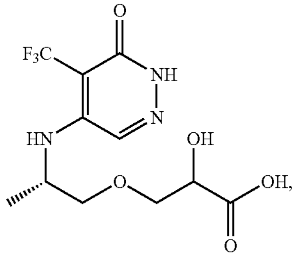
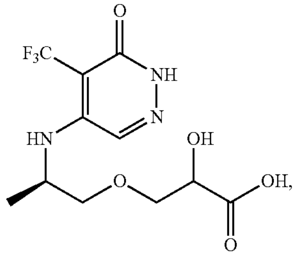
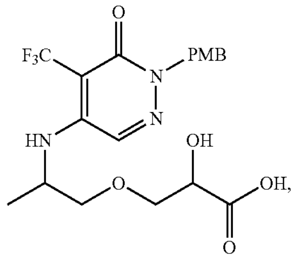
-continued
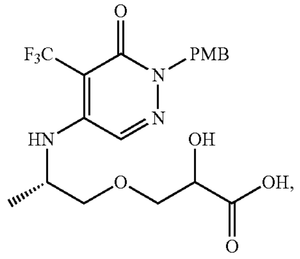
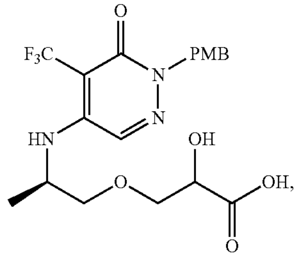
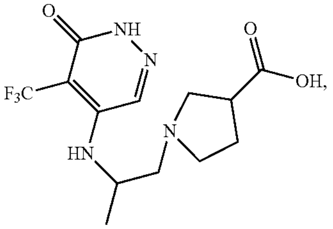
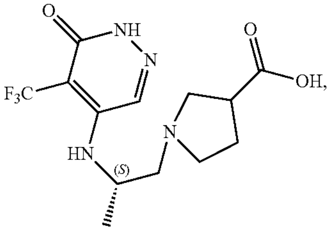
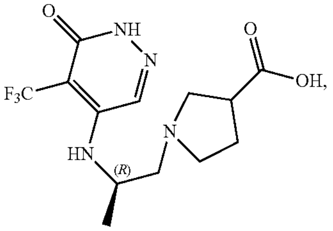
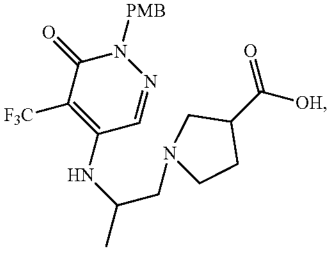
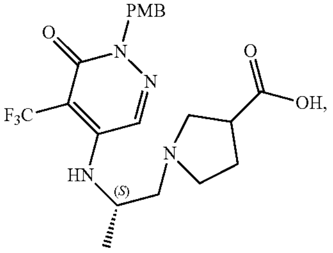

-continued
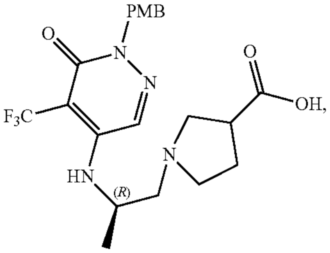
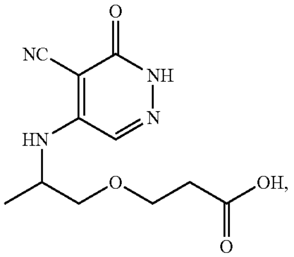
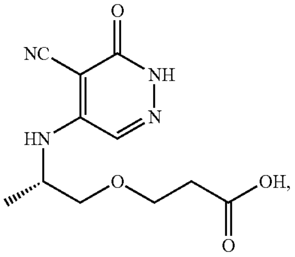
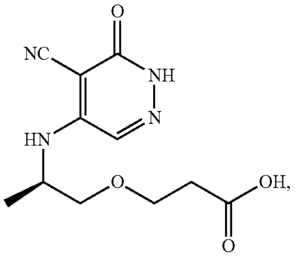
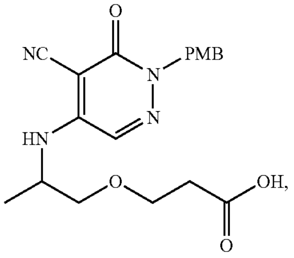
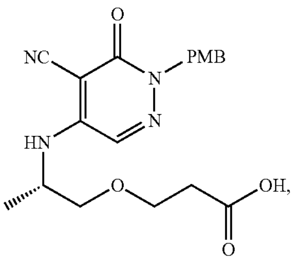
-continued
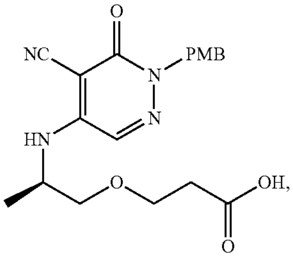
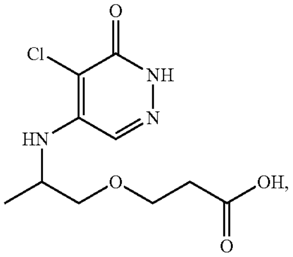
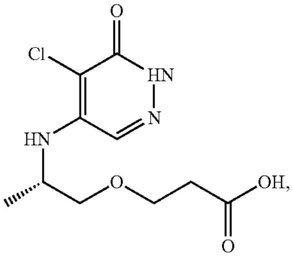
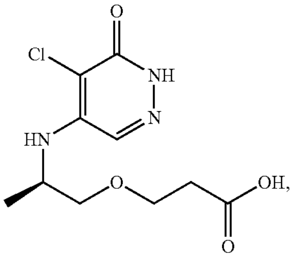
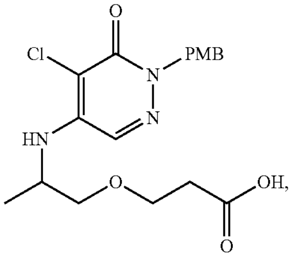
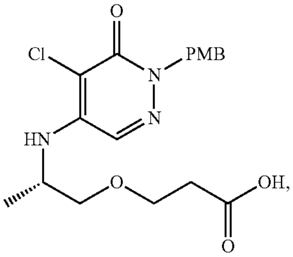

-continued
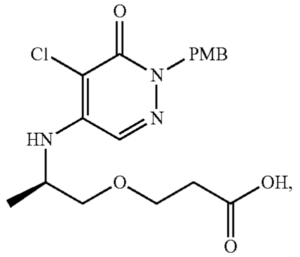
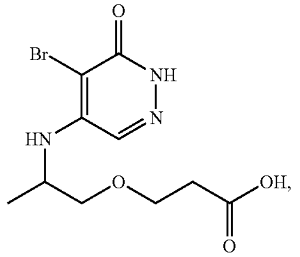
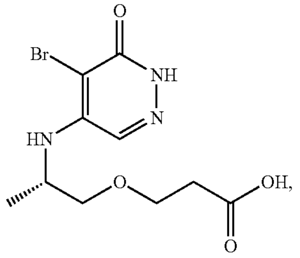
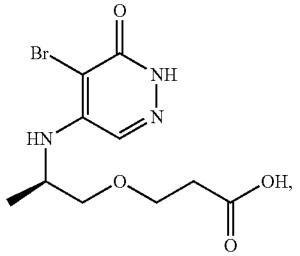
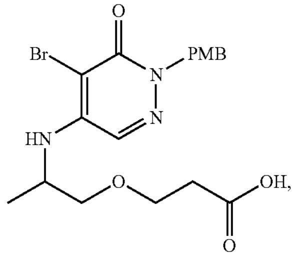
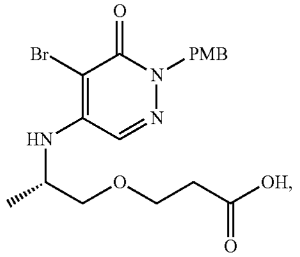
-continued
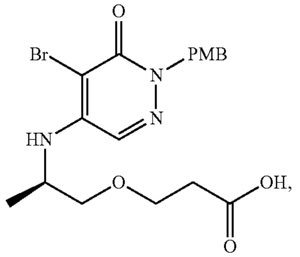
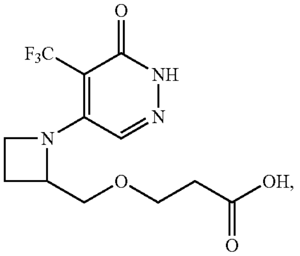
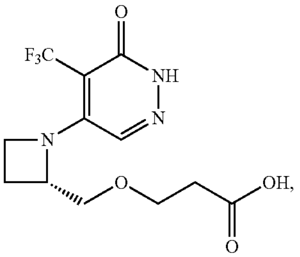
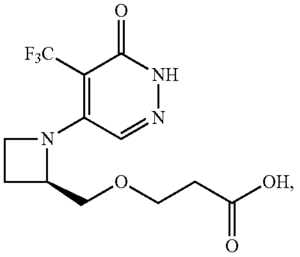
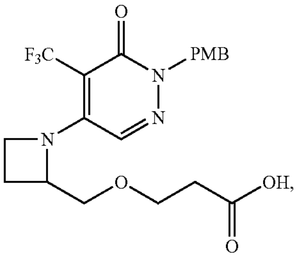
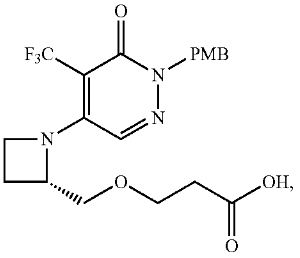

-continued
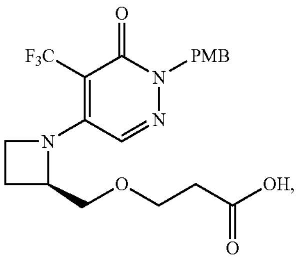
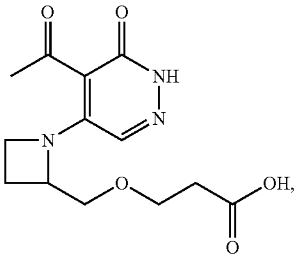
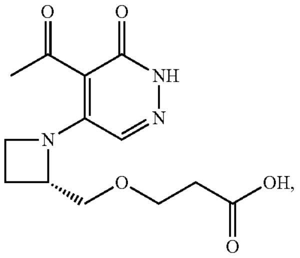
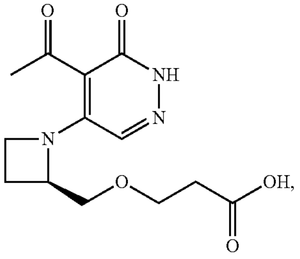
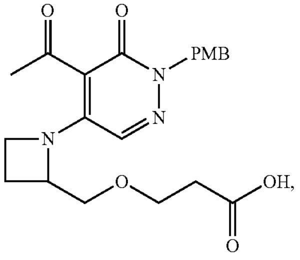
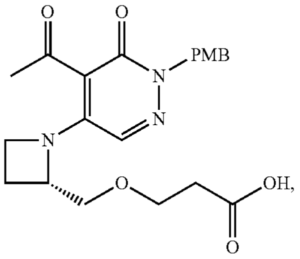
-continued
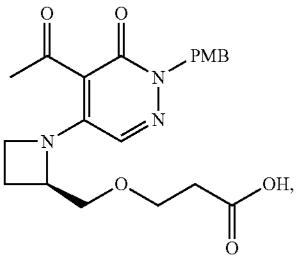
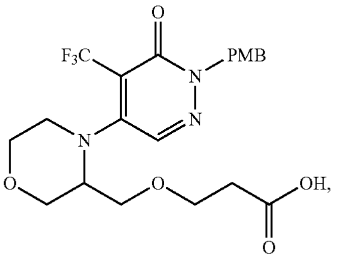
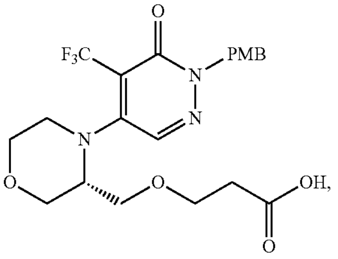
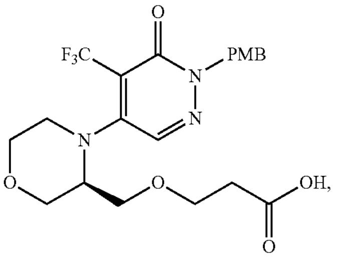
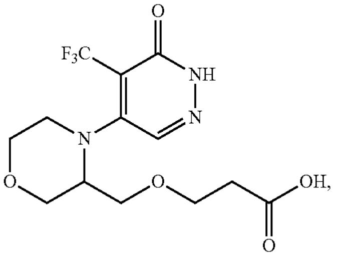
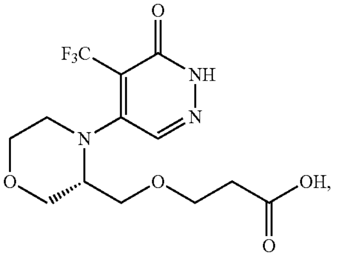

-continued
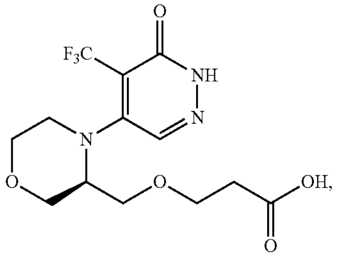
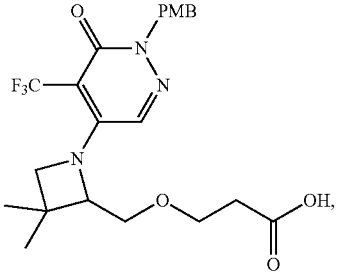
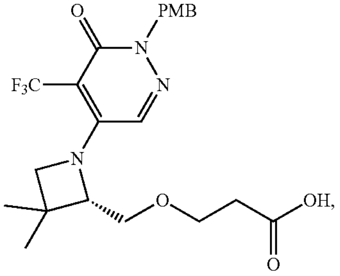
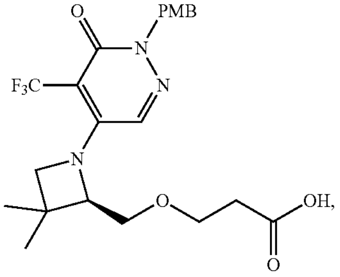
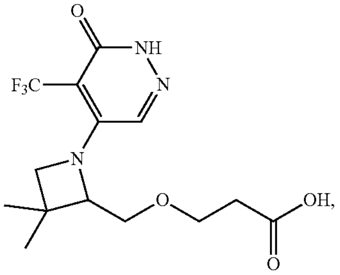
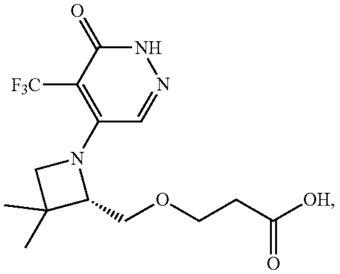
-continued
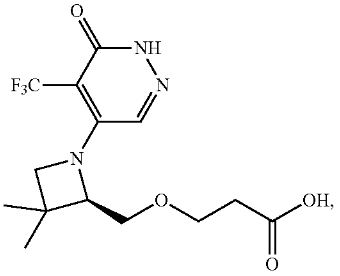
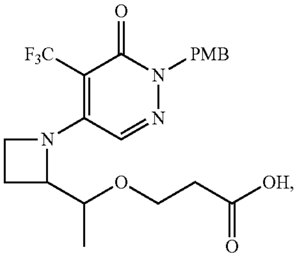
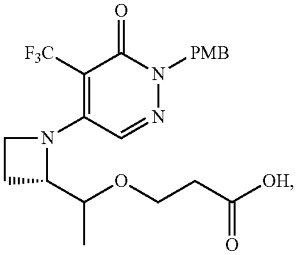
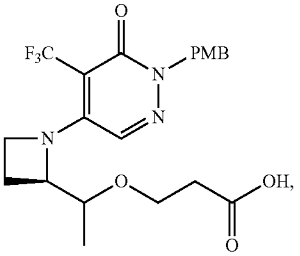
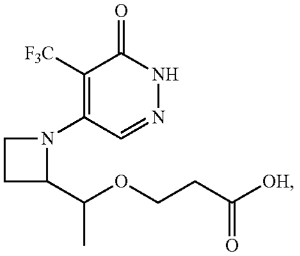
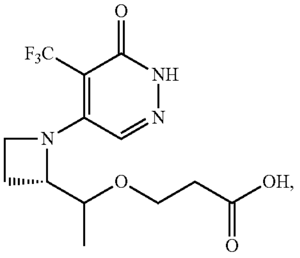

-continued
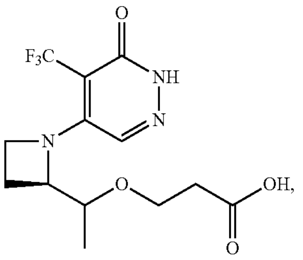
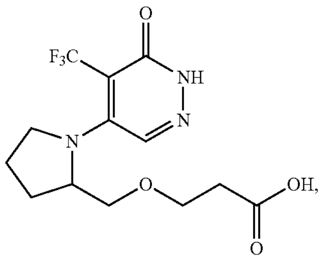
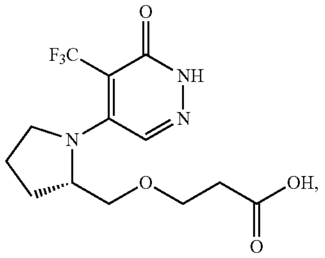
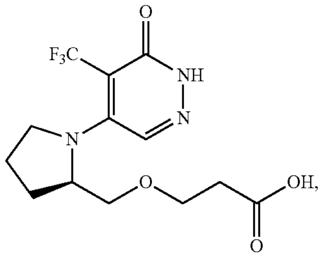
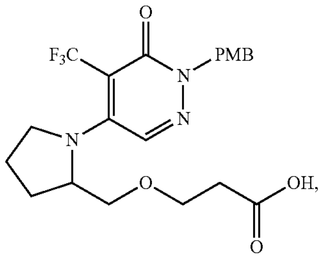
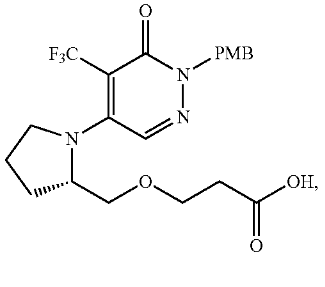
-continued
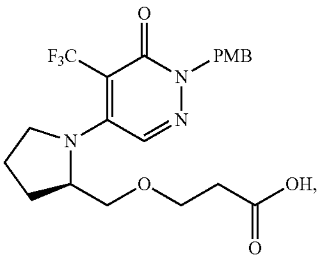
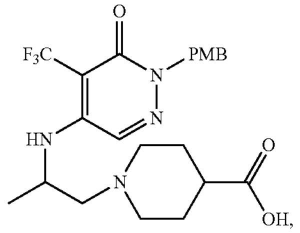
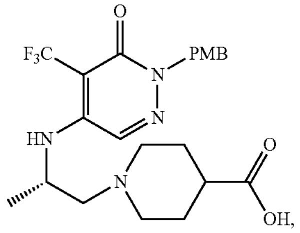
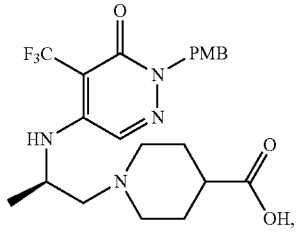
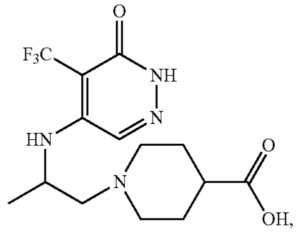
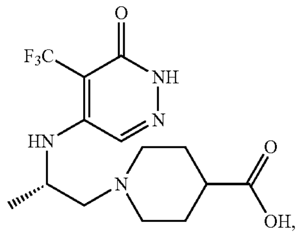
or
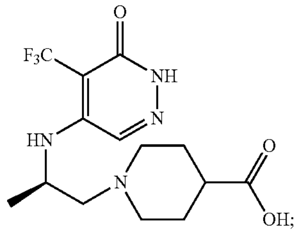

-continued
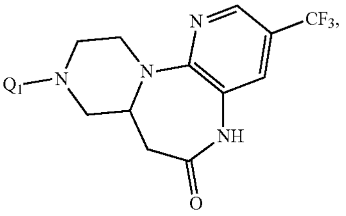
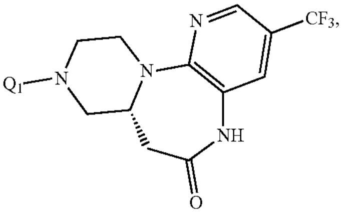
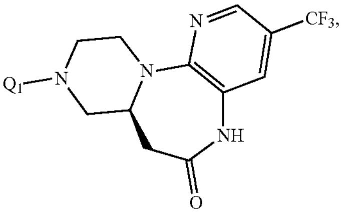
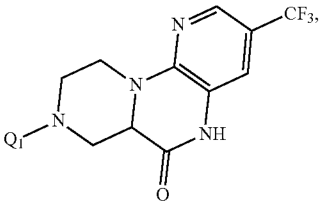
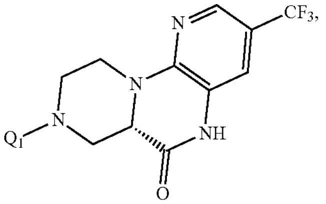
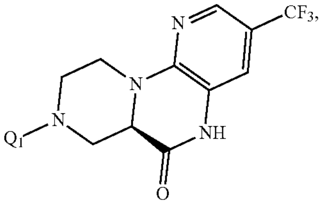
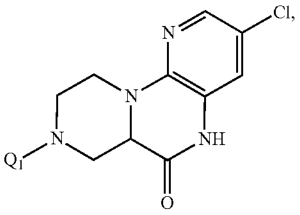
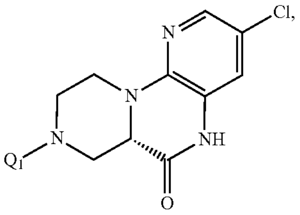
-continued
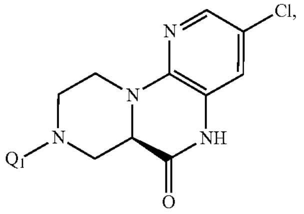
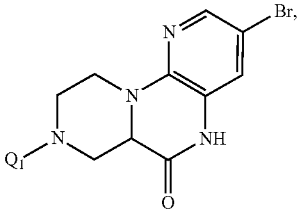
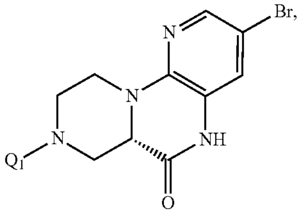
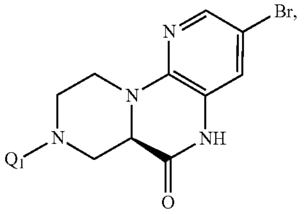
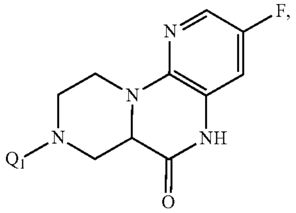
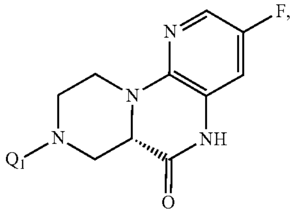
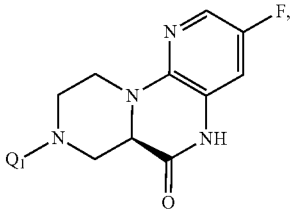
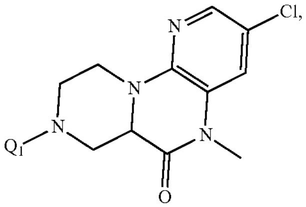

-continued
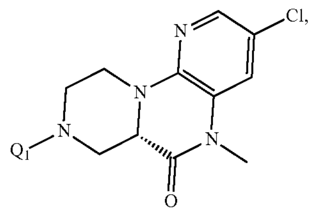
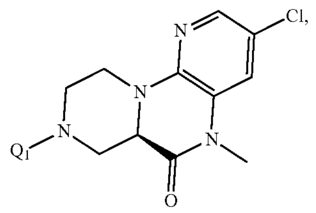
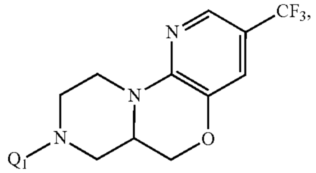
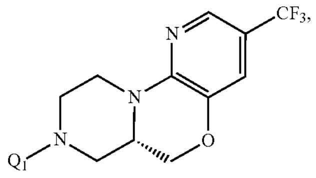
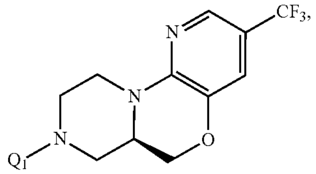
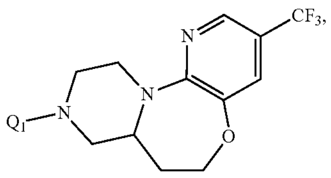
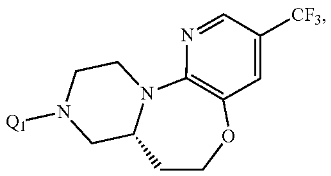
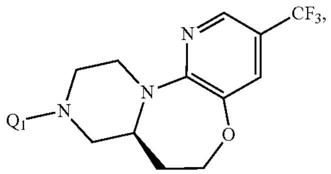
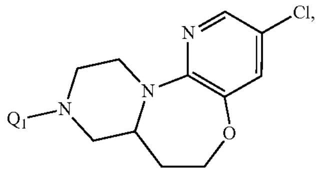
-continued
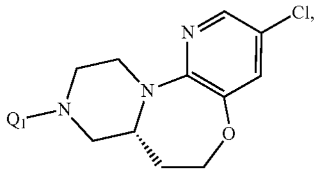
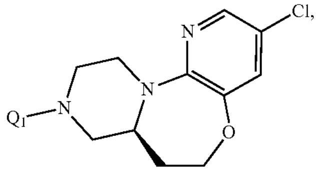
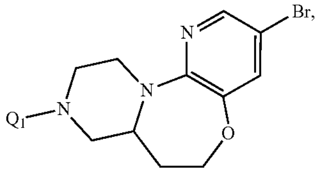
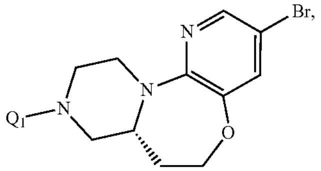
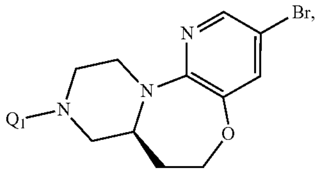
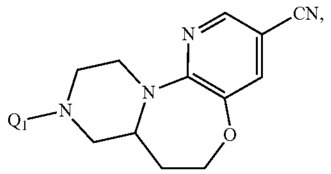
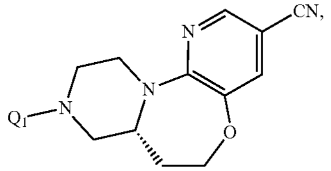
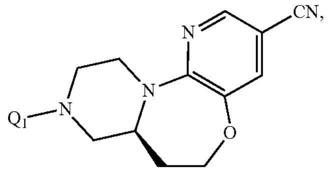
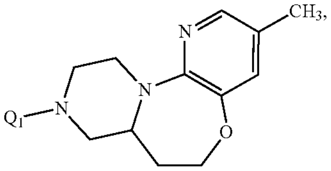
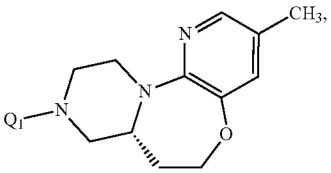

-continued
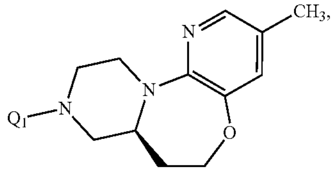
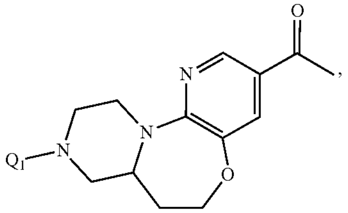
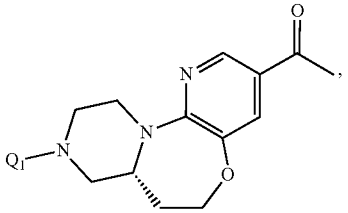
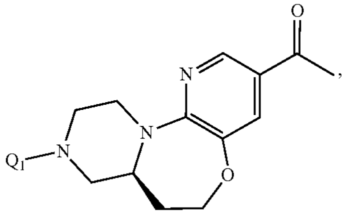
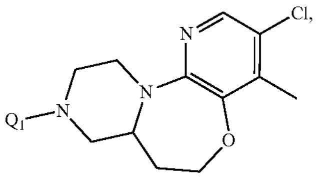
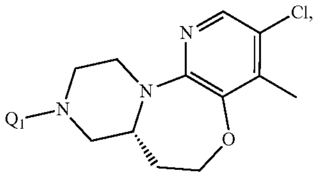
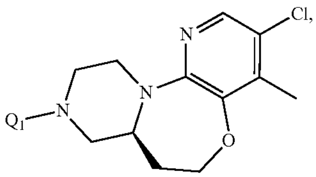
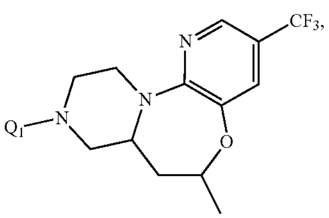
-continued
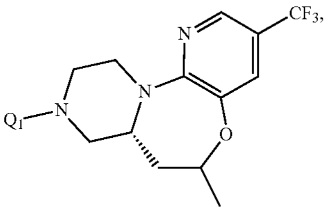
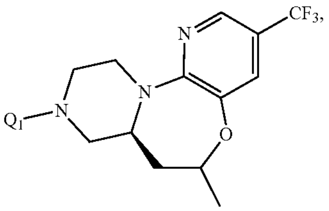
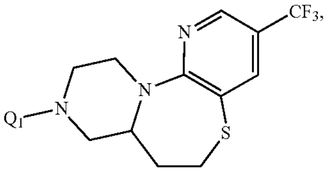
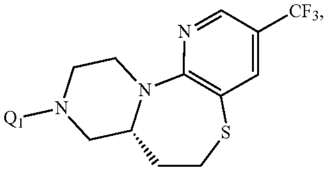
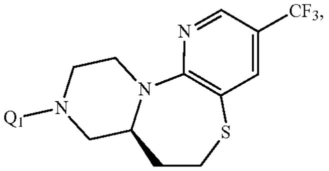
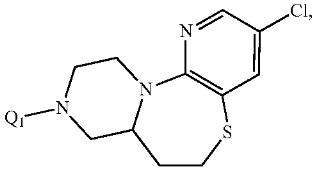
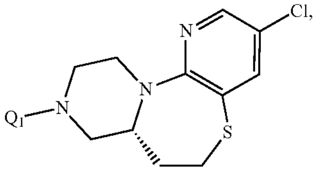
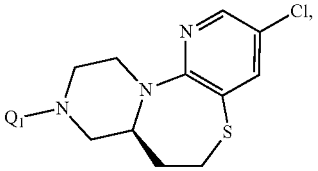
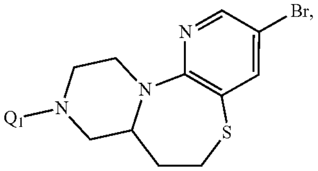

-continued
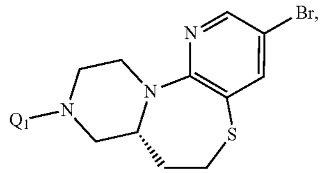
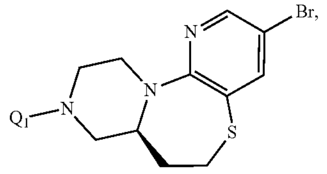
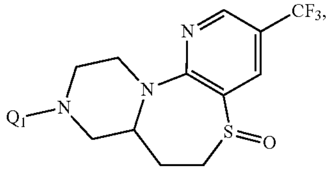
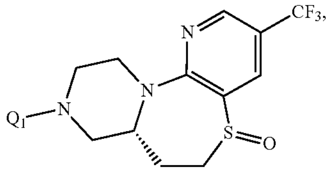
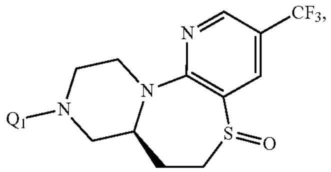
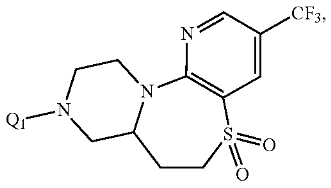
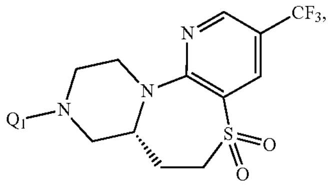
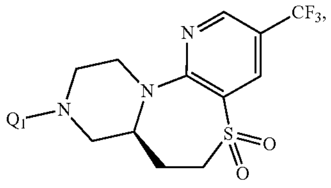
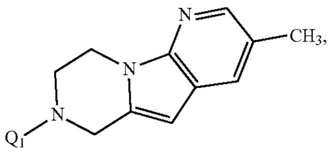
-continued
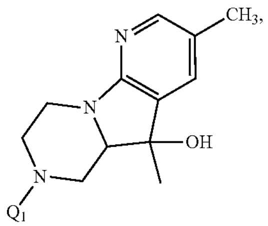
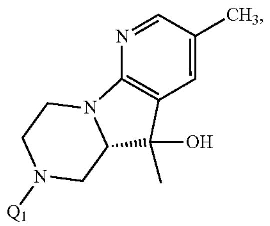
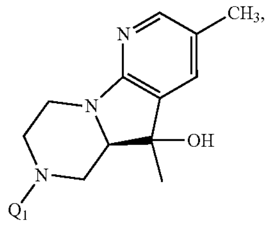
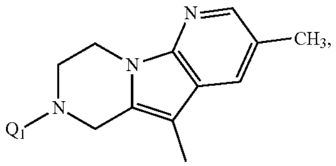
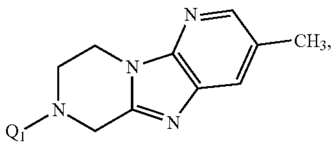
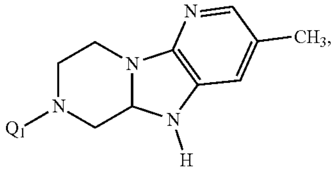
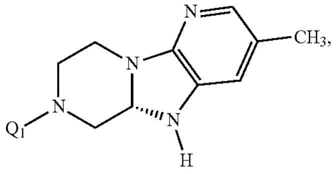
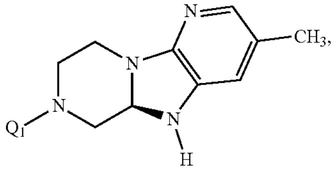
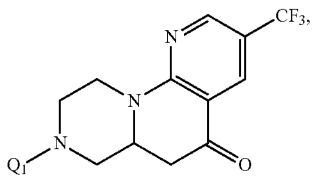
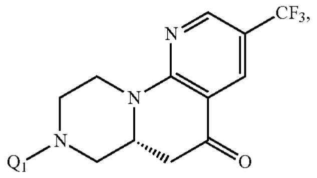

-continued
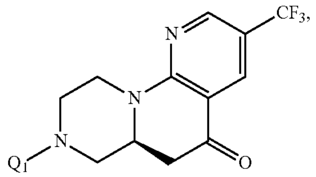
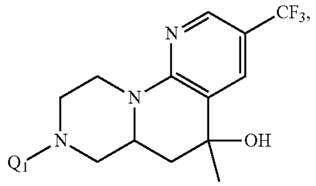
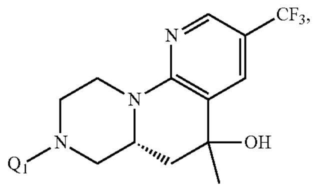
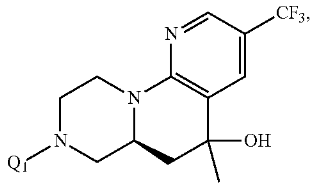
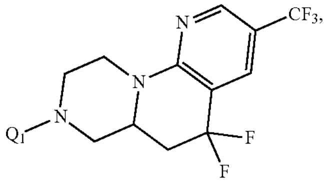
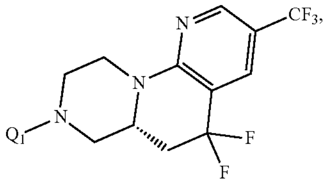
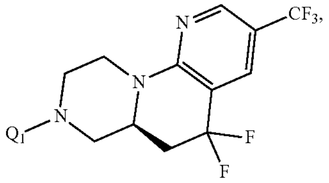
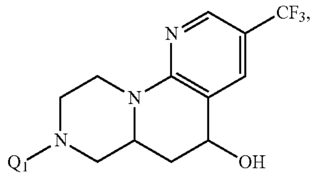
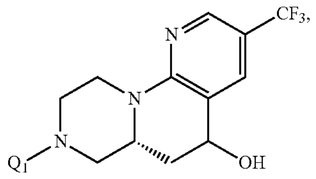
-continued
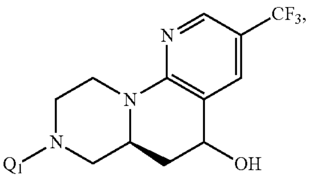
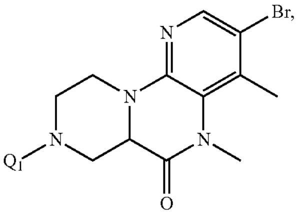
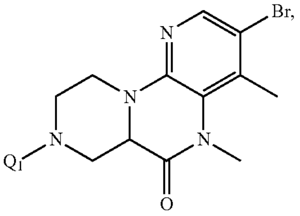
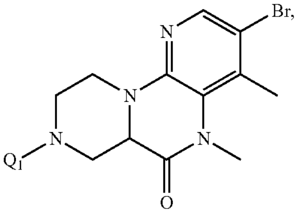
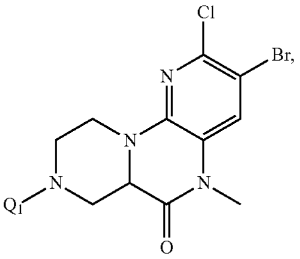
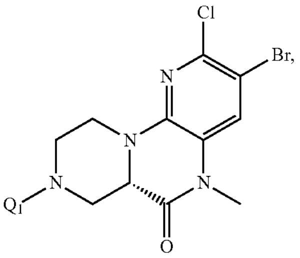
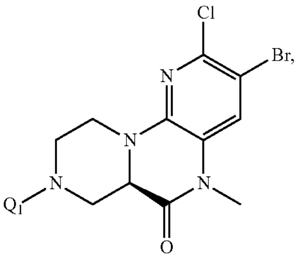

-continued
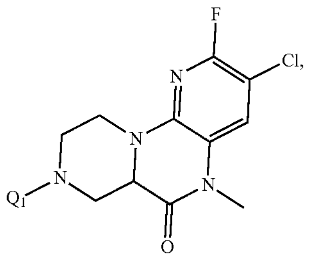
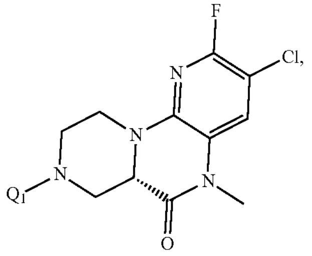
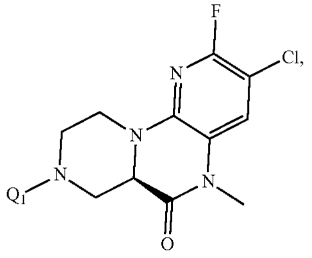
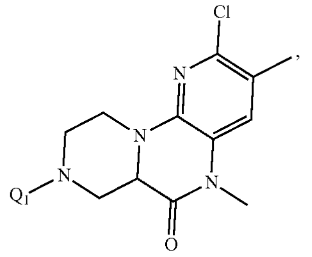
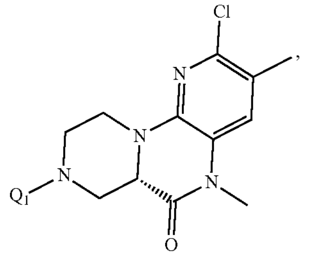
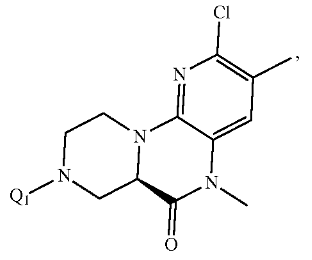
-continued
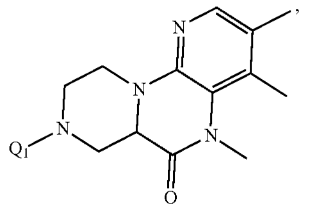
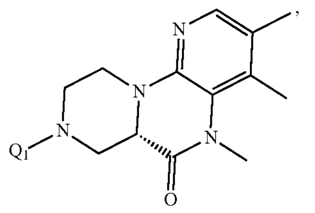
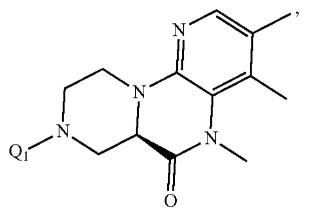
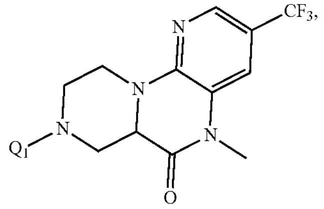
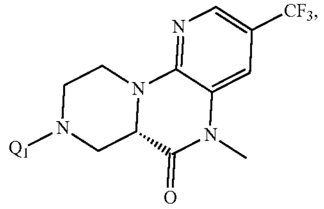
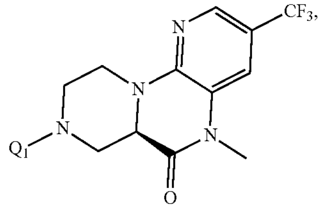
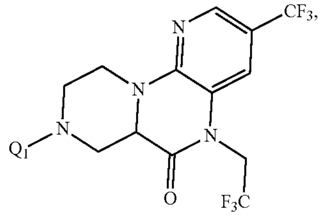
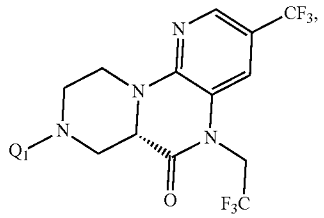

-continued
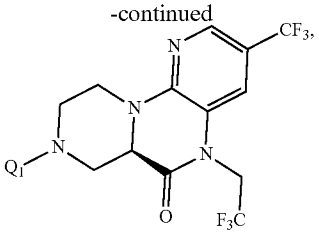
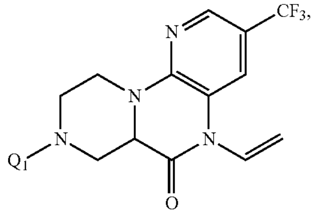
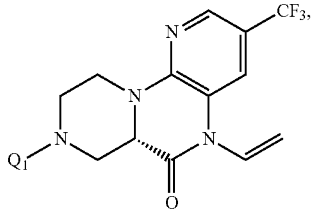
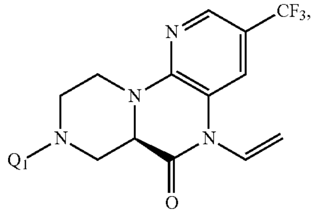
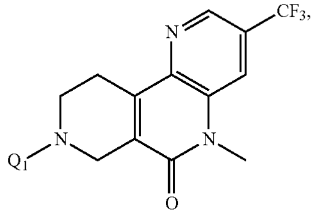
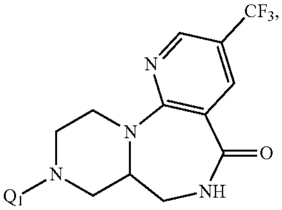
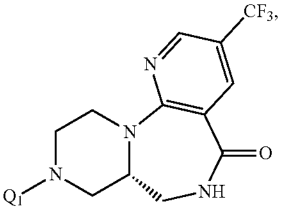
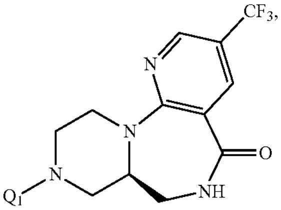
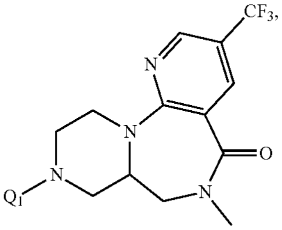
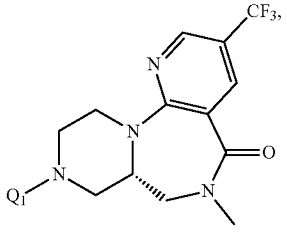
or
-continued
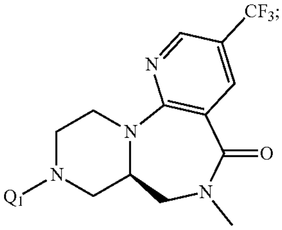
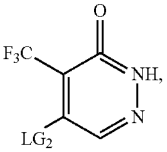
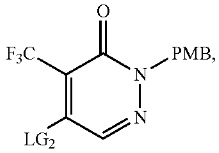
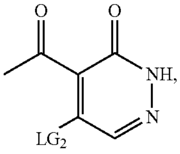
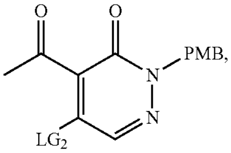
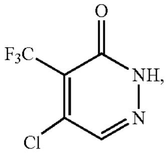
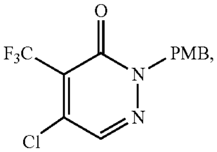
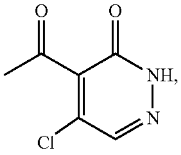
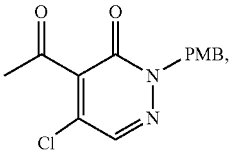
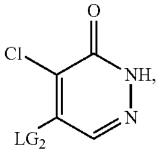
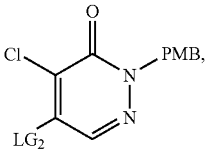
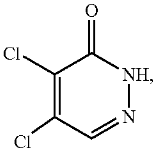
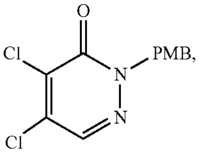
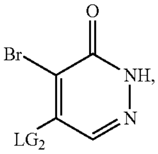
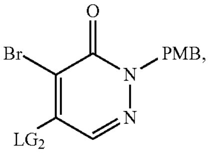
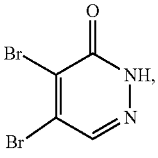
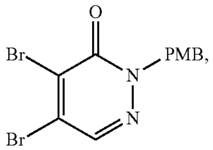
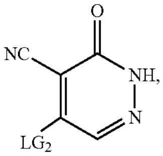

-continued
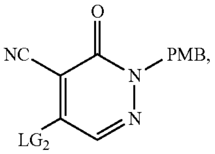
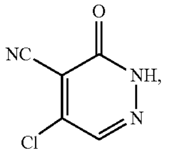
or
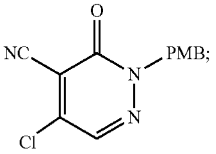
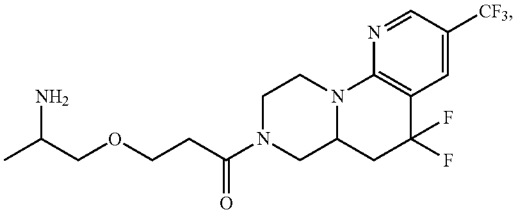
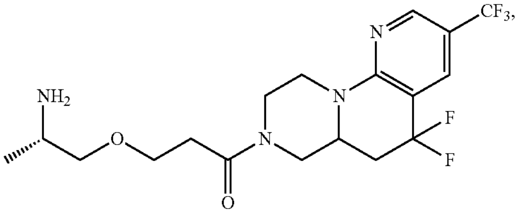
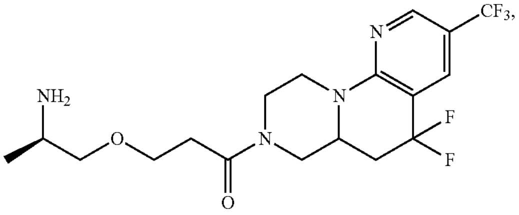
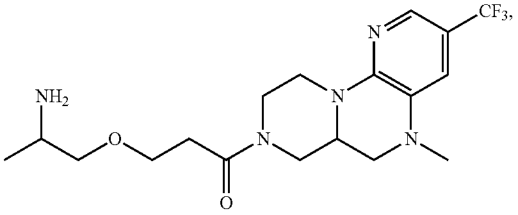
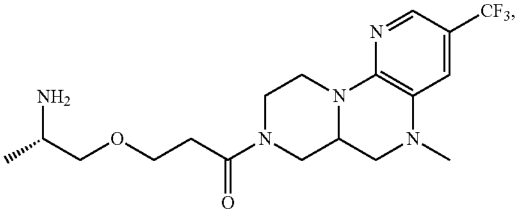
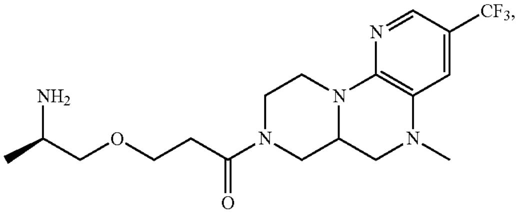
-continued
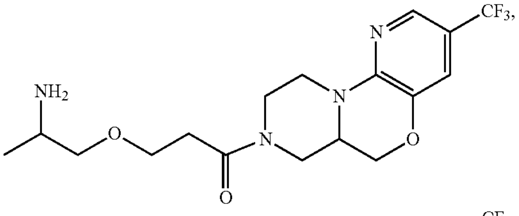
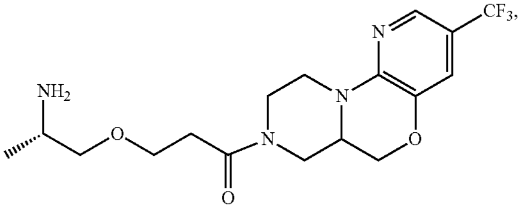
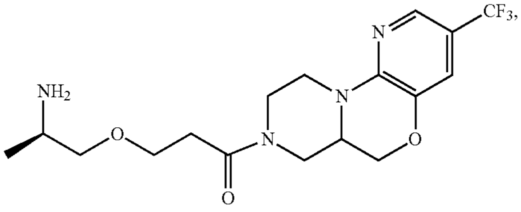
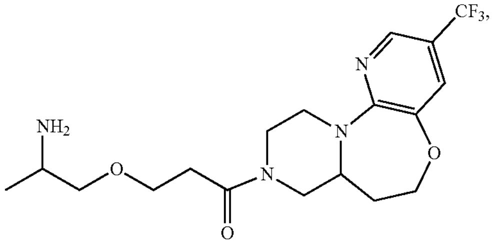
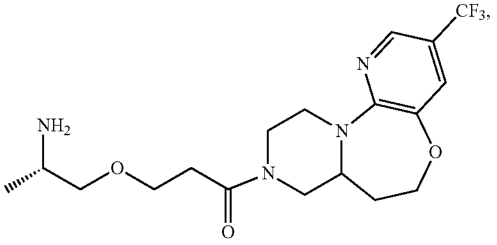
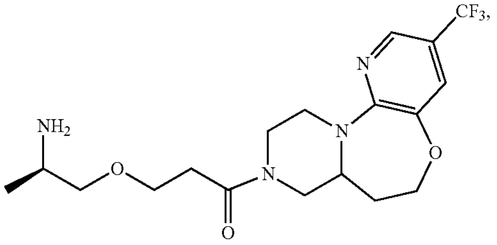
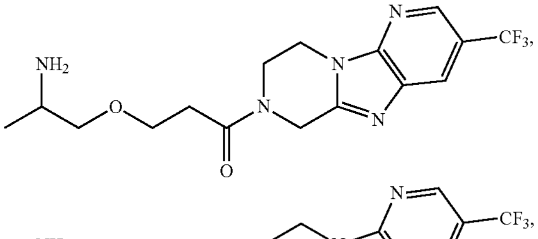
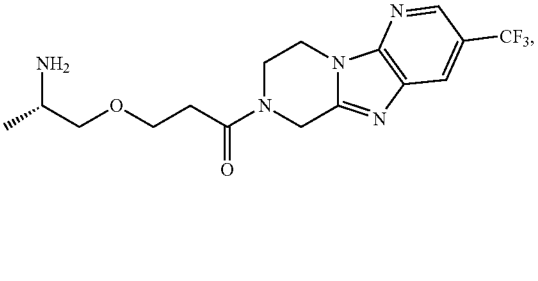

-continued
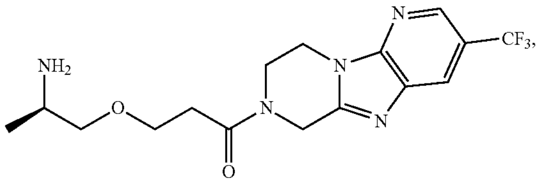,
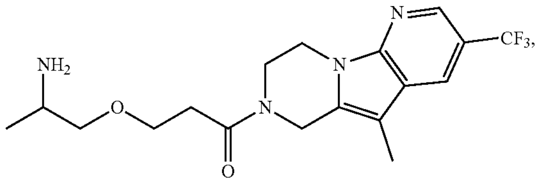,
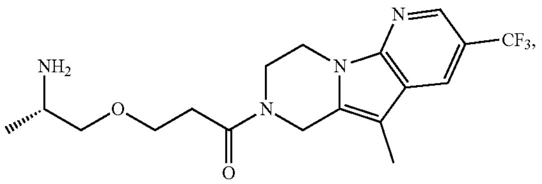,
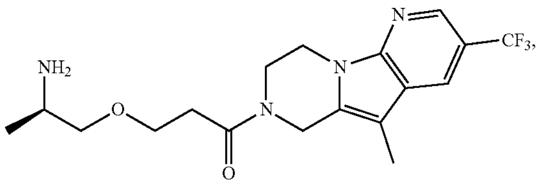,
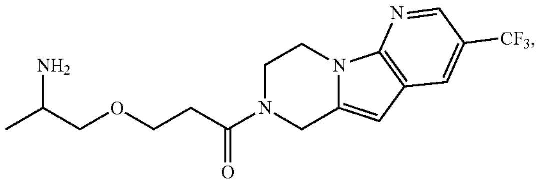,
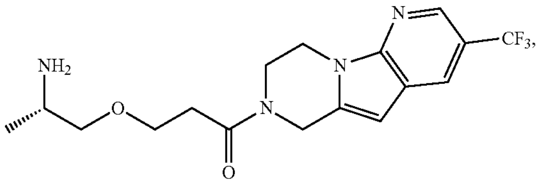,
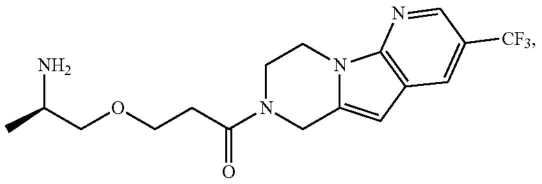,
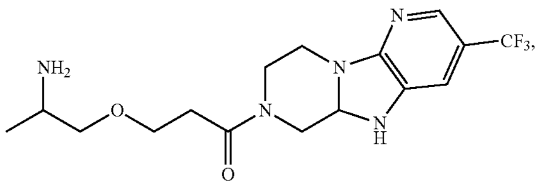,
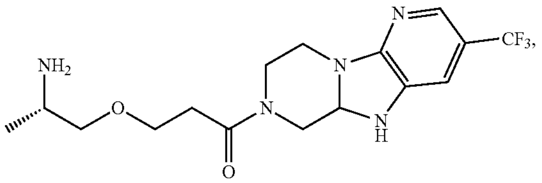,
-continued
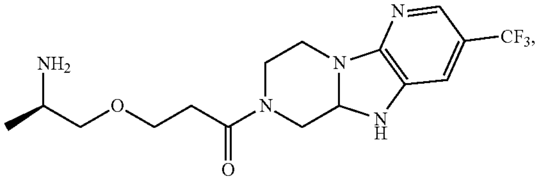,
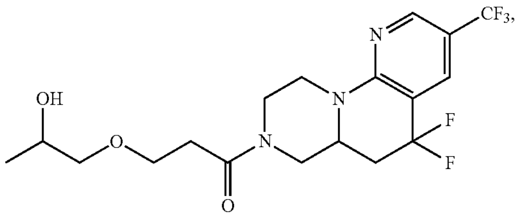,
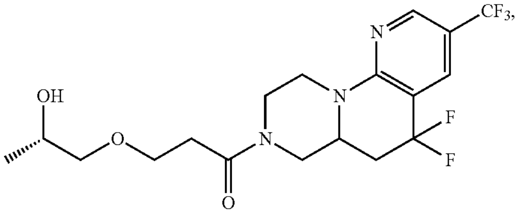,
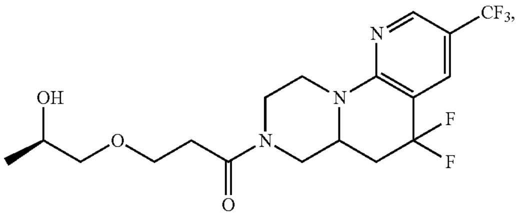,
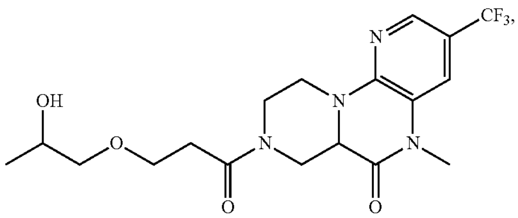,
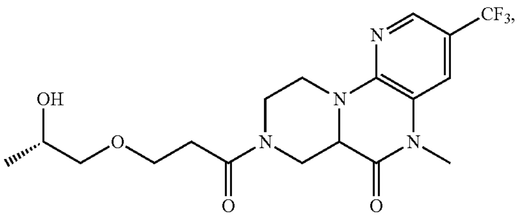,
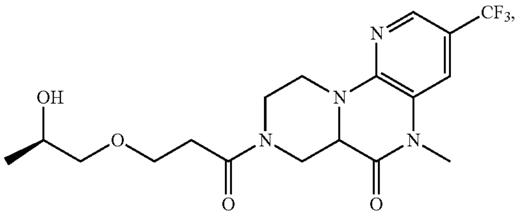,
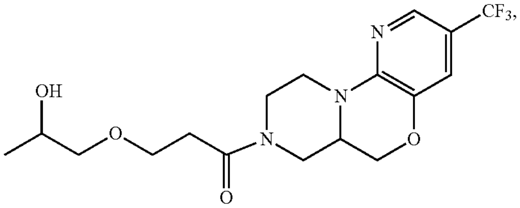, -continued
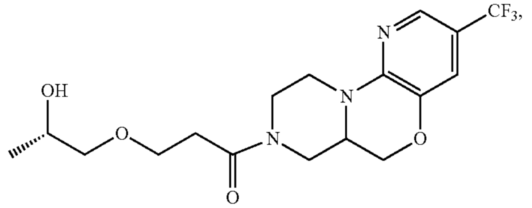
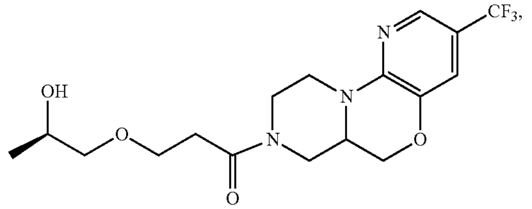
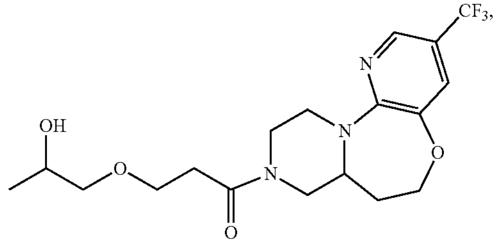
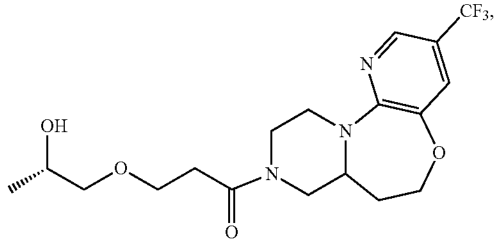
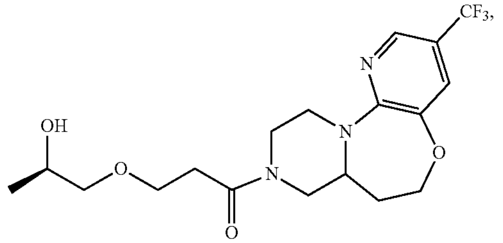
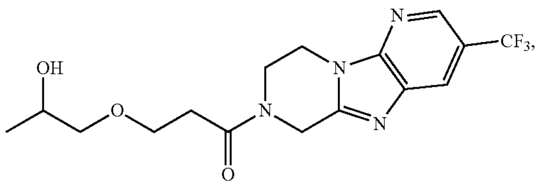
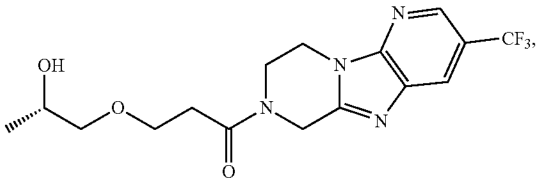
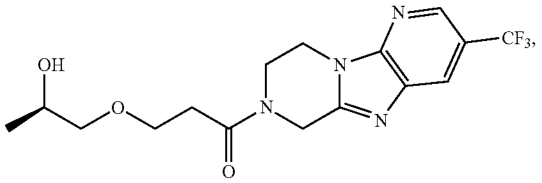
-continued
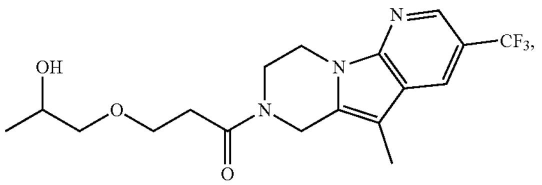
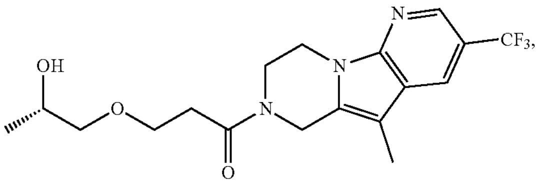
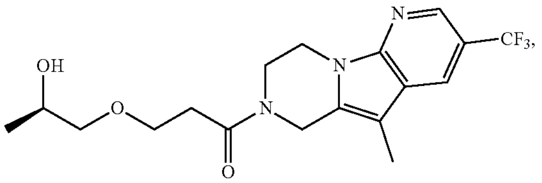
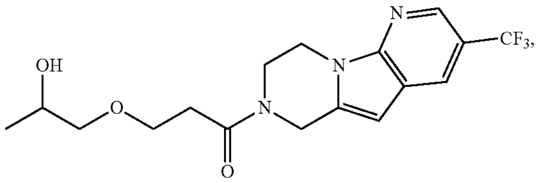
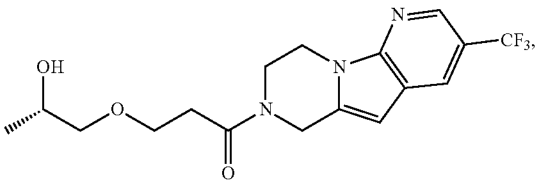
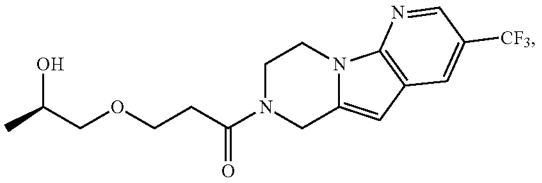
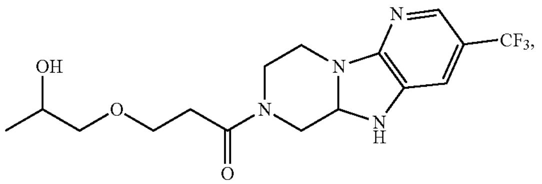
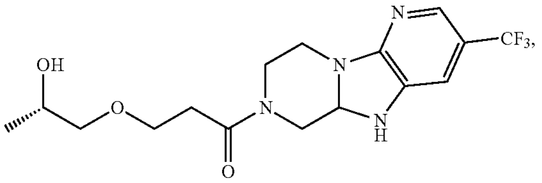
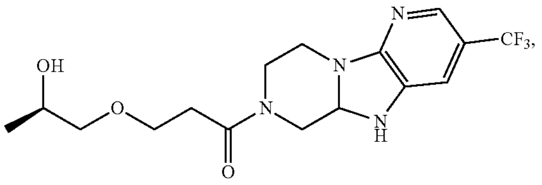

-continued
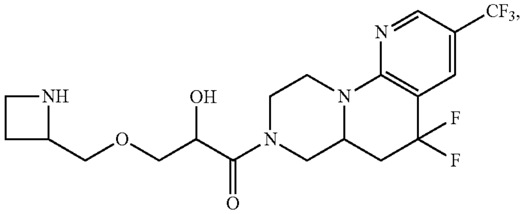
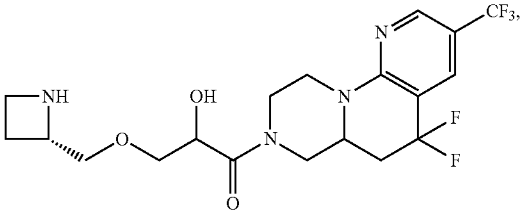
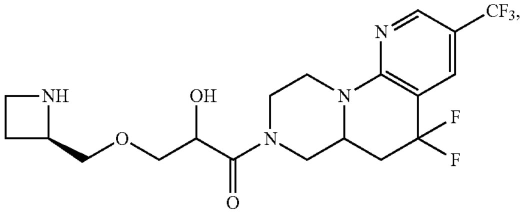
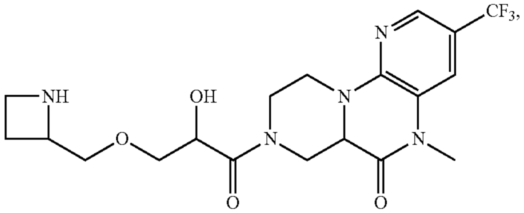
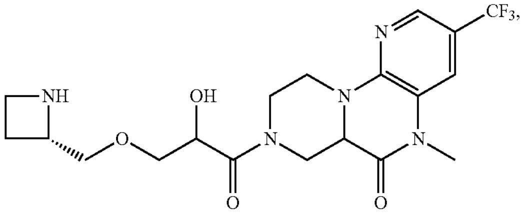
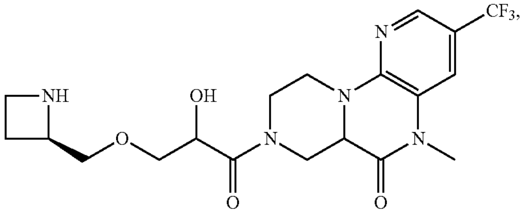
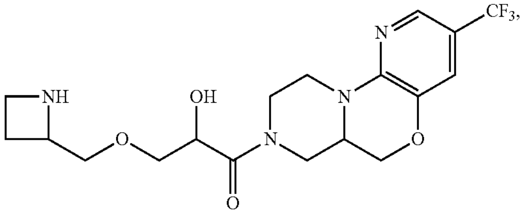
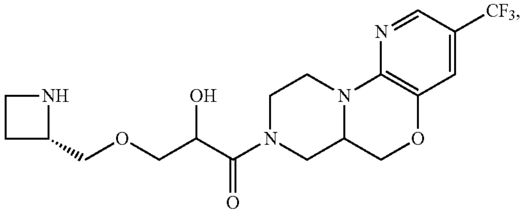
-continued
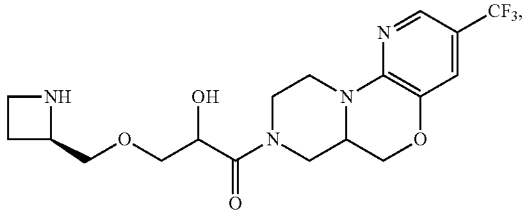
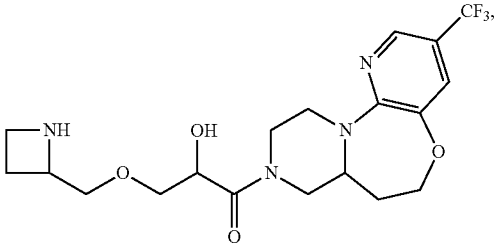
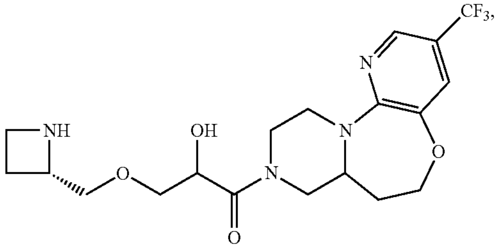
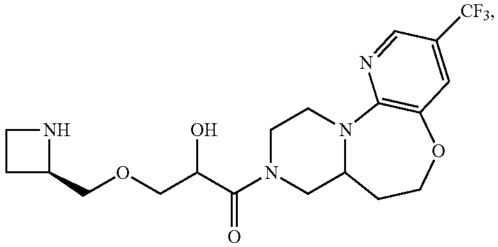
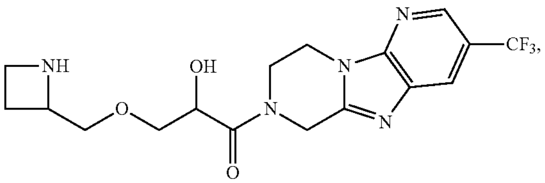
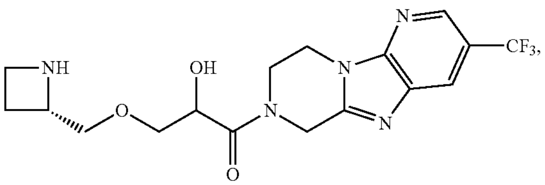
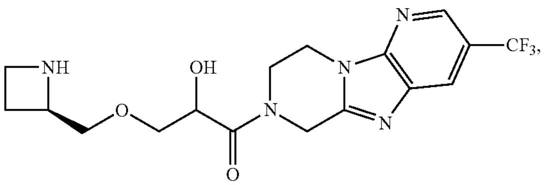

-continued
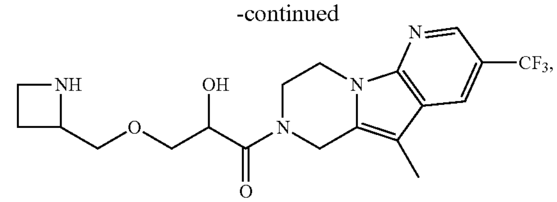
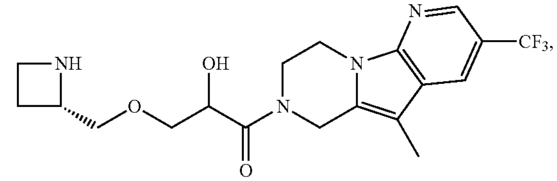
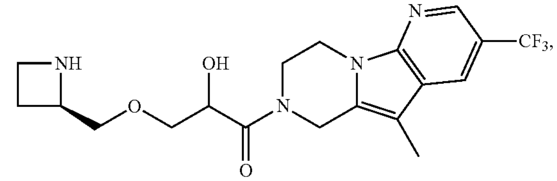
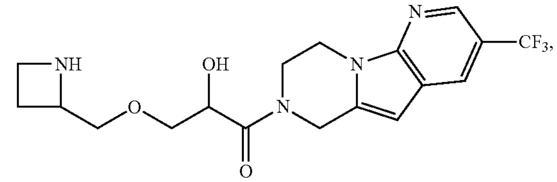
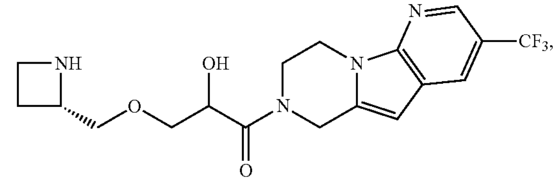
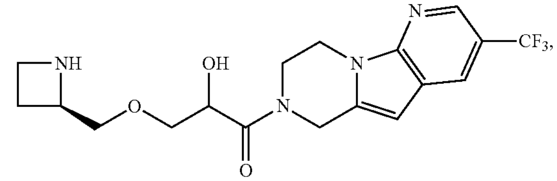
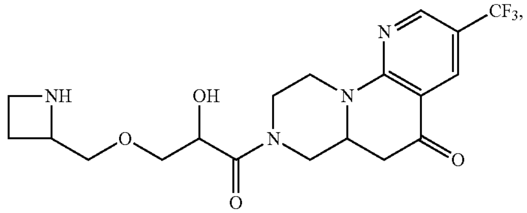
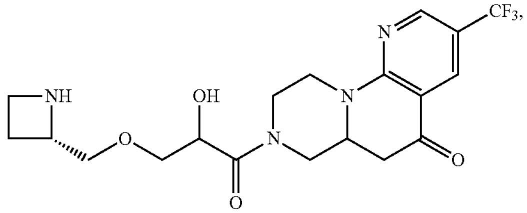
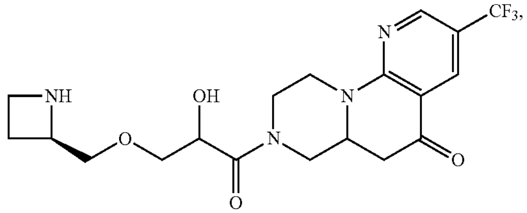
-continued
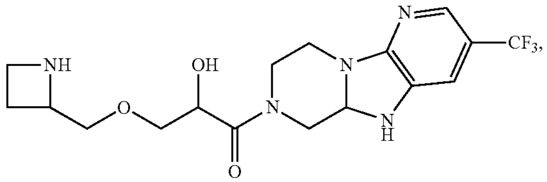
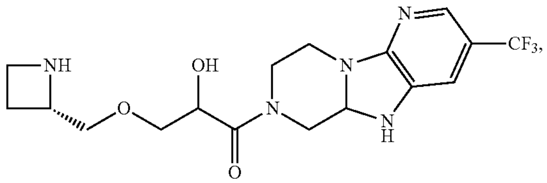
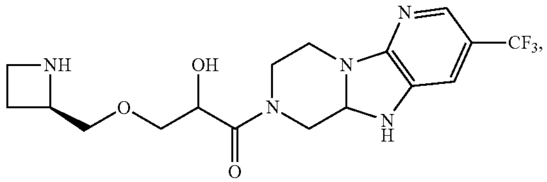
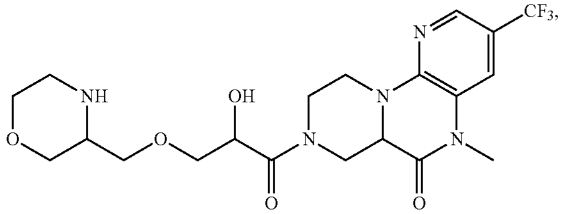
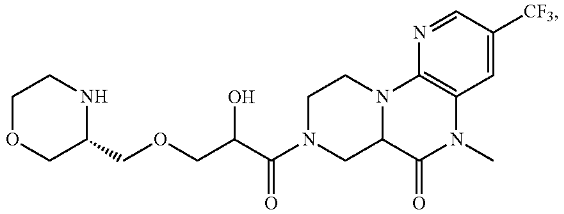
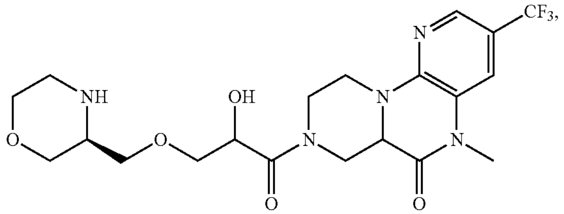
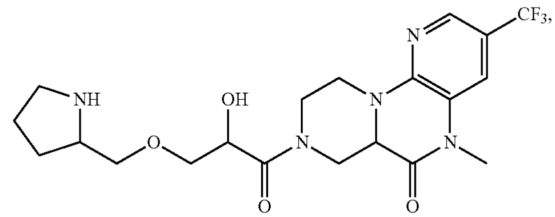
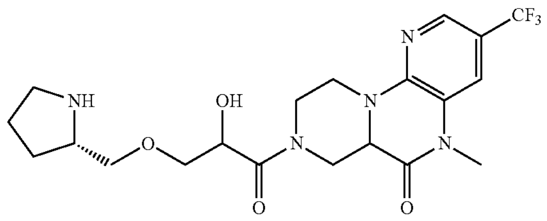
or -continued
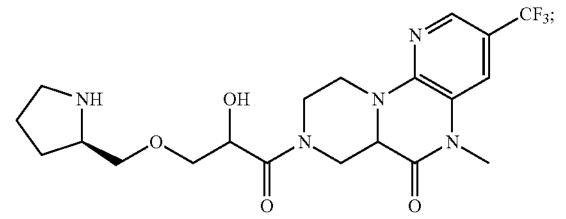
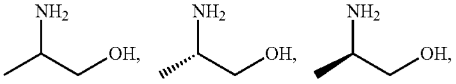
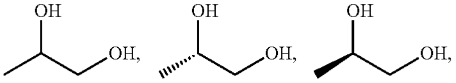
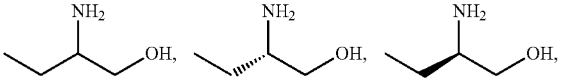
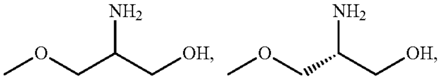
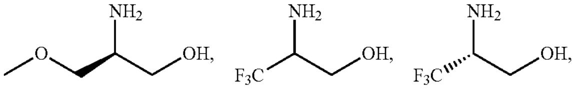
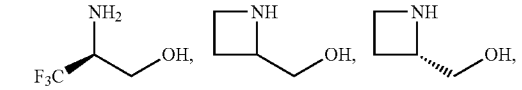
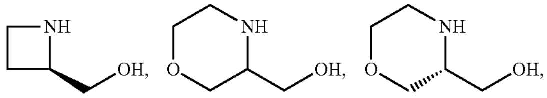
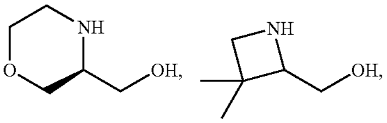
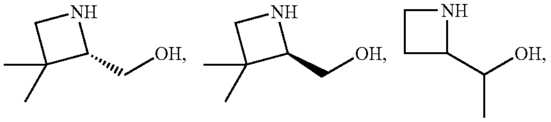
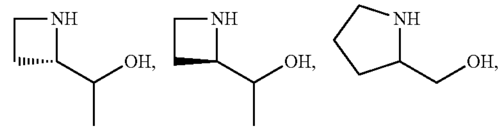
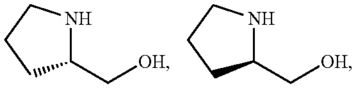
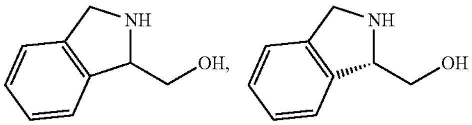 or
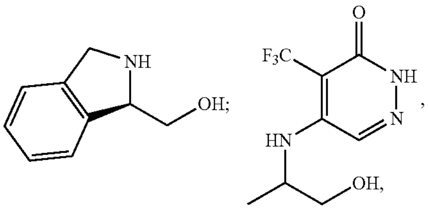
-continued
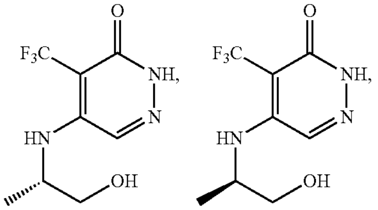
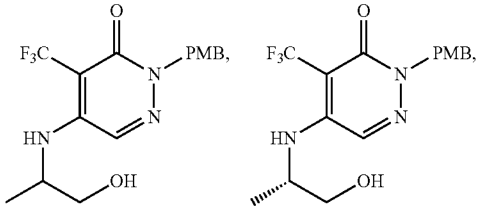
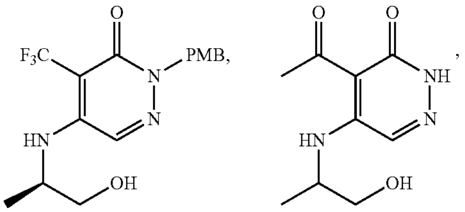
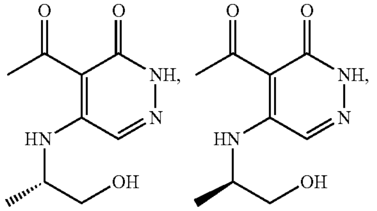
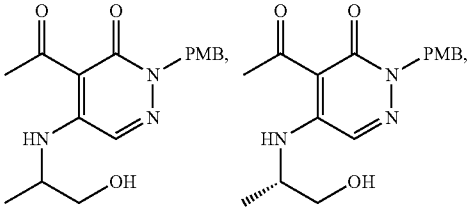
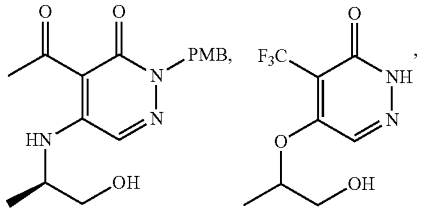
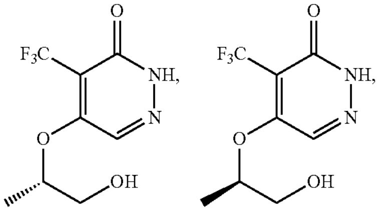
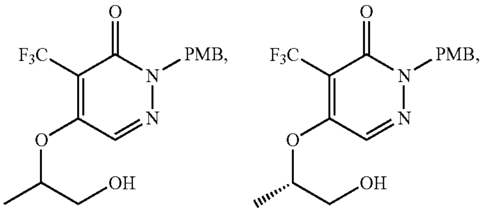

-continued
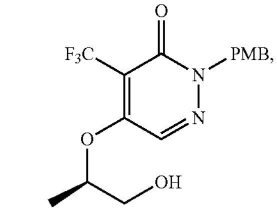
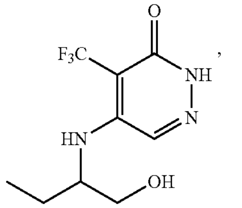
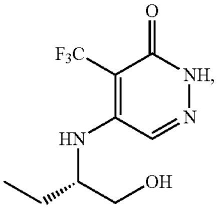
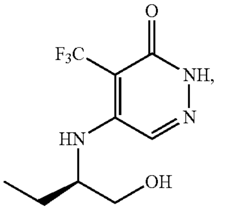
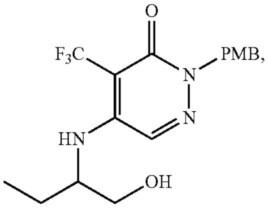
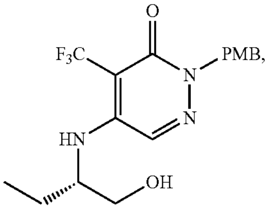
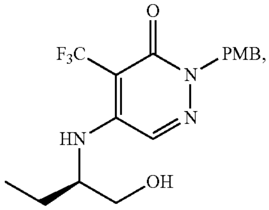
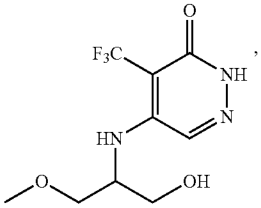
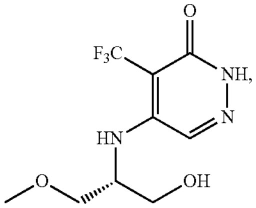
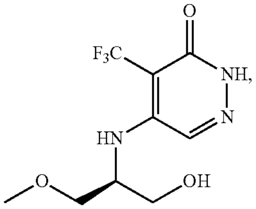
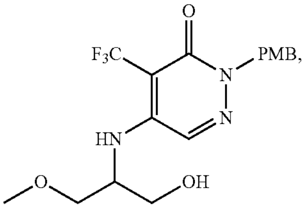
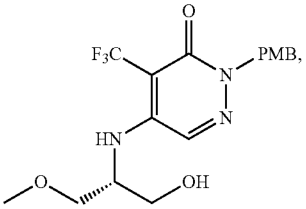
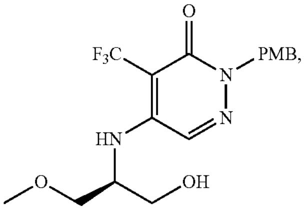
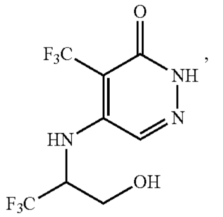
-continued
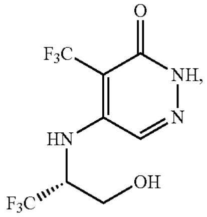
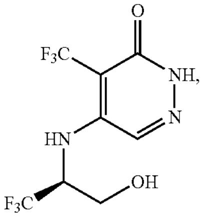
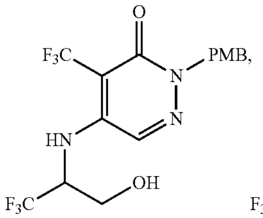
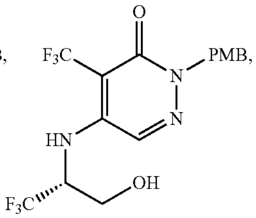
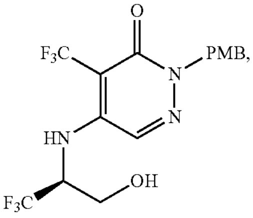
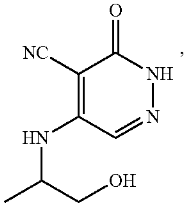
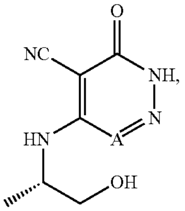
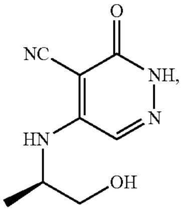
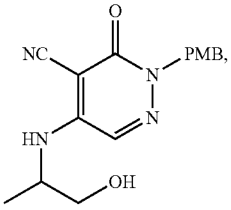
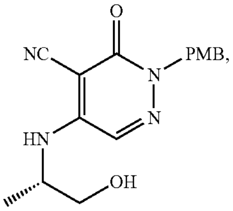
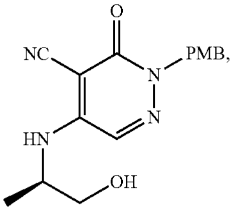
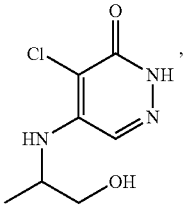
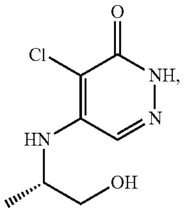
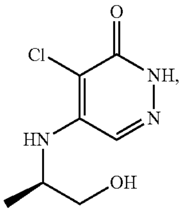
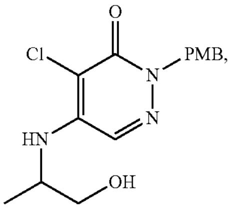
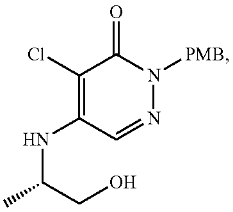

-continued
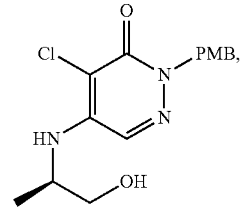
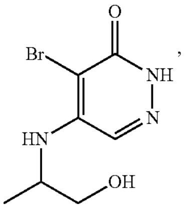
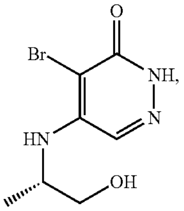
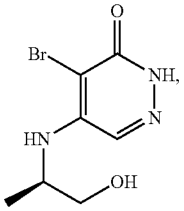
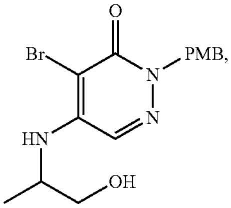
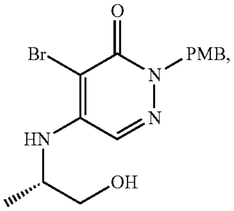
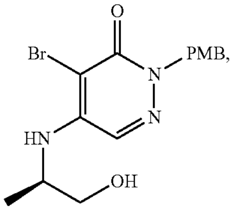
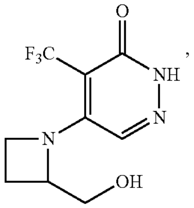
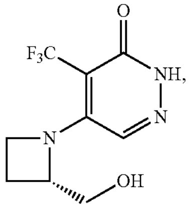
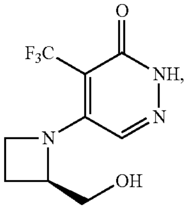
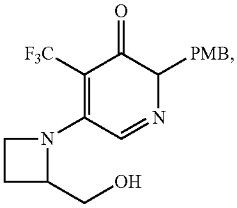
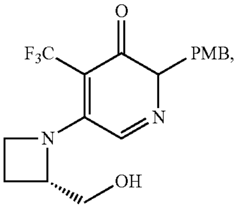
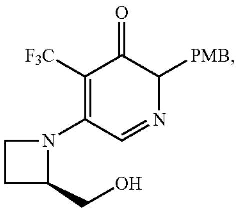
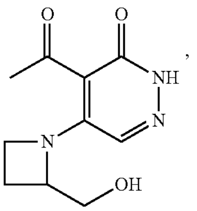
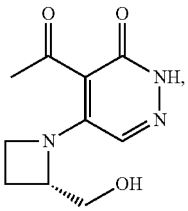
-continued
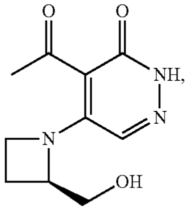
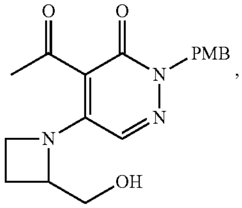
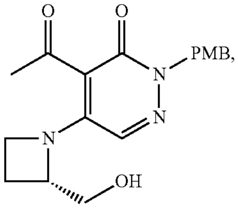
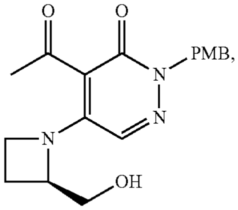
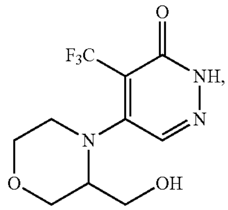
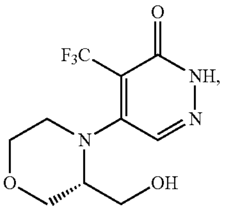
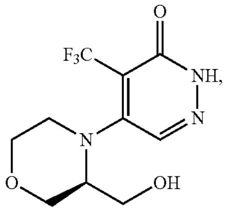
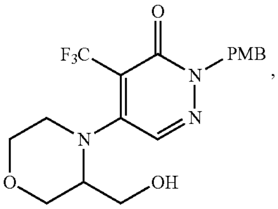
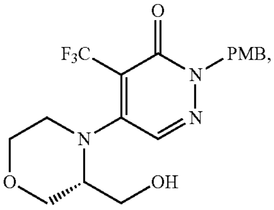
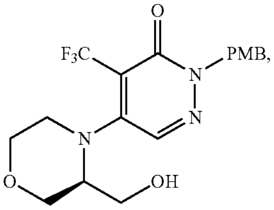
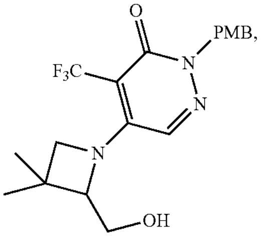
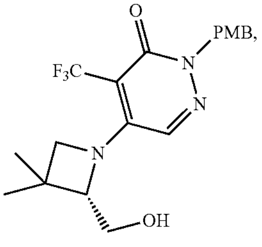
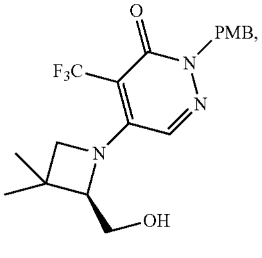
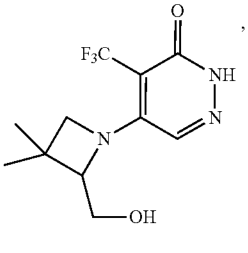

-continued
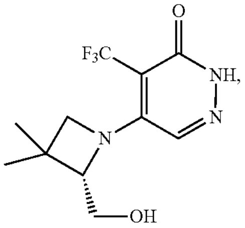
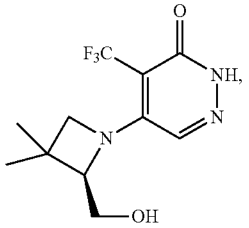
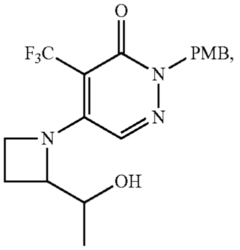
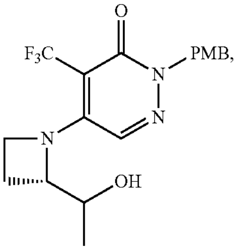
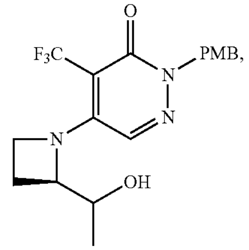
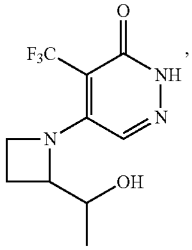
,
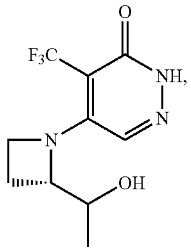
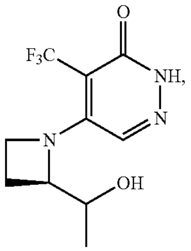
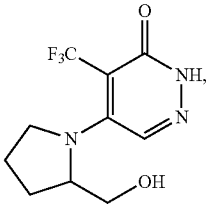
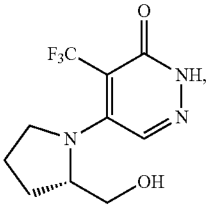
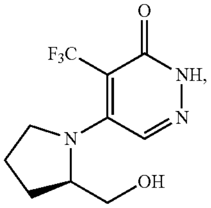
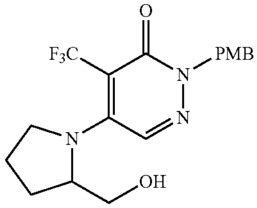
,
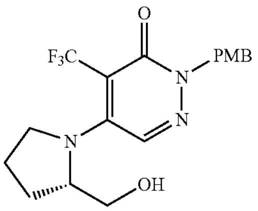
or
-continued
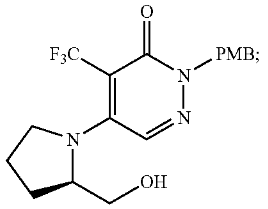
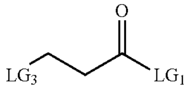
,
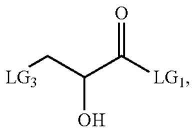
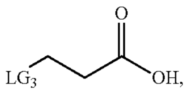
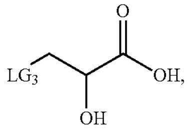
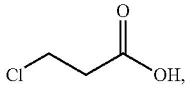
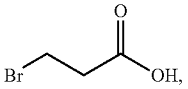
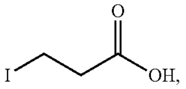
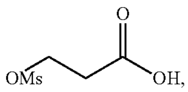
or
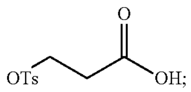
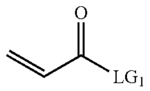
or
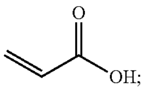
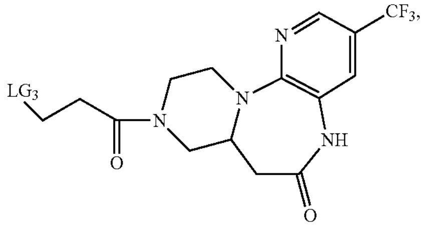
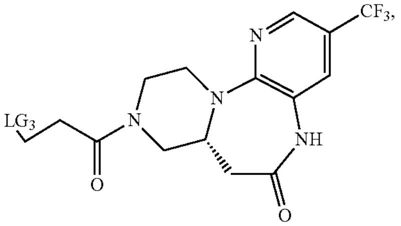
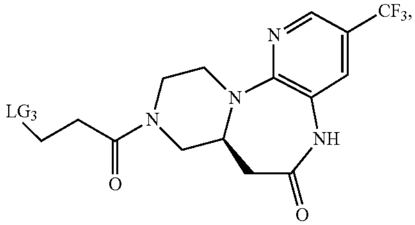
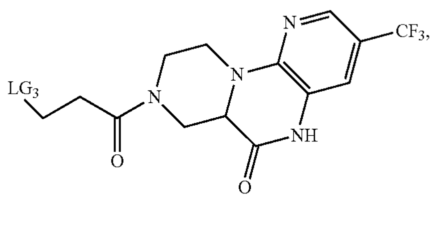

-continued
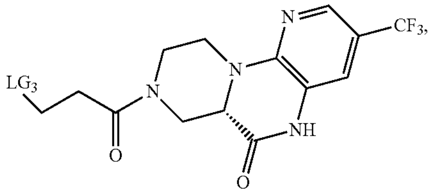
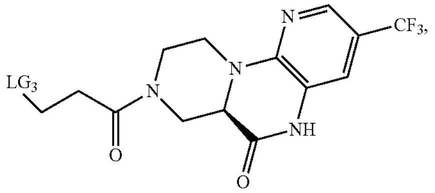
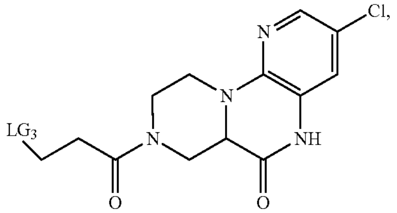
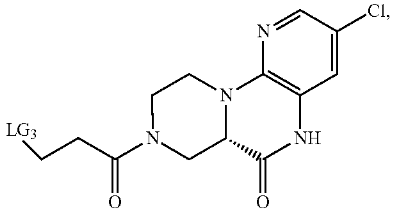
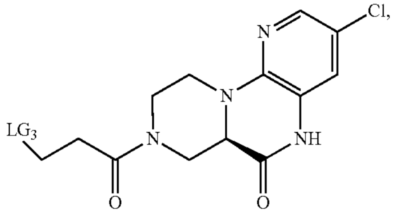
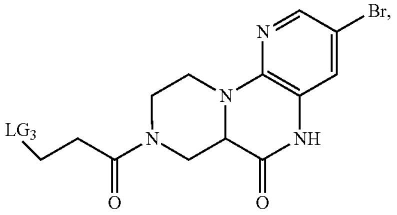
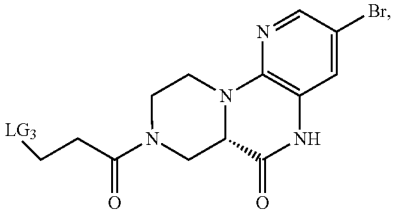
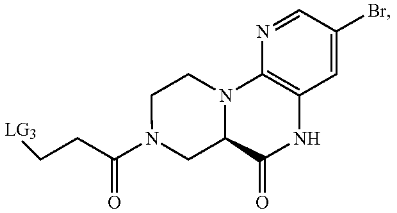
-continued
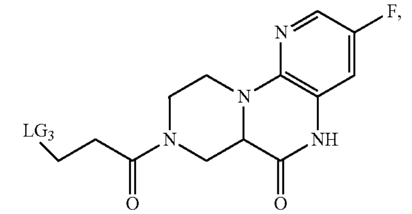
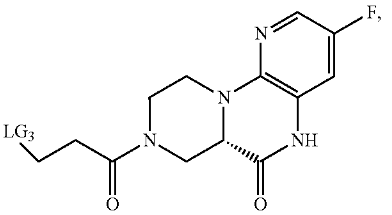
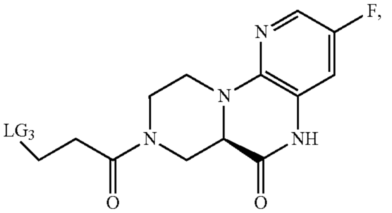
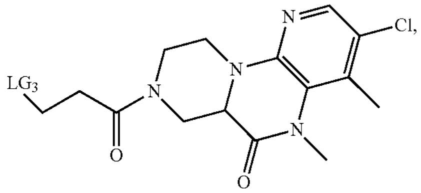
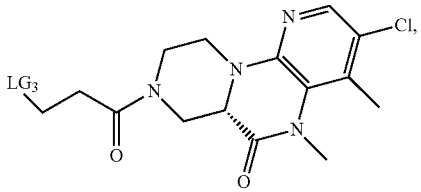
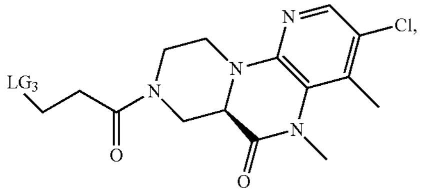
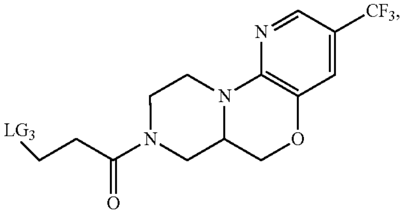
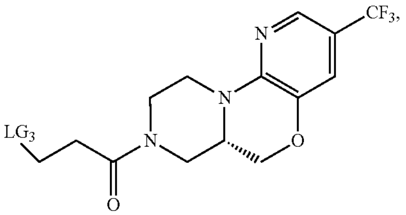

-continued
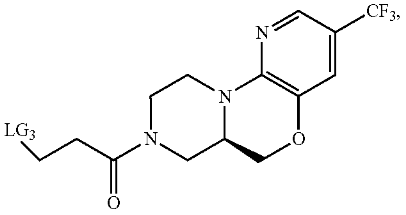
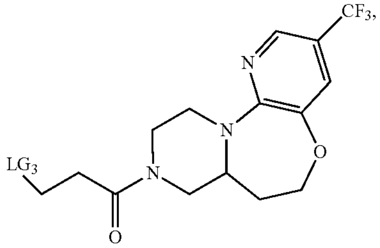
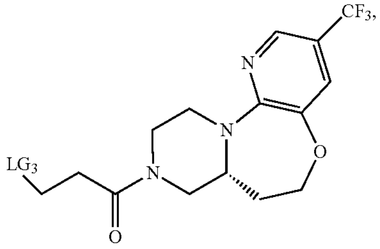
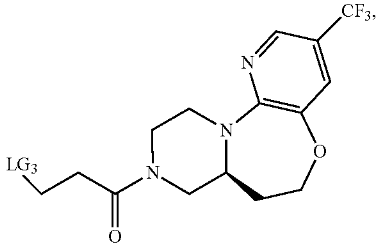
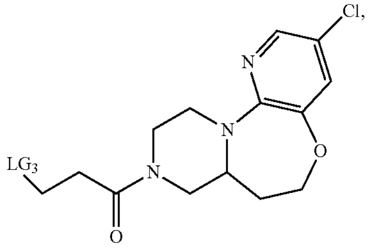
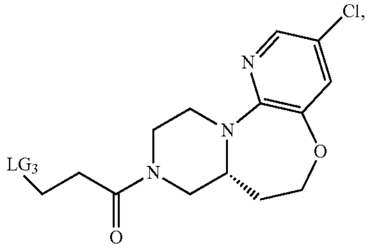
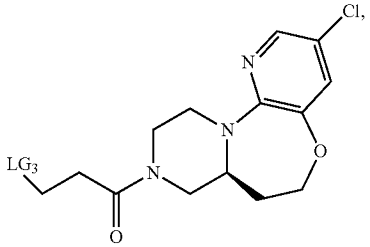
-continued
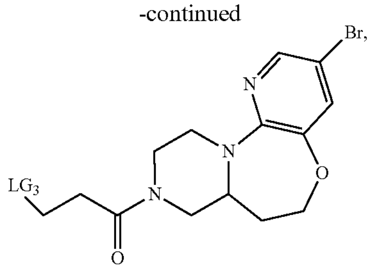
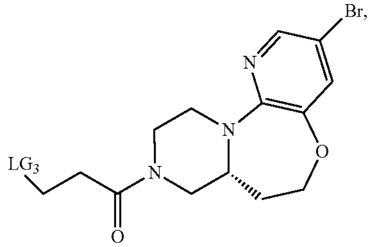
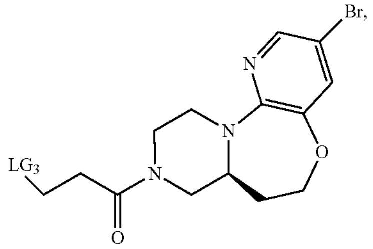
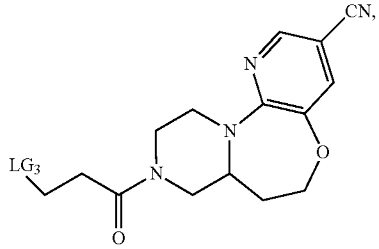
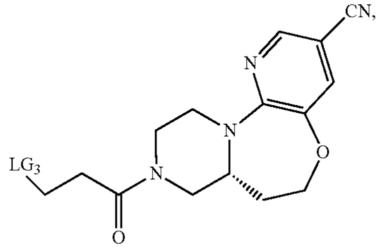
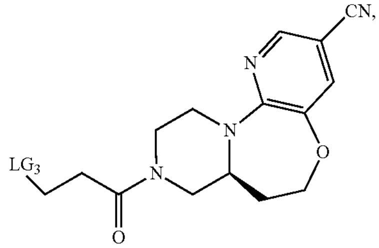
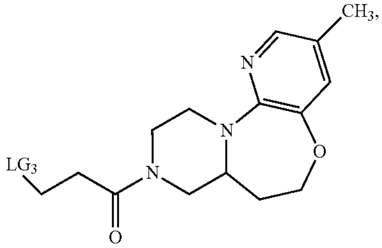

533
-continued
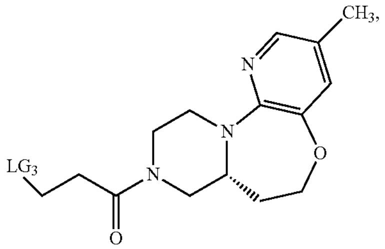
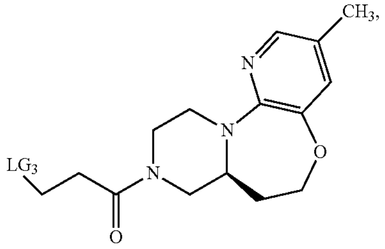
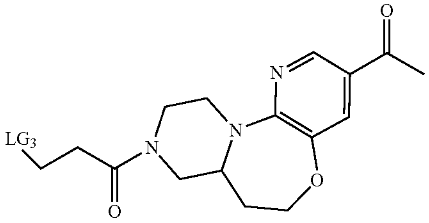
,
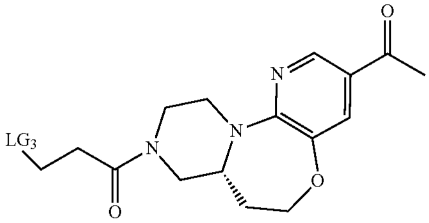
,
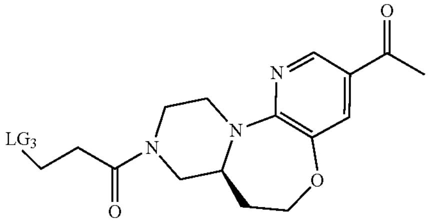
,
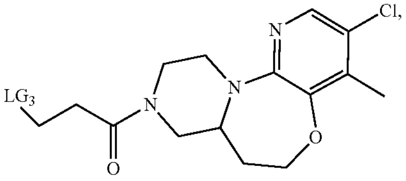
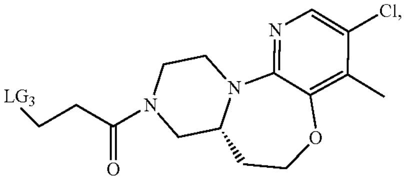
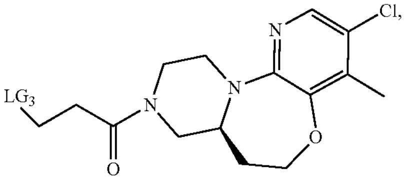
534
-continued
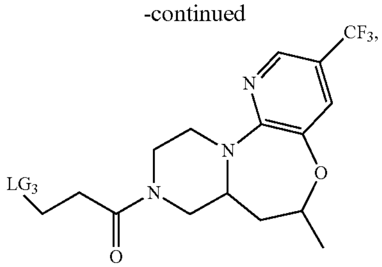
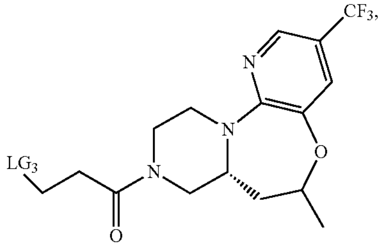
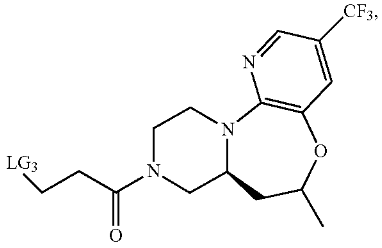
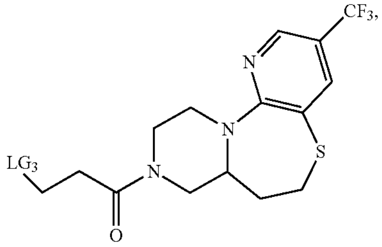
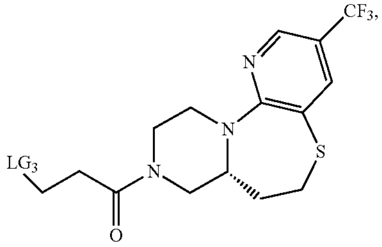
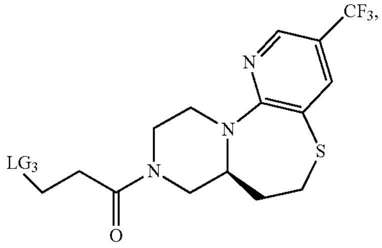
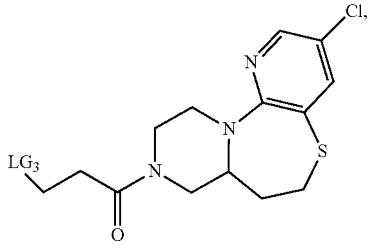

-continued
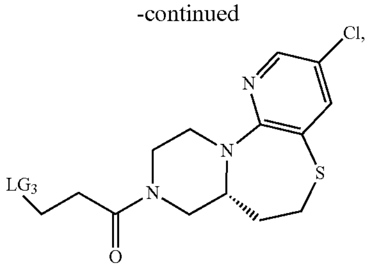
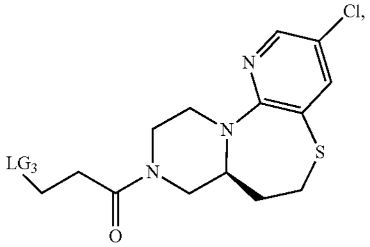
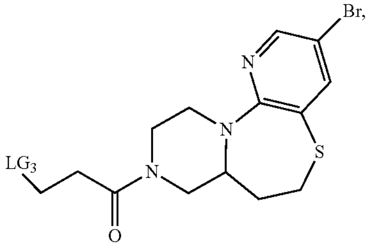
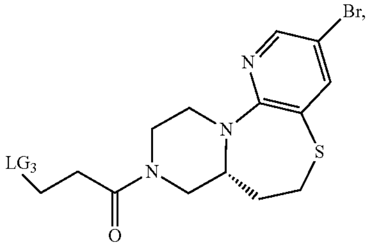
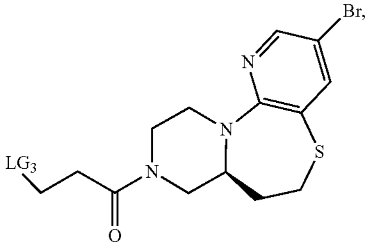
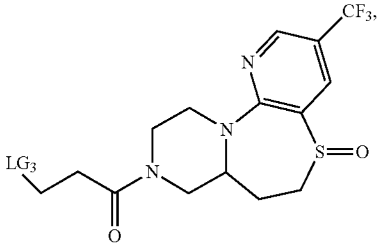
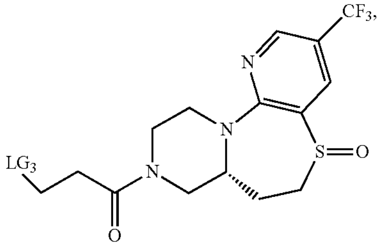
-continued
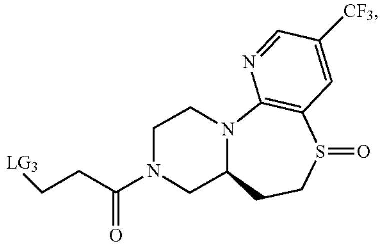
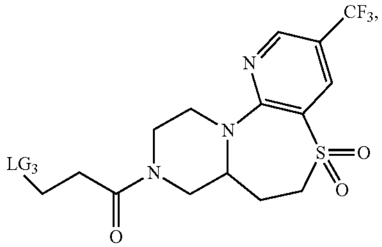
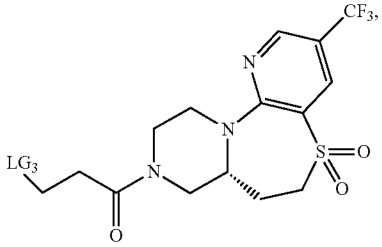
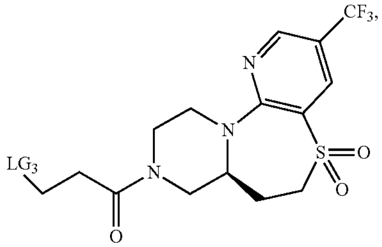
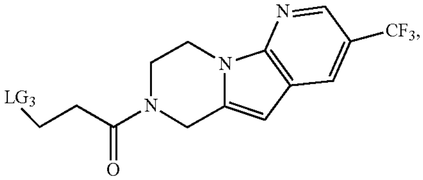
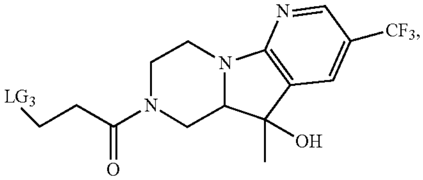
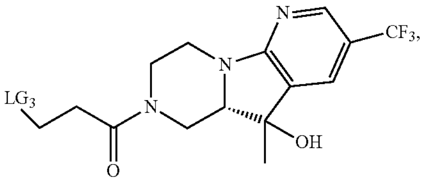
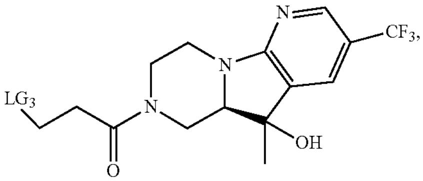

-continued
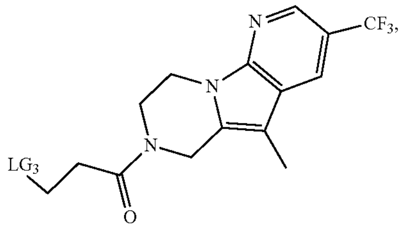
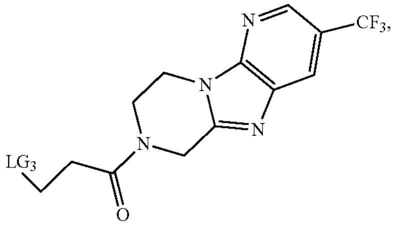
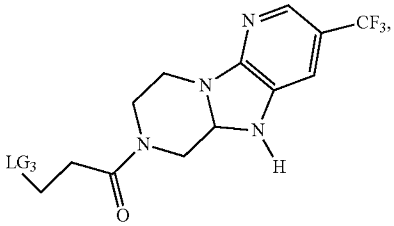
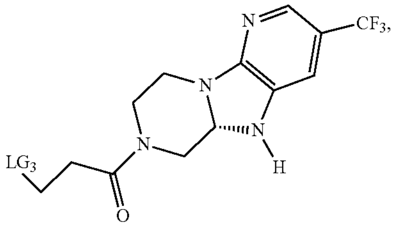
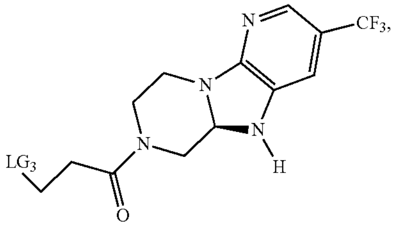
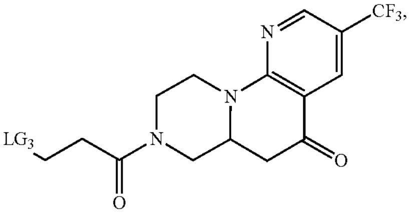
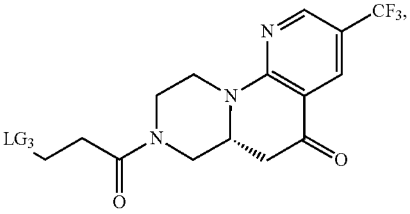
-continued
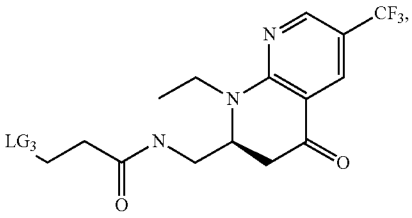
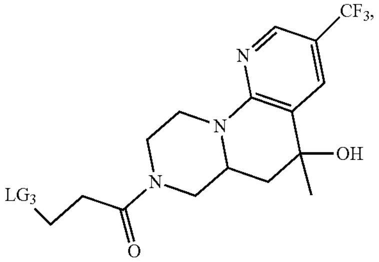
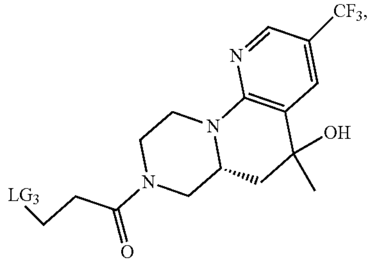
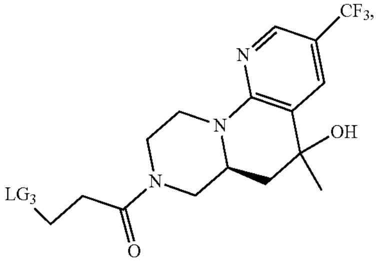
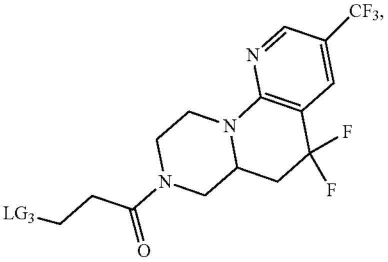
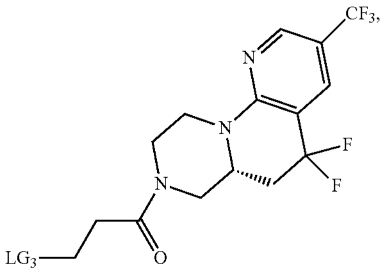

-continued
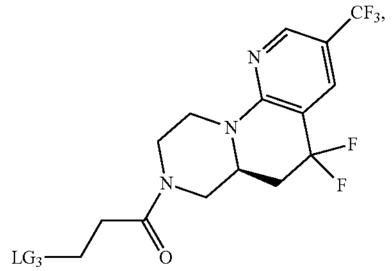
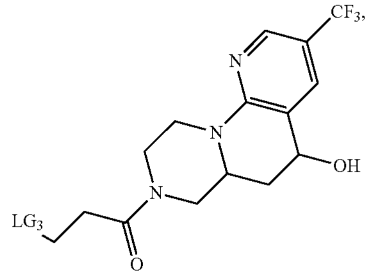
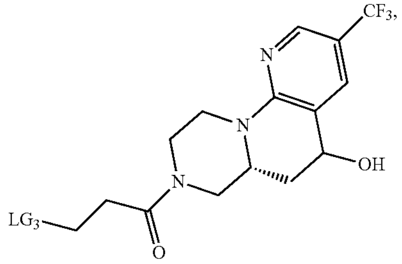
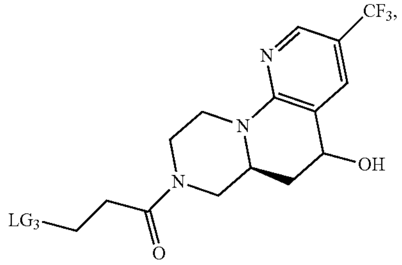
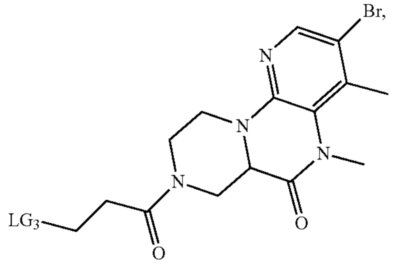
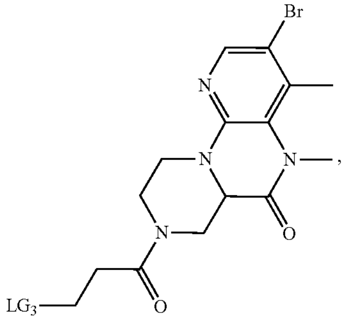
-continued
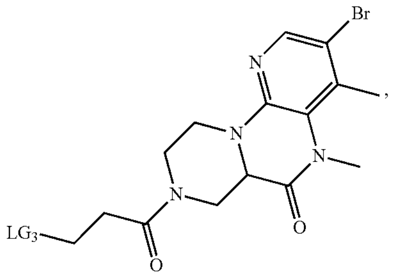
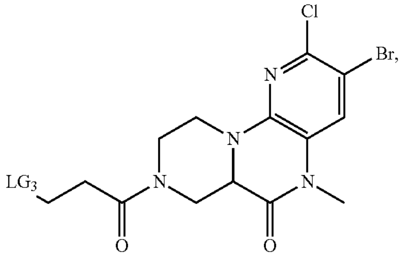
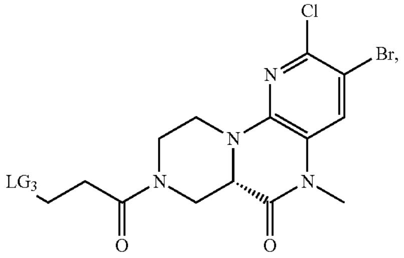
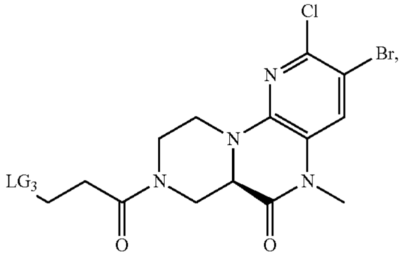
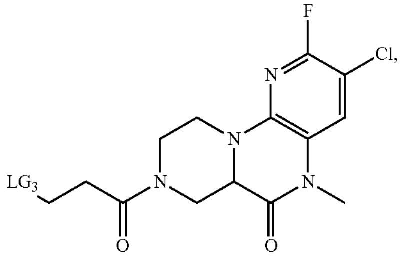
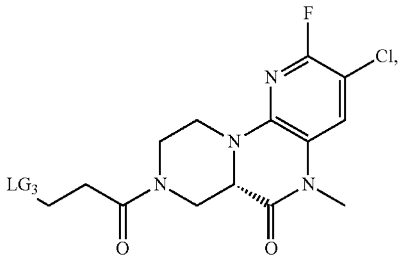

-continued
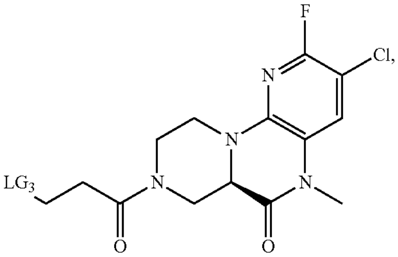
,
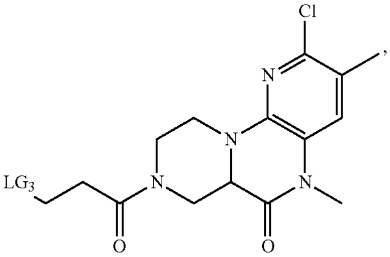
,
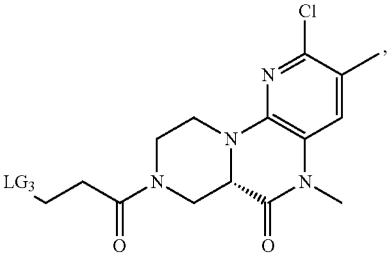
,
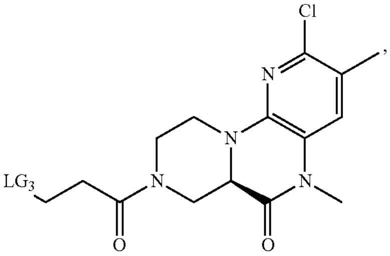
,
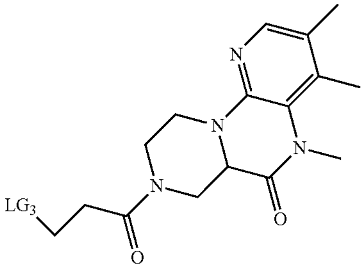
,
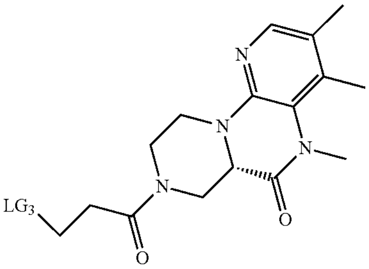
,
-continued
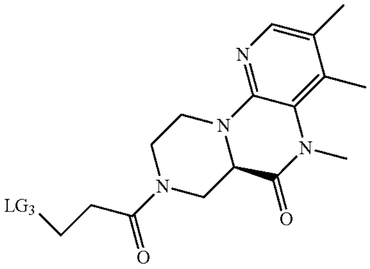
,
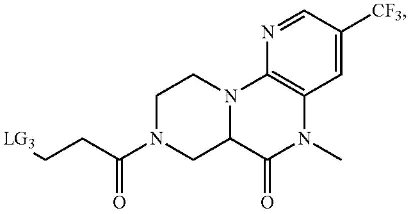
,
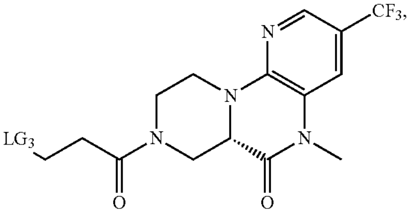
,
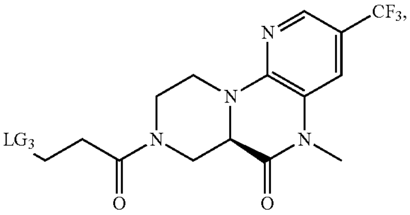
,
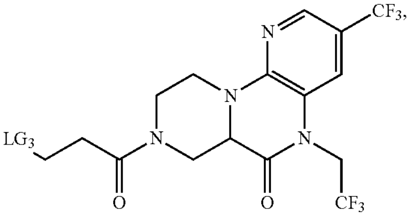
,
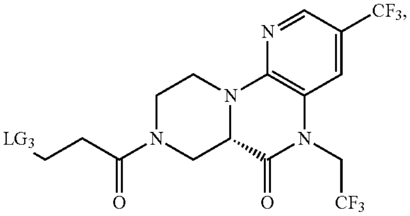
,
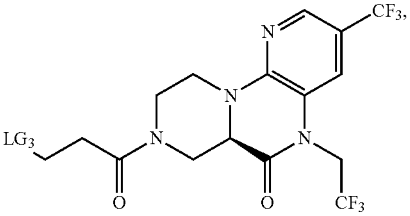
, -continued
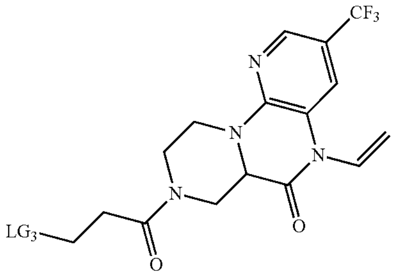
,
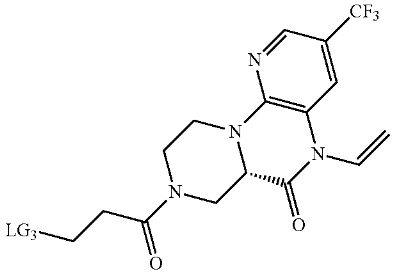
,
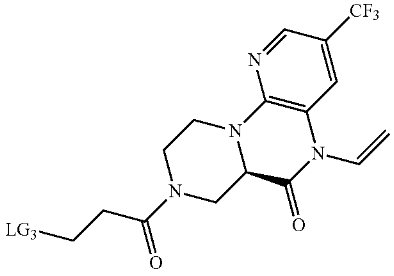
,
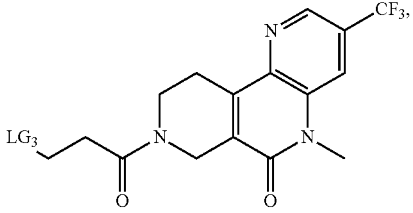
,
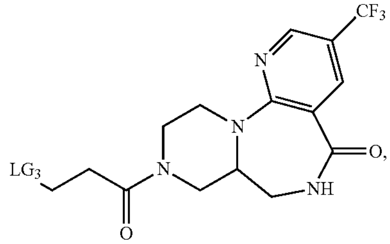
,
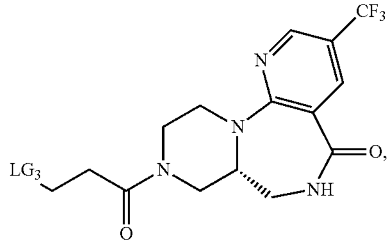
,
-continued
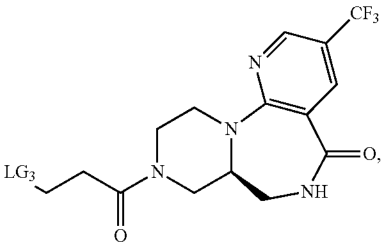
,
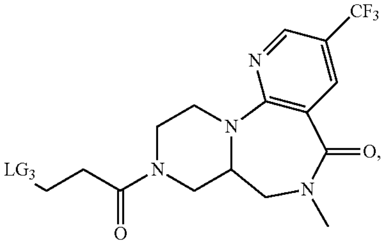
,
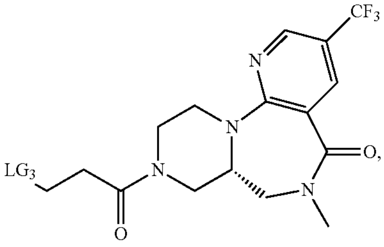
, or
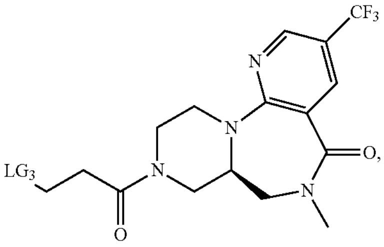
,
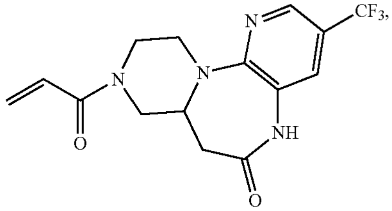
,
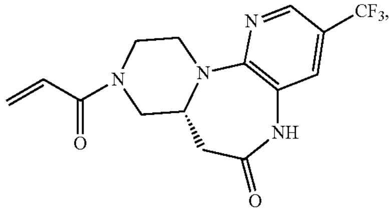
,
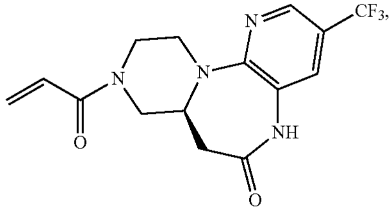
, -continued
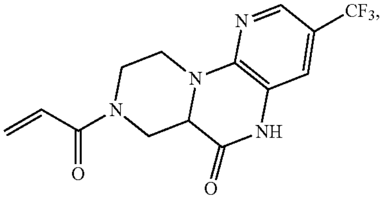
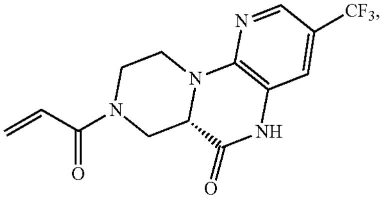
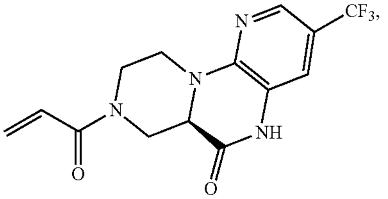
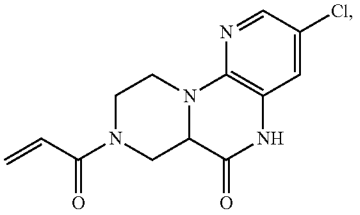
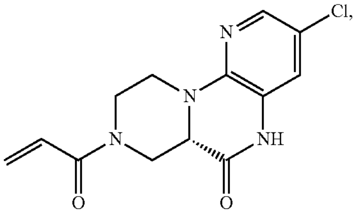
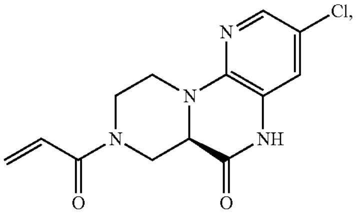
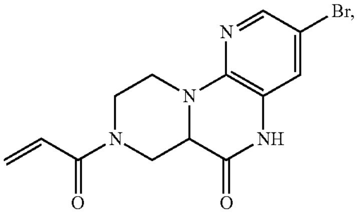
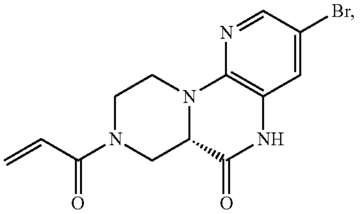
-continued
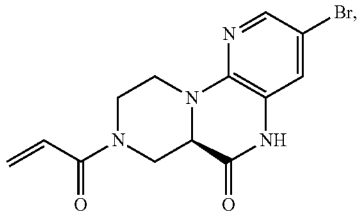
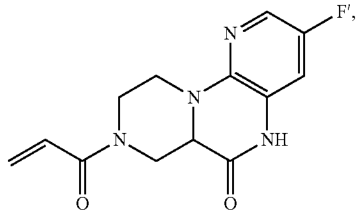
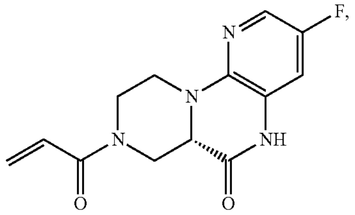
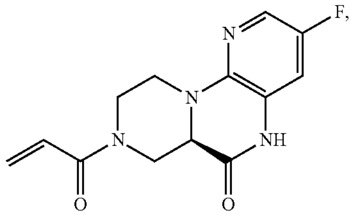
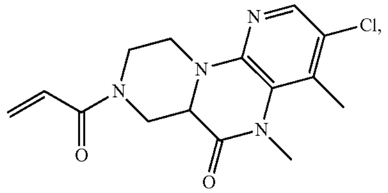
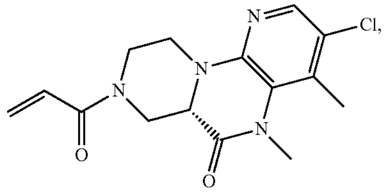
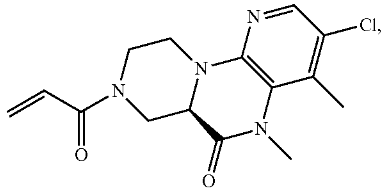
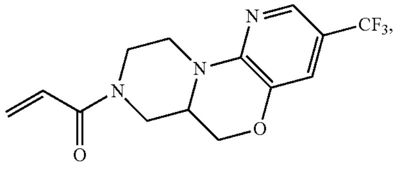

-continued
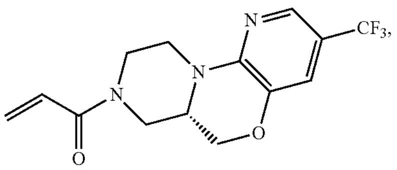
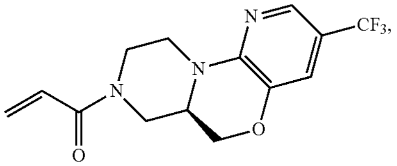
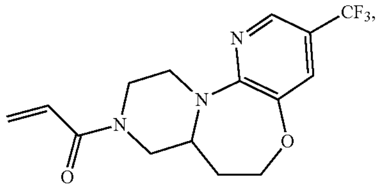
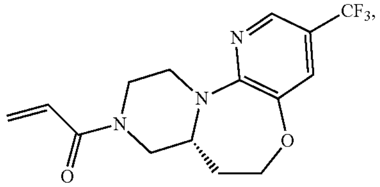
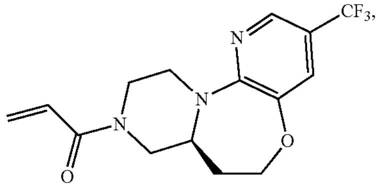
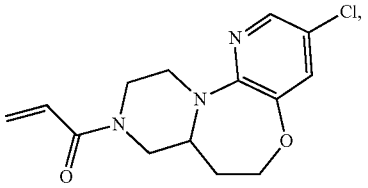
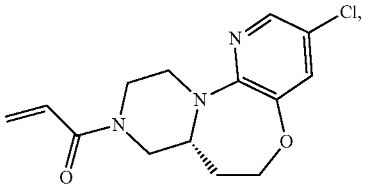
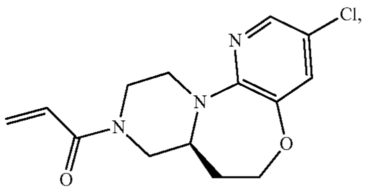
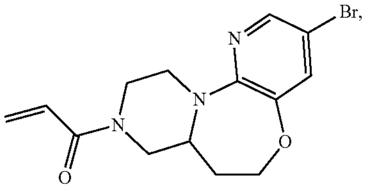
-continued
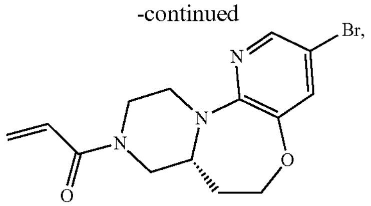
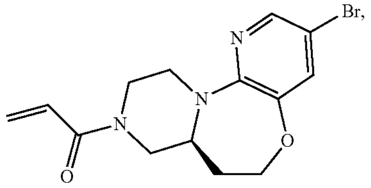
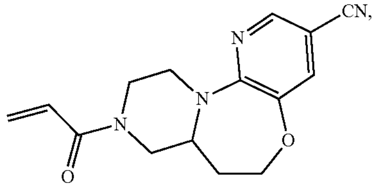
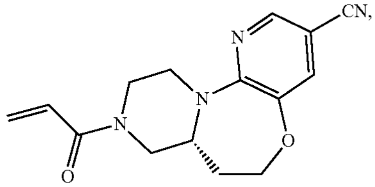
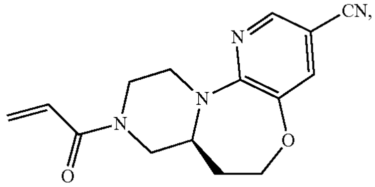
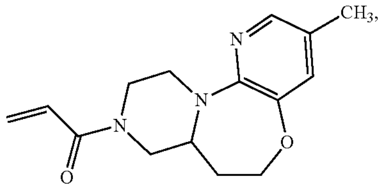
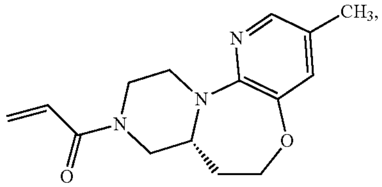
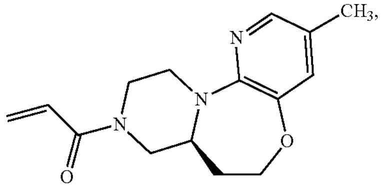
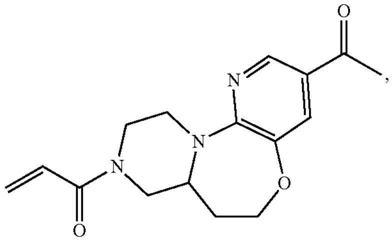

-continued
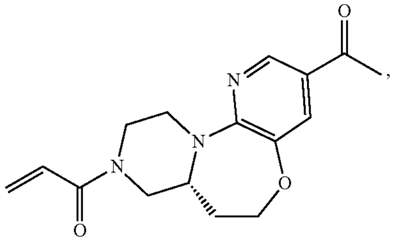
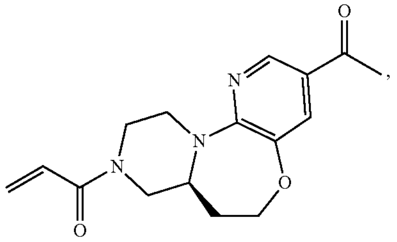
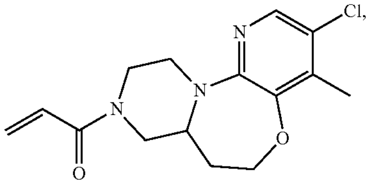
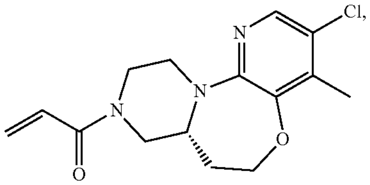
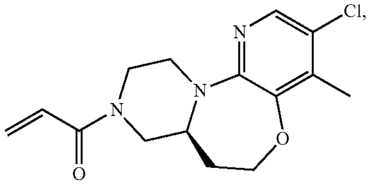
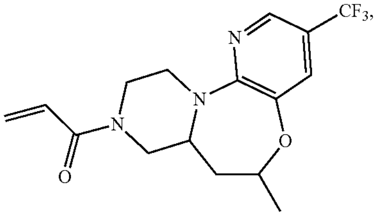
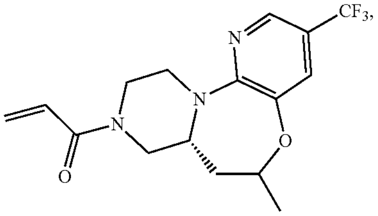
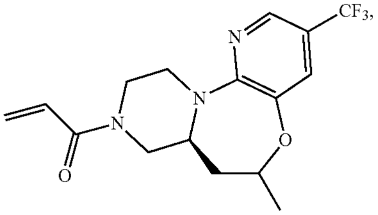
-continued
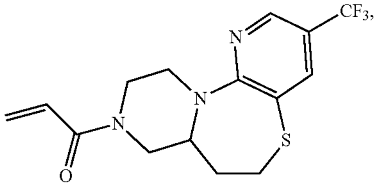
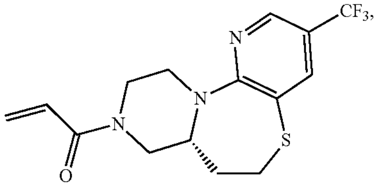
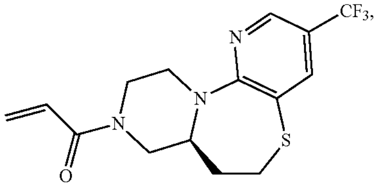
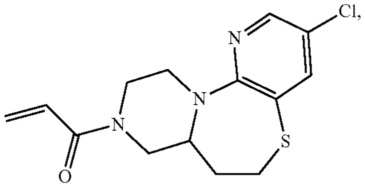
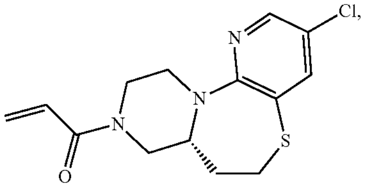
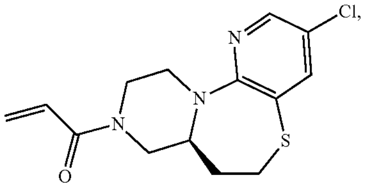
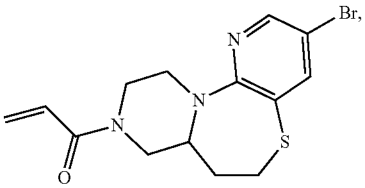
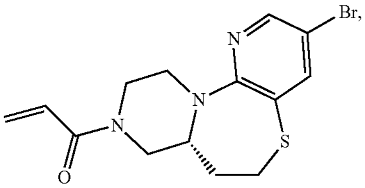
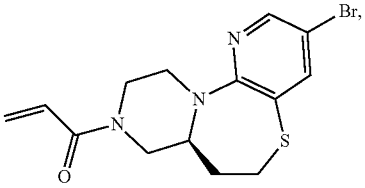

-continued
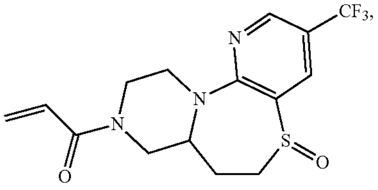
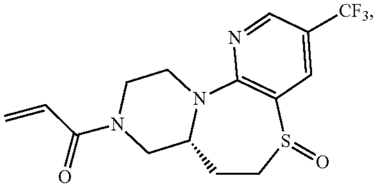
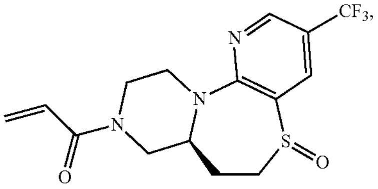
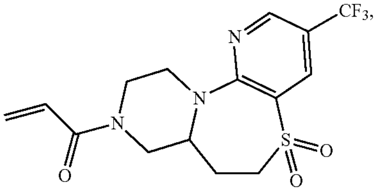
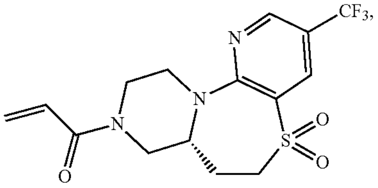
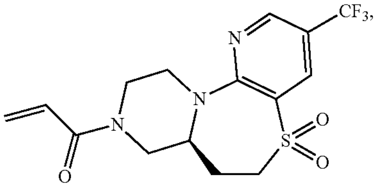
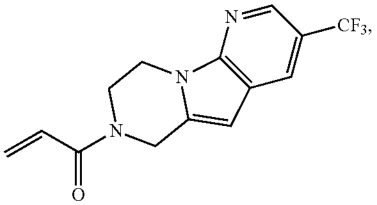
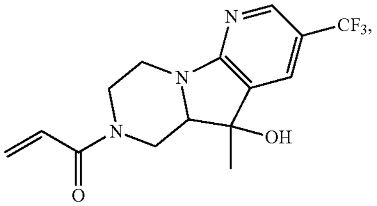
-continued
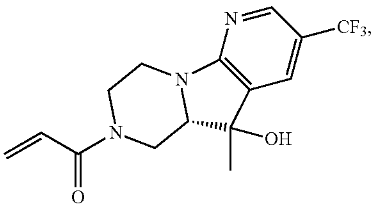
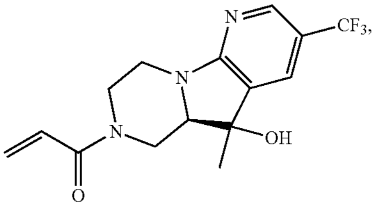
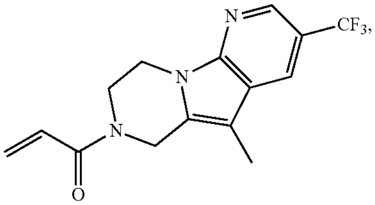
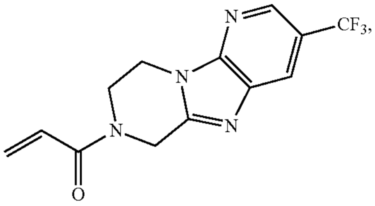
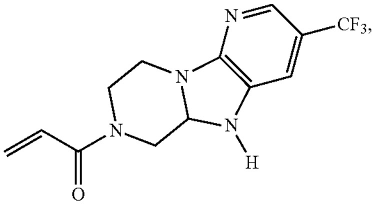
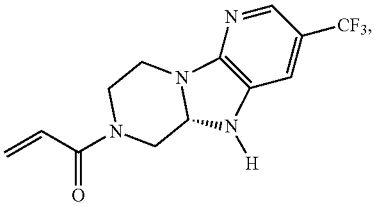
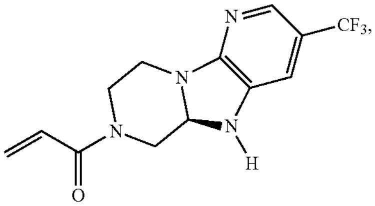
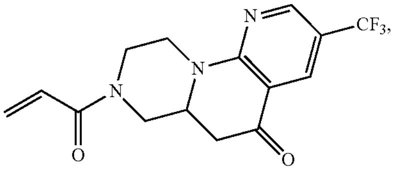

-continued
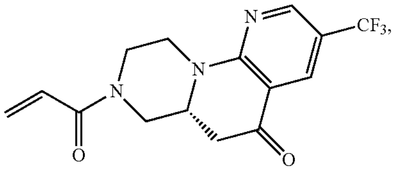
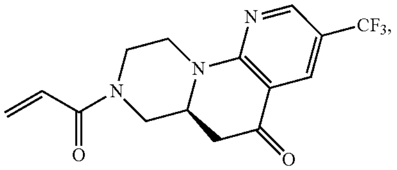
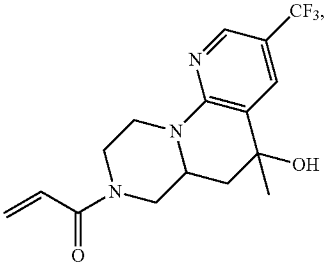
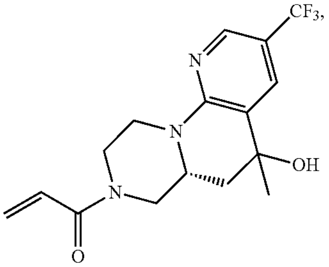
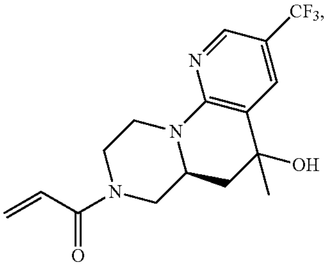
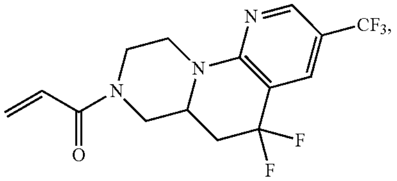
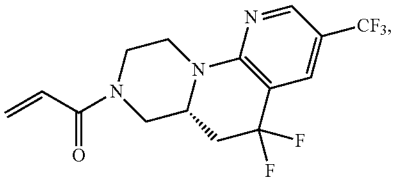
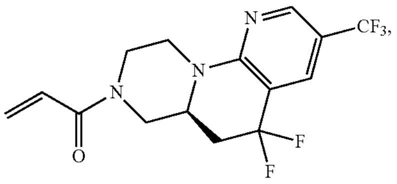
-continued
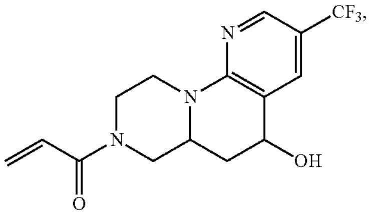
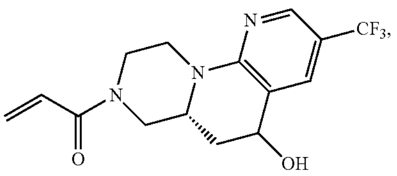
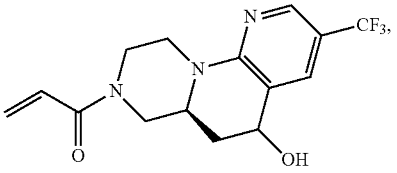
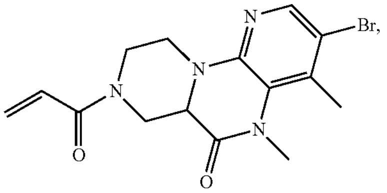
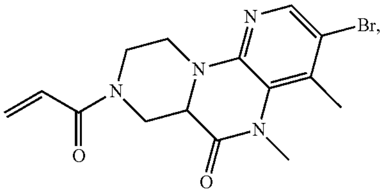
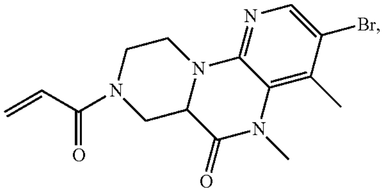
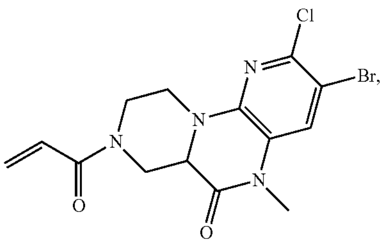
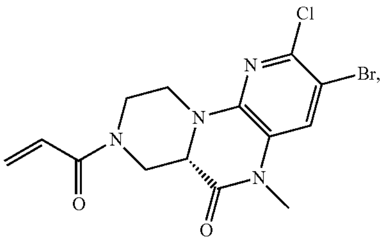

-continued
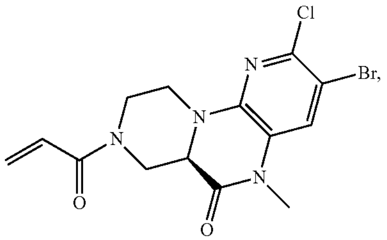
,
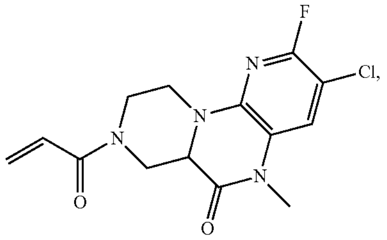
,
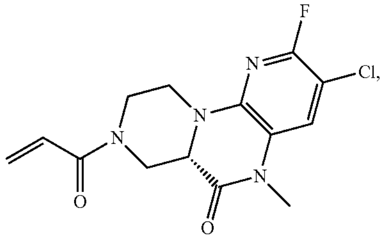
,
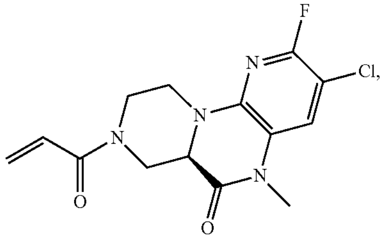
,
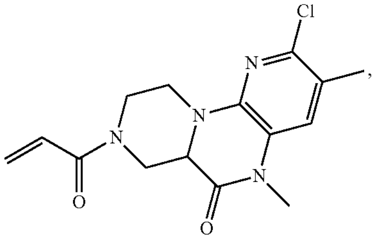
,
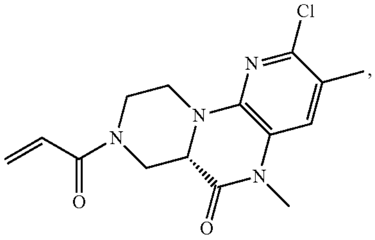
,
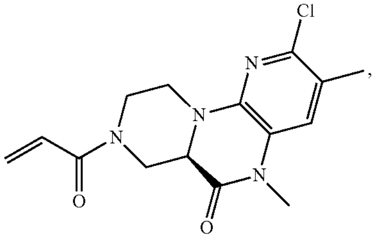
,
-continued
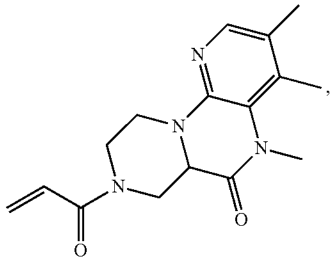
,
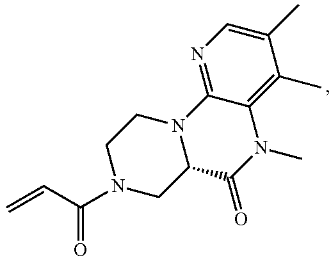
,
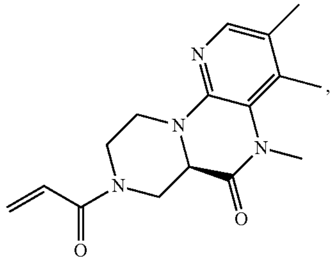
,
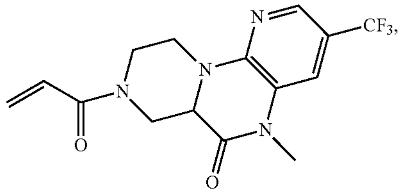
,
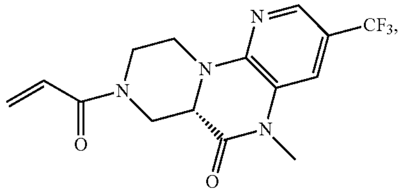
,
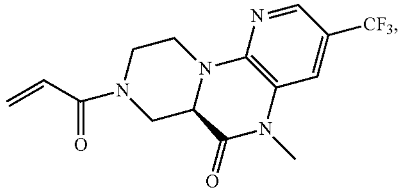
,
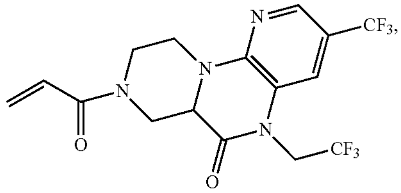

-continued
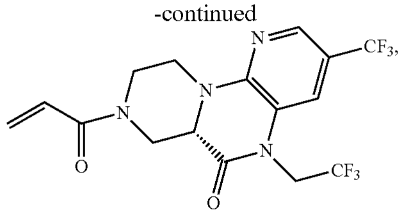
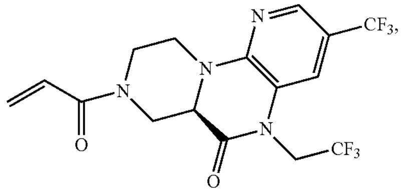
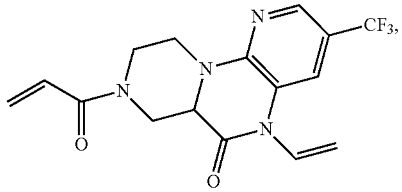
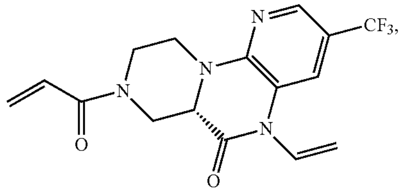
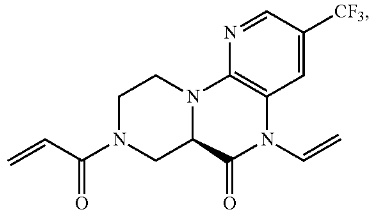
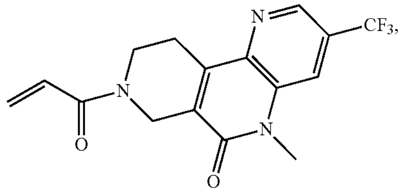
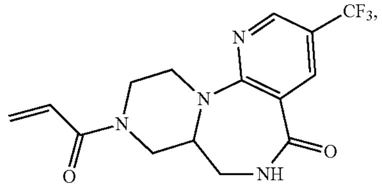
-continued
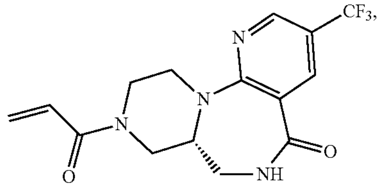
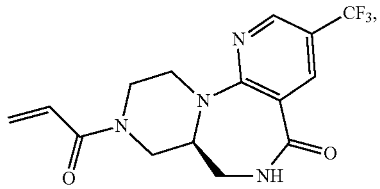
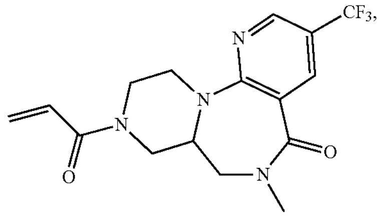
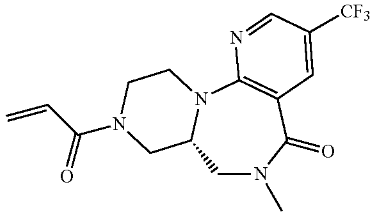
or
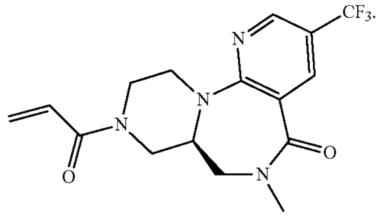
[95]. A process for preparing the compound of according to any one of [1] to [93], comprising the following Step A or Step B:
Step A: Reacting the compound of formula (I-1) with the compound of formula (I-2) by a condensation reaction to yield the compound of formula (I):
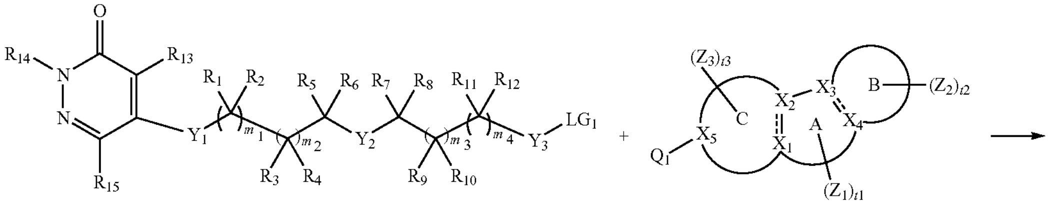
(I-1) (I-2)

-continued

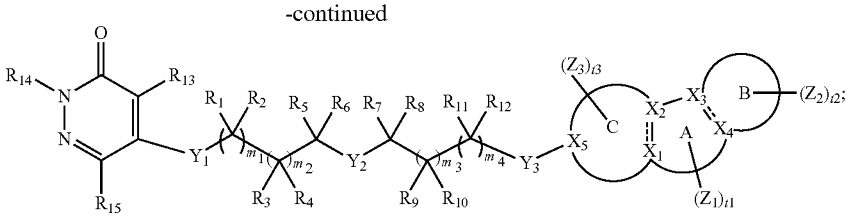

(I)

Said $LG_1$ in the compound of formula (I-1) is a leaving group or a group that can be converted to the leaving group; in some embodiments, the leaving group is selected from halogen (such as —Cl, —Br or —I), —$OS(=O)_2CH_3$ or

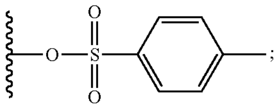 [SMILES: *OS(=O)(=O)c1ccc(C)cc1]

in some embodiments, the group that can be converted to the leaving group is selected from —OH;

When $X_5$ is selected from N, said $Q_1$ in the compound of formula (I-2) is selected from —H or a protecting group of N, in some embodiments, said protecting group of N is selected from -Boc;

Step B: reacting the compound of formula (I'-1) with the compound of formula (I'-2) by a substitution reaction or by a coupling reaction to yield the compound of formula (I);

Said $LG_2$ in the compound of formula (I'-1) is a leaving group or a group that can be converted to the leaving group; in some embodiments, the leaving group is selected from halogen (such as —Cl, —Br or —I), —$OS(=O)_2CH_3$ or

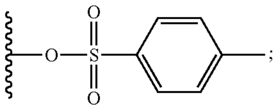 [SMILES: *OS(=O)(=O)c1ccc(C)cc1]

in some embodiments, the group that can be converted to the leaving group is selected from —OH;

Said $Q_2$ in the compound of formula (I'-2) is selected from —H;

The definition of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $Y_1$, $Y_2$, $Y_3$, $X_1$, $X_2$, $X_3$, $X_4$, $X_5$, ring A, ring B, ring C, $Z_1$, $Z_2$, $Z_3$, $m_1$, $m_2$, $m_3$, $m_4$, $t_1$, $t_2$, or $t_3$ at each occurrence in formula (I-1), formula (I-2), formula (I-1'), formula (I-2') or formula (I) is same as any one of [1] to [93];

In some embodiments, the compound of formula (I-1) is selected from any one of the following formulas:

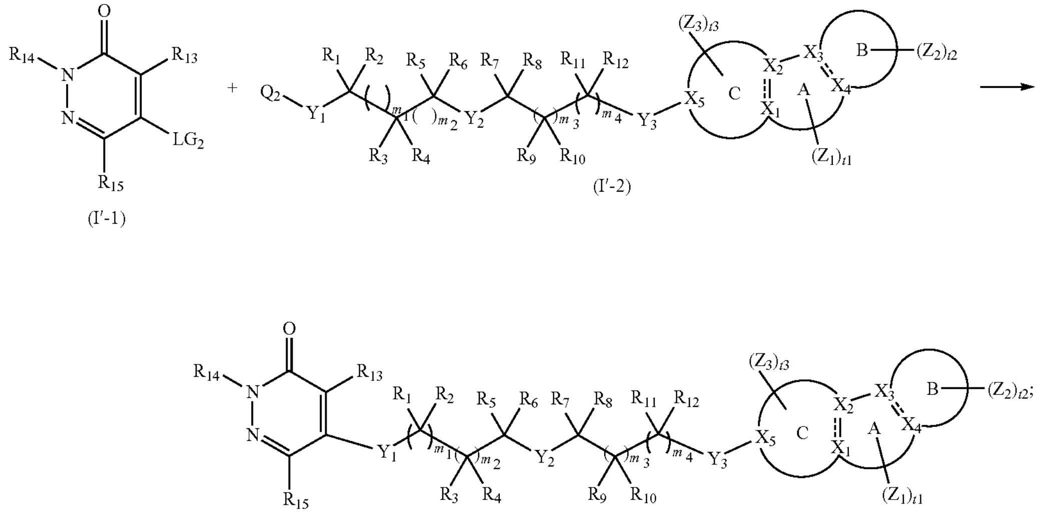

(I'-1) (I'-2)

(I)

-continued
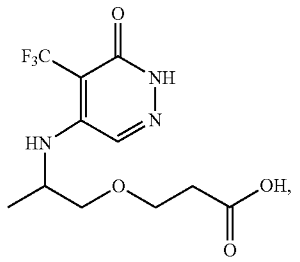
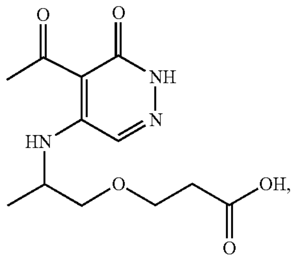
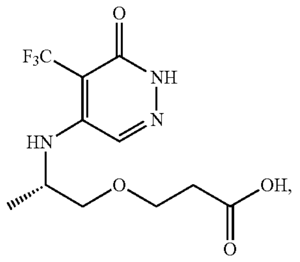
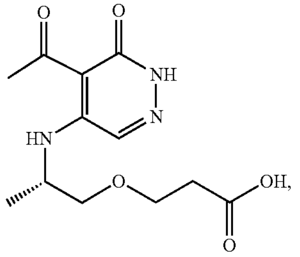
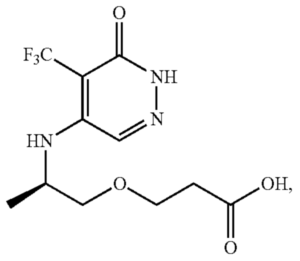
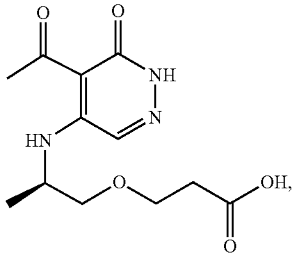
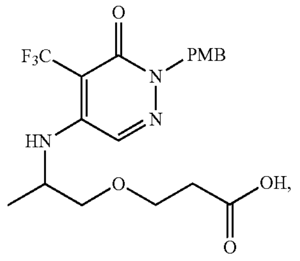
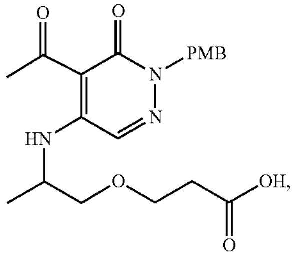
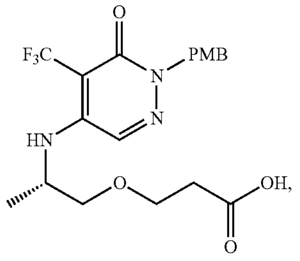
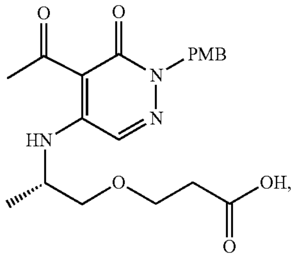
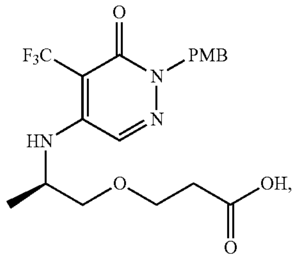
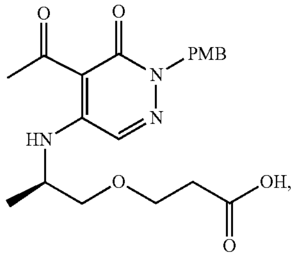

-continued
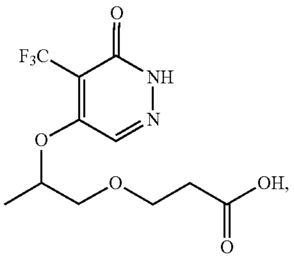
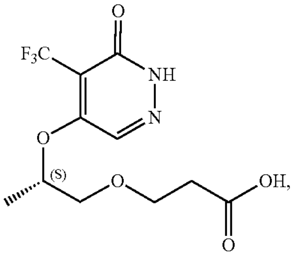
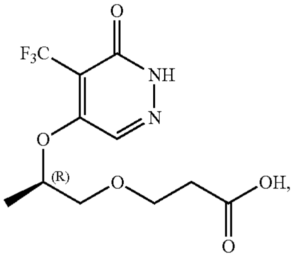
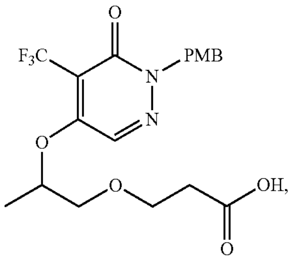
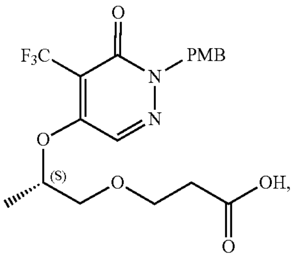
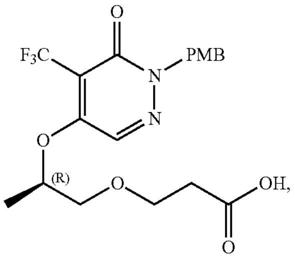
-continued
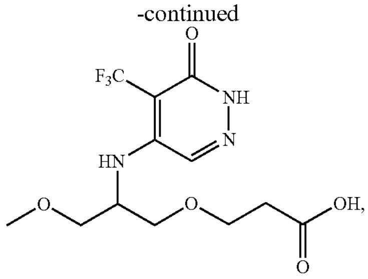
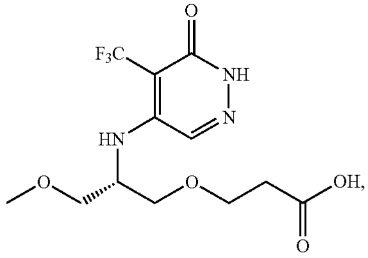
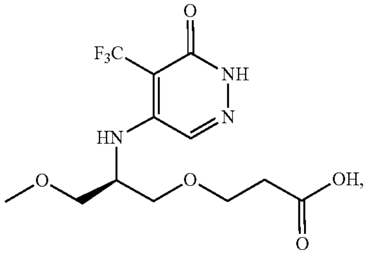
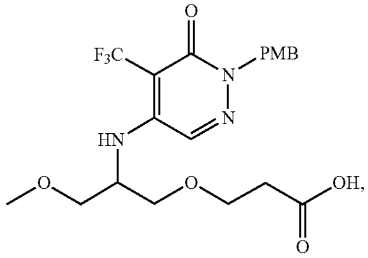
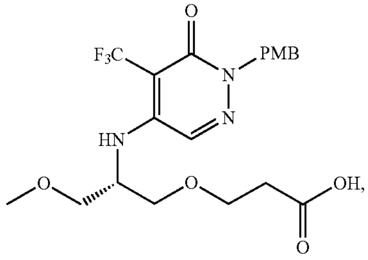
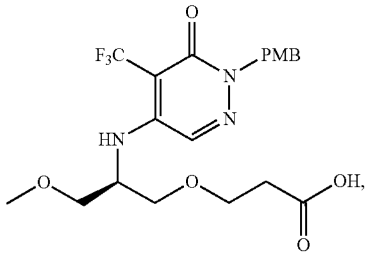

-continued
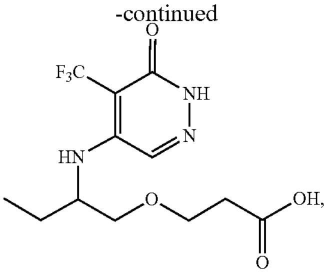
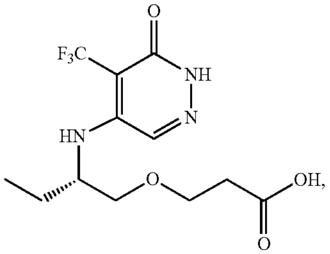
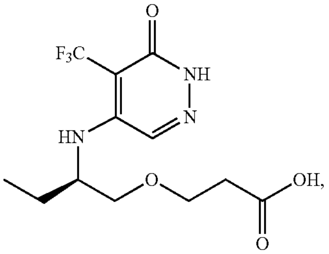
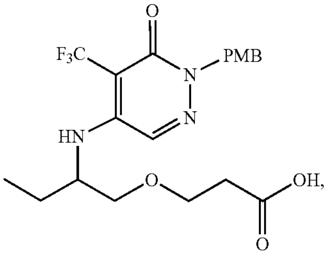
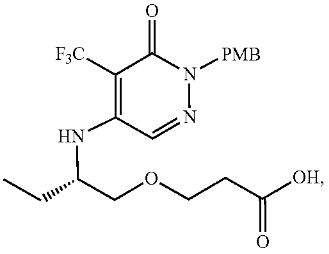
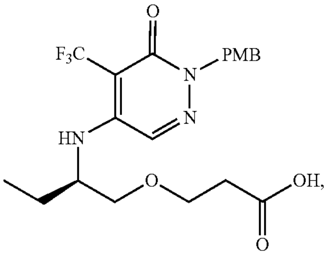
-continued
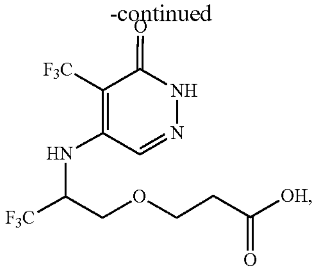
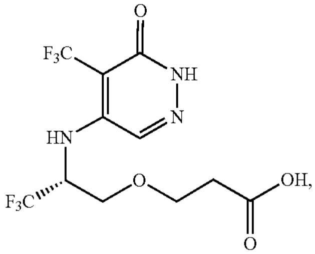
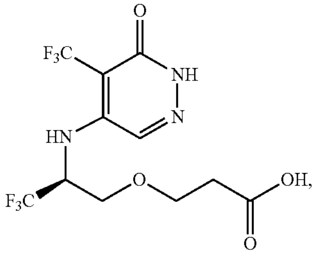
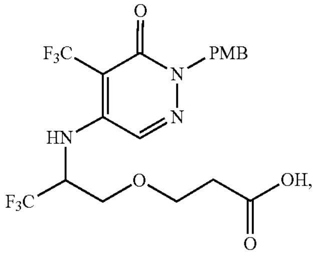
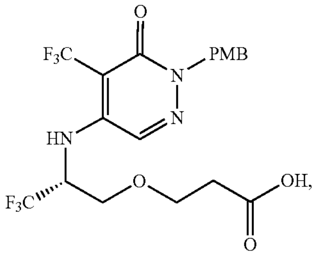
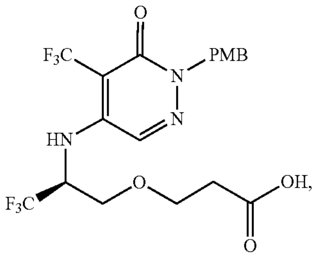

-continued
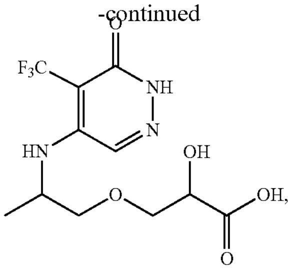
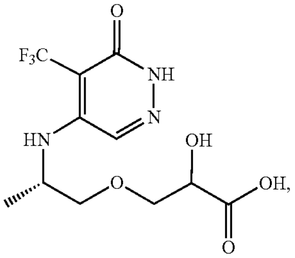
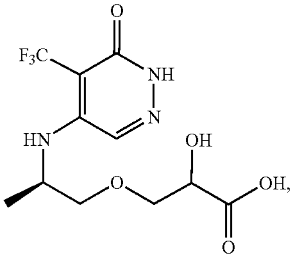
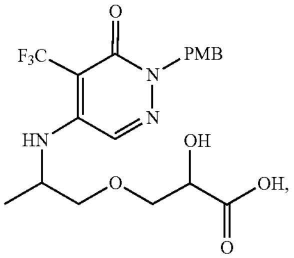
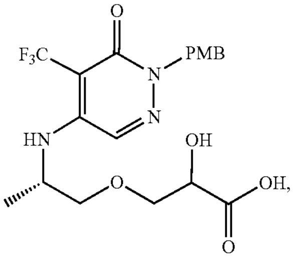
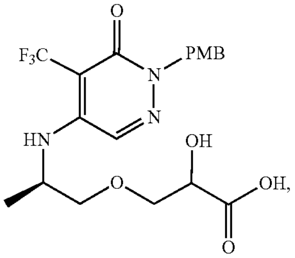
-continued
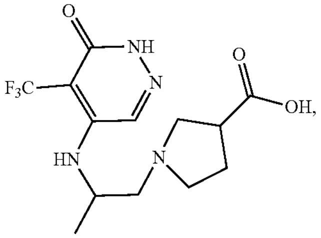
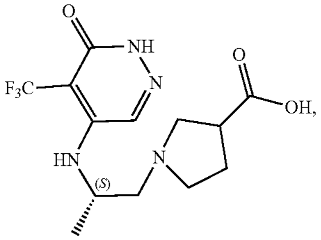
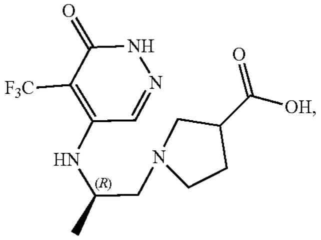
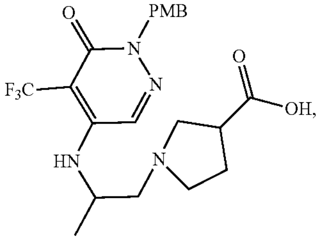
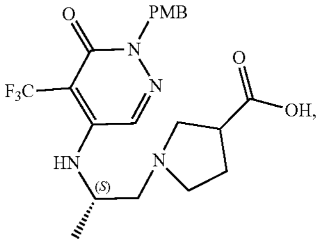
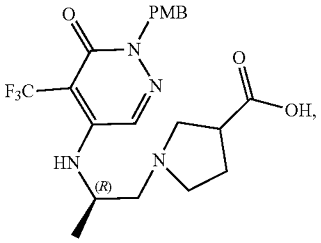
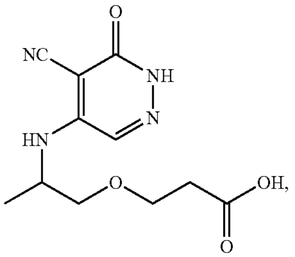

-continued
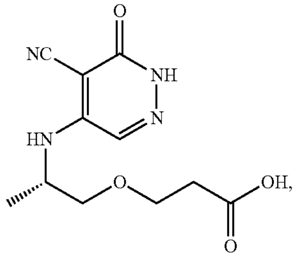
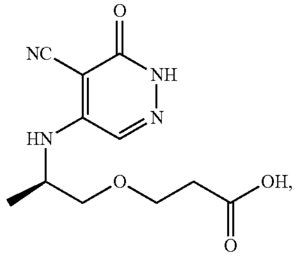
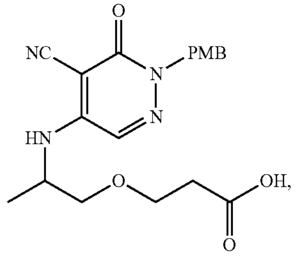
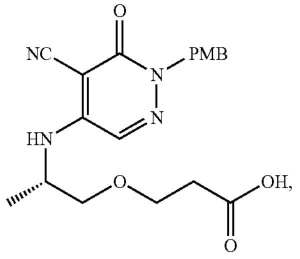
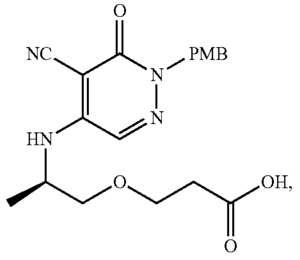
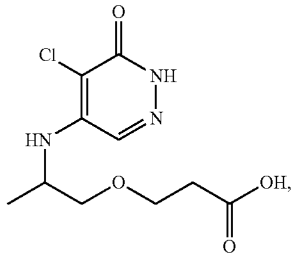
-continued
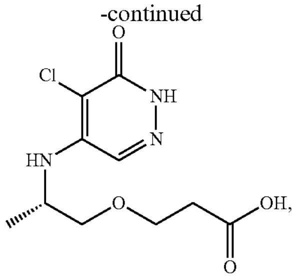
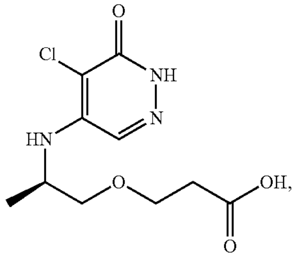
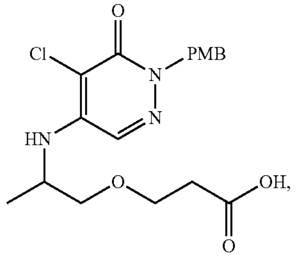
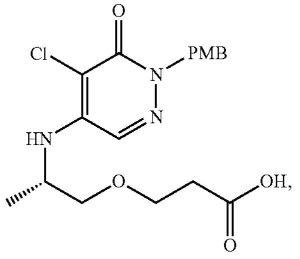
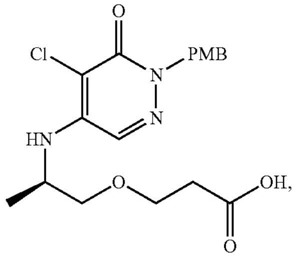
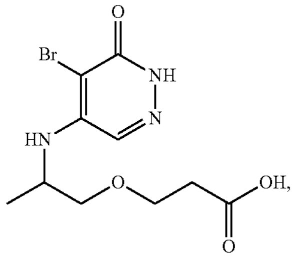

-continued
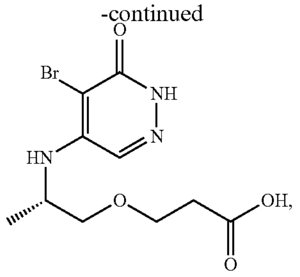
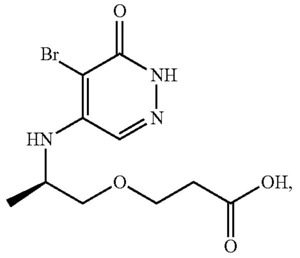
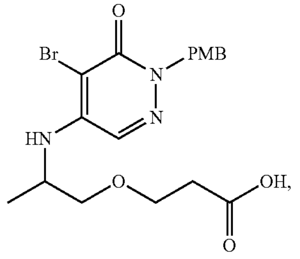
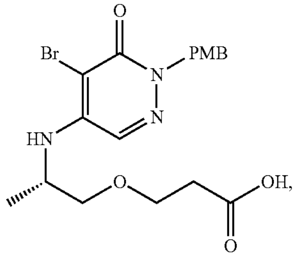
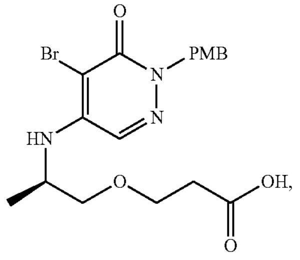
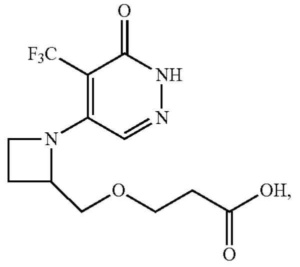
-continued
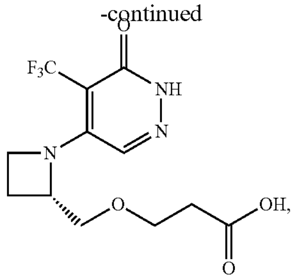
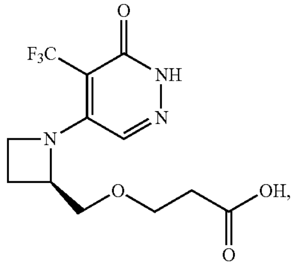
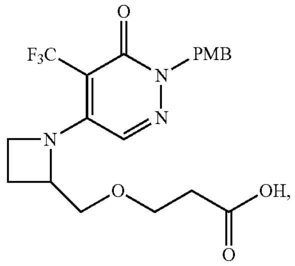
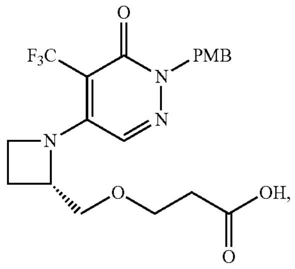
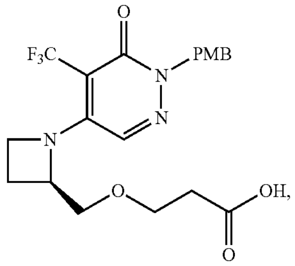
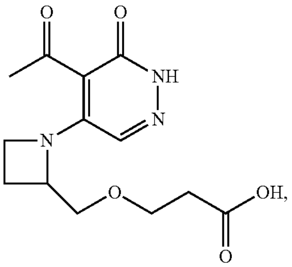

-continued
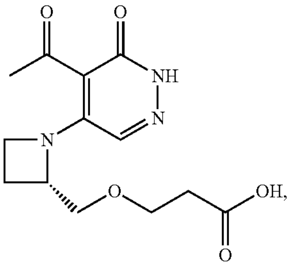
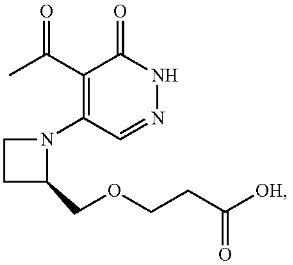
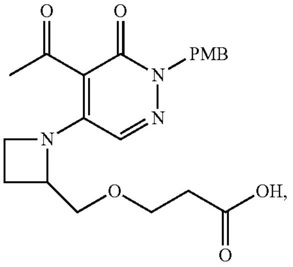
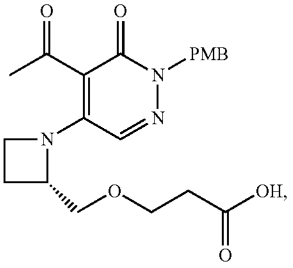
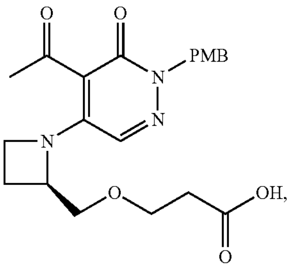
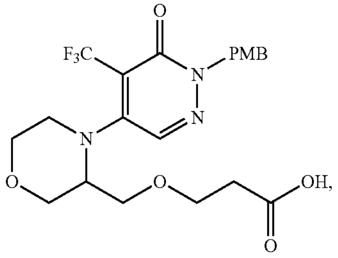
-continued
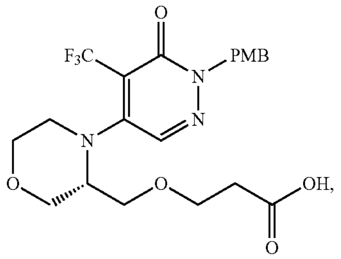
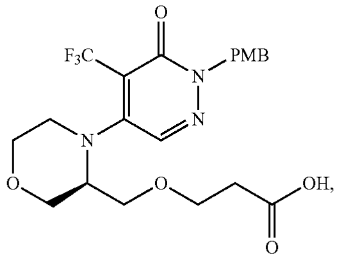
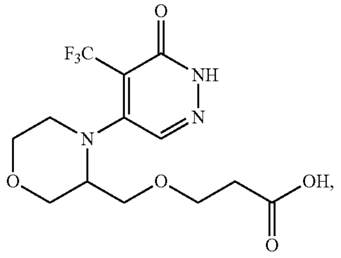
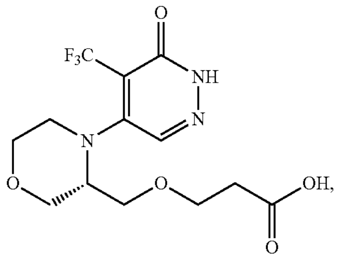
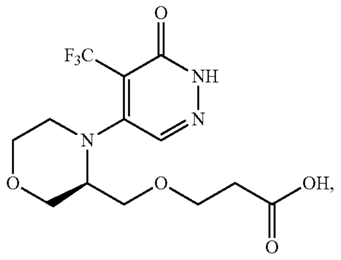

-continued
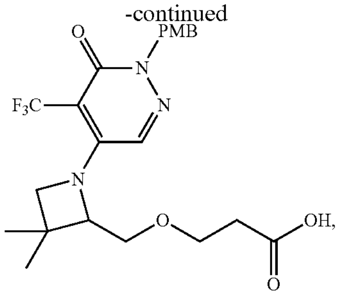
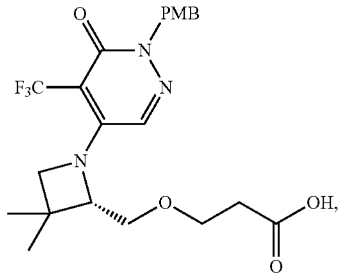
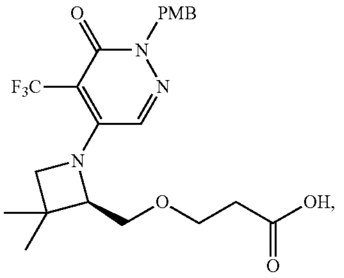
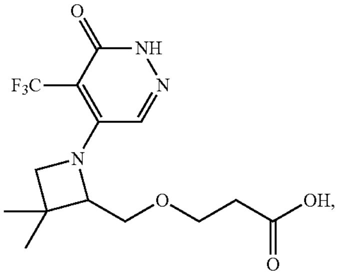
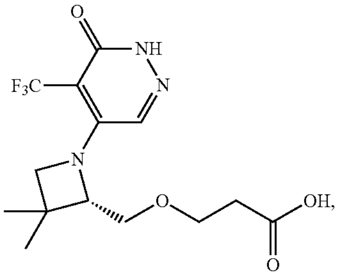
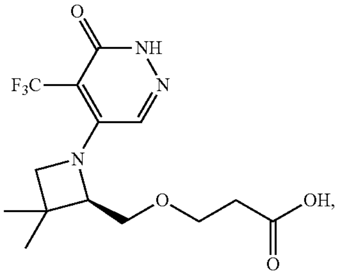
-continued
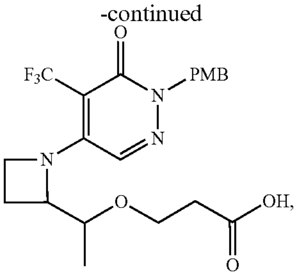
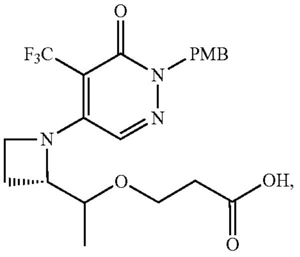
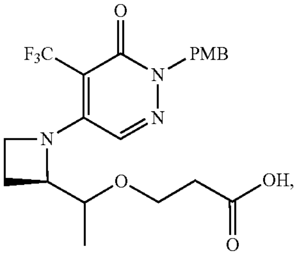
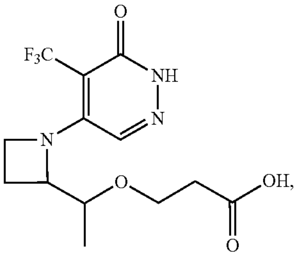
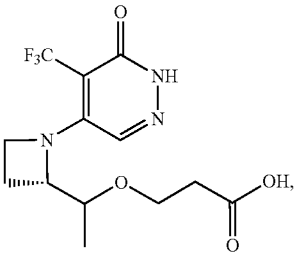
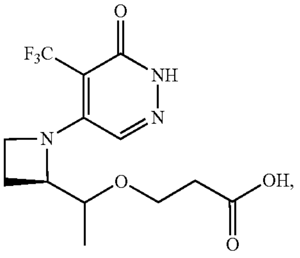

-continued
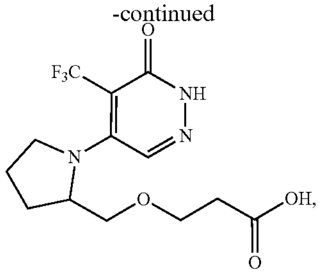
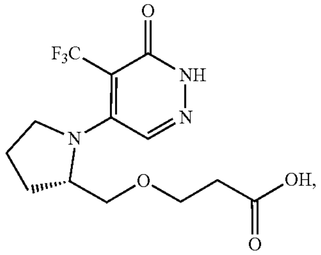
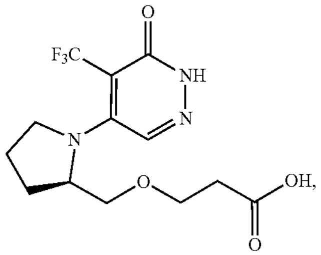
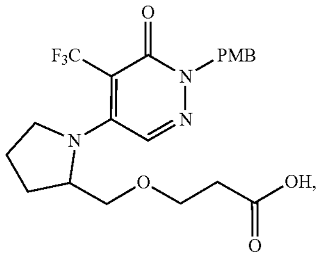
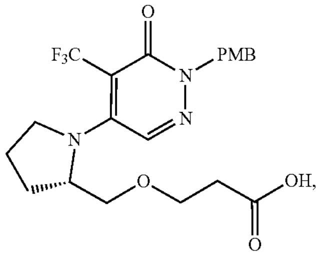
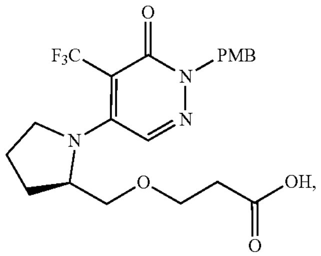
-continued
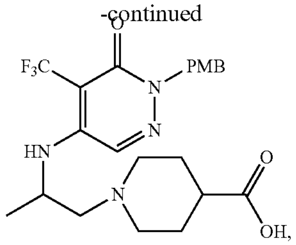
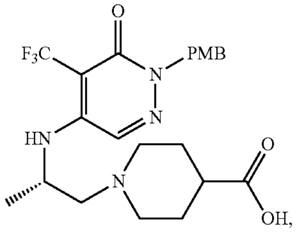
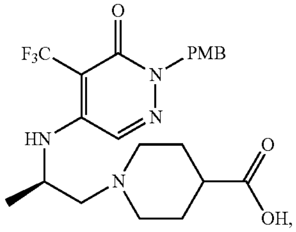
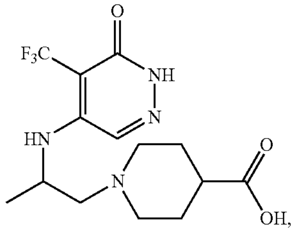
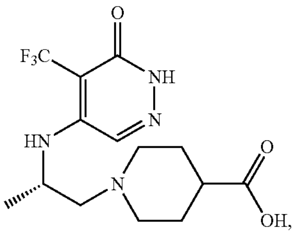
or
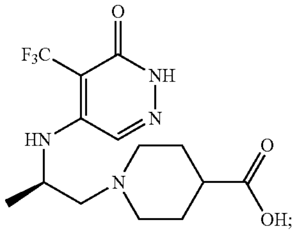
In some embodiments, the compound of formula (I-2) is selected from any one of the following formulas:

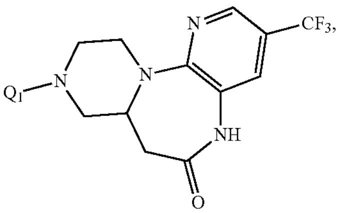
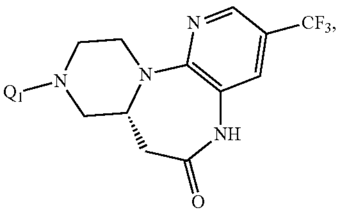
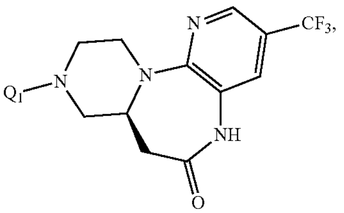
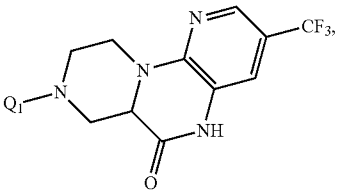
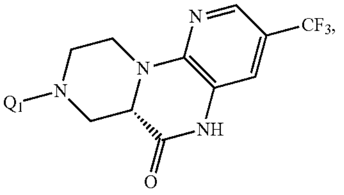
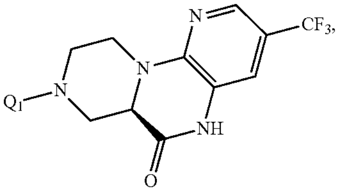
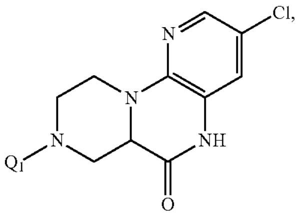
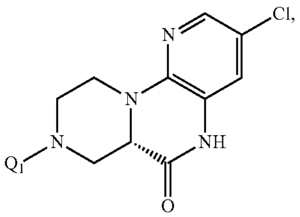
-continued
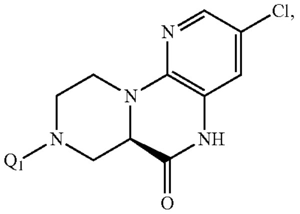
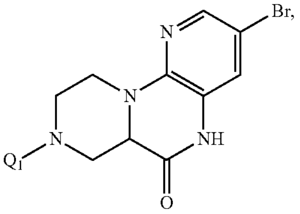
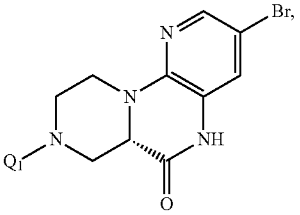
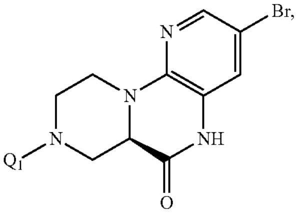
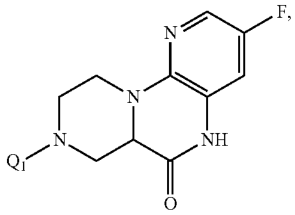
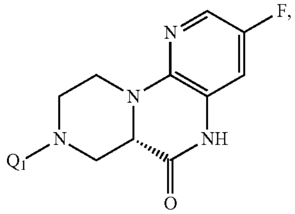
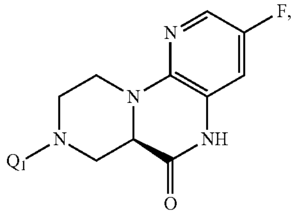
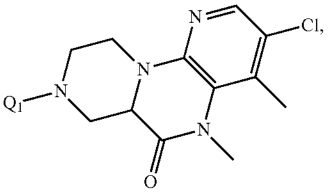

-continued
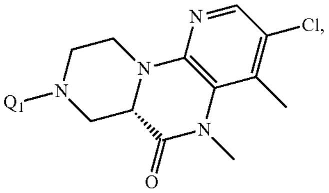
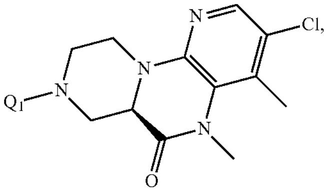
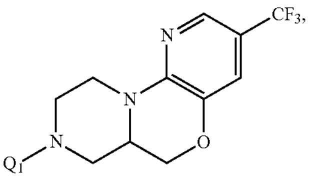
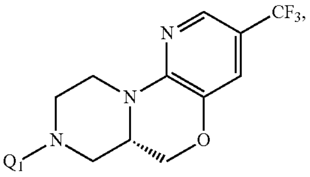
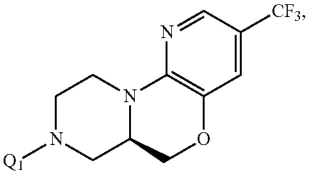
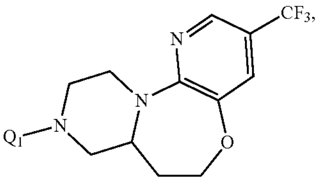
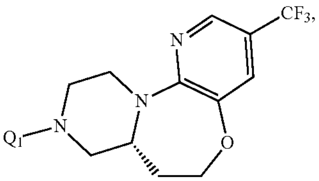
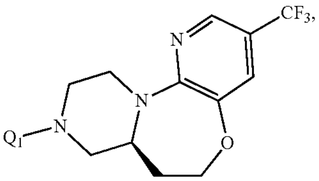
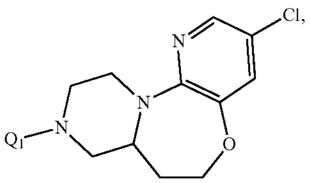
-continued
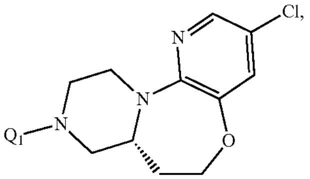
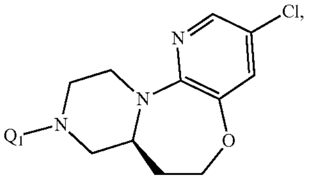
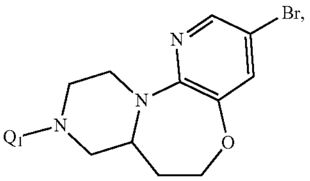
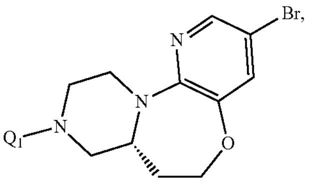
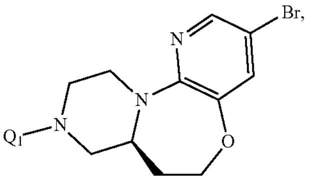
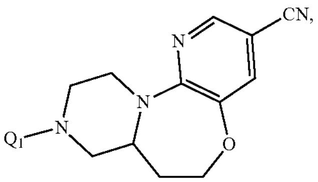
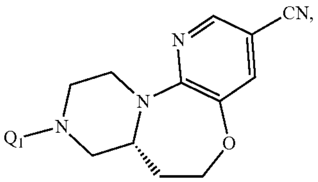
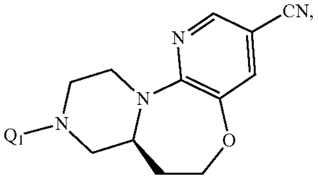
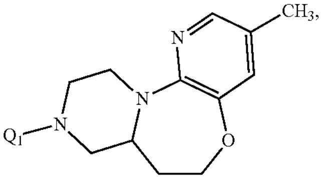

-continued
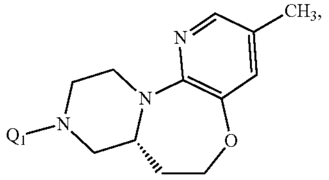
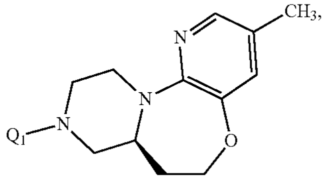
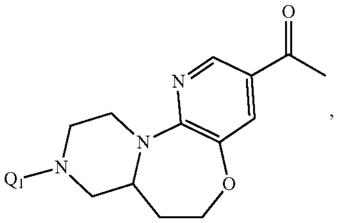
,
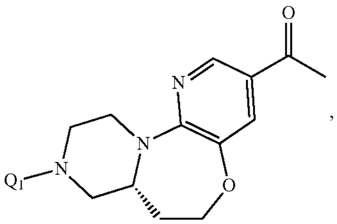
,
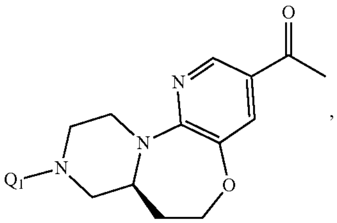
,
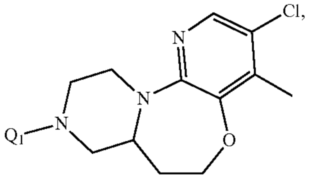
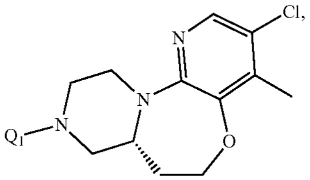
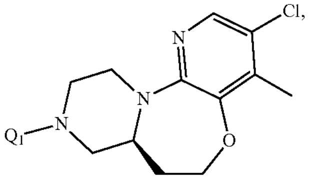
-continued
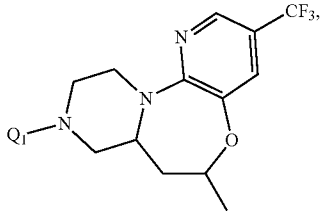
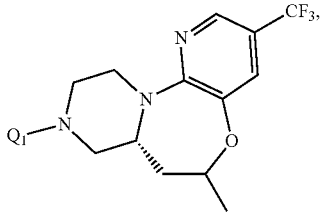
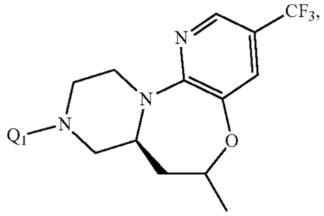
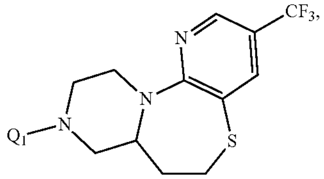
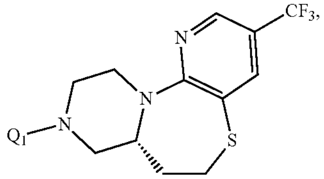
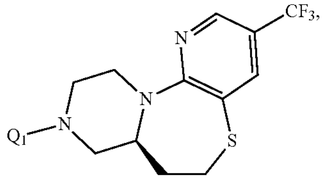
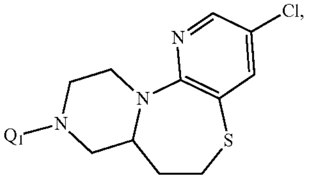
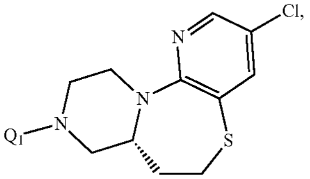
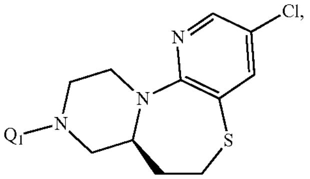

-continued
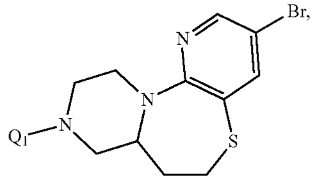
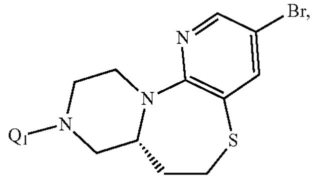
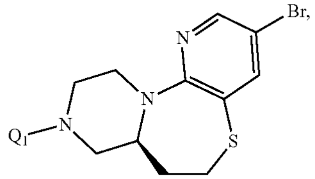
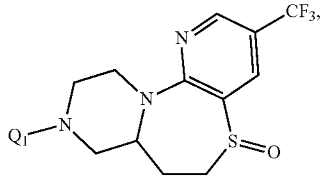
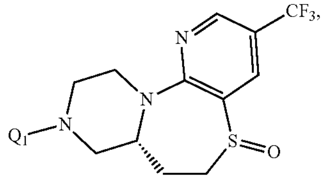
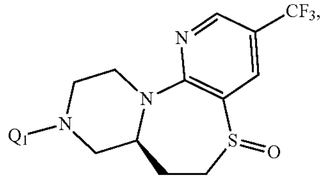
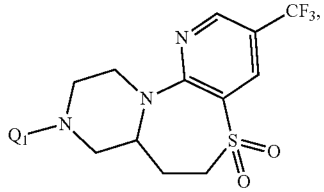
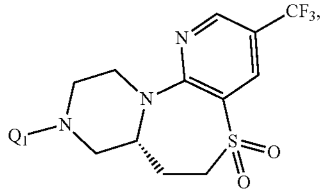
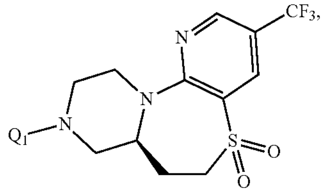
-continued
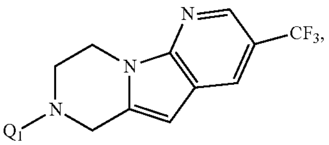
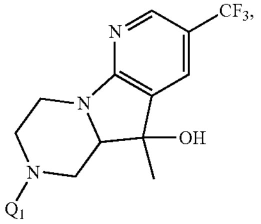
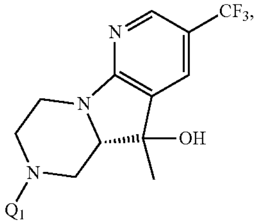
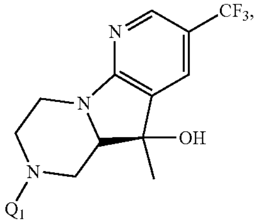
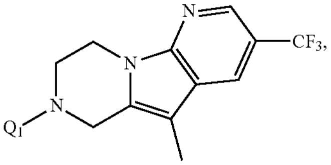
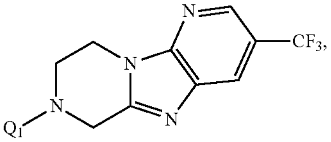
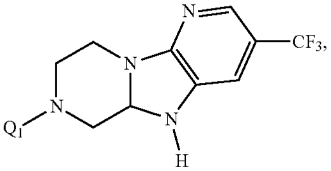
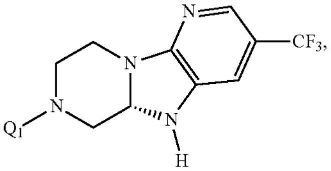
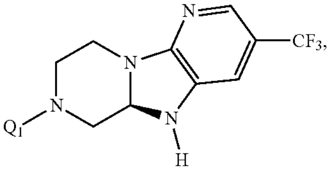

-continued
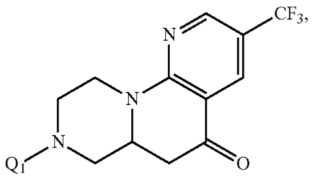
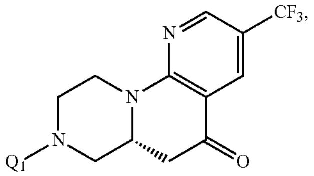
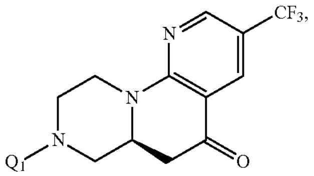
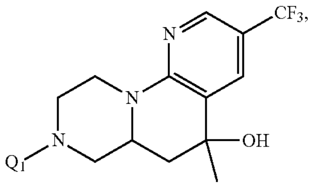
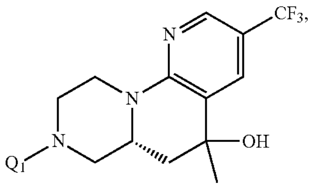
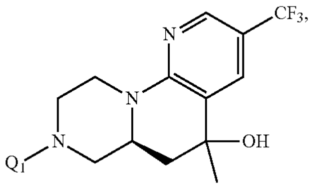
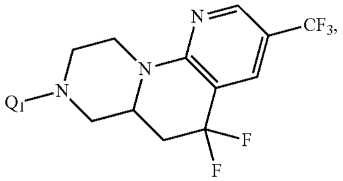
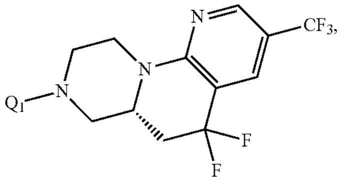
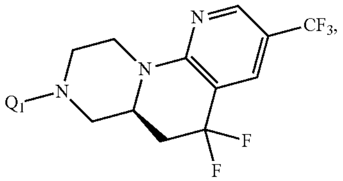
-continued
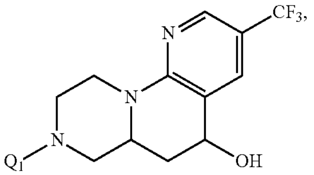
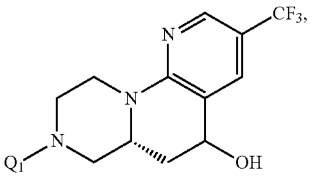
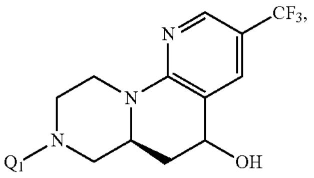
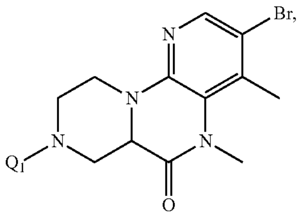
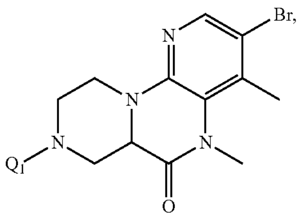
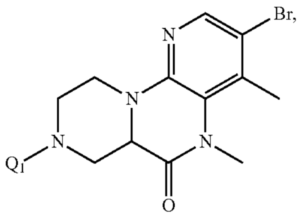
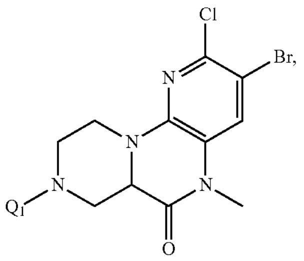
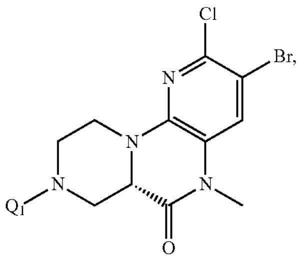

-continued
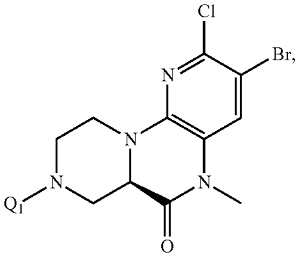
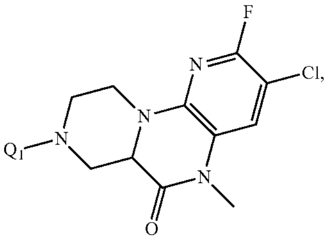
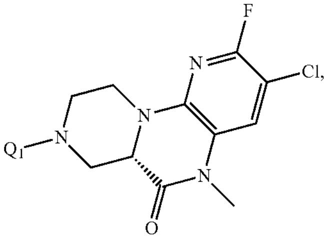
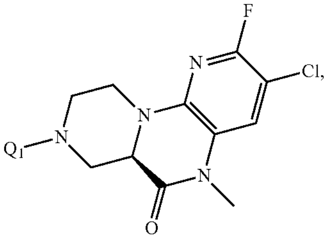
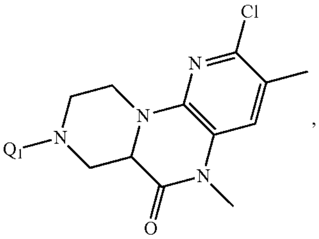
,
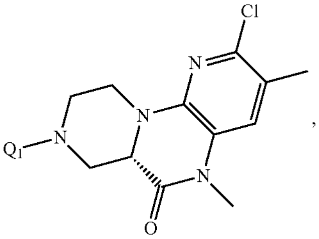
,
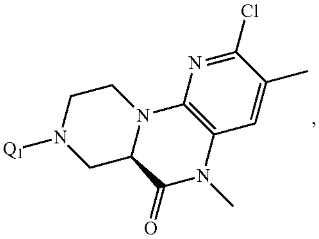
,
-continued
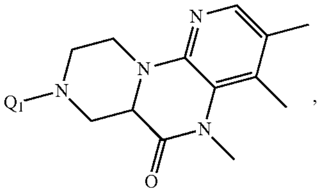
,
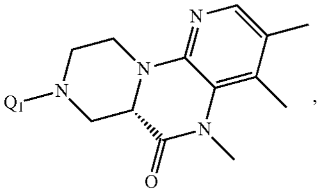
,
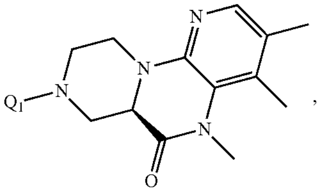
,
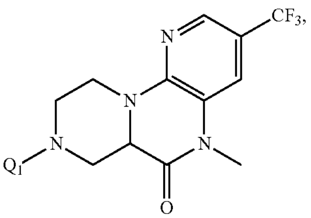
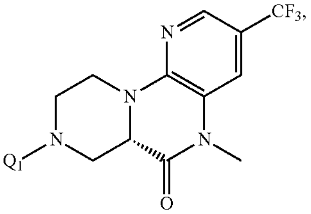
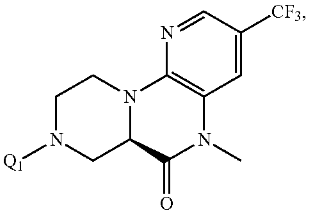
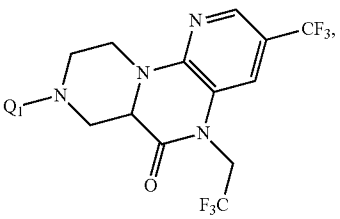
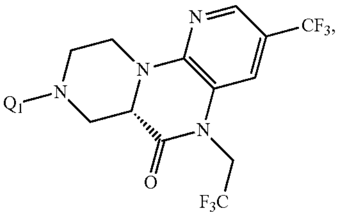

-continued
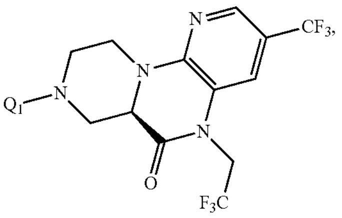
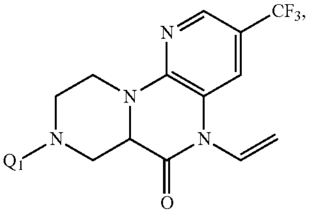
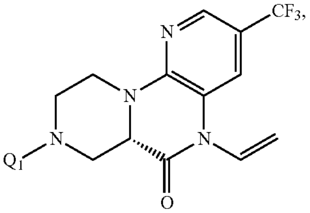
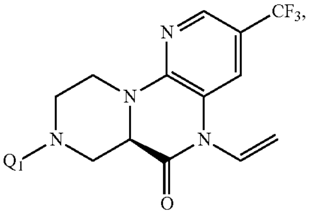
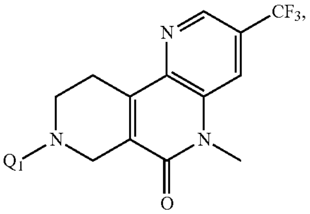
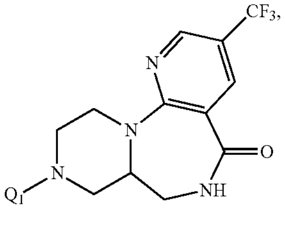
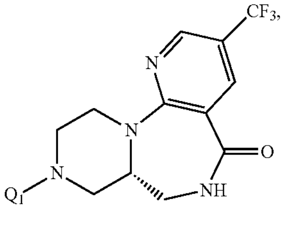
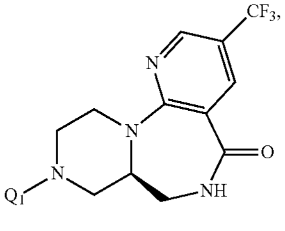
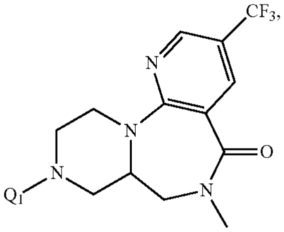
-continued
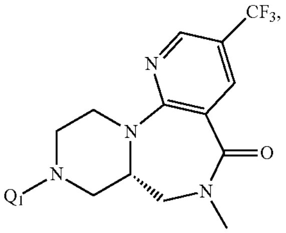
or
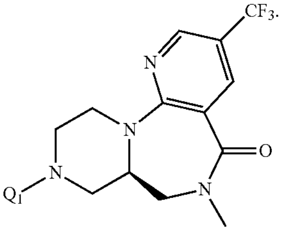
In some embodiments, the compound of formula (P-1) is selected from any one of the following formulas:
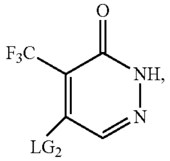
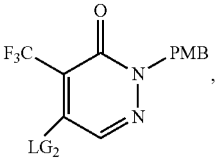
,
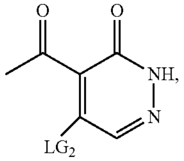
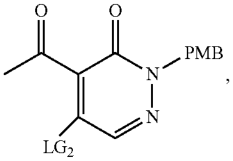
,
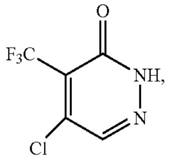
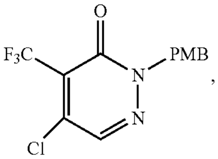
,
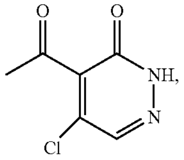
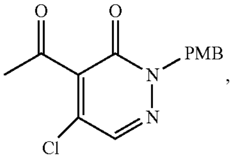
,
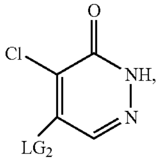
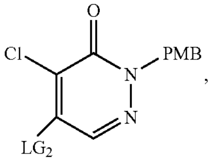
,
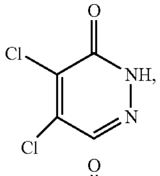
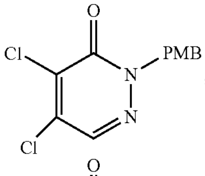
,
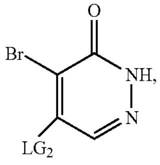
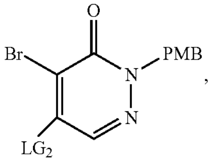
, -continued
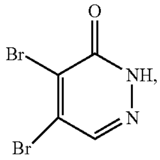
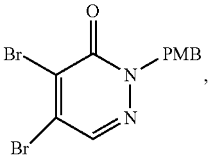
,
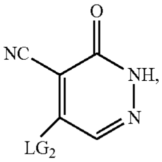
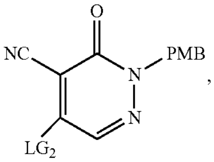
,
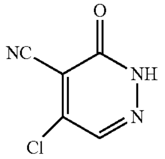
or
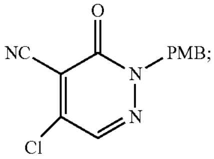
in some embodiments, the compound of formula (P-1) is selected from
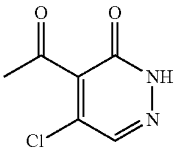
or
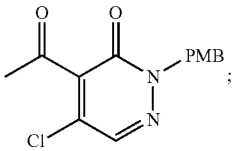
;
In some embodiments, the compound of formula (P-2) is selected from any one of the following formulas:
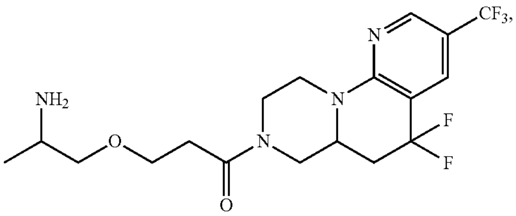
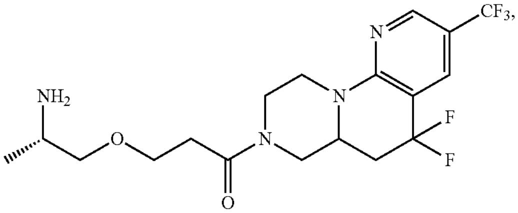
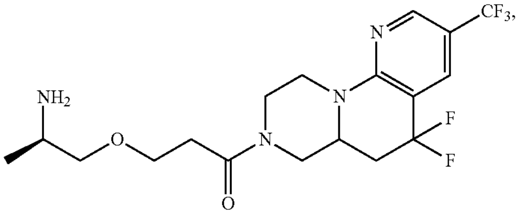
-continued
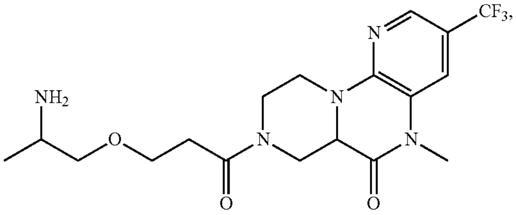
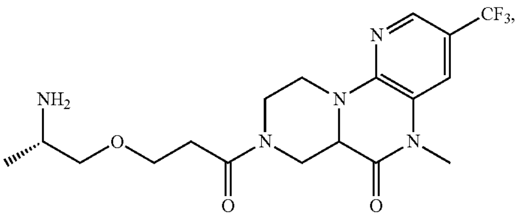
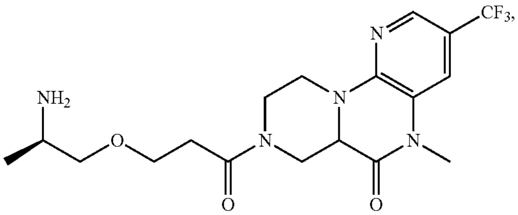
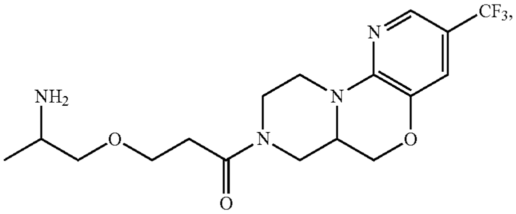
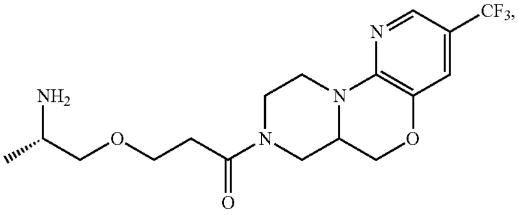
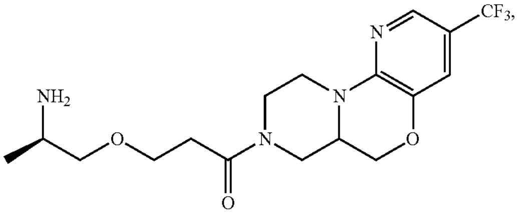
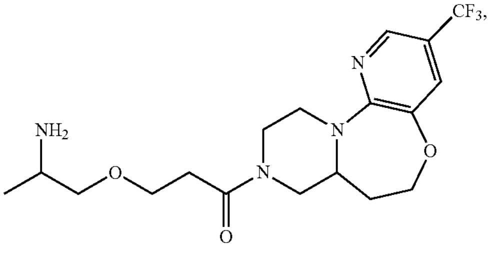

-continued
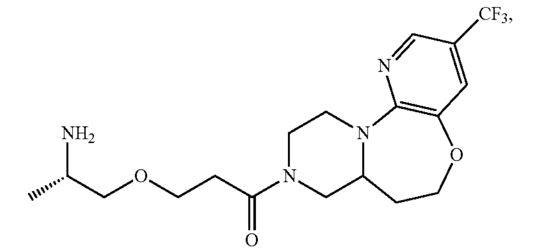
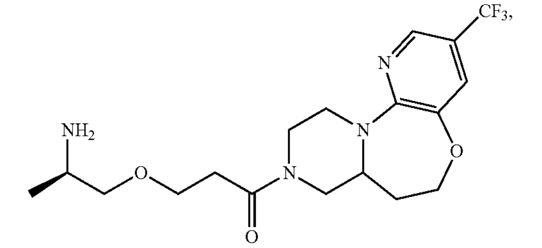
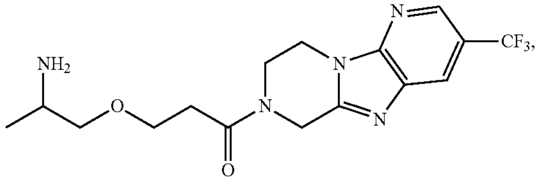
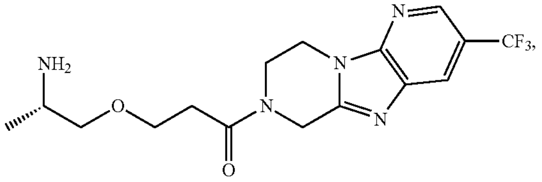
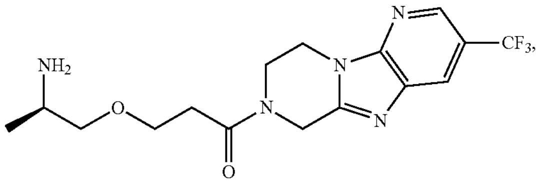
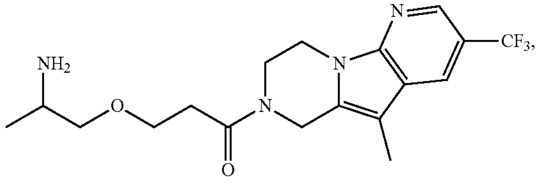
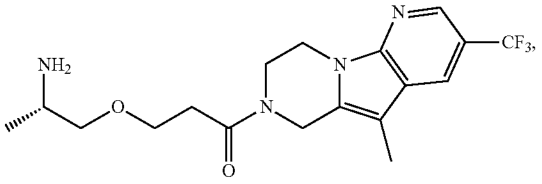
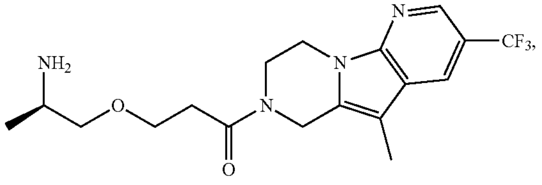
-continued
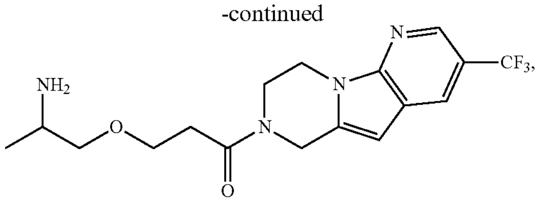
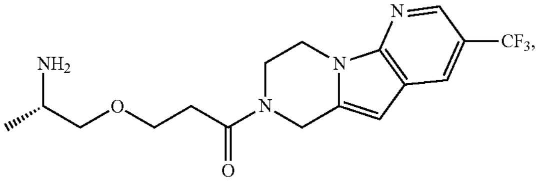
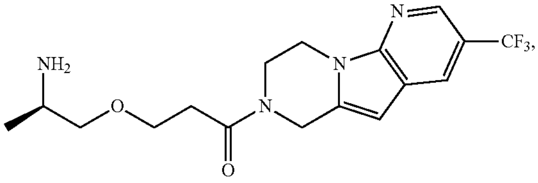
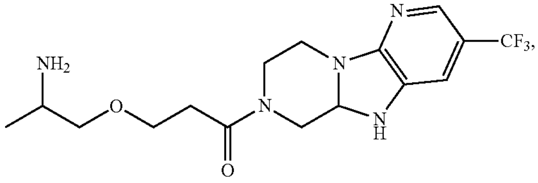
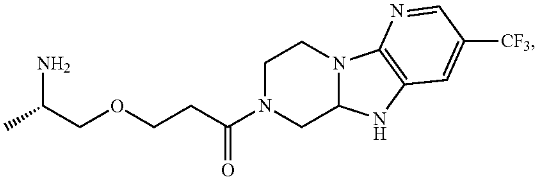
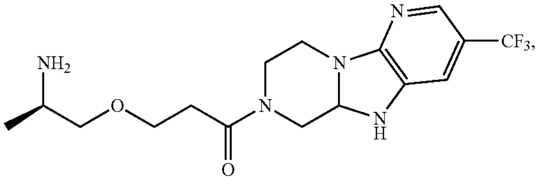
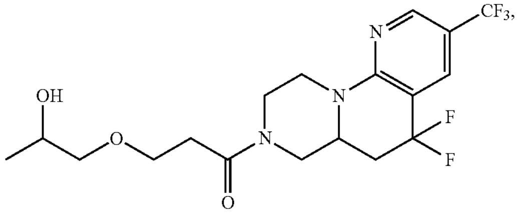
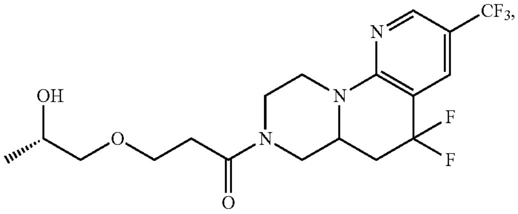
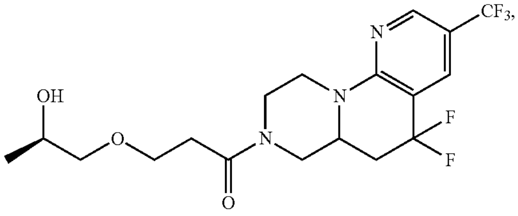

-continued
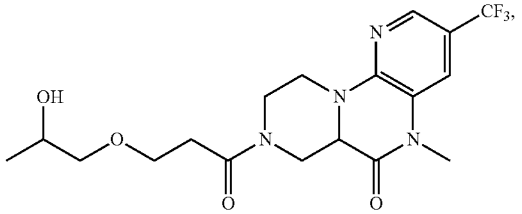
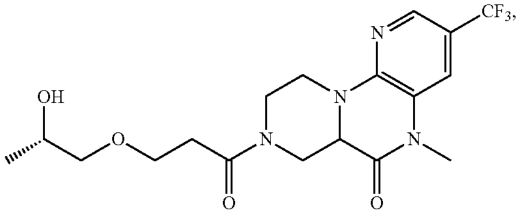
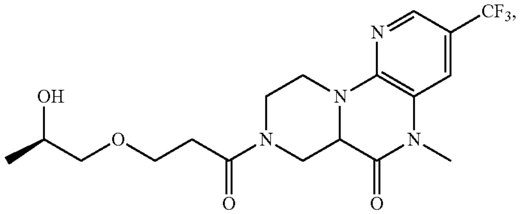
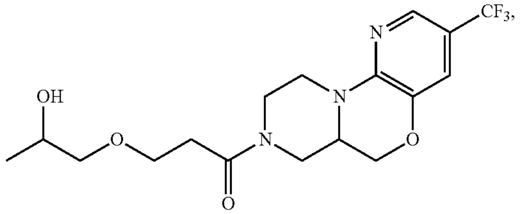
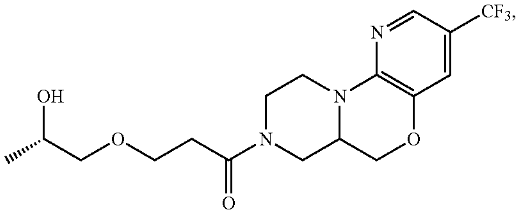
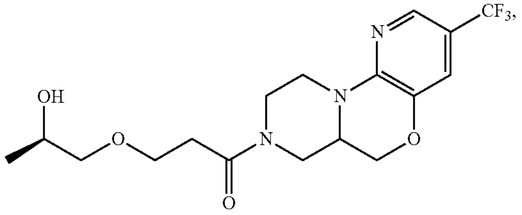
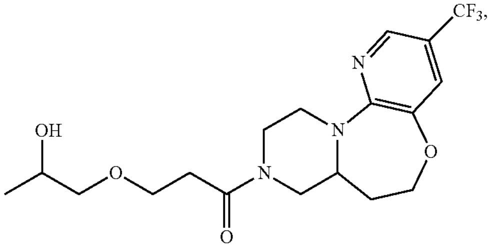
-continued
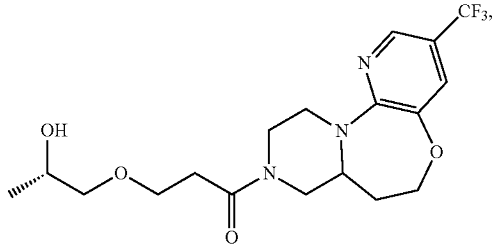
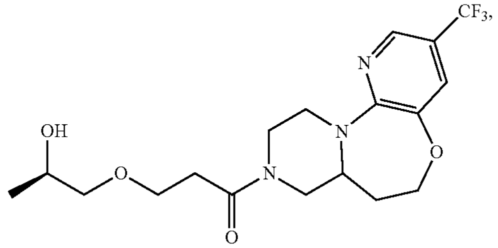
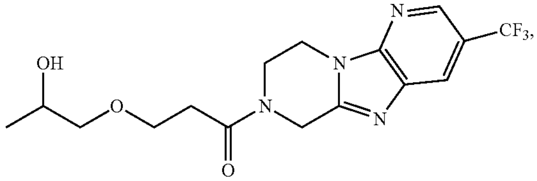
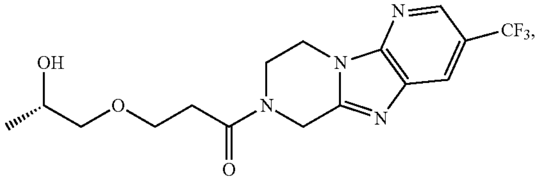
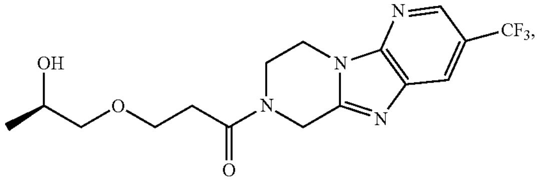
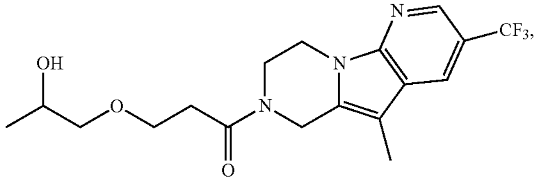
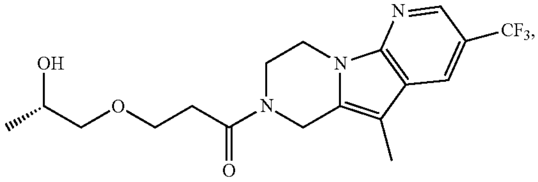
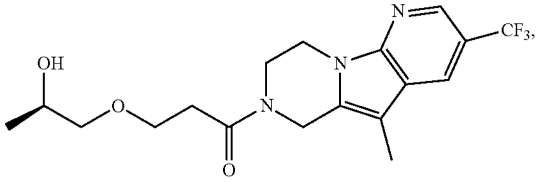

-continued
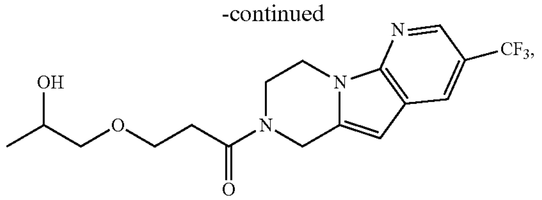
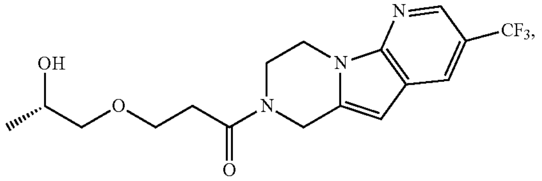
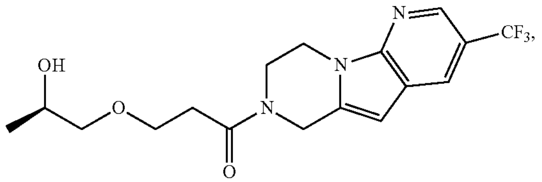
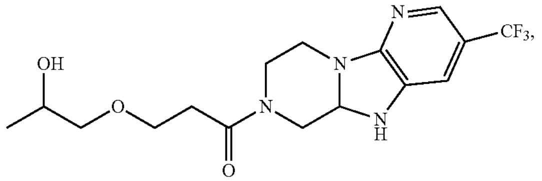
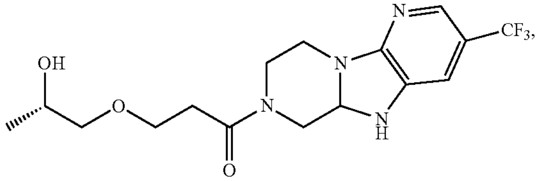
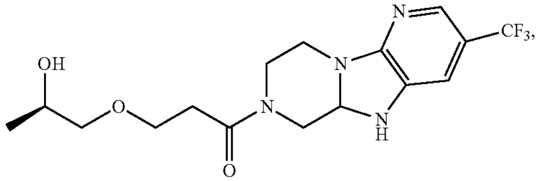
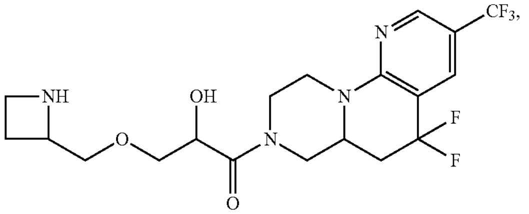
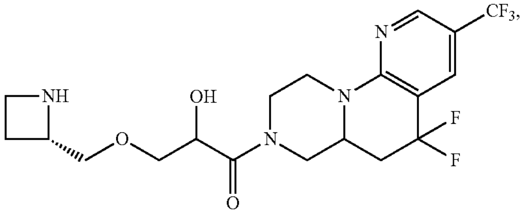
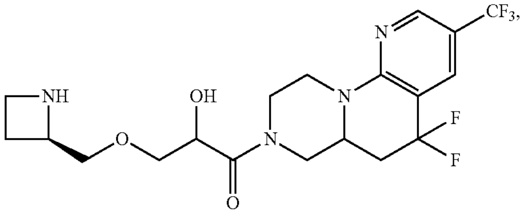
-continued
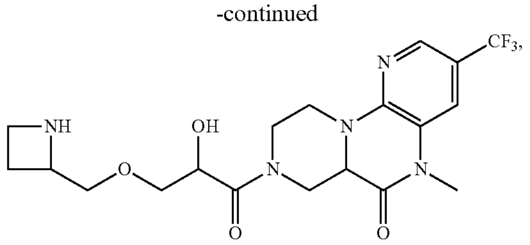
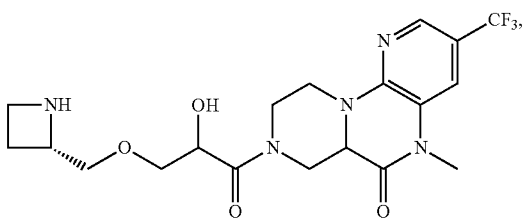
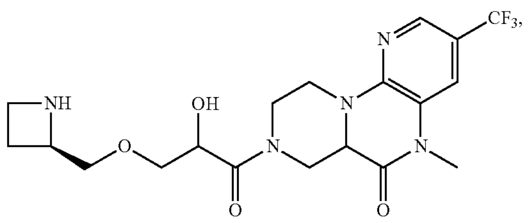
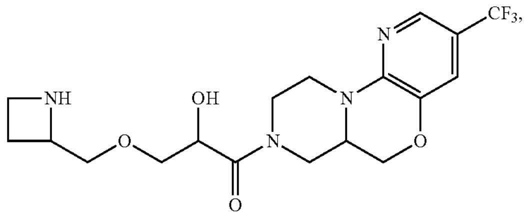
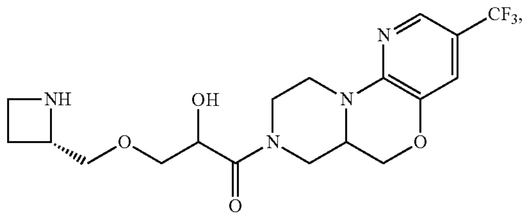
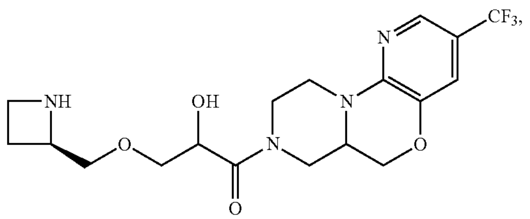
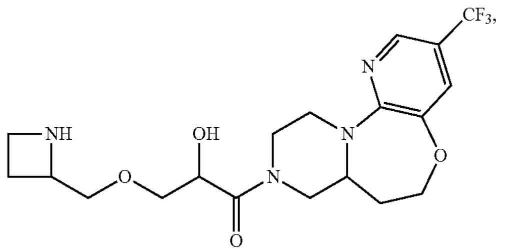

-continued
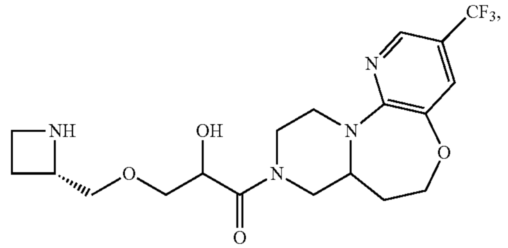
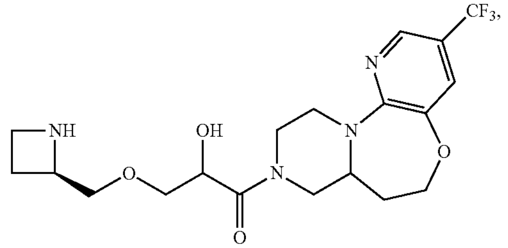
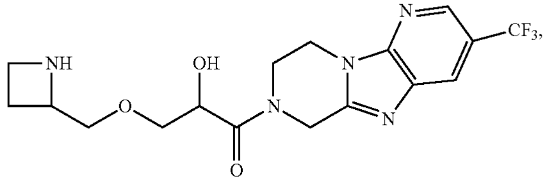
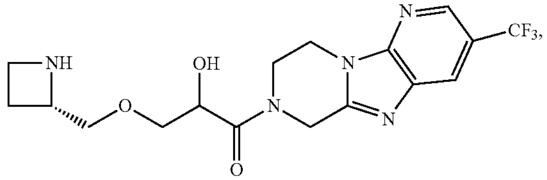
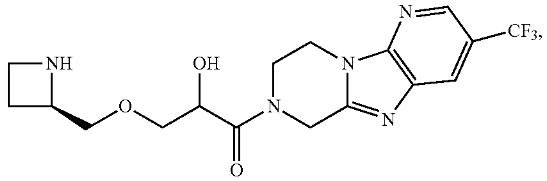
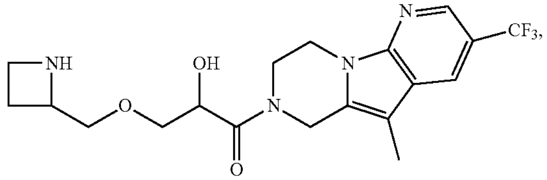
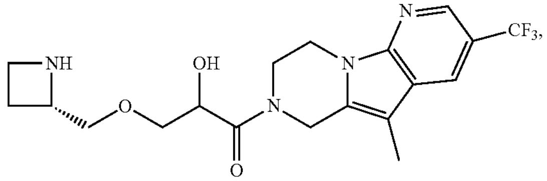
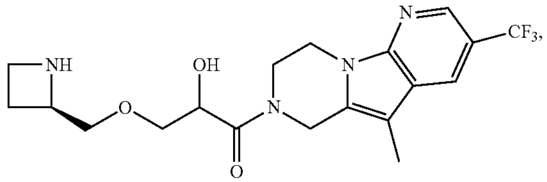
-continued
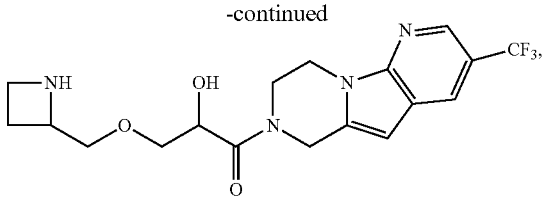
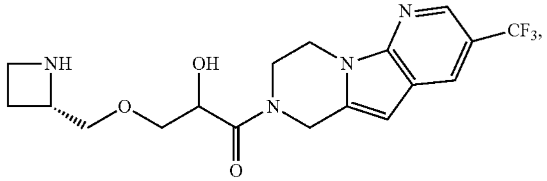
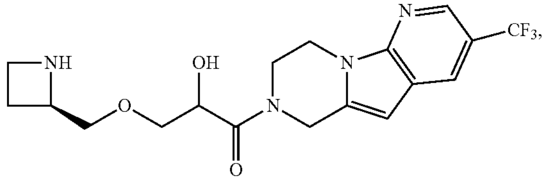
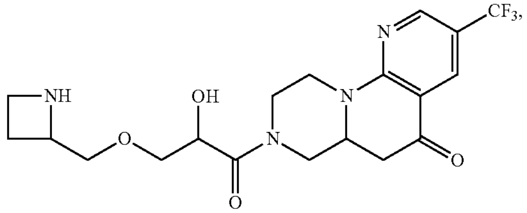
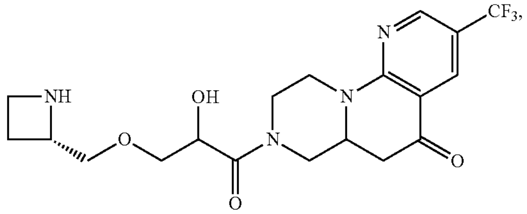
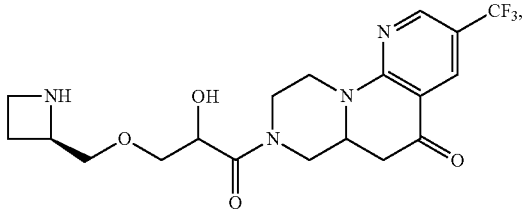
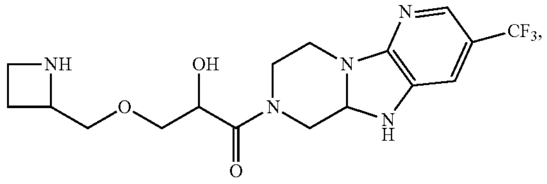
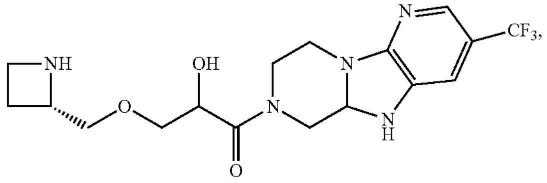
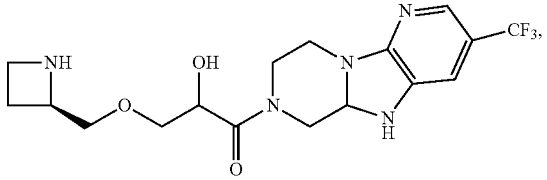

-continued

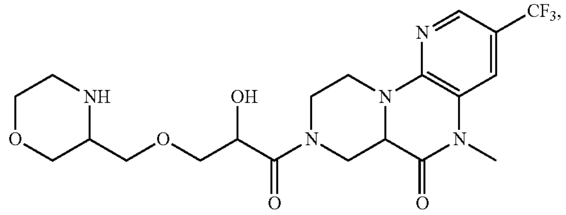

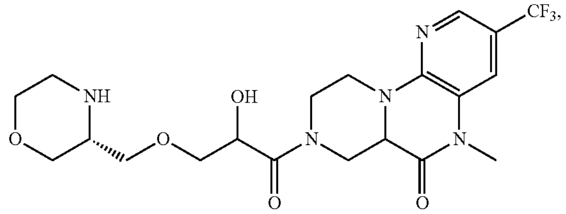

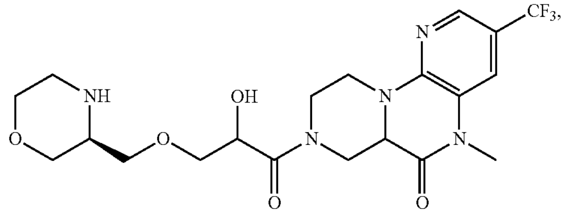

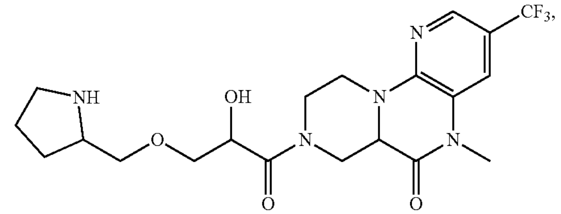

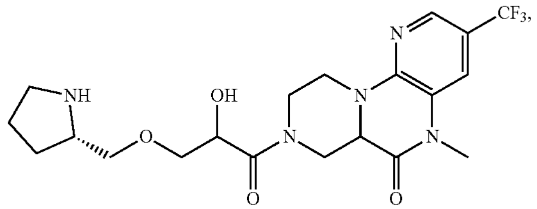

or

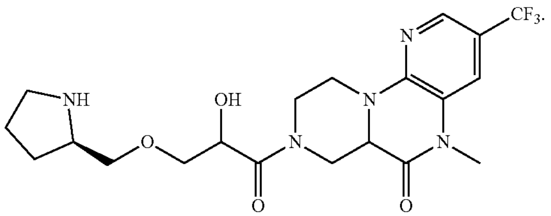

[96]. The process according to [95], wherein, the compound of formula (I-1) is prepared by the following Step C or Step D:

Step C:

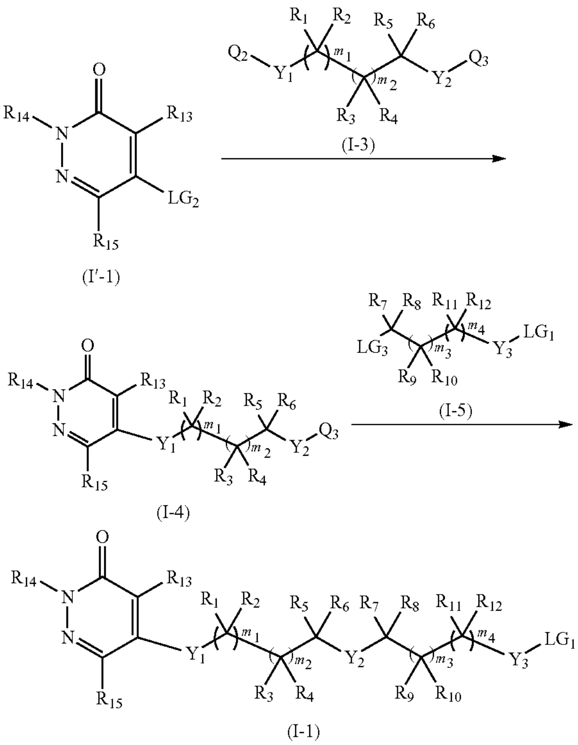

(a) Reacting the compound of formula (I'-1) with the compound of formula (I-3) by a substitution reaction or by a coupling reaction to yield the compound of formula (I-4);

Said $Q_3$ in the compound of formula (I-3) and compound of formula (I-4) is selected from —H;

(b) Reacting the compound of formula (I-4) with the compound of formula (I-5) by a substitution reaction or by a coupling reaction to yield the compound of formula (I-1);

Said $LG_3$ in the compound of formula (I-5) is a leaving group or a group that can be converted to the leaving group; in some embodiments, the leaving group is selected from halogen (such as —Cl, —Br or —I), $—OS(=O)_2CH_3$ or

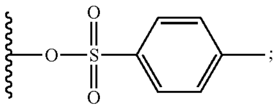 [SMILES: *OS(=O)(=O)c1ccc(C)cc1];

in some embodiments, the group that can be converted to the leaving group is selected from —OH;

In some embodiments, the compound of formula (I-3) is selected from any one of the following formulas:

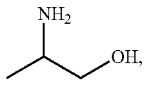 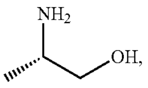 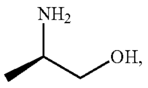

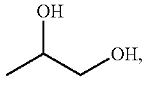 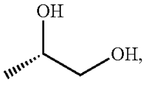 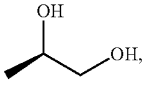

-continued
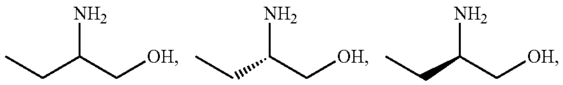
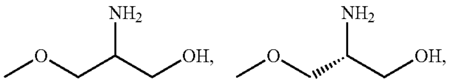
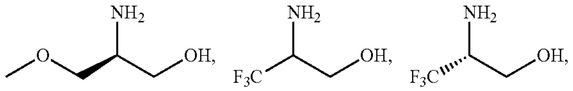
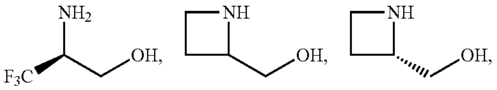
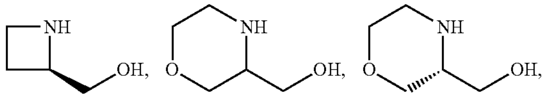
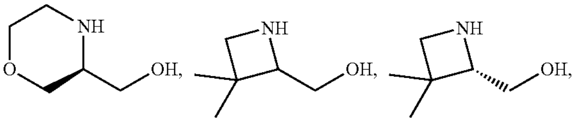
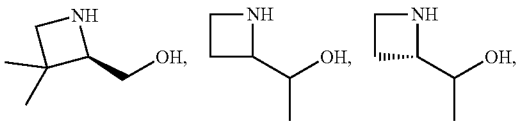
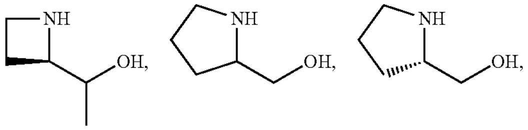
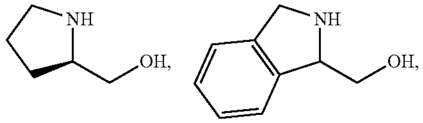
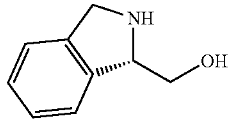 or 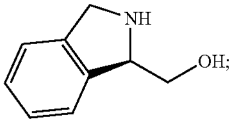
In some embodiments, the compound of formula (I-4) is selected from any one of the following formulas:
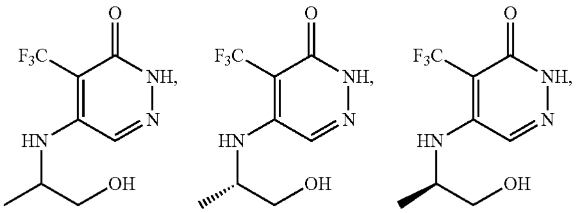
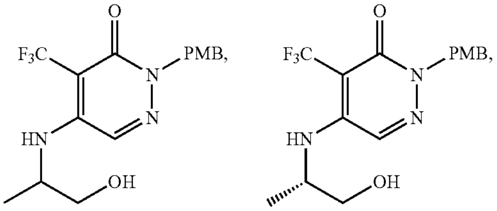
-continued
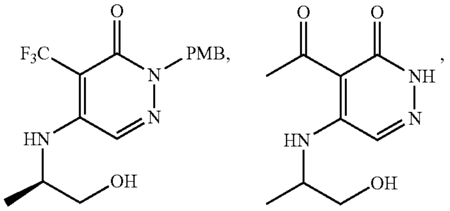
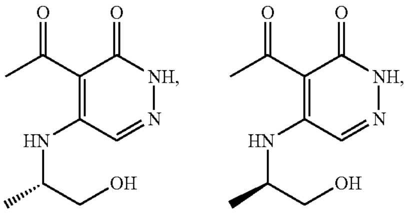
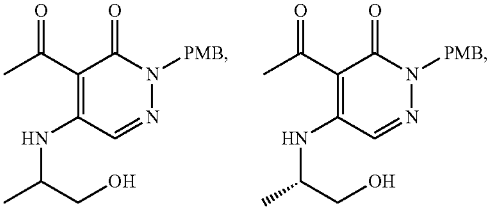
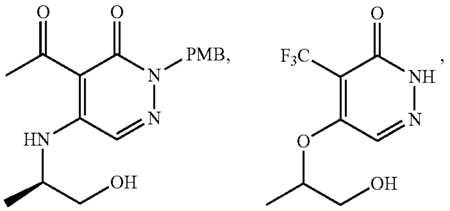
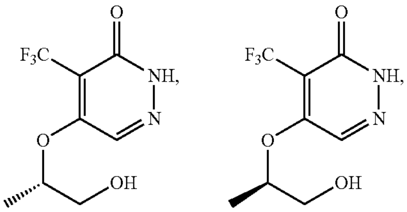
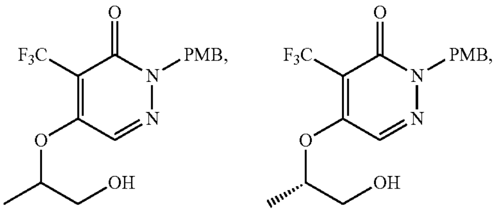
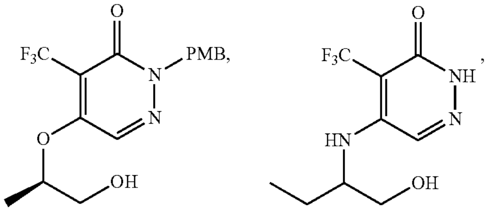
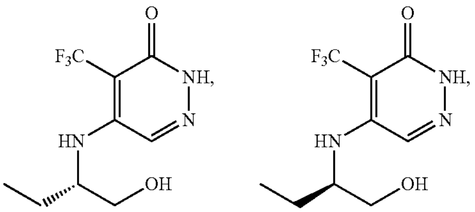

-continued
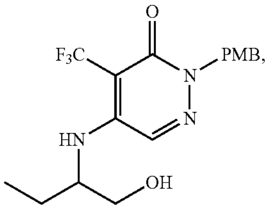
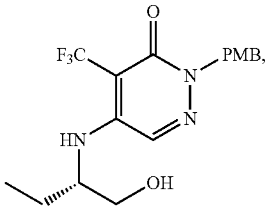
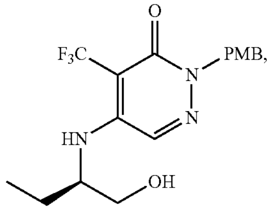
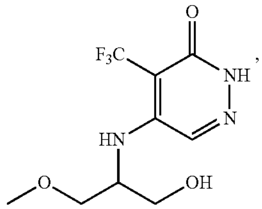
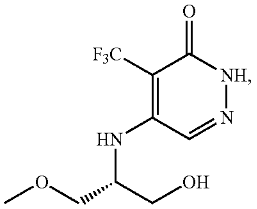
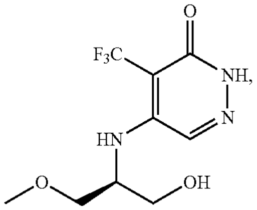
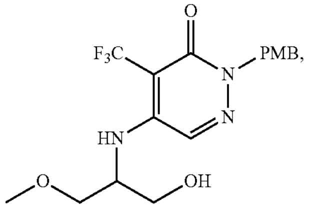
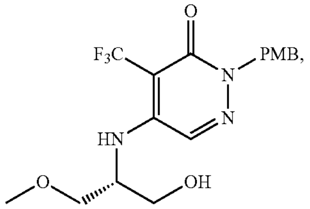
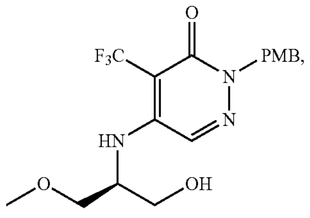
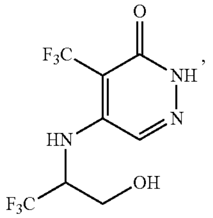
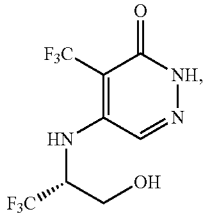
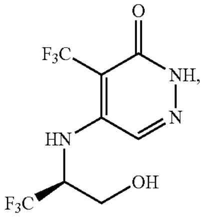
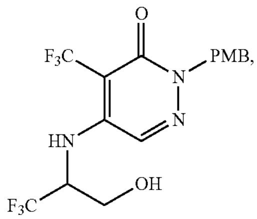
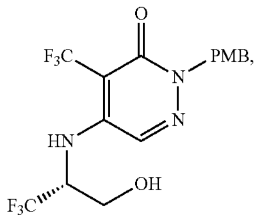
-continued
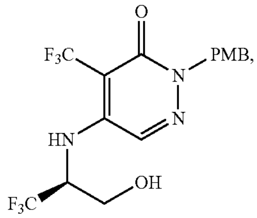
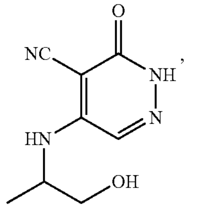
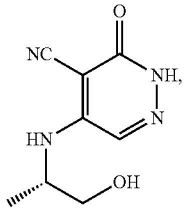
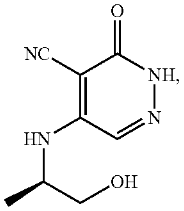
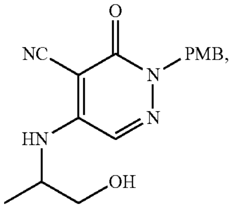
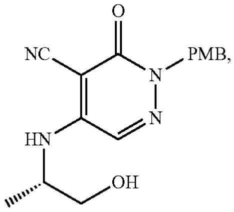
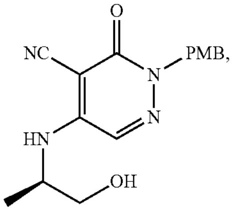
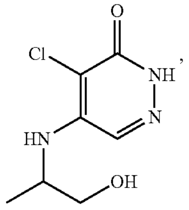
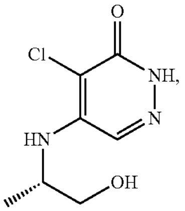
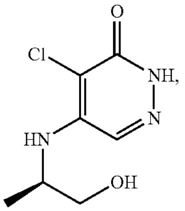
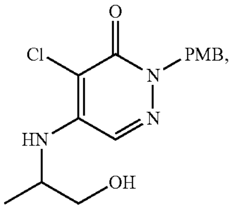
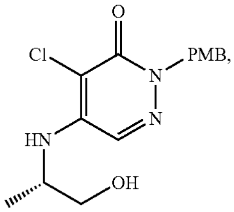
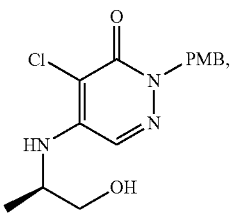
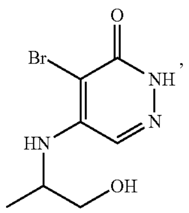
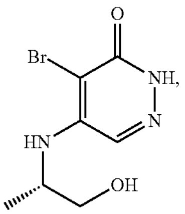
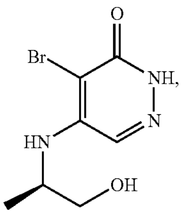

-continued
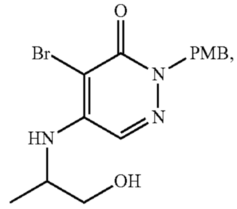
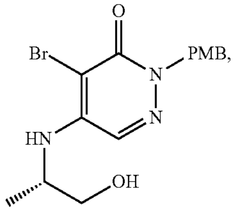
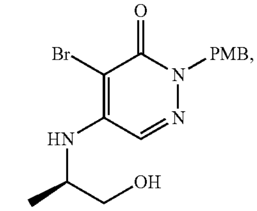
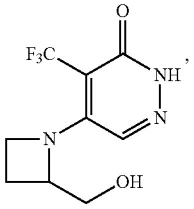
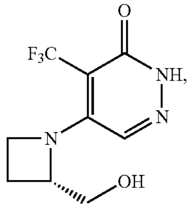
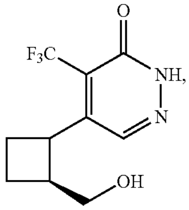
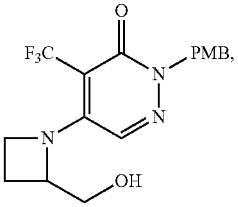
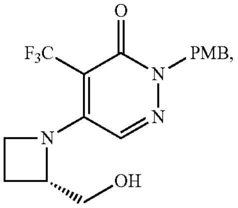
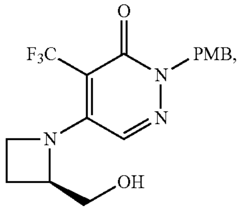
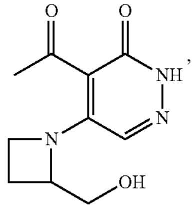
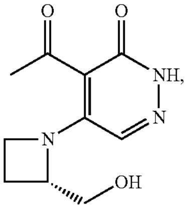
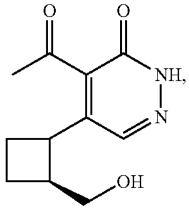
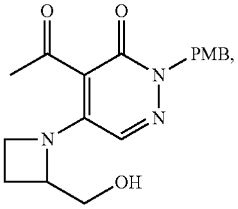
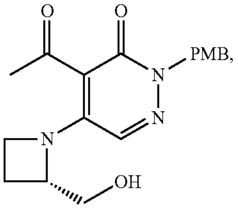
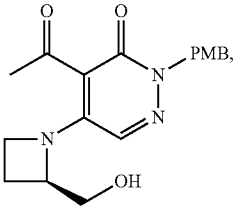
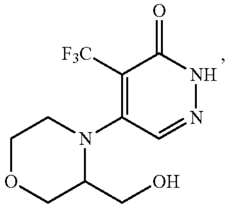
-continued
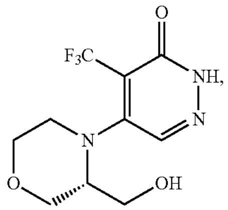
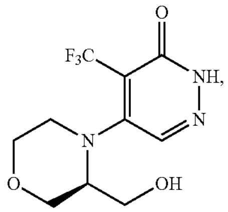
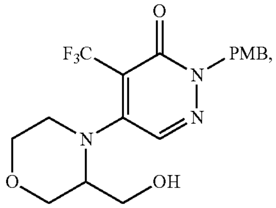
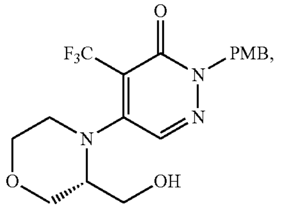
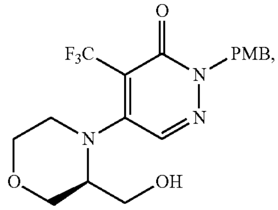
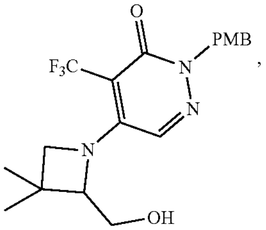
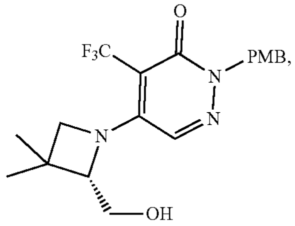
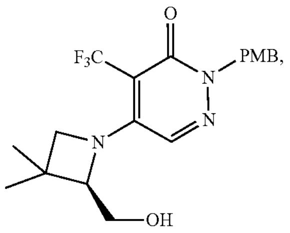
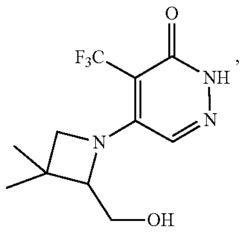
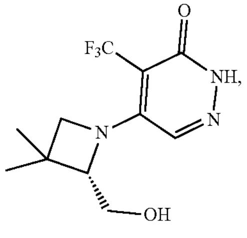
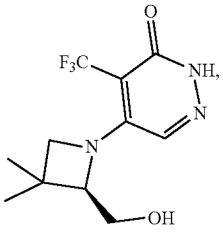
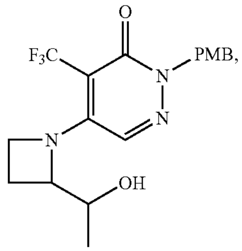
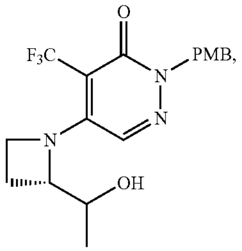

-continued

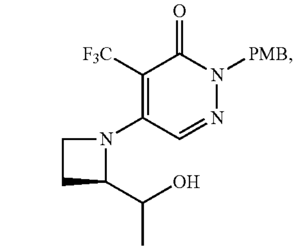
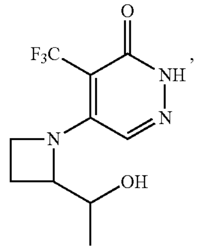
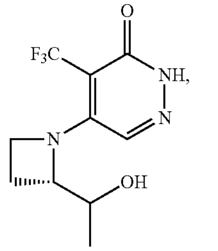
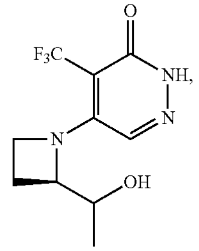
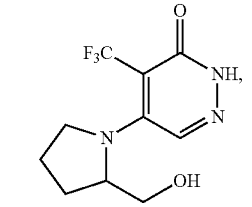
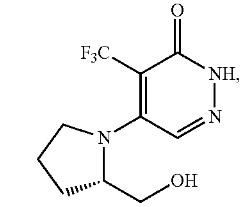
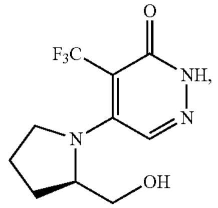
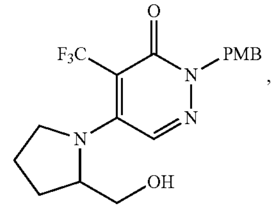
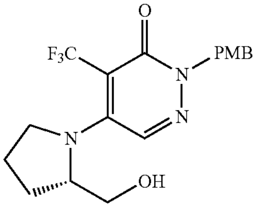
or
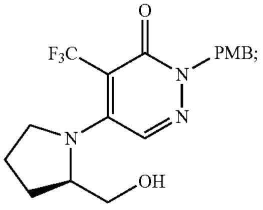

In some embodiments, the compound of formula (I-5) is selected from any one of the following formulas:

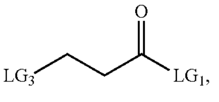
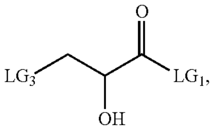
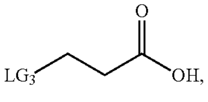
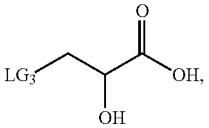
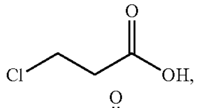
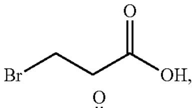
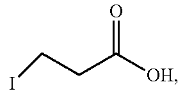
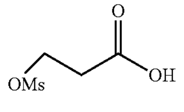
or -continued

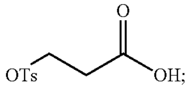

Step D:

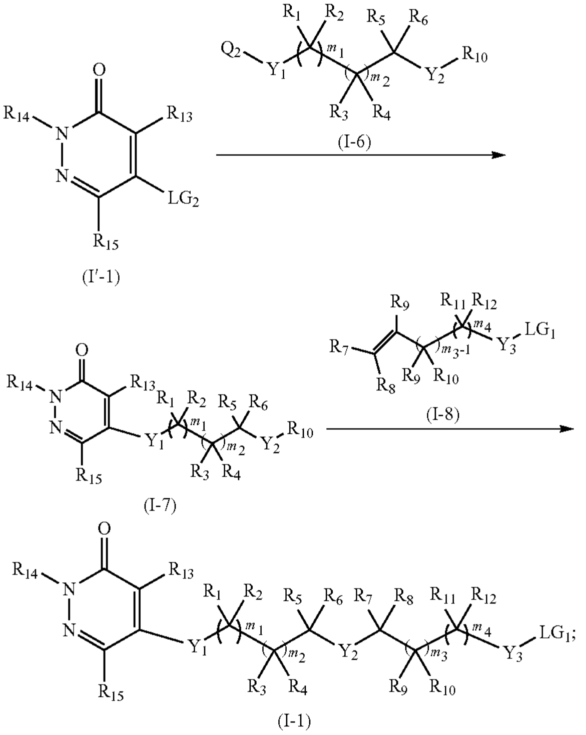

(a) Reacting the compound of formula (I'-1) with the compound of formula (I-6) by a substitution reaction or by a coupling reaction to yield the compound of formula (I-7);

(b) reacting the compound of formula (I-7) with the compound of formula (I-8) by an addition reaction to yield the compound of formula (I-I);

In some embodiments, the compound of formula (I-6) is selected from any one of the following formulas:

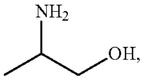
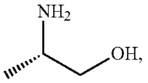
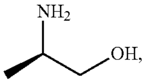
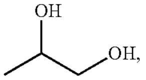
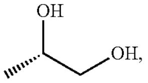
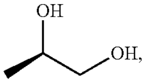
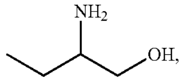
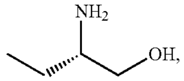
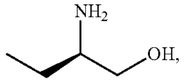
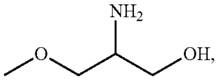
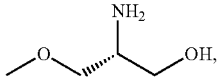
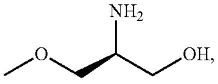

-continued
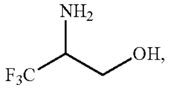
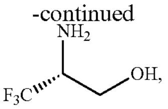
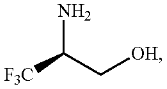
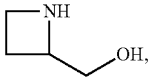
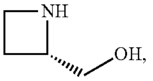
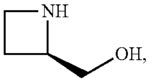
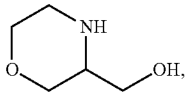
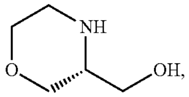
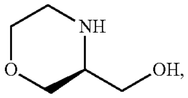
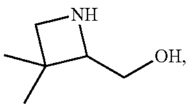
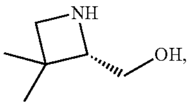
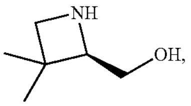
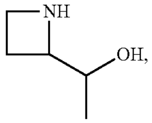
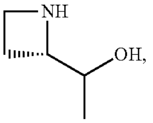
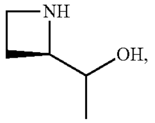
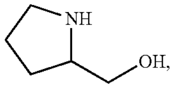
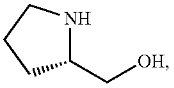
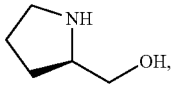
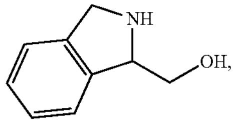
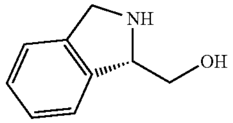
or
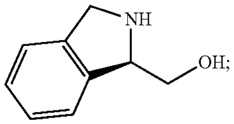
In some embodiments, the compound of formula (I-7) is selected from any one of the following formulas:
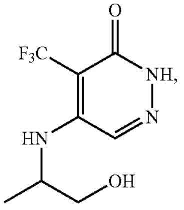
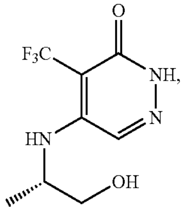
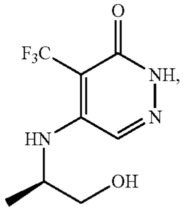
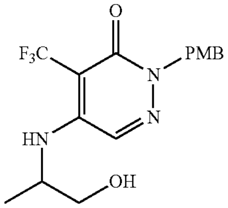
,
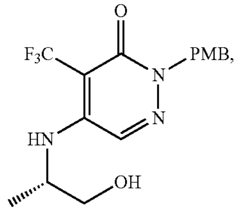
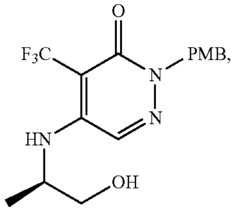
-continued
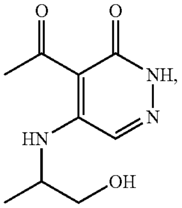
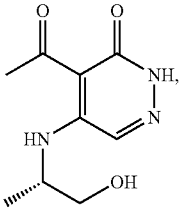
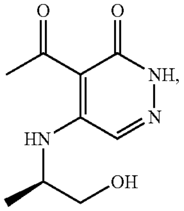
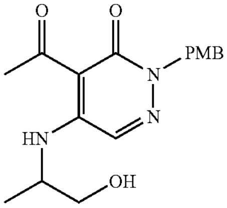
,
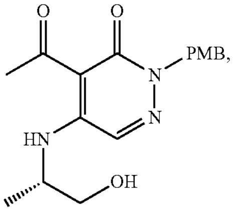
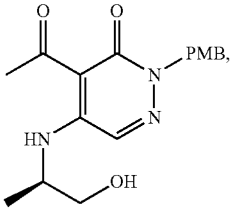
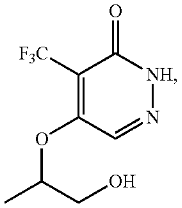
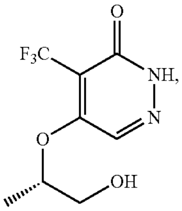
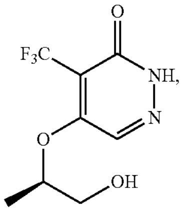
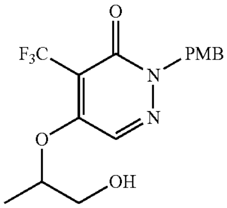
,
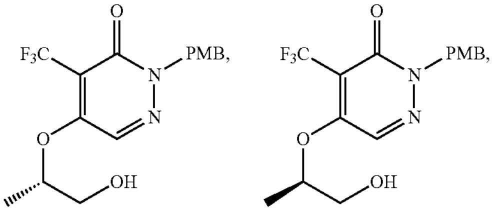
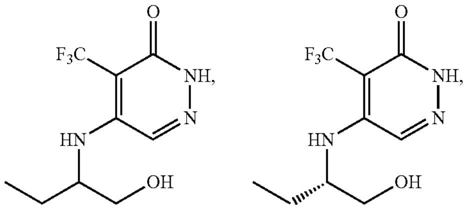
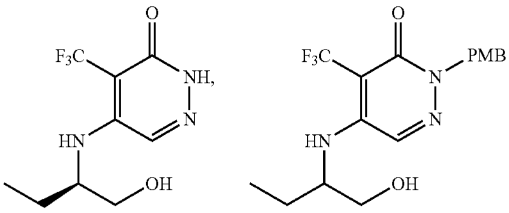
, -continued
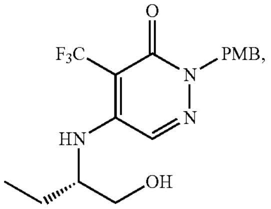
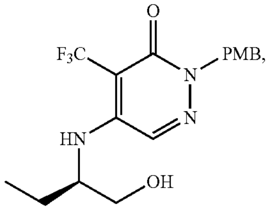
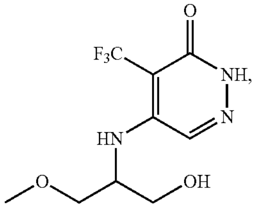
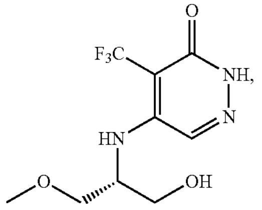
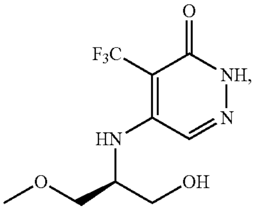
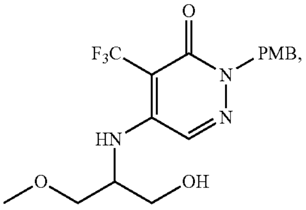
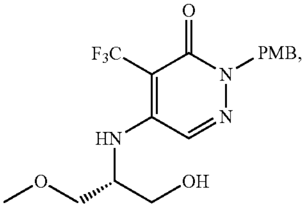
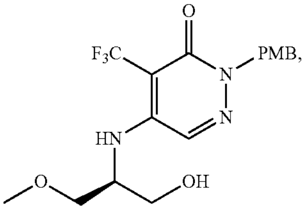
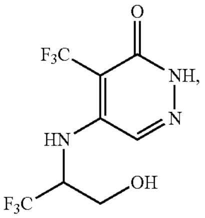
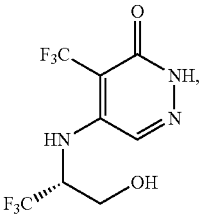
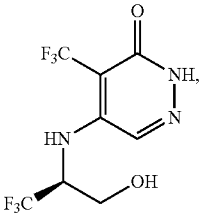
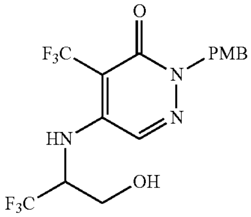
,
-continued
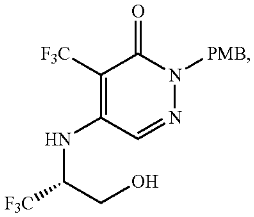
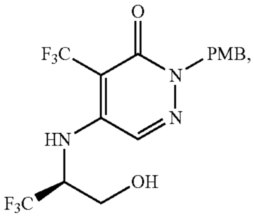
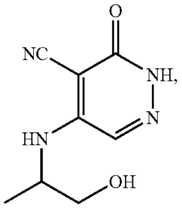
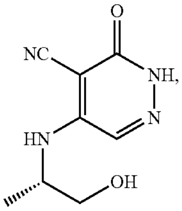
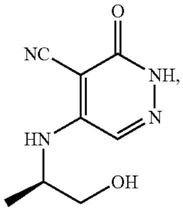
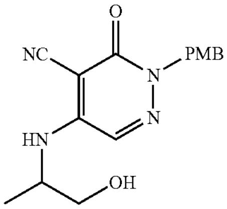
,
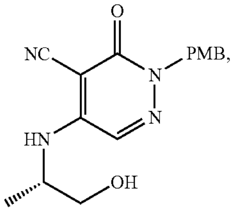
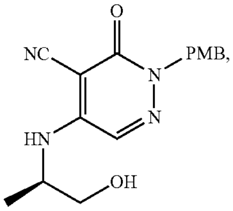
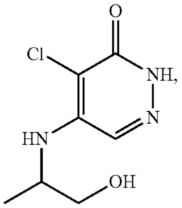
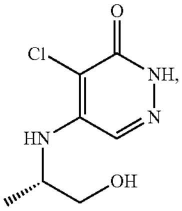
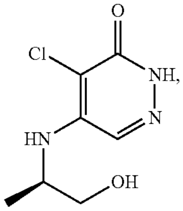
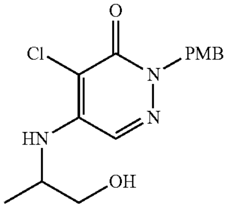
,
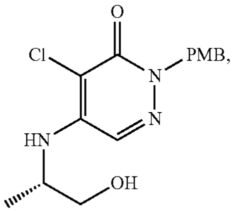
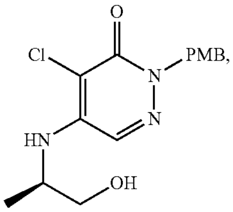
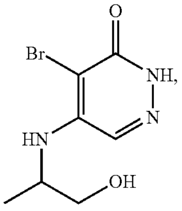
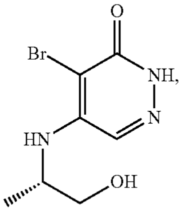

-continued
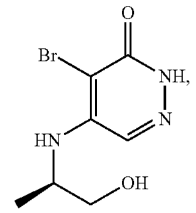
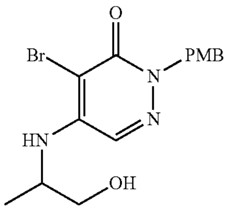
,
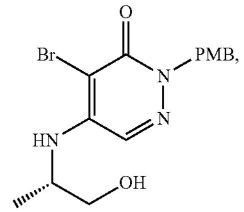
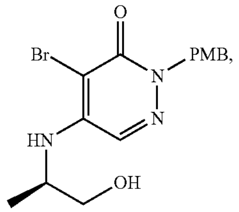
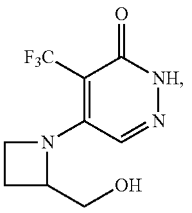
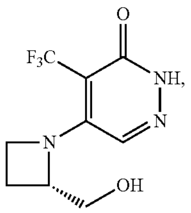
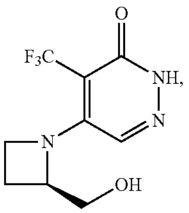
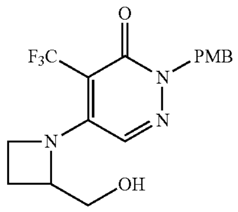
,
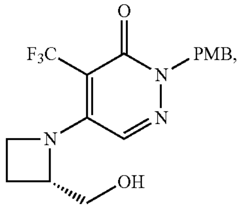
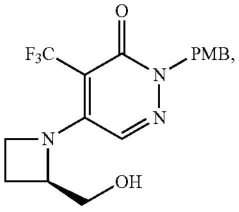
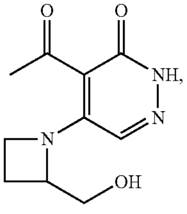
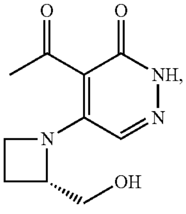
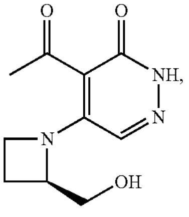
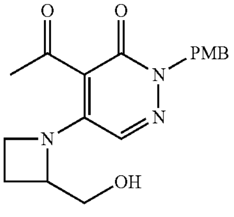
,
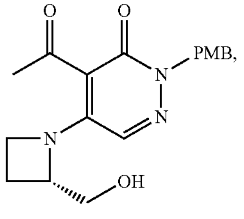
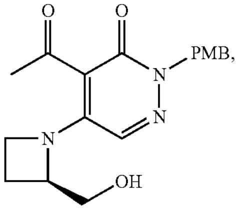
-continued
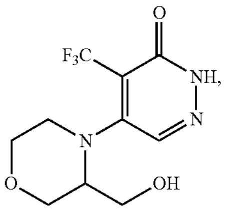
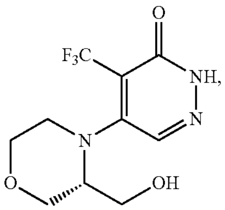
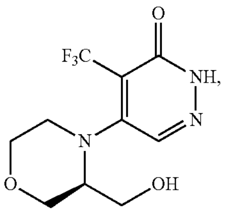
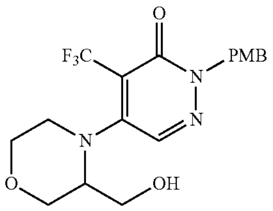
,
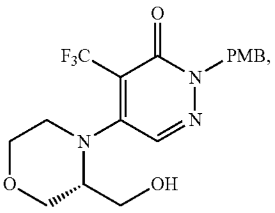
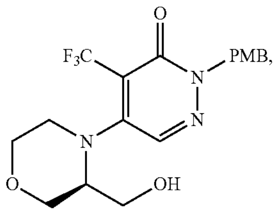
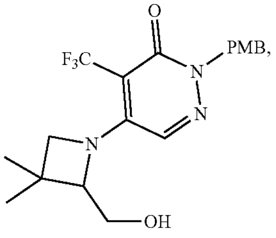
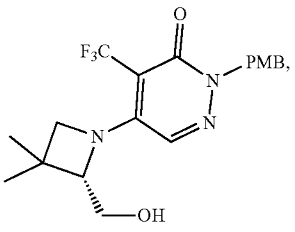
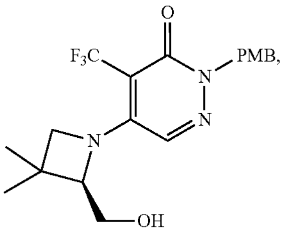
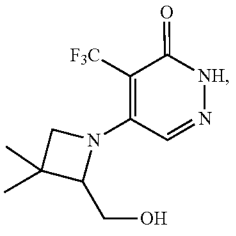

-continued
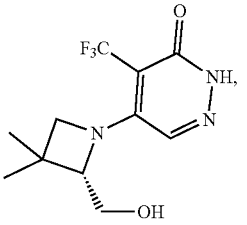
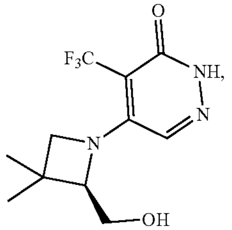
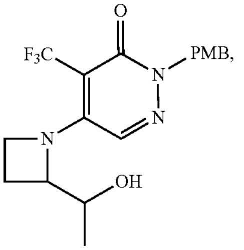
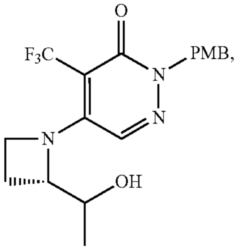
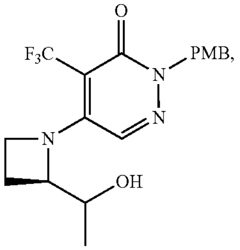
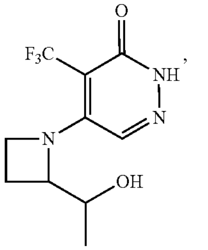,
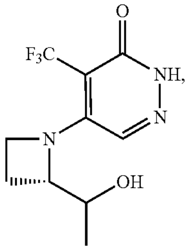
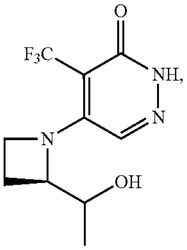
-continued
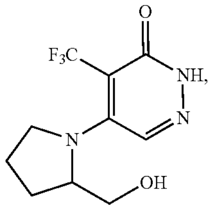
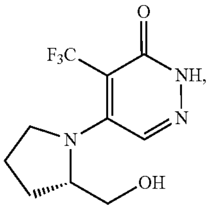
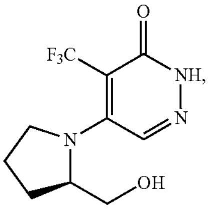
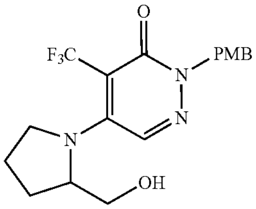,
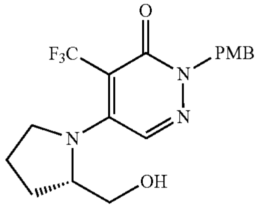
or
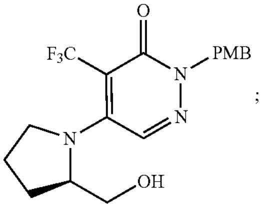
;
In some embodiments, the compound of formula (I-8) is independently selected from any one of the following formulas:
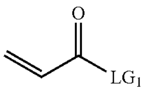
or
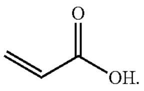
[97]. The process according to [95] or [96], wherein, the compound of formula (I'-2) is prepared by the following Step E or Step F:
Step E:
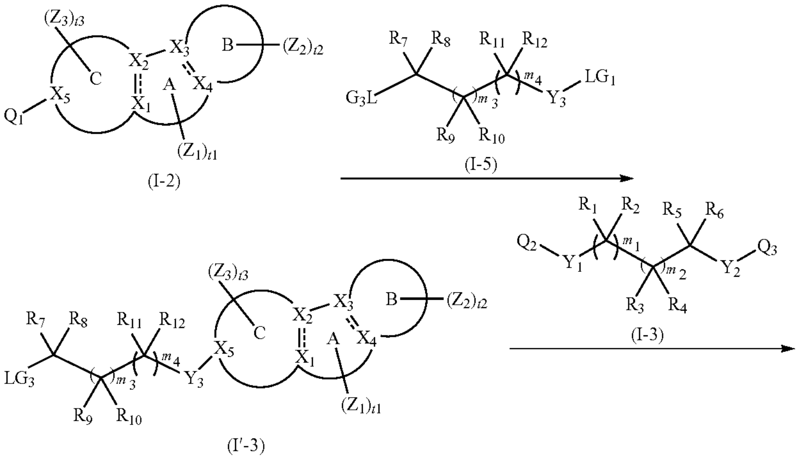
(I-2)
(I-5)
(I-3)
(I'-3)

-continued

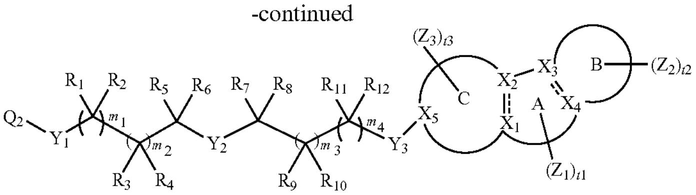

(I'-2)

(a) Reacting the compound of formula (I-2) with the compound of formula (I-5) by a condensation reaction to yield the compound of formula (I'-3):

(b) Reacting the compound of formula (I'-3) with the compound of formula (I-3) by a substitution reaction or by a coupling reaction to yield the compound of formula (I'-2);

In some embodiments, the compound of formula (I'-3) is selected from any one of the following formulas:

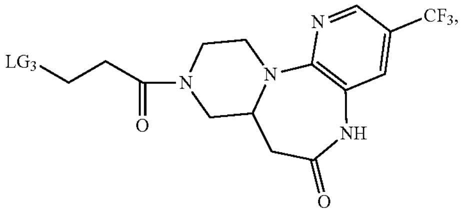

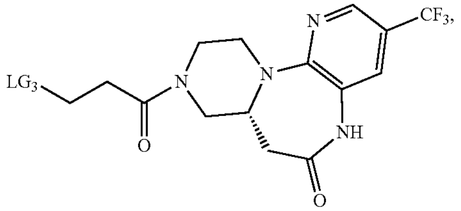

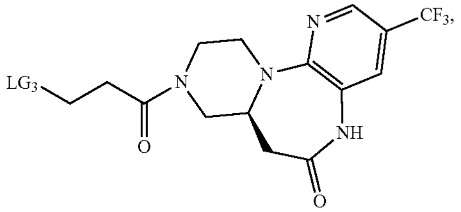

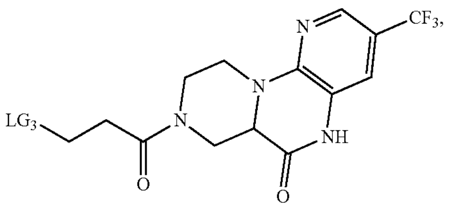

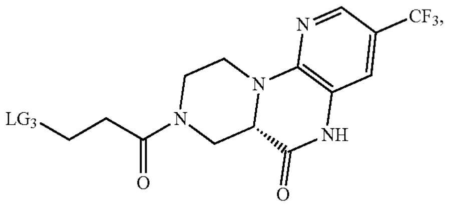

-continued

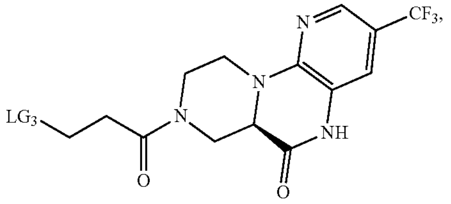

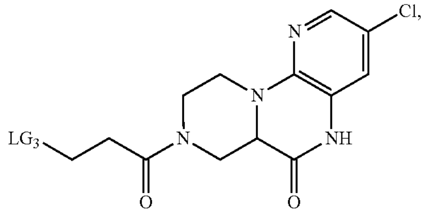

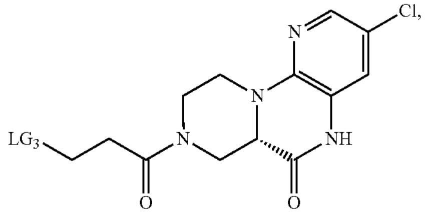

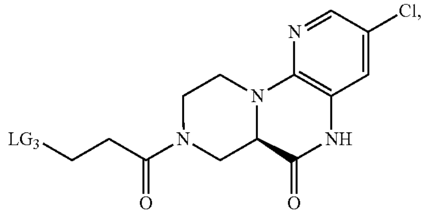

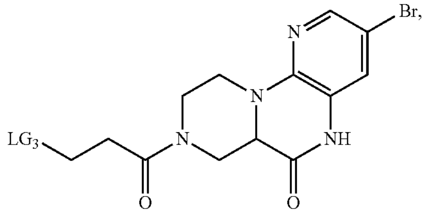

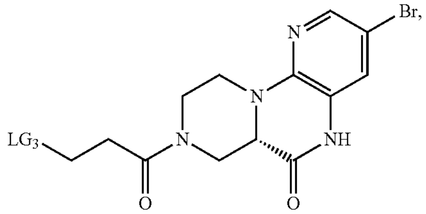

-continued
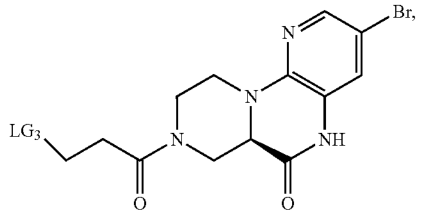
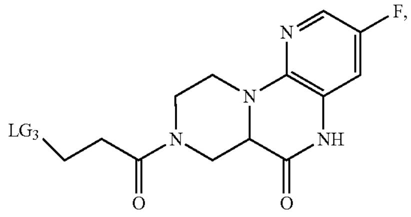
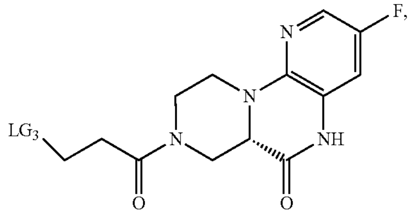
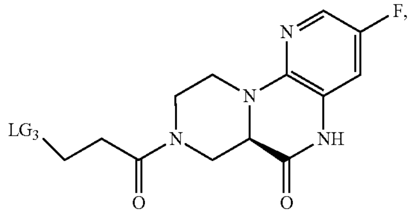
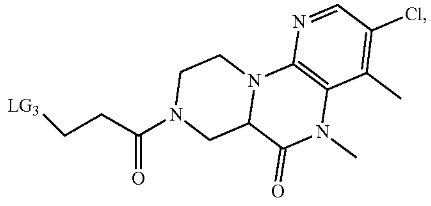
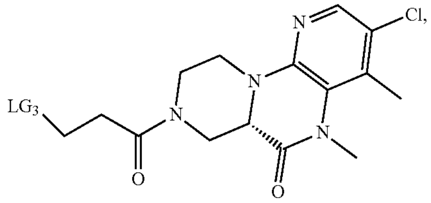
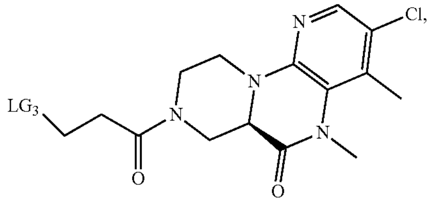
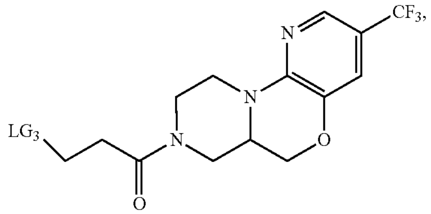
-continued
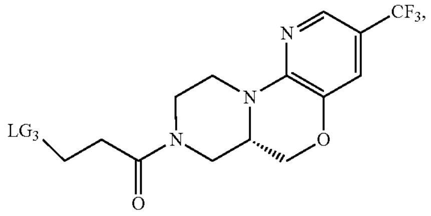
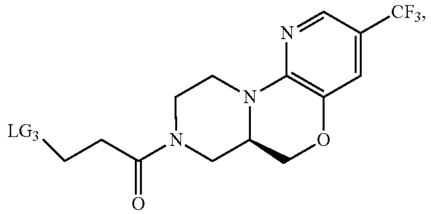
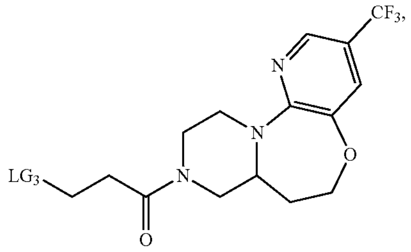
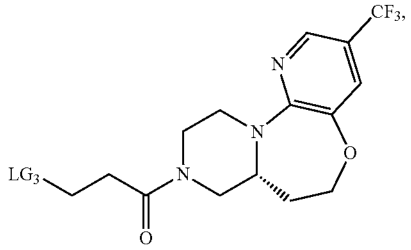
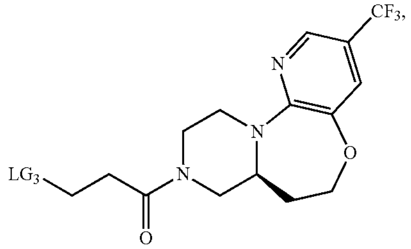
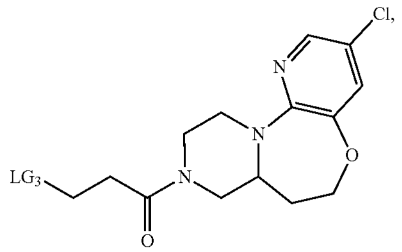
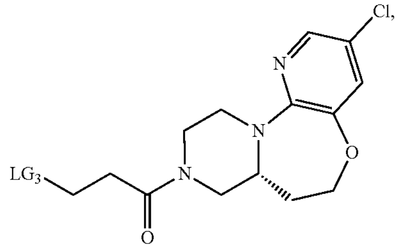

-continued
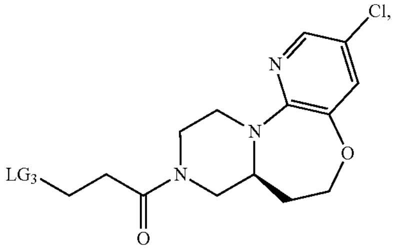
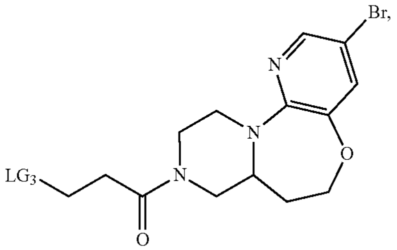
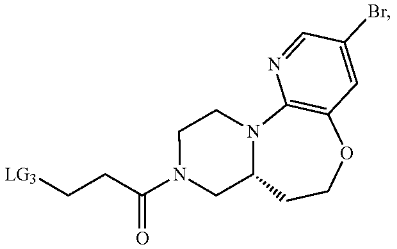
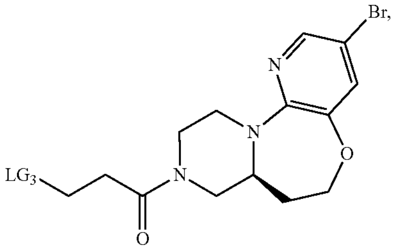
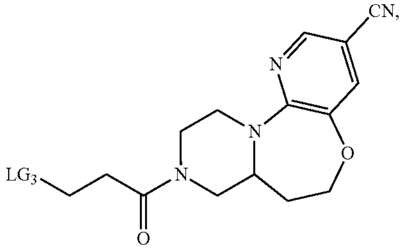
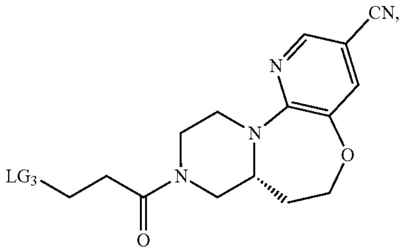
-continued
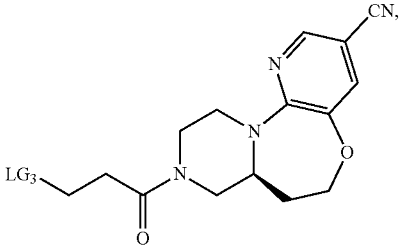
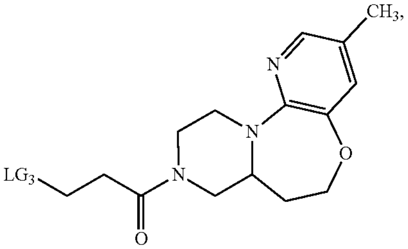
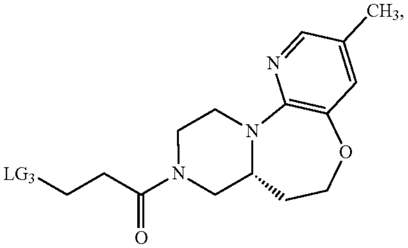
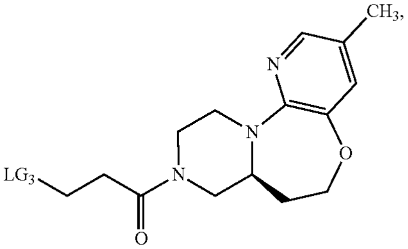
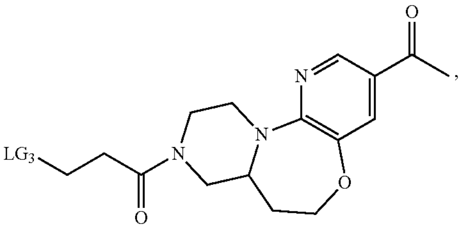
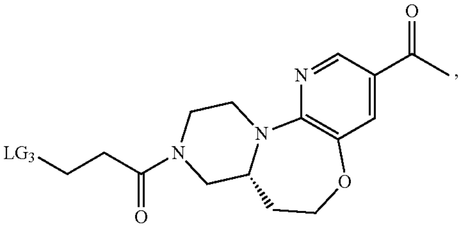
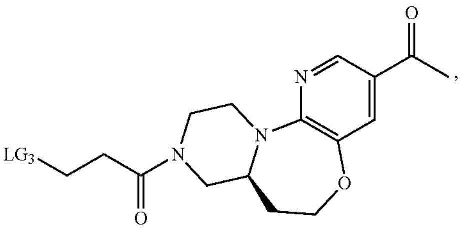

-continued
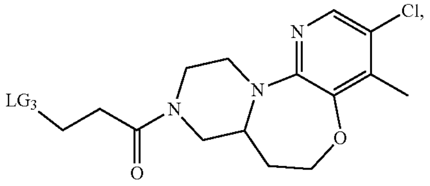
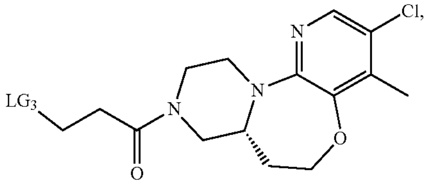
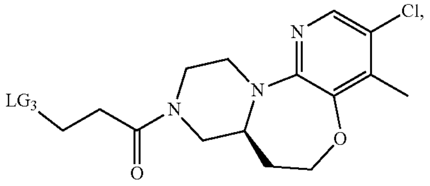
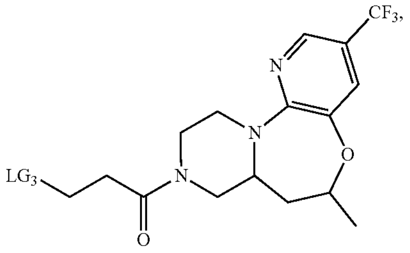
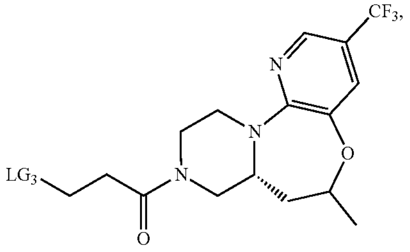
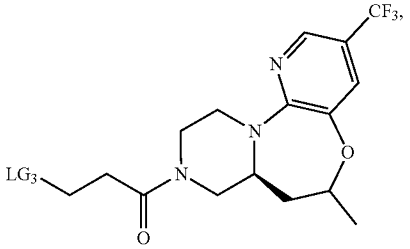
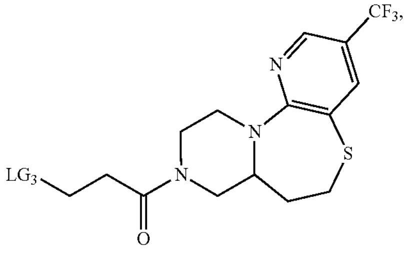
-continued
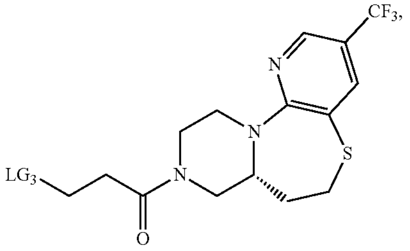
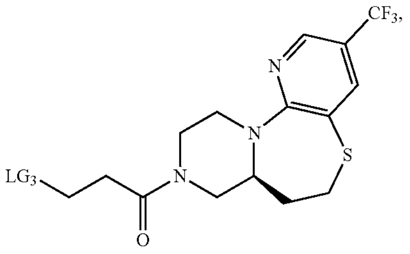
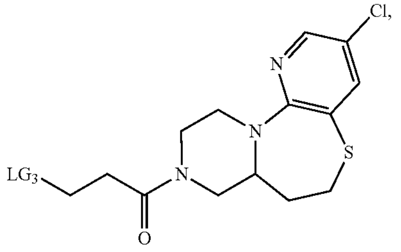
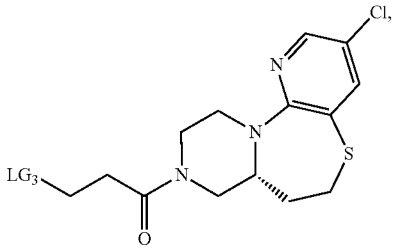
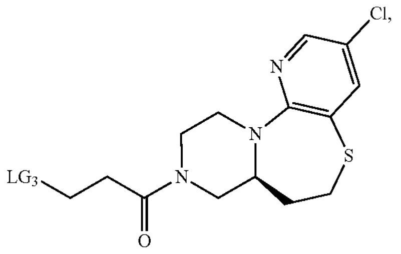
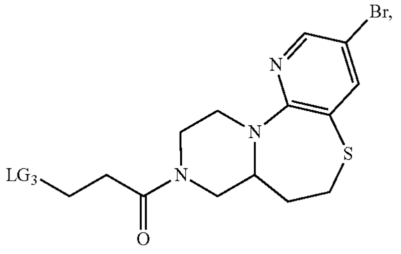

-continued
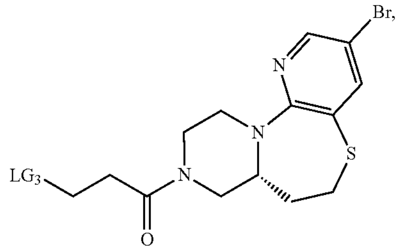
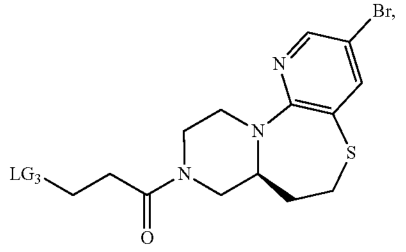
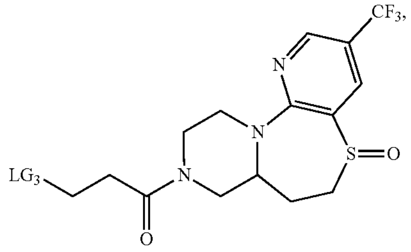
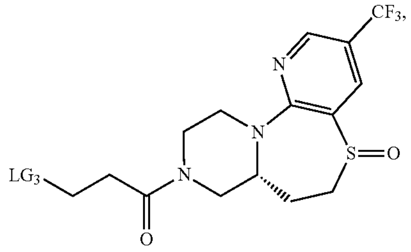
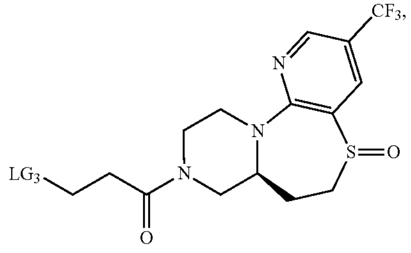
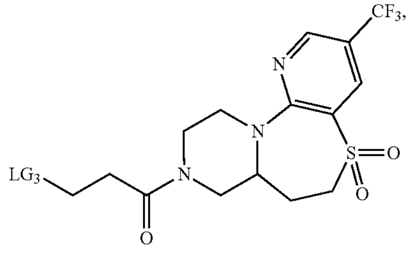
-continued
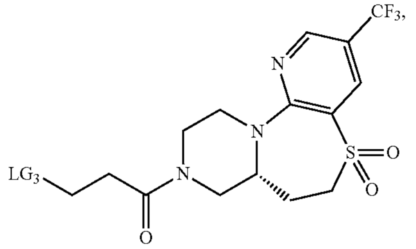
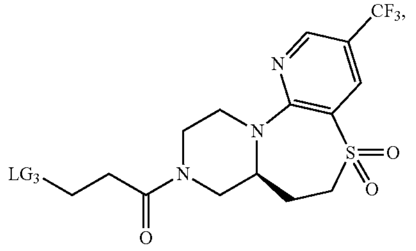
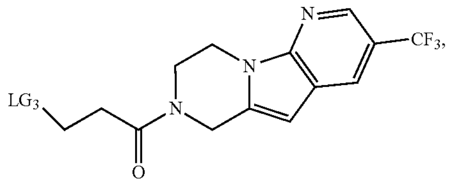
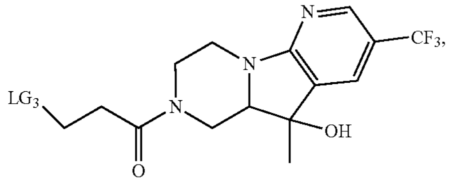
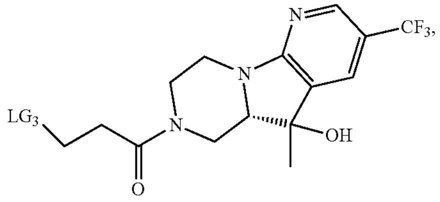
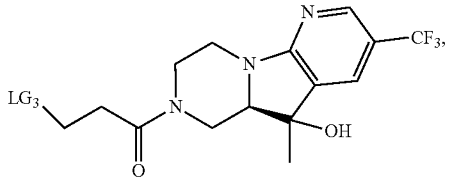
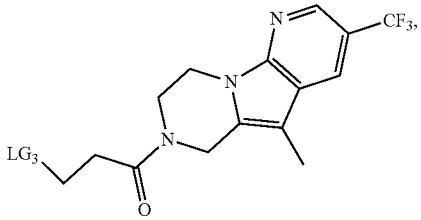
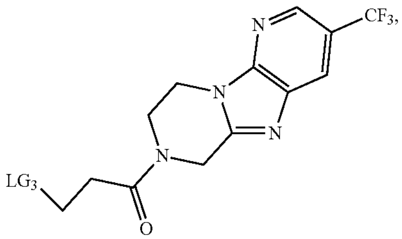

-continued
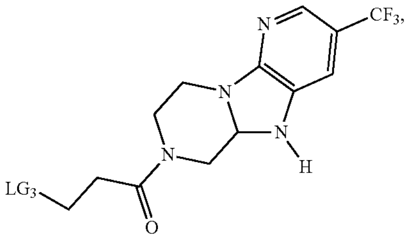
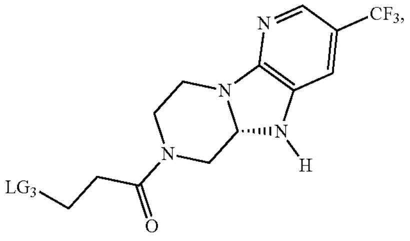
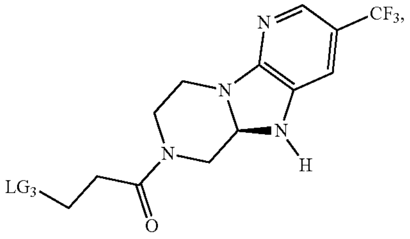
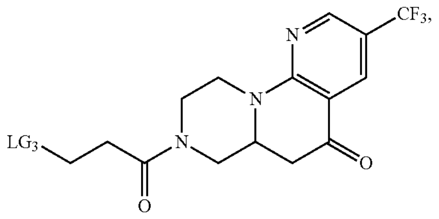
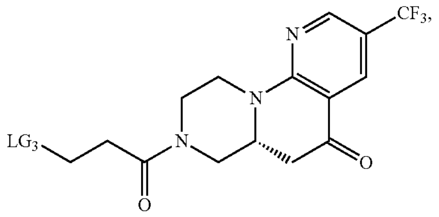
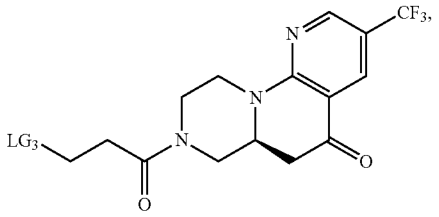
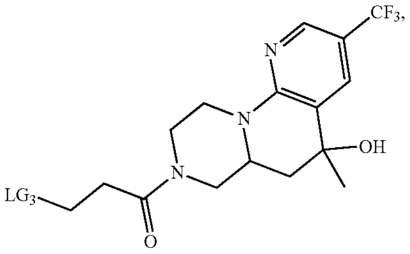
-continued
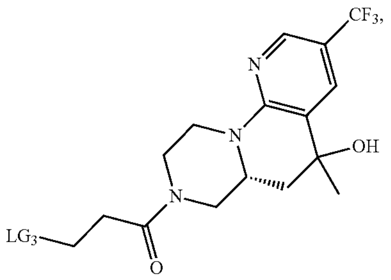
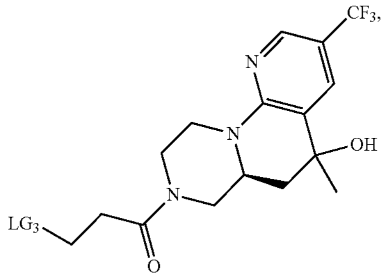
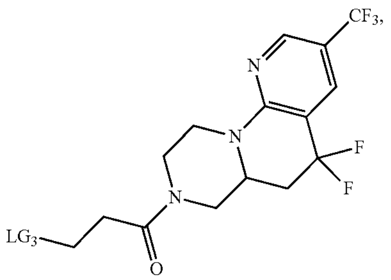
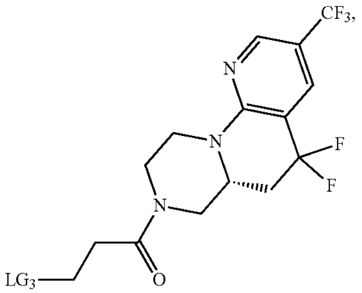
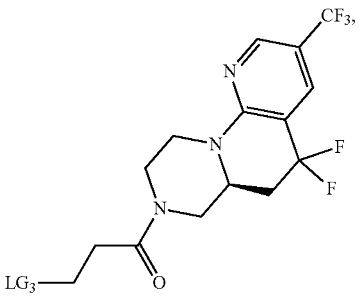
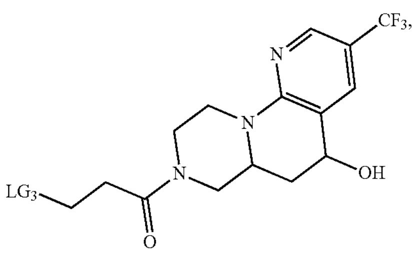

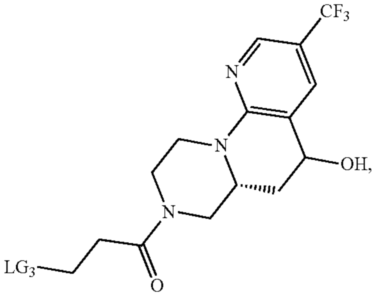
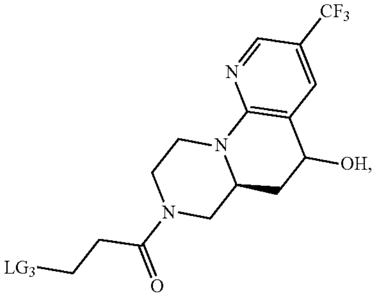
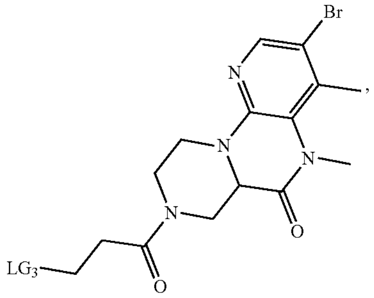
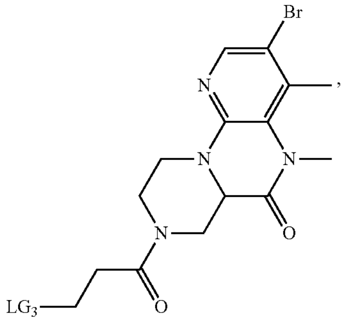
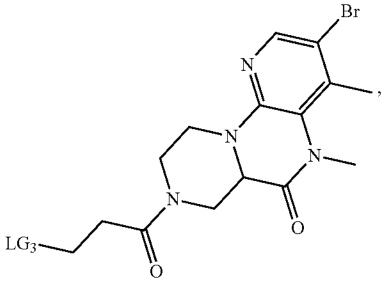
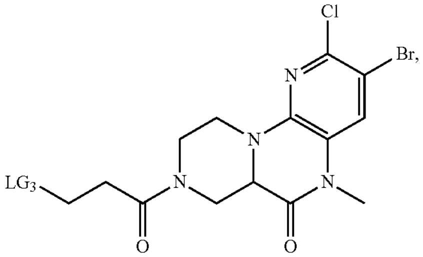
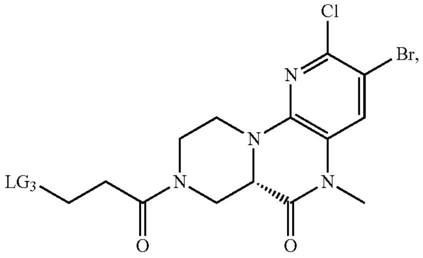
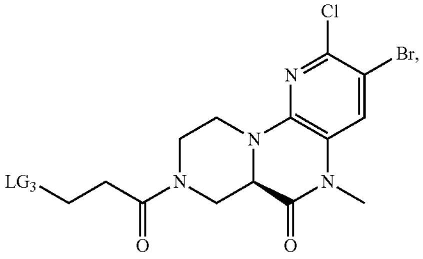
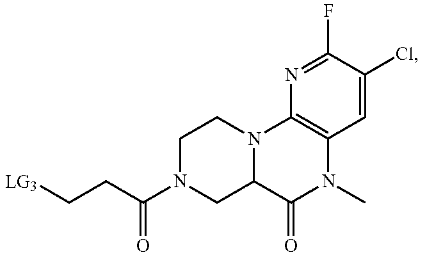
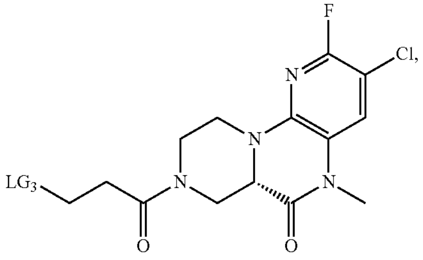
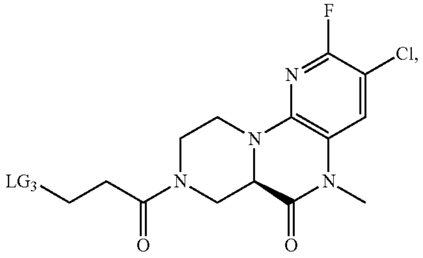

-continued
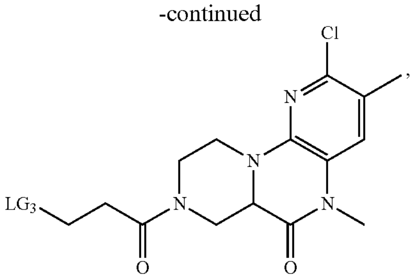
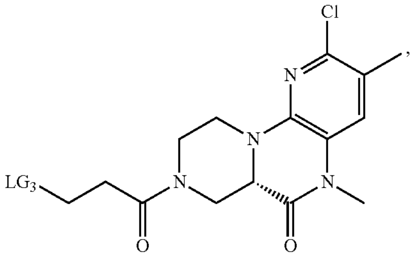
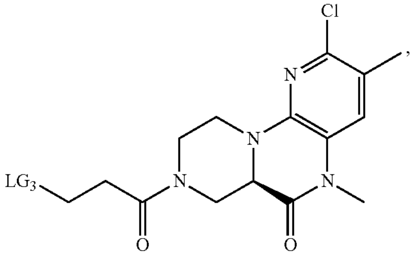
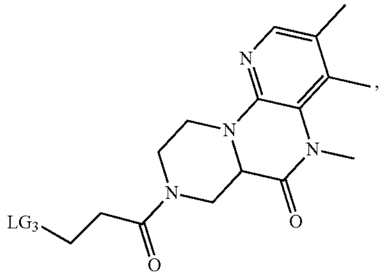
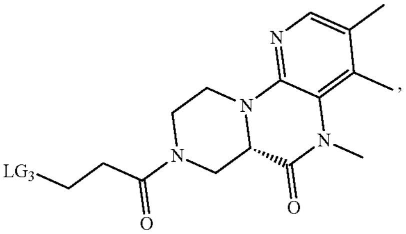
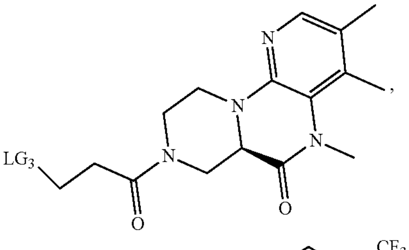
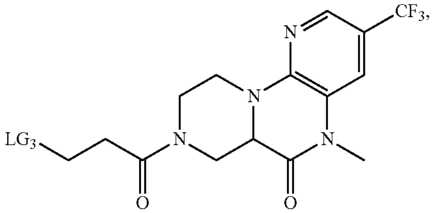
-continued
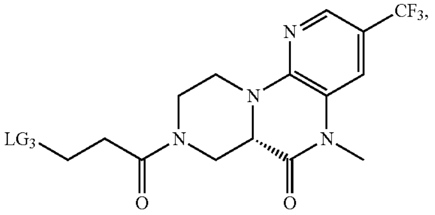
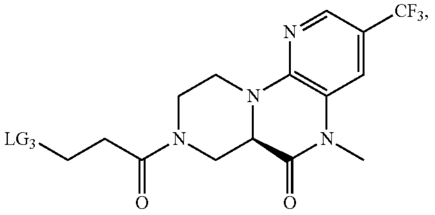
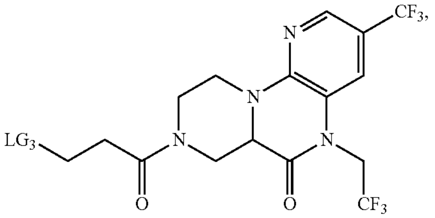
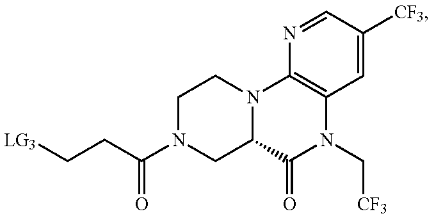
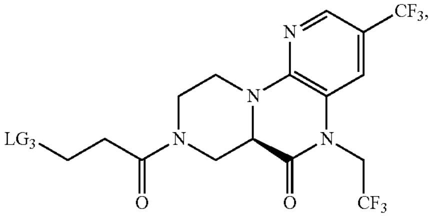
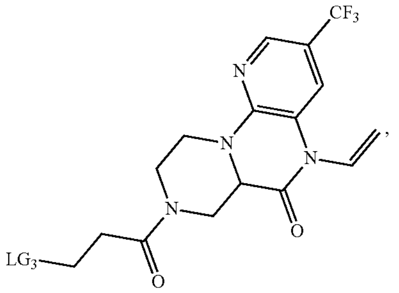
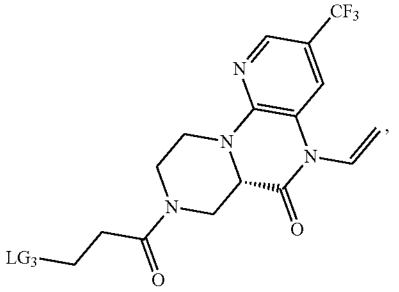

-continued
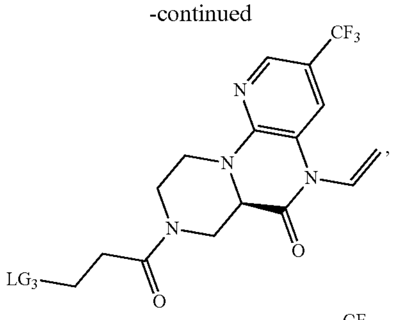
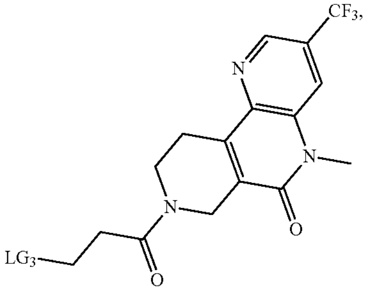
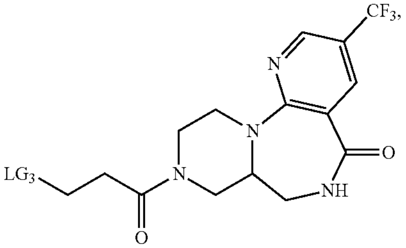
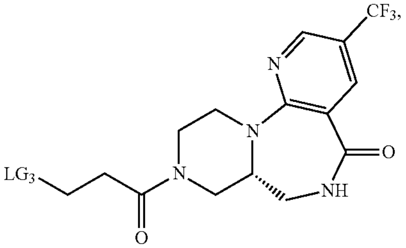
-continued
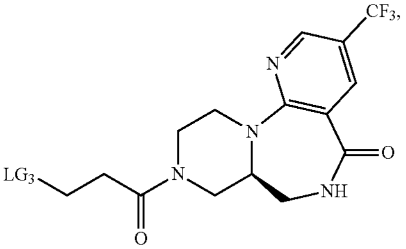
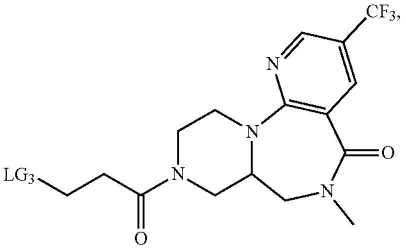
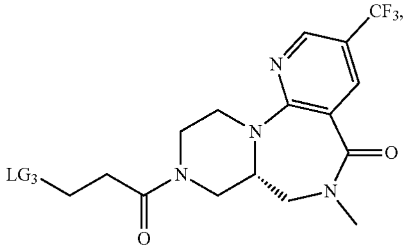
or
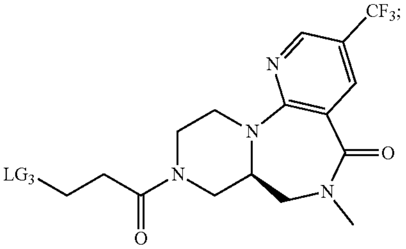
Step F:
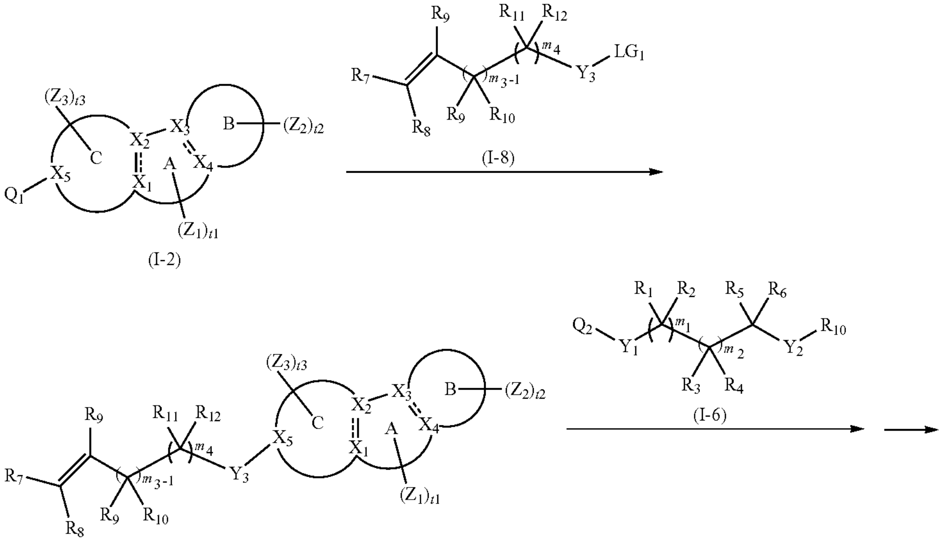
(I'-4)

-continued

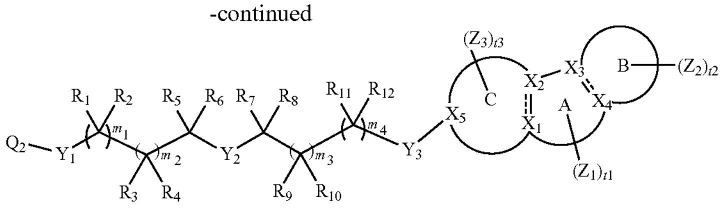

(I'-2)

(a) Reacting the compound of formula (I-2) with the compound of formula (I-8) by a condensation reaction to yield the compound of formula (P-4);

(b) Reacting the compound of formula (P-4) with the compound of formula (I-6) by an addition reaction to yield the compound of formula (P-2);

In some embodiments, the compound of formula (P-4) is selected from any one of the following formulas:

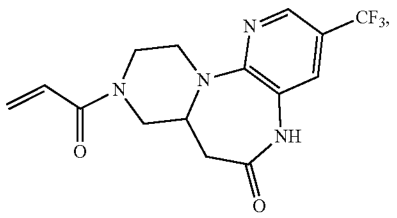

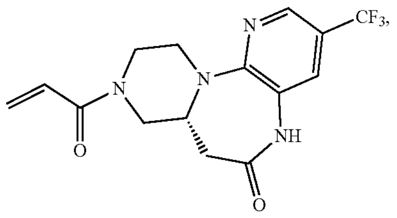

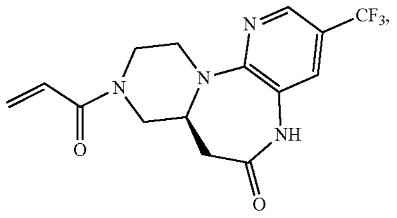

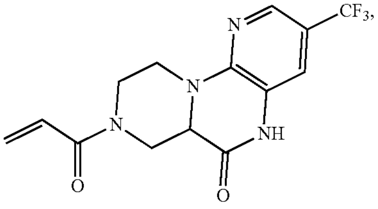

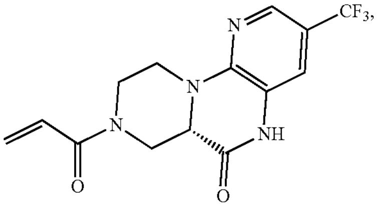

-continued

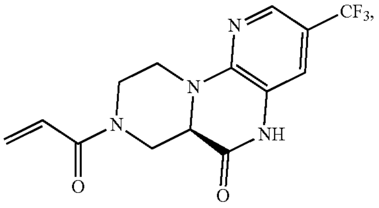

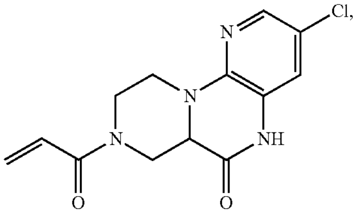

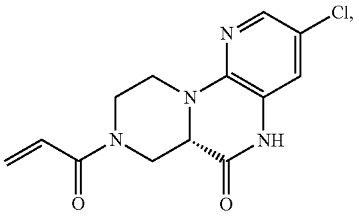

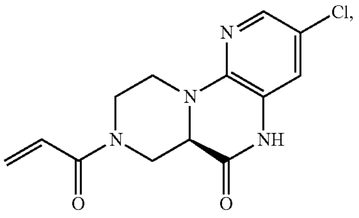

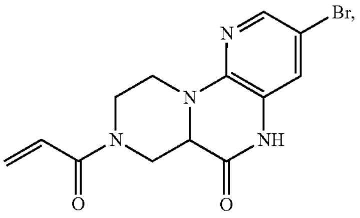

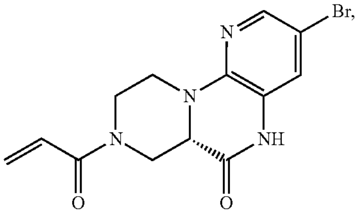

-continued
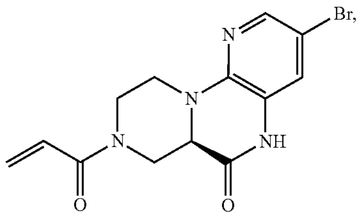
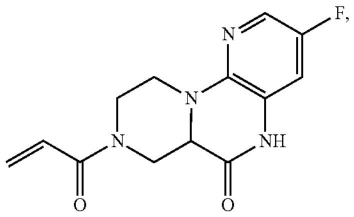
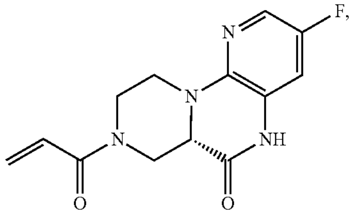
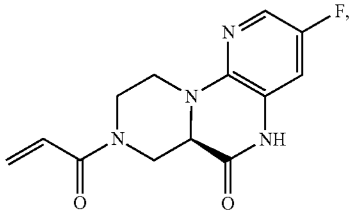
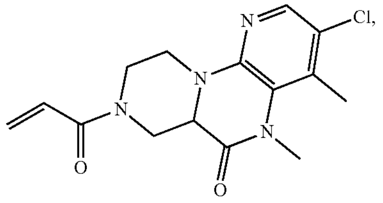
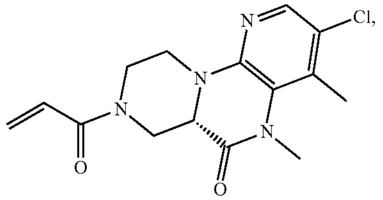
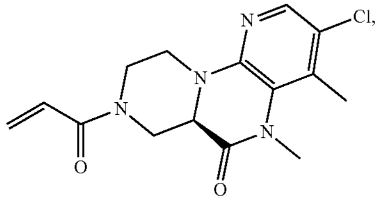
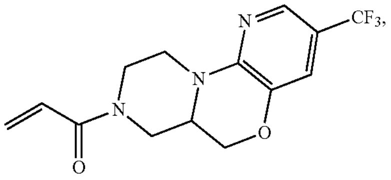
-continued
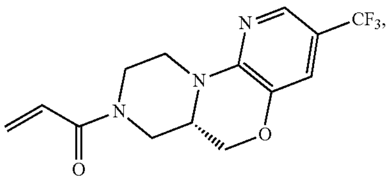
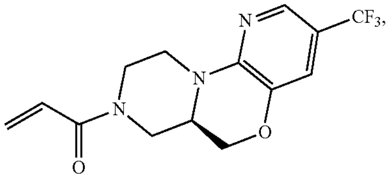
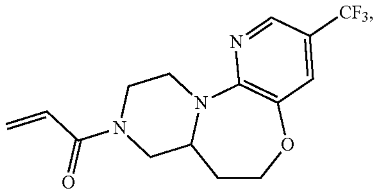
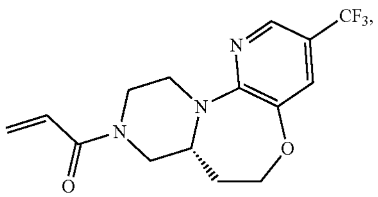
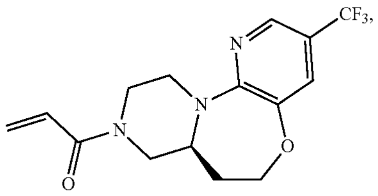
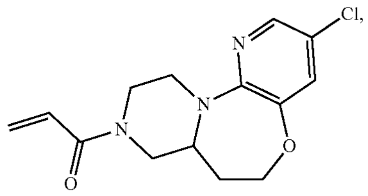
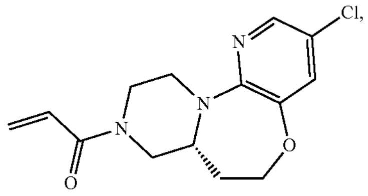
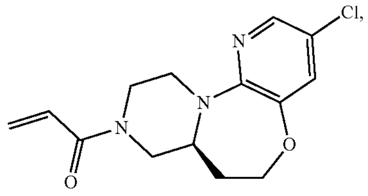

-continued
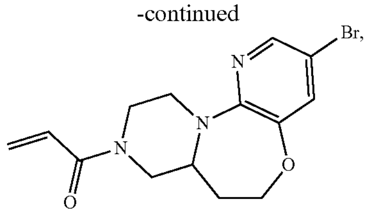
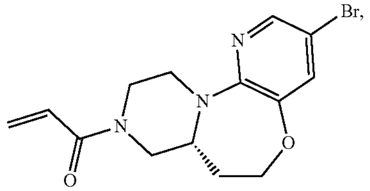
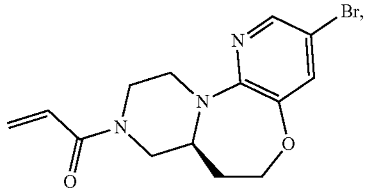
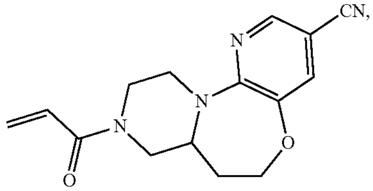
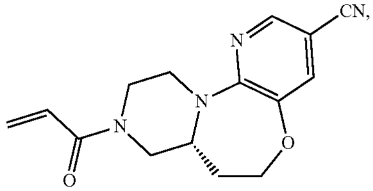
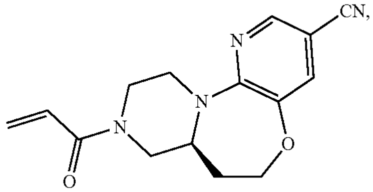
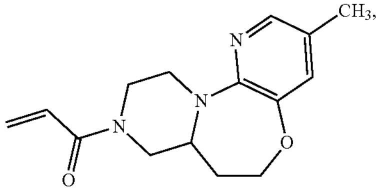
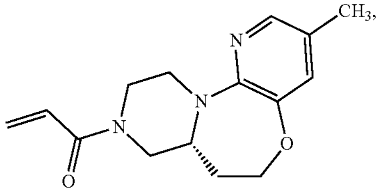
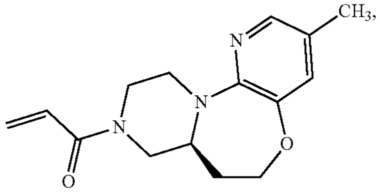
-continued
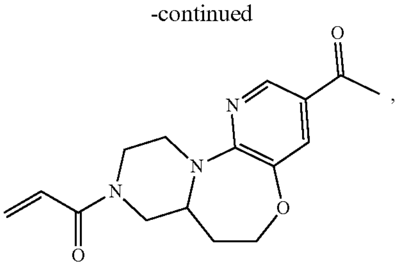
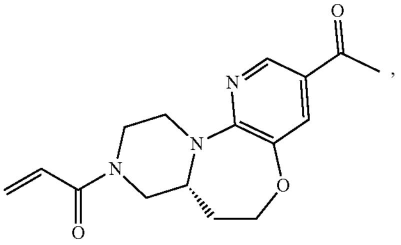
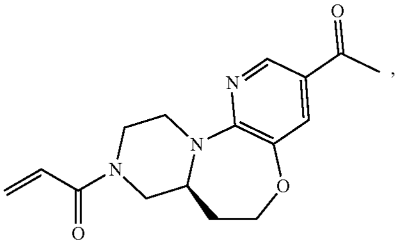
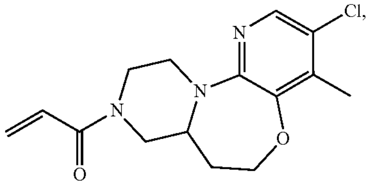
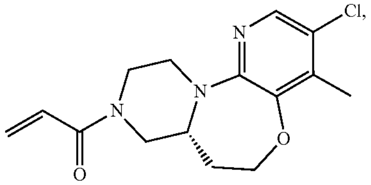
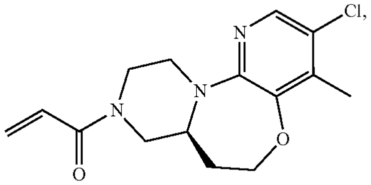
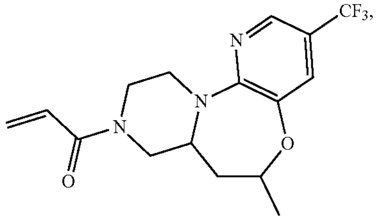
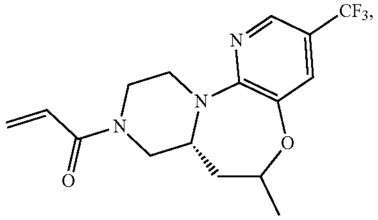

-continued
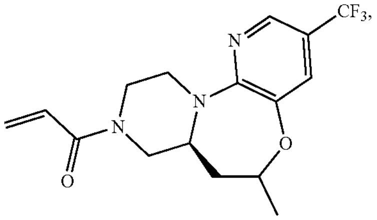
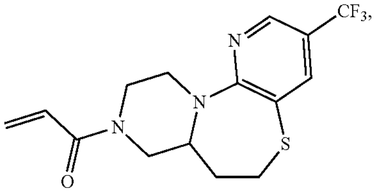
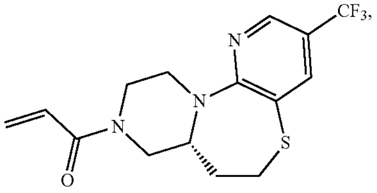
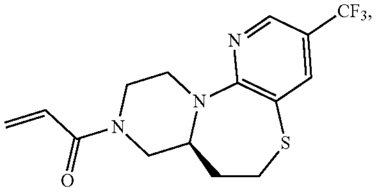
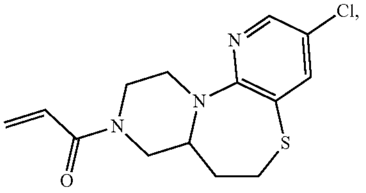
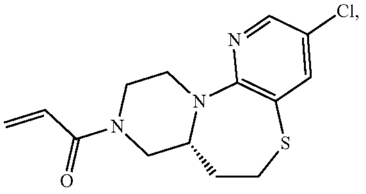
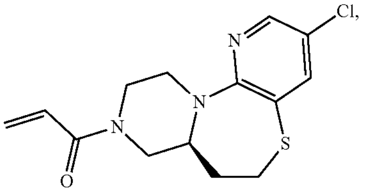
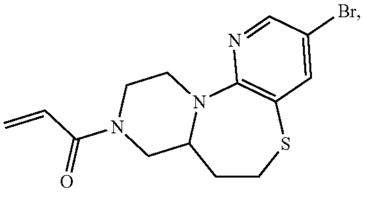
-continued
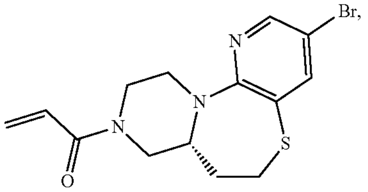
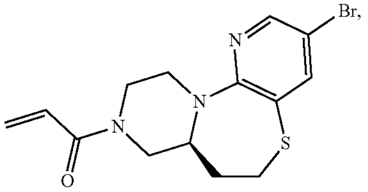
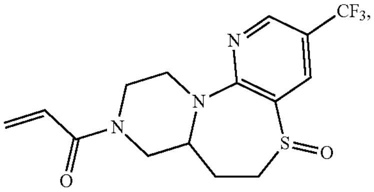
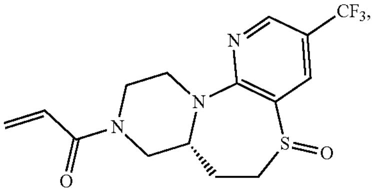
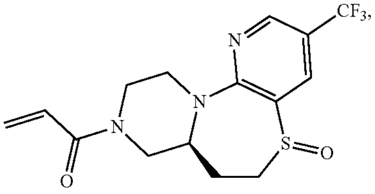
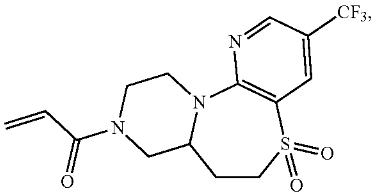
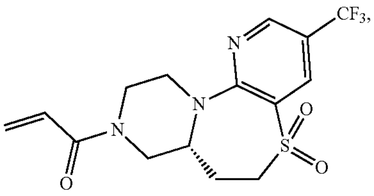
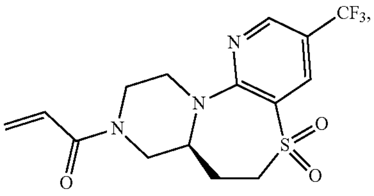

-continued
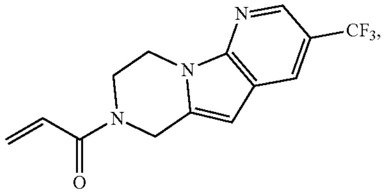
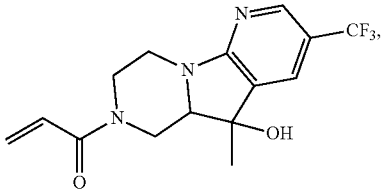
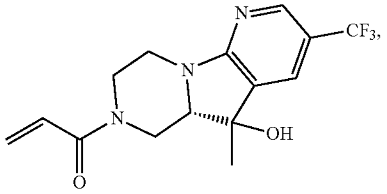
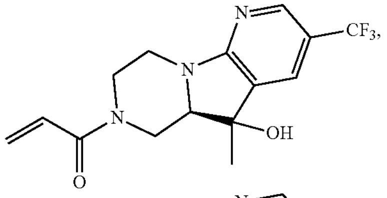
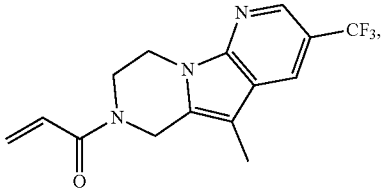
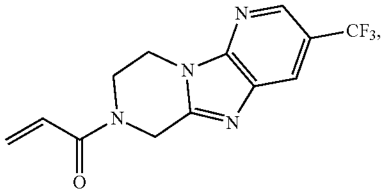
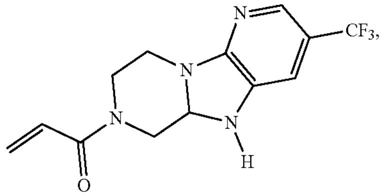
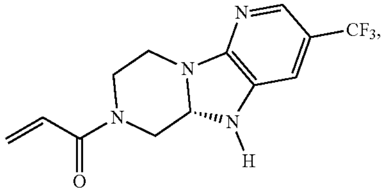
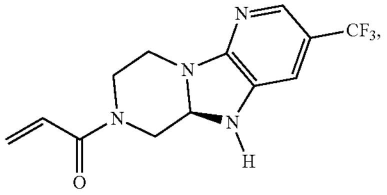
-continued
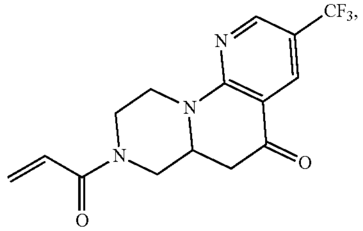
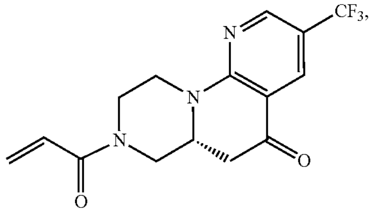
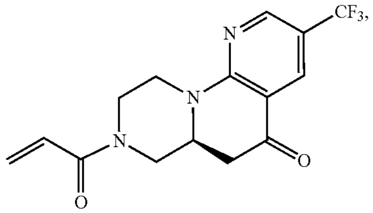
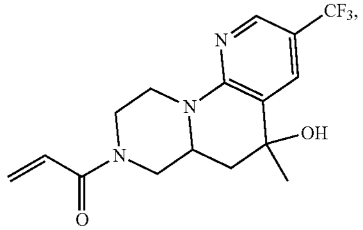
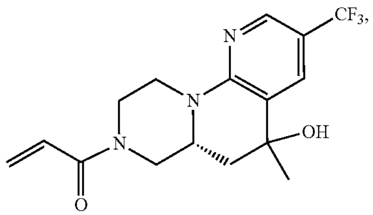
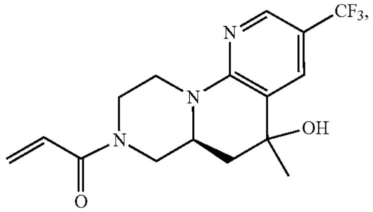
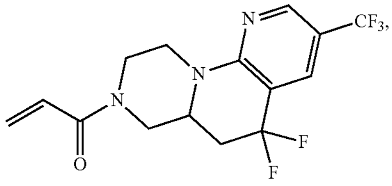
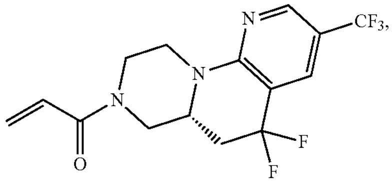

-continued
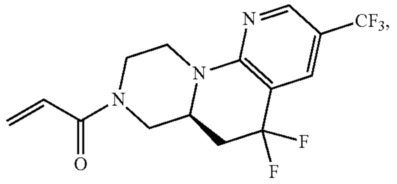
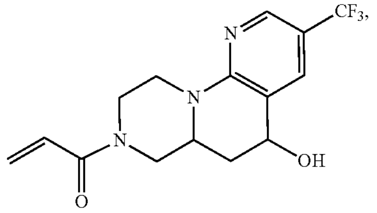
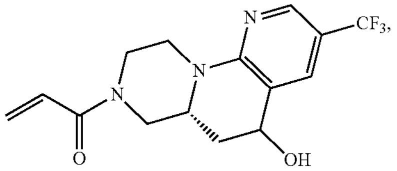
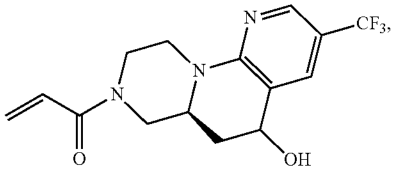
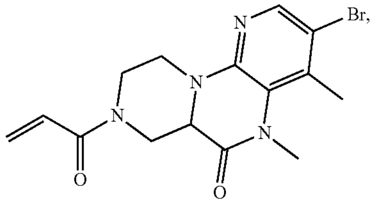
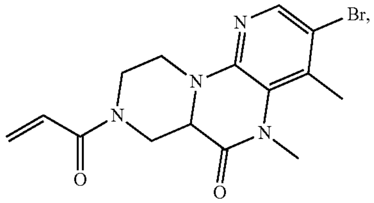
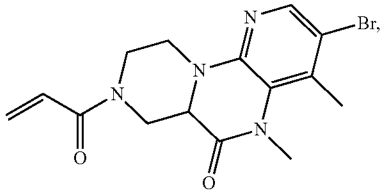
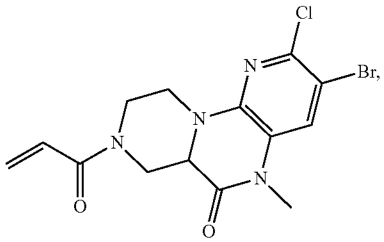
-continued
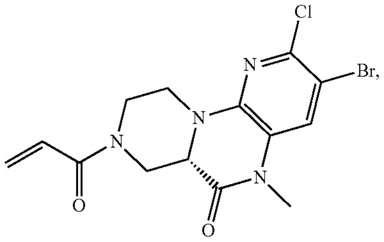
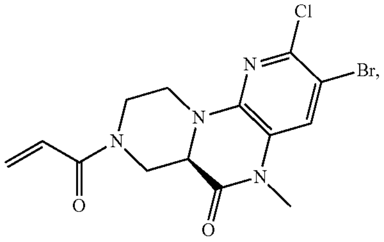
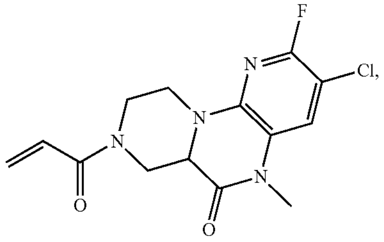
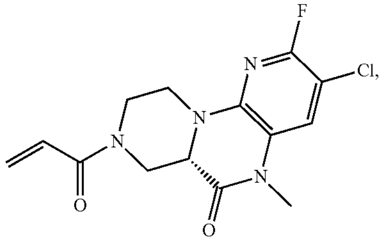
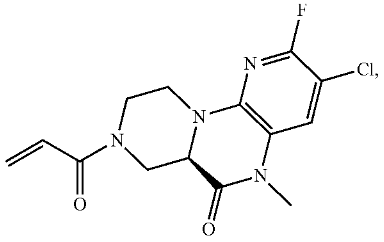
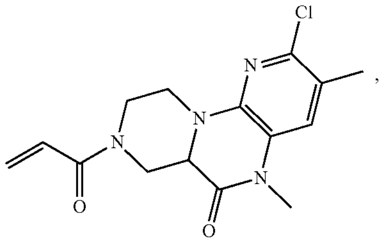
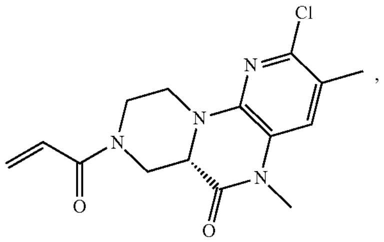

-continued
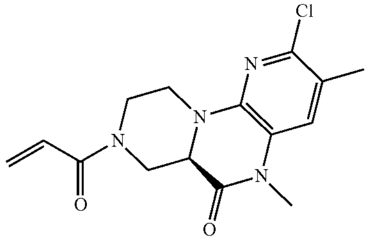
,
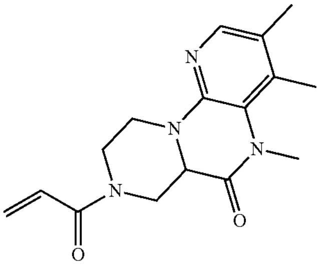
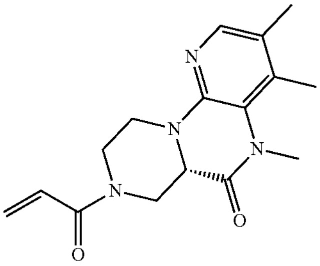
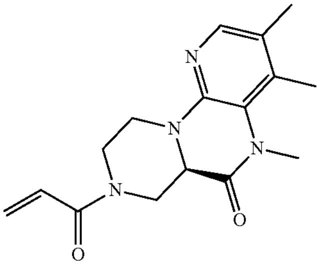
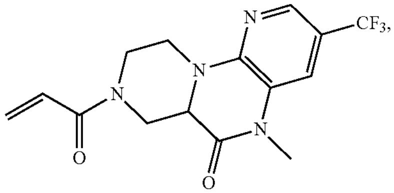
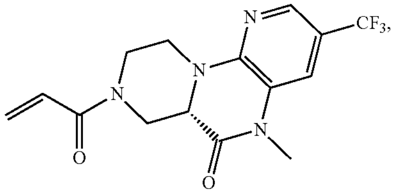
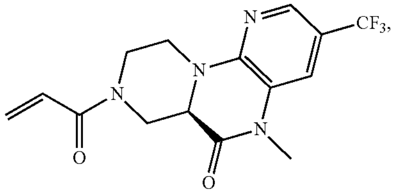
-continued
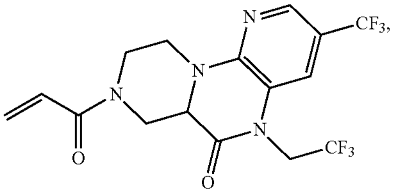
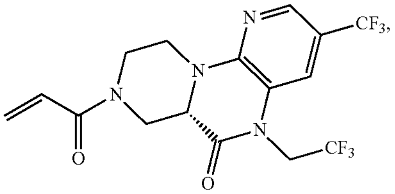
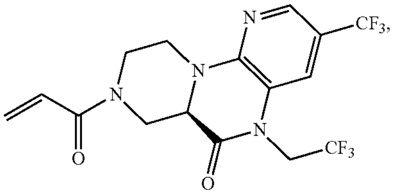
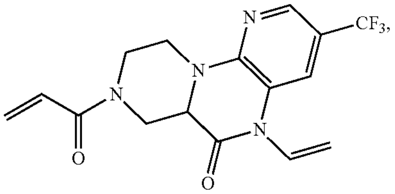
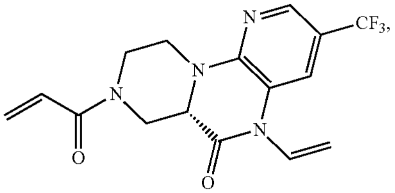
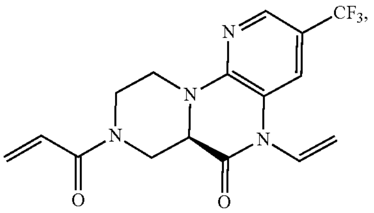
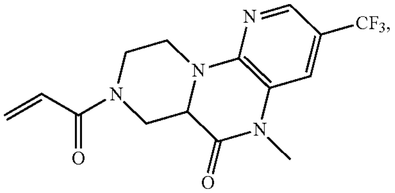
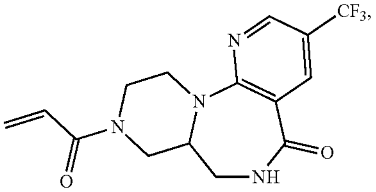

-continued

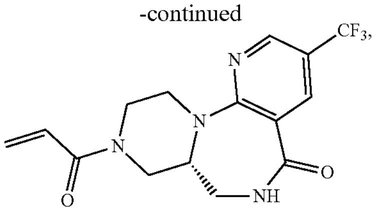

,

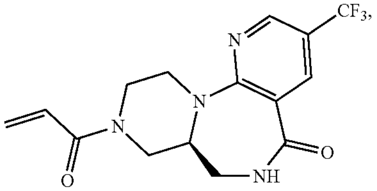

,

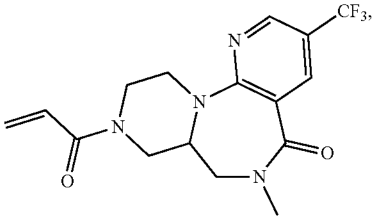

,

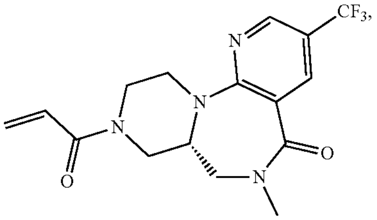

, or

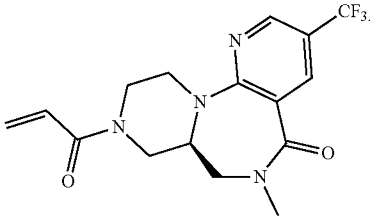

.

[98]. A use of the compound of formula (I), a stereoisomer thereof, a deuterated derivative thereof, or a pharmaceutically acceptable salt thereof according to any one of [1] to [93] as a targeting PARP7 protein ligand in a PROTAC compound acting as a degradation modulator of PARP7 protein.

[99]. A pharmaceutical composition comprising the compound of formula (I), a stereoisomer thereof, a deuterated derivative thereof, or a pharmaceutically acceptable salt thereof according to any one of [1] to [93]; and at least one pharmaceutically acceptable excipient.

[100]. A method of inhibiting the activity of PARP7 comprising contacting an effective amount of the compound of formula (I), a stereoisomer thereof, a deuterated derivative thereof, or a pharmaceutically acceptable salt thereof according to any one of [1] to [93] with PARP7 or a cell in which inhibition of PARP7 is desired.

[101]. A use of the compound of formula (I), a stereoisomer thereof, a deuterated derivative thereof, or a pharmaceutically acceptable salt thereof according to any one of [1] to [93]; or the pharmaceutical composition according to [99] for the manufacture of a medicament for the treatment of cancer;

In some embodiments, the cancer is PARP7 associated cancer;

In some embodiments, the cancer is PARP7 overexpression associated cancer;

In some embodiments, the cancer is selected from breast cancer, cancer of the central nervous system, endometrium cancer, kidney cancer, large intestine cancer, lung cancer, esophagus cancer, tongue cancer, ovarian cancer, pancreatic cancer, prostate cancer, stomach cancer, mesothelioma, melanoma, fibrosarcoma, bladder cancer, rectal cancer, lymphoma, cervical cancer, head and neck cancer, upper aerodigestive cancer, colorectal cancer, urinary tract cancer, or colon cancer. More preferably, each cancer is independently selected from adenocarcinoma, squamous cell carcinoma, mixed adenosquamous carcinoma, undifferentiated carcinoma. More preferably, the ovarian cancer comprises high grade ovarian serious adenocarcinoma, ovarian mucinous cystadenocarcinoma or malignant ovarian Brenner tumor; the kidney cancer comprises clear cell renal cell carcinoma; the tongue cancer comprises tongue squamous cell carcinoma; the lung cancer comprises lung adenocarcinoma, lung adenosquamous carcinoma, squamous cell lung carcinoma, large cell lung carcinoma, small cell lung carcinoma, papillary adenocarcinoma of the lung or non-small cell lung carcinoma; the pancreatic cancer comprises pancreatic adenocarcinoma or pancreatic ductal adenocarcinoma; the esophagus cancer comprises esophageal squamous cell carcinoma; the mesothelioma comprises biphasic mesothelioma; the cancer of the central nervous system comprises neuroglioma, glioblastoma or glioblastoma multiforme; the stomach cancer comprises gastric adenocarcinoma; the breast cancer comprises ductal breast carcinoma, breast adenocarcinoma or HR+ breast cancer; the bladder cancer comprises bladder squamous cell carcinoma; the melanoma comprises malignant melanoma; the colon cancer comprises colon adenocarcinoma; the head and neck cancer comprises head and neck small squamous cell cancer; in some embodiments, the cancer is PARP7 overexpression associated cancer.

[102]. A method of treating a subject having cancer, said method comprising administering to the subject a therapeutically effective amount of the compound of formula (I), a stereoisomer thereof, a deuterated derivative thereof, a tautomer thereof, or a pharmaceutically acceptable salt thereof according to any one of [1] to [93]; or the pharmaceutical composition according to [99];

In some embodiments, the cancer is PARP7 associated cancer;

In some embodiments, the cancer is PARP7 overexpression associated cancer;

In some embodiments, the cancer is selected from breast cancer, cancer of the central nervous system, endometrium cancer, kidney cancer, large intestine cancer, lung cancer, esophagus cancer, tongue cancer, ovarian cancer, pancreatic cancer, prostate cancer, stomach cancer, mesothelioma, melanoma, fibrosarcoma, bladder cancer, rectal cancer, lymphoma, cervical cancer, head and neck cancer, upper aerodigestive cancer, colorectal cancer, urinary tract cancer, or colon cancer. More preferably, each cancer is independently selected from adenocarcinoma, squamous cell carcinoma, mixed adenosquamous carcinoma, undifferentiated carcinoma. More preferably, the ovarian cancer comprises high grade ovarian serious adenocarcinoma, ovarian mucinous cystadenocarcinoma or malignant ovarian Brenner tumor; the kidney cancer comprises clear cell renal cell carcinoma; the tongue cancer comprises tongue squamous cell carcinoma; the lung cancer comprises lung adenocarcinoma, lung adenosquamous carcinoma, squamous cell lung carcinoma, large cell lung carcinoma, small cell lung carcinoma, papillary adenocarcinoma of the lung or non-small cell lung carcinoma; the pancreatic cancer comprises pancreatic adenocarcinoma or pancreatic ductal adenocarcinoma; the esophagus cancer comprises esophageal squamous cell carcinoma; the mesothelioma comprises biphasic mesothelioma; the cancer of the central nervous system comprises neuroglioma, glioblastoma or glioblastoma multiforme; the stomach cancer comprises gastric adenocarcinoma; the breast cancer comprises ductal breast carcinoma, breast adenocarcinoma or HR+ breast cancer; the bladder cancer comprises bladder squamous cell carcinoma; the melanoma comprises malignant melanoma; the colon cancer comprises colon adenocarcinoma; the head and neck cancer comprises head and neck small squamous cell cancer; in some embodiments, the cancer is PARP7 overexpression associated cancer.

[103]. A compound of formula (I), a stereoisomer thereof, a deuterated derivative thereof, a tautomer thereof, or a pharmaceutically acceptable salt thereof according to any one of [1] to [93]; or the pharmaceutical composition of according to [99] for use in the treatment of cancer;

In some embodiments, the cancer is PARP7 associated cancer;

In some embodiments, the cancer is PARP7 overexpression associated cancer.

In some embodiments, the cancer is selected from breast cancer, cancer of the central nervous system, endometrium cancer, kidney cancer, large intestine cancer, lung cancer, esophagus cancer, tongue cancer, ovarian cancer, pancreatic cancer, prostate cancer, stomach cancer, mesothelioma, melanoma, fibrosarcoma, bladder cancer, rectal cancer, lymphoma, cervical cancer, head and neck cancer, upper aerodigestive cancer, colorectal cancer, urinary tract cancer, or colon cancer. More preferably, each cancer is independently selected from adenocarcinoma, squamous cell carcinoma, mixed adenosquamous carcinoma, undifferentiated carcinoma. More preferably, the ovarian cancer comprises high grade ovarian serious adenocarcinoma, ovarian mucinous cystadenocarcinoma or malignant ovarian Brenner tumor; the kidney cancer comprises clear cell renal cell carcinoma; the tongue cancer comprises tongue squamous cell carcinoma; the lung cancer comprises lung adenocarcinoma, lung adenosquamous carcinoma, squamous cell lung carcinoma, large cell lung carcinoma, small cell lung carcinoma, papillary adenocarcinoma of the lung or non-small cell lung carcinoma; the pancreatic cancer comprises pancreatic adenocarcinoma or pancreatic ductal adenocarcinoma; the esophagus cancer comprises esophageal squamous cell carcinoma; the mesothelioma comprises biphasic mesothelioma; the cancer of the central nervous system comprises neuroglioma, glioblastoma or glioblastoma multiforme; the stomach cancer comprises gastric adenocarcinoma; the breast cancer comprises ductal breast carcinoma, breast adenocarcinoma or HR+ breast cancer; the bladder cancer comprises bladder squamous cell carcinoma; the melanoma comprises malignant melanoma; the colon cancer comprises colon adenocarcinoma; the head and neck cancer comprises head and neck small squamous cell cancer; in some embodiments, the cancer is PARP7 overexpression associated cancer.

Definition

The term "a", "an", "the" and similar terms, as used herein, unless otherwise indicated, are to be construed to cover both the singular and plural.

The term "halogen" or "halo", as used interchangeably herein, unless otherwise indicated, means fluoro, chloro, bromo or iodo. The preferred halogen groups include —F, —Cl and —Br.

The term "alkyl", as used herein, unless otherwise indicated, includes saturated monovalent hydrocarbon radicals having straight or branched. $C_{1-10}$ in —$C_{1-10}$alkyl is defined to identify the group having 1, 2, 3, 4, 5, 6, 7, 8, 9 or 10 carbon atoms in a linear or branched arrangement. Non-limiting alkyl includes methyl, ethyl, propyl, isopropyl, n-butyl, isobutyl, sec-butyl, t-butyl, n-pentyl, 3-(2-methyl) butyl, 2-pentyl, 2-methylbutyl, neopentyl, n-hexyl, 2-hexyl and 2-methylpentyl.

The term "haloalkyl", as used herein, unless otherwise indicated, means the above-mentioned alkyl substituted with one or more (for example 1, 2, 3, 4, 5, or 6) halogen (such as —F, —Cl or —Br). In some embodiments, the haloalkyl is interchangeable —$C_{1-10}$haloalkyl or halo$C_{1-10}$alkyl, wherein, $C_{1-10}$ in the —$C_{1-10}$haloaklyl or halo$C_{1-10}$alkyl indicates that the total carbon atoms of the alkyl are 1 to 10. In some embodiments, the —$C_{1-10}$haloalkyl is the —$C_{1-6}$haloalkyl. In some embodiments, the —$C_{1-6}$haloalkyl is the —$C_{1-3}$haloalkyl. In some embodiments, the —$C_{1-3}$haloalkyl is (methyl, ethyl, propyl or isopropyl) substituted with 1, 2, 3, 4, 5, or 6 —F; preferably, the —$C_{1-3}$haloalkyl is —$CF_3$.

The term "alkylene", as used herein, unless otherwise indicated, means a difunctional group obtained by removal of an additional hydrogen atom from an alkyl group defined above. In some embodiments, the alkylene is $C_{0-6}$alkylene. In some embodiments, the $C_{0-6}$alkylene is $C_{0-3}$alkylene. The $C_{0-6}$ in the front of the alkylene indicates the total carbon atoms in the alkylene are 0 to 6 and $C_0$ indicates the two ends of the alkylene are connected directly. Non-limiting alkylene includes methylene (i.e., —$CH_2$—), ethylene (i.e., —$CH_2$—$CH_2$— or —$CH(CH_3)$—) and propylene (i.e., —$CH_2$—$CH_2$—$CH_2$—, —CH(—$CH_2$—$CH_3$)— or —$CH_2$—CH($CH_3$)—).

The term "alkenyl", as used herein, unless otherwise indicated, means a straight or branch-chained hydrocarbon radical containing one or more double bonds and typically from 2 to 20 carbon atoms in length. In some embodiments, the alkenyl is —$C_{2-10}$alkenyl. In some embodiments, the —$C_{2-10}$alkenyl is —$C_{2-6}$alkenyl which contains from 2 to 6 carbon atoms. Non-limiting alkenyl includes ethenyl, propenyl, butenyl, 2-methyl-2-buten-1-yl, hepetenyl, octenyl and the like.

The term "haloalkenyl", as used herein, unless otherwise indicated, means the above-mentioned alkenyl substituted with one or more (for example 1, 2, 3, 4, 5, or 6) halogen (such as —F, —Cl or —Br). In some embodiments, the haloalkenyl is interchangeable —$C_{2-10}$haloalkenyl or halo$C_{2-10}$alkenyl, wherein, $C_{2-10}$ in the —$C_{2-10}$haloaklenyl or halo$C_{2-10}$alkenyl indicates that the total carbon atoms of the alkenyl are 2 to 10. In some embodiments, the —$C_{2-10}$haloalkenyl is the —$C_{2-6}$haloalkenyl. In some embodiments, the —$C_{2-6}$haloalkenyl is the —$C_{2-3}$haloalkenyl. In some embodiments, the —$C_{2-3}$haloalkenyl is (ethenyl or propenyl) substituted with 1, 2, 3, 4, 5, or 6 —F.

The term "alkynyl", as used herein, unless otherwise indicated, contains a straight or branch-chained hydrocarbon radical containing one or more triple bonds and typically from 2 to 20 carbon atoms in length. In some embodiments, the alkynyl is —$C_{2-10}$alkynyl. In some embodiments, the —$C_{2-10}$alkynyl is —$C_{2-6}$alkynyl which contains from 2 to 6 carbon atoms. Non-limiting alkynyl includes ethynyl, 1-propynyl, 1-butynyl, heptynyl, octynyl and the like.

The term "haloalkynyl", as used herein, unless otherwise indicated, means the above-mentioned alkynyl substituted with one or more (for example 1, 2, 3, 4, 5, or 6) halogen (such as —F, —Cl or —Br). In some embodiments, the haloalkynyl is interchangeable —$C_{2-10}$haloalkynyl or halo$C_{2-10}$alkynyl, wherein, $C_{2-10}$ in the —$C_{2-10}$haloaklynyl or halo$C_{2-10}$alkynyl indicates that the total carbon atoms of the alkynyl are 2 to 10. In some embodiments, the —$C_{2-10}$haloalkynyl is the —$C_{2-6}$haloalkynyl. In some embodiments, the —$C_{2-6}$haloalkynyl is the —$C_{2-3}$haloalkynyl. In some embodiments, the —$C_{2-3}$haloalkynyl is (ethynyl or propynyl) substituted with 1, 2, 3, 4, 5, or 6 —F.

The term "alkoxy", as used herein, unless otherwise indicated, are oxygen ethers formed from the previously described alkyl groups.

The term "haloalkoxy", as used herein, unless otherwise indicated, means the above-mentioned alkoxy substituted with one or more (for 1, 2, 3, 4, 5, or 6) halogen (—F, —Cl or —Br). In some embodiment, the haloalkoxy is interchangeable —$C_{1-10}$haloalkoxy or halo$C_{1-10}$alkoxy. In some embodiments, the haloalkoxy is interchangeable —$C_{1-6}$haloalkoxy or halo$C_{1-6}$alkoxy, wherein, $C_{1-6}$ in the —$C_{1-6}$haloakloxy or halo$C_{1-6}$alkoxy indicates that the total carbon atoms of the alkoxy are 1 to 6. In some embodiments, the —$C_{1-6}$haloalkoxy is the —$C_{1-3}$haloalkoxy. In some embodiments, the —$C_{1-3}$haloalkoxy is (methoxy, ethoxy, propoxy or isopropoxy) substituted with 1, 2, 3, 4, 5, or 6 —F; preferably, the —$C_{1-3}$haloalkoxy is —$OCF_3$.

The term "carbocyclic ring", as used herein, unless otherwise indicated, refers to a totally saturated or partially saturated monocyclic, bicyclic, bridged, fused, or sipiro ring non-aromatic ring only containing carbon atoms as ring members. The term "carbocyclyl" as used herein, unless otherwise indicated, means a monovalent group obtained by removal of a hydrogen atom on the ring carbon atom from the carbocyclic ring defined in the present invention. The carbocyclic ring is interchangeable with the carbocyclyl ring in the present invention. In some embodiments, the carbocyclic ring is a three to twenty membered (such as 3-, 4-, 5-, 6-, 7-, 8-, 9-, 10-, 11-, 12-, 13-, 14-, 15-, 16-, 17-, 18-, 19- or 20-membered) carbocyclic ring and is either fully saturated or has one or more degrees of unsaturation. Multiple degrees of substitution, for example, one, two, three, four, five or six, are included within the present definition. The carbocyclic ring includes a cycloalkyl ring in which all ring carbon atoms are saturated, a cycloalkenyl ring which contains at least one double bond (preferred contain one double bond), and a cycloalkynyl ring which contains at least one triple bond (preferred contain one triple bond). Exemplary cycloalkyl includes but not limited to cyclopropyl, cyclobutyl, cyclopentyl, cyclohexyl, cycloheptyl, cyclooctyl, cyclononyl, cyclodecyl and the like. Exemplary cycloalkenyl includes but not limited to cyclopentenyl, cyclohexenyl, cycloheptenyl, cyclooctenyl, cyclononenyl, cyclodecenyl and the like. The carbocyclyl ring includes a monocyclic carbocyclyl ring, and a bicyclic or polycyclic carbocyclyl ring in which one, two or three or more atoms are shared between the rings. The term "spirocyclic carbocyclic ring" refers to a carbocyclic ring in which each of the rings only shares one ring atom with the other ring. In some embodiments, the spirocyclic ring is bicyclic spirocyclic ring. The spirocyclic carbocyclic ring includes a spirocyclic cycloalkyl ring and a spirocyclic cycloalkenyl ring and a spirocyclic cycloalkynyl ring. The term "fused carbocyclic ring" refers to a carbocyclic ring in which each of the rings shares two adjacent ring atoms with the other ring. In some embodiments, the fused ring is a bicyclic fused ring. The fused carbocyclic ring includes a fused cycloalkyl ring and a fused cycloalkenyl ring and a fused cycloalkynyl ring. A monocyclic carbocyclic ring fused with an aromatic ring (such as phenyl) is included in the definition of the fused carbocyclic ring. The term "bridged carbocyclic ring" refers to a carbocyclic ring that includes at least two bridgehead carbon ring atoms and at least one bridging carbon atom. In some embodiments, the bridged ring is bicyclic bridged ring. The bridged carbocyclic ring includes a bicyclic bridged carbocyclic ring which includes two bridgehead carbon atoms and a polycyclic bridged carbocyclic ring which includes more than two bridgehead carbon atoms. The bridged carbocyclic ring includes a bridged cycloalkyl ring, a bridged cycloalkenyl ring and a bridged cycloalkynyl ring. Examples of monocyclic carbocyclyl and bicyclic carbocyclyl include but not limit to cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, and 1-cyclohex-3-enyl.

The term "heterocyclic ring", as used herein, unless otherwise indicated, refers to a totally saturated or partially saturated monocyclic, bicyclic, bridged, fused, or spiro ring non-aromatic ring containing not only carbon atoms as ring members and but also containing one or more (such as 1, 2, 3, 4, 5, or 6) heteroatoms as ring members. Preferred heteroatoms include N, O, S, N-oxides, sulfur oxides, and sulfur dioxides. The term "heterocyclyl" as used herein, unless otherwise indicated, means a monovalent group obtained by removal of a hydrogen atom on the ring carbon atom or the ring heteroatom from the heterocyclic ring defined in the present invention. The heterocyclic ring is interchangeable with the heterocyclyl ring in the present invention. In some embodiments, the heterocyclic ring is a three to twenty membered (such as 3-, 4-, 5-, 6-, 7-, 8-, 9-, 10-, 11-, 12-, 13-, 14-, 15-, 16-, 17-, 18-, 19- or 20-membered) heterocyclic ring and is either fully saturated or has one or more degrees of unsaturation. Multiple degrees of substitution, for example, one, two, three, four, five or six, are included within the present definition. The heterocyclic ring includes a heterocycloalkyl ring in which all ring carbon atoms are saturated, a heterocycloalkenyl ring which contains at least one double bond (preferred contain one double bond), and a heterocycloalkynyl ring which contains at least one triple bond (preferred contain one triple bond). The heterocyclyl ring includes a monocyclic heterocyclyl ring, and a bicyclic or polycyclic heterocyclyl ring in which one, two or three or more atoms are shared between the rings. The term "spirocyclic heterocyclic ring" refers to a heterocyclic ring in which each of the rings only shares one ring atom with the other ring. In some embodiments, the spirocyclic ring is bicyclic spirocyclic ring. The spirocyclic heterocyclic ring includes a spirocyclic heterocycloalkyl ring and a spirocyclic heterocycloalkenyl ring and a spirocyclic heterocycloalkynyl ring. The term "fused heterocyclic ring" refers to a heterocyclic ring in which each of the rings shares two adjacent ring atoms with the other ring. In some embodiments, the fused ring is a bicyclic fused ring. The fused heterocyclic ring includes a fused heterocycloalkyl ring and a fused heterocycloalkenyl ring and a fused heterocycloalkynyl ring. A monocyclic heterocyclic ring fused with an aromatic ring (such as phenyl) is included in the definition of the fused heterocyclic ring. The term "bridged heterocyclic ring" refers to a heterocyclic ring that includes at least two bridgehead ring atoms and at least one bridging atom. In some embodiments, the bridged ring is bicyclic bridged ring. The bridged heterocyclic ring includes a bicyclic bridged heterocyclic ring which includes two bridgehead atoms and a polycyclic bridged heterocyclic ring which includes more than two bridgehead atoms. The bridged heterocyclic ring includes a bridged heterocycloalkyl ring, a bridged heterocycloalkenyl ring and a bridged heterocycloalkynyl ring. Examples of such heterocyclyl include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "aryl", as used herein, unless otherwise indicated, refers to a mono or polycyclic aromatic ring system only containing carbon ring atoms. The preferred aryls are mono cyclic or bicyclic 6-10 membered aromatic rings. Phenyl and naphthyl are preferred aryls.

The term "heteroaryl", as used herein, unless otherwise indicated, represents an aromatic ring containing carbons and one or more (such as 1, 2, 3 or 4) heteroatoms selected from N, O or S. The heteroaryl may be monocyclic or polycyclic. A monocyclic heteroaryl group may have 1 to 4 heteroatoms in the ring, while a polycyclic heteroaryl may contain 1 to 10 heteroatoms. A polycyclic heteroaryl ring may contain fused ring junction, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms), preferred monocyclic heteroaryl is 5 membered heteroaryl including 1, 2, 3 or 4 heteroatoms selected from N, O or S, or 6 membered heteroaryl including 1 or 2 heteroatoms selected from N. Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyladeninyl, quinolinyl or isoquinolinyl.

The term "one or more", as used herein, unless otherwise indicated, refers to one or more than one. In some embodiments, "one or more" refers to 1, 2, 3, 4, 5 or 6. In some embodiments, "one or more" refers to 1, 2, 3 or 4. In some embodiments, "one or more" refers to 1, 2, or 3. In some embodiments, "one or more" refers to 1 or 2. In some embodiments, "one or more" refers to 1. In some embodiments, "one or more" refers to 2. In some embodiments, "one or more" refers to 3. In some embodiments, "one or more" refers to 4. In some embodiments, "one or more" refers to 5. In some embodiments, "one or more" refers to 6.

The term "substituted", as used herein, unless otherwise indicated, refers to a hydrogen on the carbon atom or a hydrogen on the nitrogen atom is replaced by a substituent. When one or more substituents are substituted on a ring in the present invention, it means that each of substituents may be respectively independently substituted on every ring atom of the ring including but not limited to a ring carbon atom or a ring nitrogen atom. In addition, when the ring is a polycyclic ring, such as a fused ring, a bridged ring or a spiro ring, each of substituents may be respectively independently substituted on every ring atom of the polycyclic ring. In some embodiments, the substitution does not occur on the fused atoms when the ring is a fused ring.

The term "oxo" refers to oxygen atom together with the attached carbon atom forms the group

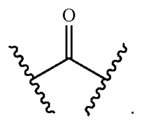 [SMILES: *C(*)=O]

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds in the present invention are intended for pharmaceutical use they are preferably provided in substantially pure form, for example at least 60% pure, more suitably at least 75% pure, especially at least 98% pure (% are on a weight for weight basis).

The present invention includes within its scope the prodrug of the compounds of this invention. In general, such prodrug will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The present invention includes all stereoisomers of the compound and pharmaceutically acceptable salts thereof. Further, mixtures of stereoisomers as well as isolated specific stereoisomers are also included. During the course of the synthetic procedures used to prepare such compounds or in using racemization or epimerization procedures known to those skilled in the art, the products of such procedures can be a mixture of stereoisomers.

The term "stereoisomer" as used in the present invention refers to an isomer in which atoms or groups of atoms in the molecule are connected to each other in the same order but differ in spatial arrangement, including conformational isomers and configuration isomers. The configuration isomers include geometric isomers and optical isomers, and optical isomers mainly include enantiomers and diastereomers. The invention includes all possible stereoisomers of the compound.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^{1}H$ (hydrogen), $^{2}H$ (deuterium) and $^{3}H$ (tritium). They are also commonly denoted as D for deuterium and T for tritium. In the application, $CD_3$ denotes a methyl group wherein all of the hydrogen atoms are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent.

The term "deuterated derivative", used herein, unless otherwise indicated, refers to a compound having the same chemical structure as a reference compound, but with one or more hydrogen atoms replaced by a deuterium atom ("D"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivative described herein. Thus, unless otherwise stated, when a reference is made to a "deuterated derivative" of a compound of the disclosure, at least one hydrogen is replaced with deuterium at well above its natural isotopic abundance (which is typically about 0.015%) In some embodiments, the deuterated derivative of the disclosure have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at lease 6333.3 (95% deuterium incorporation, at least 6466.7 (97% deuterium incorporation, or at least 6600 (99% deuterium incorporation).

When a tautomer of the compound in the present invention exists, the present invention includes any possible tautomer and pharmaceutically acceptable salts thereof, and mixtures thereof, except where specifically stated otherwise.

The compounds described herein can also inhibit PARP7 protein function through incorporation into agents that catalyze the destruction of PARP7 protein. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. Preferably, the portion of the PROTAC that engages the E3 ligase is connected to the portion of the PROTAC that engages the target protein via a linker which consists of a variable chain of atoms. Recruitment of PARP-7 protein to the E3 ligase will thus result in the destruction of the PARP-7 protein. The variable chain of atoms can include, for example, rings, heteroatoms, and/or repeating polymeric units. It can be rigid or flexible. It can be attached to the two portions described above using standard techniques in the art of organic synthesis.

The pharmaceutical compositions of the present invention comprise a compound in present invention (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds in present invention or a prodrug or a metabolite or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound in the present invention or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt. The compounds of the present invention or pharmaceutically acceptable salts thereof, can also be included in pharmaceutical compositions in combination with one or more other therapeutically active compounds.

The pharmaceutical carrier employed can be, for example, a solid, liquid or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 0.05 to about 95 percent of the total composition. Unit dosage forms will generally contain between from about 0.01 mg to about 2 g of the active ingredient, typically 0.01 mg, 0.02 mg, 1 mg, 2 mg, 3 mg, 4 mg, 5 mg, 6 mg, 7 mg, 8 mg, 9 mg, 10 mg, 25 mg, 50 mg, 100 mg, 200 mg, 300 mg, 400 mg, 500 mg, 600 mg, 800 mg, 1000 mg, 1500 mg or 2000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder or the like. Further, the compositions can be in a form suitable for use in transdermal devices. These formulations may be prepared, utilizing a compound in the present invention or a pharmaceutically acceptable salt thereof, via conventional processing methods. As an example, a cream or ointment is prepared by admixing hydrophilic material and water, together with about 0.05 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described herein or pharmaceutically acceptable salts thereof, may also be prepared in powder or liquid concentrate form.

Generally, dosage levels on the order of from about 0.001 mg/kg to about 150 mg/kg of body weight per day are useful in the treatment of the above-indicated conditions or alternatively about 0.05 mg to about 7 g per patient per day. For example, inflammation, cancer, psoriasis, allergy/asthma, disease and conditions of the immune system, disease and conditions of the central nervous system (CNS), may be effectively treated by the administration of from about 0.001 to 50 mg of the compound per kilogram of body weight per day or alternatively about 0.05 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Unless otherwise apparent from the context, when a value is expressed as "about" X or "approximately" X, the stated value of X will be understood to be accurate to ±10%, preferably, ±5%, ±2%.

The term "subject" refers to an animal. In some embodiments, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject. As used herein, a subject is "in need of" a treatment if such subject would benefit biologically, medically or in quality of life from such treatment.

The term "inhibition", "inhibiting" or "inhibit" refers to the reduction or suppression of a given condition, symptom, or disorder, or disease, or a significant decrease in the baseline activity of a biological activity or process.

The term “treat”, “treating” or “treatment” of any disease or disorder refers in one embodiment, to ameliorating the disease or disorder (i.e., slowing or arresting or reducing the development of the disease or at least one of the clinical symptoms thereof). In another embodiment, “treat”, “treating” or “treatment” refers to alleviating or ameliorating at least one physical parameter including those which may not be discernible by the patient. In yet another embodiment, “treat”, “treating” or “treatment” refers to modulating the disease or disorder, either physically, (e.g., stabilization of a discernible symptom), physiologically, (e.g., stabilization of a physical parameter), or both. In yet another embodiment, “treat”, “treating” or “treatment” refers to preventing or delaying the onset or development or progression of the disease or disorder.

All methods described herein can be performed in any suitable order unless otherwise indicated herein or otherwise clearly contradicted by context. The use of any and all examples, or exemplary language (e.g. “such as”) provided herein is intended merely to belier illuminate the invention and does not pose a limitation on the scope of the invention otherwise claimed.

These and other aspects will become apparent from the following written description of the invention.

Methods of Preparation

Compounds of the present invention can be synthesized from commercially available reagents using the synthetic methods and reaction schemes described herein. The examples which outline specific synthetic route, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

EXAMPLES

The following Examples are provided to better illustrate the present invention. All parts and percentages are by weight and all temperatures are degrees Celsius, unless explicitly stated otherwise. The following abbreviations have been used in the examples:

| | |
|---|---|
| DMF | Dimethylformamide |
| EA | Ethyl acetate |
| $CH_3CN$ | Acetonitrile |
| MeOH | Methanol |
| DCM | Dichloromethane |
| NaH | Sodium hydride |
| CuI | Cuprous iodide |
| NMP | 1-methyl-2-pyrrolidon |
| TMSI | Trimethylimidazosilane |
| THF | Tetrahydrofuran |
| Hex | Hexane |
| $Na_2SO_4$ | Sodium sulfate |
| TEA | Triethylamine |
| $H_2O$ | Water |
| LiOH | Lithium hydroxide |
| Pd/C | Palladium carbon |
| t-BuOK | Potassium tert-butoxide |
| t-BuOH | tert-Butanol |
| t-BuONa | Sodium tert-butoxide |
| PyBOP | Benzotriazole-1-yl-oxytripyrrolidino-phosphonium hexafluorophosphate |
| $Cs_2CO_3$ | Cesium carbonate |
| $K_2CO_3$ | Potassium carbonate |

-continued

| | |
|---|---|
| $Na_2CO_3$ | Sodium carbonate |
| HCl | Hydrochloric acid |
| HATU | Azabenzotriazolyl tetramethyluronium hexafluorophosphate |
| TfOH | Methanesulfonic acid |
| TFA | 2,2,2-Trifluoroacetic acid |
| $Mg(ClO_4)_2$ | Magnesium perchlorate |
| $POCl_3$ | Phosphoryl chloride |
| $NaHCO_3$ | Sodium bicarbonate |
| $NH_4Cl$ | Ammonium chloride |
| DMSO | Dimethyl sulfoxide |
| $Zn(CN)_2$ | Zinc cyanide |
| MeMgBr | Methylmagnesium bromide |
| $Pd(PPh_3)_4$ | Tetrakis(triphenylphosphine)palladium |
| $NaNO_2$ | Sodium nitrite |
| HOAc | Acetic acid |
| $CH_3I$ | Methyl iodide |
| $Pd(dppf)Cl_2$ | [1,1'-Bis(diphenylphosphino)ferrocene] dichloropalladium(II) |
| DIPEA | N,N-Diisopropylethylamine |
| CsF | Cesium fluoride |
| m-CPBA | 3-Chloroperbenzoic acid |
| $Na_2S_2O_3$ | Sodium Thiosulfate |
| MTBE | methyl tert-butyl ether |
| $LiAlH_4$ | Lithium Aluminum Hydride |
| MsCl | Methanesulfonyl chloride |
| n-BuLi | n-Butyllithium |
| $CHCl_3$ | Trichloromethane |
| DAST | Diethylaminosulphur trifluoride |
| $NaBH_4$ | Sodium borohydride |
| NCS | N-Chlorosuccinimide |
| $Cu(OAc)_2$ | Cupric Acetate Monohydrate |
| KOAc | Potassium Acetate |
| STAB | Sodium triacetoxyborohydrid |
| $T_3P$ | Propyl phosphate tricyclic anhydride |
| sat. | Saturated |
| h/hrs | Hour/hours |

Intermediate A1 (INT A1)

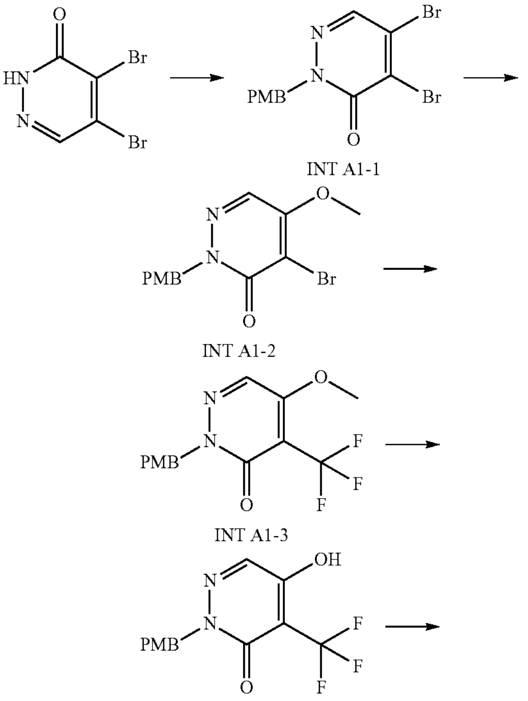

INT A1-1

INT A1-2

INT A1-3

INT A1-4

-continued

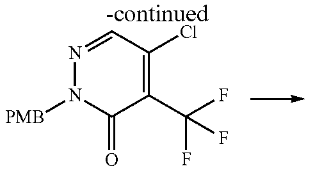

INT A1-5

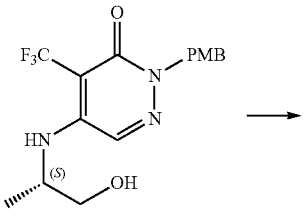

INT A1-6

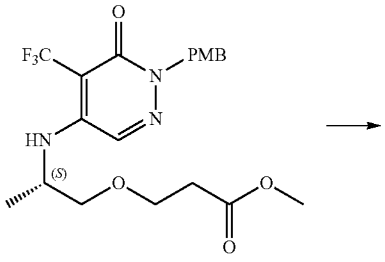

INT A1-7

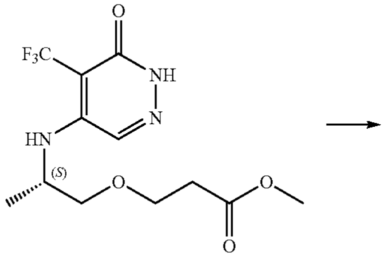

INT A1-8

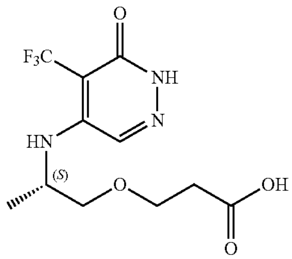

INT A1

Step 1: A solution of 4,5-dibromopyridazin-3(2H)-one (204.14 g, 0.80 mol, 1.0 eq.) dissolved in DMF (1.0 L) was purged and maintained with an inert atmosphere of nitrogen, cooled to 0~10° C., and then NaH (42.17 g, 1.05 mol, 1.31 eq.) (600% in mineral oil) was added slowly. The resulting mixture was stirred at 0° C. for 1 h, and then 1-(chloromethyl)-4-methoxybenzene (193.71 g, 1.24 mmol, 1.54 eq.) was added. The reaction mixture was stirred for 3 hrs at room temperature, quenched with water (1.5 L) and extracted with DCM (1.5 L×2). The organic layers were combined, dried over anhydrous $Na_2SO_4$, filtered, and the filtrate was concentrated under reduced pressure to obtain a residue. The residue was dispersed in MeOH (800 mL), stirred for 1 h at room temperature, and then filtered. The filter cake was dried under vacuum to afford INT A1-1 (245.01 g, yield 81%) as a solid. LCMS: m/z=375 $[M+1]^+$.

Step 2: A mixture of INT A1-1 (242.91 g, 0.65 mol, 1.0 eq.), potassium hydroxide (143.46 g, 2.56 mol, 3.94 eq.) and MeOH (2.5 L) was stirred for 4 hrs at room temperature, and then concentrated under reduced pressure to precipitate the solid. The solid was collected by filtration and then dispersed in water (1.8 L) to obtain a suspension which was stirred for 1 h at room temperature. The resulting mixture was filtered and the filter cake was dried under vacuum to afford INT A1-2 (118.86 g, yield 56%) as a solid. LCMS: m/z=325, 327 $[M+1]^+$.

Step 3: INT A1-2 (80.76 g, 0.25 mol, 1.0 eq.), methyl 2,2-difluoro-2-(fluorosulfonyl)acetate (159.59 g, 0.83 mol, 3.345 eq.), and CuI (74.04 g, 0.39 mol, 1.57 eq.) were dispersed in NMP (800 mL). The reaction mixture was purged and maintained with an inert atmosphere of nitrogen, stirred for 4.5 hrs at 100° C., quenched with water (1.5 L), and then extracted with DCM (500 mL×3). The organic layers were combined and concentrated under reduced pressure to obtain a residue. The residue was purified with silica gel column (eluted with EA/hexane) to obtain an oil which was dispersed in $H_2O$ (LOL) to precipitate the solid. The solid was obtained by filtration and washed with MeOH (100 mL), dried under vacuum to afford INT A1-3 (67.3 g, yield 86%) as a white solid. LCMS: m/z=315 $[M+1]^+$.

Step 4: A solution of INT A1-3 (60.34 g, 0.19 mol, 1.0 eq.) dissolved in NMP (600 mL) was purged and maintained with an inert atmosphere of nitrogen, and then TMSI (69.27 g, 0.35 mol, 1.80 eq.) was added dropwise at 20° C. The reaction mixture was stirred for 20 hrs at 85° C., quenched with water (850 $m_l$), and then extracted with EA (500 mL×3). The organic layers were combined, dried over anhydrous $Na_2SO_4$, and then concentrated under reduced pressure to obtain a residue which was purified with silica gel column chromatography (eluted with Hex/EA) to afford INT A1-4 (54.0 g, yield 94%) as a solid. LCMS: m/z=301 $[M+1]^+$.

Step 5: A solution of INT A1-4 (27.12 g, 90.33 mmol, 1.0 eq.) dissolved in DMF (250 mL) was purged and maintained with an inert atmosphere of nitrogen, cooled to 0-5° C., and then oxalic dichloride (33.25 g, 0.26 mol, 2.90 eq.) was added dropwise. The reaction mixture was stirred for 3 hrs at room temperature, quenched with sat. sodium carbonate aqueous (850 mL), and then extracted with EA (500 mL×3). The organic layers were combined, dried over anhydrous $Na_2SO_4$, and then concentrated under reduced pressure to obtain a residue which was purified with silica gel column (eluted with Hex/EA) to afford INT A1-5 (18.94 g, yield 66%) as a solid. LCMS: m/z=319 $[M+1]^+$.

Step 6: INT A1-5 (10.76 g, 33.76 mmol, 1.0 eq.), S-(+)-2-amino-1-propanol (3.43 g, 45.67 mmol, 1.35 eq.), and TEA (15 mL) were dissolved in $CH_3CN$ (100 mL). The reaction mixture was stirred for 18 hrs at 85° C. and concentrated under reduced pressure. The residue was purified with Prep-HPLC (C18 column, eluted with $CH_3CN$/$H_2O$) to afford INT A1-6 (10.29 g, yield 85%) as a solid. LCMS: m/z=358 $[M+1]^+$.

Step 7: INT A1-6 (9.15 g, 25.60 mmol, 1.0 eq.), methyl acrylate (15.83 g, 183.88 mmol, 7.18 eq.) and $Cs_2CO_3$ (42.73 g, 131.15 mmol, 5.12 eq.) were dispersed in $CH_3CN$ (150 mL). The reaction mixture was stirred for 8 hrs at room temperature and then filtered. The filtrate was concentrated under reduced pressure to obtain a residue which was purified with silica gel column (eluted with Hex/EA) to afford INT A1-7 (4.40 g, yield 39%) as a solid. LCMS: m/z=444 $[M+1]^+$.

Step 8: TfOH (45 mL) was added dropwise at room temperature to a solution of INT A1-7 (32.12 g, 72.44 mmol, 1.0 eq.) dissolved in TFA (200 mL). The reaction mixture was stirred for 2 hrs at room temperature, quenched with sat. sodium bicarbonate aqueous solution (850 mL) and then extracted with of EA (500 mL×3). The organic layers were combined, dried over anhydrous $Na_2SO_4$, and then concentrated under reduced pressure to obtain a residue which was purified with silica gel column (eluted with Hex/EA) to afford INT A1-8 (14.53 g, yield 62%) as a solid. LCMS: m/z=324 $[M+1]^+$.

Step 9: INT A1-8 (2.54 g, 7.86 mmol, 1.0 eq.) and LiOH (0.67 g, 24.98 mmol, 3.56 eq.) were dispersed in THF (50 mL) and water (10 mL). The reaction mixture was stirred for 4 hrs at room temperature, quenched with HCl aqueous (1N) and extracted with EA (30 mL×3). The organic layers were combined, dried over anhydrous $Na_2SO_4$, and then concentrated under reduced pressure to obtain a residue which was purified with Prep-HPLC (C18 column, eluted with $H_2O$/$CH_3CN$) to afford INT A1 (1.86 g, yield 77%). LCMS: m/z=310 $[M+1]^+$.

Intermediate A2 (INT A2)

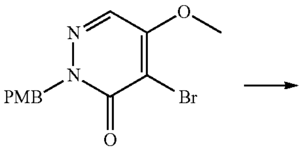

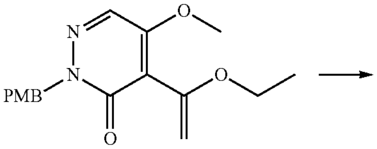

INT A2-1

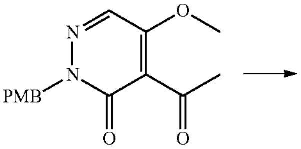

INT A2-2

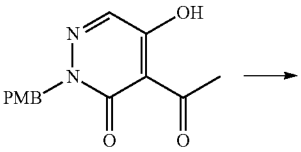

INT A2-3

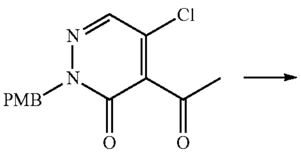

INT A2-4

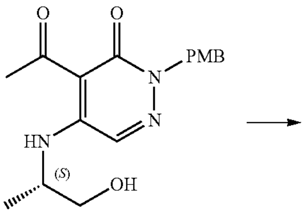

INT A2-5

-continued

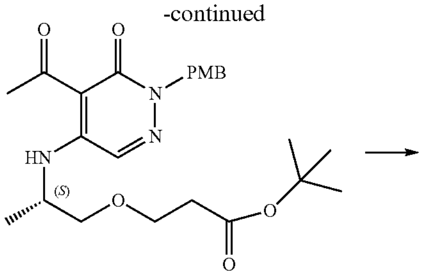

INT A2-6

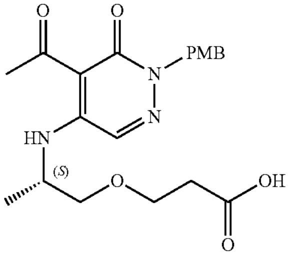

INT A2

Step 1: 4-Bromo-5-methoxy-2-(4-methoxybenzyl)pyridazin-3(2H)-one (81.14 g, 0.25 mol, 1.0 eq.), tributyl (1-ethoxyvinyl)stannane (99.34 g, 0.28 mol, 1.12 eq.), $Pd(PPh_3)_2Cl_2$ (20.39 g, 28.88 mmol, 0.12 eq.) and CsF (112.68 g, 0.74 mol, 2.96 eq.) were dispersed in 1,4-dioxane (600 mL). The reaction mixture was purged and maintained with an inert atmosphere of nitrogen, stirred for 4.5 hrs at 100° C. and then filtered. The filtrate was concentrated under reduced pressure to obtain a residue was purified with silica gel column (eluted with Hex/EA) to afford INT A2-1 (66.66 g, yield 84%). LCMS: m/z=317 $[M+1]^+$.

Step 2: 6N hydrochloric acid aqueous solution (200 mL) was added at room temperature to a solution of INT A2-1 (66.66 g, 0.21 mol, 1.0 eq.) dissolved in THF (600 mL). The reaction mixture was stirred for 3 hrs, quenched with sodium bicarbonate solution (800 mL), and then extracted with EA (800 mL×3). The organic layers were combined, dried over anhydrous $Na_2SO_4$, and then concentrated under reduce pressure to afford INT A2-2 (57.35 g, yield 94%). LCMS: m/z=289 $[M+1]^+$.

Step 3: NaOH aqueous solution (4N, 100 mL, 0.40 mol, 2.0 eq.) was added to a solution of INT A2-2 (57.35 g, 0.20 mmol, 1.0 eq.) dissolved in THF (800 mL). The reaction mixture was stirred for 3 hrs at 85° C., cooled to room temperature, quenched with HCl (2N, aq.), and then extracted with EA (500 mL×3). The organic layers were combined, dried over anhydrous $Na_2SO_4$, and then concentrated under reduced pressure to obtain a residue which was purified with a silica gel column (eluted with Hex/EA) to afford INT A2-3 (50.51 g, yield 92%). LCMS: m/z=275 $[M+1]^+$.

Step 4: A mixture of INT A2-3 (50.5 g, 0.18 mol, 1.0 eq.) and $POCl_3$ (100 mL) was stirred for 2 hrs at 95° C., cooled to room temperature, quenched with $NaHCO_3$ aqueous solution and extracted with EA (500 mL×3). The organic layers were combined, dried over anhydrous $Na_2SO_4$, and then concentrated under reduced pressure to obtain a residue which was purified with silica gel column (eluted with Hex/EA) to afford INT A2-4 (32.80 g). LCMS: m/z=293 $[M+1]^+$.

Step 5: INT A2-4 (32.80 g, 112.05 mmol, 1.0 eq.), S-(+)-2-amino-1-propanol (17.80 g, 236.99 mmol, 2.12 eq.), and TEA (35.60 g, 351.82 mmol, 3.14 eq.) were dispersed in $CH_3CN$ (200 mL). The reaction mixture was stirred for 18 hrs at 85° C., cooled to room temperature and concentrated under reduced pressure to obtain a residue which was purified with Prep-HPLC (C18 column, eluted with $H_2O$/$CH_3CN$) to afford INT A2-5 (36.08 g, yield 97%). LCMS: m/z=332 $[M+1]^+$.

Step 6: INT A2-5 (36.08 g, 108.88 mmol, 1.0 eq.), tert-butyl acrylate (65.20 g, 508.71 mmol, 4.67 eq.), and $Cs_2CO_3$ (96.70 g, 296.79 mmol, 2.73 eq.) were dispersed in $CH_3CN$ (500 mL). The reaction mixture was stirred for 8 hrs at room temperature, and then filtered. The filtrate was concentrated under reduced pressure to obtain a residue which was purified with silica gel column (eluted with Hex/EA) to afford INT A2-6 (38.87 g, yield 84%). LCMS: m/z=460 $[M+1]^+$.

Step 7: TFA (8 mL) was added dropwise at room temperature to a solution of INT A2-6 (2.83 g, 6.16 mmol, 1.0 eq.) dissolved in DCM (30 mL). The reaction mixture was stirred for 5 hrs at room temperature, quenched with saturated $NaHCO_3$ aqueous solution (100 mL), and then extracted with EA (100 mL×3). The organic layers were combined, dried over anhydrous $Na_2SO_4$ and concentrated under reduced pressure to afford a crude product (2.60 g) of INT A2 as a yellow oil which was used in next step without further purification. LCMS: m/z=404 $[M+1]^+$.

Intermediate A3 (INT A3)

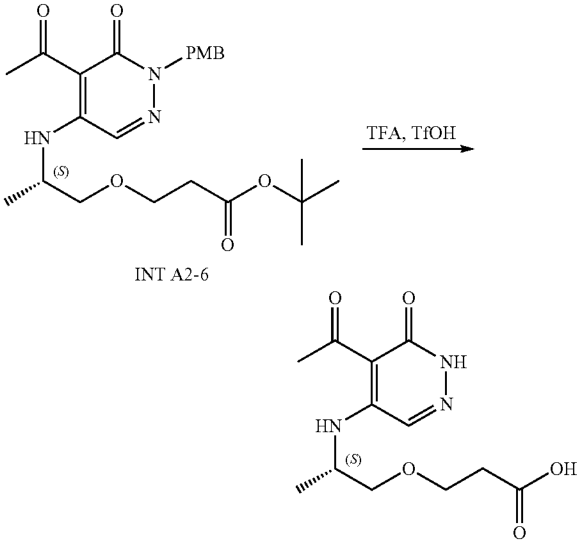

INT A2-6

INT A3

Step 1: TfOH (10 mL) was added dropwise at room temperature to a solution of INT A2-6 (43.4 g, 75.30 mmol, 1.0 eq.) dissolved in TFA (100 mL). The reaction mixture was stirred for 7 hrs at room temperature, quenched with saturated $NaHCO_3$ aqueous solution (850 mL), and extracted with EA (500 mL×3). The organic layers were combined, dried over anhydrous $Na_2SO_4$ and concentrated under reduced pressure to obtain a residue which was purified with Prep-HPLC (C18 column, eluted with $H_2O$/$CH_3CN$) to afford INT A3 (21.10 g, yield 98%). LCMS: m/z=284 $[M+1]^+$.

Intermediate A4 (INT A4)

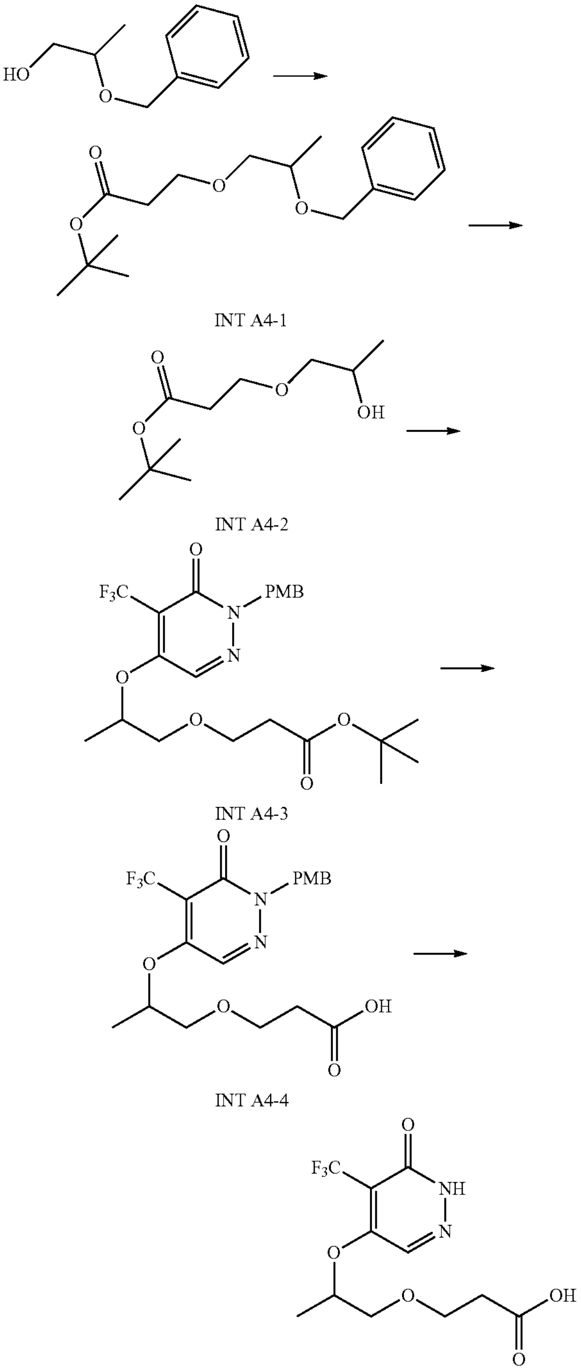
INT A4-1

INT A4-2

INT A4-3

INT A4-4

INT A4

Step 1: 2-(Benzyloxy)propan-1-ol (21.33 g, 128.33 mmol, 1.0 eq.), tert-butyl acrylate (70.84 g, 552.71 mmol, 4.31 eq.) and $Cs_2CO_3$ (125.61 g, 385.52 mmol, 3.00 eq.) were dispersed in DMSO (210 mL). The reaction mixture was stirred for 3 hrs at room temperature, poured into water (200 mL) and extracted with EA (200 mL×3). The organic layers were combined, dried over anhydrous $Na_2SO_4$, and then concentrated under reduced pressure to obtain a residue which was purified with Prep-HPLC (C18 column, eluted with $H_2O$/$CH_3CN$) to afford INT A4-1 (26.52 g). LCMS: m/z=295 $[M+1]^+$.

Step 2: A mixture of INT A4-1 (10.71 g, 36.38 mmol, 1.0 eq.), Pd/C (1.02 g, 9.58 mmol, 0.26 eq.) and MeOH (10 mL) was purged and maintained with an inert atmosphere of hydrogen, stirred for 48 hrs at room temperature, and then filtered. The filtrate was concentrated under reduced pressure to afford a crude product (9.15 g) containing INT A4-2 which was used in next step without further purification. LCMS: m/z=205 $[M+1]^+$.

Step 3: In an atmosphere of nitrogen, INT A4-2 (9.15 g, 44.80 mmol, 1.09 eq.), 5-chloro-2-(4-methoxybenzyl)-4-(trifluoromethyl)pyridazin-3(2H)-one (13.11 g, 41.14 mmol, 1.0 eq.) and t-BuONa (5.52 g, 57.44 mmol, 1.40 eq.) were dispersed in DCM (50 mL). The reaction mixture was stirred for 2 hrs at room temperature, washed with $NH_4Cl$ (aq.) and then extracted with DCM (50 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT A4-3 (12.81 g). LCMS: m/z=487 $[M+1]^+$.

Step 4: TFA (10 mL) was added dropwise at room temperature to a solution of INT A4-3 (12.81 g, 26.33 mmol, 1.0 eq.) dissolved in DCM (40 mL). The reaction mixture was stirred for 2 hrs at room temperature, quenched with saturated $NaHCO_3$ aqueous solution (50 mL), and extracted with of EA (100 mL×3). The organic layers were combined, dried over anhydrous $Na_2SO_4$, and then concentrated under reduced pressure to afford a crude product (11.33 g) of INT A4-4 which was used in next step without further purification. LCMS: m/z=431 $[M+1]^+$.

Step 5: TfOH (30 mL) was added dropwise at room temperature to a solution of INT A4-4 (12.81 g, crude) dissolved in TFA (200 mL). The reaction mixture was stirred for 2 hrs at room temperature, quenched with saturated $NaHCO_3$ aqueous solution (850 mL), and then extracted with of EA (500 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT A4 (5.23 g, yield 64%). LCMS: m/z=311 $[M+1]^+$.

The following intermediates were synthesized using the above procedure with the corresponding starting material.

| INT | Structure | Starting material | LCMS (ESI, m/z): $[M + H]^+$ |
|---|---|---|---|
| INT A5 | 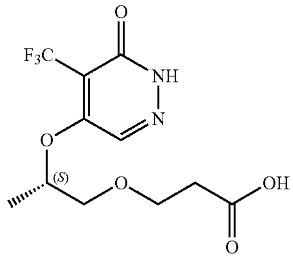 | 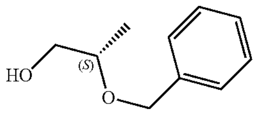 | 311 |
| INT A6 | 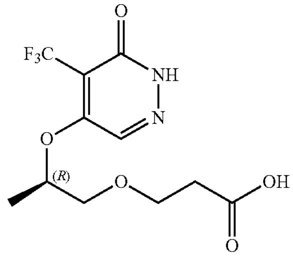 | 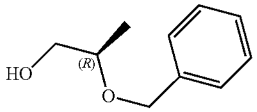 | 311 |

Intermediate A7 (INT A7)

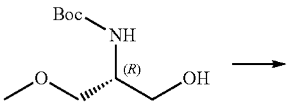

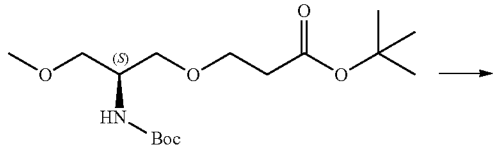

INT A7-1

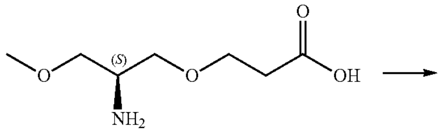

INT A7-2

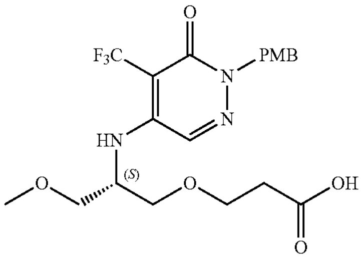

INT A7

Step 1: Tert-butyl (R)-(1-hydroxy-3-methoxypropan-2-yl) carbamate (19.29 g, 93.98 mmol, 1.0 eq.), tert-butyl acrylate (57.36 g, 447.54 mmol, 4.76 eq.) and $Cs_2CO_3$ (100.01 g, 306.95 mmol, 3.27 eq.) were dispersed in $CH_3CN$ (500 mL). The reaction mixture was stirred for 16 hrs at room temperature, poured into water (200 mL) and extracted with EA (200 mL×3). The organic layers were combined, dried over anhydrous $Na_2SO_4$, and then concentrated under reduced pressure to obtain a residue which was purified with silica gel column (eluted with Hex/EA) to afford INT A7-1 (20.76 g, yield 66%). LCMS: m/z=334 $[M+1]^+$.

Step 2: TFA (10 mL) was added dropwise at room temperature to a solution of INT A7-1 (20.66 g, 61.96 mmol, 1.0 eq.) dissolved in DCM (200 mL). The reaction mixture was stirred for 2 hrs at room temperature and then concentrated under reduced pressure to afford a crude product (23.38 g) of INT A7-2 which was used in next step without further purification. LCMS: m/z=178 $[M+1]^+$.

Step 3: In an atmosphere of nitrogen, the crude product (1.01 g) of INT A7-2, 5-chloro-2-(4-methoxybenzyl)-4-(trifluoromethyl)pyridazin-3(2H)-one (1.13 g, 3.55 mol, 1.32 eq.) and $Et_3N$ (2.88 g, 28.50 mmol, 10.63 eq.) were dispersed in $CH_3CN$ (10 mL). The reaction mixture was stirred for 5 hrs at 70° C., cooled to room temperature and then concentrated under reduced pressure to obtain a residue which was purified with Prep-HPLC (C18 column, eluted with $H_2O/CH_3CN$) to afford INT A7 (0.92 g, yield 75%). LCMS: m/z=460 $[M+1]^+$.

Intermediate A8 (INT A8)

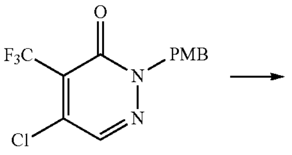

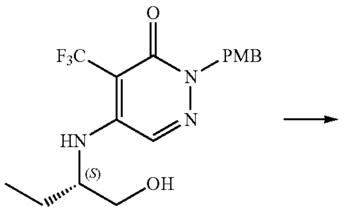

INT A8-1

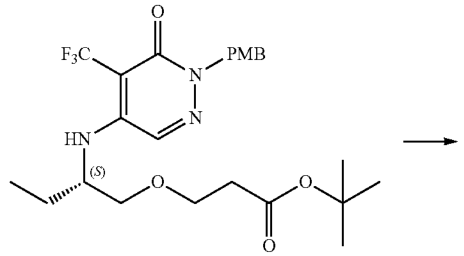

INT A8-2

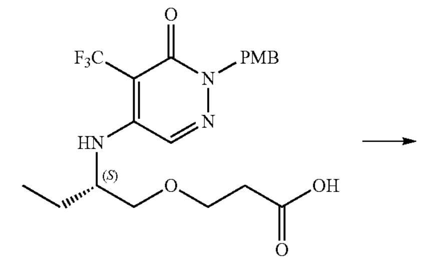

INT A8-3

-continued

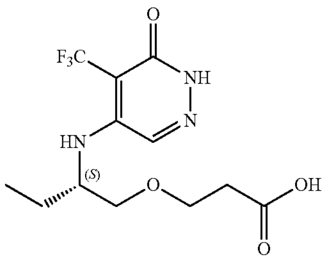

INT A8

Step 1: 5-Chloro-2-(4-methoxybenzyl)-4-(trifluoromethyl)pyridazin-3(2H)-one (10.00 g, 31.38 mmol, 1.0 eq.), (S)-2-aminobutan-1-ol (4.07 g, 45.66 mmol, 1.46 eq.) and TEA (15 mL) were dissolved in $CH_3CN$ (100 mL). The reaction mixture was stirred for 4 hrs at 70° C., cooled to room temperature and concentrated under reduced pressure to obtain a residue. The residue was purified with Prep-HPLC (C18 column, eluted with $CH_3CN/H_2O$) to afford INT A8-1 (11.05 g, yield 94%). LCMS: m/z=372 $[M+1]^+$.

Step 2: INT A8-1 (11.05 g, 29.78 mmol, 1.0 eq.), tert-butyl acrylate (19.74 g, 154.02 mmol, 5.17 eq.) and $Cs_2CO_3$ (29.13 g, 89.41 mmol, 3.00 eq.) were dispersed in DMSO (100 mL). The reaction mixture was stirred for 3 hrs at room temperature, poured into water (100 mL) and extracted with EA (100 mL×3). The organic layers were combined, dried over anhydrous $Na_2SO_4$, and concentrated under reduced pressure to obtain a residue which was purified with silica gel column (eluted with Hex/EA) to afford INT A8-2 (5.58 g, yield 37%). LCMS: m/z=500 $[M+1]^+$.

Step 3: TFA (10 mL) was added dropwise at room temperature to a solution of INT A8-2 (5.47 g, 10.95 mmol, 1.0 eq.) dissolved in DCM (50 mL). The reaction mixture was stirred for 5 hrs at room temperature, quenched with $NaHCO_3$ aqueous solution (50 mL), and then extracted with of EA (100 mL×3). The organic layers were combined, dried over anhydrous $Na_2SO_4$, and then concentrated under reduced pressure to afford a crude product (4.85 g) of INT A8-3 which was used in next step without further purification. LCMS: m/z=444 $[M+1]^+$.

Step 4: The crude product (4.85 g) of INT A8-3 was dissolved in TFA (60 mL) to obtain a solution, and then TfOH (6 mL) was added dropwise at room temperature. The reaction mixture was stirred for 2 hrs at room temperature, quenched with saturated $NaHCO_3$ aqueous solution (200 mL) and then extracted with of EA (200 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT A8 (1.41 g, yield 39%). LCMS: m/z=324 $[M+1]^+$.

Intermediate A9 (INT A9)

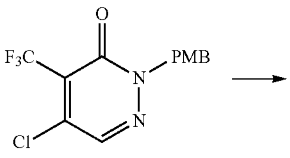

-continued

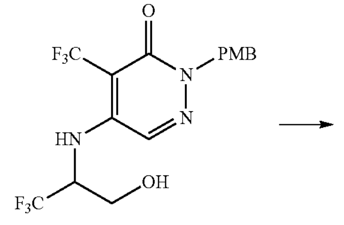

INT A9-1

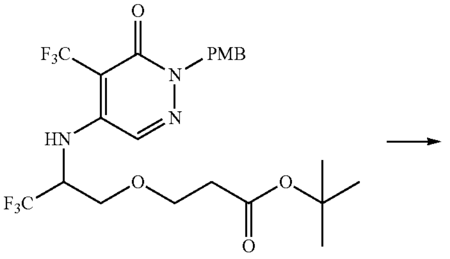

INT A9-2

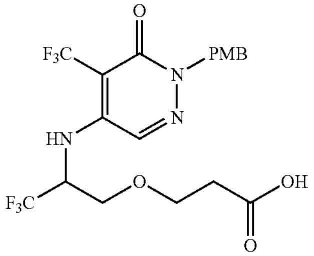

INT A9

Step 1: 5-Chloro-2-(4-methoxybenzyl)-4-(trifluoromethyl)pyridazin-3(2H)-one (12.60 μg, 39.54 mmol, 2.11 eq.), 2-amino-3,3,3-trifluoropropan-1-ol hydrochloride (3.10 g, 18.73 mmol, 1.0 eq.) and $Cs_2CO_3$ (18.0 g, 55.25 mmol, 2.95 eq.) were dissolved in $CH_3CN$ (100 mL). The reaction mixture was stirred for 16 hrs at room temperature, and then filtered. The filtrate was concentrated under reduced pressure to obtain a residue which was purified with Prep-HPLC (C18 column, eluted with $CH_3CN/H_2O$) to afford INT A9-1 (0.82 g, yield 10%). LCMS: m/z=412 $[M+1]^+$.

Step 2: INT A9-1 (0.80 g, 1.95 mmol, 1.0 eq.), tert-butyl acrylate (2.56 g, 19.97 mmol, 10.27 eq.) and $Cs_2CO_3$ (3.24 g, 9.94 mmol, 5.11 eq.) were dispersed in DMSO (8 mL). The reaction mixture was stirred for 5 hrs at room temperature, poured into water (50 mL) and extracted with EA (50 mL×3). The organic layers were combined, dried over anhydrous $Na_2SO_4$, and then concentrated under reduced pressure to obtain a residue which was purified with silica gel column (eluted with Hex/EA) to afford INT A9-2 (0.32 g, yield 30%). LCMS: m/z=540 $[M+1]^+$.

Step 3: TFA (2 mL) was added dropwise at room temperature to a solution of INT A9-2 (0.32 g, 0.59 mmol, 1.0 eq.) dissolved in DCM (10 mL). The reaction mixture was stirred for 3 hrs at room temperature, quenched with $NaHCO_3$ aqueous solution (50 mL), and then extracted with of EA (50 mL×3). The organic layers were combined, dried over anhydrous $Na_2SO_4$, and then concentrated under reduced pressure to afford a crude product (0.27 g) of INT A9 which was used in next step without further purification. LCMS: m/z=484 $[M+1]^+$.

Intermediate A10 (INT A10)

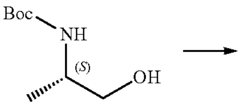

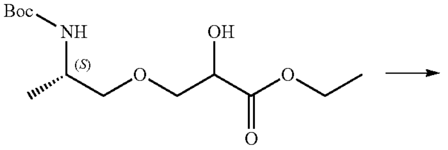

INT A10-1

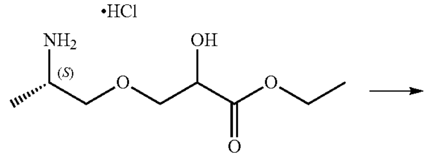

INT A10-2

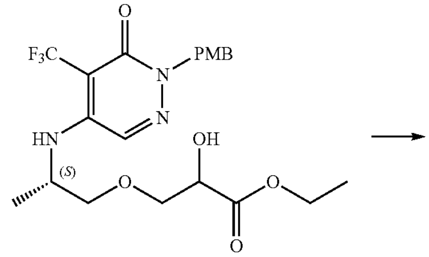

INT A10-3

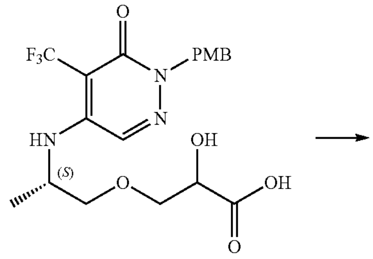

INT A10-4

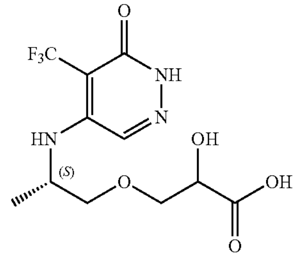

INT A10

Step 1: Ethyl oxirane-2-carboxylate (27.84 g, 239.76 mmol, 2.10 eq.), tert-butyl (S)-(1-hydroxypropan-2-yl)carbamate (20.03 g, 114.31 mmol, 1.0 eq.) and $Mg(ClO_4)_2$ (49.69 g, 222.62 mmol, 1.95 eq.) were dispersed in EA (200 mL). The reaction mixture was stirred for 64 hrs at room temperature, and then filtered. The filtrate was concentrated under reduced pressure to obtain a residue which was purified with silica gel column (eluted with Hex/EA) to afford INT A10-1 (1.10 g, yield 3%). LCMS: m/z=292 $[M+1]^+$.

Step 2: A solution of INT A10-1 (0.99 g, 3.40 mmol, 1.0 eq.) dissolved in HCl/1,4-dioxane (10 mL, 1N) was stirred for 2 hrs at room temperature and concentrated under reduced pressure to afford a crude product (0.96 g) of INT A10-2 which was used in next step without further purification. LCMS: m/z=192[M+1]$^+$.

Step 3: 5-Chloro-2-(4-methoxybenzyl)-4-(trifluoromethyl)pyridazin-3(2H)-one (1.40 g, 4.39 mmol, 1.29 eq.), INT A10-2 (0.96 g, 3.40 mmol, 1.0 eq.) and TEA (3 mL) were dissolved in $CH_3CN$ (10 mL). The reaction mixture was stirred for 2 hrs at 60° C. and then concentrated under reduced pressure to obtain a residue which as purified with Prep-HPLC (C18 column, eluted with $CH_3CN/H_2O$) to afford INT A10-3 (1.20 g, yield 62%). LCMS: m/z=474 [M+1]$^+$.

Step 4: INT A10-3 (1.20 g, 2.53 mmol, 1.0 eq.) and LiOH (0.18 g, 7.52 mmol, 2.97 eq.) were dispersed in a mixed solvent of THF (10 mL) and water (3 mL). The reaction mixture was stirred for 3 hrs at room temperature, quenched with HCl aqueous solution (1N), and extracted with EA (30 mL×3). The organic layers were combined and dried over anhydrous $Na_2SO_4$, and concentrated under reduced pressure to obtain a residue which was purified with Prep-HPLC (C18 column, eluted with $H_2O/CH_3CN$) to afford INT A10-4 (0.40 g, yield 35%). LCMS: m/z=446 [M+1]$^+$.

Step 5: TfOH (1 mL) was added dropwise at room temperature to a solution of INT A10-4 (0.40 g, 0.90 mmol, 1.0 eq.) dissolved in TFA (5 mL). The reaction mixture was stirred for 2 hrs at room temperature, quenched with saturated $NaHCO_3$ aqueous solution (850 mL), and then extracted with of EA (500 mL×3). The organic layers were combined and dried over anhydrous $Na_2SO_4$, and then concentrated under reduced pressure to afford a crude product (0.40 g) of INT A10 which was used in next step without further purification. LCMS: m/z=326 [M+1]$^+$.

Intermediate A11 (INT A11)

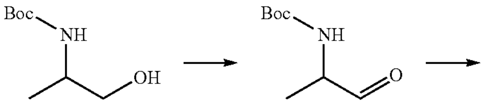

INT A11-1

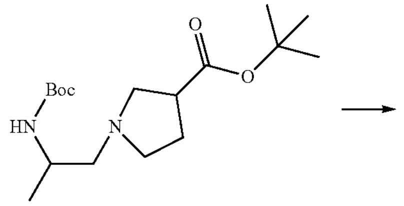

INT A11-2

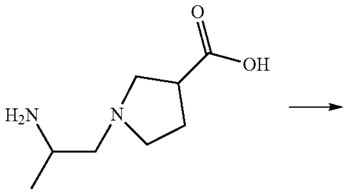

INT A11-3

-continued

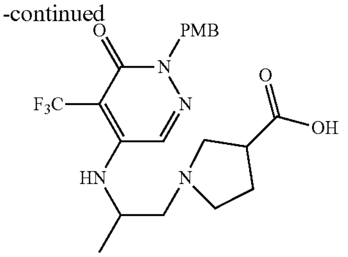

INT A11

Step 1: Dess-Martin periodinane (13.76 g, 32.44 mmol, 1.25 eq.) was added at 0° C. to a solution of tert-butyl (1-hydroxypropan-2-yl)carbamate (4.53 g, 25.85 mmol, 1.0 eq.) dissolved in DCM (90 mL). The reaction mixture was stirred for 2 hrs at room temperature, and then saturated $NaHCO_3$ aqueous solution (50 mL) was added. The resulting mixture was extracted with EA (100 mL×3). The organic layer were combined and concentrated under reduced pressure to obtain a residue which was purified with silica gel column (eluted with Hex/EA) to afford INT A11-1 (3.82 g, yield 85%). LCMS: m/z=174 [M+1]$^+$.

Step 2: INT A11-1 (3.82 g, 25.85 mmol, 1.0 eq.) and tert-butyl pyrrolidine-3-carboxylate (4.34 g, 25.35 mmol, 1.15 eq.) were dissolved in DCM (80 mL), and then STAB (6.97 g, 33.04 mmol, 1.50 eq.) was added. The reaction mixture was stirred for 4 hrs at room temperature, and then saturated $NaHCO_3$ aqueous solution (50 mL) was added. The resulting mixture was extracted with EA (100 mL×3), and the combined organic layer was concentrated under reduced pressure to obtain a residue. The residue was purified with silica gel column (eluted with Hex/EA) to afford INT A11-2 (4.07 g, yield 56%). LCMS: m/z=329 [M+1]$^+$.

Step 3: TFA (8 mL) was added dropwise at room temperature to a solution of INT A11-2 (4.07 g, 12.39 mmol, 1.00 eq.) dissolved in DCM (40 mL). The reaction mixture was stirred for 8 hrs at room temperature, quenched with $NaHCO_3$ aqueous solution (50 mL), and extracted with of EA (50 mL×3). The organic layers were combined, dried over anhydrous $Na_2SO_4$, and concentrated under reduced pressure to afford a crude product (2.13 g) of INT A11-3 which was used in next step without further purification. LCMS: m/z=173 [M+1]$^+$.

Step 4: 5-Chloro-2-(4-methoxybenzyl)-4-(trifluoromethyl)pyridazin-3(2H)-one (4.44 g, 13.93 mmol, 1.0 eq.), INT A11-3 (2.13 g, crude) and TEA (10 mL) were dissolved in $CH_3CN$ (60 mL). The reaction mixture was stirred for 4 hrs at room temperature and concentrated under reduced pressure to obtain a residue which was purified with Prep-HPLC (C18 column, eluted with $CH_3CN/H_2O$) to afford INT A11 (0.97 g, yield 17%). LCMS: m/z=455 [M+1]$^+$.

Intermediate A12 (INT A12)

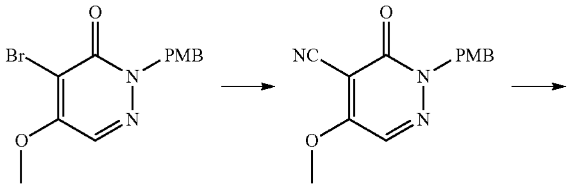

INT A12-1

-continued

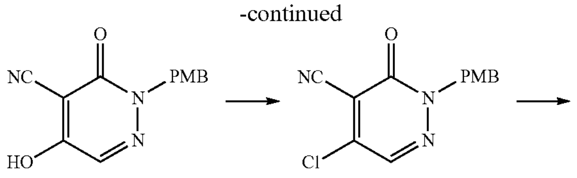

INT A12-2 INT A12-3

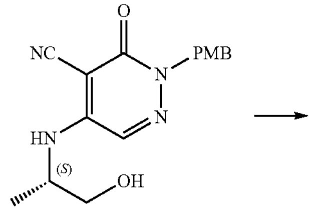

INT A12-4

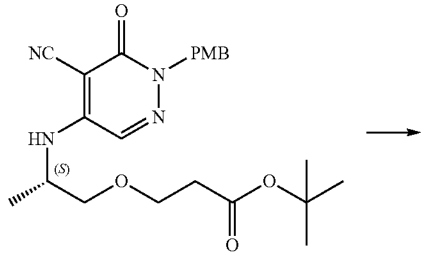

INT A12-5

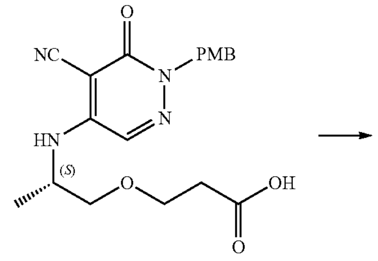

INT A12-6

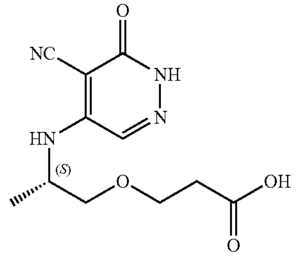

INT A12

Step 1: 4-Bromo-5-methoxy-2-(4-methoxybenzyl) pyridazin-3(2H)-one (10.12 g, 31.12 mmol, 1.0 eq.), $Zn(CN)_2$ (5.51 g, 46.92 mmol, 1.51 eq.), $Pd(PPh_3)_4$ (10.31 g, 8.92 mmol, 0.29 eq.) were dispersed in DMF (100 mL). The reaction mixture was purged and maintained with an inert atmosphere of nitrogen, stirred for 4 hrs at 130° C., cooled to room temperature, diluted with brine (100 mL) and then extracted with EA (100 mL×3). The organic layers were combined, dried over anhydrous $Na_2SO_4$ and then concentrated under reduced pressure to obtain a residue which was purified with Prep-HPLC ($C_{18}$ column, eluted with $CH_3CN/H_2O$) to afford INT A12-1 (7.83 g, yield 92%). LCMS: m/z=272 $[M+1]^+$.

Step 2: A mixture of INT A12-1 (7.83 g, 28.86 mol, 1.0 eq.) and DMF (80 mL) was purged and maintained with an inert atmosphere of nitrogen, and then TMSI (11.47 g, 57.32 mol, 1.99 eq.) was added dropwise at room temperature. The reaction mixture was stirred for 3 hrs at 85° C., cooled to room temperature, quenched with water (100 mL) and then extracted with EA (100 mL×3). The organic layers were combined, dried over anhydrous $Na_2SO_4$, and concentrated under reduced pressure to obtain a residue which was purified with Prep-HPLC (C18 column, eluted with $CH_3CN/H_2O$) to afford INT A12-2 (4.25 g, yield 57%). LCMS: m/z=258 $[M+1]^+$.

Step 3: A mixture of INT A12-2 (4.25 g, 16.52 mmol, 1.0 eq.) and DMF (50 mL) was purged and maintained with an inert atmosphere of nitrogen, cooled to 0-5° C., and then oxalic dichloride (4.10 g, 32.30 mol, 1.96 eq.) was added dropwise. The reaction mixture was stirred for 6 hrs at room temperature, quenched with saturated $Na_2CO_3$ aqueous solution (100 mL), and then extracted with EA (150 mL×3). The organic layers were combined, dried over anhydrous $Na_2SO_4$, and then concentrated under reduced pressure to afford a crude product (4.49 g) of INT A12-3 which was used in next step without further purification. LCMS: m/z=276 $[M+1]^+$.

Step 4: INT A12-3 (4.49 g, 16.29 mmol, 1.0 eq.), S-(+)-2-amino-1-propanol (2.50 g, 33.28 mmol, 2.04 eq.) and TEA (4.97 g, 49.12 mmol, 3.02 eq.) were dispersed in $CH_3CN$ (100 mL). The reaction mixture was stirred for 3 hrs at room temperature and concentrated under reduced pressure to obtain a residue which was purified with Prep-HPLC (C18 column, eluted with $CH_3CN/H_2O$) to afford INT A12-4 (4.57 g, yield 89%). LCMS: m/z=315 $[M+1]^+$.

Step 5: INT A12-4 (2.10 g, 6.68 mmol, 1.0 eq.), tert-butyl acrylate (10.0 g, 78.02 mmol, 11.68 eq.) and $Cs_2CO_3$ (3.24 g, 9.94 mmol, 1.49 eq.) were dispersed in DMSO (30 mL). The reaction mixture was stirred for 16 hrs at room temperature, poured into water (50 mL) and extracted with EA (50 mL×3). The organic layers were combined, dried over anhydrous $Na_2SO_4$, and then concentrated under reduced pressure to obtain a residue which was purified with Prep-HPLC (C18 column, eluted with $CH_3CN/H_2O$) to afford INT A12-5 (2.21 g, yield 74%). LCMS: m/z=443 $[M+1]^+$.

Step 6: TFA (10 mL) was added dropwise at room temperature to a solution of INT A12-5 (4.38 g, 9.90 mmol, 1.0 eq.) dissolved in DCM (50 mL). The reaction mixture was stirred for 6 hrs at room temperature, quenched with saturated $NaHCO_3$ aqueous solution (20 mL) and extracted with EA (50 mL×3). The organic layers were combined, dried over anhydrous $Na_2SO_4$ and concentrated under reduced pressure to afford a crude (4.27 g) of INT A12-6 as a yellow oil which was used in next step without further purification. LCMS: m/z=387 $[M+1]^+$.

Step 7: TfOH (8 mL) was added dropwise at room temperature to a solution of INT A12-6 (4.12 g, 10.66 mmol, 1.0 eq.) dissolved in TFA (30 mL). The reaction mixture was stirred for 3 hrs at room temperature, quenched with saturated $NaHCO_3$ aqueous solution (100 mL) and then extracted with of EA (100 mL×3). The organic layers were combined, dried over anhydrous $Na_2SO_4$, and concentrated under reduced pressure to obtain a residue which was purified with Prep-HPLC ($C_{18}$ column, eluted with $CH_3CN/H_2O$) to afford INT A12 (1.78 g, yield 62%). LCMS: m/z=267 $[M+1]^+$.

Intermediate A13 (INT A13)

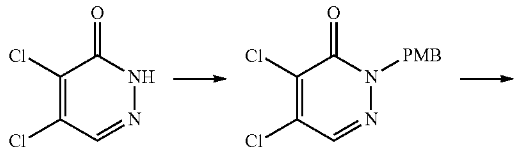

INT A13-1

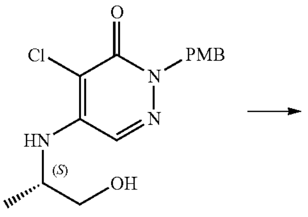

INT A13-2

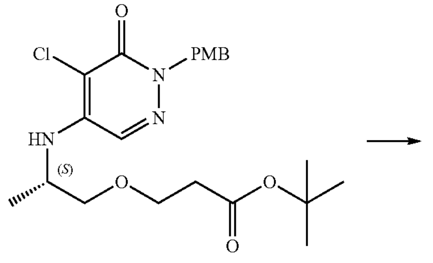

INT A13-3

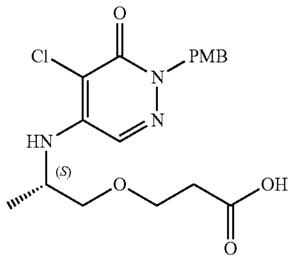

INT A13

Step 1: A solution of 4,5-dichloropyridazin-3(2H)-one (5.02 g, 30.43 mmol, 1.0 eq.) dissolved in DMF (1.0 L) was purged and maintained with an inert atmosphere of nitrogen, cooled to 0~10° C., and then NaH (1.32 g, 32.75 mmol, 1.08 eq.) (60% in mineral oil) was added slowly. The resulting mixture was stirred at 0° C. for 1 h, and then 1-(chloromethyl)-4-methoxybenzene (6.76 g, 43.16 mmol, 1.42 eq.) was added. The reaction mixture was stirred for 2 hrs at room temperature, quenched with water (50 mL), and extracted with EA (50 mLx3). The organic layers were combined, dried over anhydrous $Na_2SO_4$, and then concentrated under reduced pressure to obtain a residue. A mixture of the residue and MeOH (10 mL) was stirred for 1 h at room temperature, and then filtered. The filter cake was dried under vacuum to afford INT A13-1 (5.01 g, yield 57%) as a solid. LCMS: m/z=285[M+1]$^+$.

Step 2: INT A13-1 (2.21 g, 7.75 mmol, 1.0 eq.), S-(+)-2-amino-1-propanol (1.78 g, 23.70 mmol, 3.06 eq.) and TEA (2.03 g, 20.06 mmol, 2.59 eq.) were dissolved in $CH_3CN$ (15 mL). The reaction mixture was stirred for 18 hrs at 80° C. and concentrated under reduced pressure to obtain a residue which was purified with Prep-HPLC (C18 column, eluted with $CH_3CN/H_2O$) to afford INT A13-2 (1.58 g, yield 62%) as a solid. LCMS: m/z=324 [M+1]$^+$.

Step 3: INT A13-2 (1.36 g, 4.20 mmol, 1.0 eq.), tert-butyl acrylate (2.96 g, 23.09 mmol, 5.50 eq.) and $Cs_2CO_3$ (4.29 g, 13.17 mmol, 3.13 eq.) were dispersed in DMSO (10 mL). The reaction mixture was stirred for 3 hrs at room temperature, poured into water (50 mL) and extracted with EA (50 mLx3). The organic layers were combined, dried over anhydrous $Na_2SO_4$, and concentrated under reduced pressure to obtain a residue which was purified with silica gel column (eluted with Hex/EA) to afford INT A13-3 (1.14 g, 60%). LCMS: m/z=452 [M+1]$^+$.

Step 4: TFA (2 mL) was added dropwise at room temperature to a solution of INT A13-3 (1.14 g, 2.52 mmol, 1.0 eq.) dissolved in DCM (10 mL). The reaction mixture was stirred for 2 hrs at room temperature, quenched with saturated $NaHCO_3$ aqueous solution (20 mL), and extracted with EA (50 mLx3). The organic layers were combined, dried over anhydrous $Na_2SO_4$, and concentrated under reduced pressure to afford a crude product (0.99 g) of INT A13 as a yellow oil which was used in next step without further purification. LCMS: m/z=396 [M+1]$^+$.

Intermediate A14 (INT A14)

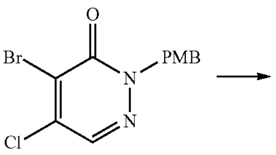

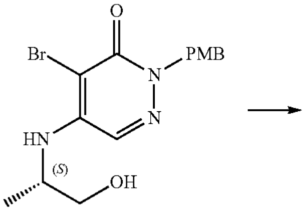

INT A14-1

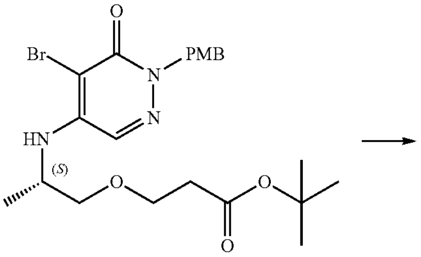

INT A14-2

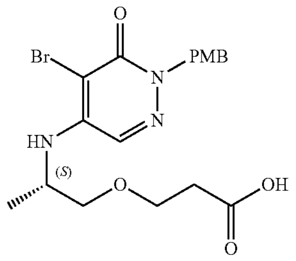

INT A14

Step 1: 4,5-Dibromo-2-(4-methoxybenzyl)pyridazin-3(2H)-one (2.56 g, 6.84 mmol, 1.0 eq.), S-(+)-2-amino-1-propanol (1.92 g, 25.56 mmol, 3.74 eq.) and TEA (4 mL) were dispersed in $CH_3CN$ (15 mL). The reaction mixture was stirred for 18 hrs at 80° C., cooled to room temperature and concentrated under reduced pressure to obtain a residue which was purified with Prep-HPLC (C18 column, eluted with $CH_3CN/H_2O$) to afford INT A14-1 (1.46 g, yield 57%) as a solid. LCMS: m/z=368, 370 $[M+1]^+$.

Step 2: INT A14-1 (1.36 g, 3.69 mmol, 1.0 eq.), tert-butyl acrylate (3.75 g, 29.26 mmol, 5.50 eq.) and $Cs_2CO_3$ (2.40 g, 7.37 mmol, 1.99 eq.) were dispersed in DMSO (15 mL). The reaction mixture was stirred for 3 hrs at room temperature, poured into water (50 mL) and extracted with EA (50 mL×3). The organic layers were combined, dried over anhydrous $Na_2SO_4$, and then concentrated under reduced pressure to obtain a residue which was purified with Prep-HPLC (C18 column, eluted with $CH_3CN/H_2O$) to afford INT A14-2 (0.83 g, yield 45%). LCMS: m/z=496, 498 $[M+1]^+$.

Step 3: TFA (2 mL) was added dropwise at room temperature to a solution of INT A14-2 (0.83 g, 1.67 mmol, 1.0 eq.) dissolved in DCM (10 mL). The reaction mixture was stirred for 2 hrs at room temperature, quenched with saturated $NaHCO_3$ aqueous solution (20 mL), and extracted with EA (50 mL×3). The organic layers were combined, dried over anhydrous $Na_2SO_4$ and then concentrated under reduced pressure to obtain a crude product (0.74 g) of INT A14 as a yellow oil which was used in next step without further purification. LCMS: m/z=440, 442 $[M+1]^+$.

Intermediate A15 (INT A15)

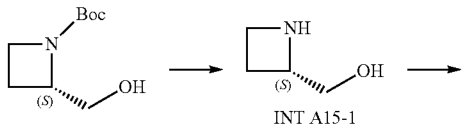

INT A15-1

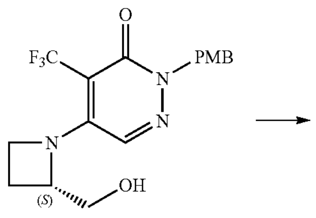

INT A15-2

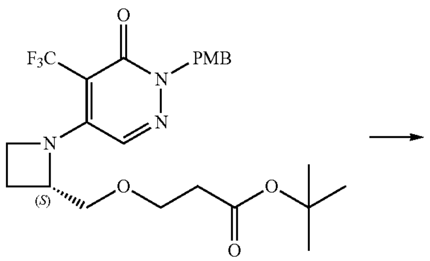

INT A15-3

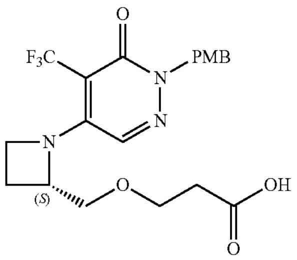

INT A15

Step 1: HCl/1,4-dioxane (100 mL, 1N) was added to a solution of tert-butyl (S)-2-(hydroxymethyl)azetidine-1-carboxylate (9.93 g, 53.03 mmol, 1.0 eq.) dissolved in 1,4-dioxane (10 mL). The reaction mixture was stirred for 2 hrs at room temperature and then concentrated under reduced pressure to afford a crude product (8.49 g) of INT A15-1 as a yellow oil which was used in next step without further purification. LCMS: m/z=88 $[M+1]^+$.

Step 2: INT A15-1 (8.49 g, 97.45 mmol, 1.0 eq.) and 5-chloro-2-(4-methoxybenzyl)-4-(trifluoro-methyl) pyridazin-3(2H)-one (17.82 g, 55.91 mmol, 0.57 eq.) were dissolved in $CH_3CN$ (120 mL), and then TEA (30.31 g, 0.29 mol, 3.07 eq.) was added. The reaction mixture was stirred for 4 hrs at 90° C., quenched with water (200 mL) and extracted with EA (200 mL×3). The organic layers were combined and concentrated under reduced pressure to obtain a residue which was purified with Prep-HPLC ($C_{18}$ column, eluted with $H_2O/CH_3CN$) to afford INT A15-2 (10.47 g, yield 29%) as a yellow oil. LCMS: m/z=370 $[M+1]^+$.

Step 3: INT A15-2 (10.36 g, 28.05 mmol, 1.0 eq.), tert-butyl acrylate (19.93 g, 155.49 mmol, 5.51 eq.) and $Cs_2CO_3$ (27.64 g, 84.83 mmol, 3.02 eq.) were dispersed in DMSO (100 mL). The reaction mixture was stirred for 8 hrs at room temperature, and then filtered. The filtrate was concentrated under reduced pressure to obtain a residue which was purified with Prep-HPLC ($C_{18}$ column, eluted with $H_2O/CH_3CN$) to afford INT A15-3 (6.51 g, yield 46%) as a yellow oil. LCMS: m/z=498 $[M+1]^+$.

Step 4: TFA (14 mL) was added dropwise at room temperature to a solution of INT A15-3 (6.51 g, 13.09 mmol, 1.0 eq.) dissolved in DCM (70 mL). The reaction mixture was stirred for 3 hrs at room temperature and then concentrated under reduced pressure to obtain a residue which was purified with Prep-HPLC (C18 column, eluted with $H_2O/CH_3CN$) to afford INT A15 (4.60 g, yield 80%). LCMS: m/z=442 $[M+1]^+$.

Intermediate A16 (INT A16)

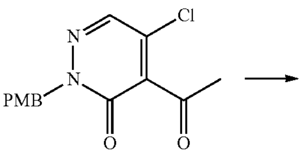

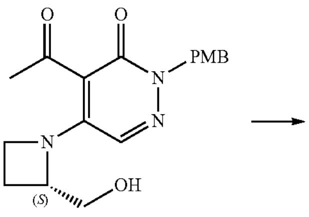

INT 16-1

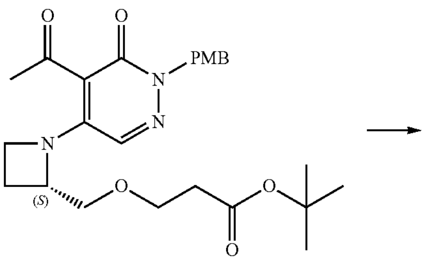

INT A16-2

-continued

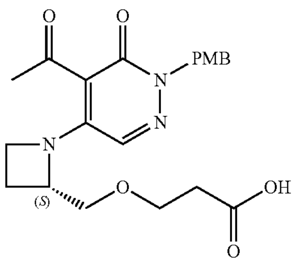

INT 16

Step 1: 4-Acetyl-5-chloro-2-(4-methoxybenzyl) pyridazin-3(2H)-one (2.16 g, 7.38 mmol, 1.0 eq.), (S)-azetidin-2-ylmethanol (1.0 g, 11.48 mmol, 1.56 eq.) and TEA (2.8 mL) were dispersed in $CH_3CN$ (20 mL). The reaction mixture was stirred for 2 hrs at 80° C., poured into water (50 mL) and extracted with EA (50 mL×3). The organic layers were combined and concentrated under reduced pressure to obtain a residue which was purified with Prep-HPLC (C18 column, eluted with $H_2O/CH_3CN$) to afford INT A16-1 (1.59 g, yield 62%). LCMS: m/z=344 $[M+1]^+$.

Step 2: INT A16-1 (1.46 g, 4.25 mmol, 1.0 eq.), tert-butyl acrylate (3.50 g, 27.31 mmol, 6.42 eq.) and $Cs_2CO_3$ (4.01 g, 12.31 mmol, 2.89 eq.) were dispersed in DMSO (15 mL). The reaction mixture was stirred for 2 hrs at room temperature, poured into water (50 mL) and extracted with EA (50 mL×3). The organic layers were combined and concentrated under reduced pressure to obtain a residue which was purified with Prep-HPLC (C18 column, eluted with $H_2O/CH_3CN$) to afford INT A16-2 (1.06 g, yield 52%). LCMS: m/z=472 $[M+1]^+$.

Step 3: TFA (2 mL) was added dropwise at room temperature to a solution of INT A16-2 (1.06 g, 2.25 mmol, 1.0 eq.) dissolved in DCM (20 mL). The reaction mixture was stirred for 3 hrs at room temperature, quenched with saturated $NaHCO_3$ aqueous solution (20 mL), and extracted with EA (50 mL×3). The organic layers were combined, dried over anhydrous $Na_2SO_4$ and then concentrated under reduced pressure to obtain a residue which was purified with Prep-HPLC (C18 column, eluted with $H_2O/CH_3CN$) to afford INT A16 (0.91 g, yield 97%). LCMS: m/z=416 $[M+1]^+$.

Intermediate A17 (INT A17)

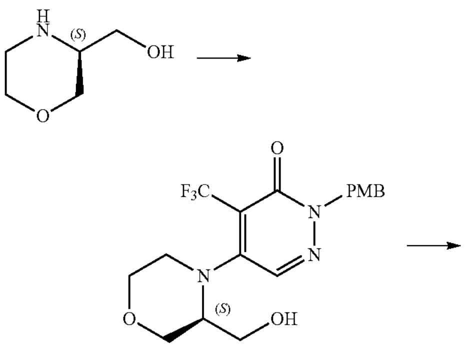

INT A17-1

-continued

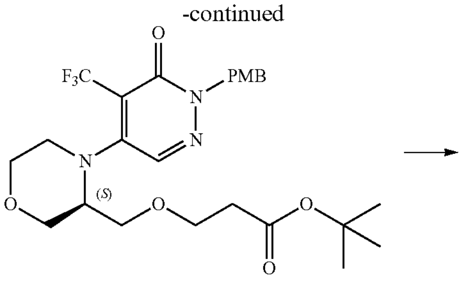

INT A17-2

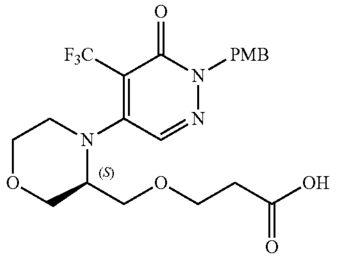

INT A17

Step 1: 5-Chloro-2-(4-methoxybenzyl)-4-(trifluoromethyl)pyridazin-3(2H)-one (9.66 g, 30.31 mmol, 1.0 eq.), (S)-morpholin-3-ylmethanol (4.13 g, 35.26 mmol, 1.16 eq.) and TEA (9.94 g, 98.23 mmol, 2.79 eq.) were dispersed in $CH_3CN$ (150 mL). The reaction mixture was stirred for 2 hrs at 80° C., cooled to room temperature and concentrated under reduced pressure to obtain a residue which was purified with Prep-HPLC (C18 column, eluted with $H_2O/CH_3CN$) to afford INT A17-1 (1.26 g, yield 10%). LCMS: m/z=400 $[M+1]^+$.

Step 2: INT A17-1 (1.12 g, 2.80 mmol, 1.0 eq.), tert-butyl acrylate (2.07 g, 16.15 mmol, 5.76 eq.) and $Cs_2CO_3$ (3.21 g, 9.85 mmol, 3.51 eq.) were dispersed in DMF (50 mL). The reaction mixture was stirred for 4.5 hrs at room temperature, poured into water (100 mL) and extracted with EA (100 mL×3). The organic layers were combined and concentrated under reduced pressure to obtain a residue which was purified with Prep-HPLC (C18 column, eluted with $H_2O/CH_3CN$) to afford INT A17-2 (200 mg, yield 13%). LCMS: m/z=528 $[M+1]^+$.

Step 3: TFA (2 mL) was added dropwise at room temperature to a solution of INT A17-2 (210 mg, 0.40 mmol, 1.0 eq.) dissolved in DCM (10 mL). The reaction mixture was stirred for 1.5 hrs at room temperature and concentrated under reduced pressure to afford a crude product (200 mg) of INT A17 which was used in next step without further purification. LCMS: m/z=472 $[M+1]^+$.

Intermediate A18 (INT A18)

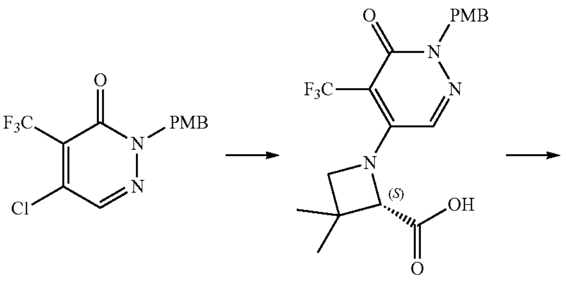

INT A18-1

-continued

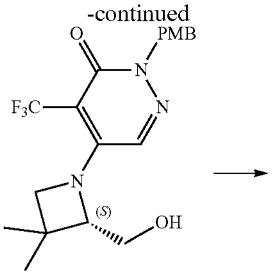

INT A18-2

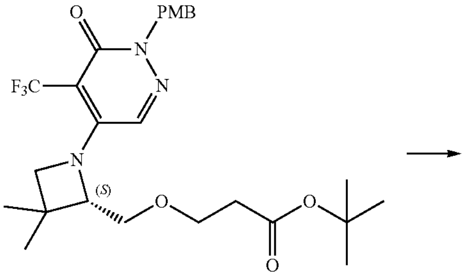

INT A18-3

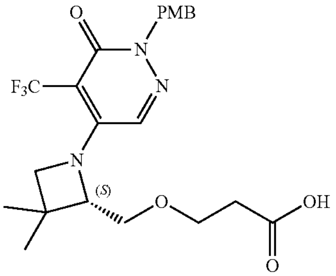

INT A18

Step 1: 5-Chloro-2-(4-methoxybenzyl)-4-(trifluoromethyl)pyridazin-3(2H)-one (1.50 g, 4.71 mmol, 1.29 eq.), (S)-3,3-dimethylazetidine-2-carboxylic acid (0.47 g, 3.64 mmol, 1.0 eq.) and TEA (3 mL) were dispersed in $CH_3CN$ (20 mL). The reaction mixture was stirred for 16 hrs at 80° C., cooled to room temperature and concentrated under reduced pressure obtain a residue which was purified with Prep-HPLC (C18 column, eluted with $H_2O/CH_3CN$) to afford INT A18-1 (1.22 g, yield 81%). LCMS: m/z=412 $[M+1]^+$.

Step 2: $BH_3$-THF (8 mL) was added at 0° C. to a solution of INT A18-1 (868 mg, 2.11 mmol, 1.0 eq.) dissolved in THF (15 mL). The reaction mixture was stirred for 5 hrs at room temperature, quenched with MeOH and concentrated under reduced pressure obtain a residue which was purified with Prep-HPLC (C18 column, eluted with $H_2O/CH_3CN$) to afford INT A18-2 (498 mg, yield 59%). LCMS: m/z=398 $[M+1]^+$.

Step 3: INT A18-2 (444 mg, 1.12 mmol, 1.0 eq.), tert-butyl acrylate (2.05 g, 15.99 mmol, 14.32 eq.) and $Cs_2CO_3$ (1.20 g, 3.68 mmol, 3.30 eq.) were dispersed in DMSO (10 mL). The reaction mixture was stirred for 7 hrs at room temperature, poured into water (20 mL) and extracted with EA (50 mL×3). The organic layers were combined and concentrated under reduced pressure to obtain a residue which was purified with Prep-HPLC (C18 column, eluted with $H_2O/CH_3CN$) to afford INT A18-3 (541 mg, yield 92%). LCMS: m/z=526 $[M+1]^+$.

Step 4: TFA (1 mL) was added dropwise at room temperature to a solution of INT A18-3 (505 mg, 0.96 mmol, 1.0 eq.) dissolved in DCM (5 mL). The reaction mixture was stirred for 1.5 hrs at room temperature and concentrated under reduced pressure to afford a crude product (581 mg) of INT A18 which was used in next step without further purification. LCMS: m/z=470 $[M+1]^+$.

Intermediate A19 (INT A19)

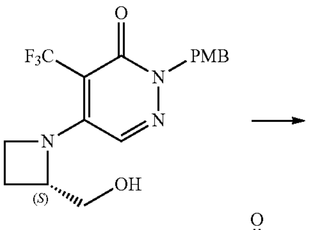

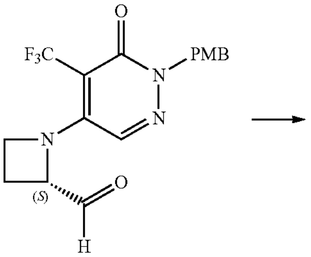

INT A19-1

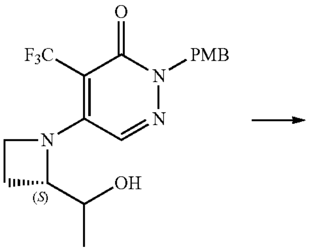

INT A19-2

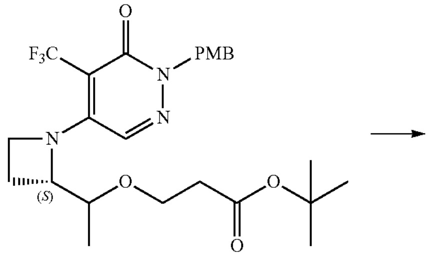

INT A19-3

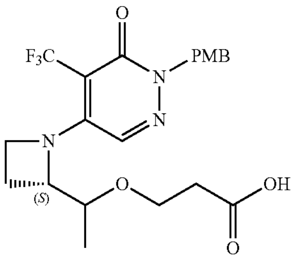

INT A19

Step 1: Dess-Martin periodinane (2.78 g, 6.55 mmol, 1.31 eq.) was added at 0° C. to a solution of (S)-5-(2-(hydroxymethyl)azetidin-1-yl)-2-(4-methoxybenzyl)-4-(trifluoromethyl)pyridazin-3(2H)-one (1.85 g, 5.01 mmol, 1.0 eq.) dissolved in DCM (20 mL). The reaction mixture was stirred for 2 hrs at room temperature, and then saturated $NaHCO_3$ aqueous solution (20 mL) was added. The resulting mixture was extracted with EA (50 mL×3), and the combined organic layer was concentrated under reduced pressure to obtain a residue which was purified with Prep-HPLC (C18 column, eluted with $H_2O/CH_3CN$) to afford INT A19-1 (1.71 g, yield 92%). LCMS: m/z=368 $[M+1]^+$.

Step 2: In an atmosphere of nitrogen, MgMeBr (7.5 mL, 22.5 mmol, 6.30 eq.) was added at 0° C. to a solution of INT A19-1 (1.31 g, 3.57 mmol, 1.0 eq.) dissolved in THF (10 mL). The reaction mixture was stirred for 3 hrs at room temperature, quenched with saturated $NH_4Cl$ aqueous solution (20 mL), and then extracted with EA (20 mL×3). The combined organic layer was concentrated under reduced pressure to obtain a residue which was purified with Prep-HPLC (C18 column, eluted with $H_2O/CH_3CN$) to afford INT A19-2 (0.43 g, yield 31%). LCMS: m/z=384 $[M+1]^+$.

Step 3: INT A19-2 (0.43 g, 1.12 mmol, 1.0 eq.), tert-butyl acrylate (718.8 mg, 5.61 mmol, 5.0 eq.) and $Cs_2CO_3$ (1.09 g, 3.55 mmol, 2.98 eq.) were dispersed in DMSO (5 mL). The reaction mixture was stirred for 3 hrs at room temperature, poured into water (20 mL) and extracted with EA (50 mL×3). The organic layers were combined and concentrated under reduced pressure to obtain a residue which was purified with Prep-HPLC (C18 column, eluted with $H_2O/CH_3CN$) to afford INT A19-3 (0.24 g, yield 41%). LCMS: m/z=512 $[M+1]^+$.

Step 4: TFA (3 mL) was added dropwise at room temperature to a solution of INT A19-3 (0.24 g, 0.47 mmol, 1.0 eq.) dissolved in DCM (5 mL). The reaction mixture was stirred for 2 hrs at room temperature and concentrated under reduced pressure to afford a crude product (0.35 g) of INT A19 which was used in next step without further purification. LCMS: m/z=456 $[M+1]^+$.

Intermediate A20 (INT A20)

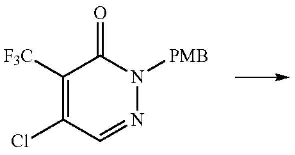

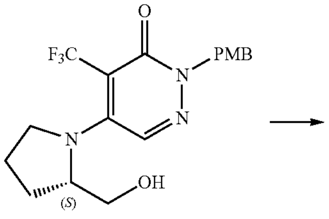

INT 20-1

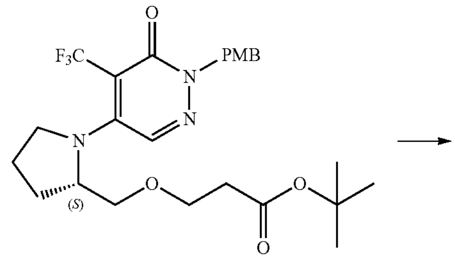

INT 20-2

-continued

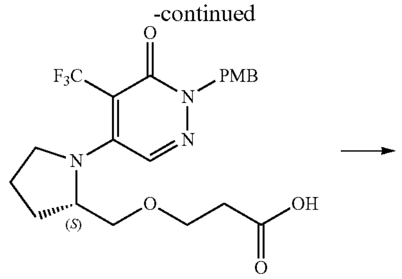

INT 20-3

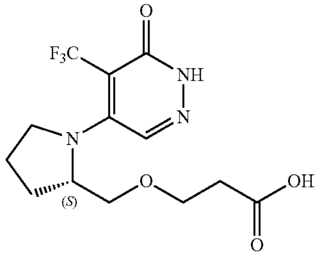

INT 20

Step 1: 5-Chloro-2-(4-methoxybenzyl)-4-(trifluoromethyl)pyridazin-3(2H)-one (10.0 g, 31.38 mmol, 1.0 eq.), (S)-pyrrolidin-2-ylmethanol (3.82 g, 37.77 mmol, 1.20 eq.) and TEA (7.20 g, 71.15 mmol, 2.27 eq.) were dispersed in $CH_3CN$ (60 mL). The reaction mixture was stirred for 3.5 hrs at 80° C., cooled to room temperature and concentrated under reduced pressure to obtain a residue. The residue was purified with Prep-HPLC (C18 column, eluted with $H_2O/CH_3CN$) to afford INT A20-1 (11.16 g, yield 92%). LCMS: m/z=384 $[M+1]^+$.

Step 2: INT A20-1 (11.16 g, 29.11 mmol, 1.0 eq.), tert-butyl acrylate (22.79 g, 177.81 mmol, 6.11 eq.) and $Cs_2CO_3$ (28.34 g, 86.98 mmol, 2.99 eq.) were dispersed in DMSO (100 mL). The reaction mixture was stirred for 3.5 hrs at room temperature, poured into water (100 mL) and extracted with EA (100 mL×3). The organic layers were combined and concentrated under reduced pressure to obtain a residue which was purified with Prep-HPLC (C18 column, eluted with $H_2O/CH_3CN$) to afford INT A20-2 (6.20 g, yield 41%). LCMS: m/z=512 $[M+1]^+$.

Step 3: TFA (10 mL) was added dropwise at room temperature to a solution of INT A20-2 (6.20 g, 12.12 mmol, 1.0 eq.) dissolved in DCM (100 mL). The reaction mixture was stirred for 4 hrs at room temperature and concentrated under reduced pressure to afford a crude product (6.12 g) of INT A20-3 which was used in next step without further purification. LCMS: m/z=456 $[M+1]^+$.

Step 4: TfOH (2 mL) was added dropwise at room temperature to a solution of INT A20-3 (6.12 g, crude) dissolved in TFA (20 mL). The reaction mixture was stirred for 4 hrs at room temperature, quenched with $NaHCO_3$ aqueous solution (100 mL) and then extracted with of EA (100 mL×3). The organic layers were combined, dried over anhydrous $Na_2SO_4$, and concentrated under reduced pressure obtain a residue which was purified with Prep-HPLC (C18 column, eluted with $CH_3CN/H_2O$) to afford INT A20 (2.66 g, yield of two steps 65%). LCMS: m/z=336 $[M+1]^+$.

Intermediate A21 (INT A21)

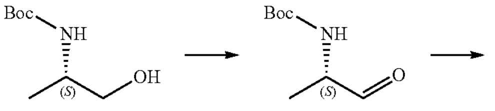

INT A21-1

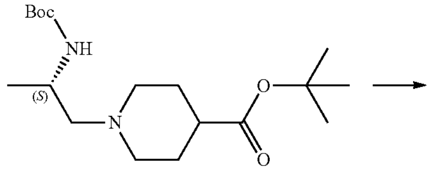

INT A21-2

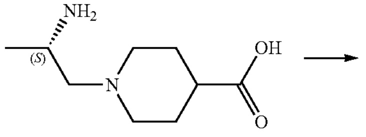

INT A21-3

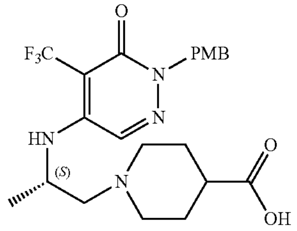

INT A21

Step 1: Dess-Martin periodinane (13.76 g, 32.44 mmol, 1.25 eq.) was added at 0° C. to a solution of tert-butyl (S)-(1-hydroxypropan-2-yl)carbamate (4.53 g, 25.85 mmol, 1.0 eq.) dissolved in DCM (90 mL). The reaction mixture was stirred for 2 hrs at room temperature, and then saturated $Na_2S_2O_3$ aqueous solution (50 mL) was added. The resulting mixture was extracted with DCM (100 mLx3). The combined organic layers were concentrated under reduced pressure to obtain a residue which was purified with Prep-HPLC (C18 column, eluted with $CH_3CN/H_2O$) to afford INT A21-1 (3.82 g, yield 85%). LCMS: m/z=174 $[M+1]^+$.

Step 2: INT A21-1 (883 mg, 25.85 mmol, 1.0 eq.) and tert-butyl piperidine-4-carboxylate (1.13 g, 5.10 mmol, 1.0 eq.) were dissolved in DCM (15 mL), and then STAB (1.69 g, 8.01 mmol, 1.57 eq.) was added. The reaction mixture was stirred for 2 hrs at room temperature and saturated $NaHCO_3$ aqueous solution (50 mL) was added. The resulting mixture was extracted with EA (100 mLx3). The organic layers were combined and concentrated under reduced pressure to obtain a residue which was purified with silica gel column (eluted with Hex/EA) to afford INT A21-2 (1.50 g, yield 85%). LCMS: m/z=343 $[M+1]^+$.

Step 3: TFA (3 mL) was added dropwise at room temperature to a solution of INT A21-2 (1.13 g, 3.30 mmol, 1.00 eq.) dissolved in DCM (15 mL). The reaction mixture was stirred for 16 hrs at room temperature and concentrated under reduced pressure to afford a crude product (2.75 g) of INT A21-3 which was used in next step without further purification. LCMS: m/z=187 $[M+1]^+$.

Step 4: 5-Chloro-2-(4-methoxybenzyl)-4-(trifluoromethyl)pyridazin-3(2H)-one (1.41 g, 4.42 mmol, 1.34 eq.), a crude product (2.75 g) of INT A21-3 and TEA (5 mL) were dissolved in $CH_3CN$ (20 mL). The reaction mixture was stirred for 2.5 hrs at room temperature and concentrated under reduced pressure to obtain a residue which was purified with Prep-HPLC (C18 column, eluted with $CH_3CN/H_2O$) to afford INT A21 (1.01 g, yield 65%). LCMS: m/z=469 $[M+1]^+$.

Intermediate B1 (INT B1)

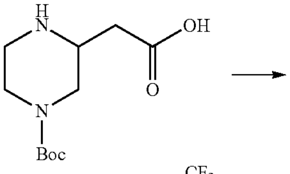

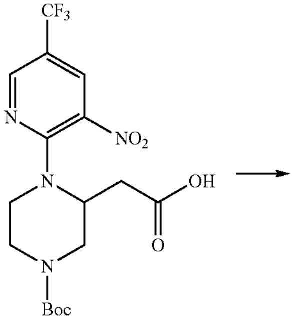

INT B1-1

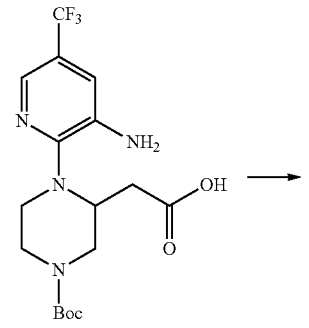

INT B1-2

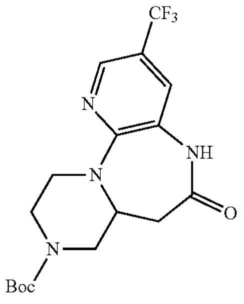

INT B1

Step 1: 2-(4-(Tert-butoxycarbonyl)piperazin-2-yl)acetic acid (5.25 g, 23.17 mmol, 1.1 eq.) and 2-chloro-3-nitro-5-(trifluoromethyl)pyridine (5.13 g, 21.00 mmol, 1.0 eq.) were dissolved in a mixed solution of DMF (20 mL) and THF (60 mL), and then TEA (10.53 g, 104.04 mmol, 4.95 eq.) was added at room temperature. The reaction mixture was stirred for 4 hrs at 55° C., quenched with water (20 mL), and extracted with DCM (50 mLx3). The organic layers were combined and concentrated under reduced pressure to obtain a residue which was purified with silica gel column (eluted with Hex/EA) to afford INT B1-1 (6.45 g, yield 71%). LCMS: m/z=435 $[M+1]^+$.

Step 2: INT B1-1 (5.13 g, 11.78 mmol, 1.0 eq.) and Pd/C (2.22 g, 20.86 mmol, 1.77 eq.) were dispersed in MeOH (40 mL). The reaction mixture was purged and maintained with an inert atmosphere of hydrogen, stirred for 4 hrs at room temperature, and then filtered. The filtrate was concentrated under vacuum to obtain a residue which was purified with silica gel column (eluted with Hex/EA) to afford INT B1-2 (5.2 g, yield 93%). LCMS: m/z=405 $[M+1]^+$.

Step 3: INT B1-2 (5.2 g, 12.87 mmol, 1.0 eq.) and TEA (5.07 g, 50.10 mmol, 3.89 eq.) were dissolved in DCM (250 mL), and then HATU (7.35 g, 19.33 mmol, 1.5 eq.) was added. The reaction mixture was stirred for 2 hrs at room temperature, quenched with water (20 mL), and extracted with DCM (50 mL×3). The organic layers were combined and concentrated under reduced pressure to obtain a residue which was purified with silica gel column (eluted with Hex/EA) to afford INT B1 (3.26 g, yield 58%). LCMS: m/z=387 $[M+1]^+$.

Intermediate B2 (INT B2)

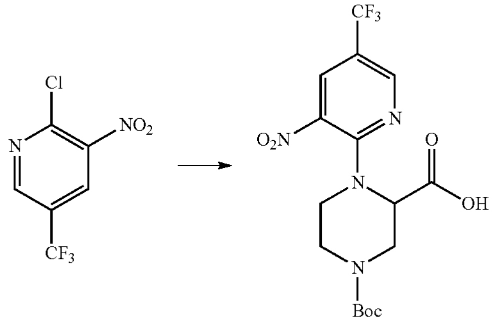

INT B2-1

-continued

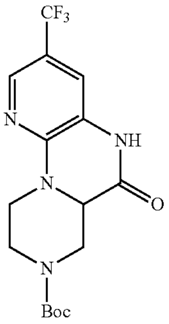

INT B2

Step 1: 4-(tert-butoxycarbonyl)piperazine-2-carboxylic acid (47.15 g, 0.20 mol, 1.25 eq.) and 2-chloro-3-nitro-5-(trifluoromethyl)pyridine (37.15 g, 0.16 mol, 1.0 eq.) were dissolved in DMF (300 mL) and THF (1000 mL), and then TEA (109.67 g, 1.08 mol, 6.61 eq.) was added at room temperature. The reaction mixture was stirred for 4 hrs at 55° C., poured into water (1000 mL), and extracted with EA (500 mL×3). The organic layers were combined and concentrated under reduced pressure to obtain a residue which was purified with silica gel column (eluted with Hex/EA) to afford INT B2-1 (63.95 g, yield 92%). LCMS: m/z=421 $[M+1]^+$.

Step 2: INT B2-1 (28.38 g, 67.52 mmol, 1.0 eq.) and the powder of Fe (22.48 g, 402.54 mmol, 5.96 eq.) were dispersed in HOAc (400 mL). The reaction mixture was stirred for 16 hrs at room temperature, and then filtered. The filtrate was concentrated under vacuum to obtain a residue which was purified with silica gel column (eluted with Hex/EA) to afford INT B2 (9.63 g, yield 38%). LCMS: m/z=373 $[M+1]^+$.

The following intermediates were synthesized using the above procedure with the corresponding starting material.

| INT | Structure | Starting material | LCMS (ESI, m/z): $[M + H]^+$ |
|---|---|---|---|
| INT B3 | 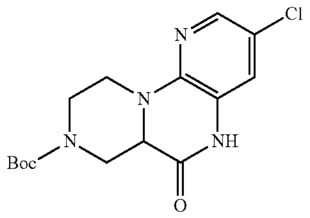 [SMILES: CC(C)(C)OC(=O)N1CCN2c3ncc(Cl)cc3NC(=O)C2C1] | 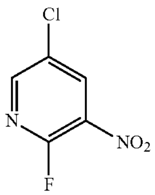 [SMILES: O=[N+]([O-])c1cc(Cl)cnc1F] | 339 |
| INT B4 | 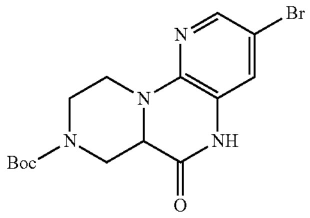 | 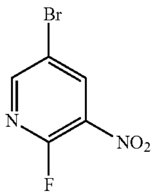 [SMILES: O=[N+]([O-])c1cc(Br)cnc1F] | 383, 385 |
| INT B5 | 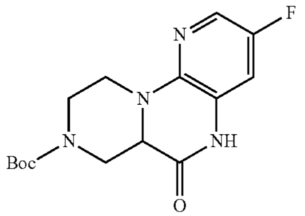 [SMILES: CC(C)(C)OC(=O)N1CCN2c3ncc(F)cc3NC(=O)C2C1] | 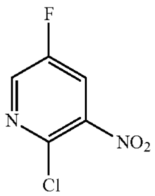 [SMILES: O=[N+]([O-])c1cc(F)cnc1Cl] | 323 |

Intermediate B6 (INT B6)

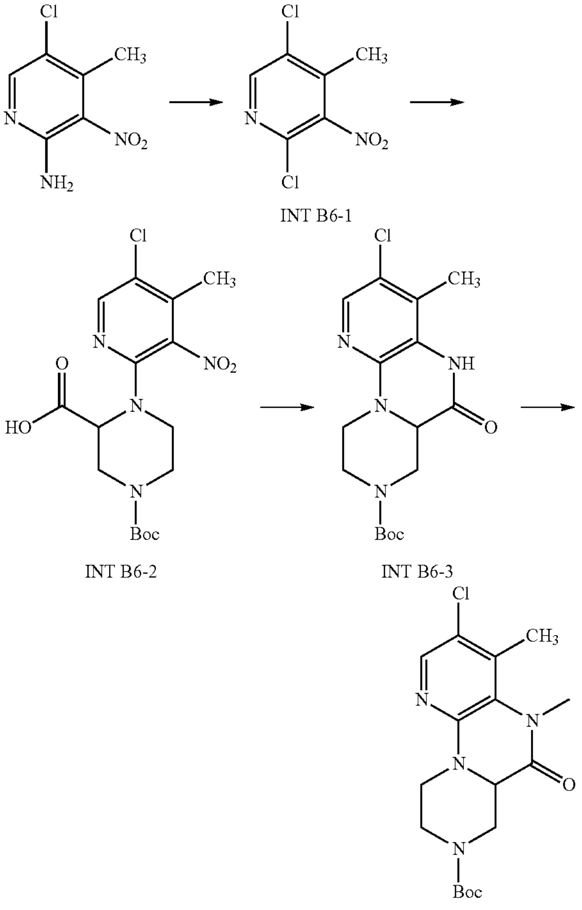

INT B6-1

INT B6-2

INT B6-3

INT B6

Step 1: A mixture of 5-chloro-4-methyl-3-nitropyridin-2-amine (1.09 g, 5.81 mmol, 1.0 eq.) dispersed in concentrated HCl (10 mL) was cooled to 0° C., and then $NaNO_2$ (0.83 g, 12.03 mmol, 2.07 eq.) was added. The reaction mixture was stirred for 16 hrs at room temperature, and then extracted with EA (50 mL×3). The organic layers were combined and concentrated under reduced pressure to obtain a residue which was purified with silica gel column (eluted with Hex/EA) to afford INT B6-1 (1.03 g, yield 85%). LCMS: m/z=207 $[M+1]^+$.

Step 2: 2-(4-(Tert-butoxycarbonyl)piperazin-2-yl)acetic acid (1.21 g, 5.25 mmol, 1.1 eq.) and INT B6-1 (1.03 g, 4.98 mmol, 1.0 eq.) were dissolved in DMF (20 mL), and then $Et_3N$ (1.56 g, 15.42 mmol, 3.10 eq.) was added at room temperature. The reaction mixture was stirred for 16 hrs at 100° C., poured into water (50 mL), and then extracted with EA (50 mL×3). The organic layers were combined and concentrated under reduced pressure to obtain a residue which was purified with silica gel column (eluted with Hex/EA) to afford INT B6-2 (1.17 g, yield 58%). LCMS: m/z=401 $[M+1]^+$.

Step 3: INT B6-2 (1.17 g, 2.92 mmol, 1.0 eq.) and the powder of iron (0.82 g, 14.68 mmol, 5.03 eq.) were dispersed in HOAc (15 mL). The reaction mixture was stirred for 4 hrs at room temperature, and then filtered. The filtrate was concentrated under vacuum to obtain a residue which was purified with silica gel column (eluted with Hex/EA) to afford INT B6-3 (0.76 g, yield 73%). LCMS: m/z=353 $[M+1]^+$.

Step 4: NaH (0.10 g, 4.17 mmol, 2.23 eq.) (60% in mineral oil) was added at 0° C. to a solution of INT B6-3 dissolved in THF (5 mL). The resulting mixture was stirred for 30 mins at 0° C., and then $CH_3I$ (0.71 g, 5.00 mmol, 2.67 eq.) was added. The reaction mixture was stirred for 2 hrs at room temperature, quenched with water (20 mL), and then extracted with EA (50 mL×3). The organic layers were combined and concentrated under reduced pressure to obtain a residue which was purified with silica gel column (eluted with Hex/EA) to afford INT B6 (0.53 g (yield 77%). LCMS: m/z=367 $[M+1]^+$.

Intermediate B7 (INT B7)

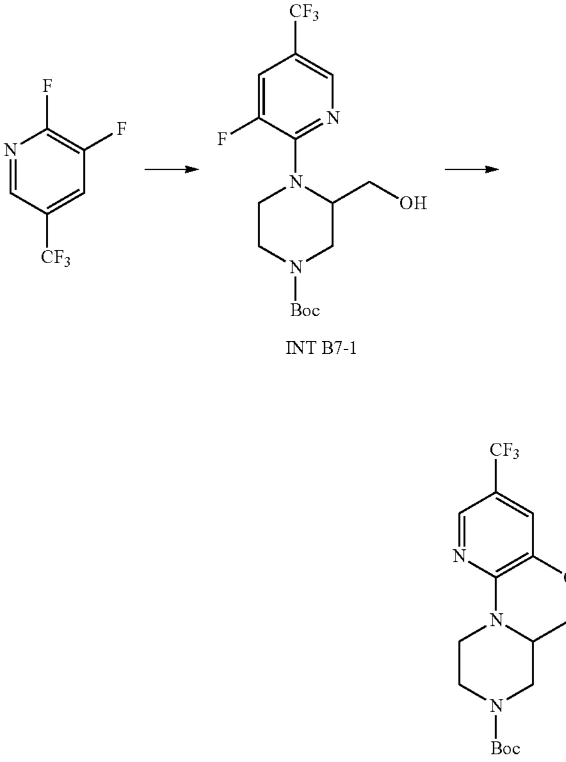

INT B7-1

INT B7

Step 1: 2,3-Difluoro-5-(trifluoromethyl)pyridine (1.06 g, 5.79 mmol, 1.0 eq.), tert-butyl 3-(hydroxymethyl)piperazine-1-carboxylate (1.27 g, 5.87 mmol, 1.0 eq.) and TEA (3 mL) were dissolved in $CH_3CN$ (8 mL). The reaction mixture was stirred overnight at 80° C., and then concentrated under reduced pressure to obtain a residue which was purified with silica gel column (eluted with Hex/EA) to afford INT B7-1 (1.38 g, yield 68%). LCMS: m/z=380 $[M+1]^+$.

Step 2: A mixture of INT B7-1 (230 mg, 0.61 mmol, 1.0 eq.), t-BuOK (255 mg, 2.27 mmol, 3.72 eq.) and t-BuOH (5 mL) was stirred for 2 hrs at 80° C., and then concentrated under reduced pressure to obtain a residue. The residue was purified with silica gel column (eluted with Hex/EA) to afford INT B7 (180 mg, yield 83%). LCMS: m/z=360 $[M+1]^+$.

The following intermediates were synthesized using the above procedure with the corresponding starting material.

| INT | Structure | Starting material | LCMS (ESI, m/z): [M + H]+ |
|---|---|---|---|
| INT B8 | 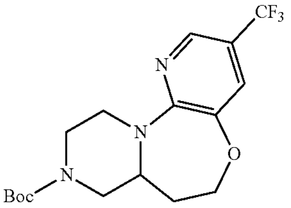 [SMILES: CC(C)(C)OC(=O)N1CCN2c3ncc(C(F)(F)F)cc3OCCC2C1] | 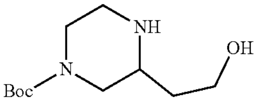 [SMILES: CC(C)(C)OC(=O)N1CCNC(CCO)C1] | 374 |
| INT B9 | 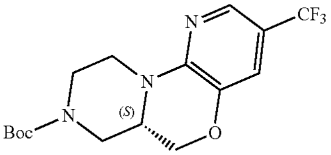 | 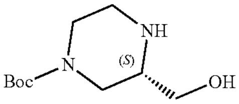 | 360 |
| INT B10 | 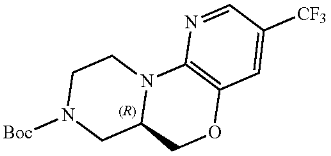 | 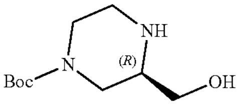 | 360 |

Intermediate B11 (INT B11)

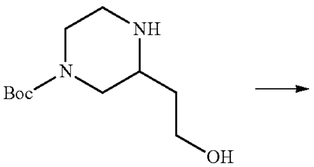

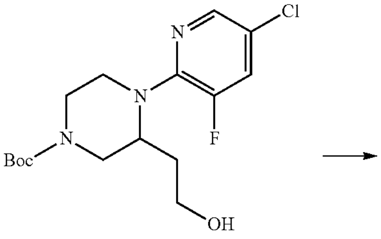

INT B11-1

-continued

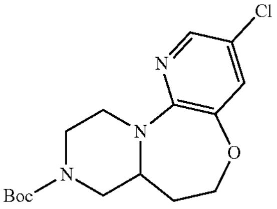

INT B11

Step 1: 5-Chloro-2,3-difluoropyridine (1.31 g, 8.76 mmol, 1.75 eq.), tert-butyl 3-(2-hydroxyethyl) piperazine-1-carboxylate (1.10 g, 4.99 mmol, 1.0 eq.) and DIPEA (2 mL) were dissolved in DMSO (10 mL). The reaction mixture was stirred overnight at 130° C., quenched with water (20 mL), and then extracted with EA (50 mL×3). The organic layers were combined and concentrated under reduced pressure to obtain a residue which was purified with silica gel column (eluted with Hex/EA) to afford INT B11-1 (0.96 g, yield 53%). LCMS: m/z=360 $[M+1]^+$.

Step 2: INT B11-1 (530 mg, 1.47 mmol, 1.0 eq.) and t-BuOK (570 mg, 5.08 mmol, 3.45 eq.) were dispersed in t-BuOH (10 mL). The reaction mixture was stirred overnight at 120° C., and then concentrated under reduced pressure to obtain a residue which was purified with silica gel column (eluted with Hex/EA) to afford INT B11 (300 mg, yield 59%). LCMS: m/z=340 $[M+1]^+$.

The following intermediate was synthesized using the above procedure with the corresponding starting material.

| INT | Structure | Starting material | LCMS (ESI, m/z): [M + H]$^+$ |
| --- | --- | --- | --- |
| INT B12 | 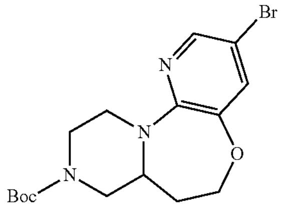 [SMILES: CC(C)(C)OC(=O)N1CCN2c3ncc(Br)cc3OCCC2C1] | 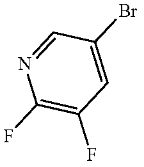 | 384, 386 |

Intermediate B13 (INT B13)

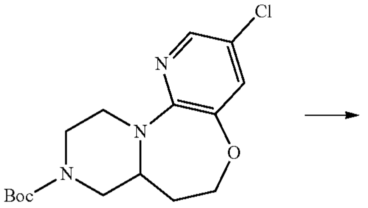

INT B11

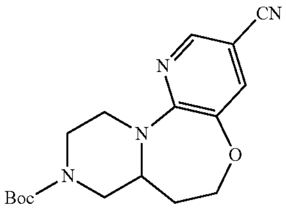

INT B13

Step 1: INT B11 (250 mg, 0.74 mmol, 1.0 eq.), $Zn(CN)_2$ (230 mg, 1.96 mmol, 2.66 eq.) and $Pd(PPh_3)_4$ (180 mg, 0.16 mmol, 0.21 eq.) were dispersed in DMF (10 mL). The reaction mixture was purged and maintained with an inert atmosphere of nitrogen, stirred for 4 hrs at 130° C., cooled to room temperature, diluted with brine and extracted with EA (50 mL×3). The organic layers were combined, dried over anhydrous $Na_2SO_4$ and then concentrated under reduced pressure to obtain a residue which was purified with Prep-HPLC (C18 column, eluted with $H_2O/CH_3CN$) to afford INT B13 (160 mg, yield 65%). LCMS: m/z=331 [M+1]$^+$.

Intermediate B14 (INT B14)

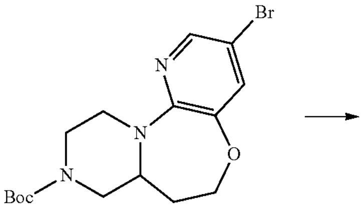

INT B12

-continued

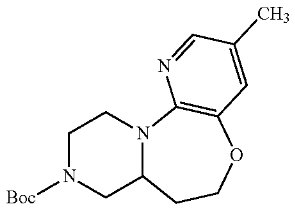

INT B14

Step 1: INT B12 (340 mg, 0.88 mmol, 1.0 eq.), 2,4,6-trimethyl-1,3,5,2,4,6-trioxatriborinane (190 mg, 1.51 mmol, 1.71 eq.), $Pd(dppf)Cl_2$ (200 mg, 0.27 mmol, 0.31 eq.) and $Na_2CO_3$ (240 mg, 1.74 mmol, 1.96 eq.) were dispersed in a mixed solvent of 1,4-dioxane and $H_2O$ (v/v=20 mL:2 mL). The reaction mixture was purged and maintained with an inert atmosphere of nitrogen, stirred for 1 h at 120° C., cooled to room temperature, diluted with brine and extracted with EA (50 mL×3). The organic layers were combined and dried over anhydrous $Na_2SO_4$ and then filtered. The filtrate was concentrated under reduced pressure to obtain a residue which was purified with silica gel column (eluted with Hex/EA) to afford INT B14 (240 mg, yield 84%) as a white solid. LCMS: m/z=320 [M+1]$^+$.

Intermediate B15 (INT B15)

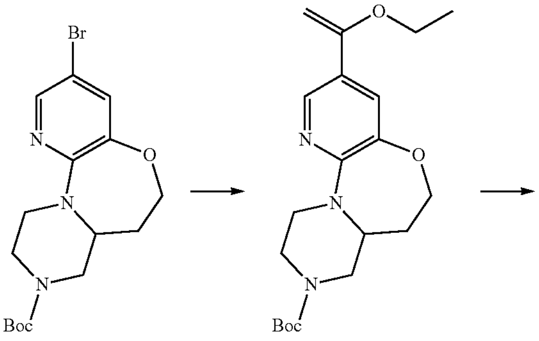

INT B12 INT B15-1

-continued

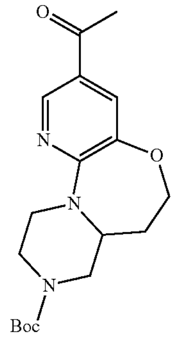

INT B15

Step 1: INT B12 (1.30 g, 3.38 mmol, 1.0 eq.), tributyl(1-ethoxyvinyl)stannane (1.70 g, 4.70 mmol, 1.39 eq.), $Pd(PPh_3)_2Cl_2$ (0.39 g, 0.55 mmol, 0.16 eq.) and CsF (1.09 g, 7.18 mmol, 2.12 eq.) were dispersed in 1,4-dioxane (20 mL). The reaction mixture was purged and maintained with an inert atmosphere of nitrogen, stirred for 2 hrs at 90° C., and then filtered. The filtrate was concentrated under reduced pressure to afford a crude product (1.27 g) of INT B15-1 which was used in next step without further purification. LCMS: m/z=376 $[M+1]^+$.

Step 2: The crude product (1.27 g) of INT B15-1 was dissolved in THF (20 mL), then HCl (12 mL, 6N, aq.) was added at room temperature. The reaction mixture was stirred for 3 hrs, quenched with $NaHCO_3$ aqueous solution (100 mL), and then extracted with EA (50 mL×3). The organic layers were combined, dried over anhydrous $Na_2SO_4$, and then filtrated. The filtrate was concentrated under reduce pressure to obtain a residue which was purified with silica gel column (eluted with Hex/EA) to afford INT B15 (0.37 g, yield 31%). LCMS: m/z=348 $[M+1]^+$.

Intermediate B16 (INT B16)

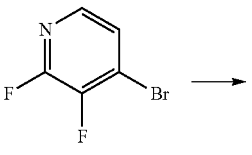

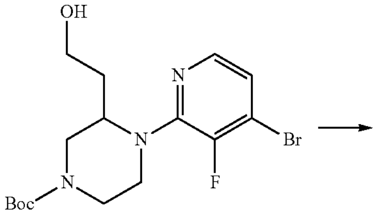

INT B16-1

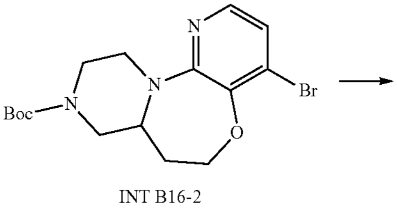

INT B16-2

-continued

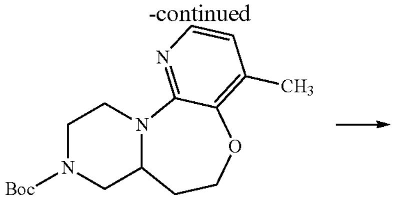

INT B16-3

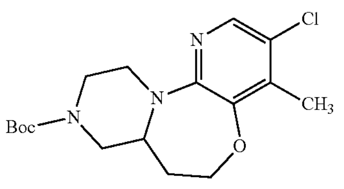

INT B16

Step 1: 4-Bromo-2,3-difluoropyridine (4.81 g, 24.80 mmol, 1.75 eq.), tert-butyl 3-(2-hydroxyethyl)piperazine-1-carboxylate (6.48 g, 28.14 mmol, 1.13 eq.) and $K_2CO_3$ (7.13 g, 51.59 mmol, 2.08 eq.) were dispersed in NMP (60 mL). The reaction mixture was stirred overnight at 120° C., poured into water (100 mL), and then extracted with EA (100 mL×3). The organic layers were combined and concentrated under reduced pressure to obtain a residue which was purified with silica gel column (eluted with Hex/EA) to afford INT B16-1 (1.60 g, yield 15%). LCMS: m/z=404, 406 $[M+1]^+$.

Step 2: A mixture of INT B16-1 (1.53 g, 3.78 mmol, 1.0 eq.), t-BuOK (1.34 g, 11.94 mmol, 3.16 eq.) and t-BuOH (30 mL) was stirred at 120° C. for 3 hrs, and then concentrated under reduced pressure to obtain a residue. The residue was purified with Prep-HPLC (C18 column, eluted with $H_2O$/$CH_3CN$) to afford INT B16-2 (0.91 g, yield 62%). LCMS: m/z=384, 386 $[M+1]^+$.

Step 3: INT B16-2 (2.01 g, 5.23 mmol, 1.0 eq.), 2,4,6-trimethyl-1,3,5,2,4,6-trioxatriborinane (2.04 g, 8.13 mmol, 1.55 eq.), $Pd(dppf)Cl_2$ (2.06 g, 2.82 mmol, 0.54 eq.) and $Na_2CO_3$ (1.80 g, 13.02 mmol, 2.49 eq.) were dispersed in a mixed solvent of 1,4-dioxane and $H_2O$ (v/v=40 mL:4 mL). The reaction mixture was purged and maintained with an inert atmosphere of nitrogen, stirred for 3 hrs at 90° C., cooled to room temperature, diluted with brine and extracted with EA (100 mL×3). The organic layers were combined, dried over anhydrous $Na_2SO_4$ and then concentrated under reduced pressure to obtain a residue which was purified with silica gel column (eluted with Hex/EA) to afford INT B16-3 (1.07 g, yield 64%) as white solid. LCMS: m/z=320 $[M+1]^+$.

Step 4: INT B16-3 (0.87 g, 2.72 mmol, 1.0 eq.) and NCS (0.55 g, 4.12 mmol, 1.51 eq.) were dispersed in $CH_3CN$ (20 mL). The reaction mixture was purged and maintained with an inert atmosphere of nitrogen, stirred for 3 hrs at 80° C., cooled to room temperature, diluted with brine and extracted with EA (100 mL×3). The organic layers were combined, dried over anhydrous $Na_2SO_4$, filtered and then concentrated under reduced pressure to obtain a residue which was purified with Prep-HPLC (C18 column, eluted with $H_2O$/$CH_3CN$) to afford INT B16 (0.50 g, yield 51%). LCMS: m/z=354 $[M+1]^+$.

Intermediate B17 (INT B17)

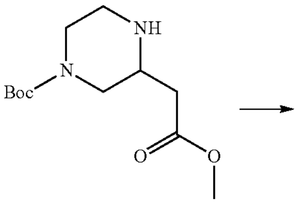

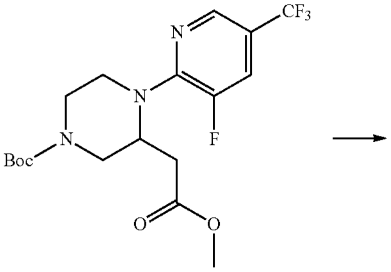

INT B17-1

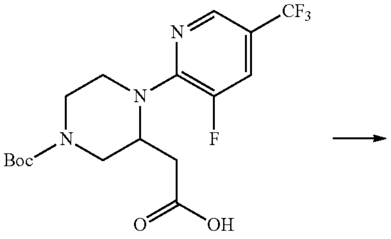

INT B17-2

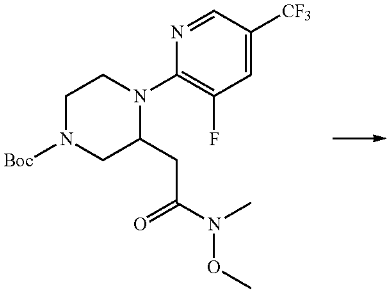

INT B17-3

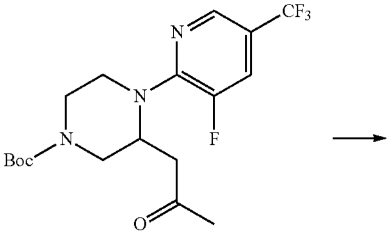

INT B17-4

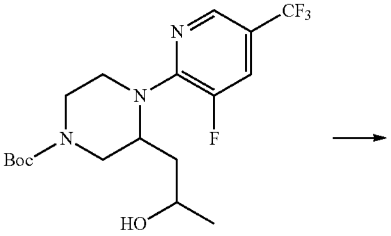

INT B17-5

-continued

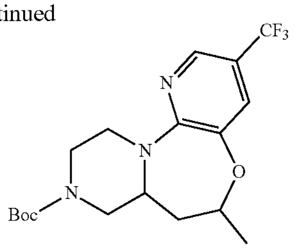

INT B17

Step 1: 2,3-Difluoro-5-(trifluoromethyl)pyridine (11.91 g, 65.05 mmol, 1.89 eq.), tert-butyl 3-(2-methoxy-2-oxoethyl) piperazine-1-carboxylate (8.90 g, 34.45 mmol, 1.0 eq.) and DIPEA (15 mL) were dissolved in DMSO (70 mL). The reaction mixture was stirred overnight at 130° C., poured into water (100 mL), and then extracted with EA (100 mL×3). The organic layers were combined and concentrated under reduced pressure to obtain a residue which was purified with Prep-HPLC (C18 column, eluted with $H_2O/CH_3CN$) to afford INT B17-1 (13.59 g, yield 93%). LCMS: m/z=422 $[M+1]^+$.

Step 2: INT B17-1 (13.59 g, 32.25 mmol, 1.0 eq.) and LiOH (2.82 g, 117.71 mmol, 3.65 eq.) were dispersed in a mixed solvent of THF (100 mL) and water (30 mL). The reaction mixture was stirred for 3 hrs at room temperature, quenched with HCl aqueous solution (1N), and extracted with EA (100 mL×3). The organic layers were combined, dried over anhydrous $Na_2SO_4$, and then concentrated under reduced pressure to afford a crude product (16.78 g) of INT B17-2 which was used in next step without further purification. LCMS: m/z=408 $[M+1]^+$.

Step 3: The crude product (16.37 g) of INT B17-2, N,O-dimethylhydroxylamine hydrochloride (8.90 g, 91.24 mmol, 2.83 eq.) and DIPEA (20 mL) were dissolved in $CH_3CN$ (200 mL), and then HATU (17.66 g, 46.45 mmol, 1.44 eq.) was added. The reaction mixture was stirred for 4 hrs at room temperature, poured into water (200 mL), and extracted with EA (200 mL×3). The organic layers were combined and concentrated under reduced pressure to obtain a residue which was purified with Prep-HPLC (C18 column, eluted with $H_2O/CH_3CN$) to afford INT B17-3 (13.05 g, yield 89%). LCMS: m/z=451 $[M+1]^+$.

Step 4: In an atmosphere of nitrogen, MgMeBr (15 mL, 45 mmol, 1.56 eq.) was added at 0° C. to a solution of INT B17-3 (12.98 g, 28.82 mmol, 1.0 eq.) dissolved in THF (300 mL). The reaction solution was stirred for 2 hrs at room temperature, quenched with saturated $NH_4Cl$ aqueous solution (200 mL) and then extracted with EA (200 mL×3). The organic layers were combined and then concentrated under reduced pressure to obtain a residue which was purified with Prep-HPLC (C18 column, eluted with $H_2O/CH_3CN$) to afford INT B17-4 (9.99, yield 85%). LCMS: m/z=406 $[M+1]^+$.

Step 5: INT B17-4 (9.63 g, 23.75 mmol, 1.0 eq.) was dissolved in THF (150 mL), and $NaBH_4$ (10.94 g, 28.77 mmol, 1.21 eq.) was added at room temperature. The reaction mixture was stirred at room temperature for 5 hrs, poured into water (200 mL), and extracted with EA (200 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT B17-5 (9.20 g, yield 95%). LCMS: m/z=408 $[M+1]^+$.

Step 6: INT B17-5 (4.15 g, 10.19 mmol, 1.0 eq.) and t-BuOK (3.12 g, 27.80 mmol, 2.73 eq.) were dispersed in t-BuOH (40 mL). The reaction mixture was stirred at 120° C. for 3 hrs, and then concentrated under reduced pressure to obtain a residue which was purified with Prep-HPLC (C18 column, eluted with $H_2O/CH_3CN$) to afford INT B17 (2.40 g, yield 60%). LCMS: m/z=388 $[M+1]^+$.

Intermediate B18 (INT B18)

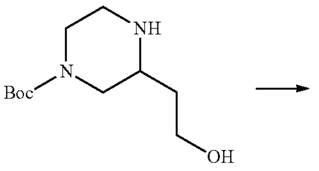

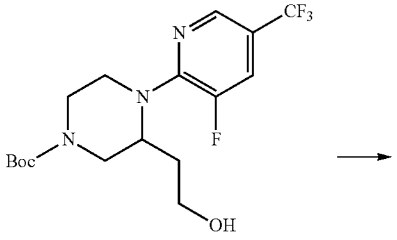

INT B18-1

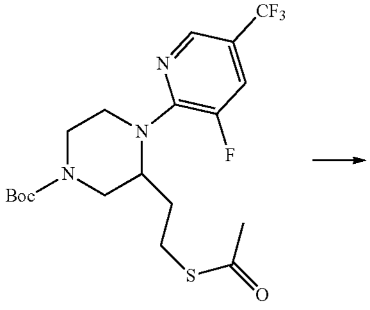

INT B18-2

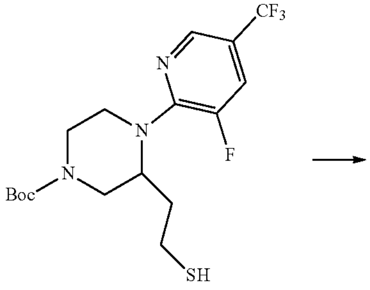

INT B18-3

-continued

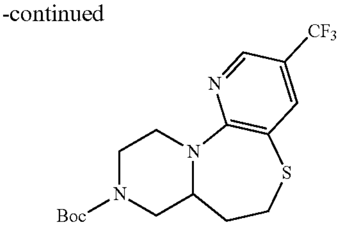

INT B18

Step 1: 2,3-Difluoro-5-(trifluoromethyl)pyridine (6.92 g, 37.80 mmol, 1.15 eq.), tert-butyl 3-(2-hydroxyethyl)piperazine-1-carboxylate (7.54 g, 32.74 mmol, 1.0 eq.) and TEA (14.84 g, 146.66 mmol, 4.48 eq.) were dissolved in DMF (100 mL). The reaction mixture was stirred overnight at 85° C. and then concentrated under reduced pressure to obtain a residue which was purified with Prep-HPLC (C18 column, eluted with $H_2O/CH_3CN$) to afford INT B18-1 (11.33 g, yield 87%). LCMS: m/z=394 $[M+1]^+$.

Step 2: A mixture of INT B18-1 (4.03 g, 10.24 mmol, 1.0 eq.), triphenylphosphine (9.32 g, 35.54 mmol, 3.47 eq.) and THF (80 mL) was purged and maintained with an inert atmosphere of nitrogen, cooled to −10° C., and then diisopropyl azodicarboxylate, (6.15 g, 30.41 mmol, 2.97 eq.) was added dropwise. The resulting mixture was stirred at −10° C. for 30 min and then ethanethioic acid (1.75 g, 22.99 mmol, 2.25 eq.) was added dropwise at −10° C. The reaction mixture was stirred at −10° C. for 2 hrs, quenched with water (20 mL), and then extracted with EA (100 mL×3). The organic layers were combined and concentrated under reduced pressure to obtain a residue which was purified with silica gel column (eluted with Hex/EA) to afford INT B18-2 (4.45 g, yield 96%). LCMS: m/z=452 $[M+1]^+$.

Step 3: INT B18-2 (7.28 g, 16.12 mmol, 1.0 eq.) and NaOH (1.95 g, 48.75 mmol, 3.02 eq.) were dispersed in a mixed solvent of MeOH (70 mL) and water (10 mL). The reaction mixture was stirred for 30 min at room temperature, quenched with HCl aqueous solution (1N), and extracted with EA (100 mL×3). The organic layers were combined, dried over anhydrous $Na_2SO_4$, and then concentrated under vacuum to afford a crude product (6.60 g) of INT B18-3 which was used in next step without further purification. LCMS: m/z=410 $[M+1]^+$.

Step 4: The crude product (6.60 g) of INT B18-3 and LiOH (1.22 g, 50.94 mmol, 3.06 eq.) were dispersed in a mixed solvent of DMF (10 mL) and THF (30 mL). The reaction mixture was purged and maintained with an inert atmosphere of nitrogen, stirred for 3 hrs at 80° C., and then concentrated under reduced pressure to obtain a residue which was purified with Prep-HPLC (C18 column, eluted with $H_2O/CH_3CN$) to afford INT B18 (4.65 g, yield 72%). LCMS: m/z=390 $[M+1]^+$.

The following intermediates were synthesized using the above procedure with the corresponding starting material.

| INT | Structure | Starting material | LCMS (ESI, m/z): $[M + H]^+$ |
|---|---|---|---|
| INT B19 | 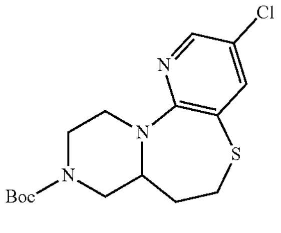 | 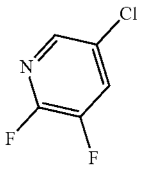 | 356 |

-continued

| INT | Structure | Starting material | LCMS (ESI, m/z): [M + H]+ |
|---|---|---|---|
| INT B20 | 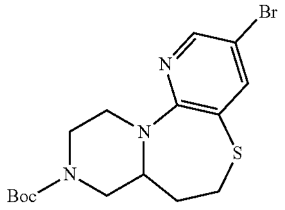 [SMILES: CC(C)(C)OC(=O)N1CCN2c3ncc(Br)cc3SCCC2C1] | 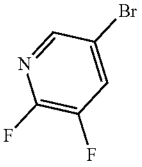 | 400, 402 |

Intermediate B21 (INT B21)

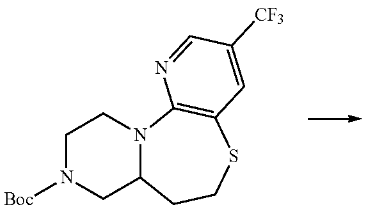

INT B18

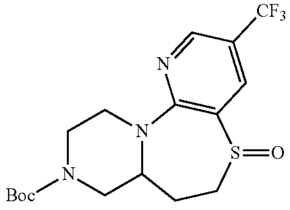

INT B21

Step 1: m-CPBA (150 mg, 0.87 mmol, 1.14 eq.) was added at 0° C. to a mixture of INT B18 (296 mg, 0.76 mmol, 1.0 eq.) and DCM (10 mL). The reaction mixture was stirred for 2 hrs at 0° C., quenched with saturated $Na_2S_2O_3$ aqueous solution (20 mL) and extracted with EA (50 mL×3). The organic layers were combined, dried over anhydrous $Na_2SO_4$ and then concentrated under reduced pressure to obtain a residue which was purified with silica gel column (eluted with Hex/EA) to afford INT B21 (250 mg, yield 81%). LCMS: m/z=406 $[M+1]^+$.

Intermediate B22 (INT B22)

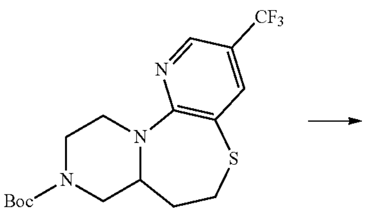

INT B18

-continued

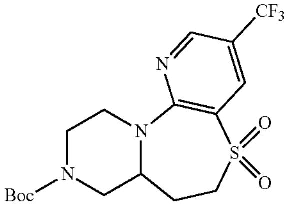

INT B22

Step 1: m-CPBA (559 mg, 3.24 mmol, 4.21 eq.) was added at 0° C. to a mixture of INT B18 (300 mg, 0.77 mmol, 1.0 eq.) and DCM (10 mL). The reaction mixture was stirred for 2 hrs at 0° C., quenched with saturated $Na_2S_2O_3$ aqueous solution (20 mL) and extracted with EA (50 mL×3). The organic layers were combined, dried over anhydrous $Na_2SO_4$ and then concentrated under reduced pressure to obtain a residue which was purified with silica gel column (eluted with Hex/EA) to afford INT B22 (305 mg, yield 94%). LCMS: m/z=422 $[M+1]^+$.

Intermediate B23 (INT B23)

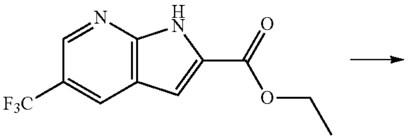

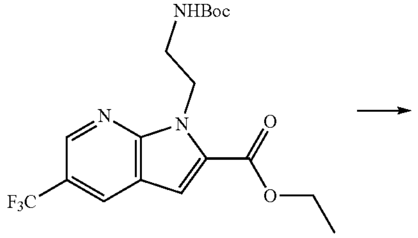

INT B23-1

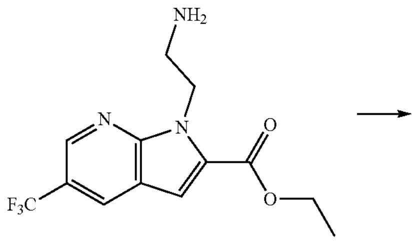

INT B23-2

-continued

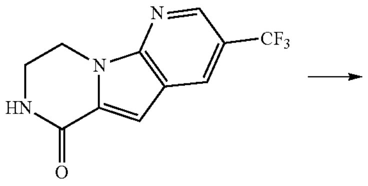

INT B23-3

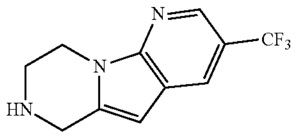

INT B23

Step 1: Ethyl 5-(trifluoromethyl)-1H-pyrrolo[2,3-b]pyridine-2-carboxylate (10.01 g, 38.77 mmol, 1.0 eq.) and t-BuOK (4.80 g, 42.78 mmol, 1.10 eq.) were dispersed in DMF (200 mL) at 0° C. The resulting mixture was stirred for 1 h, and then tert-butyl 1,2,3-oxathiazolidine-3-carboxylate 2,2-dioxide (9.58 g, 42.91 mmol, 1.11 eq.) was added. The reaction mixture was stirred for 2 hrs at room temperature, quenched with water (100 mL) and extracted with EA (100 mL×3). The organic layers were combined and concentrated under vacuum to obtain a residue which was purified with Prep-HPLC (C18 column, eluted with $H_2O/CH_3CN$) to afford INT B23-1 (14.17 g). LCMS: m/z=402 $[M+1]^+$.

Step 2: TFA (10 mL) was added dropwise at room temperature to a solution of INT B23-1 (13.16 g, 32.79 mmol, 1.0 eq.) dissolved in DCM (80 mL). The reaction mixture was stirred for 2 hrs at room temperature, quenched with saturated $NaHCO_3$ aqueous solution (50 mL) and extracted with EA (100 mL×3). The organic layer were combined, dried over anhydrous $Na_2SO_4$, and then concentrated under reduced pressure to afford a crude product (9.57 g) of INT B23-2 which was used in next step without further purification. LCMS: m/z=302 $[M+1]^+$.

Step 3: In an atmosphere of nitrogen, INT B23-2 (9.60 g, 31.87 mmol, 1.0 eq.) and $K_2CO_3$ (22.23 g, 160.85 mmol, 5.05 eq.) were dispersed in MeOH (150 mL). The reaction mixture was stirred for 16 hrs at room temperature and then concentrated under vacuum to obtain a residue. A mixture of the residue and water (100 mL) was stirred and then filtered. The filter cake was washed with water (100 mL×3), and dried to afford a crude product (8.24 g) of INT B23-3 which was used in next step without further purification. LCMS: m/z=256 $[M+1]^+$.

Step 4: INT B23-3 (2.08 g, 8.15 mmol, 1.0 eq.) was dispersed in MTBE (50 mL), and then $LiAlH_4$ (640 mg, 16.86 mmol, 2.07 eq.) was added at room temperature. The reaction mixture was stirred for 2 hrs at 55° C., quenched with water (50 mL) and extracted with EA (100 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT B23 (950 mg). LCMS: m/z=242 $[M+1]^+$.

Intermediate B24 (INT B24)

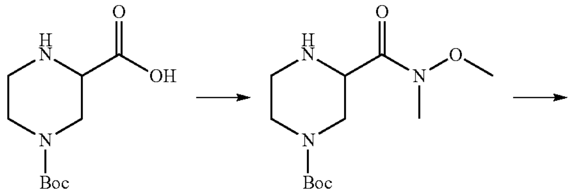

INT B24-1

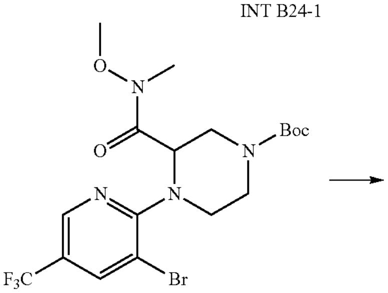

INT B24-2

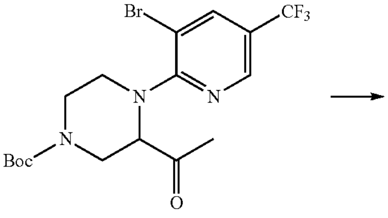

INT B24-3

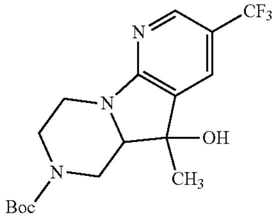

INT B24

Step 1: 4-(Tert-butoxycarbonyl)piperazine-2-carboxylic acid (21.59 g, 93.76 mmol, 1.0 eq.), N,O-dimethylhydroxylamine hydrochloride (21.55 g, 220.93 mmol, 2.36 eq.), DIPEA (42.43 g, 328.30 mmol, 3.50 eq.) and HATU (43.87 g, 115.38 mmol, 1.23 eq.) were dispersed in $CH_3CN$ (200 mL). The reaction mixture was stirred for 3 hrs at room temperature and then concentrated under reduced pressure to obtain a residue which was purified with Prep-HPLC (C18 column, eluted with $H_2O/CH_3CN$) to afford INT B24-1 (12.68 g, yield 49%). LCMS: m/z=274 $[M+1]^+$.

Step 2: 3-bromo-2-fluoro-5-(trifluoromethyl)pyridine (19.09 g, 78.24 mmol, 1.25 eq.), INT B24-1 (17.10 g, 62.56 mmol, 1.0 eq.) and DIPEA (9.22 g, 71.34 mmol, 1.14 eq.) were dispersed in DMF (100 mL) at room temperature. The reaction mixture was stirred for 16 hrs at 80° C., poured into water (100 mL), and extracted with DCM (100 mL×3). The organic layers were combined and concentrated under reduced pressure to obtain a residue which was purified with silica gel column (eluted with Hex/EA) to afford INT B24-2 (15.59 g, yield 50%). LCMS: m/z=497, 499 $[M+1]^+$.

Step 3: In an atmosphere of nitrogen, MeMgBr (14 mL, 42 mmol, 1.54 eq.) was added at −20° C. to a solution of INT B24-2 (13.59 g, 27.33 mmol, 1.0 eq.) dissolved in THF (140 mL). The reaction mixture was stirred for 3 hrs at −20° C., quenched with saturated $NH_4Cl$ aqueous solution (200 mL), and extracted with EA (200 mL×3). The organic layers were combined and then concentrated under reduced pressure to obtain a residue which was purified with Prep-HPLC (C18 column, eluted with $H_2O/CH_3CN$) to afford INT B24-3 (10.9 g, yield 88%). LCMS: m/z=452, 454 $[M+1]^+$.

Step 4: In an atmosphere of nitrogen, n-BuLi (14 mL, 42.0 mmol, 1.74 eq.) was added dropwise at −78° C. to a solution of INT B24-3 (10.9 g, 24.10 mmol, 1.0 eq.) dissolved in THF (100 mL). The reaction mixture was stirred for 1 h at −78° C., quenched with saturated $NH_4Cl$ aqueous solution (200 mL), and then extracted with EA (200 mL×3). The organic layers were combined and then concentrated under reduced pressure to obtain a residue which was purified with Prep-HPLC (C18 column, eluted with $H_2O/CH_3CN$) to afford INT B24 (2.76 g, yield 30%). LCMS: m/z=374 $[M+1]^+$.

Intermediate B25 (INT B25)

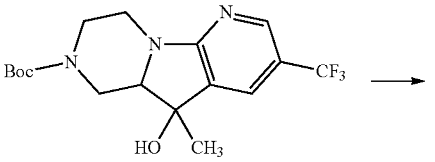

INT B24

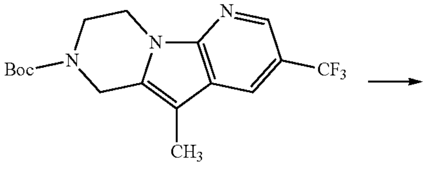

INT B25-1

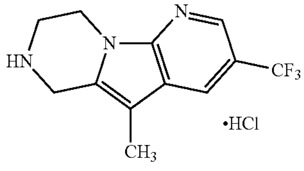

INT B25

Step 1: A mixture of INT B24 (6.19 g, 16.58 mmol, 1.0 eq.), $Et_3N$ (3.69 g, 36.47 mmol, 2.20 eq.), DMAP (122 mg, 0.99 mmol, 0.06 eq.) and DCM (100 mL) was cooled to 0° C., and then MsCl (2.94 g, 25.67 mmol, 1.55 eq.) was added dropwise. The reaction mixture was stirred for 1 h at 0° C., poured into saturated $NaHCO_3$ aqueous solution (100 mL), and then extracted with DCM (100 mL×3). The organic layers were combined and then concentrated under reduced pressure to obtain a residue which was purified with silica gel column (eluted with Hex/EA) to afford INT B25-1 (5.40 g, yield 91%). LCMS: m/z=356 $[M+1]^+$.

Step 2: A mixture of INT B25-1 (5.05 g, 14.21 mmol, 1.0 eq.) and HCl/1,4-dioxane (100 mL, 1N) was stirred for 3 hrs at room temperature and then concentrated under reduced pressure to afford a crude product (6.72 g) of a hydrochloride of INT B25 which was used in next step without further purification.

LCMS: m/z=256 $[M+1]^+$.

Intermediate B26 and Intermediate B27 (INT B26 and INT B27)

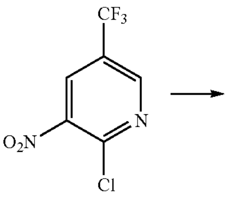

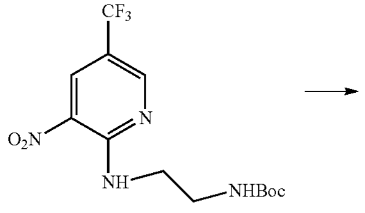

INT B26-1

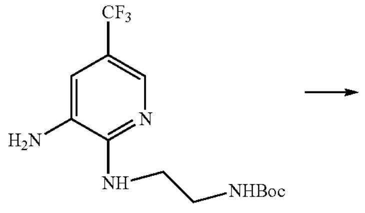

INT B26-2

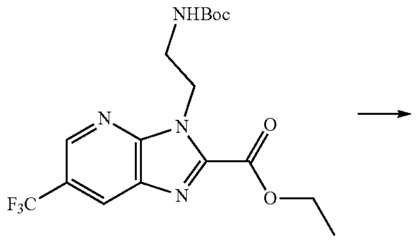

INT B26-3

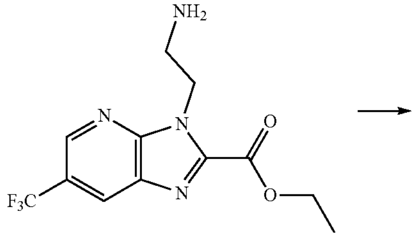

INT B26-4

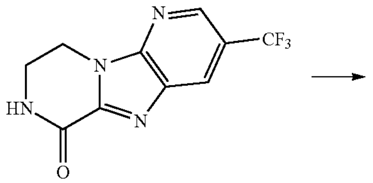

INT B26-5

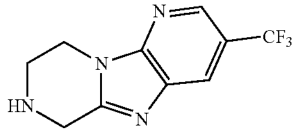

+

INT B26

-continued

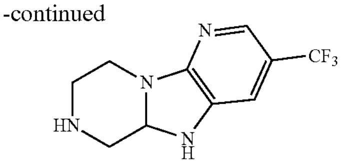

INT B27

Step 1: 2-Chloro-3-nitro-5-(trifluoromethyl)pyridine (10.1 g, 44.58 mmol, 1.0 eq.), tert-butyl (2-aminoethyl) carbamate (7.15 g, 44.58 mmol, 1.0 eq.) and TEA (9.02 g, 89.17 mmol, 2.0 eq.) were dispersed in $CH_3CN$ (100 mL) at room temperature. The reaction mixture was stirred for 4 hrs at 110° C., cooled to room temperature and concentrated under reduced pressure to obtain a residue. A mixture of the residue and EA (5 mL) was stirred and then filtered. The filter cake was washed with EA (1 mL), and dried under vacuum to afford INT B26-1 (11.20 g, yield 71%). LCMS: m/z=351 $[M+1]^+$.

Step 2: INT B26-1 (11.73 g, 33.49 mmol, 1.0 eq.), Pd/C (2.10 g, 0.18 w/w.) were dispersed in MeOH (40 mL). The reaction mixture was purged and maintained with an inert atmosphere of hydrogen, stirred for 2 hrs at room temperature, and then filtered. The filtrate was concentrated under reduced pressure to afford a crude product (5.42 g) of INT B26-2 which was used in next step without further purification. LCMS: m/z=321 $[M+1]^+$.

Step 3: A crude product (5.41 g) of INT B26-2, ethyl 2-chloro-2-oxoacetate (2.98 g, 21.83 mmol, 1.29 eq.) and $Et_3N$ (3.94 g, 38.94 mmol, 2.31 eq.) were dispersed in DCM (70 mL). The reaction mixture was stirred for 1 h at room temperature, poured into water (70 mL) and extracted with EA (100 mL×3). The organic layers were combined, dried over anhydrous $Na_2SO_4$, and then concentrated under reduced pressure to obtain a residue. A mixture of the residue and toluene (70 mL) was stirred for 16 hrs at 110° C., cooled to room temperature and then concentrated under reduced pressure to obtain a crude product which was purified with Prep-HPLC (C18 column, eluted with $H_2O/CH_3CN$) to afford INT B26-3 (0.56 g, yield 8%). LCMS: m/z=403 $[M+1]^+$.

Step 4: TFA (3 mL) was added dropwise at room temperature to a solution of INT B26-3 (0.55 g, 1.37 mmol, 1.0 eq.) dissolved in DCM (12 mL). The reaction mixture was stirred for 1 h at room temperature and concentrated under reduced pressure to afford a crude product (0.40 g) of INT B26-4 which was used in next step without further purification. LCMS: m/z=303 $[M+1]^+$.

Step 5: The crude product (0.40 g) of INT B26-4 (0.40 g, 1.32 mmol, 1.0 eq.) and $K_2CO_3$ (0.96 g, 6.95 mmol, 5.25 eq.) were dispersed in MeOH (30 mL). The reaction mixture was stirred for 16 hrs at room temperature and concentrated under reduced pressure to obtain a residue. A mixture of the residue and water (20 mL) was stirred and then filtered. The filter cake was washed with water (10 mL), and dried under vacuum to afford INT B26-5 (0.22 g, yield 64%). LCMS: m/z=257 $[M+1]^+$.

Step 6: INT B26-5 (0.42 g, crude) was dispersed in MTBE (20 mL), $LiAlH_4$ (0.11 g, 2.90 mmol, 1.77 eq.) was added at room temperature. The reaction mixture was stirred for 2 hrs at 55° C., quenched with water (50 mL) and extracted with EA (100 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT B26 (20 mg), LCMS: m/z=243 $[M+1]^+$; and INT B27 (200 mg), LCMS: m/z=245 $[M+1]^+$.

Intermediate B28 (INT B28)

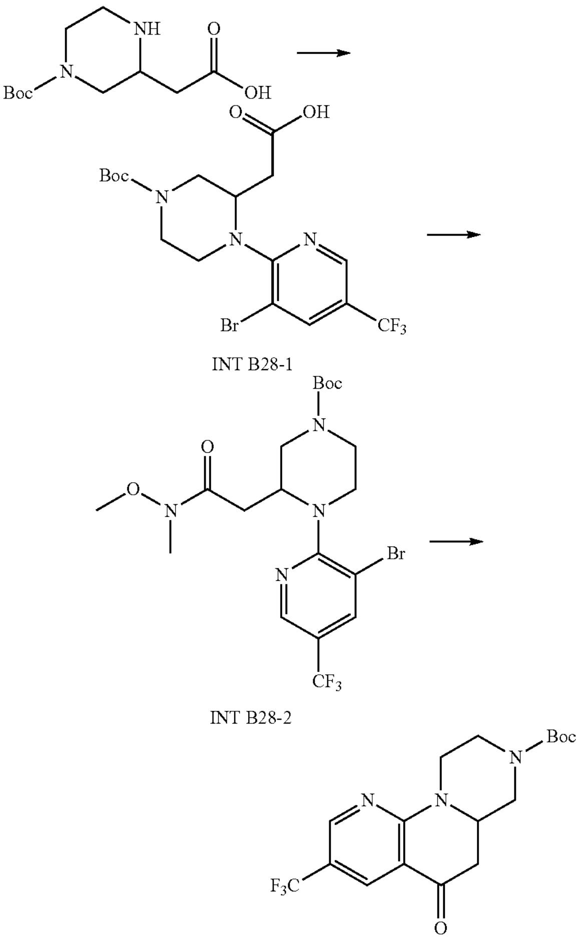

INT B28-1

INT B28-2

INT B28

Step 1: 2-(4-(Tert-butoxycarbonyl)piperazin-2-yl)acetic acid (6.39 g, 28.37 mmol, 1.0 eq.), 3-bromo-2-fluoro-5-(trifluoromethyl)pyridine (11.19 g, 45.86 mmol, 1.62 eq.), TEA (17 mL) were dispersed in $CH_3CN$ (120 mL) at room temperature. The reaction mixture was stirred for 16 hrs at 90° C., cooled to room temperature and concentrated under reduced pressure to obtain a residue which was purified with Prep-HPLC (C18 column, eluted with $H_2O/CH_3CN$) to afford INT B28-1 (12.54 g, yield 94%). LCMS: m z=468, 470 $[M+1]^+$.

Step 2: INT B28-1 (12.54 g, 26.78 mmol, 1.0 eq.), N,O-dimethylhydroxylamine hydrochloride (3.86 g, 39.57 mmol, 1.48 eq.), TEA (12.72 g, 125.70 mmol, 4.69 eq.) and HATU (13.79 g, 32.27 mmol, 1.21 eq.) were dispersed in DCM (100 mL). The reaction mixture was stirred for 3 hrs at room temperature, washed with water (100 mL) and then concentrated under reduced pressure to obtain a residue which was purified with Prep-HPLC (C18 column, eluted with $H_2O/CH_3CN$) to afford INT B28-2 (7.99 g, yield 58%). LCMS: m/z=511, 513 $[M+1]^+$.

Step 3: In an atmosphere of nitrogen, n-BuLi (8 mL, 24.0 mmol, 3.31 eq.) was added dropwise at −78° C. to a solution of INT B28-2 (3.7 g, 7.24 mmol, 1.0 eq.) dissolved in THF (40 mL). The reaction mixture was stirred for 2.5 hrs at −78°

C., quenched with saturated $NH_4Cl$ aqueous solution (100 mL), and then extracted with EA (100 mL×3). The organic layers were combined and concentrated under reduced pressure to obtain a residue which was purified with Prep-HPLC (C18 column, eluted with $H_2O/CH_3CN$) to afford INT B28 (2.20 g, yield 81%). LCMS: m/z=372 $[M+1]^+$.

Intermediate B29 (INT B29)

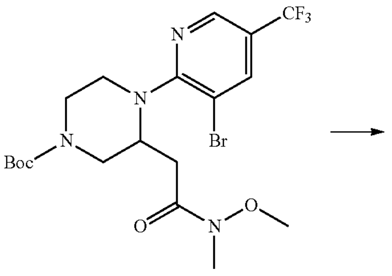

INT B28-2

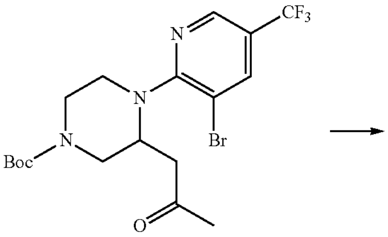

INT B29-1

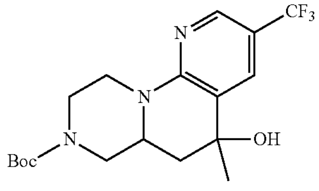

INT B29

Step 1: In an atmosphere of nitrogen, MgMeBr (1 mL, 3.0 mmol, 1.40 eq.) was added at −20° C. to a solution of INT B28-2 (1.10 g, 2.15 mmol, 1.0 eq.) dissolved in THF (20 mL). The reaction mixture was stirred for 4.5 hrs at −20° C., quenched with saturated $NH_4Cl$ aqueous solution (50 mL), and then extracted with EA (50 mL×3). The organic layers were combined and concentrated under reduced pressure to obtain a residue which was purified with Prep-HPLC (C18 column, eluted with $H_2O/CH_3CN$) to afford INT B29-1 (0.68 g, yield 67%). LCMS: m/z=466, 468 $[M+1]^+$.

Step 2: In an atmosphere of nitrogen, n-BuLi (0.6 mL, 1.8 mmol, 1.23 eq.) was added dropwise at −78° C. to a solution of INT B29-1 (0.68 g, 1.46 mmol, 1.0 eq.) dissolved in THF (10 mL). The reaction mixture was stirred for 1 h at −78° C., quenched with saturated $NH_4Cl$ aqueous solution (10 mL), and then extracted with EA (20 mL×3). The organic layers were combined and concentrated under reduced pressure to obtain a residue which was purified with Prep-HPLC (C18 column, eluted with $H_2O/CH_3CN$) to afford INT B29 (0.19 g, yield 33%). LCMS: m/z=388 $[M+1]^+$.

Intermediate B30 (INT B30)

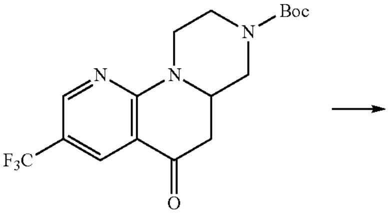

INT B28

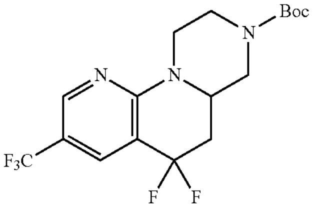

INT B30

Step 1: INT B28 (332.6 mg, 0.90 mmol, 1.0 eq.), DAST (1.44 g, 8.93 mmol, 9.97 eq.) were dispersed in $CHCl_3$ (3 mL) at room temperature. The reaction mixture was stirred for 5 hrs at 70° C., cooled to room temperature and concentrated under reduced pressure to obtain a residue which was purified with silica gel column (eluted with Hex/EA) to afford INT B30 (331 mg, yield 93%). LCMS: m/z=394 $[M+1]^+$.

Intermediate B31 (INT B31)

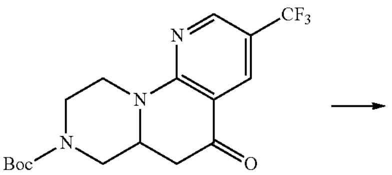

INT B28

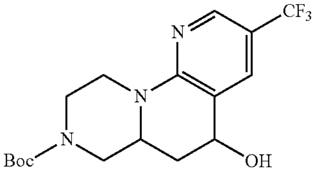

INT B31

Step 1: INT B28 (1.01 g, 2.72 mmol, 1.0 eq.) and $NaBH_4$ (0.57 g, 15.07 mmol, 5.54 eq.) were dispersed in THF (10 mL) at room temperature. The reaction mixture was stirred for 1 h at room temperature, poured into water (10 mL) and extracted with EA (20 mL×3). The organic layers were combined and concentrated under reduced pressure to afford a crude product (1.02 g) of INT B31 which was used in next step without further purification. LCMS: m/z=374 $[M+1]^+$.

Intermediate B32 (INT B32)

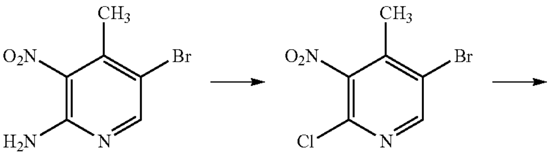

INT B32-1

-continued

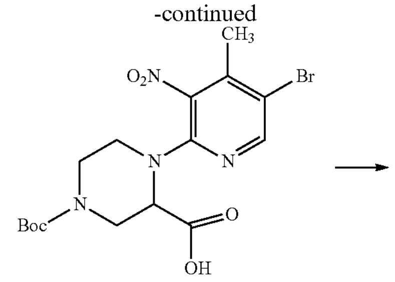

INT B32-2

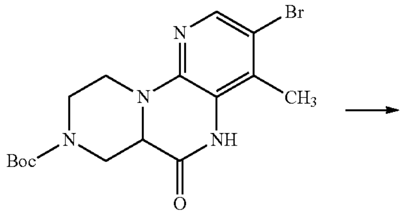

INT B32-3

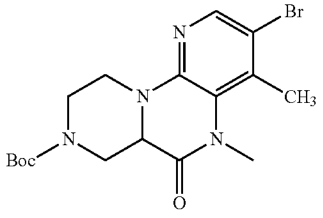

INT B32

Step 1: A mixture of 5-bromo-4-methyl-3-nitropyridin-2-amine (2.03 g, 8.75 mmol, 1.0 eq.) dispersed in concentrated HCl (50 mL) was cooled to 0° C., and then $NaNO_2$ (1.43 g, 20.73 mmol, 2.37 eq.) was added. The reaction mixture was stirred for 16 hrs at room temperature, and then extracted with EA (100 mL×3). The organic layers were combined and concentrated under reduced pressure to obtain a residue which was purified with silica gel column (eluted with Hex/EA) to afford INT B32-1 (1.32 g, yield 60%). LCMS: m/z=251, 253 $[M+1]^+$.

Step 2: 2-(4-(Tert-butoxycarbonyl)piperazin-2-yl)acetic acid (2.67 g, 11.60 mmol, 1.39 eq.), INT B32-1 (2.10 g, 8.35 mmol, 1.0 eq.) and $Et_3N$ (2.69 g, 26.58 mmol, 3.18 eq.) were dispersed in DMF (50 mL) at room temperature. The reaction mixture was stirred for 16 hrs at 100° C., poured into water (50 mL) and then extracted with EA (50 mL×3). The organic layers were combined and concentrated under reduced pressure to obtain a residue which was purified with silica gel column (eluted with Hex/EA) to afford INT B32-2 (1.07 g, yield 28%). LCMS: m/z=445, 447 $[M+1]^+$.

Step 3: INT B32-2 (1.02 g, 2.29 mmol, 1.0 eq.) and the powder of Fe (0.49 g, 8.77 mmol, 3.83 eq.) were dispersed in HOAc (20 mL). The reaction mixture was stirred for 16 hrs at room temperature, and then filtered. The filtrate was concentrated under vacuum to obtain a residue which was purified with silica gel column (eluted with Hex/EA) to afford INT B32-3 (0.21 g, yield 23%). LCMS: m/z=397, 399 $[M+1]^+$.

Step 4: INT B32-3 (1.14 g, 2.87 mmol, 1.0 eq.), $K_2CO_3$ (0.70 g, 5.06 mmol, 1.77 eq.) and $CH_3I$ (0.91 g, 6.41 mmol, 2.23 eq.) were dispersed in DMF (30 mL). The reaction mixture was stirred for 1 h at 60° C., poured into water (50 mL), and extracted with EA (50 mL×3). The organic layers were combined, dried over anhydrous $Na_2SO_4$, and then concentrated under reduced pressure to obtain a residue which was purified with silica gel column chromatography (eluted with Hex/EA) to afford INT B32 (0.94 g, yield 79%). LCMS: m/z=411, 413 $[M+1]^+$.

Intermediate B33 (INT B33)

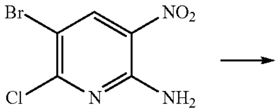

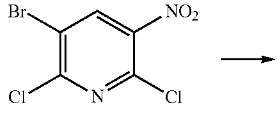

INT B33-1

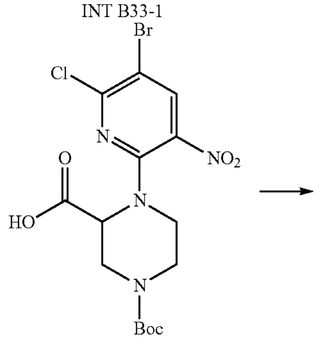

INT B33-2

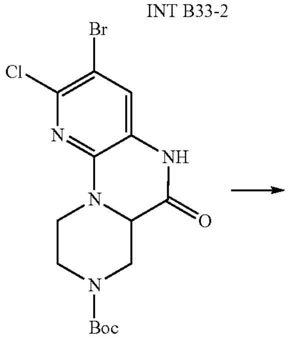

INT B33-3

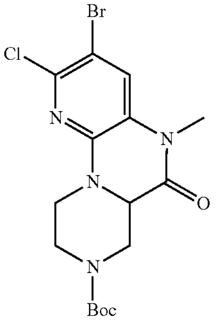

INT B33

Step 1: A mixture of 5-bromo-6-chloro-3-nitropyridin-2-amine (2.02 g, 8.00 mmol, 1.0 eq.) dispersed in concentrated HCl (50 mL) was cooled to 0° C., and then $NaNO_2$ (1.10 g, 15.94 mmol, 1.99 eq.) was added. The reaction mixture was stirred for 16 hrs at room temperature, and then extracted with EA (100 mL×3). The organic layers were combined and concentrated under reduced pressure to obtain a residue which was purified with silica gel column (eluted with Hex/EA) to afford INT B33-1 (1.59 g, yield 73%). LCMS: m/z=271, 273 $[M+1]^+$.

Step 2: 2-(4-(Tert-butoxycarbonyl)piperazin-2-yl)acetic acid (2.07 g, 8.99 mmol, 1.06 eq.), INT B33-1 (2.31 g, 8.50 mmol, 1.0 eq.) and TEA (6 mL) were dispersed in DMF (20 mL) at room temperature. The reaction mixture was stirred for 1 h at 60° C., poured into water (50 mL) and then extracted with EA (50 mL×3). The organic layers were combined and concentrated under reduced pressure to obtain a residue which was purified with Prep-HPLC (C18 column, eluted with $H_2O/CH_3CN$) to afford INT B33-2 (3.75 g, yield 94%). LCMS: m/z=465, 467 $[M+1]^+$.

Step 3: INT B33-2 (3.75 g, 8.05 mmol, 1.0 eq.) and the powder of iron (2.77 g, 49.60 mmol, 6.16 eq.) were dispersed in HOAc (50 mL). The reaction mixture was stirred for 16 hrs at room temperature, and then filtered. The filtrate was concentrated under vacuum to obtain a residue which was purified with silica gel column (eluted with Hex/EA) to afford INT B33-3 (1.31 g, yield 38%). LCMS: m/z=417, 419 $[M+1]^+$.

Step 4: A mixture of INT B33-3 (1.2 g, 2.87 mmol, 1.0 eq.) and THF (20 mL) was purged and maintained with an inert atmosphere of nitrogen, cooled to 0~10° C., and then NaH (0.29 g, 7.25 mmol, 2.52 eq.) (60% in mineral oil) was added slowly. The resulting mixture was stirred for 0.5 h, and then $CH_3I$ (1.24 g, 8.74 mmol, 3.04 eq.) was added. The reaction mixture was warmed to room temperature and stirred for 3 hrs, quenched with water (20 mL), and then extracted with EA (50 mL×3). The organic layers were combined, dried over anhydrous $Na_2SO_4$, and concentrated under reduced pressure to obtain a residue which was purified with silica gel column chromatography (eluted with Hex/EA) to afford INT B33 (0.89 g, yield 71%). LCMS: m/z=431, 433 $[M+1]^+$.

Intermediate B34 (INT B34)

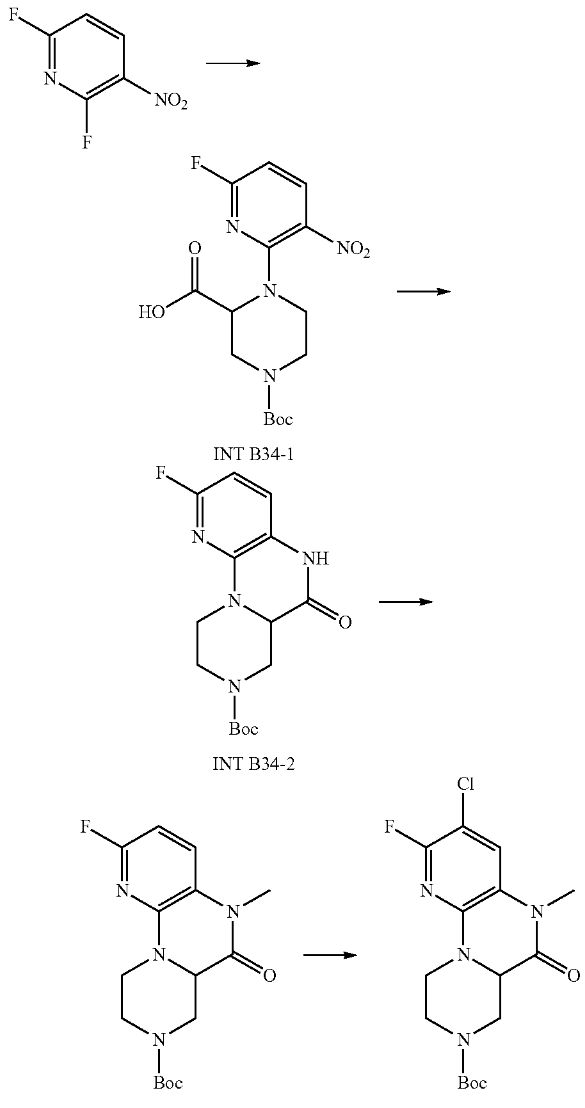

INT B34-1

INT B34-2

INT B34-3

INT B34

Step 1: 2-(4-(Tert-butoxycarbonyl)piperazin-2-yl)acetic acid (3.09 g, 13.42 mmol, 0.98 eq.), 2,6-difluoro-3-nitropyridine (2.17 g, 13.56 mmol, 1.0 eq.) and TEA (4 mL) were dispersed in DMF (20 mL) at room temperature. The reaction mixture was stirred for 1 h at room temperature, poured into water (50 mL) and then extracted with EA (50 mL×3). The organic layers were combined and concentrated under reduced pressure to obtain a residue which was purified with Prep-HPLC (C18 column, eluted with $H_2O/CH_3CN$) to afford INT B34-1 (4.66 g, yield 92%). LCMS: m/z=371 $[M+1]^+$.

Step 2: INT B34-1 (3.20 g, 8.64 mmol, 1.0 eq.) and Pd/C (0.45 g, 0.14 w/w.) were dispersed in MeOH (40 mL). The reaction mixture was purged and maintained with an inert atmosphere of hydrogen, stirred for 24 hrs at room temperature, and then filtered. The filtrate was concentrated under vacuum to afford a crude product (2.10 g) of INT B34-2. LCMS: m/z=323 $[M+1]^+$.

Step 3: A mixture of INT B34-2 (2.10 g, 6.52 mmol, 1.0 eq.) dissolved in THF (30 mL) was purged and maintained with an inert atmosphere of nitrogen, cooled to 0~10° C., and then NaH (0.32 g, 13.33 mmol, 2.05 eq.) (60% in mineral oil) was added slowly. The resulting mixture was stirred for 0.5 h and then $CH_3I$ (4.13 g, 29.10 mmol, 4.47 eq.) was added. The reaction mixture was stirred for 2 hrs at room temperature, quenched with water (20 mL), and extracted with EA (50 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT B34-3 (1.14 g, yield 52%). LCMS: m/z=337 $[M+1]^+$.

Step 4: INT B34-3 (1.14 g, 3.39 mmol, 1.0 eq.) and NCS (0.60 g, 4.49 mmol, 1.33 eq.) were dispersed in DMF (15 mL). The reaction mixture was stirred for 1 h at room temperature, diluted with brine (50 mL) and then extracted with EA (50 mL×3). The organic layers were combined, dried over anhydrous $Na_2SO_4$ and then concentrated under reduced pressure to obtain a residue which was purified with Prep-HPLC (C18 column, eluted with $H_2O/CH_3CN$) to afford INT B34 (0.88 g, yield 70%). LCMS: m/z=371 $[M+1]^+$.

Intermediate B35 (INT B35)

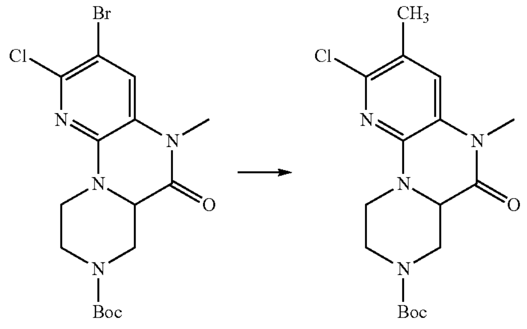

INT B33 INT B35

Step 1: INT B33 (0.50 g, 1.16 mmol, 1.0 eq.), 2,4,6-trimethyl-1,3,5,2,4,6-trioxatriborinane (1.06 g, 8.44 mmol, 7.29 eq.), $Pd(dppf)Cl_2$ (0.30 g, 0.41 mmol, 0.35 eq.) and $K_2CO_3$ (0.82 g, 5.93 mmol, 5.12 eq.) were dispersed in a mixed solvent of 1,4-dioxane and $H_2O$ (v/v=5 mL:1 mL). The reaction mixture was purged and maintained with an inert atmosphere of nitrogen, stirred for 4 hrs at 100° C., cooled to room temperature, diluted with brine and then extracted with EA (50 mL×3). The organic layers were combined and dried over anhydrous $Na_2SO_4$ and then concentrated under reduced pressure to obtain a residue which was purified with Prep-HPLC (C18 column, eluted with $H_2O/CH_3CN$) to afford INT B35 (0.21 g, yield 49%) as a white solid. LCMS: m/z=367 $[M+1]^+$.

Intermediate B36 (INT B36)

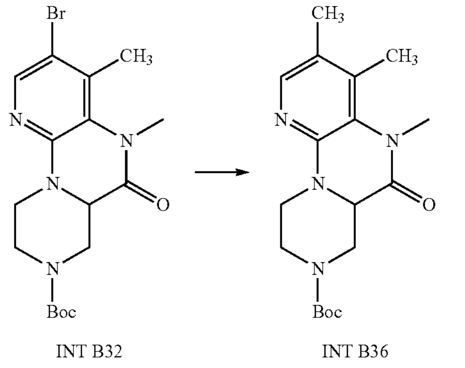

Step 1: INT B32 (410 mg, 1.00 mmol, 1.0 eq.), 2,4,6-trimethyl-1,3,5,2,4,6-trioxatriborinane (260 mg, 2.07 mmol, 2.07 eq.), Pd(dppf)$Cl_2$ (260 mg, 0.36 mmol, 0.36 eq.) and $K_2CO_3$ (310 mg, 2.24 mmol, 2.24 eq.) were dispersed in a mixed solvent of 1,4-dioxane and $H_2O$ (v/v=5 mL:1 mL). The reaction mixture was purged and maintained with an inert atmosphere of nitrogen, stirred for 2 hrs at 120° C., cooled to room temperature, diluted with brine and then extracted with EA (50 mL×3). The organic layers were combined, dried over anhydrous $Na_2SO_4$ and then concentrated under reduced pressure to obtain a residue which was purified with Prep-HPLC (C18 column, eluted with $H_2O/CH_3CN$) to afford INT B36 (220 mg, yield 66%) as a white solid. LCMS: m/z=347 $[M+1]^+$.

Intermediate B37 (INT B37)

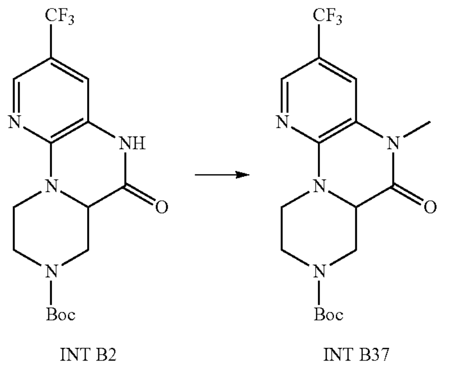

Method A: NaH (2.31 g, 57.75 mmol, 2.05 eq.) (60% in mineral oil) was added slowly at 0~10° C. to a solution of INT B2 (10.48 g, 28.14 mmol, 1.0 eq.) dissolved in THF (100 mL). The resulting mixture was stirred for 0.5 h, and then $CH_3I$ (8.41 g, 59.25 mmol, 2.11 eq.) was added. The reaction mixture was stirred for 3 hrs at room temperature, quenched with water (200 mL), and extracted with DCM (200 mL×3). The organic layers were combined, dried over anhydrous $Na_2SO_4$, and then concentrated under reduced pressure to obtain a residue which was purified with silica gel column chromatography (eluted with Hex/EA) to afford INT B37 (6.20 g, yield 57%). LCMS: m/z=387 $[M+1]^+$.

Method B: INT B2 (10.26 g, 27.56 mmol, 1.0 eq.), methyl iodide (28.01 g, 197.34 mmol, 7.16 eq.) and $K_2CO_3$ (7.91 g, 57.23 mmol, 2.08 eq.) were dispersed in DMF (100 mL). The reaction mixture was stirred for 2 hrs at 65° C., quenched with water (200 mL) and then extracted with EA (200 mL×3). The organic layers were combined and concentrated under reduced pressure to obtain a residue which was purified with Prep-HPLC (C18 column, eluted with $H_2O/CH_3CN$) to afford INT B37 (10.40 g, yield 97%). LCMS: m/z=387 $[M+1]^+$.

Intermediate B38 (INT B38)

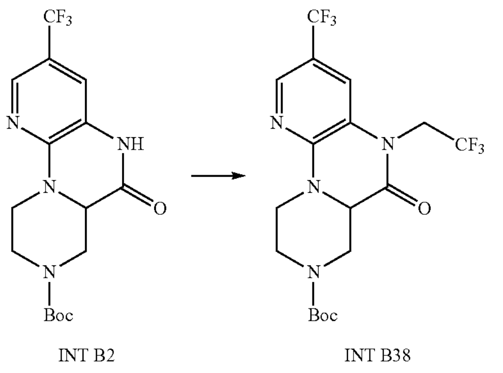

Step 1: INT B2 (0.61 g, 1.64 mmol, 1.0 eq.), 2,2,2-trifluoroethyl trifluoromethanesulfonate (1.22 g, 5.26 mmol, 3.21 eq.) and $Cs_2CO_3$ (2.20 g, 6.75 mmol, 4.12 eq.) were dispersed in DMF (10 mL). The reaction mixture was stirred for 2 hrs at room temperature, poured into water (20 mL) and then extracted with EA (20 mL×3). The organic layers were combined and concentrated under reduced pressure to obtain a residue which was purified with Prep-HPLC (C18 column, eluted with $H_2O/CH_3CN$) to afford INT B38 (0.48 g, yield 64%). LCMS: m/z=455 $[M+1]^+$.

Intermediate B39 (INT B39)

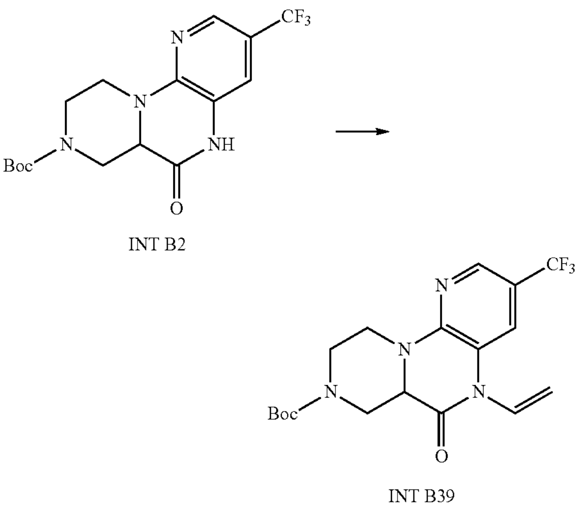

Step 1: INT B2 (2.01 g, 5.40 mmol, 1.0 eq.), potassium trifluoro(vinyl)borate (3.03 g, 22.62 mmol, 4.19 eq.), pyridine (2.85 g, 36.03 mmol, 6.67 eq.) and $Cu(OAc)_2$ (4.44 g, 24.44 mmol, 4.53 eq.) were dispersed in 1,4-dioxane (100 mL). The reaction mixture was stirred for 18 hrs at 110° C. and then filtered. The filtrate was concentrated under reduced pressure to obtain a residue which h was purified with silica gel column (eluted with Hex/EA) to afford INT B39 (0.85 g, yield 39%). LCMS: m/z=399 $[M+1]^+$.

Intermediate B40 (INT B40)

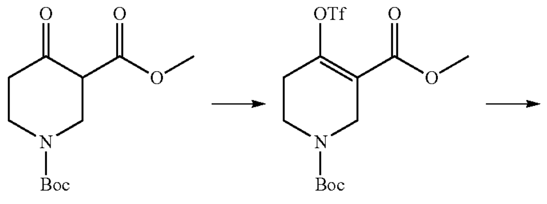

INT 40-1

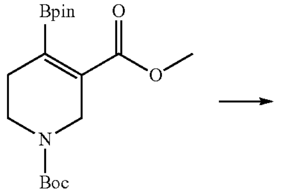

INT 40-2

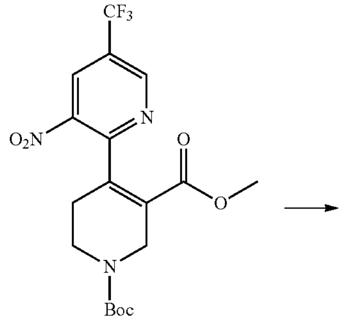

INT 40-3

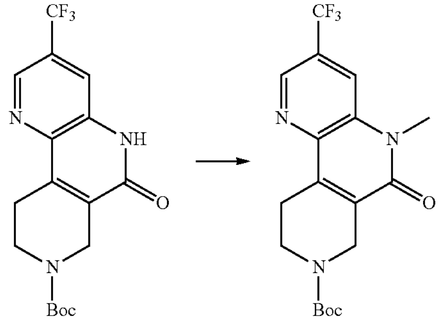

INT 40-4 INT 40

Step 1: In an atmosphere of nitrogen, a mixture of 1-(tert-butyl)-3-methyl 4-oxopiperidine-1,3-dicarboxylate (2.03 g, 7.48 mmol, 1.0 eq.) dissolved in toluene (20 mL) was cooled to −70° C., and then DIPEA (3.68 g, 28.47 mmol, 3.81 eq.) and trifluoromethanesulfonic anhydride (3.31 g, 11.73 mmol, 1.57 eq.) were added. The reaction mixture was stirred for 1 h at room temperature, quenched with saturated $Na_2CO_3$ aqueous solution (20 mL) and then extracted with EA (50 mL×3). The organic layers were combined, dried over anhydrous $Na_2SO_4$ and then concentrated under reduced pressure to obtain a residue which was purified with silica gel column (eluted with Hex/EA) to afford INT B40-1 (3.08 g). LCMS: m/z=390 $[M+1]^+$.

Step 2: 4,4,4',4',5,5,5',5'-octamethyl-2,2'-bi(1,3,2-dioxaborolane) (6.45 g, 25.40 mmol, 1.28 eq.), INT B40-1 (8.01 g, 19.86 mmol, 1.0 eq.), $Pd(dppf)Cl_2$ (2.81 g, 3.84 mmol, 0.19 eq.) and KOAc (5.88 g, 59.91 mmol, 3.02 eq.) were dispersed in 1,4-dioxane (150 mL). The reaction mixture was purged and maintained with an inert atmosphere of nitrogen, stirred for 16 hrs at 80° C., cooled to room temperature and concentrated under reduced pressure to obtain a residue. The residue was purified with silica gel column (eluted with Hex/EA) to afford INT B40-2 (6.85 g). LCMS: m/z=368 $[M+1]^+$.

Step 3: INT B40-2 (0.95 g, 2.49 mmol, 1.06 eq.), 2-chloro-3-nitro-5-(trifluoromethyl)pyridine (0.53 g, 2.34 mmol, 1.0 eq.), $Pd(dppf)Cl_2$ (0.34 g, 0.46 mmol, 0.20 eq.) and $Na_2CO_3$ (0.71 g, 6.70 mmol, 2.86 eq.) were dispersed in a mixed solvent of 1,4-dioxane and $H_2O$ (v/v=30 mL:3 mL). The reaction mixture was purged and maintained with an inert atmosphere of nitrogen, stirred for 16 hrs at 120° C., cooled to room temperature and then concentrated under reduced pressure to obtain a residue. The residue was purified with silica gel column (eluted with Hex/EA) to afford INT B40-3 (0.67 g). LCMS: m/z=432 $[M+1]^+$.

Step 4: INT B40-3 (1.80 g, 4.04 mmol, 1.0 eq.) and the powder of iron (1.09 g, 19.52 mmol, 4.83 eq.) were dispersed in HOAc (50 mL). The reaction mixture was stirred for 2 hrs at room temperature, and then filtered. The filtrate was concentrated under reduced pressure to obtain a residue which was purified with silica gel column (eluted with Hex/EA) to afford INT B40-4 (0.90 g, yield 60%). LCMS: m/z=370 $[M+1]^+$.

Step 5: A mixture of INT B40-4 (0.55 g, 1.49 mmol, 1.0 eq.) dissolved in THF (30 mL) was purged and maintained with an inert atmosphere of nitrogen, cooled to 0~10° C., and NaH (120 mg, 3.0 mmol, 2.01 eq.) (60% in mineral oil) was added slowly. The resulting mixture was stirred for 0.5 h and $CH_3I$ (1.0 g, 7.05 mmol, 4.73 eq.) was added. The reaction mixture was stirred for 16 hrs at room temperature, quenched with water (50 mL), and extracted with EA (50 mL×3). The organic layers were combined, dried over anhydrous $Na_2SO_4$, and then concentrated under reduced pressure to obtain a residue which was purified with silica gel column chromatography (eluted with Hex/EA) to afford INT B40 (0.30 g, yield 52%). LCMS: m/z=384 $[M+1]^+$.

Intermediate B41 (INT B41)

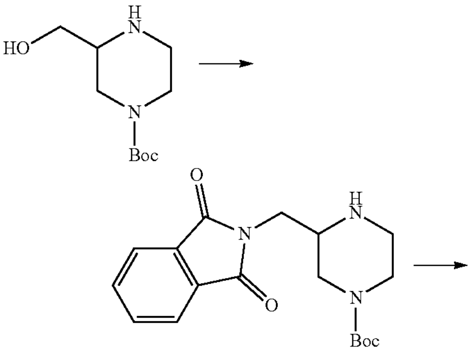

INT B41-1

-continued

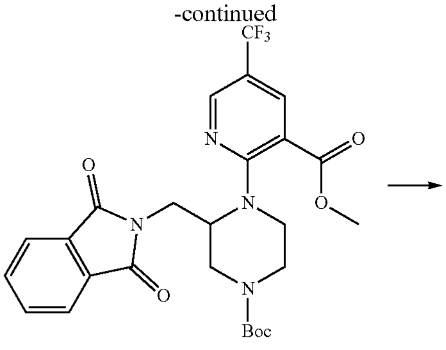

INT B41-2

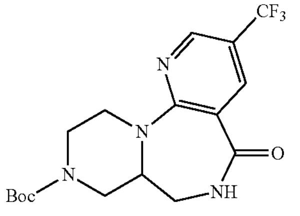

INT B41

Step 1: A mixture of tert-butyl 3-(hydroxymethyl)piperazine-1-carboxylate (2.06 g, 9.52 mmol, 1.0 eq.), triphenylphosphine (7.43 g, 28.33 mmol, 2.97 eq.) and toluene (80 mL) was purged and maintained with an inert atmosphere of nitrogen, cooled to 0° C., and then diisopropyl azodicarboxylate, (3.97 g, 19.63 mmol, 2.06 eq.) was added dropwise at 0° C. The resulting mixture was stirred at 0° C. for 30 min, and then isoindoline-1,3-dione (1.65 g, 11.21 mmol, 1.18 eq.) was added dropwise at 0° C. The reaction mixture was stirred for 16 hrs at room temperature, quenched with water (50 mL) and then extracted with EA (100 mLx3). The organic layers were combined and concentrated under reduced pressure to obtain a residue which was purified with Prep-HPLC (C18 column, eluted with $H_2O/CH_3CN$) to afford INT B41-1 (2.82 g, yield 86%). LCMS: m/z=346 $[M+1]^+$.

Step 2: INT B41-1 (1.61 g, 4.66 mmol, 1.0 eq.) and methyl 2-chloro-5-(trifluoromethyl)nicotinate (2.17 g, 9.06 mmol, 1.94 eq.), KI (1.85 g, 11.14 mmol, 2.39 eq.) and $Et_3N$ (3 mL) were dispersed in DMF (30 mL) at room temperature. The reaction mixture was stirred for 16 hrs at 80° C., cooled to room temperature, poured into water (50 mL) and then extracted with EA (50 mLx3). The organic layers were combined and concentrated under reduced pressure to obtain a residue which was purified with Prep-HPLC (C18 column, eluted with $H_2O$/MeOH) to afford INT B41-2 (866 mg, yield 33%). LCMS: m/z=549 $[M+1]^+$.

Step 3: INT B41-2 (843 mg, 1.50 mmol, 1.0 eq.) was dispersed in methylamine (40% solution in methanol) (15 mL) at room temperature. The reaction mixture was stirred for 16 hrs at room temperature and concentrated under reduced pressure to obtain a residue. The residue was purified with Prep-HPLC (C18 column, eluted with $H_2O/CH_3CN$) to afford INT B41 (409 mg, yield 70%). LCMS: m/z=387 $[M+1]^+$.

Intermediate B42 (INT B42)

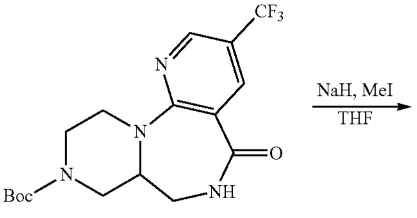

INT B41

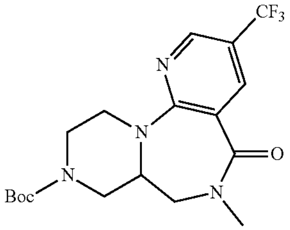

INT B42

Step 1: A mixture of INT B41 (172 mg, 0.45 mmol, 1.0 eq.) and THF (7 mL) was purged and maintained with an inert atmosphere of nitrogen, cooled to 0~10° C., and then NaH (31 mg, 0.78 mmol, 1.73 eq.) (60% in mineral oil) was added slowly. The resulting mixture was stirred for 0.5 h and then $CH_3I$ (134 mg, 0.94 mmol, 2.09 eq.) was added. The reaction mixture was stirred for 16 hrs at room temperature, quenched with saturated $NH_4Cl$ aqueous (10 mL) and extracted with EA (20 mLx3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford INT B42 (132 mg, yield 73%). LCMS: m/z=401 $[M+1]^+$.

Example 1

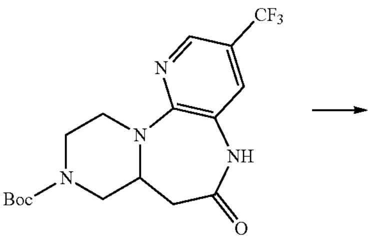

INT B41

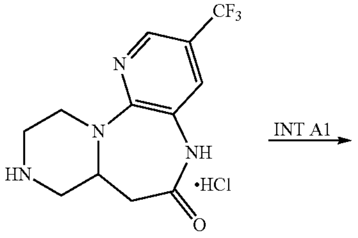

Compound 1-1

-continued

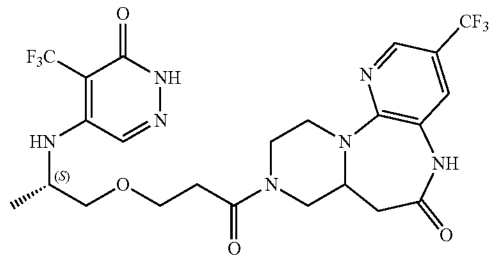

Compound 1

Step 1: HCl/1,4-dioxane (2 mL, 1N) was added to a solution of the INT B1 (60 mg, 0.15 mmol, 1.0 eq.) dissolved in 1,4-dioxane (2 mL). The reaction mixture was stirred for 1 h at room temperature, and then concentrated under reduced pressure to afford Compound 1-1 (40 mg, yield 82%). LCMS: m/z=287 $[M+1]^+$.

Step 2: PyBOP (70 mg, 0.13 mmol, 1.18 eq.) was added to a solution of Compound 1-1 (36 mg, 0.11 mmol, 1.0 eq.), INT A1 (42 mg, 0.14 mmol, 1.27 eq.) and TEA (3 mL) dissolved in DMF (10 mL). The reaction mixture was stirred for 1 h at room temperature, and then concentrated under reduced pressure to obtain a residue which was purified with Prep-HPLC (C18 column, eluted with $H_2O/CH_3CN$) to afford Compound 1 (21 mg, yield 33%). LCMS: m/z=578 $[M+1]^+$.

$^1H$ NMR (400 MHz, DMSO-$d_6$) δ 12.45 (s, 1H), 9.89 (s, 1H), 8.41 (s, 1H), 7.92 (s, 1H), 7.49 (s, 1H), 6.28 (s, 1H), 4.36 (t, 1H), 4.14 (s, 1H), 3.96-3.85 (m, 2H), 3.74-3.61 (m, 3H), 3.49 (d, J=4.4 Hz, 2H), 3.32-3.18 (m, 1H), 3.10-2.88 (m, 2H), 2.80-2.55 (m, 3H), 2.45-2.33 (m, 1H), 1.15 (d, J=6.0 Hz, 3H).

Example 2

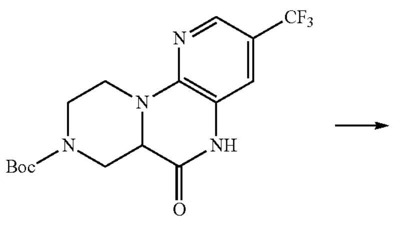

INT B2

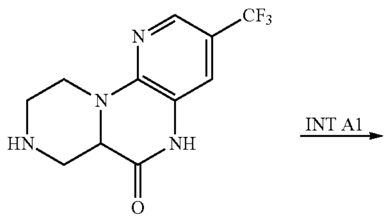

Compound 2-1

-continued

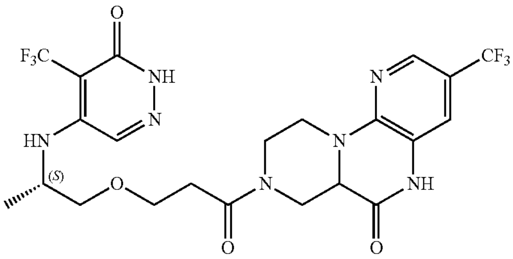

Compound 2

Step 1: TFA (1 mL) was added dropwise to a solution of INT B2 (106 mg, 0.28 mmol, 1.0 eq.) dissolved in DCM (4 mL). The reaction mixture was stirred for 1 h at room temperature, poured into sat. $NaHCO_3$ aqueous solution (1 mL) and then extracted with EA (20 mL×3). The organic layers were combined and concentrated under reduced pressure to obtain a residue which was purified with Prep-HPLC (C18 column, eluted with $H_2O/CH_3CN$) to afford Compound 2-1 (70 mg, yield 90%). LCMS: m/z=273 $[M+1]^+$.

Step 2: Following an analogous procedure described in step 2 of Example 1, Compound 2-1 (70 mg, 0.26 mmol, 1.0 eq.) and INT A1 (79 mg, 0.26 mmol, 1.0 eq.) were used as reactants to synthesize Compound 2 (38.7 mg, yield 26%). LCMS: m/z=564 $[M+1]^+$.

$^1H$ NMR (400 MHz, MeOH-$d_4$) δ 8.08 (s, 1H), 7.94 (s, 0.5H), 7.91 (s, 0.5H), 7.18 (s, 1H), 5.06 (d, J=13.2 Hz, 0.5H), 4.72-4.56 (m, 1.5H), 4.47 (d, J=12.8 Hz, 0.5H), 4.21-4.07 (m, 2H), 4.02 (d, J=10.0 Hz, 0.5H), 3.86-3.69 (m, 2H), 3.66-3.58 (m, 1H), 3.56-3.45 (m, 1H), 3.30-3.12 (m, 1H), 3.03-2.64 (m, 4H), 1.25 (d, J=6.0 Hz, 3H).

Example 3

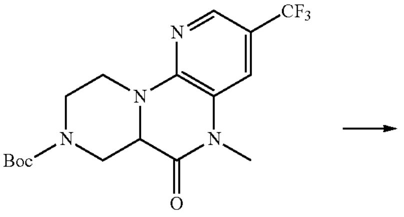

INT B37

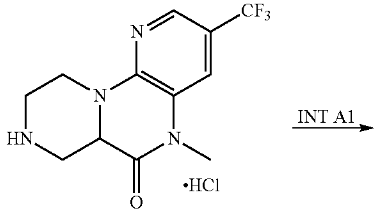

Compound 3-1

-continued

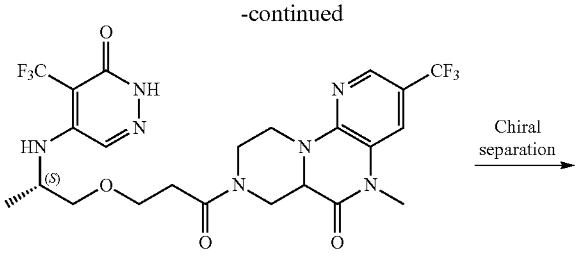

Compound 3

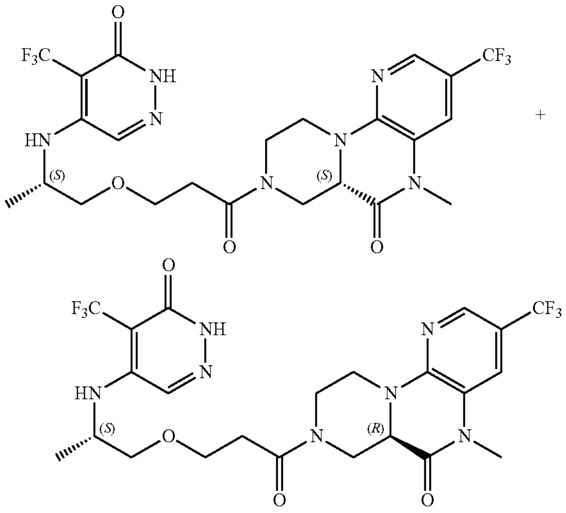

Step 1: HCl/1,4-dioxane (50 mL, 1N) was added to a solution of INT B37 (10.03 g, 25.96 m mol, 1.0 eq.) dissolved in 1,4-dioxane (10 mL). The reaction mixture was stirred for 3 hrs at room temperature, and then concentrated under reduced pressure to afford a crude product (9.98 g) of Compound 3-1. LCMS: m/z=287 $[M+1]^+$.

Step 2: Compound 3-1 (5.94 g, crude), INT A1 (5.04 g, 16.30 mmol, 1.0 eq.) and TEA (15 mL) were dissolved in DMF (100 mL) to form a solution. PyBOP (12.60 g, 24.21 mmol, 1.49 eq.) was added to the solution. The reaction mixture was stirred for 1.5 hrs at room temperature, poured into water (500 mL) and then extracted with EA (500 mL×3). The organic layers were combined and concentrated under reduced pressure to obtain a residue which was purified with Prep-HPLC (C18 column, eluted with $H_2O$/$CH_3CN$) to afford Compound 3 (7.89 g, yield 83%). LCMS: m/z=578 $[M+1]^+$.

$^1$H NMR (400 MHz, MeOH-$d_4$) δ 8.16 (s, 1H), 7.93 (d, J=17.4 Hz, 1H), 7.43 (s, 1H), 5.10 (d, J=12.7 Hz, 0.5H), 4.66 (d, J=10.8 Hz, 1H), 4.61 (s, 0.5H), 4.53 (d, J=13.8 Hz, 0.5H), 4.23-4.06 (m, 2H), 4.01 (d, J=10.6 Hz, 0.5H), 3.88-3.74 (m, 2H), 3.63 (d, J=9.0 Hz, 1H), 3.54 (m, 1H), 3.38 (s, 3H), 3.26 (m, 1H), 2.92-2.63 (m, 4H), 1.26 (d, J=6.1 Hz, 3H).

The chiral separation of the Compound 3 (7.84 g) was performed by Chiral-Prep-HPLC with the following conditions: Equipment: Prep-HPLC-Gilson; Column: CHIRAL ART Cellulose SB 2 cm×25 cm, 5 um; Mobile Phase A: (Hex:DCM=3:1)(0.2% 2M $NH_3$-MeOH); Mobile Phase B: MeOH; $V_{Mobile\ Phase\ A}$:$V_{Mobile\ Phase\ B}$=75:25; Flow Rate: 20 mL/min; Detector Wavelength: 220 nm. This resulted in the first eluting stereoisomer (Compound 3A, 2.4510 g, Retention time: 6.92 min) and the second eluting stereoisomer (Compound 3B, 2.3618 g, Retention time: 10.74 min).

Example 4

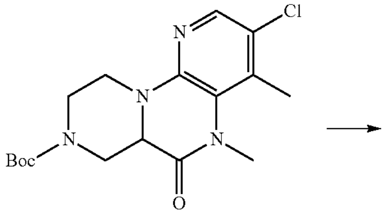

INT B6

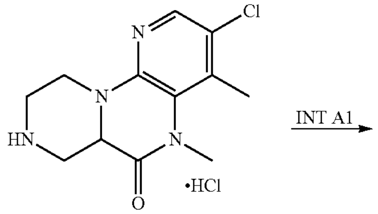

Compound 4-1

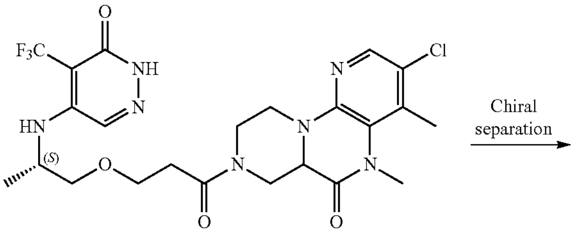

Compound 4

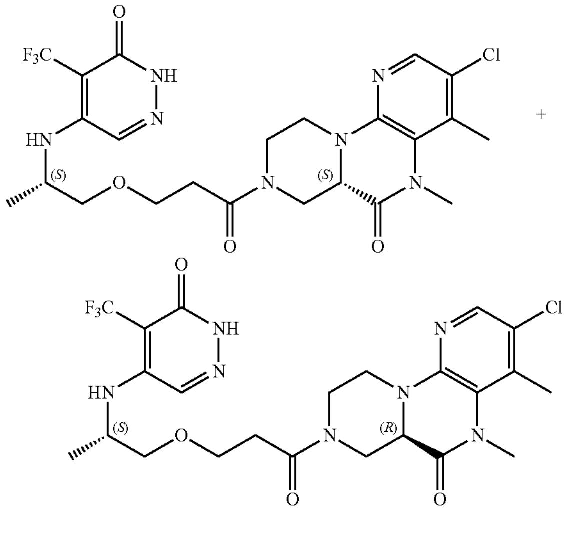

Step 1: Following an analogous procedure described in step 1 of Example 1, INT B6 (0.25 g, 0.68 mmol, 1.0 eq.) and HCl/1,4-dioxane (5 mL, 1N) were used as reactants to synthesize Compound 4-1 (181 mg, yield 87%). LCMS: m/z=267 $[M+1]^+$.

Step 2: Following an analogous procedure described in step 2 of Example 1, Compound 4-1 (181 mg, 0.60 mmol, 0.92 eq.) and INT A1 (0.20 g, 0.65 mmol, 1.0 eq.) were used as reactants to synthesize Compound 4 (0.28 g, yield 77%). LCMS: m/z=558 $[M+1]^+$.

$^1$H NMR (400 MHz, MeOH-$d_4$) δ 7.92 (d, J=10.4 Hz, 1H), 7.89 (s, 1H), 5.00 (d, J=12.0 Hz, 0.5H), 4.62 (d, J=12.8 Hz, 0.5H), 4.43 (d, J=13.2 Hz, 0.5H), 4.19-4.06 (m, 2.5H), 3.83-3.74 (m, 2H), 3.60 (dd, 1H), 3.56-3.40 (m, 2H), 3.30-3.28 (m, 3H), 3.27-3.19 (m, 1H), 2.93-2.62 (m, 4H), 2.43 (s, 3H), 1.22 (t, J=8.4 Hz, 3H).

The chiral separation of the Compound 4 (0.28 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 4A, 103.1 mg, Retention time: 6.23 min) and the second eluting stereoisomer (Compound 4B, 105.2 mg, Retention time: 8.67 min).

Example 5

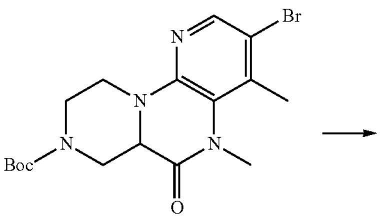

INT B32

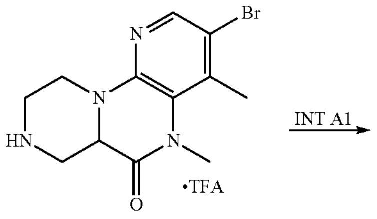

Compound 5-1

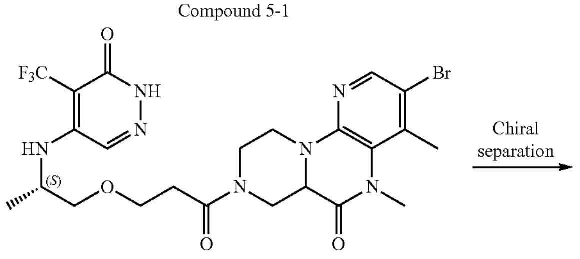

Compound 5

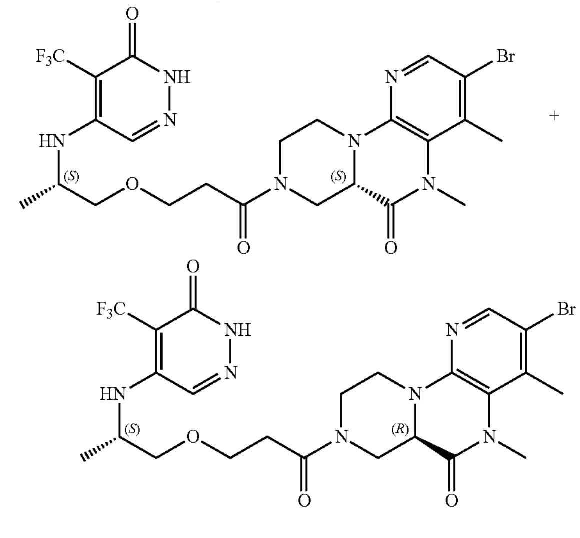

Step 1: Following an analogous procedure described in step 1 of Example 2, INT B32 (0.30 g, 0.73 mmol, 1.0 eq.) and TFA (1 mL) were used as reactants to synthesize Compound 5-1 (230 mg, yield 77%). LCMS: m/z=311, 313 $[M+1]^+$.

Step 2: Following an analogous procedure described in step 2 of Example 1, Compound 5-1 (220 mg, 0.54 mmol, 1.0 eq.) and INT A1 (0.40 g, 1.29 mmol, 2.39 eq.) were used as reactants to synthesize Compound 5 (0.19 g, yield 58%). LCMS: m/z=602, 604 $[M+1]^+$.

$^1H$ NMR (400 MHz, MeOH-$d_4$) δ 8.05 (s, 1H), 7.90 (d, J=13.2 Hz, 1H), 5.03-4.95 (m, 0.5H), 4.63 (d, J=13.2 Hz, 0.5H), 4.43 (d, J=13.2 Hz, 0.5H), 4.19-4.06 (m, 2.5H), 3.83-3.73 (m, 2H), 3.62-3.54 (m, 1H), 3.54-3.41 (m, 2H), 3.32-3.30 (m, 3.5H), 3.27-3.21 (m, 0.5H), 2.92-2.62 (m, 4H), 2.44 (d, J=2.0 Hz, 3H), 1.23 (t, J=7.2 Hz, 3H).

The chiral separation of the Compound 5 (0.19 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=55:45; Flow Rate: 20 mL/min; Detector Wavelength: 220 nm. This resulted in the first eluting stereoisomer (Compound 5A, 83.1 mg, Retention time: 6.95 min) and the second eluting stereoisomer (Compound 5B, 63.2 mg, Retention time: 9.27 min).

Example 6

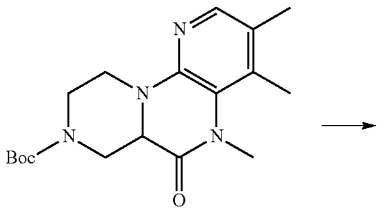

INT B36

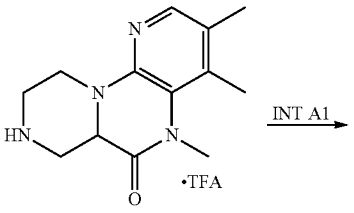

Compound 6-1

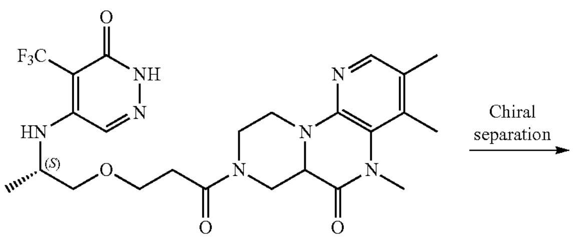

Compound 6

-continued

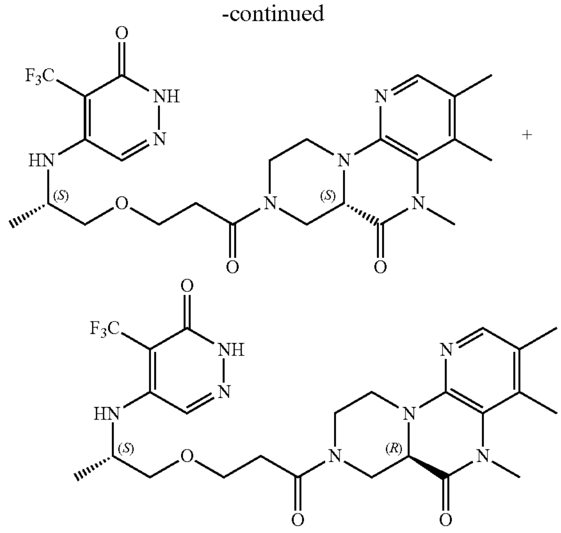

Step 1: Following an analogous procedure described in step 1 of Example 2, INT B36 (0.22 g, 0.66 mmol, 1.0 eq.) and TFA (1 mL) were used as reactants to synthesize Compound 6-1 (197 mg, yield 90%). LCMS: m/z=247 $[M+1]^+$.

Step 2: Following an analogous procedure described in step 2 of Example 1, Compound 6-1 (0.19 g, 0.55 mmol, 1.0 eq.) and INT A1 (0.36 g, 1.16 mmol, 2.11 eq.) were used as reactants to synthesize Compound 6 (0.17 g, yield 57%). LCMS: m/z=538 $[M+1]^+$.

$^1$H NMR (400 MHz, MeOH-$d_4$) δ 7.89 (d, J=18.8 Hz, 1H), 7.74 (s, 1H), 5.02-4.94 (m, 0.5H), 4.64 (d, J=13.2 Hz, 0.5H), 4.46-4.39 (m, 0.5H), 4.18-4.03 (m, 2.5H), 3.84-3.72 (m, 2H), 3.62-3.55 (m, 1H), 3.53-3.47 (m, 1H), 3.46-3.35 (m, 1H), 3.32-3.30 (m, 3H), 3.28-3.22 (m, 0.5H), 2.92-2.62 (m, 4.5H), 2.29 (d, J=4.8 Hz, 3H), 2.21 (s, 3H), 1.22 (dd, 3H).

The chiral separation of the Compound 6 (0.17 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=55:45; Flow Rate: 20 mL/min; Detector Wavelength: 220 nm. This resulted in the first eluting stereoisomer (Compound 6A, 67.4 mg, Retention time: 5.66 min) and the second eluting stereoisomer (Compound 6B, 67.7 mg, Retention time: 7.81 min).

Example 7

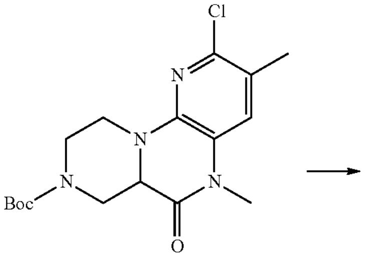

INT B35

-continued

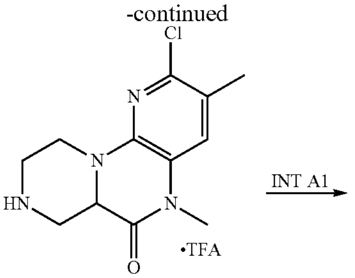

Compound 7-1

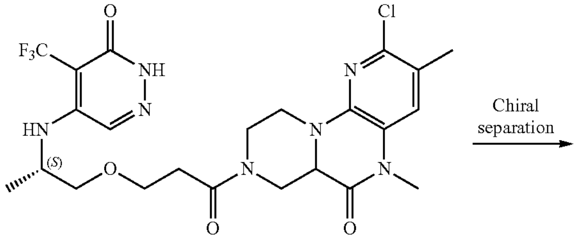

Compound 7

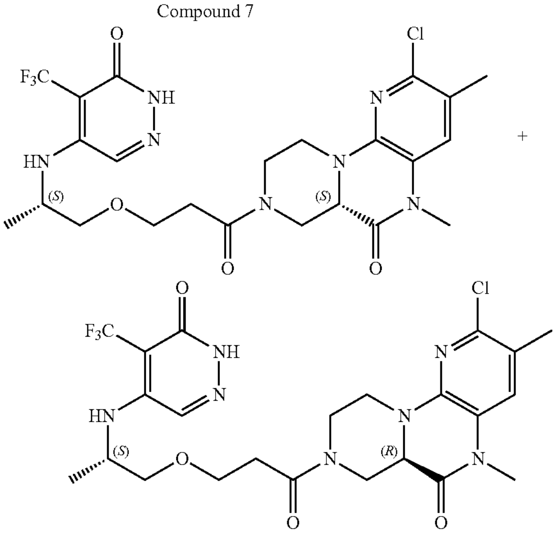

Step 1: Following an analogous procedure described in step 1 of Example 1, INT B35 (0.21 g, 0.57 mmol, 1.0 eq.) and HCl/1,4-dioxane (5 mL, 1N) were used as reactants to synthesize Compound 7-1 (152 mg, 88% yield). LCMS: m/z=267 $[M+1]^+$.

Step 2: Following an analogous procedure described in step 2 of Example 1, Compound 7-1 (0.21 g, 0.69 mmol, 0.88 eq.) and INT A1 (0.24 g, 0.78 mmol, 1.0 eq.) were used as reactants to synthesize Compound 7 (0.18 g, yield 41%). LCMS: m/z=558 $[M+1]^+$.

$^1$H NMR (400 MHz, MeOH-$d_4$) δ 7.90 (d, J=26.4 Hz, 1H), 7.22 (d, J=13.6 Hz, 1H), 5.04 (d, J=12.4 Hz, 0.5H), 4.63 (d, J=13.2 Hz, 0.5H), 4.55-4.46 (m, 0.5H), 4.37-4.28 (m, 1H), 4.15-4.09 (m, 1.5H), 3.86-3.71 (m, 3H), 3.65-3.46 (m, 2H), 3.31-3.29 (m, 3H), 3.27-3.16 (m, 1H), 2.86-2.56 (m, 4H), 2.27 (s, 3H), 1.24 (dd, 3H).

The chiral separation of the Compound 7 (0.18 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 7A, 68.5 mg, Retention time: 6.85 min) and the second eluting stereoisomer (Compound 7B, 71.4 mg, Retention time: 9.58 min).

Example 8

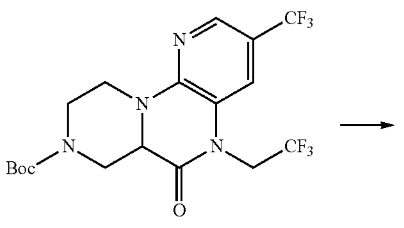

INT B38

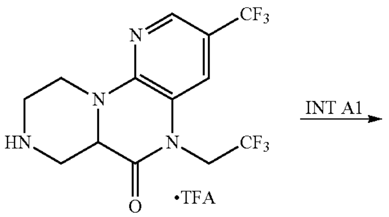

Compound 8-1

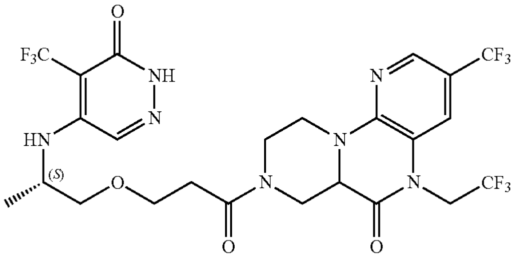

Compound 8

Step 1: Following an analogous procedure described in step 1 of Example 2, INT B38 (0.48 g, 1.06 mmol, 1.0 eq.) and TFA (5 mL) were used as reactants to synthesize Compound 8-1 (crude, 0.68 g). LCMS: m/z=355 $[M+1]^+$.

Step 2: Following an analogous procedure described in step 2 of Example 1, the crude Compound 8-1 (0.68 g, crude) and INT A1 (0.36 g, 1.16 mmol, 1.0 eq.) were used as reactants to synthesize Compound 8 (228 mg, yield 30%). LCMS: m/z=646 $[M+1]^+$.

$^1$H NMR (400 MHz, DMSO-$d_6$) δ=12.25 (s, 1H), 10.71 (d, J=8.4 Hz, 1H), 8.77 (s, 2H), 7.94 (s, 1H), 4.84-4.73 (m, 2H), 4.36 (d, J=12.8 Hz, 1H), 4.26-4.15 (m, 1H), 3.93 (d, J=14.0 Hz, 1H), 3.81-3.67 (m, 2H), 3.57-3.50 (m, 1H), 3.49-3.41 (m, 1H), 3.37-3.34 (m, 3H), 3.30 (s, 1H), 2.85 (dd, 1H), 2.76-2.60 (m, 2H), 1.09 (d, J=4.8 Hz, 3H).

Example 9

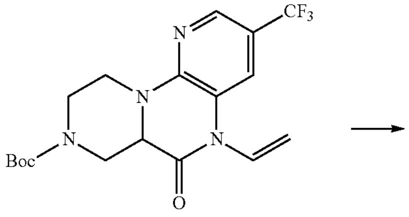

INT B39

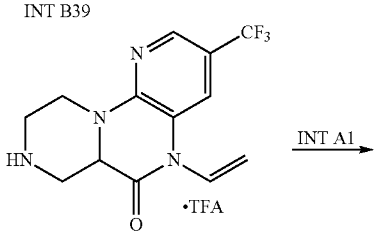

Compound 9-1

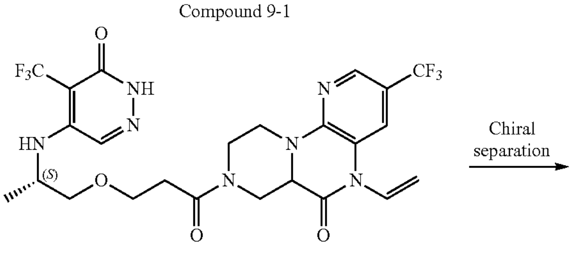

Compound 9

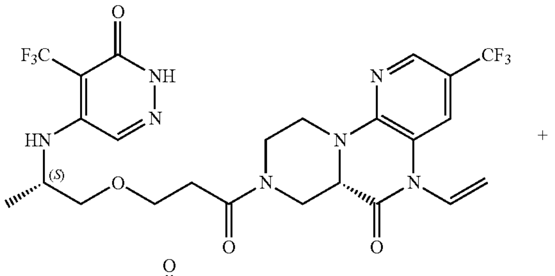

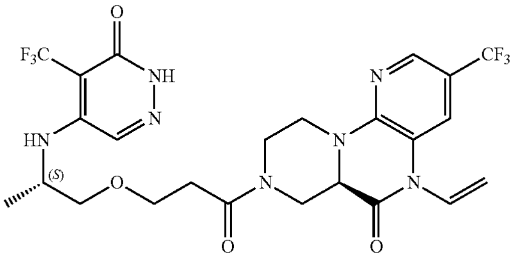

Step 1: Following an analogous procedure described in step 1 of Example 2, INT B39 (174 mg, 0.44 mmol, 1.0 eq.) and TFA (2 mL) were used as reactants to synthesize Compound 9-1 (crude, 150 mg). LCMS: m/z=299 $[M+1]^+$.

Step 2: Following an analogous procedure described in step 2 of Example 1, the crude Compound 9-1 (150 mg, crude) and INT A1 (0.17 g, 0.55 mmol, 1.45 eq.) were used as reactants to synthesize Compound 9 (75 mg, yield 33%). LCMS: m/z=590 $[M+1]^+$.

$^1$H NMR (400 MHz, MeOH-$d_4$) δ8.20 (s, 1H), 7.92 (d, J=14.4, 1H), 7.54 (s, 1H), 6.56 (dd, 1H), 5.63-5.52 (m, 2H), 5.07 (d, J=12.8 Hz, 0.5H), 4.66 (d, J=10.4 Hz, 0.5H), 4.57-4.49 (m, 1.5H), 4.19-4.10 (m, 1.5H), 4.09-4.02 (m, 0.5H), 3.00-3.94 (m, 0.5H), 3.84-3.74 (m, 2H), 3.62-3.57 (m, 1H), 3.55-3.48 (m, 1H), 3.3-3.24 (m, 1H), 2.92-2.62 (m, 4H), 1.24 (d, J=6.4 Hz, 3H).

The chiral separation of the Compound 9 (75 mg) was performed by Chiral-Prep-HPLC with the following conditions: Equipment: Prep-HPLC-Gilson; Column: CHIRALPAK ID 2 cm×25 cm, 5 um; Mobile Phase A: MTBE, Mobile Phase B: EtOH, $V_{Mobile\ Phase\ A}$:$V_{Mobile\ Phase\ B}$=60:40; Flow Rate: 20 mL/min; Detector Wavelength: 220 nm. This resulted in the first eluting stereoisomer (Compound 9A, 24.7 mg, Retention time: 4.79 min) and the second eluting stereoisomer (Compound 9B, 26.2 mg, Retention time: 6.09 min).

Example 10

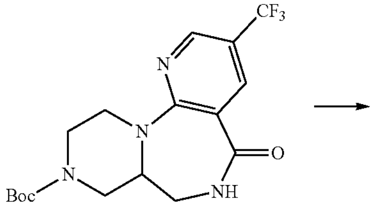

INT B41

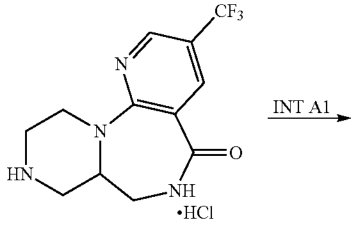

Compound 10-1

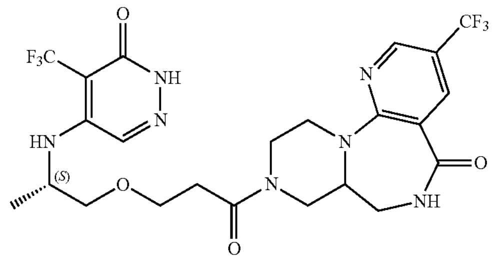

Compound 10

Step 1: Following an analogous procedure described in step 1 of Example 1, INT B41 (54 mg, 0.14 mmol, 1.0 eq.) and HCl/1,4-dioxane (2 mL, 1N) were used as reactants to synthesize Compound 10-1 (crude, 39 mg). LCMS: m/z=287 $[M+1]^+$.

Step 2: Following an analogous procedure described in step 2 of Example 1, the crude Compound 10-1 (39 mg, crude) and INT A1 (44 mg, 0.14 mmol, 1.0 eq.) were used as reactants to synthesize Compound 10 (30 mg, yield 37%). LCMS: m/z=578 $[M+1]^+$.

$^1$H NMR (400 MHz, MeOH-$d_4$) δ 8.61 (s, 1H), 8.15 (s, 1H), 7.94 (s, 1H), 4.47 (dd, 1H), 4.34-4.25 (m, 1H), 4.20-4.10 (m, 1H), 4.06-3.88 (m, 1H), 3.84-3.71 (m, 2H), 3.66-3.54 (m, 2H), 3.53-3.45 (m, 2H), 3.40-3.21 (m, 1H), 3.18-3.00 (m, 1H), 2.96-2.79 (m, 2H), 2.78-2.58 (m, 2H), 1.25 (d, J=6.4 Hz, 3H).

Example 11

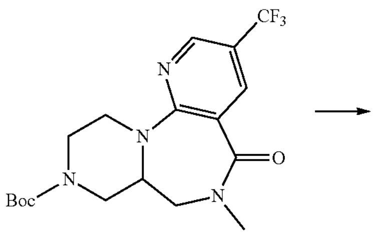

INT B42

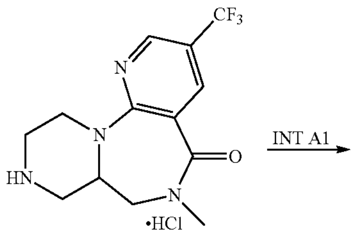

Compound 11-1

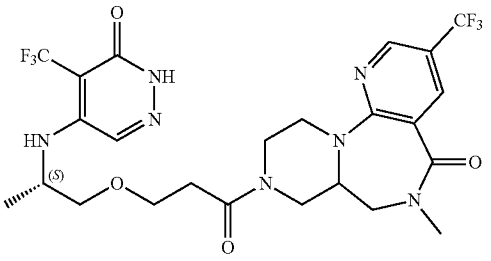

Compound 11

Step 1: Following an analogous procedure described in step 1 of Example 1, INT B42 (74 mg, 0.18 mmol, 1.0 eq.) and HCl/1,4-dioxane (3 mL, 1N) were used as reactants to synthesize Compound 11-1 (crude, 69 mg). LCMS: m/z=301 $[M+1]^+$.

Step 2: Following an analogous procedure described in step 2 of Example 1, the crude Compound 11-1 (69 mg, crude) and INT A1 (65 mg, 0.21 mmol, 1.0 eq.) were used as reactants to synthesize Compound 11 (41 mg, yield 32%). LCMS: m/z=592 $[M+1]^+$.

$^1$H NMR (400 MHz, MeOH-$d_4$) δ 8.50 (s, 1H), 8.03 (d, J=2.0 Hz, 1H), 7.85 (s, 1H), 4.50-4.38 (m, 1H), 4.21 (d, J=13.2 Hz, 1H), 4.12-4.00 (m, 1H), 3.99-3.88 (m, 1H), 3.77-3.61 (m, 3H), 3.59-3.37 (m, 3H), 3.31-3.23 (m, 1H), 3.13 (s, 3H), 3.11-2.89 (m, 1H), 2.89-2.75 (m, 1H), 2.69-2.51 (m, 3H), 1.17 (d, J=6.4 Hz, 3H).

Example 12

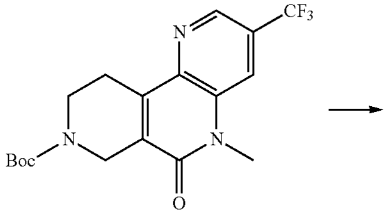

INT B40

-continued

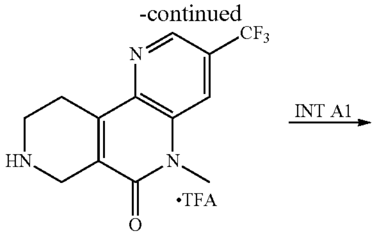

Compound 12-1

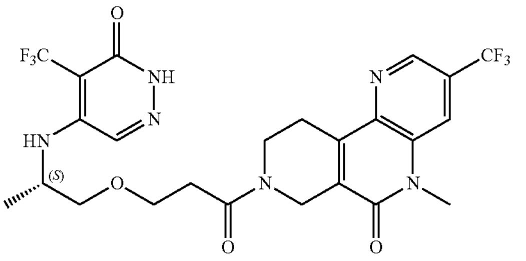

Compound 12

Step 1: Following an analogous procedure described in step 1 of Example 2, INT B40 (0.27 g, 0.70 mmol, 1.0 eq.) and TFA (1 mL) were used as reactants to synthesize Compound 12-1 (crude, 73 mg). LCMS: m/z=284 $[M+1]^+$.

Step 2: Following an analogous procedure described in step 2 of Example 1, the crude Compound 12-1 (73 mg, crude) and INT A1 (105 mg, 0.34 mmol, 1.0 eq.) were used as reactants to synthesize Compound 12 (18.5 mg, yield 16%). LCMS: m/z=575 $[M+1]^+$.

$^1H$ NMR (400 MHz, MeOH-$d_4$) δ 8.81 (d, J=13.2 Hz, 1H), 8.23 (d, J=7.6 Hz, 1H), 7.86 (s, 1H), 4.64-4.58 (m, 2H), 4.16-4.03 (m, 1H), 3.93-3.79 (m, 4H), 3.78 (s, 3H), 3.65-3.56 (m, 1H), 3.54-3.46 (m, 1H), 3.27-3.13 (m, 2H), 2.84-2.74 (m, 2H), 1.21 (t, J=6.4 Hz, 3H).

The following compounds were synthesized using the above procedure or modification procedure using the corresponding intermediates.

| Example | Compound | Chiral separation | Structure | INT | $^1H$ NMR and MS: $(M + H)^+$ |
|---|---|---|---|---|---|
| 13 | 13A & 13B | Column: CHIRAL ART Cellulose SB 2 cm x 25 cm, 5 um; Mobile Phase A: MTBE, Mobile Phase B: EtOH, $V_{Mobile\ Phase\ A}$: $V_{Mobile\ Phase\ B}$ = 50:50; Flow Rate: 20 mL/min Compound 13A: Retention time: 8.18 min; Compound 13B: Retention time: 9.84 min. | 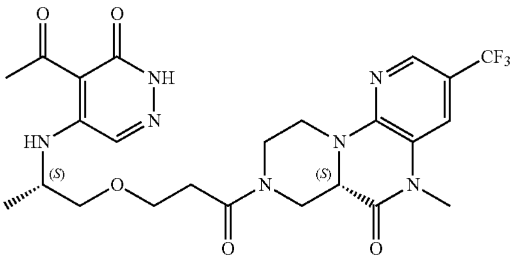 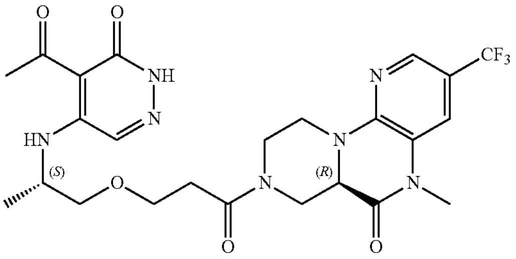 | A2 & B37 | MS: 552 $(M + H)^+$. Compound 13A: $^1H$ NMR (400 MHz, MeOH-$d_4$) δ 8.13 (s, 1H), 7.89 (d, J = 27.2 Hz, 1H), 7.39 (d, J = 20.4 Hz, 1H), 5.07 (d, J = 13.2 Hz, 0.5H), 4.64 (d, J = 11.2 Hz, 1H), 4.60-4.52 (m, 1H), 4.21-4.13 (m, 1.5H), 4.06-4.00 (m, 1H), 3.89-3.73 (m, 2H), 3.64 (dd, 1H), 3.54-3.45 (m, 1H), 3.37 (s, 1H), 3.30-3.18 (m, 2H), 2.97-2.75 (m, 3H), 2.74-2.56 (m, 2H), 2.46 (d, J = 40.0 Hz, 3H), 1.25 (dd, 3H); Compound 13B: $^1H$ NMR (400 MHz, MeOH-$d_4$) δ 8.15 (d, J = 9.6 Hz, 1H), 7.93 (s, 1H), 7.43 (d, J = 1.6 Hz, 1H), 5.11-5.04 (m, 0.5H), 4.70-4.51 (m, 2H), 4.23-4.14 (m, 1.5H), 4.10 (dd, 0.5H), 4.00 (dd, 0.5H), 3.91-3.76 (m, 2H), 3.66 (dd, 1H), 3.54-3.47 (m, 1H), 3.38 (d, J = 3.6 Hz, 3H), 3.31-3.22 (m, 1H), 2.92-2.75 (m, 3H), 2.74-2.65 (m, 1H), 2.52 (d, J = 18.8 Hz, 3H), 1.28 (dd, 3H). |

-continued

| Example | Compound | Chiral separation | Structure | INT | $^1H$ NMR and MS: $(M + H)^+$ |
|---|---|---|---|---|---|
| 14 | 14A & 14B | Column: CHIRAL ART Cellulose SB 2 cm × 25 cm, 5 um; Mobile Phase A: MTBE, Mobile Phase B: EtOH, $V_{Mobile\ Phase\ A}$: $V_{Mobile\ Phase\ B}$ = 50:50; Flow Rate: 20 mL/min Compound 14A: Retention time: 7.34 min; Compound 14B: Retention time: 9.60 min | 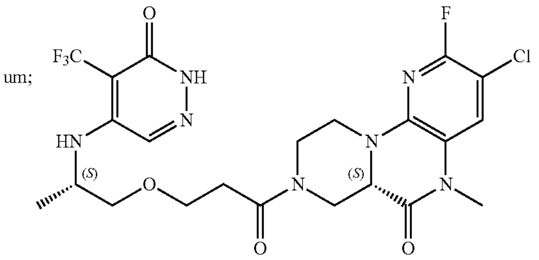 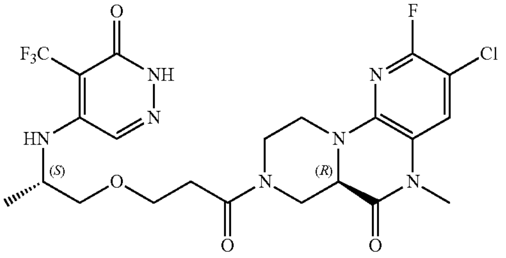 | A1 & B34 | MS: $(M + H)^+$ 562. Compound 14A: $^1H$ NMR (400 MHz, MeOH-$d_4$) δ 7.90 (d, J = 23.2 Hz, 1H), 7.51-7.43 (m, 1H), 5.05 (d, J = 13.2 Hz, 0.5H), 4.86-4.85 (m, 2H), 4.63 (d, J = 12.4 Hz, 0.5H), 4.50 (d, J = 13.6 Hz, 0.5H), 4.37-4.27 (m, 1H), 4.19-4.05 (m, 1.5H), 3.99-3.85 (m, 1H), 3.85-3.72 (m, 2H), 3.64-3.46 (m, 2H), 3.28-3.11 (m, 1H), 2.86-2.60 (m, 4H), 2.03 (s, 1H), 1.24 (t, J = 6.8 Hz, 3H); Compound 14B: $^1H$ NMR (400 MHz, MeOH-$d_4$) δ 7.91 (s, 1H), 7.47 (d, J = 7.2 Hz, 1H), 5.06 (d, J = 13.2 Hz, 0.5H), 4.86-4.85 (m, 2H), 4.63 (d, J = 10.8, 0.5H), 4.48 (d, J = 13.6 Hz, 0.5H), 4.35-4.26 (m, 1H), 4.19-4.07 (m, 1.5H), 3.99-3.92 (m, 0.5H), 3.90-3.83 (m, 0.5H), 3.81-3.72 (m, 2H), 3.65-3.56 (m, 1H), 3.54-3.46 (m, 1H), 3.33-3.18 (m, 2H), 2.85-2.61 (m, 4H), 1.27-1.20 (m, 3H). |
| 15 | 15A & 15B | Column: CHIRAL ART Cellulose SB 2 cm × 25 cm, 5 um; Mobile Phase A: MTBE, Mobile Phase B: EtOH, $V_{Mobile\ Phase\ A}$: $V_{Mobile\ Phase\ B}$ = 60:40; Flow Rate: 20 mL/min Compound 15A: Retention time: 6.37 min; Compound 15B: Retention time: 7.40 min | 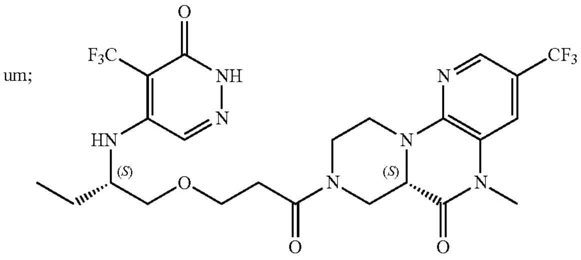 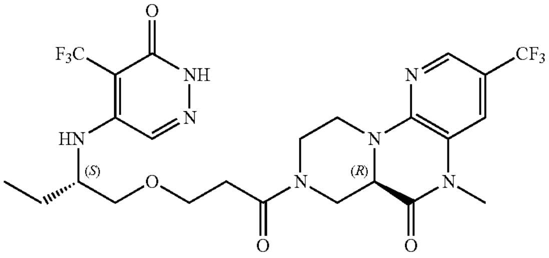 | A6 & B37 | MS: $(M + H)^+$ 592. Compound 15A: $^1H$ NMR (400 MHz, MeOH-$d_4$) δ 8.14 (s, 1H), 7.92 (d, J = 15.6 Hz, 1H), 7.42 (s, 1H), 5.07 (d, J = 13.6 Hz, 0.5H), 4.67-4.58 (m, 1.5H), 4.49 (d, J = 13.1, 0.5H), 4.14-4.04 (m, 1H), 4.01-3.92 (m, 1.5H), 3.85-3.71 (m, 2H), 3.66-3.46 (m, 2H), 3.37 (s, 3H), 3.30-3.18 (m, 1H), 2.89-2.63 (m, 4H), 1.75-1.51 (m, 2H), 0.96 (t, J = 7.4, 3H); Compound 15B: $^1H$ NMR (400 MHz, MeOH-$d_4$) δ 8.15 (s, 1H), 7.94 (d, J = 3.2 Hz, 1H), 7.42 (s, 1H), 5.07 (d, J = 13.2 Hz, 0.5H), 4.69-4.58 (m, 1.5H), 4.49 (d, J = 13.6 Hz, 0.5H), 4.16-4.04 (m, 1H), 4.02-3.90 (m, 1.5H), 3.85-3.72 (m, 2H), 3.65-3.59 (m, 1H), 3.58-3.49 (m, 1H), 3.37 (s, 3H), 3.30-3.16 (m, 1H), 2.90-2.64 (m, 4H), 1.74-1.51 (m, 2H), 0.96 (t, J = 6.4 Hz, 3H). |

Example 16

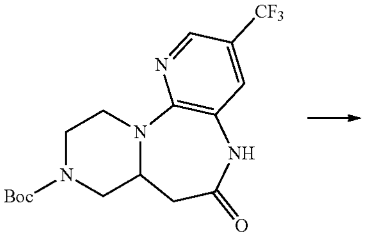

INT B1

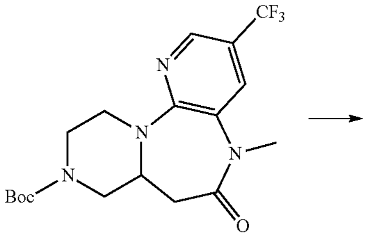

Compound 16-1

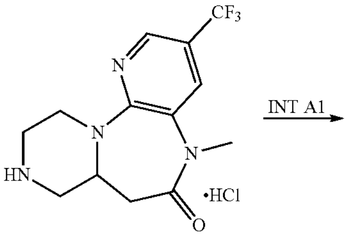

Compound 16-2

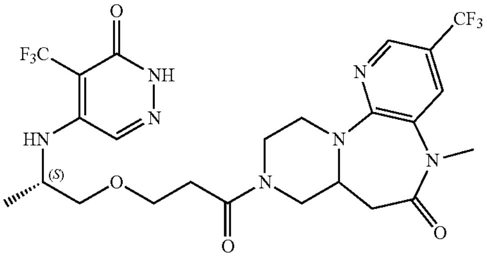

Compound 16

Step 1: A solution of INT B1 (141 mg, 0.36 mmol, 1.0 eq.) dissolved in THF (4 mL) was purged and maintained with an inert atmosphere of nitrogen, cooled to 0° C., and then NaH (23 mg, 0.56 mmol, 1.56 eq.) (60% in oil) was added slowly. The resulting mixture was stirred for 0.5 h and then $CH_3I$ (110 mg, 0.77 mmol, 2.12 eq.) was added. The reaction mixture was warmed to room temperature and stirred for 3 hrs, quenched with water (20 mL), and extracted with DCM (50 mL×3). The organic layers were combined, dried over anhydrous $Na_2SO_4$, and then filtered. The filtrate was concentrated under reduced pressure to obtain a residue which was purified with silica gel column chromatography eluted with Hex/EA to afford Compound 16-1 (130 mg, yield 88%). LCMS: m/z=401 $[M+1]^+$.

Step 2: Following an analogous procedure described in step 1 of Example 1, Compound 16-1 (130 mg, 0.32 mmol, 1.0 eq.) and HCl/1,4-dioxane (6 mL, 1N) were used as reactants to synthesize Compound 16-2 (crude, 140 mg). LCMS: m/z=301 $[M+1]^+$.

Step 3: Following an analogous procedure described in step 2 of Example 1, the crude Compound 16-2 (140 mg, crude) and INT A1 (99 mg, 0.32 mmol, 1.0 eq.) were used as reactants to synthesize Compound 16 (72.1 mg, yield 26%). LCMS: m/z=592 $[M+1]^+$.

$^1H$ NMR (400 MHz, DMSO-$d_6$) δ 12.44 (s, 1H), 8.50 (s, 1H), 8.02 (s, 1H), 7.91 (s, 1H), 6.27 (s, 1H), 4.38 (dd, 1H), 4.20-4.09 (m, 1H), 3.97-3.88 (m, 1H), 3.77 (t, J=13.6 Hz, 1H), 3.72-3.56 (m, 2H), 3.49 (d, J=5.2 Hz, 2H), 3.30 (s, 1H), 3.24 (s, 3H), 3.09-2.87 (m, 2H), 2.81-2.61 (m, 3H), 2.60-2.54 (m, 1H), 2.47-2.31 (m, 1H), 1.15 (d, J=6.4 Hz, 3H).

Example 17

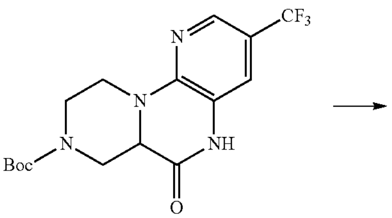

INT B2

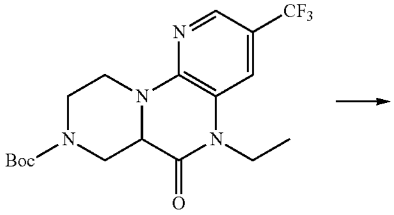

Compound 17-1

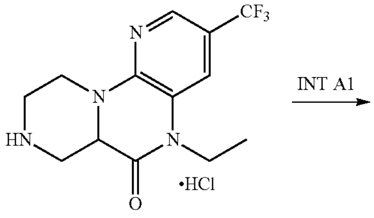

Compound 17-2

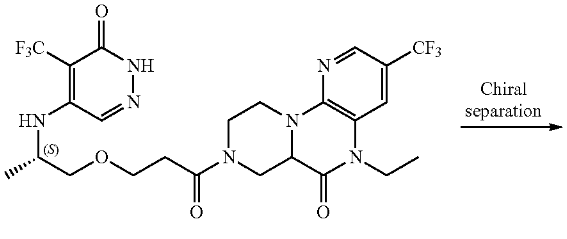

Compound 17

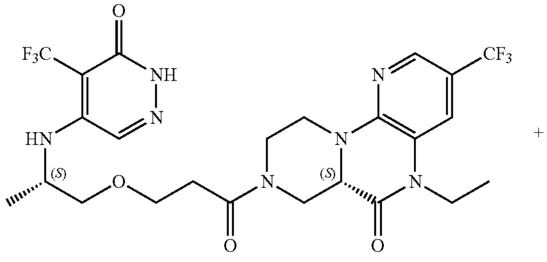

-continued

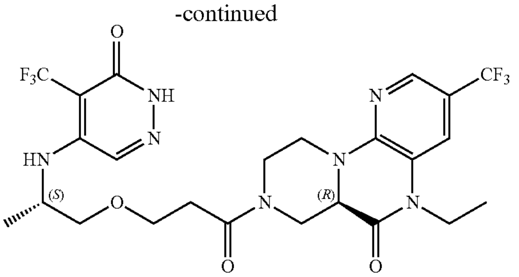

Step 1: A mixture of INT B2 (5.09 g, 13.67 mmol, 1.0 eq.), EtI (4.10 g, 26.29 mmol, 1.92 eq.), $K_2CO_3$ (5.81 g, 42.04 mmol, 3.08 eq.) and DMF (5 mL) was stirred for 3.5 hrs at 65° C., poured into water (100 mL), and then extracted with EA (100 mL×3). The organic layers were combined and concentrated under reduced pressure to obtain a residue which was purified with Prep-HPLC (C18 column, eluted with $H_2O/CH_3CN$) to afford Compound 17-1 (5.40 g, yield 98%). LCMS: m/z=401 $[M+1]^+$.

Step 2: Following an analogous procedure described in step 1 of Example 1, Compound 17-1 (5.40 g, 13.49 mmol, 1.0 eq.) and HCl/1,4-dioxane (50 mL, 1N) were used as reactants to synthesize Compound 17-2 (crude, 5.52 g). LCMS: m/z=301 $[M+1]^+$.

Step 3: Following an analogous procedure described in step 2 of Example 1, the crude Compound 17-2 (5.52 g, crude) and INT A1 (5.51 g, 17.82 mmol, 1.0 eq.) were used as reactants to synthesize Compound 17 (7.29 g, yield 91%). LCMS: m/z=592 $[M+1]^+$.

$^1H$ NMR (400 MHz, MeOH-$d_4$) δ8.16 (d, J=7.2 Hz, 1H), 7.95 (d, J=4.0 Hz, 1H), 7.46 (s, 1H), 5.08 (d, J=13.2 Hz, 0.5H), 4.68-4.58 (m, 1.5H), 4.51 (d, J=14.0 Hz, 0.5H), 4.21-3.96 (m, 4.5H), 3.88-3.76 (m, 2H), 3.64 (dd, 1H), 3.53 (dd, 1H), 3.31-3.21 (m, 1H), 2.92-2.66 (m, 4H), 1.29-1.20 (m, 6H).

The chiral separation of the Compound 17 (7.29 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=70:30; Flow Rate: 20 mL/min; Detector Wavelength: 220 nm. This resulted in the first eluting stereoisomer (Compound 17A, 2.6508 g, Retention time: 7.60 min) and the second eluting stereoisomer (Compound 17B, 2.6455 g, Retention time: 9.88 min).

The following compounds were synthesized using the above procedure or modification procedure using the corresponding intermediates.

| Example | Compound | Chiral separation | Structure | INT | $^1H$ NMR and MS: $(M + H)^+$ |
|---|---|---|---|---|---|
| 18 | 18A & 18B | Column: CHIRAL ART Cellulose SB 2 cm x 25 cm, 5um; Mobile Phase A: Hex: DCM = 3: 1, Mobile Phase B: EtOH, $V_{Mobile\ Phase\ A}$: $V_{Mobile\ Phase\ B}$ = 50:50; Flow Rate: 20 mL/min Compound 18A: Retention time: 8.18 min; Compound 18B: Retention time: 9.84 min. | 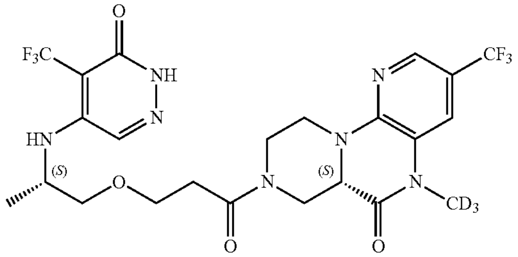 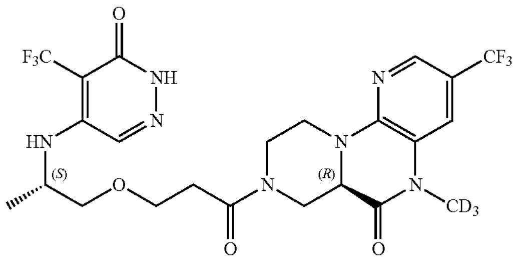 | A1 & B2 | MS: $(M + H)^+$ 581. Compound 18A: $^1H$ NMR (400 MHz, MeOH-$d_4$) δ 8.16 (s, 1H), 7.93 (d, J = 17.4 Hz, 1H), 7.43 (s, 1H), 5.10 (d, J = 12.7 Hz, 0.5H), 4.66 (d, J = 10.8 Hz, 1H), 4.61 (s, 0.5H), 4.53 (d, J = 13.8 Hz, 0.5H), 4.23-4.06 (m, 2H), 4.01 (d, J = 10.6 Hz, 0.5H), 3.88-3.74 (m, 2H), 3.63 (d, J = 9.0 Hz, 1H), 3.54 (m, 1H), 3.26 (m, 1H), 2.92-2.63 (m, 4H), 1.26 (d, J = 6.1 Hz, 3H); Compound 18B: $^1H$ NMR (400 MHz, MeOH-$d_4$) δ 8.14 (d, J = 5.6 Hz, 1H), 7.93 (s, 1H), 7.42 (s, 1H), 5.11-5.04 (m, 0.5H), 4.67-4.59 (m, 1.5H), 4.53-4.46 (m, 0.5H), 4.19-4.05 (m, 2H), 3.99 (dd, 0.5H), 3.85-3.73 (m, 2H), 3.61 (dd, 1H), 3.54-3.46 (m, 1H), 3.29-3.18 (m, 1H), 2.90-2.64 (m, 4H), 1.24 (dd, 3H). |

-continued

| Example | Compound | Chiral separation | Structure | INT | $^1$H NMR and MS: $(M + H)^+$ |
|---|---|---|---|---|---|
| 19 | 19A & 19B | Column: CHIRAL ART Cellulose SB 2 cm × 25 cm, 5um; Mobile Phase A: MTBE, Mobile Phase B: EtOH, $V_{Mobile\ Phase\ A}$: $V_{Mobile\ Phase\ B}$ = 50:50; Flow Rate: 20 mL/min Compound 19A: Retention time: 7.35 min; Compound 19B: Retention time: 10.50 min. | 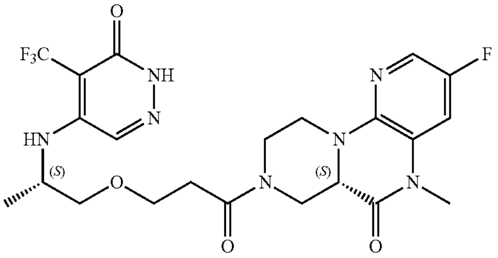 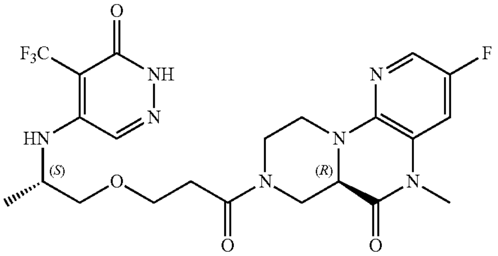 | A1 & B5 | MS: $(M + H)^+$ 528. Compound 19A: $^1$H NMR (400 MHz, MeOH-$d_4$) δ 7.92 (d, J = 23.2 Hz, 1H), 7.78 (d, J = 2.4 Hz, 1H), 7.30-7.23 (m, 1H), 5.08 (d, J = 14.4 Hz, 0.5H), 4.66 (d, J = 13.2, 0.5H), 4.53 (d, J = 13.2, 0.5H), 4.39-4.29 (m, 1H), 4.20-4.10 (m, 1.5H), 3.87-3.69 (m, 3H), 3.66-3.58 (m, 1H), 3.57-3.50 (m, 1H), 3.31-3.30 (m, 3H), 3.28-3.20 (m, 1H), 2.87-2.61 (m, 4H), 1.26 (t, J = 6.8 Hz, 3H); Compound 19B: $^1$H NMR (400 MHz, MeOH-$d_4$) δ 7.92 (s, 1H), 7.78 (dd, 1H), 7.27 (dd, 1H), 5.12-5.04 (m, 0.5H), 4.71-4.62 (m, 0.5H), 4.55-4.46 (m, 0.5H), 4.38-4.29 (m, 1H), 4.21-4.08 (m, 1.5H), 3.87-3.76 (m, 2.5H), 3.71 (dd, 0.5H), 3.67-3.58 (m, 1H), 3.56-3.48 (m, 1H), 3.33-3.31 (m,3H), 3.30-3.20 (m, 1H), 2.85-2.62 (m, 4H), 1.26 (dd, 3H). |

-continued

| Example | Compound | Chiral separation | Structure | INT | $^1$H NMR and MS: (M + H)$^+$ |
|---|---|---|---|---|---|
| 20 | 20A & 20B | Column: CHIRAL ART Cellulose SB 2 cm × 25 cm, 5um; Mobile Phase A: MTBE, Mobile Phase B: EtOH, $V_{MobilePhase\ A}$: $V_{Mobile\ Phase\ B}$ = 55:45; Flow Rate: 20 mL/min Compound 20A: Retention time: 6.61 min; Compound 20B: Retention time: 8.21 min. | 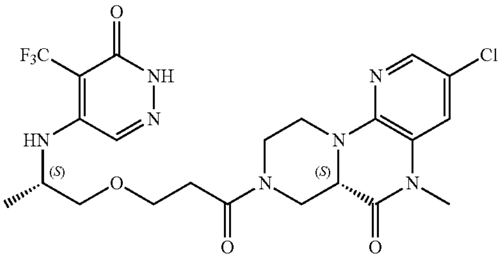 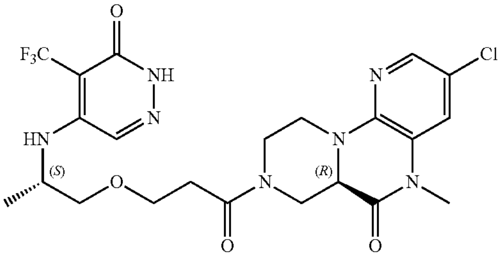 | A1 & B3 | MS: (M + H)$^+$ 544. Compound 20A: $^1$H NMR (400 MHz, MeOH-d$_4$) δ 7.90 (d, J = 20.4 Hz, 1H), 7.82 (s, 1H), 7.32 (d, J = 4.4 Hz, 1H), 5.05 (d, J = 13.2 Hz, 0.5H), 4.63 (d, J = 12.8 Hz, 0.5H), 4.50 (d, J = 13.4 Hz, 0.5H), 4.38 (t, J = 11.6 Hz, 1H), 4.19-4.06 (m, 1.5H), 3.91-3.72 (m, 3H), 3.64-3.47 (m, 2H), 3.31-3.28 (m, 3H), 3.24-3.18 (m, 1H), 2.84-2.62 (m, 4H), 1.24 (t, J = 5.6 Hz, 3H); Compound 20B: $^1$H NMR (400 MHz, MeOH-d$_4$) δ 7.93 (s, 1H), 7.85 (dd, 1H), 7.36 (s, 1H), 5.13-5.05 (m, 0.5H), 4.69-4.63 (m, 0.5H), 4.50 (d, J = 13.4 Hz, 0.5H), 4.38 (t, J = 11.6 Hz, 1H), 4.19-4.06 (m, 1.5H), 3.91-3.72 (m, 3H), 3.64-3.47 (m, 2H), 3.31-3.27 (m, 3H), 3.24-3.18 (m, 1H), 2.86-2.63 (m, 4H), 1.26 (dd, 3H). |
| 21 | 21A & 21B | Column: CHIRAL ART Cellulose SB 2 cm × 25 cm, 5um; Mobile Phase A: MTBE, Mobile Phase B: EtOH, $V_{Mobile\ Phase\ A}$: $V_{Mobile\ Phase\ B}$ = 75:25; Flow Rate: 20 mL/min Compound 21A: Retention time: 6.71 min; Compound 21B: Retention time: 9.28 min. | 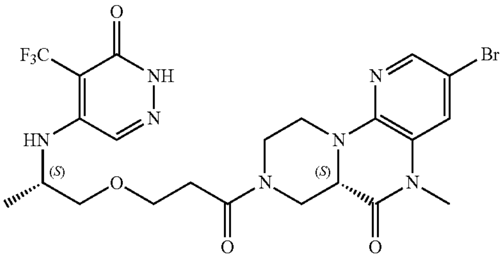 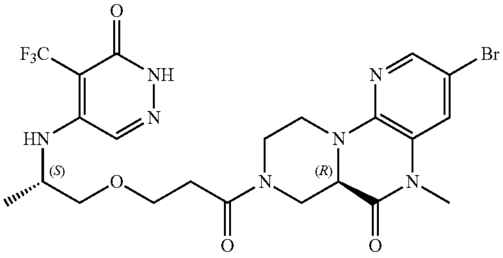 | A1 & B4 | MS: (M + H)$^+$ 588, 590. Compound 21A: $^1$H NMR (400 MHz, MeOH-d$_4$) δ 7.94-7.86 (m, 2H), 7.42 (s, 1H), 5.06 (d, J = 12.4 Hz, 0.5H), 4.63 (d, J = 13.2, 0.5H), 4.50 (d, J = 13.6 Hz, 0.5H), 4.39 (t, J = 11.6 Hz, 1H), 4.18-4.06 (m, 1.5H), 3.91-3.73 (m, 3H), 3.65-3.46 (m, 2H), 3.31-3.28 (m, 3H), 3.26-3.16 (m, 1H), 2.84-2.60 (m, 4H), 1.24 (s, 3H); Compound 21B: $^1$H NMR (400 MHz, MeOH-d$_4$) δ 7.94-7.87 (m, 2H), 7.43 (s, 1H), 5.06 (d, J = 12.4 Hz, 0.5H), 4.63 (d, J = 12.0 Hz, 0.5H), 4.48 (d, J = 13.2 Hz, 0.5H), 4.44-4.36 (m, 1H), 4.19-4.05 (m, 1.5H), 3.90 (d, J = 10.4 Hz, 0.5H), 3.85-3.73 (m, 2.5H), 3.64-3.56 (m, 1H), 3.54-3.46 (m, 1H), 3.33-3.17 (m, 4H), 2.84-2.61 (m, 4H), 1.27-1.20 (m, 3H). |

-continued

| Example | Compound | Chiral separation | Structure | INT | $^1$H NMR and MS: $(M + H)^+$ |
|---|---|---|---|---|---|
| 22 | 22A & 22B | Column: CHIRAL ART Cellulose SB 2 cm × 25 cm, 5um; Mobile Phase A: MTBE, Mobile Phase B: MeOH, $V_{Mobile\ Phase\ A}$: $V_{Mobile\ Phase\ B}$ = 80:20; Flow Rate: 20 mL/min Compound 22A: Retention time: 6.64 min; Compound 22B: Retention time: 8.66 min. | 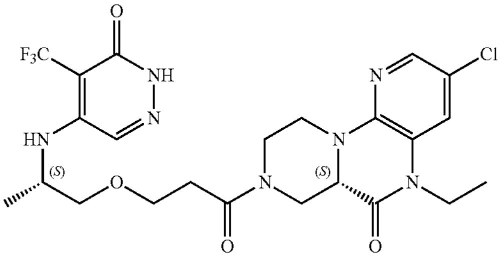 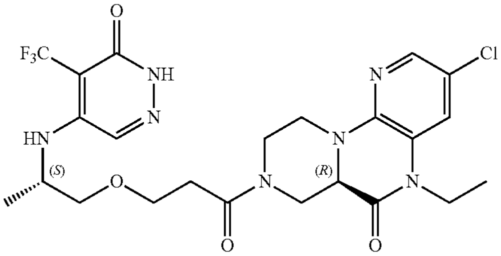 | A1 & B3 | MS: $(M + H)^+$ 558. Compound 22A: $^1$H NMR (400 MHz, MeOH-$d_4$) δ 7.90 (d, J = 16.4 Hz, 1H), 7.82 (s, 1H), 7.36 (s, 1H), 5.05 (d, J = 13.2 Hz, 0.5H), 4.63 (d, J = 12.8 Hz, 0.5H), 4.48 (d, J = 13.2 Hz, 0.5H), 4.37 (t, J = 11.2 Hz, 1H), 4.18-4.09 (m, 1.5H), 4.01-3.91 (m, 2H), 3.90-3.72 (m, 3H), 3.61-3.48 (m, 2H), 3.28-3.18 (m, 1H), 2.82-2.60 (m, 4H), 1.25-1.19 (m, 6H); Compound 22B: $^1$H NMR (400 MHz, MeOH-$d_4$) δ 7.91 (s, 1H), 7.83 (d, J = 9.2 Hz, 1H), 7.37 (s, 1H), 5.05 (d, J = 13.6 Hz, 0.5H), 4.63 (d, J = 12.4 Hz, 0.5H), 4.47 (d, J = 13.6 Hz, 0.5H), 4.42-4.32 (m, 1H), 4.19-4.05 (m, 1.5H), 4.05-3.92 (m, 2H), 3.91-3.72 (m, 3H), 3.65-3.56 (m, 1H), 3.55-3.44 (m, 1H), 3.31-3.16 (m, 1H), 2.84-2.60 (m, 4H), 1.28-1.16 (m, 6H). |

-continued

| Example | Compound | Chiral separation | Structure | INT | $^1$H NMR and MS: $(M + H)^+$ |
| --- | --- | --- | --- | --- | --- |
| 23 | 23A & 23B | Column: CHIRAL ART Cellulose SB 2 cm × 25 cm, 5um; Mobile Phase A: MTBE, Mobile Phase B: MeOH, $V_{MobilePhase\ A}$: $V_{Mobile\ Phase\ B}$ = 75:25; Flow Rate: 20 mL/min Compound 23A: Retention time: 5.99 min; Compound 23B: Retention time: 8.33 min. | 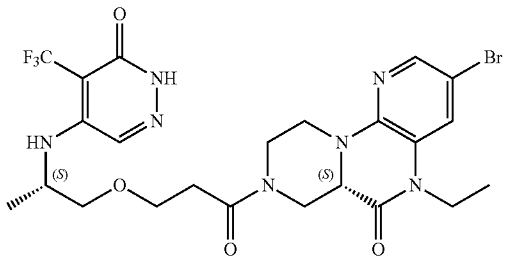 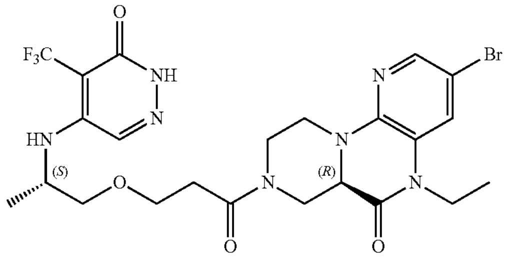 | A1 & B4 | MS: $(M + H)^+$ 602, 604. Compound 23A: $^1$H NMR (400 MHz, MeOH-$d_4$) δ 7.95-7.86 (m, 2H), 7.45 (s, 1H), 5.05 (d, J = 12.8 Hz, 0.5H), 4.63 (d, J = 12.4 Hz, 0.5H), 4.48 (d, J = 13.2 Hz, 0.5H), 4.37 (t, J = 10.8 Hz, 1H), 4.21-4.06 (m, 1.5H), 3.90-3.71 (m, 2H), 3.91-3.70 (m, 3H), 3.67-3.44 (m, 2H), 3.29-3.14 (m, 1H), 2.88-2.57 (m, 4H), 1.31-1.14 (m, 6H); Compound 23B: $^1$H NMR (400 MHz, MeOH-$d_4$) δ 7.96-7.87 (m, 2H), 7.46 (s, 1H), 5.05 (d, J = 12.8 Hz, 0.5H), 4.63 (d, J = 12.4 Hz, 0.5H), 4.47 (d, J = 13.2 Hz, 0.5H), 4.43-4.31 (m, 1H), 4.20-4.05 (m, 1.5H), 4.04-3.85 (m, 2.5H), 3.85-3.72 (m, 2.5H), 3.60 (dd, 1H), 3.54-3.44 (m, 1H), 3.30-3.17 (m, 1H), 2.84-2.60 (m, 4H), 1.28-1.15 (m, 6H). |

-continued

| Example | Compound | Chiral separation | Structure | INT | $^1H$ NMR and MS: $(M + H)^+$ |
|---|---|---|---|---|---|
| 24 | 24A & 24B | Column: CHIRAL ART Cellulose SB 2 cm × 25 cm, 5um; Mobile Phase A: MTBE, Mobile Phase B: EtOH, $V_{Mobile\ Phase\ A}$: $V_{Mobile\ Phase\ B}$ = 60:40; Flow Rate: 20 mL/min Compound 24A: Retention time: 6.18 min; Compound 24B: Retention time: 7.16 min. | 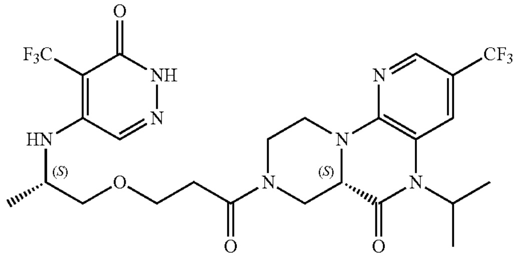 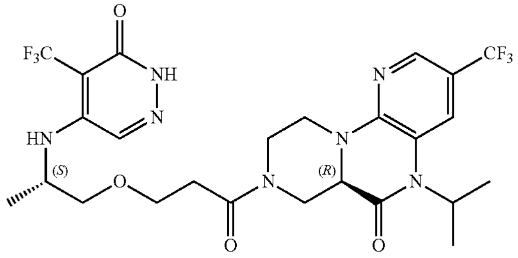 | A1 & B2 | MS: $(M + H)^+$ 606. Compound 24A: $^1H$ NMR (400 MHz, MeOH-$d_4$) δ 8.16 (s, 1H), 7.92 (d, J = 11.6 Hz, 1H), 7.53 (s, 1H), 5.04 (d, J = 13.2 Hz, 0.5H), 4.72-4.59 (m, 1.5H), 4.52-4.40 (m, 1.5H), 4.19-4.07 (m, 1.5H), 3.90 (d, J = 8.4 Hz, 0.5H), 3.84-3.79 (m, 2.5H), 3.62-3.48 (m, 2H), 3.30-3.21 (m, 1H), 2.88-2.61 (m, 4H), 1.55 (d, J = 6.8 Hz, 3H), 1.51 (d, J = 6.8 Hz, 3H), 1.25 (d, J = 6.4 Hz, 3H); Compound 24B: $^1H$ NMR (400 MHz, MeOH-$d_4$) δ 8.14 (d, J = 6.0 Hz, 1H), 7.93 (s, 1H), 7.40 (s, 1H), 5.07 (d, J = 13.2 Hz, 0.5H), 4.67-4.56 (m, 1.5H), 4.49 (d, J = 13.2 Hz, 0.5H), 4.19-4.05 (m, 2H), 4.04-3.88 (m, 2.5H), 3.86-3.73 (m, 2H), 3.61 (dd, 1H), 3.50 (dd, 1H), 3.29-3.18 (m, 1H), 2.90-2.62 (m, 4H), 1.72-1.56 (m, 2H), 1.24 (d, J = 6.4 Hz, 3H), 0.96 (t, J = 7.2 Hz, 3H). |

-continued

| Example | Compound | Chiral separation | Structure | INT | $^1$H NMR and MS: $(M + H)^+$ |
|---|---|---|---|---|---|
| 25 | 25A & 25B | Column: CHIRAL ART Cellulose SA 2 cm × 25 cm, 5um; Mobile Phase A: MTBE, Mobile Phase B: EtOH, $V_{Mobile\ Phase\ A}$: $V_{Mobile\ Phase\ B}$ = 78:22; Flow Rate: 20 mL/min Compound 25A: Retention time: 6.52 min; Compound 25B: Retention time: 8.35 min. | 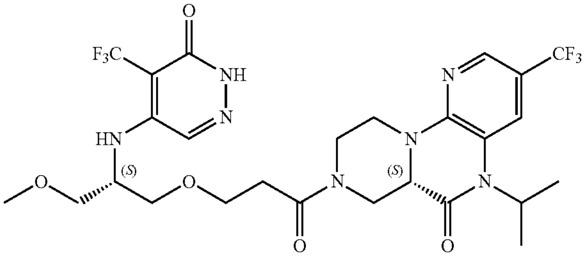 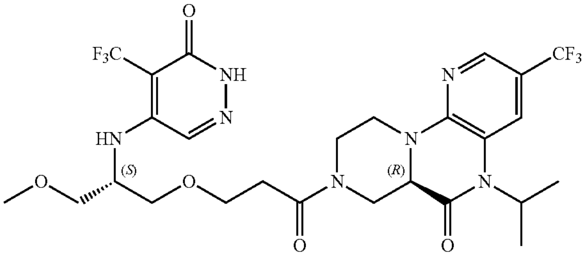 | A5 & B2 | MS: $(M + H)^+$ 636. Compound 25A: $^1$H NMR (400 MHz, MeOH-$d_4$) δ 8.17 (s, 1H), 7.94 (d, J = 8.6, 1H), 7.54 (s, 1H), 5.04 (d, J = 14.0 Hz, 0.5H), 4.71-4.61 (m, 1.5H), 4.51-4.42 (m, 1.5H), 4.23-4.16 (m, 1H), 4.12 (d, J = 13.2 Hz, 0.5H), 3.93-3.87 (m, 0.5H), 3.84-3.73 (m, 2.5H), 3.69-3.59 (m, 2H), 3.56-3.52 (m, 2H), 3.36 (s, 3H), 3.30-3.20 (m, 1H), 2.89-2.64 (m, 4H), 1.55 (d, J = 6.8 Hz, 3H), 1.51 (d, J = 6.8 Hz, 3H); Compound 25B: $^1$H NMR (400 MHz, MeOH-$d_4$) δ 8.17 (d, J = 4.4 Hz, 1H), 7.95 (d, J = 7.2 Hz, 1H), 7.54 (s, 1H), 5.04 (d, J = 14.0, 0.5H), 4.69-4.61 (m, 1.5H), 4.51-4.43 (m, 1.5H), 4.22-4.17 (m, 1H), 4.12 (d, J = 13.2 Hz, 0.5H), 3.93-3.87 (m, 0.5H), 3.83-3.75 (m, 2.5H), 3.68-3.60 (m, 2H), 3.54 (d, J = 4.8 Hz, 2H), 3.36 (s, 3H), 3.29-3.21 (m, 1H), 2.90-2.67 (m, 4H), 1.55 (d, J = 6.8 Hz, 3H), 1.51 (d, J = 6.8 Hz, 3H). |

Example 26

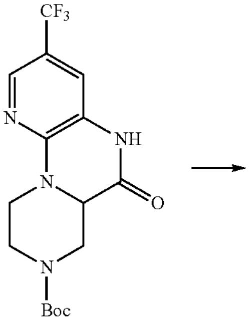

INT B2

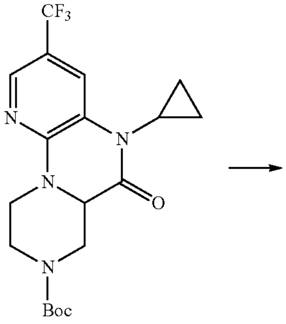

Compound 26-1

-continued

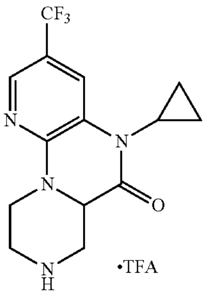

Compound 26-2

-continued

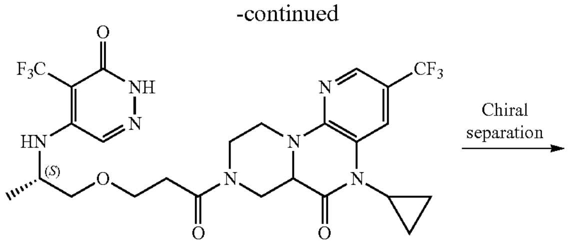

Compound 26

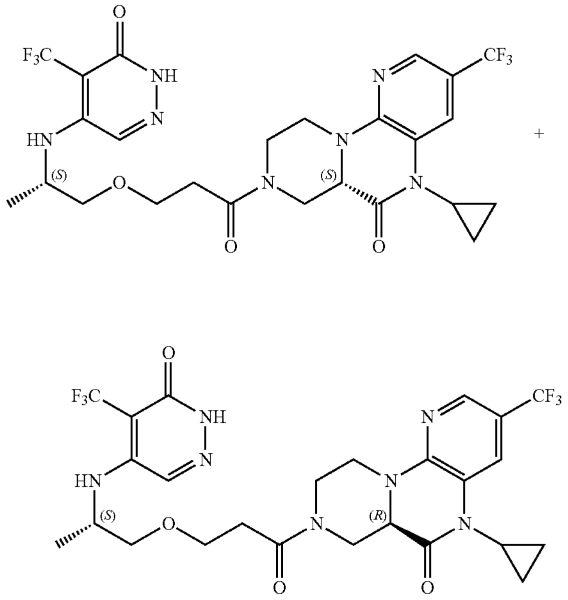

Step 1: INT B2 (352 mg, 0.95 mmol, 1.0 eq.), cyclopropylboronic acid (292 mg, 3.40 mmol, 3.70 eq.), pyridine (373 mg, 4.72 mmol, 4.97 eq.), $Cs_2CO_3$ (156 mg, 0.48 mmol, 0.51 eq.) and $Cu(OAc)_2$ (377 mg, 2.08 mmol, 2.19 eq.) were dispersed in toluene (15 mL). The reaction mixture was stirred overnight at 110° C., and then filtered. The filtrate was concentrated under reduced pressure to obtain a residue which was purified with silica gel column chromatography eluted with Hex/EA to afford Compound 26-1 (377 mg, yield 96%). LCMS: m/z=413 $[M+1]^+$.

Step 2: Following an analogous procedure described in step 1 of Example 2, the Compound 26-1 (377 mg, 0.91 mmol, 1.0 eq.) and TFA (5 mL) were used as reactants to synthesize Compound 26-2 (crude, 409 mg). LCMS: m/z=313 $[M+1]^+$.

Step 3: Following an analogous procedure described in step 2 of Example 1, the crude Compound 26-2 (409 mg, crude) and INT A1 (304 mg, 0.98 mmol, 1.0 eq.) were used as reactants to synthesize Compound 26 (188 mg, yield 34%). LCMS: m/z=604 $[M+1]^+$.

$^1$H NMR (400 MHz, MeOH-$d_4$) δ 8.18 (d, 15.9 Hz, 1H), 7.95 (s, 1H), 7.75 (s, 1H), 5.07 (d, J=13.0 Hz, 0.5H), 4.66 (d, J=9.1 Hz, 0.5H), 4.57-4.43 (m, 1.5H), 4.13 (d, J=17.8 Hz, 1.5H), 4.02 (d, J=10.7 Hz, 0.5H), 3.92 (d, J=8.3 Hz, 0.5H), 3.82 (d, J=5.6 Hz, 2H), 3.63 (d, J=6.4 Hz, 1H), 3.56-3.47 (m, 1H), 3.26 (dd, 1H), 2.91-2.65 (m, 5H), 1.31 (s, 1H), 1.27 (d, J=6.5 Hz, 3H), 1.21-1.10 (m, 1H), 0.87 (s, 1H), 0.56 (s, 1H).

The chiral separation of the Compound 26 (188 mg) was performed by Chiral-Prep-HPLC with the following conditions: Equipment: Prep-HPLC-Gilson; Column: CHIRAL ART Cellulose SB 2 cm×25 cm, 5 um; Mobile Phase A: Hex:DCM=3:1, Mobile Phase B: EtOH; $V_{Mobile\ Phase\ A}$: $V_{Mobile\ Phase\ B}$=70:30; Flow Rate: 20 mL/min; Detector Wavelength: 220 nm. This resulted in the first eluting stereoisomer (Compound 26A, 75 mg, Retention time: 5.410 min) and the second eluting stereoisomer (Compound 26B, 71 mg, Retention time: 5.84 min).

The following compounds were synthesized using the above procedure or modification procedure using the corresponding intermediates.

| Example | Compound | Chiral separation | Structure | INT | $^1$H NMR and MS: $(M + H)^+$ |
|---|---|---|---|---|---|
| 27 | 27 | N/A | 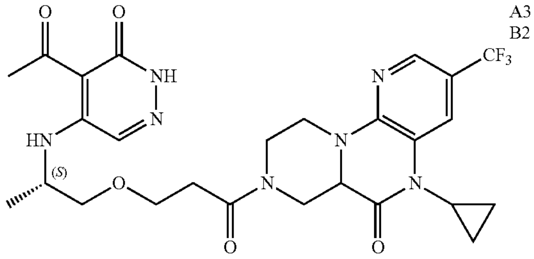 | A3 & B2 | $^1$H NMR (400 MHz, DMSO-$d_6$) δ 12.25 (s, 1H), 10.70 (d, J = 8.2, 1H), 8.21 (s, 1H), 7.93 (d, J = 8.9, 1H), 7.66 (s, 1H), 4.81 (d, J = 13.2 Hz, 0.5H), 4.55-4.31 (m, 1.5H), 4.31-4.14 (m, 1.5H), 4.14-3.92 (m, 1.5H), 3.76-3.66 (m, 2H), 3.56-3.50 (m, 1H), 3.49-3.41 (m, 1H), 3.27-3.04 (m, 1H), 2.86-2.56 (m, 5H), 2.49-2.40 (m, 3H), 1.25-1.13 (m, 4H), 1.12-1.03 (m, 1H), 0.81-0.70 (m, 1H), 0.50-0.43 (m, 1H); MS: $(M + H)^+$ 578. |

-continued

| Example | Compound | Chiral separation | Structure | INT | $^1H$ NMR and MS: $(M + H)^+$ |
| --- | --- | --- | --- | --- | --- |
| 28 | 28A & 28B | Column: CHIRAL ART Cellulose SA 2 cm × 25 cm, 5um; Mobile Phase A: MTBE, Mobile Phase B: EtOH, $V_{Mobile\ Phase\ A}$: $V_{Mobile\ Phase\ B}$ = 50:50; Flow Rate: 20 mL/min Compound 28A: Retention time: 5.75 min; Compound 28B: Retention time: 6.99 min. | 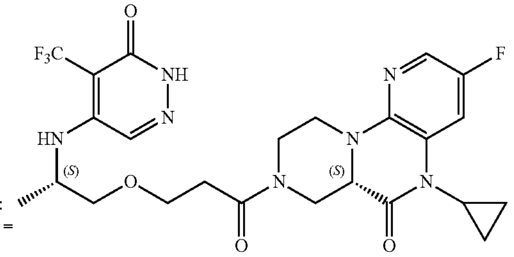 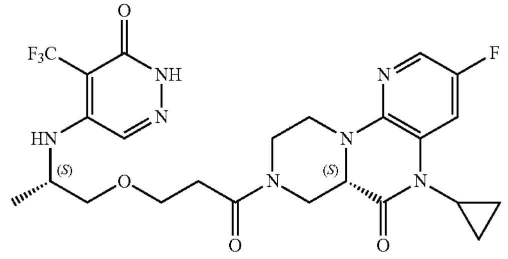 | A1 & B5 | MS: $(M + H)^+$ 554. Compound 28A: $^1H$ NMR (400 MHz, MeOH-$d_4$) δ 7.92 (d, J = 22.0 Hz, 1H), 7.80 (d, J = 1.6 Hz, 1H), 7.54-7.49 (m, 1H), 5.08-5.02 (m, 0.5H), 4.66 (d, J = 12.6 Hz, 0.5H), 4.55-4.46 (m, 0.5H), 4.28-4.19 (m, 1H), 4.18-4.10 (m, 1.5H), 3.87-3.76 (m, 2H), 3.73 (dd, 0.5H), 3.70-3.59 (m, 1.5H), 3.58-3.49 (m, 1H), 3.28-3.17 (m, 1H), 2.87-2.60 (m, 5H), 1.30-1.23 (m, 3H), 1.21 (s, 1H), 1.16-1.09 (m, 1H), 0.93-0.86 (m, 1H), 0.55-0.49 (m, 1H); Compound 28B: $^1H$ NMR (400 MHz, MeOH-$d_4$) δ 7.81 (s, 1H), 7.68 (dd, 1H), 7.41 (dd, 1H), 4.99-4.91 (m, 0.5H), 4.54 (d, J = 12.4 Hz, 0.5H), 4.41-4.32 (m, 0.5H), 4.16-4.09 (m, 1H), 4.08-3.97 (m, 1.5H), 3.76-3.60 (m, 2.5H), 3.57-3.48 (m, 1.5H), 3.45-3.37 (m, 1H), 3.18-3.07 (m, 1H), 2.72-2.50 (m, 5H), 1.20-1.11 (m, 3H), 1.10 (s, 1H), 1.06-0.96 (m, 1H), 0.84-0.73 (m, 1H), 0.45-0.35 (m, 1H). |

Example 29

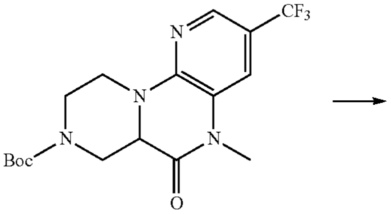

INT B37

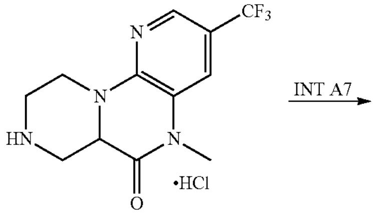

Compound 29-1

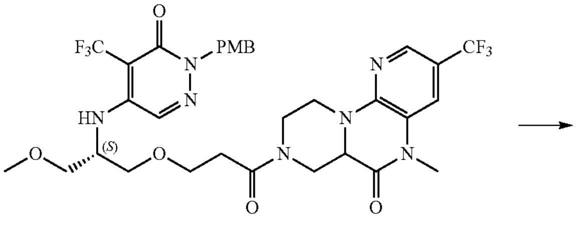

Compound 29-2

-continued

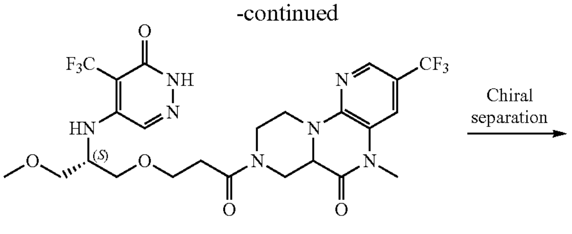

Compound 29

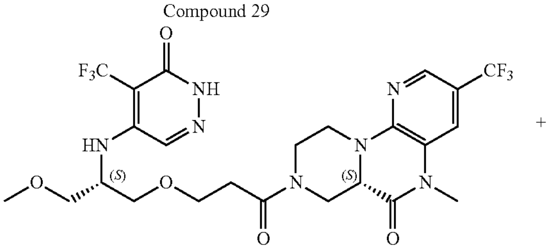

+

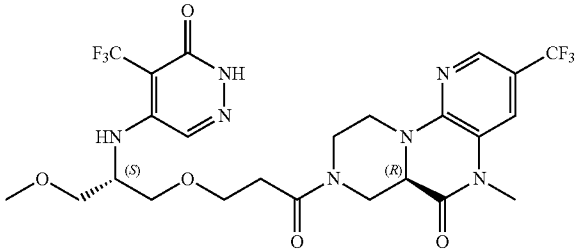

Step 1: Following an analogous procedure described in step 1 of Example 1, INT B37 (588 mg, 1.52 mmol, 1.0 eq.) and HCl/1,4-dioxane (5 mL, 1N) were used as reactants to synthesize Compound 29-1 (400 mg, yield 81%). LCMS: m/z=287 $[M+1]^+$.

Step 2: Following an analogous procedure described in step 2 of Example 1, the Compound 29-1 (400 mg, 1.24 mmol, 1.29 eq.) and INT A7 (440 mg, 0.96 mmol, 1.0 eq.) were used as reactants to synthesize Compound 29-2 (320 mg, yield 45%). LCMS: m/z=728 $[M+1]^+$.

Step 3: TfOH (2 mL) was added dropwise at room temperature to a solution of the Compound 29-2 (320 mg, 0.44 mmol, 1.0 eq.) dissolved in TFA (10 mL). After stirring for 2 hrs at room temperature, the pH of the reaction mixture was adjusted to 7-8 with sodium bicarbonate aqueous solution. The resulting mixture was extracted with EA (100 mL×2). The combined organic layers were dried over anhydrous $Na_2SO_4$, and then concentrated under reduced pressure to obtain a residue which was purified with C18 column eluted with $H_2O/CH_3CN$ to afford Compound 29 (226 mg, yield 84%). LCMS: m/z=608 $[M+1]^+$.

$^1H$ NMR (400 MHz, MeOH-$d_4$) δ 8.15 (s, 1H), 7.94 (d, J=13.2 Hz, 1H), 7.42 (s, 1H), 5.08 (d, J=13.2 Hz, 0.5H), 4.68-4.59 (m, 1.5H), 4.50 (d, J=13.2 Hz, 0.5H), 4.25-4.16 (m, 1H), 4.14-4.06 (m, 1H), 4.04-3.97 (m, 0.5H), 3.86-3.74 (m, 2H), 3.70-3.59 (m, 2H), 3.54 (d, J=4.8 Hz, 2H), 3.37 (s, 6H), 3.28-3.16 (m, 1H), 2.89-2.63 (m, 4H).

The chiral separation of the Compound 29 (226 mg) was performed by Chiral-Prep-HPLC with the following conditions: Equipment: Prep-HPLC-Gilson; Column: CHIRALPAK ID 2 cm×25 cm, 5 um; Mobile Phase A: MTBE, Mobile Phase B: EtOH, $V_{Mobile\ Phase\ A}$:$V_{Mobile\ Phase\ B}$=55:45; Flow Rate: 18 mL/min; Detector Wavelength: 220 nm. This resulted in the first eluting stereoisomer (Compound 29A, 77.5 mg, Retention time: 5.45 min) and the second eluting stereoisomer (Compound 29B, 77.3 mg, Retention time: 6.24 min).

The following compounds were synthesized using the above procedure or modification procedure using the corresponding intermediates.

| Example | Compound | Chiral separation | Structure | INT | $^1H$ NMR and MS: $(M + H)^+$ |
|---|---|---|---|---|---|
| 30 | 30A & 30B & 30C & 30D | Column: CHIRAL ART Cellulose SB 2 cm x 25 cm, 5 um; Mobile Phase A: MTBE, Mobile Phase B: EtOH, $V_{MobilePhaseA}$:$V_{MobilePhaseB}$ = 50:50; Flow Rate: 20 mL/min Mixture of 30A & 30B Retention time: 4.66 min; Compound 30C: Retention time: 7.47 min; Compound 30D: Retention time: 9.01 min. Column: CHIRALPAK IG 2 cm x 25 cm, 5 um; Mobile Phase A: Hex, Mobile Phase B: EtOH, $V_{MobilePhaseA}$:$V_{MobilePhaseB}$ = 50:50; Flow Rate: 20 mL/min; Detector Wavelength: 220 nm Compound 30A: Retention time: 8.71 min; Compound 30B: Retention time: 9.91 min. | 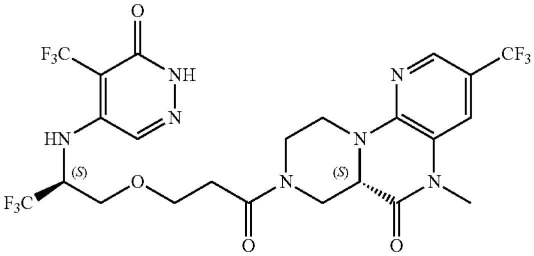 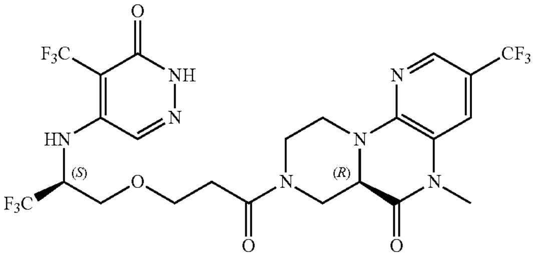 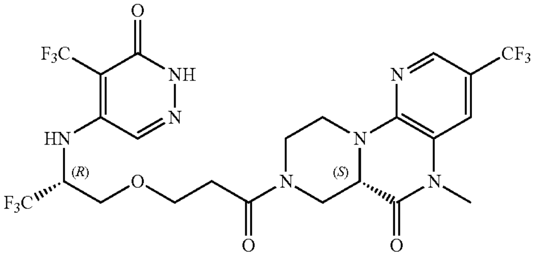 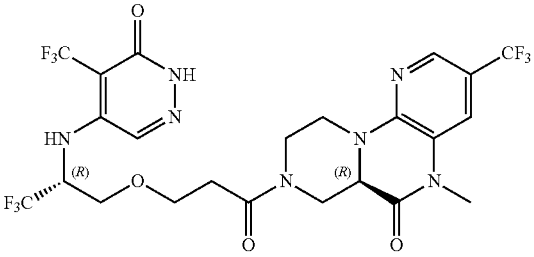 | A9 & B37 | MS: $(M + H)^+$ 632. Compound 30A: $^1H$ NMR (400 M Hz, MeOH-$d_4$) δ 8.15 (d, J = 3.2 Hz, 1H), 8.01 (s, 1H), 7.43 (s, 1H), 5.07 (d, J = 13.6 Hz, 1H), 5.03-4.94 (m, 2H), 4.64 (d, J = 10.0 Hz, 1H), 4.49 (d, J = 13.6 Hz, 0.5H), 4.16-4.02 (m, 1H), 4.00-3.92 (m, 1.5H), 3.90-3.82 (m, 2H), 3.37 (s, 3H), 3.28-3.11 (m, 1H), 2.91-2.69 (m, 4H); Compound 30B: $^1H$ NMR (400 M Hz, MeOH-$d_4$) δ 8.15 (s, 1H), 8.00 (d, J = 6.4 Hz, 1H), 7.43 (s, 1H), 5.07 (d, J = 13.6 Hz, 1H), 5.03-4.94 (m, 2H), 4.64 (d, J = 10.0 Hz, 1H), 4.49 (d, J = 13.6 Hz, 0.5H), 4.16-4.02 (m, 1H), 4.00-3.92 (m, 1.5H), 3.89-3.81 (m, 2H), 3.37 (s, 3H), 3.28-3.11 (m, 1H), 2.89-2.68 (m, 4H); Compound 30C: $^1H$ NMR (400 M Hz, MeOH-$d_4$) δ 8.15 (s, 1H), 8.00 (d, J = 6.4 Hz, 1H), 7.43 (s, 1H), 5.07 (d, J = 13.6 Hz, 1H), 5.03-4.94 (m, 2H), 4.64 (d, J = 10.0 Hz, 1H), 4.49 (d, J = 13.6 Hz, 0.5H), 4.16-4.02 (m, 1H), 4.01-3.92 (m, 1.5H), 3.90-3.81 (m, 2H), 3.37 (s, 3H), 3.28-3.19 (m, 1H), 2.88-2.68 (m, 4H); Compound 30D: $^1H$ NMR (400 M Hz, MeOH-$d_4$) δ 8.15 (d, J = 3.2 Hz, 1H), 8.01 (s, 1H), 7.43 (s, 1H), 5.07 (d, J = 13.6 Hz, 1H), 5.03-4.94 (m, 2H), 4.64 (d, J = 10.0 Hz, 1H), 4.49 (d, J = 13.6 Hz, 0.5H), 4.17-4.05 (m, 1H), 4.02-3.91 (m, 1.5H), 3.90-3.81 (m, 2H), 3.37 (s, 3H), 3.28-3.19 (m, 1H), 2.91-2.70 (m, 4H) |

-continued

| Example | Compound | Chiral separation | Structure | INT | $^1$H NMR and MS: (M + H)$^+$ |
|---|---|---|---|---|---|
| 31 | 31A & 31B | Column: CHIRALPAK ID 2 cm × 25 cm, 5 um; Mobile Phase A: MTBE, Mobile Phase B: EtOH, $V_{MobilePhaseA}$: $V_{MobilePhaseB}$ = 50:50; Flow Rate: 16 mL/min; Detector Wavelength: 220 nm Compound 31A: Retention time: 8.78 min; Compound 31B: Retention time: 11.12 min. | 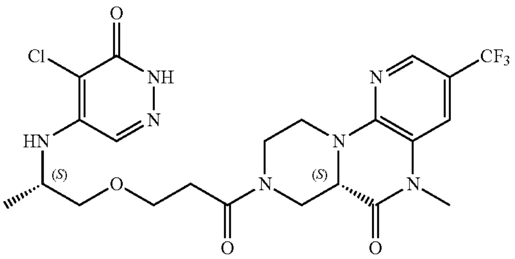<br>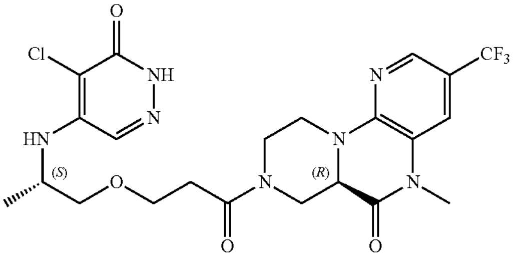 | A13 & B37 | MS: (M + H)$^+$ 544. Compound 31A: $^1$H NMR (400 M Hz, MeOH-$d_4$) δ 8.13 (s, 1H), 7.86 (d, J = 30.8 Hz, 1H), 7.39 (d, J = 13.2 Hz, 1H), 5.06 (d, J = 13.2 Hz, 0.5H), 4.69-4.47 (m, 2H), 4.15-4.01 (m, 2H), 3.96 (d, J = 9.2 Hz, 0.5H), 3.86-3.68 (m, 2H), 3.63-3.45 (m, 2H), 3.36 (d, J = 10.4 Hz, 3H), 3.30-3.16 (m, 1H), 2.90-2.55 (m, 4H), 1.30-1.16 (m, 3H); Compound 31B: $^1$H NMR (400 M Hz, MeOH-$d_4$) δ 8.12 (d, J = 9.6 Hz, 1H), 7.87 (d, J = 3.2 Hz, 1H), 7.40 (s, 1H), 5.07 (d, J = 13.2 Hz, 0.5H), 4.68-4.54 (m, 1.5H), 4.50 (d, J = 13.6 Hz, 0.5H), 4.14-4.02 (m, 2H), 4.01-3.93 (m, 0.5H), 3.86-3.71 (m, 2H), 3.63-3.56 (m, 1H), 3.55-3.46 (m, 1H), 3.36 (s, 3H), 3.30-3.16 (m, 1H), 2.89-2.56 (m, 4H), 1.23 (d, J = 6.4 Hz, 3H). |
| 32 | 32A & 32B | Column: CHIRALPAK ID 2 cm × 25 cm, 5 um; Mobile Phase A: MTBE, Mobile Phase B: EtOH, $V_{MobilePhaseA}$: $V_{Mobile PhaseB}$ = 50:50; Flow Rate: 16 mL/min; Detector Wavelength: 220 nm Compound 32A: Retention time: 10.42 min; Compound 32B: Retention time: 13.99 min. | 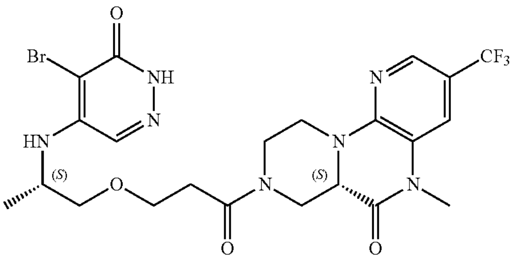<br>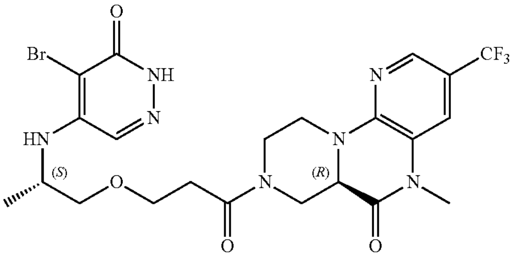 | A14 & B37 | MS: (M + H)$^+$ 588, 590. Compound 32A: $^1$H NMR (400 M Hz, MeOH-$d_4$) δ 8.13 (s, 1H), 7.77 (d, J = 30.0 Hz, 1H), 7.40 (d, J = 14.0 Hz, 1H), 5.06 (d, J = 13.2 Hz, 0.5H), 4.67-4.47 (m, 2H), 4.13-4.02 (m, 2H), 3.99-3.93 (m, 0.5H), 3.87-3.71 (m, 2H), 3.65-3.45 (m, 2H), 3.35 (d, J = 12.0 Hz, 3H), 3.28-3.09 (m, 1H), 2.89-2.58 (m, 4H), 1.26-1.22 (m, 3H); Compound 32B: $^1$H NMR (400 M Hz, MeOH-$d_4$) δ 8.13 (d, J = 9.6 Hz, 1H), 7.78 (d, J = 4.0 Hz, 1H), 7.41 (s, 1H), 5.07 (d, J = 13.2 Hz, 0.5H), 4.67-4.55 (m, 1.5H), 4.50 (d, J = 12.4 Hz, 0.5H), 4.14-4.03 (m, 2H), 4.02-3.95 (m, 0.5H), 3.87-3.72 (m, 2H), 3.64-3.57 (m, 1H), 3.55-3.47 (m, 1H), 3.36 (s, 3H), 3.27-3.17 (m, 1H), 2.88-2.58 (m, 4H), 1.24 (d, J = 6.4 Hz, 3H). |

Example 33

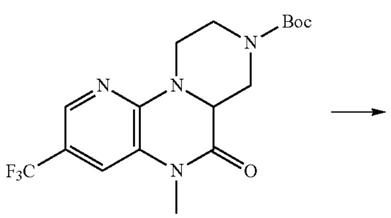

INT B37

-continued

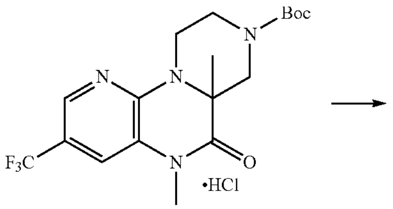

Compound 33-1

-continued

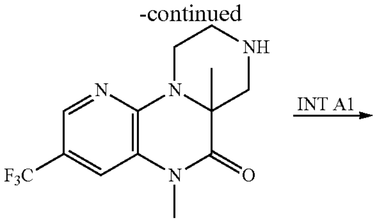

Compound 33-2

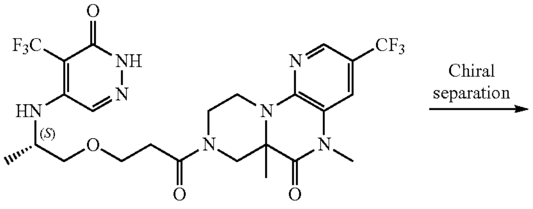

Compound 33

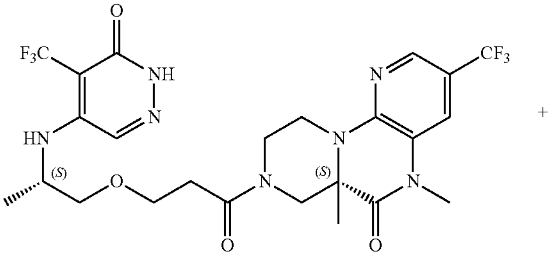

+

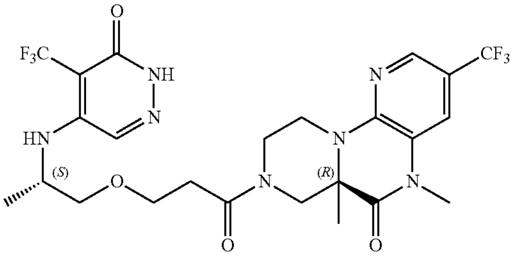

Step 1: A solution of diisopropylamine (531 mg, 5.25 mmol, 6.87 eq.) dissolved in THF (6 mL) was purged and maintained with an inert atmosphere of nitrogen, cooled to −70° C., and then n-BuLi (2 mL) was added dropwise at −70° C. The mixture was stirred for 1 h at −10° C., cooled to −70° C., and a solution of INT B37 (295 mg, 0.76 mmol, 1.0 eq.) dissolved in THF (4 mL) was added. The resulting mixture was stirred at −30° C. for 30 min, and then $CH_3I$ (577 mg, 4.07 mmol, 5.32 eq.) was added. The reaction mixture was stirred for 2.5 hrs at 0° C., quenched with saturated $NH_4Cl$ aqueous solution (10 mL) and extracted with EA (20 mL×3). The organic layers were combined, dried over anhydrous $Na_2SO_4$, and then concentrated under reduced pressure to obtain a residue which was purified with Prep-HPLC (C18 column, eluted with $H_2O/CH_3CN$) to afford Compound 33-1 (90 mg, yield 29%). LCMS: m/z=401 $[M+1]^+$.

Step 2: Following an analogous procedure described in step 1 of Example 1, the Compound 33-1 (90 mg, 0.22 mmol, 1.0 eq.) and HCl/1,4-dioxane (10 mL, 1N) were used as reactants to synthesize Compound 33-2 (crude, 79 mg). LCMS: m/z=301 $[M+1]^+$.

Step 3: Following an analogous procedure described in step 2 of Example 1, the crude Compound 33-2 (79 mg, crude) and INT A1 (81 mg, 0.26 mmol, 1.0 eq.) were used as reactants to synthesize Compound 33 (78 mg, yield 59%). LCMS: m/z=592 $[M+1]^+$.

$^1H$ NMR (400 MHz, MeOH-$d_4$) δ 8.19 (s, 1H), 7.95 (s, 1H), 7.50 (d, J=6.9, 1H), 4.97 (d, J=12.8 Hz, 0.5H), 4.69 (d, J=12.8 Hz, 0.5H), 4.35-4.27 (m, 1H), 4.26-4.11 (m, 2H), 3.91-3.76 (m, 2H), 3.67-3.60 (m, 1H), 3.58-3.49 (m, 1H), 3.41 (d, J=4.7, 3H), 3.30-3.24 (m, 0.5H), 3.20-2.98 (m, 1.5H), 2.92-2.62 (m, 3H), 1.27 (t, J=5.6 Hz, 3H), 1.18 (d, J=24.0 Hz, 3H).

The chiral separation of the Compound 33 (78 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=70:30; Flow Rate: 20 mL/min; Detector Wavelength: 220 nm. This resulted in the first eluting stereoisomer (Compound 33A, 17.9 mg, Retention time: 4.98 min) and the second eluting stereoisomer (Compound 33B, 17.0 mg, Retention time: 6.74 min).

Example 34

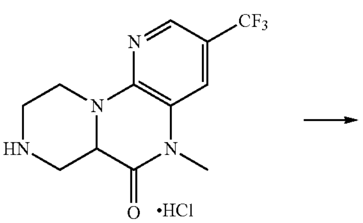

Compound 3-1

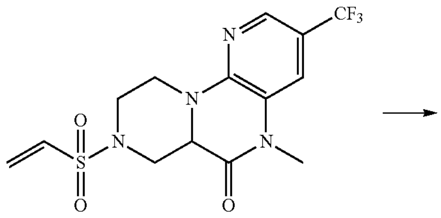

Compound 34-1

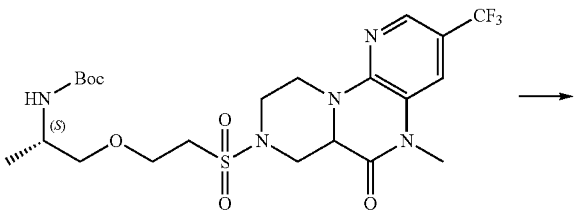

Compound 34-2

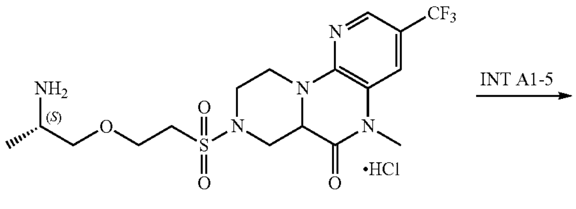

Compound 34-3

-continued

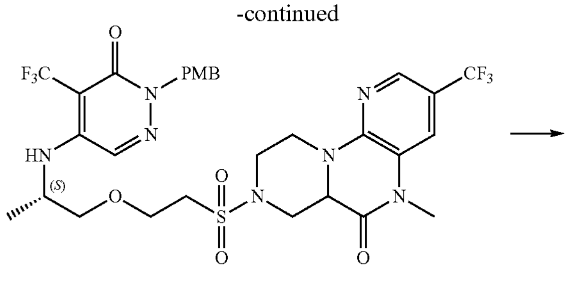

Compound 34-4

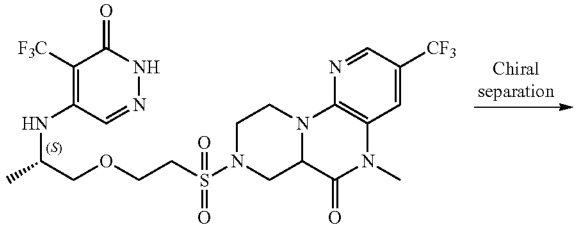

Compound 34

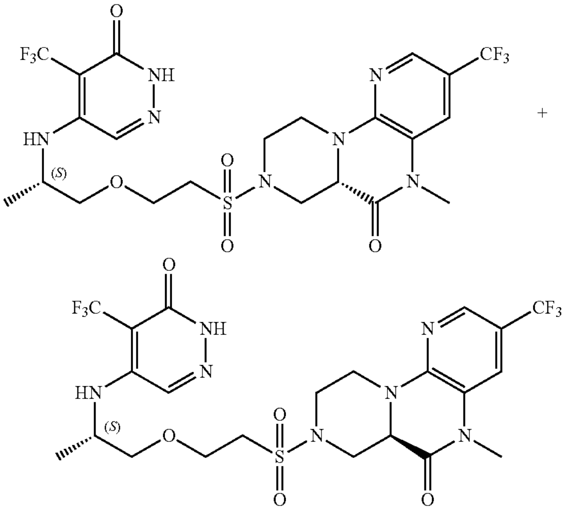

Step 1: Compound 3-1 (687 mg, 2.13 mmol, 1.0 eq.) and TEA (2.56 g, 25.25 mmol, 11.85 eq.) were dissolved in DCM (15 mL), and then ethenesulfonyl chloride (639 mg, 5.05 mmol, 2.37 eq.) was added dropwise at 0° C. The reaction mixture was stirred for 2 hrs at room temperature, poured into water (50 mL) and then extracted with EA (50 mL×3). The combined organic layers were concentrated under reduced pressure to obtain a residue which was purified with Prep-HPLC (C18 column, eluted with $H_2O/CH_3CN$) to afford Compound 34-1 (335 mg, yield 41%). LCMS: m/z=377 $[M+1]^+$.

Step 2: The Compound 34-1 (335 mg, 0.89 mmol, 1.0 eq.), N-Boc-L-alaninol (323 mg, 1.84 mmol, 2.07 eq.) and $Cs_2CO_3$ (356 mg, 1.09 mmol, 1.23 eq.) were dispersed in $CH_3CN$ (6 mL). The reaction mixture was stirred for 8 hrs at room temperature, poured into water (20 mL) and extracted with EA (20 mL×3). The combined organic layers were dried over anhydrous $Na_2SO_4$, and then filtered. The filtrate was concentrated under reduced pressure to obtain a residue which was purified with Prep-HPLC (C18 column, eluted with $H_2O/CH_3CN$) to afford Compound 34-2 (384 mg, yield 78%). LCMS: m/z=552 $[M+1]^+$.

Step 3: HCl/1,4-dioxane (5 mL, 1N) was added to a solution of the Compound 34-2 (384 mg, 0.70 mmol, 1.0 eq.) dissolved in 1,4-dioxane (2 mL). The reaction mixture was stirred for 2 hrs at room temperature, and then concentrated under reduced pressure to afford Compound 34-3 (crude, 314 mg). LCMS: m/z=452 $[M+1]^+$.

Step 4: A mixture of INT A1-5 (371 mg, 1.16 mmol, 1.66 eq.), crude Compound 34-3 (314 mg, 0.70 mmol, 1.0 eq.), TEA (2 mL) and $CH_3CN$ (10 mL) was stirred for 4 hrs at room temperature, and then concentrated under reduced pressure to obtain a residue. The residue was purified with Prep-HPLC (C18 column, eluted with $CH_3CN/H_2O$) to afford Compound 34-4 (268 mg, yield 52%). LCMS: m/z=734 $[M+1]^+$.

Step 5: TfOH (1 mL) was added dropwise at room temperature to a solution of the Compound 34-4 (268 mg, 0.37 mmol, 1.0 eq.) dissolved in TFA (5 mL). The reaction mixture was stirred for 1 h at room temperature, quenched with sodium bicarbonate aqueous solution (50 mL) and then extracted with of EA (50 mL×3). The combined organic layers were dried over anhydrous $Na_2SO_4$, and then filtered. The filtrate was concentrated under reduced pressure to obtain a residue which was purified with Prep-HPLC(C18 column, eluted with $CH_3CN/H_2O$) to afford Compound 34 (126 mg, yield 84%). LCMS: m/z=614 $[M+1]^+$.

$^1H$ NMR (400 MHz, MeOH-$d_4$) δ 8.15 (s, 1H), 7.90 (s, 1H), 7.42 (s, 1H), 4.67 (d, J=12.2 Hz, 1H), 4.23-4.10 (m, 3H), 3.94-3.78 (m, 3H), 3.64-3.52 (m, 2H), 3.39-3.33 (m, 5H), 3.03-2.83 (m, 3H), 1.24 (d, J=6.4 Hz, 3H).

The chiral separation of the Compound 34 (126 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereo isomer (Compound 34A, 49.0 mg, Retention time: 5.48 min) and the second eluting stereoisomer (Compound 34B, 47.6 mg, Retention time: 6.83 min).

Example 35

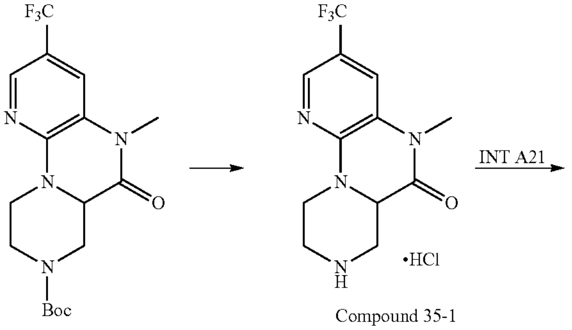

Compound 35-1

INT B37

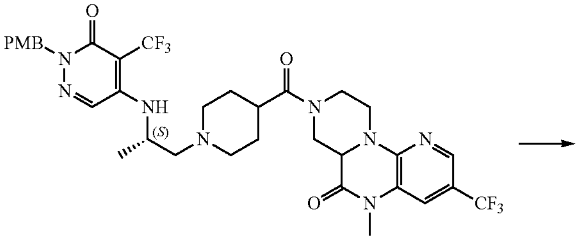

Compound 35-2

-continued

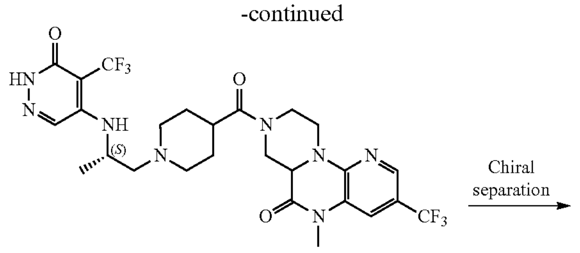

Compound 35

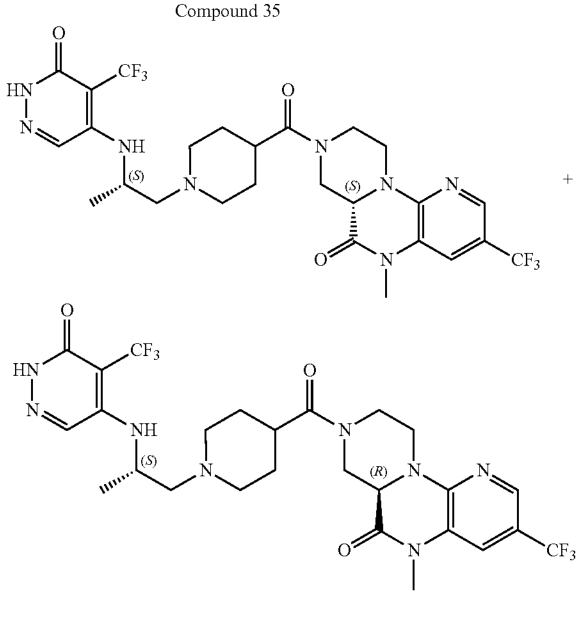

Step 1: Following an analogous procedure described in step 1 of Example 1, INT B37 (588 mg, 1.52 mmol, 1.0 eq.) and HCl/1,4-dioxane (5 mL, 1N) were used as reactants to synthesize Compound 35-1 (400 mg, yield 81%). LCMS: m/z=287 $[M+1]^+$.

Step 2: Following an analogous procedure described in step 2 of Example 1, the Compound 35-1 (0.70 g, 2.17 mmol, 2.26 eq.) and INT A21 (452 mg, 0.96 mmol, 1.0 eq.) were used as reactants to synthesize Compound 35-2 (0.35 g, yield 49%). LCMS: m/z=737 $[M+1]^+$.

Step 3: TfOH (0.5 mL) was added dropwise at room temperature to a solution of the Compound 35-2 (0.35 g, 0.48 mmol, 1.0 eq.) dissolved in TFA (5 mL). After stirring for 2 hrs at room temperature, the pH of reaction mixture was adjusted to 7-8 with sodium bicarbonate aqueous solution. The resulting mixture was extracted with EA (100 mL×2). The combined organic layers were dried over anhydrous $Na_2SO_4$ and then filtered. The filtrate was concentrated under reduced pressure to obtain a residue which was purified with (C18 column, eluted with $H_2O/CH_3CN$) to afford Compound 35 (0.28 g, yield 960). LCMS: m/z=617 [M+1]).

$^1$H NMR (400 MHz, $CD_3OD$) δ 8.14 (s, 1H), 7.93 (s, 1H), 7.43 (s, 1H), 5.07 (d, J=12.81 Hz, 0.5H), 4.70-4.59 (m, 1.51H), 4.49 (d, J=11.61 Hz, 0.5H), 4.21-3.96 (m, 2.5H), 3.37 (d, J=5.2 Hz, 3H), 3.30-3.21 (m, 1H), 3.01-2.67 (m, 5H), 2.52 (d, J=6.4 Hz, 2H), 2.37-2.13 (m, 2H), 1.81-1.63 (m, 4H), 1.26 (d, J=6.4 Hz, 3H).

The chiral separation of the Compound 35 (0.28 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}:V_{Mobile\ Phase\ B}$=60:40; Flow Rate: 20 mL/min; Detector Wavelength: 220 nm. This resulted in the first eluting stereoisomer (Compound 35A, 119.9 mg, Retention time: 4.82 min) and the second eluting stereoisomer (Compound 35B3, 120.2 mg, Retention time: 6.61 min).

Example 36

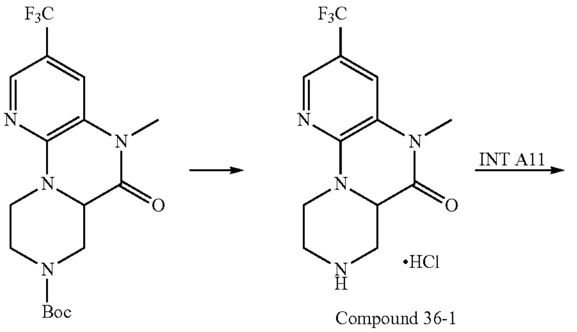

INT B37

Compound 36-1

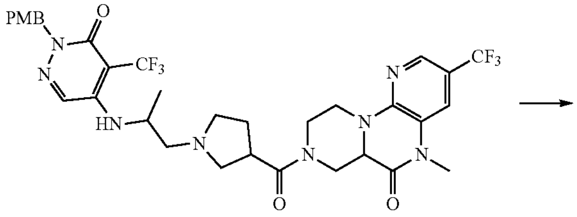

Compound 36-2

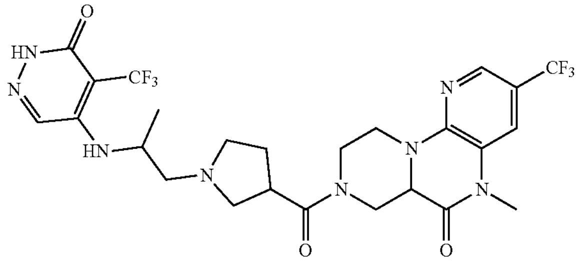

Compound 36

Step 1: Following an analogous procedure described in step 1 of Example 1, INT B37 (1.02 g, 2.64 mmol, 1.0 eq.) and HCl/1,4-dioxane (5 mL, 1N) were used as reactants to synthesize Compound 36-1 (crude, 1.22 g). LCMS: m/z=287 $[M+1]^+$.

Step 2: Following an analogous procedure described in step 2 of Example 1, the crude Compound 36-1 (1.22 g, crude) and INT A11 (0.97 g, 2.13 mmol, 1.0 eq.) were used as reactants to synthesize Compound 36-2 (883 mg, yield 57%). LCMS: m/z=723 $[M+1]^+$.

Step 3: Following an analogous procedure described in step 3 of Example 35, the Compound 36-2 (883 mg, 1.22 mmol, 1.0 eq.), TFA (5 mL) and TfOH (0.5 mL) were used as reactants to synthesize Compound 36 (607 mg, yield 82%). LCMS: m/z=603 $[M+1]^+$.

$^1$H NMR (400 MHz, $CD_3OD$) δ 8.15 (s, 1H), 7.93 (s, 1H), 7.43 (s, 1H), 5.07 (d, J=14.0 Hz, 0.5H), 4.67-4.61 (m, 1.5H), 4.52-4.45 (m, 0.5H), 4.19-3.99 (m, 2.5H), 3.37 (s, 3H), 3.30-3.21 (m, 1H), 3.01-2.93 (m, 1H), 2.92-2.73 (m, 5H), 2.71-2.60 (m, 3H), 2.17-1.98 (m, 2H), 1.28 (d, J=6.0 Hz, 3H).

Example 37

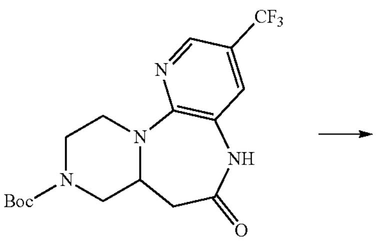

INT B1

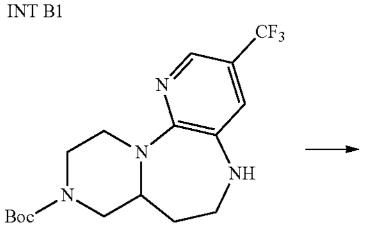

Compound 37-1

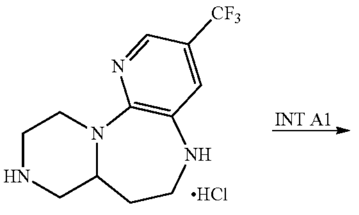

Compound 37-2

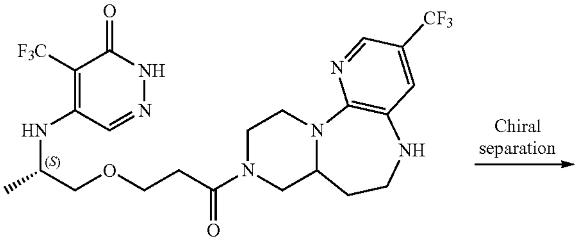

Compound 37

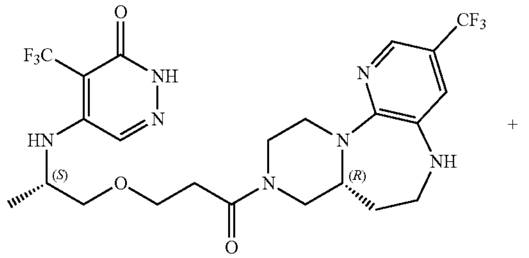

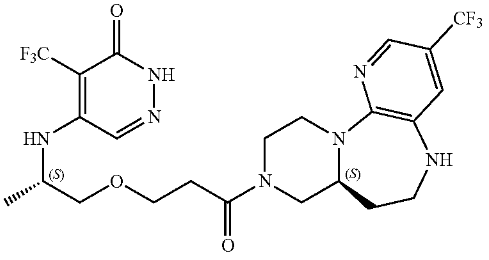

Step 1: $BH_3$-THF (85 mL) was added dropwise at room temperature to a solution of INT B1 (3.26 g, 8.44 mmol, 1.0 eq.) dissolved in THF (150 mL). The reaction mixture was stirred overnight at room temperature, quenched with MeOH, and then extracted with EA (50 mL×3). The organic layers were combined, dried over anhydrous $Na_2SO_4$, filtrated and concentrated under reduced pressure to afford Compound 37-1 (3.10 g, yield 99%). LCMS: m/z=373 $[M+1]^+$.

Step 2: Following an analogous procedure described in step 1 of Example 1, the Compound 37-1 (231 mg, 0.62 mmol, 1.0 eq.) and HCl/1,4-dioxane (6 mL, 1N) were used as reactants to synthesize Compound 37-2 (168 mg, 87%). LCMS: m/z=273 $[M+1]^+$.

Step 3: Following an analogous procedure described in step 2 of Example 1, the Compound 37-2 (168 mg, 0.54 mmol, 1.0 eq.) and INT A1 (179 mg, 0.58 mmol, 1.07 eq.) were used as reactants to synthesize Compound 37 (265 mg, yield 87%). LCMS: m/z=564 $[M+1]^+$.

$^1$H NMR (400 MHz, MeOH-$d_4$) δ 7.94 (d, J=6.4 Hz, 1H), 7.79 (d, J=6.4 Hz, 1H), 6.99 (s, 1H), 4.18-4.09 (m, 1H), 4.05-3.87 (m, 1H), 3.86-3.74 (m, 4H), 3.72-3.45 (m, 7H), 3.29-3.21 (m, 1H), 2.69-2.61 (m, 2H), 1.99-1.87 (m 1H), 1.82-1.74 (m, 1H), 1.24 (t, J=6.4 Hz, 3H).

The chiral separation of the Compound 37 (265 mg) was performed by Chiral-Prep-HPLC with the following conditions: Equipment: Prep-HPLC-Gilson; Column: CHIRALPAK IE 2 cm×25 cm, 5 um; Mobile Phase A: (Hex:DCM=3:1)(0.5% 2M $NH_3$-MeOH), Mobile Phase B: MeOH; $V_{Mobile\ Phase\ A}$:$V_{Mobile\ Phase\ B}$=80:20; Flow Rate: 20 mL/min; Detector Wavelength: 220 nm. This resulted in the first eluting stereoisomer (Compound 37A, 63 mg, Retention time: 2.46 min) and the second eluting stereoisomer (Compound 37B, 58 mg, Retention time: 3.03 min).

Example 38

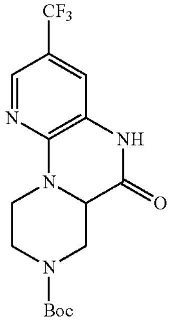

INT B2

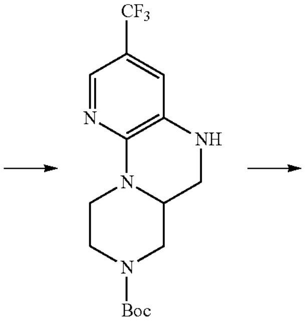

Compound 38-1

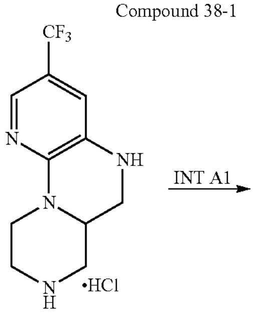

Compound 38-2

-continued

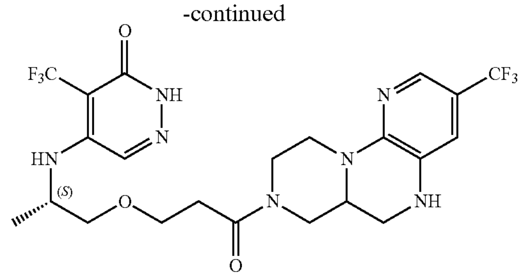

Compound 38

Step 1: Following an analogous procedure described in step 1 of Example 37, INT B2 (0.51 g, 1.37 mmol, 1.0 eq.) and $BH_3$-THF (8 mL) were used as reactants to synthesize Compound 38-1 (crude, 490 mg). LCMS: m/z=359 $[M+1]^+$.

Step 2: Following an analogous procedure described in step 1 of Example 1, the Compound 38-1 (225 mg, crude) and HCl/1,4-dioxane (5 mL, 1N) were used as reactants to synthesize Compound 38-2 (crude, 162 mg). LCMS: m/z=259 $[M+1]^+$.

Step 3: Following an analogous procedure described in step 2 of Example 1, the crude Compound 38-2 (162 mg, crude) and INT A1 (180 mg, 0.58 mmol, 1.0 eq.) were used as reactants to synthesize Compound 38 (113 mg, yield 35%). LCMS: m/z=550 $[M+1]^+$.

$^1$H NMR (400 MHz, DMSO-$d_6$) δ 12.47 (s, 1H), 7.92 (s, 1H), 7.70 (s, 1H), 6.79 (s, 1H), 6.29 (brs, 1H), 6.24 (s, 1H), 4.56-4.39 (m, 2H), 4.21-4.10 (m, 1H), 3.99 (d, J=12.0 Hz, 1H), 3.74-3.61 (m, 2H), 3.51-3.45 (m, 2H), 3.43-3.38 (m, 1H), 3.25-3.00 (m, 2H), 2.99-2.73 (m, 2H), 2.71-2.56 (m, 3H), 1.15 (d, J=5.6 Hz, 3H).

Example 39

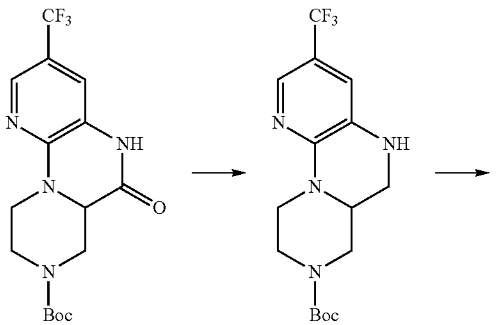

INT B2

Compound 39-1

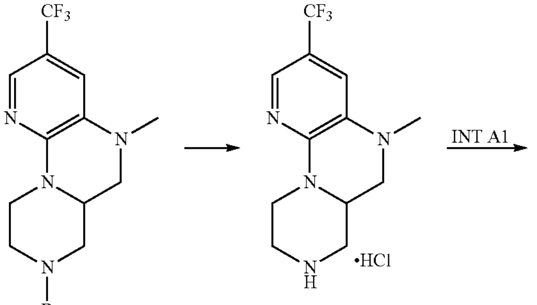

Compound 39-2

Compound 39-3

-continued

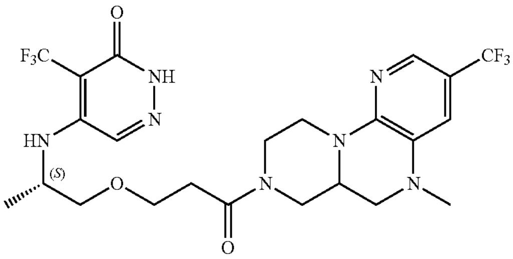

Compound 39

Step 1: Following an analogous procedure described in step 1 of Example 37, INT B2 (0.51 g, 1.37 mmol, 1.0 eq.) and $BH_3$-THF (8 mL) were used as reactants to synthesize Compound 39-1 (crude, 490 mg). LCMS: m/z=359 $[M+1]^+$.

Step 2: A mixture of the Compound 39-1 (crude, 0.25 g), $CH_3I$ (0.52 g, 3.66 mmol, 5.25 eq.), $K_2CO_3$ (0.26 g, 1.88 mmol, 2.70 eq.) and $CH_3CN$ (5 mL) was stirred for 20 hrs at 65° C., poured into water (20 mL), and then extracted with EA (50 mL×3). The organic layers were combined and concentrated under reduced pressure to obtain a residue which was purified with Prep-HPLC ($C_{18}$ column, eluted with $H_2O/CH_3CN$) to afford Compound 39-2 (0.22 g, yield 84%). LCMS: m/z=373 $[M+1]^+$.

Step 3: Following an analogous procedure described in step 1 of Example 1, the Compound 39-2 (0.22 g, 0.59 mmol, 1.0 eq.) and HCl/1,4-dioxane (10 mL, 1N) were used as reactants to synthesize Compound 39-3 (crude, 0.16 g). LCMS: m/z=273 $[M+1]^+$.

Step 4: Following an analogous procedure described in step 2 of Example 1, the Compound 39-3 (0.16 g, crude) and INT A1 (161 mg, 0.52 mmol, 1.0 eq.) were used as reactants to synthesize to afford Compound 39 (116.5 mg, yield 39%). LCMS: m/z=564 $[M+1]^+$.

$^1$H NMR (400 MHz, MeOH-$d_4$) δ 7.93 (s, 0.5H), 7.91 (s, 0.5H), 7.72 (s, 1H), 6.75 (s, 1H), 4.65 (d, J=11.2 Hz, 1H), 4.58-4.54 (m, 1H), 4.19-4.02 (m, 2H), 3.86-3.72 (m, 2H), 3.65-3.58 (m, 1H), 3.56-3.41 (m, 2H), 3.37 (d, J=11.6 Hz, 1H), 3.16-3.05 (m, 1H), 3.03-2.93 (m, 1H), 2.87 (s, 3H), 2.85-2.80 (m, 1H), 2.74-2.65 (m, 2H), 2.62-2.52 (m, 1H), 1.25 (d, J=6.4 Hz, 3H).

Example 40

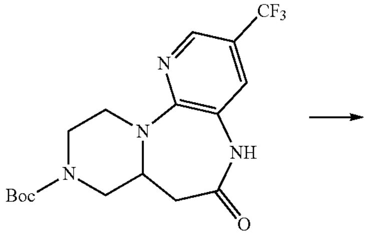

INT B1

-continued

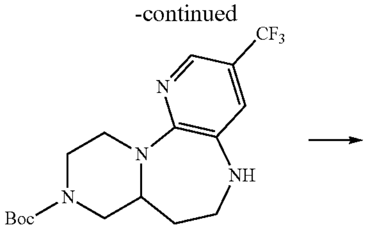

Compound 40-1

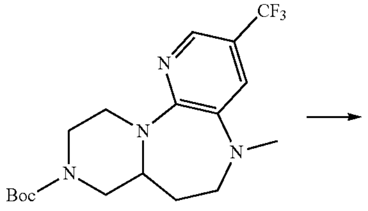

Compound 40-2

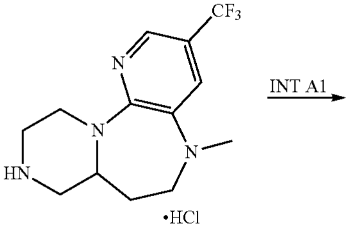

Compound 40-3

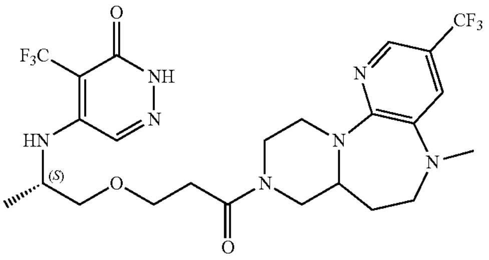

Compound 40

Step 1: $BH_3$-THF (85 mL) was added dropwise at room temperature to a solution of INT B1 (3.26 g, 8.44 mmol, 1.0 eq.) dissolved in THF (150 mL). The reaction mixture was stirred overnight at room temperature, quenched with MeOH, and extracted with EA (50 mL×3). The organic layers were combined, dried over anhydrous $Na_2SO_4$, and then concentrated under reduced pressure to afford Compound 40-1 (3.10 g, yield 99%). LCMS: m/z=373 $[M+1]^+$.

Step 2: A solution of the Compound 40-1 (261 mg, 0.70 mmol, 1.0 eq.) dissolved in THF (10 mL) was purged and maintained with an inert atmosphere of nitrogen, cooled to 0~10° C., and then NaH (82 mg, 3.40 mmol, 4.87 eq.) (60% in oil) was added slowly. The resulting mixture was stirred for 0.5 h and $CH_3I$ (200 mg, 1.44 mmol, 2.01 eq.) was added. The reaction mixture was stirred for 3 hrs at room temperature, quenched with water (20 mL), and extracted with DCM (50 mL×2). The organic layers were combined, dried over anhydrous $Na_2SO_4$, and then filtered. The filtrate was concentrated under reduced pressure to obtain a residue which was purified with silica gel column chromatography (eluted with Hex/EA) to afford Compound 40-2 (121 mg, yield 46%). LCMS: m/z=387 $[M+1]^+$.

Step 3: Following an analogous procedure described in step 1 of Example 1, the Compound 40-2 (100 mg, 0.26 mmol, 1.0 eq.) and HCl/1,4-dioxane (5 mL, 1N) were used as reactants to synthesize Compound 40-3 (70 mg, yield 83%). LCMS: m/z=287 $[M+1]^+$.

Step 4: Following an analogous procedure described in step 2 of Example 1, the Compound 40-3 (70 mg, 0.22 mmol, 1.0 eq.) and INT A1 (90 mg, 0.29 mmol, 1.32 eq.) were used as reactants to synthesize Compound 40 (53 mg, yield 41%). LCMS: m/z=578 $[M+1]^+$.

$^1H$ NMR (400 MHz, DMSO-$d_6$) δ 12.47 (s, 1H), 7.95 (s, 0.5H), 7.94 (s, 0.5H), 7.92 (s, 1H), 7.01 (s, 0.5H), 6.98 (s, 0.5H), 6.28 (s, 1H), 4.19-4.10 (m, 1H), 3.99-3.86 (m, 1H), 3.80-3.61 (m, 5H), 3.48 (d, J=5.2 Hz, 2H), 3.45-3.34 (m, 1H), 3.32-3.21 (m, 2H), 3.21-3.07 (m, 2H), 2.78 (s, 3H), 2.60-2.54 (m, 2H), 1.97-1.84 (m, 1H), 1.70-1.59 (m, 1H), 1.15 (d, J=6.4 Hz, 3H).

Example 41

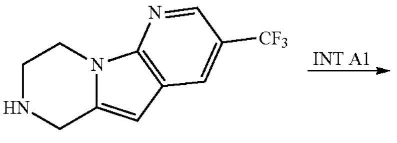

INT B23

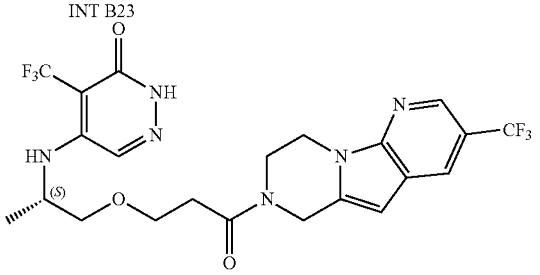

Compound 41

Step 1: Following an analogous procedure described in step 2 of example 1, INT B23 (180 mg, 0.75 mmol, 1.0 eq.) and INT A1 (390 mg, 1.26 mmol, 1.68 eq.) were used as reactants to synthesize Compound 41 (314.8 mg, yield 79%). LCMS: m/z=533 $[M+1]^+$.

$^1H$ NMR (400 MHz, MeOH-$d_4$) δ 8.47 (s, 1H), 8.22 (s, 1H), 7.87 (d, J=20.4 Hz, 1H), 6.50 (s, 1H), 5.06 (s, 1H), 5.01 (d, J=4.8 Hz, 1H), 4.36 (t, J=5.2 Hz, 1H), 4.29 (t, J=5.2 Hz, 1H), 4.17-3.99 (m, 3H), 3.88-3.74 (m, 2H), 3.65-3.54 (m, 1H), 3.53-3.43 (m, 1H), 2.83-2.74 (m, 2H), 1.18 (dd, 3H).

Example 42

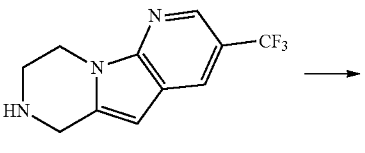

INT B23

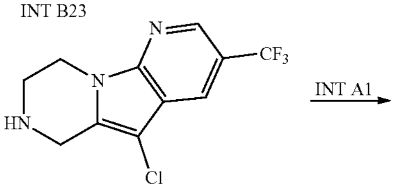

Compound 42-1

-continued

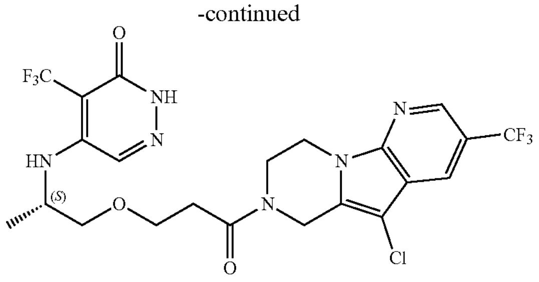

Compound 42

Step 1: INT B23 (290 mg, 1.20 mmol, 1.0 eq.) and NCS (180 mg, 1.35 mmol, 1.12 eq.) were dispersed in DCM (20 mL) at −10° C. The reaction mixture stirred for 5 min at −10° C., diluted with brine and extracted with EA (20 mL×3). The organic layers were combined, dried over anhydrous $Na_2SO_4$ and then filtered. The filtrate was concentrated under reduced pressure to obtain a residue which was purified with Prep-HPLC (C18 column, eluted with $H_2O/CH_3CN$) to afford Compound 42-1 (220 mg, yield 66%). LCMS: m/z=276 $[M+1]^+$.

Step 2: Following an analogous procedure described in step 2 of example 1, the Compound 42-1 (160 mg, 0.58 mmol, 1.79 eq.) and INT A1 (100 mg, 0.32 mmol, 1.0 eq.) were used as reactants to synthesize Compound 42 (40.6 mg, yield 22%). LCMS: m/z=567 $[M+1]^+$.

$^1$H NMR (400 MHz, MeOH-$d_4$) δ 8.56 (s, 1H), 8.21 (s, 1H), 7.87 (d, J=24.2, 1H), 5.04-4.95 (m, 2H), 4.39-4.27 (m, 2H), 4.17-4.00 (m, 3H), 3.90-3.77 (m, 2H), 3.65-3.55 (m, 1H), 3.54-3.46 (m, 1H), 2.82 (t, J=5.7, 2H), 1.19 (dd, 3H).

Example 43

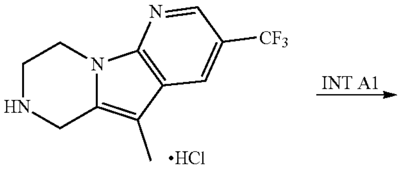

INT B25

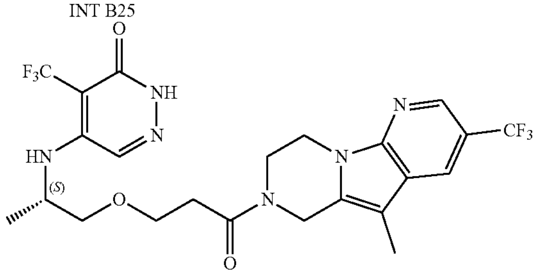

Compound 43

Step 1: Following an analogous procedure described in step 2 of example 1, INT B25 (97 mg, 0.33 mmol, 0.94 eq.) and INT A1 (109 mg, 0.35 mmol, 1.0 eq.) were used as reactants to synthesize Compound 43 (100.5 mg, yield 52%). LCMS: m/z=547 $[M+1]^+$.

$^1$H NMR (400 MHz, MeOH-$d_4$) δ 8.43 (s, 1H), 8.18 (s, 1H), 7.87 (d, J=15.6 Hz, 1H), 5.00-4.90 (m, 2H), 4.36-4.21 (m, 2H), 4.16-4.00 (m, 3H), 3.90-3.75 (m, 2H), 3.66-3.55 (m, 1H), 3.54-3.45 (m, 1H), 2.81 (t, J=5.6 Hz, 2H), 2.28 (d, J=8.0 Hz, 3H), 1.21 (dd, 3H).

Example 44

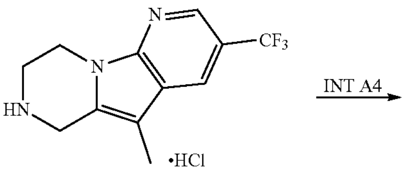

INT B25

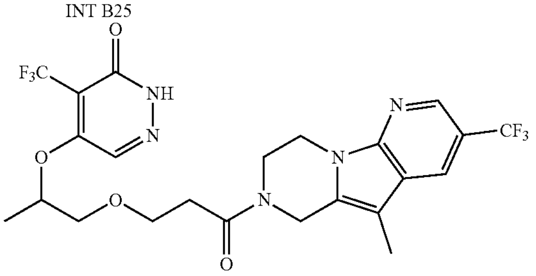

Compound 44

Step 1: INT B25 (232 mg, 0.80 mmol, 1.23 eq.), INT A4 (201 mg, 0.65 mmol, 1.0 eq.) and TEA (414 mg, 4.09 mmol, 6.31 eq.) were dissolved in DMF (2 mL) to form a solution, and then PyBOP (442 mg, 0.85 mmol, 1.31 eq.) was added to the solution. The reaction mixture was stirred for 2 hrs at room temperature and purified with Prep-HPLC (C18 column, eluted with $H_2O/CH_3CN$) to afford Compound 44 (304 mg, yield 85%). LCMS: m/z=548 $[M+1]^+$.

$^1$H NMR (400 MHz, MeOH-$d_4$) δ8.43 (s, 1H), 8.18 (s, 1H), 8.14 (d, J=20.0 Hz, 1H), 5.12-4.98 (m, 1H), 4.97-4.95 (m, 1H), 4.91 (d, J=10.4 Hz, 1H), 4.34-4.20 (m, 2H), 4.12-3.96 (m, 2H), 3.89-3.82 (m, 1H), 3.79-3.74 (m, 1H), 3.70-3.54 (m, 2H), 2.77-2.74 (m, 2H), 2.27 (d, J=6.0 Hz, 3H), 1.32-1.27 (m, 3H).

Example 45

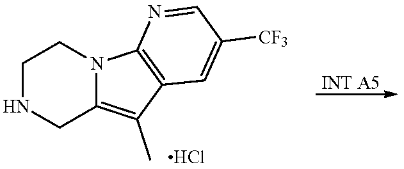

INT B25

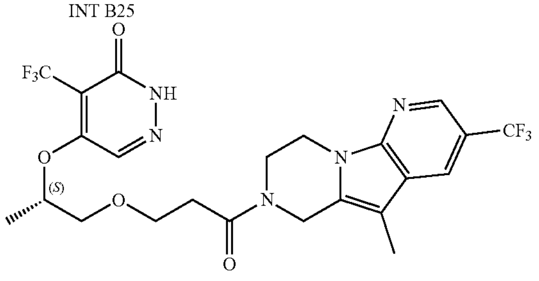

Compound 45

Step 1: INT A5 (99 mg, 0.32 mmol, 1.0 eq.), INT B25 (104 mg, 0.36 mmol, 1.13 eq.), and TEA (194 mg, 1.92 mmol, 6.00 eq.) were dissolved in THF (1 mL) to form a solution, and then $T_3P$ (312 mg, 0.98 mmol, 3.06 eq.)(50% in EA) was added to the solution. The reaction mixture was stirred for 1 h at room temperature. The resulting solution was diluted with water (2 mL), extracted with EA (2×3 mL) and the organic layer was combined, washed with brine (3 mL) and concentrated under vacuum. The residue was purified with Prep-HPLC (C18 column, eluted with $H_2O/CH_3CN$) to afford Compound 45 (149.5 mg, 85% yield). LCMS: m/z=548 $[M+1]^+$.

$^1H$ NMR (400 MHz, $CD_3OD$) δ 8.43 (s, 1H), 8.18 (s, 1H), 8.14 (d, J=19.8 Hz, 1H), 5.12-4.98 (m, 1H), 4.89-4.96 (m, 2H), 4.23-4.30 (m, 2H), 4.11-3.98 (m, 2H), 3.90-3.81 (m, 1H), 3.77 (m, 1H), 3.72-3.54 (m, 2H), 2.76 (t, 2H), 2.27 (d, J=6.2 Hz, 3H), 1.27-1.32 (m, 3H).

The following compound was synthesized using the above procedure or modification procedure using the corresponding intermediate.

-continued

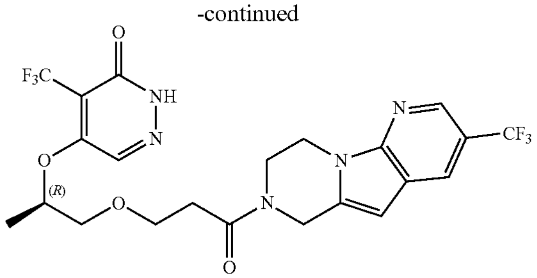

Compound 47B

Step 1: INT B23 (431 mg, 1.79 mmol, 1.20 eq.), INT A4 (463 mg, 1.49 mmol, 1.0 eq.) and TEA (317 mg, 3.13 mmol, 3.17 eq.) were dissolved in DMF (5 mL), and then PyBOP (713 mg, 1.37 mmol, 1.38 eq.) was added. The reaction mixture was stirred for 3 hrs at room temperature and

| Example | Compound | Structure | INT | $^1H$ NMR and MS: $(M + H)^+$ |
|---|---|---|---|---|
| 46 | 46 | 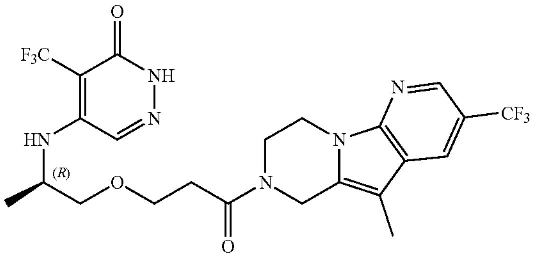 Compound 46 | A6 & B25 | $^1H$ NMR (400 MHz, DMSO-$d_6$) δ 12.33 (s, 1H), 7.89 (s, 1H), 7.65 (s, 1H), 7.44 (s, 1H), 4.84 (d, J = 10.4 Hz, 2H), 4.48 (d, J = 10.8 Hz, 1H), 4.28 (d, J = 12.0 Hz, 2H), 4.02 (t, J = 10.8 Hz, 1H), 3.87 (d, J = 7.6 Hz, 2H), 3.81-3.65 (m, 4H), 3.25 (d, J = 10.8 Hz, 3H), 2.76-2.56 (m, 4H), 1.99 (s, 1H), 1.31-1.14 (m, 1H). MS: $(M + H)^+$ 556. |

Example 47

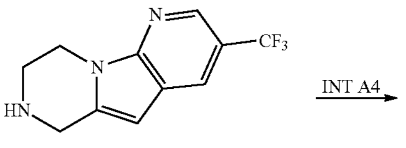

INT B23

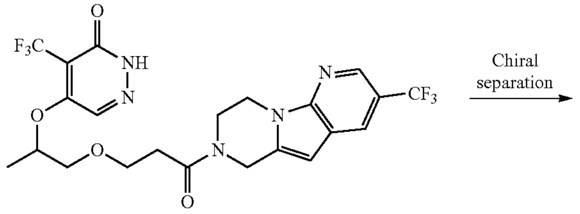

Compound 47

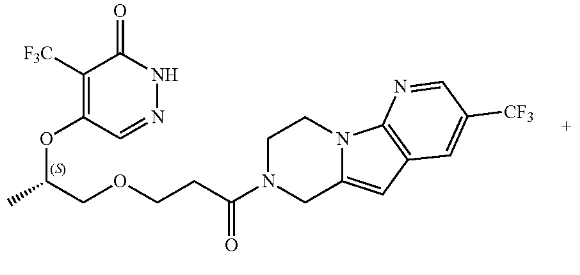

Compound 47A purified with Prep-HPLC (C18 column, eluted with $H_2O/CH_3CN$) to afford Compound 47 (0.69 g, yield 86%). LCMS: m/z=534 $[M+1]^+$.

$^1H$ NMR (400 MHz, MeOH-$d_4$) δ 8.46 (s, 1H), 8.20 (s, 1H), 8.14 (d, J=20.0 Hz, 1H), 6.47 (d, J=4.0 Hz, 1H), 5.07-5.01 (m, 3H), 4.37-4.26 (m, 2H), 4.14-3.99 (m, 2H), 3.94-3.72 (m, 2H), 3.70-3.53 (m, 2H), 2.76-2.71 (m, 2H), 1.32-1.28 (m, 3H).

The chiral separation of the Compound 47 (0.69 g) was performed by Chiral-Prep-HPLC with the following conditions: Equipment: Prep-HPLC-Gilson; Column: CHIRALPAK-IG column 2 cm×25 cm, 5 um; Mobile Phase A: (Hex:DCM=3:1), Mobile Phase B: EtOH, $V_{Mobile\ Phase\ A}:V_{Mobile\ Phase\ B}$=50:50; Flow Rate: 20 mL/min; Detector Wavelength: 220 nm. This resulted in the first eluting stereoisomer (Compound 47A, 323.8 mg, Retention time: 6.16 min), and the second eluting stereoisomer (Compound 47B, 105.1 mg, Retention time: 7.26 min).

Example 48

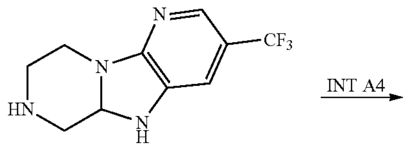

INT B27

-continued

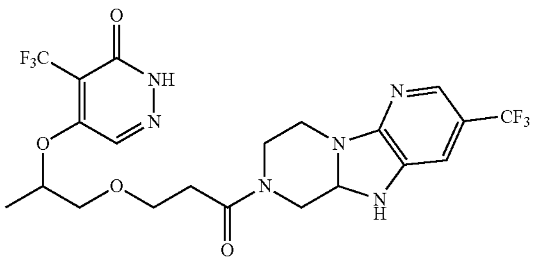

Compound 48

Step 1: Following an analogous procedure described in step 2 of example 1, INT B27 (290 mg, 1.19 mmol, 1.84 eq.) and INT A4 (200 mg, 0.64 mmol, 1.0 eq.) were used as reactants to synthesize Compound 48 (215 mg, yield 62%). LCMS: m/z=537 $[M+1]^+$.

$^1H$ NMR (400 MHz, MeOH-$d_4$) δ8.21 (s, 1H), 7.45 (s, 1H), 6.45 (d, J=5.6 Hz, 1H), 5.27-5.04 (m, 2H), 4.56 (dd, 1H), 4.09 (d, J=10.8 Hz, 1H), 3.99 (t, J=12.4 Hz, 1H), 3.85-3.76 (m, 1H), 3.75-3.64 (m, 2H), 3.63-3.54 (m, 1H), 3.21-3.00 (m, 2H), 2.79-2.52 (m, 3H), 1.35 (d, J=6.4 Hz, 3H).

Example 49

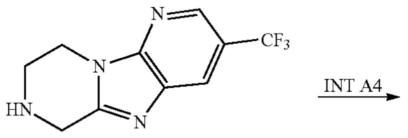

INT B26

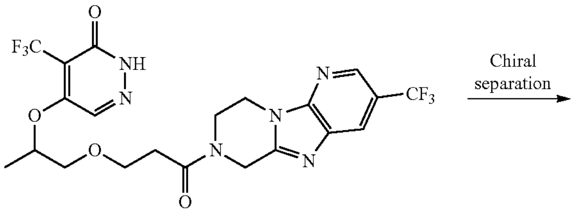

Compound 49

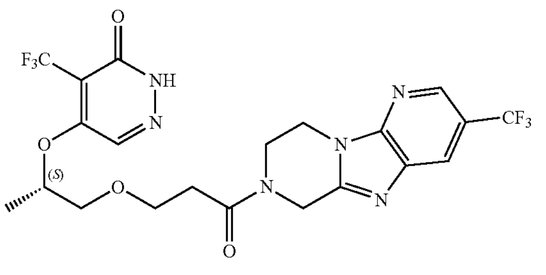

Compound 49A

+

-continued

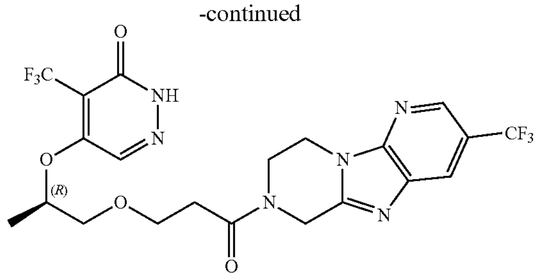

Compound 49B

Step 1: Following an analogous procedure described in step 2 of example 1, INT B26 (18 mg, 0.07 mmol, 1.0 eq.) and INT A4 (28 mg, 0.09 mmol, 1.21 eq.) were used as reactants to synthesize Compound 49 (36 mg, yield 90%). LCMS: m/z=535 $[M+1]^+$.

$^1H$ NMR (400 MHz, MeOH-$d_4$) δ8.66 (s, 1H), 8.27 (s, 1H), 8.15 (d, J=19.2 Hz, 1H), 5.15-4.96 (m, 3H), 4.41-4.28 (m, 2H), 4.19-4.10 (m, 2H), 3.91-3.82 (m, 1H), 3.80-3.73 (m, 1H), 3.71-3.52 (m, 2H), 2.83-2.70 (m, 2H), 1.36-1.24 (m, 3H).

The chiral separation of the Compound 49 (36 mg) was performed by Chiral-Prep-HPLC with the following conditions: Equipment: Prep-HPLC-Gilson; Column: CHIRALPAK-IG column 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 49A, 27.0 mg, Retention time: 4.99 min), and the second eluting stereoisomer (Compound 49B, 8.6 mg, Retention time: 8.94 min).

Example 50

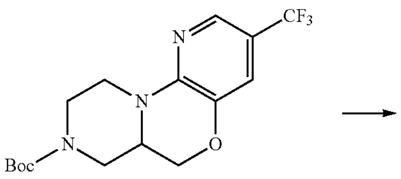

INT B7

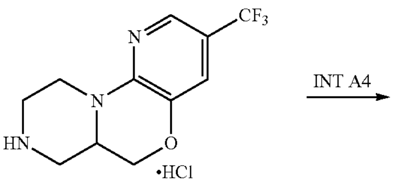

Compound 50-1

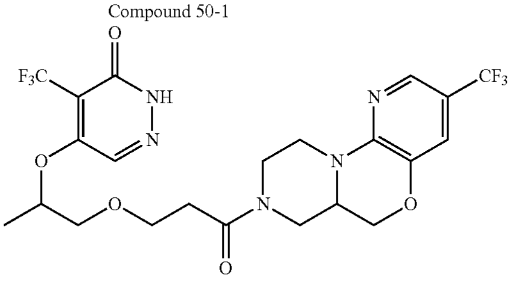

Compound 50

Step 1: HCl/1,4-dioxane (80 mL, 1N) was added to a solution of INT B7 (8.08 g, 22.49 mmol, 1.0 eq.) dissolved in 1,4-dioxane (10 mL). The reaction mixture was stirred for 1 h at room temperature, and then concentrated under reduced pressure to afford Compound 50-1 (crude, 8.92 g). LCMS: m/z=260 $[M+1]^+$.

Step 2: PyBOP (2.77 g, 5.32 mmol, 1.66 eq.) was added to a solution of the crude Compound 50-1 (1.12 g, crude), INT A4 (993 mg, 3.20 mmol, 1.0 eq.), and TEA (2.65 g, 26.19 mmol, 8.18 eq.) dissolved in DMF (15 mL). The reaction mixture was stirred for 2 hrs at room temperature, and then concentrated under reduced pressure to obtain a residue. The residue was purified by Prep-HPLC (C18 column, eluted with $H_2O/CH_3CN$) to afford Compound 50 (685 mg, yield 38%). LCMS: m/z=552 $[M+1]^+$.

$^1$H NMR (400 MHz, MeOH-$d_4$) δ8.20 (s, 1H), 8.00 (s, 1H), 7.16 (s, 1H), 5.16-5.06 (m, 1H), 4.67-4.51 (m, 2H), 4.39-4.34 (m, 1H), 4.11-3.94 (m, 2H), 3.86-3.78 (m, 1H), 3.77-3.64 (m, 2H), 3.63-3.55 (m, 1H), 3.54-3.37 (m, 1H), 3.28-3.21 (m, 0.5H), 3.03-2.89 (m, 1H), 2.88-2.77 (m, 1H), 2.75-2.61 (m, 2H), 2.55 (t, J=12 Hz, 0.5H), 1.34 (d, J=6.0, 3H).

Example 51

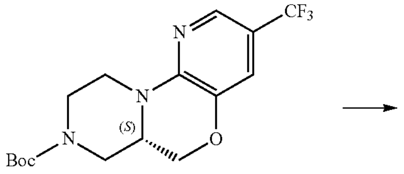

INT B9

-continued

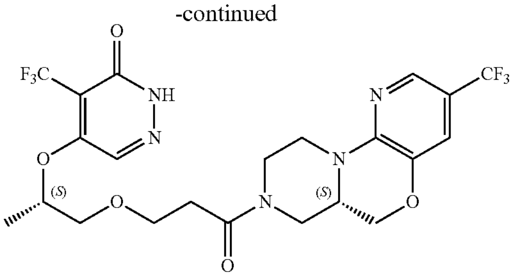

Compound 51

Step 1: HCl/1,4-dioxane (150 mL, 1N) was added to a solution of INT B9 (14.91 g, 41.49 mmol, 1.0 eq.) dissolved in 1,4-dioxane (100 mL). The reaction mixture was stirred for 1 h at room temperature, and then concentrated under reduced pressure to afford Compound 51-1 (crude, 14.96 g). LCMS: m/z=260 $[M+1]^+$.

Step 2: PyBOP (4.40 g, 8.46 mmol, 1.29 eq.) was added to a solution of Compound 51-1 (2.34 g, crude), INT A5 (2.03 g, 6.54 mmol, 1.0 eq.), and TEA (1.976 g, 19.53 mmol, 2.99 eq.) dissolved in DMF (20 mL). The reaction mixture was stirred for 2 hrs at room temperature, and then concentrated under reduced pressure. The residue was purified by Prep-HPLC (C18 column, eluted with $H_2O/CH_3CN$) to afford Compound 51 (2.12 g, yield 59%). LCMS: m/z=552 $[M+1]^+$.

$^1$H NMR (400 MHz, MeOH-$d_4$) δ 8.21 (s, 1H), 7.99 (s, 1H), 7.16 (s, 1H), 5.16-5.05 (m, 1H), 4.67-4.51 (m, 2H), 4.39-4.34 (m, 1H), 4.10-3.96 (m, 2H), 3.85-3.78 (m, 1H), 3.75-3.65 (m, 2H), 3.61-3.56 (m, 1H), 3.54-3.37 (m, 1H), 3.29-3.19 (m, 0.5H), 2.99-2.85 (m, 1H), 2.80-2.77 (m, 1H), 2.70-2.61 (m, 2H), 2.51-2.54 (m, 0.5H), 1.33-1.35 (d, J=6.0, 3H).

The following compound was synthesized using the above procedure or modification procedure using the corresponding intermediate.

| Example | Compound | Structure | INT | $^1$H NMR and MS: $(M + H)^+$ |
|---|---|---|---|---|
| 52 | 52 | 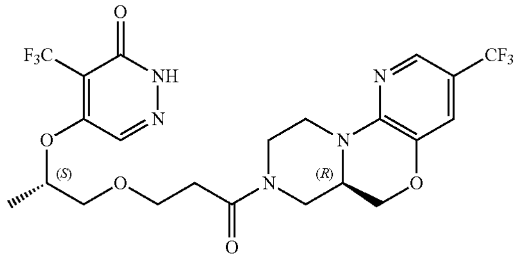 Compound 52 | A5 & B10 | $^1$H NMR (400 MHz, DMSO-$d_6$) δ 12.33 (s, 1H), 7.89 (s, 1H), 7.65 (s, 1H), 7.44 (s, 1H), 4.84 (d, J = 10.4 Hz, 2H), 4.48 (d, J = 10.8 Hz, 1H), 4.28 (d, J = 12.0 Hz, 2H), 4.02 (t, J = 10.8 Hz, 1H), 3.87 (d, J = 7.6 Hz, 2H), 3.81- 3.65 (m, 4H), 3.25 (d, J = 10.8 Hz, 3H), 2.76-2.56 (m, 4H), 1.99 (s, 1H), 1.31-1.14 (m, 1H). MS: $(M + H)^+$ 556. |

-continued

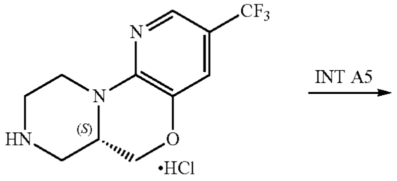

Compound 51-1

Example 53

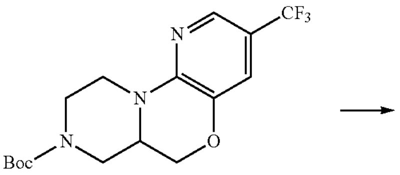

INT B7

-continued

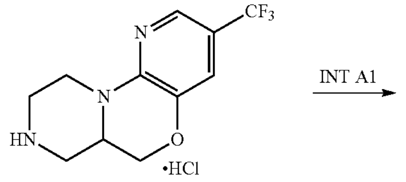

Compound 53-1

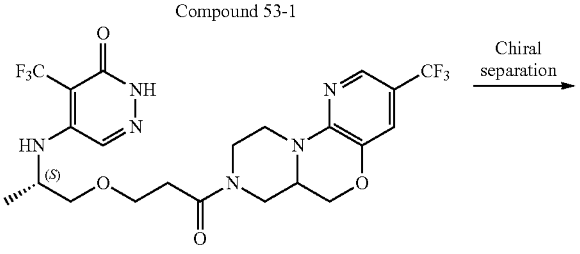

Compound 53

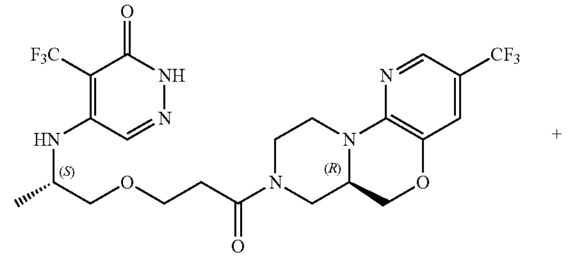

Compound 53A

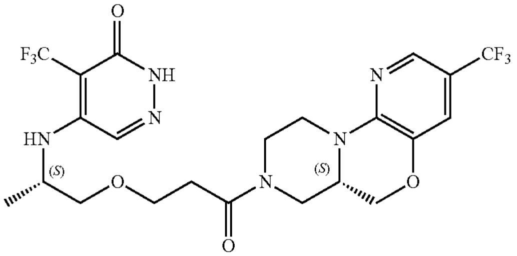

Compound 53B

Step 1: Following an analogous procedure described in step 1 of Example 1, INT B7 (312 mg, 0.87 mmol, 1.0 eq.) and HCl/1,4-dioxane (20 mL, 1N) were used as reactants to synthesize to afford Compound 53-1 (209 mg, yield 81%). LCMS: m/z=260 $[M+1]^+$.

Step 2: Following an analogous procedure described in step 2 of Example 1, the Compound 53-1 (209 mg, 0.71 mmol, 1.0 eq.) and INT A1 (260 mg, 0.84 mmol, 1.18 eq.) were used as reactants to synthesize Compound 53 (277 mg, yield 71%). LCMS: m/z=551 $[M+1]^+$.

$^1$H NMR (400 MHz, MeOH-$d_4$) δ 8.00 (s, 1H), 7.93 (s, 1H), 7.16 (s, 1H), 4.65-4.55 (m, 2H), 4.37 (d, J=10.8 Hz, 1H), 4.21-3.94 (m, 3H), 3.87-3.71 (m, 2H), 3.67-3.56 (m, 1H), 3.57-3.40 (m, 2H), 3.29-3.18 (m, 1H), 3.04-2.79 (m, 2H), 2.71 (s, 2H), 2.62-2.50 (m, 1H), 1.25 (d, J=4.8 Hz, 3H).

The chiral separation of the Compound 53 (277 mg) was performed by Chiral-Prep-HPLC with the following conditions: Equipment: Prep-HPLC-Gilson; Column: CHIRALPAK AD 3 cm×25 cm, 5 um; Mobile Phase A: $CO_2$, Mobile Phase B: MeOH (0.5%2 mM $NH_3$-MeOH); Flow Rate: 20 mL/min; Detector Wavelength: 220 nm. This resulted in the first eluting stereoisomer (Compound 53A, 75 mg, Retention time: 0.59 min) and the second eluting stereoisomer (Compound 53B, 71 mg, Retention time: 1.25 min).

Example 54

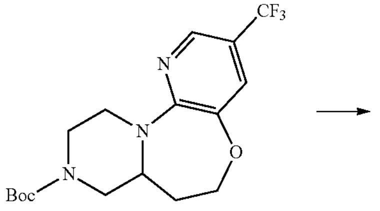

INT B8

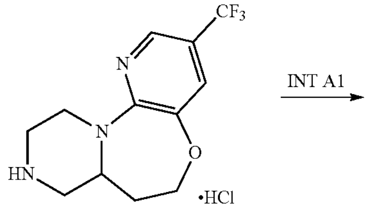

Compound 54-1

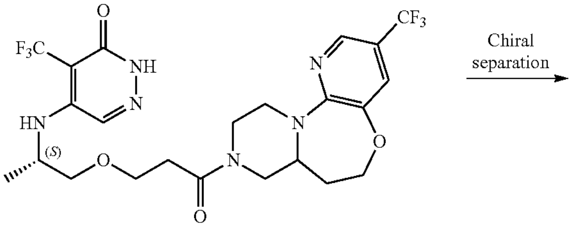

Compound 54

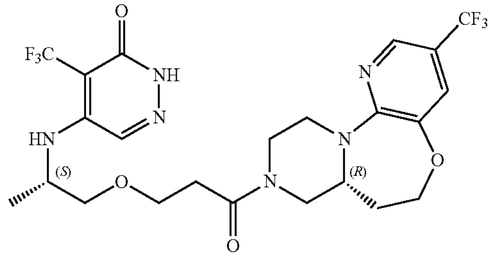

+

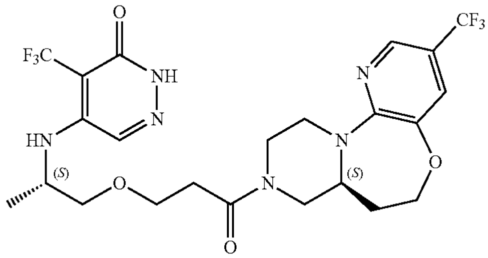

Step 1: HCl/1,4-dioxane (20 mL, 1N) was added to a solution of INT B8 (4.07 g, 10.90 mmol, 1.0 eq.) dissolved in 1,4-dioxane (5 mL). The reaction mixture was stirred for 2 hrs at room temperature, and then concentrated under reduced pressure to afford Compound 54-1 (crude, 4.01 g). LCMS: m/z=274 $[M+1]^+$.

Step 2: PyBOP (2.51 g, 4.82 mmol, 1.41 eq.) was added to a solution of the crude Compound 54-1 (1.30 g, crude), INT A1 (1.06 g, 3.43 mmol, 1.0 eq.) and TEA (2 mL) dissolved in DMF (15 mL). The reaction mixture was stirred for 1 h at room temperature, and then concentrated under reduced pressure to obtain a residue. The residue was purified with P-rep-HPLC(C18 column, eluted with $H_2O$/$CH_3CN$) to afford Compound 54 (1.68 g, yield 86%). LCMS: m/z=565 $[M+1]^+$.

$^1$H NMR (400 MHz, MeOH-$d_4$) δ 8.08 (d, J=7.2 Hz, 1H), 7.95 (d, J=7.6 Hz, 1H), 7.28 (s, 1H), 4.35 (s, 2H), 4.15 (s, 2H), 3.91 (d, J=9.2 Hz, 2H), 3.83 (s, 4H), 3.62 (d, J=10.8 Hz, 2H), 3.52 (d, J=7.6 Hz, 2H), 2.67 (s, 2H), 2.17 (s, 1H), 1.99 (s, 1H), 1.25 (t, 3H).

The chiral separation of the Compound 54 (1.68 g) was performed by Chiral-Prep-HPLC with the following conditions: Equipment: Prep-HPLC-Gilson; Column: CHIRALPAK ID 2 cm×25 cm, 5 um; Mobile Phase A: MTBE (0.2% IPA), Mobile Phase B: MeOH/DCM=1:1, $V_{Mobile\ Phase\ A}$:$V_{Mobile\ Phase\ B}$=50:50; Flow Rate: 20 mL/min; Detector Wavelength: 220 nm. This resulted in the first eluting stereoisomer (Compound 54A, 0.54 g, Retention time: 6.12 min) and the second eluting stereoisomer (Compound 54B, 0.57 g, Retention time: 7.04 min).

Example 55

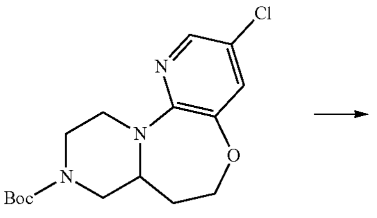

INT B11

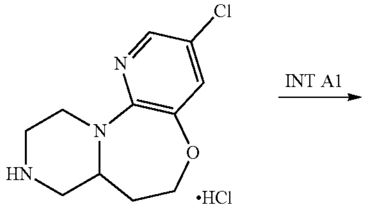

Compound 55-1

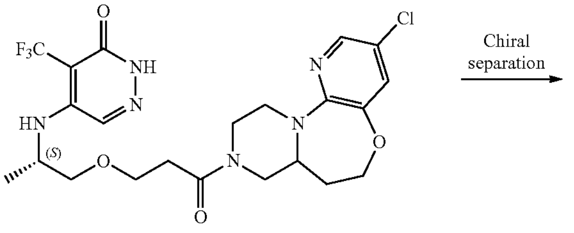

Compound 55

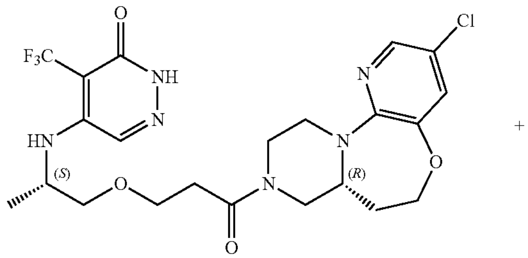

-continued

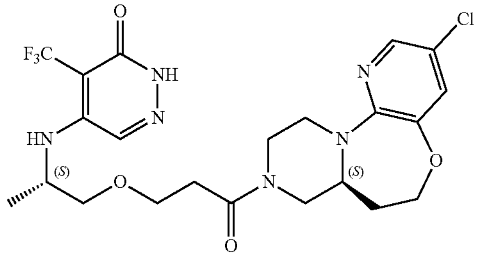

Step 1: Following an analogous procedure described in step 1 of Example 1, INT B11 (270 mg, 0.79 mmol, 1.0 eq.) and HCl/1,4-dioxane (20 mL, 1N) to afford Compound 55-1 (crude, 220 mg). LCMS: m/z=240 $[M+1]^+$.

Step 2: Following an analogous procedure described in step 2 of Example 1, the crude Compound 55-1 (220 mg, crude) and INT A1 (251 mg, 0.81 mmol, 1.03 eq.) were used as reactants to synthesize Compound 55 (242 mg, yield 58%). LCMS: m/z=531 $[M+1]^+$.

$^1$H NMR (400 MHz, MeOH-$d_4$) δ 7.84 (s, 1H), 7.69 (t, J=1.6 Hz, 1H), 7.03 (d, J=2.0 Hz, 1H), 4.28-4.14 (m, 2H), 4.08-4.01 (m, 1H), 3.87-3.77 (m, 1H), 3.76-3.61 (m, 5H), 3.61-3.44 (m, 3H), 3.44-3.33 (m, 3H), 2.58-2.54 (m, 2H), 2.10-1.97 (m, 1H), 1.88-1.77 (m, 1H), 1.15 (d, J=6.4 Hz, 3H).

The chiral separation of the Compound 55 (242 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$:$V_{Mobile\ Phase\ B}$=50:50; Flow Rate: 20 mL/min; Detector Wavelength: 220 nm. This resulted in the first eluting stereoisomer (Compound 55A, 76.3 mg, Retention time: 5.14 min) and the second eluting stereoisomer (Compound 55B, 76.7 mg, Retention time: 6.29 min).

Example 56

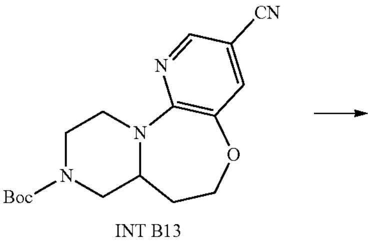

INT B13

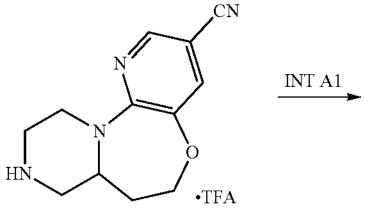

Compound 56-1

-continued

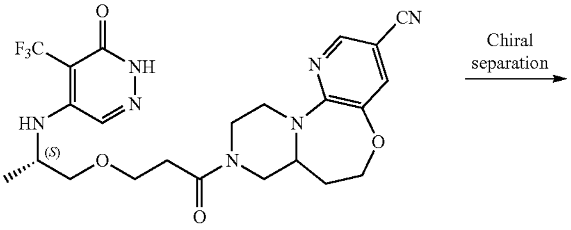

Compound 56

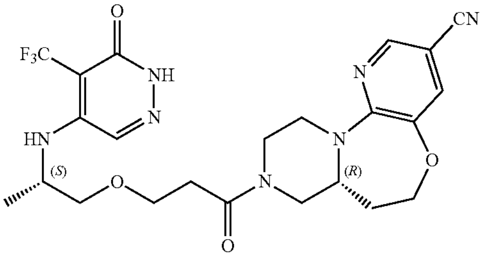

+

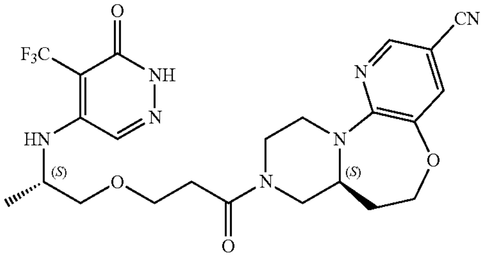

Step 1: Following an analogous procedure described in step 1 of Example 2, INT B13 (150 mg, 0.45 mmol, 1.0 eq.) and TFA (1 mL) were used as reactants to synthesize Compound 56-1 (crude, 155 mg). LCMS: m/z=231 $[M+1]^+$.

Step 2: Following an analogous procedure described in step 2 of Example 1, the crude Compound 56-1 (155 mg, crude) and INT A1 (270 mg, 0.87 mmol, 1.0 eq.) were used as reactants to synthesize Compound 56 (74 mg, yield 32%). LCMS: m/z=522 $[M+1]^+$.

$^1$H NMR (400 MHz, MeOH-$d_4$) 8.12 (d, J=7.2 Hz, 1H), 7.93 (d, J=6.4 Hz, 1H), 7.29 (s, 1H), 4.38-4.30 (m, 1H), 4.30-4.08 (m, 3H), 4.01-3.85 (m, 3H), 3.84-3.67 (m, 4H), 3.66-3.57 (m, 1.5H), 3.55-3.44 (m, 1.5H), 2.71-2.57 (m, 2H), 2.21-2.07 (m, 1H), 2.04-1.92 (m, 1H), 1.25 (d, J=8.8 Hz, 3H).

The chiral separation of the Compound 56 (74 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 56A, 32.8 mg, Retention time: 5.79 min) and the second eluting stereoisomer (Compound 56B, 29.1 mg, Retention time: 8.68 min).

Example 57

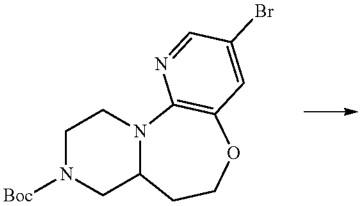

INT B12

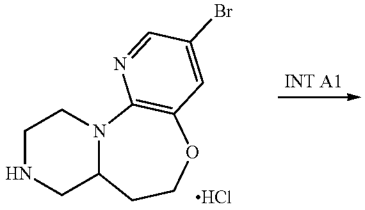

Compound 57-1

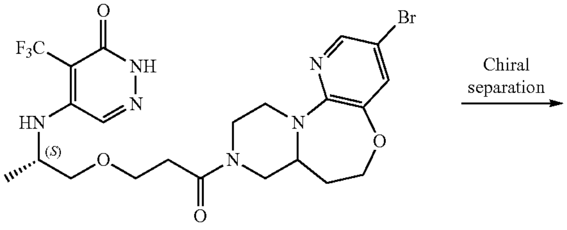

Compound 57

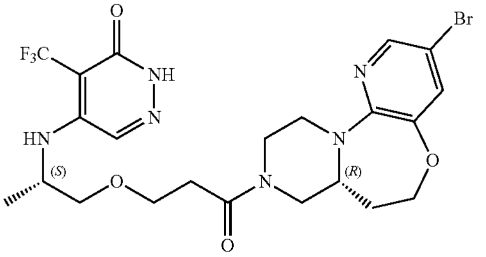

+

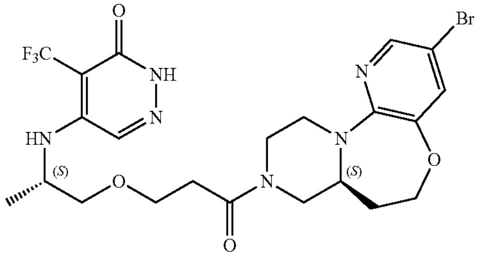

Step 1: Following an analogous procedure described in step 1 of Example 1, INT B12 (7.28 g, 18.95 mmol, 1.0 eq.) and HCl/1,4-dioxane (80 mL, 1N) were used as reactants to synthesize Compound 57-1 (crude, 6.38 g). LCMS: m/z=284, 286 $[M+1]^+$.

Step 2: Following an analogous procedure described in step 2 of Example 1, the crude Compound 57-1 (6.38 g, crude) and INT A1 (5.60 g, 18.11 mmol, 1.0 eq.) were used as reactants to synthesize Compound 57 (7.72 g, yield 74%). LCMS: m/z=575, 577 $[M+1]^+$.

$^1$H NMR (400 MHz, MeOH-$d_4$) δ 7.92 (d, J=6.4 Hz, 1H), 7.85 (d, J=8.8 Hz, 1H), 7.24 (s, 1H), 4.37-4.23 (m, 2H), 4.13 (s, 1H), 3.92 (d, J=13.2 Hz, 1H), 3.86-3.72 (m, 4H), 3.72-

3.57 (m, 3H), 3.57-3.43 (m, 3H), 2.72-2.57 (m, 2H), 2.20-2.05 (m, 1H), 2.00-1.86 (m, 1H), 1.24 (t, J=7.2 Hz, 3H).

The chiral separation of the Compound 57 (7.72 g) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=55:45; Flow Rate: 20 mL/min; Detector Wavelength: 220 nm. This resulted in the first eluting stereoisomer (Compound 57A, 3.3288 g, Retention time: 5.61 min) and the second eluting stereoisomer (Compound 57B, 3.2059 g, Retention time: 7.62 min).

Example 58

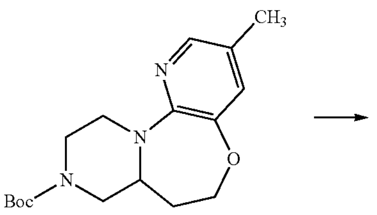

INT B14

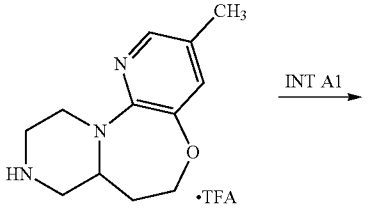

Compound 58-1

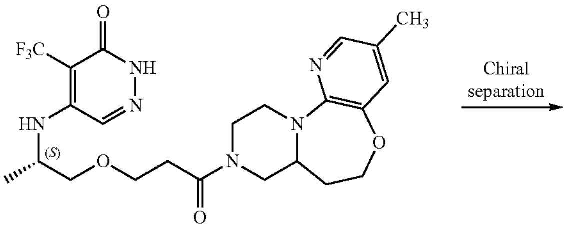

Compound 58

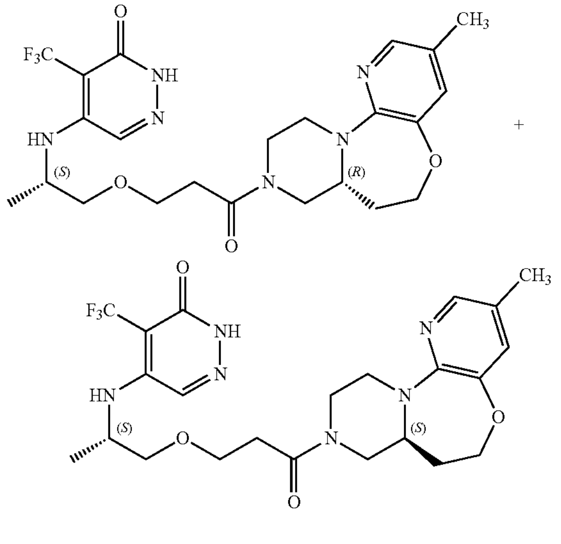

Step 1: Following an analogous procedure described in step 1 of Example 2, INT B14 (160 mg, 0.50 mmol, 1.0 eq.) and TFA (1 mL) were used as reactants to synthesize Compound 58-1 (crude, 210 mg). LCMS: m/z=220 $[M+1]^+$.

Step 2: Following an analogous procedure described in step 2 of Example 1, Compound 58-1 (210 mg, crude) and INT A1 (430 mg, 1.39 mmol, 1.0 eq.) were used as reactants to synthesize Compound 58 (121 mg, yield 47%). LCMS: m/z=511 $[M+1]^+$.

$^1$H NMR (400 MHz, MeOH-$d_4$) δ 7.96 (s, 1H), 7.69 (s, 1H), 7.01 (s, 1H), 4.33-4.21 (m, 2H), 4.20-4.11 (m, 1H), 3.95-3.87 (m, 1H), 3.86-3.75 (m, 3H), 3.73-3.57 (m, 4H), 3.57-3.45 (m, 3H), 2.72-2.64 (m, 2H), 2.21 (s, 3H), 2.17-2.06 (m, 1H), 2.01-1.89 (m, 1H), 1.27 (d, J=6.4 Hz, 3H).

The chiral separation of the Compound 58 (121 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 58A, 51.5 mg, Retention time: 9.79 min) and the second eluting stereoisomer (Compound 58B, 22.6 mg, Retention time: 13.92 min).

Example 59

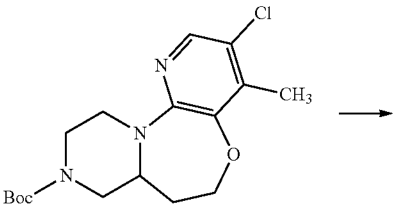

INT B16

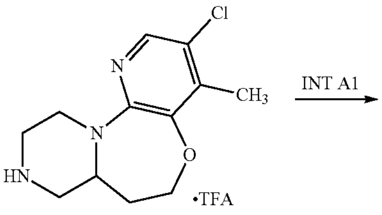

Compound 59-1

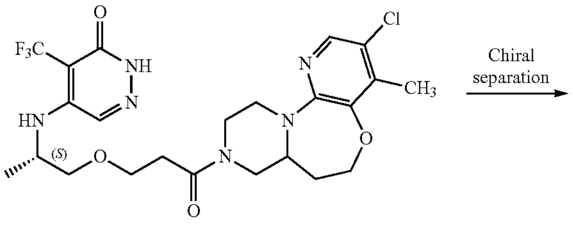

Compound 59

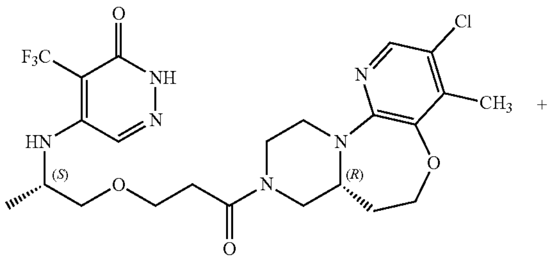

-continued

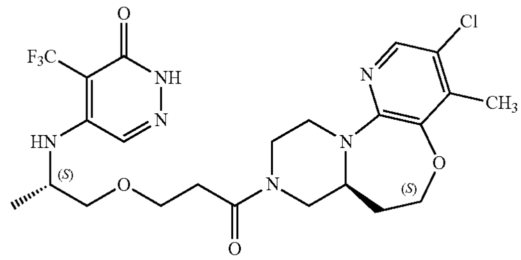

Step 1: Following an analogous procedure described in step 1 of Example 2, INT B16 (0.22 g, 0.62 mmol, 1.0 eq.) and TFA (2 mL) were used as reactants to synthesize Compound 59-1 (crude, 230 mg). LCMS: m/z=254 $[M+1]^+$.

Step 2: Following an analogous procedure described in step 2 of Example 1, Compound 59-1 (230 mg, crude) and INT A1 (0.16 g, 0.52 mmol, 1.0 eq.) were used as reactants to synthesize Compound 59 (81 mg, yield 28%). LCMS: m/z=545 $[M+1]^+$.

$^1$H NMR (400 MHz, MeOH-$d_4$) δ 7.93 (d, J=8.0 Hz, 1H), 7.79 (d, J=7.2 Hz, 1H), 4.35-4.27 (m, 2H), 4.18-4.08 (m, 1H), 3.93-3.86 (m, 1H), 3.84-3.72 (m, 4H), 3.71-3.57 (m, 3H), 3.54-3.45 (m, 3H), 2.70-2.61 (m, 2H), 2.22 (s, 3H), 2.15-2.01 (m, 1H), 2.00-1.88 (m, 1H), 1.24 (t, J=6.8 Hz, 3H).

The chiral separation of the Compound 59 (81 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: Hexane (0.1% IPA), Mobile Phase B: EtOH, $V_{Mobile\ Phase\ A}$:$V_{Mobile\ Phase\ B}$=50:50; Flow Rate: 20 mL/min; Detector Wavelength: 220 nm. This resulted in the first eluting stereoisomer (Compound 59A, 26.2 mg, Retention time: 9.25 min) and the second eluting stereoisomer (Compound 59B, 34.9 mg, Retention time: 10.37 min).

Example 60

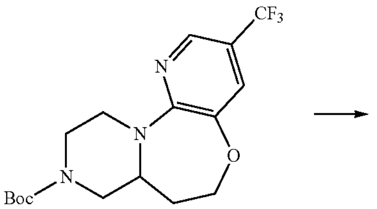

INT B8

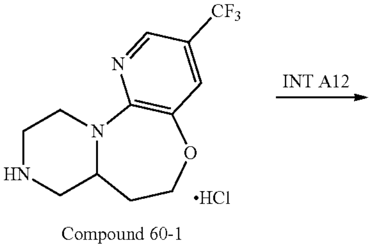

Compound 60-1

-continued

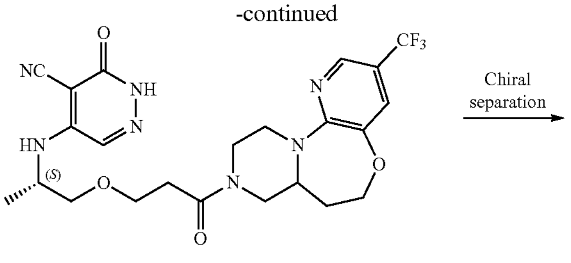

Compound 60

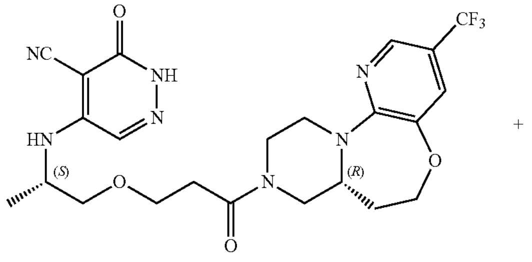

+

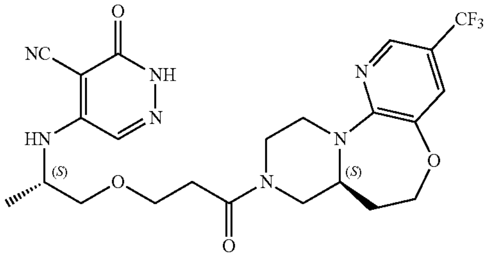

Step 1: Following an analogous procedure described in step 1 of Example 1, INT B8 (4.07 g, 10.90 mmol, 1.0 eq.) and HCl/1,4-dioxane (100 mL, 1N) were used as reactants to synthesize Compound 60-1 (crude, 2.98 g). LCMS: m/z=274 $[M+1]^+$.

Step 2: Following an analogous procedure described in step 2 of Example 1, the crude Compound 60-1 (0.49 g, crude) and INT A12 (0.24 g, 0.90 mmol, 1.0 eq.) were used as reactants to synthesize Compound 60 (324 mg, yield 68%). LCMS: m/z=522 $[M+1]^+$.

$^1$H NMR (400 MHz, MeOH-$d_4$) δ 8.06 (s, 1H), 7.72 (brs, 1H), 7.26 (s, 1H), 4.39-4.25 (m, 2H), 4.14-4.01 (m, 1H), 3.97-3.86 (m, 2H), 3.85-3.64 (m, 5H), 3.64-3.55 (m, 1.5H), 3.54-3.46 (m, 1.5H), 2.69-2.61 (m, 2H), 2.22-2.07 (m, 1H), 2.01-1.90 (m, 1H), 1.29-1.22 (m, 4H).

The chiral separation of the Compound 60 (324 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$:$V_{Mobile\ Phase\ B}$=50:50; Flow Rate: 20 mL/min; Detector Wavelength: 220 nm. This resulted in the first eluting stereoisomer (Compound 60A, 101.5 mg, Retention time: 5.24 min) and the second eluting stereoisomer (Compound 60B, 98.9 mg, Retention time: 6.79 min).

Example 61

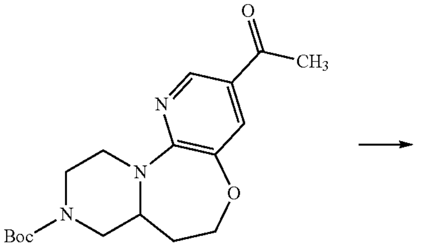

INT B15

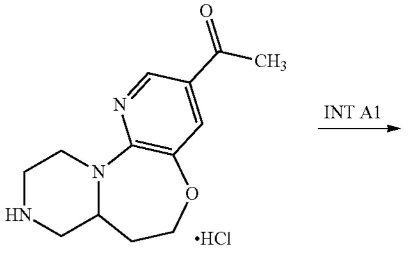

Compound 61-1

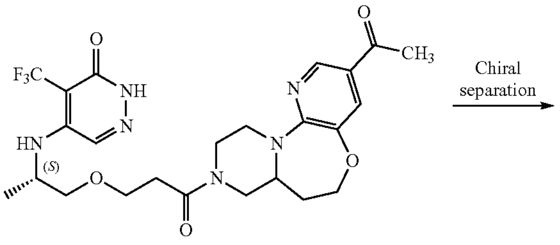

Compound 61

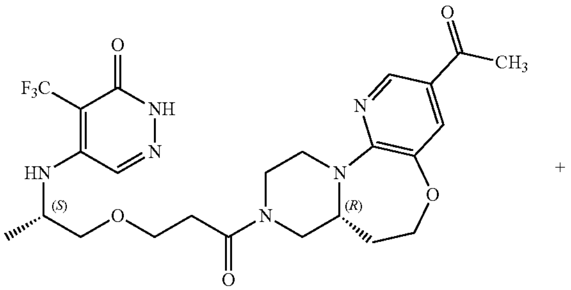

+

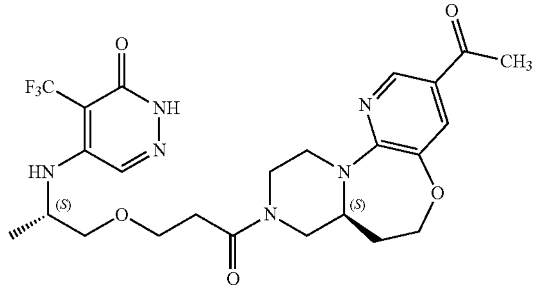

Step 1: Following an analogous procedure described in step 1 of Example 1, INT B15 (0.37 g, 1.07 mmol, 1.0 eq.) and HCl/1,4-dioxane (10 mL, 1N) were used as reactants to synthesize Compound 61-1 (crude, 0.32 g). LCMS: m/z=248 [M+1]$^+$.

Step 2: Following an analogous procedure described in step 2 of Example 1, the crude Compound 61-1 (0.32 g, crude) and INT A1 (0.39 g, 1.26 mmol, 1.18 eq.) were used as reactants to synthesize Compound 61 (0.47 g, yield 81%). LCMS: m/z=539 [M+1]$^+$.

$^1$H NMR (400 MHz, MeOH-$d_4$) δ 8.45 (d, J=8.8 Hz, 1H), 7.92 (d, J=8.8 Hz, 1H), 7.54 (s, 1H), 4.38-4.29 (m, 1H), 4.27-4.08 (m, 3H), 4.03-3.66 (m, 7H), 3.65-3.43 (m, 3H), 2.72-2.58 (m, 2H), 2.49 (s, 3H), 2.19-2.08 (m, 1H), 2.04-1.92 (m, 1H), 1.23 (dd, 3H).

The chiral separation of the Compound 61 (100 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 61A, 42.5 mg, Retention time: 5.70 min) and the second eluting stereoisomer (Compound 62B, 42.8 mg, Retention time: 7.16 min).

Example 62

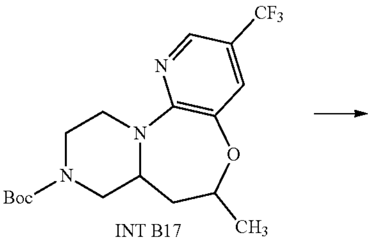

INT B17

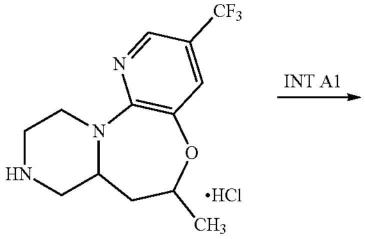

Compound 62-1

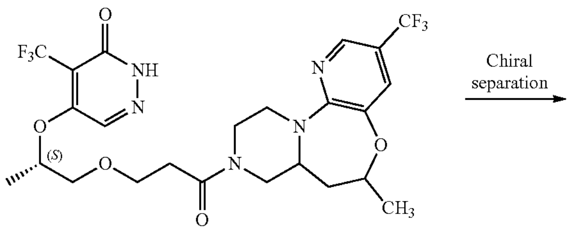

Compound 62

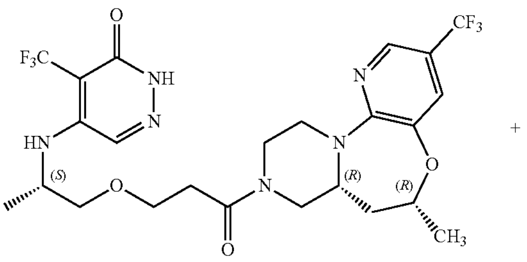

+

-continued

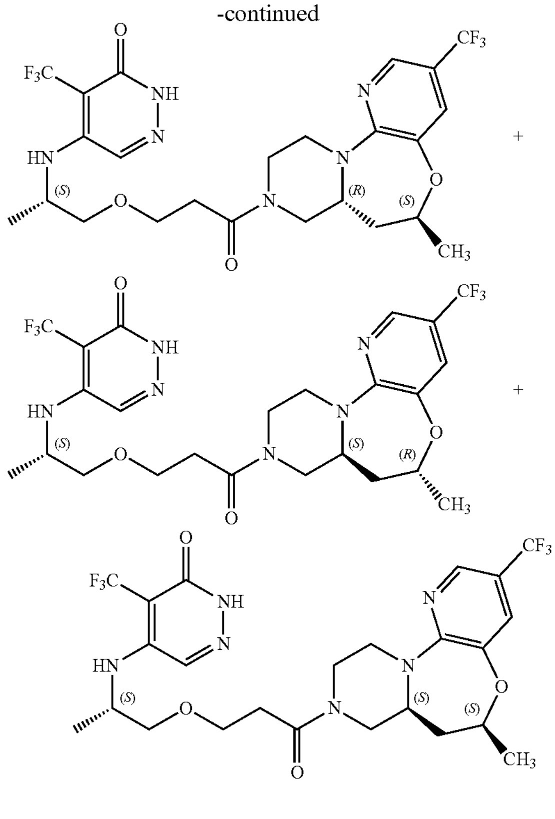

Step 1: Following an analogous procedure described in step 1 of Example 1, INT B17 (2.49 g, 6.43 mmol, 1.0 eq.) and HCl/1,4-dioxane (20 mL, 1N) were used as reactants to synthesize Compound 62-1 (crude, 2.72 g). LCMS: m/z=288 $[M+1]^+$.

Step 2: Following an analogous procedure described in step 2 of Example 1, the crude Compound 62-1 (2.72 g, crude) and INT A1 (2.32 g, 7.50 mmol, 1.17 eq.) were used as reactants to synthesize Compound 62 (3.61 g, yield 97%). LCMS: m/z=579 $[M+1]^+$.

$^1$H NMR (400 MHz, MeOH-$d_4$) δ 8.04 (d, J=8.4 Hz, 1H), 7.92 (d, J=7.6 Hz, 1H), 7.24 (s, 1H), 4.54-4.43 (m, 1H), 4.18-4.07 (m, 2H), 3.94-3.72 (m, 7H), 3.69-3.54 (m, 2H), 3.51-3.45 (m, 1H), 2.72-2.57 (m, 2H), 2.17-2.06 (m, 1H), 1.89-1.75 (m, 1H), 1.36 (d, J=6.0 Hz, 3H), 1.23 (dd, 3H).

The chiral separation of the Compound 62 (3.61 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=80:20; Flow Rate: 20 mL/min; Detector Wavelength: 220 nm. This resulted in the first eluting stereoisomer (Compound 62A, 0.6077 g, Retention time: 5.12 min), the second eluting stereoisomer (Compound 62B, 0.5359 g, Retention time: 6.02 min), a third eluting stereoisomer (Compound 62C, 0.5514, Retention time: 8.00 min), and a fourth eluting stereoisomer (Compound 62D, 0.5719 g, Retention time: 9.63 min).

Example 63

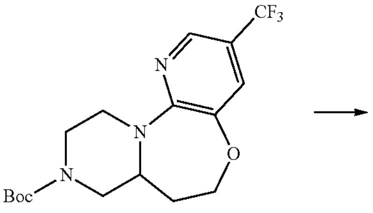

INT B8

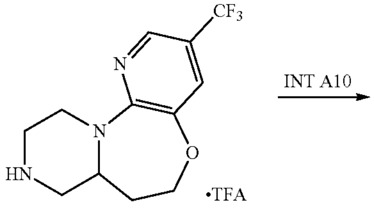

Compound 63-1

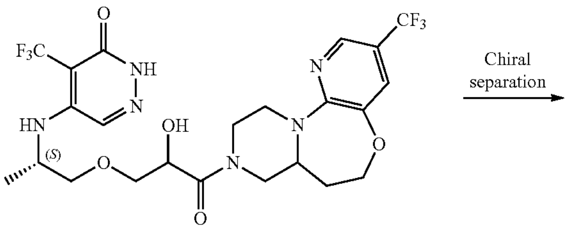

Compound 63

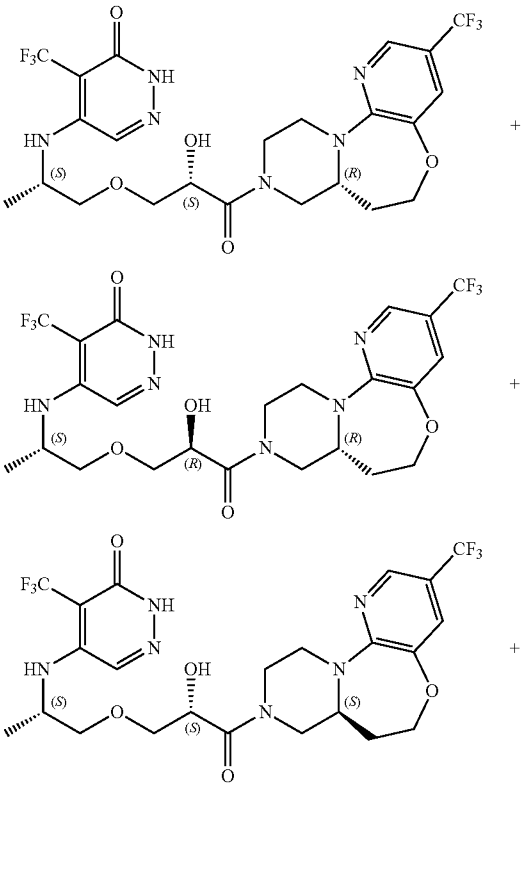

-continued

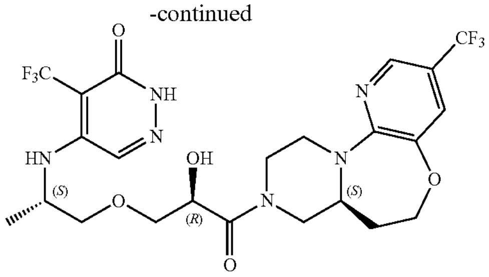

Step 1: Following an analogous procedure described in step 1 of Example 2, INT B8 (330 mg, 0.88 mmol, 1.0 eq.) and TFA (1 mL) were used as reactants to synthesize Compound 63-1 (crude, 330 mg). LCMS: m/z=274 $[M+1]^+$.

Step 2: Following an analogous procedure described in step 2 of Example 1, the crude Compound 63-1 (330 mg, crude) and INT A10 (200 mg, 0.61 mmol, 1.0 eq.) were used as reactants to synthesize Compound 63 (49 mg, yield 13%). LCMS: m/z=581 $[M+1]^+$.

The chiral separation of the Compound 63 (49 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=75:25; Flow Rate: 20 mL/min; Detector Wavelength: 220 nm. This resulted in the first eluting stereo isomer (Compound 63A, 7.0 mg, Retention time: 4.95 min), the second eluting stereoisomer (Compound 63B, 7.0 mg, Retention time: 5.51 min), a third eluting stereoisomer (Compound 63C, 7.8 mg, Retention time: 5.68 min), and a fourth eluting stereoisomer (Compound 63D, 7.8 mg, Retention time: 6.06 min).

The following examples were synthesized using the above procedure or modification procedure using the corresponding intermediate.

| Example | Compound | Chiral separation | Structure | INT | $^1$H NMR and MS: $(M + H)^+$ |
|---|---|---|---|---|---|
| 64 | 64A & 64B | Column: CHIRAL ART Cellulose SA 2 cm × 25 cm, 5 um; Mobile Phase A: MTBE, Mobile Phase B: EtOH, $V_{MobilePhaseA}$: $V_{Mobile\ PhaseB}$ = 75:25; Flow Rate: 20 mL/min Compound 64A: Retention time: 6.78 min; Compound 64B: Retention time: 7.79 min. | 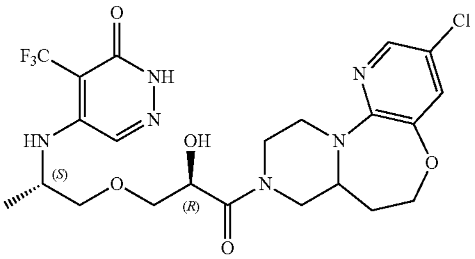 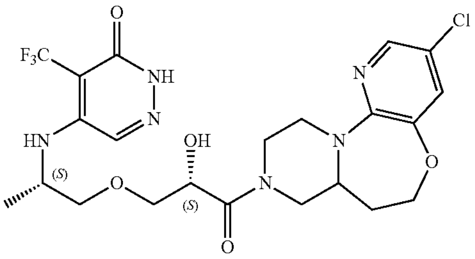 | A10 & B11 | MS: $(M + H)^+$ 547. Compound 64A: $^1$H NMR (400 MHz, MeOH-$d_4$) δ 7.92 (s, 1H), 7.80 (s, 1H), 7.14 (d, J = 6.4 Hz, 1H), 4.66-4.55 (m, 1H), 4.38-4.24 (m, 2H), 4.18-4.10 (m, 1H), 4.01-3.84 (m, 2H), 3.78-3.63 (m, 5H), 3.61-3.46 (m, 3H), 3.40-3.32 (m, 1H), 2.20-2.07 (m, 1H), 2.01-1.89 (m, 1H), 1.25 (d, J = 6.4 Hz, 3H); Compound 64B: $^1$H NMR (400 MHz, MeOH-$d_4$) δ 7.93 (s, 1H), 7.80 (s, 1H), 7.14 (s, 1H), 4.65-4.54 (m, 1H), 4.40-4.23 (m, 2H), 4.20-4.08 (m, 1H), 4.03-3.82 (m, 2H), 3.80-3.61 (m, 6H), 3.60-3.35 (m, 4H), 2.19-2.07 (m, 1H), 2.02-1.87 (m, 1H), 1.25 (d, J = 6.4 Hz, 3H). |

-continued

| Example | Compound | Chiral separation | Structure | INT | $^{1}H$ NMR and MS: $(M + H)^{+}$ |
|---|---|---|---|---|---|
| 65 | 65A & 65B & 65C & 65D | Column: CHIRALPAK ID 2 cm × 25 cm, 5 um; Mobile Phase A: MTBE, Mobile Phase B: EtOH, $V_{MobilePhaseA}$: $V_{MobilePhaseB}$ = 55:45; Flow Rate: 18 mL/min; Detector Wavelength: 220 nm Compound 65A: Retention time: 5.50 min; Mixture of 65B & 65C Retention time: 6.22 min; Compound 65D: Retention time: 8.20 min. Column CHIRAL ART Cellulose SC 2 cm × 25 cm, 5 um; Mobile Phase A: MTBE, Mobile Phase B: EtOH, $V_{MobilePhaseA}$: $V_{MobilePhaseB}$ = 50:50; Flow Rate: 20 mL/min; Detector Wavelength: 220 nm Compound 65B: Retention time: 6.45 min; Compound 65C: Retention time: 8.78 min. | 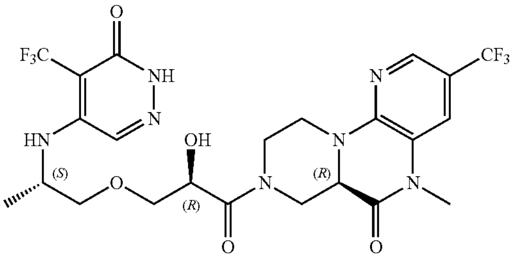 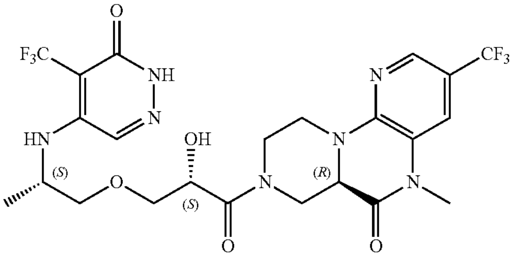 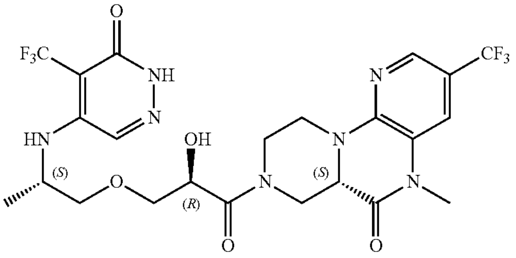 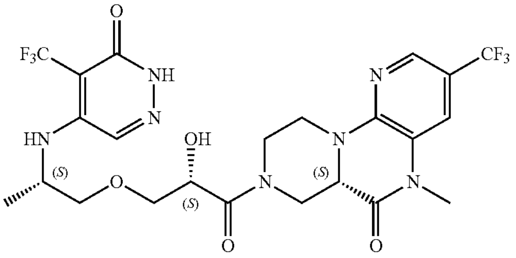 | A10 & B37 | $^{1}H$ NMR (400 MHz, MeOH-$d_4$) δ 8.14 (s, 1H), 7.94 (s, 1H), 7.42 (s, 1H), 5.02 (s, 0.5H), 4.72-4.55 (m, 3H), 4.33-4.24 (m, 0.5H), 4.21-4.07 (m, 1.5H), 3.02-3.94 (m, 0.5H), 3.71 (d, J = 5.2 Hz, 2H), 3.67-3.61 (m, 1H), 3.61-3.53 (m, 1H), 3.37 (s, 3H), 3.30-3.18 (m, 1H), 2.93-2.73 (m, 2H), 1.25 (d, J = 6.5, 3H); MS: $(M + H)^{+}$ 594. |

Example 66

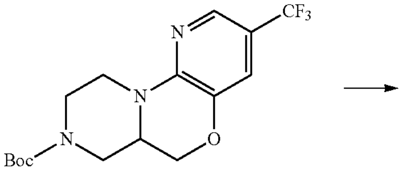

INT B7

-continued

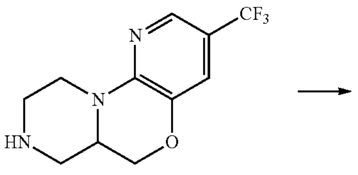

•HCl

Compound 66-1

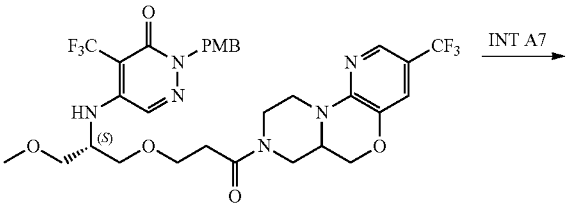

Compound 66-2

-continued

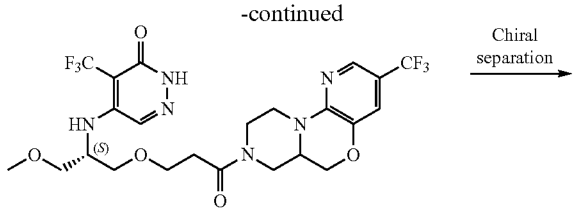

Compound 66

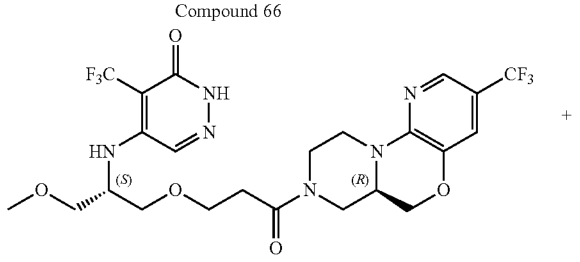

Compound 66A

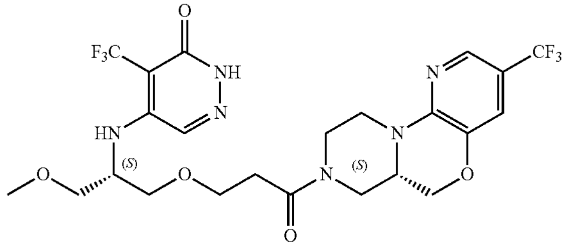

Compound 66B

Step 1: Following an analogous procedure described in step 1 of Example 1, INT B7 (2.31 g, 1.90 mmol, 1.0 eq.) and HCl/1,4-dioxane (50 mL, 1N) were used as reactants to synthesize Compound 66-1 (crude, 2.73 g). LCMS: m/z=260 $[M+1]^+$.

Step 2: Following an analogous procedure described in step 2 of Example 1, the crude Compound 66-1 (397 mg, crude) and INT A7 (364 mg, 0.79 mmol, 1.0 eq.) were used as reactants to synthesize Compound 66-2 (467 mg, yield 84%). LCMS: m/z=701 $[M+1]^+$.

Step 3: Following an analogous procedure described in step 3 of Example 35, the Compound 66-2 (467 mg, 0.67 mmol, 1.0 eq.), TFA (5 mL) and TfOH (0.5 mL) were used as reactants to synthesize Compound 66 (332 mg, yield 85%). LCMS: m/z=581 $[M+1]^+$.

$^1$H NMR (400 MHz, $CD_3OD$) δ 8.00 (s, 1H), 7.94 (d, J=3.2 Hz, 1H), 7.17 (s, 1H), 4.67-4.55 (m, 2H), 4.42-4.35 (m, 1H), 4.23-4.15 (m, 1H), 4.15-4.05 m, 1H), 4.04-3.96 (m, 1H), 3.85-3.72 (m, 2H), 3.70-3.58 (m, 2H), 3.53 (d, J=4.8 Hz, 2H), 3.49-3.39 (m, 1H), 3.36 (s, 3H), 3.30-3.22 (m, 1H), 3.02-2.80 (m, 2H), 2.74-2.67 (m, 1H), 2.57 (t, J=12.0 Hz, 1H).

The chiral separation of the Compound 66 (332 mg) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: IPA, $V_{Mobile\ Phase\ A}$: $V_{Mobile\ Phase\ B}$=85:15; Flow Rate: 20 mL/min; Detector Wavelength: 220 nm. This resulted in the first eluting stereo isomer (Compound 66A, 131.1 mg, Retention time: 12.22 min) and the second eluting stereoisomer (Compound 66B, 130.2 mg, Retention time: 13.34 min).

The following compounds were synthesized using the above procedure or modification procedure using the corresponding intermediates.

| Example | Compound | Chiral separation | Structure | INT | $^1$H NMR and MS: $(M + H)^+$ |
|---|---|---|---|---|---|
| 67 | 67A & 67B | Column: CHIRAL ART Cellulose SA 2 cm × 25 cm, 5 um; Mobile Phase A: MTBE, Mobile Phase B: EtOH, $V_{MobilePhaseA}$: $V_{MobilePhaseB}$ = 75:25; Flow Rate: 20 mL/min Compound 67A: Retention time: 7.50 min; Compound 67B: Retention time: 9.46 min. | 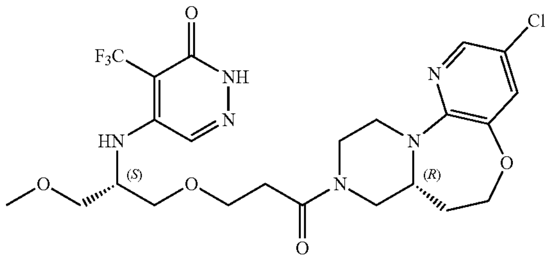 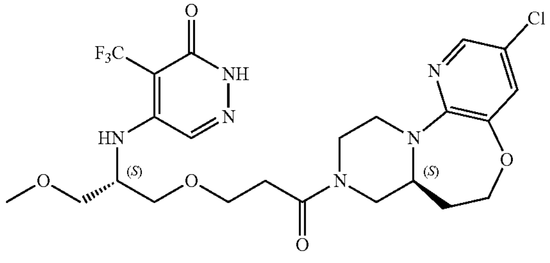 | A7 & B11 | MS: $(M + H)^+$ 561. Compound 67A: $^1$H NMR (400 MHz, MeOH-$d_4$) δ 7.94 (s, 1H), 7.79 (d, J = 4.8 Hz, 1H), 7.13 (s, 1H), 4.39-4.24 (m, 2H), 4.23-4.14 (m, 1H), 3.97-3.88 (m, 1H), 3.86-3.71 (m, 5H), 3.70-3.58 (m, 3H), 3.56-3.43 (m, 4H), 3.37 (s, 3H), 2.72-2.61 (m, 2H), 2.21-2.07 (m, 1H), 1.99-1.87 (m, 1H); Compound 67B: $^1$H NMR (400 MHz, MeOH-$d_4$) δ 7.95 (s, 1H), 7.79 (s, 1H), 7.13 (d, J = 2.0 Hz, 1H), 4.39-4.24 (m, 2H), 4.23-4.15 (m, 1H), 3.98-3.87 (m, 1H), 3.86-3.69 (m, 5H), 3.69-3.58 (m, 3H), 3.57-3.43 (m, 4H), 3.37 (s, 3H), 2.70-2.60 (m, 2H), 2.21-2.06 (m, 1H), 1.99-1.87 (m, 1H). |

-continued

| Example | Compound | Chiral separation | Structure | INT | $^1H$ NMR and MS: $(M + H)^+$ |
|---|---|---|---|---|---|
| 68 | 68A & 68B | Column: CHIRAL ART Cellulose SA 2 cm × 25 cm, 5 um; Mobile Phase A: MTBE, Mobile Phase B: EtOH, $V_{MobilePhaseA}$: $V_{MobilePhaseB}$ = 80:20; Flow Rate: 20 mL/min Compound 68A: Retention time: 6.33 min; Compound 68B: Retention time: 7.72 min. | 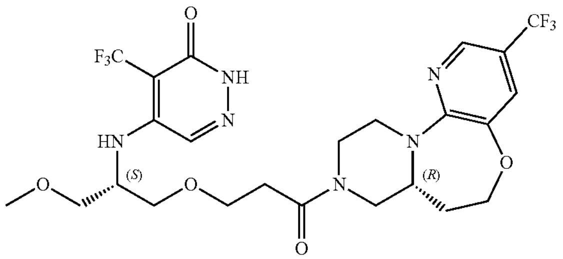 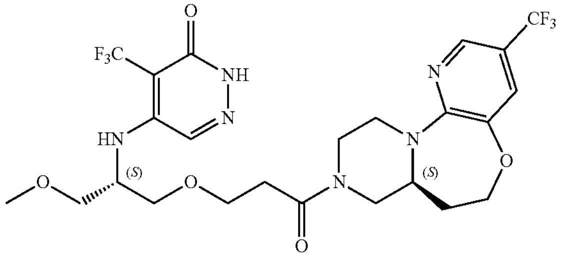 | A7 & B8 | MS: $(M + H)^+$ 595. Compound 68A: $^1H$ NMR (400 MHz, MeOH-$d_4$) δ 8.07 (d, J = 6.8 Hz, 1H), 7.94 (d, J = 6.8 Hz, 1H), 7.26 (s, 1H), 4.39-4.26 (m, 2H), 4.23-4.15 (m, 1H), 4.14-4.03 (m, 1H), 3.97-3.87 (m, 2H), 3.86-3.73 (m, 4H), 3.72-3.56 (m, 4H), 3.54-3.49 (m, 2H), 3.37 (d, J = 1.6 Hz, 3H), 2.71-2.57 (m, 2H), 2.23-2.07 (m, 1H), 2.04-1.91 (m, 1H); Compound 68B: $^1H$ NMR (400 MHz, MeOH-$d_4$) δ 8.07 (s, 1H), 7.95 (s, 1H), 7.26 (s, 1H), 4.38-4.26 (m, 2H), 4.23-4.16 (m, 1H), 4.15-4.03 (m, 1H), 3.98-3.87 (m, 2H), 3.86-3.73 (m, 4H), 3.71-3.55 (m, 4H), 3.54-3.50 (m, 2H), 3.37 (s, 3H), 2.69-2.62 (m, 2H), 2.22-2.08 (m, 1H), 2.01-1.91 (m, 1H). |

Example 69

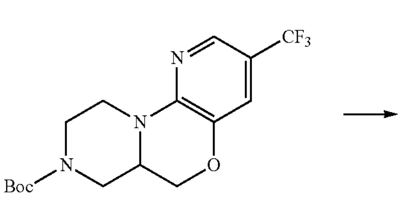

INT B7

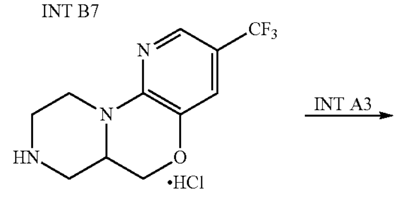

Compound 69-1

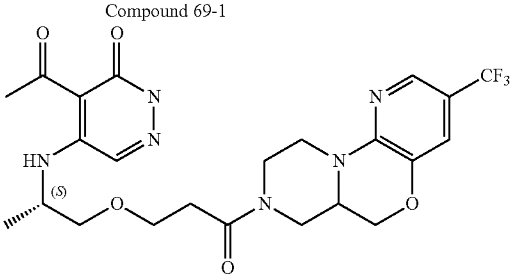

Compound 69

Step 1: Following an analogous procedure described in step 1 of Example 1, INT B7 (2.311 g, 6.43 mmol, 1.0 eq.) and HCl/1,4-dioxane (20 mL, 1N) were used as reactants to synthesize Compound 69-1 (crude, 2.73 g). LCMS: m/z=260 $[M+1]^+$.

Step 2: Following an analogous procedure described in step 2 of Example 1, the crude Compound 69-1 (218 mg, crude) and INT A3 (182 mg, 0.64 mmol, 1.0 eq.) were used as reactants to synthesize Compound 69 (126.7 mg, yield 37%). LCMS: m/z=525 $[M+1]^+$.

$^1H$ NMR (400 MHz, MeOH-$d_4$) δ 7.99 (s, 1H), 7.91 (s, 1H), 7.15 (d, J=8.4 Hz, 1H), 4.67-4.53 (m, 2H), 4.40-4.31 (m, 1H), 4.22-4.11 (m, 2H), 4.04-3.94 (m, 1H), 3.86-3.73 (m, 2H), 3.67-3.60 (m, 1H), 3.57-3.40 (m, 1H), 3.29-3.21 (m, 1H), 3.07-2.57 (m, 5H), 2.54 (d, J=5.6 Hz, 3H), 1.26 (d, J=6.0 Hz, 3H).

Example 70

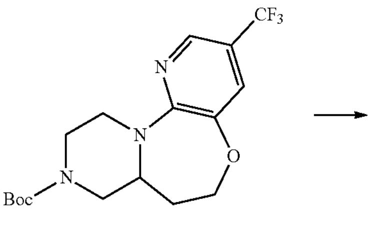

INT B8

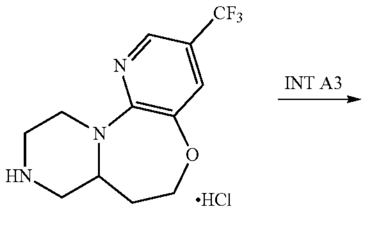

Compound 70-1

-continued

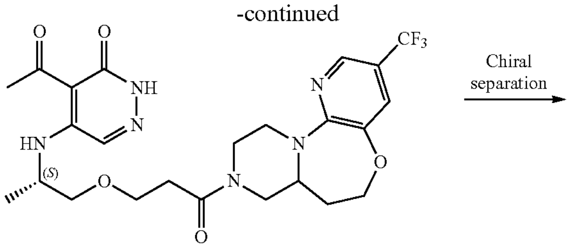

Compound 70

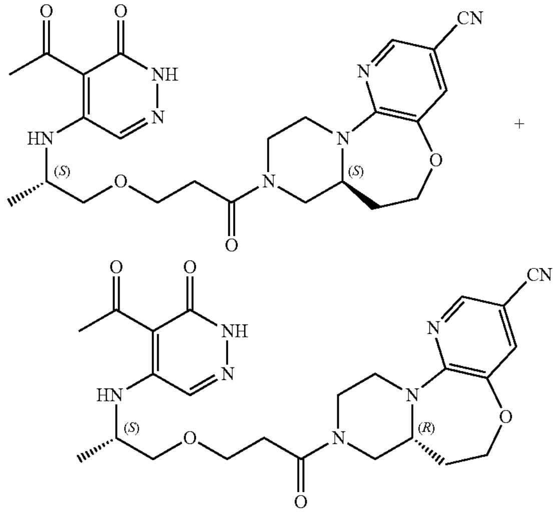

Step 1: Following an analogous procedure described in step 1 of Example 1, INT B8 (4.07 g, 10.90 mmol, 1.0 eq.) and HCl/1,4-dioxane (100 mL, 1N) were used as reactants to synthesize Compound 70-1 (crude, 2.98 g). LCMS: m/z=274 $[M+1]^+$.

Step 2: Following an analogous procedure described in step 2 of Example 1, the crude Compound 70-1 (578 mg, crude) and INT A3 (640 mg, 2.26 mmol, 1.0 eq.) were used as reactants to synthesize Compound 70 (875 mg, yield 87%). LCMS: m/z=539 $[M+1]^+$.

$^1H$ NMR (400 MHz, MeOH-$d_4$) δ 8.05 (d, J=15.2 Hz, 1H), 7.93 (d, J=8.8 Hz, 1H), 7.26-7.23 (m, 1H), 4.37-4.24 (m, 2H), 4.22-4.03 (m, 2H), 3.97-3.71 (m, 7H), 3.69-3.59 (m, 2H), 3.56-3.42 (m, 1H), 2.77-2.61 (m, 2H), 2.58 (d, J=6.0 Hz, 3H), 2.22-2.08 (m, 1H), 2.04-1.91 (m, 1H), 1.25 (dd, 3H).

The chiral separation of the Compound 70 (875 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH; $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 70A, 211.8 mg, Retention time: 6.12 min) and the second eluting stereoisomer (Compound 70B, 213.2 mg, Retention time: 7.77 min).

Example 71

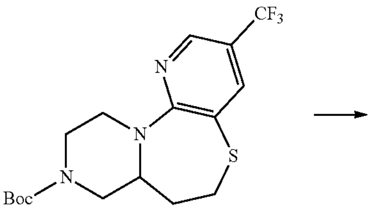

INT B18

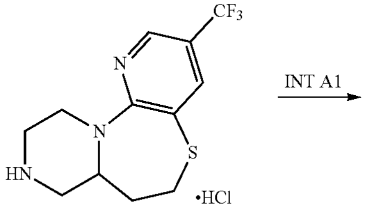

Compound 71-1

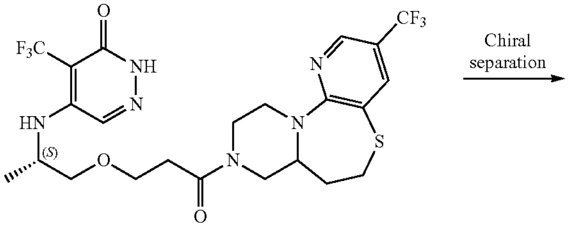

Compound 71

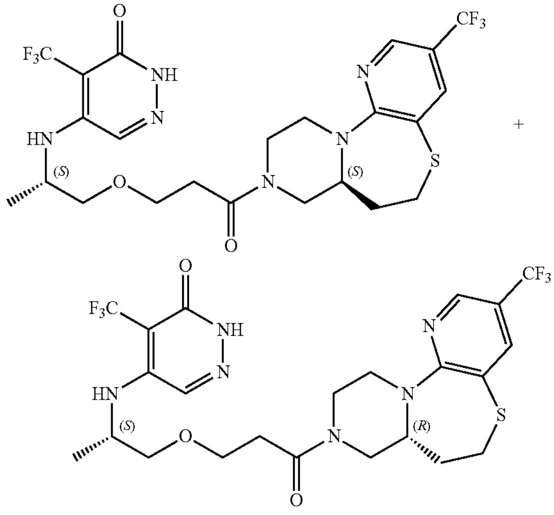

Step 1: Following an analogous procedure described in step 1 of Example 1, INT B18 (6.23 g, 16.20 mmol, 1.0 eq.) and HCl/1,4-dioxane (80 mL, 1N) were used as reactants to synthesize Compound 71-1 (crude, 10.22 g). LCMS: m/z=290 $[M+1]^+$.

Step 2: Following an analogous procedure described in step 2 of Example 1, the crude Compound 71-1 (6.92 g, crude) and INT A1 (5.12 g, 16.56 mmol, 1.0 eq.) were used as reactants to synthesize Compound 71 (8.42 g, yield 87% E). LCMS: m/z=581 $[M+1]^+$.

$^1H$ NMR (400 MHz, MeOH-$d_4$) δ 8.15 (s, 1H), 7.93 (d, J=5.5, 1H), 7.58 (s, 1H), 4.18-4.09 (m, 1H), 4.08-3.92 (m, 2H), 3.86-3.70 (m, 5H), 3.69-3.53 (m, 4H), 3.52-3.43 (m,

1H), 2.93 (dd, 1H), 2.71-2.57 (m, 2H), 2.17-2.06 (m, 1H), 1.98-1.82 (m, 1H), 1.23 (t, J=6.8 Hz, 3H).

The chiral separation of the Compound 71 (8.42 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=75:25; Flow Rate: 20 mL/min; Detector Wavelength: 220 nm. This resulted in the first eluting stereoisomer (Compound 71A, 2.7416 g, Retention time: 5.10 min) and the second eluting stereoisomer (Compound 71B, 2.7269 g, Retention time: 5.99 min.

Example 72

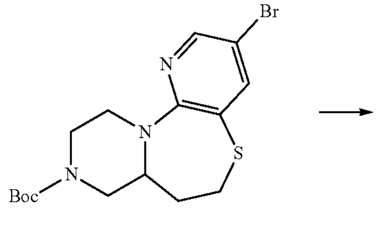

INT B20

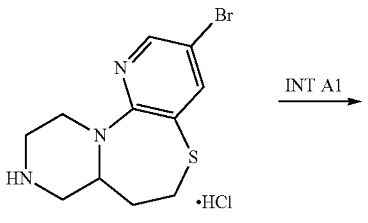

Compound 72-1

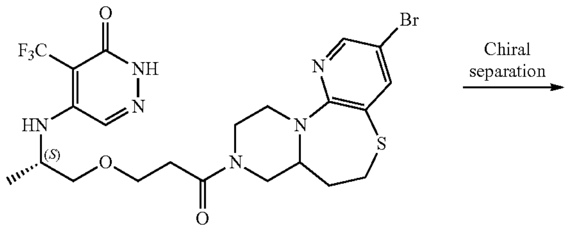

Compound 72

-continued

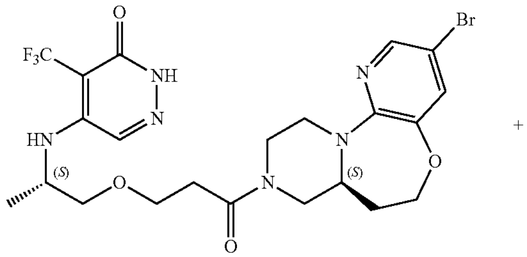

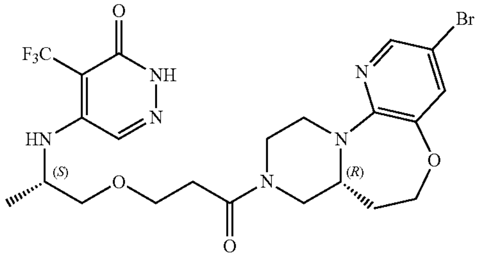

Step 1: Following an analogous procedure described in step 1 of example 1, INT B20 (1.72 g, 4.30 mmol, 1.0 eq.) and HCl/1,4-dioxane (20 mL, 1N) were used as reactants to synthesize Compound 72-1 (crude, 1.76 g). LCMS: m/z=300, 302 $[M+1]^+$.

Step 2: Following an analogous procedure described in step 2 of example 1, the crude Compound 72-1 (1.76 g, crude) and INT A1 (1.15 g, 3.72 mmol, 1.0 eq.) were used as reactants to synthesize Compound 72 (1.79 g, yield 81%). LCMS: m/z=591, 593 $[M+1]^+$.

$^1$H NMR (400 MHz, MeOH-$d_4$) δ 7.97-2.90 (m, 2H), 7.54 (s, 1H), 4.59-4.46 (m, 1H), 4.19-4.06 (m, 1H), 3.93-3.67 (m, 6H), 3.67-3.55 (m, 2H), 3.55-3.42 (m, 3H), 2.93-2.83 (m, 1H), 2.70-2.57 (m, 2H), 2.12-2.01 (m, 1H), 1.97-1.81 (m, 1H), 1.23 (t, J=6.8 Hz, 3H).

The chiral separation of the Compound 72 (1.79 g) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 72A, 693.8 mg, Retention time: 5.24 min) and the second eluting stereoisomer (Compound 72B, 662.9 mg, Retention time: 8.57 min).

The following compounds were synthesized using the above procedure or modification procedure using the corresponding intermediate.

| Example | Compound | Chiral separation | Structure | INT | $^1$H NMR and MS: $(M + H)^+$ |
|---|---|---|---|---|---|
| 73 | 73A & 73B | Column: CHIRAL ART Cellulose SA 2 cm × 25 cm, 5 um; Mobile Phase A: MTBE, Mobile Phase B: EtOH, $V_{MobilePhaseA}$: $V_{MobilePhaseB}$ = 50:50; Flow Rate: 20 mL/min Compound 73A: Retention time: 5.09 min; Compound 73B: Retention time: 6.74 min. | 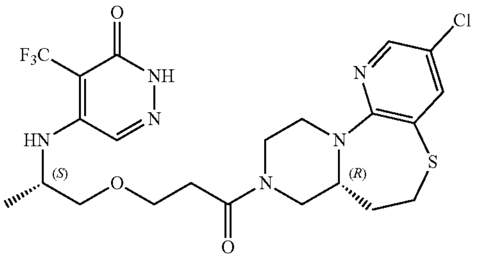 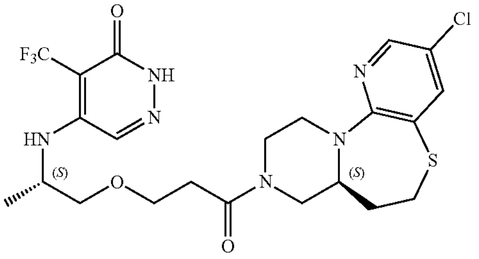 | A1 & B19 | MS: $(M + H)^+$ 547. Compound 73A: $^1$H NMR (400 MHz, MeOH-$d_4$) δ 7.92 (d, J = 4.4 Hz, 1H), 7.87 (s, 1H), 7.43 (s, 1H), 4.56-4.42 (m, 1H), 4.18-4.06 (m, 1H), 3.92-3.70 (m, 6H), 3.70-3.55 (m, 2H), 3.55-3.41 (m, 3H), 2.92-2.84 (m, 1H), 2.70-2.56 (m, 2H), 2.13-2.02 (m, 1H), 1.96-1.76 (m, 1H), 1.24 (t, J = 6.4 Hz, 3H); Compound 73B: $^1$H NMR (400 MHz, MeOH-$d_4$) δ 7.93 (d, J = 4.0 Hz, 1H), 7.88 (s, 1H), 7.44 (s, 1H), 4.58-4.42 (m, 1H), 4.18-4.08 (m, 1H), 3.91-3.65 (m, 6H), 3.64-3.53 (m, 2H), 3.52-3.42 (m, 3H), 2.93-2.82 (m, 1H), 2.70-2.57 (m, 2H), 2.12-1.99 (m, 1H), 1.96-1.80 (m, 1H), 1.24 (d, J = 5.6 Hz, 3H). |

Example 74

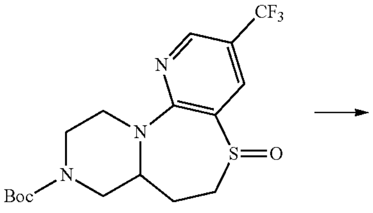

INT B21

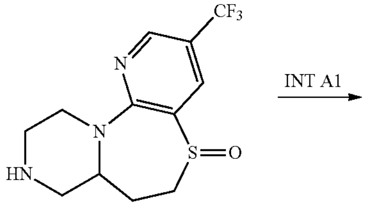

Compound 74-1

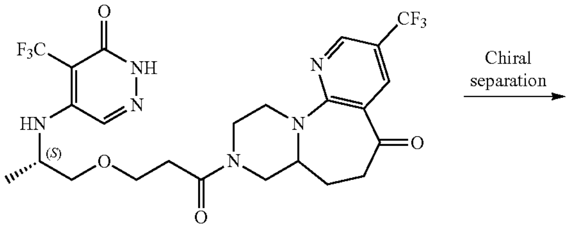

Compound 74

-continued

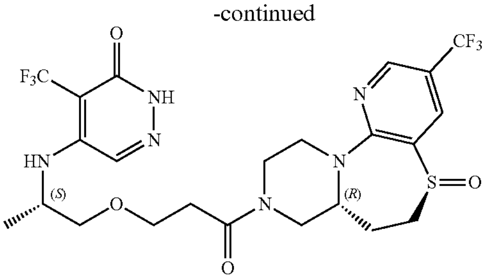

+

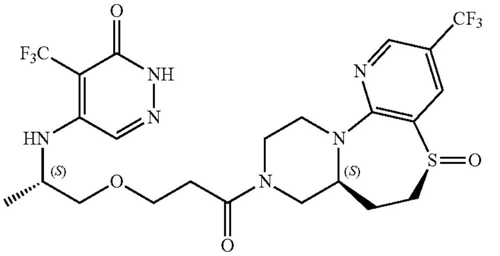

+

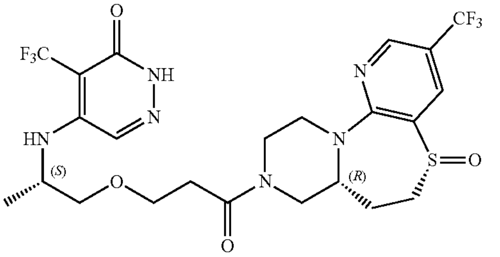

+

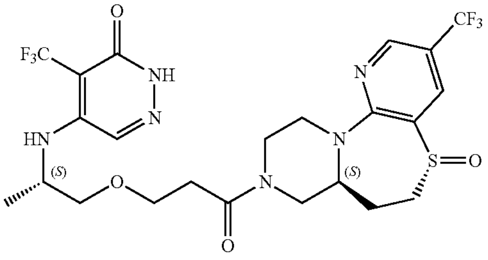

Step 1: Following an analogous procedure described in step 1 of example 1, INT B21 (230 mg, 0.57 mmol, 1.0 eq.) and HCl/1,4-dioxane (5 mL, 1N) were used as reactants to synthesize Compound 74-1 (crude, 221 mg). LCMS: m/z=306 $[M+1]^+$.

Step 2: Following an analogous procedure described in step 2 of example 1, the crude Compound 74-1 (221 mg, crude) and INT A1 (268 mg, 0.87 mmol, 1.0 eq.) were used as reactants to synthesize Compound 74 (253 mg, yield 74%). LCMS: m/z=597 $[M+1]^+$.

$^1$H NMR (400 MHz, MeOH-$d_4$) δ 8.47 (s, 1H), 8.06 (s, 1H), 7.93 (d, J=6.8 Hz, 1H), 4.19-3.86 (m, 4H), 3.86-3.66 (m, 5H), 3.64-3.53 (m, 3H), 3.52-3.42 (m, 1H), 3.36-3.31 (m, 1H), 2.68-2.57 (m, 2H), 2.52-2.38 (m, 1H), 2.34-2.21 (m, 1H), 1.23 (dd, 3H).

The chiral separation of the Compound 74 (253 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH; $V_{Mobile\ Phase\ A}$: $V_{Mobile\ Phase\ B}$=50:50; Flow Rate: 20 mL/min; Detector Wavelength: 220 nm. This resulted in the first eluting stereo isomer (Compound 74A, 42 mg, Retention time: 4.38 min), the second eluting stereoisomer (Compound 74B, 46 mg, Retention time: 5.02 min), a third eluting stereoisomer (Compound 74C, 45 mg, Retention time: 5.92 min), and a fourth eluting stereoisomer (Compound 74D, 40 mg, Retention time: 7.71 min).

Example 75

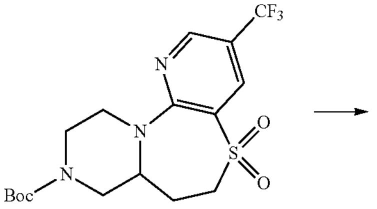

INT B22

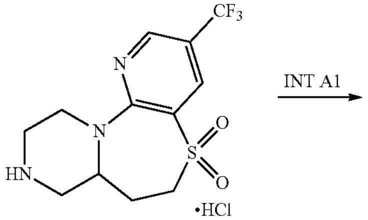

•HCl

Compound 75-1

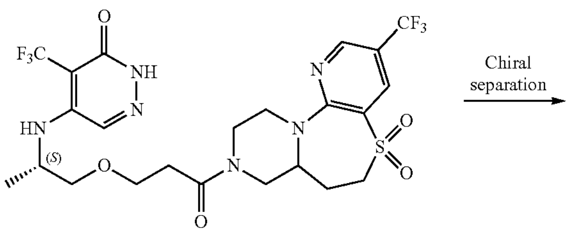

Compound 75

-continued

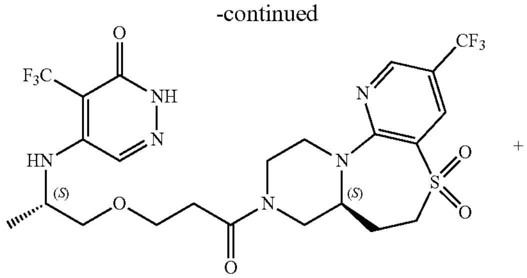

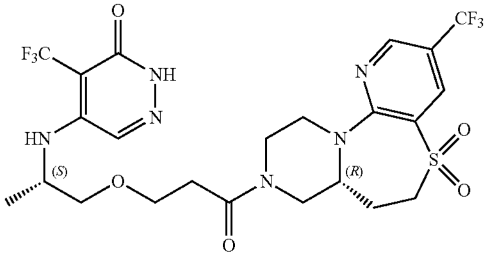

Step 1: Following an analogous procedure described in step 1 of example 1, INT B22 (381 mg, 0.90 mmol, 1.0 eq.) and HCl/1,4-dioxane (3 mL, 1N) were used as reactants to synthesize Compound 75-1 (crude, 431 mg). LCMS: m/z=322 $[M+1]^+$.

Step 2: Following an analogous procedure described in step 2 of example 1, the crude Compound 75-1 (431 mg, crude) and INT A1 (403 mg, 1.30 mmol, 1.0 eq.) were used as reactants to synthesize Compound 75 (252 mg, yield 45%). LCMS: m/z=613 $[M+1]^+$.

$^1$H NMR (400 MHz, MeOH-$d_4$) δ 8.62 (s, 1H), 8.34 (s, 1H), 7.92 (s, 1H), 4.35-4.18 (m, 1H), 4.18-3.87 (m, 5H), 3.85-3.65 (m, 5H), 3.64-3.42 (m, 3H), 2.64 (d, J=4.1, 2H), 2.29-2.14 (m, 2H), 1.22 (s, 3H).

The chiral separation of the Compound 75 (252 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH; $V_{Mobile\ Phase\ A}$: $V_{Mobile\ Phase\ B}$=60:40; Flow Rate: 20 mL/min; Detector Wavelength: 220 nm. This resulted in the first eluting stereoisomer (Compound 75A, 130 mg, Retention time: 4.39 min) and the second eluting stereoisomer (Compound 75B, 62 mg, Retention time: 5.28 min).

Example 76

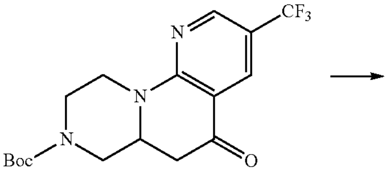

INT B28

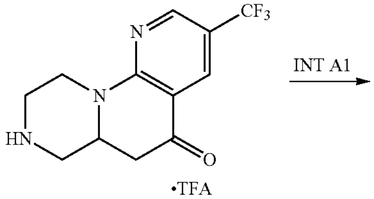

•TFA

Compound 76-1

-continued

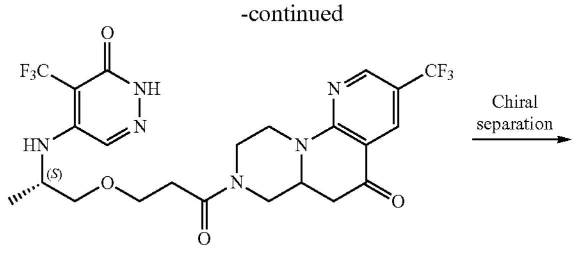

Compound 76

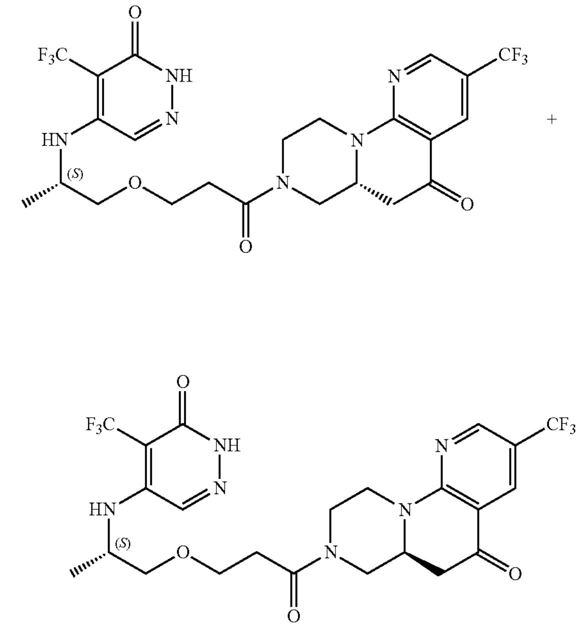

Step 1: Following an analogous procedure described in step 1 of example 2, INT B28 (261 mg, 0.70 mmol, 1.0 eq.) and TFA (1 mL) were used as reactants to synthesize Compound 76-1 (crude, 0.27 g). LCMS: m/z=272 $[M+1]^+$.

Step 2: Following an analogous procedure described in step 2 of example 1, the crude Compound 76-1 (0.27 g, crude) and INT A1 (258 mg, 0.83 mmol, 1.0 eq.) were used as reactants to synthesize Compound 76 (225 mg, yield 57%). LCMS: m/z=563 $[M+1]^+$.

$^1H$ NMR (400 MHz, MeOH-$d_4$) δ 8.62 (s, 1H), 8.24 (s, 1H), 7.92 (s, 1H), 4.82-4.74 (m, 1H), 4.63 (d, J=13.2 Hz, 1H), 4.21-4.08 (m, 2H), 3.85-3.72 (m, 2H), 3.70-3.56 (m, 2H), 3.52-3.45 (m, 1H), 3.42-3.32 (m, 0.5H), 3.27-3.15 (m, 0.5H), 3.01-2.90 (m, 1H), 2.89-2.74 (m, 2H), 2.73-2.66 (m, 3H), 1.24 (d, J=6.4 Hz, 3H).

The chiral separation of the Compound 76 (225 mg) was performed by Chiral-Prep-HPLC with the following conditions: Equipment: Prep-HPLC-Gilson; Column: CHIRALPAK ID 2 cm×25 cm, 5 um; Mobile Phase A: MTBE, Mobile Phase B: EtOH, $V_{Mobile\ Phase\ A}$:$V_{Mobile\ Phase\ B}$=60:40; Flow Rate: 16 mL/min; Detector Wavelength: 220 nm. This resulted in the first eluting stereoisomer (Compound 76A, 87.3 mg, Retention time: 4.60 min) and the second eluting stereoisomer (Compound 76B, 87.5 mg, Retention time: 5.31 min).

Example 77

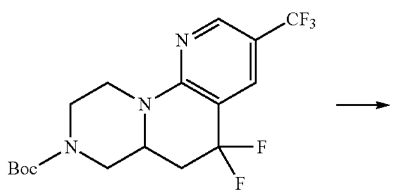

INT B30

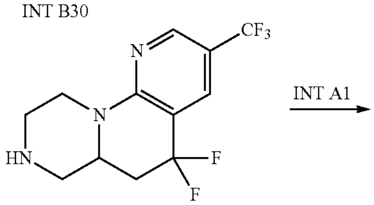

•TFA

Compound 77-1

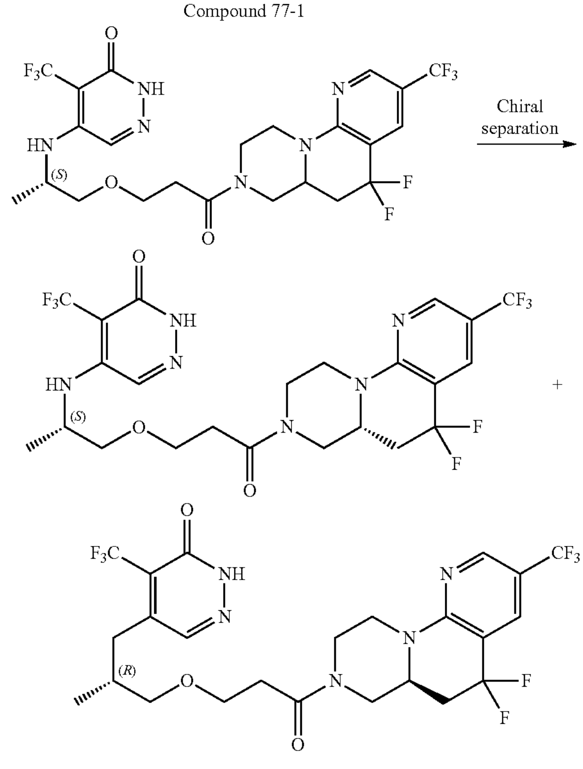

Step 1: Following an analogous procedure described in step 1 of example 2, INT B30 (331 mg, 0.84 mmol, 1.0 eq.) and TFA (1 mL) were used as reactants to synthesize Compound 77-1 (crude, 510 mg). LCMS: m/z=294 $[M+1]^+$.

Step 2: Following an analogous procedure described in step 2 of example 1, the crude Compound 77-1 (510 mg, crude) and INT A1 (276 mg, 0.89 mmol, 1.06 eq.) were used as reactants to synthesize Compound 77 (89 mg, yield 18%). LCMS: m/z=585 $[M+1]^+$.

The chiral separation of the Compound 77 (89 mg) was performed by Chiral-Prep-HPLC with the following conditions: Equipment: Prep-HPLC-Gilson; Column: CHIRALPAK ID 2 cm×25 cm, 5 um; Mobile Phase A: MTBE, Mobile Phase B: EtOH; $V_{Mobile\ Phase\ A}$:$V_{Mobile\ Phase\ B}$=70:30; Flow Rate: 16 mL/min; Detector Wavelength: 220 nm. This resulted in the first eluting stereoisomer (Compound 77A, 30.4 mg, Retention time: 4.60 min) and the second eluting stereoisomer (Compound 77B, 30.3 mg, Retention time: 5.31 min).

Example 78

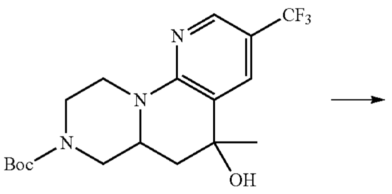
INT B29

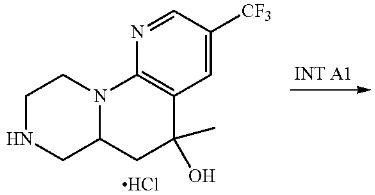

Compound 78-1

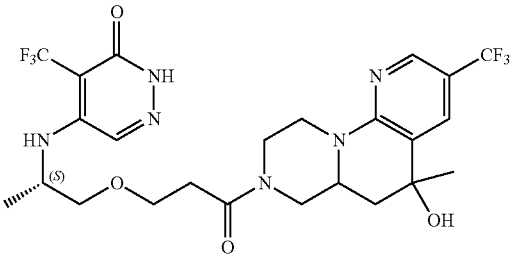
Compound 78

Step 1: Following an analogous procedure described in step 1 of example 1, INT B29 (190 mg, 0.49 mmol, 1.0 eq.) and HCl/1,4-dioxane (3 mL, 1N) were used as reactants to synthesize Compound 78-1 (crude, 245 mg). LCMS: m/z=288 $[M+1]^+$.

Step 2: Following an analogous procedure described in step 2 of example 1, the crude Compound 78-1 (245 mg, crude) and INT A1 (183 mg, 0.59 mmol, 1.20 eq.) were used as reactants to synthesize Compound 78 (203 mg, yield 71%). LCMS: m/z=579 $[M+1]^+$.

$^1H$ NMR (400 MHz, DMSO-$d_6$) δ 12.46 (s, 1H), 8.35 (s, 1H), 7.92 (s, 1H), 7.77 (s, 1H), 6.32-6.25 (m, 1H), 5.27 (d, J=17.2 Hz, 1H), 4.76-4.66 (m, 1H), 4.46-4.37 (m, 1H), 4.20-4.11 (m, 1H), 4.06-3.97 (m, 1H), 3.74-3.64 (m, 2H), 3.49 (d, J=5.2 Hz, 2H), 3.05-2.99 (m, 11H), 2.96-2.83 (m, 1H), 2.82-2.66 (m, 11H), 2.65-2.58 (m, 2H), 1.99-1.88 (m, 11H), 1.77-1.70 (m, 11H), 1.65-1.56 (m, 11H), 1.54 (s, 3H), 1.16 (d, J=6.4, 3H).

The following compounds were synthesized using the above procedure or modification procedure using the corresponding intermediates.

| Example | Compound | Chiral separation | Structure | INT | $^1$H NMR and MS: (M + H)$^+$ |
|---|---|---|---|---|---|
| 79 | 79A & 79B & 79C & 79D | Column: CHIRALPAK IG 2 cm × 25 cm, 5 um; Mobile Phase A: Hex: MTBE = 3:1, Mobile Phase B: EtOH, $V_{MobilePhaseA}$:$V_{MobilePhaseB}$ = 60:40; Flow Rate: 20 mL/min; Detector Wavelength: 220 nm Mixture of 79A & 79B Retention time: 3.36 min. Compound 79C: Retention time: 4.76 min; Compound 79D: Retention time: 6.51 min. Column: CHIRAL ART Cellulose SA 2 cm × 25 cm, 5 um; Mobile Phase A: Hex, Mobile Phase B: EtOH, $V_{MobilePhaseA}$:$V_{MobilePhaseB}$ = 80:20; Flow Rate: 20 mL/min Compound 79A: Retention time: 10.21 min; Compound 79B: Retention time: 11.27 min. | 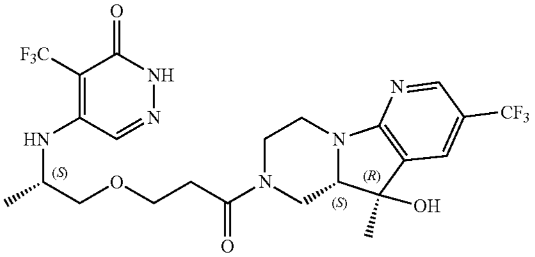<br>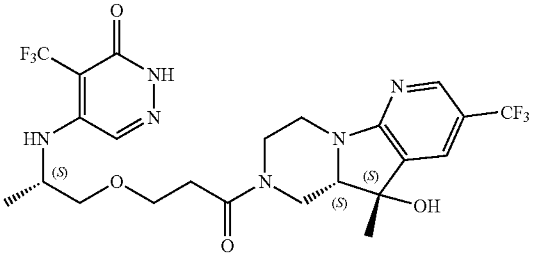<br>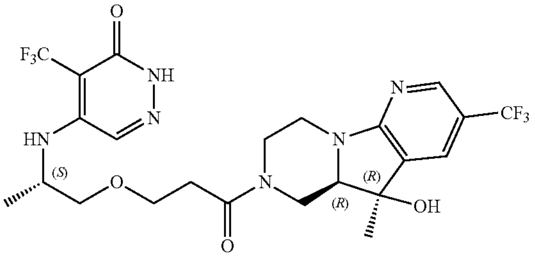<br>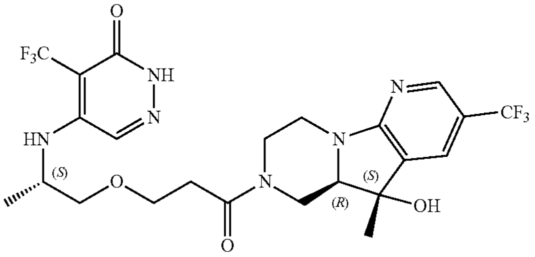 | A1 & B24 | MS: (M + H)$^+$ 565. Compound 79A: $^1$H NMR (400 MHz, DMSO-$d_6$) δ 12.34 (s, 1H), 8.25 (s, 1H), 7.92 (s, 1H), 7.64 (s, 1H), 6.32-6.24 (m, 1H), 5.60 (s, 1H), 4.49 (dd, 1H), 4.20-4.10 (m, 1H), 4.09-3.99 (m, 1H), 3.98-3.89 (m, 1H), 3.74-3.63 (m, 2H), 3.48 (d, J = 4.8 Hz, 2H), 3.41-3.35 (m, 1H), 3.27-3.17 (m, 1H), 3.15-2.83 (m, 2H), 2.71-2.53 (m, 2H), 1.52 (d, J = 11.2 Hz, 3H), 1.16 (d, J = 6.4 Hz, 3H); Compound 79B: $^1$H NMR (400 MHz, DMSO-$d_6$) δ 12.44 (s, 1H), 8.26 (s, 1H), 7.92 (s, 1H), 7.63 (s, 1H), 6.32-6.24 (m, 1H), 5.60 (s, 1H), 4.49 (dd, 1H), 4.21-4.10 (m, 1H), 4.08-4.00 (m, 1H), 3.98-3.89 (m, 1H), 3.74-3.64 (m, 2H), 3.49 (d, J = 4.8 Hz, 2H), 3.41-3.35 (m, 1H), 3.27-3.16 (m, 1H), 3.08-2.81 (m, 2H), 2.71-2.53 (m, 2H), 1.39 (d, J = 11.2 Hz, 3H), 1.15 (d, J = 6.4 Hz, 3H); Compound 79C: $^1$H NMR (400 MHz, DMSO-$d_6$) δ 12.44 (s, 1H), 8.25 (s, 1H), 7.92 (s, 1H), 7.63 (s, 1H), 6.32-6.24 (m, 1H), 5.60 (s, 1H), 4.49 (dd, 1H), 4.20-4.10 (m, 1H), 4.08-3.99 (m, 1H), 3.98-3.89 (m, 1H), 3.74-3.64 (m, 2H), 3.48 (d, J = 4.8 Hz, 2H), 3.41-3.35 (m, 1H), 3.27-3.16 (m, 1H), 3.16-2.84 (m, 2H), 2.71-2.53 (m, 2H), 1.52 (d, J = 11.2 Hz, 3H), 1.16 (d, J = 6.4 Hz, 3H); Compound 79D: $^1$H NMR (400 MHz, DMSO-$d_6$) δ 12.44 (s, 1H), 8.26 (s, 1H), 7.91 (s, 1H), 7.64 (s, 1H), 6.34-6.24 (m, 1H), 5.76 (s, 1H), 4.57 (dd, 1H), 4.22-4.10 (m, 1H), 4.08-3.99 (m, 1H), 3.98-3.89 (m, 1H), 3.74-3.64 (m, 2H), 3.48 (d, J = 4.8 Hz, 2H), 3.41-3.35 (m, 1H), 3.27-3.16 (m, 1H), 3.16-2.84 (m, 2H), 2.71-2.53 (m, 2H), 1.39 (d, J = 11.2 Hz, 3H), 1.16 (d, J = 6.4 Hz, 3H). |

Example 80

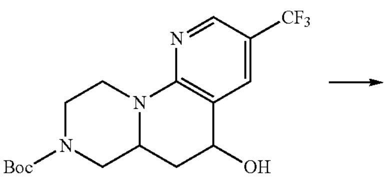

INT B31

-continued

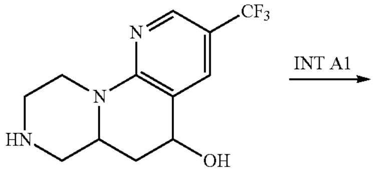

•TFA

Compound 80-1

-continued

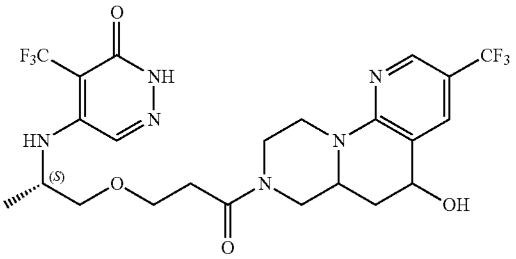

Compound 80

Step 1: Following an analogous procedure described in step 1 of example 2, INT B31 (0.31 g, 0.83 mmol, 1.0 eq.) and TFA (3 mL, 1N) were used as reactants to synthesize Compound 80-1 (crude, 0.42 g). LCMS: m/z=274 [M+1]$^+$.

Step 2: Following an analogous procedure described in step 2 of example 1, the Compound 80-1 (0.42 g, crude) and INT A1 (0.56 g, 1.81 mmol, 1.0 eq.) were used as reactants to synthesize Compound 80 (0.40 g, yield 85%). LCMS: m/z=565 [M+1]$^+$.

$^1$H NMR (400 MHz, DMSO-d$_6$) δ 12.44 (s, 1H), 8.28 (s, 1H), 7.91 (s, 1H), 7.71 (s, 1H), 6.32-6.24 (m, 1H), 5.79 (t, J=5.2 Hz, 1H), 4.72-4.62 (m, 2H), 4.50-4.34 (m, 1H), 4.20-4.10 (m, 1H), 4.08-3.93 (m, 1H), 3.73-3.63 (m, 2H), 3.49 (d, J=5.2 Hz, 3H), 3.45-3.37 (m, 0.5H), 3.17-3.08 (m, 0.5H), 2.96-2.78 (m, 1H), 2.77-2.67 (m, 1H), 2.66-2.55 (m, 2H), 2.31-2.17 (m, 1H), 1.61-1.47 (m, 1H), 1.19-1.12 (m, 3H).

Example 81

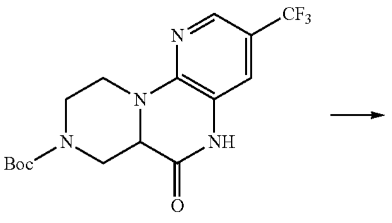

INT B2

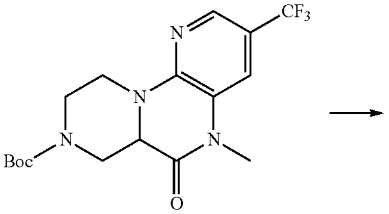

Compound 81-1

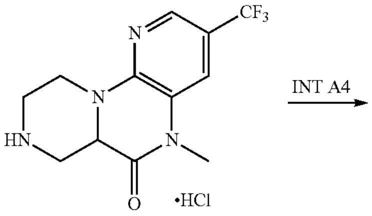

Compound 81-2

-continued

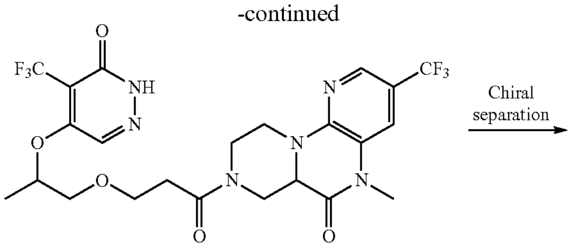

Compound 81

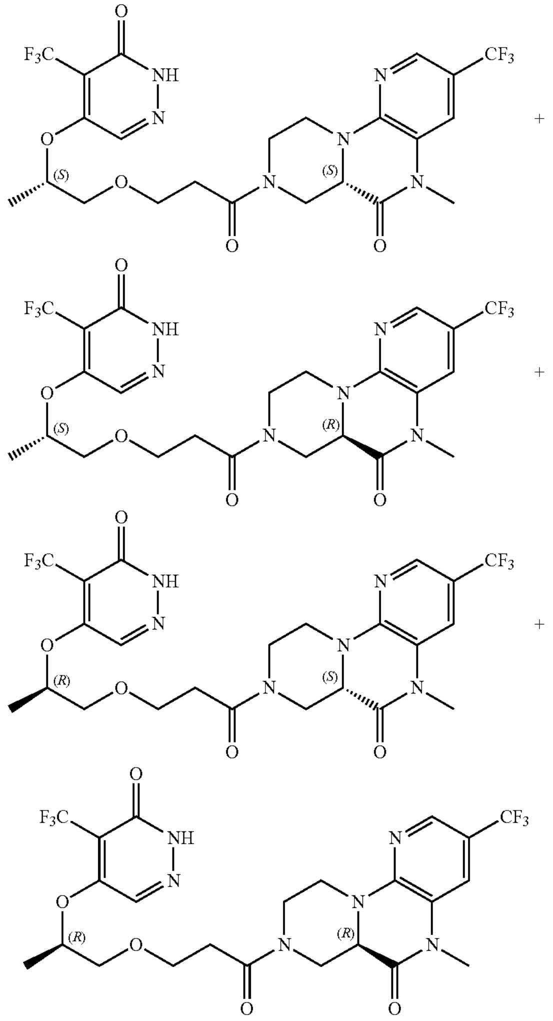

Step 1: A mixture of INT B2 (10.26 g, 27.56 mmol, 1.0 eq.), methyl iodide (28.01 g, 197.34 mmol, 7.16 eq.), $K_2CO_3$ (7.91 g, 57.23 mmol, 2.08 eq.) and DMF (100 mL) was stirred for 2 hrs at 65° C., quenched with water (200 mL) and extracted with EA (200 mL×3). The combined organic layers were concentrated under reduced pressure to obtain a residue which was purified with Prep-HPLC (C18 column, eluted with $H_2O/CH_3CN$) to afford Compound 81-1 (10.40 g, yield 97%). LCMS: m/z=387 [M+1]$^+$.

Step 2: Following an analogous procedure described in step 1 of example 1, the Compound 81-1 (10.03 g, 25.96 mmol, 1.0 eq.) and HCl/1,4-dioxane (50 mL, 1N) were used as reactants to synthesize Compound 81-2 (7.42 g, yield 88%). LCMS: m/z=287 [M+1]$^+$.

Step 3: Following an analogous procedure described in step 2 of example 1, the Compound 81-2 (1.69 g, 5.24 mmol, 1.20 eq.) and INT A4 (1.36 g, 4.38 mmol, 1.0 eq.) were used as reactants to synthesize Compound 81 (1.40 g, yield 55%). LCMS: m/z=579 $[M+1]^+$.

$^1$H NMR (400 MHz, MeOH-$d_4$) δ 8.21 (s, 1H), 8.14 (d, J=4.6, 1H), 7.42 (s, 1H), 5.18-5.00 (m, 2.5H), 4.66-4.55 (m, 0.5H), 4.52-4.45 (m, 0.5H), 4.11-4.04 (m, 1H), 4.03-3.97 (m, 0.5H), 3.86-3.79 (m, 1H), 3.79-3.70 (m, 1H), 3.71-3.64 (m, 1H), 3.63-3.56 (m, 1H), 3.37 (s, 3H), 3.27-3.11 (m, 1H), 2.90-2.58 (m, 4H), 1.34 (t, J=5.7, 3H).

The chiral separation of the Compound 81 (1.40 g) was performed by Chiral-Prep-HPLC with the following conditions: Equipment: Prep-HPLC-Gilson; Column: CHIRALPAK ID 2 cm×25 cm, Sum; Mobile Phase A: (Hex:DCM=3:1), Mobile Phase B: IPA, $V_{Mobile\ Phase\ A}$:$V_{Mobile\ Phase\ B}$=70:30; Flow Rate: 20 mL/min; Detector Wavelength: 220 nm. This resulted in the first eluting stereoisomer (Compound 81A, 32.5 mg, Retention time: 6.38 min), the second eluting stereoisomer (Compound 81B, 30.3 mg, Retention time: 7.04 min), a third eluting stereoisomer (Compound 81C, 51.4 mg, Retention time: 8.01 min), and a fourth eluting stereoisomer (Compound 81D, 44.5 mg, Retention time: 9.02 min).

The following compounds were synthesized using the above procedure or modification procedure using the corresponding intermediates.

| Example | Compound | Chiral separation | Structure | INT | $^1$H NMR and MS: $(M + H)^+$ |
|---|---|---|---|---|---|
| 82 | 82A & 82B & 82C & 82D | Column: CHIRAL ART Cellulose SA 2 cm × 25 cm, 5 um; Mobile Phase A: MTBE, Mobile Phase B: EtOH, $V_{MobilePhaseA}$:$V_{MobilePhaseB}$ = 50:50; Flow Rate: 20 mL/min Compound 82A: Retention time: 6.24 min; Compound 82B: Retention time: 6.82 min; Compound 82C: Retention time: 9.27 min; Compound 82D: Retention time: 10.04 min | 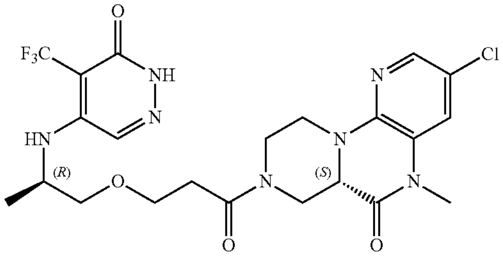<br>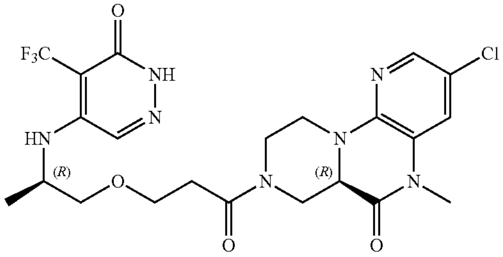<br>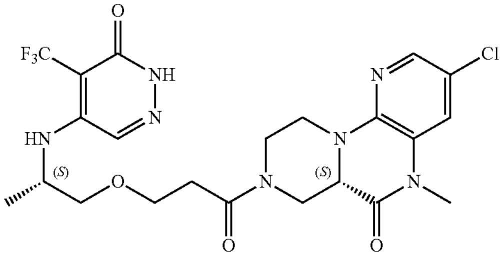<br>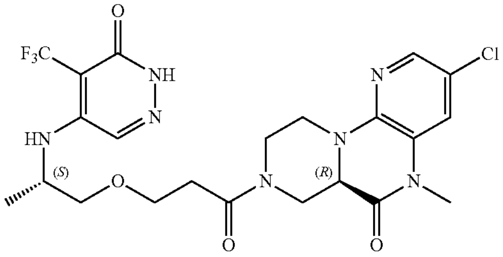 | A4 & B3 | MS: $(M + H)^+$ 545. Compound 82A: $^1$H NMR (400 MHz, MeOH-$d_4$) δ 8.18 (d, J = 21.6 Hz, 1H), 7.83 (s, 1H), 7.33 (d, J = 12.8 Hz, 1H), 5.14-5.00 (m, 1.5H), 4.87-4.86 (m, 1H), 4.61-4.59 (m, 0.5H), 4.53-4.45 (m, 0.5H), 4.43-4.32 (m, 1H), 4.12-4.04 (m, 0.5H), 3.90-3.70 (m, 3H), 3.69-3.56 (m, 2H), 3.32-3.30 (m, 2H), 3.22-3.13 (m, 1H), 2.82-2.55 (m, 4H), 1.33 (t, J = 7.2 Hz, 3H); Compound 82B: $^1$H NMR (400 MHz, MeOH-$d_4$) δ 8.19 (s, 1H), 7.82 (d, J = 6.4 Hz, 1H), 7.34 (s, 1H), 5.15-5.00 (m, 1.5H), 4.87-4.86 (m, 1H), 4.61-4.59 (m, 0.5H), 4.53-4.45 (m, 0.5H), 4.43-4.32 (m, 1H), 4.12-4.04 (m, 0.5H), 3.91-3.72 (m, 3H), 3.69-3.56 (m, 2H), 3.32-3.30 (m, 2H), 3.26-3.10 (m, 1H), 2.82-2.56 (m, 4H), 1.33 (t, J = 7.2 Hz, 3H); Compound 82C: $^1$H NMR (400 MHz, MeOH-$d_4$) δ 8.19 (s, 1H), 7.82 (d, J = 6.4 Hz, 1H), 7.34 (s, 1H), 5.15-5.00 (m, 1.5H), 4.87-4.86 (m, 1H), 4.66-4.58 (m, 0.5H), 4.51-4.44 (m, 0.5H), 4.43-4.33 (m, 1H), 4.11-4.03 (m, 0.5H), 3.91-3.72 (m, 3H), 3.69-3.56 (m, 2H), 3.32-3.30 (m, 2H), 3.27-3.13 (m, 1H), 2.83-2.56 (m, 4H), 1.33 (t, J = 7.2 Hz, 3H); Compound 82D: $^1$H NMR (400 MHz, MeOH-$d_4$) δ 8.18 (d, J = 22.0 Hz, 1H), 7.83 (s, 1H), 7.33 (d, J = 12.8 Hz, 1H), 5.14-5.00 (m, 1.5H), 4.87-4.86 (m, 1H), 4.66-4.59 (m, 0.5H), 4.54-4.44 (m, 0.5H), 4.43-4.33 (m, 1H), 4.11-4.03 (m, 0.5H), 3.91-3.72 (m, 3H), 3.69-3.56 (m, 2H), 3.32-3.30 (m, 2H), 3.27-3.13 (m, 1H), 2.83-2.55 (m, 4H), 1.33 (t, J = 7.2 Hz, 3H). |

-continued

| Example | Compound | Chiral separation | Structure | INT | $^1$H NMR and MS: $(M + H)^+$ |
|---|---|---|---|---|---|
| 83 | 83A & 83B & 83C & 83D | Column: CHIRALPAK IG 2 cm × 25 cm, 5 um; Mobile Phase A: Hex: DCM = 3:1, Mobile Phase B: EtOH, $V_{MobilePhaseA}$: $V_{MobilePhaseB}$ = 65:35; Flow Rate: 20 mL/min; Detector Wavelength: 220 nm Compound 83A: Retention time: 4.82 min; Compound 83B: Retention time: 5.32 min; Compound 83C: Retention time: 6.78 min; Compound 83D: Retention time: 8.06 min. | 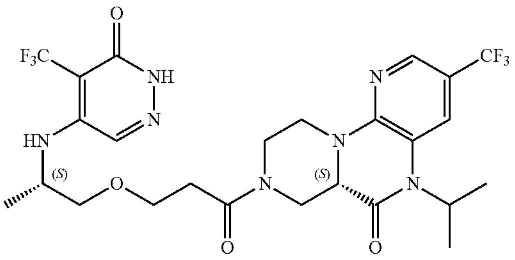<br>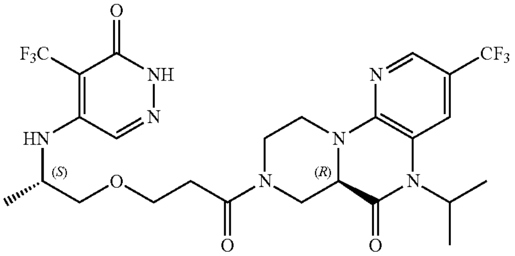<br>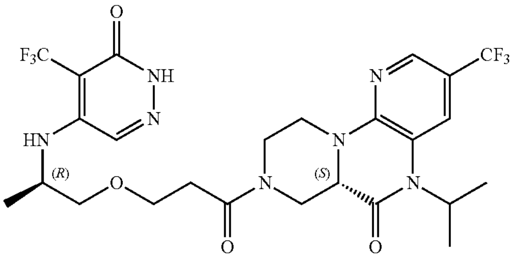<br>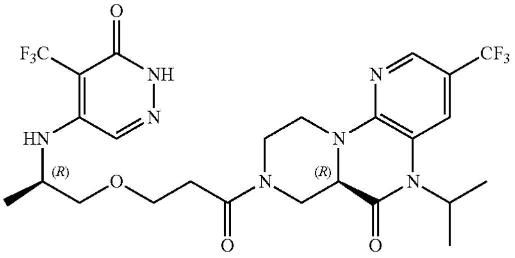 | A4 & B2 | MS: $(M + H)^+$ 607. Compound 83A: $^1$H NMR (400 MHz, MeOH-$d_4$) δ 8.23-8.14 (m, 2H), 7.53 (s, 1H), 5.15-5.06 (m, 1H), 5.02 (d, J = 13.6 Hz, 0.5H), 4.71-4.59 (m, 1.5H), 4.51-4.38 (m, 1.5H), 4.09 (d, J = 13.6 Hz, 0.5H), 3.92-3.70 (m, 3H), 3.70-3.56 (m, 2H), 3.27-3.18 (m, 1H), 2.86-2.55 (m, 4H), 1.55 (d, J-6.8 Hz, 3H), 1.51 (d, J = 6.8 Hz, 3H), 1.34 (d, J = 6.4 Hz, 3H); Compound 83B: $^1$H NMR (400 MHz, MeOH-$d_4$) δ 8.21 (s, 1H), 8.16 (d, J = 5.6 Hz, 1H), 7.53 (s, 1H), 5.15-5.06 (m, 1H), 5.05-4.98 (m, 0.5H), 4.70-4.59 (m, 1.5H), 4.50-4.41 (m, 1.5H), 4.12-4.05 (m, 0.5H), 3.92-3.64 (m, 4H), 3.63-3.55 (m, 1H), 3.27-3.18 (m, 1H), 2.88-2.62 (m, 4H), 1.55 (d, J = 6.8 Hz, 3H), 1.51 (d, J = 6.8 Hz, 3H), 1.34 (d, J = 6.4 Hz, 3H); Compound 83C: $^1$H NMR (400 MHz, MeOH-$d_4$) δ 8.21 (s, 1H), 8.16 (d, J = 5.6 Hz, 1H), 7.53 (s, 1H), 5.15-5.07 (m, 1H), 5.05-4.98 (m, 0.5H), 4.71-4.57 (m, 1.5H), 4.49-4.40 (m, 1.5H), 4.12-4.04 (m, 0.5H), 3.91-3.64 (m, 4H), 3.63-3.55 (m, 1H), 3.27-3.18 (m, 1H), 2.88-2.59 (m, 4H), 1.55 (d, J = 6.8 Hz, 3H), 1.51 (d, J = 6.8 Hz, 3H), 1.34 (d, J = 6.0 Hz, 3H) Compound 83D: $^1$H NMR (400 MHz, MeOH-$d_4$) δ 8.23-8.14 (m, 2H), 7.53 (s, 1H), 5.15-5.06 (m, 1H), 5.02 (d, J = 13.2 Hz, 0.5H), 4.70-4.58 (m, 1.5H), 4.50-4.38 (m, 1.5H), 4.09 (d, J = 14.0 Hz, 0.5H), 3.92-3.70 (m, 3H), 3.70-3.56 (m, 2H), 3.29-3.18 (m, 1H), 2.86-2.54 (m, 4H), 1.55 (d, J = 6.8 Hz, 3H), 1.51 (d, J = 6.8 Hz, 3H), 1.34 (d, J = 6.4 Hz, 3H). |

Example 84

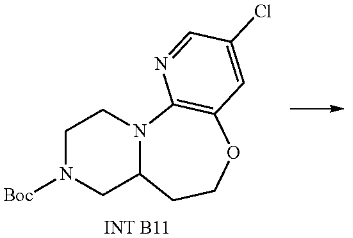

INT B11

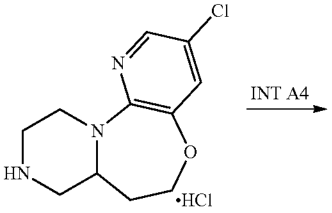

Compound 84-1

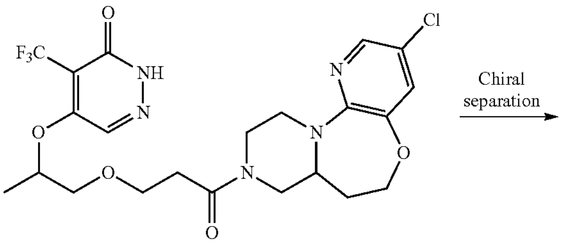

Compound 84

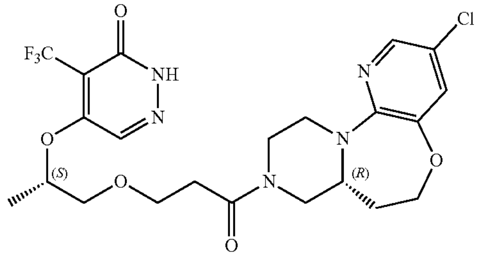

+

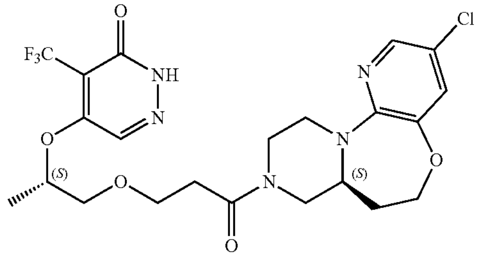

+

-continued

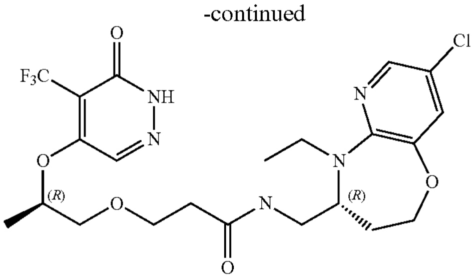

+

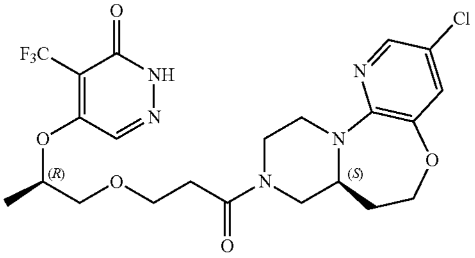

Step 1: HCl/1,4-dioxane (10 mL, 1N) was added to a solution of INT B11 (0.97 g, 2.85 mmol, 1.0 eq.) dissolved in 1,4-dioxane (2 mL). The reaction mixture was stirred for 1 h at room temperature, and then concentrated under reduced pressure to afford crude Compound 84-1 (crude, 0.85 g). LCMS: m/z=240 $[M+1]^+$.

Step 2: Compound 84-1 (0.85 g, crude), INT A4 (0.60 g, 1.93 mmol, 1.0 eq.) and TEA (1 mL) were dissolved in DMF (6 mL) to form a solution, and then PyBOP (1.32 g, 2.53 mmol, 1.31 eq.) was added to the solution. The reaction mixture was stirred for 2 hrs at room temperature and water (1 mL) was added. The resulting mixture was purified with Prep-HPLC (C18 column, eluted with $H_2O/CH_3CN$) to afford Compound 84 (1.01 g, yield 98%). LCMS: m/z=532 $[M+1]^+$.

$^1H$ NMR (400 MHz, MeOH-$d_4$) δ8.20 (d, J=4.4, 1H), 7.79 (s, 1H), 7.13 (s, 1H), 5.10 (s, 1H), 4.40-4.24 (m, 2H), 3.95-3.39 (m, 11H), 2.69-2.52 (m, 2H), 2.20-2.05 (m, 1H), 2.00-1.87 (m, 1H), 1.34 (d, J=6.0 Hz, 3H).

The chiral separation of the Compound 84 (1.01 g) was performed by Chiral-Prep-HPLC with the following conditions: Equipment: Prep-HPLC-Gilson; Column: CHIRAL ART Cellulose SB 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 84A, 265.0 mg, Retention time: 4.69 min), the second eluting stereoisomer (Compound 84B, 245.0 mg, Retention time: 5.93 min), a third eluting stereoisomer (Compound 84C, 135.8 mg, Retention time: 8.16 min), and a fourth eluting stereoisomer (Compound 84D, 153.3 mg, Retention time: 8.90 min).

The following compounds were synthesized using the above procedure or modification procedure using the corresponding intermediates.

| Example | Compound | Chiral separation | Structure | INT | $^1$H NMR and MS: (M + H)$^+$ |
|---|---|---|---|---|---|
| 85 | 85A & 85B & 85C & 86D | Column: CHIRALPAK IG 2 cm × 25 cm, 5 um; Mobile Phase A: MTBE, Mobile Phase B: EtOH, $V_{MobilePhaseA}$: $V_{MobilePhaseB}$ = 50:50; Flow Rate: 20 mL/min; Detector Wavelength: 220 nm Compound 85A: Retention time: 4.53 min; Compound 85B: Retention time: 5.35 min; Compound 85C: Retention time: 6.80 min; Compound 85D: Retention time: 9.81 min. | 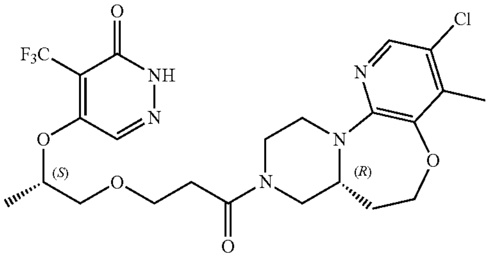 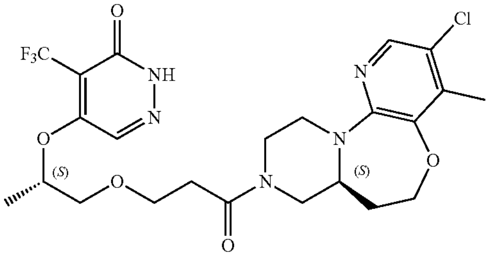 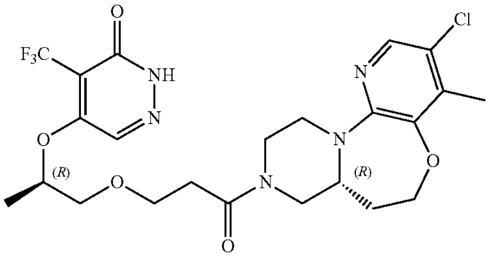 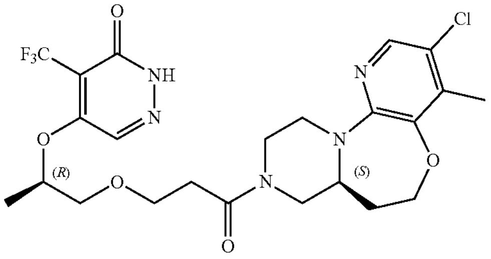 | A4 & B16 | MS: (M + H)$^+$ 546. Compound 85A: $^1$H NMR (400 MHz, MeOH-$d_4$) δ 8.20 (d, J = 6.8 Hz, 1H), 7.79 (d, J = 3.6 Hz, 1H), 5.10 (s, 1H), 4.35-4.27 (m, 2H), 3.91-3.41 (m, 11H), 2.67-2.51 (m, 2H), 2.22 (s, 3H), 2.14-2.02 (m, 1H), 1.99-1.87 (m, 1H), 1.34 (d, J = 6.4 Hz, 3H); Compound 85B: $^1$H NMR (400 MHz, MeOH-$d_4$) δ 8.22 (s, 1H), 7.79 (s, 1H), 5.15-5.06 (m, 1H), 4.35-4.24 (m, 2H), 3.92-3.63 (m, 7H), 3.62-3.54 (m, 2H), 3.53-3.41 (m, 2H), 2.67-2.53 (m, 2H), 2.22 (s, 3H), 2.14-2.02 (m, 1H), 2.00-1.87 (m, 1H), 1.34 (d, J = 6.0 Hz, 3H); Compound 85C: $^1$H NMR (400 MHz, MeOH-$d_4$) δ 8.22 (s, 1H), 7.79 (s, 1H), 5.16-5.06 (m, 1H), 4.35-4.24 (m, 2H), 3.92-3.63 (m, 7H), 3.62-3.54 (m, 2H), 3.53-3.41 (m, 2H), 2.68-2.54 (m, 2H), 2.22 (s, 3H), 2.14-2.01 (m, 1H), 1.98-1.85 (m, 1H), 1.34 (d, J = 6.0 Hz, 3H); Compound 85D: $^1$H NMR (400 MHz, MeOH-$d_4$) δ 8.20 (d, J = 6.8 Hz, 1H), 7.79 (d, J = 3.6 Hz, 1H), 5.15-5.06 (m, 1H), 4.35-4.24 (m, 2H), 3.91-3.62 (m, 7H), 3.62-3.52 (m, 2H), 3.52-3.41 (m, 2H), 2.67-2.51 (m, 2H), 2.22 (s, 3H), 2.14-2.01 (m, 1H), 2.00-1.88 (m, 1H), 1.34 (d, J = 6.4 Hz, 3H). |

-continued

| Example | Compound | Chiral separation | Structure | INT | $^1$H NMR and MS: (M + H)$^+$ |
|---|---|---|---|---|---|
| 86 | 86A & 86B & 86C & 86D | Column: CHIRAL ART Cellulose SA 2 cm × 25 cm, 5 um; Mobile Phase A: Hex: DCM = 3:1, Mobile Phase B: EtOH, $V_{MobilePhaseA}$: $V_{MobilePhaseB}$ = 75:25; Flow Rate: 20 mL/min Compound 86A: Retention time: 4.66 min; Compound 86B: Retention time: 5.02 min; Compound 86C: Retention time: 5.61 min; Compound 86D: Retention time: 5.88 min | 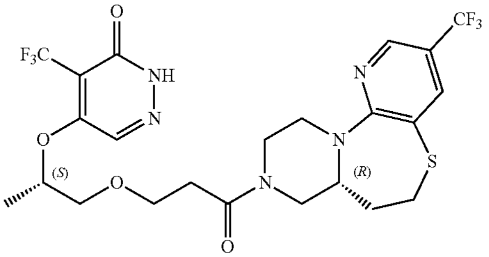 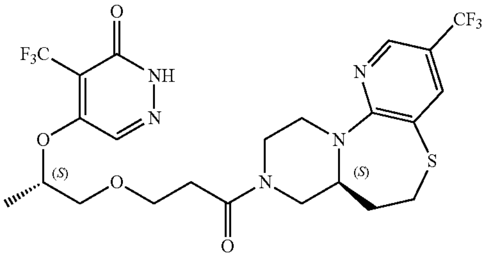 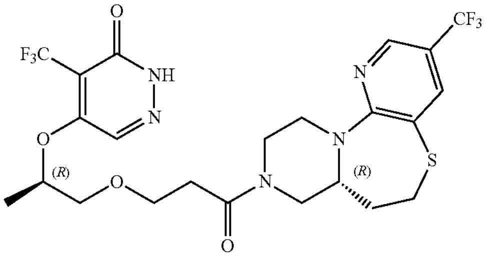 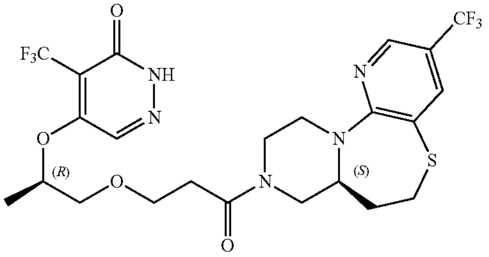 | A4 & B18 | MS: (M + H)$^+$ 582. Compound 86A: $^1$H NMR (400 MHz, MeOH-$d_4$) δ 8.21 (s, 1H), 8.15 (s, 1H), 7.59 (d, J = 2.0 Hz, 1H), 5.14-5.05 (m, 1H), 4.06-3.93 (m, 2H), 3.86-3.53 (m, 10H), 2.98-2.90 (m, 1H), 2.58 (t, J = 5.6 Hz, 2H), 2.15-2.06 (m, 1H), 1.98-1.82 (m, 1H), 1.34 (d, J-6.2 Hz, 3H); Compound 86B: $^1$H NMR (400 MHz, MeOH-$d_4$) δ 8.22 (d, J = 5.6 Hz, 1H), 8.15 (s, 1H), 7.59 (s, 1H), 5.14-5.05 (m, 1H), 4.04-3.91 (m, 2H), 3.85-3.52 (m, 10H), 2.98-2.89 (m, 1H), 2.66-2.51 (m, 2H), 2.13-2.02 (m, 1H), 1.95-1.82 (m, 1H), 1.34 (d, J = 6.2 Hz, 3H); Compound 86C: $^1$H NMR (400 MHz, MeOH-$d_4$) δ 8.22 (d, J = 5.6 Hz, 1H), 8.15 (s, 1H), 7.59 (s, 1H), 5.15-5.05 (m, 1H), 4.04-3.90 (m, 2H), 3.85-3.51 (m, 10H), 2.98-2.89 (m, 1H), 2.66-2.51 (m, 2H), 2.13-2.03 (m, 1H), 1.96-1.82 (m, 1H), 1.34 (d, J = 6.2 Hz, 3H); Compound 86D: $^1$H NMR (400 MHz, MeOH-$d_4$) δ 8.21 (s, 1H), 8.15 (s, 1H), 7.59 (d, J = 2.0 Hz, 1H), 5.15-5.05 (m, 1H), 4.05-3.93 (m, 2H), 3.86-3.53 (m, 10H), 2.99-2.90 (m, 1H), 2.64-2.53 (m, 2H), 2.16-2.04 (m, 1H), 1.98-1.82 (m, 1H), 1.34 (d, J = 6.2 Hz, 3H). |

Example 87

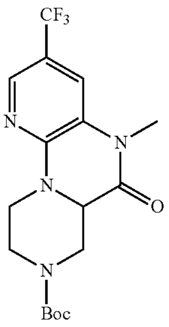

INT B37

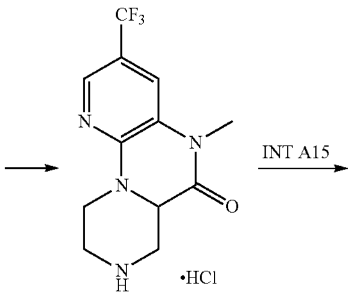

Compound 87-1

-continued

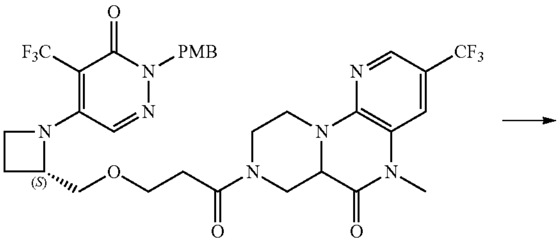

Compound 87-2

-continued

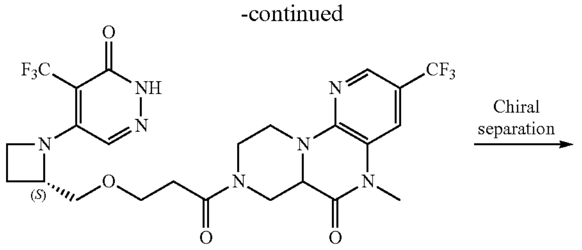

Compound 87

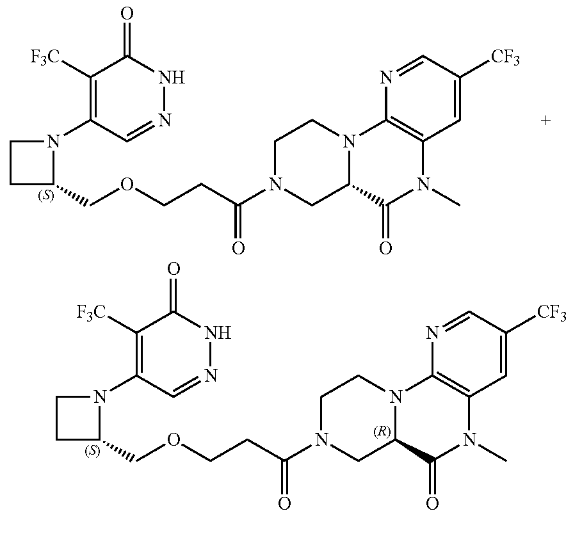

Step 1: Following an analogous procedure described in step 1 of example 1, INT B37 (10.03 g, 25.96 mmol, 1.0 eq.) and HCl/1,4-dioxane (50 mL, 1N) were used as reactants to synthesize Compound 87-1 (7.42 g, yield 88%). LCMS: m/z=287 $[M+1]^+$.

Step 2: Following an analogous procedure described in step 2 of example 1, Compound 87-1 (2.56 g, 7.93 mmol, 1.20 eq.) and INT A15 (2.94 g, 6.66 mmol, 1.0 eq.) were used as reactants to synthesize Compound 87-2 (2.13 g, yield 45%). LCMS: m/z=710 $[M+1]^+$.

Step 3: TfOH (3 mL) was added dropwise at −20° C. to a solution of Compound 87-2 (2.16 g, 3.04 mmol, 1.0 eq.) dissolved in TFA (10 mL). After stirring for 2 hrs at −20° C., the pH of the reaction mixture was adjusted to 7-8 with sodium bicarbonate aqueous solution. The resulting mixture was extracted with EA (100 mL×2). The combined organic layers were dried over anhydrous $Na_2SO_4$, and then concentrated under reduced pressure to obtain a residue which was purified with Prep-HPLC (C18 column, eluted with $H_2O/CH_3CN$) to afford Compound 87 (1.41 g, yield 78). LCMS: m/z=590 $[M+1]^+$.

$^1H$ NMR (400 MHz, $CD_3OD$) δ 8.14 (s, 11H), 7.79 (d, J=8.8 Hz, 11H), 7.42 (s, 11H), 5.06 (d, J=13.2 Hz, 1H), 4.69-4.37 (m, 3H), 4.17-4.09 (m, 1H), 3.99 (d, J=7.6 Hz, 2H), 3.91-3.76 (m, 4H), 3.37 (s, 3H), 2.93-2.66 (m, 4H), 2.64-2.47 (m, 1H), 2.18-1.96 (m, 1H), 1.35-1.18 (m, 1H).

The chiral separation of the Compound 87 (1.41 g) was performed by Chiral-Prep-HPLC with the following conditions: Equipment: Prep-HPLC-Gilson; Column: CHIRALPAK IE 2 cm×25 cm, 5 um; Mobile Phase A: MTBE, Mobile Phase B: EtOH, $V_{Mobile\ Phase\ A}$:$V_{Mobile\ Phase\ B}$=50:50; Flow Rate: 16 mL/min; Detector Wavelength: 220 nm. This resulted in the first eluting stereoisomer (Compound 87A, 805.7 mg, Retention time: 9.12 min), and the second eluting stereoisomer (Compound 87B, 794.7 mg, Retention time: 11.38 min).

The following compounds were synthesized using the above procedure or modification procedure using the corresponding intermediates.

| Example | Compound | Chiral separation | Structure | INT | $^1H$ NMR and MS: $(M + H)^+$ |
|---|---|---|---|---|---|
| 88 | 88A & 88B | Column: CHIRALPAK IG 2 cm × 25 cm, 5 um; Mobile Phase A: MTBE, Mobile Phase B: EtOH, $V_{MobilePhaseA}$: $V_{MobilePhaseB}$ = 45:55; Flow Rate: 20 mL/min; Detector Wavelength: 220 nm Compound 88A: Retention time: 12.21 min; Compound 88B: Retention time: 15.41 min. | 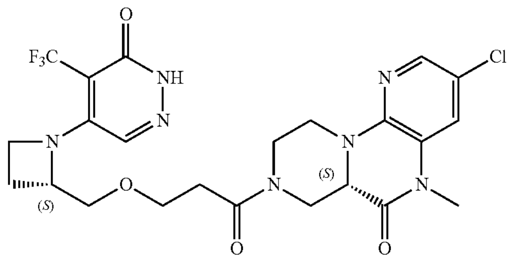 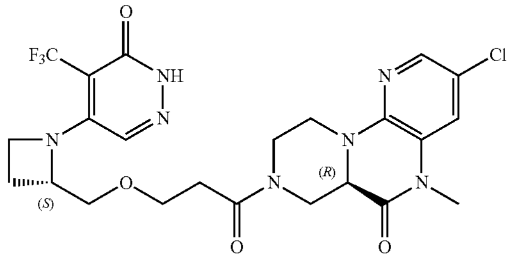 | A15 & B3 | MS: $(M + H)^+$ 556. Compound 88A: $^1H$ NMR (400 MHz, DMSO-$d_6$) δ 12.33 (s, 1H), 7.89 (s, 1H), 7.65 (s, 1H), 7.44 (s, 1H), 4.89-4.77 (m, 1.5H), 4.53-4.42 (m, 0.5H), 4.35-4.23 (m, 2.5H), 4.05-3.97 (m, 1H), 3.93-3.81 (m, 1.5H), 3.81-3.65 (m, 5H), 3.25 (d, J = 10.8 Hz, 3H), 2.76-2.56 (m, 4H), 1.99 (s, 1H), 1.31-1.14 (m, 1H); Compound 88B: $^1H$ NMR (400 MHz, MeOH-$d_4$) δ 7.84 (s, 1H), 7.80 (s, 1H), 7.35 (s, 1H), 5.04 (d, J = 13.2 Hz, 0.5H), 4.91-4.87 (m, 1H), 4.62 (d, J = 12.4 Hz, 0.5H), 4.52-4.35 (m, 2.5H), 4.13 (d, J = 13.8 Hz, 0.5H), 4.04-3.94 (m, 1H), 3.94-3.75 (m, 5H), 4.89-4.77 (m, 1H), 3.36-3.32(m, 1H), 3.29-3.18 (m, 2H), 2.83-2.62 (m,4H), 2.61-2.49 (m, 1H), 2.12-2.01 (m, 1H). |

-continued

| Example | Compound | Chiral separation | Structure | INT | $^1$H NMR and MS: $(M + H)^+$ |
|---|---|---|---|---|---|
| 89 | 89A & 89B | Column: CHIRAL ART Cellulose SB 2 cm × 25 cm, 5 um; Mobile Phase A: MTBE, Mobile Phase B: MeOH, $V_{MobilePhaseA}$: $V_{MobilePhaseB}$ = 60:40; Flow Rate: 20 mL/min Compound 89A: Retention time: 7.36 min; Compound 89B: Retention time: 9.55 min. | 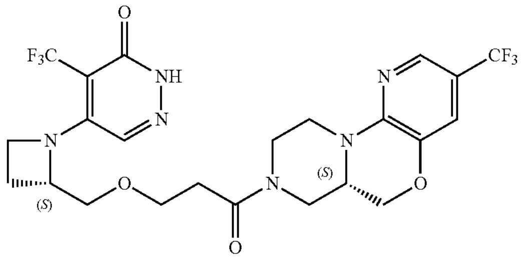 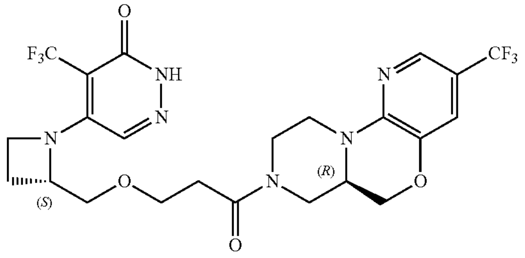 | A15 & B7 | MS: $(M + H)^+$ 563. Compound 89A: $^1$H NMR (400 MHz, MeOH-$d_4$) δ 8.00 (s, 1H), 7.80 (s, 1H), 7.17 (s, 1H), 4.63-4.55 (m, 2H), 4.51-4.32 (m, 2H), 4.12 (t, J = 11.2 Hz, 1H), 4.03-3.98 (m, 2H), 3.90-3.74 (m, 4H), 3.51-3.45 (m, 1H), 3.29-3.22 (m, 1H), 3.10-2.80 (m, 2H), 2.80-2.69 (m, 2H), 2.60-2.51 (m, 2H), 2.11-2.00 (m, 1H); Compound 89B: $^1$H NMR (400 MHz, MeOH-$d_4$) δ 8.00 (s, 1H), 7.80 (s, 1H), 7.16 (s, 1H), 4.67-4.52 (m, 2H), 4.49-4.34 (m, 2H), 4.13 (t, J = 13.2 Hz, 1H), 4.06-3.94 (m, 2H), 3.89-3.75 (m, 4H), 3.56-3.37 (m, 1H), 3.29-3.23 (m, 1H), 3.06-2.80 (m, 2H), 2.78-2.68 (m, 2H), 2.61-2.49 (m, 2H), 2.11-2.00 (m, 1H). |
| 90 | 90A & 90B | Column: CHIRAL ART Cellulose SA 2 cm × 25 cm, 5 um; Mobile Phase A: MTBE, Mobile Phase B: EtOH, $V_{MobilePhaseA}$: $V_{MobilePhaseB}$ = 60:40; Flow Rate: 20 mL/min Compound 90A: Retention time: 7.51 min; Compound 90B: Retention time: 9.35 min. | 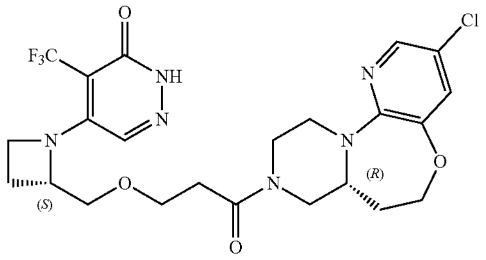 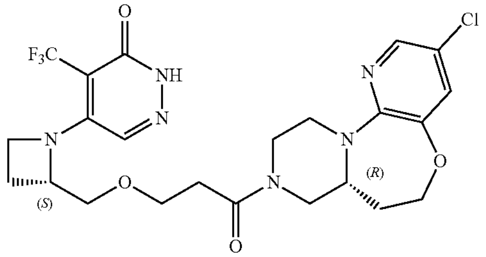 | A13 & B11 | MS: $(M + H)^+$ 543. Compound 90A: $^1$H NMR (400 MHz, MeOH-$d_4$) δ 7.83-7.77 (m, 2H), 7.13 (s, 1H), 4.50-4.39 (m, 1H), 4.39-4.24 (m, 2H), 4.05-3.94 (m, 1H), 3.93-3.74 (m, 8H), 3.74-3.60 (m, 2H), 3.58-3.40 (m, 2H), 2.73-2.65 (m, 2H), 2.61-2.50 (m, 1H), 2.21-1.87 (m, 3H); Compound 90B: $^1$H NMR (400 MHz, MeOH-$d_4$) δ 7.81 (s, 1H), 7.79 (s, 1H), 7.13 (s, 1H), 4.50-4.39 (m, 1H), 4.38-4.23 (m, 2H), 4.04-3.95 (m, 1H), 3.92-3.76 (m, 7H), 3.74-3.459 (m, 5H), 2.74-2.62 (m, 2H), 2.61-2.49 (m, 1H), 2.22-2.01 (m, 2H), 1.98-1.89 (m, 1H). |
| 91 | 91 | N/A | 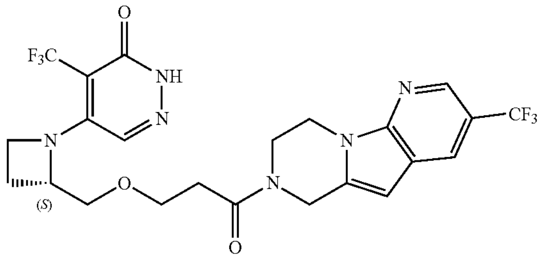 | A15 & B23 | $^1$H NMR (400 MHz, MeOH-$d_4$) δ 8.47 (s, 1H), 8.22 (s, 1H), 7.75 (d, J = 10.0 Hz, 1H), 6.50 (d, J = 9.2 Hz, 1H), 5.10-5.05 (m, 1H), 4.99 (d, J = 23.2 Hz, 1H), 4.80-4.75 (m, 1H), 4.44-4.27 (m, 3H), 4.18-4.04 (m, 2H), 4.00-3.82 (m, 3H), 3.83-3.74 (m, 2H), 2.88-2.76 (m, 2H), 2.57-2.43 (m, 1H), 2.13-1.95 (m, 1H); MS: $(M + H)^+$ 545. |
| 92 | 92 | N/A | 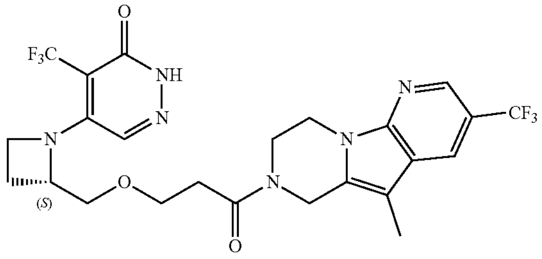 | A15 & B25 | $^1$H NMR (400 MHz, DMSO-$d_6$) δ 12.33 (s, 1H), 8.52 (s, 1H), 8.32 (s, 1H), 7.65 (s, 1H), 4.96-4.72 (m, 3H), 4.36-4.13 (m, 3H), 4.05-3.92 (m, 2H), 3.88-3.67 (m, 5H), 2.78 (s, 2H), 2.49-2.32 (m, 1H), 2.25 (d, J = 11.0, 3H), 2.04-1.90 (m, 1H); MS: $(M + H)^+$ 559. |

-continued

| Example | Compound | Chiral separation | Structure | INT | $^1H$ NMR and MS: $(M + H)^+$ |
|---|---|---|---|---|---|
| 93 | 93A & 93B | Column: CHIRAL ART Cellulose SB 2 cm × 25 cm, 5 um; Mobile Phase A: MTBE, Mobile Phase B: EtOH, $V_{MobilePhaseA}$: $V_{MobilePhaseB}$ = 50:50; Flow Rate: 20 mL/min Compound 93A: Retention time: 5.51 min; Compound 93B: Retention time: 7.34 min. | 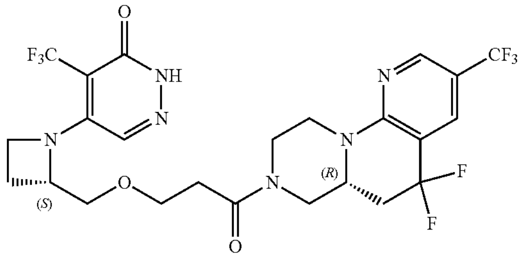 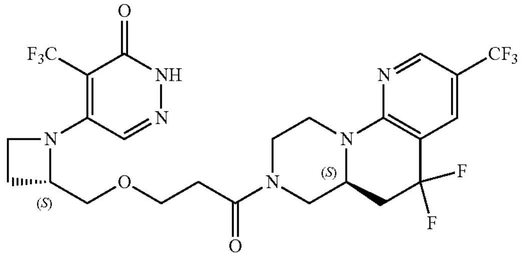 | A15 & B30 | Compound 93: $^1H$ NMR (400 MHz, DMSO-$d_6$) δ 12.47 (s, 1H), 7.92 (s, 1H), 7.70 (s, 1H), 6.79 (s, 1H), 6.29 (s, 1H), 6.24 (s, 1H), 4.56-4.39 (m, 2H), 4.21-4.10 (m, 1H), 3.99 (d, J = 12.0 Hz, 1 H), 3.74-3.61 (m, 2H), 3.51-3.45 (m, 3H), 3.43-3.38 (m, 1H), 3.25-3.00 (m, 2H), 2.99-2.73 (m, 2H), 2.71-2.56 (m, 3 H), 1.15 (d, J = 5.6 Hz, 3H); MS: $(M + H)^+$ 597. |

Example 94

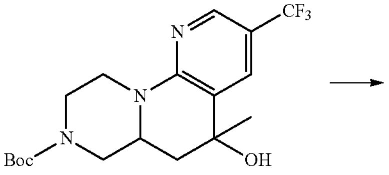

INT B29

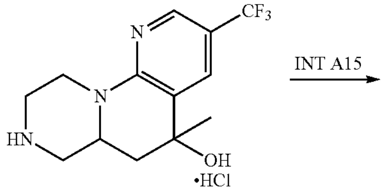

Compound 94-1

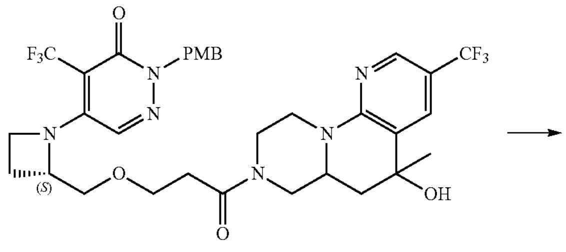

Compound 94-2

-continued

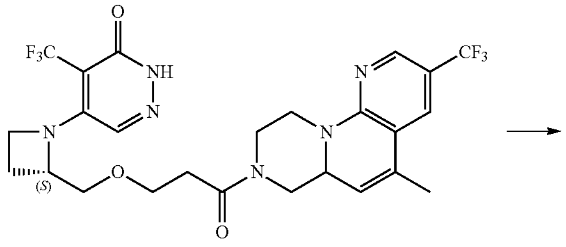

Compound 94-3

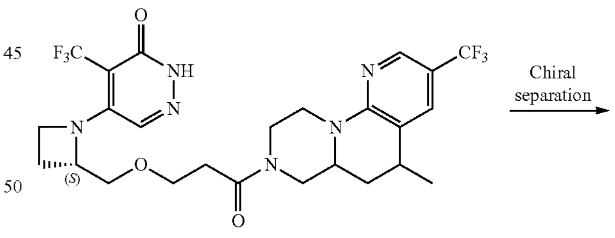

Compound 94

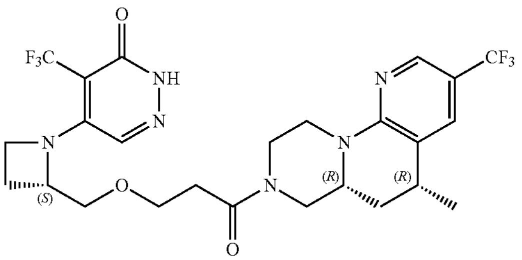

+

-continued

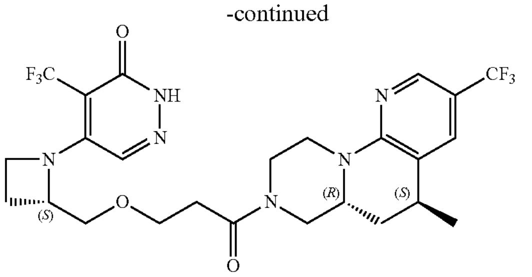

+

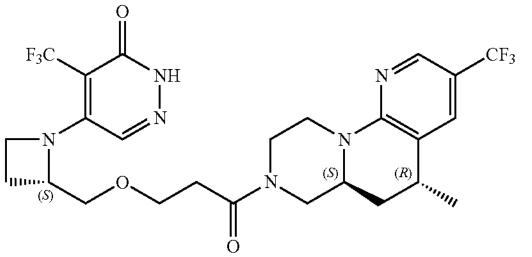

+

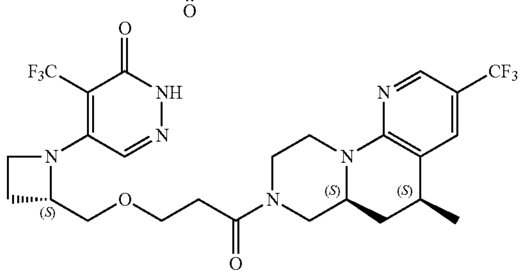

Step 1: Following an analogous procedure described in step 1 of example 1, INT B29 (225 mg, 0.58 mmol, 1.0 eq.) and HCl/1,4-dioxane (10 mL, 1N) were used as reactants to synthesize Compound 94-1 (crude, 0.20 g). LCMS: m/z=288 $[M+1]^+$.

Step 2: Following an analogous procedure described in step 2 of example 1, Compound 94-1 (0.20 g, crude) and INT A15 (287 mg, 0.65 mmol, 1.0 eq.) were used as reactants to synthesize Compound 94-2 (316 mg, yield 76%). LCMS: m/z=711 $[M+1]^+$.

Step 3: Following an analogous procedure described in step 3 of example 83, the Compound 94-2 (316 mg, 0.44 mmol, 1.0 eq.), TFA (2 mL) and TfOH (0.5 mL) were used as reactants to synthesize Compound 94-3 (186 mg, yield 73%). LCMS: m/z=573 $[M+1]^+$.

Step 4: A mixture of the Compound 94-3 (186 mg, 0.32 mmol, 1.0 eq.), Pd/C (89 mg, 0.48 w/w.) and MeOH (10 mL) was purged and maintained with an inert atmosphere of hydrogen, stirred for 5 hrs at room temperature, and then filtered. The filtrate was concentrated under reduced pressure to obtain a residue which was purified with Prep-HPLC (C18 column, eluted with $H_2O/CH_3CN$) to afford Compound 94 (130 mg, yield 72%). LCMS: m/z=575 $[M+1]^+$.

$^1$H NMR (400 MHz, MeOH-$d_4$) δ8.17 (s, 1H), 7.81 (s, 1H), 7.51 (s, 1H), 4.80-4.72 (m, 1H), 4.58-4.39 (m, 2H), 4.09 (d, J=13.0, 1H), 4.04-3.94 (m, 1H), 3.91-3.75 (m, 4H), 3.58-3.34 (m, 1H), 3.29-3.24 (m, 1H), 3.00-2.83 (m, 3H), 2.72 (t, J=5.6 Hz, 2H), 2.62-2.44 (m, 2H), 2.15-2.00 (m, 2H), 1.47-1.32 (m, 4H).

The chiral separation of the Compound 94 (130 mg) was performed by Chiral-Prep-HPLC with the following conditions: Equipment: Prep-HPLC-Gilson; Column: CHIRALPAK-ID column 2 cm×25 cm, 5 um; Mobile Phase A: MTBE, Mobile Phase B: EtOH, $V_{Mobile\ Phase\ A}$: $V_{Mobile\ Phase\ B}$=70:30; Flow Rate: 16 mL/min; Detector Wavelength: 220 nm. This resulted in the first eluting stereoisomer (Compound 94A, 6.2 mg, Retention time: 6.83 min), the second eluting stereoisomer (Compound 94B, 50.9 mg, Retention time: 7.02 min), a third eluting stereoisomer (Compound 94C, 9.3 mg, Retention time: 7.69 min), and a fourth eluting stereoisomer (Compound 94D, 51.2 mg, Retention time: 8.15 min).

Example 95

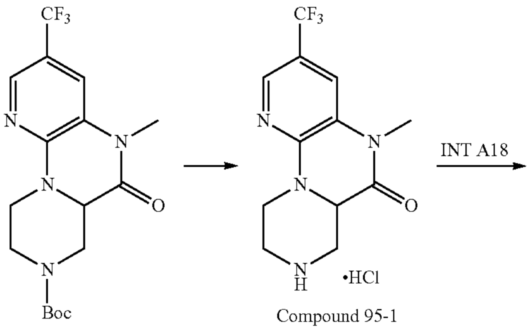

INT B37

Compound 95-1

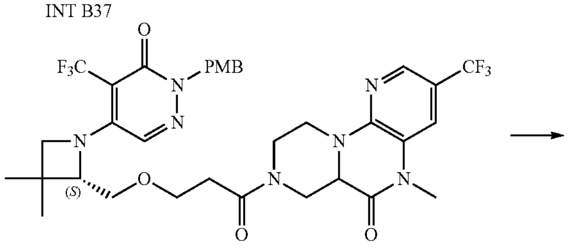

Compound 95-2

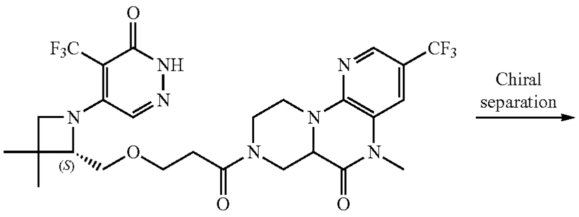

Compound 95

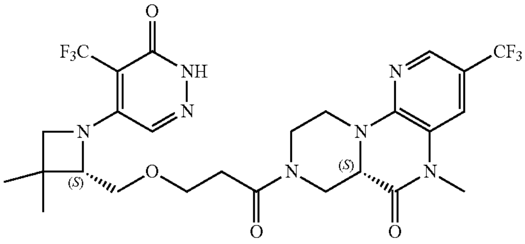

+

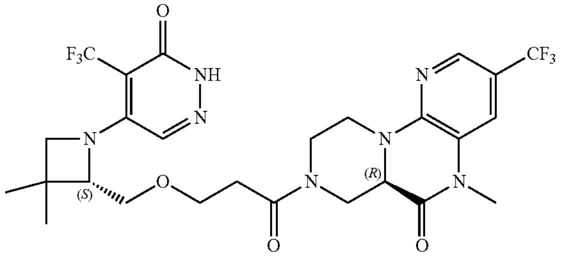

Step 1: Following an analogous procedure described in step 1 of example 1, INT B37 (10.03 g, 25.96 mmol, 1.0 eq.)

and HCl/1,4-dioxane (50 mL, 1N) were used as reactants to synthesize Compound 95-1 (7.42 g, yield 88%). LCMS: m/z=287 [M+1]$^+$.

Step 2: Following an analogous procedure described in step 2 of example 1, the Compound 95-1 (807 mg, 2.50 mmol, 2.02 eq.) and INT A18 (581 mg, 1.24 mmol, 1.0 eq.) were used as reactants to synthesize Compound 95-2 (186 mg, yield 20%). LCMS: m/z=738 [M+1]$^+$.

Step 3: Following an analogous procedure described in step 3 of example 83, the Compound 95-2 (186 mg, 0.25 mmol, 1.0 eq.), TFA (5 mL) and TfOH (0.5 mL) were used as reactants to synthesize Compound 95 (140 mg, yield 89%). LCMS: m/z=618 [M+1]$^+$.

$^1$H NMR (400 MHz, $CD_3OD$) δ 8.15 (s, 1H), 7.85 (s, 1H), 7.43 (s, 1H), 5.09-5.04 (m, 1H), 4.66-3.29 (m, 1.5H), 4.54-1.16 (m, 0.5H), 4.39-4.32 (m, 1H), 4.22-4.08 (m, 1.5H), 4.06-3.99 (m, 0.5H), 3.88-3.79 (m, 4H), 3.66-3.60 (m, 1H), 3.38 (d, J=3.2 Hz, 3H), 3.26-3.19 (m, 1H), 2.91-2.69 (m, 4H), 1.32-1.27 (m, 3H), 1.20 (s, 3H).

The chiral separation of the Compound 95 (140 mg) was performed by Chiral-Prep-HPLC with the following conditions: Equipment: Prep-HPLC-Gilson; Column: CHIRAL ART Cellulose SA 2 cm×25 cm, 5 um; Mobile Phase A: MTBE, Mobile Phase B: EtOH, $V_{Mobile\ Phase\ A}$: $V_{Mobile\ Phase\ B}$=50:50; Flow Rate: 20 mL/min; Detector Wavelength: 220 nm. This resulted in the first eluting stereoisomer (Compound 95A, 49.7 mg, Retention time 6.31 min), and the second eluting stereoisomer (Compound 95B, 51.1 mg, Retention time 7.72 min).

Example 96

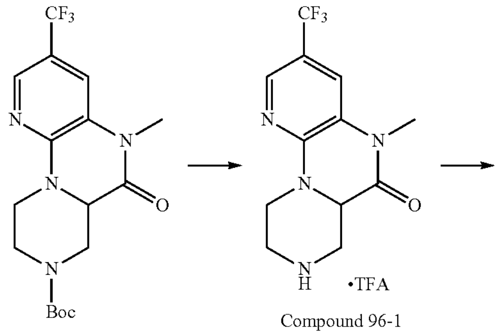

INT B37

Compound 96-1

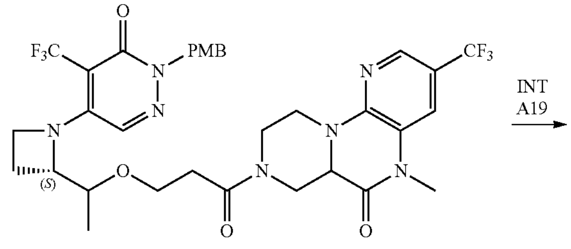

Compound 96-2

-continued

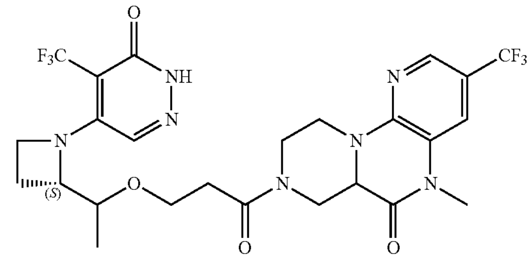

Compound 96

Step 1: Following an analogous procedure described in step 1 of example 2, INT B37 (0.65 g, 1.68 mmol, 1.0 eq.) and TFA (4 mL) were used as reactants to synthesize Compound 96-1 (crude, 1.22 g). LCMS: m/z=287 [M+1]$^+$.

Step 2: Following an analogous procedure described in step 2 of example 1, Compound 96-1 (0.25 g, crude) and INT A19 (0.35 g, 0.77 mmol, 1.0 eq.) were used as reactants to synthesize Compound 96-2 (0.14 g, yield 29%). LCMS: m/z=724 [M+1]$^+$.

Step 3: Following an analogous procedure described in step 3 of example 83, Compound 96-2 (0.14 g, 0.19 mmol, 1.0 eq.), TFA (5 mL) and TfOH (1 mL) were used as reactants to synthesize Compound 96 (32 mg, yield 27%). LCMS: m/z=604 [M+1]$^+$.

$^1$H NMR (400 MHz, $CD_3OD$) δ 8.14 (s, 1H), 7.92 (d, J=7.2 Hz, 0.5H), 7.75 (d, J=8.8 Hz, 0.5H), 7.43 (s, 1H), 5.11-4.97 (m, 0.5H), 4.83-4.76 (m, 0.5H), 4.68-4.33 (m, 4H), 4.19-3.84 (m, 5H), 3.84-3.44 (m, 2H), 3.27-3.11 (m, 1H), 2.92-2.42 (m, 5H), 2.18 (s, 1H), 1.98 (s, 1H), 1.19 (t, J=8.0 Hz, 3H).

Example 97

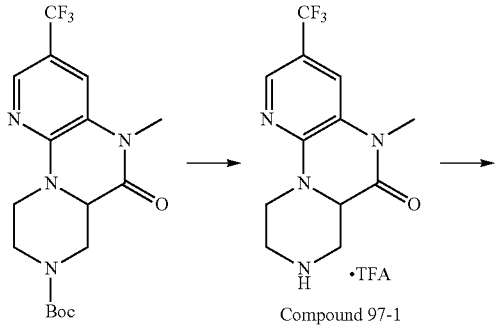

INT B37

Compound 97-1

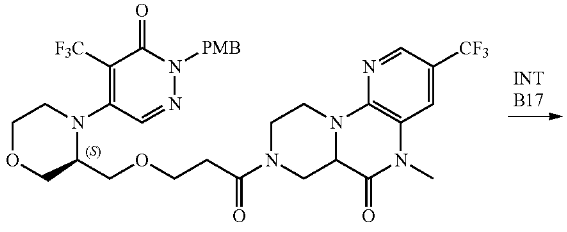

Compound 97-2

-continued

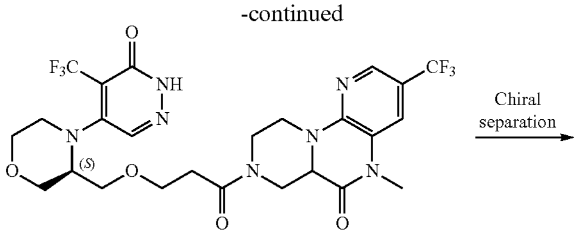

Compound 97

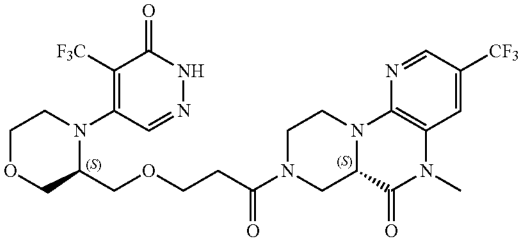

+

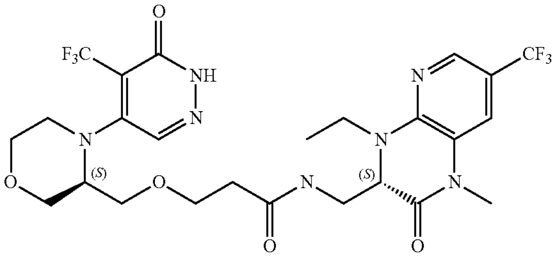

Step 1: Following an analogous procedure described in step 1 of example 2, INT B37 (0.65 g, 1.68 mmol, 1.0 eq.) and TFA (4 mL) were used as reactants to synthesize Compound 97-1 (crude, 1.22 g). LCMS: m/z=287 $[M+1]^+$.

Step 2: Following an analogous procedure described in step 2 of example 1, Compound 97-1 (490 mg, crude) and INT A17 (150 mg, 0.32 mmol, 1.0 eq.) were used as reactants to synthesize Compound 97-2 (crude, 270 mg). LCMS: m/z=740 $[M+1]^+$.

Step 3: Following an analogous procedure described in step 3 of example 83, Compound 97-2 (crude, 270 mg), TFA (10 mL) and TfOH (1 mL) were used as reactants to synthesize Compound 97 (163 mg, yield 72%). LCMS: m/z=620 $[M+1]^+$.

$^1$H NMR (400 MHz, $CD_3OD$) δ 8.15 (s, 1H), 7.91 (d, J=5.7, 1H), 7.43 (d, J=4.4 Hz, 1H), 5.05 (d, J=13.6 Hz, 0.5H), 4.68-4.60 (m, 1H), 4.39 (d, J=13.2 Hz, 0.5H), 4.13-3.84 (m, 5H), 3.84-3.66 (m, 5H), 3.65-3.56 (m, 2H), 3.38 (d, J=5.6 Hz, 3H), 3.25-3.13 (m, 2H), 2.94-2.74 (m, 2H), 2.59-2.51 (m, 2H).

The chiral separation of the Compound 97 (163 mg) was performed by Chiral-Prep-HPLC with the following conditions: Equipment: Prep-HPLC-Gilson; Column: CHIRALPAK ID 2 cm×25 cm, 5 um; Mobile Phase A: MTBE, Mobile Phase B: EtOH, $V_{Mobile\ Phase\ A}$:$V_{Mobile\ Phase\ B}$=60:40; Flow Rate: 16 mL/min; Detector Wavelength: 220 nm. This resulted in the first eluting stereoisomer (Compound 97A, 64.0 mg, Retention time 7.21 min), and the second eluting stereoisomer (Compound 97B, 64.9 mg, Retention time 8.05 min).

Example 98

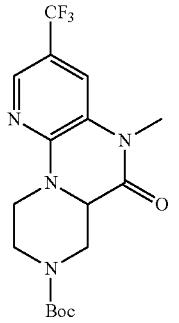

INT B37

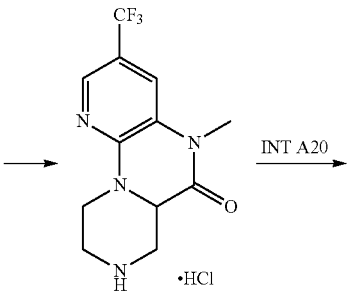

Compound 98-1

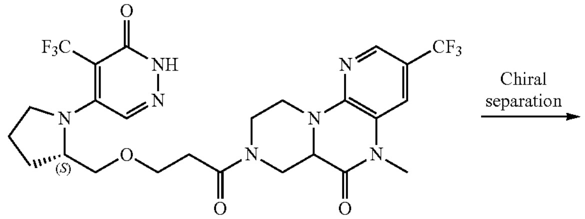

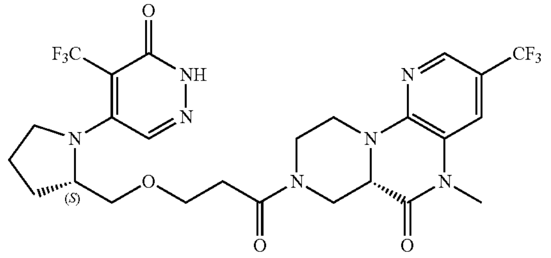

+

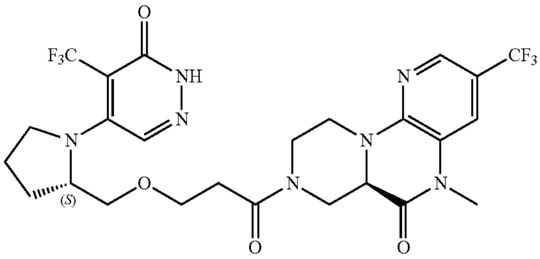

Step 1: Following an analogous procedure described in step 1 of example 1, INT B37 (5.31 g, 13.74 mmol, 1.0 eq.) and HCl/1,4-dioxane (20 mL, 1N) were used as reactants to synthesize Compound 98-1 (crude, 5.56 g). LCMS: m/z=287 $[M+1]^+$.

Step 2: Following an analogous procedure described in step 2 of example 1, the crude Compound 98-1 (1.95 g, crude) and INT A20 (2.27 g, 6.77 mmol, 1.0 eq.) were used as reactants to synthesize Compound 98 (2.50 g, yield 68%). LCMS: m/z=604 $[M+1]^+$.

$^1$H NMR (400 MHz, MeOD-$d_4$) δ 8.14 (s, 1H), 8.11 (d, J=10.0 Hz, 1H), 7.42 (s, 1H), 5.06 (d, J=13.2 Hz, 0.5H), 4.68-4.52 (m, 2.5H), 4.44 (d, J=13.6 Hz, 0.5H), 4.13-3.98 (m, 1.5H), 3.85-3.58 (m, 4H), 3.51-3.41 (m, 1H), 3.40-3.34 (m, 4H), 3.30-3.16 (m, 1H), 2.90-2.74 (m, 2H), 2.70-2.60 (m, 2H), 2.26-2.16 (m, 1H), 2.01-1.92 (m, 1H), 1.78-1.61 (m, 2H).

The chiral separation of the Compound 98 (260 mg) was performed by Chiral-Prep-HPLC with the following conditions: Equipment: Prep-HPLC-Gilson; Column: CHIRALPAK-ID column 2 cm×25 cm, 5 um; Mobile Phase A:

MTBE, Mobile Phase B: EtOH, $V_{Mobile\ Phase\ A}$:$V_{Mobile\ Phase\ B}$=60:40; Flow Rate: 18 mL/min; Detector Wavelength: 220 nm. This resulted in the first eluting stereoisomer (Compound 98A, 81.0 mg, Retention time 7.72 min), and the second eluting stereoisomer (Compound 98B, 86.4 mg, Retention time 8.95 min).

Pharmacological Experiments

1. PARP7 Enzymatic Experiments

The PARP7 enzyme inhibitory activity of each compound was tested using HTRF (homogeneous time resolved fluorescence) assay, and the half inhibitory concentration $IC_{50}$ thereof was obtained.

(1) Each compound to be tested was prepared using gradient dilution method with DMSO and water to obtain a solution with the concentration of 50 nM, 10 nM, 2 nM, 0.4 nM, and 0.08 nM. The concentration of DMSO in the solution of each compound to be tested was 2%.

(2) PARP7 enzyme (Cell Chemical Biology 27, 877-887, Jul. 16, 2020; the fusion tags was N-His6-TEV-Avi-MHHHHHHSSGVDLGTENLYFQSNAGLNDIFEAQK-IEWHE) was dissolved in the buffer solution (the pH of the buffer solution was 7.4, and the buffer solution contained 25 mM HEPES (N-(2-hydroxyethyl) piperazine-N'-2-sulfonic acid), 120 mM NaCl, 5 mM $MgCl_2$, 2 mM DTT (Dithiothreitol), 0.002% (ml/ml) Tween-20, 0.1% (ml/ml) BSA (bovine serum albumin) and water) to obtain a PARP7 enzyme solution with the concentration of 6 nM.

(3) The RBN011147 (Cell Chemical Biology 27, 877-887, Jul. 16, 2020), MAb Anti His-T b cryptate Gold (Cisbio, Cat. No 61GSTTLF, Lot. No 09A), and Streptavidin-d2 (Cisbio, Cat. No 610SADLF, Lot. No 19G) were diluted with buffer solution (the pH of the buffer solution was 7.4, and the buffer solution contained 25 mM HEPES (N-(2-hydroxyethyl) piperazine-N'-2-sulfonic acid), 120 mM NaCl, 5 mM $MgCl_2$, 2 mM DTT (Dithiothreitol), 0.002% (ml/ml) Tween-20, 0.1% (ml/ml) BSA (bovine serum albumin) and water) to obtain the solution containing fluorophore with the concentration of 10 nM, 0.7 nM, and 2.5 nM respectively. The MAb Anti His-Tb cryptate Gold was the donor fluorophore, and the Streptavidin-d2 was the acceptor fluorophore.

(4) 2.5 μl of the solution of the compound to be tested was transferred into 384-well plate, 2.5 μl of the PARP7 enzyme solution was added. The resulting solution was incubated for 15 mins, and then 5 μl of the solution containing fluorophore was added. The resulting mixture was incubated at 25° C. for 3 hrs to obtain the final solution to be tested.

(5) The fluorescence signal was read on SPARK plate reader (Tecan), the wavelength of the excitation spectrum of the SPARK plate reader was 320 nm, and the wavelength of the emission spectrum of the SPARK plate reader was 620 nm and 665 nm. The ratio of absorbance at 620 nm to absorbance at 665 nm was calculated for the solution in each well. The ratio was calculated according to the following formula: Ratio=absorbance at 665 nm/absorbance at 620 nm×104.

(6) The activation of the compounds to be tested was calculated according to the following formula: Activation (%)=100×($ratio_{compound}$−$ratio_{negative}$)/($ratio_{positive}$−$ratio_{negative}$). Inhibition (%)=100−Activation (%). The positive control was the whole reaction system containing PARP7 enzyme, RBN011147, MAb Anti His-Tb cryptate Gold, and Streptavidin-d2, but with DMSO instead of compound. The negative control was the whole reaction system containing RBN011147, MAb Anti His-Tb cryptate Gold, Streptavidin-d2, and DMSO instead of compound, with no PARP7 enzyme.

The $IC_{50}$ value was obtained by 4 Parameter Logistic (4PL 1/y2) model fitting, and the measured results are shown in Table 1:

TABLE 1

| Compound | PARP7 Enzyme ($IC_{50}$ μM) |
|---|---|
| Compound 1A | 0.0343 |
| Compound 2 | 0.000584 |
| Compound 3 | 0.000966 |
| Compound 3A | 0.001224 |
| Compound 3B | 0.001832 |
| Compound 4A | 0.016590 |
| Compound 4B | 0.167339 |
| Compound 5A | 0.002537 |
| Compound 5B | 0.001596 |
| Compound 6A | 0.013694 |
| Compound 6B | 0.003205 |
| Compound 7A | 0.003702 |
| Compound 7B | 0.002247 |
| Compound 8 | 0.001875 |
| Compound 9A | 0.000648 |
| Compound 9B | 0.001173 |
| Compound 10 | 0.048308 |
| Compound 11 | 0.011116 |
| Compound 12 | 0.002923 |
| Compound 13A | 0.001356 |
| Compound 13B | 0.001730 |
| Compound 14A | 0.010570 |
| Compound 14B | 0.039933 |
| Compound 15A | 0.001925 |
| Compound 15B | 0.002857 |
| Compound 16 | 0.123706 |
| Compound 17A | 0.001146 |
| Compound 17B | 0.001399 |
| Compound 18 | 0.000806 |
| Compound 18A | 0.001082 |
| Compound 18B | 0.001784 |
| Compound 19A | 0.001701 |
| Compound 19B | 0.002749 |
| Compound 20A | 0.001514 |
| Compound 20B | 0.001852 |
| Compound 21A | 0.000424 |
| Compound 21B | 0.000812 |
| Compound 22A | 0.000846 |
| Compound 22B | 0.000969 |
| Compound 23A | 0.000804 |
| Compound 23B | 0.000863 |
| Compound 24A | 0.002072 |
| Compound 24B | 0.003173 |
| Compound 25A | 0.003717 |
| Compound 25B | 0.005357 |
| Compound 26A | 0.001539 |
| Compound 26B | 0.003404 |
| Compound 27 | 0.006984 |
| Compound 28A | 0.007527 |
| Compound 28B | 0.00787 |
| Compound 29A | 0.000861 |
| Compound 29B | 0.001085 |
| Compound 31A | 0.025768 |
| Compound 31B | 0.059047 |
| Compound 32A | 0.008253 |
| Compound 32B | 0.020015 |
| Compound 33A | 0.003947 |
| Compound 33B | 0.008650 |
| Compound 34 A | 0.001039 |
| Compound 34B | 0.015222 |
| Compound 35A | 0.1966 |
| Compound 36 | 0.11527 |
| Compound 37 | 0.003106 |
| Compound 37A | 0.004146 |
| Compound 37B | 0.001306 |
| Compound 39 | 0.003645 |
| Compound 40 | 0.00961 |
| Compound 41 | 0.002309 |
| Compound 42 | 0.002767 |
| Compound 43 | 0.002023 |
| Compound 45 | 0.001582 |
| Compound 47A | 0.001292 |

TABLE 1-continued

| Compound | PARP7 Enzyme ($IC_{50}$ μM) |
|---|---|
| Compound 48 | 0.000802 |
| Compound 49A | 0.000967 |
| Compound 49B | 0.110179 |
| Compound 51 | 0.001243 |
| Compound 53 | 0.002131 |
| Compound 53A | 0.001445 |
| Compound 53B | 0.001127 |
| Compound 54 | 0.002555 |
| Compound 54A | 0.000726 |
| Compound 54B | 0.001789 |
| Compound 55A | 0.000676 |
| Compound 55B | 0.002783 |
| Compound 56A | 0.000939 |
| Compound 56B | 0.003686 |
| Compound 57A | 0.000617 |
| Compound 57B | 0.000897 |
| Compound 58A | 0.00845 |
| Compound 58B | 0.001532 |
| Compound 59A | 0.001123 |
| Compound 59B | 0.005295 |
| Compound 60A | 0.014599 |
| Compound 60B | 0.117505 |
| Compound 61A | 0.000828 |
| Compound 61B | 0.002322 |
| Compound 62A | 0.001532 |
| Compound 62B | 0.008187 |
| Compound 62C | 0.001821 |
| Compound 62D | 0.007456 |
| Compound 63A | 0.001766 |
| Compound 63B | 0.001062 |
| Compound 63C | 0.00359 |
| Compound 63D | 0.003009 |
| Compound 64A | 0.001502 |
| Compound 64B | 0.009459 |
| Compound 62A | 0.001772 |
| Compound 62B | 0.041523 |
| Compound 62C | 0.001324 |
| Compound 62D | 0.03863 |
| Compound 66A | 0.002053 |
| Compound 66B | 0.001823 |
| Compound 67A | 0.001658 |
| Compound 67B | 0.007318 |
| Compound 68A | 0.001595 |
| Compound 68B | 0.004285 |
| Compound 69 | 0.003925 |
| Compound 70A | 0.001497 |
| Compound 70B | 0.007535 |
| Compound 71A | 0.001526 |
| Compound 71B | 0.014942 |
| Compound 72A | 0.000837 |
| Compound 72B | 0.007241 |
| Compound 73A | 0.000769 |
| Compound 73B | 0.017879 |
| Compound 74A | 0.002158 |
| Compound 74B | 0.002231 |
| Compound 74C | 0.05543 |
| Compound 74D | 0.072204 |
| Compound 75A | 0.00364 |
| Compound 75B | 0.013493 |
| Compound 76A | 0.003307 |
| Compound 76B | 0.005036 |
| Compound 77A | 0.012557 |
| Compound 77B | 0.004 |
| Compound 78 | 0.002833 |
| Compound 79A | 0.007246 |
| Compound 79B | 0.004671 |
| Compound 79C | 0.004774 |
| Compound 79D | 0.003184 |
| Compound 80 | 0.000946 |
| Compound 81A | 0.113747 |
| Compound 81C | 0.001291 |
| Compound 81D | 0.001489 |
| Compound 82A | 0.000744 |
| Compound 82B | 0.000892 |
| Compound 83A | 0.003786 |
| Compound 83B | 0.003635 |
| Compound 84A | 0.001006 |

TABLE 1-continued

| Compound | PARP7 Enzyme ($IC_{50}$ μM) |
|---|---|
| Compound 84 | 0.004006 |
| Compound 85A | 0.002031 |
| Compound 85B | 0.007836 |
| Compound 86A | 0.002496 |
| Compound 86B | 0.020518 |
| Compound 87A | 0.0006114 |
| Compound 87B | 0.00087 |
| Compound 88A | 0.000416 |
| Compound 88B | 0.000446 |
| Compound 89A | 0.000696 |
| Compound 89B | 0.000658 |
| Compound 90A | 0.000592 |
| Compound 90B | 0.000792 |
| Compound 91 | 0.000496 |
| Compound 92 | 0.000686 |
| Compound 93A | 0.002818 |
| Compound 93B | 0.002089 |
| Compound 94A | 0.002368 |
| Compound 94B | 0.002937 |
| Compound 94C | 0.002098 |
| Compound 94D | 0.0035515 |
| Compound 95A | 0.003565 |
| Compound 95B | 0.005881 |
| Compound 96 | 0.003272 |
| Compound 98A | 0.001246 |
| Compound 98B | 0.001355 |

From Table 1, it can be seen that the representative compounds of the present invention have good inhibitory effect on PARP7 enzyme.

2. Lung Cancer Cell Proliferation Inhibition Experiment

In this experiment, the CTG method was used to test the inhibition of the compounds on the proliferation of lung cancer cell line H1373 (high expression of PARP7), and half inhibitory concentration $IC_{50}$ of the compound to H1373 was obtained. The H1373 cell line was purchased from ATCC, the complete culture medium was ATCC modified RPMI 1640 medium+10% FBS (Fetal bovine serum)+1% PS (Penicillin-Streptomycin Liquid). RPMI 1640 cell culture medium, fetal bovine serum, and trypsin were purchased from Gibco, and cell culture flasks were purchased from Greiner, disposable Cell Counting Plate, and trypan Blue Solution purchased from Bio-Rad.

(1) 100 μl of H1373 cells suspension was seeded in a 96-well cell culture plate, and the density of the suspension in each well was $1.5\times10^4$ cells/ml. The culture plate was incubated in incubator for 16-24 h (37° C., 5% $CO_2$);

(2) The solution of each compound to be tested with different concentration was obtained using gradient dilution. 2 d of the solution of each compound to be tested was mixed with 198 μl RPMI 1640 containing 1% PS to obtain the final solution. The final solution was transferred to the culture plate (25 μl/well, 2 parallel wells per concentration), and the culture plate was incubated for 144 hrs in incubator (37° C., 5% $CO_2$). Cell Titer Glo reagent was added into each well of the culture plate, and then the culture plate was shaken for 2 mins and incubated for an additional 10 mins at room temperature.

(3) The luminescence signal of each well was measured on SPARK plate reader.

(4) The inhibition rate was calculated by the luminescence signal value.

(5) The curve was fitted with the inhibition rate of different concentrations, and then the $IC_{50}$ of compounds were calculated.

The measured results were shown in Table 2:

TABLE 2

| Compound | H1373 ($IC_{50}$ μM) |
|---|---|
| Compound 2 | 0.425632 |
| Compound 3 | 0.15987 |
| Compound 3A | 0.024442 |
| Compound 3B | 0.050294 |
| Compound 5A | 0.340704 |
| Compound 5B | 0.135359 |
| Compound 8 | 0.203275 |
| Compound 9A | 0.041912 |
| Compound 9B | 0.104576 |
| Compound 13A | 0.035744 |
| Compound 13B | 0.052152 |
| Compound 15A | 0.082417 |
| Compound 15B | 0.187225 |
| Compound 17A | 0.0452895 |
| Compound 17B | 0.0572675 |
| Compound 18 | 0.099634 |
| Compound 18A | 0.085869 |
| Compound 18B | 0.129752 |
| Compound 19A | 0.268735 |
| Compound 19B | 0.221383 |
| Compound 20A | 0.053902 |
| Compound 20B | 0.057425 |
| Compound 21A | 0.080858 |
| Compound 21B | 0.043634 |
| Compound 22A | 0.139165 |
| Compound 22B | 0.06408 |
| Compound 23A | 0.11735 |
| Compound 23B | 0.046067 |
| Compound 25A | 0.038062 |
| Compound 25B | 0.053354 |
| Compound 26A | 0.1979765 |
| Compound 26B | 0.318014 |
| Compound 27 | 0.441354 |
| Compound 28A | 0.274546 |
| Compound 28B | 0.760526 |
| Compound 29A | 0.016434 |
| Compound 29B | 0.03036 |
| Compound 33A | 0.127720 |
| Compound 33B | 0.261216 |
| Compound 34 A | 0.073872 |
| Compound 37 | 0.202894 |
| Compound 37B | 0.08597 |
| Compound 39 | 0.107573 |
| Compound 40 | 0.259922 |
| Compound 41 | 0.275535 |
| Compound 42 | 0.137707 |
| Compound 43 | 0.105045 |
| Compound 45 | 0.013012 |
| Compound 47A | 0.060916 |
| Compound 48 | 0.070813 |
| Compound 49A | 0.184699 |
| Compound 51 | 0.0345895 |
| Compound 53 | 0.079704 |
| Compound 53A | 0.295638 |
| Compound 53B | 0.213736 |
| Compound 54 | 0.063638 |
| Compound 54A | 0.033237 |
| Compound 54B | 0.802165 |
| Compound 55A | 0.028923 |
| Compound 55B | 0.614607 |
| Compound 56A | 0.117204 |
| Compound 57A | 0.013156 |
| Compound 57B | 0.304514 |
| Compound 58B | 0.103693 |
| Compound 59A | 0.05042 |
| Compound 59B | 0.42533 |
| Compound 61A | 0.328345 |
| Compound 62A | 0.014046 |
| Compound 62B | 0.329203 |
| Compound 62C | 0.253659 |
| Compound 63A | 0.189412 |
| Compound 63B | 0.069637 |
| Compound 63C | 0.652201 |
| Compound 64A | 0.207681 |
| Compound 62A | 0.451993 |

TABLE 2-continued

| Compound | H1373 ($IC_{50}$ μM) |
|---|---|
| Compound 62C | 0.531244 |
| Compound 66A | 0.085499 |
| Compound 66B | 0.070357 |
| Compound 67A | 0.026568 |
| Compound 67B | 0.842469 |
| Compound 68A | 0.014175 |
| Compound 68B | 0.234648 |
| Compound 69 | 0.482841 |
| Compound 70A | 0.028667 |
| Compound 70B | 0.342008 |
| Compound 71A | 0.013942 |
| Compound 71B | 0.912377 |
| Compound 72A | 0.013269 |
| Compound 73A | 0.022269 |
| Compound 76A | 0.359512 |
| Compound 76B | 0.403923 |
| Compound 77A | 0.349191 |
| Compound 77B | 0.333648 |
| Compound 79A | 0.572421 |
| Compound 79B | 0.34133 |
| Compound 79C | 0.45571 |
| Compound 79D | 0.742494 |
| Compound 80 | 0.150968 |
| Compound 81C | 0.01924 |
| Compound 81D | 0.012291 |
| Compound 82A | 0.047498 |
| Compound 82B | 0.021573 |
| Compound 83A | 0.142545 |
| Compound 83B | 0.46832 |
| Compound 84A | 0.021542 |
| Compound 84B | 0.43221 |
| Compound 85A | 0.020722 |
| Compound 85B | 0.311436 |
| Compound 86A | 0.011892 |
| Compound 86B | 0.245727 |
| Compound 87A | 0.0058 |
| Compound 87B | 0.005351 |
| Compound 88A | 0.002165 |
| Compound 88B | 0.002935 |
| Compound 89A | 0.010582 |
| Compound 89B | 0.006924 |
| Compound 90A | 0.005117 |
| Compound 90B | 0.041809 |
| Compound 91 | 0.011266 |
| Compound 92 | 0.0080165 |
| Compound 93A | 0.015647 |
| Compound 93B | 0.010418 |
| Compound 94A | 0.008513 |
| Compound 94B | 0.013253 |
| Compound 94C | 0.007027 |
| Compound 94D | 0.015805 |
| Compound 95A | 0.039918 |
| Compound 95B | 0.048516 |
| Compound 96 | 0.022103 |
| Compound 98A | 0.055522 |
| Compound 98B | 0.037055 |

From the Table 2, it can be seen that the representative compounds of the present invention have good inhibitory effect on the proliferation of H1373 cell.

3. Mouse Pharmacokinetic Study

The purpose of this study was to evaluate the pharmacokinetic properties of compounds in Balb/c mouse (Y) following single dose administration. Six mice were needed for each compound and the six mice were divided into two groups (n=3/group), group A and group B. Mice in group A were treated with a single 3 mg/kg dose of compound (i.v.). Mice in group B were treated with a single 100 mg/kg dose of compound (p.o.). For each mouse in group A, blood samples were collected at pre-dose, and at the time point of 0.083, 0.5, 1, 4, 8 and 24 h post-dose. For each mouse in group B, blood samples were collected at pre-dose, and at the time point of 0.25, 0.5, 1, 4 and 8 h post-dose. Blood samples were placed on ice until centrifugation to obtain plasma samples. The plasma samples were stored at −80° C. until analysis. The concentration of compound in plasma samples was determined using a LC-MS/MS method. The results are in the following Table 3:

TABLE 3

| | 3 mg/kg, i.v. | | 100 mg/kg, p.o. | | |
|---|---|---|---|---|---|
| Compound | CL (mL/min/kg) | Vss (L/kg) | $C_{max}$ (ng/ml) | $AUC_{last}$ (ng · h/mL) | Oral BA (F %) |
| Compound 82A | 32 | 0.4 | 21733 | 26442 | 48 |
| Compound 51 | 22 | 0.5 | 38233 | 91379 | 121 |
| Compound 84A | 41 | 0.5 | 15033 | 43382 | 106 |
| Compound 47A | 16 | 0.5 | 41100 | 95227 | 90 |
| Compound 85A | 60 | 0.5 | 24200 | 86095 | 301 |
| Compound 86A | 54 | 1.4 | 7857 | 20321 | 66 |

From the Table 3, it can be seen that the representative compounds of the present invention have good pharmacokinetic properties, such as high $AUC_{last}$, $C_{max}$ and oral BA. Others compounds, such as Compound 14A, Compound 20A, Compound 24A, Compound 29A, Compound 45, Compound 57A, Compound 59A, Compound 67A, Compound 71A processes good pharmacokinetic properties as well.

It should be understood that if the present invention quotes any prior art publication, it should be understood that: such quotation does not mean that the publication is recognized as part of the common knowledge in the field in any country. Although for the sake of clear understanding, the present invention has been described in detail by way of examples, it is obvious to those skilled in the art that certain minor changes and modifications will be made. Therefore, the description and examples should not be construed as limiting the scope of the present invention.

What is claimed is:

1. A compound, a stereoisomer thereof, a deuterated derivative thereof, or a pharmaceutically acceptable salt thereof, wherein, the compound is selected from any one of the following compounds:

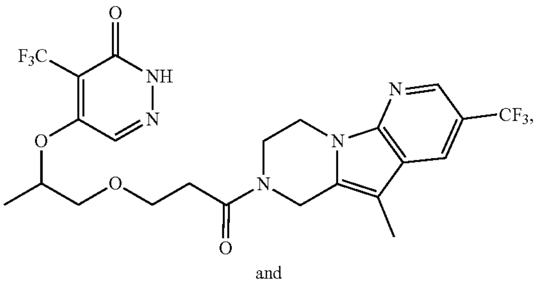

and

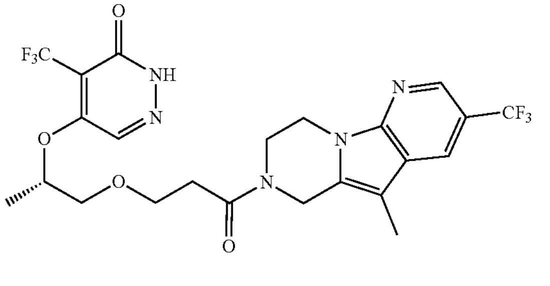

2. A pharmaceutical composition comprising the compound according to claim 1, a stereoisomer thereof, a deuterated derivative thereof, or a pharmaceutically acceptable salt thereof; and at least one pharmaceutically acceptable excipient.

3. A method of inhibiting the activity of PARP7 comprising contacting an effective amount of the compound according to claim 1, a stereoisomer thereof, a deuterated derivative thereof, or a pharmaceutically acceptable salt thereof with PARP7 or a cell in which inhibition of PARP7 is desired.

4. The compound according to claim 1, a stereoisomer thereof, a deuterated derivative thereof, or a pharmaceutically acceptable salt thereof, wherein, the compound is:

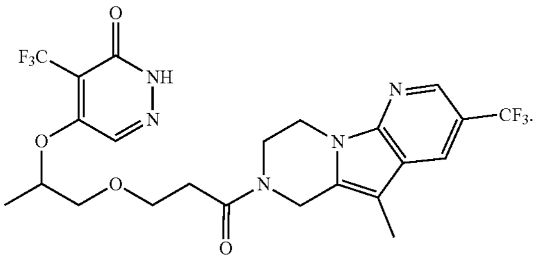 [SMILES: Cc1c2n(c3ncc(C(F)(F)F)cc13)CCN(C(=O)CCOCC(C)Oc1cn[nH]c(=O)c1C(F)(F)F)C2]

5. The compound according to claim 1, a stereoisomer thereof, a deuterated derivative thereof, or a pharmaceutically acceptable salt thereof, wherein, the compound is:

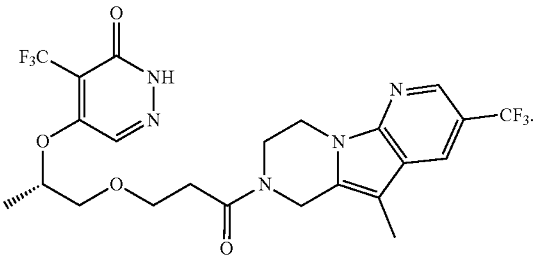 [SMILES: Cc1c2n(c3ncc(C(F)(F)F)cc13)CCN(C(=O)CCOC[C@H](C)Oc1cn[nH]c(=O)c1C(F)(F)F)C2]

6. A method of treating a subject having cancer, said method comprising administering to the subject a therapeutically effective amount of the compound according to claim 1, a stereoisomer thereof, a deuterated derivative thereof, or a pharmaceutically acceptable salt thereof.

7. The method according to claim 6, wherein, the cancer is selected from breast cancer, cancer of the central nervous system, endometrium cancer, kidney cancer, large intestine cancer, lung cancer, esophagus cancer, tongue cancer, ovarian cancer, pancreatic cancer, prostate cancer, stomach cancer, mesothelioma, melanoma, fibrosarcoma, bladder cancer, rectal cancer, lymphoma, cervical cancer, head and neck cancer, upper aerodigestive cancer, colorectal cancer, urinary tract cancer, and colon cancer.

8. The method according to claim 7, wherein, each cancer is independently selected from adenocarcinoma, squamous cell carcinoma, mixed adenosquamous carcinoma, and undifferentiated carcinoma.

9. The method according to claim 7, wherein, the ovarian cancer is selected from the group consisting of high grade ovarian serious adenocarcinoma, ovarian mucinous cystadenocarcinoma or malignant ovarian Brenner tumor; the kidney cancer is clear cell renal cell carcinoma; the tongue cancer is tongue squamous cell carcinoma; the lung cancer is selected from the group consisting of lung adenocarcinoma, lung adenosquamous carcinoma, squamous cell lung carcinoma, large cell lung carcinoma, small cell lung carcinoma, papillary adenocarcinoma of the lung or non-small cell lung carcinoma; the pancreatic cancer is selected from the group consisting of pancreatic adenocarcinoma or pancreatic ductal adenocarcinoma; the esophagus cancer is esophageal squamous cell carcinoma; the mesothelioma is biphasic mesothelioma; the cancer of the central nervous system is selected from the group consisting of neuroglioma, glioblastoma or glioblastoma multiforme; the stomach cancer is gastric adenocarcinoma; the breast cancer is selected from the group consisting of ductal breast carcinoma, breast adenocarcinoma or $HR_+$ breast cancer; the bladder cancer is bladder squamous cell carcinoma; the melanoma is malignant melanoma; the colon cancer is colon adenocarcinoma; the head and neck cancer is head and neck small squamous cell cancer.

10. The method according to claim 7, wherein, the cancer is PARP7 overexpression associated cancer.

11. A method of treating a subject having cancer, said method comprising administering to the subject a therapeutically effective amount of the pharmaceutical composition according to claim 2.

* * * * *